United States Patent
Jin et al.

(10) Patent No.: US 12,110,295 B2
(45) Date of Patent: Oct. 8, 2024

(54) WD40 REPEAT DOMAIN PROTEIN 5 (WDR5) DEGRADATION/DISRUPTION COMPOUNDS AND METHODS OF USE

(71) Applicants: Icahn School of Medicine at Mount Sinai, New York, NY (US); The University of North Carolina at Chapel Hill, Chapel Hill, NC (US)

(72) Inventors: Jian Jin, New York, NY (US); Gang Wang, Chapel Hill, NC (US); Jing Liu, New York, NY (US); Xufen Yu, New York, NY (US); Dongxu Li, Chapel Hill, NC (US)

(73) Assignees: Icahn School of Medicine at Mount Sinai, New York, NY (US); The University of North Carolina at Chapel Hill, Chapel Hill, NC (US)

( * ) Notice: Subject to any disclaimer, the term of this patent is extended or adjusted under 35 U.S.C. 154(b) by 258 days.

(21) Appl. No.: 17/254,345

(22) PCT Filed: Jun. 21, 2019

(86) PCT No.: PCT/US2019/038560
§ 371 (c)(1),
(2) Date: Dec. 21, 2020

(87) PCT Pub. No.: WO2019/246570
PCT Pub. Date: Dec. 26, 2019

(65) Prior Publication Data
US 2022/0348580 A1 Nov. 3, 2022

Related U.S. Application Data

(60) Provisional application No. 62/688,343, filed on Jun. 21, 2018.

(51) Int. Cl.
*C07D 487/04* (2006.01)
*C07D 401/14* (2006.01)
*C07D 417/14* (2006.01)

(52) U.S. Cl.
CPC ......... *C07D 487/04* (2013.01); *C07D 401/14* (2013.01); *C07D 417/14* (2013.01)

(58) Field of Classification Search
CPC ... C07D 487/04; C07D 401/14; C07D 417/14
USPC ....................................................... 514/249
See application file for complete search history.

(56) References Cited

U.S. PATENT DOCUMENTS

| | | |
|---|---|---|
| 5,691,147 A | 10/1997 | Draetta et al. |
| 8,377,937 B2 | 2/2013 | Bencsik et al. |
| 8,648,096 B2 | 2/2014 | Muller et al. |
| 9,809,603 B1 | 11/2017 | Jacques |
| 9,822,094 B2 | 11/2017 | Man et al. |
| 2002/0098161 A1 | 7/2002 | Uhrich |
| 2004/0063773 A1 | 4/2004 | Tang et al. |
| 2011/0172107 A1 | 7/2011 | Katz et al. |
| 2011/0196150 A1 | 8/2011 | Man et al. |
| 2014/0031325 A1 | 1/2014 | Bartlett et al. |
| 2014/0356322 A1 | 12/2014 | Crews et al. |
| 2015/0119435 A1 | 4/2015 | Crews et al. |
| 2015/0274738 A1 | 10/2015 | Gray et al. |
| 2015/0291562 A1 | 10/2015 | Crew et al. |
| 2016/0045504 A1 | 2/2016 | Grembecka et al. |
| 2017/0008904 A1 | 1/2017 | Crew et al. |
| 2017/0114098 A1 | 4/2017 | Aivado et al. |
| 2017/0121321 A1 | 5/2017 | Crews et al. |
| 2017/0224685 A1 | 8/2017 | Duncan et al. |
| 2017/0283807 A1 | 10/2017 | Mounir et al. |
| 2018/0072741 A1 | 3/2018 | Vechorkin et al. |
| 2018/0086767 A1 | 3/2018 | Fesik et al. |
| 2018/0134684 A1 | 5/2018 | Bradner et al. |
| 2018/0186800 A1 | 7/2018 | Yamamoto et al. |
| 2019/0092768 A1 | 3/2019 | Gray et al. |
| 2019/0255041 A1 | 8/2019 | Jin et al. |
| 2019/0336503 A1 | 11/2019 | Jin et al. |
| 2019/0367525 A1 | 12/2019 | Ioannidis et al. |
| 2020/0338070 A1 | 10/2020 | Jin et al. |
| 2020/0399266 A1 | 12/2020 | Jin et al. |
| 2021/0261538 A1 | 8/2021 | Jin et al. |
| 2021/0283261 A1 | 9/2021 | Jin et al. |
| 2021/0355140 A1 | 11/2021 | Shunatona et al. |
| 2021/0395244 A1 | 12/2021 | Jin et al. |
| 2022/0054488 A1 | 2/2022 | Jin et al. |
| 2023/0022524 A1 | 1/2023 | Jin et al. |
| 2023/0070613 A1 | 3/2023 | Jin et al. |
| 2023/0167106 A1 | 6/2023 | Jin et al. |

FOREIGN PATENT DOCUMENTS

| | | |
|---|---|---|
| CN | 102822165 | 12/2012 |
| CN | 103189067 | 7/2013 |
| CN | 104736569 | 6/2015 |

(Continued)

OTHER PUBLICATIONS

PCT International Search Report and Written Opinion in International Appln. No. PCT/US2022/013225, dated Jun. 6, 2022, 24 pages.
EP Extended European Search Report in European Appln. No. 19821826.5, dated May 3, 2022, 10 pages.
Fisher et al., "Targeted protein degradation and the enzymology of degraders," Current Opinion in Chemical Biology, 2018, 44:47-55.
CN Office Action in Chinese Appln. No. 201780085879.6, dated Jun. 27, 2022, 15 pages (with English Translation).
JP Office Action in Japanese Appln. No. 2019-522841, dated Jul. 12, 2022, 8 pages (with English Translation).
U.S. Appl. No. 16/345,591, filed Apr. 26, 2019, Jian Jin.
U.S. Appl. No. 16/926,418, filed Jul. 10, 2020, Jian Jin.
U.S. Appl. No. 17/978,696, filed Nov. 1, 2022, Jian Jin.
U.S. Appl. No. 16/467,888, filed Jun. 7, 2019, Jian Jin.
U.S. Appl. No. 17/453,619, filed Nov. 4, 2021, Jian Jin.

(Continued)

*Primary Examiner* — Kahsay Habte
(74) *Attorney, Agent, or Firm* — Fish & Richardson P.C.

(57) ABSTRACT

Disclosed herein are WD40 repeat domain protein 5 (WDR5) degradation/disruption compounds including a WDR5 ligand, a degradation/disruption tag, and a linker, and methods of using such compounds in the treatment of WDR5-mediated diseases.

15 Claims, 28 Drawing Sheets

(56) References Cited

FOREIGN PATENT DOCUMENTS

| | | |
|---|---|---|
| CN | 105085620 | 11/2015 |
| CN | 105175284 | 12/2015 |
| CN | 108137507 | 6/2018 |
| CN | 109071552 | 12/2018 |
| CN | 109790143 | 5/2019 |
| CN | 112778303 | 5/2021 |
| JP | 2007-512364 | 5/2007 |
| JP | 2008-525526 | 7/2008 |
| JP | 2009-542721 | 12/2009 |
| JP | 2009-542723 | 12/2009 |
| JP | 2010-532386 | 10/2010 |
| JP | 2010-532387 | 10/2010 |
| JP | 2015-508414 | 3/2015 |
| JP | 2016-540811 | 12/2016 |
| JP | 2017-513862 | 6/2017 |
| JP | 2018-502097 | 1/2018 |
| JP | 2018-526430 | 9/2018 |
| JP | 2019-514883 | 5/2020 |
| MX | 2018000471 | 4/2018 |
| MX | 2018000360 | 6/2018 |
| WO | WO 2008/109104 | 9/2008 |
| WO | WO 2014/100719 | 6/2014 |
| WO | WO 2015/101293 | 7/2015 |
| WO | WO 2015/104677 | 7/2015 |
| WO | WO 2015/192123 | 12/2015 |
| WO | WO 2016/073956 | 5/2016 |
| WO | WO 2016/105518 | 6/2016 |
| WO | WO 2016/106518 | 7/2016 |
| WO | WO 2016/115480 | 7/2016 |
| WO | WO 2016/149668 | 9/2016 |
| WO | WO 2016/168992 | 10/2016 |
| WO | WO 2016/174130 | 11/2016 |
| WO | WO 2016/197032 | 12/2016 |
| WO | WO 2016/208595 | 12/2016 |
| WO | WO 2017/011371 | 1/2017 |
| WO | WO 2017/011590 | 1/2017 |
| WO | WO 2017/024317 | 2/2017 |
| WO | WO 2017/024319 | 2/2017 |
| WO | WO 2017/079267 | 5/2017 |
| WO | WO 2017/147700 | 9/2017 |
| WO | WO 2017/147701 | 9/2017 |
| WO | WO 2017/185031 | 10/2017 |
| WO | WO 2017/197051 | 11/2017 |
| WO | WO 2017/197055 | 11/2017 |
| WO | WO 2018/049200 | 3/2018 |
| WO | WO 2018/098280 | 5/2018 |
| WO | WO 2018/106870 | 6/2018 |
| WO | WO 2018/117177 | 6/2018 |
| WO | WO 2018/119441 | 6/2018 |
| WO | WO 2019/084030 | 5/2019 |
| WO | WO 2019/222380 | 11/2019 |
| WO | WO 2019/246570 | 12/2019 |
| WO | WO 2020/252043 | 12/2020 |
| WO | WO 2021/021904 | 2/2021 |
| WO | WO 2021/057872 | 4/2021 |
| WO | WO 2023/006063 | 2/2023 |

OTHER PUBLICATIONS

U.S. Appl. No. 16/769,326, filed Jun. 3, 2020, Jian Jin.
U.S. Appl. No. 16/970,305, filed Aug. 14, 2020, Jian Jin.
U.S. Appl. No. 16/977,654, filed Sep. 2, 2020, Jian Jin.
U.S. Appl. No. 17/938,502, filed Oct. 6, 2022, Jian Jin.
U.S. Appl. No. 17/256,516, filed Dec. 28, 2020, Jian Jin.
U.S. Appl. No. 17/604,636, filed Oct. 18, 2021, Jian Jin.
U.S. Appl. No. 17/336,059, filed Jun. 1, 2021, Jian Jin.
AU Office Action in Australian Appln. No. 2022201488, dated Feb. 14, 2023, 6 pages.
CN Office Action in Chinese Appln. No. 201980030599.4, dated Jan. 5, 2023, 13 pages (with English Translation).
EP Extended European Search Report in European Appln. No. 20802303.6, dated Dec. 23, 2022, 6 pages.
EP Office Action in European Appln. No. 17863645.2, dated Nov. 11, 2022, 6 pages.
Fioravanti et al., "Six years (2012-2018) of researches on catalytic EZH2 inhibitors: The boom of the 2-pyridone compounds," Manuscript, The Chemical Record, 2018, 18(12):1818-1832.
Kumar et al., "EZH2 Inhibitor GSK126 for Cancer Treatment: Metabolism, drug transporter and rat pharmacokinetic studies," Medical Research Archives, 2015, Issue 3, 31 pages.
PCT Invitation to Pay Additional Fees in International Appln. No. PCT/US2022/050929, dated Feb. 6, 2023, 3 pages.
Stazi et al., "EZH2 inhibitors: a patent review (2014-2016)," Expert Opinion on Therapeutic Patents, 2017, 27(7):797-813.
EP Office Action in European Appln. No. 17877800.7, dated May 24, 2022, 6 pages.
Abramovich et al., "Hox regulation of normal and leukemic hematopoietic stem cells," Curr. Opin. Hematol., May 2005, 12(3):210-216.
Addie et al., "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases," J. Med. Chem., Mar. 2013, 56(5):2059-2073.
Aguilar et al., "Discovery of 4-((3'R,4'S,5'R)-6"-Chloro-4'-(3-chloro-2-fluorophenyl)l'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," Journal of Medicinal Chemistry, Mar. 2017, 60(7):2819-2839.
Alinari et al., "Selective inhibition of protein arginine methyltransferase 5 blocks initiation and maintenance of B-cell transformation," Blood, Apr. 2015, 125(16):2530-2543.
Alzabin et al., "Hematopoietic progenitor kinase 1 is a critical component of prostaglandin E2- mediated suppression of the antitumor immune response," Cancer Immunol. Immunother., 2010, 59:419-429.
Alzabin et al., "Hematopoietic Progenitor Kinase 1 Is a Negative Regulator of Dendritic Cell Activation," J Immunol, 2009, 182:6187-6194.
Anders et al., "Differential expression analysis for sequence count data," Genome Biol., 2010 11:R106.
Armstrong et al., "MLL translocations specify a distinct gene expression profile that distinguishes a unique leukemia," Nat Genet., Jan. 2002, 30:41-47.
Artinger et al., "An MLL-dependent network sustains hematopoiesis," Proc. Natl. Acad. Sci. USA, Jul. 2013, 110(29):12000-12005.
Asiaban et al., "Cell-Based Ligand Discovery for the ENL YEATS Domain," ACS Chem. Biol., Apr. 2020, 15(4):895-903.
AU Notice of Allowance in Australian Appln. No. 2017348322, dated Dec. 14, 2021, 3 pages.
AU Office Action in Australian Appln. No. 2017348322, dated Dec. 10, 2020, 7 pages.
AU Office Action in Australian Appln. No. 2017348322, dated Sep. 27, 2021, 2 pages.
Ayton et al., "Molecular mechanisms of leukemogenesis mediated by MLL fusion proteins," Oncogene, Oct. 2001, 20:5695-5707.
Bachman et al., "EZH2 Expression Is Associated With High Proliferation Rate and Aggressive Tumor Subgroups in Cutaneous Melanoma and Cancers of the Endometrium, Prostate, and Breast," J. Clin. Oncol., 2006, 24(2):268-273.
Bai et al., "Targeted degradation of BET proteins in triple-negative breast cancer," Cancer Res., May 1, 2017, 77(9):2476-2487.
Basiorka et al. "Lenalidomide Stabilizes the Erythropoietin Receptor by Inhibiting the E3 Ubiquitin Ligase RNF41," Cancer Res., Apr. 2016, 76:3531-3540.
Bennett et al., "The Role of Nuclear Receptor-Binding SET Domain Family Histone Lysine Methyltransferases in Cancer," Cold Spring Harb. Perspect. Med., Jun. 2017, 7(6):a026708.
Berge et al., "Pharmaceutical Salts," Journal of Pharmaceutical Science, 1997, 66:1-19.
Bilsland et al., "Behavioral and neurochemical alterations in mice deficient in anaplastic lymphoma kinase suggest therapeutic potential for psychiatric indications," Neuropsychopharmacology, 2008, 33:685-700.

(56) References Cited

OTHER PUBLICATIONS

Biondi et al., "Biological and therapeutic aspects of infant leukemia.," Blood, Jul. 2000, 96:24-33.
Biswas et al., "Function of leukemogenic mixed lineage leukemia 1 (MLL) fusion proteins through distinct partner protein complexes," Proc. Natl. Acad. Sci. USA, Sep. 2011, 108(38):15751-15756.
Bitoun et al., "The mixed-lineage leukemia fusion partner 10 AF4 stimulates RNA polymerase II transcriptional elongation and mediates coordinated chromatin remodeling," Human Molecular Genetics, Jan. 2007, 16:92-106.
Blake et al., "Discovery and preclinical pharmacology of a selective ATP-competitive Akt inhibitor (GDC-0068) for the treatment of human tumors," J. Med. Chem., Sep. 2012, 55(18):8110-8127.
Bolshan et al., "Synthesis, optimization, and evaluation of novel small molecules as antagonists of WDR5-MLL interaction," ACS Medicinal Chemistry Letters, Mar. 2013, 4(3):353-357.
Bondeson et al., "Catalytic in vivo protein knockdown by small-molecule PROTACs," Nature Chemical Biology, 2015, 11(8):611-617.
Bondeson et al., "Lessons in PROTAC design from selective degradation with a promiscuous warhead," Cell Chem. Biol., Jan. 2018, 25:78-87e5.
Bottcher et al., "Fragment-based discovery of a chemical probe for the PWWP1 domain of NSD3," Nat. Chem. Biol., Aug. 2019, 15:822-829.
Bourdi et al., "Safety Assessment of Metarrestin in Dogs: A Clinical Candidate Targeting a Subnuclear Structure Unique to Metastatic Cancer Cell," Regul. Toxicol. Pharmacol., Aug. 2020, 116:104716.
Bracken et al., "EZH2 is downstream of the pRB-E2F pathway, essential for proliferation and amplified in cancer," EMBO J., 2003, 22(20)5323-5335.
Bradley et al., "EZH2 Inhibitor Efficacy in Non-Hodgkin's Lymphoma Does Not Require Suppression of H3K27 Monomethylation," Chem. Biol., 2014, 21(11):1463-1475.
Brand et al., "Homolog-selective degradation as a strategy to probe the function of CDK6 in AML," Cell Chem. Biol., Feb. 2019, 26(2):300-306e9.
Brauer et al., "Building a better understanding of the intracellular tyrosine kinase PTK6—BRK by BRK," Biochim. Biophys. Acta., Aug. 2010, 1806:66-73.
Braun et al., "Coordinated Splicing of Regulatory Detained Introns within Oncogenic Transcripts Creates an Exploitable Vulnerability in Malignant Glioma," Cancer Cell, Oct. 2017, 32(4):411-426.
Broooun et al., "Polycomb repressive complex 2 structure with inhibitor reveals a mechanism of activation and drug resistance," Nat. Commun., Apr. 28, 2016, 7:11384, 12 pages.
Browne et al., "Regulation of peptide-chain elongation in mammalian cells," Eur. J. Biochem., Nov. 2002, 269:5360-5368.
Buckley et al., "HaloPROTACS: use of small molecule PROTACs to induce degradation of HaloTag fusion proteins," ACS Chemical Biology, Aug. 2015, 10(8):1831-1837.
Buckley et al., "Small-molecule control of intracellular protein levels through modulation of the ubiquitin proteasome system," Angew Chem. Int. Ed. Engl., 2014, 53(9):2312-2330.
Buckley et al., "Small-molecule inhibitors of the interaction between the E3 ligase VHL and HIF1α," Angew Chem Int. Ed. Engl., 2012, 51(46):11463-11467.
Buckley et al., "Targeting the von Hippel-Lindau E3 ubiquitin ligase using small molecules to disrupt the VHL/HIF-1α interaction," Journal of the American Chemical Society, 2012, 134(10):4465-4468.
Burkhart et al., "Cellular mechanisms of tumour suppression by the retinoblastoma gene," Nature Reviews Cancer, 2008, 8(9):671-682.
Burnet, "The concept of immunological surveillance," Progress Exp. Tumor Res., 1970, 13:1-27.
Burslem et al., "Small-molecule modulation of protein homeostasis," Chem. Rev., Aug. 2017, 117(17):11269-11301.
Burslem et al., "The advantages of targeted protein degradation over inhibition: An RTK case study," Cell Chem. Biol., Jan. 2018, 25:67-77e3.

Cai et al., "Subunit composition and substrate specificity of a MOF-containing histone acetyltransferase distinct from the male-specific lethal (MSL) complex," The Journal of Biological Chemistry, Feb. 2010, 285(7):4268-4272.
Cai et al., "ZFX Mediates Non-canonical Oncogenic Functions of the Androgen Receptor Splice Variant 7 in Castrate-Resistant Prostate Cancer," 2018, Mol. Cell 72, 341-354 e346.
Campbell et al., "EPZ011989, A Potent, Orally-Available EZH2 Inhibitor with Robust in Vivo Activity," ACS Med. Chem. Lett., 2015, 6(5):491-495.
Cao et al., "Regulation and functional role of eEF1A2 in pancreatic carcinoma," Biochem. Biophys. Res. Commun., 2009, 380(1):11-16.
Cao et al., "Role of Histone H3 Lysine 27 Methylation in Polycomb-Group Silencing," Science, 2002, 298(5595):1039-1043.
Cao et al., "Targeting MLL1 H3K4 methyltransferase activity in mixed-lineage leukemia," Molecular Cell, Jan. 2014, 53(2):247-261.
Cappuzzo et al., "Erlotinib as maintenance treatment in advanced non-small-cell lung cancer: a multicentre, randomised, placebo-controlled phase 3 study," Lancet Oncol., Jun. 2010, 11:521-529.
Cardenas et al., "Enantioselective Synthesis of Pyrrolopyrimidine Scaffolds through Cation-Directed Nucleophilic Aromatic Substitution," Org. Lett., Mar. 2018, 20:2037-2041.
Carugo et al., "In vivo functional platform targeting patient-derived xenografts identifies WDR5-Myc association as a critical determinant of pancreatic cancer," Cell Reports, Jun. 2016, 16(1):133-147.
Castro et al., "Breast tumor kinase and extracellular signal-regulated kinase 5 mediate Met receptor signaling to cell migration in breast cancer cells," Breast Cancer Research, 2010, 12:R60, 15 pages.
Chamberlain et al., "Structure of the human Cereblon-DDB1-lenalidomide complex reveals basis for responsiveness to thalidomide analogs," Nat. Struct. Mol. Biol., 2014, 21(9):803-809.
Chang et al., "EZH2 promotes expansion of breast tumor initiating cells through activation of RAF1-β- catenin signaling," Cancer Cell, 2011, 19(1):86-100.
Chan-Penebre et al., "A selective inhibitor of PRMT5 with in vivo and in vitro potency in MCL models," Nature Chemical Biology, Apr. 2015, 11:432-437.
Chau et al., "An Anatomical Site and Genetic-Base Prognostic Model for Patients With Nuclear Protein in Testis (NUT) Midline Carcinoma: Analysis of 124 Patients," JNCI Cancer Spectr 4, 2020, pkz094 2020.
Chawade et al., "Normalyzer: a tool for rapid evaluation of normalization methods for omics data sets," J. Proteome. Res., 2014, 13:3114-31202014.
Chen et al., "Design, synthesis, and initial evaluation of affinity-based small molecular probe for detection of WDR5," Bioorganic Chemistry, Feb. 2018, 76:380-385.
Chen et al., "Gene expression profiling of WDR5 regulated genes in bladder cancer," Genomics Data, Sep. 2015, 5:27-29.
Chen et al., "PTK6 promotes hepatocellular carcinoma cell proliferation and invasion," Am. J. Transl. Res., Oct. 2016, (10):4354-4361.
Chen et al., "Upregulated WDR5 promotes proliferation, self-renewal and chemoresistance in bladder cancer via mediating H3K4 trimethylation," Scientific Reports, Feb. 2015, 5: 12 pages.
Chi et al., "Covalent histone modifications—miswritten, misinterpreted and mis-erased in human cancers," Nat. Rev. Cancer, 2010, 10:457-469.
Choi et al., "EML4-ALK mutations in lung cancer that confer resistance to ALK inhibitors," N. Engl. J. Med., Oct. 2010, 363(18):1734-1739.
Choi et al., "Identification of novel isoforms of the EML4-ALK transforming gene in non-small cell lung cancer," Cancer Res., Jul. 2008, 68(13):4971-4976.
Christott et al., "Discovery of a Selective Inhibitor for the YEATS Domains of ENL/AF9.," SLAS Discov., 2019, 24:133-141.
Chung et al., "Cbx8 acts non-canonically with Wdr5 to promote mammary tumorigenesis," Cell Reports, Jul. 2016, 16(2):472-486.

(56) References Cited

OTHER PUBLICATIONS

Clinicaltrials.gov [online], "Metarrestin (ML-246) in Subjects with Metastatic Solid Tumors," Jan. 10, 2020, retrieved on Mar. 16, 2022, retrieved from URL<https://clinicaltrials.gov/ct2/show/NCT04222413>, 12 pages.
CN Office Action in Chinese Appln. No. 201780081246.8, dated Dec. 2, 2021, 18 pages (with English Translation).
CN Office Action in Chinese Appln. No. 201780081246.8, dated Jun. 4, 2021, 19 pages (with English Translation).
CN Office Action in Chinese Appln. No. 201780085879.6, dated Jan. 5, 2022, 18 pages (with English Translation).
Corthay, "Does the immune system naturally protect against cancer?" Front. Immunol., May 2014, 5(197):1-8.
Cromm et al., "Addressing kinase-independent functions of Fak via PROTAC-mediated degradation," J. Am. Chem. Soc., Nov. 2018, 140(49):17019-17026.
Cromm et al., "Targeted protein degradation: from chemical biology to drug discovery," Cell Chem. Biol., Sep. 2017, 24(9):1181-1190.
Czermin et al., "*Drosophila* enhancer of Zeste/ESC complexes have a histone H3 methyltransferase activity that marks chromosomal Polycomb sites," Cell, 2002, 111(2):185-196.
Dai et al., "WDR5 expression is prognostic of breast cancer outcome," PLoS One, Sep. 2015, 10: 15 pages.
Davies et al., "Monoacidic Inhibitors of the Kelch-like ECH-Associated Protein 1: Nuclear Factor Erythroid 2-Related Factor 2 (KEAP1 :NRF2) Protein-Protein Interaction with High Cell Potency Identified by Fragment-Based Discovery," Journal of Medicinal Chemistry, Apr. 2016, 59(8):3991-4006.
Dawson et al., "Inhibition of BET recruitment to chromatin as an effective treatment for MLL-fusion leukaemia," Nature, 2011, 478:529-15 533.
Deng et al., "Protein arginine methyltransferase 5 functions as an epigenetic activator of the androgen receptor to promote prostate cancer cell growth," Oncogene, 2017, 36:1223-1231.
Derry et al., "Altered localization and activity of the intracellular tyrosine kinase BRK/Sik in prostate tumor cells," Oncogene, Jul. 2003, 22:4212-4220.
Deshpande et al., "Chromatin modifications as therapeutic targets in MLL-rearranged leukemia," Trends Immunol., Nov. 2012, 33(11):563-570.
Dias et al., "Structural analysis of the KANSL1/WDR5/KANSL2 complex reveals that WDR5 is required for efficient assembly and chromatin targeting of the NSL complex," Genes & Development, May 2014, 28(9):929-942.
Douglass, Jr. et al., "A comprehensive mathematical model for three-body binding equilibria," J. Am. Chem. Soc., Apr. 2013, 135(16):6092-6099.
Du et al., "FOXC1, a target of polycomb, inhibits metastasis of breast cancer cells," Breast Cancer Res. Treat., 2012, 131(1):65-73.
Duanmin et al., "eEF1A2 protein expression correlates with lymph node metastasis and decreased survival in pancreatic ductal adenocarcinoma," Hepatogastroenterology, Jun. 2013, 60(124):870-875.
Dumble et al., "Discovery of novel AKT inhibitors with enhanced anti-tumor effects in combination with the MEK inhibitor," PloS One, Jun. 2014, 9(6), 11 pages.
EA Office Action in Eurasian Appln. No. 201991071, dated Jun. 10, 2020, 4 pages (with English translation).
Ee et al., "An embryonic stem cell-specific NuRD complex functions through interaction with WDR5," Stem Cell Reports, Jun. 2017, 8(6): 9 pages.
EP Extended European Search Report in European Appln. No. 17863645.2, dated Aug. 6, 2020, 10 pages.
EP Extended European Search Report in European Appln. No. 17877800.7, dated Feb. 19, 2021, 9 pages.
EP Extended European Search Report in European Appln. No. 19757825.5, dated Jan. 26, 2022, 14 pages.
EP Extended European Search Report in European Appln. No. 19763958.6, dated Dec. 8, 2021, 12 pages.
EP Extended European Search Report in European Appln. No. 19830269.7, dated Mar. 7, 2022, 6 pages.
EP Office Action in European Appln. No. 17863645.2, dated Apr. 6, 2021, 7 pages.
EP Office Action in European Appln. No. 17863645.2, dated Mar. 11, 2022, 5 pages.
EP Office Action in European Appln. No. 19821826.5, dated Jan. 13, 2022, 4 pages.
EP Partial Supplementary Search Report in European Appln. No. 19757825.5, dated Oct. 18, 2021, 16 pages.
Erb et al. (2017). Transcription control by the ENL YEATS domain in acute leukaemia. Nature 543, 270-274.
Fabian et al., "A small molecule-kinase interaction map for clinical kinase inhibitors," Nat. Biotechnol., Mar. 2005, 23(3):329-336.
Fan et al., "A Kinase Inhibitor Targeted to mTORC1 Drives Regression in Glioblastoma," Cancer Cell, Mar. 2017, 31(3):424-435.
Fan et al., "BAHCC1 binds H3K27me3 via a conserved BAH module to mediate gene silencing and oncogenesis," Nature genetics, 2020, 52:1384-1396.
fda.gov [online], "Data Standards Manual (Monographs)," Feb. 27, 2018, retrieved on Feb. 7, 2022, retrieved from URL <https://www.fda.gov/drugs/electronic-regulatory-submission-and-review/data-standards-manual-monographs>, 1 page.
fda.gov [online], "Development & Approval Process | Drugs," Oct. 28, 2019, retrieved on Feb. 4, 2022, retrieved from URL <https://www.fda.gov/drugs/development-approval-process-drugs>, 4 pages.
Fei et al., "PROTAC and its Application in the Treatment of Cancer," Chemistry of Life, Aug. 2014, 34(4):549-554 (with English abstract).
Ferguson et al., "Kinase inhibitors: the road ahead," Nat. Rev. Drug Discov., May 2018, 17:353-377.
Ferrando et al., "Gene expression signatures in MLL-rearranged T-lineage and B-precursor acute leukemias: dominance of HOX dysregulation," Blood, Jul. 2003, 102(1):262-268.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," The Lancet Oncology, 2015, 16(1):25-35.
Fischer et al., "Structure of the DDB1-CRBN E3 ubiquitin ligase in complex with thalidomide," Nature, Aug. 2014, 512(7512):49-53.
Frankowski et al., "Metarrestin, a perinucleolar compartment inhibitor, effectively suppresses metastasis," Science Translational Medicine, May 2018, 10(441), 13 pages.
Frost et al., "Potent and selective chemical probe of hypoxic signalling downstream of HIF-α hydroxylation via VHL inhibition," Nat. Commun., Nov. 2016, 7:13312, 12 pages.
Fujii et al., "MEKERK pathway regulates EZH2 overexpression in association with aggressive breast cancer subtypes," Oncogene, 2011, 30(39):4118-4128.
Gadd et al., "A Children's Oncology Group and TARGET initiative exploring the genetic landscape of Wilms tumor," Nat. Genet., Oct. 2017, 49:1487-1494.
Galdeano et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities," J. Med. Chem., 2014, 57(20):8657-8663.
Gao et al., "ZLD1122, a novel EZH2 and EZH1 small molecular inhibitor, blocks H3K27 methylation and diffuse large B cell lymphoma cell growth," RSC Adv., 2016, 6:28512-28521.
Garapaty-Rao et al., "Identification of EZH2 and EZH1 small molecule inhibitors with selective impact on diffuse large B cell lymphoma cell growth," Chem. Biol., 2013, 20(11):1329-1339.
Garnar-Wortzel et al., "Chemical Inhibition of ENL/AF9 YEATS Domains in Acute Leukemia," ACS Central Science, Apr. 2021, 7(5):815-830.
Ge et al., "WDR5 high expression and its effect on tumorigenesis in leukemia," Oncotarget, Jun. 2016, 7(25):37740-37754.
Gehling et al., "Discovery, design, and synthesis of indole-based EZH2 inhibitors," Bioorg. Med. Chem. Lett., 2015, 25(17):3644-3649.

(56) References Cited

OTHER PUBLICATIONS

Genscript.com [online], "Gen Script Make Research Easy," available on or before Mar. 3, 2015, retrieved on Mar. 17, 2022, retrieved from URL<https://www.genscript.com/gRNAdatabase.html>.
Getlik et al., "Structure-based optimization of a small molecule antagonist of the interaction between WD repeat-containing protein 5 (WDR5) and mixed-lineage leukemia 1 (MLL1)," Journal of Medicinal Chemistry, Mar. 2016, 59(6):2478-2496.
Gillis et al., "Biochemical and biological characterization of lymphocyte regulatory molecules; V. Identification of an interleukin 2-producing human leukemia T cell line," The Journal of experimental medicine, Dec. 1980,152:1709-1719.
Github.com [online], "PreprocessCore," Oct. 26, 2021, retrieved on Mar. 17, 2022, retrieved from URL<Gihttps://github.com/bmbolstad/preprocessCore>, 1 pages.
Github.com [online], "ProteiNorm," Jul. 27, 2020, retrieved on Mar. 17, 2022, retrieved from URL <https://github.com/ByrumLab/proteiNorm>, 3 page.
Gluz et al., "Triplenegative breast cancer—current status and future directions," Ann. Oncol., 2009, 20(12):1913-1927.
Godin-Heymann et al., "The T790M 'gatekeeper' mutation in EGFR mediates resistance to low concentrations of an irreversible EGFR inhibitor," Mol. Cancer Ther., Apr. 2008, 7(4):874-879.
Gonzalez et al., "Downregulation of EZH2 decreases growth of estrogen receptor-negative invasive breast carcinoma and requires BRCA1," Oncogene, 2009, 28(6):843-853.
Gonzalez et al., "EZH2 expands breast stem cells through activation of NOTCH1 signaling," Proc. Natl. Acad. Sci. USA, 2014, 111(8):3098-3103.
Grabe et al., "C797S Resistance: The undruggable EGFR mutation in non-small cell lung cancer?" ACS Med. Chem. Lett., 2018, 9:779-782.
Grebien et al., "Pharmacological targeting of the Wdr5-MLL interaction in C/EBPα N-terminal leukemia," Nature Chemical Biology, Aug. 2015, 11(8): 11 pages.
Guarnaccia et al., "Moonlighting with WDR5: A cellular multitasker," Journal of Clinical Medicine, Feb. 2018, 7(2): 17 pages.
Gullà et al., "Protein arginine methyltransferase 5 has prognostic relevance and is a druggable target in multiple myeloma," Leukemia, 2018, 32:996-1002.
Haegebarth et al., "Protein tyrosine kinase 6 negatively regulates growth and promotes enterocyte differentiation in the small intestine," Mol. Cell Biol., Jul. 2006, 26:4949-4957.
Hallberg et al., "Mechanistic insight into ALK receptor tyrosine kinase in human cancer biology," Nature Reviews Cancer, Oct. 2013, 13:685-700.
Hamilton et al., "Targeting CDK4/6 in patients with cancer," Cancer Treatment Reviews, 2016, 45:129-138.
Han et al., "Discovery of ARD-69 as a Highly Potent Proteolysis Targeting Chimera (PROTAC) Degrader of Androgen Receptor (AR) for the Treatment of Prostate Cancer," Journal of Medicinal Chemistry, Jan. 2019, 62:941-964.
Harvey et al., "Brk protects breast cancer cells from autophagic cell death induced by loss of anchorage," The American Journal of Pathology, Sep. 2009, 175:1226-1234.
Harvey et al., "Use of RNA interference to validate Brk as a novel therapeutic target in breast cancer: Brk promotes breast carcinoma cell proliferation," Oncogene, Aug. 2003, 22:5006-5010.
He et al., "HIV-1 Tat and Host AFF4 Recruit Two Transcription Elongation Factors into a Bifunctional Complex for Coordinated Activation of HIV-I Transcription," Mol. Cell., May 2010, 38(3):428-438.
He et al., "Human Polymerase-Associated Factor complex (PAFc) connects the Super Elongation Complex (SEC) to RNA polymerase II on chromatin," Proc. Natl. Acad. Sci. USA, Sep. 2011, 108(36):E636-E645.
Heerding et al., "Identification of 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol (GSK690693), a novel inhibitor of AKT kinase," Journal of Medicinal Chemistry, Sep. 2008, 51(18):5663-5679.
Heidenreich et al., "Structure-Based Approach toward Identification of Inhibitory Fragments for Eleven-Nineteen-Leukemia Protein (ENL)," J. Med. Chem., Nov. 2018, 61(23):10929-10934.
Henning et al., "Degradation of Akt using protein-catalyzed capture agent," Journal of Peptide Science, 2016, 22:196-200.
Herbst et al., "Gefitinib—a novel targeted approach to treating cancer," Nat. Rev. Cancer, Dec. 2004, 4:956-965.
Hernandez et al., "The Kinase Activity of Hematopoietic Progenitor Kinase 1 Is Essential for the Regulation of T Cell Function," Cell reports, Oct. 2018, 25:80-94.
Herrera-Abreu et al., "Early adaptation and acquired resistance to CDK4/6 inhibition in estrogen receptor-positive breast cancer," Cancer Research, 2016, 76(8):2301-2313.
Hess, "MLL: a histone methyltransferase disrupted in leukemia," Trends Mol. Med., Oct. 2004, 10(10):500-507.
Higa et al., "CUL4-DDB 1 ubiquitin ligase interacts with multiple WD40-repeat proteins and regulates histone methylation," Nature Cell Biology, Nov. 2006, 8(11):1277-1283.
Hirai et al., "MK-2206, an allosteric Akt inhibitor, enhances antitumor efficacy by standard chemotherapeutic agents or molecular targeted drugs in vitro and in vivo," Molecular Cancer Therapeutics, Jul. 2010, 9(7):1956-1967.
Hiroyuki et al., "The structure of bestatin," The Journal of Antibiotics, Jan. 1976, 29(1):100-101.
Hirsch et al., "Lung cancer: current therapies and new targeted treatments," Lancet, Jan. 2017, 389:299-311.
Holm et al., "Global H3K27 trimethylation and EZH2 abundance in breast tumor subtypes," Mol. Oncol., 2012, 6(5):494-506.
Hsu et al., "Recognition of histone acetylation by the GAS41 YEATS domain promotes H2A.Z deposition in non-small cell lung cancer," Genes Dev., 2018, 32:58-69.
Hu et al., "Human HPK1, a novel human hematopoietic progenitor kinase that activates the JNK/SAPK kinase cascade," Genes Dev., Sep. 1996, 10:225 1-2264.
Hu et al., "Small Molecule Inhibitors of Protein Arginine Methyltransferases," Expert Opinion Investigational Drugs, 2016, 25:335-358.
Huang et al., "A Chemoproteomic Approach to Query the Degradable Kinome Using a Multi-kinase Degrader," Cell Chemical Biology, Jan. 2018, 25(1):88-99.
Huang et al., "Covalent inhibition of NSD1 histone methyltransferase," Nat. Chem. Biol, 2020, 16:1403-1410.
Huber et al., "Variance stabilization applied to microarray data calibration and to the quantification of differential expression," Bioinformatics, 2002, 18 Suppl 1:S96-104.
IN Office Action in Indian Appln. No. 201917020814, dated Jun. 23, 2021, 6 pages (with English Translation).
Irie et al., "PTK6 regulates IGF-1-induced anchorage-independent survival," PLoS One, Jul. 2010, 5(7):e11729.
Ito et al., "Identification of a primary target of thalidomide teratogenicity," Science, Mar. 2010, 327(5971):1345-1350.
Ito et al., "PTK6 Inhibition Suppresses Metastases of Triple-Negative Breast Cancer via SNAIL-Dependent E-Cadherin regulation," Cancer Res., Aug. 2016, 76:4406-4417.
Ito et al., "PTK6 regulates growth and survival of endocrine therapy-resistant ER+ breast cancer cells," NPJ Breast Cancer, Nov. 2017, 3:45.
Iwahara et al., "Molecular characterization of ALK, a receptor tyrosine kinase expressed specifically in the nervous system," Oncogene, Jan. 30, 1997, 14:439-449.
Jakobsson et al., "The dual methyltransferase METTL13 targets N terminus and Lys55 of eEF1A and modulates codon-specific translation rates," Nature Communications, Aug. 2018, 15 pages.
Jiang et al., "Development of dual and selective degraders of cyclin-dependent kinases 4 and 6," Angew. Chem. Int. Ed. Engl., May 2019, 58(19):6321-6326.
Jiang et al., "Targeting BRK-Positive Breast Cancers with Small-Molecule Kinase Inhibitors," Cancer Res., Jan. 2017, 77:175-186.

(56) References Cited

OTHER PUBLICATIONS

Jiao et al., "Structural basis of histone H3K27 trimethylation by an active polycomb repressive complex 2," Science, 2015, 350(6258):aac4383.

Jin et al., "Targeting methyltransferase PRMT5 eliminates leukemia stem cells in chronic myelogenous leukemia," The Journal of Clinical Investigation, Oct. 2016, 126:3961-3980.

JP Office Action in Japanese Appln. No. 2019-522841, dated Oct. 5, 2021, 14 pages (with English Translation).

JP Office Action in Japanese Appln. No. 2019-530811, dated Dec. 14, 2021, 4 pages (with English Translation).

Jude et al., "Unique and independent roles for MLL in adult hematopoietic stem cells and progenitors," Cell Stem Cell, Sep. 2007, 1(3):324-337.

Justin et al., "Structural basis of oncogenic histone H3K27M inhibition of human polycomb repressive complex 2," Nat. Commun., 2016, 7:11316.

Kanda et al., "Protein arginine methyltransferase 5 is associated with malignant phenotype and peritoneal metastasis in gastric cancer," International Journal of Oncology, Jun. 2016, 49:1195-1202.

Kanis et al., "A small molecule inhibitor of the perinucleolar compartment, ML246, attenuates growth and spread of ovarian cancer," Gynecol. Oncol. Res. Pract., 2018, 5:7.

Kanis et al., "Metarrestin: A novel compound active against ovarian cancer," Gynecol Oncol., Oct. 2015, 139(1):190.

Kaniskan et al., "Inhibitors of Protein Methyltransferases and Demethylases," Chem. Rev., 2018, 118(3):989-1068.

Kaniskan et al., "Selective inhibitors of protein methyltransferases," Journal of Medicinal Chemistry, 2015, 58:1596-1629.

Karatas et al., "Discovery of a highly potent, cell-permeable macrocyclic peptidomimetic (MM-589) targeting the WD repeat domain 5 protein (WDR5)-mixed lineage leukemia (MLL) protein-protein interaction," Journal of Medicinal Chemistry, Jun. 2017, 60(12):4818-4839.

Khalyfa et al., "Characterization of elongation factor-1A (eEF1A-1) and eEF1A-2/S1 protein expression in normal and wasted mice," Journal of Biological Chemistry, 2001, 276:22915-22922.

Kiefer et al., "HPK1, a hematopoietic protein kinase activating the SAPK/JNK pathway," EMBO J., Dec. 1996, 15(24):7013-7025.

Kim et al. "Targeted disruption of the EZH2-EED complex inhibits EZH2-dependent cancer" Nature Chemical Biology, 2013, 9:643-650.

Kim et al., "Targeting EZH2 in cancer," Nat. Med., 2016, 22(2):128-134.

Kleer et al., "EZH2 is a marker of aggressive breast cancer and promotes neoplastic transformation of breast epithelial cells," PNAS, 2003, 100(20):11606-11611.

Klein et al., "Yaf9 subunit of the NuA4 and SWR1 complexes targets histone H3K27ac through its YEATS domain," Nucleic Acids Res., Jan. 2018, 46:421-430.

Knutson et al., "A selective inhibitor of EZH2 blocks H3K27 methylation and kills mutant lymphoma cells," Nat. Chem. Biol., 8(11):890-896.

Knutson et al., "Durable tumor regression in genetically altered malignant rhabdoid tumors by inhibition of methyltransferase EZH2," Proc. Natl. Acad. Sci. USA., 2013, 110(19):7922-7927.

Kobayashi et al., "EGFR mutation and resistance of non-small-cell lung cancer to gefitinib," N. Engl. J. Med., Feb. 2005, 352(8):786-792.

Koivunen et al., "EML4-ALK fusion gene and efficacy of an ALK kinase inhibitor in lung cancer," Clinical Cancer Research, Jul. 1, 2008, 14(13):4275-4283.

Konze et al., "An Orally Bioavailable Chemical Probe of the Lysine Methyltransferases EZH2 and EZH1," ACS Chem. Biol., 2013, 8(6):1324-1334.

Krause et al., "Tyrosine kinases as targets for cancer therapy," N. Engl. J. Med., Jul. 2005, 353(2):172-187.

Krivtsov et al., "MLL translocations, histone modifications and leukaemia stem-cell development," Nat. Rev. Cancer, Nov. 2007, 7:823-833.

Kryukov et al., "MTAP deletion confers enhanced dependency on the PRMT5 arginine methyltransferase in cancer cells," Science, 2016, 351(6278):1214-1218.

Kuenzi et al., "Polypharmacology-based ceritinib repurposing using integrated functional proteomics," Nat. Chem. Biol., Dec. 2017, 13(12): 1222-1231.

Kung et al., "Design and Synthesis of Pyridone-Containing 3,4-Dihydroisoquinoline-1(2H)-ones as a Novel Class of Enhancer of Zeste Homolog 2 (EZH2) Inhibitors," J. Med. Chem., 2016, 59(18):8306-8325.

Kuzmichev et al., "Histone methyltransferase activity associated with a human multiprotein complex containing the Enhancer of Zeste protein," Genes Dev., 2002, 16(22):2893-2905.

Kwak et al., "Anaplastic lymphoma kinase inhibition in non-small-cell lung cancer," New England Journal of Medicine, Oct. 28, 2010, 363(18):1693-1703.

Lai et al., "Induced protein degradation: an emerging drug discovery paradigm," Nat. Rev. Drug Discov., Feb. 2017, 16(2):101-114.

Lai et al., "Modular PROTAC design for the degradation of oncogenic BCR-ABL," Angewandte Chemie International Edition English, Jan. 2016, 55(2):807-810.

Lapierre et al., "Discovery of 3-(3-(4-(1-Aminocyclobutyl)phenyl)-5-phenyl-3H-imidazo[4,5-b]pyridin-2-yl)pyridin-2-amine (ARQ 092): An orally bioavailable, selective, and potent allosteric AKT inhibitor," Journal of Medicinal Chemistry, 2016, 59:6455-6469.

Lebraud et al., "Protein Degradation by In-Cell Self-Assembly of Proteolysis Targeting Chimeras," ACS Central Science, 2016, 2:927-934.

Li et al., "AF9 YEATS domain links histone acetylation to DOT1L-mediated H3K79 methylation," Cell, Oct. 2014, 159(3):558-571.

Li et al., "Discovery of MD-224 as a first-in-class, highly potent, and efficacious proteolysis targeting chimera Murine Double Minute 2 degrader capable of achieving complete and durable tumor regression," J. Med. Chem., 2019, 62(2):448-466.

Li et al., "Discovery of potent and noncovalent reversible EGFR kinase inhibitors of $EGFR^{L858R/T790M/C797S}$," ACS Med. Chem. Lett., Jun. 2019, 10(6):869-873.

Li et al., "High-affinity small molecular blockers of mixed lineage leukemia 1 (MLL1)-WDR5 interaction inhibit MILL1 complex H3K4 methyltransferase activity," European Journal of Medicinal Chemistry, Nov. 2016, 124:480-489.

Li et al., "Molecular Coupling of Histone Crotonylation and Active Transcription by AF9 YEATS Domain," Mol. Cell., Apr. 2016, 62(2):181-193.

Li et al., "RSEM: accurate transcript quantification from RNA-Seq data with or without a reference genome," BMC Bioinformatics, 2011, 12:323.

Li et al., "Structure-based design and synthesis of small molecular inhibitors disturbing the interaction of MILL1-WDR5," European Journal of Medicinal Chemistry, Aug. 2016, 118:1-8.

Li et al., "Structure-guided development of YEATS domain inhibitors by targeting ππ stacking," Nat. Chem. Biol., Dec. 2018, 14:1140-1149.

Li et al., "The OncoPPi network of cancer-focused protein-protein interactions to inform biological insights and therapeutic strategies," Nat. Commun., Feb. 2017, 8:14356.

Li et al., "Understanding histone H3 lysine 36 methylation and its deregulation in disease," Cell. Mol. Life Sci., Aug. 2019, 76(15):2899-2916.

Li et al., "ZMYND11-MBTD1 induces leukemogenesis through hijacking NuA4/TIP60 acetyltransferase complex and a PWWP-mediated chromatin association mechanism," Nat. Commun., 2021, 12(1), 18 pages.

Lim et al., "CDK4/6 inhibitors: promising opportunities beyond breast cancer," Cancer Discovery, 2016, 6(7):697-699.

Lin et al., "AFF4, a component of the ELL/PTEFb elongation complex and a shared subunit of MLL chimeras, can link transcription elongation to leukemia," Mol. Cell., Feb. 2010, 37(3):429-437.

(56) References Cited

OTHER PUBLICATIONS

Lin et al., "Clinicopathologic features, patterns of recurrence, and survival among women with triple-negative breast cancer in the National Comprehensive Cancer Network," Cancer, 2012, 118(22):5463-5472.
Lin et al., "Targeting ALK: Precision Medicine Takes on Drug Resistance," Cancer Discovery, Feb. 2017, 7(2):137-155.
Ling et al., "Involvement of hematopoietic progenitor kinase 1 in T cell receptor signaling," The Journal of biological chemistry, Jun. 2001, 276:18908-18914.
Liou et al., "HPK1 is activated by lymphocyte antigen receptors and negatively regulates AP-1," Immunity, Apr. 2000, 12(4):399-408.
Liu et al., "Calcineurin is a common target of cyclophilin-cyclosporin A and FKBP-FK506 complexes," Cell, Aug. 1991, 66(4):807-815.
Liu et al., "Critical role of kinase activity of hematopoietic progenitor kinase 1 in anti-tumor immune surveillance," PloS one, Mar. 2019, 14:e02 12670.
Liu et al., "METTL13 Methylation of eEF1A Increases Translational Output to Promote Tumorigenesis," Cell, Jan. 2019, 176:491-504.e421.
Liu et al., "Widening Synthesis Bottlenecks: Realization of Ultrafast and Continuous-Flow Synthesis of High-Silica Zeolite SSZ-13 for NOx Removal," Angew. Chem., May 4, 2015, 127(19):5775-5779.
Losada et al., "Binding of eEF1A2 to the RNA-dependent protein kinase PKR modulates its activity and promotes tumour cell survival," British Journal of Cancer, Nov. 2018, 119(11):1410-1420.
Lu et al., "Epigenetic Perturbations by Arg882-Mutated DNMT3A Potentiate Aberrant Stem Cell Gene-Expression Program and Acute Leukemia Development," Cancer Cell, 2016, 30:92-107.
Lu et al., "Hijacking the E3 ubiquitin ligase cereblon to efficiently target BRD4," Chemistry & Biology, Jun. 2015, 22(6):755-763.
Lu et al., "Targeting EGFR$^{L858R/T790M}$ and EGFR$^{L858R/T790M/C797S}$ resistance mutations in NSCLC: Current developments in medicinal chemistry," Med. Res. Rev., Jan. 2018, 38(5):1550-1581.
Mahara et al., "HIFI-α activation underlies a functional switch in the paradoxical role of Ezh2/PRC2 in breast cancer," PNAS, 2016, 113(26):E3735-E3744.
Mahmoud et al., "Discovery of 4-anilino α-carbolines as novel Brk inhibitors," Bioorganic & Medicinal Chemistry Letters, Apr. 2014, 24:1948-1951.
Majer et al., "A687V EZH2 is a gain-offunction mutation found in lymphoma patients," FEBS Lett., 2012, 586(19):3448-3451.
Maniaci et al., "Homo-PROTACs: bivalent small-molecule dimerizers of the VHL E3 ubiquitin ligase to induce self-degradation," Nature Communication, Oct. 2017, 8, 14 pages.
Manning et al., "AKT/PKB signaling: navigating the network," Cell, Apr. 2017, 169(3):381-405.
Marjon et al., "MTAP Deletions in Cancer Create Vulnerability to Targeting of the MAT2A/PRMT5/RIOK1 Axis," Cell Reports, Apr. 2016, 15:574-587.
Marschalek, "MLL Leukemia and Future Treatment Strategies," Arch. Pharm. Chem. Life Sci., Apr. 2015, 348(4):221-228.
Matsushime et al., "Identification and properties of an atypical catalytic subunit (p34$^{PSK-J3}$/cdk4) for mammalian D type G1 cyclins," Cell, 1992, 71(2):323-334.
Mavrakis et al., "Disordered methionine metabolism in MTAP/CDKN2A-deleted cancers leads to dependence on PRMT5," Science, Feb. 2016, 351(6278):1208-1213.
Mcalpine et al., "Abstract 4857: Discovery of PF-06855800, a SAM competitive PRMT5 inhibitor with potent antitumor activity," American Association for Cancer Research Annual Meeting, 2018, 78(13 Supplement), 4 pages.
McCabe et al., "EZH2 inhibition as a therapeutic strategy for lymphoma with EZH2-activating mutations," Nature, 2012, 492(7427):108-112.
McCabe et al., "Mutation of A677 in histone methyltransferase EZH2 in human B-cell lymphoma promotes hypertrimethylation of histone H3 on lysine 27 (H3K27)," Proc. Natl. Acad. Sci. USA, 2012, 109(8):2989-2994.

Meyer et al., "New insights to the MLL recombinome of acute leukemias," Leukemia, Aug. 2009, 23:1490-1499.
Meyer et al., "The MLL recombinome of acute leukemias in 2013," Leukemia, Nov. 2013, 27:2165-2176.
Meyer et al., "The MLL recombinome of acute leukemias," Leukemia, May 2006, 20:777-784.
Meyerson et al., "Identification of G1 kinase activity for cdk6, a novel cyclin D partner," Molecular and Cellular Biology. 1994, 14(3):2077-2086.
Mi et al., "YEATS2 links histone acetylation to tumorigenesis of non-small cell lung cancer," Nat. Commun., Oct. 2017, 8:1088, 14 pages.
Migliori et al., "Symmetric dimethylation of H3R2 is a newly identified histone mark that supports euchromatin maintenance," Nature Structural and Molecular Biology, Feb. 2012, 19(2):136-144.
Miller et al., "COMPASS: a complex of proteins associated with atrithorax-related SET domain protein," Proceedings of the National Academy of Sciences, Nov. 2001, 98(23):12902-12907.
Mitchell et al., "Cloning and characterisation of cDNAs encoding a novel non-receptor tyrosine kinase, brk, expressed in human breast tumours," Oncogene, Aug. 1994, 9:2383-2390.
Mohan et al., "Licensed to elongate: a molecular mechanism for MLL-based leukaemogenesis," Nat. Rev. Cancer, Oct. 2010, 10:721-728.
Mohan et al., "Linking H3K79 trimethylation to Wnt signaling through a novel Dot1-containing complex (DotCom)," Genes Dev., 2010, 24:574-589.
Molander et al., "Efficient hydrolysis of organotrifluoroborates via silica gel and water," Journal of Organic Chemistry, Oct. 2009, 74(19):364-7369.
Morin et al., "Somatic mutations altering EZH2 (Y641) in follicular and diffuse large B-cell lymphomas of germinal-center origin," Nat. Genet., 2010, 42(2):181-185.
Morris et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," Oncogene, Mar. 8, 1997, 14:2175-2188.
Morris et al., "Fusion of a kinase gene, ALK, to a nucleolar protein gene, NPM, in non-Hodgkin's lymphoma," Science, Mar. 4, 1994, 263(5151):1281-1284.
Moustakim et al., "Discovery of an MLLT1/3 YEATS Domain Chemical Probe," Angew. Chem. Int. Ed. Engl., Dec. 2018, 57(50):16302-16307.
Mueller et al., "A role for the MLL fusion partner ENL in transcriptional elongation and chromatin modification," Blood, Dec. 2007, 110(13):4445-4454.
Mueller et al., "Misguided Transcriptional Elongation Causes Mixed Lineage Leukemia," Plos Biol., Nov. 2009, 7(11):e1000249, 15 pages.
Müller et al., "Histone methyltransferase activity of a *Drosophila* Poly comb group repressor complex," Cell, 2002, 111(2):197-208.
MX Office Action in Mexican Appln. No. MX/a/2019/004950, dated Aug. 6, 2021, 6 pages (with English translation).
MX Office Action in Mexican Appln. No. MX/a/2019/004950, dated Nov. 23, 2021, 8 pages (with English Translation).
Nadeem Abbas et al., "Advances in targeting the epidermal growth factor receptor pathway by synthetic products and its regulation by epigenetic modulators as a therapy for glioblastoma," Cells, Apr. 2019, 8:350, 22 pages.
Neklesa et al., "Small-molecule hydrophobic tagging induced degradation of HaloTag fusion proteins," Nat. Chem. Biol., 2011, 7(8):538-543.
Ni et al., "Structural Insights into Interaction Mechanisms of Alternative Piperazine-urea YEATS Domain Binders in MLLTI," ACS Med. Chem. Lett., Dec. 2019, 10(12):1661-1666.
Nicholson et al., "EGFR and cancer prognosis," Eur. J. Cancer, Sep. 2001, 37(Supp. 4):9-15.
Noble et al., "Protein kinase inhibitors: insights into drug design from structure," Science, Mar. 2004, 303:1800-1805.
Odho et al., "Characterization of a novel WDR5-binding site that recruits RbBP5 through a conserved motif to enhance methylation

(56) References Cited

OTHER PUBLICATIONS of histone H3 lysine 4 by mixed lineage leukemia protein-1," Journal of Biological Chemistry, Oct. 2010, 285(43):32967-32976.
Ohoka et al., "In vivo knockdown of pathogenic proteins via specific and nongenetic inhibitor of apoptosis protein (IAP)-dependent protein erasers (SNIPERs)," Journal of Biological Chemistry, Mar. 2017, 292(11):4556-4570.
Okada et al., "hDOTIL links histone methylation to leukemogenesis," Cell, Apr. 2005, 121(2):167-178.
Okuhira et al., "Specific degradation of CRABP-II via cIAP1-mediated ubiquitylation induced by hybrid molecules that crosslink cIAP1 and the target protein," FEBS Lett., Apr. 2011, 585(8):1147-1152.
Olson et al., "Pharmacological perturbation of CDK9 using selective CDK9 inhibition or degradation," Nat. Chem. Biol., Feb. 2018, 14:163-170.
Ono et al., "PTK6 promotes cancer migration and invasion in pancreatic cancer cells dependent on ERK signaling," PLoS One, 2014, 9:e96060.
Ostrander et al., "Brk/PTK6 signaling in normal and cancer cell models," Curr. Opin. Phannacol., 2010, 10:662-669.
Ottis et al., "Proteolysis-targeting chimeras: induced protein degradation as a therapeutic strategy," ACS Chem. Biol., Mar. 2017, 12(4):892-898.
Paez et al., "EGFR mutations in lung cancer: correlation with clinical response to gefitinib therapy," Science, Jun. 2004, 304:1497-500.
Pao et al., "Acquired resistance of lung adenocarcinomas to gefitinib or erlotinib is associated with a second mutation in the EGFR kinase domain," PLoS Med., Feb. 2005, 2(3):e73.
Papazimas et al., "A General Strategy for the Preparation of Thalidomide-Conjugate Linkers," Synlett, Aug. 23, 2017, 28:2881-2885.
Park et al., "Discovery of EGF receptor inhibitors that are selective for the d746-750/T790M/C797S mutant through structure-based de novo design," Angew. Chem. Int. Ed., Jun. 2017, 56(26):7634-7638.
Park et al., "PTK6 inhibition promotes apoptosis of Lapatinib-resistant Her2+ breast cancer cells by inducing Bim," Breast Cancer Res, 2015, 17:86.
Patel et al., "A conserved arginine-containing motif crucial for the assembly and enzymatic activity of the mixed lineage leukemia protein-I core complex," The Journal of Biological Chemistry, Nov. 2008, 283(47):32162-32175.
Patel et al., "Recent updates on third generation EGFR inhibitors and emergence of fourth generation EGFR inhibitors to combat C797S resistance," Eur. J. Med. Chem., Dec. 2017, 142:32-47.
Patel et al., "Structure of WDR5 bound to mixed lineage leukemia protein-I peptide," The Journal of Biological Chemistry, Nov. 2008, 283(47):32158-32161.
PCT International Preliminary Report on Patentability in International Appln No. PCT/US2018/063847, dated Jun. 18, 2020, 8 pages.
PCT International Preliminary Report on Patentability in International Appln. No. PCT/US2019/019123, dated Aug. 27, 2020, 10 pages.
PCT International Preliminary Report on Patentability in International Appln. No. PCT/US2019/038560, dated Dec. 30, 2020, 9 pages.
PCT International Preliminary Report on Patentability in International Appln. No. PCT/US2019/040507, dated Jan. 5, 2021, 7 pages.
PCT International Preliminary Report on Patentability in International Appln. No. PCT/US2020/031527, dated Nov. 2, 2021, 8 pages.
PCT International Search Report and Written Opinion in International Appln. No. PCT/US2017/058718, dated Jan. 28, 2018, 8 pages.
PCT International Search Report and Written Opinion in International Appln. No. PCT/US2017/065027, dated Mar. 6, 2018, 8 pages.
PCT International Search Report and Written Opinion in International Appln. No. PCT/US2018/063847, dated Mar. 27, 2019, 11 pages.
PCT International Search Report and Written Opinion in International Appln. No. PCT/US2019/019123, dated Jun. 20, 2019, 15 pages.
PCT International Search Report and Written Opinion in International Appln. No. PCT/US2019/021014, dated Jun. 27, 2019, 11 pages.
PCT International Search Report and Written Opinion in International Appln. No. PCT/US2019/038560, dated Oct. 10, 2019, 12 pages.
PCT International Search Report and Written Opinion in International Appln. No. PCT/US2019/040507, dated Nov. 12, 2019, 10 pages.
PCT International Search Report and Written Opinion in International Appln. No. PCT/US2020/031527, dated Sep. 14, 2020, 11 pages.
PCT International Search Report and Written Opinion in International Appln. No. PCT/US2021/055574, dated Feb. 25, 2022, 11 pages.
PCT Invitation to Pay Additional Fees in International Appln. No. PCT/US2019/019123, dated Apr. 8, 2019, 3 pages.
PCT Invitation to Pay Additional Fees in International Appln. No. PCT/US2019/021014, dated Apr. 22, 2019, 2 pages.
PCT Invitation to Pay Additional Fees in International Appln. No. PCT/US2019/038560, dated Aug. 14, 2019, 2 pages.
PCT Invitation to Pay Additional Fees in International Appln. No. PCT/US2021/055574, dated Dec. 22, 2021, 2 pages.
Pellegrino et al., "EEF1A2 inactivates p53 by way of PI3K/AKT/mTOR-dependent stabilization of MDM4 in hepatocellular carcinoma," Hepatology, May 2014, 59(5):1886-1899.
Peng et al, "Protein tyrosine kinase 6 promotes ERBB2-induced mammary gland tumorigenesis in the mouse," Cell Death Dis., 2015, 6:e1848.
Perlman et al., "MLLT1 YEATS domain mutations in clinically distinctive Favourable Histology Wilms tumours," Nat. Commun., Dec. 2015, 6:10013, 10 pages.
Peters et al., "Alectinib versus Crizotinib in Untreated ALK Positive Non-Small-Cell Lung Cancer," New England Journal of Medicine, Aug. 31, 2017, 377(9):829-838.
Pettersson et al., "PROteolysis TArgeting Chimeras (PROTACs)—past, present and future," Drug Discov. Today Technol., Apr. 2019, 31:15-27.
Pieters et al., "A treatment protocol for infants younger than 1 year with acute lymphoblastic leukaemia (Interfant-99): an observational study and a multicentre randomised trial," Lancet, Jul. 2007, 370:240-250.
Prabhu et al., "Adapting AlphaLISA high throughput screen to discover a novel small-molecule inhibitor targeting protein arginine methyltransferase 5 in pancreatic and colorectal cancers," Oncotarget, May 2017, 8(25):39963-39977.
Prêtre et al., "Inhibition of Akt and other AGC kinases: A target for clinical cancer therapy?," Accepted Manuscript, Seminars in Cancer Biology, 2018, 48:70-77.
PubChem-CID-44631912, NIH, National Center for Biotechnology Information, Create Date: Mar. 8, 2010, 30 pages.
Pui et al., "Treating Childhood Acute Lymphoblastic Leukemia without Cranial Irradiation," N. Engl. J. Med., Jun. 2009, 360(26):2730-2741.
Pulford et al., "Detection of anaplastic lymphoma kinase (ALK) and nucleolar protein nucleophosmin (NPM)-ALK proteins in normal and neoplastic cells with the monoclonal antibody ALK1," Blood, Feb. 15, 1997, 89(4):1394-1404.
Qi et al., "Selective inhibition of Ezh2 by a small molecule inhibitor blocks tumor cells proliferation," Proc. Natl. Acad. Sci. USA, 2012, 109(52):21360-21365.
Quentmeier et al., "EZH2 Y641 mutations in follicular lymphoma," Leukemia, 2011, 25(4):726-729.
Raina et al., "PROTACinduced BET protein degradation as a therapy for castration-resistant prostate cancer," Proceedings of the National Academy of Sciences of the United States of America, Jun. 2016, 113(26):7124-7129.

(56) References Cited

OTHER PUBLICATIONS

Rao et al., "Hijacked in cancer: the KMT2 (MLL) family of methyltransferases," Nat. Rev. Cancer, Jun. 2015, 15:334-346.
Ren et al., "PHF19 promotes multiple myeloma tumorigenicity through PRC2 activation and broad H3K27me3 domain formation," Blood, 2019, 134:1176-1189.
Ren et al., "Polycomb protein EZH2 regulates tumor invasion via the transcriptional repression of the metastasis suppressor RKIP in breast and prostate cancer," Cancer Res., 2012, 72(12):3091-3104.
Ribas et al., "Cancer immunotherapy using checkpoint blockade," Science (New York, NY), Mar. 2018, 359(6382):1350-1355.
Rikova et al., "Global survey of phosphotyrosine signaling identifies oncogenic kinases in lung cancer," Cell, Dec. 14, 2007, 131(6):1190-1203.
Ritchie et al., "limma powers differential expression analyses for RNA-sequencing and microarray studies," Nucleic Acids Res., 2015, 43(7):e47.
Rodrik-Outmezguine et al., "Overcoming mTOR resistance mutations with a new-generation mTOR inhibitor," Nature, Jun. 2016, 534:272-276.
Roguev et al., "The *Saccharomyces cerevisiae* Set1 complex includes an ash2 homologue and methylates histone 3 lysine," The EMBO journal, Dec. 2001, 20(24):7137-7148.
Rosati et al., "NUP98 is fused to the NSD3 gene in acute myeloid leukemia associated with t(8;11)(p11.2;p15)," Blood, 2002, 99:3857-3860.
Sakamoto et al., "Protacs: chimeric molecules that target proteins to the Skp1-Cullin-F box complex for ubiquitination and degradation," Proc. Natl. Acad. Sci. USA, Jul. 2001, 98(15):8554-8559.
Salami et al., "Waste disposal—An attractive strategy for cancer therapy," Science, Mar. 2017, 355:1163-1167.
Saura et al., "A first-in-human phase I study of the ATP-competitive AKT inhibitor ipatasertib demonstrates robust and safe targeting of AKT in patients with solid tumors," Cancer Discovery, Jan. 2017, 7(1):102-113.
Sauvageau et al., "Poly comb group proteins: multi-faceted regulators of somatic stem cells and cancer," Cell Stem Cell., 2010, 7(3):299-313.
Sawasdikosol et al., "Hematopoietic progenitor kinase 1 (HPK1) regulates prostaglandin $E_2$-induced fos gene transcription," Blood, May 2003, 101(9):3687-3689.
Sawasdikosol et al., "HPK1 as a novel target for cancer immunotherapy," Immunologic Research, Dec. 2012, 54(1-3):262-265.
Sawasdikosol et al., "Prostaglandin $E_2$ activates HPK 1 kinase activity via a PKA-dependent pathway," The Journal of biological chemistry, Nov. 2007, 282(48):34693-34699.
Schapira et al., "Targeted protein degradation: expanding the toolbox," Nat. Rev. Drug Discov., Dec. 2019, 18(12):949-963.
Schmandt et al., "The BRK tyrosine kinase is expressed in high-grade serous carcinoma of the ovary," Cancer Biol. Ther., 2006, 5:1136-1141.
Schneider et al. "Characterization of EBV-genome negative 'null' and 'T' cell lines derived from children with acute lymphoblastic leukemia and leukemic transformed non-Hodgkin lymphoma," International Journal of Cancer, May 1977, 19(5): 621-626.
Schramm et al., "Novel BQCA- and TBPB-derived M1 receptor hybrid ligands: orthosteric carbachol differentially regulates partial agonism," ChemMedChem, Jul. 2019, 14(14):1349-1358.
Senisterra et al., "Small-molecule inhibition of MLL activity by disruption of its interaction with WDR5," Biochemical Journal, Jan. 2013, 449(1):151-159.
Seshacharyulu et al., "Targeting the EGFR signaling pathway in cancer therapy," Expert Opin. Ther. Targets, Jan. 2012, 16:15-31.
Shanle et al., "Association of Taf14 with acetylated histone H3 directs gene transcription and the DNA damage response," Genes Dev., 2015, 29:1795-1800.
Sharma et al., "Epidermal growth factor receptor mutations in lung cancer," Nat. Rev. Cancer, Mar. 2007, 7:169-181.
Shaw et al., "Ceritinib in ALK-rearranged non-small-cell lung cancer," New England Journal of Medicine, Mar. 27, 2014, 370(13):1189-1197.
Shen et al., "Identification of LEM-14 inhibitor of the oncoprotein NSD2," Biochem Biophys. Res. Commun., Jan. 2019, 508(1):102-108.
Shen et al., "NSD3-Short Is an Adaptor Protein that Couples BRD4 to the CHD8 Chromatin Remodeler," Mol. Cell., Dec. 2015, 60(6):847-859.
Shen et al., "Structure-based design of 5-methylpyrimidopyridone derivatives as new wild-type sparing inhibitors of the epidermal growth factor receptor triple mutant (EGFR$^{L858R/T790M/C797S}$), " J. Med. Chem., Jul. 2019, 62:7302-7308.
Sherr et al., "Targeting CDK4 and CDK6: from discovery to therapy," Cancer Discovery, 2016, 6(4):353-367.
Shibata et al., "Development of protein degradation inducers of oncogenic BCR-ABL protein by conjugation of ABL kinase inhibitors and IAP ligands," Cancer Science, Aug. 2017, 108(8):1657-1666.
Shimizu et al., "The protein arginine methyltransferase 5 promotes malignant phenotype of hepatocellular carcinoma cells and is associated with adverse patient outcomes after curative hepatectomy," International Journal of Oncology, Jan. 2017, 50(2):381-386.
Shiota et al., "Hyperphosphorylation of a novel 80 kDa protein-tyrosine kinase similar to Ltk in a human 40 Ki-1 lymphoma cell line, AMS3," Oncogene, Jun. 1994, 9(6):1567-1574.
Shui et al., "Hematopoietic progenitor kinase 1 negatively regulates T-cell receptor signaling and T cell-mediated immune responses," Nature Immunology, Jan. 2007, 8(1):84-91.
Slany, "When epigenetics kills: MLL fusion proteins in leukemia," Hematol. Oncol., Mar. 2005, 23:1-9.
Sneeringer et al., "Coordinated activities of wild-type plus mutant EZH2 drive tumor-associated hypertrimethylation oflysine 27 on histone H3 (H3K27) in human B-cell lymphomas," Proc. Natl. Acad. Sci. USA, Dec. 7, 2010, 107(49): 20980-20985.
Soda et al., "Identification of the transforming EML4-ALK fusion gene in non-small-cell lung cancer," Nature, Aug. 2, 2007, 448:561-566.
Solomon et al., "First-line crizotinib versus chemotherapy in ALK-positive lung cancer," New England Journal of Medicine, Dec. 4, 2014, 371(23):2167-2177.
Song et al., "Selective inhibition of EZH2 by ZLD1039 blocks H3K27methylation and leads to potent anti-tumor activity in breast cancer," Sci. Rep., 2016, 6:20864.
Song et al., "WDR5 interacts with mixed lineage leukemia (MLL) protein via the histone HJ-binding pocket," The Journal of Biological Chemistry, Dec. 2008, 283(50):35258-35264.
Soucy et al., "An inhibitor of NEDD8-activating enzyme as a new approach to treat cancer," Nature, Apr. 2009, 458:732-736.
Subramanian et al., "Gene set enrichment analysis: a knowledge-based approach for interpreting genome-wide expression profiles," Proc. Natl. Acad. Sci. USA, Sep. 2005, 102(43):15545-15550.
Suda et al., "The structure of bestatin," The Journal of Antibiotic, Jan. 1976, 29(1):100-101.
Sun et al., "Discovery of AMG 232, a potent, selective, and orally bioavailable MDM2-p53 inhibitor in clinical development," Journal of Medicinal Chemistry, Feb. 2014, 57(4):1454-1472.
Sun et al., "PROTAC-induced BTK degradation as a novel therapy for mutated BTK C481S induced ibrutinib-resistant B-cell malignancies," Cell Research, Jul. 2018, 28(7):779-781.
Sun et al., "Up-regulated WDR5 promotes gastric cancer formation by induced cyclin D1 expression," Journal of Cellular Biochemistry, Apr. 2018, 119(4): 28 pages.
Sun et al., "WDR5 supports an N-Myc transcriptional complex that drives a protumorigenic gene expression signature in neuroblastoma," Cancer Research, Dec. 2015 75(23):5143-5154.
Tahirovic et al., "Discovery of N-alkyl piperazine side chain based CXCR4 antagonists with improved drug-like properties," ACS Med. Chem. Lett., May 2018, 9(5):446-451.
Takeuchi et al., "KIF5B-ALK, a novel fusion oncokinase identified by an immunohistochemistry-based diagnostic system for ALK-positive lung cancer," Clinical Cancer Research, May 1, 2009, 15(9):3143-3149.

(56) References Cited

OTHER PUBLICATIONS

Tan et al., "A kinase-independent role for EGF receptor in autophagy initiation," Cell, Jan. 2015, 160(1-2):145-160.
Tan et al., "Next-generation epidermal growth factor receptor tyrosine kinase inhibitors in epidermal growth factor receptor-mutant non-small cell lung cancer," Lung Cancer, Mar. 2016, 93:59-68.
Tan et al., "PBK/AKT-mediated upregulation of WDR5 promotes colorectal cancer metastasis by directly targeting ZNF407," Cell Death and Disease, Mar. 2017, 8(3): 12 pages.
Taniguchi et al., "Silencing of Kruppel-like factor 2 by the histone methyltransferase EZH2 in human cancer," Oncogene, 2012, 31(15):1988-1994.
Tarighat et al., "The dual epigenetic role of PRMT5 in acute myeloid leukemia: gene activation and repression via histone arginine methylation," Leukemia, Nov. 2016, 30:789-799.
Thomas et al., "Interaction with WDR5 promotes target gene recognition and tumorigenesis by MYC," Molecular Cell, May 2015, 58(3):440-452.
Thomas et al., "The MYC-WDR5 nexus and cancer," Cancer Research, Oct. 2015, 75(19):4012-4015.
Thress et al., "Acquired EGFR C797S mutation mediates resistance to AZD9291 in non-small cell lung cancer harboring EGFR T790M," Nat. Med., May 2015, 21:560-562.
Toure et al., "Small-Molecule PROTACS: New Approaches to Protein Degradation," Angewandte Chemie—International Edition, Feb. 2016, 55(6):1966-1973.
Trievel et al., "WDR5, a complexed protein," Nature Structural & Molecular Biology, Jul. 2009, 16(7):678-680.
Turner et al., "Palbociclib in hormone-receptor-positive advanced breast cancer," New England Journal of Medicine, 2015, 373(3):209-219.
Turner-Ivey et al., "Development of mammary hyperplasia, dysplasia, and invasive ductal carcinoma in transgenic mice expressing the 8p11 amplicon oncogene NSD3," Breast Cancer Res. Treat., Jul. 2017, 164(2):349-358.
Varambally et al., "The polycomb group protein EZH2 is involved in progression of prostate cancer," Nature, 2002, 419(6907):624-629.
Varfolomeev et al., "IAP antagonists induce autoubiquitination of c-IAPs, NF-κB activation, and TNFα-dependent apoptosis," Cell, Nov. 2007, 131(4):669-681.
Vassilev et al., "In vivo activation of the p53 pathway by small-molecule antagonists of MDM2," Science, Feb. 2004, 303(5659):844-848.
Verma et al., "Identification of Potent, Selective, Cell-Active Inhibitors of the Histone Lysine Methyltransferase EZH2," Acs Med. Chem. Lett., 2012, 3(12):1091-1096.
Vivanco et al., "A kinase-independent function of AKT promotes cancer cell survival," eLIFE, 2014, 3:e03751.
Vu et al., "Discovery of RG7112: a small-molecule MDM2 inhibitor in clinical development," ACS Medicinal Chemistry Letters, May 2013, 4(5):466-469.
Wakeling, "Use of pure antioestrogens to elucidate the mode of action of oestrogens," Biochemical Pharmacology, May 1995, 49(11):1545-1549.
Wan et al., "ENL links histone acetylation to oncogenic gene expression in acute myeloid leukaemia," Nature, Mar. 2017, 543:265-269.
Wan et al., "Impaired cell fate through gain-of-function mutations in a chromatin reader," Nature, Jan. 2020, 577:121-126.
Wang et al., "EAI045: The fourth-generation EGFR inhibitor overcoming T790M and C797S resistance," Cancer Lett., Jan. 2017, 385:51-54.
Wang et al., "MapSplice: accurate mapping of RNA-seq reads for splice junction discovery," Nucleic Acids Res., 2010, 38:e178.
Wang et al., "NUP98-NSD1 links H3K36 methylation to Hox-A gene activation and leukaemogenesis," Nat. Cell. Biol., Jul. 2007, 9(7):804-812.
Wang et al., "Polycomb genes, miRNA, and their deregulation in B-cell malignancies," Blood, 2015, 125(8):1217-1225.

Wei et al., "Protein arginine methylation of non-histone proteins and its role in diseases," Cell Cycle, 2014, 13(1):32-41.
Weisberg et al., "Smac mimetics: implications for enhancement of targeted therapies in leukemia," Leukemia, Dec. 2010, 24:2100-2109.
Weiss et al., "Anaplastic lymphoma kinase and leukocyte tyrosine kinase: functions and genetic interactions in learning, memory and adult neurogenesis," Pharmacology, Biochemistry and Behavior, Jan. 2012, 100(3):566-574.
Weiss et al., "The role of T3 surface molecules in the activation of human T cells: a two-stimulus requirement for IL 2 production reflects events occurring at a pre-translational level," Journal of Immunology, Aug. 1984, 133(1):123-128.
Wieduwilt et al., "The epidermal growth factor receptor family: biology driving targeted therapeutics," Cell. Mol. Life Sci., May 2008, 65(10):1566-1584.
Winter et al., "Phthalimide conjugation as a strategy for in vivo target protein degradation," Science, May 2015, 348(6241):1376-1381.
Wood et al., "Lack of the t(2;5) or other mutations resulting in expression of anaplastic lymphoma kinase catalytic domain in CD30$^+$primary cutaneous lymphoproliferative disorders and Hodgkin's disease," Blood, Sep. 1, 1996, 88(5):1765-1770.
Wu et al., "Overexpression of WD repeat domain 5 associates with aggressive clinicopathological features and unfavorable prognosis in head neck squamous cell carcinoma," International Association of Oral Pathologists and the American Academy of Oral Pathology, Apr. 2018, 47(5): 27 pages.
Xie et al., "Pharmacological targeting of the pseudokinase Her3," Nature Chemical Biology, Dec. 2014, 10(12):1006-1012.
Xie et al., "WDR5 positively regulates p53 stability by inhibiting p53 ubiquitination," Biochemical and Biophysical Research Communications, May 2017, 487(2):333-338.
Xu et al., "eEF1A2 promotes cell migration, invasion and metastasis in pancreatic cancer by upregulating MMP-9 expression through Akt activation," Clin. Exp. Metastasis, May 2013, 30(7):933-944.
Xu et al., "Selective inhibition of EZH2 and EZH1 enzymatic activity by a small molecule suppresses MLL-rearranged leukemia," Blood, Jan. 2015, 125:346-357.
Xu et al., "Targeting EZH2 and PRC2 dependence as novel anticancer therapy," Exp. Hematol., 2015, 43(8):698-712.
Yang et al., "Structure-Activity Relationship Studies for Enhancer of Zeste Homologue 2 (EZH2) and Enhancer of Zeste Homologue 1 (EZH1) Inhibitors," J. Med. Chem., 2016, 59(16):7617-7633.
Yokoyama et al., "A Higher-Order Complex Containing AF4 and ENL Family Proteins with P-TEFb Facilitates Oncogenic and Physiologic MLL-Dependent Transcription," Cancer Cell, Feb. 2010, 17(2):198-212.
You et al., "Discovery of an AKT degrader with prolonged inhibition of downstream signaling," Cell Chemical Biology, 2020, 27(1):66-73.
Yu et al., "Altered Hox Expression and Segmental Identity in Mll-Mutant Mice," Nature, Nov. 1995, 378:505-508.
Yu et al., "Requirement for CDK4 kinase function in breast cancer," Cancer Cell, 2006, 9(1):23-32.
Yu et al., "Targeting AKT1-E17K and the PI3K/AKT pathway with an allosteric AKT inhibitor, ARQ 092," PLOS One, Oct. 2015, 10(10):e0140479.
Yun et al., "The T790M mutation in EGFR kinase causes drug resistance by increasing the affinity for ATP," Proc. Natl. Acad. Sci. USA, Feb. 2008, 105(6):2070-2075.
Zeng et al., "Discovery of novel imidazo[1,2-a]pyrazin-8-amines as Brk/PTK6 inhibitors," Bioorg. Med. Chem. Lett., Oct. 2011, 21(19):5870-5875.
Zengerle et al., "Selective Small Molecule Induced Degradation of the BET Bromodomain Protein BRD4," ACS Chemical Biology, Jun. 2015, 10(8):1770-1777.
Zhang et al., "Proteolysis targeting chimeras (PROTACs) of anaplastic lymphoma linase (ALK)," Eur. J. Med. Chem., May 2018, 151:304-314.
Zhang et al., "Structural Insights into Histone Crotonyl-Lysine Recognition by the AF9 YEATS Domain," Structure, Sep. 2016, 24(9):1606-1612.

(56) References Cited

OTHER PUBLICATIONS

Zhao et al., "PROTACs suppression of CDK4/6, crucial kinases for cell cycle regulation in cancer," Chem. Commun. (Camb)., 2019, 55:2704-2707.
Zhao et al., "The language of chromatin modification in human cancers," Nat. Rev. Cancer, Jul. 2021, 21:413-430.
Zheng et al., "PTK6 activation at the membrane regulates epithelial-mesenchymal transition in prostate cancer," Cancer Res., Sep. 2013, 73(17):5426-5437.
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, 2018, 61(2):462-481.
Zuber et al., "RNAi screen identifies Brd4 as a therapeutic target in acute myeloid leukaemia," Nature, 2011, 478:524-528.
CN Office Action in Chinese Appln. No. 201780081246.8, dated Mar. 4, 2023, 16 pages (with English Translation).
EP Office Action in European Appln. No. 17877800.7, dated Apr. 13, 2023, 7 pages.
EP Office Action in European Appln. No. 19763958.6, dated May 10, 2023, 4 pages.
EP Office Action in European Appln. No. 19821826.5, dated Apr. 12, 2023, 4 pages.
JP Office Action in Japanese Appln. No. 2020-546159, dated May 9, 2023, 14 pages (with English Translation).
PCT International Preliminary Report on Patentability in International Appln. No. PCT/US2021/055574, dated May 4, 2023, 8 pages.
PCT International Search Report and Written Opinion in International Appln. No. PCT/US2022/050929, dated Apr. 7, 2023, 13 pages.
Popow et al., "Highly selective PTK2 proteolysis targeting chimeras to probe focal adhesion kinase scaffolding functions," Journal of Medicinal Chemistry, 2019, 62(5):2508-2520.
Wei et al., "Discovery of a first-in-class mitogen-activated protein kinase kinase 1/2 degrader," Journal of Medicinal Chemistry, 2019, 62(23):10897-10911.
Xue et al., "Protein degradation through covalent inhibitor-based PROTACs," Chemical Communications, 2020, 56(10):1521-1524.
U.S. Appl. No. 18/032,758, filed Apr. 19, 2023, Jian Jin.
Office Action in Chinese Appln. No. 201980054694.8, mailed on Sep. 1, 2023, 21 pages (with Machine translation).
Office Action in U.S. Appl. No. 16/970,305, mailed on Sep. 8, 2023, 22 pages.
JP Office Action in Japanese Appln. No. 2020-570728, dated Jun. 27, 2023, 11 pages (with English Translation).
JP Office Action in Japanese Appln. No. 2021-500187, dated Jul. 4, 2023, 12 pages (with English Translation).
Wang et al., "Discovery of potent 2-Aryl-6,7-dihydro-5$H$-pyrrolo[1,2-α] imidazoles as WDR5-WIN- site inhibitors using fragment-based methods and structure-based design," Journal of Medicinal Chemistry, 2018, 61(13):5623-5642.
Ishoey et al., "Translation Termination Factor GSPT1 Is a Phenotypically Relevant Off-Target of Heterobifunctional Phtalimide Degraders," ACS Chemical Biology, Jan. 22, 2018, 13(3):533-560.
Office Action in Chinese Appln. No 202080049386.9, mailed on Feb. 2, 2024, 23 pages (with Machine translation).

WD40 REPEAT DOMAIN PROTEIN 5 (WDR5) DEGRADATION/DISRUPTION COMPOUNDS AND METHODS OF USE

CROSS-REFERENCE TO RELATED APPLICATION

This application is a U.S. National Stage application, and claims priority of International Application No. PCT/US2019/038560, filed Jun. 21, 2019, which claims the benefit of U.S. Provisional Application Ser. No. 62/688,343 filed Jun. 21, 2018. The entire contents of the foregoing are incorporated herein by reference.

TECHNICAL FIELD

This disclosure relates to bivalent compounds (e.g., bifunctional small molecule compounds) which degrade and/or disrupt the WD40 repeat domain protein 5 (WDR5) compositions comprising one or more of the bivalent compounds, and to methods of use thereof for the treatment of WDR5-mediated disease in a subject in need thereof. The disclosure also relates to methods for designing such bivalent compounds.

BACKGROUND OF THE INVENTION

WD40 repeat domain protein 5 (WDR5) plays vital roles in a variety of cellular processes that include gene regulation, cell cycle progression, and apoptosis. The best characterized function of WDR5 is to act as a scaffolding and core subunit of human trithorax-like family of histone methyl-transferase (HMT) complexes, which include the Su(var)3-9 enhancer of zeste trithorax 1 (SET1) proteins, such as mixed lineage leukemia 1 (MLL1) protein, and the cofactors ASH2L and RbBP5 (Miller et al., 2001; Roguev et al., 2001; Trievel and Shilatifard, 2009). These WDR5-containing HMT complexes catalyze formation of mono, di- and tri-methylation at histone H3 lysine-4 (H3K4me1/2/3) on chromatin to promote epigenetic transcriptional gene activation (Miller et al., 2001; Roguev et al., 2001; Trievel and Shilatifard, 2009). For instance, WDR5 association with MLL1 is required to activate the developmental Hox genes in early development and hematopoeisis (Higa et al., 2006).

Like other WD40 repeat proteins, WDR5 has a donut-shaped propeller structure that provides a platform to recruit multiple binding partners through protein-protein interactions. Owing to this core structure, WDR5 interacts with a diverse set of regulatory proteins. In addition to the MLL1 complex, WDR5 forms complexes with other epigenetic modulators such as H3R2 (Migliori et al, 2012), NSL/MOF (Cai et al, 2010), C/EBPa (Grebien et al, 2015), NuRD (Ee et al., 2017), and the oncoprotein MYC (Thomas et al., 2015a) (Carugo et al., 2016; Thomas et al., 2015b). Not surprisingly, perturbation of these epigenetic regulatory complexes is associated with human illnesses, including cancer (Chung et al., 2016; Ge et al., 2016; Tan et al., 2017; Thomas et al., 2015a). Generally, WDR5 contributes to tumorigenesis when a binding partner is aberrantly amplified or constitutively active, leading to increased methylation and dysregulation of target genes. For example, the WDR5-MLL1 protein-protein interaction is required for effective association of the MLL1 core complex to its target genes in acute myelogenous leukemia (AML) cells, and disruption of the WDR5-MLL1 interaction results in a dramatic decrease in MLL1 methylation activity, relieving inhibition of myeloid differentiation and decreasing leukemogenesis (Bolshan et al., 2013; Getlik et al., 2016; Grebien et al., 2015; Li et al., 2016a; Li et al., 2016b; Patel et al., 2008a; Patel et al., 2008b; Song and Kingston, 2008). In addition, WDR5 upregulation has been directly associated with human cancers, such as gastric cancer (Sun et al., 2018), head neck squamous cell carcinoma (HNSCC) (Wu et al., 2018), colorectal cancer (CRC) (Tan et al., 2017), lung cancer (Xie et al., 2017), leukemia (Ge et al., 2016), pancreatic cancer (Carugo et al., 2016), bladder cancer (Chen et al., 2015a; Chen et al., 2015b), breast cancer (Dai et al., 2015), and neuroblastomas (Sun et al., 2015). Therefore, mounting evidence has shown WDR5 to be a valid drug target for anti-cancer therapies (Bolshan et al., 2013; Getlik et al., 2016; Grebien et al., 2015; Li et al., 2016a; Li et al., 2016b; Patel et al., 2008a; Patel et al., 2008b; Song and Kingston, 2008).

While many epigenetic regulatory proteins, including WDR5 and associated complexes, are appealing targets for drug discovery, developing small molecule inhibitors to disrupt the protein-protein interactions of these complexes has been a challenge. Certain inhibitors have been developed against WDR5, albeit at preclinical development stages (Guarnaccia and Tansey, 2018). Two binding motifs recognized by WDR5 on binding partners have been identified. The WBM site on MYC proteins and the Win site on MLL1 and other SET1-related proteins have been proposed to be targetable sites by small inhibitors (Dias et al., 2014; Guarnaccia and Tansey, 2018; Odho et al., 2010). (Carugo et al., 2016; Thomas et al., 2015b). While inhibitors exploiting the WBM site have not been reported to date, two types of inhibitors that are specific for the Win site have been reported—one cyclic peptidomimetic, MM-401 that mimics the arginine of the Win motif, thereby interfering with WDR5-cofactor interactions (Cao et al., 2014). The other inhibitor, OICR-9429, belongs to a set of more traditional small-molecule inhibitors that disrupt WDR5-MLL1 interactions (Bolshan et al., 2013; Chen et al., 2018; Grebien et al., 2015; Li et al., 2016a; Li et al., 2016b; Senisterra et al., 2013). OICR-9429 is a potent (Zd=30 nM) and selective WDR5 chemical probe. Recent studies have demonstrated that OICR-9429 or its analogs effectively reduced the growth of a number of disease-associated cells, such as patient AML cells, MLL translocation cells, Li-Fraumeni Syndrome (LFS) fibroblasts, pancreatic ductal adenocarcinoma (PDAC), neuroblastoma cell, and aged myofiber-associated satellite cells. Recently, dihydro-5H-pyrrolo[1,2-c]imidazoles have been disclosed as a new type of WDR5 inhibitors (US20180086767A1).

A drawback of current WDR5 inhibitors is that inhibition of protein-protein interactions is inherently unstable and rely on low on/off rates of the inhibitor to block binding of the protein partner. Thus, full inhibition is not easily achieved. In contrast, complete removal of WDR5 is likely to have greater efficacy in this context. Thus, proposed herein are small molecule degraders of WDR5.

SUMMARY OF THE INVENTION

Unlike the above WDR5 inhibitors, which inhibit the interaction of WDR5 with its binding partners, the WDR5 degradation/disruption compounds ("WDR5 degraders") disclosed herein bind and induce degradation of WDR5, thus eliminating any scaffolding functions of WDR5. The WDR5 degraders disclosed herein are bivalent compounds, including a WDR5 ligand conjugated to a degradation/disruption tag via a linker.

The WDR5 degraders disclosed herein offer a novel mechanism for treating WDR5-mediated diseases. In particular, the ability of the WDR5 degraders to target WDR5 for degradation, as opposed to merely disrupt WDR5 interactions with its binding partners.

In an aspect, this disclosure provides a method of treating WDR5-mediated diseases, the method including administering one or more WDR5 degraders to a subject who has a WDR5-mediated disease, the WDR5 degraders being bivalent compounds including a WDR5 ligand conjugated to a degradation/disruption tag via a linker. The WDR5-mediated disease can be a disease resulting from WDR5 expression. The WDR5-mediated disease can have elevated WDR5 expression relative to a wild-type tissue of the same species and tissue type. Non-limiting examples of WDR5-mediated diseases include leukemia, lymphoma, ovarian cancer, stomach cancer, cervical cancer, uterine cancer, gastric cancer, head neck squamous cell carcinoma (HNSCC), colorectal cancer (CRC), lung cancer, pancreatic cancer, bladder cancer, breast cancer, and neuroblastoma.

The WDR5-mediated cancer can include, e.g., a relapsed cancer. The WDR5-mediated cancer can, e.g., be refractory to one or more previous treatments.

The present disclosure relates generally to bivalent compounds (e.g., bi-functional small molecule compounds) which degrade and/or disrupt WDR5, and to methods for the treatment of WDR5-mediated cancer (i.e., a cancer which depends on WDR5 protein; or cancer having elevated levels of WDR5, or WDR5 activity relative to a wild-type tissue of the same species and tissue type). Because the WDR5 degraders/disruptors have dual functions (protein-protein interaction inhibition plus protein degradation/disruption), the bivalent compounds of the present disclosure can be significantly more effective therapeutic agents than current WDR5 inhibitors, which inhibit the protein-protein interaction involving WDR5, but do not affect WDR5 protein levels. The present disclosure further provides methods for identifying WDR5 degrader s/disruptors as described herein.

More specifically, the present disclosure provides a bivalent compound including a WDR5 ligand conjugated to a degradation/disruption tag via a linker.

In some aspects, the WDR5 degraders/disruptors have the form "PI-Linker-EL", as shown below:

wherein PI (a ligand for a "protein of interest," i.e., the protein to be degraded) comprises a WDR5 ligand (e.g., a WDR5 protein-protein inhibitor), and EL (e.g., a ligand for an E3 ligase) comprises a degradation/disruption tag (e.g., E3 ligase ligand). Exemplary WDR5 ligands (PI), exemplary degradation/disruption tags (EL), and exemplary linkers (Linker) are illustrated below:

WDR5 Ligands

WDR5 Ligands include but are not limited to:

FORMULA 1

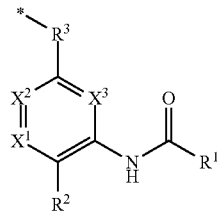

Wherein
*: Connect to "Linker".

$R^1$ is $C_6$-$C_{10}$ aryl or $C_5$-$C_{10}$ heteroaryl. $R^1$ is unsubstituted or substituted with one or more of groups selected from halo, =O, =S, CN, $NO_2$, $C_{1-8}$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_1$-$C_8$ alkyleneOR$^4$, $C_1$-$C_8$alkyleneSR$^5$, $C_1$-$C_8$alkylene NR$^6$R$^7$, $C_2$-$C_8$ alkenyl, $C_2$-$C_8$ alkynyl, OR$^4$, SR$^5$, NR$^6$R$^7$.

$R^2$ is heterocycloalkyl, which contains one or more nitrogen atoms. $R^2$ is unsubstituted or substituted with one or more of groups selected from halo, =O, =S, CN, $NO_2$, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_2$-$C_8$ alkenyl, $C_2$-$C_8$ alkynyl, OR$^8$, SR$^9$, NR$^{10}$R$^{11}$, $C_1$-$C_8$ alkyleneOR$^8$, $C_1$-$C_8$ alkyleneSR$^9$, $C_1$-$C_8$ alkyleneNR$^{10}$R$^{11}$.

$R^3$ is selected from $C_6$-$C_{10}$ aryl, $C_5$-$C_{10}$ heteroaryl, or heterocycloalkyl, heterocycloalkenyl. $R^3$ is unsubstituted or substituted with one or more of groups selected from halo, CN, $NO_2$, =O, =S, OR$^{12}$, SR$^{13}$, $SO_2$R$^{14}$, NR$^{15}$R$^{16}$, R$^{17}$, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_2$-$C_8$ alkenyl, $C_2$-$C_8$ alkynyl, $C_1$-$C_8$ alkyleneR$^{17}$, $C_2$-$C_8$ alkenyleneR$^{17}$, $C_2$-$C_8$ alkynyleneR$^{17}$, OC$_1$-$C_8$ alkyleneR$^{17}$, SC$_1$-$C_8$ alkyleneR$^{17}$, $C_1$-$C_8$ alkyleneOR$^{12}$, $C_1$-$C_8$ alkyleneSR$^{13}$, $C_1$-$C_8$ alkyleneNR$^{15}$R$^{16}$, OC$_1$-$C_8$ alkyleneOR$^{12}$, OC$_1$-$C_8$ alkyleneSR$^{13}$, OC$_1$-$C_8$ alkyleneNR$^{15}$R$^{16}$, SC$_1$-$C_8$ alkyleneOR$^{12}$, SC$_1$-$C_8$ alkyleneSR$^{13}$, SC$_1$-$C_8$ alkyleneNR$^{15}$R$^{16}$, C(O)R$^{12}$, C(O)OR$^{12}$, C(S)OR$^{12}$, C(O)NR$^{15}$R$^{16}$, C(S) NR$^{15}$R$^{16}$, NR$^{15}$C(O)R$^{12}$, NR$^{15}$S(O)R$^{12}$, NR$^{15}$S(O)OR$^{12}$, S(O)R$^{13}$, S(O)OR$^{12}$, and S(O)ONR$^{15}$R$^{16}$.

$R^4$, $R^5$, $R^6$, $R^7$, $R^8$, $R^9$, $R^{10}$, and $R^{11}$ are independently selected from H, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, C(O)C$_1$-$C_8$ alkyl, C(O)C$_1$-$C_8$ haloalkyl, C(O)C$_1$-$C_8$ hydroxyalkyl, C(O)C$_3$-$C_{10}$ cycloalkyl, and C(O)C$_3$-$C_{10}$ heterocyclyl, or $R^6$ and $R^7$; $R^{10}$ and $R^{11}$ together with the nitrogen atom to which they are connected can independently form 3-10 membered heterocyclyl rings.

$R^{12}$, $R^{13}$, and $R^{14}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_8$ cycloalkyl, $C_3$-$C_7$ heterocycloalkyl, $C_6$-$C_{10}$ aryl, $C_5$-$C_{10}$ heteroaryl, C(O)C$_1$-$C_8$ alkyl, C(O)C$_1$-$C_8$ haloalkyl, C(O)C$_1$-$C_8$ hydroxyalkyl, C(O)C$_1$-$C_8$ alkoxyalkyl, C(O)C$_3$-$C_{10}$ cycloalkyl, C(O) C$_3$-$C_{10}$ heterocyclyl, C(O)C$_6$-$C_{10}$ aryl, C(O)C$_5$-$C_{10}$ heteroaryl, $C_1$-$C_8$ alkyleneC$_3$-$C_{10}$ cycloalkyl, $C_1$-$C_8$ alkyleneC$_3$-$C_{10}$ heterocycloalkyl, $C_1$-$C_8$ alkyleneC$_6$-$C_{10}$ aryl, $C_1$-$C_8$ alkyleneC$_5$-$C_{10}$ heteroaryl.

$R^{15}$ and $R^{16}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_{10}$ cycloalkyl, $C_3$-$C_{10}$ heterocloalkyl, $C_6$-$C_{10}$ aryl, $C_5$-$C_{10}$ heteroaryl, C(O)C$_1$-$C_8$ alkyl, C(O)C$_1$-$C_8$ haloalkyl, C(O)C$_1$-$C_8$ hydroxyalkyl, C(O)C$_1$-$C_8$ alkoxyalkyl, C(O)C$_3$-$C_{10}$ cycloalkyl, C(O) C$_3$-$C_{10}$ heterocycloalkyl, C(O)C$_6$-$C_{10}$ aryl, C(O)C$_5$-$C_{10}$ heteroaryl, C(O)OC$_1$-$C_8$ alkyl, C(O)OC$_1$-$C_8$ haloalkyl, C(O)OC$_1$-$C_8$ hydroxyalkyl, C(O)OC$_1$-$C_8$ alkoxyalkyl, C(O)OC$_3$-$C_{10}$ cycloalkyl, C(O)OC$_3$-$C_{10}$ heterocyclyl, C(O)OC$_6$-$C_{10}$ aryl, C(O)OC$_5$-$C_{10}$ heteroaryl, C(O)NC$_1$-$C_8$ alkyl, C(O)NC$_1$-$C_8$ haloalkyl, C(O)NC$_1$-$C_8$ hydroxyalkyl, C(O)NC$_1$-$C_8$ alkoxyalkyl, C(O)NC$_3$-$C_{10}$ cycloalkyl, C(O)NC$_3$-$C_{10}$ heterocyclyl, C(O)NC$_6$-$C_{10}$ aryl, C(O)NC$_5$-$C_{10}$ heteroaryl, $SO_2$C$_1$-$C_8$ alkyl, $SO_2$C$_1$-$C_8$ haloalkyl, $SO_2$C$_1$-$C_8$ hydroxyalkyl, SO$_2$C$_1$-C$_8$ alkoxyalkyl, SO$_2$C$_3$-C$_{10}$ cycloalkyl, SO$_2$C$_3$-C$_{10}$ heterocyclyl, SO$_2$C$_6$-C$_{10}$ aryl, SO$_2$C$_5$-C$_{10}$ heteroaryl, C$_1$-C$_8$ alkyleneC$_3$-C$_{10}$ cycloalkyl, C$_1$-C$_8$ alkyleneC$_3$-C$_{10}$ heterocycloalkyl, C$_1$-C$_8$ alkyleneC$_6$-C$_{10}$ aryl, C$_1$-C$_8$ alkyleneC$_5$-C$_{10}$ heteroaryl, or R$^{15}$ and R$^{16}$ together with the nitrogen atom to which they are connected can independently form 3-10 membered heterocyclyl rings.

R$^{17}$ is selected from C$_3$-C$_{10}$ cycloalkyl, C$_3$-C$_{10}$ heterocloalkyl, C$_6$-C$_{10}$ aryl, C$_5$-C$_{10}$ heteroaryl, C(O)C$_1$-C$_8$ alkyl, C(O)C$_1$-C$_8$ haloalkyl, C(O)C$_1$-C$_8$ hydroxyalkyl, C(O)C$_1$-C$_8$ alkoxyalkyl, C(O)C$_3$-C$_{10}$ cycloalkyl, C(O)C$_3$-C$_{10}$ heterocycloalkyl, C(O)C$_6$-C$_{10}$ aryl, and C(O)C$_5$-C$_{10}$ heteroaryl.

X1, X2, and X3 are independently selected from CR$^{18}$, and N.

R$^{18}$ is selected from H, F, Cl, C$_{1-8}$ alkyl, C$_1$-C$_8$ haloalkyl, C$_1$-C$_8$ alkoxyalkyl, or C$_3$-C$_8$ cycloalkyl In some aspects of Formula I, R$^1$ has a structure of:

FORMULA 1-1A

FORMULA 1-1B

FORMULA 1-1C

FORMULA 1-1D

FORMULA 1-1E

FORMULA 1-1F

FORMULA 1-1G

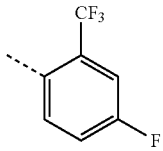

FORMULA 1-1H

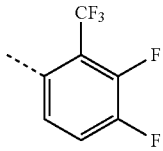

FORMULA 1-1I

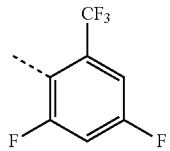

FORMULA 1-1J

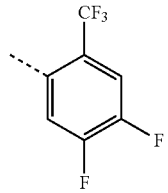

In some aspects of Formula I, R$^2$ has a structure of:

FORMULA 1-2A

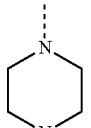

FORMULA 1-2B

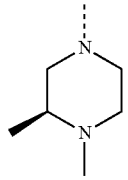

FORMULA 1-2C

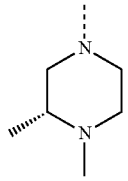

FORMULA 1-2D

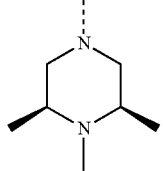

FORMULA 1-2E
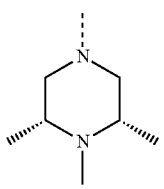
FORMULA 1-2F
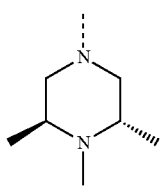
FORMULA 1-2G
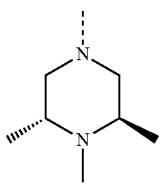
FORMULA 1-2H
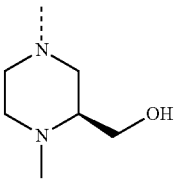
FORMULA 1-2I
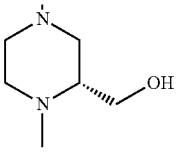
In some aspects of Formula I, $R^3$ has a structure of:
FORMULA 1-3A
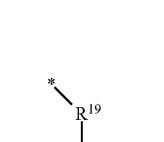
FORMULA 1-3B
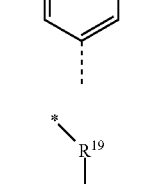
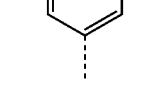
FORMULA 1-3C
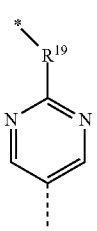
FORMULA 1-3D
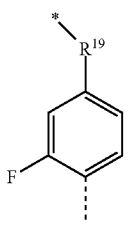
FORMULA 1-3E
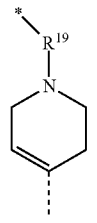
FORMULA 1-3F
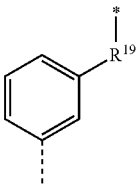
FORMULA 1-3G
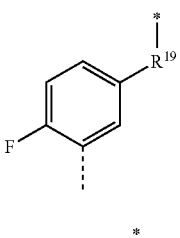
FORMULA 1-3H
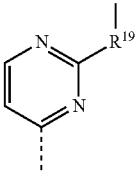
FORMULA 1-3I
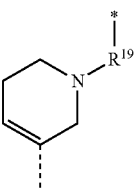

-continued

FORMULA 1-3J

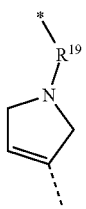

*: connect to "Linker".

$R^{19}$ is selected from a bond, $C_1$-$C_8$ alkyl, $C_1$-$C_8$ haloalkyl, $OR^{20}$, $SR^{20}$, $SO_2R^{20}$, $NR^{21}R^{22}$, $R^{23}$, $C_1$-$C_8$ alkyleneR$^{23}$, $C_2$-$C_8$ alkenyleneR$^{23}$, $OC_1$-$C_8$ alkyleneR$^{23}$, $SC_1$-$C_8$ alkyleneR$^{23}$, $C_1$-$C_8$ alkyleneOR$^{20}$, $C_1$-$C_8$ alkyleneSR$^{20}$, $C_1$-$C_8$ alkyleneNR$^{21}R^{22}$, $OC_1$-$C_8$ alkyleneOR$^{20}$, $OC_1$-$C_8$ alkyleneSR$^{20}$, $OC_1$-$C_8$ alkyleneNR$^{21}R^{22}$, $SC_1$-$C_8$ alkyleneOR$^{20}$, $SC_1$-$C_8$ alkyleneSR$^{20}$, $SC_1$-$C_8$ alkyleneNR$^{21}R^{22}$, $C(O)OR^{20}$, $C(S)OR^{20}$, $C(O)$ $NR^{21}R^{22}$, $C(S)$ $NR^{21}R^{22}$.

$R^{20}$ is selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_8$ cycloalkyl, $C_3$-$C_7$ heterocycloalkyl, $C_6$-$C_{10}$ aryl, $C_5$-$C_{10}$ heteroaryl, $C(O)C_1$-$C_8$ alkyl, $C(O)C_1$-$C_8$ haloalkyl, $C(O)C_1$-$C_8$ hydroxyalkyl, $C(O)C_1$-$C_8$ alkoxyalkyl, $C(O)C_3$-$C_{10}$ cycloalkyl, $C(O)C_3$-$C_{10}$ heterocyclyl, $C(O)C_6$-$C_{10}$ aryl, $C(O)C_5$-$C_{10}$ heteroaryl, $C_1$-$C_8$ alkyleneC$_3$-$C_{10}$ cycloalkyl, $C_1$-$C_8$ alkyleneC$_3$-$C_{10}$ heterocycloalkyl, $C_1$-$C_8$ alkyleneC$_6$-$C_{10}$ aryl, $C_1$-$C_8$ alkyleneC$_5$-$C_{10}$ heteroaryl.

$R^{21}$ and $R^{22}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_{10}$ cycloalkyl, $C_3$-$C_{10}$ heterocycloalkyl, $C_6$-$C_{10}$ aryl, $C_5$-$C_{10}$ heteroaryl, $C(O)C_1$-$C_8$ alkyl, $C(O)C_1$-$C_8$ haloalkyl, $C(O)C_1$-$C_8$ hydroxyalkyl, $C(O)C_1$-$C_8$ alkoxyalkyl, $C(O)C_3$-$C_{10}$ cycloalkyl, $C(O)$ $C_3$-$C_{10}$ heterocycloalkyl, $C(O)C_6$-$C_{10}$ aryl, $C(O)C_5$-$C_{10}$ heteroaryl, $C(O)OC_1$-$C_8$ alkyl, $C(O)OC_1$-$C_8$ haloalkyl, $C(O)OC_1$-$C_8$ hydroxyalkyl, $C(O)OC_1$-$C_8$ alkoxyalkyl, $C(O)OC_3$-$C_{10}$ cycloalkyl, $C(O)OC_3$-$C_{10}$ heterocyclyl, $C(O)OC_6$-$C_{10}$ aryl, $C(O)OC_5$-$C_{10}$ heteroaryl, $C(O)NC_1$-$C_8$ alkyl, $C(O)NC_1$-$C_8$ haloalkyl, $C(O)NC_1$-$C_8$ hydroxyalkyl, $C(O)NC_1$-$C_8$ alkoxyalkyl, $C(O)NC_3$-$C_{10}$ cycloalkyl, $C(O)NC_3$-$C_{10}$ heterocyclyl, $C(O)NC_6$-$C_{10}$ aryl, $C(O)NC_5$-$C_{10}$ heteroaryl, $SO_2C_1$-$C_8$ alkyl, $SO_2C_1$-$C_8$ haloalkyl, $SO_2C_1$-$C_8$ hydroxyalkyl, $SO_2C_1$-$C_8$ alkoxyalkyl, $SO_2C_3$-$C_{10}$ cycloalkyl, $SO_2C_3$-$C_{10}$ heterocyclyl, $SO_2C_6$-$C_{10}$ aryl, $SO_2C_5$-$C_{10}$ heteroaryl, $C_1$-$C_8$ alkyleneC$_3$-$C_{10}$ cycloalkyl, $C_1$-$C_8$ alkyleneC$_3$-$C_{10}$ heterocycloalkyl, $C_1$-$C_8$ alkyleneC$_6$-$C_{10}$ aryl, $C_1$-$C_8$ alkyleneC$_5$-$C_{10}$ heteroaryl, or $R^{21}$ and $R^{22}$ together with the nitrogen atom to which they are connected can independently form 3-10 membered heterocyclyl rings.

$R^{23}$ is selected from $C_3$-$C_{10}$ cycloalkyl, $C_3$-$C_{10}$ heterocycloalkyl, $C_6$-$C_{10}$ aryl, $C_5$-$C_{10}$ heteroaryl, $C(O)C_1$-$C_8$ alkyl, $C(O)C_1$-$C_8$ haloalkyl, $C(O)C_1$-$C_8$ hydroxyalkyl, $C(O)C_1$-$C_8$ alkoxyalkyl, $C(O)C_3$-$C_{10}$ cycloalkyl, $C(O)$ $C_3$-$C_{10}$ heterocycloalkyl, $C(O)C_6$-$C_{10}$ aryl, and $C(O)$ $C_5$-$C_{10}$ heteroaryl.

WDR5 Ligands include but are not limited to:

FORMULA 2A

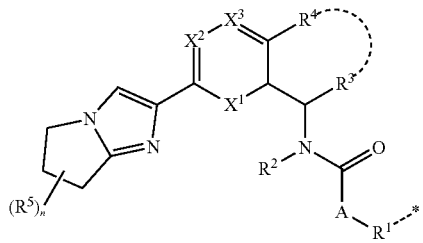

FORMULA 2B

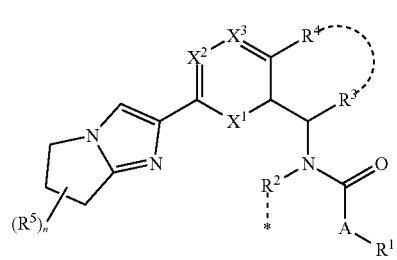

FORMULA 2C

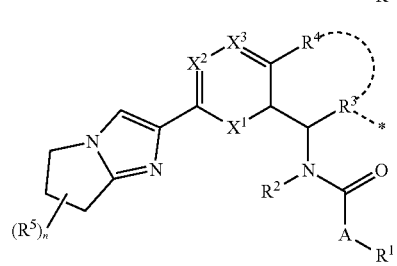

Wherein

*: Connect to "Linker".

$X^1$, $X^2$, and $X^3$ are independently selected from null, $CR^6$, and N, wherein $R^6$, at each occurrence, is independently selected from hydrogen, halogen, cyano, nitro, optionally substituted $C_1$-$C_8$ alkyl, optionally substituted $C_1$-$C_8$ haloalkyl, optionally substituted $C_1$-$C_8$ alkoxy, optionally substituted $C_1$-$C_8$ haloalkoxy, optionally substituted $C_1$-$C_8$ alkylamino, optionally substituted $C_1$-$C_8$ haloalkylamino, optionally substituted $C_1$-$C_8$ alkoxycarbonyl, optionally substituted $C_1$-$C_8$ haloalkoxycarbonyl, optionally substituted $C_1$-$C_8$ alkylaminocarbonyl, optionally substituted $C_1$-$C_8$ haloalkylaminocarbonyl, optionally substituted $C_3$-$C_8$ carbocyclyl, and optionally substituted $C_4$-$C_8$ heterocyclyl;

A is selected from null, optionally substituted $C_1$-$C_8$ alkylene, optionally substituted $C_1$-$C_8$ haloalkylene, optionally substituted $C_1$-$C_8$ alkylamino, optionally substituted $C_1$-$C_8$ alkyleneamino, optionally substituted $C_1$-$C_8$ haloalkylamino, optionally substituted $C_2$-$C_8$ alkenylene, optionally substituted $C_2$-$C_8$ haloalkenylene, optionally substituted $C_2$-$C_8$ alkenyleneamino, optionally substituted $C_2$-$C_8$ haloalkenyleneamino, optionally substituted $C_2$-$C_8$ alkynylene, optionally substituted $C_2$-$C_8$ haloalkynylene, optionally substituted $C_2$-$C_8$ alkynyleneamino, optionally substituted $C_2$-$C_8$ haloalkynyleneamino, optionally substituted $C_3$-$C_8$ carbocyclyl, and optionally substituted $C_4$-$C_8$ heterocyclyl;

$R^1$ is selected from selected from null, carbocyclyl, heterocyclyl, aryl, and heteroaryl, which are optionally substituted with one or more substituents independently selected from hydrogen, halogen, oxo, CN, $NO_2$, $OR^7$, $SR^7$, $NR^7R^8$, $OCOR^7$, $OCO_2R^7$, $OCON(R^7)R^8$, $COR^7$, $CO_2R^7$, $CON(R^7)R^8$, $SOR^7$, $SO_2R^7$, $SO_2N(R^7)R^8$, $NR^9CO_2R^7$, $NR^9COR^7$, $NR^9C(O)N(R^7)R^8$, $NR^9SOR^7$, $NR^9SO_2R^7$, $NR^9SO_2N(R^7)R^8$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted 4-10 membered heterocyclyl$C_1$-$C_8$alkyl, optionally substituted 3-10 membered carbocyclyl$C_1$-$C_8$alkyl, optionally substituted 3-10 membered carbocyclyl, optionally substituted 4-10 membered heterocyclyl, optionally substituted aryl, and optionally substituted heteroaryl, wherein $R^7$, $R^8$, and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-10 membered carbocyclyl$C_1$-$C_8$alkyl, optionally substituted 4-10 membered heterocyclyl$C_1$-$C_8$alkyl, optionally substituted 3-10 membered carbocyclyl, optionally substituted 4-10 membered heterocyclyl, optionally substituted aryl, and optionally substituted heteroaryl, or $R^7$ and $R^8$, $R^7$ and $R^9$ together with the atom to which they are connected form a 4-20 membered heterocyclyl ring;

$R^2$ is selected from null, hydrogen, optionally substituted $C_1$-$C_8$ alkyl, optionally substituted $C_1$-$C_8$haloalkyl, optionally substituted $C_3$-$C_8$ carbocyclyl, optionally substituted $C_4$-$C_8$ heterocyclyl, optionally substituted aryl, and optionally substituted heteroaryl;

$R^3$ is selected from null, hydrogen, halogen, cyano, nitro, optionally substituted $C_1$-$C_8$ alkyl, optionally substituted $C_1$-$C_8$ haloalkyl, optionally substituted $C_3$-$C_8$ carbocyclyl, optionally substituted $C_4$-$C_8$ heterocyclyl, optionally substituted $C_2$-$C_8$ alkenylene, optionally substituted $C_2$-$C_8$ alkynylene, optionally substituted aryl, and optionally substituted heteroaryl;

$R^4$ is selected from null, hydrogen, halogen, cyano, nitro, $OR^{10}$, $NR^{10}R^{11}$, optionally substituted $C_1$-$C_8$ alkyl, optionally substituted $C_3$-$C_8$ carbocyclyl, optionally substituted $C_4$-$C_8$ heterocyclyl, optionally substituted $C_2$-$C_8$ alkenylene, optionally substituted $C_2$-$C_8$ alkynylene, optionally substituted aryl, and optionally substituted heteroaryl, wherein $R^{10}$, and $R^{11}$, are independently selected from hydrogen, optionally substituted $C_1$-$C_8$ alkyl, optionally substituted $C_3$-$C_8$ carbocyclyl, optionally substituted $C_4$-$C_8$ heterocyclyl, optionally substituted $C_2$-$C_8$ alkenylene, optionally substituted $C_2$-$C_8$ alkynylene, optionally substituted aryl, and optionally substituted heteroaryl;

$R^3$ and $R^4$, together with the atoms to which they are connected optionally form a 4-8 membered carbocyclyl ring, or 4-8 membered heterocyclyl ring;

$R^5$, at each occurrence, is independently selected from hydrogen, halogen, hydroxyl, cyano, nitro, optionally substituted $C_1$-$C_8$ alkyl, optionally substituted $C_1$-$C_8$ haloalkyl, optionally substituted $C_1$-$C_8$ alkoxy, optionally substituted $C_1$-$C_8$ alkylamino, optionally substituted $C_1$-$C_8$ haloalkylamino, optionally substituted $C_3$-$C_8$ carbocyclyl, and optionally substituted $C_4$-$C_8$ heterocyclyl; and n=0-6.

In some aspects of Formulae 2A, 2B and 2C, $X^1$, $X^2$, and $X^3$ are $CR^6$.

In some aspects of Formulae 2A, 2B and 2C, $X^1$ and $X^3$ are $CR^6$; and $X^3$ is N.

In some aspects of Formulae 2A, 2B and 2C, $R^6$ is selected from hydrogen, halogen, optionally substituted $C_1$-$C_8$ alkyl, optionally substituted $C_1$-$C_8$ alkoxy, optionally substituted $C_1$-$C_8$ alkylamino, optionally substituted $C_1$-$C_8$ alkoxycarbonyl, optionally substituted $C_3$-$C_8$ carbocyclyl, and optionally substituted $C_4$-$C_8$ heterocyclyl.

In some aspects of Formulae 2A, 2B and 2C, $R^6$ is selected from H, F, Cl, Br, $CH_3$, $CH_3O$, and $CH_3O(CO)$—.

In some aspects of Formulae 2A, 2B and 2C, $R^6$ is H.

In some aspects of Formulae 2A, 2B and 2C, A is selected from null, optionally substituted $C_1$-$C_8$ alkylene, optionally substituted $C_1$-$C_8$ alkylamino, optionally substituted $C_1$-$C_8$ alkyleneamino, optionally substituted $C_2$-$C_8$ alkenylene, optionally substituted $C_2$-$C_8$ alkenyleneamino, optionally substituted $C_2$-$C_8$ alkynylene, and optionally substituted $C_2$-$C_8$ alkynyleneamino.

In some aspects of Formulae 2A, 2B and 2C, A is selected from null, and optionally substituted $C_1$-$C_8$ alkylene.

In some aspects of Formulae 2A, 2B and 2C, A is null.

In some aspects of Formulae 2A, 2B and 2C, A is $CH_2$.

In some aspects of Formulae 2A, 2B and 2C, $R^1$ is selected from selected from null, carbocyclyl, heterocyclyl, aryl, and heteroaryl, which are optionally substituted with one or more substituents independently selected from hydrogen, halogen, oxo, CN, $NO_2$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$alkoxy, optionally substituted $C_1$-$C_8$alkylamino, optionally substituted 4-10 membered heterocyclyl$C_1$-$C_8$alkyl, optionally substituted 3-10 membered carbocyclyl$C_1$-$C_8$alkyl, optionally substituted 4-10 membered heterocyclyloxy, optionally substituted 3-10 membered carbocyclyloxy, optionally substituted 3-10 membered carbocyclyl, and optionally substituted 4-membered heterocyclyl.

In some aspects of Formulae 2A, 2B and 2C, $R^1$ is selected from aryl and heteroaryl, which are optionally substituted with one or more substituents independently selected from hydrogen, halogen, oxo, CN, $NO_2$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$alkoxy, optionally substituted $C_1$-$C_8$alkylamino, optionally substituted 4-10 membered heterocyclyl$C_1$-$C_8$alkyl, optionally substituted 3-10 membered carbocyclyl$C_1$-$C_8$alkyl, optionally substituted 4-10 membered heterocyclyloxy, optionally substituted 3-10 membered carbocyclyloxy, optionally substituted 3-membered carbocyclyl, and optionally substituted 4-10 membered heterocyclyl.

In some aspects of Formulae 2A, 2B and 2C, $R^2$ is selected from null, hydrogen, optionally substituted $C_1$-$C_8$ alkyl, optionally substituted $C_1$-$C_8$ haloalkyl, optionally substituted C3-C8 cycloalkyl, optionally substituted $C_4$-$C_8$ heterocycloalkyl, optionally substituted aryl, and optionally substituted heteroaryl.

In some aspects of Formulae 2A, 2B and 2C, $R^2$ is selected from null, hydrogen, optionally substituted $C_1$-$C_8$ alkyl, optionally substituted $C_3$-$C_8$ cycloalkyl, and optionally substituted $C_3$-$C_8$ cycloalkyl$C_1$-$C_8$ alkyl.

In some aspects of Formulae 2A, 2B and 2C, $R^3$ is selected from null, hydrogen, and optionally substituted $C_1$-$C_8$ alkyl.

In some aspects of Formulae 2A, 2B and 2C, $R^3$ is selected from null, hydrogen, methyl, methylene, ethyl, ethylene, isopropyl, and cyclopropyl.

In some aspects of Formulae 2A, 2B and 2C, $R^4$ is selected from null, hydrogen, halogen, optionally substituted $C_1$-$C_8$ alkyl, optionally substituted $C_1$-$C_8$ alkoxy, optionally substituted $C_1$-$C_8$ alkylamino, optionally substituted $C_3$-$C_8$ cycloalkyl, optionally substituted $C_3$-$C_8$ cycloalkoxy, optionally substituted $C_3$-$C_8$ cycloalkylamino, optionally substituted $C_4$-$C_8$ heterocyclyl, optionally substituted $C_2$-$C_8$ alkenylene, optionally substituted $C_2$-$C_8$ alkynylene, optionally substituted aryl, optionally substituted aryloxy, optionally substituted arylamino, and optionally substituted heteroaryl.

In some aspects of Formulae 2A, 2B and 2C, $R^3$ and $R^4$, together with the atoms to which they are connected optionally form a 5-membered carbocyclyl ring, 6-membered carbocyclyl ring, 5-membered heterocyclyl ring, or 6-membered heterocyclyl ring.

In some aspects of Formulae 2A, 2B and 2C, $R^3$ and $R^4$, together with the atoms to which they are connected optionally form a 5-membered carbocyclyl ring.

In some aspects of Formulae 2A, 2B and 2C, $R^5$, at each occurrence, is independently selected from hydrogen, halogen, optionally substituted $C_1$-$C_8$ alkyl, optionally substituted $C_1$-$C_8$ alkoxy, optionally substituted $C_1$-$C_8$ alkylamino, optionally substituted $C_3$-$C_8$ carbocyclyl, and optionally substituted $C_4$-$C_8$ heterocyclyl.

In some aspects of Formulae 2A, 2B and 2C, $R^5$ is hydrogen.

In some aspects, the WDR5 ligand can be derivatives of following compounds:

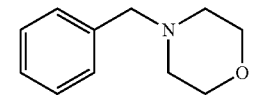

OICR-9429

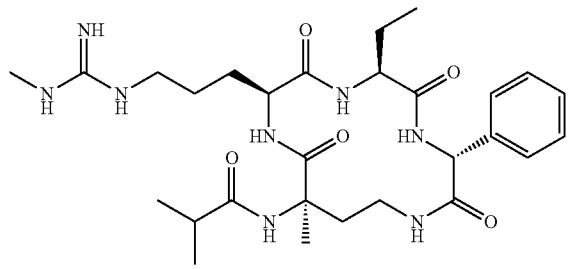

MM-589

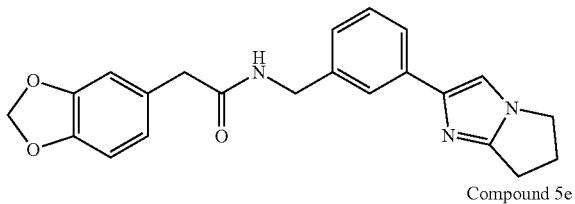

Compound B154

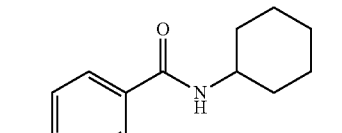

Compound 5e

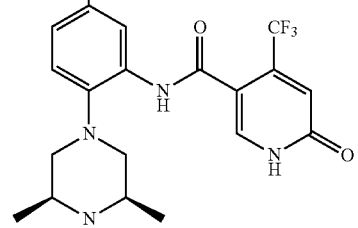

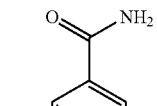

Compound 5f

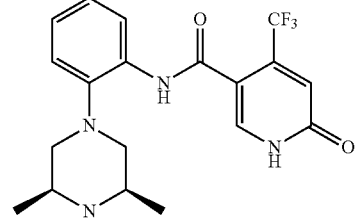

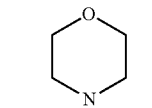

Compound 5g

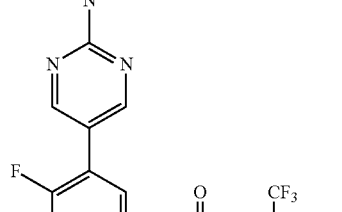

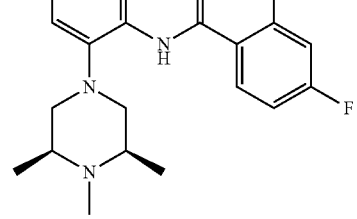

Compound 5h
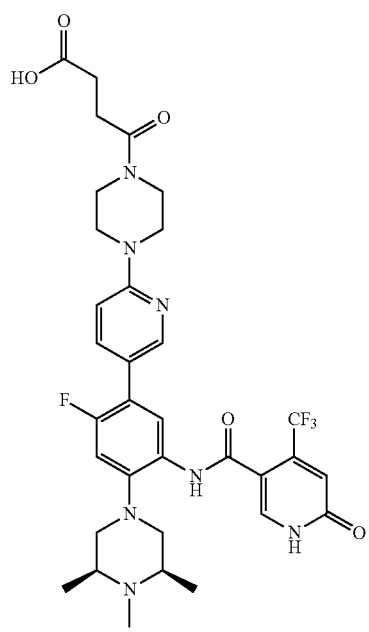
Compound 5j
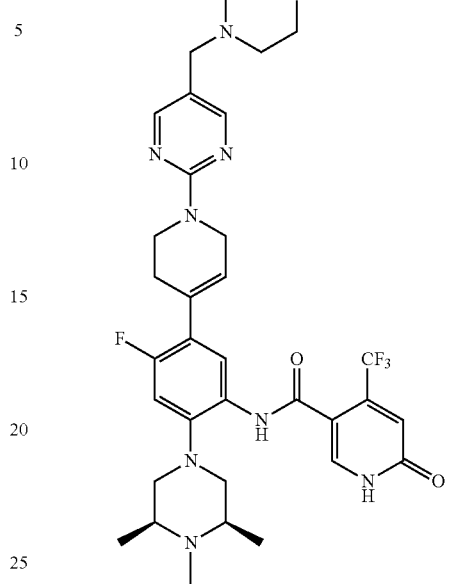
Compound 5k
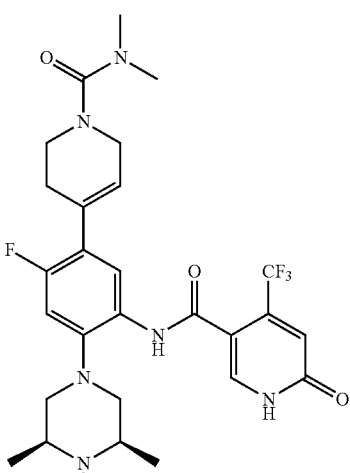
Compound 5i
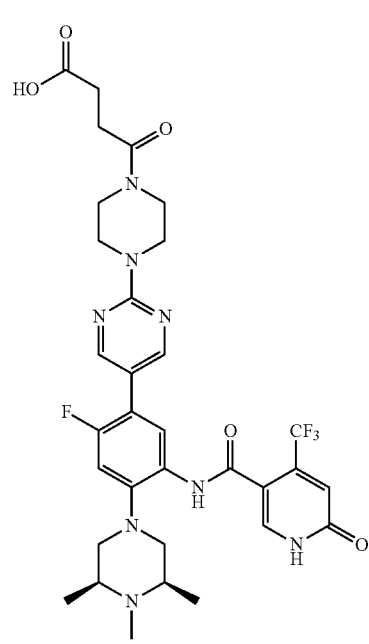
Compound 5l
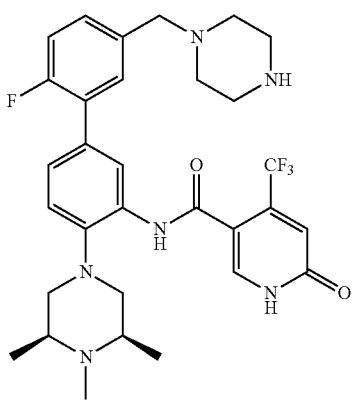

Compound 5m
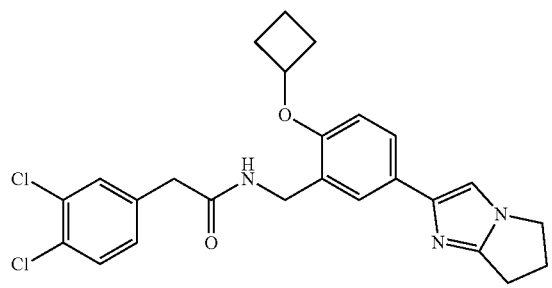
Compound 5o
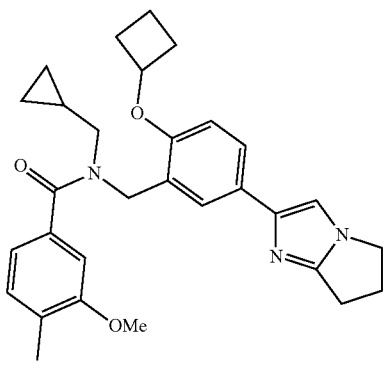
Compound 6a
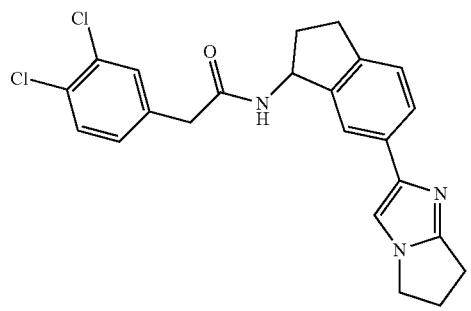
Compound 6b
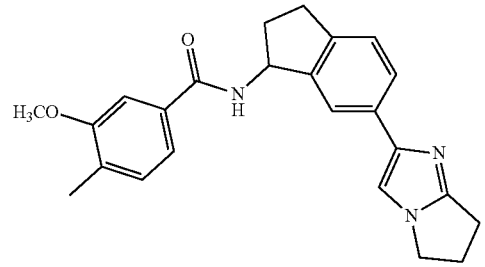
Compound 6c
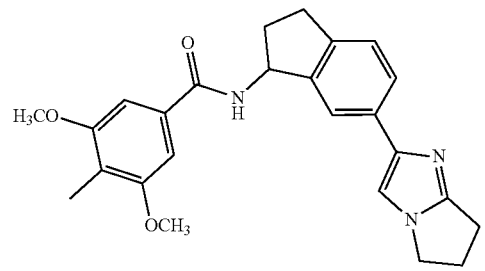
Compound C3
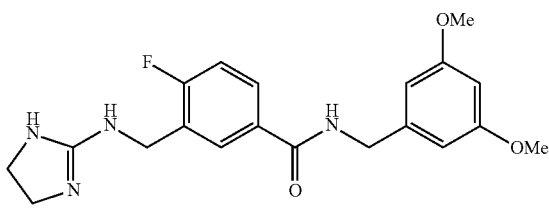
Compound C6
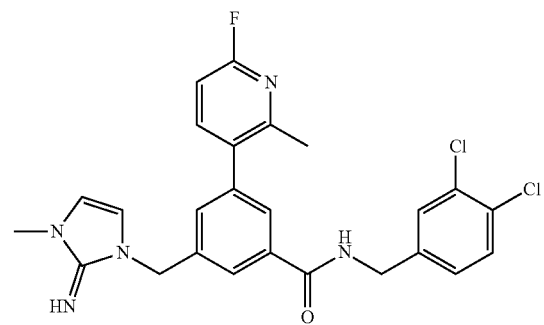
In some aspects, the WDR5 ligand can be, e.g.:
FORMULA 1A
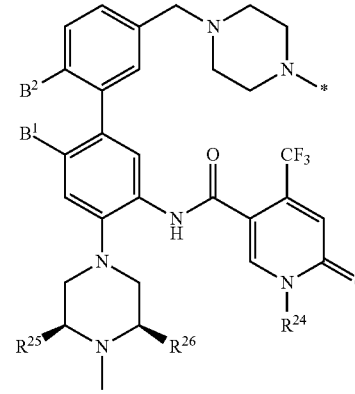
FORMULA 1B
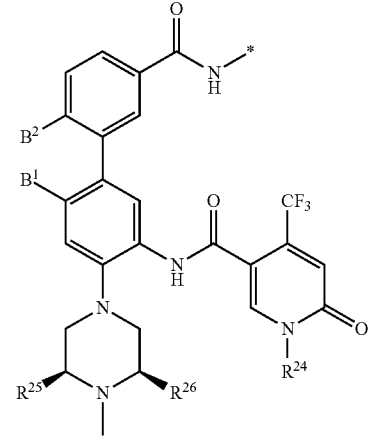

FORMULA 1C
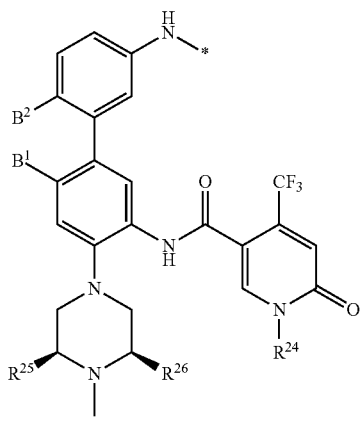
FORMULA 1D
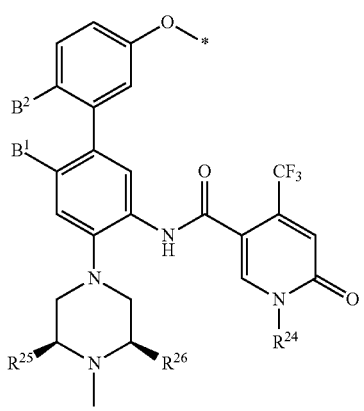
FORMULA 1E
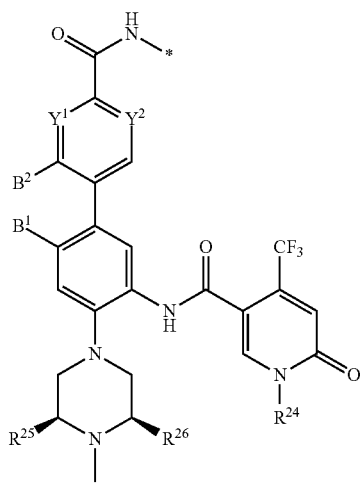
FORMULA 1F
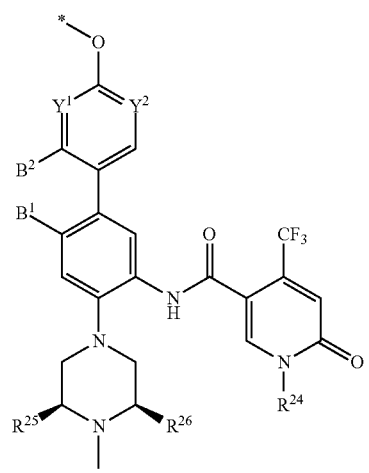
FORMULA 1G
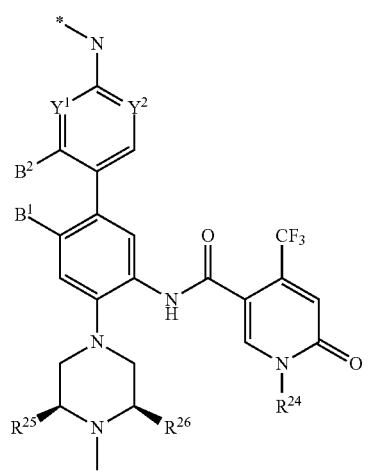
FORMULA 1H
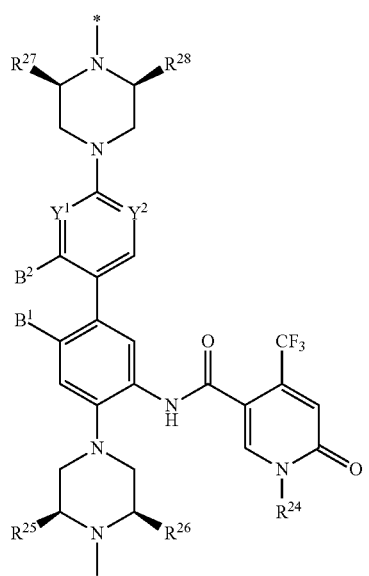

-continued
FORMULA 1I
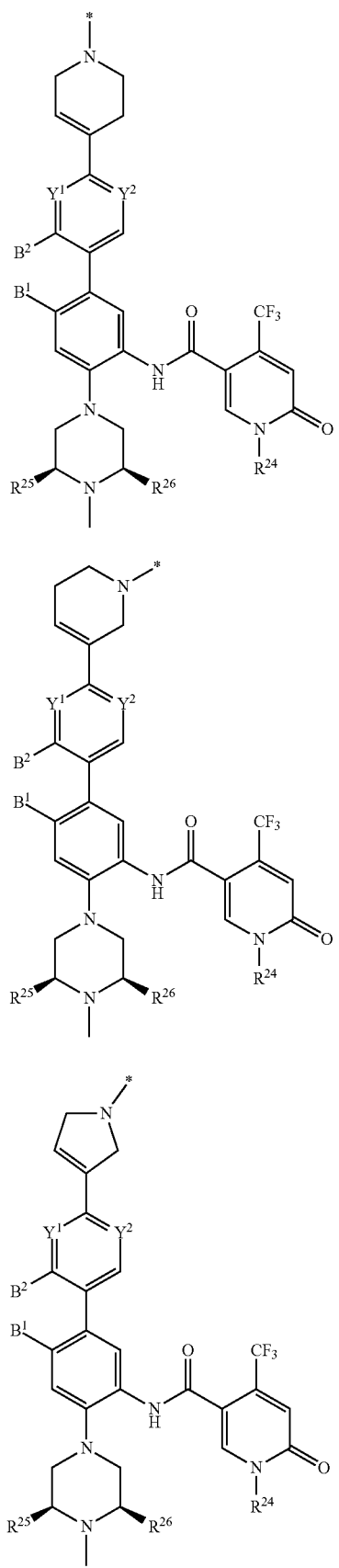
FORMULA 1J
FORMULA 1K
-continued
FORMULA 1L
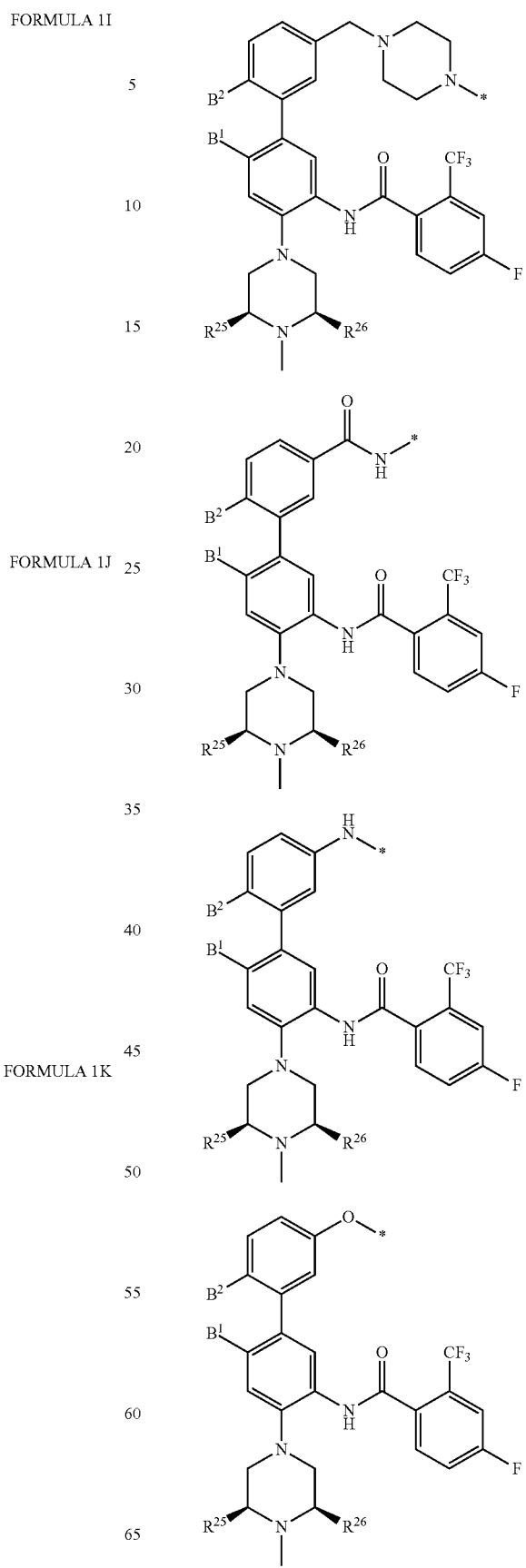
FORMULA 1M
FORMULA 1N
FORMULA 1O 23
-continued
FORMULA 1P
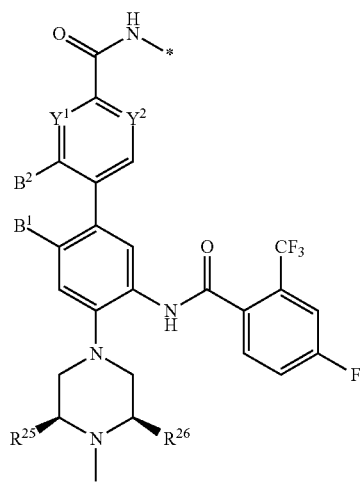
FORMULA 1Q
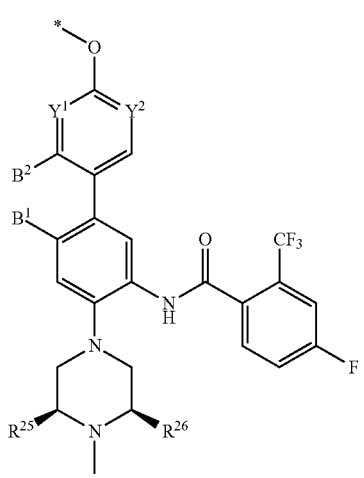
FORMULA 1R
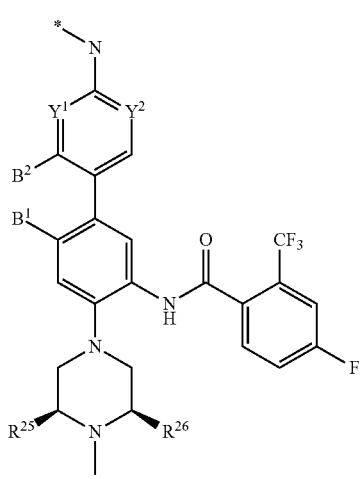
24
-continued
FORMULA 1S
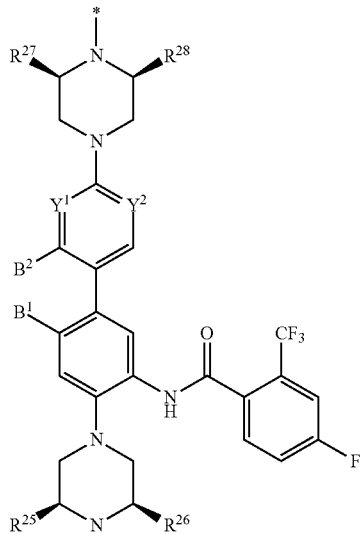
FORMULA 1T
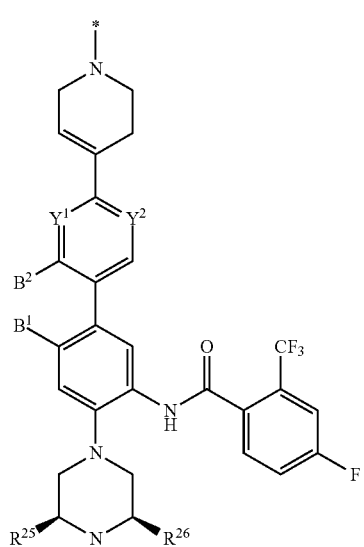
FORMULA 1U
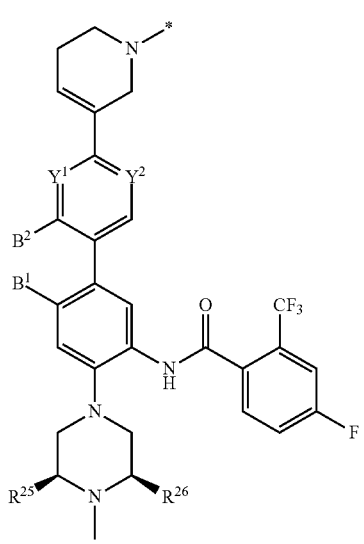

FORMULA 1V
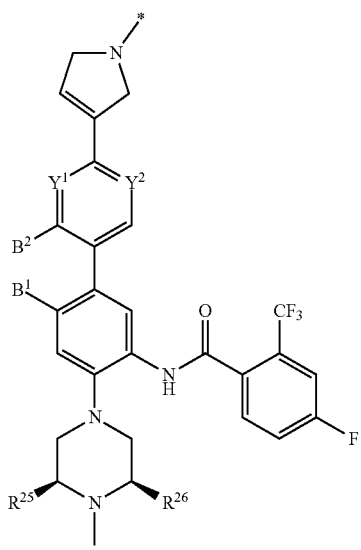
FORMULA 1W
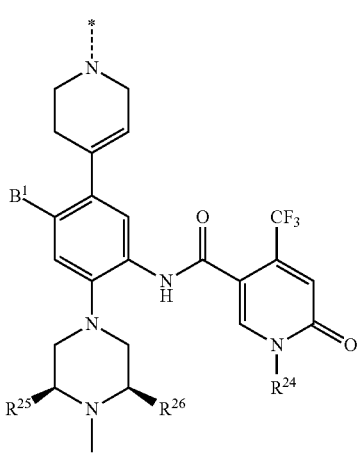
FORMULA 1X
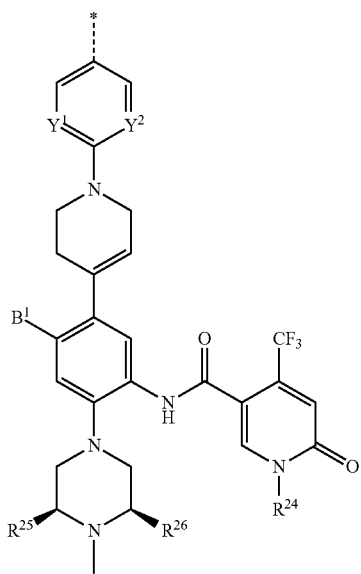
FORMULA 1Y
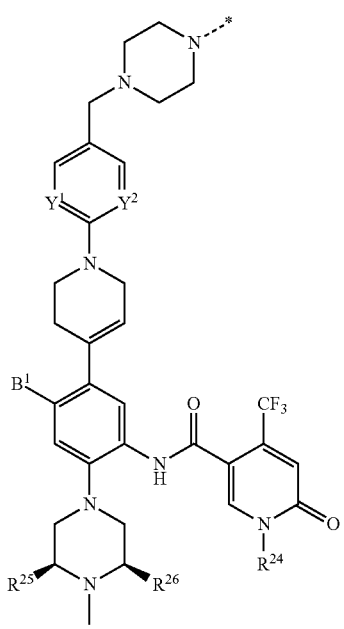
FORMULA 1Z FORMULA 1AA
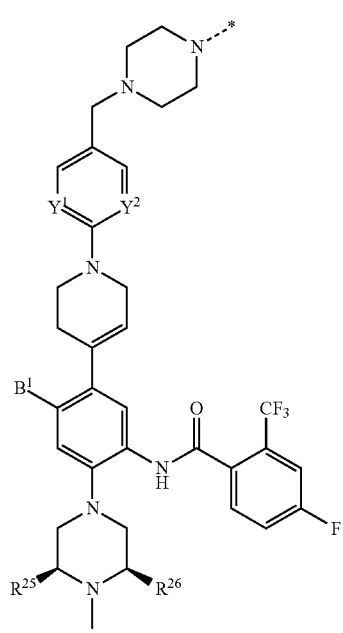
FORMULA 1AB
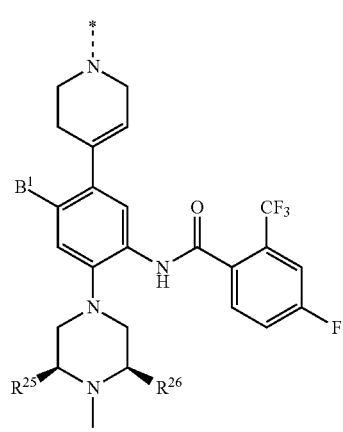
FORMULA 1AC

FORMULA 1AD
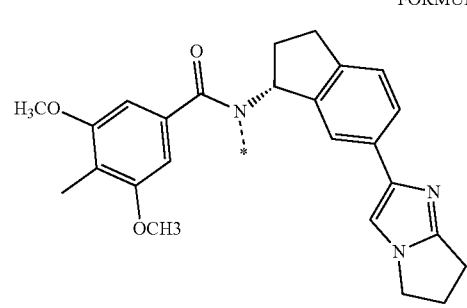
FORMULA 1AE
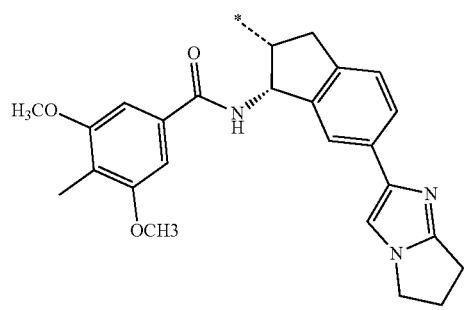
FORMULA 1AF
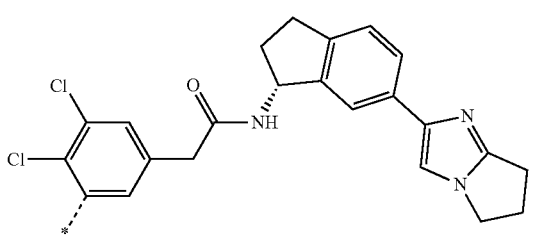
FORMULA 1AG
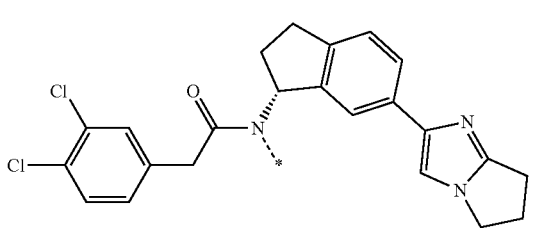
FORMULA 1AH
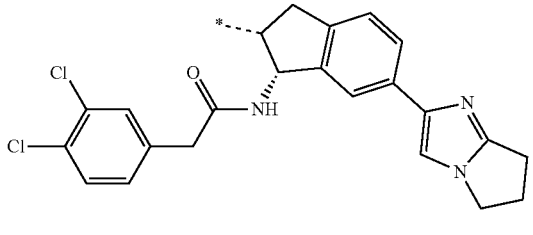
FORMULA 1AI
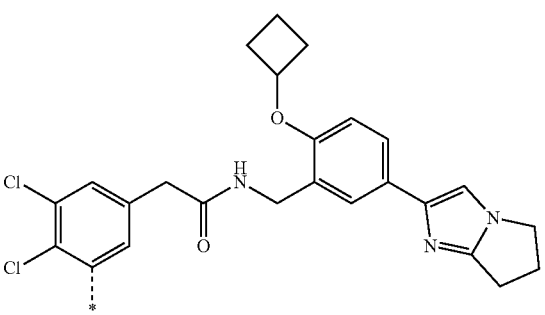

FORMULA 1AJ

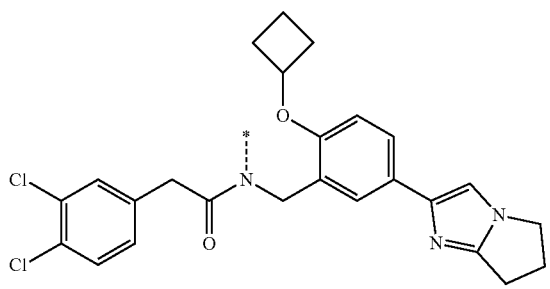

FORMULA 1AK

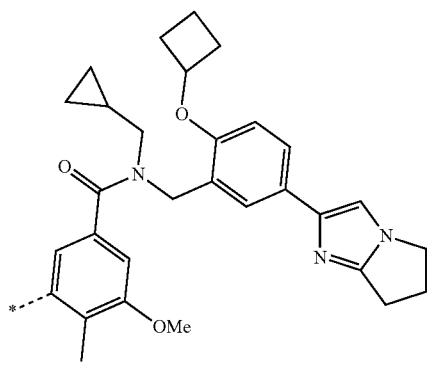

FORMULA 1AL

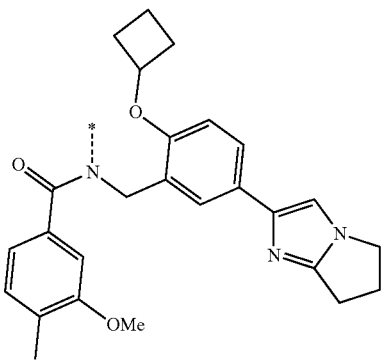

FORMULA 1AM

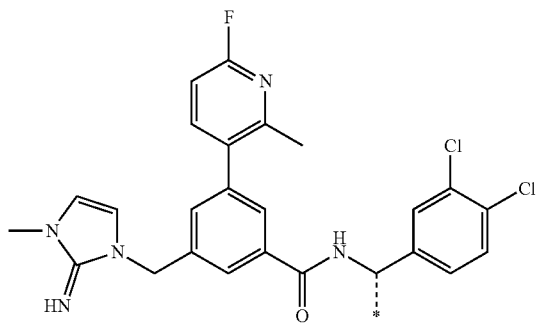

FORMULA 1AN

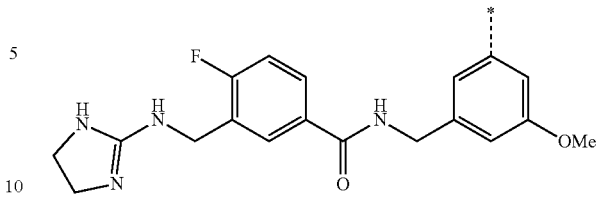

*: Connect to "Linker".
$R^{24}$, $R^{25}$, $R^{26}$, $R^{27}$, and $R^{28}$ are independently selected from H and $CH_3$.
$B^1$ and $B^2$ are independently selected from H and F.
$Y^1$ and $Y^2$ are independently selected from CH and N.
The WDR5 ligand can be bound to WDR5 and/or WDR5 mutant proteins.

Degradation/Disruption Tags

Degradation/Disruption Tags (EL) include but are not limited to:

FORMULA 4A

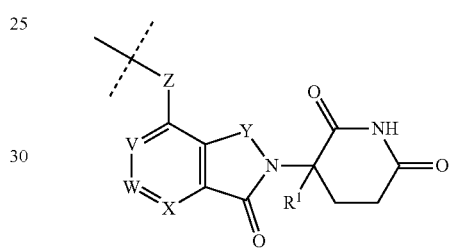

FORMULA 4B

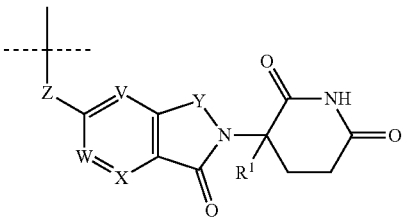

FORMULA 4C

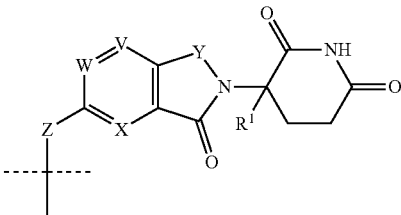

FORMULA 4D

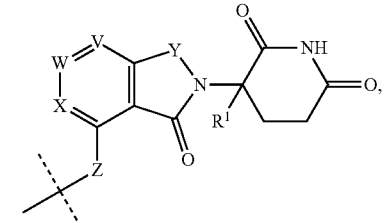

wherein
V, W, and X are independently selected from $CR^2$ and N;
Y is selected from CO, $CR^3R^4$, and N=N;
Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH=CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In an embodiment, the compounds of Formulas 4A-4D, may include the following:

FORMULA 4A

FORMULA 4B

FORMULA 4C

FORMULA 4D

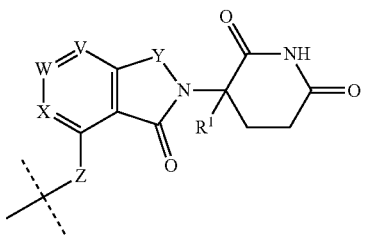

wherein
V, W, and X are independently $CR^2$ or N,
Y is CO or $CH_2$,
Z is $CH_2$, NH, or O,
$R^1$ is hydrogen, methyl, or fluoro, and
$R^2$ is hydrogen, halogen, or $C_1$-$C_5$ alkyl.

FORMULA 4E

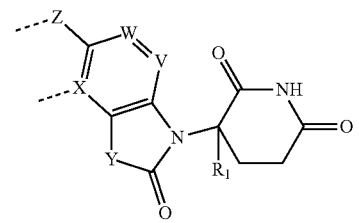

FORMULA 4F

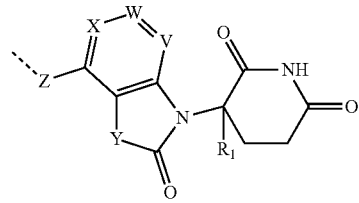

FORMULA 4G

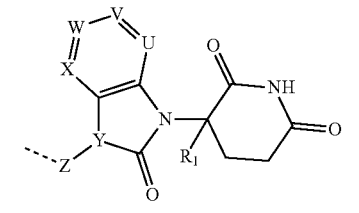

FORMULA 4H

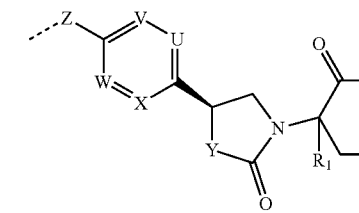

FORMULA 4I

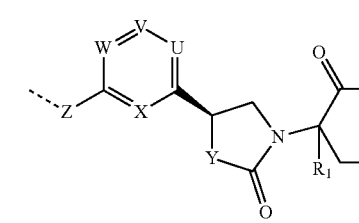

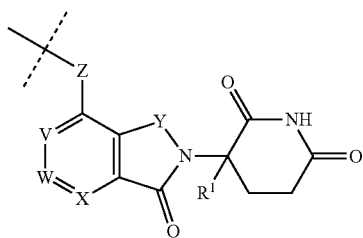

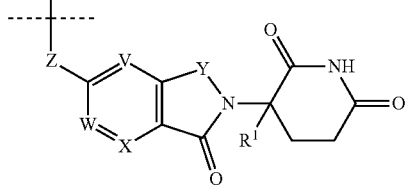

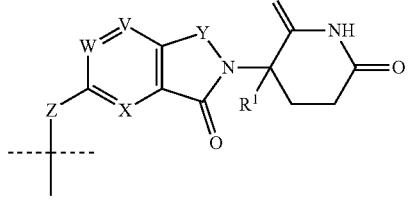

wherein
- U, V, W, and X are independently selected from $CR^2$ and N;
- Y is selected from $CR^3R^4$, $NR^3$ and O; preferably, Y is selected from $CH_2$, NH, $NCH_3$ and O;
- Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH=CH, C≡C, NH and O;
- $R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;
- $R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and
- $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

FORMULA 5A


wherein
- $R^1$ and $R^2$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_1$-$C_8$ aminoalkyl, $C_1$-$C_8$ alkylaminoalkyl, $C_3$-$C_7$ cycloalkyl, $C_3$-$C_7$ heterocyclyl, $C_2$-$C_8$ alkenyl, or $C_2$-$C_8$ alkynyl;
- $R^3$ is H, $C(O)C_1$-$C_8$ alkyl, $C(O)C_1$-$C_8$ alkoxyalkyl, $C(O)C_1$-$C_8$ haloalkyl, $C(O)C_1$-$C_8$ hydroxyalkyl, $C(O)C_1$-$C_8$ aminoalkyl, $C(O)C_1$-$C_8$ alkylaminoalkyl, $C(O)C_3$-$C_7$ cycloalkyl, $C(O)C_3$-$C_7$ heterocyclyl, $C(O)C_2$-$C_8$ alkenyl, $C(O)C_2$-$C_8$ alkynyl, $C(O)OC_1$-$C_8$ alkoxyalkyl, $C(O)OC_1$-$C_8$ haloalkyl, $C(O)OC_1$-$C_8$ hydroxyalkyl, $C(O)OC_1$-$C_8$ aminoalkyl, $C(O)OC_1$-$C_8$ alkylaminoalkyl, $C(O)OC_3$-$C_7$ cycloalkyl, $C(O)OC_3$-$C_7$ heterocyclyl, $C(O)OC_2$-$C_8$ alkenyl, $C(O)OC_2$-$C_8$ alkynyl, $C(O)NC_1$-$C_8$ alkoxyalkyl, $C(O)NC_1$-$C_8$ haloalkyl, $C(O)NC_1$-$C_8$ hydroxyalkyl, $C(O)NC_1$-$C_8$ aminoalkyl, $C(O)NC_1$-$C_8$ alkylaminoalkyl, $C(O)NC_3$-$C_7$ cycloalkyl, $C(O)NC_3$-$C_7$ heterocyclyl, $C(O)NC_2$-$C_8$ alkenyl, $C(O)NC_2$-$C_8$ alkynyl, $P(O)(OH)_2$, $P(O)(OC_1$-$C_8$ alkyl$)_2$, or $P(O)(OC_1$-$C_8$ aryl$)_2$.

FORMULA 5B

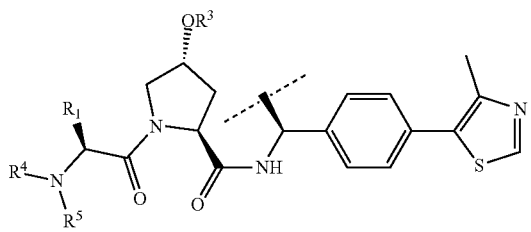

FORMULA 5C

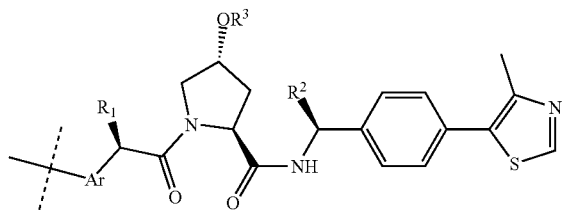

FORMULA 5D

FORMULA 5E

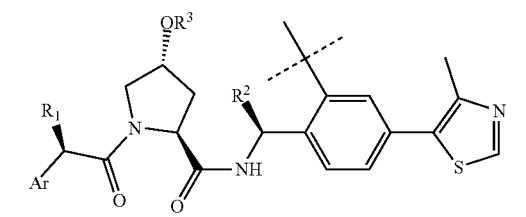

FORMULA 5F

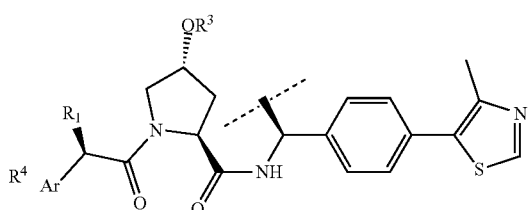

wherein
- $R^1$ and $R^2$ are independently selected from hydrogen, halogen, OH, $NH_2$, ON, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, $R^1$ is selected from iso-propyl or tert-butyl; and
- $R^2$ is selected from hydrogen or methyl).

R³ is hydrogen, optionally substituted C(O)C₁-C₈ alkyl, optionally substituted C(O)C₁-C₈alkoxyC₁-C₈alkyl, optionally substituted C(O)C₁-C₈ haloalkyl, optionally substituted C(O)C₁-C₈ hydroxyalkyl, optionally substituted C(O)C₁-C₈ aminoalkyl, optionally substituted C(O)C₁-C₈alkylaminoC₁-C₈alkyl, optionally substituted C(O)C₃-C₇ cycloalkyl, optionally substituted C(O)(3-7 membered heterocyclyl), optionally substituted C(O)C₂-C₈ alkenyl, optionally substituted C(O)C₂-C₈ alkynyl, optionally substituted C(O)OC₁-C₈alkoxyC₁-C₈alkyl, optionally substituted C(O)OC₁-C₈ haloalkyl, optionally substituted C(O)OC₁-C₈ hydroxyalkyl, optionally substituted C(O)OC₁-C₈ aminoalkyl, optionally substituted C(O)OC₁-C₈alkylaminoC₁-C₈alkyl, optionally substituted C(O)OC₃-C₇ cycloalkyl, optionally substituted C(O)O(3-7 membered heterocyclyl), optionally substituted C(O)OC₂-C₈ alkenyl, optionally substituted C(O)OC₂-C₈ alkynyl, optionally substituted C(O)NC₁-C₈alkoxyC₁-C₈alkyl, optionally substituted C(O)NC₁-C₈ haloalkyl, optionally substituted C(O)NC₁-C₈ hydroxyalkyl, optionally substituted C(O)NC₁-C₈ aminoalkyl, optionally substituted C(O)NC₁-C₈alkylaminoC₁-C₈alkyl, optionally substituted C(O)NC₃-C₇ cycloalkyl, optionally substituted C(O)N(3-7 membered heterocyclyl), optionally substituted C(O)NC₂-C₈ alkenyl, optionally substituted C(O)NC₂-C₈ alkynyl, optionally substituted P(O)(OH)₂, optionally substituted P(O)(OC₁-C₈ alkyl)₂, and optionally substituted P(O)(OC₁-C₈ aryl)₂; and R⁴ and R⁵ are independently selected from hydrogen, COR⁶, CO₂R⁶, CONR⁶R⁷, SOR⁶, SO₂R⁶, SO₂NR⁶R⁷, optionally substituted C₁-C₈ alkyl, optionally substituted C₁-C₈alkoxyC₁-C₈alkyl, optionally substituted C₁-C₈alkylaminoC₁-C₈alkyl, optionally substituted 3-8 membered cycloalkyl, optionally substituted 3-8 membered heterocyclyl, optionally substituted aryl, and optionally substituted heteroaryl, wherein R⁶ and R⁷ are independently selected from hydrogen, optionally substituted C₁-C₈ alkyl, optionally substituted C₁-C₈ alkoxy, optionally substituted C₁-C₈alkoxyC₁-C₈alkyl, optionally substituted C₁-C₈alkylaminoC₁-C₈alkyl, optionally substituted 3-8 membered cycloalkyl, optionally substituted 3-8 membered heterocyclyl, optionally substituted aryl, and optionally substituted heteroaryl, or R⁴ and R⁵; R⁶ and R⁷ together with the atom to which they are connected form a 4-8 membered cycloalkyl or heterocyclyl ring;

Ar is selected from aryl and heteroaryl, each of which is optionally substituted with one or more substituents independently selected from F, Cl, CN, NO₂, OR⁸, NR⁸R⁹, COR⁸, CO₂R⁸, CONR⁸R⁹, SOR⁸, SO₂R⁸, SO₂NR⁹R¹⁰, NR⁹COR¹⁰, NR⁸C(O)NR⁹R¹⁰, NR⁹SOR¹⁰, NR⁹SO₂R¹⁰, optionally substituted C₁-C₆ alkyl, optionally substituted C₁-C₆ alkoxyalkyl, optionally substituted C₁-C₆ haloalkyl, optionally substituted C₁-C₆ hydroxyalkyl, optionally substituted C₁-C₆alkylaminoC₁-C₆alkyl, optionally substituted C₃-C₇ cycloalkyl, optionally substituted 3-7 membered heterocyclyl, optionally substituted C₂-C₆ alkenyl, optionally substituted C₂-C₆ alkynyl, optionally substituted aryl, and optionally substituted C₄-C₅ heteroaryl, wherein R⁸, R⁹, and R¹⁰ are independently selected from null, hydrogen, optionally substituted C₁-C₆ alkyl, optionally substituted C₂-C₆ alkenyl, optionally substituted C₂-C₆ alkynyl, optionally substituted C₃-C₇ cycloalkyl, optionally substituted 3-7 membered heterocyclyl, optionally substituted aryl, and optionally substituted heteroaryl, or R⁸ and R⁹; R⁹ and R¹⁰ together with the atom to which they are connected form a 4-8 membered cycloalkyl or heterocyclyl ring.

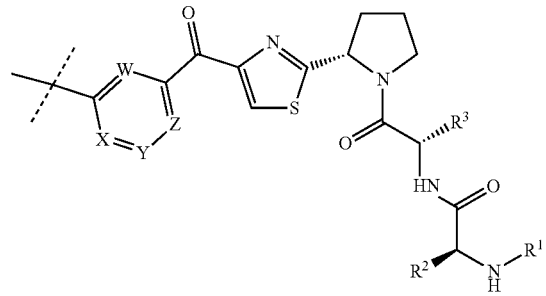

FORMULA 6A wherein

R¹, R², R³, and R⁴ are independently hydrogen, C₁-C₈ alkyl, C₁-C₈ alkoxyalkyl, C₁-C₈ haloalkyl, C₁-C₈ hydroxyalkyl, C₃-C₇ cycloalkyl, C₃-C₇ heterocyclyl, C₂-C₈ alkenyl, or C₂-C₈ alkynyl, and V, W, X, and Z are independently CR⁴ or N.

And

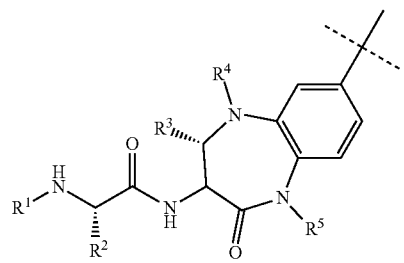

FORMULA 6B wherein

R¹, R², and R³ are independently selected from hydrogen, halogene, optionally substituted C₁-C₈ alkyl, optionally substituted C₁-C₈alkoxyC₁-C₈alkyl, optionally substituted C₁-C₈ haloalkyl, optionally substituted C₁-C₈ hydroxyalkyl, optionally substituted C₃-C₇ cycloalkyl, optionally substituted 3-7 membered heterocyclyl, optionally substituted C₂-C₈ alkenyl, and optionally substituted C₂-C₈ alkynyl;

R⁴ and R⁵ are independently selected from hydrogen, COR⁶, CO₂R⁶, CONR⁶R⁷, SOR⁶, SO₂R⁶, SO₂NR⁶R⁷, optionally substituted C₁-C₈ alkyl, optionally substituted C₁-C₈alkoxyC₁-C₈alkyl, optionally substituted C₁-C₈alkylaminoC₁-C₈alkyl, optionally substituted aryl-C₁-C₈alkyl, optionally substituted 3-8 membered cycloalkyl, optionally substituted 3-8 membered heterocyclyl, optionally substituted aryl, and optionally substituted heteroaryl, wherein R⁶ and R⁷ are independently selected from hydrogen, optionally substituted C₁-C₈ alkyl, optionally substituted C₁-C₈alkoxyC₁-C₈alkyl, optionally substituted C₁-C₈alkylaminoC₁-C₈alkyl, optionally substituted 3-8 membered cycloalkyl, optionally substituted 3-8 membered heterocyclyl, optionally substituted aryl, and optionally substituted heteroaryl, or R⁶ and R⁷ together with the atom to which they are connected form a 4-8 membered cycloalkyl or heterocyclyl ring.

In some aspects, the degradation/disruption tag can be, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Fliroyuki Suda et al., 1976), MV1 (Varfolomeev et al., 2007), LCL161 (Weisberg et al., 2010), FK506 (Liu et al., 1991) rapamycin (Fan et al., 2017; Rodrik-Outmezguine et al., 2016) and/or analogs thereof.

In some aspects, the degradation/disruption tag can be, e.g., one of the following structures:

FORMULA 7A

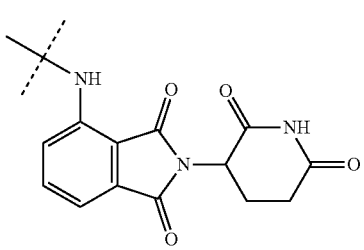

FORMULA 7B

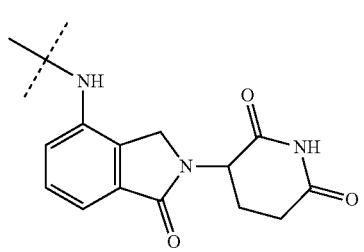

FORMULA 7C

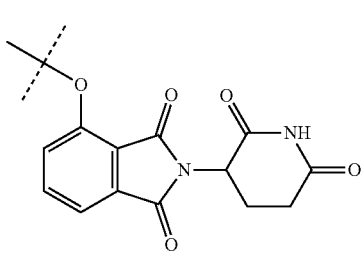

FORMULA 7D

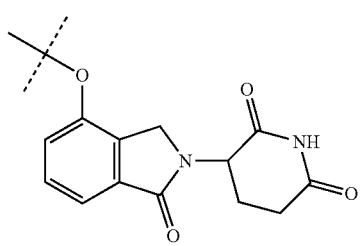

FORMULA 7E

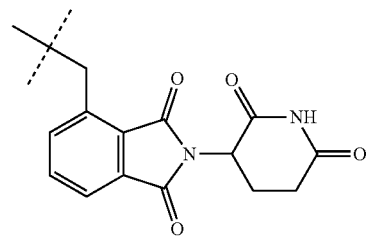

FORMULA 7F

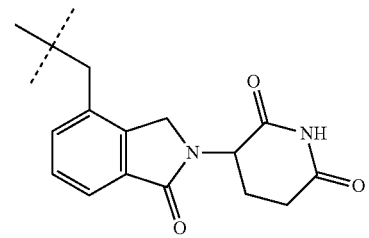

FORMULA 7G

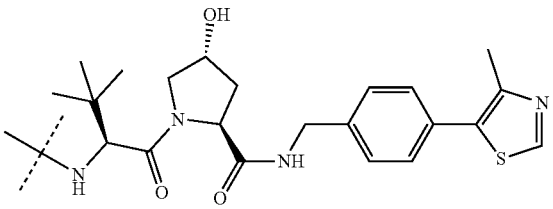

FORMULA 7H

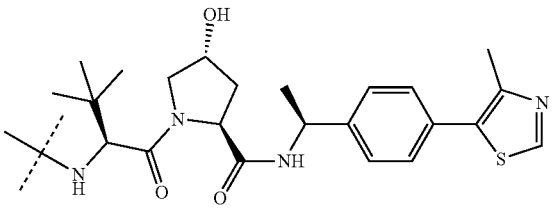

FORMULA 7I

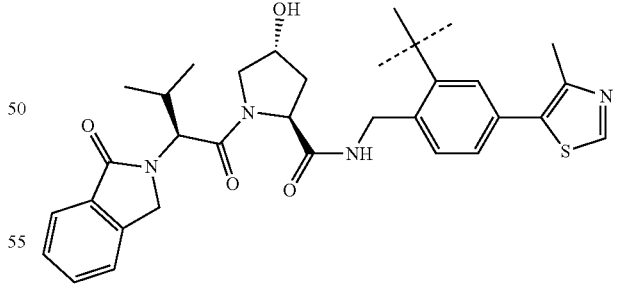

FORMULA 7J

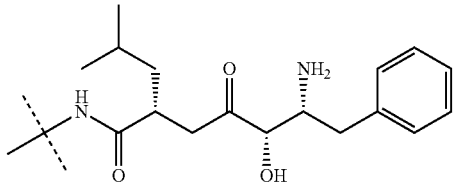

FORMULA 7K
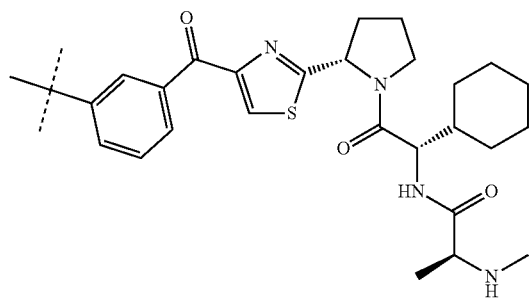
FORMULA 7L
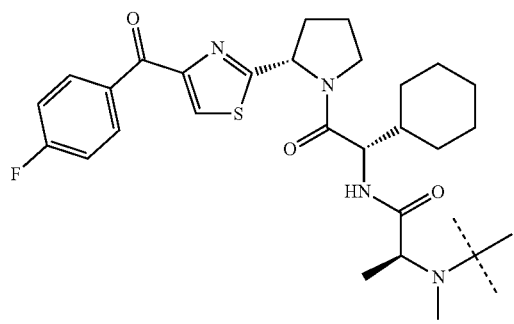
FORMULA 7M
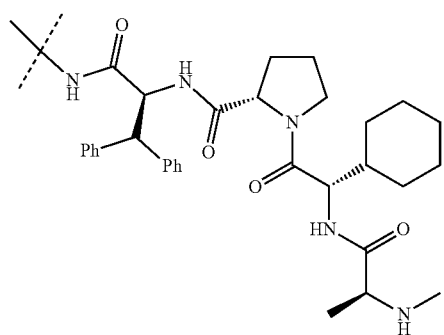
FORMULA 7N
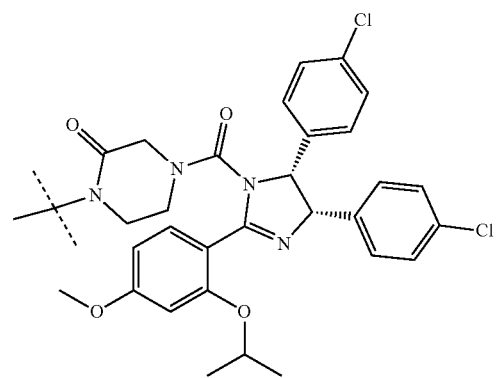
FORMULA 7O
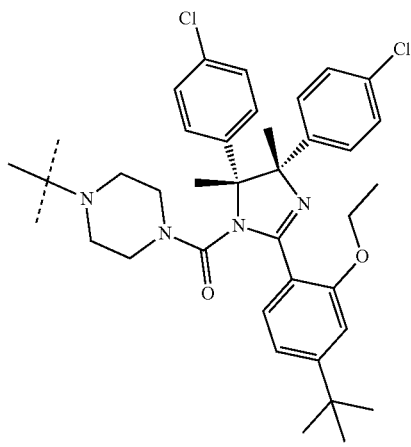
FORMULA 7P
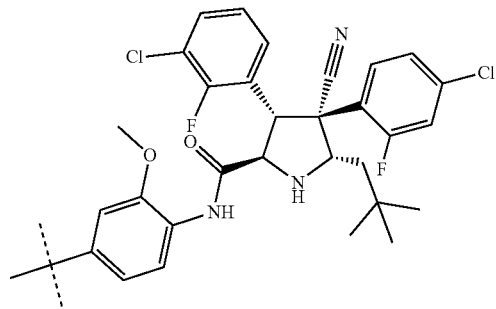
FORMULA 7Q
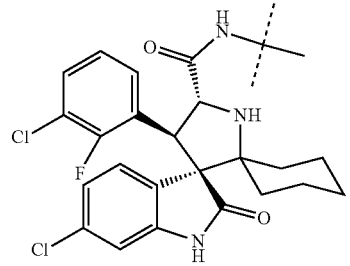
FORMULA 7R
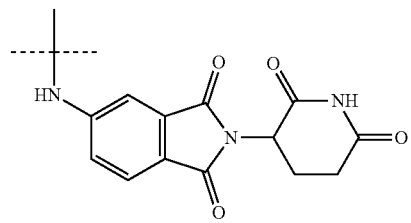
FORMULA 7S
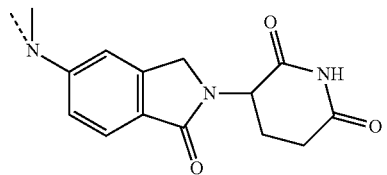

FORMULA 7T
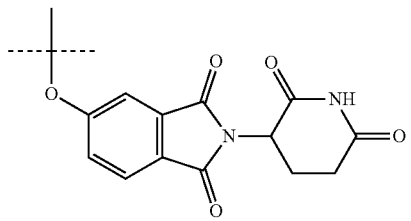
FORMULA 7U
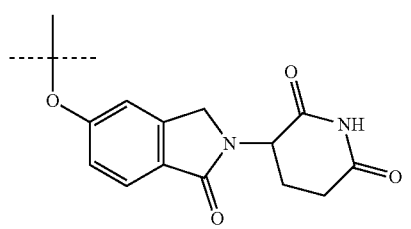
FORMULA 7V
FORMULA 7W
FORMULA 7X
FORMULA 7Y
FORMULA 7Z
FORMULA 7AA
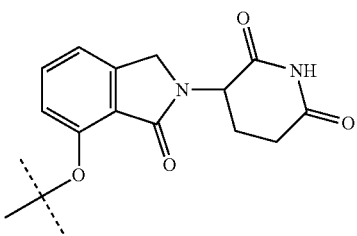
FORMULA 7AB
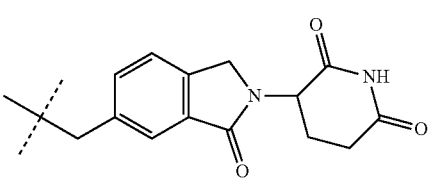
FORMULA 7AC
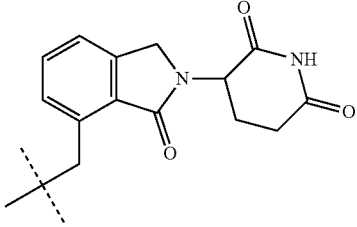
FORMULA 7AD
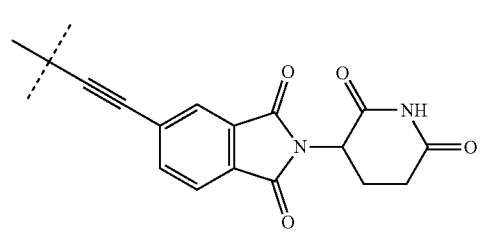
FORMULA 7AE
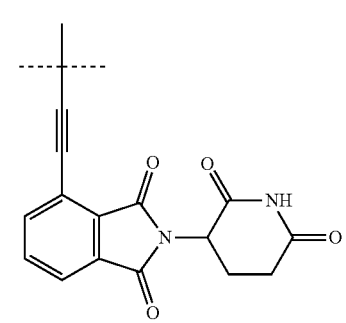
FORMULA 7AF
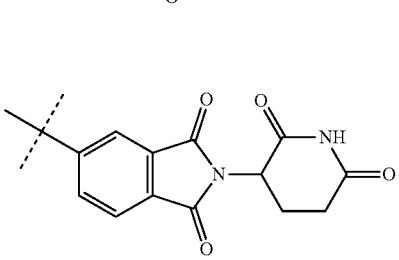

FORMULA 7AG
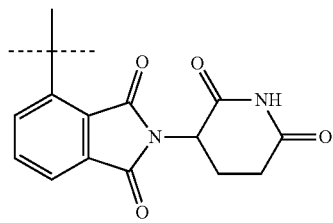
FORMULA 7AH
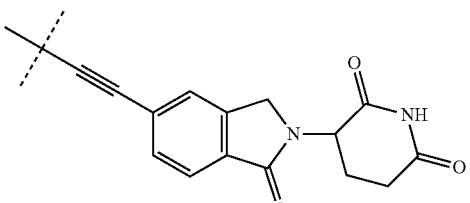
FORMULA 7AI
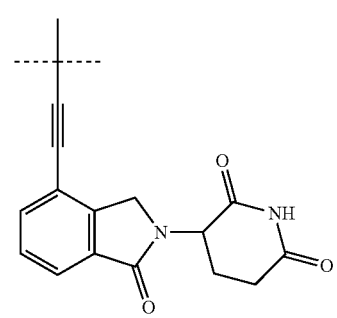
FORMULA 7AJ
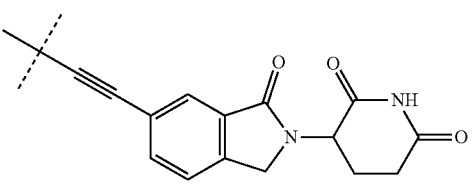
FORMULA 7AK
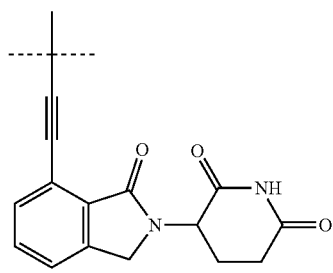
FORMULA 7AL
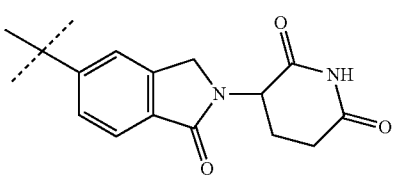
FORMULA 7AM
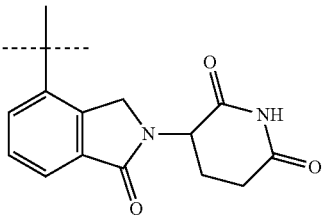
FORMULA 7AN
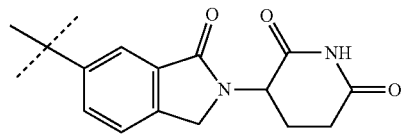
FORMULA 7AO
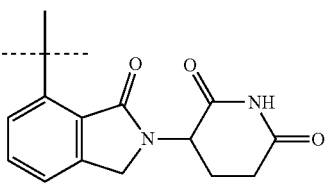
FORMULA 7AP
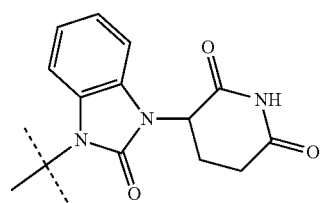
FORMULA 7AQ
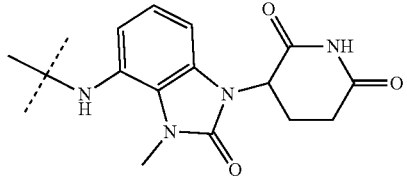
FORMULA 7AR
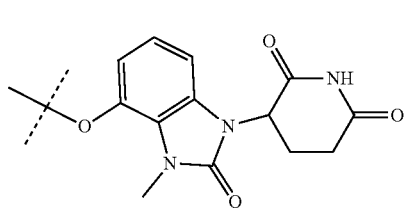
FORMULA 7AS
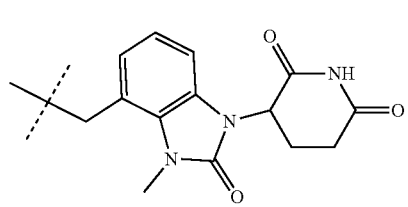
FORMULA 7AT
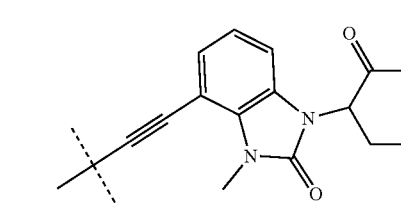

FORMULA 7AU
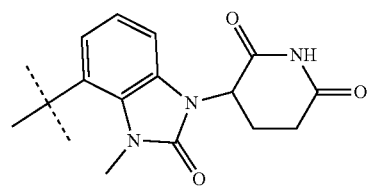
FORMULA 7AV
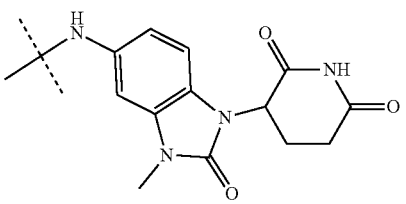
FORMULA 7AW
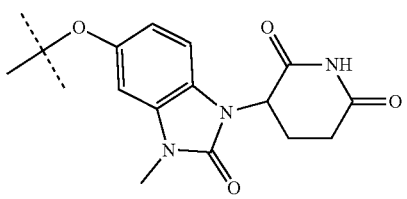
FORMULA 7AX
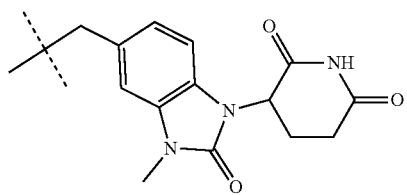
FORMULA 7AY
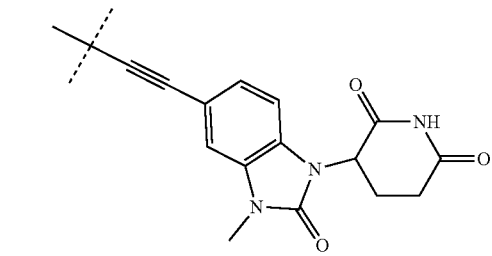
FORMULA 7AZ
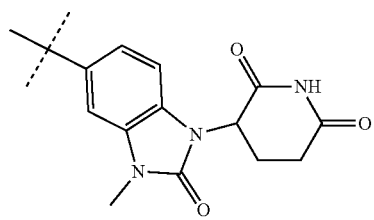
FORMULA 7BA
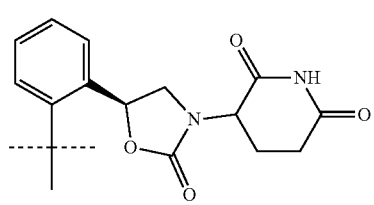
FORMULA 7BB
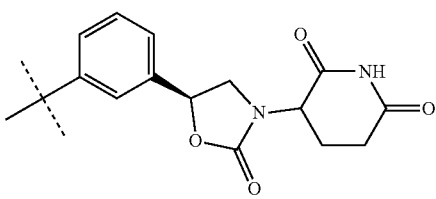
FORMULA 7BC
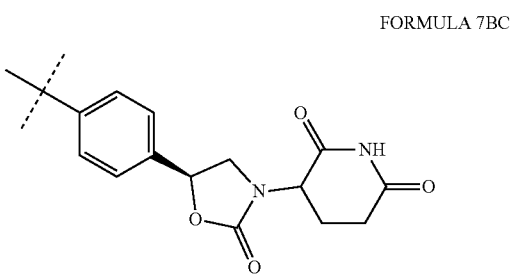
FORMULA 7BD
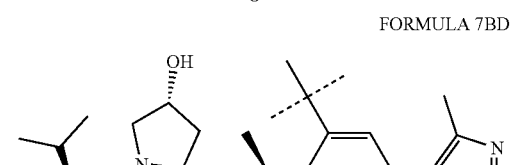
FORMULA 7BE
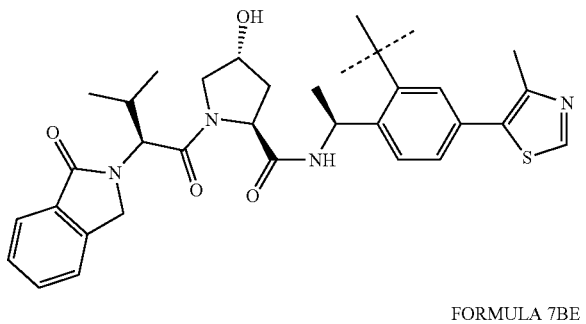
FORMULA 7BF
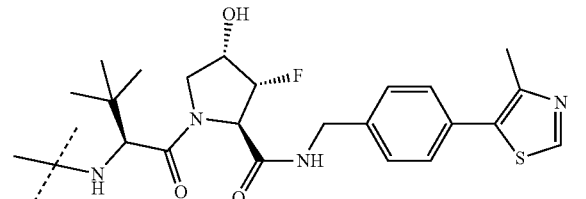
FORMULA 7BG
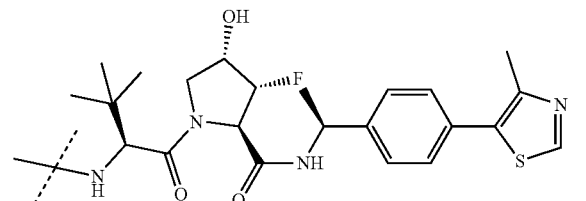

47
-continued
FORMULA 7BH
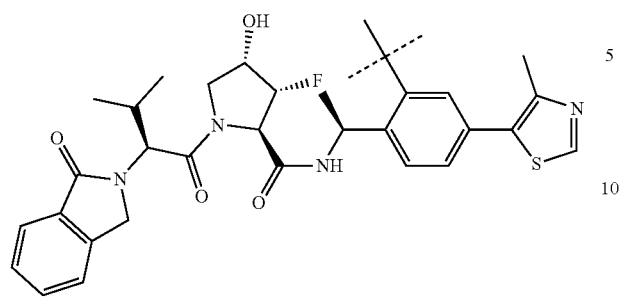
FORMULA 7BI

FORMULA 7BJ

FORMULA 7BK
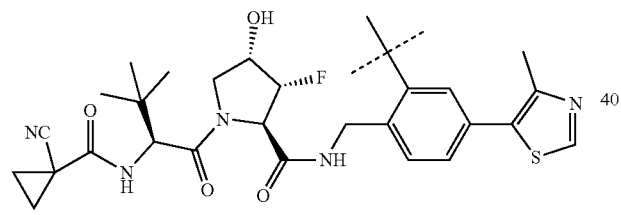
FORMULA 7BL
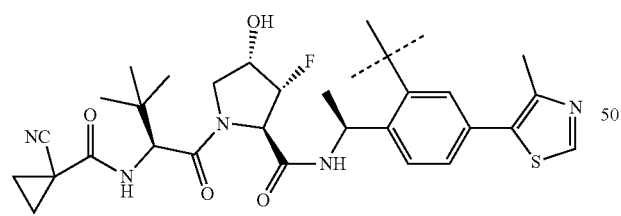
FORMULA 7BM
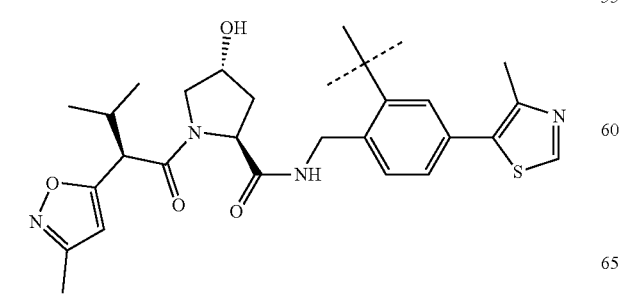
48
-continued
FORMULA 7BN
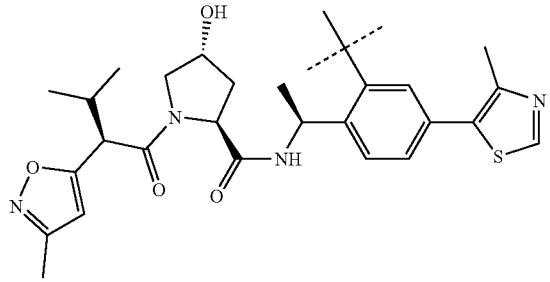
FORMULA 7BO
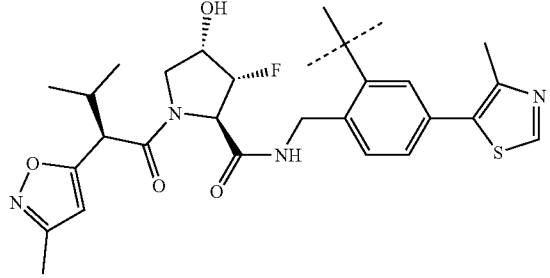
FORMULA 7BP
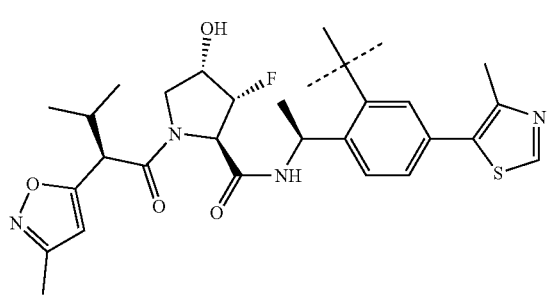
FORMULA 7BQ
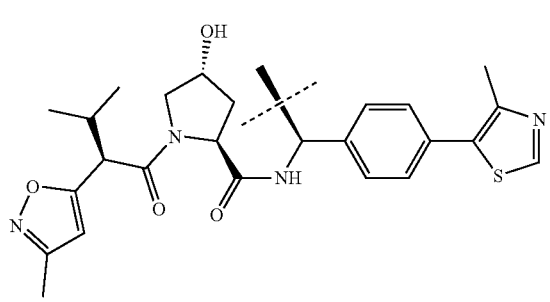
FORMULA 7BR
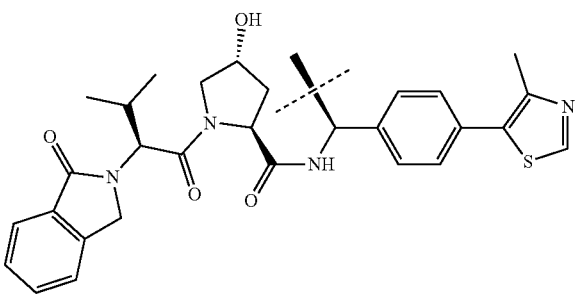

FORMULA 7BS
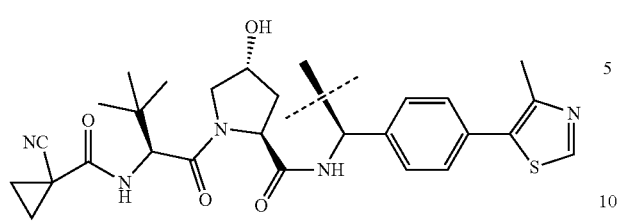
FORMULA 7BT
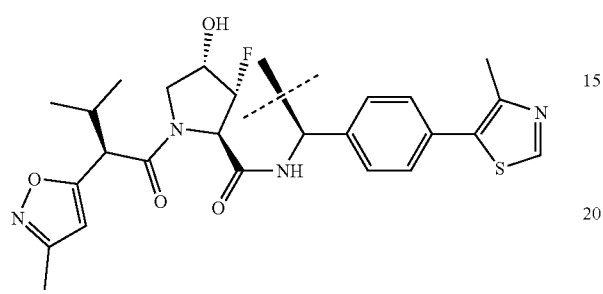
FORMULA 7BU
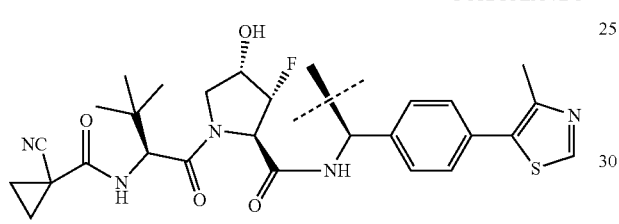
FORMULA 7BV
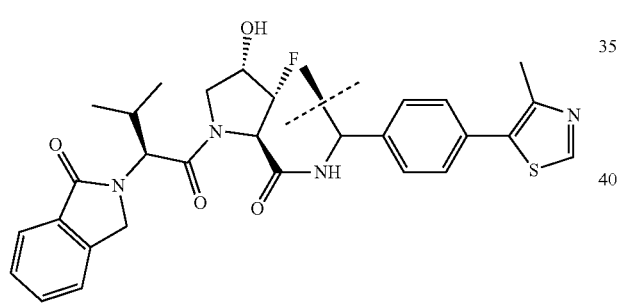
FORMULA 7BW
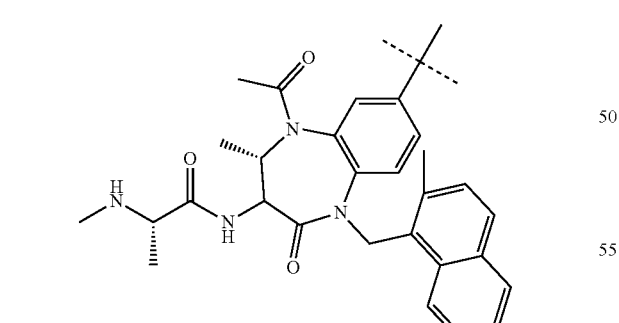
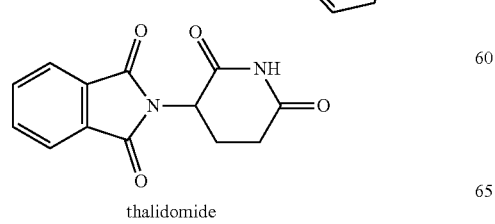
thalidomide
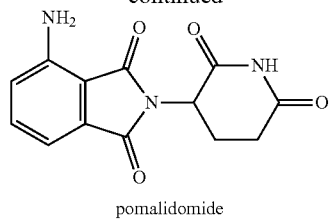
pomalidomide
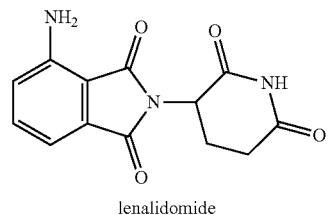
lenalidomide
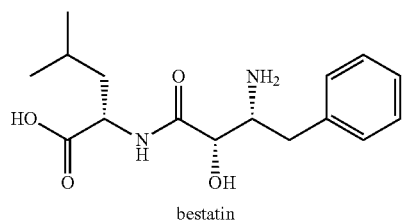
bestatin
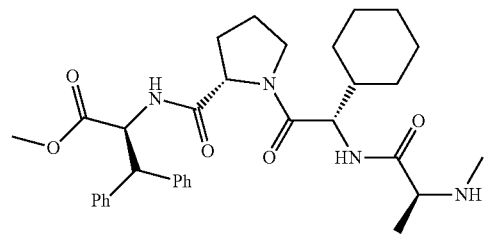
MV1
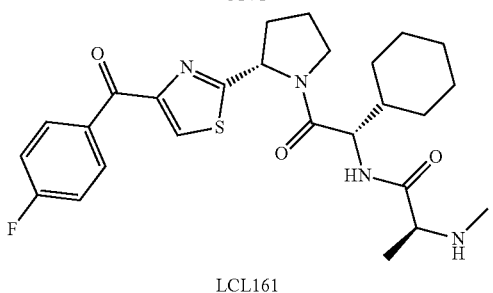
LCL161
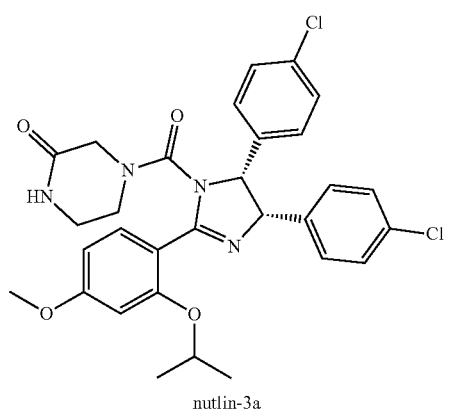
nutlin-3a -continued
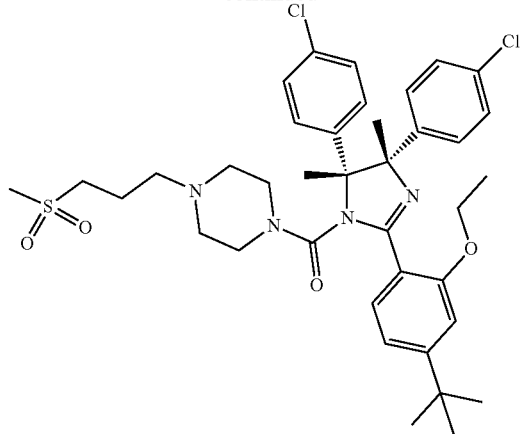
RG7112
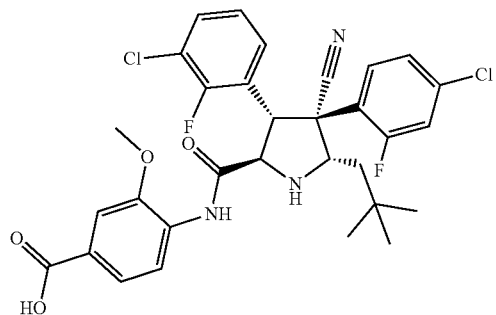
RG7338
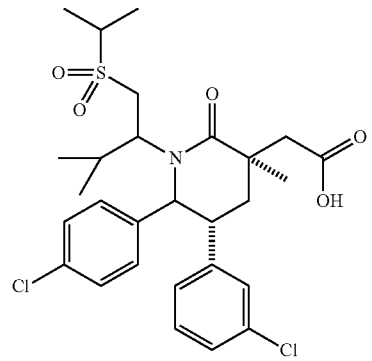
AMG232
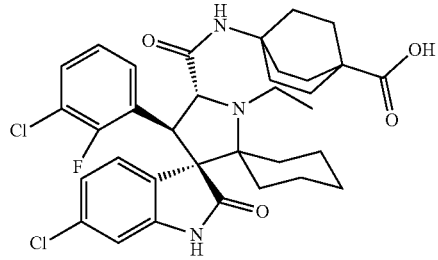
AA-115
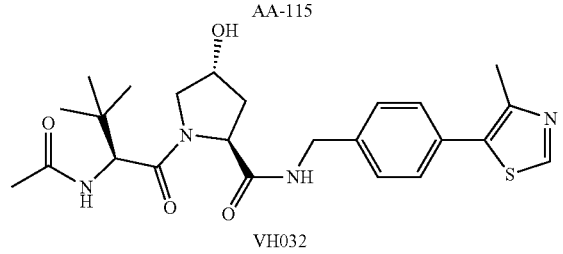
VH032
-continued
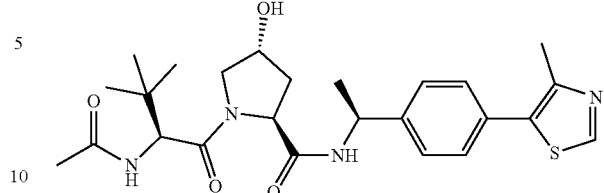
Compound W1
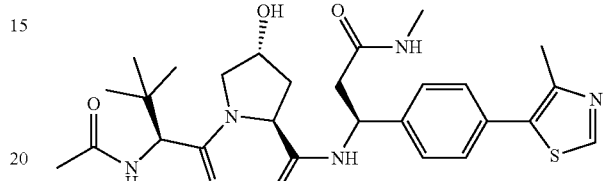
Wompound W2
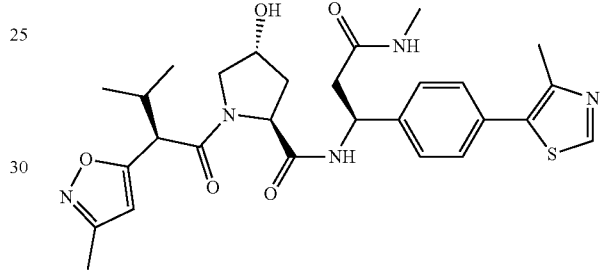
Compound W3
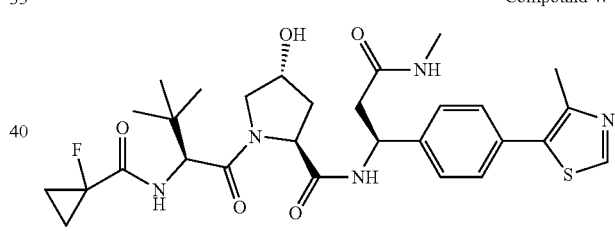
Compound W4
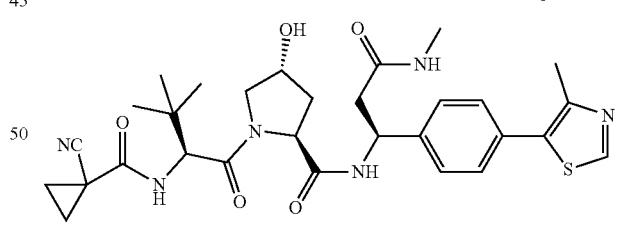
Compound W5
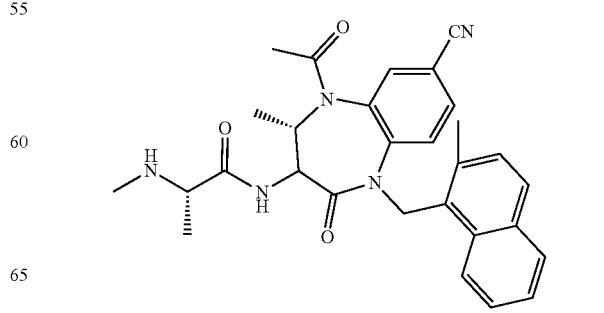
Compound W6

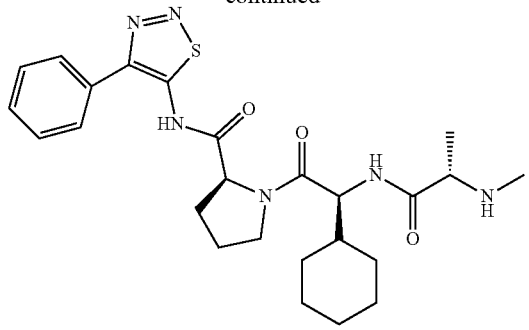

GDC-0152

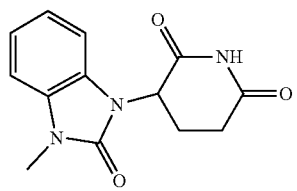

Compound W7

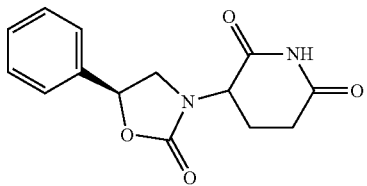

Compound W8

In some aspects, the degradation/disruption tag can bind to a ubiquitin ligase (e.g., an E3 ligase such as a cereblon E3 ligase, a VHL E3 ligase, a MDM2 ligase, a TRIM21 ligase, a TRIM24 ligase, a KEAP1 ligase and/or an IAP ligase) and/or serve as a hydrophobic group or a tag group that leads to WDR5 protein misfolding.

Linkers

In all of the above-described compounds, the WDR5 ligand is conjugated to the degradation/disruption tag through a linker. The linker can include, for example, acyclic or cyclic saturated or unsaturated carbon, ethylene glycol, amide, amino, ether, urea, carbamate, aromatic, heteroaromatic, heterocyclic and/or carbonyl containing groups with different lengths.

In some aspects, the linker can be a moiety of:

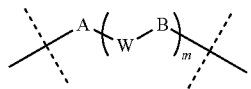

FORMULA 8 wherein

A, W and B, at each occurrence, are independently selected from null, or bivalent moiety selected from R'-R", R'COR", R'CO$_2$R", R'C(O)N(R$^1$)R", R'C(S)N(R$^1$)R", R'OR", R'OC(O)R", R'OC(O)OR", R'OCON(R$^1$)R", R'SR", R'SOR", R'SO$_2$R", R'SO$_2$N(R$^1$)R", R'N(R$^1$)R", R'NR$^1$COR", R'NR$^1$C(O)OR", R'NR$^1$CON(R$^2$)R", R'NR$^1$C(S)R", R'NR$^2$S(O)R", R'NR$^1$S(O)$_2$R", and R'NR$^1$S(O)$_2$N(R$^2$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^1$ and R$^2$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^1$ and R$^2$, R' and R$^1$, R' and R$^2$, R" and R$^1$, R" and R$^2$ together with the atom to which they are connected form a 3-20 membered cycloalkyl or 4-20 membered heterocyclyl ring; and m is 0 to 15.

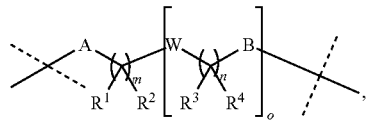

FORMULA 8A wherein

R$^1$, R$^2$, R$^3$ and R$^4$, at each occurrence, are independently selected from hydrogen, halogen, hydroxyl, amino, cyano, nitro, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$ alkylamino, and optionally substituted C$_1$-C$_8$ alkylaminoC$_1$-C$_8$ alkyl, optionally substituted 3-10 membered carbocyclyl, optionally substituted 3-8 membered cycloalkoxy, optionally substituted 3-10 membered carbocyclylamino, optionally substituted 4-8 membered membered heterocyclyl, optionally substituted aryl, and optionally substituted heteroaryl, or $R^1$ and $R^2$, $R^3$ and $R^4$ together with the atom to which they are connected form a 3-20 membered cycloalkyl or 4-20 membered heterocyclyl ring;

A, W and B, at each occurrence, are independently selected from null, or bivalent moiety selected from R'-R", R'COR", R'CO$_2$R", R'C(O)N(R$^5$)R", R'C(S)N(R$^5$)R", R'OR", R'OC(O)R", R'OC(O)OR", R'OCONR$^5$R", R'SR", R'SOR", R'SO$_2$R", R'SO$_2$N(R$^5$)R", R'N(R$^5$)R", R'NR$^5$COR", R'NR$^5$C(O)OR", R'NR$^5$CON(R$^6$)R", R'NR$^5$C(S)R", R'NR$^5$S(O)R", R'NR$^5$S(O)$_2$R", and R'NR$^5$S(O)$_2$N(R$^6$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

$R^5$ and $R^6$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^5$ and R$^6$, R' and R$^5$, R' and R$^6$, R" and R$^5$, R" and R$^6$ together with the atom to which they are connected form a 3-20 membered cycloalkyl or 4-20 membered heterocyclyl ring;

m is 0 to 15;

n, at each occurrence, is 0 to 15; and is 0 to 15.

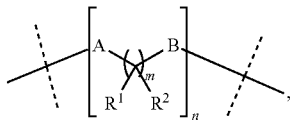

FORMULA 8B wherein $R^1$ and $R^2$, at each occurrence, are independently selected from hydrogen, halogen, hydroxyl, amino, cyano, nitro, and optionally substituted C$_1$-C$_8$ alkyl, optionally substituted C$_1$-C$_8$ alkoxy, optionally substituted C$_1$-C$_8$ alkoxy C$_1$-C$_8$ alkyl, optionally substituted C$_1$-C$_8$ haloalkyl, optionally substituted C$_1$-C$_8$ hydroxyalkyl, optionally substituted C$_1$-C$_8$ alkylamino, C$_1$-C$_8$alkylaminoC$_1$-C$_8$alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'-R", R'COR", R'CO$_2$R", R'C(O)N(R$^3$)R", R'C(S)N(R$^3$)R", R'OR", R'OC(O)R", R'OC(O)OR", R'OCON(R$^3$)R", R'SR", R'SOR", R'SO$_2$R", R'SO$_2$N(R$^3$)R", R'N(R$^3$)R", R'NR$^3$COR", R'NR$^3$C(O)OR", R'NR$^3$CON(R$^4$)R', R'NR$^3$C(S)R", R'NR$^3$S(O)R", R'NR$^3$S(O)$_2$R", and R'NR$^3$S(O)$_2$N(R$^4$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

$R^3$ and $R^4$ are independently selected from hydrogen, optionally substituted C$_1$-C$_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

m, at each occurrence, is 0 to 15; and n is 0 to 15.

FORMULA 8C

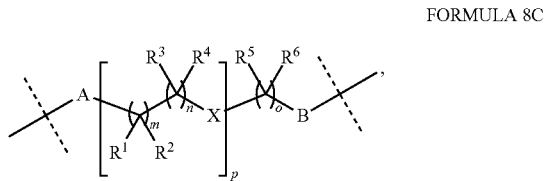

wherein

X is selected from O, NH, and $NR^7$;

$R^1$, $R^2$, $R^3$, $R^4$, $R^5$, and $R^6$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'-R", R'COR", R'$CO_2$R", R'C(O)N($R^8$)R", R'C(S)N($R^8$)R", R'OR", R'OC(O)R", R'OC(O)OR", R'OCON($R^8$)R", R'SR", R'SOR", R'$SO_2$R", R'$SO_2$N($R^8$)R", R'N($R^8$)R", R'$NR^8$COR", R'$NR^8$C(O)OR", R'$NR^8$CON($R^9$)R", R'$NR^8$C(S)R", R'$NR^8$S(O)R", R'$NR^8$S(O)$_2$R", and R'$NR^8$S(O)$_2$N($R^9$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^7$, $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^8$ and $R^9$, R' and $R^8$, R' and $R^9$, R" and $R^8$, R" and $R^9$ together with the atom to which they are connected form a 3-20 membered cycloalkyl or 4-20 membered heterocyclyl ring;

m, at each occurrence, is 0 to 15;

n, at each occurrence, is 0 to 15;

is 0 to 15; and p is 0 to 15.

In some aspects of Formulae 8, 8A, 8B, and 8C, the linker moiety comprises a ring selected from the group consisting of a 3 to 13 membered ring, a 3 to 13 membered fused ring, a 3 to 13 membered bridged ring, and a 3 to 13 membered spiro ring.

In some aspects of Formulae 8, 8A, 8B, and 8C, the linker moiety comprises a ring selected from the group consisting of Formula C1, C2, C3, C4 and C5:

Formula C1

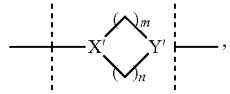

X' = N or CH
Y' = N or CH
m = 0-5
n = 0-5

Formula C2

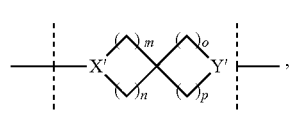

X' = N or CH
Y' = N or CH
m = 0-5
n = 0-5
o = 0-5
p = 0-5

-continued

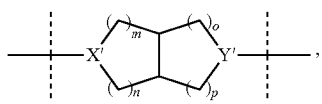

X' = N or CH
Y' = N or CH
m = 0-5
n = 0-5
o = 0-5
p = 0-5

Formula C3

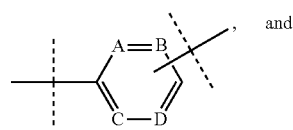, and

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N Formula C4

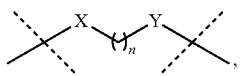

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3alkyl), O, S Formula C5

In some aspects, the linker can also be a moiety of:

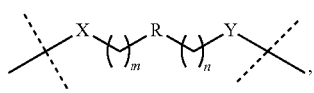

Formula A wherein X is C=O or CH$_2$,
Y is C=O or CH$_2$, and
n is 0-15;

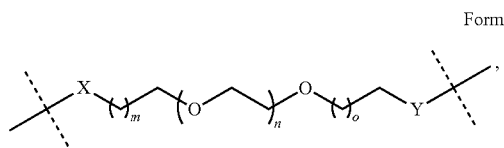

Formula B wherein X is C=O or CH$_2$,
Y is C=O or CH$_2$,
m is 0-15,
n is 0-6, and
is 0-15; or

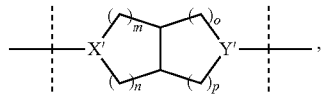

Formula C wherein
X is C=O or CH$_2$,
Y is C=O or CH$_2$,
R is —CH$_2$—, —CF$_2$—, —CH(C$_{1-3}$ alkyl)-, —C(C$_{1-3}$ alkyl)(C$_{1-3}$ alkyl)-, —CH=CH—, —C(C$_{1-3}$ alkyl)=C(C$_{1-3}$ alkyl)-, —C≡C—, —O—, —NH—, —N(C$_{1-3}$ alkyl)-, —C(O)NH—, —C(O)N(C$_{1-3}$ alkyl)-, a 3-13 membered ring, a 3-13 membered fused ring, a 3-13 membered bridged ring, and/or a 3-13 membered spiro ring,
m is 0-15, and
n is 0-15.

In some aspects of Formula C, R is a 3-13 membered ring, a 3-13 membered fused ring, a 3-13 membered bridged ring, and/or a 3-13 membered spiro ring, one or more of which can contain one or more heteroatoms.

In some aspects of Formula C, R has a structure of:

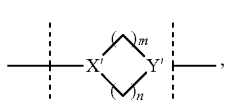

Formula C1

X' = N or CH
Y' = N or CH
m = 0-5
n = 0-5

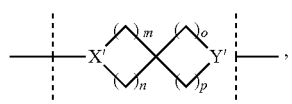

Formula C2

X' = N or CH
Y' = N or CH
m = 0-5
n = 0-5
o = 0-5
p = 0-5

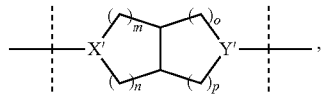

Formula C3

X' = N or CH
Y' = N or CH
m = 0-5
n = 0-5
o = 0-5
p = 0-5

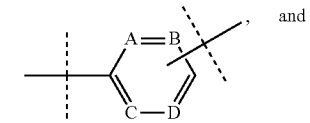, and

Formula C4

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N -continued

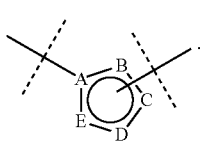
Formula C5

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3alkyl), O, S In some aspects, the bivalent compound is a compound selected from the following compounds, as identified in Table 1 below: XF048-117, XF048-118, XF048-119, XF048-120, XF048-121, XF048-122, XF048-123, XF048-124, XF048-125, XF048-126, XF048-127, XF048-128, XF048-129, XF048-130, XF048-131, XF048-132, XF048-133, XF048-134, XF048-135, XF048-136, XF048-137, XF048-138, XF048-139, XF048-140, XF048-141, XF048-142, XF048-143, XF048-144, XF048-145, XF050-166, XF050-169, XF050-165, XF050-159, XF050-160, XF050-161, XF050-162, XF050-156, XF050-164, XF050-158, XF056-23, XF056-25, XF056-26, XF056-24, XF056-32, XF056-72, XF056-38, XF056-39, XF056-104, XF056-118, XF061-111, XF067-66, XF056-124, XF056-125, XF056-126, XF056-127, XF056-128, XF056-129, XF056-130, XF056-131, XF056-132, XF056-133, XF056-134, XF056-135, XF056-136, XF056-137, XF056-138, XF056-139, XF056-140, XF056-141, XF056-142, XF056-143, XF056-144, XF056-145, XF056-146, XF056-147, XF056-148, XF056-149, XF056-150, XF056-151, XF056-152, XF056-153, XF056-157, XF056-158, XF056-159, XF056-160, XF056-161, XF056-162, XF056-163, XF056-164, XF056-165, XF056-166, XF056-167, XF056-168, XF056-169, XF056-170, XF056-171, XF056-172, XF056-173, XF056-174, XF056-175, XF056-176, XF056-177, XF056-178, XF056-179, XF056-180, XF056-181, XF056-182, XF056-183, XF056-184, XF056-185, XF056-186, XF061-104, XF067-67, XF067-68, XF067-131, XF067-133, XF067-134, XF067-140, XF067-141, XF067-142, XF067-143, XF067-144, XF067-145, XF067-146, XF067-147, XF067-148, XF067-149, XF067-150, XF067-151, XF067-152, XF067-153, XF067-154, XF067-155, XF067-156, XF067-157, XF067-158, XF067-159, XF067-160, XF067-161, XF067-162, XF067-163, XF067-164, XF067-165, XF067-166, XF067-167, XF067-168, XF067-169, XF078-1, XF078-2, XF078-3, XF078-4, XF078-5, XF078-6, XF078-7, XF078-8, XF078-9, XF078-10, XF078-11, XF078-12, XF078-13, XF078-14, XF078-15, XF078-16, XF078-17, XF078-18, XF078-19, XF078-20, XF078-21, XF078-22, XF078-23, XF078-24, XF078-25, XF078-26, XF078-27, XF078-28, XF078-29, XF078-30, XF078-31, XF078-32, XF078-33, XF078-34, XF078-35, XF078-36, XF078-37, XF078-38, XF078-39, XF078-40, XF078-41, XF078-42, XF078-43, XF078-44, XF078-45, XF078-46, XF078-47, XF078-48, XF078-49, XF078-50, XF078-51, XF078-52, XF078-53, XF078-54, XF078-55, XF078-56, XF078-57, XF078-58, XF078-61, XF078-62, XF078-63, XF078-64, XF078-65, XF078-66, XF078-67, XF078-68, XF078-69, XF078-70, XF078-71, XF078-72, XF078-73, XF078-74, XF078-75, XF078-76, XF078-77, XF078-78, XF078-79, XF078-80, XF078-81, XF078-82, XF078-83, XF078-84, XF078-85, XF078-86, XF078-87, XF078-88, XF078-89, XF078-90, XF078-99, XF078-100, XF078-101, XF078-102, XF078-103, XF078-104, XF078-105, XF078-106, XF078-107, XF078-108, XF078-109, XF078-110, XF078-111, XF078-112, XF078-113, XF078-114, XF078-115, XF078-116, XF078-117, XF078-118, XF078-119, XF078-120, XF078-121, XF078-122, XF078-123, XF078-124, XF078-125, XF078-126, XF078-127, XF078-132, XF078-133, XF078-134, XF078-135, XF078-136, XF078-137, XF078-138, XF078-139, XF078-140, XF078-141, XF078-142, XF078-143, XF078-144, XF078-145, XF078-146, XF078-147, XF078-148, XF078-149, XF078-150, XF078-151, XF078-152, XF078-153, XF078-154, XF078-155, XF078-156, XF078-157, XF078-158, XF078-159, XF078-160, XF061-33, XF061-34, XF061-35, XF061-36, XF061-37, XF061-38, XF061-39, XF061-40, XF061-41, XF061-42, XF061-43, XF061-44, XF061-45, XF061-46, XF061-47, XF061-48, XF061-49, XF061-50, XF061-51, XF061-52, XF061-53, XF061-54, XF061-55, XF061-56, XF061-57, XF061-58, XF061-59, XF061-60, XF061-61, XF082-33, XF082-34, and examples 369-432 or analogs thereof.

In some aspects, this disclosure provides a method of treating WDR5-mediated cancers, the method including administering to a subject in need thereof one or more bivalent compounds including a WDR5 ligand conjugated to a degradation/disruption tag via a linker. The WDR5-mediated cancer can be a cancer resulting from (aberrant) WDR5 activation. The WDR5-mediated cancer can have elevated WDR5 expression relative to a wild-type tissue of the same species and tissue type. Non-limiting examples of WDR5-mediated diseases include leukemia, lymphoma, ovarian cancer, stomach cancer, cervical cancer, uterine cancer, gastric cancer, head neck squamous cell carcinoma (HN-SCC), colorectal cancer (CRC), lung cancer, pancreatic cancer, bladder cancer, breast cancer, and neuroblastoma.

The WDR5-mediated cancer can be a relapsed cancer. The WDR5-mediated cancer can have been refractory to one or more previous treatments by different therapies.

In any of the above-described methods, the bivalent compounds can be XF048-117, XF048-118, XF048-119, XF048-120, XF048-121, XF048-122, XF048-123, XF048-124, XF048-125, XF048-126, XF048-127, XF048-128, XF048-129, XF048-130, XF048-131, XF048-132, XF048-133, XF048-134, XF048-135, XF048-136, XF048-137, XF048-138, XF048-139, XF048-140, XF048-141, XF048-142, XF048-143, XF048-144, XF048-145, XF050-166, XF050-169, XF050-165, XF050-159, XF050-160, XF050-161, XF050-162, XF050-156, XF050-164, XF050-158, XF056-23, XF056-25, XF056-26, XF056-24, XF056-32, XF056-72, XF056-38, XF056-39, XF056-104, XF056-118, XF061-111, XF067-66, XF056-124, XF056-125, XF056-126, XF056-127, XF056-128, XF056-129, XF056-130, XF056-131, XF056-132, XF056-133, XF056-134, XF056-135, XF056-136, XF056-137, XF056-138, XF056-139, XF056-140, XF056-141, XF056-142, XF056-143, XF056-144, XF056-145, XF056-146, XF056-147, XF056-148, XF056-149, XF056-150, XF056-151, XF056-152, XF056-153, XF056-157, XF056-158, XF056-159, XF056-160, XF056-161, XF056-162, XF056-163, XF056-164, XF056-165, XF056-166, XF056-167, XF056-168, XF056-169, XF056-170, XF056-171, XF056-172, XF056-173, XF056-174, XF056-175, XF056-176, XF056-177, XF056-178, XF056-179, XF056-180, XF056-181, XF056-182, XF056-183, XF056-184, XF056-185, XF056-186, XF061-104, XF067-67, XF067-68, XF067-131, XF067-133, XF067-134, XF067-140, XF067-141, XF067-142, XF067-143, XF067-144, XF067-145, XF067-146, XF067-147, XF067-148, XF067-149, XF067-150, XF067-151, XF067-152, XF067-153, XF067-154, XF067-155, XF067-156, XF067-157, XF067-158, XF067-159, XF067-160, XF067-161, XF067-162, XF067-163, XF067-164, XF067-165, XF067-166, XF067-167, XF067-168, XF067-169, XF078-1, XF078-2, XF078-3, XF078-4, XF078-5, XF078-6, XF078-7, XF078-8, XF078-9, XF078-10, XF078-11, XF078-12, XF078-13, XF078-14, XF078-15, XF078-16, XF078-17, XF078-18, XF078-19, XF078-20, XF078-21, XF078-22, XF078-23, XF078-24, XF078-25, XF078-26, XF078-27, XF078-28, XF078-29, XF078-30, XF078-31, XF078-32, XF078-33, XF078-34, XF078-35, XF078-36, XF078-37, XF078-38, XF078-39, XF078-40, XF078-41, XF078-42, XF078-43, XF078-44, XF078-45, XF078-46, XF078-47, XF078-48, XF078-49, XF078-50, XF078-51, XF078-52, XF078-53, XF078-54, XF078-55, XF078-56, XF078-57, XF078-58, XF078-61, XF078-62, XF078-63, XF078-64, XF078-65, XF078-66, XF078-67, XF078-68, XF078-69, XF078-70, XF078-71, XF078-72, XF078-73, XF078-74, XF078-75, XF078-76, XF078-77, XF078-78, XF078-79, XF078-80, XF078-81, XF078-82, XF078-83, XF078-84, XF078-85, XF078-86, XF078-87, XF078-88, XF078-89, XF078-90, XF078-99, XF078-100, XF078-101, XF078-102, XF078-103, XF078-104, XF078-105, XF078-106, XF078-107, XF078-108, XF078-109, XF078-110, XF078-111, XF078-112, XF078-113, XF078-114, XF078-115, XF078-116, XF078-117, XF078-118, XF078-119, XF078-120, XF078-121, XF078-122, XF078-123, XF078-124, XF078-125, XF078-126, XF078-127, XF078-132, XF078-133, XF078-134, XF078-135, XF078-136, XF078-137, XF078-138, XF078-139, XF078-140, XF078-141, XF078-142, XF078-143, XF078-144, XF078-145, XF078-146, XF078-147, XF078-148, XF078-149, XF078-150, XF078-151, XF078-152, XF078-153, XF078-154, XF078-155, XF078-156, XF078-157, XF078-158, XF078-159, XF078-160, XF061-33, XF061-34, XF061-35, XF061-36, XF061-37, XF061-38, XF061-39, XF061-40, XF061-41, XF061-42, XF061-43, XF061-44, XF061-45, XF061-46, XF061-47, XF061-48, XF061-49, XF061-50, XF061-51, XF061-52, XF061-53, XF061-54, XF061-55, XF061-56, XF061-57, XF061-58, XF061-59, XF061-60, XF061-61, XF082-33, XF082-34, and examples 369-432, or analogs thereof.

In some aspects of the methods described herein, the bivalent compounds can be administered, e.g., orally, parenterally, intradermally, subcutaneously, topically, and/or rectally.

Any of the above-described methods can further include treating a subject with one or more additional therapeutic regimens for treating cancer. The one or more additional therapeutic regimens for treating cancer can be, e.g., one or more of surgery, chemotherapy, radiation therapy, hormone therapy, or immunotherapy.

This disclosure additionally provides a method for identifying a bivalent compound which mediates degradation/disruption of WDR5, the method including providing a heterobifunctional test compound including a WDR5 ligand conjugated to a degradation/disruption tag via a linker, contacting the heterobifunctional test compound with a cell (e.g., a cancer cell such as a WDR5-mediated cancer cell) including a ubiquitin ligase and WDR5.

As used herein, the terms "about" and "approximately" are defined as being within plus or minus 10% of a given value or state, preferably within plus or minus 5% of said value or state. The terms "bivalent" and "bi-functional" are used interchangeably herein. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
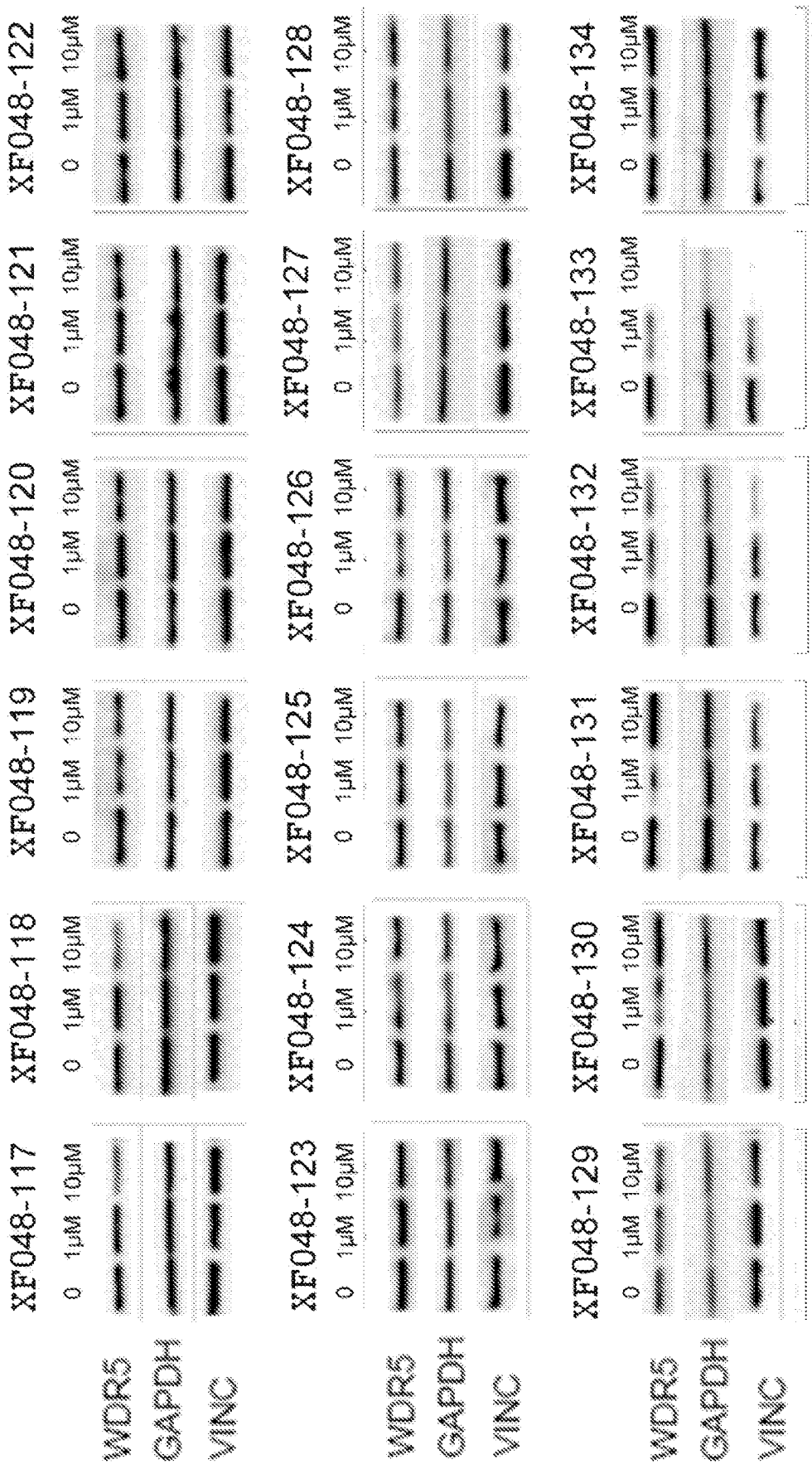
FIGS. 1A-1C are a series of Western blots showing the effect of various WDR5 degraders in reducing WDR5 levels at 0, 1 µM, and 10 µM in MV4;11 cells or at 1 µM in Hela cells after 18 h treatment.

The present disclosure is based in part, on the discovery that novel heterobifunctional small molecules which degrade WDR5 and/or WDR5 mutant proteins are useful in the treatment of WDR5-mediated diseases, particularly leukemia, lymphoma, ovarian cancer, stomach cancer, cervical cancer, uterine cancer, gastric cancer, head neck squamous cell carcinoma (HNSCC), colorectal cancer (CRC), lung cancer, pancreatic cancer, bladder cancer, breast cancer, and neuroblastoma.

Successful strategies for selective degradation/disruption of the target protein induced by a bifunctional small molecule include recruiting an E3 ubiquitin ligase and mimicking protein misfolding with a hydrophobic tag (Buckley and Crews, 2014). The bifunctional molecules have three moieties: one E3-binder moiety that binds an E3 ubiquitin ligase; one targeted protein-binder moiety that binds the protein target of interest; and a linker moiety that connects the E3-binder and the targeted protein-binder moieties (Buckley and Crews, 2014). The induced proximity leads to selective ubiquitination of the target followed by its degradation at the proteasome. Several types of high affinity small-molecule E3 ligase ligands have been identified/developed. They include (1) immunomodulatory drugs (IMiDs) such as thalidomide and pomalidomide, which bind cereblon (CRBN or CRL4CRBN), a component of a culfin-RING ubiquitin ligase (CRL) complex (Bondeson et al., 2015; Chamberlain et al., 2014; Fischer et al., 2014; Ito et al., 2010; Winter et al., 2015); (2) VHL-1, a hydroxyproline-containing ligand, which binds van Hippel-Lindau protein (VHL or CRL2VHL), a component of another CRL complex (Bondeson et al., 2015; Buckley et al., 2012a; Buckley et al., 2012b; Galdeano et al., 2014; Zengerle et al., 2015); (3) compound 7, which selectively binds KEAP1, a component of a CRL3 complex (Davies et al., 2016); (4) AMG232, which selectively binds MDM2, a heterodimeric RING E3 ligase (Sun et al., 2014); and (5) LCL161, which selectively binds IAP, a homodimeric RING E3 ligase (Ohoka et al., 2017; Okuhira et al., 2011; Shibata et al., 2017). The technology has been successfully applied to degradation of multiple targets (Bondeson et al., 2015; Buckley et al., 2015; Lai et al., 2016; Lu et al., 2015; Winter et al., 2015; Zengerle et al., 2015), but not to degradation of WDR5 or WDR5 mutant proteins. In addition, a hydrophobic tagging approach, which utilizes a bulky and hydrophobic adamantyl group, has been developed to mimic protein misfolding, leading to the degradation of the target protein by proteasome (Buckley and Crews, 2014). This approach has been successfully applied to selective degradation of the pseudokinase Her3 (Xie et al., 2014), but not to degradation of WDR5 or WDR5 mutant proteins.

As discussed in the following examples, this disclosure provides specific examples of novel WDR5 degraders/disruptors, and examines the effect of exemplary degraders/disruptors in inhibiting/disrupting WDR5 function, suppressing WDR5 expression, and inhibiting cancer cell proliferation. The results indicate that these novel small molecules can be beneficial in treating human disease, especially leukemia, lymphoma, ovarian cancer, stomach cancer, cervical cancer, uterine cancer, gastric cancer, head neck squamous cell carcinoma (HNSCC), colorectal cancer (CRC), lung cancer, pancreatic cancer, bladder cancer, breast cancer, and neuroblastoma.

A number of selective small-molecule WDR5 protein-protein interaction inhibitors, such as OICR-9429 (Getlik et al., 2016), MM-589 (Karatas et al., 2017), and compound B154 (US20180086767A1) have been reported.

Currently available small molecules targeting WDR5 focus on inhibition of the interaction with its binders. In the present disclosure, a different approach is taken: to develop compounds that directly and selectively target not only the protein-protein interaction of WDR5, but also its level of expression at the protein level. Strategies for inducing protein degradation include recruiting E3 ubiquitin ligases, mimicking protein misfolding with hydrophobic tags, and inhibiting chaperones. For example, a thalidomide-JQ1 bivalent compound has been used to hijack the cereblon E3 ligase, inducing highly selective BET protein degradation in vitro and in vivo and resulting in a demonstrated delay in leukemia progression in mice (Winter et al., 2015). Similarly, BET protein degradation has also been induced via another E3 ligase, VHL (Zengerle et al., 2015). Partial degradation of Her3 has been induced using an adamantane-modified compound (Xie et al., 2014). Such an approach, based on the use of bivalent small molecule compounds, permits more flexible regulation of protein expression in vitro and in vivo compared with techniques such as gene knockout or shRNA (short hairpin RNA) knockdown. Unlike gene knockout or shRNA knockdown, a small molecule approach further provides an opportunity to study dose and time dependency in a disease model through varying the concentrations and frequencies of administration of the relevant small molecule.

This disclosure includes all stereoisomers, geometric isomers, tautomers and isotopes of the structures depicted and compounds named herein. This disclosure also includes compounds described herein, regardless of how they are prepared, e.g., synthetically, through biological process (e.g., metabolism or enzyme conversion), or a combination thereof.

This disclosure includes pharmaceutically acceptable salts of the structures depicted and compounds named herein.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms. In some embodiments, the compound includes at least one fluorine atom. In some embodiments, the compound includes two or more fluorine atoms. In some embodiments, the compound includes 1-2, 1-3, 1-4, 1-5, or 1-6 fluorine atoms. In some embodiments, all of the hydrogen atoms in a compound can be replaced or substituted by fluorine atoms.

Degraders

In some aspects, the present disclosure provides bivalent compounds, also referred to herein as degraders, comprising an WDR5 ligand (or targeting moiety) conjugated to a degradation tag. Linkage of the WDR5 ligand to the degradation tag can be direct, or indirect via a linker.

As used herein, the terms "WD40 repeat domain protein 5 (WDR5) ligand" or "WDR5 ligand" or "WDR5 targeting moiety" are to be construed broadly, and encompass a wide variety of molecules ranging from small molecules to large proteins that associate with or bind to WDR5.

The WDR5 ligand or targeting moiety can be, for example, a small molecule compound (i.e., a molecule of molecular weight less than about 1.5 kilodaltons (kDa)), a peptide or polypeptide, nucleic acid or oligonucleotide, carbohydrate such as oligosaccharides, or an antibody or fragment thereof.

The WDR5 ligand or targeting moiety can be a WDR5 protein-protein inhibitor (e.g., OICR-9429 (Getlik et al., 2016), MM-589 (Karatas et al., 2017), compound B154 (US20180086767A1), and analogs thereof), which is capable of interfering with the protein-protein interaction of WDR5 with its binders. As used herein, a "WDR5 protein-protein inhibitor" refers to an agent that restrains, retards, or otherwise causes inhibition of a physiological, chemical or enzymatic action or function and causes a decrease in binding of at least 5%. An inhibitor can also or alternately refer to a drug, compound, or agent that prevents or reduces the expression, transcription, or translation of a gene or protein. An inhibitor can reduce or prevent the function of a protein, e.g., by binding to or activating/inactivating another protein or receptor.

Exemplary WDR5 ligands include, but are not limited to, the compounds listed below:

OICR-9429

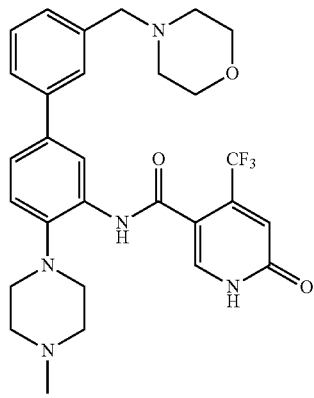

MM-589

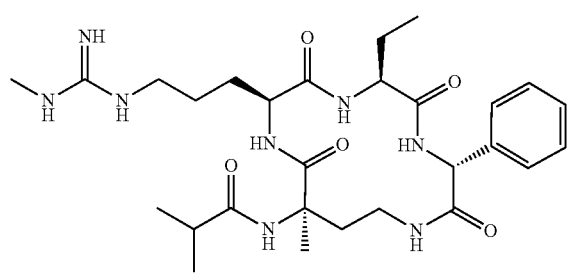

Compound B154

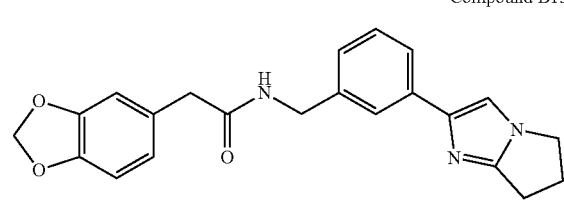

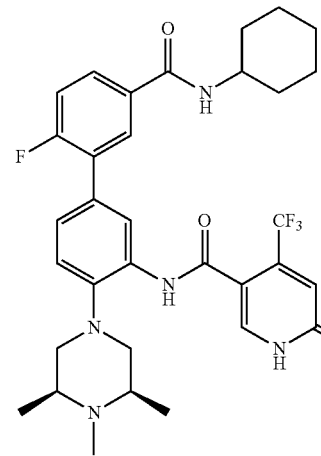

-continued

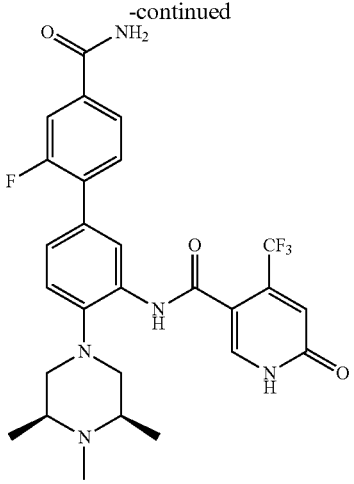

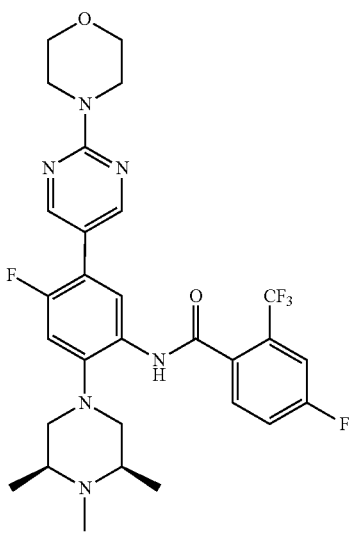

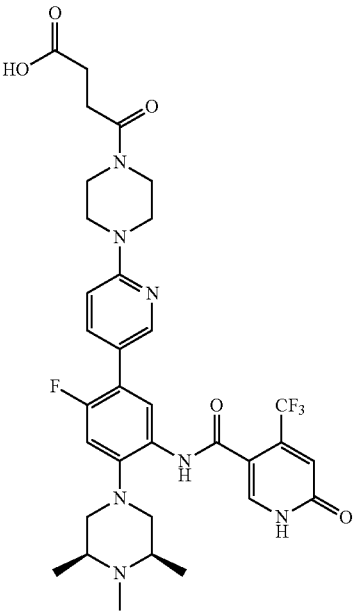

69
-continued
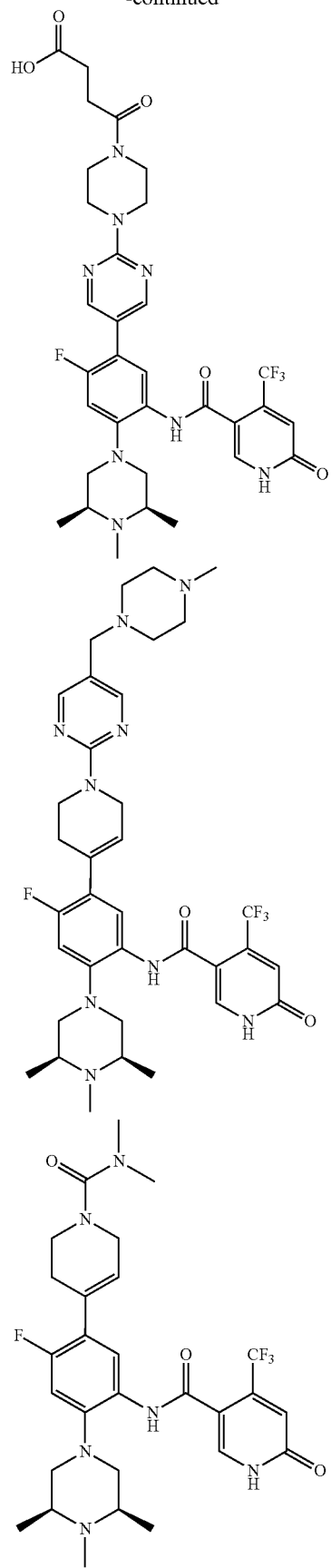
70
-continued
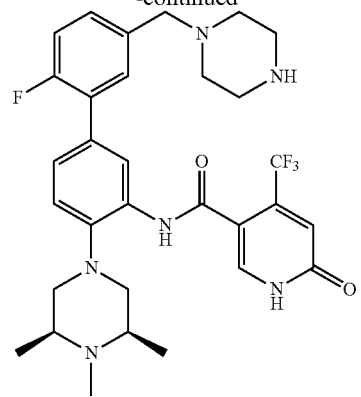
Compound 5m
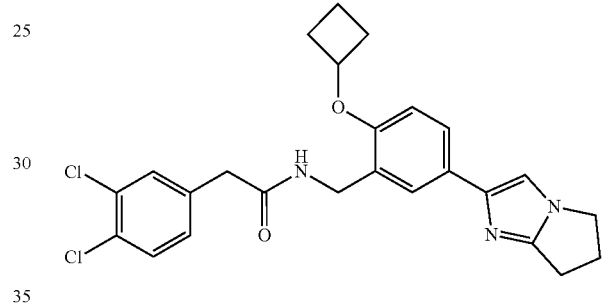
Compound 5o
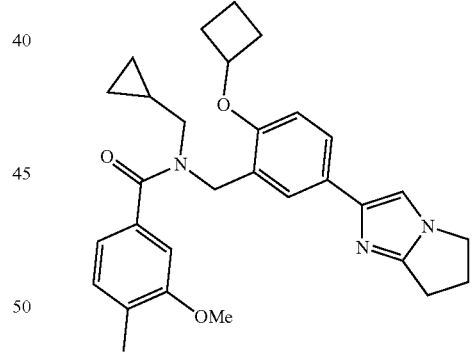
Compound 6a
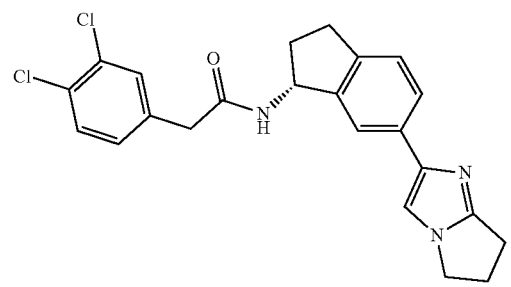

Compound 6b

Compound 6e

Compound C3

Compound C6

FORMULA 1A

FORMULA 1B

FORMULA 1C

FORMULA 1D

FORMULA 1E
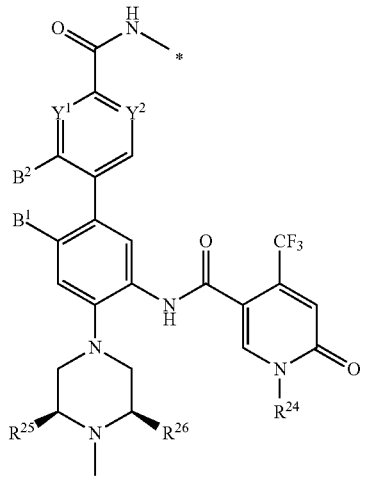
FORMULA 1H
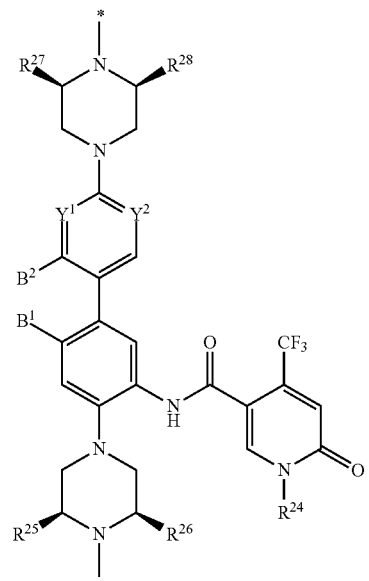
FORMULA 1F
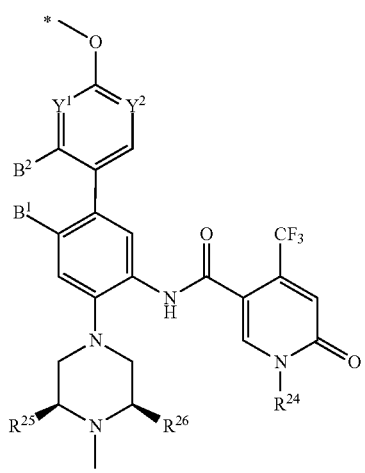
FORMULA 1G
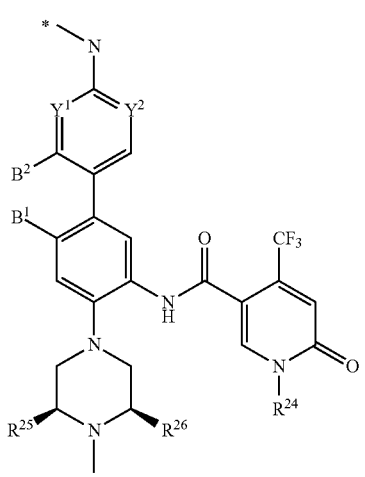
FORMULA 1I
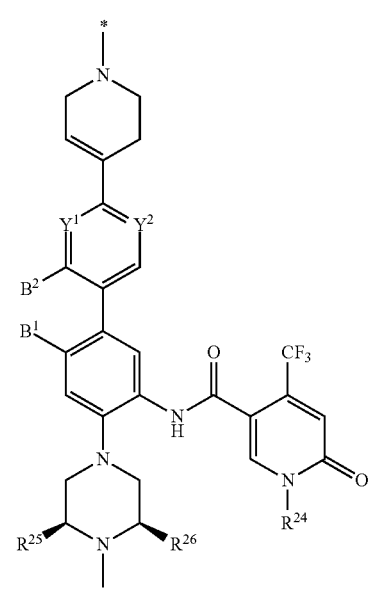

FORMULA 1J
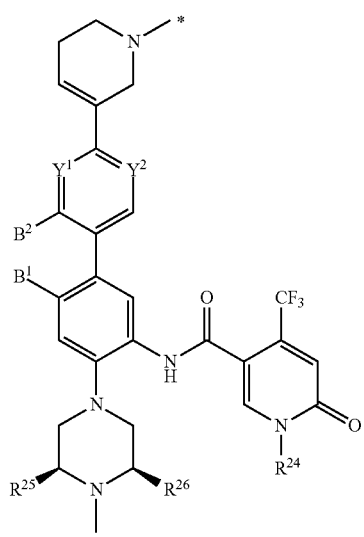
FORMULA 1K
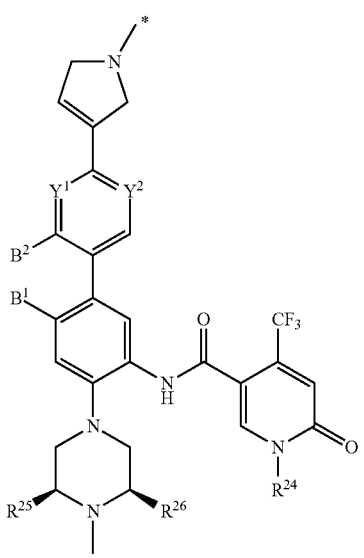
FORMULA 1L
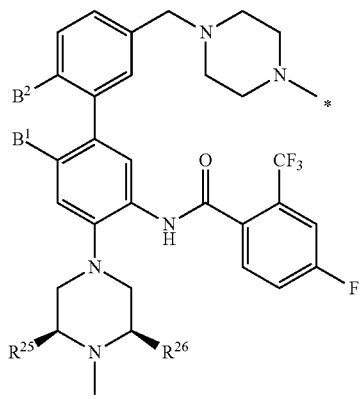
FORMULA 1M
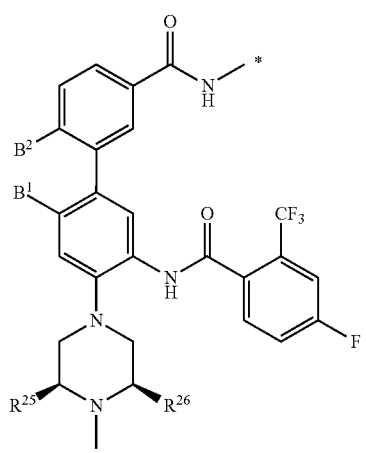
FORMULA 1N
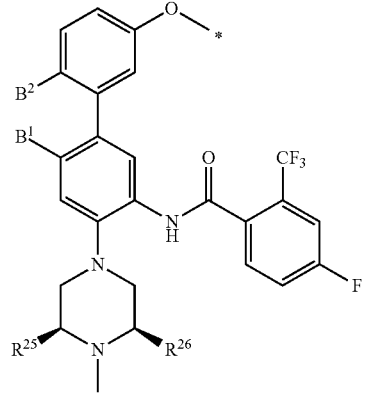
FORMULA 1O FORMULA 1P
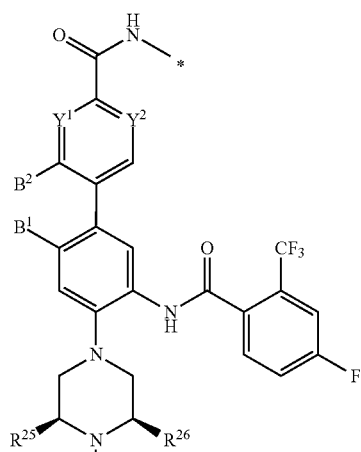
FORMULA 1Q
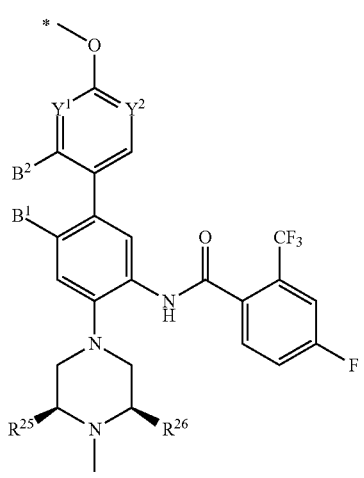
FORMULA 1R
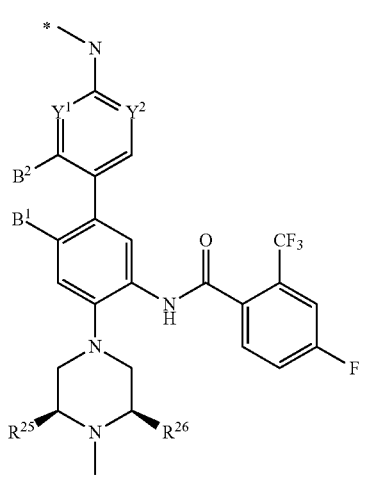
FORMULA 1S
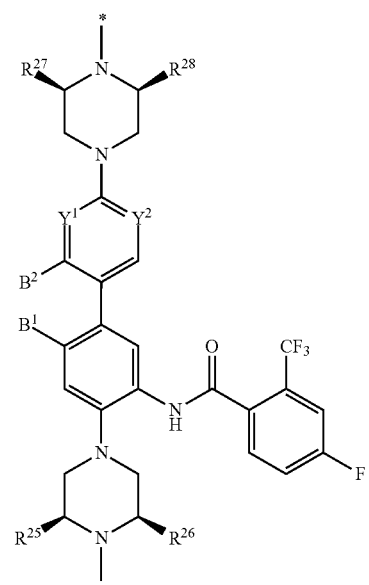
FORMULA 1T
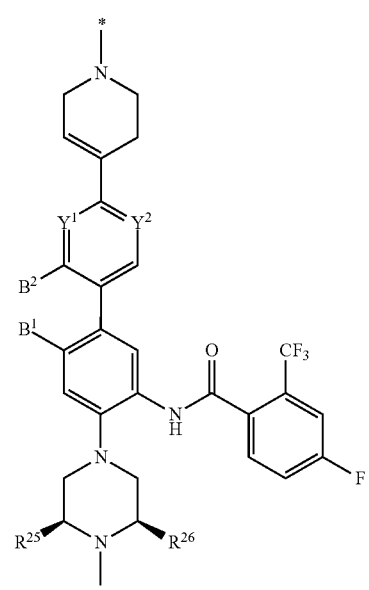

FORMULA 1U
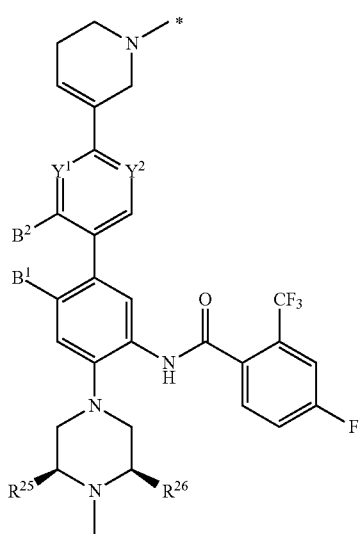
FORMULA 1V
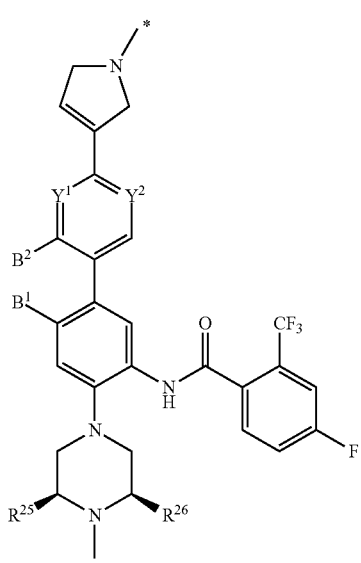
FORMULA 1W
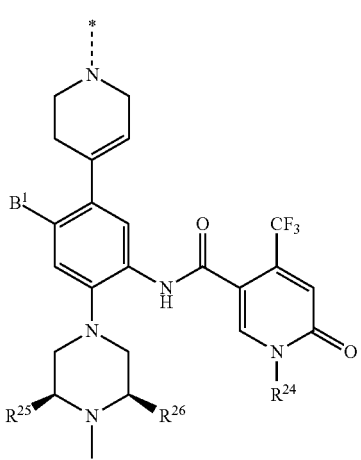
FORMULA 1X
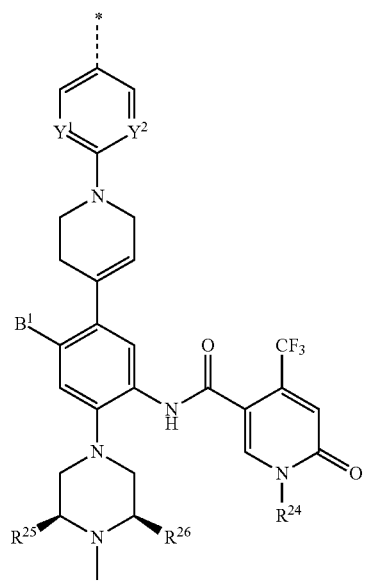
FORMULA 1Y
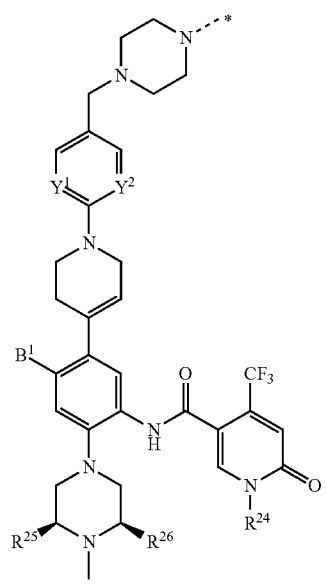

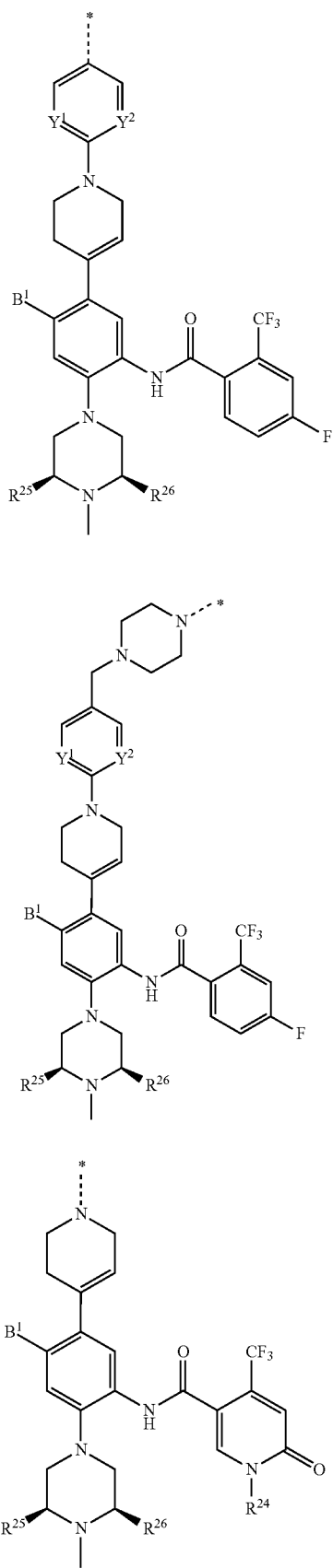

FORMULA 1AH

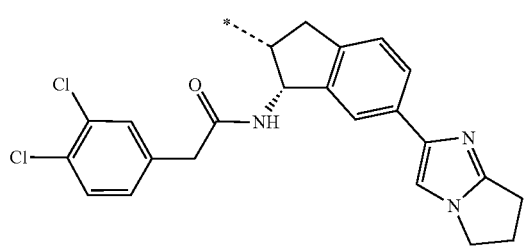

FORMULA 1AL

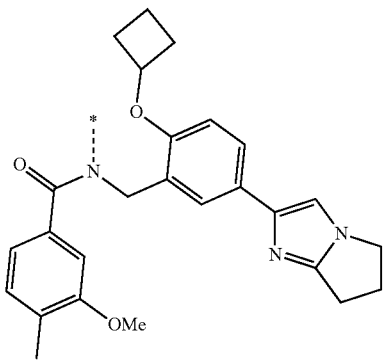

FORMULA 1AI

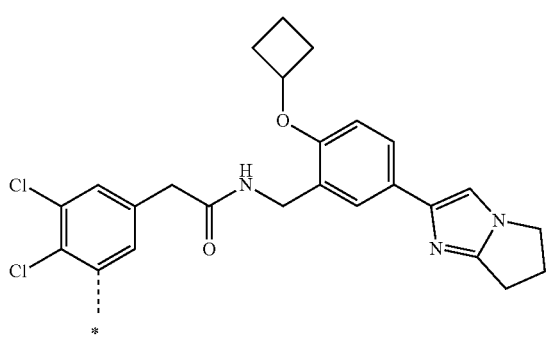

FORMULA 1AM

FORMULA 1AJ

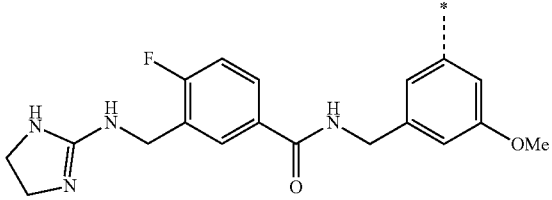

FORMULA 1AN

FORMULA 1AK

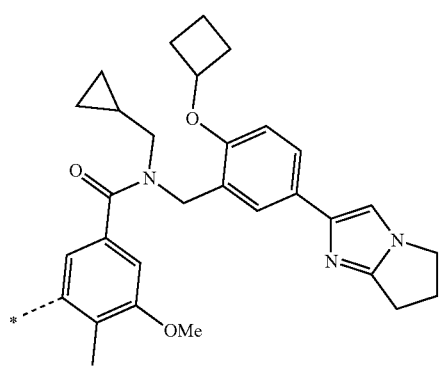

*: Connect to "Linker".
$R^{24}$, $R^{25}$, $R^{26}$, $R^{27}$, and $R^{28}$ are independently selected from H and $CH_3$.
$B^1$ and $B^2$ are independently selected from H and F.
$Y^1$ and $Y^2$ are independently selected from CH and N.

As used herein, the term "degradation/disruption tag" refers to a compound, which associates with or binds to a ubiquitin ligase for recruitment of the corresponding ubiquitination machinery to WDR5 or induces WDR5 protein misfolding and subsequent degradation at the proteasome or loss of function.

In some aspects, the degradation/disruption tags of the present disclosure include, e.g., pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4, 4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Fliroyuki Suda et al., 1976), MV1 (Varfolomeev et al., 2007), LCL161 (Weisberg et al., 2010), FK506 (Liu et al., 1991) rapamycin (Fan et al., 2017; Rodrik-Outmezguine et al., 2016), and/or analogs thereof.

As used herein, a "linker" is a bond, molecule, or group of molecules that binds two separate entities to one another. Linkers provide for optimal spacing of the two entities. The term "linker" in some aspects refers to any agent or molecule that bridges the WDR5 ligand to the degradation/disruption tag. One of ordinary skill in the art recognizes that sites on the WDR5 ligand or the degradation/disruption tag, which are not necessary for the function of the degraders of the present disclosure, are ideal sites for attaching a linker, provided that the linker, once attached to the conjugate of the present disclosures, does not interfere with the function of the WDR5 ligand, i.e., its ability to bind WDR5, or the function of the degradation/disruption tag, i.e., its ability to recruit a ubiquitin ligase.

The length of the linker of the bivalent compound can be adjusted to minimize the molecular weight of the disruptors/degraders and avoid the clash of the WDR5 ligand or targeting moiety with the ubiquitin ligase or induce WDR5 misfolding by the hydrophobic tag at the same time.

In some aspects, the degradation/disruption tags of the present disclosure include, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), FK506 (Liu et al., 1991) rapamycin (Fan et al., 2017; Rodrik-Outmezguine et al., 2016), and analogs thereof. The degradation/disruption tags can be attached to each portion of interest in the structure of a WDR5 ligand or targeting moiety (e.g., OICR-9429 (Getlik et al., 2016), MM-589 (Karatas et al., 2017), compound B154 (US20180086767A1), and analogs thereof) with linkers of different types and lengths in order to generate effective bivalent compounds. In particular, attaching pomalidomide or VHL-1 to either portion of the molecule can recruit the cereblon E3 ligase or VHL E3 ligase to WDR5.

The bivalent compounds disclosed herein can selectively affect WDR5-mediated disease cells compared to WT (wild type) cells (i.e., a WDR5 degrader/disruptor able to kill or inhibit the growth of a WDR5-mediated disease cell while also having a relatively low ability to lyse or inhibit the growth of a WT cell), e.g., possess a $GI_{50}$ for one or more WDR5-mediated disease cells more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than its $GI_{50}$ for one or more WT cells, e.g., WT cells of the same species and tissue type as the WDR5-mediated disease cells.

Additional bivalent compounds (i.e., WDR5 degraders/disruptors) can be developed using the principles and methods disclosed herein. For example, other linkers, degradation/disruption tags, and WDR5 binding/inhibiting moieties (not limited to OICR-9429 (Getlik et al., 2016), MM-589 (Karatas et al., 2017), compound B154 (US20180086767A1), and analogs thereof) can be synthesized and tested.

In some aspects, the WDR5 degraders/disruptors have the form "PI-Linker-EL", as shown below:

wherein PI (a ligand for a "protein of interest," i.e., the protein to be degraded) comprises a WDR5 ligand (e.g., a WDR5 protein-protein inhibitor), and EL (e.g., a ligand for an E3 ligase) comprises a degradation/disruption tag (e.g., E3 ligase ligand). Exemplary WDR5 ligands (PI), exemplary degradation/disruption tags (EL), and exemplary linkers (Linker) are illustrated below:

WDR5 Ligands

WDR5 Ligands include but are not limited to:

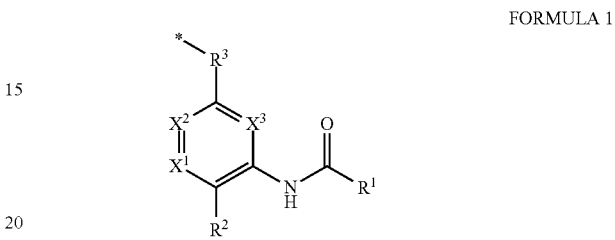

FORMULA 1

Wherein

*: Connect to "Linker".

$R^1$ is $C_6$-$C_{10}$ aryl or $C_5$-$C_{10}$ heteroaryl. $R^1$ is unsubstituted or substituted with one or more of groups selected from halo, =O, =S, CN, $NO_2$, $C_{1-8}$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_1$-$C_8$ alkyleneOR$^4$, $C_1$-$C_8$alkyleneSR$^5$, $C_1$-$C_8$alkylene NR$^6$R$^7$, $C_2$-$C_8$ alkenyl, $C_2$-$C_8$ alkynyl, OR$^4$, SR$^5$, NR$^6$R$^7$.

$R^2$ is heterocycloalkyl, which contains one or more nitrogen atoms. $R^2$ is unsubstituted or substituted with one or more of groups selected from halo, =O, =S, CN, $NO_2$, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_2$-$C_8$ alkenyl, $C_2$-$C_8$ alkynyl, OR$^8$, SR$^9$, NR$^{10}$R$^{11}$, $C_1$-$C_8$ alkyleneOR$^8$, $C_1$-$C_8$ alkyleneSR$^9$, $C_1$-$C_8$ alkyleneNR$^{10}$R$^{11}$.

$R^3$ is selected from $C_6$-$C_{10}$ aryl, $C_5$-$C_{10}$ heteroaryl, or heterocycloalkyl, heterocycloalkenyl. $R^3$ is unsubstituted or substituted with one or more of groups selected from halo, CN, $NO_2$, =O, =S, OR$^{12}$, SR$^{13}$, $SO_2$R$^{14}$, NR$^{15}$R$^{16}$, R$^{17}$, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, $C_2$-$C_8$ alkenyl, $C_2$-$C_8$ alkynyl, $C_1$-$C_8$ alkyleneR$^{17}$, $C_2$-$C_8$ alkenyleneR$^{17}$, $C_2$-$C_8$ alkynyleneR$^{17}$, OC$_1$-$C_8$ alkyleneR$^{17}$, SC$_1$-$C_8$ alkyleneR$^{17}$, $C_1$-$C_8$ alkyleneOR$^{12}$, $C_1$-$C_8$ alkyleneSR$^{13}$, $C_1$-$C_8$ alkyleneNR$^{15}$R$^{16}$, OC$_1$-$C_8$ alkyleneOR$^{12}$, OC$_1$-$C_8$ alkyleneSR$^{13}$, OC$_1$-$C_8$ alkyleneNR$^{15}$R$^{16}$, SC$_1$-$C_8$ alkyleneOR$^{12}$, SC$_1$-$C_8$ alkyleneSR$^{13}$, SC$_1$-$C_8$ alkyleneNR$^{15}$R$^{16}$, C(O)R$^{12}$, C(O)OR$^{12}$, C(S)OR$^{12}$, C(O)NR$^{15}$R$^{16}$, C(S) NR$^{15}$R$^{16}$, NR$^{15}$C(O)R$^{12}$, NR$^{15}$S(O)R$^{12}$, NR$^{15}$S(O)OR$^{12}$, S(O) R$^{13}$, S(O)OR$^{12}$, and S(O)ONR$^{15}$R$^{16}$.

$R^4$, $R^5$, $R^6$, $R^7$, $R^8$, $R^9$, $R^{10}$, and $R^{11}$ are independently selected from H, $C_1$-$C_8$ alkyl, $C_1$-$C_8$ haloalkyl, $C_1$-$C_8$ hydroxyalkyl, $C_3$-$C_{10}$ cycloalkyl, $C_3$-$C_{10}$ heterocyclyl, C(O)C$_1$-$C_8$ alkyl, C(O)C$_1$-$C_8$ haloalkyl, C(O)C$_1$-$C_8$ hydroxyalkyl, C(O)C$_3$-$C_{10}$ cycloalkyl, and C(O)C$_3$-$C_{10}$ heterocyclyl, or $R^6$ and $R^7$; $R^{10}$ and $R^{11}$ together with the nitrogen atom to which they are connected can independently form 3-10 membered heterocyclyl rings.

$R^{12}$, $R^{13}$, and $R^{14}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_8$ cycloalkyl, $C_3$-$C_7$ heterocycloalkyl, $C_6$-$C_{10}$ aryl, $C_5$-$C_{10}$ heteroaryl, C(O)C$_1$-$C_8$ alkyl, C(O)C$_1$-C$_8$ haloalkyl, C(O)C$_1$-C$_8$ hydroxyalkyl, C(O)C$_1$-C$_8$ alkoxyalkyl, C(O)C$_3$-C$_{10}$ cycloalkyl, C(O)C$_3$-C$_{10}$ heterocyclyl, C(O)C$_6$-C$_{10}$ aryl, C(O)C$_5$-C$_{10}$ heteroaryl, C$_1$-C$_8$ alkyleneC$_3$-C$_{10}$ cycloalkyl, C$_1$-C$_8$ alkyleneC$_3$-C$_{10}$ heterocycloalkyl, C$_1$-C$_8$ alkyleneC$_6$-C$_{10}$ aryl, C$_1$-C$_8$ alkyleneC$_5$-C$_{10}$ heteroaryl.

R$^{15}$ and R$^{16}$ are independently selected from H, C$_1$-C$_8$ alkyl, C$_1$-C$_8$ haloalkyl, C$_1$-C$_8$ alkoxyalkyl, C$_1$-C$_8$ hydroxyalkyl, C$_3$-C$_{10}$ cycloalkyl, C$_3$-C$_{10}$ heterocloalkyl, C$_6$-C$_{10}$ aryl, C$_5$-C$_{10}$ heteroaryl, C(O)C$_1$-C$_8$ alkyl, C(O)C$_1$-C$_8$ haloalkyl, C(O)C$_1$-C$_8$ hydroxyalkyl, C(O)C$_1$-C$_8$ alkoxyalkyl, C(O)C$_3$-C$_{10}$ cycloalkyl, C(O)C$_3$-C$_{10}$ heterocycloalkyl, C(O)C$_6$-C$_{10}$ aryl, C(O)C$_5$-C$_{10}$ heteroaryl, C(O)OC$_1$-C$_8$ alkyl, C(O)OC$_1$-C$_8$ haloalkyl, C(O)OC$_1$-C$_8$ hydroxyalkyl, C(O)OC$_1$-C$_8$ alkoxyalkyl, C(O)OC$_3$-C$_{10}$ cycloalkyl, C(O)OC$_3$-C$_{10}$ heterocyclyl, C(O)OC$_6$-C$_{10}$ aryl, C(O)OC$_5$-C$_{10}$ heteroaryl, C(O)NC$_1$-C$_8$ alkyl, C(O)NC$_1$-C$_8$ haloalkyl, C(O)NC$_1$-C$_8$ hydroxyalkyl, C(O)NC$_1$-C$_8$ alkoxyalkyl, C(O)NC$_3$-C$_{10}$ cycloalkyl, C(O)NC$_3$-C$_{10}$ heterocyclyl, C(O)NC$_6$-C$_{10}$ aryl, C(O)NC$_5$-C$_{10}$ heteroaryl, SO$_2$C$_1$-C$_8$ alkyl, SO$_2$C$_1$-C$_8$ haloalkyl, SO$_2$C$_1$-C$_8$ hydroxyalkyl, SO$_2$C$_1$-C$_8$ alkoxyalkyl, SO$_2$C$_3$-C$_{10}$ cycloalkyl, SO$_2$C$_3$-C$_{10}$ heterocyclyl, SO$_2$C$_6$-C$_{10}$ aryl, SO$_2$C$_5$-C$_{10}$ heteroaryl, C$_1$-C$_8$ alkyleneC$_3$-C$_{10}$ cycloalkyl, C$_1$-C$_8$ alkyleneC$_3$-C$_{10}$ heterocycloalkyl, C$_1$-C$_8$ alkyleneC$_6$-C$_{10}$ aryl, C$_1$-C$_8$ alkyleneC$_5$-C$_{10}$ heteroaryl, or R$^{15}$ and R$^{16}$ together with the nitrogen atom to which they are connected can independently form 3-10 membered heterocyclyl rings.

R$^{17}$ is selected from C$_3$-C$_{10}$ cycloalkyl, C$_3$-C$_{10}$ heterocycloalkyl, C$_6$-C$_{10}$ aryl, C$_5$-C$_{10}$ heteroaryl, C(O)C$_1$-C$_8$ alkyl, C(O)C$_1$-C$_8$ haloalkyl, C(O)C$_1$-C$_8$ hydroxyalkyl, C(O)C$_1$-C$_8$ alkoxyalkyl, C(O)C$_3$-C$_{10}$ cycloalkyl, C(O)C$_3$-C$_{10}$ heterocycloalkyl, C(O)C$_6$-C$_{10}$ aryl, and C(O)C$_5$-C$_{10}$ heteroaryl.

X1, X2, and X3 are independently selected from CR$^{18}$, and N.

R$^{18}$ is selected from H, F, Cl, C$_{1-8}$ alkyl, C$_1$-C$_8$ haloalkyl, C$_1$-C$_8$ alkoxyalkyl, or C$_3$-C$_8$ cycloalkyl.

In some aspects of Formula I, R$^1$ has a structure of:

FORMULA 1-1A

FORMULA 1-1B

FORMULA 1-1C

FORMULA 1-1D
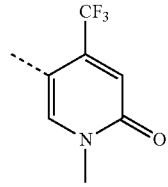

FORMULA 1-1E
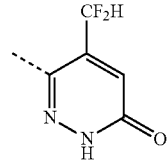

FORMULA 1-1F
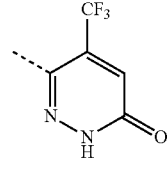

FORMULA 1-1G
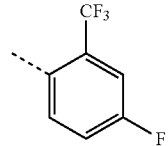

FORMULA 1-1H
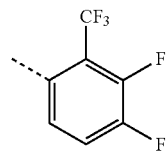

FORMULA 1-1I
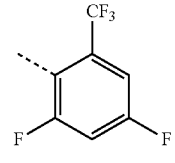

FORMULA 1-1J
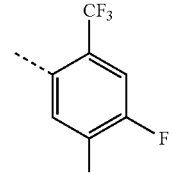

In some aspects of Formula I, R$^2$ has a structure of:

Formula 1-2A
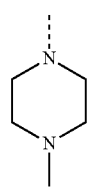

-continued
Formula 1-2B
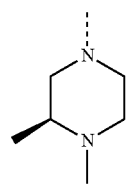
Formula 1-2C
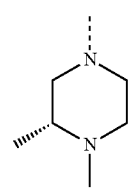
Formula 1-2D
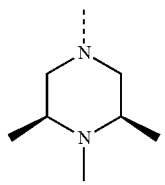
Formula 1-2E
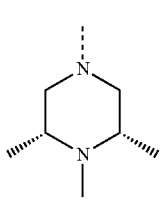
Formula 1-2F
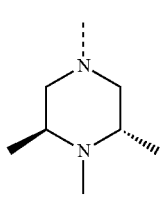
Formula 1-2G
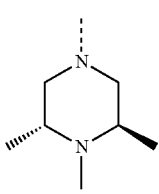
Formula 1-2H
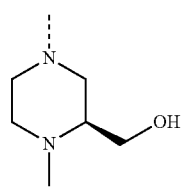
Formula 1-2I
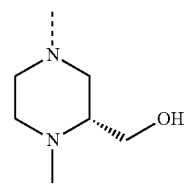
In some aspects of Formula I, $R^3$ has a structure of:
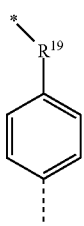
FORMULA 1-3A
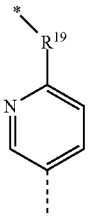
FORMULA 1-3B
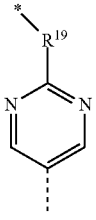
FORMULA 1-3C
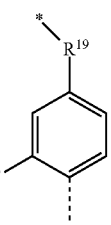
FORMULA 1-3D
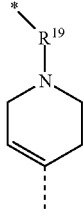
FORMULA 1-3E
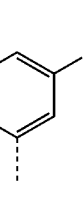
FORMULA 1-3F
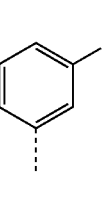
FORMULA 1-3G -continued

FORMULA 1-3H

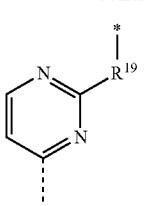

FORMULA 1-3I

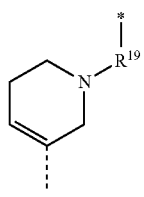

FORMULA 1-3J

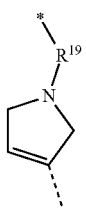

*: connect to "Linker".

$R^{19}$ is selected from a bond, $C_1$-$C_8$ alkyl, $C_1$-$C_8$ haloalkyl, $OR^{20}$, $SR^{20}$, $SO_2R^{20}$, $NR^{21}R^{22}$, $R^{23}$, $C_1$-$C_8$ alkylene$R^{23}$, $C_2$-$C_8$ alkenylene$R^{23}$, $OC_1$-$C_8$ alkylene$R^{23}$, $SC_1$-$C_8$ alkylene$R^{23}$, $C_1$-$C_8$ alkyleneO$R^{20}$, $C_1$-$C_8$ alkyleneS$R^{20}$, $C_1$-$C_8$ alkyleneN$R^{21}R^{22}$, $OC_1$-$C_8$ alkyleneO$R^{20}$, $OC_1$-$C_8$ alkyleneS$R^{20}$, $OC_1$-$C_8$ alkyleneN$R^{21}R^{22}$, $SC_1$-$C_8$ alkyleneO$R^{20}$, $SC_1$-$C_8$ alkyleneS$R^{20}$, $SC_1$-$C_8$ alkyleneN$R^{21}R^{22}$, $C(O)OR^{20}$, $C(S)OR^{20}$, $C(O) NR^{21}R^{22}$, $C(S) NR^{21}R^{22}$.

$R^{20}$ is selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_8$ cycloalkyl, $C_3$-$C_7$ heterocycloalkyl, $C_6$-$C_{10}$ aryl, $C_5$-$C_{10}$ heteroaryl, $C(O)C_1$-$C_8$ alkyl, $C(O)C_1$-$C_8$ haloalkyl, $C(O)C_1$-$C_8$ hydroxyalkyl, $C(O)C_1$-$C_8$ alkoxyalkyl, $C(O)C_3$-$C_{10}$ cycloalkyl, $C(O)C_3$-$C_{10}$ heterocyclyl, $C(O)C_6$-$C_{10}$ aryl, $C(O)C_5$-$C_{10}$ heteroaryl, $C_1$-$C_8$ alkylene$C_3$-$C_{10}$ cycloalkyl, $C_1$-$C_8$ alkylene$C_3$-$C_{10}$ heterocycloalkyl, $C_1$-$C_8$ alkylene$C_6$-$C_{10}$ aryl, $C_1$-$C_8$ alkylene$C_5$-$C_{10}$ heteroaryl.

$R^{21}$ and $R^{22}$ are independently selected from H, $C_1$-$C_8$ alkyl, $C_1$-$C_8$ haloalkyl, $C_1$-$C_8$ alkoxyalkyl, $C_1$-$C_8$ hydroxyalkyl, $C_3$-$C_{10}$ cycloalkyl, $C_3$-$C_{10}$ heterocycloalkyl, $C_6$-$C_{10}$ aryl, $C_5$-$C_{10}$ heteroaryl, $C(O)C_1$-$C_8$ alkyl, $C(O)C_1$-$C_8$ haloalkyl, $C(O)C_1$-$C_8$ hydroxyalkyl, $C(O)C_1$-$C_8$ alkoxyalkyl, $C(O)C_3$-$C_{10}$ cycloalkyl, $C(O) C_3$-$C_{10}$ heterocycloalkyl, $C(O)C_6$-$C_{10}$ aryl, $C(O)C_5$-$C_{10}$ heteroaryl, $C(O)OC_1$-$C_8$ alkyl, $C(O)OC_1$-$C_8$ haloalkyl, $C(O)OC_1$-$C_8$ hydroxyalkyl, $C(O)OC_1$-$C_8$ alkoxyalkyl, $C(O)OC_3$-$C_{10}$ cycloalkyl, $C(O)OC_3$-$C_{10}$ heterocyclyl, $C(O)OC_6$-$C_{10}$ aryl, $C(O)OC_5$-$C_{10}$ heteroaryl, $C(O)NC_1$-$C_8$ alkyl, $C(O)NC_1$-$C_8$ haloalkyl, $C(O)NC_1$-$C_8$ hydroxyalkyl, $C(O)NC_1$-$C_8$ alkoxyalkyl, $C(O)NC_3$-$C_{10}$ cycloalkyl, $C(O)NC_3$-$C_{10}$ heterocyclyl, $C(O)NC_6$-$C_{10}$ aryl, $C(O)NC_5$-$C_{10}$ heteroaryl, $SO_2C_1$-$C_8$ alkyl, $SO_2C_1$-$C_8$ haloalkyl, $SO_2C_1$-$C_8$ hydroxyalkyl, $SO_2C_1$-$C_8$ alkoxyalkyl, $SO_2C_3$-$C_{10}$ cycloalkyl, $SO_2C_3$-$C_{10}$ heterocyclyl, $SO_2C_6$-$C_{10}$ aryl, $SO_2C_5$-$C_{10}$ heteroaryl, $C_1$-$C_8$ alkylene$C_3$-$C_{10}$ cycloalkyl, $C_1$-$C_8$ alkylene$C_3$-$C_{10}$ heterocycloalkyl, $C_1$-$C_8$ alkylene$C_6$-$C_{10}$ aryl, $C_1$-$C_8$ alkylene$C_5$-$C_{10}$ heteroaryl, or $R^{21}$ and $R^{22}$ together with the nitrogen atom to which they are connected can independently form 3-10 membered heterocyclyl rings.

$R^{23}$ is selected from $C_3$-$C_{10}$ cycloalkyl, $C_3$-$C_{10}$ heterocloalkyl, $C_6$-$C_{10}$ aryl, $C_5$-$C_{10}$ heteroaryl, $C(O)C_1$-$C_8$ alkyl, $C(O)C_1$-$C_8$ haloalkyl, $C(O)C_1$-$C_8$ hydroxyalkyl, $C(O)C_1$-$C_8$ alkoxyalkyl, $C(O)C_3$-$C_{10}$ cycloalkyl, $C(O) C_3$-$C_{10}$ heterocycloalkyl, $C(O)C_6$-$C_{10}$ aryl, and $C(O) C_5$-$C_{10}$ heteroaryl.

WDR5 Ligands include but are not limited to:

FORMULA 2A

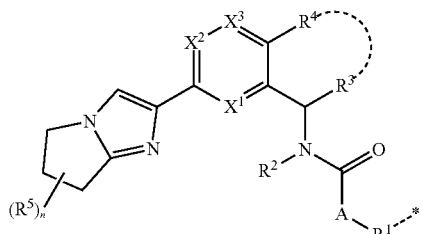

FORMULA 2B

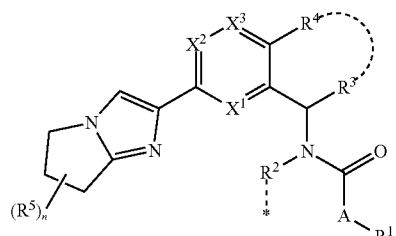

FORMULA 2C

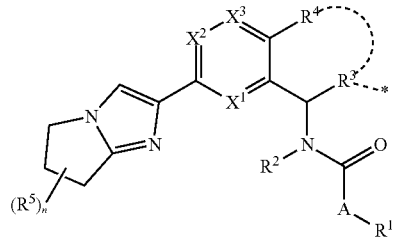

Wherein
*: Connect to "Linker".

$X^1$, $X^2$, and $X^3$ are independently selected from null, $CR^6$, and N, wherein $R^6$, at each occurrence, is independently selected from hydrogen, halogen, cyano, nitro, optionally substituted $C_1$-$C_8$ alkyl, optionally substituted $C_1$-$C_8$ haloalkyl, optionally substituted $C_1$-$C_8$ alkoxy, optionally substituted $C_1$-$C_8$ haloalkoxy, optionally substituted $C_1$-$C_8$ alkylamino, optionally substituted $C_1$-$C_8$haloalkylamino, optionally substituted $C_1$-$C_8$alkoxycarbonyl, optionally substituted $C_1$-$C_8$haloalkoxycarbonyl, optionally substituted $C_1$-$C_8$ alkylaminocarbonyl, optionally substituted $C_1$-$C_8$ haloalkylaminocarbonyl, optionally substituted $C_3$-$C_8$ carbocyclyl, and optionally substituted $C_4$-$C_8$ heterocyclyl;

A is selected from null, optionally substituted $C_1$-$C_8$ alkylene, optionally substituted $C_1$-$C_8$ haloalkylene, optionally substituted $C_1$-$C_8$ alkylamino, optionally substituted $C_1$-$C_8$ alkyleneamino, optionally substituted $C_1$-$C_8$ haloalkylamino, optionally substituted $C_2$-$C_8$ alkenylene, optionally substituted $C_2$-$C_8$ haloalkenylene, optionally substituted $C_2$-$C_8$ alkenyleneamino, optionally substituted $C_2$-$C_8$ haloalkenyleneamino, optionally substituted $C_2$-$C_8$ alkynylene, optionally substituted $C_2$-$C_8$ haloalkynylene, optionally substituted $C_2$-$C_8$ alkynyleneamino, optionally substituted $C_2$-$C_8$ haloalkynyleneamino, optionally substituted $C_3$-$C_8$ carbocyclyl, and optionally substituted $C_4$-$C_8$ heterocyclyl;

$R^1$ is selected from selected from null, carbocyclyl, heterocyclyl, aryl, and heteroaryl, which are optionally substituted with one or more substituents independently selected from hydrogen, halogen, oxo, CN, $NO_2$, $OR^7$, $SR^7$, $NR^7R^8$, $OCOR^7$, $OCO_2R^7$, $OCON(R^7)R^8$, $COR^7$, $CO_2R^7$, $CON(R^7)R^8$, $SOR^7$, $SO_2R^7$, $SO_2N(R^7)R^8$, $NR^9CO_2R^7$, $NR^9COR^7$, $NR^9C(O)N(R^7)R^8$, $NR^9SOR^7$, $NR^9SO_2R^7$, $NR^9SO_2N(R^7)R^8$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted 4-10 membered heterocyclyl$C_1$-$C_8$alkyl, optionally substituted 3-10 membered carbocyclyl$C_1$-$C_8$alkyl, optionally substituted 3-10 membered carbocyclyl, optionally substituted 4-10 membered heterocyclyl, optionally substituted aryl, and optionally substituted heteroaryl, wherein $R^7$, $R^8$, and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-10 membered carbocyclyl$C_1$-$C_8$alkyl, optionally substituted 4-10 membered heterocyclyl$C_1$-$C_8$alkyl, optionally substituted 3-10 membered carbocyclyl, optionally substituted 4-10 membered heterocyclyl, optionally substituted aryl, and optionally substituted heteroaryl, or $R^7$ and $R^8$, $R^7$ and $R^9$ together with the atom to which they are connected form a 4-20 membered heterocyclyl ring;

$R^2$ is selected from null, hydrogen, optionally substituted $C_1$-$C_8$ alkyl, optionally substituted $C_1$-$C_8$haloalkyl, optionally substituted $C_3$-$C_8$ carbocyclyl, optionally substituted $C_4$-$C_8$ heterocyclyl, optionally substituted aryl, and optionally substituted heteroaryl;

$R^3$ is selected from null, hydrogen, halogen, cyano, nitro, optionally substituted $C_1$-$C_8$ alkyl, optionally substituted $C_1$-$C_8$ haloalkyl, optionally substituted $C_3$-$C_8$ carbocyclyl, optionally substituted $C_4$-$C_8$ heterocyclyl, optionally substituted $C_2$-$C_8$ alkenylene, optionally substituted $C_2$-$C_8$ alkynylene, optionally substituted aryl, and optionally substituted heteroaryl;

$R^4$ is selected from null, hydrogen, halogen, cyano, nitro, $OR^{10}$, $NR^{10}R^{11}$, optionally substituted $C_1$-$C_8$ alkyl, optionally substituted $C_3$-$C_8$ carbocyclyl, optionally substituted $C_4$-$C_8$ heterocyclyl, optionally substituted $C_2$-$C_8$ alkenylene, optionally substituted $C_2$-$C_8$ alkynylene, optionally substituted aryl, and optionally substituted heteroaryl, wherein $R^{10}$, and $R^{11}$, are independently selected from hydrogen, optionally substituted $C_1$-$C_8$ alkyl, optionally substituted $C3$-$C_8$ carbocyclyl, optionally substituted $C_4$-$C_8$ heterocyclyl, optionally substituted $C_2$-$C_8$ alkenylene, optionally substituted $C_2$-$C_8$ alkynylene, optionally substituted aryl, and optionally substituted heteroaryl;

$R^3$ and $R^4$, together with the atoms to which they are connected optionally form a 4-8 membered carbocyclyl ring, or 4-8 membered heterocyclyl ring;

$R^5$, at each occurrence, is independently selected from hydrogen, halogen, hydroxyl, cyano, nitro, optionally substituted $C_1$-$C_8$ alkyl, optionally substituted $C_1$-$C_8$ haloalkyl, optionally substituted $C_1$-$C_8$ alkoxy, optionally substituted $C_1$-$C_8$ alkylamino, optionally substituted $C_1$-$C_8$ haloalkylamino, optionally substituted $C_3$-$C_8$ carbocyclyl, and optionally substituted $C_4$-$C_8$ heterocyclyl; and n=0-6.

In some aspects of Formulae 2A, 2B and 2C, $X^1$, $X^2$, and $X^3$ are $CR^6$.

In some aspects of Formulae 2A, 2B and 2C, $X^1$ and $X^3$ are $CR^6$; and $X^3$ is N.

In some aspects of Formulae 2A, 2B and 2C, $R^6$ is selected from hydrogen, halogen, optionally substituted $C_1$-$C_8$ alkyl, optionally substituted $C_1$-$C_8$ alkoxy, optionally substituted $C_1$-$C_8$ alkylamino, optionally substituted $C_1$-$C_8$ alkoxycarbonyl, optionally substituted $C_3$-$C_8$ carbocyclyl, and optionally substituted $C_4$-$C_8$ heterocyclyl.

In some aspects of Formulae 2A, 2B and 2C, $R^6$ is selected from H, F, Cl, Br, $CH_3$, $CH_3O$, and $CH_3O(CO)$—.

In some aspects of Formulae 2A, 2B and 2C, $R^6$ is H.

In some aspects of Formulae 2A, 2B and 2C, A is selected from null, optionally substituted $C_1$-$C_8$ alkylene, optionally substituted $C_1$-$C_8$ alkylamino, optionally substituted $C_1$-$C_8$ alkyleneamino, optionally substituted $C_2$-$C_8$ alkenylene, optionally substituted $C_2$-$C_8$ alkenyleneamino, optionally substituted $C_2$-$C_8$ alkynylene, and optionally substituted $C_2$-$C_8$ alkynyleneamino.

In some aspects of Formulae 2A, 2B and 2C, A is selected from null, and optionally substituted $C_1$-$C_8$ alkylene.

In some aspects of Formulae 2A, 2B and 2C, A is null.

In some aspects of Formulae 2A, 2B and 2C, A is $CH_2$.

In some aspects of Formulae 2A, 2B and 2C, $R^1$ is selected from selected from null, carbocyclyl, heterocyclyl, aryl, and heteroaryl, which are optionally substituted with one or more substituents independently selected from hydrogen, halogen, oxo, CN, $NO_2$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$alkoxy, optionally substituted $C_1$-$C_8$alkylamino, optionally substituted 4-10 membered heterocyclyl$C_1$-$C_8$alkyl, optionally substituted 3-10 membered carbocyclyl$C_1$-$C_8$alkyl, optionally substituted 4-10 membered heterocyclyloxy, optionally substituted 3-10 membered carbocyclyloxy, optionally substituted 3-10 membered carbocyclyl, and optionally substituted 4-membered heterocyclyl.

In some aspects of Formulae 2A, 2B and 2C, $R^1$ is selected from aryl and heteroaryl, which are optionally substituted with one or more substituents independently selected from hydrogen, halogen, oxo, CN, $NO_2$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$alkoxy, optionally substituted $C_1$-$C_8$alkylamino, optionally substituted 4-10 membered heterocyclyl$C_1$-$C_8$alkyl, optionally substituted 3-10 membered carbocyclyl$C_1$-$C_8$alkyl, optionally substituted 4-10 membered heterocyclyloxy, optionally substituted 3-10 membered carbocyclyloxy, optionally substituted 3-membered carbocyclyl, and optionally substituted 4-10 membered heterocyclyl.

In some aspects of Formulae 2A, 2B and 2C, $R^2$ is selected from null, hydrogen, optionally substituted $C_1$-$C_8$ alkyl, optionally substituted $C_1$-$C_8$ haloalkyl, optionally substituted C3-C8 cycloalkyl, optionally substituted $C_4$-$C_8$ heterocycloalkyl, optionally substituted aryl, and optionally substituted heteroaryl.

In some aspects of Formulae 2A, 2B and 2C, $R^2$ is selected from null, hydrogen, optionally substituted $C_1$-$C_8$ alkyl, optionally substituted $C_3$-$C_8$ cycloalkyl, and optionally substituted $C_3$-$C_8$ cycloalkyl$C_1$-$C_8$ alkyl.

In some aspects of Formulae 2A, 2B and 2C, $R^3$ is selected from null, hydrogen, and optionally substituted $C_1$-$C_8$ alkyl.

In some aspects of Formulae 2A, 2B and 2C, $R^3$ is selected from null, hydrogen, methyl, methylene, ethyl, ethylene, isopropyl, and cyclopropyl.

In some aspects of Formulae 2A, 2B and 2C, $R^4$ is selected from null, hydrogen, halogen, optionally substituted $C_1$-$C_8$ alkyl, optionally substituted $C_1$-$C_8$ alkoxy, optionally substituted $C_1$-$C_8$ alkylamino, optionally substituted $C_3$-$C_8$ cycloalkyl, optionally substituted $C_3$-$C_8$ cycloalkoxy, optionally substituted $C_3$-$C_8$ cycloalkylamino, optionally substituted $C_4$-$C_8$ heterocyclyl, optionally substituted $C_2$-$C_8$ alkenylene, optionally substituted $C_2$-$C_8$ alkynylene, optionally substituted aryl, optionally substituted aryloxy, optionally substituted arylamino, and optionally substituted heteroaryl.

In some aspects of Formulae 2A, 2B and 2C, $R^3$ and $R^4$, together with the atoms to which they are connected optionally form a 5-membered carbocyclyl ring, 6-membered carbocyclyl ring, 5-membered heterocyclyl ring, or 6-membered heterocyclyl ring.

In some aspects of Formulae 2A, 2B and 2C, $R^3$ and $R^4$, together with the atoms to which they are connected optionally form a 5-membered carbocyclyl ring.

In some aspects of Formulae 2A, 2B and 2C, $R^5$, at each occurrence, is independently selected from hydrogen, halogen, optionally substituted $C_1$-$C_8$ alkyl, optionally substituted $C_1$-$C_8$ alkoxy, optionally substituted $C_1$-$C_8$ alkylamino, optionally substituted $C_3$-$C_8$ carbocyclyl, and optionally substituted $C_4$-$C_8$heterocyclyl.

In some aspects of Formulae 2A, 2B and 2C, $R^5$ is hydrogen.

In some aspects, the WDR5 ligand can be derivatives of following compounds:

OICR-9429

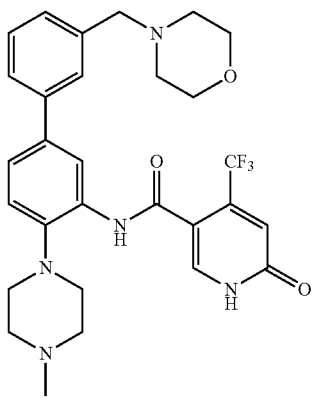

MM-589

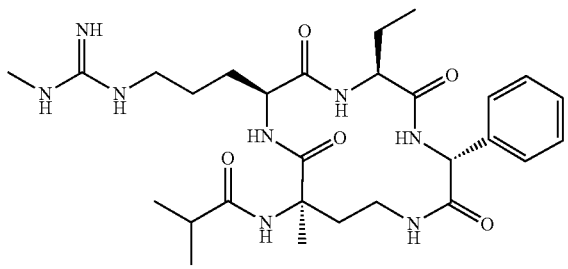

Compound B154

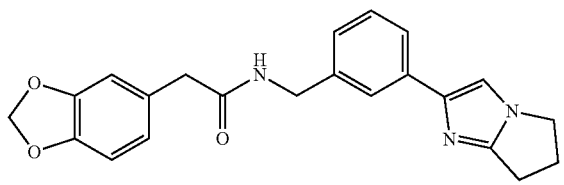

Compound 5e

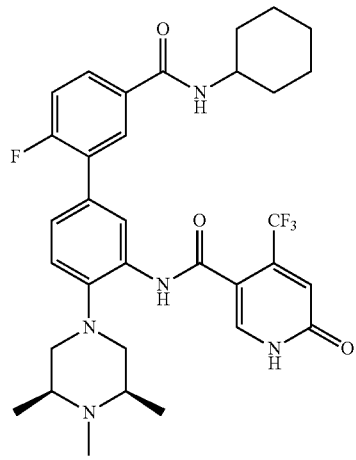

Compound 5f

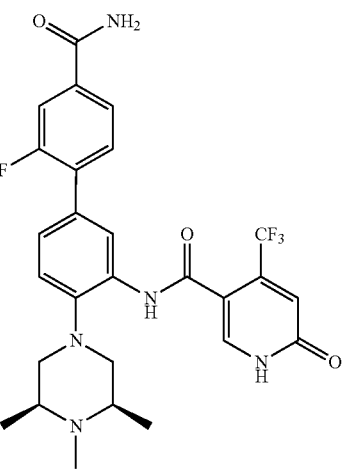

Compound 5g
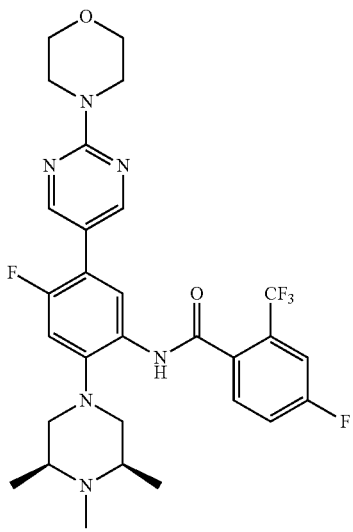
Compound 5h
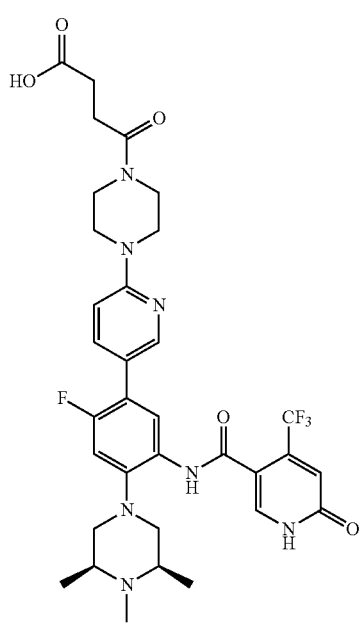
Compound 5i
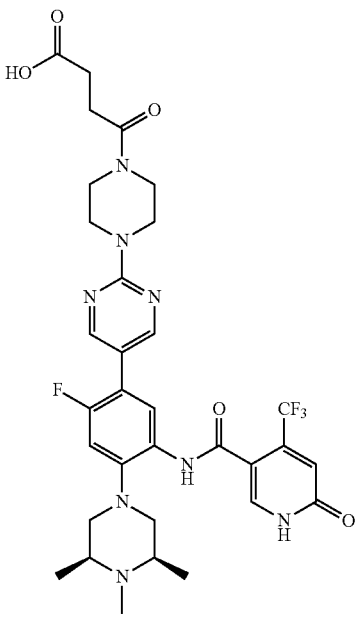
Compound 5j
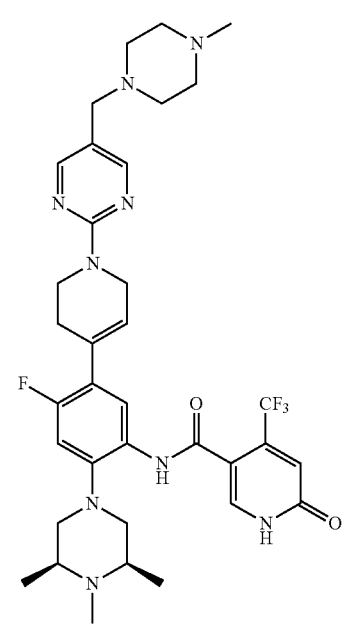

Compound 5k
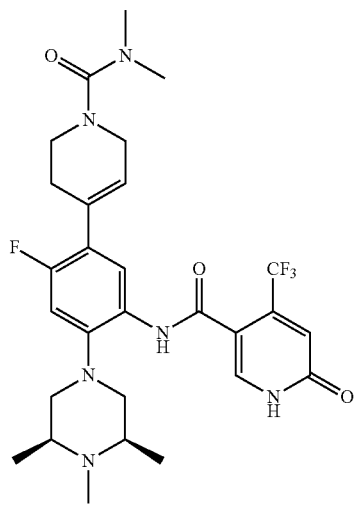
Compound 6a
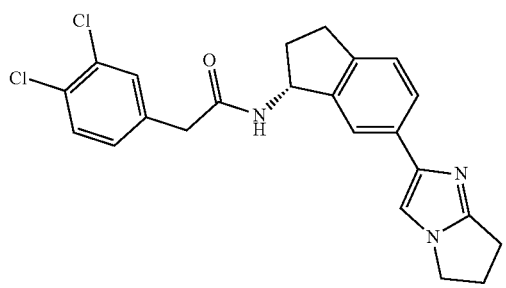
Compound 5l
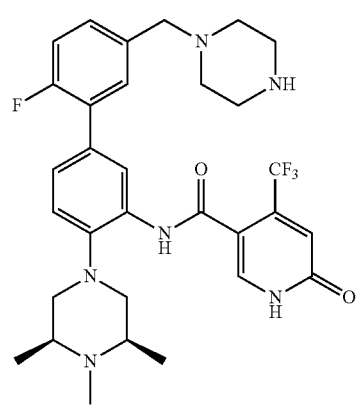
Compound 6b
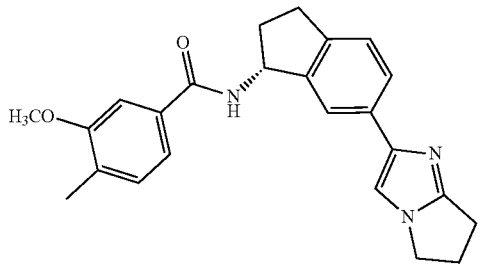
Compound 6e
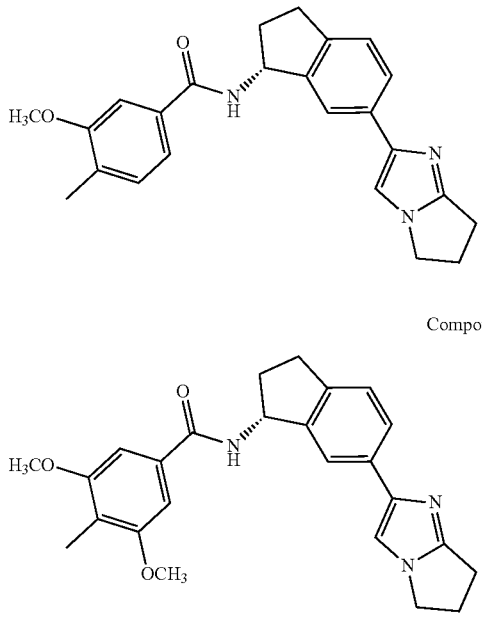
Compound 5m
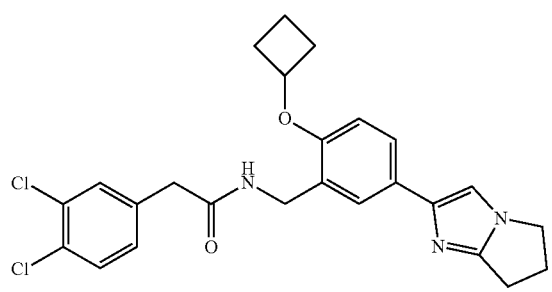
Compound C3
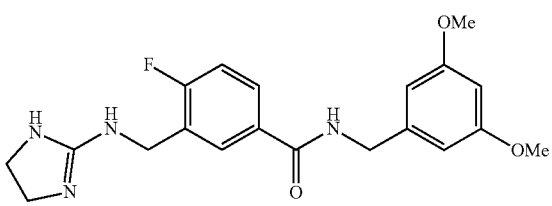
Compound 5o
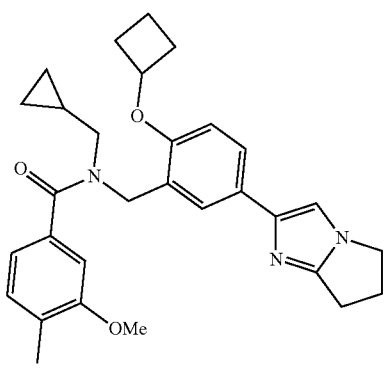
Compound C6

In some aspects, the WDR5 ligand can be, e.g.:
FORMULA 1A
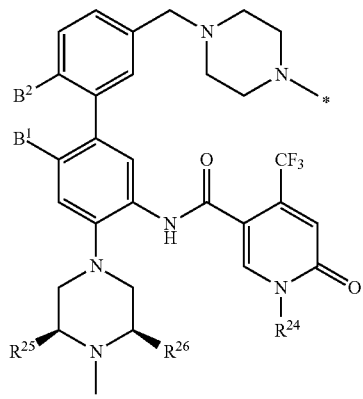
FORMULA 1B
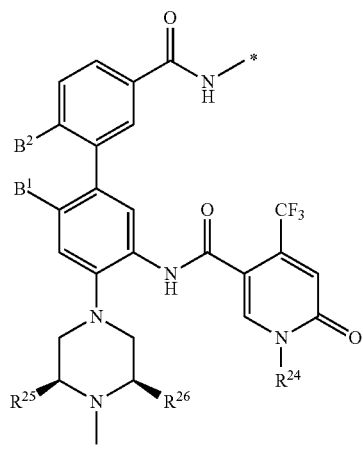
FORMULA 1C
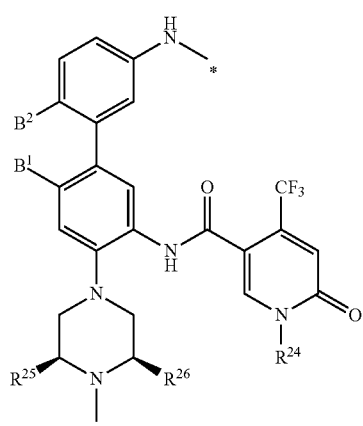
-continued
FORMULA 1D
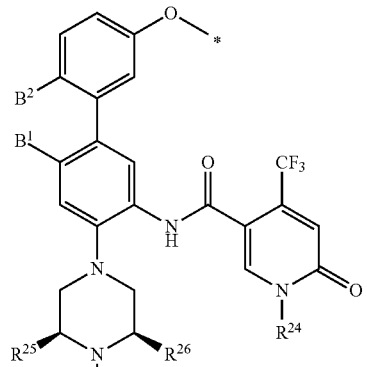
FORMULA 1E
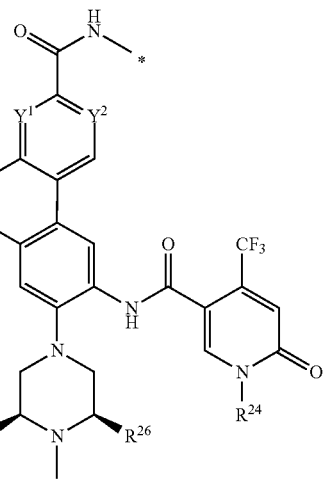
FORMULA 1F
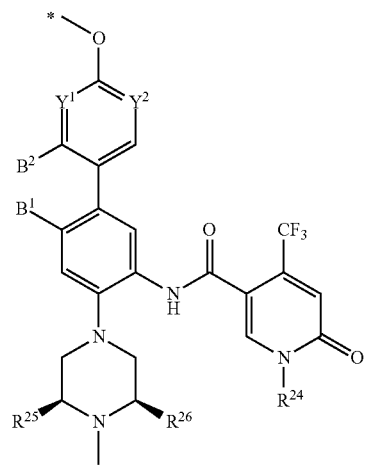

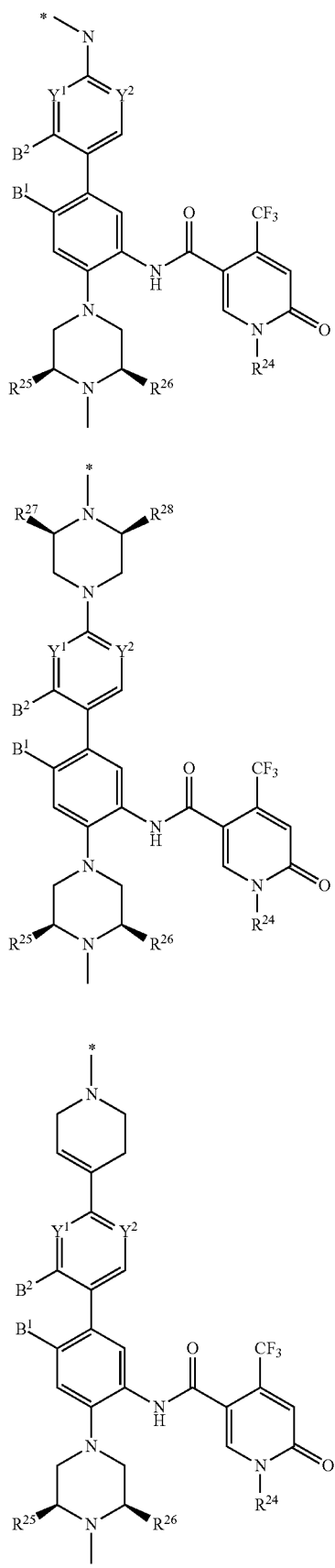
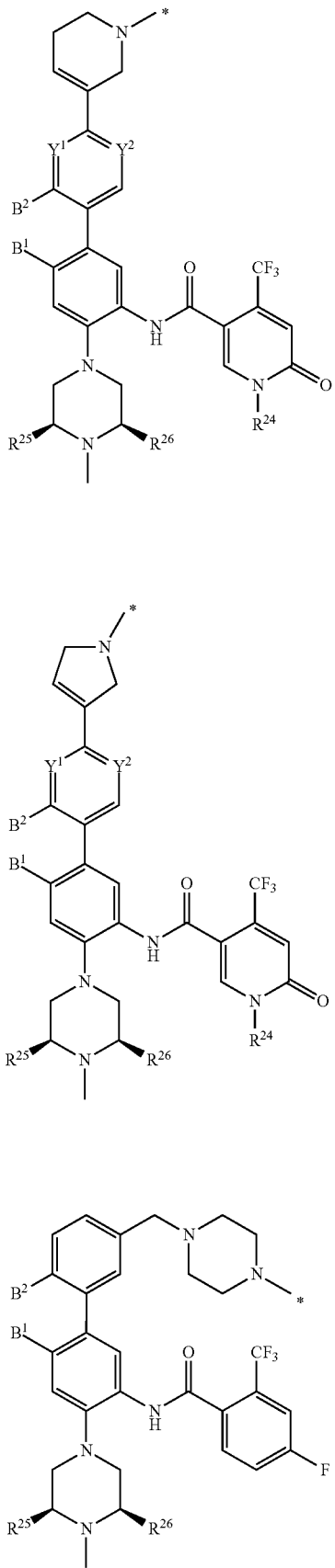

FORMULA 1M
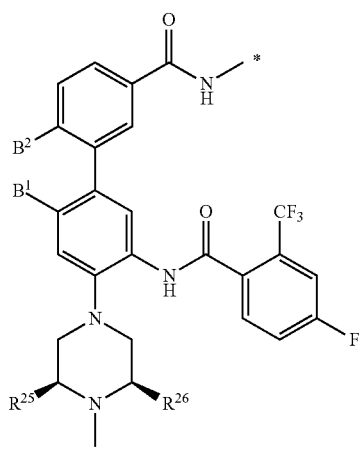
FORMULA 1P
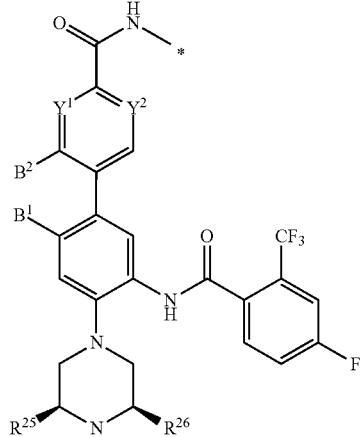
FORMULA 1N
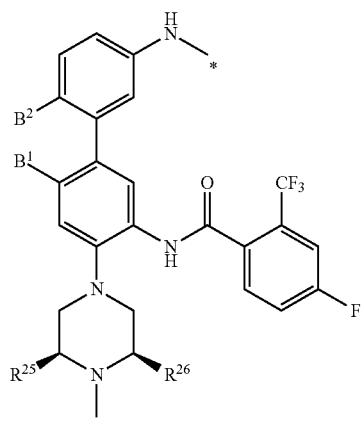
FORMULA 1Q
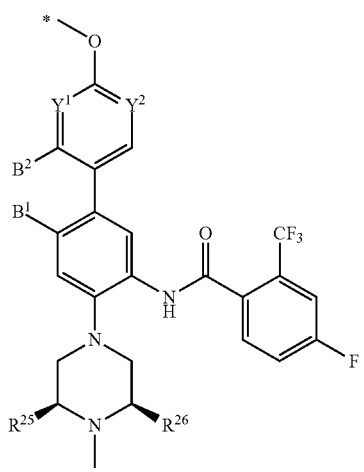
FORMULA 1O
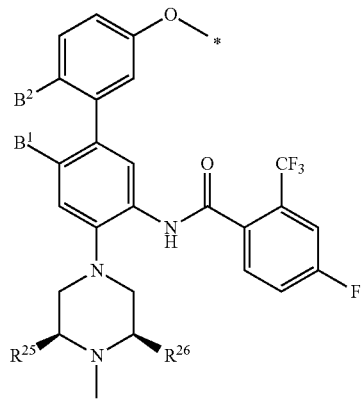
FORMULA 1R
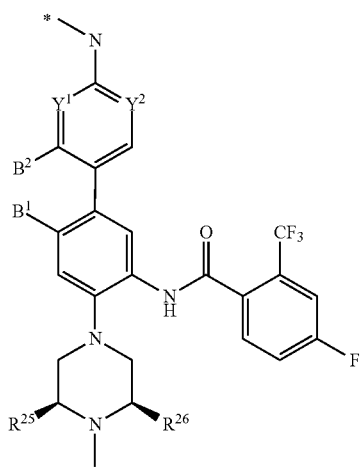

FORMULA 1S
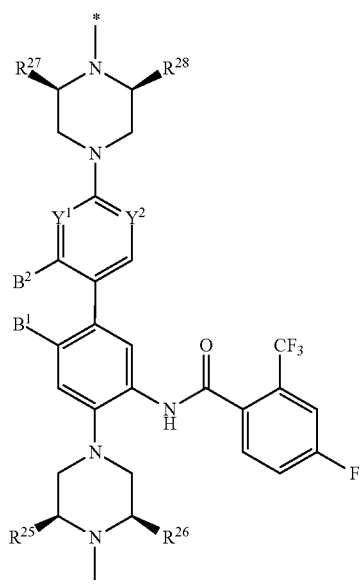
FORMULA 1T
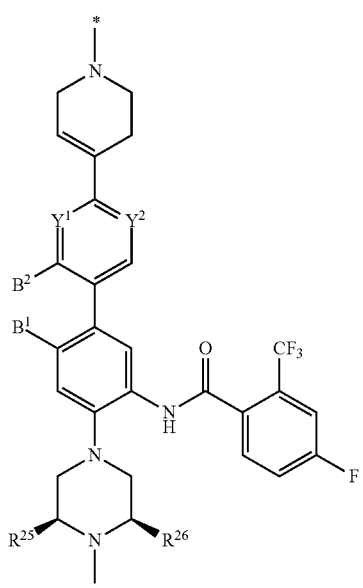
FORMULA 1U
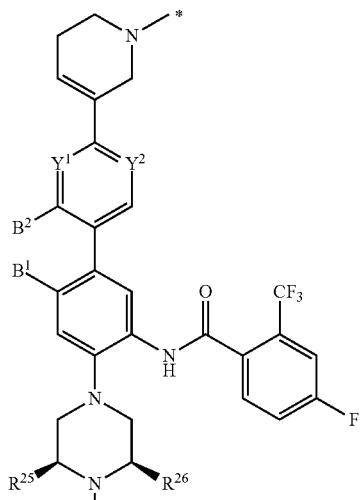
FORMULA 1V
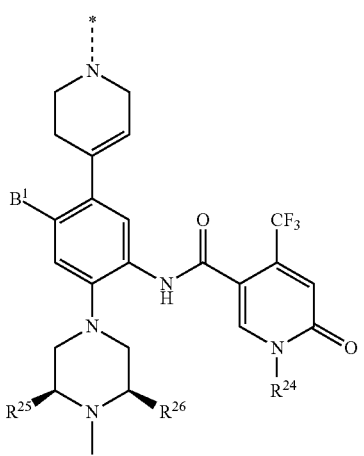
FORMULA 1W FORMULA 1X
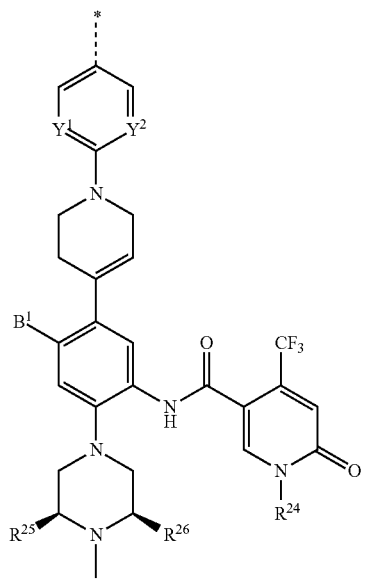
FORMULA 1Y
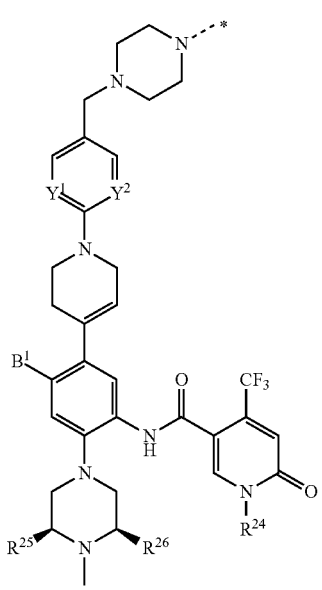
FORMULA 1Z
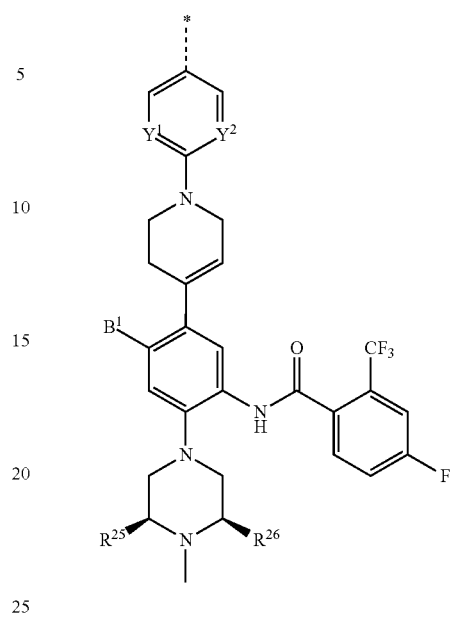
FORMULA 1AA
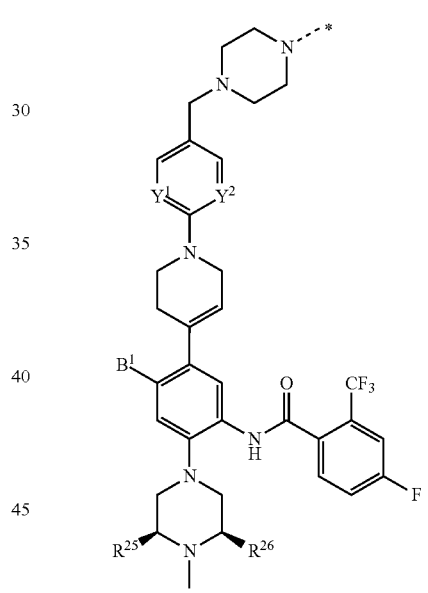
FORMULA 1AB
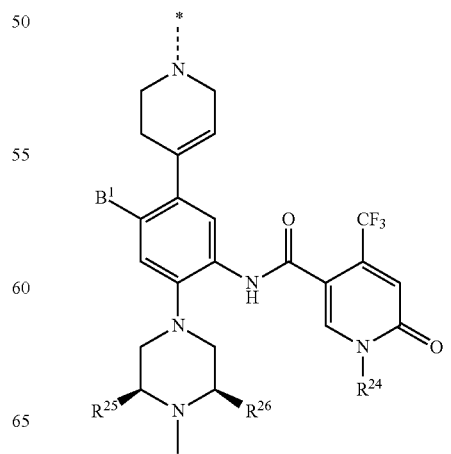

FORMULA 1AC
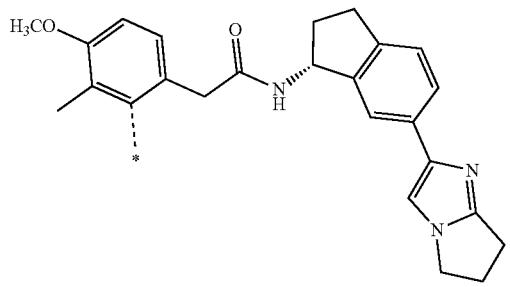
FORMULA 1AD
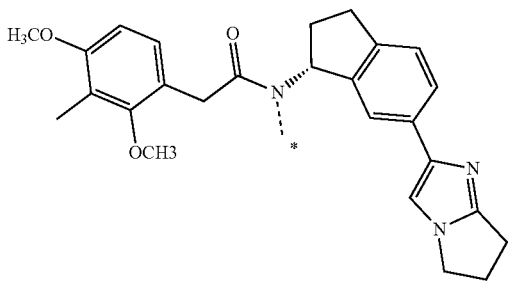
FORMULA 1AE
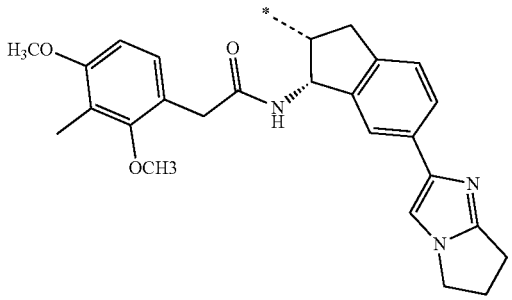
FORMULA 1AF
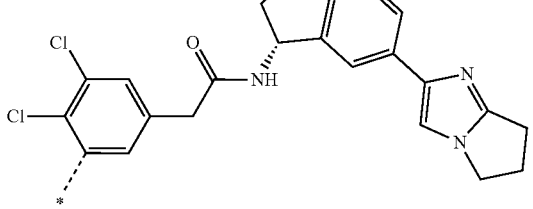
FORMULA 1AG
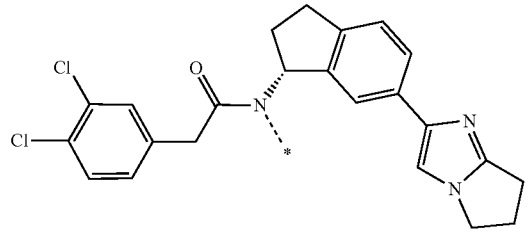
FORMULA 1AH
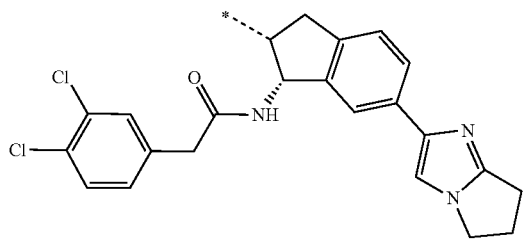
FORMULA 1AI
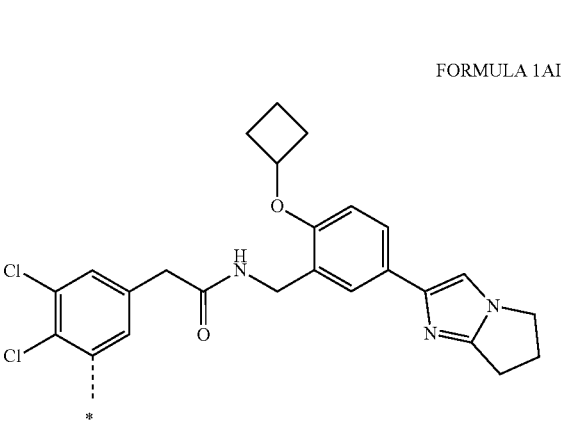
FORMULA 1AJ
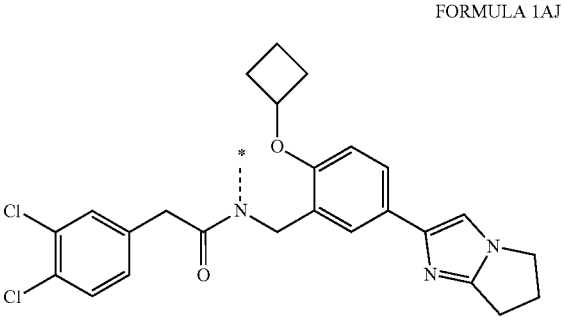
FORMULA 1AK
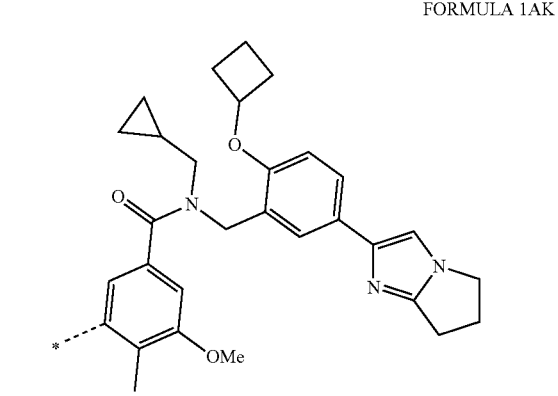

FORMULA 1AL

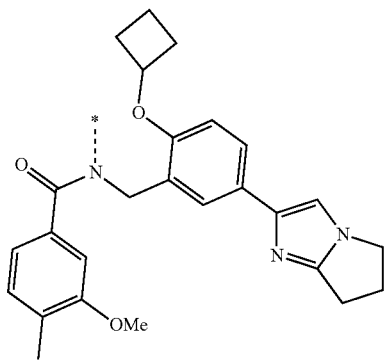

FORMULA 1AM

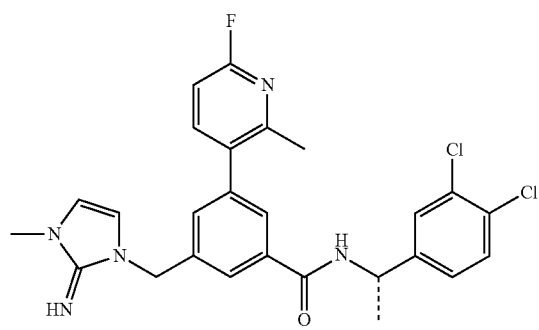

FORMULA 1AN

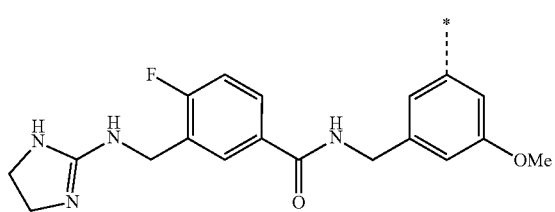

*: Connect to "Linker".

$R^{24}$, $R^{25}$, $R^{26}$, $R^{27}$, and $R^{28}$ are independently selected from H and $CH_3$.

$B^1$ and $B^2$ are independently selected from H and F.

$Y^1$ and $Y^2$ are independently selected from CH and N.

The WDR5 ligand can be bound to WDR5 and/or WDR5 mutant proteins.

Degradation/Disruption Tags

Degradation/Disruption Tags (EL) include but are not limited to:

FORMULA 4A

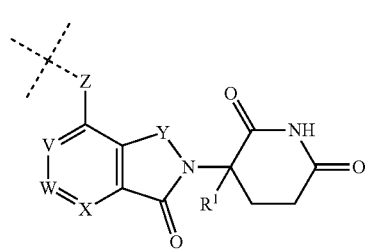

FORMULA 4B

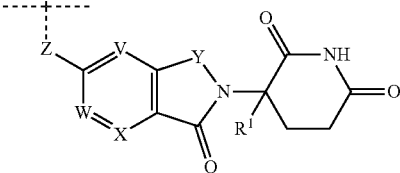

FORMULA 4C

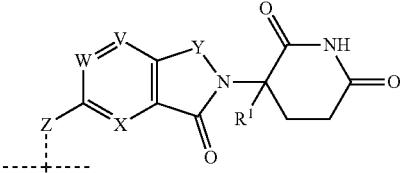

FORMULA 4D

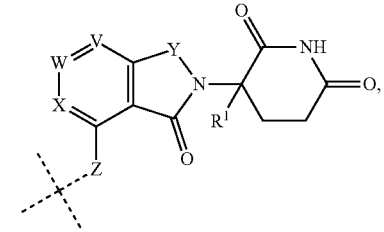

wherein
V, W, and X are independently selected from $CR^2$ and N;
Y is selected from CO, $CR^3R^4$, and N=N;
Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH=CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In an embodiment, the compounds of Formulas 4A-4D may include the following:

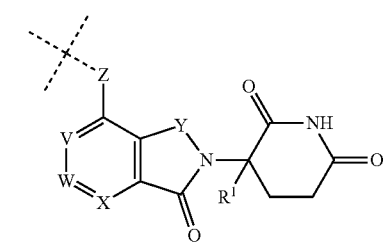

FORMULA 4A

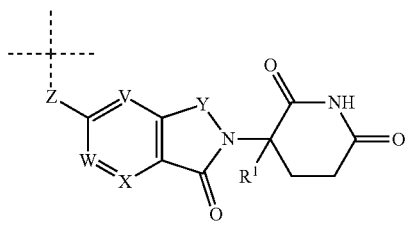

FORMULA 4B

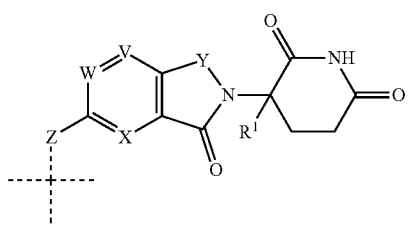

FORMULA 4C

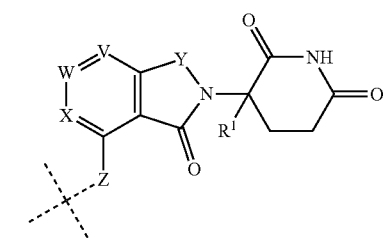

FORMULA 4D wherein
V, W, and X are independently $CR^2$ or N,
Y is CO or $CH_2$,
Z is $CH_2$, NH, or O,
$R^1$ is hydrogen, methyl, or fluoro, and
$R^2$ is hydrogen, halogen, or $C_1$-$C_5$ alkyl.

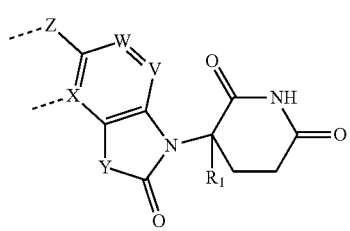

FORMULA 4E

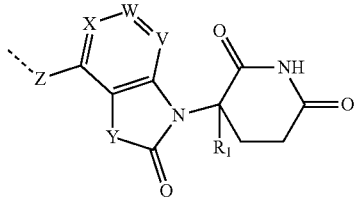

FORMULA 4F

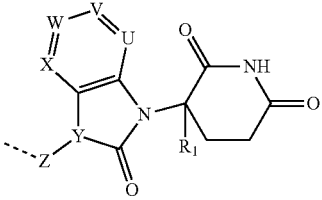

FORMULA 4G

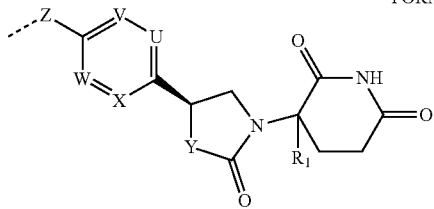

FORMULA 4H

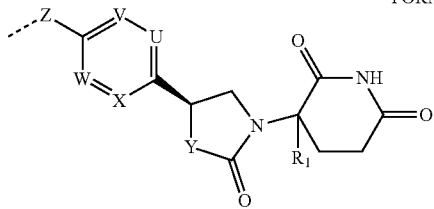

FORMULA 4I wherein
U, V, W, and X are independently selected from $CR^2$ and N;
Y is selected from $CR^3R^4$, $NR^3$ and O; preferably, Y is selected from $CH_2$, NH, $NCH_3$ and O;
Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH=CH, C≡C, NH and O;
$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;
$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

FORMULA 5A

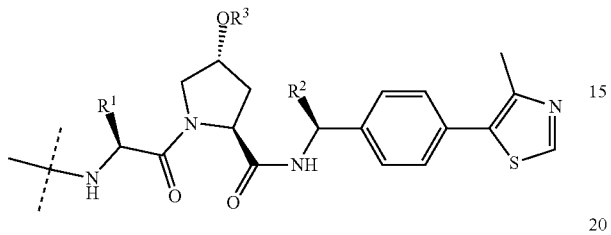

wherein
- $R^1$ and $R^2$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_1$-$C_8$ aminoalkyl, $C_1$-$C_8$ alkylaminoalkyl, $C_3$-$C_7$ cycloalkyl, $C_3$-$C_7$ heterocyclyl, $C_2$-$C_8$ alkenyl, or $C_2$-$C_8$ alkynyl;
- $R^3$ is H, C(O)$C_1$-$C_8$ alkyl, C(O)$C_1$-$C_8$ alkoxyalkyl, C(O)$C_1$-$C_8$ haloalkyl, C(O)$C_1$-$C_8$ hydroxyalkyl, C(O)$C_1$-$C_8$ aminoalkyl, C(O)$C_1$-$C_8$ alkylaminoalkyl, C(O)$C_3$-$C_7$ cycloalkyl, C(O)$C_3$-$C_7$ heterocyclyl, C(O)$C_2$-$C_8$ alkenyl, C(O)$C_2$-$C_8$ alkynyl, C(O)O$C_1$-$C_8$ alkoxyalkyl, C(O)O$C_1$-$C_8$ haloalkyl, C(O)O$C_1$-$C_8$ hydroxyalkyl, C(O)O$C_1$-$C_8$ aminoalkyl, C(O)O$C_1$-$C_8$ alkylaminoalkyl, C(O)O$C_3$-$C_7$ cycloalkyl, C(O)O$C_3$-$C_7$ heterocyclyl, C(O)O$C_2$-$C_8$ alkenyl, C(O)O$C_2$-$C_8$ alkynyl, C(O)N$C_1$-$C_8$ alkoxyalkyl, C(O)N$C_1$-$C_8$ haloalkyl, C(O)N$C_1$-$C_8$ hydroxyalkyl, C(O)N$C_1$-$C_8$ aminoalkyl, C(O)N$C_1$-$C_8$ alkylaminoalkyl, C(O)N$C_3$-$C_7$ cycloalkyl, C(O)N$C_3$-$C_7$ heterocyclyl, C(O)N$C_2$-$C_8$ alkenyl, C(O)N$C_2$-$C_8$ alkynyl, P(O)(OH)$_2$, P(O)(O$C_1$-$C_8$ alkyl)$_2$, or P(O)(O$C_1$-$C_8$ aryl)$_2$.

FORMULA 5B

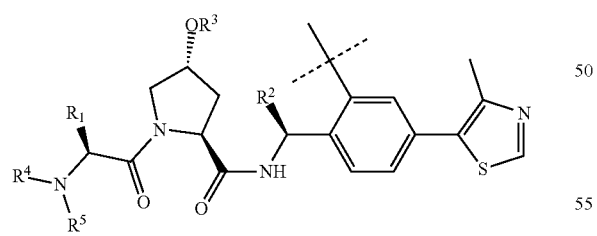

FORMULA 5C

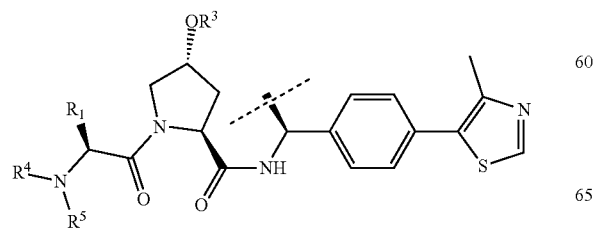

FORMULA 5D

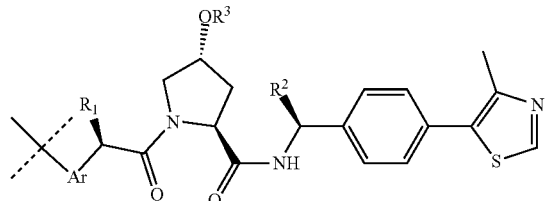

FORMULA 5E

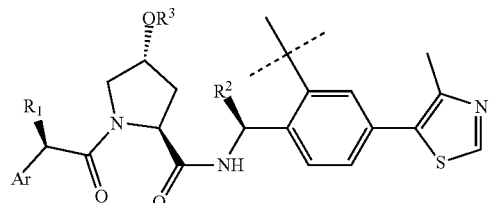

FORMULA 5F

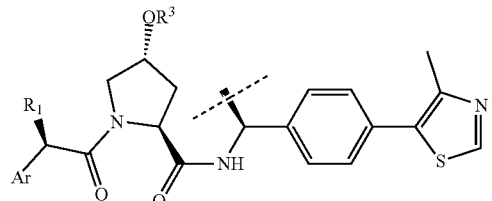

wherein
- $R^1$ and $R^2$ are independently selected from hydrogen, halogen, OH, NH$_2$, CN, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, $R^1$ is selected from iso-propyl or tert-butyl; and $R^2$ is selected from hydrogen or methyl).
- $R^3$ is hydrogen, optionally substituted C(O)$C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)$C_3$-$C_7$ cycloalkyl, optionally substituted C(O)(3-7 membered heterocyclyl), optionally substituted C(O)$C_2$-$C_8$ alkenyl, optionally substituted C(O) $C_2$-$C_8$ alkynyl, optionally substituted C(O)O$C_1$-$C_8$alkoxy$C_1$-$C_8$alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O)O$C_1$-$C_8$alkylamino$C_1$-$C_8$alkyl, optionally substituted C(O) O$C_3$-$C_7$ cycloalkyl, optionally substituted C(O)O(3-7 membered heterocyclyl), optionally substituted C(O) O$C_2$-$C_8$ alkenyl, optionally substituted C(O)O$C_2$-$C_8$ alkynyl, optionally substituted C(O)N$C_1$-$C_8$alkoxy$C_1$-$C_8$alkyl, optionally substituted C(O)N$C_1$-$C_8$ haloalkyl, optionally substituted C(O)N$C_1$-$C_8$ hydroxyalkyl, optionally substituted C(O)N$C_1$-$C_8$ aminoalkyl, optionally substituted C(O)N$C_1$-$C_8$alkylamino$C_1$-$C_8$alkyl, optionally substituted C(O)NC$_3$-C$_7$ cycloalkyl, optionally substituted C(O)N(3-7 membered heterocyclyl), optionally substituted C(O)NC$_2$-C$_8$ alkenyl, optionally substituted C(O)NC$_2$-C$_8$ alkynyl, optionally substituted P(O)(OH)$_2$, optionally substituted P(O)(OC$_1$-C$_8$ alkyl)$_2$, and optionally substituted P(O)(OC$_1$-C$_8$ aryl)$_2$; and R$^4$ and R$^5$ are independently selected from hydrogen, COR$^6$, CO$_2$R$^6$, CONR$^6$R$^7$, SOR$^6$, SO$_2$R$^6$, SO$_2$NR$^6$R$^7$, optionally substituted C$_1$-C$_8$ alkyl, optionally substituted C$_1$-C$_8$alkoxyC$_1$-C$_8$alkyl, optionally substituted C$_1$-C$_8$alkylaminoC$_1$-C$_8$alkyl, optionally substituted 3-8 membered cycloalkyl, optionally substituted 3-8 membered heterocyclyl, optionally substituted aryl, and optionally substituted heteroaryl, wherein R$^6$ and R$^7$ are independently selected from hydrogen, optionally substituted C$_1$-C$_8$ alkyl, optionally substituted C$_1$-C$_8$ alkoxy, optionally substituted C$_1$-C$_8$alkoxyC$_1$-C$_8$alkyl, optionally substituted C$_1$-C$_8$alkylaminoC$_1$-C$_8$alkyl, optionally substituted 3-8 membered cycloalkyl, optionally substituted 3-8 membered heterocyclyl, optionally substituted aryl, and optionally substituted heteroaryl, or R$^4$ and R$^5$; R$^6$ and R$^7$ together with the atom to which they are connected form a 4-8 membered cycloalkyl or heterocyclyl ring;

Ar is selected from aryl and heteroaryl, each of which is optionally substituted with one or more substituents independently selected from F, Cl, CN, NO$_2$, OR$^8$, NR$^8$R$^9$, COR$^8$, CO$_2$R$^8$, CONR$^8$R$^9$, SOR$^8$, SO$_2$R$^8$, SO$_2$NR$^9$R$^{10}$, NR$^9$COR$^{10}$, NR$^8$C(O)NR$^9$R$^{10}$, NR$^9$SOR$^{10}$, NR$^9$SO$_2$R$^{10}$, optionally substituted C$_1$-C$_6$ alkyl, optionally substituted C$_1$-C$_6$ alkoxyalkyl, optionally substituted C$_1$-C$_6$ haloalkyl, optionally substituted C$_1$-C$_6$ hydroxyalkyl, optionally substituted C$_1$-C$_6$alkylaminoC$_1$-C$_6$alkyl, optionally substituted C$_3$-C$_7$ cycloalkyl, optionally substituted 3-7 membered heterocyclyl, optionally substituted C$_2$-C$_6$ alkenyl, optionally substituted C$_2$-C$_6$ alkynyl, optionally substituted aryl, and optionally substituted C$_4$-C$_5$ heteroaryl, wherein R$^8$, R$^9$, and R$^{10}$ are independently selected from null, hydrogen, optionally substituted C$_1$-C$_6$ alkyl, optionally substituted C$_2$-C$_6$ alkenyl, optionally substituted C$_2$-C$_6$ alkynyl, optionally substituted C$_3$-C$_7$ cycloalkyl, optionally substituted 3-7 membered heterocyclyl, optionally substituted aryl, and optionally substituted heteroaryl, or R$^8$ and R$^9$; R$^9$ and R$^{10}$ together with the atom to which they are connected form a 4-8 membered cycloalkyl or heterocyclyl ring.

FORMULA 6A

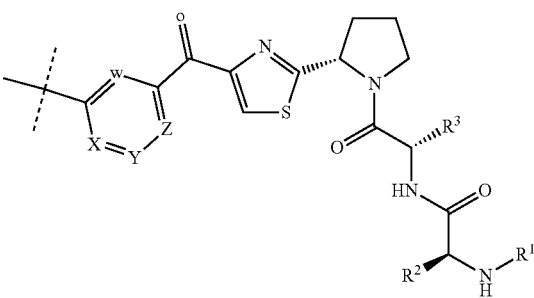

wherein

R$^1$, R$^2$, R$^3$, and R$^4$ are independently hydrogen, C$_1$-C$_8$ alkyl, C$_1$-C$_8$ alkoxyalkyl, C$_1$-C$_8$ haloalkyl, C$_1$-C$_8$ hydroxyalkyl, C$_3$-C$_7$ cycloalkyl, C$_3$-C$_7$ heterocyclyl, C$_2$-C$_8$ alkenyl, or C$_2$-C$_8$ alkynyl, and V, W, X, and Z are independently CR$^4$ or N.

And

FORMULA 6B

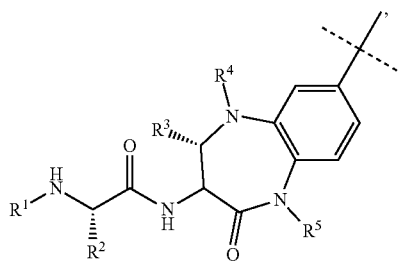

wherein

R$^1$, R$^2$, and R$^3$ are independently selected from hydrogen, halogene, optionally substituted C$_1$-C$_8$ alkyl, optionally substituted C$_1$-C$_8$alkoxyC$_1$-C$_8$alkyl, optionally substituted C$_1$-C$_8$ haloalkyl, optionally substituted C$_1$-C$_8$ hydroxyalkyl, optionally substituted C$_3$-C$_7$ cycloalkyl, optionally substituted 3-7 membered heterocyclyl, optionally substituted C$_2$-C$_8$ alkenyl, and optionally substituted C$_2$-C$_8$ alkynyl;

R$^4$ and R$^5$ are independently selected from hydrogen, COR$^6$, CO$_2$R$^6$, CONR$^6$R$^7$, SOR$^6$, SO$_2$R$^6$, SO$_2$NR$^6$R$^7$, optionally substituted C$_1$-C$_8$ alkyl, optionally substituted C$_1$-C$_8$alkoxyC$_1$-C$_8$alkyl optionally substituted C$_1$-C$_8$alkylaminoC$_1$-C$_8$alkyl, optionally substituted aryl-C$_1$-C$_8$alkyl, optionally substituted 3-8 membered cycloalkyl, optionally substituted 3-8 membered heterocyclyl, optionally substituted aryl, and optionally substituted heteroaryl, wherein R$^6$ and R$^7$ are independently selected from hydrogen, optionally substituted C$_1$-C$_8$ alkyl, optionally substituted C$_1$-C$_8$alkoxyC$_1$-C$_8$alkyl, optionally substituted C$_1$-C$_8$alkylaminoC$_1$-C$_8$alkyl, optionally substituted 3-8 membered cycloalkyl, optionally substituted 3-8 membered heterocyclyl, optionally substituted aryl, and optionally substituted heteroaryl, or R$^6$ and R$^7$ together with the atom to which they are connected form a 4-8 membered cycloalkyl or heterocyclyl ring.

In some aspects, the degradation/disruption tag can be, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Fliroyuki Suda et al., 1976), MV1 (Varfolomeev et al., 2007), LCL161 (Weisberg et al., 2010), FK506 (Liu et al., 1991) rapamycin (Fan et al., 2017; Rodrik-Outmezguine et al., 2016), and/or analogs thereof.

In some aspects, the degradation/disruption tag can be, e.g., one of the following structures:
FORMULA 7A
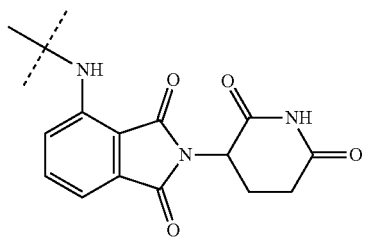
FORMULA 7B
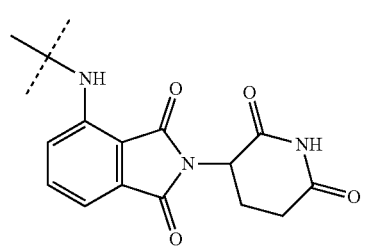
FORMULA 7C
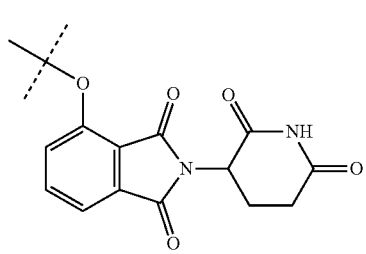
FORMULA 7D
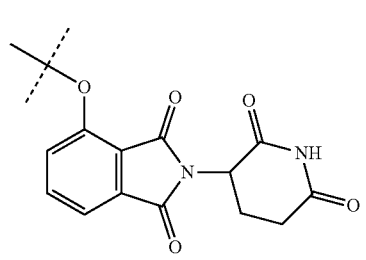
FORMULA 7E
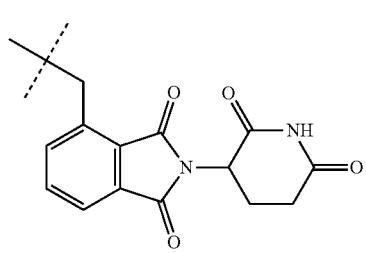
FORMULA 7F
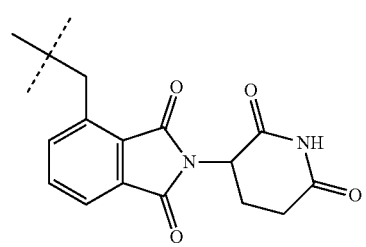
FORMULA 7G
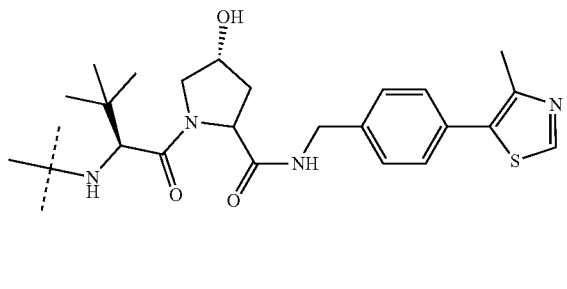
FORMULA 7H
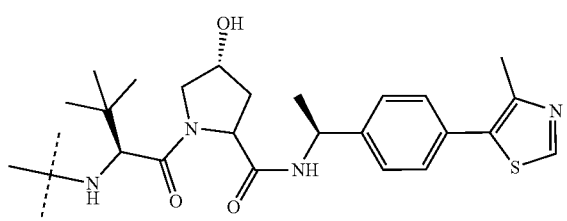
FORMULA 7I
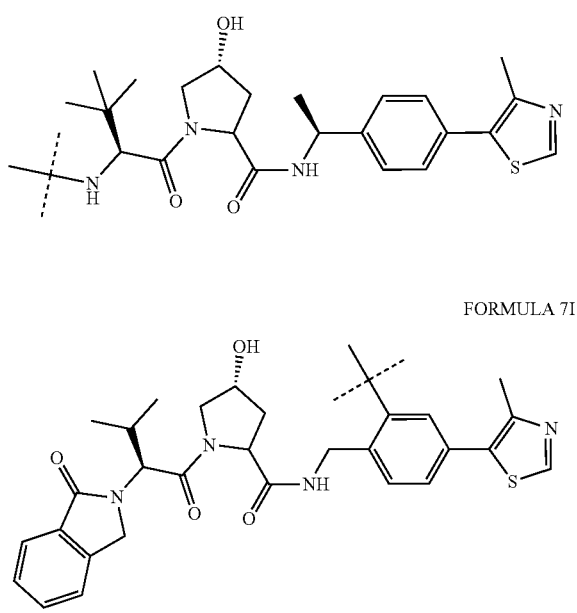
FORMULA 7J
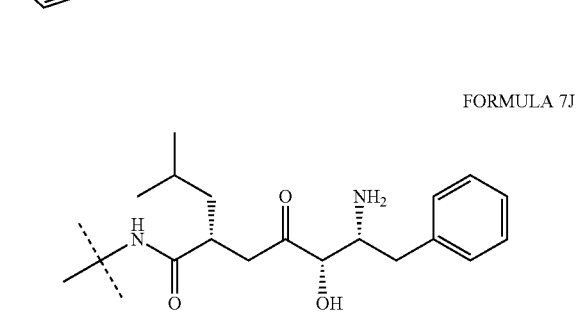
FORMULA 7K
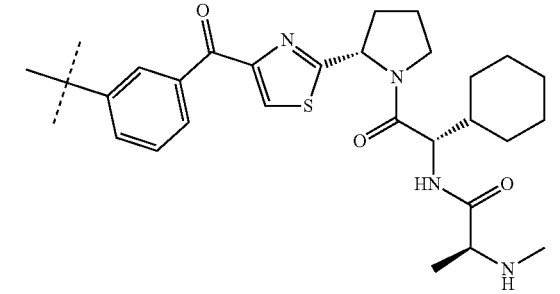

-continued

FORMULA 7L

FORMULA 7M

FORMULA 7N

FORMULA 7O

-continued

FORMULA 7P

FORMULA 7Q

FORMULA 7R

FORMULA 7S

FORMULA 7T

FORMULA 7U

FORMULA 7V
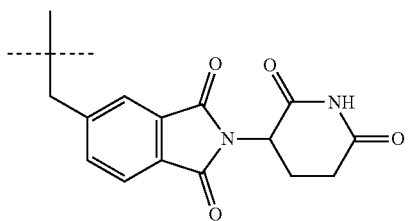
FORMULA 7W
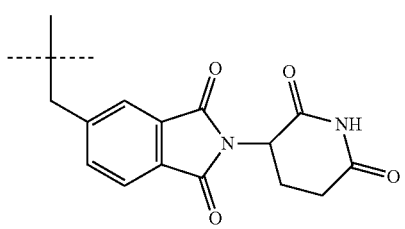
FORMULA 7X
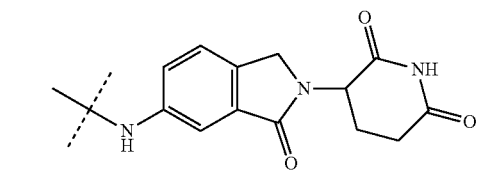
FORMULA 7Y
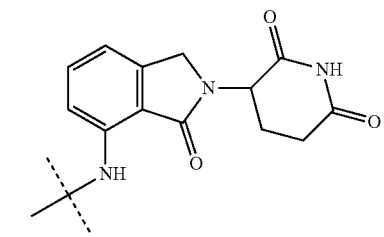
FORMULA 7Z
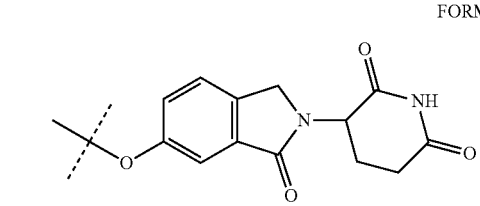
FORMULA 7AA
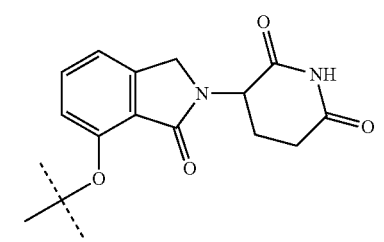
FORMULA 7AB
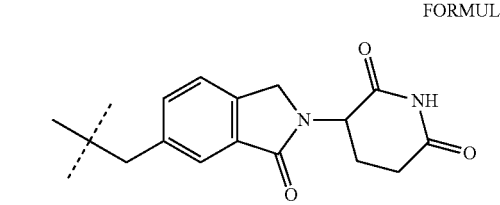
FORMULA 7AC
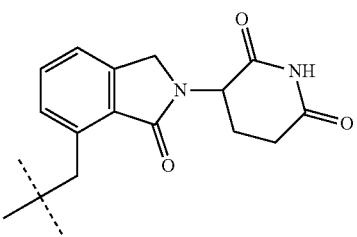
FORMULA 7AD
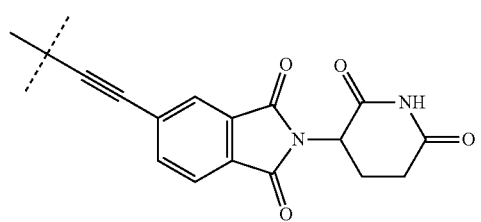
FORMULA 7AE
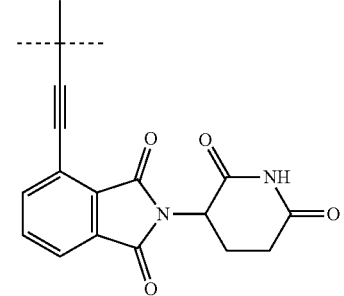
FORMULA 7AF
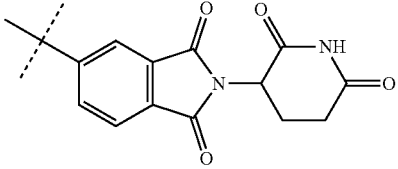
FORMULA 7AG
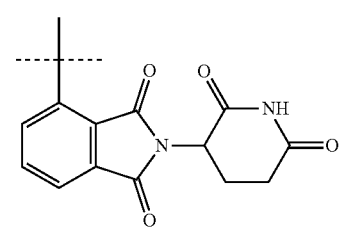
FORMULA 7AH
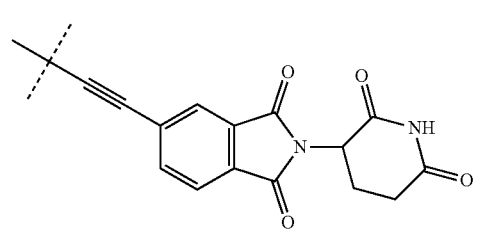

FORMULA 7AI
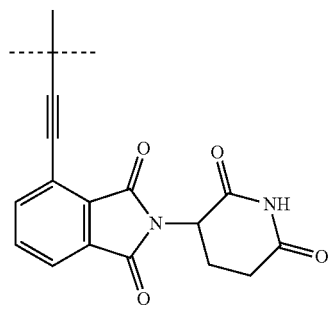
FORMULA 7AJ
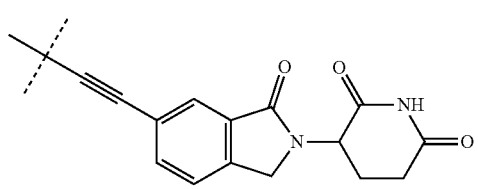
FORMULA 7AK
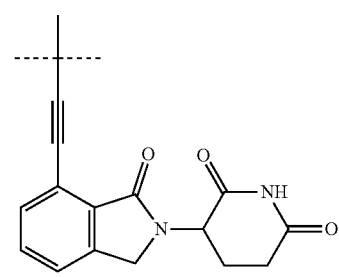
FORMULA 7AL
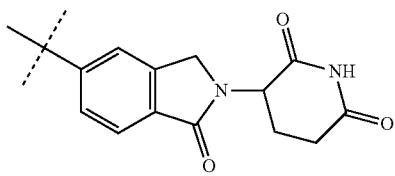
FORMULA 7AM
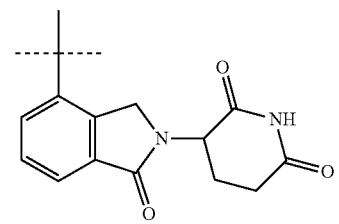
FORMULA 7AN
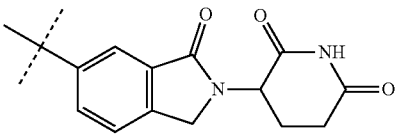
FORMULA 7AO
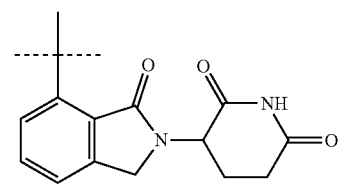
FORMULA 7AP
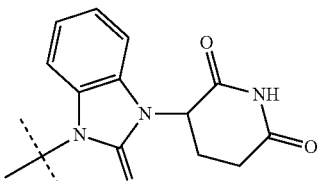
FORMULA 7AQ
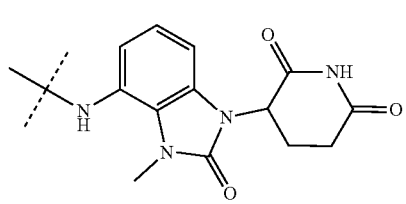
FORMULA 7AR
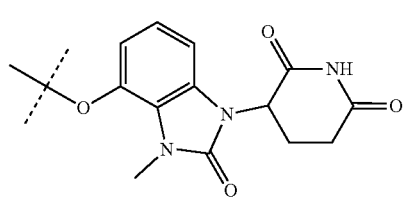
FORMULA 7AS
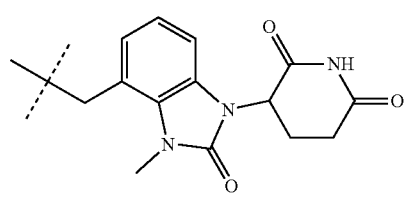
FORMULA 7AT
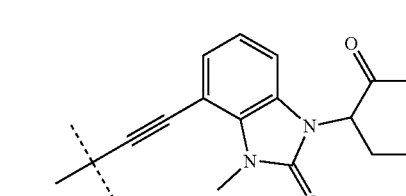
FORMULA 7AU
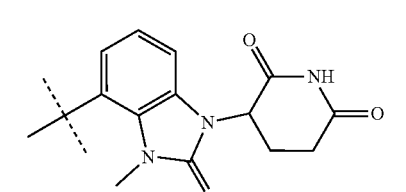
FORMULA 7AV
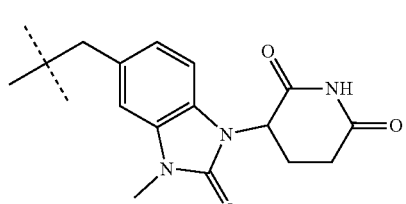
FORMULA 7AW
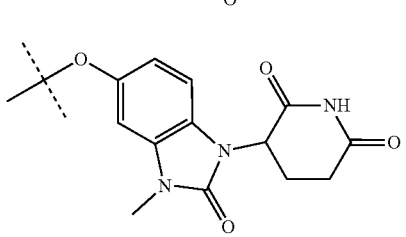

FORMULA 7AX
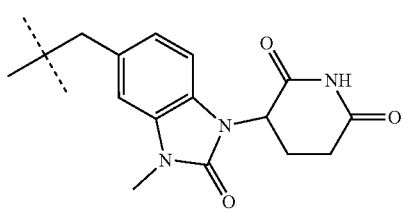
FORMULA 7AY
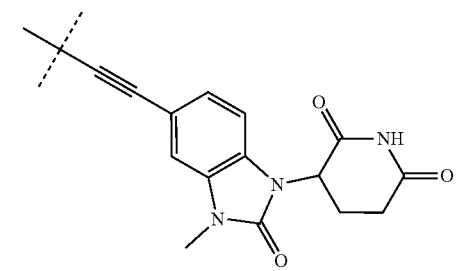
FORMULA 7AZ
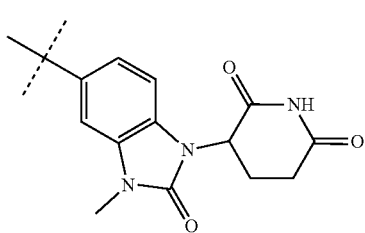
FORMULA 7BA
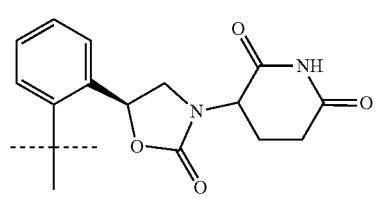
FORMULA 7BB
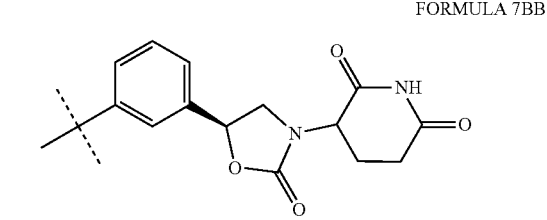
FORMULA 7BC
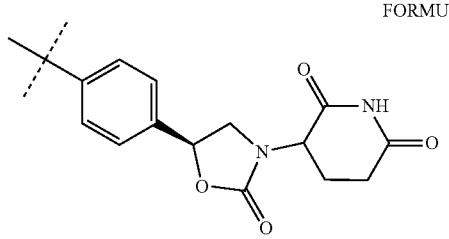
FORMULA 7BD
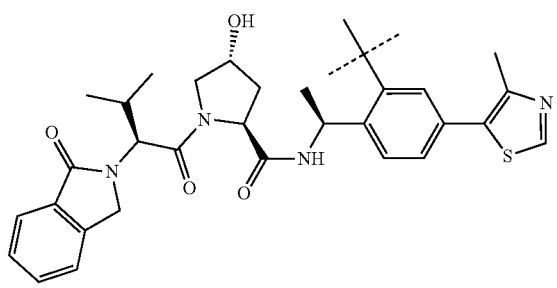
FORMULA 7BE
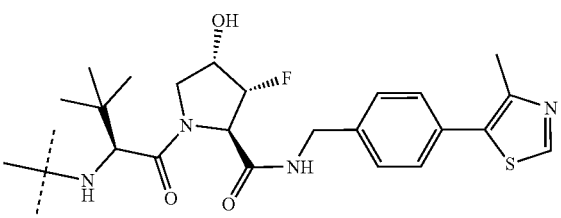
FORMULA 7BF
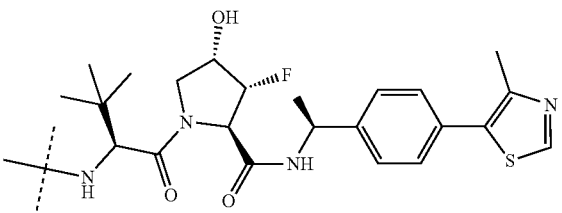
FORMULA 7BG
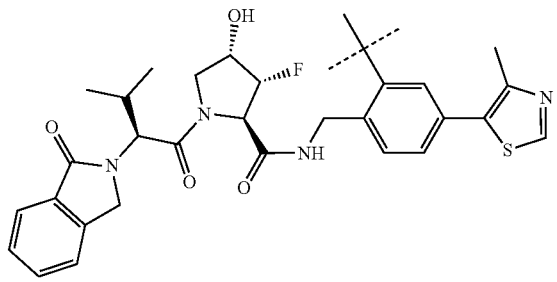
FORMULA 7BH
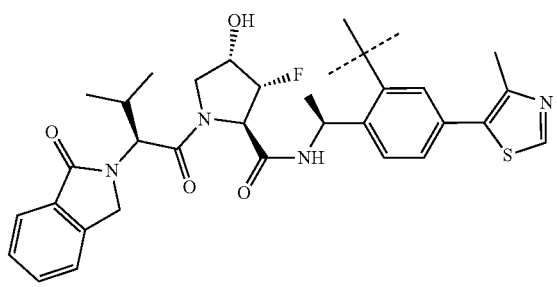
FORMULA 7BI
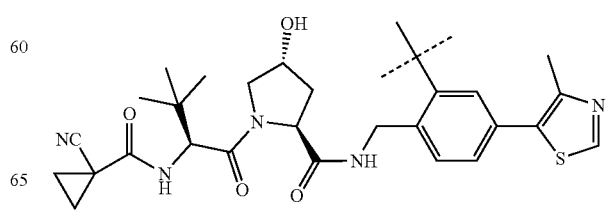

FORMULA 7BJ

FORMULA 7BK
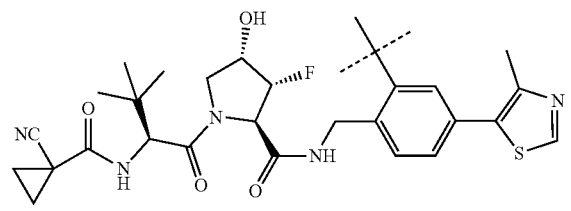
FORMULA 7BL
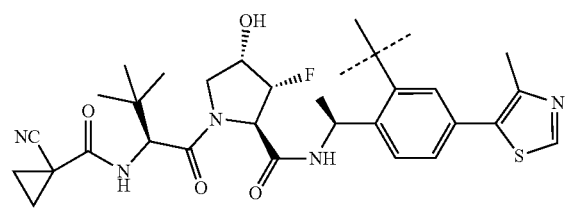
FORMULA 7BM

FORMULA 7BN
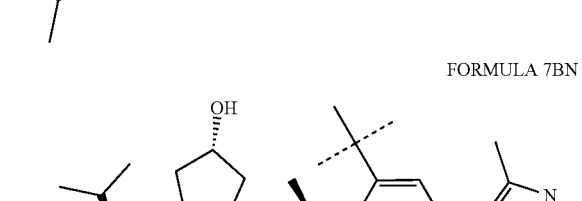
FORMULA 7BO
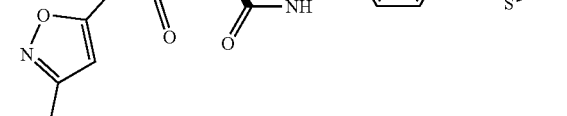
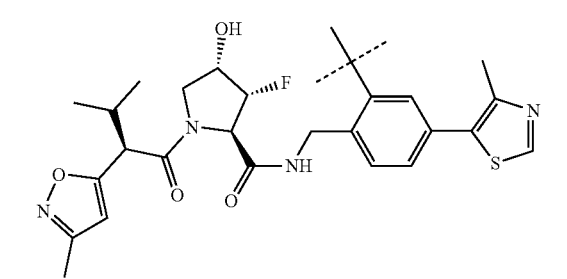
FORMULA 7BP
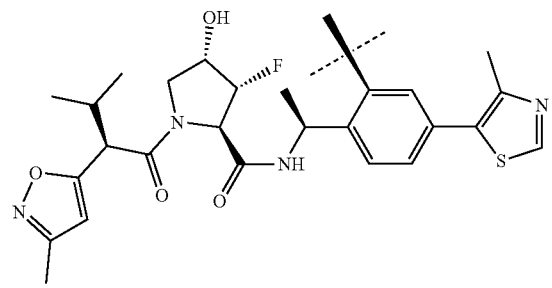
FORMULA 7BQ
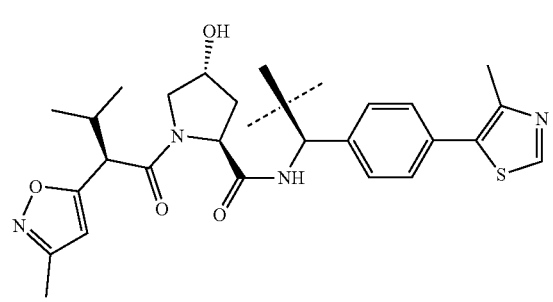
FORMULA 7BR
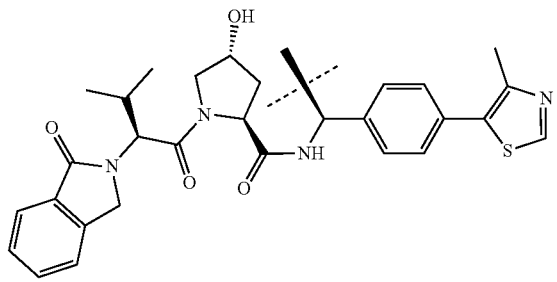
FORMULA 7BS
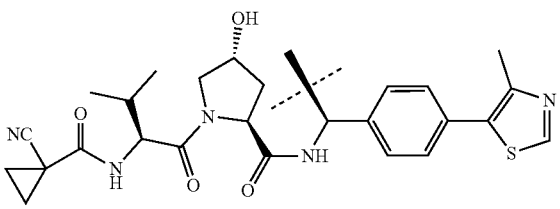
FORMULA 7BT
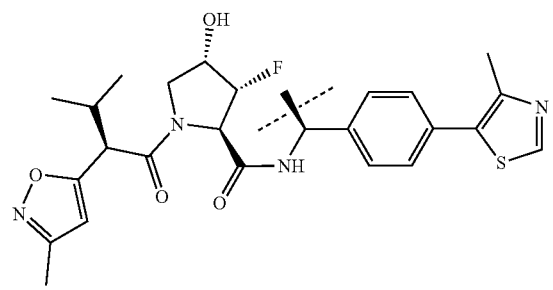

-continued
FORMULA 7BU
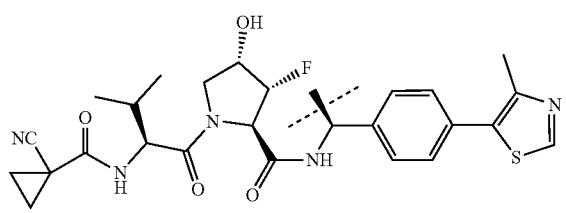
FORMULA 7BV
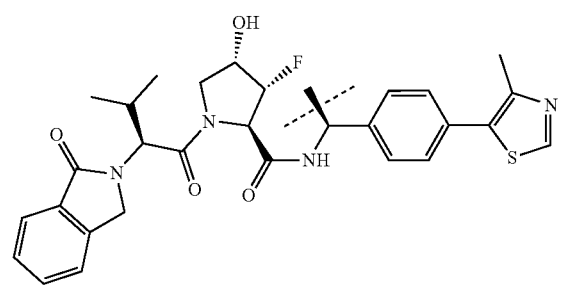
FORMULA 7BW
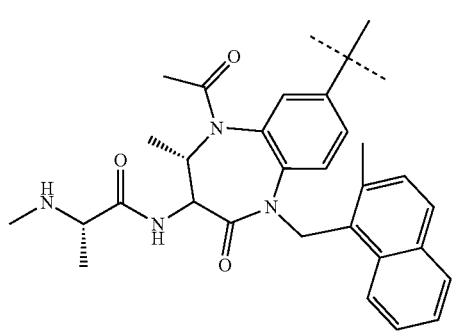
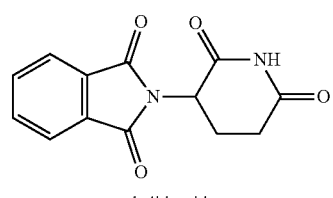
thalidomide
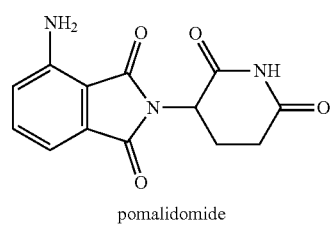
pomalidomide
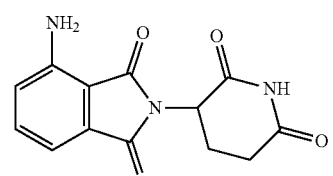
lenalidomide
-continued
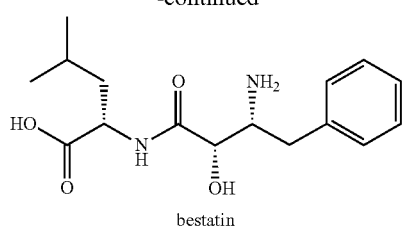
bestatin
MV1
LCL161
nutlin-3a
RG7112

135
-continued
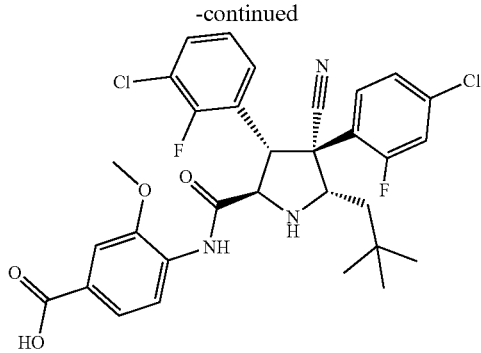
RG7338
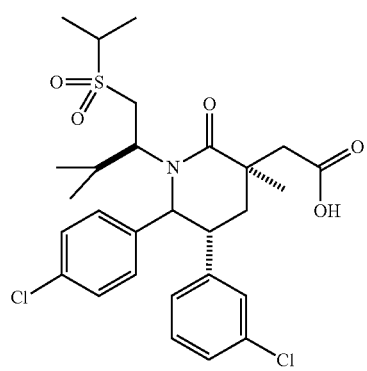
AMG232
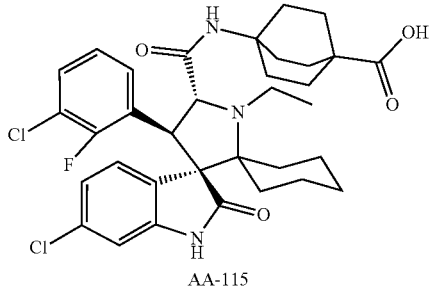
AA-115
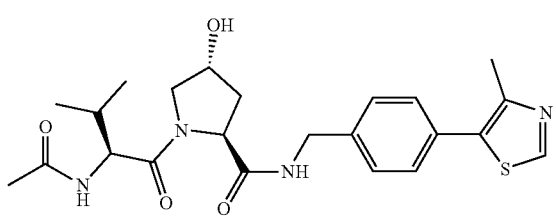
VH032
136
-continued
Compound W2
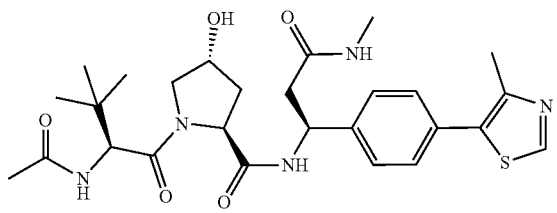
Compound W3
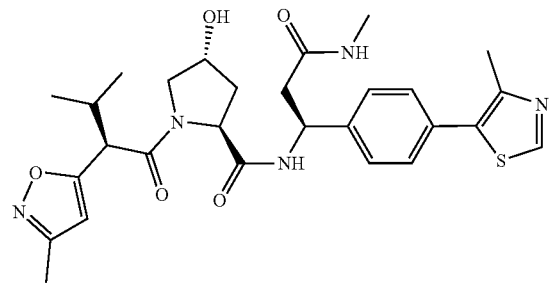
Compound W4
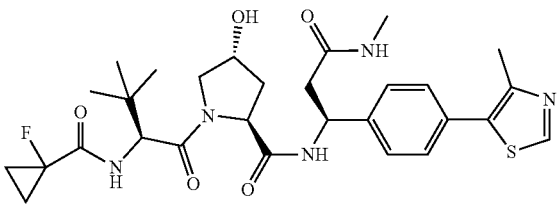
Compound W5
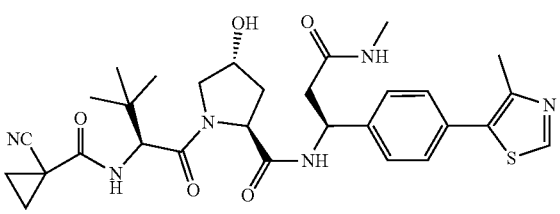
Compound W6
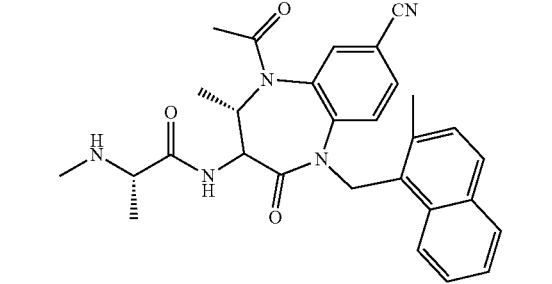
Compound W1

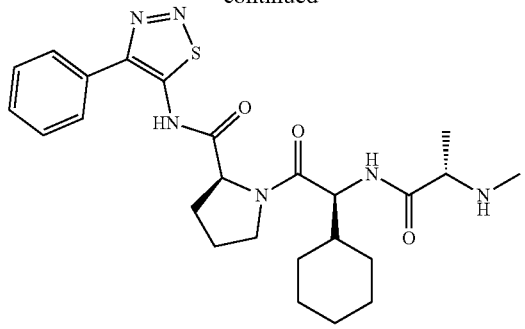

GDC-0152

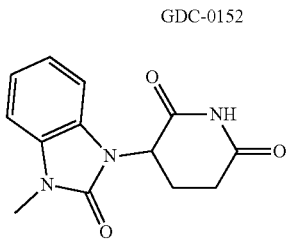

Compound W7

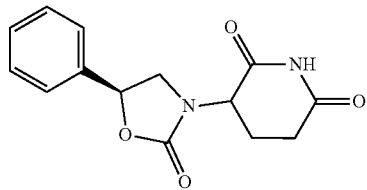

Compound W8

In some aspects, the degradation/disruption tag can bind to a ubiquitin ligase (e.g., an E3 ligase such as a cereblon E3 ligase, a VHL E3 ligase, a MDM2 ligase, a TRIM21 ligase, a TRIM24 ligase, a KEAP1 E3 ligase and/or an IAP ligase) and/or serve as a hydrophobic group or a tag that leads to WDR5 protein misfolding.

Linkers

In all of the above-described compounds, the WDR5 ligand is conjugated to the degradation/disruption tag through a linker. The linker can include, for example, acyclic or cyclic saturated or unsaturated carbon, ethylene glycol, amide, amino, ether, urea, carbamate, aromatic, heteroaromatic, heterocyclic and/or carbonyl containing groups with different lengths.

In some aspects, the linker can be a moiety of:

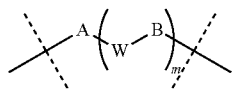

FORMULA 8 wherein

A, W and B, at each occurrence, are independently selected from null, or bivalent moiety selected from R'-R", R'COR", R'CO$_2$R", R'C(O)N(R$^1$)R", R'C(S)N (R$^1$)R", R'OR", R'OC(O)R", R'OC(O)OR", R'OCON (R$^1$)R", R'SR", R'SOR", R'SO$_2$R", R'SO$_2$N(R$^1$)R", R'N (R$^1$)R", R'NR$^1$COR", R'NR$^1$C(O)OR", R'NR$^1$CON (R$^2$)R", R'NR$^1$C(S)R", R'NR$^2$S(O)R", R'NR$^1$S(O)$_2$R", and R'NR$^1$S(O)$_2$N(R$^2$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^1$ and R$^2$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^1$ and R$^2$, R' and R$^1$, R' and R$^2$, R" and R$^1$, R" and R$^2$ together with the atom to which they are connected form a 3-20 membered cycloalkyl or 4-20 membered heterocyclyl ring; and m is 0 to 15.

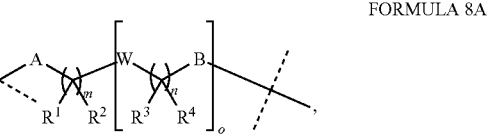

FORMULA 8A wherein

R$^1$, R$^2$, R$^3$ and R$^4$, at each occurrence, are independently selected from hydrogen, halogen, hydroxyl, amino, cyano, nitro, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$ alkylamino, and optionally substituted C$_1$-C$_8$ alkylaminoC$_1$-C$_8$ alkyl, optionally substituted 3-10 membered carbocyclyl, optionally substituted 3-8 membered cycloalkoxy, optionally substituted 3-10 membered carbocyclylamino, optionally substituted 4-8 membered membered heterocyclyl, optionally substituted aryl, and optionally substituted heteroaryl, or $R^1$ and $R^2$, $R^3$ and $R^4$ together with the atom to which they are connected form a 3-20 membered cycloalkyl or 4-20 membered heterocyclyl ring;

A, W and B, at each occurrence, are independently selected from null, or bivalent moiety selected from R'-R", R'COR", R'CO$_2$R", R'C(O)N($R^5$)R", R'C(S)N($R^5$)R", R'OR", R'OC(O)R", R'OC(O)OR", R'OCONR$^5$R", R'SR", R'SOR", R'SO$_2$R", R'SO$_2$N($R^5$)R", R'N($R^5$)R", R'NR$^5$COR", R'NR$^5$C(O)OR", R'NR$^5$CON($R^6$)R", R'NR$^5$C(S)R", R'NR$^6$S(O)R", R'NR$^5$S(O)$_2$R", and R'NR$^5$S(O)$_2$N($R^6$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;

n, at each occurrence, is 0 to 15; and is 0 to 15.

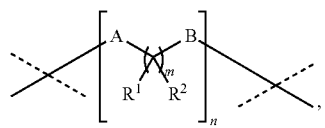

FORMULA 8B wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'-R", R'COR", R'CO$_2$R", R'C(O)N($R^3$)R", R'C(S)N($R^3$)R", R'OR", R'OC(O)R", R'OC(O)OR", R'OCON($R^3$)R", R'SR", R'SOR", R'SO$_2$R", R'SO$_2$N($R^3$)R", R'N($R^3$)R", R'NR$^3$COR", R'NR$^3$C(O)OR", R'NR$^3$CON($R^4$)R", R'NR$^3$C(S)R", R'NR$^4$S(O)R", R'NR$^3$S(O)$_2$R", and R'NR$^3$S(O)$_2$N($R^4$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^3$ and $R^4$ are independently selected from hydrogen, optionally substituted $C_1$-$C_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R'', R$^3$ and R$^4$, R' and R$^3$, R' and R$^4$, R'' and R$^3$, R'' and R$^4$ together with the atom to which they are connected form a 3-20 membered cycloalkyl or 4-20 membered heterocyclyl ring;

m, at each occurrence, is 0 to 15; and n is 0 to 15.

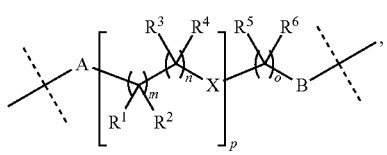

FORMULA 8C wherein

X is selected from O, NH, and NR$^7$;

R$^1$, R$^2$, R$^3$, R$^4$, R$^5$, and R$^6$, at each occurrence, are independently selected from hydrogen, halogen, hydroxyl, amino, cyano, nitro, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxy C$_1$-C$_8$ alkyl, optionally substituted C$_1$-C$_8$ haloalkyl, optionally substituted C$_1$-C$_8$ hydroxyalkyl, optionally substituted C$_1$-C$_8$ alkylamino, optionally substituted C$_1$-C$_8$ alkylaminoC$_1$-C$_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'-R'', R'COR'', R'CO$_2$R'', R'C(O)N(R$^8$)R'', R'C(S)N(R$^8$)R'', R'OR'', R'OC(O)R'', R'OC(O)OR'', R'OCON(R$^8$)R'', R'SR'', R'SOR'', R'SO$_2$R'', R'SO$_2$N(R$^8$)R'', R'N(R$^8$)R'', R'NR$^8$COR'', R'NR$^8$C(O)OR'', R'NR$^8$CON(R$^9$)R'', R'NR$^8$C(S)R'', R'NR$^8$S(O)R'', R'NR$^8$S(O)$_2$R'', and R'NR$^8$S(O)$_2$N(R$^9$)R'', wherein R' and R'' are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^7$, R$^8$ and R$^9$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R'', R$^8$ and R$^9$, R' and R$^8$, R' and R$^9$, R'' and R$^8$, R'' and R$^9$ together with the atom to which they are connected form a 3-20 membered cycloalkyl or 4-20 membered heterocyclyl ring;

m, at each occurrence, is 0 to 15;

n, at each occurrence, is 0 to 15;

is 0 to 15; and p is 0 to 15.

In some aspects of Formulae 8, 8A, 8B, and 8C, the linker moiety comprises a ring selected from the group consisting of a 3 to 13 membered ring, a 3 to 13 membered fused ring, a 3 to 13 membered bridged ring, and a 3 to 13 membered spiro ring.

In some aspects of Formulae 8, 8A, 8B, and 8C, the linker moiety comprises a ring selected from the group consisting of Formula C1, C2, C3, C4 and C5:

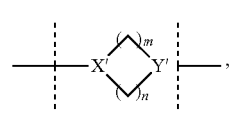

Formula C1

X' = N or CH
Y' = N or CH
m = 0-5
n = 0-5

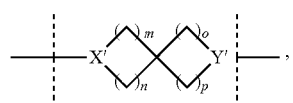

Formula C2

X' = N or CH
Y' = N or CH
m = 0-5
n = 0-5
o = 0-5
p = 0-5

-continued

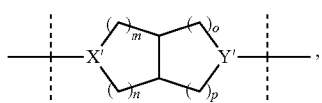

X' = N or CH
Y' = N or CH
m = 0-5
n = 0-5
o = 0-5
p = 0-5

Formula C3

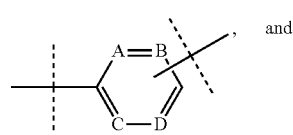
and

Formula C4

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N

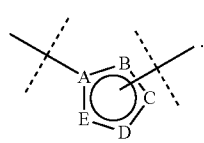

Formula C5

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3alkyl), O, S In some aspects, the linker can also be a moiety of:

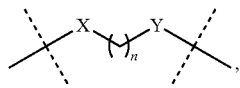

Formula A wherein X is C=O or CH$_2$,
Y is C=O or CH$_2$, and
n is 0-15;

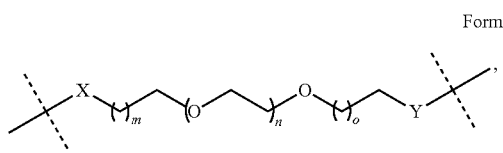

Formula B wherein X is C=O or CH$_2$,
Y is C=O or CH$_2$,
m is 0-15,
n is 0-6, and
is 0-15; or

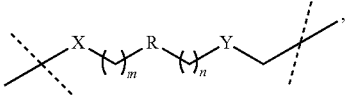

Formula C wherein
X is C=O or CH$_2$,
Y is C=O or CH$_2$,
R is —CH$_2$—, —CF$_2$—, —CH(C$_{1-3}$ alkyl)-, —C(C$_{1-3}$ alkyl)(C$_{1-3}$ alkyl)-, —CH=CH—, —C(C$_{1-3}$ alkyl)=C(C$_{1-3}$ alkyl)-, —C≡C—, —O—, —NH—, —N(C$_{1-3}$ alkyl)-, —C(O)NH—, —C(O)N(C$_{1-3}$ alkyl)-, a 3-13 membered ring, a 3-13 membered fused ring, a 3-13 membered bridged ring, and/or a 3-13 membered spiro ring,
m is 0-15, and
n is 0-15.

In some aspects of Formula C, R is a 3-13 membered ring, a 3-13 membered fused ring, a 3-13 membered bridged ring, and/or a 3-13 membered spiro ring, one or more of which can contain one or more heteroatoms.

In some aspects of Formula C, R has a structure of:

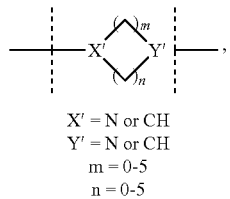

Formula C1

X' = N or CH
Y' = N or CH
m = 0-5
n = 0-5

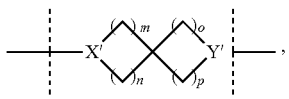

Formula C2

X' = N or CH
Y' = N or CH
m = 0-5
n = 0-5
o = 0-5
p = 0-5

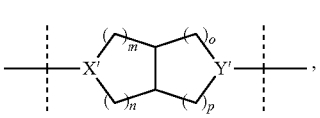

Formula C3

X' = N or CH
Y' = N or CH
m = 0-5
n = 0-5
o = 0-5
p = 0-5

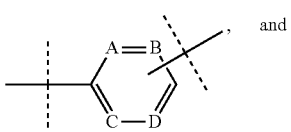
and

Formula C4

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N -continued

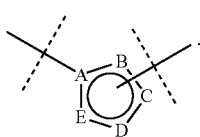

Formula C5

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3alkyl), O, S Synthesis and Testing of Bivalent Compounds The binding affinity of novel synthesized bivalent compounds (i.e., WDR5 degraders/disruptors) can be assessed using standard biophysical assays known in the art (e.g., isothermal titration calorimetry (ITC), surface plasmon resonance (SPR)). Cellular assays can then be used to assess the bivalent compound's ability to induce WDR5 degradation and inhibit cancer cell proliferation. Besides evaluating a bivalent compound's induced changes in the protein expression of WDR5 or WDR5 mutant proteins, enzymatic activity of WDR5 complexes (e.g., WDR5-MLL1 complex) can also be assessed. Assays suitable for use in any or all of these steps are known in the art, and include, e.g., Western blotting, quantitative mass spectrometry (MS) analysis, flow cytometry, enzymatic inhibition, ITC, SPR, cell growth inhibition and xenograft and PDX models. Suitable cell lines for use in any or all of these steps are known in the art and include, e.g., patient AML cells, MLL translocation cells, Li-Fraumeni Syndrome (LFS) fibroblasts, pancreatic ductal adenocarcinoma (PDAC), neuroblastoma cell, and aged myofibre-associated satellite cells.

By way of non-limiting example, detailed synthesis protocols are described in the Examples for specific exemplary WDR5 degraders/disruptors.

Pharmaceutically acceptable isotopic variations of the compounds disclosed herein are contemplated and can be synthesized using conventional methods known in the art or methods corresponding to those described in the Examples (substituting appropriate reagents with appropriate isotopic variations of those reagents). Specifically, an isotopic variation is a compound in which at least one atom is replaced by an atom having the same atomic number, but an atomic mass different from the atomic mass usually found in nature. Useful isotopes are known in the art and include, for example, isotopes of hydrogen, carbon, nitrogen, oxygen, phosphorus, sulfur, fluorine, and chlorine. Exemplary isotopes thus include, e.g., $^2$H, $^3$H, $^{13}$C, $^{14}$C, $^{15}$N, $^{17}$O, $^{18}$O, $^{32}$P, $^{35}$S, $^{18}$F, and $^{36}$Cl.

Isotopic variations (e.g., isotopic variations containing $^2$H) can provide therapeutic advantages resulting from greater metabolic stability, e.g., increased in vivo half-life or reduced dosage requirements. In addition, certain isotopic variations (particularly those containing a radioactive isotope) can be used in drug or substrate tissue distribution studies. The radioactive isotopes tritium ($^3$H) and carbon-14 ($^{14}$C) are particularly useful for this purpose in view of their ease of incorporation and ready means of detection.

Pharmaceutically acceptable solvates of the compounds disclosed herein are contemplated. A solvate can be generated, e.g., by substituting a solvent used to crystallize a compound disclosed herein with an isotopic variation (e.g., D$_2$O in place of H$_2$O, d$_6$-acetone in place of acetone, or de-DMSO in place of DMSO).

Pharmaceutically acceptable fluorinated variations of the compounds disclosed herein are contemplated and can be synthesized using conventional methods known in the art or methods corresponding to those described in the Examples (substituting appropriate reagents with appropriate fluorinated variations of those reagents). Specifically, a fluorinated variation is a compound in which at least one hydrogen atom is replaced by a fluoro atom. Fluorinated variations can provide therapeutic advantages resulting from greater metabolic stability, e.g., increased in vivo half-life or reduced dosage requirements.

Pharmaceutically acceptable prodrugs of the compounds disclosed herein are contemplated and can be synthesized using conventional methods known in the art or methods corresponding to those described in the Examples (e.g., converting hydroxyl groups or carboxylic acid groups to ester groups). As used herein, a "prodrug" refers to a compound that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

Characterization of Exemplary WDR5 Degraders/Disruptors

Figure 1B:
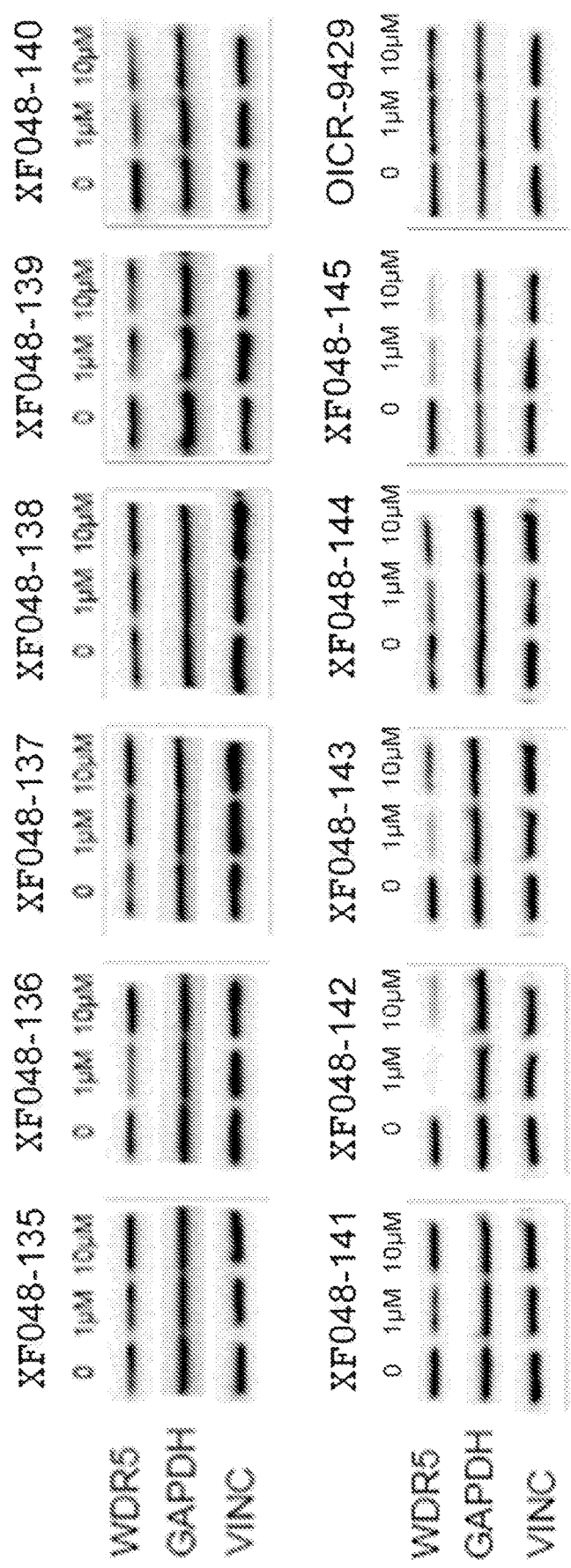
Figure 1C:
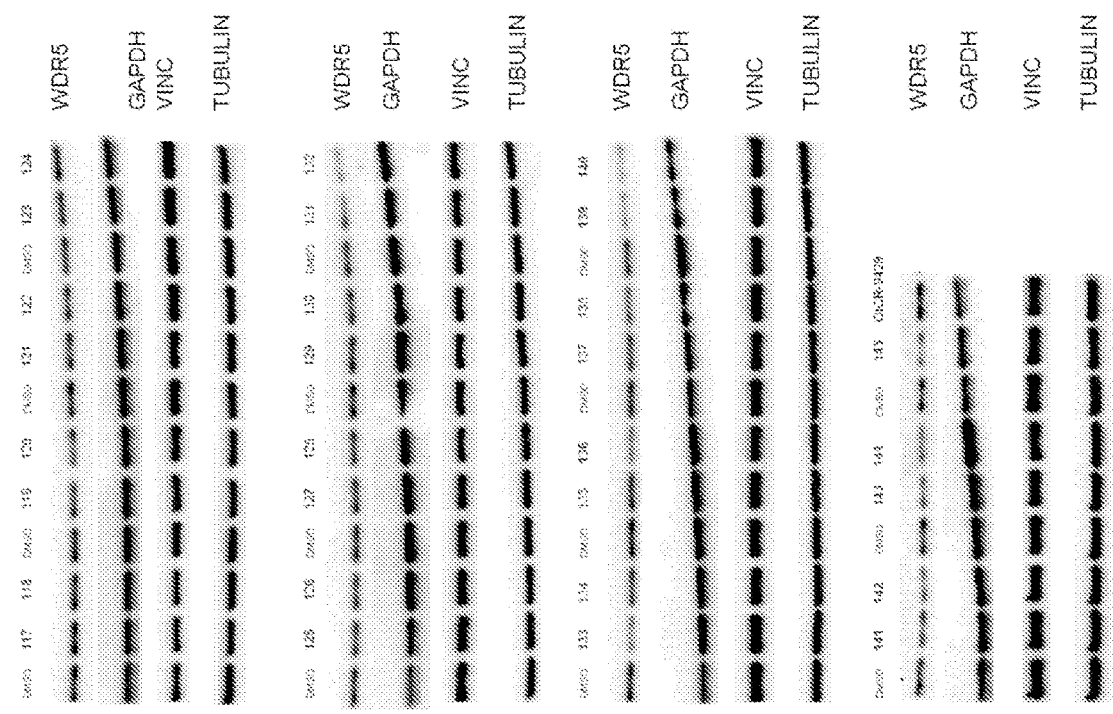
Figure 2:
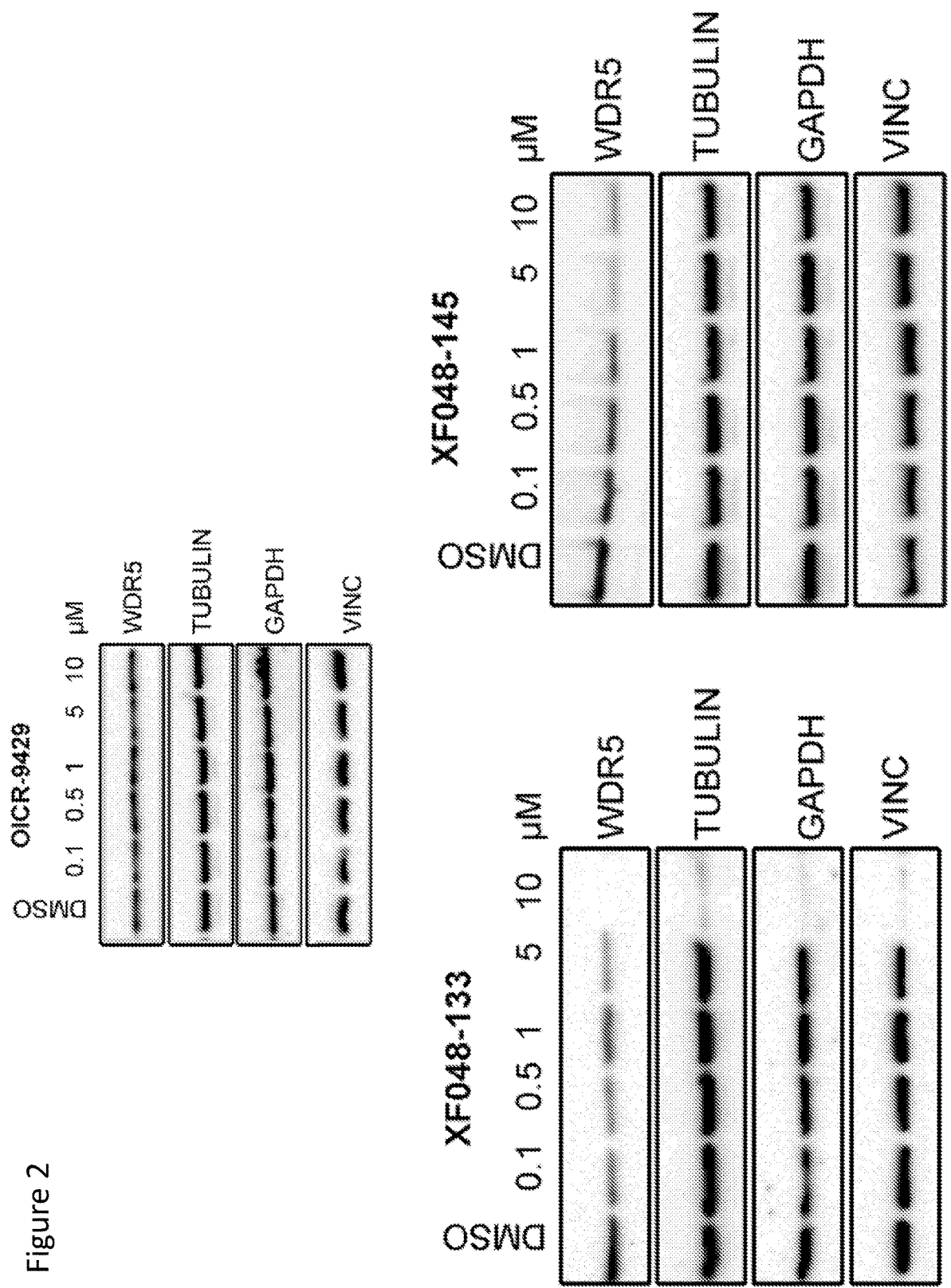
FIG. 2 is a series of Western blots showing that XF048-133 and XF048-145, but not OICR-9429, concentration-dependently reduced WDR5 levels in MV4;11 cells after 18 h treatment.
Figure 3A:
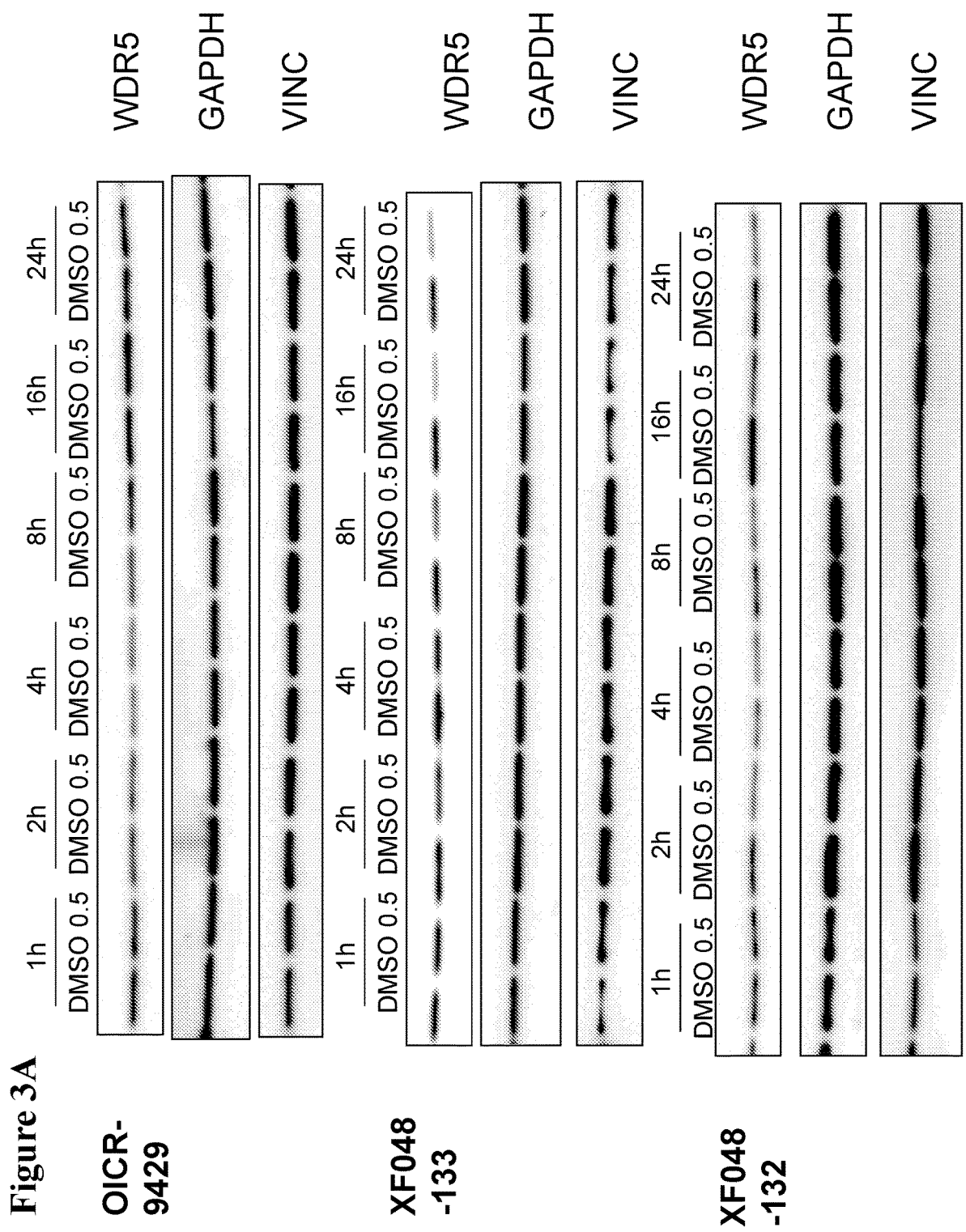
FIG. 3A-B are a series of Western blots showing that the indicated WDR5 degraders, but not OICR-9429, time-dependently reduced WDR5 levels in MV4;11 cells.
Figure 3B:
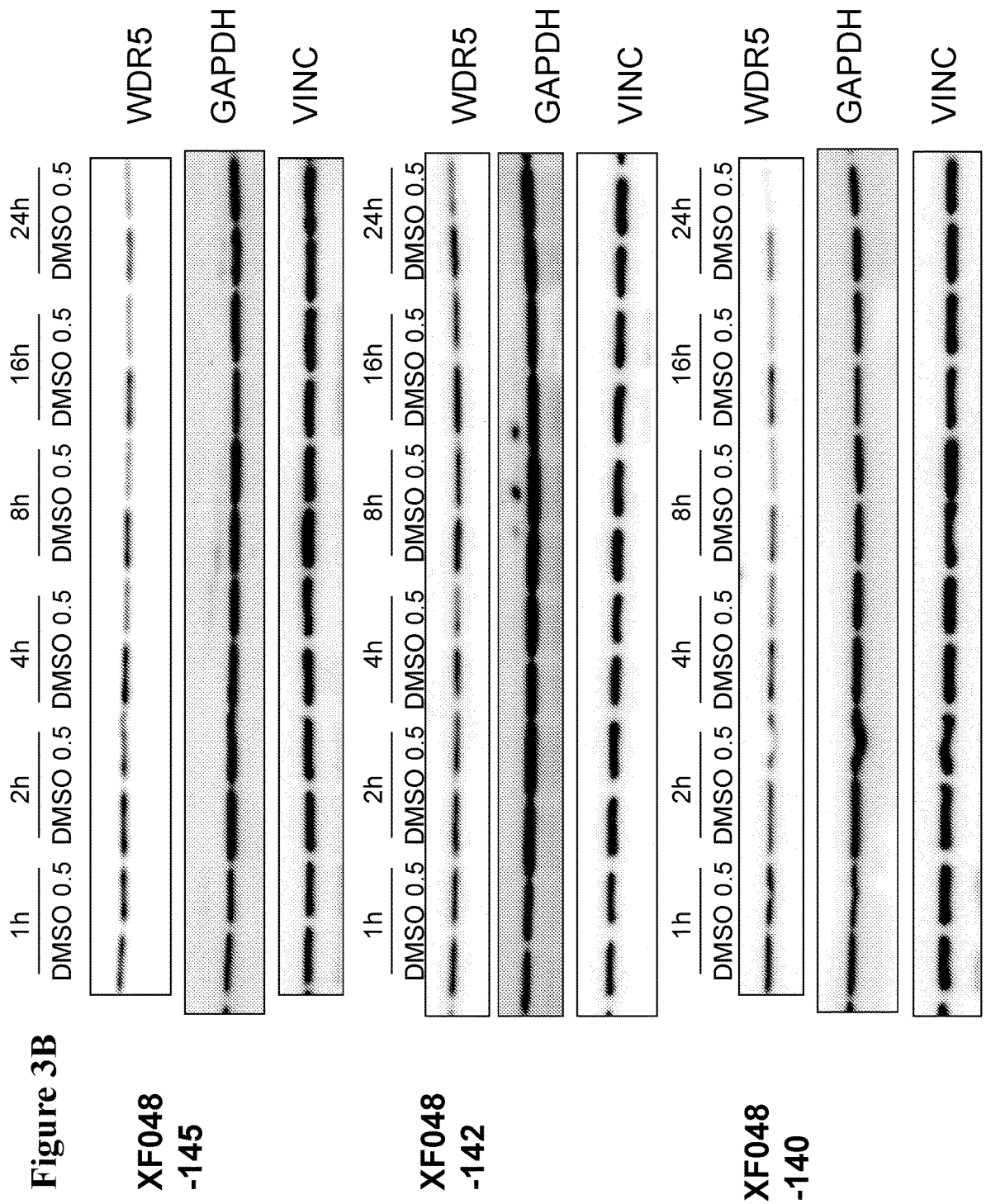
Figure 4:
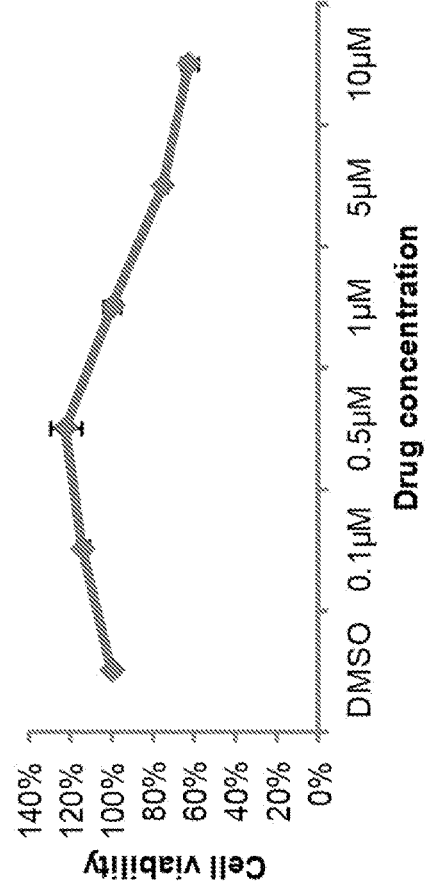
FIG. 4 shows that XF048-133 reduced the viability of MV4;11 cells much more significantly than OICR-9429 after 72 h treatment at indicated concentrations.
Figure 4:
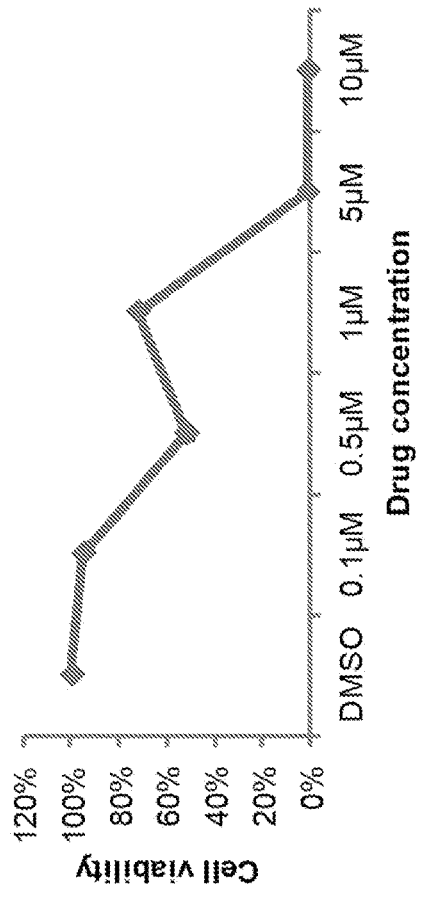
Figure 5:
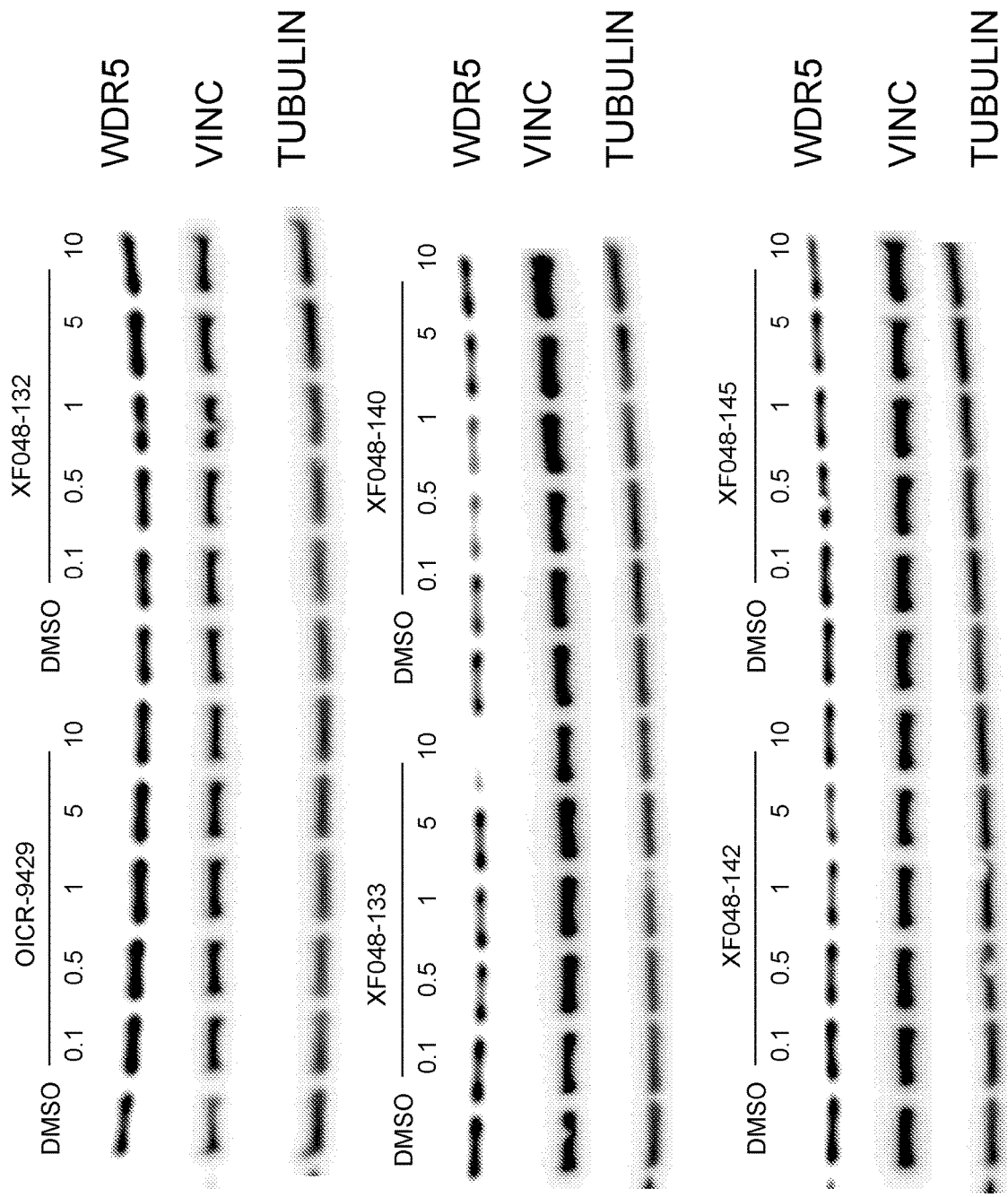
FIG. 5 is a series of Western blots showing that indicated WDR5 degraders concentration-dependently reduced WDR5 levels in MIAPACA2 cells after 18 h treatment.

Specific exemplary WDR5 degraders/disruptors were characterized in MV4;11 and MIAPACA2 cells (Examples 433-442, FIGS. 1-10). Bifunctional compounds XF048-133, XF048-142, and XF048-145 in particular were found to be effective in reducing WDR5 protein levels in MV4;11 cells in a concentration- and time-dependent manner while the WDR5 inhibitor OICR-9419 had no effect on reducing WDR5 protein levels (FIGS. 1-3). In addition, The WDR5 degrader XF048-133 reduced the viability of MV4;11 cells much more significantly than the WDR5 inhibitor OICR-9419. Moreover, XF048-140 and XF048-133 reduced WDR5 protein levels in MIAPACA2 cells (FIG. 5). By screening large number of putative WDR5 degraders (FIGS. 6-10), multiple compounds, such as XF048-133, XF048-140, XF050-161, XF050-162, XF050-166, XF056-39, XF056-132, XF056-171, XF056-173, XF056-186, XF061-105, XF067-133, XF067-134, XF067-140, XF067-142, XF067-146, XF078-1, XF078-2, XF078-6, XF078-8, XF078-12, XF078-13, XF078-14, XF078-15, XF078-20, XF078-21, XF078-22, XF078-23, XF078-24, XF078-25, XF078-26, XF078-27, XF078-28, XF078-29, XF078-30, XF078-41, XF078-42, XF078-43, XF078-44, XF078-45, XF078-46, XF078-61, XF078-99, XF078-101, XF078-102, XF078-103, XF078-105, XF078-106, XF078-110, XF078-111, XF078-112, XF078-113, XF078-114, XF078-115, XF078-121, XF078-125, XF078-126, XF078-127, XF078-132, XF078-133, XF078-134, XF078-135, XF078-136, XF078-137, XF078-138, XF078-139, XF078-141, XF078-142, XF078-143, XF078-144, XF078-145, XF078-146, XF078-147, XF078-148, XF078-149, XF078-150, XF078-157, XF078-158, XF078-159, and XF078-160, were found to be able to effectively degrade WDR5 in MV4;11 and/or MIAPACA2 cells.

Definition of Terms

As used herein, the terms "comprising" and "including" are used in their open, non-limiting sense.

"Alkyl" refers to a straight or branched hydrocarbon chain radical consisting solely of carbon and hydrogen atoms, containing no unsaturation. An alkyl may comprise one, two, three, four, five, six, seven, eight, nine, ten, eleven, twelve, thirteen, fourteen, fifteen, or sixteen carbon atoms. In certain embodiments, an alkyl comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), pentyl, 3-methylhexyl, 2-methylhexyl, and the like.

"Alkenyl" refers to a straight or branched hydrocarbon chain radical group consisting solely of carbon and hydrogen atoms, containing at least one double bond. An alkenyl may comprise two, three, four, five, six, seven, eight, nine, ten, eleven, twelve, thirteen, fourteen, fifteen, or sixteen carbon atoms. In certain embodiments, an alkenyl comprises two to twelve carbon atoms (e.g., $C_2$-$C_{12}$ alkenyl). In certain embodiments, an alkenyl comprises two to eight carbon atoms (e.g., $C_2$-$C_8$ alkenyl). In certain embodiments, an alkenyl comprises two to six carbon atoms (e.g., $C_2$-$C_6$ alkenyl). In other embodiments, an alkenyl comprises two to four carbon atoms (e.g., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "allyl," as used herein, means a —$CH_2CH=CH_2$ group.

As used herein, the term "alkynyl" refers to a straight or branched hydrocarbon chain radical group consisting solely of carbon and hydrogen atoms, containing at least one triple bond. An alkynyl may comprise two, three, four, five, six, seven, eight, nine, ten, eleven, twelve, thirteen, fourteen, fifteen, or sixteen carbon atoms. In certain embodiments, an alkynyl comprises two to twelve carbon atoms (e.g., $C_2$-$C_{12}$ alkynyl). In certain embodiments, an alkynyl comprises two to eight carbon atoms (e.g., $C_2$-$C_8$ alkynyl). In other embodiments, an alkynyl has two to six carbon atoms (e.g., $C_2$-$C_6$ alkynyl). In other embodiments, an alkynyl has two to four carbon atoms (e.g., $C_2$-$C_4$ alkynyl). The alkynyl is attached to the rest of the molecule by a single bond. Examples of such groups include, but are not limited to, ethynyl, propynyl, 1-butynyl, 2-butynyl, 1-pentynyl, 2-pentynyl, 1-hexynyl, 2-hexynyl, 3-hexynyl, and the like.

The term "alkoxy", as used herein, means an alkyl group as defined herein which is attached to the rest of the molecule via an oxygen atom. Examples of such groups include, but are not limited to, methoxy, ethoxy, n-propyloxy, iso-propyloxy, n-butoxy, iso-butoxy, tert-butoxy, pentyloxy, hexyloxy, and the like.

The term "aryl", as used herein, "refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms. An aryl may comprise from six to eighteen carbon atoms, where at least one of the rings in the ring system is fully unsaturated, i.e., it contains a cyclic, delocalized (4n+2) π-electron system in accordance with the Hückel theory. In certain embodiments, an aryl comprises six to fourteen carbon atoms ($C_6$-$C_{14}$ aryl). In certain embodiments, an aryl comprises six to ten carbon atoms ($C_6$-$C_{10}$ aryl). Examples of such groups include, but are not limited to, phenyl, fluorenyl and naphthyl. The terms "Ph" and "phenyl," as used herein, mean a —$C_6H_5$ group.

The term "heteroaryl", refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In certain embodiments, a heteroaryl refers to a radical derived from a 3- to 10-membered aromatic ring radical (3-10 membered heteroaryl). In certain embodiments, a heteroaryl refers to a radical derived from 5- to 7-membered aromatic ring (5-7 membered heteroaryl). Heteroaryl includes fused or bridged ring systems. The heteroatom(s) in the heteroaryl radical is optionally oxidized.

One or more nitrogen atoms, if present, are optionally quaternized. The heteroaryl is attached to the rest of the molecule through any atom of the ring(s). Examples of such groups include, but not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. In certain embodiments, an heteroaryl is attached to the rest of the molecule via a ring carbon atom. In certain embodiments, an heteroaryl is attached to the rest of the molecule via a nitrogen atom (N-attached) or a carbon atom (C-attached). For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "heterocyclyl", as used herein, means a non-aromatic, monocyclic, bicyclic, tricyclic, or tetracyclic radical having a total of from 4, 5, 6, 7, 8, 9, 10, 11, 12, or 13 atoms in its ring system, and containing from 3 to 12 carbon atoms and from 1 to 4 heteroatoms each independently selected from O, S and N, and with the proviso that the ring of said group does not contain two adjacent O atoms or two adjacent S atoms. A heterocyclyl group may include fused, bridged or spirocyclic ring systems. In certain embodiments, a heterocyclyl group comprises 3 to ring atoms (3-10 membered heterocyclyl). In certain embodiments, a heterocyclyl group comprises 3 to 8 ring atoms (3-8 membered heterocyclyl). In certain embodiments, a heterocyclyl group comprises 4 to 8 ring atoms (4-8 membered heterocyclyl). In certain embodiments, a heterocyclyl group comprises 3 to 6 ring atoms (3-6 membered heterocyclyl). A heterocyclyl group may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocyclyl group contains a sulfur atom, said sulfur atom may be oxidized with one or two oxygen atoms to afford either a sulfoxide or sulfone. An example of a 4 membered heterocyclyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such heterocyclyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. A heteroaryl group may be attached to the rest of molecular via a carbon atom (C-attached) or a nitrogen atom (N-attached). For instance, a group derived from piperazine may be piperazin-1-yl (N-attached) or piperazin-2-yl (C-attached).

The term "cycloalkyl" means a saturated, monocyclic, bicyclic, tricyclic, or tetracyclic radical having a total of from 4, 5, 6, 7, 8, 9, 10, 11, 12, or 13 carbon atoms in its ring system. A cycloalkyl may be fused, bridged or spirocyclic. In certain embodiments, a cycloalkyl comprises 3 to 8 carbon ring atoms ($C_3$-$C_8$ cycloalkyl). In certain embodiments, a cycloalkyl comprises 3 to 6 carbon ring atoms ($C_3$-$C_6$ cycloalkyl). Examples of such groups include, but are not limited to, cyclopropyl, cyclobutyl, cyclopentyl, cyclopentenyl, cyclohexyl, cycloheptyl, adamantyl, and the like.

The term "cycloalkylene" is a bidentate radical obtained by removing a hydrogen atom from a cycloalkyl ring as defined above. Examples of such groups include, but are not limited to, cyclopropylene, cyclobutylene, cyclopentylene, cyclopentenylene, cyclohexylene, cycloheptylene, and the like.

The term "spirocyclic" as used herein has its conventional meaning, that is, any ring system containing two or more rings wherein two of the rings have one ring carbon in common. Each ring of the spirocyclic ring system, as herein defined, independently comprises 3 to 20 ring atoms. Preferably, they have 3 to 10 ring atoms. Non-limiting examples of a spirocyclic system include spiro[3.3]heptane, spiro[3.4]octane, and spiro[4.5]decane.

The term "cyano" refers to a —C≡N group.

An "aldehyde" group refers to a —C(O)H group.

An "alkoxy" group refers to both an —O-alkyl, as defined herein.

An "alkoxycarbonyl" refers to a —C(O)-alkoxy, as defined herein.

An "alkylaminoalkyl" group refers to an -alkyl-NR-alkyl group, as defined herein.

An "alkylsulfonyl" group refer to a —$SO_2$alkyl, as defined herein.

An "amino" group refers to an optionally substituted —$NH_2$.

An "aminoalkyl" group refers to an -alky-amino group, as defined herein.

An "aminocarbonyl" refers to a —C(O)-amino, as defined herein.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)-aryloxy, as defined herein.

An "arylsulfonyl" group refers to a —$SO_2$aryl, as defined herein.

A "carbonyl" group refers to a —C(O)— group, as defined herein.

A "carboxylic acid" group refers to a —C(O)OH group.

A "cycloalkoxy" refers to a —O-cycloalkyl group, as defined herein.

A "halo" or "halogen" group refers to fluorine, chlorine, bromine or iodine.

A "haloalkyl" group refers to an alkyl group substituted with one or more halogen atoms.

A "hydroxy" group refers to an —OH group.

A "nitro" group refers to a —$NO_2$ group.

An "oxo" group refers to the =O substituent.

A "trihalomethyl" group refers to a methyl substituted with three halogen atoms.

The term "substituted," means that the specified group or moiety bears one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "null" means the absence of an atom or moiety, and there is a bond between adjacent atoms in the structure.

The term "optionally substituted" means that the specified group may be either unsubstituted or substituted by one or more substituents as defined herein. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one at which the remainder of the compound of the present invention is attached to and an additional substituent, remaining 4 positions open). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

As used herein, the same symbol in different FORMULA means different definition, for example, the definition of R1 in FORMULA 1 is as defined with respect to FORMULA 1 and the definition of R1 in FORMULA 6 is as defined with respect to FORMULA 6.

As used herein, when m (or n or o or p) is defined by a range, for example, "m is 0 to 15" or "m=0-3" mean that m is an integer from 0 to 15 (i.e. m is 0, 1, 2, 3, 4, 5, 6, 7, 8, 9, 10, 11, 12, 13, 14, or 15) or m is an integer from 0 to 3 (i.e. m is 0, 1, 2, or 3) or is any integer in the defined range.

"Pharmaceutically acceptable salt" includes both acid and base addition salts. A pharmaceutically acceptable salt of any one of the bivalent compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, the same symbol in different FORMULA means different definition, for example, the definition of $R^1$ in FORMULA 1 is different from that in FORMULA 6.

As used herein, when m (or n or o or p) is defnited as, for example, "m is 0 to 15" or "m=0-5" mean m is m is an integer from 0 to 15 (or 0 to 5).

Pharmaceutical Compositions

In some aspects, the compositions and methods described herein include the manufacture and use of pharmaceutical compositions and medicaments that include one or more bivalent compounds as disclosed herein. Also included are the pharmaceutical compositions themselves.

In some aspects, the compositions disclosed herein can include other compounds, drugs, or agents used for the treatment of cancer. For example, in some instances, pharmaceutical compositions disclosed herein can be combined with one or more (e.g., one, two, three, four, five, or less than ten) compounds. Such additional compounds can include, e.g., conventional chemotherapeutic agents known in the art. When co-administered, WDR5 degraders/disruptors disclosed herein can operate in conjunction with conventional chemotherapeutic agents to produce mechanistically additive or synergistic therapeutic effects.

In some aspects, the pH of the compositions disclosed herein can be adjusted with pharmaceutically acceptable acids, bases, or buffers to enhance the stability of the WDR5 degraders/disruptor or its delivery form.

Pharmaceutical compositions typically include a pharmaceutically acceptable carrier, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable carrier, adjuvant, or vehicle is a composition that can be administered to a patient, together with a compound of the invention, and which does not destroy the pharmacological activity thereof and is nontoxic when administered in doses sufficient to deliver a therapeutic amount of the compound. Exemplary conventional nontoxic pharmaceutically acceptable carriers, adjuvants, and vehicles include saline, solvents, dispersion media, coatings, antibacterial and antifungal agents, isotonic and absorption delaying agents, and the like, compatible with pharmaceutical administration.

In particular, pharmaceutically acceptable carriers, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

As used herein, the WDR5 degraders/disruptors disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives.

The WDR5 degraders/disruptors disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivatives thereof.

In particular, pharmaceutically acceptable salts of the WDR5 degraders/disruptors disclosed herein include, e.g., those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, e.g., alkali metal (e.g., sodium), alkaline earth metal (e.g., magnesium), ammonium and N-(alkyl)4+ salts. The invention also envisions the quaternization of any basic nitrogen-containing groups of the WDR5 degraders/disruptors disclosed herein. Water or oil-soluble or dispersible products can be obtained by such quaternization.

In some aspects, the pharmaceutical compositions disclosed herein can include an effective amount of one or more WDR5 degraders/disruptors. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer). In some aspects, pharmaceutical compositions can further include one or more additional compounds, drugs, or agents used for the treatment of cancer (e.g., conventional chemotherapeutic agents) in amounts effective for causing an intended effect or physiological outcome (e.g., treatment or prevention of cell growth, cell proliferation, or cancer).

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/Forms-SubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, e.g., topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, e.g., as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. Fatty acids, such as oleic acid and its glyceride derivatives are useful in the preparation of injectables, as are natural pharmaceutically-acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of a compound of the formulae described herein (e.g., a WDR5 degraders/disruptors) and one or more additional compounds (e.g., one or more additional compounds, drugs, or agents used for the treatment of cancer or any other condition or disease, including conditions or diseases known to be associated with or caused by cancer), both the compound and the additional compound should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, the present disclosure provides methods for using a composition comprising a WDR5 degrader/disruptor, including pharmaceutical compositions (indicated below as 'X') disclosed herein in the following methods: Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of cancer.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition from which the subject is suffering (e.g., a WDR5-mediated disease). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the compositions and methods of the present invention. In some embodiments, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

As used herein, the term "treating cancer" means causing a partial or complete decrease in the rate of growth of a tumor, and/or in the size of the tumor and/or in the rate of local or distant tumor metastasis, and/or the overall tumor burden in a subject, and/or any decrease in tumor survival, in the presence of a degrader/disruptor (e.g., a WDR5 degrader/disruptor) described herein.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention. Exemplary WDR5-mediated diseases that can be treated with WDR5 degraders/disruptors include, for example, leukemia, lymphoma, ovarian cancer, stomach cancer, cervical cancer, uterine cancer, gastric cancer, head neck squamous cell carcinoma (HNSCC), colorectal cancer (CRC), lung cancer, pancreatic cancer, bladder cancer, breast cancer, and neuroblastoma.

As used herein, the term "preventing a disease" (e.g., preventing cancer) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

The present disclosure is also described and demonstrated by way of the following examples. However, the use of these and other examples anywhere in the specification is illustrative only and in no way limits the scope and meaning of the invention or of any exemplified term. Likewise, the invention is not limited to any particular preferred embodiment or aspect described herein. Indeed, many modifications and variations may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLES

Example 1: Synthesis of Intermediate 1

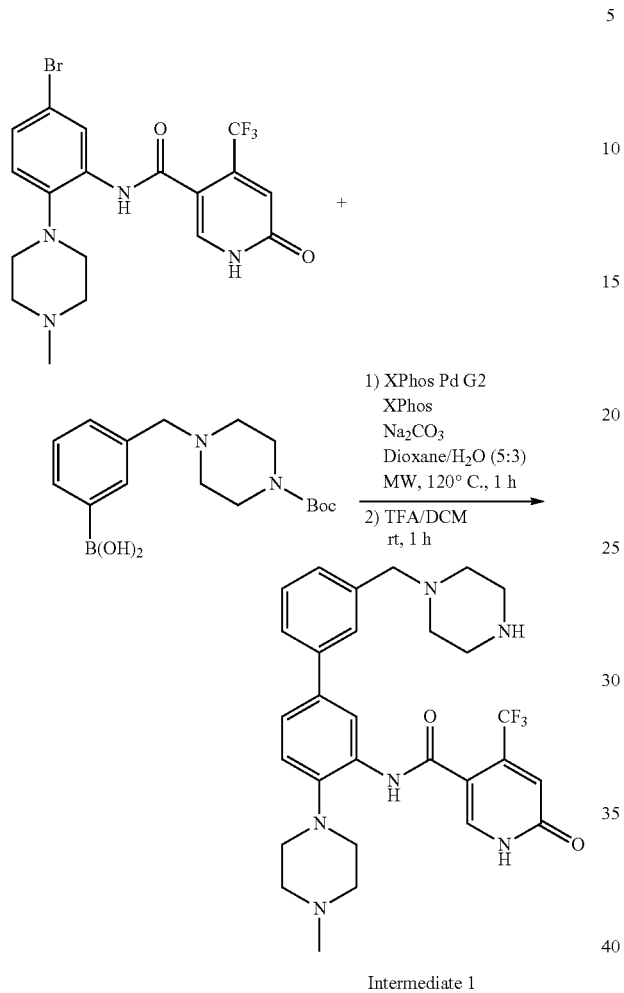

To a solution of N-(5-bromo-2-(4-methylpiperazin-1-yl) phenyl)-6-oxo-4-(trifluoromethyl)-1,6-dihydropyridine-3-carboxamide (Getlik et al., 2016) (348.6 mg, 0.76 mmol) and (3-((4-(tert-butoxycarbonyl)piperazin-1-yl)methyl)phenyl)boronic acid (729 mg, 2.27 mmol, 3.0 euqiv) in 8 mL of 1,4-dioxane/$H_2O$ (5:3) were added sodium carbonate (805.6 mg, 7.6 mmol, 10 equiv), XPhos (85 mg, 0.15 mmol, 0.2 equiv), and XPhos Pd G2 (141 mg, 0.15 mmol, 0.2 equiv). The reaction was heated to 120° C. for 1 h under Microwave. The solvent was removed and purified by reverse phase ISCO (10%-100% methanol/0.1% TFA in $H_2O$) to afford product as white solid in TFA salt form (350 mg, 70% yield). This product was dissolved in DCM (5 mL) and TFA (5 mL). The resulting mixture was stirring for 30 minutes. Then, it was concentrated and purified by reverse phase ISCO (10%-100% methanol/0.1% TFA in $H_2O$) to afford Intermediate 1 as white solid in TFA salt form (290 mg, yield 98%). $^1$H NMR (500 MHz, $CD_3OD$) δ 8.27 (dd, J=3.8, 2.2 Hz, 1H), 8.04 (d, J=3.7 Hz, 1H), 7.76-7.63 (m, 2H), 7.60-7.47 (m, 2H), 7.45-7.32 (m, 2H), 6.96 (d, J=5.7 Hz, 1H), 4.12-4.00 (m, 2H), 3.67-3.60 (m, 2H), 3.40 (dt, J=10.4, 5.0 Hz, 4H), 3.24-3.01 (m, 11H), 2.98 (d, J=5.2 Hz, 2H). HRMS (m/z) for $C_{29}H_{34}F_3N_6O_2^+$ [M+H]$^+$: calculated 555.2690. found 555.2674.

Example 2: Synthesis of Intermediate 2

To a solution of intermediate 1 (238 mg, 0.43 mmol) (Getlik et al., 2016), and tert-butyl (2-oxoethyl)carbamate (137 mg, 0.86 mmol, 2.0 equiv) in dichloromethane (10 mL) was added sodium triacetoxyborohydride (183 mg, 0.86 mmol). After stirring overnight, saturated sodium bicarbonate was added to quench reaction. The mixture was extracted with DCM (3×10 mL), dried over $Na_2SO_4$, filtered and concentrated. The crude product was purified by reverse phase ISCO (10%-100% methanol/0.1% TFA in $H_2O$) to afford intermediate 2 as white solid in TFA salt form (251 mg, 84% yield). This product was dissolved in DCM (5 mL) and TFA (5 mL). The resulting mixture was stirred for 30 minutes. Then, it was concentrated and purified by preparative HPLC (10%-100% methanol/0.1% TFA in $H_2O$) to afford Intermediate 2 (XF048-115) as white solid in TFA salt form (214 mg, yield 99%). $^1$H NMR (600 MHz, $CD_3OD$) δ 8.27 (d, J=2.1 Hz, 1H), 8.03 (d, J=3.3 Hz, 1H), 7.85-7.71 (m, 2H), 7.63-7.45 (m, 3H), 7.39 (d, J=8.3 Hz, 1H), 6.93 (s, 1H), 4.43 (s, 2H), 3.61 (d, J=11.8 Hz, 3H), 3.28 (s, 4H), 3.17 (t, J=12.9 Hz, 4H), 3.07 (t, J=5.7 Hz, 4H), 2.96 (d, J=1.8 Hz, 4H), 2.71 (q, J=5.7, 5.1 Hz, 4H). HRMS (m/z) for $C_{31}H_{39}F_3N_7O_2^+$ [M+H]$^+$: calculated 598.3112. found 598.3119.

Example 3: Synthesis of XF048-117

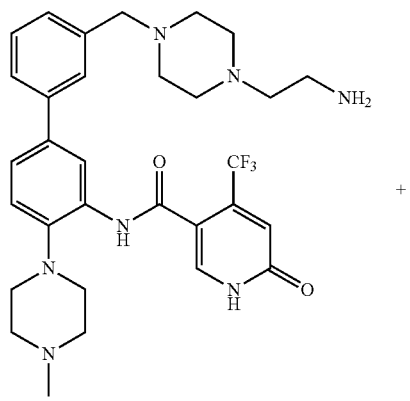

Intermediate 2

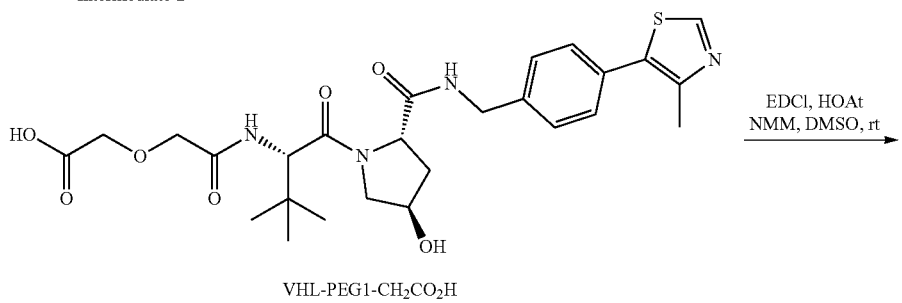

VHL-PEG1-CH$_2$CO$_2$H

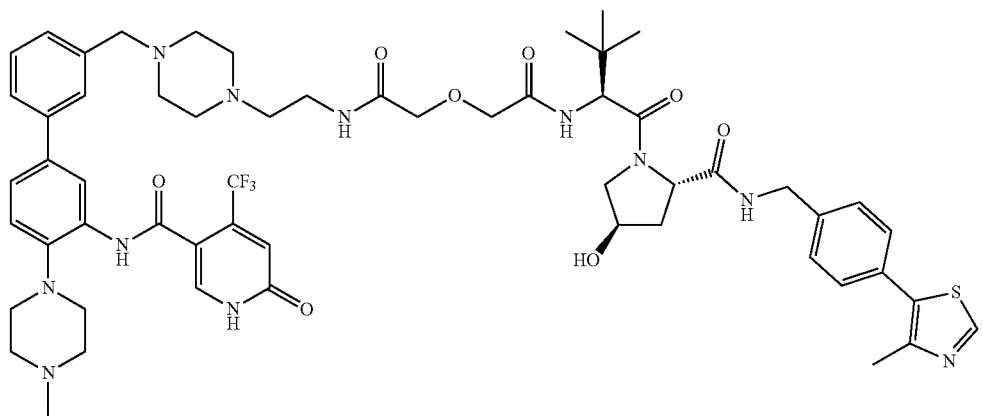

XF048-117

To the solution of intermediate 2 (13.0 mg, 0.018 mmol) in DMSO (1 mL) were added VHL-PEG1-CH$_2$COOH (9.8 mg, 0.018 mmol, 1.0 equiv), EDCI (1-ethyl-3-(3-dimethyl-aminopropyl)carbodiimide) (5.3 mg, 0.027 mmol, 1.5 equiv), HOAt (1-hydroxy-7-azabenzo-triazole) (3.7 mg, 0.027 mmol, 1.5 equiv), and NMM (N-Methylmorpholine) (5.5 mg, 0.054 mmol, 3.0 equiv). After being stirred overnight at room temperature, the resulting mixture was purified by preparative HPLC (10%-100% methanol/0.1% TFA in H$_2$O) to afford XF048-117 as white solid in TFA salt form (15.8 mg, yield 78%). $^1$H NMR (600 MHz, CD$_3$OD) δ 8.99 (s, 1H), 8.26 (d, J=2.2 Hz, 1H), 8.03 (s, 1H), 7.83 (d, J=9.2 Hz, 1H), 7.77-7.68 (m, 2H), 7.54 (ddd, J=7.8, 4.7, 2.5 Hz, 2H), 7.47-7.42 (m, 3H), 7.41 (d, J=8.3 Hz, 1H), 7.38 (d, J=8.4 Hz, 1H), 6.94 (s, 1H), 4.72-4.67 (m, 1H), 4.56 (dd, J=9.4, 7.7 Hz, 1H), 4.52-4.45 (m, 2H), 4.35 (d, J=15.4 Hz, 1H), 4.23 (s, 2H), 4.18-4.04 (m, 5H), 3.89 (d, J=11.0 Hz, 1H), 3.80 (dd, J=11.0, 3.8 Hz, 1H), 3.61 (d, J=11.9 Hz, 3H), 3.57-3.51 (m, 2H), 3.30-3.21 (m, 9H), 3.16 (t, J=13.0 Hz, 3H), 3.06 (t, J=5.9 Hz, 2H), 2.96 (s, 3H), 2.47 (s, 3H), 2.28-2.19 (m, 1H), 2.11-2.04 (m, 1H), 1.04 (s, 9H). HRMS (m/z) for C$_{57}$H$_{71}$F$_3$N$_{11}$O$_8$S$^+$ [M+H]$^+$: calculated 1126.5154, found 1126.5126.

Example 4: Synthesis of XF048-118

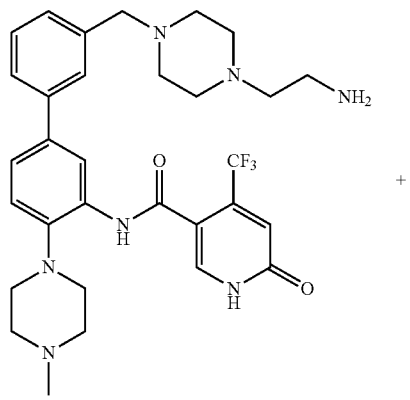

Intermediate 2

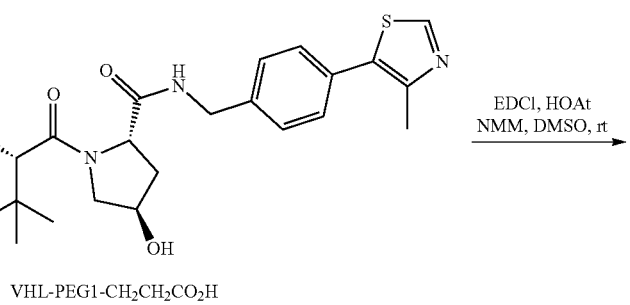

VHL-PEG1-CH₂CH₂CO₂H

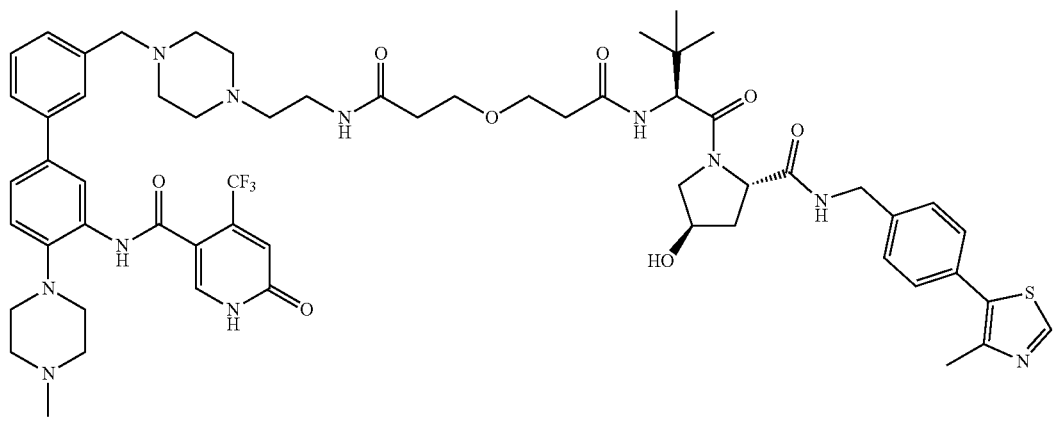

XF048-118

XF048-118 was synthesized following the standard procedures for preparing XF048-117 from intermediate 2 (13.0 mg, 0.018 mmol), VHL-PEG1-CH₂CH₂COOH (10.3 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-118 was obtained as white solid in TFA salt form (12.1 mg, yield 58%). $^1$H NMR (600 MHz, CD$_3$OD) δ 8.91 (s, 1H), 8.26 (d, J=2.2 Hz, 1H), 8.03 (s, 1H), 7.89 (d, J=9.0 Hz, 1H), 7.74-7.69 (m, 1H), 7.67 (dt, J=7.9, 1.4 Hz, 1H), 7.54-7.48 (m, 2H), 7.47-7.35 (m, 5H), 6.94 (s, 1H), 4.65-4.61 (m, 1H), 4.57-4.46 (m, 3H), 4.36 (d, J=15.5 Hz, 1H), 4.12 (s, 2H), 3.87 (d, J=11.0 Hz, 1H), 3.79 (dd, J=11.0, 3.9 Hz, 1H), 3.73-3.65 (m, 5H), 3.61 (d, J=11.6 Hz, 2H), 3.46 (t, J=6.0 Hz, 2H), 3.29 (d, J=10.4 Hz, 3H), 3.16 (t, J=12.7 Hz, 10H), 3.00 (t, J=6.1 Hz, 2H), 2.96 (s, 3H), 2.57-2.41 (m, 7H), 2.22 (ddt, J=13.1, 7.5, 2.0 Hz, 1H), 2.07 (ddd, J=13.3, 9.3, 4.4 Hz, 1H), 1.03 (s, 9H). HRMS (m/z) for $C_{59}H_{75}F_3N_{11}O_8S^+$ [M+H]$^+$: calculated 1154.5467. found 1154.5472.

Example 5: Synthesis of XF048-119

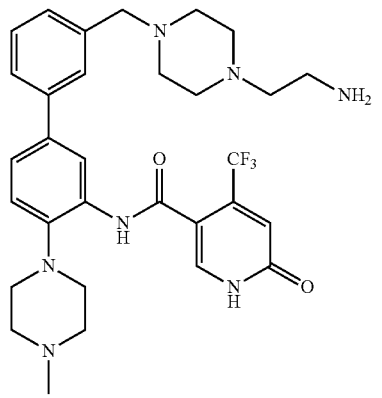

Intermediate 2

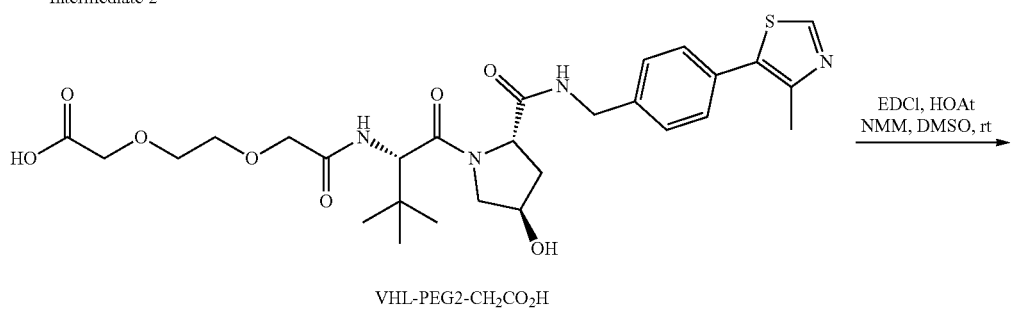

VHL-PEG2-CH2CO2H

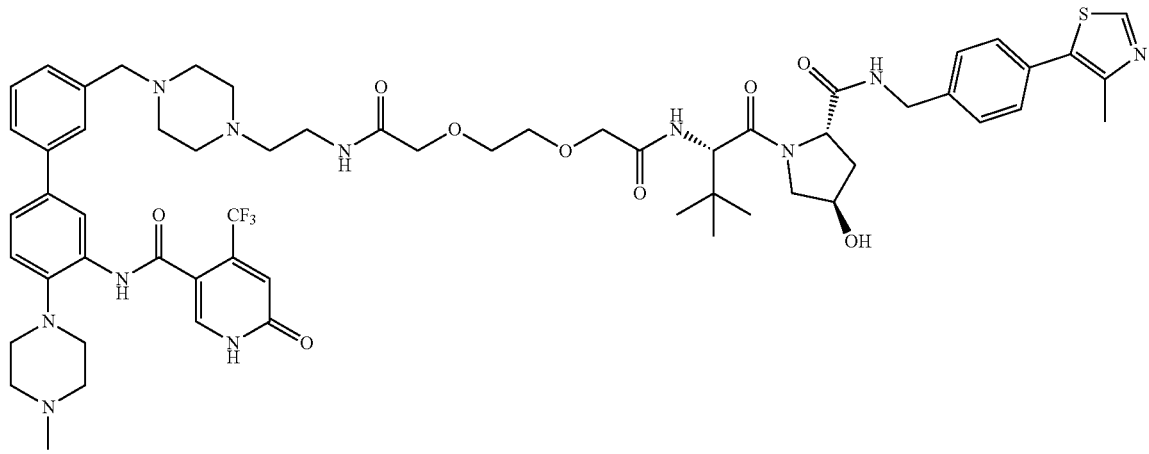

XF048-119

XF048-119 was synthesized following the standard procedures for preparing XF048-117 from intermediate 2 (13.0 mg, 0.018 mmol), VTIL-PEG2-CH$_2$COOH (10.6 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-119 was obtained as white solid in TFA salt form (10.8 mg, yield 51%). $^1$H NMR (600 MHz, CD$_3$OD) δ 8.95 (s, 1H), 8.26 (d, J=2.2 Hz, 1H), 8.03 (s, 1H), 7.74 (d, J=1.8 Hz, 1H), 7.72-7.67 (m, 1H), 7.53 (td, J=8.0, 2.6 Hz, 2H), 7.47-7.39 (m, 5H), 7.38 (d, J=8.4 Hz, 1H), 6.93 (s, 1H), 4.69 (s, 1H), 4.54 (dd, J=9.2, 7.3 Hz, 1H), 4.50-4.44 (m, 2H), 4.39 (d, J=15.5 Hz, 1H), 4.20 (s, 2H), 4.14-3.96 (m, 5H), 3.86 (d, J=11.1 Hz, 1H), 3.82-3.70 (m, 6H), 3.61 (d, J=11.7 Hz, 3H), 3.54-3.47 (m, 2H), 3.29-3.26 (m, 3H), 3.25-3.13 (m, 8H), 3.03 (q, J=5.4 Hz, 2H), 2.96 (s, 3H), 2.47 (d, J=2.6 Hz, 3H), 2.28-2.21 (m, 1H), 2.06 (ddd, J=13.4, 9.5, 4.3 Hz, 1H), 1.03 (s, 9H). HRMS (m/z) for C$_{59}$H$_{75}$F$_3$N$^{11}$O$_9$S$^+$ [M+H]$^+$: calculated 1170.5417. found 1170.5439.

2Example 6: Synthesis of XF048-120

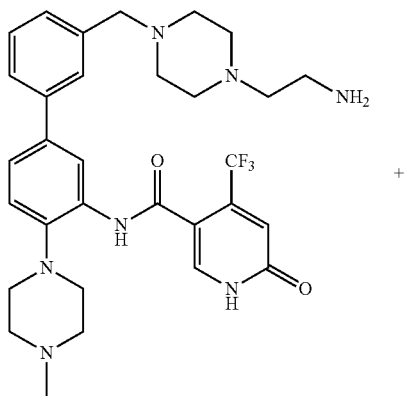

Intermediate 2

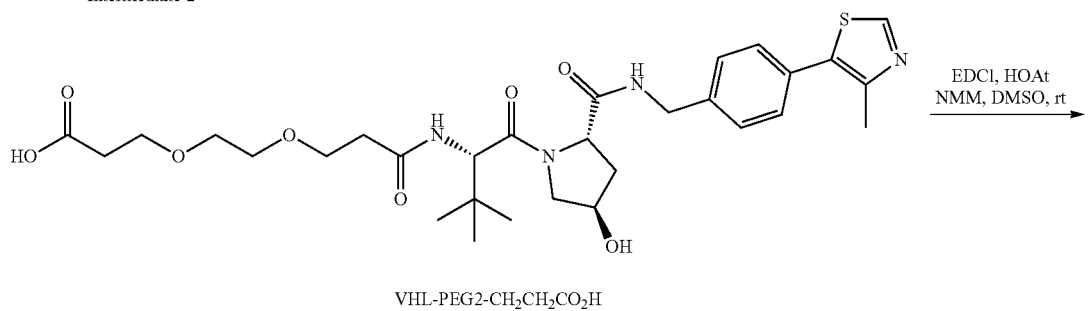

VHL-PEG2-CH₂CH₂CO₂H

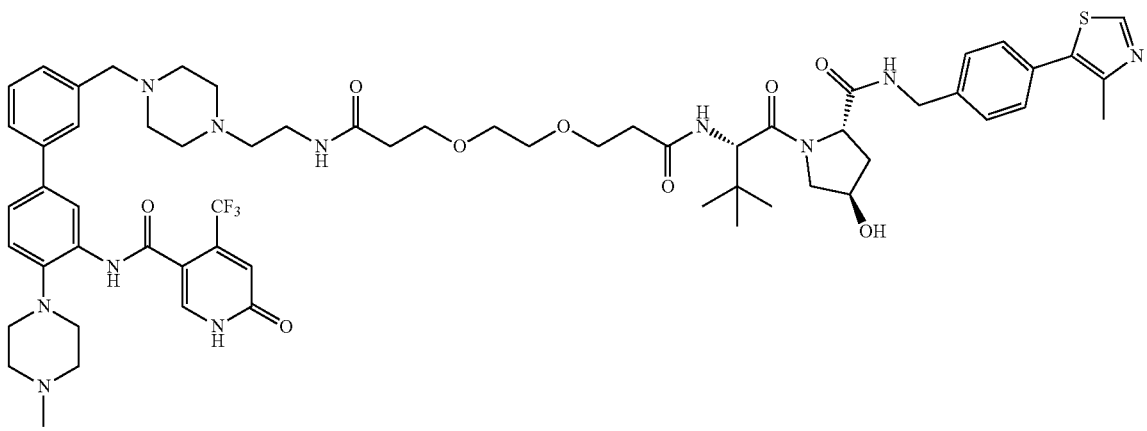

XF048-120

XF048-120 was synthesized following the standard procedures for preparing XF048-117 from intermediate 2 (13.0 mg, 0.018 mmol), VHL-PEG2-CH₂CH₂COOH (11.1 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-120 was obtained as white solid in TFA salt form (15.4 mg, yield 71%). $^1$H NMR (600 MHz, CD$_3$OD) δ 8.97 (s, 1H), 8.26 (d, J=2.2 Hz, 1H), 8.03 (s, 1H), 7.74 (d, J=1.8 Hz, 1H), 7.69 (dt, J=7.8, 1.4 Hz, 1H), 7.55-7.50 (m, 2H), 7.48-7.42 (m, 3H), 7.42-7.39 (m, 2H), 7.38 (d, J=8.4 Hz, 1H), 6.94 (s, 1H), 4.63 (s, 1H), 4.58-4.44 (m, 3H), 4.36 (d, J=15.5 Hz, 1H), 4.18 (s, 2H), 3.88 (d, J=10.9 Hz, 1H), 3.78 (dd, J=11.0, 3.9 Hz, 1H), 3.74-3.64 (m, 5H), 3.64-3.53 (m, 7H), 3.48 (t, J=6.0 Hz, 2H), 3.30-3.26 (m, 5H), 3.26-3.10 (m, 7H), 3.06 (t, J=6.0 Hz, 2H), 2.96 (s, 3H), 2.54 (ddd, J=15.1, 7.1, 5.2 Hz, 1H), 2.50-2.41 (m, 6H), 2.22 (ddt, J=13.1, 7.6, 1.9 Hz, 1H), 2.07 (ddd, J=13.4, 9.3, 4.4 Hz, 1H), 1.02 (s, 9H). HRMS (m/z) for C$_{61}$H$_{79}$F$_3$N$_{11}$O$_9$S$^+$ [M+H]$^+$: calculated 1198.5730, found 1198.5736.

Example 7: Synthesis of XF048-121

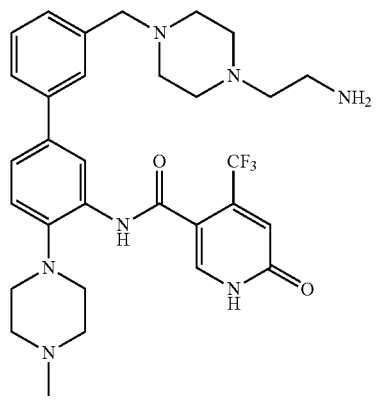

Intermediate 2

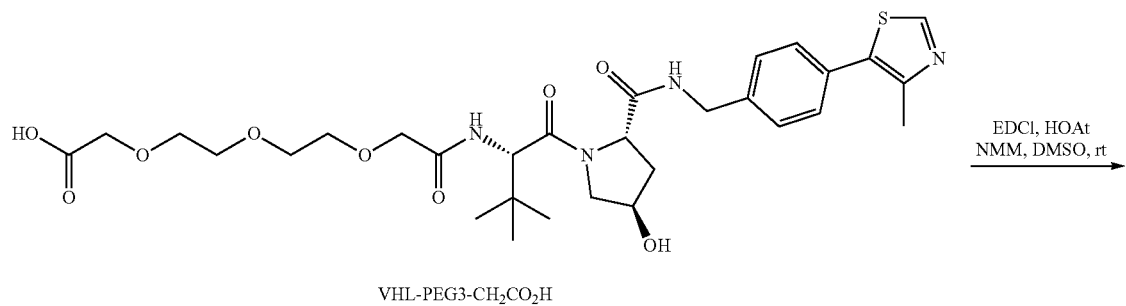

VHL-PEG3-CH$_2$CO$_2$H

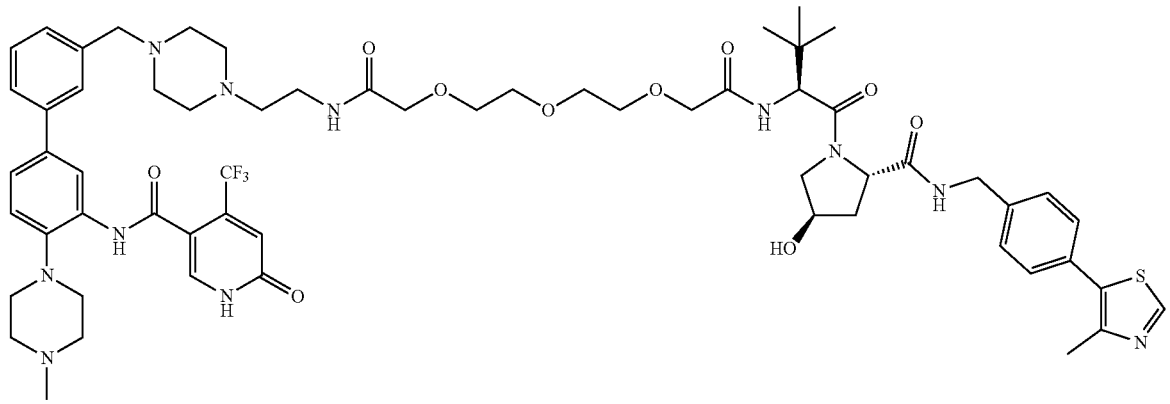

XF048-121

XF048-121 was synthesized following the standard procedures for preparing XF048-117 from intermediate 2 (13.0 mg, 0.018 mmol), VHL-PEG3-CH$_2$COOH (11.4 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-121 was obtained as white solid in TFA salt form (11.9 mg, yield 54%). $^1$H NMR (600 MHz, CD$_3$OD) δ 8.94 (s, 1H), 8.26 (s, 1H), 8.03 (s, 1H), 7.73 (s, 1H), 7.69 (d, J=8.1 Hz, 1H), 7.52 (t, J=8.3 Hz, 2H), 7.47-7.39 (m, 5H), 7.38 (d, J=8.3 Hz, 1H), 6.94 (s, 1H), 4.66 (s, 1H), 4.58-4.44 (m, 3H), 4.35 (d, J=15.4 Hz, 1H), 4.17 (s, 2H), 4.11-3.90 (m, 5H), 3.85 (d, J=11.0 Hz, 1H), 3.80-3.76 (m, 1H), 3.75-3.65 (m, 8H), 3.61 (d, J=11.5 Hz, 2H), 3.52 (s, 2H), 3.30-3.10 (m, 13H), 3.06-3.00 (m, 2H), 2.96 (s, 3H), 2.47 (s, 3H), 2.22 (dd, J=13.2, 7.7 Hz, 1H), 2.11-2.03 (m, 1H), 1.03 (s, 9H). HRMS (m/z) for C$_{61}$H$_{79}$F$_3$N$_{11}$O$_{10}$S$^+$ [M+H]$^+$: calculated 1214.5679. found 1214.5682.

Example 8: Synthesis of XF048-122

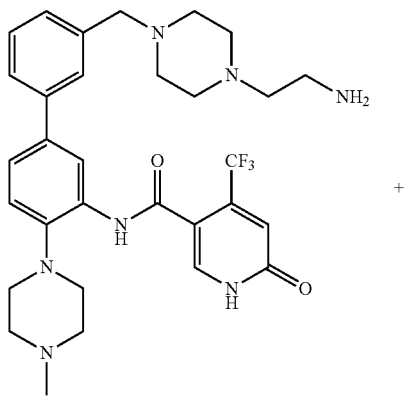

Intermediate 2

+

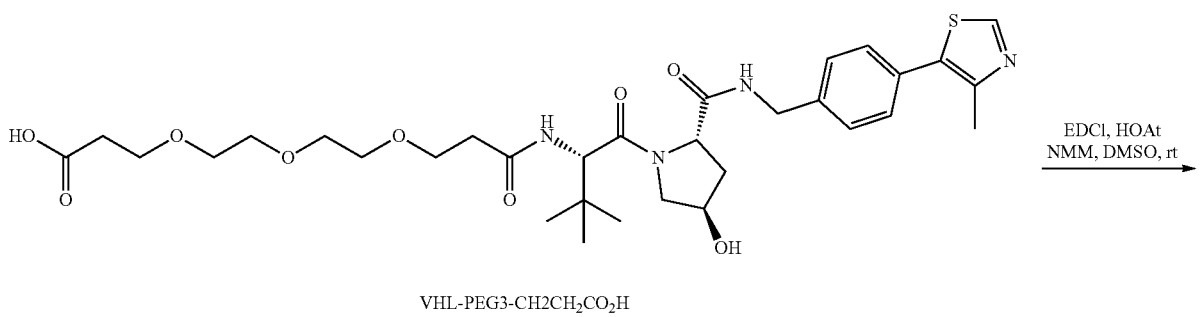

VHL-PEG3-CH2CH2CO2H

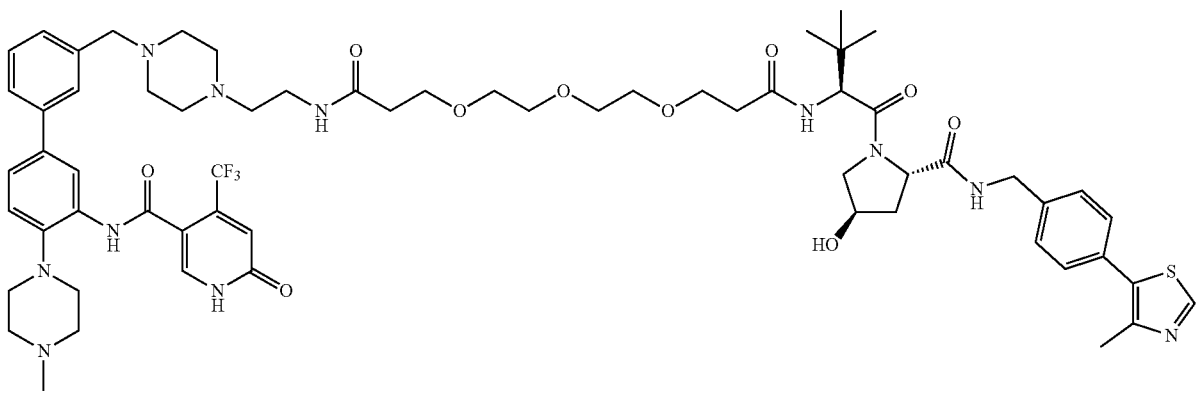

XF048-122

XF048-122 was synthesized following the standard procedures for preparing XF048-117 from intermediate 2 (13.0 mg, 0.018 mmol), VHL-PEG3-CH$_2$CH$_2$COOH (12.0 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-122 was obtained as white solid in TFA salt form (14.4 mg, yield 64%). $^1$H NMR (600 MHz, CD$_3$OD) δ 9.01 (s, 1H), 8.26 (d, J=2.4 Hz, 1H), 8.03 (s, 1H), 7.82-7.62 (m, 2H), 7.59-7.21 (m, 8H), 6.94 (s, 1H), 4.62 (s, 1H), 4.58-4.42 (m, 3H), 4.36 (d, J=15.5 Hz, 1H), 4.25 (s, 2H), 3.87 (d, J=11.0 Hz, 1H), 3.78 (dd, J=10.9, 4.0 Hz, 1H), 3.74-3.64 (m, 4H), 3.64-3.45 (m, 13H), 3.39 (s, 4H), 3.29-3.03 (m, 11H), 2.99-2.84 (m, 3H), 2.56 (ddd, J=15.5, 7.3, 5.4 Hz, 1H), 2.50-2.30 (m, 6H), 2.24-2.14 (m, 1H), 2.07 (ddd, J=13.4, 9.2, 4.5 Hz, 1H), 1.06-0.92 (m, 9H). HRMS (m/z) for C$_{63}$H$_{83}$F$_3$N$_{11}$O$_{10}$S$^+$ [M+H]$^+$: calculated 1242.5992. found 1242.5989.

Example 9: Synthesis of XF048-123

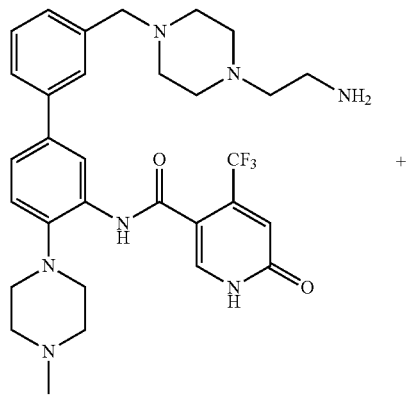

Intermediate 2

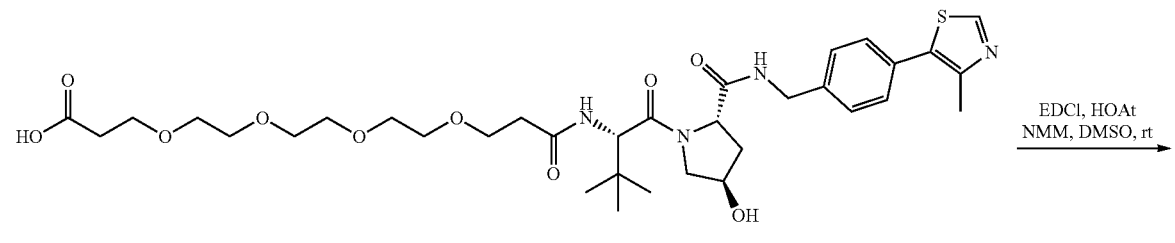

VHL-PEG4-CH₂CH₂CO₂H

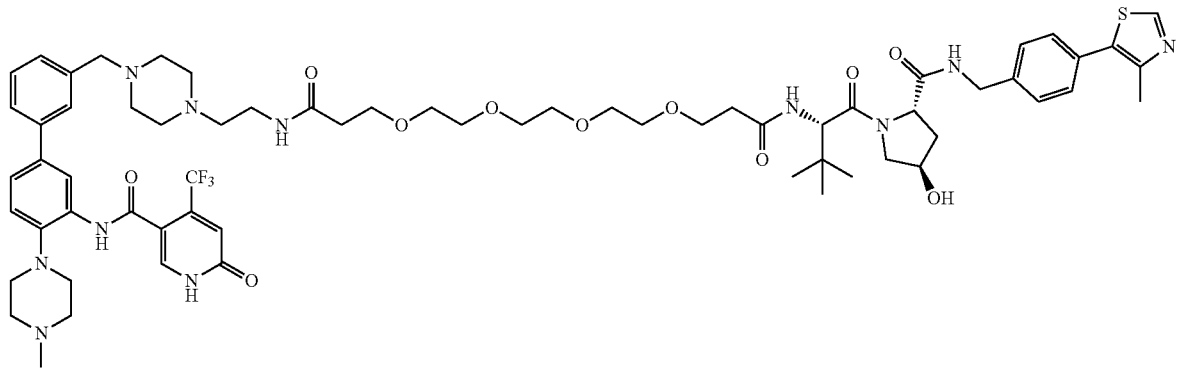

XF048-123

XF048-123 was synthesized following the standard procedures for preparing XF048-117 from intermediate 2 (13.0 mg, 0.018 mmol), VHL-PEG4-CH$_2$CH$_2$COOH (12.7 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-123 was obtained as white solid in TFA salt form (15.4 mg, yield 67%). $^1$H NMR (600 MHz, CD$_3$OD) δ 9.04 (s, 1H), 8.26 (t, J=2.2 Hz, 1H), 8.03 (d, J=2.1 Hz, 1H), 7.78 (d, J=2.3 Hz, 1H), 7.72 (d, J=7.8 Hz, 1H), 7.54 (ddt, J=7.8, 4.1, 2.4 Hz, 2H), 7.47 (dd, J=8.3, 2.1 Hz, 3H), 7.42 (dd, J=8.3, 2.2 Hz, 2H), 7.38 (dd, J=8.4, 2.2 Hz, 1H), 6.93 (d, J=2.1 Hz, 1H), 4.62 (d, J=2.2 Hz, 1H), 4.58-4.46 (m, 3H), 4.36 (dd, J=15.6, 2.2 Hz, 1H), 4.30 (d, J=2.1 Hz, 2H), 3.87 (d, J=11.0 Hz, 1H), 3.81-3.75 (m, 1H), 3.75-3.65 (m, 5H), 3.64-3.51 (m, 19H), 3.51-3.34 (m, 8H), 3.22-3.15 (m, 4H), 2.96 (d, J=2.0 Hz, 3H), 2.60-2.51 (m, 1H), 2.51-2.41 (m, 6H), 2.22 (dd, J=13.4, 7.9 Hz, 1H), 2.07 (ddt, J=13.4, 9.4, 2.2 Hz, 1H), 1.03 (d, J=2.2 Hz, 9H). HRMS (m/z) for C$_{65}$H$_{87}$F$_3$N$_1$O$_{11}$S$^+$ [M+H]$^+$: calculated 1286.6254. found 1286.6241.

Example 10: Synthesis of XF048-124

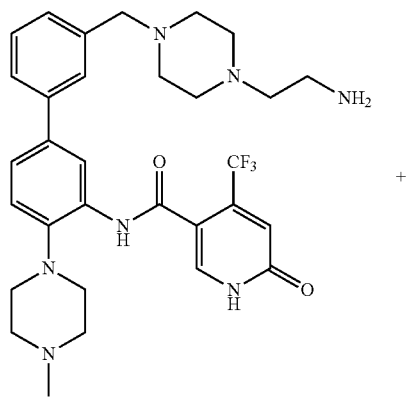

Intermediate 2

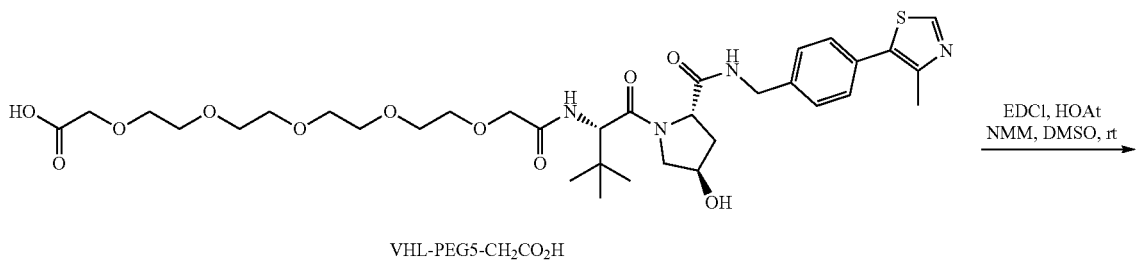

VHL-PEG5-CH₂CO₂H

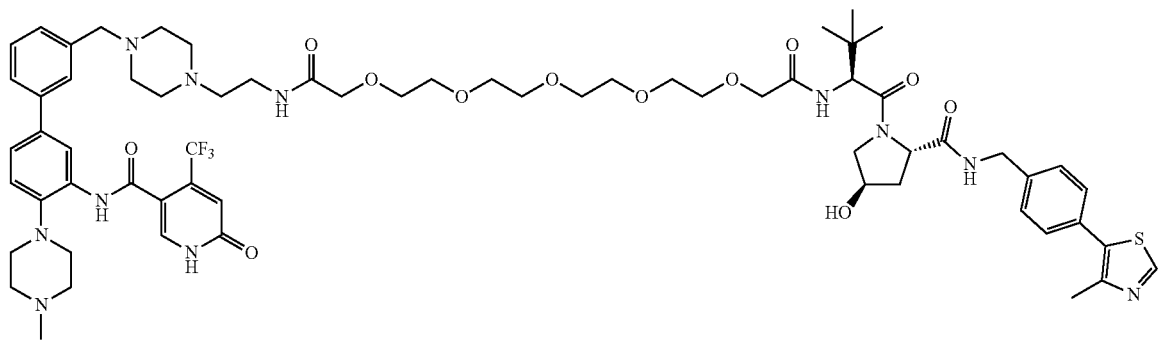

XF048-124

XF048-124 was synthesized following the standard procedures for preparing XF048-117 from intermediate 2 (13.0 mg, 0.018 mmol), VHL-PEG5-CH₂COOH (13.0 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-124 was obtained as white solid in TFA salt form (13.9 mg, yield 59%). $^1$H NMR (600 MHz, CD$_3$OD) δ 8.92 (s, 1H), 8.26 (d, J=2.2 Hz, 1H), 8.03 (s, 1H), 7.74 (d, J=2.5 Hz, 1H), 7.71-7.67 (m, 1H), 7.56-7.50 (m, 2H), 7.47-7.34 (m, 6H), 6.94 (s, 1H), 4.63 (s, 1H), 4.58-4.45 (m, 3H), 4.35 (d, J=15.5 Hz, 1H), 4.18 (s, 2H), 4.10-3.94 (m, 5H), 3.86 (d, J=11.1 Hz, 1H), 3.78 (dd, J=11.0, 3.7 Hz, 1H), 3.67-3.60 (m, 18H), 3.53 (t, J=6.1 Hz, 2H), 3.28 (s, 4H), 3.24-3.11 (m, 9H), 3.04 (t, J=5.7 Hz, 2H), 2.96 (s, 3H), 2.46 (d, J=1.1 Hz, 3H), 2.26-2.19 (m, 1H), 2.07 (ddd, J=13.4, 9.5, 4.4 Hz, 1H), 1.04 (s, 9H). HRMS (m/z) for $C_{65}H_{87}F_3N_{11}O_{12}S^+$ [M+H]$^+$: calculated 1302.6203. found 1302.6202.

Example 11: Synthesis of XF048-125

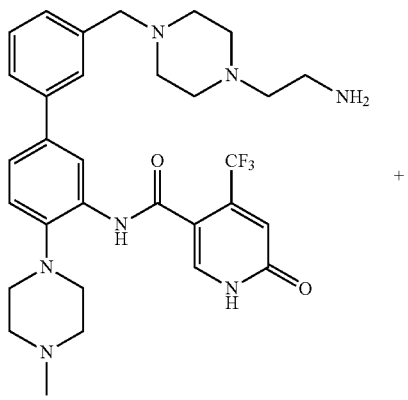

Intermediate 2

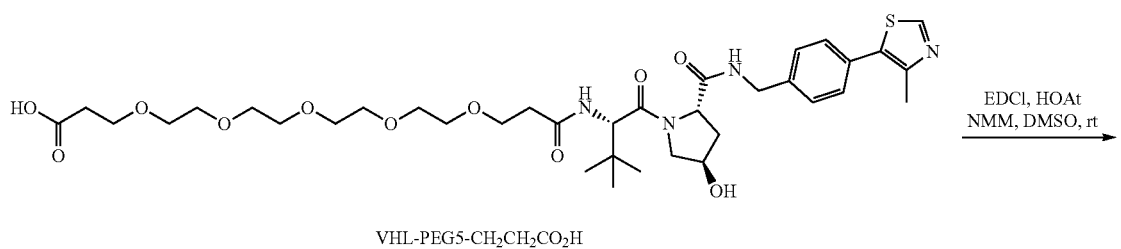

VHL-PEG5-CH₂CH₂CO₂H

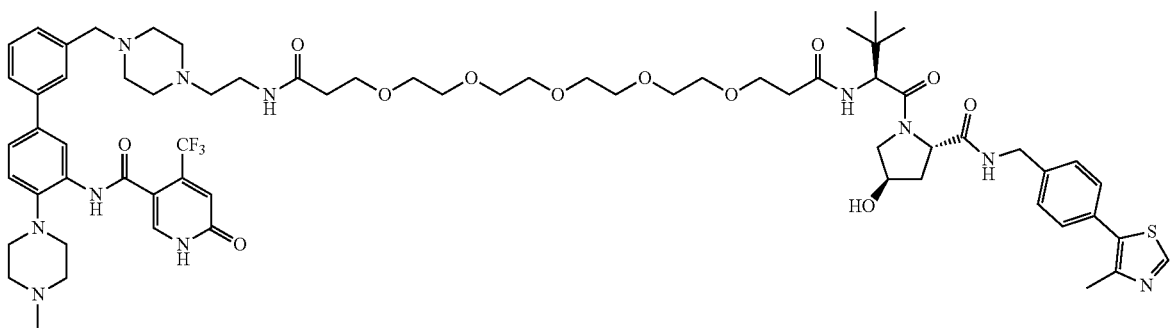

XF048-125

XF048-125 was synthesized following the standard procedures for preparing XF048-117 from intermediate 2 (13.0 mg, 0.018 mmol), VHL-PEG5-CH₂CH₂COOH (13.5 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-125 was obtained as white solid in TFA salt form (12.1 mg, yield 51%). $^1$H NMR (600 MHz, CD$_3$OD) δ 8.93 (s, 1H), 8.26 (d, J=2.2 Hz, 1H), 8.03 (s, 1H), 7.73 (d, J=2.1 Hz, 1H), 7.68 (d, J=7.8 Hz, 1H), 7.53 (ddt, J=11.2, 7.8, 4.0 Hz, 2H), 7.48-7.32 (m, 6H), 6.94 (s, 1H), 4.63 (d, J=1.7 Hz, 1H), 4.58-4.46 (m, 3H), 4.35 (d, J=15.4 Hz, 1H), 4.14 (s, 2H), 3.87 (d, J=11.0 Hz, 1H), 3.79 (dd, J=11.0, 3.8 Hz, 1H), 3.75-3.65 (m, 5H), 3.58 (ddt, J=7.3, 5.6, 2.7 Hz, 18H), 3.49 (t, J=6.0 Hz, 2H), 3.28 (s, 6H), 3.16 (t, J=12.3 Hz, 7H), 3.05 (t, J=5.8 Hz, 2H), 2.96 (d, J=1.9 Hz, 3H), 2.56 (ddd, J=15.3, 7.4, 5.2 Hz, 1H), 2.49-2.41 (m, 6H), 2.25-2.17 (m, 1H), 2.07 (ddd, J=13.3, 9.1, 4.4 Hz, 1H), 1.02 (d, J=1.8 Hz, 9H). HRMS (m/z) for $C_{67}H_{91}F_3N_{11}O_{12}S^+$ [M+H]$^+$: calculated 1330.6516, found 1330.6502.

Example 12: Synthesis of XF048-126

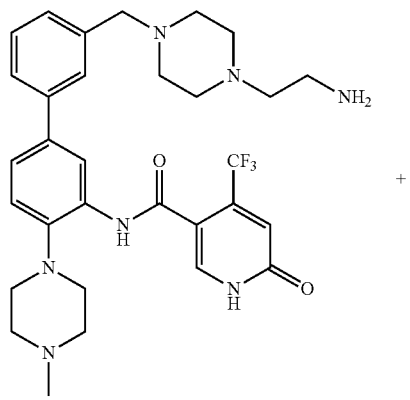

Intermediate 2

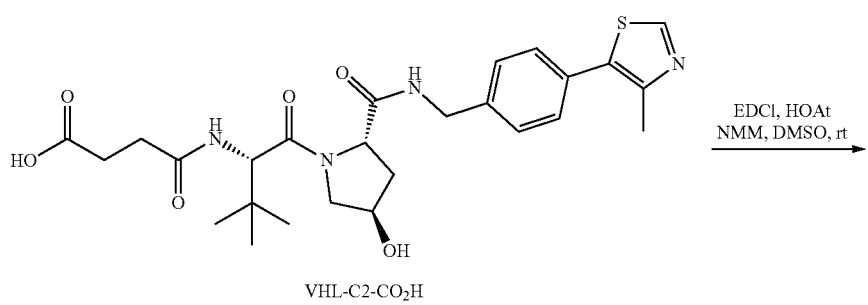

VHL-C2-CO₂H

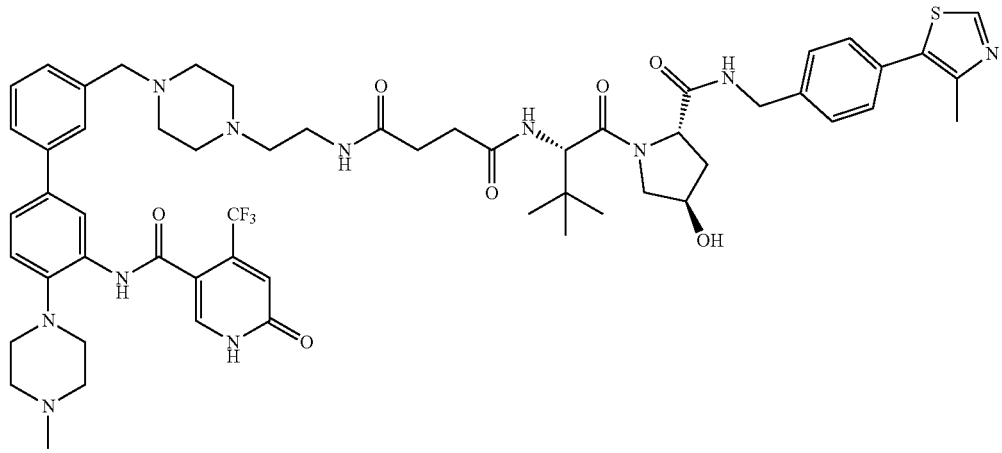

XF048-126

XF048-126 was synthesized following the standard procedures for preparing XF048-117 from intermediate 2 (13.0 mg, 0.018 mmol), VHL-C2-COOH (9.6 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-126 was obtained as white solid in TFA salt form (13.5 mg, yield 68%). $^1$H NMR (600 MHz, CD$_3$OD) δ 8.92 (s, 1H), 8.26 (d, J=2.1 Hz, 1H), 8.03 (s, 1H), 7.71 (d, J=1.8 Hz, 1H), 7.66 (d, J=7.7 Hz, 1H), 7.54-7.47 (m, 2H), 7.47-7.34 (m, 6H), 6.93 (s, 1H), 4.57-4.49 (m, 3H), 4.46 (s, 1H), 4.34 (d, J=15.5 Hz, 1H), 4.08 (q, J=12.9 Hz, 2H), 3.82 (d, J=10.9 Hz, 1H), 3.74 (dd, J=10.9, 3.8 Hz, 1H), 3.66-3.51 (m, 4H), 3.47 (dt, J=14.9, 5.5 Hz, 2H), 3.40-3.33 (m, 2H), 3.30-3.24 (m, 4H), 3.24-3.00 (m, 8H), 2.95 (s, 3H), 2.68-2.51 (m, 3H), 2.47-2.42 (m, 4H), 2.21 (dd, J=13.3, 7.5 Hz, 1H), 2.05 (ddd, J=13.3, 9.3, 4.3 Hz, 1H), 1.03 (s, 9H). HRMS (m/z) for C$_{57}$H$_{71}$F$_3$N$^{11}$O$_7$S$^+$ [M+H]$^+$: calculated 1110.5205. found 1110.5188.

Example 13: Synthesis of XF048-127

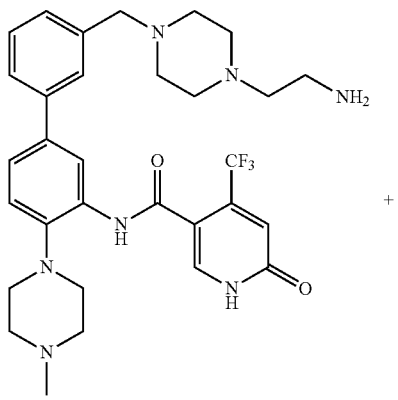
Intermediate 2

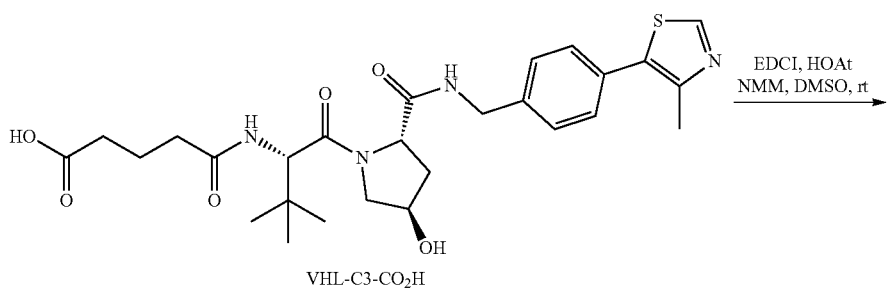
VHL-C3-CO₂H

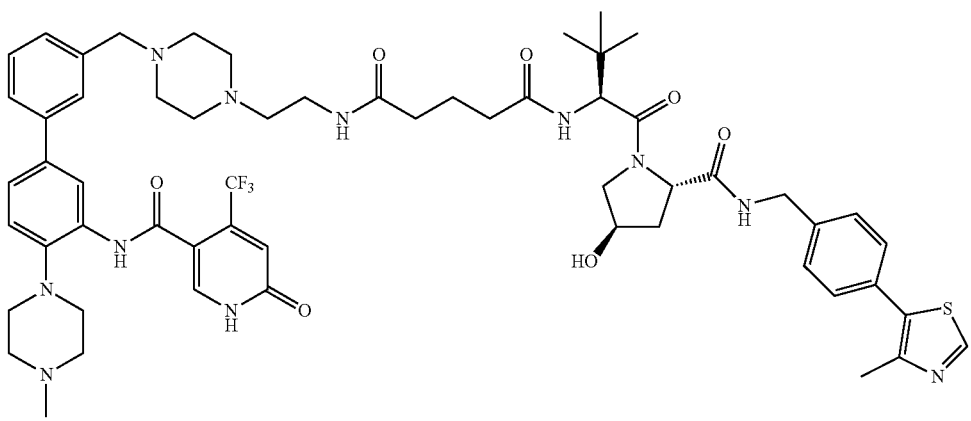
XF048-127

XF048-127 was synthesized following the standard procedures for preparing XF048-117 from intermediate 2 (13.0 mg, 0.018 mmol), VHL-C3-COOH (9.8 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-127 was obtained as white solid in TFA salt form (10.5 mg, yield 52%). $^1$H NMR (600 MHz, CD$_3$OD) δ 8.91 (d, J=3.9 Hz, 1H), 8.26 (d, J=2.2 Hz, 1H), 8.03 (s, 1H), 7.72 (d, J=1.8 Hz, 1H), 7.68 (dt, J=7.8, 1.4 Hz, 1H), 7.55-7.48 (m, 2H), 7.46-7.41 (m, 3H), 7.41-7.35 (m, 3H), 6.94 (s, 1H), 4.60 (s, 1H), 4.58-4.51 (m, 2H), 4.51-4.47 (m, 1H), 4.35 (d, J=15.5 Hz, 1H), 4.13 (s, 2H), 3.93-3.86 (m, 1H), 3.79 (dd, J=10.9, 3.9 Hz, 1H), 3.61 (d, J=11.5 Hz, 2H), 3.45 (td, J=6.0, 2.3 Hz, 2H), 3.36-3.32 (m, 1H), 3.28 (s, 4H), 3.23-3.08 (m, 9H), 3.00-2.94 (m, 5H), 2.46 (s, 3H), 2.34-2.27 (m, 2H), 2.22 (dtd, J=9.1, 7.5, 2.2 Hz, 3H), 2.07 (ddd, J=13.3, 9.3, 4.4 Hz, 1H), 1.89 (p, J=7.3 Hz, 2H), 1.03 (s, 9H). HRMS (m/z) for $C_{58}H_{73}F_3N^{11}O_7S^+$ [M+H]$^+$: calculated 1124.5362. found 1124.5349.

Example 14: Synthesis of XF048-128

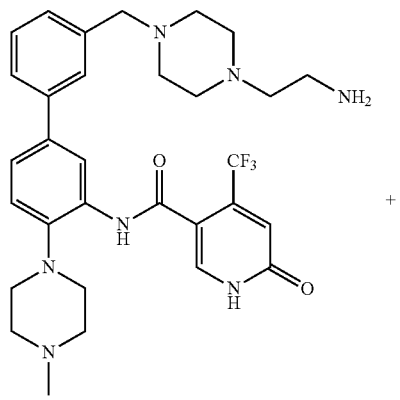
Intermediate 2

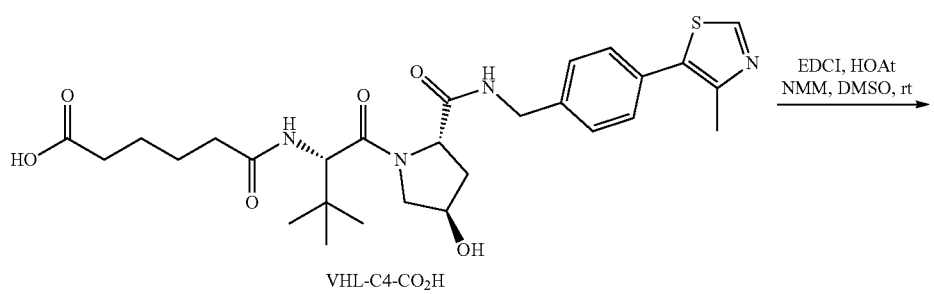
VHL-C4-CO2H

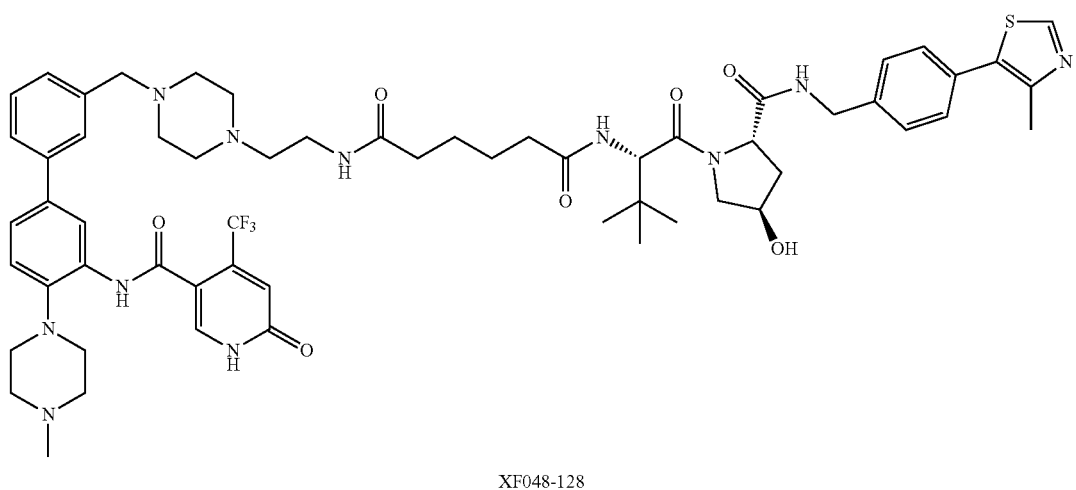
XF048-128

XF048-128 was synthesized following the standard procedures for preparing XF048-117 from intermediate 2 (13.0 mg, 0.018 mmol), VHL-C4-COOH (10.0 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-128 was obtained as white solid in TFA salt form (11.2 mg, yield 55%). $^1$H NMR (600 MHz, CD$_3$OD) δ 8.94 (d, J=2.9 Hz, 1H), 8.26 (d, J=3.6 Hz, 1H), 8.03 (s, 1H), 7.71 (d, J=30.9 Hz, 2H), 7.53 (t, J=7.7 Hz, 2H), 7.47-7.28 (m, 6H), 6.94 (s, 1H), 4.61 (s, 1H), 4.58-4.40 (m, 3H), 4.36 (d, J=14.6 Hz, 1H), 4.18 (s, 2H), 3.88 (d, J=11.2 Hz, 1H), 3.78 (d, J=10.7 Hz, 1H), 3.61 (d, J=12.4 Hz, 2H), 3.49-3.36 (m, 2H), 3.28 (s, 4H), 3.18 (s, 10H), 3.00-2.91 (m, 5H), 2.50-2.40 (m, 3H), 2.34-2.13 (m, 5H), 2.07 (dd, J=14.0, 8.9 Hz, 1H), 1.61 (d, 4H), 1.02 (s, 9H). HRMS (m/z) for $C_{59}H_{75}F_3N_{11}O_7S^+$ [M+H]$^+$: calculated 1138.5518. found 1138.5509.

Example 15: Synthesis of XF048-129

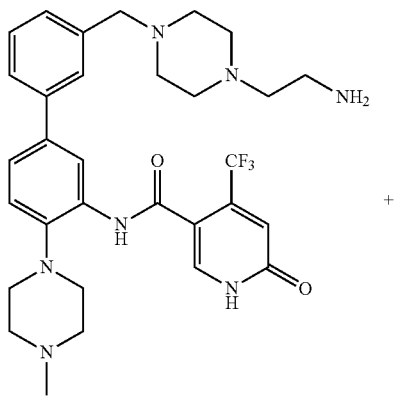

Intermediate 2

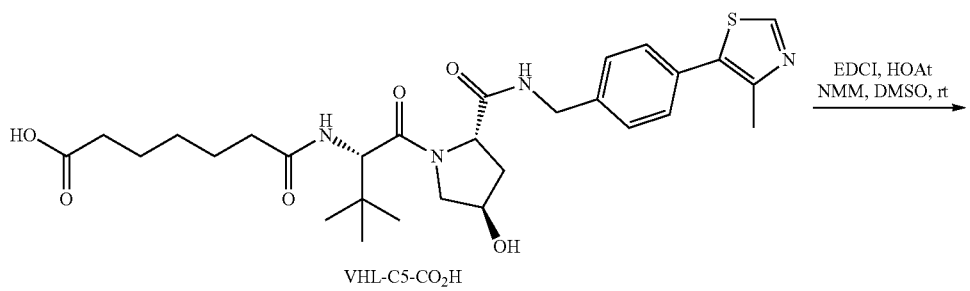

VHL-C5-CO₂H

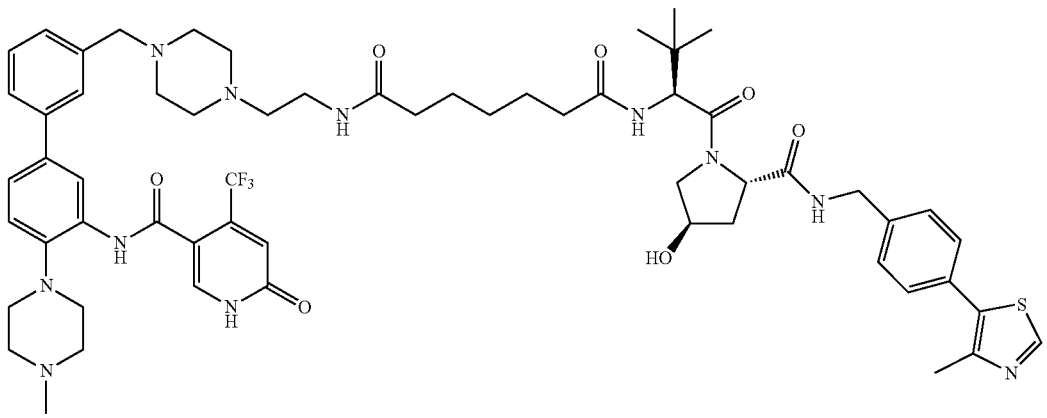

XF048-129

XF048-129 was synthesized following the standard procedures for preparing XF048-117 from intermediate 2 (13.0 mg, 0.018 mmol), VHL-C5-COOH (10.3 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-129 was obtained as white solid in TFA salt form (10.8 mg, yield 52%). $^1$H NMR (600 MHz, CD$_3$OD) δ 8.94 (s, 1H), 8.26 (d, J=2.1 Hz, 1H), 8.03 (s, 1H), 7.73 (q, J=3.4, 2.6 Hz, 1H), 7.69 (dt, J=7.9, 1.4 Hz, 1H), 7.55-7.49 (m, 2H), 7.48-7.36 (m, 6H), 6.94 (s, 1H), 4.62 (s, 1H), 4.59-4.46 (m, 3H), 4.36 (d, J=15.5 Hz, 1H), 4.17 (s, 2H), 3.89 (d, J=10.7 Hz, 1H), 3.79 (dd, J=10.9, 3.9 Hz, 1H), 3.64-3.58 (m, 2H), 3.45 (t, J=6.1 Hz, 2H), 3.36-3.31 (m, 1H), 3.28 (s, 3H), 3.26-3.08 (m, 10H), 2.99 (t, J=6.1 Hz, 2H), 2.96 (s, 3H), 2.47 (s, 3H), 2.32-2.18 (m, 5H), 2.07 (ddd, J=13.3, 9.2, 4.5 Hz, 1H), 1.61 (dp, J=7.8, 5.6, 3.8 Hz, 4H), 1.33 (dq, J=17.1, 9.4, 8.6 Hz, 2H), 1.02 (s, 9H). HRMS (m/z) for $C_{60}H_{77}F_3N^{11}O_7S^+$ [M+H]$^+$: calculated 1152.5675. found 1152.5677.

Example 16: Synthesis of XF048-130

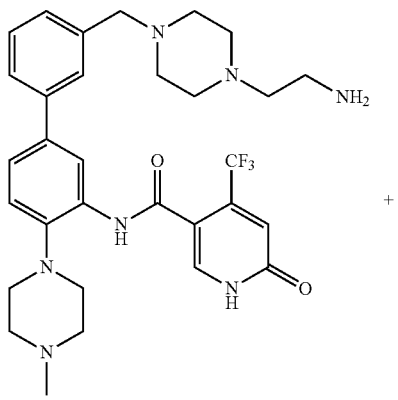

Intermediate 2

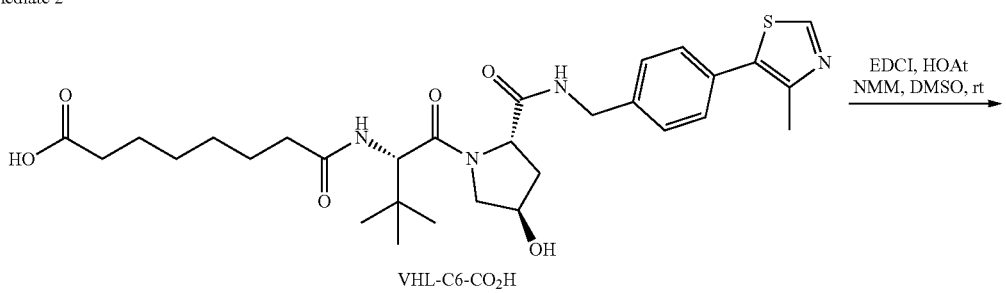

VHL-C6-CO$_2$H

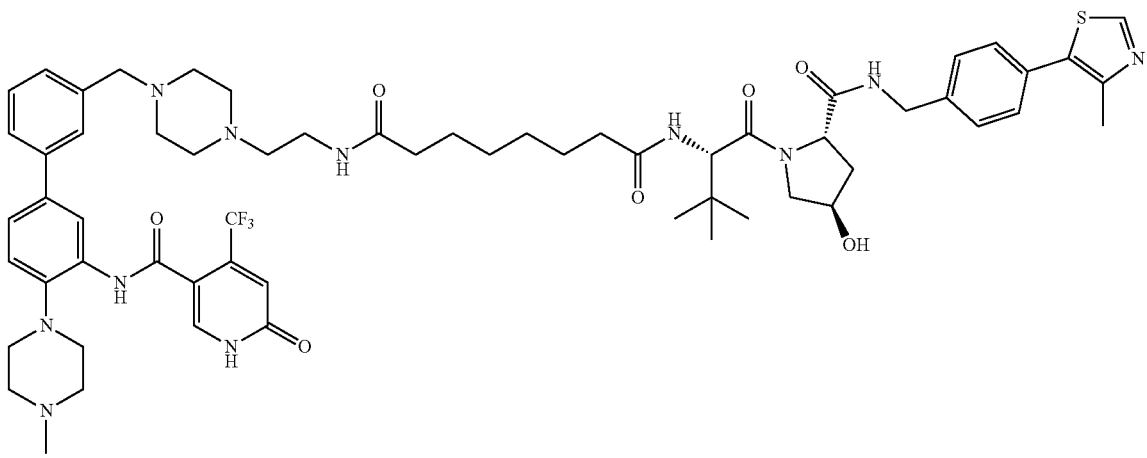

XF048-130

XF048-130 was synthesized following the standard procedures for preparing XF048-117 from intermediate 2 (13.0 mg, 0.018 mmol), VHL-C6-COOH (10.5 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-130 was obtained as white solid in TFA salt form (11.5 mg, yield 55%). $^1$H NMR (600 MHz, CD$_3$OD) δ 8.92 (s, 1H), 8.26 (d, J=2.2 Hz, 1H), 8.03 (s, 1H), 7.73 (d, J=2.0 Hz, 1H), 7.68 (d, J=7.9 Hz, 1H), 7.53 (ddt, J=11.4, 7.8, 3.4 Hz, 2H), 7.48-7.33 (m, 6H), 6.94 (s, 1H), 4.63 (s, 1H), 4.60-4.44 (m, 3H), 4.36 (d, J=15.5 Hz, 1H), 4.13 (s, 2H), 3.89 (d, J=10.9 Hz, 1H), 3.79 (dd, J=10.9, 4.0 Hz, 1H), 3.61 (d, J=11.7 Hz, 2H), 3.43 (t, J=6.1 Hz, 2H), 3.35-3.31 (m, 1H), 3.28 (s, 3H), 3.24-3.04 (m, 10H), 2.98-2.92 (m, 5H), 2.48-2.43 (m, 3H), 2.33-2.16 (m, 5H), 2.07 (ddd, J=13.3, 9.2, 4.5 Hz, 1H), 1.59 (s, 4H), 1.36-1.29 (m, 4H), 1.02 (s, 9H). HRMS (m/z) for C$_{61}$H$_{79}$F$_3$N$_{11}$O$_7$S$^+$ [M+H]$^+$: calculated 1166.5831. found 1166.5842.

Example 17: Synthesis of XF048-131

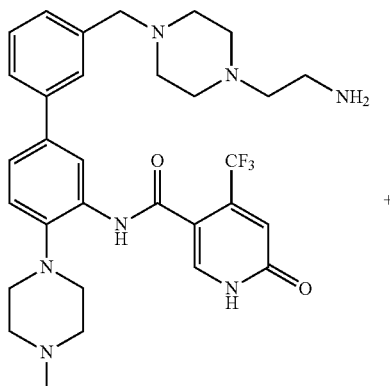

Intermediate 2

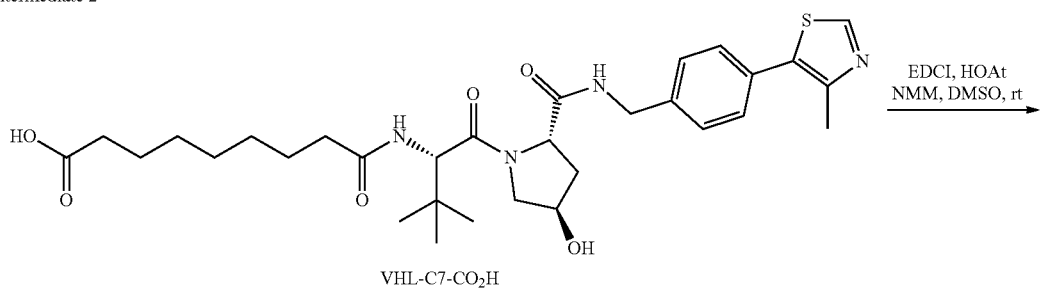

VHL-C7-CO$_2$H

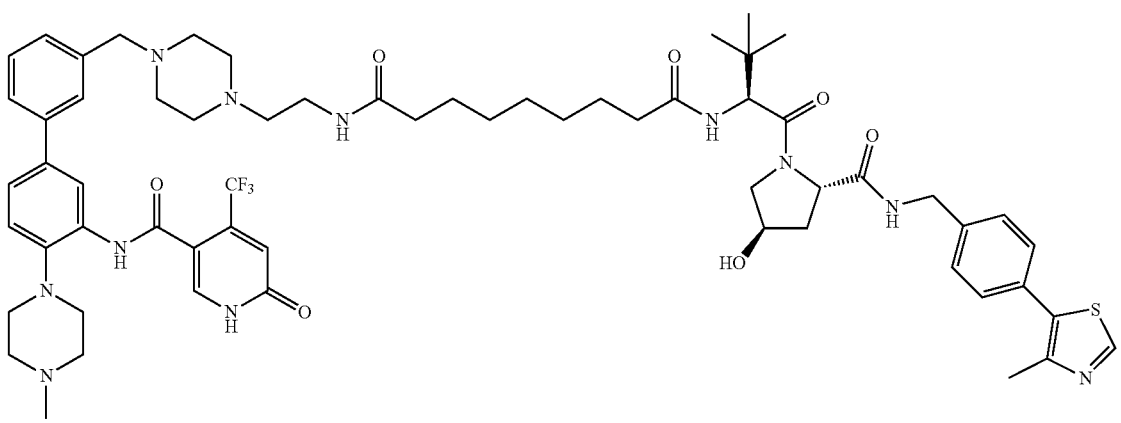

XF048-131

XF048-131 was synthesized following the standard procedures for preparing XF048-117 from intermediate 2 (13.0 mg, 0.018 mmol), VHL-C7-COOH (10.5 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-131 was obtained as white solid in TFA salt form (10.4 mg, yield 49%). $^1$H NMR (600 MHz, CD$_3$OD) δ 8.92 (s, 1H), 8.26 (d, J=2.6 Hz, 1H), 8.03 (s, 1H), 7.76-7.70 (m, 1H), 7.68 (d, J=7.9 Hz, 1H), 7.56-7.49 (m, 2H), 7.49-7.34 (m, 6H), 6.94 (s, 1H), 4.62 (s, 1H), 4.60-4.46 (m, 3H), 4.36 (d, J=15.8 Hz, 1H), 4.13 (s, 2H), 3.89 (d, J=10.7 Hz, 1H), 3.79 (dd, J=11.0, 4.0 Hz, 1H), 3.61 (d, J=11.5 Hz, 2H), 3.43 (t, J=6.2 Hz, 2H), 3.37-3.33 (m, 1H), 3.28 (s, 3H), 3.24-3.05 (m, 10H), 2.99-2.93 (m, 5H), 2.50-2.45 (m, 3H), 2.32-2.17 (m, 5H), 2.07 (ddd, J=13.3, 9.2, 4.5 Hz, 1H), 1.66-1.54 (m, 4H), 1.35-1.29 (m, 6H), 1.03 (s, 9H). HRMS (m/z) for C$_{62}$H$_{81}$F$_3$N$^{11}$O$_7$S$^+$ [M+H]$^+$: calculated 1180.5988, found 1180.5976.

Example 18: Synthesis of XF048-132

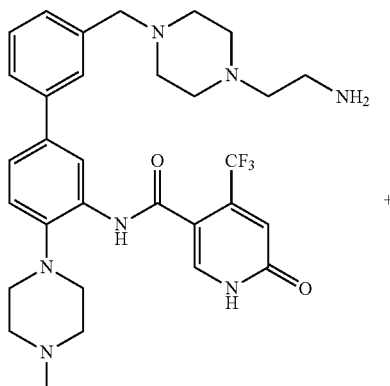

Intermediate 2

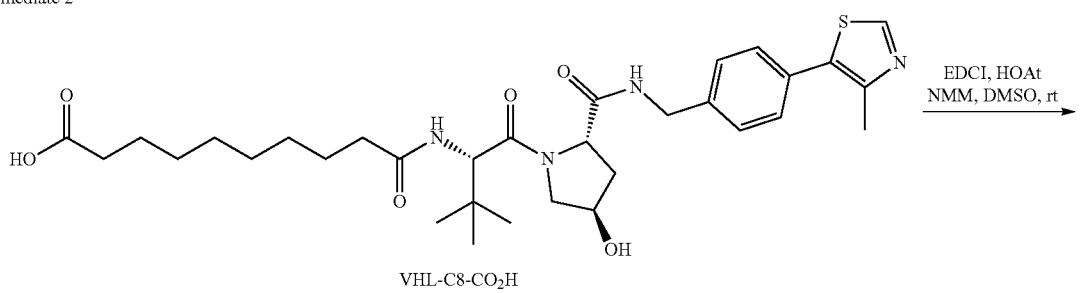

VHL-C8-CO2H

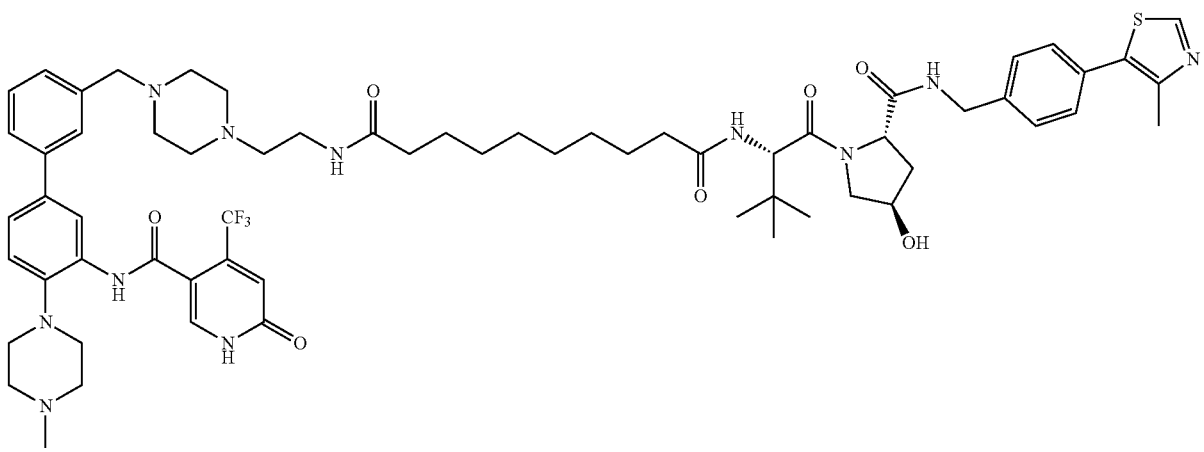

XF048-132

XF048-132 was synthesized following the standard procedures for preparing XF048-117 from intermediate 2 (13.0 mg, 0.018 mmol), VHL-C8-COOH (11.1 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-132 was obtained as white solid in TFA salt form (7.2 mg, yield 34%). $^1$H NMR (600 MHz, CD$_3$OD) δ 8.91 (d, J=1.9 Hz, 1H), 8.28-8.24 (m, 1H), 8.03 (d, J=1.8 Hz, 1H), 7.75-7.70 (m, 1H), 7.68 (d, J=7.7 Hz, 1H), 7.53 (ddt, J=9.9, 7.7, 4.0 Hz, 2H), 7.48-7.34 (m, 6H), 6.94 (d, J=3.9 Hz, 1H), 4.63 (d, J=1.8 Hz, 1H), 4.59-4.46 (m, 3H), 4.35 (d, J=15.8 Hz, 1H), 4.13 (s, 2H), 3.92-3.86 (m, 1H), 3.82-3.77 (m, 1H), 3.61 (d, J=11.6 Hz, 2H), 3.43 (dt, J=6.1, 3.1 Hz, 2H), 3.34 (t, J=1.6 Hz, 1H), 3.28 (s, 3H), 3.25-3.03 (m, 10H), 2.98-2.92 (m, 5H), 2.47 (dd, J=3.8, 1.6 Hz, 3H), 2.32-2.16 (m, 5H), 2.12-2.04 (m, 1H), 1.58 (s, 4H), 1.31 (s, 8H), 1.03 (s, 9H). HRMS (m/z) for $C_{63}H_{83}F_3N_{11}O_7S^+$ [M+H]$^+$: calculated 1194.6144. found 1194.6112.

Example 19: Synthesis of XF048-133

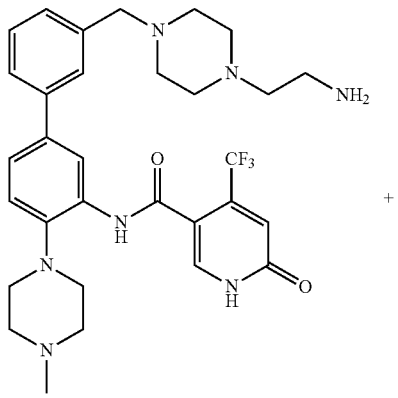
Intermediate 2

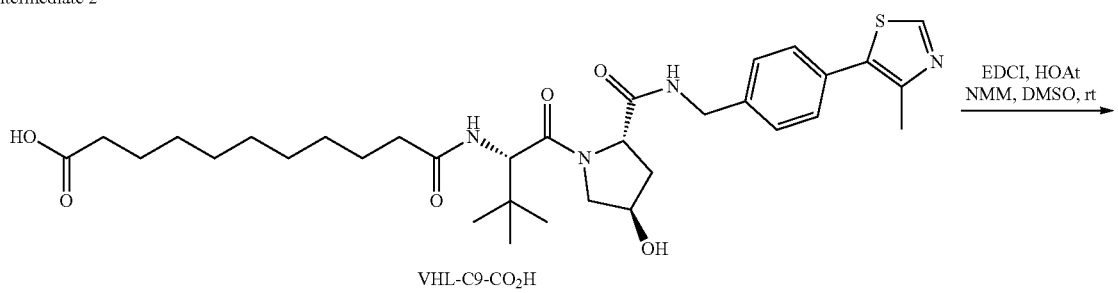
VHL-C9-CO₂H

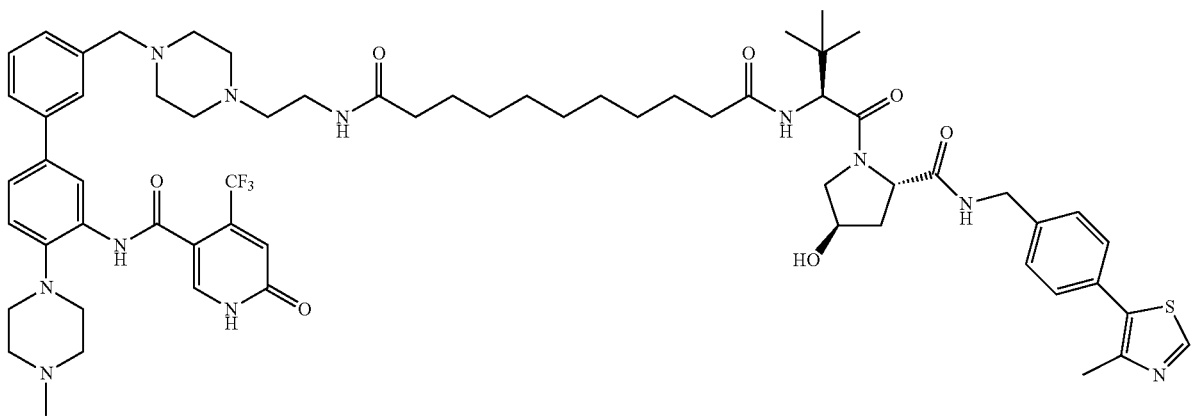
XF048-133

XF048-133 was synthesized following the standard procedures for preparing XF048-117 from intermediate 2 (13.0 mg, 0.018 mmol), VHL-C9-COOH (11.3 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-133 was obtained as white solid in TFA salt form (7.7 mg, yield 35%). $^1$H NMR (600 MHz, CD$_3$OD) δ 8.94 (s, 1H), 8.26 (d, J=2.1 Hz, 1H), 8.03 (s, 1H), 7.73 (d, J=1.9 Hz, 1H), 7.69 (dt, J=7.8, 1.5 Hz, 1H), 7.56-7.50 (m, 2H), 7.49-7.35 (m, 6H), 6.94 (s, 1H), 4.63 (s, 1H), 4.59-4.46 (m, 3H), 4.36 (d, J=15.5 Hz, 1H), 4.15 (s, 2H), 3.89 (dt, J=11.3, 1.8 Hz, 1H), 3.80 (dd, J=11.0, 3.9 Hz, 1H), 3.61 (d, J=11.5 Hz, 2H), 3.44 (t, J=6.1 Hz, 2H), 3.33 (d, J=14.8 Hz, 1H), 3.28 (s, 3H), 3.25-3.07 (m, 10H), 2.99-2.94 (m, 5H), 2.47 (s, 3H), 2.31-2.17 (m, 5H), 2.07 (ddd, J=13.3, 9.1, 4.5 Hz, 1H), 1.59 (d, J=7.5 Hz, 4H), 1.30 (s, 10H), 1.03 (s, 9H). HRMS (m/z) for $C_{64}H_{85}F_3N^{11}O_7S^+$ [M+H]$^+$: calculated 1208.6301. found 1208.6323.

Example 20: Synthesis of XF048-134

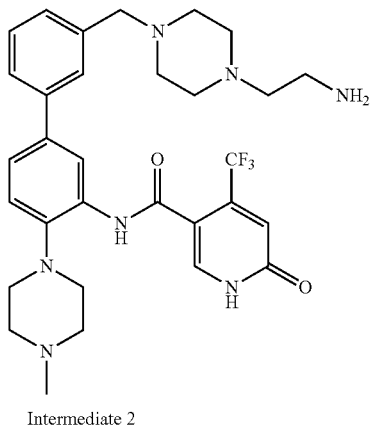

Intermediate 2

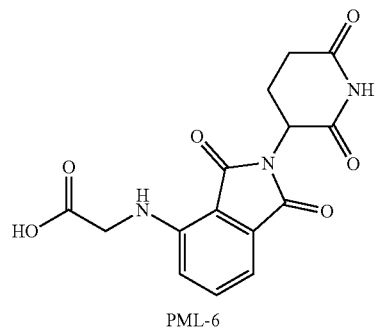

PML-6

EDCI, HOAt
NMM, DMSO, rt →

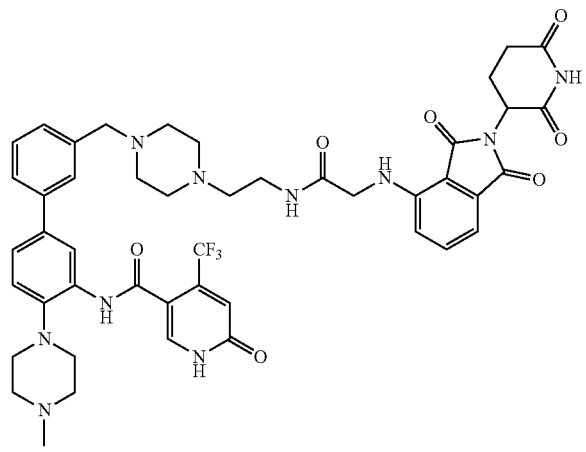

XF048-134

XF048-134 was synthesized following the standard procedures for preparing XF048-117 from intermediate 2 (13.0 mg, 0.018 mmol), PML-6 (6.0 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-134 was obtained as yellow solid in TFA salt form (8.2 mg, yield 50%). $^1$H NMR (600 MHz, CD$_3$OD) δ 8.26 (d, J=2.2 Hz, 1H), 8.02 (s, 1H), 7.71 (dd, J=7.7, 1.3 Hz, 2H), 7.56-7.51 (m, 3H), 7.43 (dt, J=7.6, 1.4 Hz, 1H), 7.38 (d, J=8.3 Hz, 1H), 7.10 (d, J=7.1 Hz, 1H), 6.93 (s, 1H), 6.89 (d, J=8.5 Hz, 1H), 5.09 (dd, J=12.4, 5.5 Hz, 1H), 4.22-4.13 (m, 2H), 4.04-3.98 (m, 2H), 3.64-3.56 (m, 2H), 3.44 (td, J=5.4, 2.8 Hz, 2H), 3.36-3.32 (m, 1H), 3.29 (s, 3H), 3.16 (t, J=12.8 Hz, 8H), 2.96 (s, 3H), 2.87-2.78 (m, 3H), 2.77-2.68 (m, 2H), 2.67-2.62 (m, 2H), 2.11 (ddd, J=10.2, 7.8, 3.7 Hz, 1H). HRMS (m/z) for $C_{46}H_{50}F_3N_{10}O_7^+$ [M+H]$^+$: calculated 911.3811. found 911.3806.

Example 21: Synthesis of XF048-135

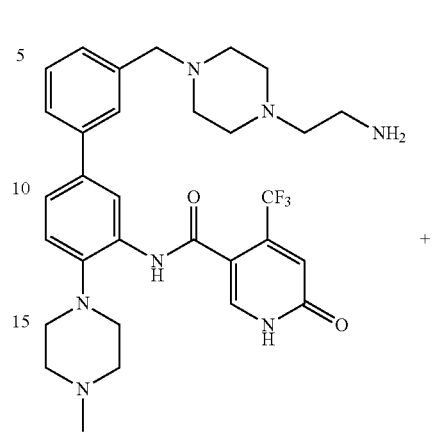

Intermediate 2

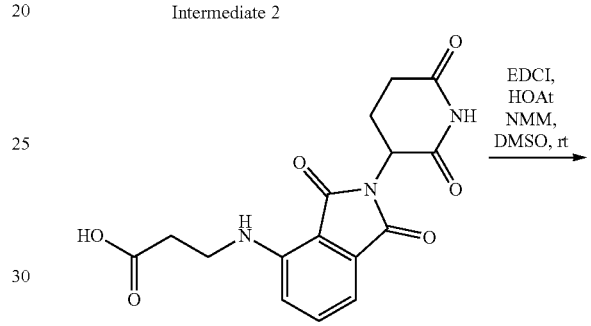

PML-7

EDCI, HOAt NMM, DMSO, rt →

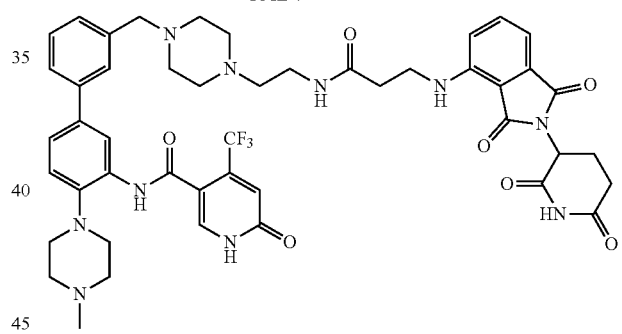

XF048-135

XF048-135 was synthesized following the standard procedures for preparing XF048-117 from intermediate 2 (13.0 mg, 0.018 mmol), PML-7 (6.2 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-135 was obtained as yellow solid in TFA salt form (8.2 mg, yield 49%). $^1$H NMR (600 MHz, CD$_3$OD) δ 8.25 (d, J=2.2 Hz, 1H), 8.02 (s, 1H), 7.72 (t, J=1.8 Hz, 1H), 7.69 (d, J=7.9 Hz, 1H), 7.58-7.47 (m, 3H), 7.41 (d, J=7.5 Hz, 1H), 7.37 (dd, J=8.4, 1.4 Hz, 1H), 7.10 (d, J=8.5 Hz, 1H), 7.07-7.01 (m, 1H), 6.92 (s, 1H), 5.01 (dd, J=12.6, 5.4 Hz, 1H), 4.17-4.06 (m, 2H), 3.66-3.57 (m, 4H), 3.43 (q, J=5.7, 5.2 Hz, 2H), 3.35-3.31 (m, 1H), 3.28 (s, 3H), 3.14 (d, J=19.4 Hz, 9H), 2.96 (s, 3H), 2.90 (t, J=6.0 Hz, 2H), 2.83-2.74 (m, 1H), 2.72-2.61 (m, 3H), 2.54 (t, J=6.2 Hz, 2H), 2.11-2.01 (m, 1H). HRMS (m/z) for $C_{47}H_{52}F_3N_{10}O_7^+$ [M+H]$^+$: calculated 925.3967. found 925.3964.

Example 22: Synthesis of XF048-136

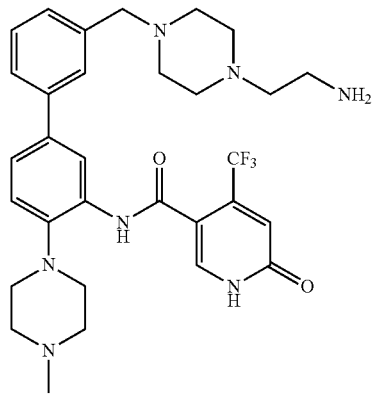

Intermediate 2

+

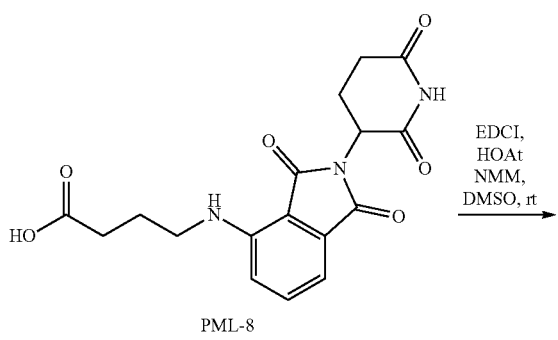

PML-8

EDCI, HOAt NMM, DMSO, rt

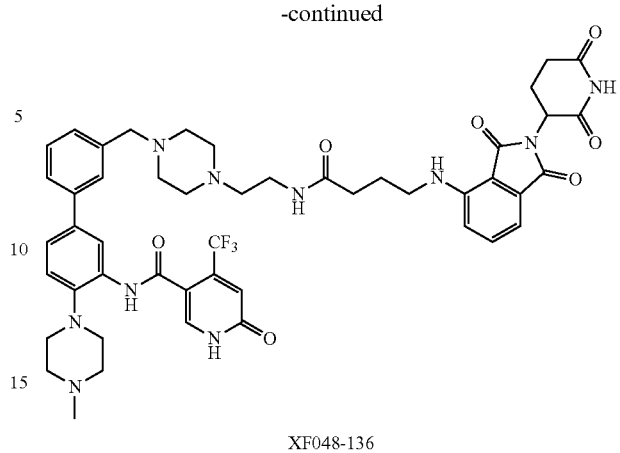

XF048-136

XF048-136 was synthesized following the standard procedures for preparing XF048-117 from intermediate 2 (13.0 mg, 0.018 mmol), PML-8 (6.5 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-136 was obtained as yellow solid in TFA salt form (7.5 mg, yield 44%). $^1$H NMR (600 MHz, CD$_3$OD) δ 8.24 (d, J=2.3 Hz, 1H), 8.02 (d, J=1.9 Hz, 1H), 7.71 (d, J=1.9 Hz, 1H), 7.68 (dd, J=7.8, 1.8 Hz, 1H), 7.52 (dtd, J=9.2, 5.0, 3.1 Hz, 3H), 7.44-7.39 (m, 1H), 7.36 (dd, J=8.1, 1.9 Hz, 1H), 7.02 (ddd, J=16.5, 7.8, 2.0 Hz, 2H), 6.93 (s, 1H), 5.04 (ddd, J=12.4, 5.2, 1.7 Hz, 1H), 4.12 (s, 2H), 3.61 (d, J=11.8 Hz, 2H), 3.44-3.37 (m, 2H), 3.37-3.31 (m, 3H), 3.28 (s, 3H), 3.23-2.99 (m, 9H), 2.96 (d, J=2.0 Hz, 3H), 2.92 (t, J=6.0 Hz, 2H), 2.83 (ddd, J=17.9, 14.0, 5.3 Hz, 1H), 2.75-2.61 (m, 3H), 2.33 (t, J=7.1 Hz, 2H), 2.07 (ddt, J=13.2, 6.2, 2.9 Hz, 1H), 2.00-1.90 (m, 2H). HRMS (m/z) for C$_{48}$H$_{54}$F$_3$N$_{10}$O$_7^+$ [M+H]$^+$: calculated 939.4124. found 939.4123.

Example 23: Synthesis of XF048-137

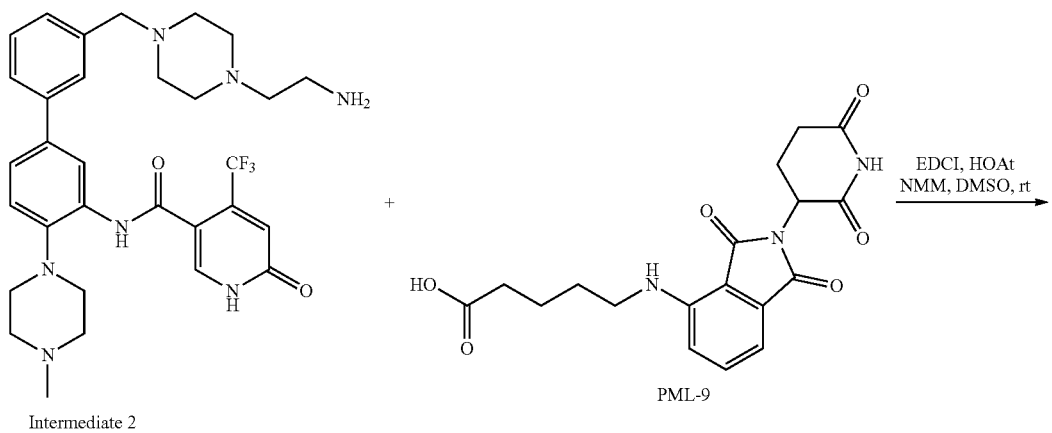

Intermediate 2

PML-9

EDCI, HOAt NMM, DMSO, rt

-continued

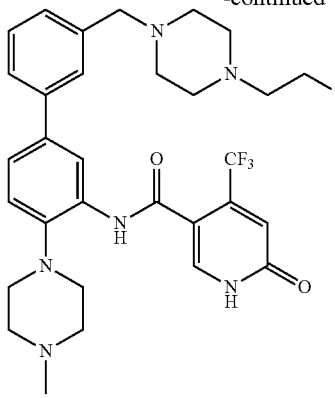 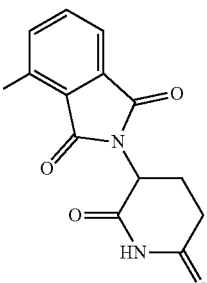

XF048-137

XF048-137 was synthesized following the standard procedures for preparing XF048-117 from intermediate 2 (13.0 mg, 0.018 mmol), PML-9 (6.7 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-137 was obtained as yellow solid in TFA salt form (12.2 mg, yield 71%). $^1$H NMR (600 MHz, CD$_3$OD) δ 8.25 (d, J=2.2 Hz, 1H), 8.02 (s, 1H), 7.72 (d, J=1.8 Hz, 1H), 7.69 (dt, J=7.8, 1.4 Hz, 1H), 7.55-7.49 (m, 3H), 7.41 (dt, J=7.6, 1.4 Hz, 1H), 7.36 (d, J=8.4 Hz, 1H), 7.02 (dd, J=7.8, 4.2 Hz, 2H), 6.93 (s, 1H), 5.02 (dd, J=12.5, 5.5 Hz, 1H), 4.15 (s, 2H), 3.61 (d, J=11.7 Hz, 2H), 3.42 (t, J=6.0 Hz, 2H), 3.36-3.31 (m, 3H), 3.27 (s, 3H), 3.22-3.00 (m, 9H), 2.96 (s, 3H), 2.89 (t, J=5.9 Hz, 2H), 2.80 (ddd, J=18.1, 14.3, 5.5 Hz, 1H), 2.73-2.61 (m, 3H), 2.26 (t, J=7.1 Hz, 2H), 2.10-2.02 (m, 1H), 1.76-1.61 (m, 4H). HRMS (m/z) for $C_{49}H_{56}F_3N_{10}O_7^+$ [M+H]$^+$: calculated 953.4280. found 953.4292.

Example 24: Synthesis of XF048-138

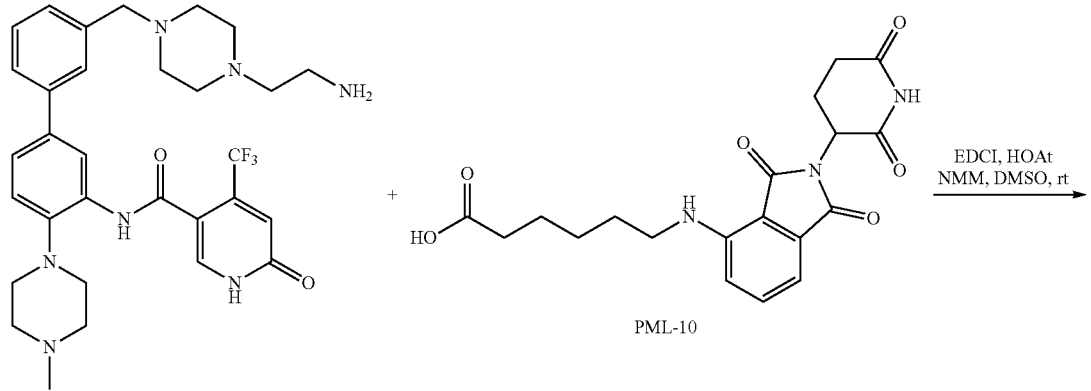

Intermediate 2     PML-10

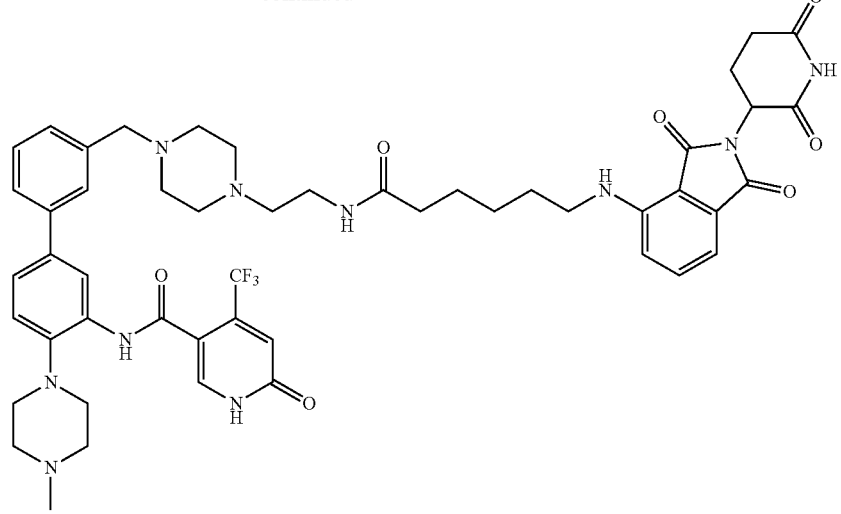

XF048-138

XF048-138 was synthesized following the standard procedures for preparing XF048-117 from intermediate 2 (13.0 mg, 0.018 mmol), PML-10 (7.2 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-138 was obtained as yellow solid in TFA salt form (11.5 mg, yield 66%). $^1$H NMR (600 MHz, CD$_3$OD) δ 8.24 (t, J=3.0 Hz, 1H), 8.02 (s, 1H), 7.74-7.70 (m, 1H), 7.69 (d, J=8.0 Hz, 1H), 7.52 (ddt, J=10.7, 8.3, 2.9 Hz, 3H), 7.42 (d, J=7.4 Hz, 1H), 7.36 (d, J=8.3 Hz, 1H), 7.03-6.95 (m, 2H), 6.93 (s, 1H), 5.06-4.98 (m, 1H), 4.13 (s, 2H), 3.60 (d, J=11.8 Hz, 2H), 3.42 (t, J=6.0 Hz, 2H), 3.35-3.30 (m, 3H), 3.27 (s, 3H), 3.22-3.00 (m, 9H), 2.98-2.88 (m, 5H), 2.83 (ddd, J=17.7, 13.9, 5.4 Hz, 1H), 2.74-2.60 (m, 3H), 2.23 (t, J=7.3 Hz, 2H), 2.11-2.03 (m, 1H), 1.65 (ddt, J=14.8, 9.6, 5.4 Hz, 4H), 1.47-1.36 (m, 2H). HRMS (m/z) for C$_{50}$H$_{58}$F$_3$N$_{10}$O$_7^+$ [M+H]$^+$: calculated 967.4437. found 967.4441.

Example 25: Synthesis of XF048-139

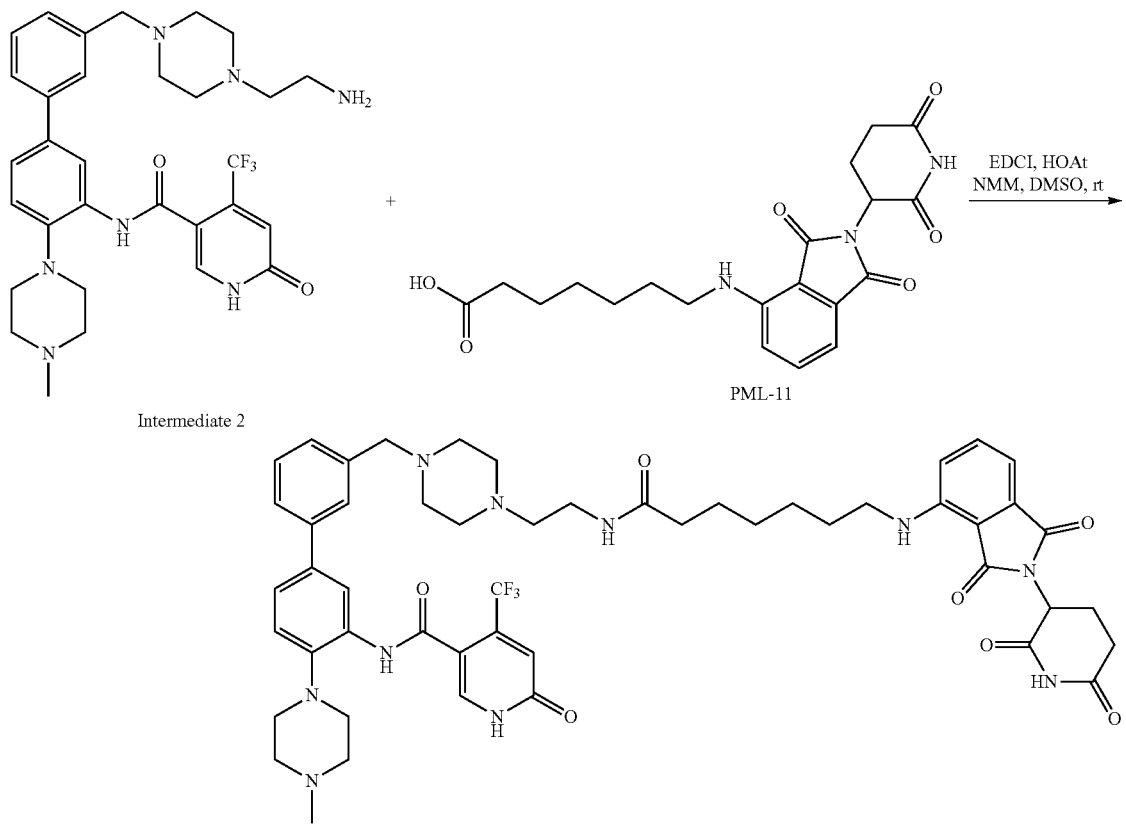

XF048-139

XF048-139 was synthesized following the standard procedures for preparing XF048-117 from intermediate 2 (13.0 mg, 0.018 mmol), PML-11 (7.2 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-139 was obtained as yellow solid in TFA salt form (10.5 mg, yield 59%). $^1$H NMR (600 MHz, CD$_3$OD) δ 8.25 (d, J=2.2 Hz, 1H), 8.02 (d, J=4.0 Hz, 1H), 7.72 (s, 1H), 7.68 (d, J=7.6 Hz, 1H), 7.52 (ddd, J=11.3, 6.2, 2.9 Hz, 3H), 7.42 (d, J=7.4 Hz, 1H), 7.39-7.32 (m, 1H), 7.01 (dd, J=9.4, 3.1 Hz, 2H), 6.93 (d, J=4.1 Hz, 1H), 5.03 (dd, J=12.7, 5.5 Hz, 1H), 4.12 (s, 2H), 3.60 (d, J=11.8 Hz, 2H), 3.42 (t, J=5.9 Hz, 2H), 3.35-3.30 (m, 3H), 3.28-3.23 (m, 3H), 3.22-3.03 (m, 9H), 2.96 (s, 3H), 2.94-2.88 (m, 2H), 2.83 (ddd, J=18.1, 13.7, 5.3 Hz, 1H), 2.74-2.63 (m, 3H), 2.21 (t, J=7.1 Hz, 2H), 2.12-2.03 (m, 1H), 1.63 (dp, J=15.1, 7.3 Hz, 4H), 1.47-1.32 (m, 4H). HRMS (m/z) for $C_{51}H_{60}F_3N_{10}O_7^+$ [M+H]$^+$: calculated 981.4593. found 981.4573.

Example 26: Synthesis of XF048-140

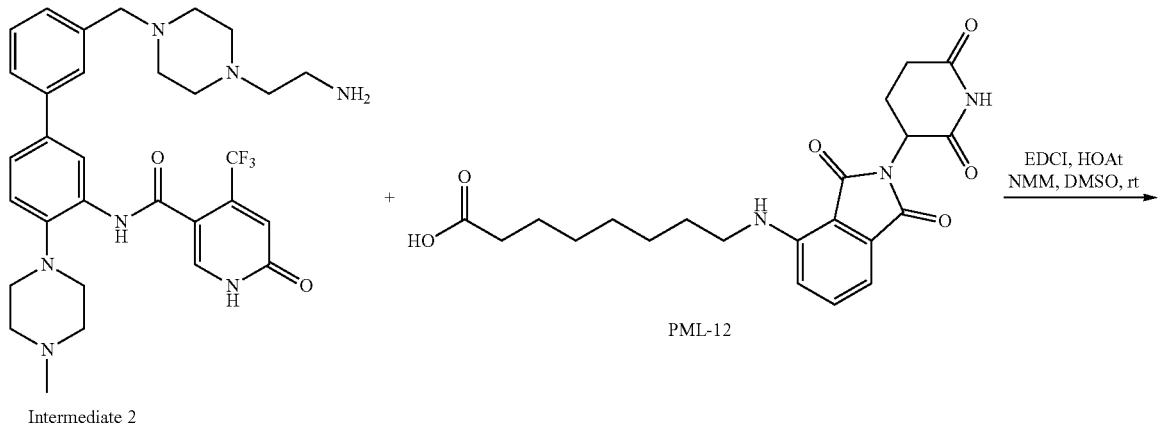

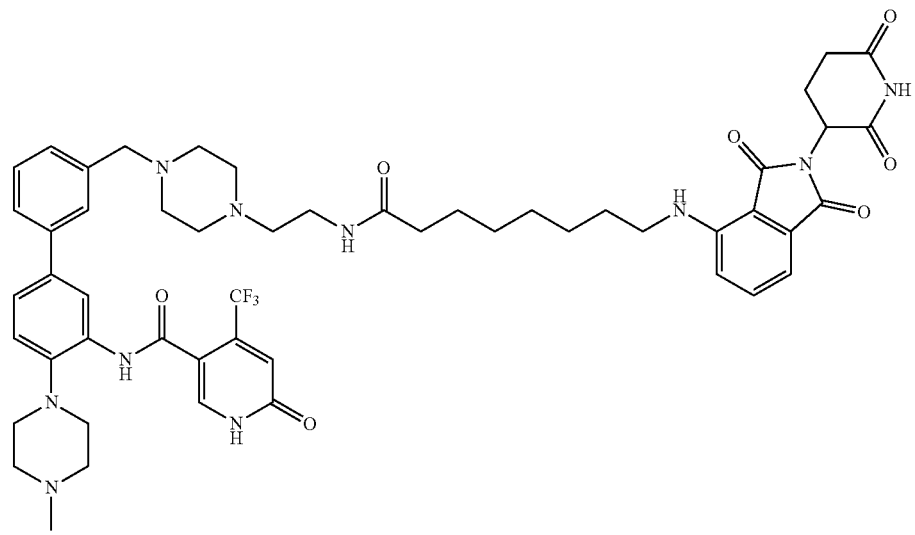

XF048-140

XF048-140 was synthesized following the standard procedures for preparing XF048-117 from intermediate 2 (13.0 mg, 0.018 mmol), PML-12 (7.5 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-140 was obtained as yellow solid in TFA salt form (12.5 mg, yield 70%). $^1$H NMR (600 MHz, CD$_3$OD) δ 8.25 (d, J=2.2 Hz, 1H), 8.02 (s, 1H), 7.72 (d, J=1.8 Hz, 1H), 7.68 (dt, J=7.9, 1.4 Hz, 1H), 7.55-7.48 (m, 3H), 7.42 (dt, J=7.7, 1.3 Hz, 1H), 7.36 (d, J=8.3 Hz, 1H), 7.02-6.98 (m, 2H), 6.93 (s, 1H), 5.03 (dd, J=12.7, 5.5 Hz, 1H), 4.13 (s, 2H), 3.60 (d, J=11.8 Hz, 2H), 3.43 (t, J=6.0 Hz, 2H), 3.28 (d, J=7.3 Hz, 6H), 3.15 (t, J=12.3 Hz, 9H), 2.97-2.89 (m, 5H), 2.83 (ddd, J=17.5, 13.9, 5.3 Hz, 1H), 2.75-2.59 (m, 3H), 2.20 (t, J=7.4 Hz, 2H), 2.11-2.03 (m, 1H), 1.61 (dp, J=22.5, 7.2 Hz, 4H), 1.45-1.26 (m, 6H). HRMS (m/z) for $C_{52}H_{62}F_3N_{10}O_7^+$ [M+H]$^+$: calculated 995.4750. found 995.4763.

Example 27: Synthesis of XF048-141

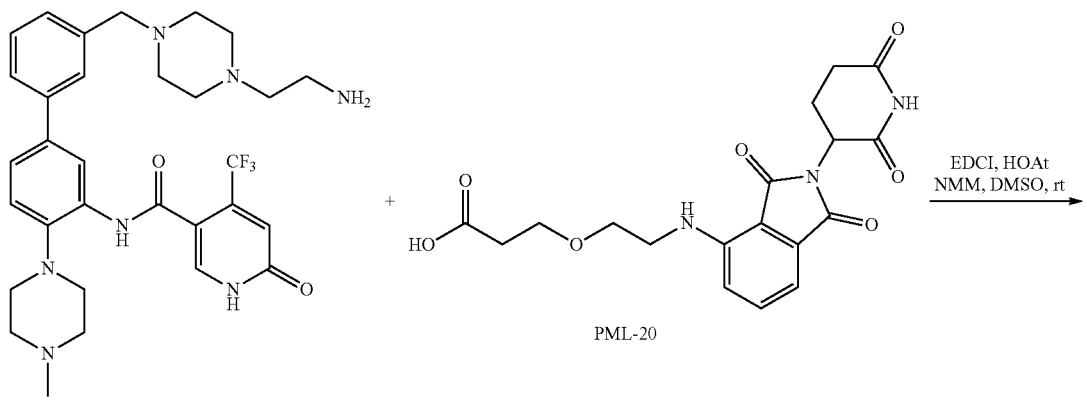

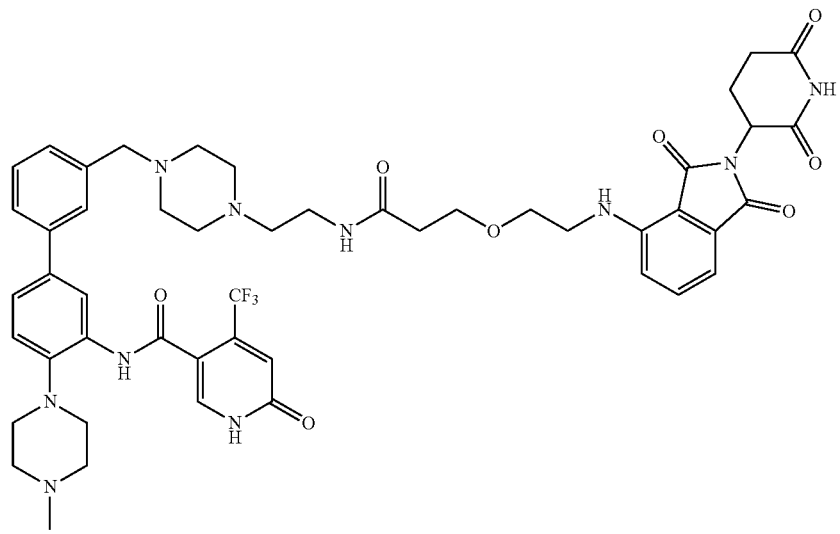

XF048-141

XF048-141 was synthesized following the standard procedures for preparing XF048-117 from intermediate 2 (13.0 mg, 0.018 mmol), PML-20 (7.0 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-141 was obtained as yellow solid in TFA salt form (16.5 mg, yield 95%). $^1$H NMR (600 MHz, CD$_3$OD) δ 8.23 (d, J=2.6 Hz, 1H), 8.03 (s, 1H), 7.73-7.69 (m, 1H), 7.67 (d, J=8.0 Hz, 1H), 7.54-7.45 (m, 3H), 7.40 (d, J=7.5 Hz, 1H), 7.37-7.31 (m, 1H), 7.07-6.98 (m, 2H), 6.93 (s, 1H), 5.07-4.97 (m, 1H), 4.10 (s, 2H), 3.74 (q, J=4.3, 2.6 Hz, 2H), 3.69-3.53 (m, 4H), 3.43 (q, J=5.5, 4.8 Hz, 4H), 3.29-3.03 (m, 13H), 3.03-2.90 (m, 5H), 2.87-2.76 (m, 1H), 2.74-2.59 (m, 3H), 2.47 (t, J=5.7 Hz, 2H), 2.12-2.02 (m, 1H). HRMS (m/z) for C$_{49}$H$_{56}$F$_3$N$_{10}$O$_8$$^+$ [M+H]$^+$: calculated 969.4229. found 969.4228.

Example 28: Synthesis of XF048-142

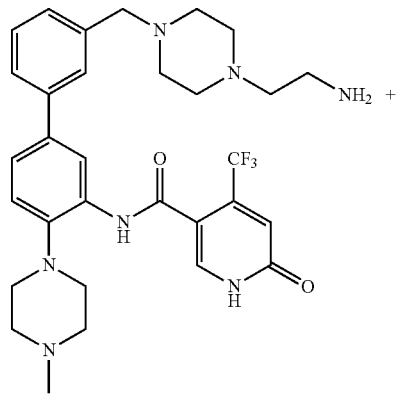

Intermediate 2

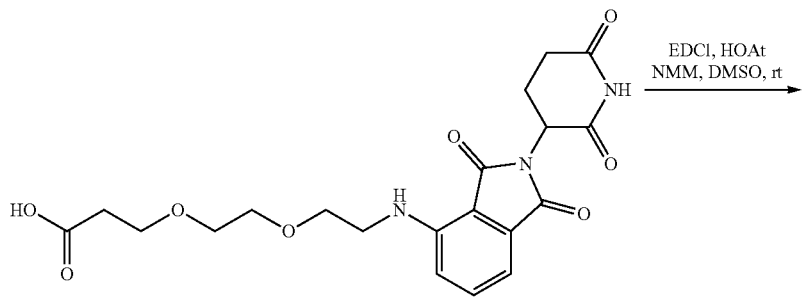

PML-21

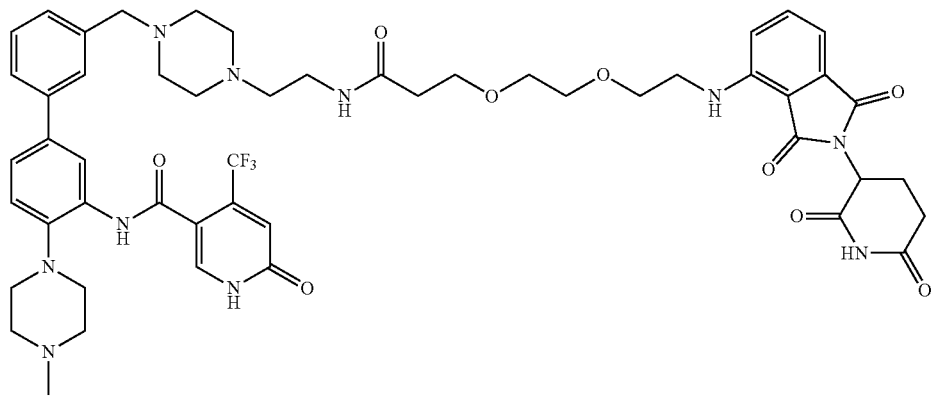

XF048-142

XF048-142 was synthesized following the standard procedures for preparing XF048-117 from intermediate 2 (13.0 mg, 0.018 mmol), PML-21 (7.8 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-142 was obtained as yellow solid in TFA salt form (14.4 mg, yield 79%). $^1$H NMR (600 MHz, CD$_3$OD) δ 8.24 (d, J=2.2 Hz, 1H), 8.02 (s, 1H), 7.70 (d, J=1.8 Hz, 1H), 7.67 (dt, J=7.8, 1.3 Hz, 1H), 7.54-7.46 (m, 3H), 7.40 (dt, J=7.7, 1.3 Hz, 1H), 7.35 (d, J=8.4 Hz, 1H), 7.02 (dd, J=10.5, 7.8 Hz, 2H), 6.93 (s, 1H), 5.03 (dd, J=12.8, 5.5 Hz, 1H), 4.09 (s, 2H), 3.72 (t, J=5.9 Hz, 2H), 3.66 (t, J=5.2 Hz, 2H), 3.64-3.55 (m, 6H), 3.44 (q, J=5.3 Hz, 4H), 3.30-3.04 (m, 13H), 2.97 (d, J=15.8 Hz, 5H), 2.82 (ddd, J=17.5, 14.0, 5.3 Hz, 1H), 2.74-2.60 (m, 3H), 2.44 (t, J=5.9 Hz, 2H), 2.12-2.03 (m, 1H). HRMS (m/z) for C$_{51}$H$_{60}$F$_3$N$_{10}$O$_9^+$ [M+H]$^+$: calculated 1013.4491. found 1013.4499.

Example 29: Synthesis of XF048-143

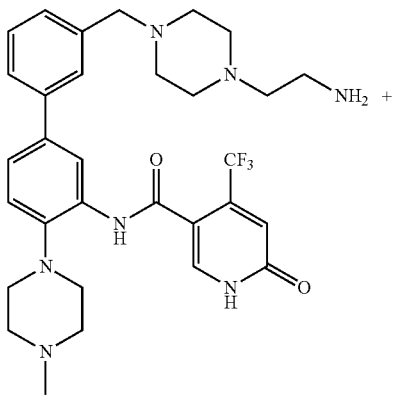

Intermediate 2

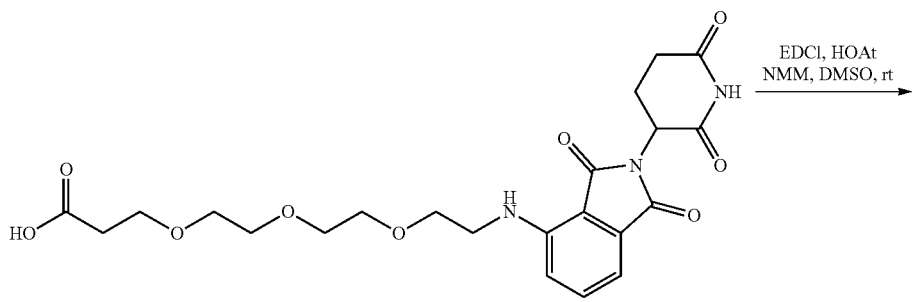

PML-22

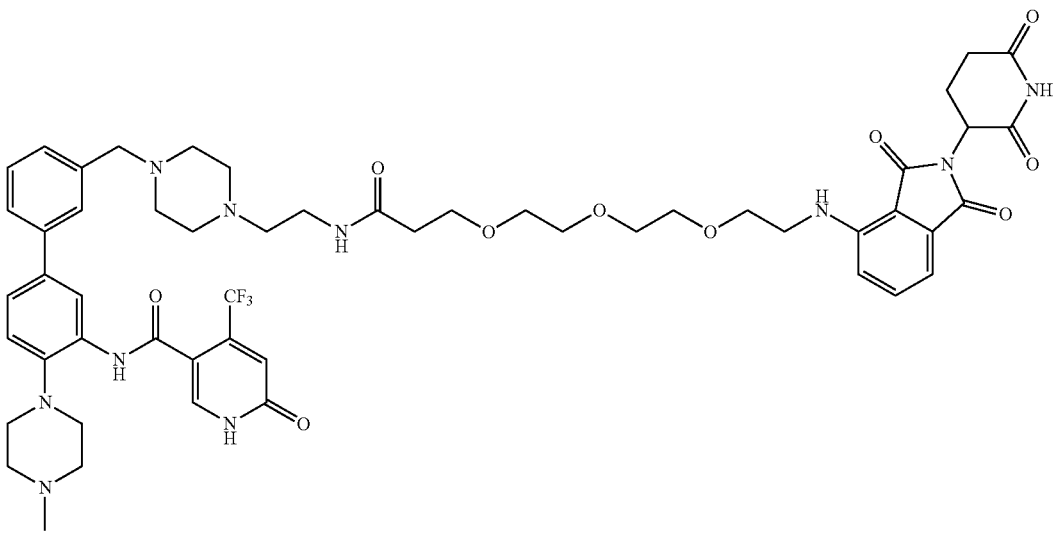

XF048-143

XF048-143 was synthesized following the standard procedures for preparing XF048-117 from intermediate 2 (13.0 mg, 0.018 mmol), PML-22 (8.6 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-143 was obtained as yellow solid in TFA salt form (12.0 mg, yield 63%). $^1$H NMR (600 MHz, CD$_3$OD) δ 8.23 (d, J=2.2 Hz, 1H), 8.03 (s, 1H), 7.71 (d, J=1.8 Hz, 1H), 7.68 (s, 1H), 7.54-7.46 (m, 3H), 7.42-7.37 (m, 1H), 7.35 (d, J=8.3 Hz, 1H), 7.01 (t, J=7.6 Hz, 2H), 6.93 (s, 1H), 5.04 (dd, J=12.8, 5.5 Hz, 1H), 4.13 (s, 2H), 3.69 (dt, J=12.7, 5.5 Hz, 4H), 3.66-3.53 (m, 10H), 3.52-3.41 (m, 4H), 3.28 (d, J=13.0 Hz, 7H), 3.16 (d, J=13.9 Hz, 6H), 3.06 (t, J=5.8 Hz, 2H), 2.96 (s, 3H), 2.83 (ddd, J=17.5, 14.0, 5.3 Hz, 1H), 2.75-2.62 (m, 3H), 2.44 (t, J=5.9 Hz, 2H), 2.08 (ddt, J=12.8, 5.4, 3.0 Hz, 1H). HRMS (m/z) for C$_{53}$H$_{64}$F$_3$N$_{10}$O$_{10}$$^+$ [M+H]$^+$: calculated 1057.4753. found 1057.4757.

Example 30: Synthesis of XF048-144

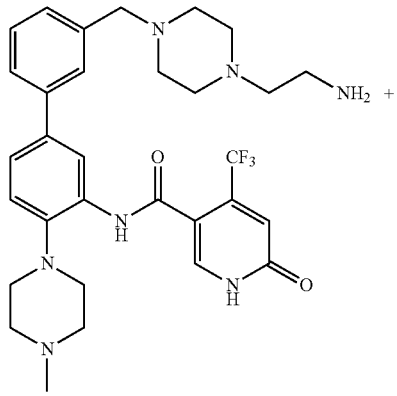

Intermediate 2

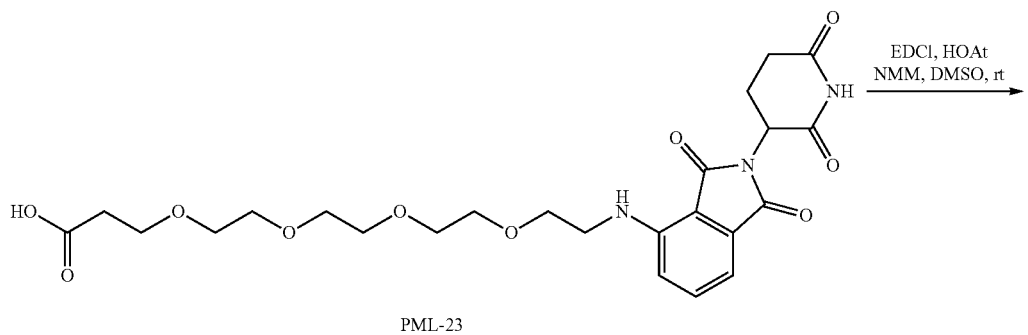

PML-23

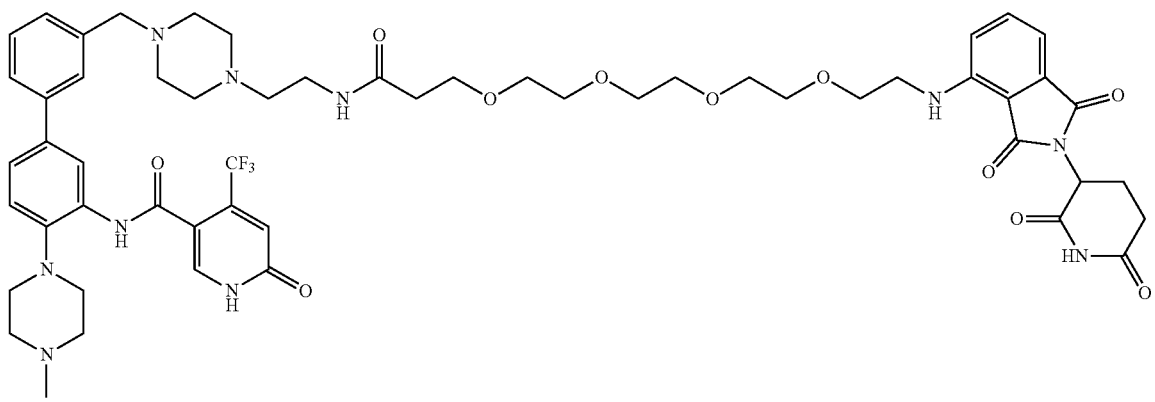

XF048-144

XF048-144 was synthesized following the standard procedures for preparing XF048-117 from intermediate 2 (13.0 mg, 0.018 mmol), PML-23 (9.4 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-144 was obtained as yellow solid in TFA salt form (14.4 mg, yield 73%). $^1$H NMR (600 MHz, CD$_3$OD) δ 8.23 (d, J=2.2 Hz, 1H), 8.03 (s, 1H), 7.72 (d, J=1.8 Hz, 1H), 7.67 (dt, J=7.8, 1.4 Hz, 1H), 7.53-7.46 (m, 3H), 7.43-7.39 (m, 1H), 7.35 (d, J=8.4 Hz, 1H), 7.01 (dd, J=7.8, 4.8 Hz, 2H), 6.93 (s, 1H), 5.04 (dd, J=12.8, 5.4 Hz, 1H), 4.19-4.11 (m, 2H), 3.74-3.65 (m, 4H), 3.64-3.53 (m, 14H), 3.49 (td, J=5.6, 2.4 Hz, 2H), 3.42 (t, J=5.2 Hz, 2H), 3.30-3.24 (m, 7H), 3.24-3.11 (m, 6H), 3.08 (t, J=5.7 Hz, 2H), 2.96 (s, 3H), 2.83 (ddd, J=17.6, 14.0, 5.3 Hz, 1H), 2.74-2.64 (m, 3H), 2.45 (t, J=5.8 Hz, 2H), 2.11-2.04 (m, 1H). HRMS (m/z) for C$_{55}$H$_{68}$F$_3$N$_{10}$O$_{11}$$^+$ [M+H]$^+$: calculated 1101.5016. found 1101.5006.

Example 31: Synthesis of XF048-145

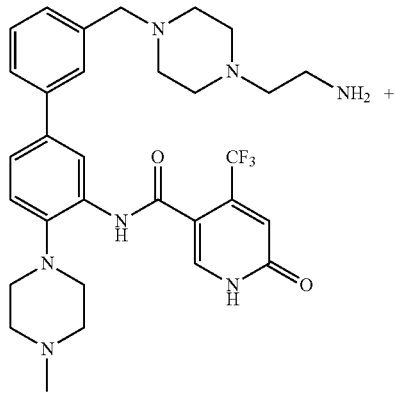

Intermediate 2

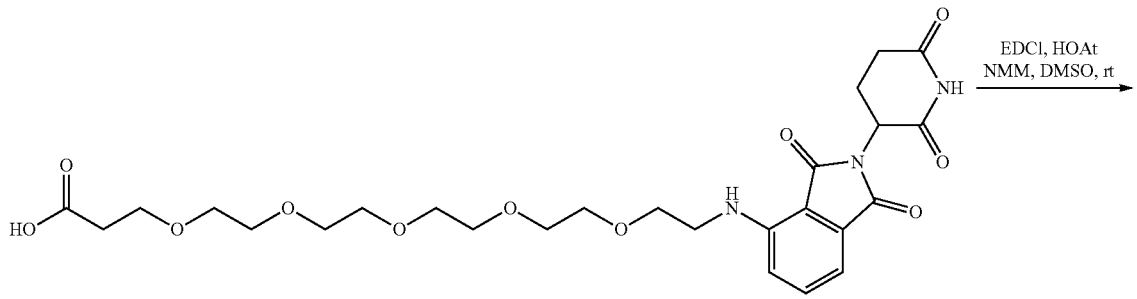

PML-24

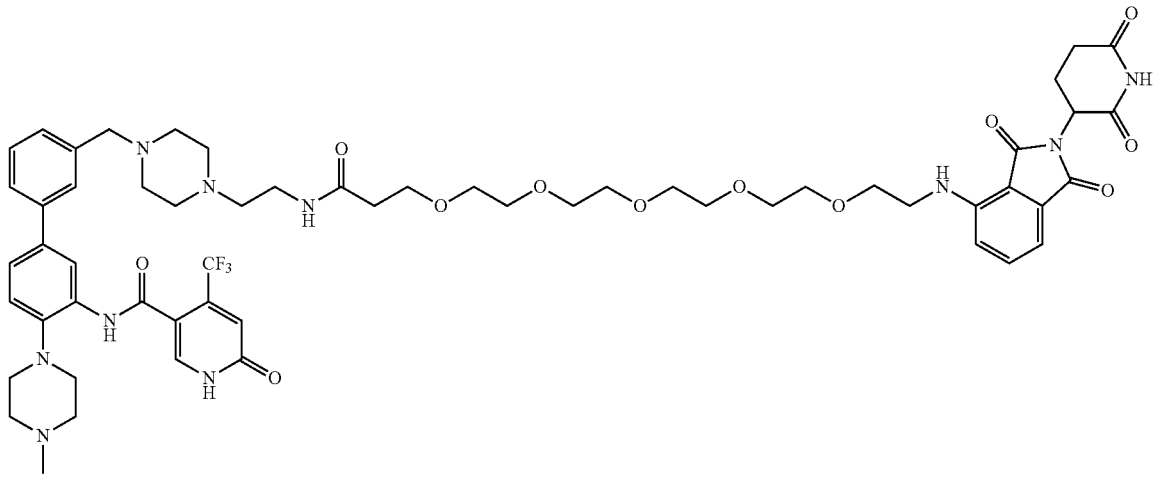

XF048-145

XF048-145 was synthesized following the standard procedures for preparing XF048-117 from intermediate 2 (13.0 mg, 0.018 mmol), PML-24 (10.2 mg, 0.018 mmol, 1.0 equiv), EDCI (5.3 mg, 0.027 mmol, 1.5 equiv), HOAt (3.7 mg, 0.027 mmol, 1.5 equiv), and NMM (5.6 mg, 0.054 mmol, 3.0 equiv) in DMSO (1 mL). XF048-145 was obtained as yellow solid in TFA salt form (6.2 mg, yield 30%). $^1$H NMR (600 MHz, CD$_3$OD) δ 8.24 (d, J=2.1 Hz, 1H), 8.02 (s, 1H), 7.69 (s, 1H), 7.65 (d, J=7.8 Hz, 1H), 7.53-7.44 (m, 3H), 7.40 (d, J=7.6 Hz, 1H), 7.35 (d, J=8.4 Hz, 1H), 7.05-6.98 (m, 2H), 6.94 (s, 1H), 5.03 (dd, J=12.8, 5.5 Hz, 1H), 4.03 (s, 2H), 3.69 (dt, J=14.9, 5.6 Hz, 4H), 3.65-3.53 (m, 18H), 3.45 (dt, J=17.9, 5.6 Hz, 4H), 3.30-3.24 (m, 5H), 3.24-3.02 (m, 8H), 3.02-2.98 (m, 2H), 2.96 (s, 3H), 2.83 (ddd, J=17.6, 14.0, 5.4 Hz, 1H), 2.74-2.65 (m, 3H), 2.44 (t, J=5.8 Hz, 2H), 2.12-2.03 (m, 1H). HRMS (m/z) for C$_{57}$H$_{72}$F$_3$N$_{10}$O$_{12}$$^+$ [M+H]$^+$: calculated 1145.5278. found 1145.5275.

Example 32: Synthesis of XF050-166

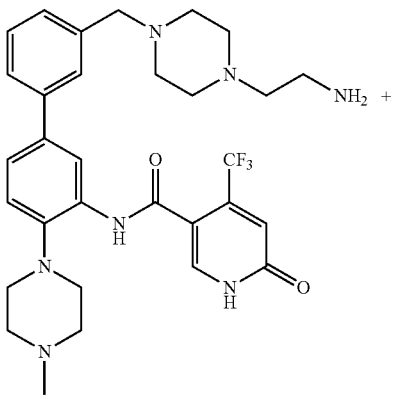

Intermediate 2

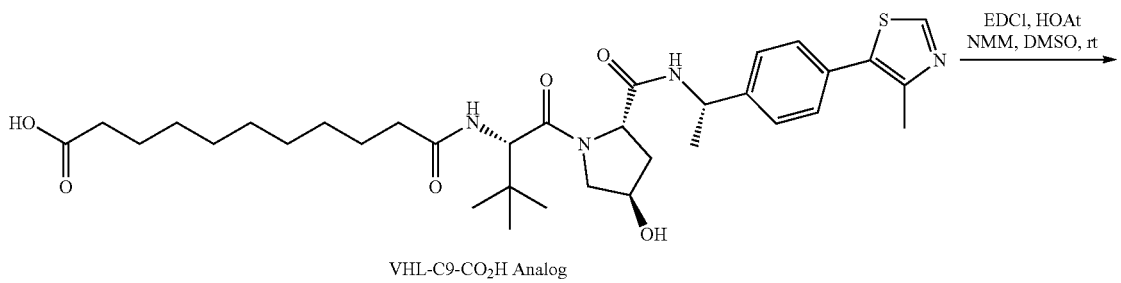

VHL-C9-CO$_2$H Analog

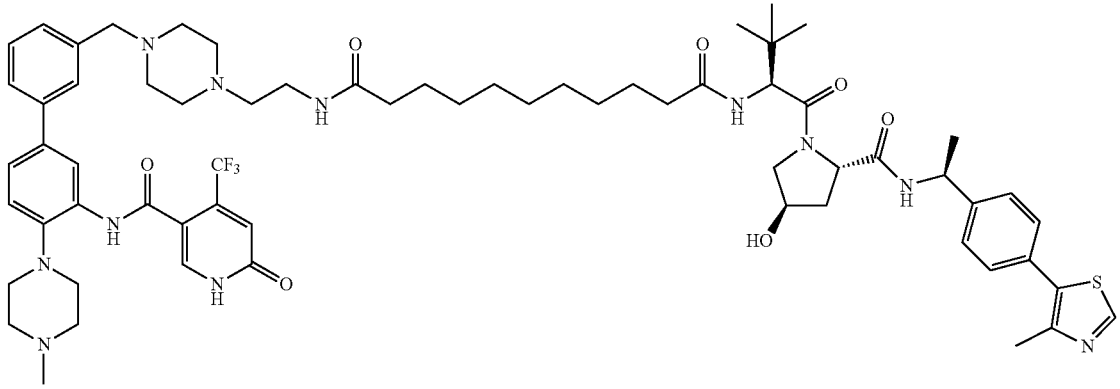

XF050-166

XF050-166 was synthesized following the standard procedures for preparing XF048-117 from intermediate 2 (9.2 mg, 0.015 mmol), VHL-C9-CO$_2$H Analog (9.9 mg, 0.015 mmol, 1.0 equiv), EDCI (4.3 mg, 0.023 mmol, 1.5 equiv), HOAt (3.1 mg, 0.023 mmol, 1.5 equiv), and NMM (4.6 mg, 0.046 mmol, 3.0 equiv) in DMSO (1 mL). XF050-166 was obtained as white solid in TFA salt form (10.6 mg, yield 58%). $^1$H NMR (600 MHz, CD$_3$OD) δ 8.98 (s, 1H), 8.26 (d, J=2.2 Hz, 1H), 8.03 (s, 1H), 7.84-7.66 (m, 2H), 7.53 (td, J=8.0, 3.3 Hz, 2H), 7.50-7.30 (m, 6H), 6.94 (s, 1H), 5.00 (q, J=7.0 Hz, 1H), 4.62 (s, 1H), 4.59-4.52 (m, 1H), 4.42 (dp, J=4.2, 2.0 Hz, 1H), 4.18 (d, J=6.9 Hz, 3H), 3.87 (dt, J=11.3, 1.8 Hz, 1H), 3.74 (dd, J=11.0, 4.0 Hz, 1H), 3.61 (d, J=11.6 Hz, 2H), 3.46 (t, J=6.1 Hz, 2H), 3.37-3.09 (m, 13H), 3.02 (t, J=6.0 Hz, 2H), 2.96 (s, 3H), 2.48 (s, 3H), 2.33-2.15 (m, 5H), 1.95 (ddd, J=13.3, 9.1, 4.6 Hz, 1H), 1.65-1.52 (m, 4H), 1.50 (d, J=7.0 Hz, 3H), 1.38-1.20 (m, 10H), 1.03 (s, 9H). HRMS (m/z) for C$_{65}$H$_{87}$F$_3$N$^{11}$O$_7$S$^+$ [M+H]$^+$: calculated 1222.6457. found 1222.6474.

Example 33: Synthesis of Intermediate 3

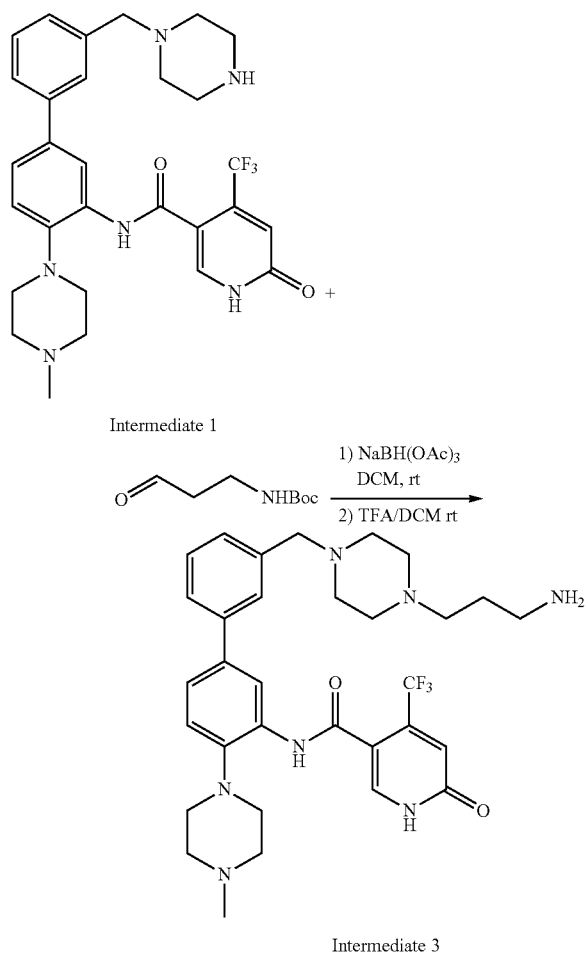

Intermediate 1

Intermediate 3

Intermediate 3 was synthesized following the standard procedures for preparing intermediate 2 from intermediate 1 (55.4 mg, 0.1 mmol), tert-butyl (3-oxopropyl)carbamate (34.6 mg, 0.2 mmol, 2.0 equiv) sodium triacetoxyborohydride (42.2 mg, 0.2 mmol, 2.0 equiv) in DCM (3 mL).

Intermediate 3 was obtained as white solid in TFA salt form (10.2 mg, yield 16%). $^1$H NMR (600 MHz, CD$_3$OD) δ 8.26 (d, J=2.2 Hz, 1H), 8.03 (s, 1H), 7.81-7.69 (m, 2H), 7.58-7.52 (m, 2H), 7.47 (dt, J=7.6, 1.4 Hz, 1H), 7.39 (d, J=8.3 Hz, 1H), 6.94 (s, 1H), 4.28 (s, 2H), 3.61 (d, J=11.1 Hz, 2H), 3.36-3.30 (m, 5H), 3.29-3.21 (m, 7H), 3.20-3.12 (m, 2H), 3.02 (t, J=7.4 Hz, 2H), 2.96 (s, 3H), 2.80 (t, J=7.1 Hz, 2H), 1.93 (p, J=7.2 Hz, 2H). HRMS (m/z) for C$_{32}$H$_{41}$F$_3$N$_7$O$_2$$^+$ [M+H]$^+$: calculated 612.3268. found 612.3287.

Example 34: Synthesis of Intermediate 4

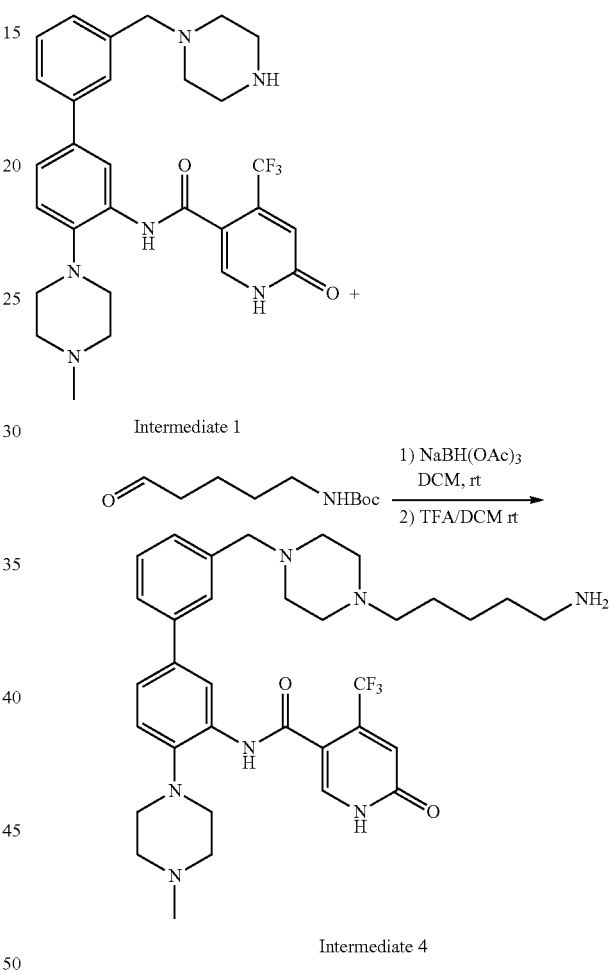

Intermediate 1

Intermediate 4

Intermediate 4 was synthesized following the standard procedures for preparing intermediate 2 from intermediate 1 (55.4 mg, 0.1 mmol), tert-butyl (5-oxopentyl)carbamate (40.2 mg, 0.2 mmol, 2.0 equiv) sodium triacetoxyborohydride (42.2 mg, 0.2 mmol, 2.0 equiv) in DCM (3 mL). Intermediate 4 was obtained as white solid in TFA salt form (15.3 mg, yield 24%). $^1$H NMR (600 MHz, CD$_3$OD) δ 8.25 (d, J=2.2 Hz, 1H), 8.03 (s, 1H), 7.76 (d, J=1.8 Hz, 1H), 7.70 (dt, J=7.8, 1.4 Hz, 1H), 7.56-7.50 (m, 2H), 7.46 (dt, J=7.7, 1.3 Hz, 1H), 7.37 (d, J=8.3 Hz, 1H), 6.94 (s, 1H), 4.23 (s, 2H), 3.61 (d, J=11.8 Hz, 2H), 3.50 (s, 4H), 3.40-3.30 (m, 4H), 3.31-3.23 (m, 4H), 3.22-3.11 (m, 4H), 2.96 (s, 3H), 2.93 (t, J=7.7 Hz, 2H), 1.83-1.74 (m, 2H), 1.74-1.63 (m, 2H), 1.45 (p, J=7.7 Hz, 2H). HRMS (m/z) for C$_{34}$H$_{45}$F$_3$N$_7$O$_2$$^+$ [M+H]$^+$: calculated 640.3581. found 640.3567.

Example 35: Synthesis of Intermediate 5

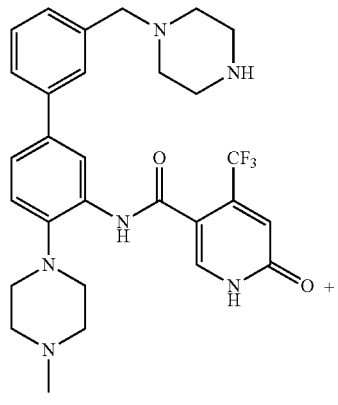

Intermediate 1

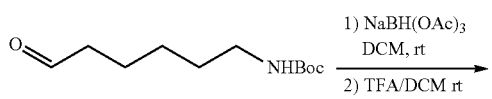

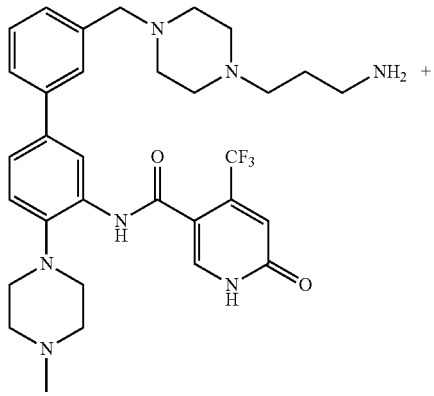

Intermediate 3

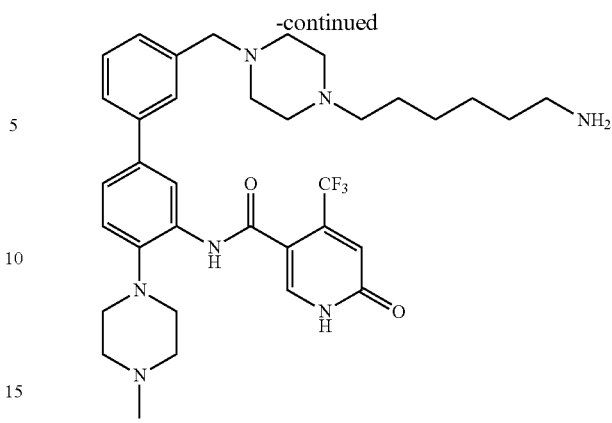

Intermediate 5

Intermediate 5 was synthesized following the standard procedures for preparing intermediate 2 from intermediate 1 (55.4 mg, 0.1 mmol), tert-butyl (6-oxohexyl)carbamate (43 mg, 0.2 mmol, 2.0 equiv) sodium triacetoxyborohydride (42.2 mg, 0.2 mmol, 2.0 equiv) in DCM (3 mL). Intermediate 5 was obtained as white solid in TFA salt form (20 mg, yield 31%). $^1$H NMR (600 MHz, CD$_3$OD) δ 8.25 (d, J=2.2 Hz, 1H), 8.03 (s, 1H), 7.75 (d, J=1.9 Hz, 1H), 7.71-7.66 (m, 1H), 7.56-7.49 (m, 2H), 7.45 (d, J=7.6 Hz, 1H), 7.37 (d, J=8.3 Hz, 1H), 6.93 (s, 1H), 4.19 (s, 2H), 3.61 (d, J=11.7 Hz, 2H), 3.49 (s, 4H), 3.37-3.24 (m, 8H), 3.21-3.10 (m, 4H), 2.96 (s, 3H), 2.91 (t, J=7.7 Hz, 2H), 1.80-1.70 (m, 2H), 1.70-1.61 (m, 2H), 1.43 (dt, J=8.4, 4.4 Hz, 4H). HRMS (m/z) for C$_{35}$H$_{47}$F$_3$N$_7$O$_2$$^+$ [M+H]$^+$: calculated 654.3738. found 654.3763.

Example 36: Synthesis of XF050-169

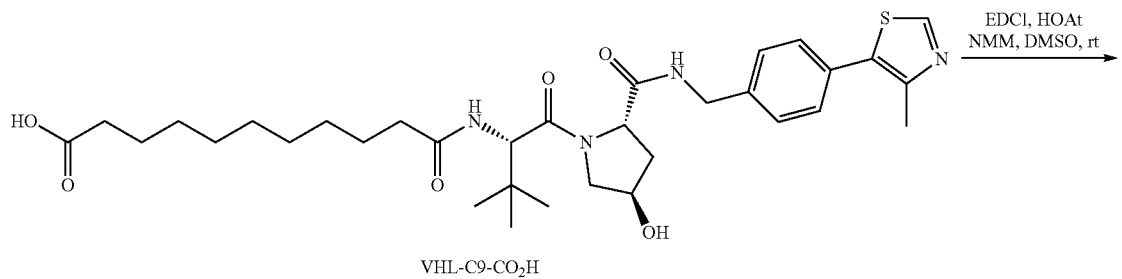

VHL-C9-CO$_2$H

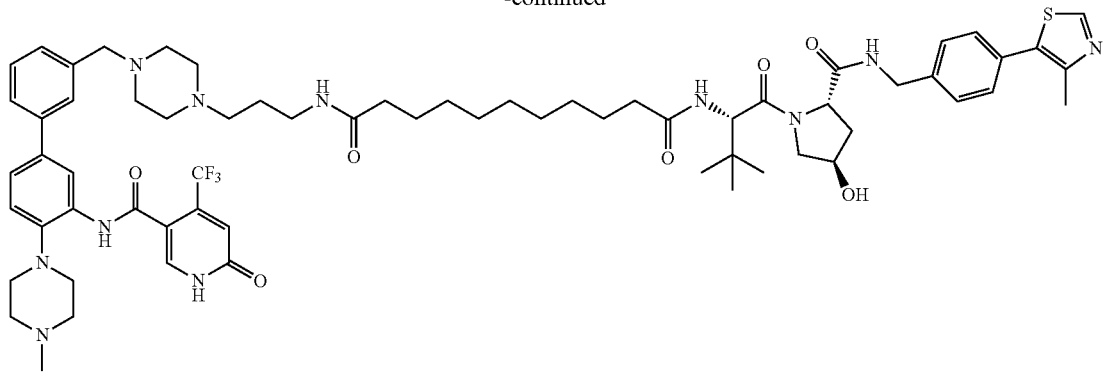

XF050-169

XF050-169 was synthesized following the standard procedures for preparing XF048-117 from intermediate 3 (16 mg, 0.025 mmol), VHL-C9-CO$_2$H (15.7 mg, 0.025 mmol, 1.0 equiv), EDCI (7.2 mg, 0.038 mmol, 1.5 equiv), HOAt (5.2 mg, 0.038 mmol, 1.5 equiv), and NMM (7.7 mg, 0.076 mmol, 3.0 equiv) in DMSO (1 mL). XF050-169 was obtained as white solid in TFA salt form (15.6 mg, yield 51%). $^1$H NMR (600 MHz, CD$_3$OD) δ 8.77 (s, 1H), 8.11-7.98 (m, 1H), 7.81 (s, 1H), 7.51 (s, 1H), 7.45 (d, J=8.9 Hz, 1H), 7.37-7.27 (m, 1H), 7.26-7.11 (m, 7H), 6.72 (s, 1H), 4.41 (s, 1H), 4.37-4.20 (m, 3H), 4.14 (d, J=16.1 Hz, 1H), 3.90 (s, 2H), 3.67 (d, J=12.1 Hz, 1H), 3.62-3.54 (m, 1H), 3.47-3.32 (m, 2H), 3.34-2.77 (m, 18H), 2.26 (s, 3H), 2.14-1.76 (m, 8H), 1.68 (p, J=7.4 Hz, 1H), 1.53-1.26 (m, 6H), 1.08 (s, 10H), 0.81 (s, 9H). HRMS (m/z) for C$_{65}$H$_{87}$F$_3$N$^{11}$O$_7$S$^+$ [M+H]$^+$: calculated 1222.6457. found 1222.6486.

Example 37: Synthesis of XF050-165

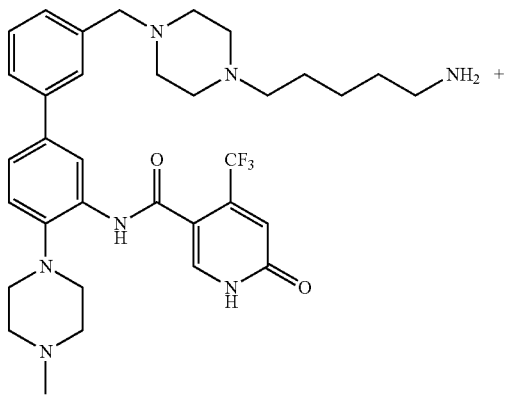

Intermediate 4

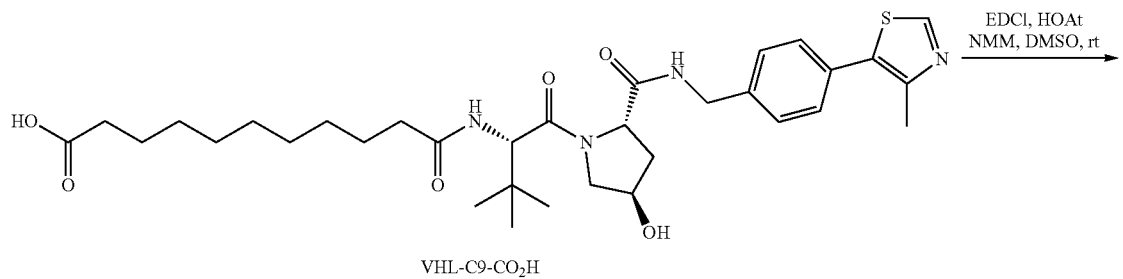

VHL-C9-CO$_2$H

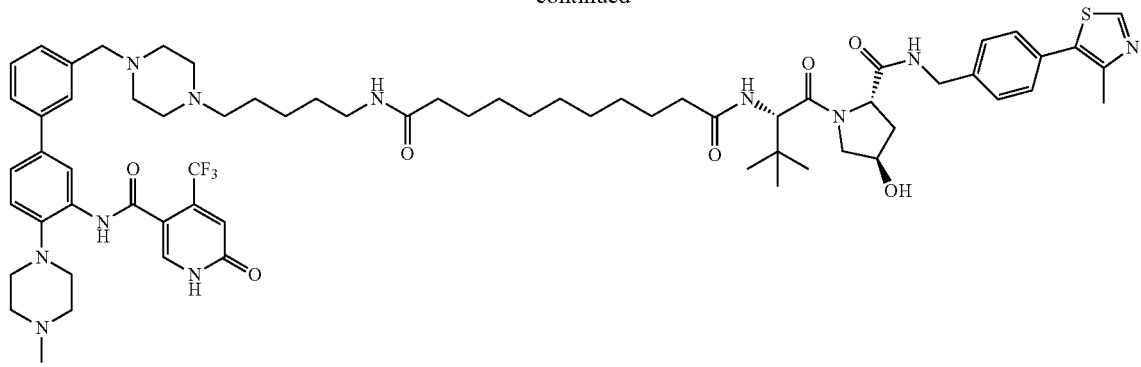

XF050-165

XF050-165 was synthesized following the standard procedures for preparing XF048-117 from intermediate 4 (7 mg, 0.011 mmol), VHL-C9-CO$_2$H (7 mg, 0.011 mmol, 1.0 equiv), EDCI (3.1 mg, 0.016 mmol, 1.5 equiv), HOAt (2.2 mg, 0.016 mmol, 1.5 equiv), and NMM (3.2 mg, 0.032 mmol, 3.0 equiv) in DMSO (1 mL). XF050-165 was obtained as white solid in TFA salt form (7.4 mg, yield 54%). $^1$H NMR (600 MHz, CD$_3$OD) δ 8.94 (s, 1H), 8.25 (d, J=2.1 Hz, 1H), 8.03 (s, 1H), 7.69 (t, J=1.8 Hz, 1H), 7.63 (dt, J=7.8, 1.5 Hz, 1H), 7.52 (dq, J=8.2, 1.8 Hz, 1H), 7.50-7.44 (m, 3H), 7.44-7.36 (m, 4H), 6.94 (s, 1H), 4.62 (s, 1H), 4.60-4.47 (m, 3H), 4.35 (d, J=15.5 Hz, 1H), 3.97 (s, 2H), 3.92-3.83 (m, 1H), 3.79 (dd, J=11.0, 3.9 Hz, 1H), 3.68-3.60 (m, 2H), 3.50-3.21 (m, 14H), 3.21-2.98 (m, 10H), 2.47 (s, 3H), 2.34-2.19 (m, 3H), 2.18-2.12 (m, 2H), 2.11-2.02 (m, 1H), 1.77-1.69 (m, 1H), 1.65-1.49 (m, 3H), 1.42-1.23 (m, 13H), 1.03 (s, 9H). HRMS (m/z) for C$_{67}$H$_{91}$F$_3$N$^{11}$O$_7$S$^+$ [M+H]$^+$: calculated 1250.6770. found 1250.6754.

Example 38: Synthesis of XF050-159

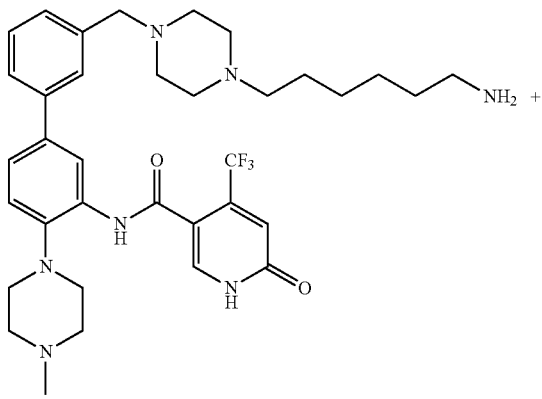

Intermediate 5

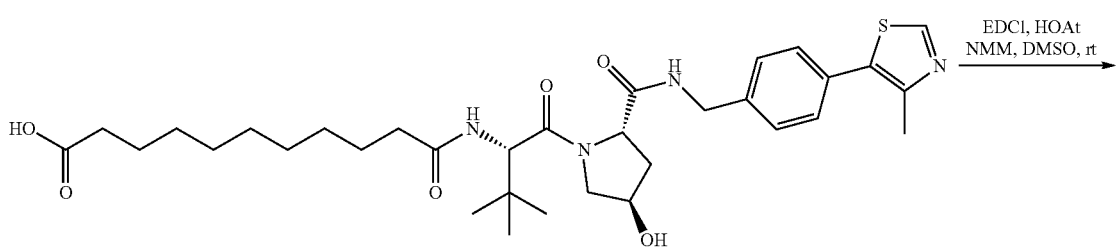

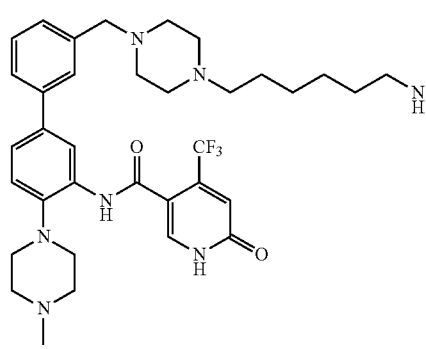
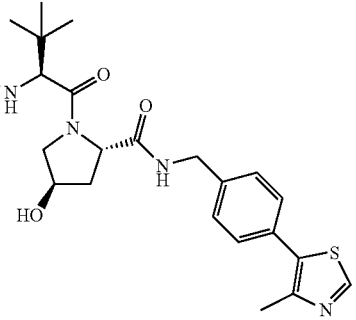

XF050-159

XF050-159 was synthesized following the standard procedures for preparing XF048-117 from intermediate 5 (7 mg, 0.011 mmol), VHL-C9-CO$_2$H (7 mg, 0.011 mmol, 1.0 equiv), EDCI (3.1 mg, 0.016 mmol, 1.5 equiv), HOAt (2.2 mg, 0.016 mmol, 1.5 equiv), and NMM (3.2 mg, 0.032 mmol, 3.0 equiv) in DMSO (1 mL). XF050-159 was obtained as white solid in TFA salt form (8.6 mg, yield 62%). $^1$H NMR (600 MHz, CD$_3$OD) δ 8.94 (s, 1H), 8.25 (s, 1H), 8.03 (s, 1H), 7.69 (s, 1H), 7.63 (d, J=7.8 Hz, 1H), 7.55-7.51 (m, 1H), 7.51-7.44 (m, 3H), 7.44-7.35 (m, 4H), 6.94 (s, 1H), 4.63 (s, 1H), 4.58-4.45 (m, 3H), 4.35 (d, J=15.4 Hz, 1H), 3.97 (s, 2H), 3.89 (d, J=11.0 Hz, 1H), 3.80 (dd, J=11.0, 3.9 Hz, 1H), 3.61 (d, J=11.4 Hz, 2H), 3.50-3.22 (m, 13H), 3.21-2.99 (m, 8H), 2.47 (s, 3H), 2.31-2.03 (m, 6H), 1.75-1.66 (m, 2H), 1.66-1.45 (m, 6H), 1.45-1.23 (m, 14H), 1.03 (s, 9H). HRMS (m/z) for C$_{68}$H$_{93}$F$_3$N$^{11}$O$_7$S$^+$ [M+H]$^+$: calculated 1264.6927. found 1264.6911.

Example 39: Synthesis of XF050-160

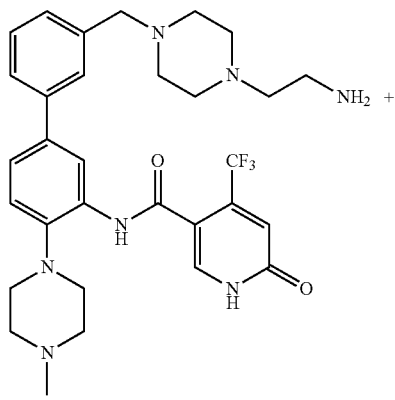

Intermediate 2

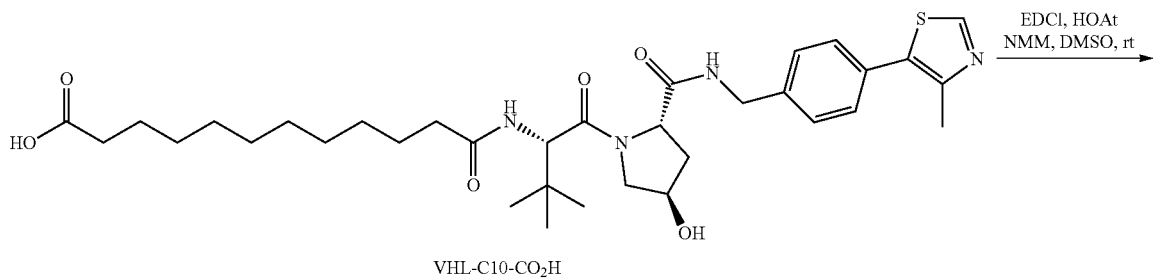

VHL-C10-CO$_2$H

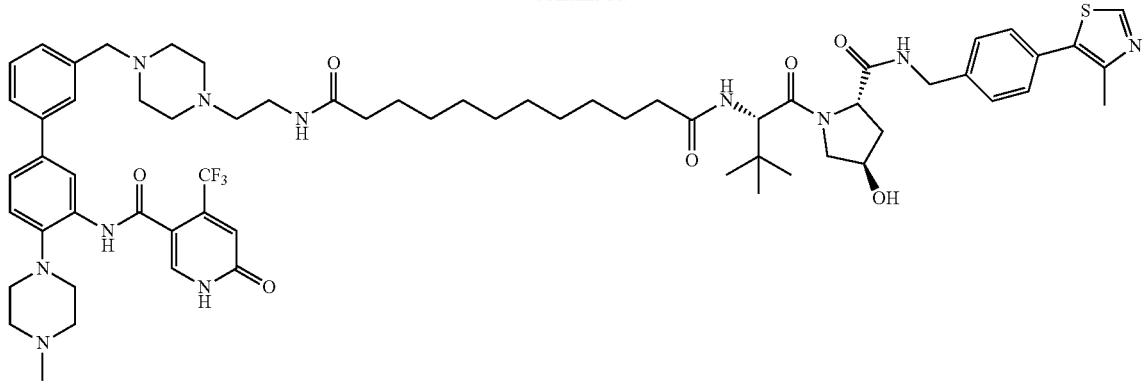

XF050-160

XF050-160 was synthesized following the standard procedures for preparing XF048-117 from intermediate 2 (10 mg, 0.017 mmol), VHL-C10-CO$_2$H (11 mg, 0.017 mmol, 1.0 equiv), EDCI (4.9 mg, 0.026 mmol, 1.5 equiv), HOAt (3.5 mg, 0.026 mmol, 1.5 equiv), and NMM (5.3 mg, 0.052 mmol, 3.0 equiv) in DMSO (1 mL). XF050-160 was obtained as white solid in TFA salt form (11.6 mg, yield 56%). $^1$H NMR (600 MHz, CD$_3$OD) δ 8.96 (s, 1H), 8.26 (d, J=2.2 Hz, 1H), 8.03 (s, 1H), 7.74 (t, J=1.9 Hz, 1H), 7.70 (dt, J=7.9, 1.4 Hz, 1H), 7.55-7.51 (m, 2H), 7.48-7.37 (m, 6H), 6.94 (s, 1H), 4.63 (s, 1H), 4.60-4.46 (m, 3H), 4.36 (d, J=15.4 Hz, 1H), 4.18 (s, 2H), 3.92-3.86 (m, 1H), 3.80 (dd, J=11.0, 3.9 Hz, 1H), 3.64-3.60 (m, 2H), 3.45 (t, J=6.1 Hz, 2H), 3.34-3.11 (m, 14H), 3.01 (t, J=6.2 Hz, 2H), 2.96 (s, 3H), 2.48 (s, 3H), 2.32-2.15 (m, 5H), 2.11-2.04 (m, 1H), 1.64-1.54 (m, 4H), 1.34-1.26 (m, 12H), 1.03 (s, 9H). HRMS (m/z) for C$_{65}$H$_{87}$F$_3$N$^{11}$O$_7$S$^+$ [M+H]$^+$: calculated 1222.6457. found 1222.6447.

Example 40: Synthesis of XF050-161

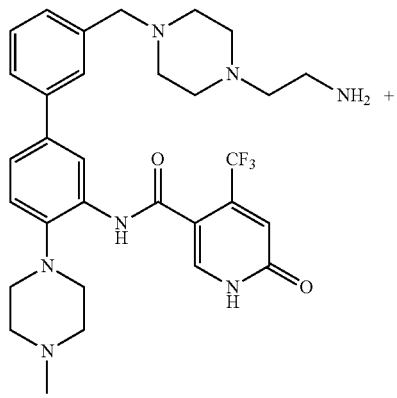

Intermediate 2

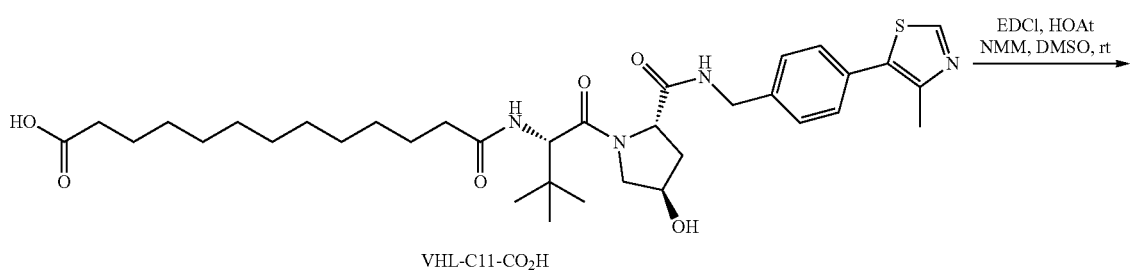

VHL-C11-CO$_2$H

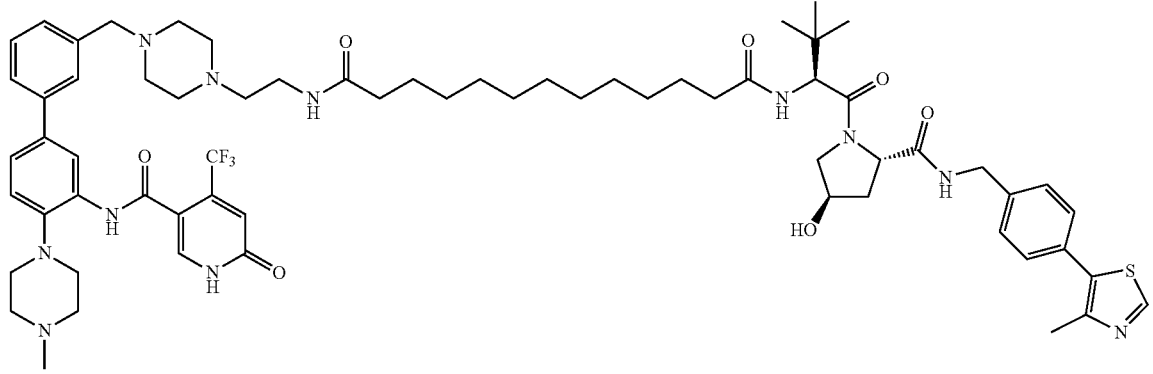

XF050-161

XF050-161 was synthesized following the standard procedures for preparing XF048-117 from intermediate 2 (10 mg, 0.017 mmol), VHL-C11-CO$_2$H (11.2 mg, 0.017 mmol, 1.0 equiv), EDCI (4.9 mg, 0.026 mmol, 1.5 equiv), HOAt (3.5 mg, 0.026 mmol, 1.5 equiv), and NMM (5.3 mg, 0.052 mmol, 3.0 equiv) in DMSO (1 mL). XF050-161 was obtained as white solid in TFA salt form (15.6 mg, yield 74%). $^1$H NMR (600 MHz, CD$_3$OD) δ 8.93 (s, 1H), 8.26 (s, 1H), 8.03 (s, 1H), 7.73 (s, 1H), 7.69 (d, J=7.9 Hz, 1H), 7.56-7.49 (m, 2H), 7.49-7.36 (m, 6H), 6.94 (s, 1H), 4.63 (s, 1H), 4.59-4.47 (m, 3H), 4.35 (d, J=15.5 Hz, 1H), 4.15 (s, 2H), 3.89 (d, J=10.9 Hz, 1H), 3.80 (dd, J=11.0, 3.7 Hz, 1H), 3.61 (d, J=11.5 Hz, 2H), 3.46-3.43 (m, 2H), 3.37-3.01 (m, 19H), 2.47 (s, 3H), 2.33-2.16 (m, 5H), 2.11-2.04 (m, 1H), 1.65-1.54 (m, 4H), 1.32-1.27 (m, 14H), 1.03 (s, 9H). HRMS (m/z) for C$_{66}$H$_{89}$F$_3$N$_1$O$_7$S$^+$ [M+H]$^+$: calculated 1236.6614, found 1236.6612.

Example 41: Synthesis of XF050-162

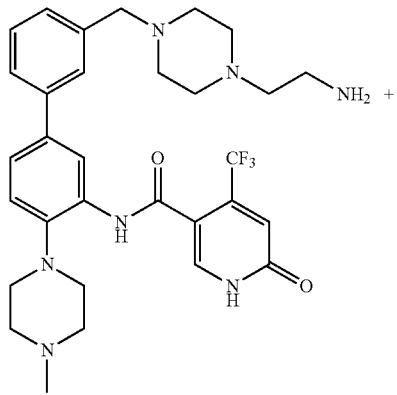

Intermediate 2

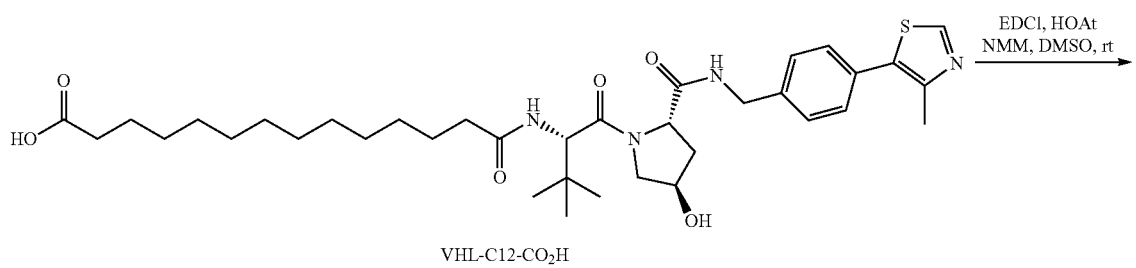

VHL-C12-CO$_2$H

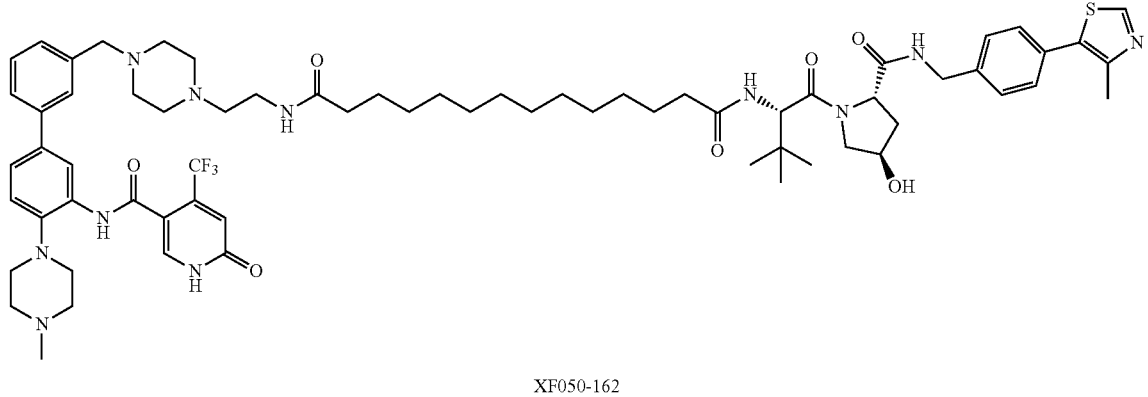

XF050-162

XF050-162 was synthesized following the standard procedures for preparing XF048-117 from intermediate 2 (10 mg, 0.017 mmol), VHL-C12-CO$_2$H (11.4 mg, 0.017 mmol, 1.0 equiv), EDCI (4.9 mg, 0.026 mmol, 1.5 equiv), HOAt (3.5 mg, 0.026 mmol, 1.5 equiv), and NMM (5.3 mg, 0.052 mmol, 3.0 equiv) in DMSO (1 mL). XF050-162 was obtained as white solid in TFA salt form (19 mg, yield 89%). $^1$H NMR (600 MHz, CD$_3$OD) δ 9.00 (s, 1H), 8.26 (d, J=2.2 Hz, 1H), 8.03 (s, 1H), 7.75 (d, J=1.9 Hz, 1H), 7.70 (dt, J=7.8, 1.4 Hz, 1H), 7.57-7.51 (m, 2H), 7.49-7.40 (m, 5H), 7.38 (d, J=8.3 Hz, 1H), 6.94 (s, 1H), 4.63 (s, 1H), 4.57-4.46 (m, 3H), 4.36 (d, J=15.5 Hz, 1H), 4.21 (s, 2H), 3.90 (dt, J=11.2, 1.8 Hz, 1H), 3.80 (dd, J=11.0, 3.9 Hz, 1H), 3.66-3.58 (m, 2H), 3.47 (t, J=6.0 Hz, 2H), 3.38-3.10 (m, 17H), 3.04 (t, J=6.1 Hz, 2H), 2.48 (s, 3H), 2.33-2.17 (m, 5H), 2.10-2.04 (m, 1H), 1.65-1.53 (m, 4H), 1.41-1.20 (m, 16H), 1.03 (s, 9H). HRMS (m/z) for C$_{67}$H$_{91}$F$_3$N$^{11}$O$_7$S$^+$ [M+H]$^+$: calculated 1250.6770. found 1250.6798.

Example 42: Synthesis of XF050-156

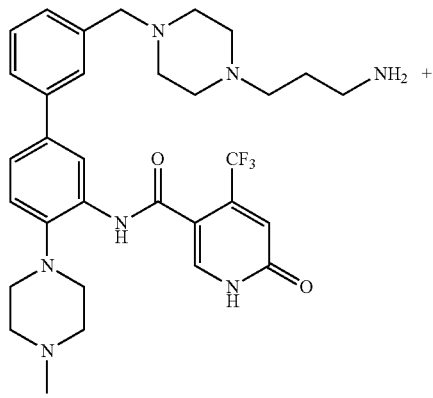

Intermediate 3

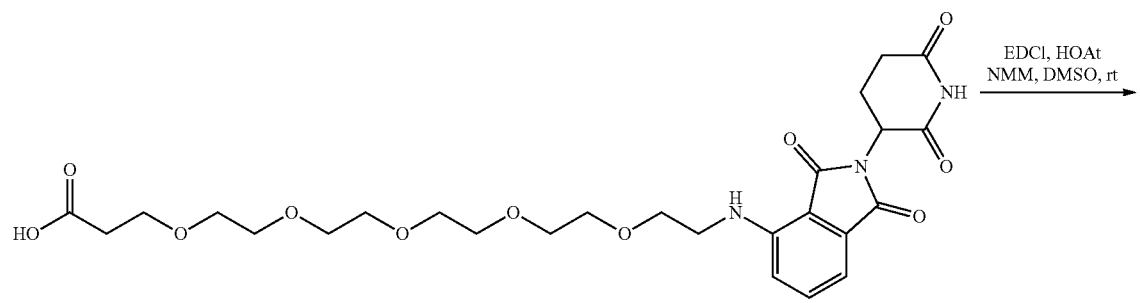

PML-24

233

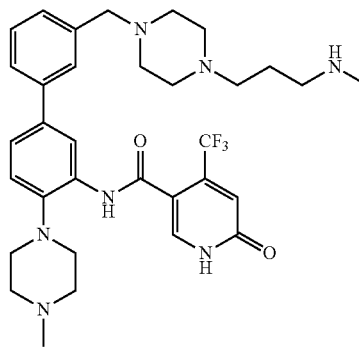

-continued

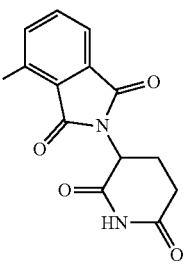

XF050-156

XF050-156 was synthesized following the standard procedures for preparing XF048-117 from intermediate 3 (10 mg, 0.016 mmol), PML-24 (9.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF050-156 was obtained as yellow solid in TFA salt form (5.6 mg, yield 30%). $^1$H NMR (600 MHz, CD$_3$OD) δ 8.22 (d, J=2.2 Hz, 1H), 8.02 (s, 1H), 7.66 (t, J=1.8 Hz, 1H), 7.60 (dt, J=7.8, 1.3 Hz, 1H), 7.54-7.44 (m, 3H), 7.35 (dd, J=10.5, 7.5 Hz, 2H), 7.01 (dd, J=7.8, 4.2 Hz, 2H), 6.93 (s, 1H), 5.12-4.99 (m, 1H), 3.89 (t, J=9.0 Hz, 2H), 3.75-3.49 (m, 22H), 3.47-3.37 (m, 2H), 3.21-2.59 (m, 24H), 2.45 (t, J=5.8 Hz, 2H), 2.15-2.01 (m, 1H), 1.92-1.84 (m, 2H). HRMS (m/z) for C$_{58}$H$_{74}$F$_3$N$_{10}$O$_{12}^+$ [M+H]$^+$: calculated 1159.5434. found 1159.5475.

Example 43: Synthesis of XF050-164

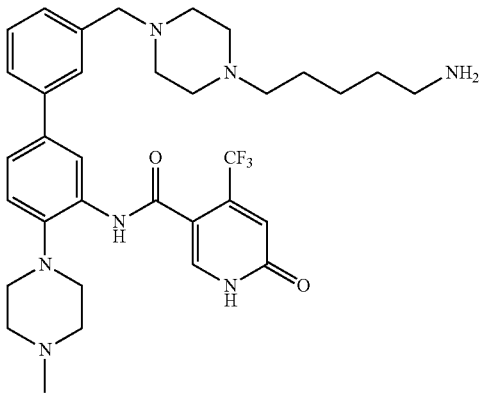

Intermediate 4

+

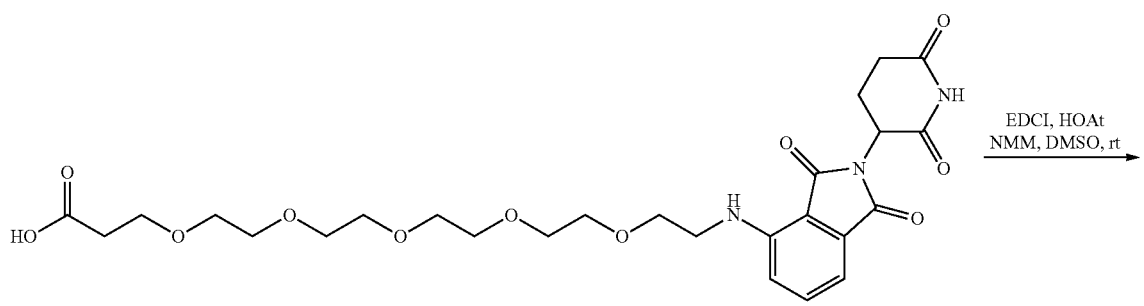

PML-24

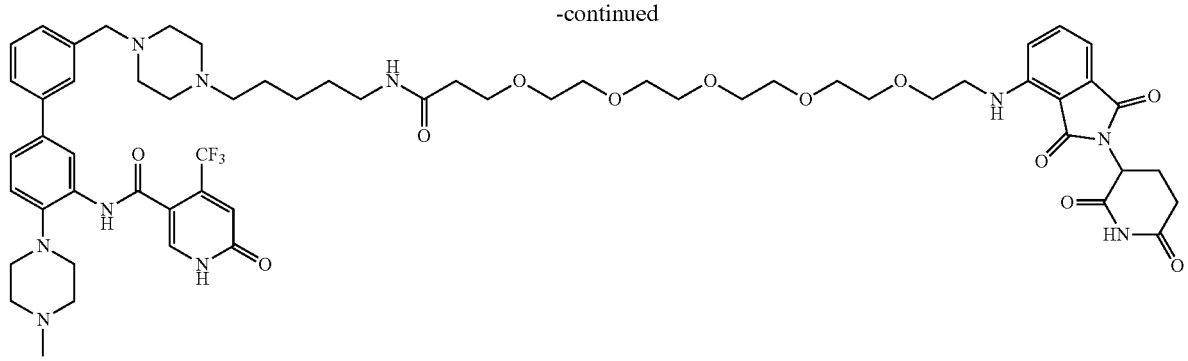

XF050-164

XF050-164 was synthesized following the standard procedures for preparing XF048-117 from intermediate 4 (7 mg, 0.011 mmol), PML-24 (6.2 mg, 0.011 mmol, 1.0 equiv), EDCI (3.1 mg, 0.016 mmol, 1.5 equiv), HOAt (2.2 mg, 0.016 mmol, 1.5 equiv), and NMM (3.2 mg, 0.032 mmol, 3.0 equiv) in DMSO (1 mL). XF050-164 was obtained as yellow solid in TFA salt form (2.6 mg, yield 20%). $^1$H NMR (600 MHz, CD$_3$OD) δ 8.23 (d, J=2.1 Hz, 1H), 8.02 (d, J=4.0 Hz, 1H), 7.71-7.29 (m, 7H), 7.14-7.00 (m, 2H), 6.94 (d, J=4.9 Hz, 1H), 5.10-4.99 (m, 1H), 3.83-3.52 (m, 28H), 3.46 (t, J=5.2 Hz, 2H), 3.22-3.09 (m, 12H), 3.07-3.01 (m, 2H), 2.96 (s, 3H), 2.90-2.79 (m, 1H), 2.78-2.61 (m, 2H), 2.40 (t, J=5.9 Hz, 2H), 2.09 (ddd, J=12.6, 6.8, 2.7 Hz, 1H), 1.78-1.65 (m, 2H), 1.53 (p, J=7.0 Hz, 2H), 1.42-1.32 (m, 2H). HRMS (m/z) for $C_{60}H_{78}F_3N_{10}O_{12}^+$ [M+H]$^+$: calculated 1187.5747. found 1187.5721.

Example 44: Synthesis of XF050-158

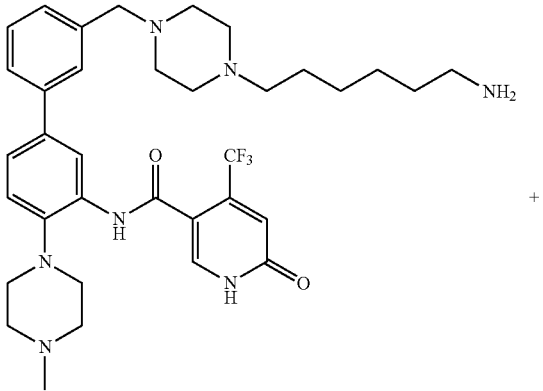

Intermediate 5

+

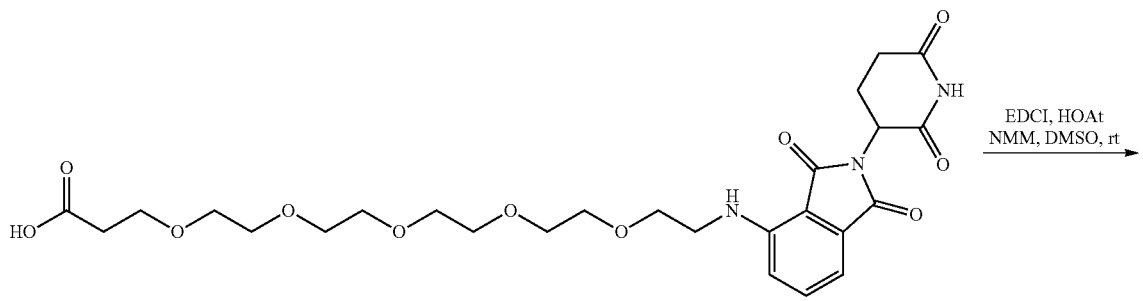

PML-24

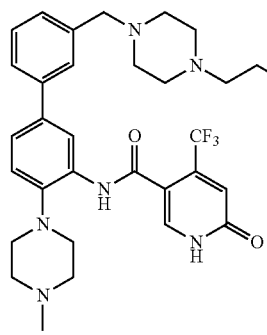

XF050-158

XF050-158 was synthesized following the standard procedures for preparing XF048-117 from intermediate 5 (7 mg, 0.011 mmol), PML-24 (6.2 mg, 0.011 mmol, 1.0 equiv), EDCI (3.1 mg, 0.016 mmol, 1.5 equiv), HOAt (2.2 mg, 0.016 mmol, 1.5 equiv), and NMM (3.2 mg, 0.032 mmol, 3.0 equiv) in DMSO (1 mL). XF050-158 was obtained as yellow solid in TFA salt form (12.8 mg, yield 96%). $^1$H NMR (600 MHz, CD$_3$OD) δ 8.29-8.22 (m, 1H), 8.08-7.98 (m, 1H), 7.77-7.58 (m, 2H), 7.58-7.45 (m, 3H), 7.46-7.33 (m, 2H), 7.13-7.00 (m, 2H), 6.94 (t, J=3.2 Hz, 1H), 5.04 (ddt, J=12.4, 6.1, 3.3 Hz, 1H), 4.09-3.96 (m, 2H), 3.78-3.02 (m, 42H), 2.96 (s, 3H), 2.89-2.78 (m, 1H), 2.77-2.61 (m, 2H), 2.45-2.35 (m, 2H), 2.12-2.05 (m, 1H), 1.75-1.65 (m, 2H), 1.54-1.46 (m, 2H), 1.43-1.31 (m, 4H). HRMS (m/z) for $C_{61}H_{80}F_3N_{10}O_{12}^+$ [M+H]$^+$: calculated 1201.5904. found 1201.5943.

Example 45: Synthesis of XF056-23

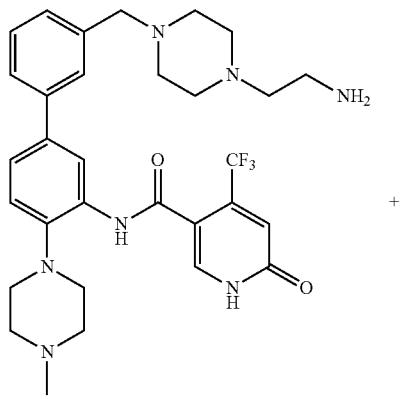

Intermediate 2

+

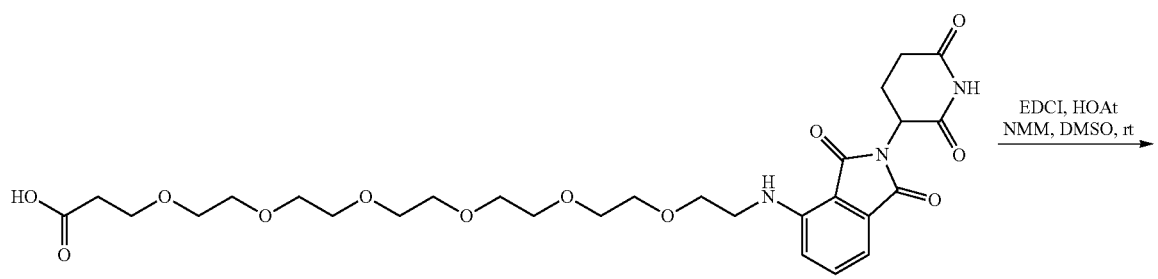

PML-25

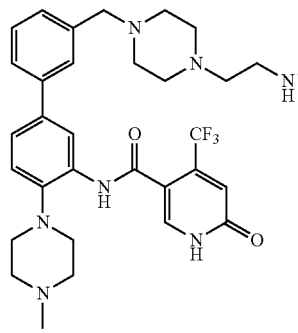
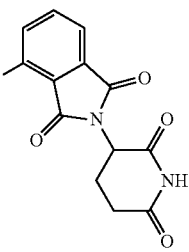

XF056-23

XF056-23 was synthesized following the standard procedures for preparing XF048-117 from intermediate 2 (8.4 mg, 0.014 mmol), PML-25 (8.5 mg, 0.014 mmol, 1.0 equiv), EDCI (4.1 mg, 0.021 mmol, 1.5 equiv), HOAt (2.9 mg, 0.021 mmol, 1.5 equiv), and NMM (4.2 mg, 0.042 mmol, 3.0 equiv) in DMSO (1 mL). XF056-23 was obtained as yellow solid in TFA salt form (6 mg, yield 36%). $^1$H NMR (600 MHz, CD$_3$OD) δ 8.25 (d, J=8.8 Hz, 1H), 8.02 (s, 1H), 7.75-7.58 (m, 2H), 7.59-7.45 (m, 4H), 7.45-7.30 (m, 2H), 7.15-6.97 (m, 1H), 6.93 (d, J=3.5 Hz, 1H), 5.04 (dd, J=12.8, 5.5 Hz, 1H), 4.11-4.04 (m, 2H), 3.81-3.77 (t, J=5.7 Hz, 1H), 3.75-3.39 (m, 30H), 3.35-2.90 (m, 14H), 2.83 (ddd, J=18.6, 14.0, 5.3 Hz, 1H), 2.76-2.65 (m, 2H), 2.49-2.42 (m, 2H), 2.13-2.05 (m, 1H). HRMS (m/z) for $C_{59}H_{76}F_3N_{10}O_{13}^+$ [M+H]$^+$: calculated 1189.5540. found 1189.5523.

Example 46: Synthesis of XF056-25

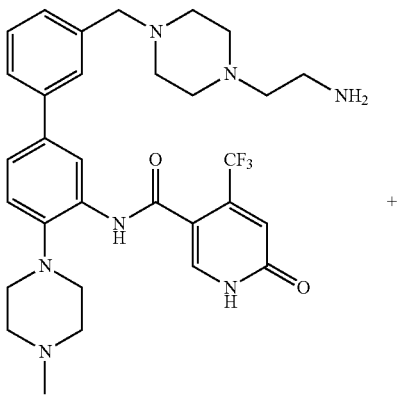

Intermediate 2

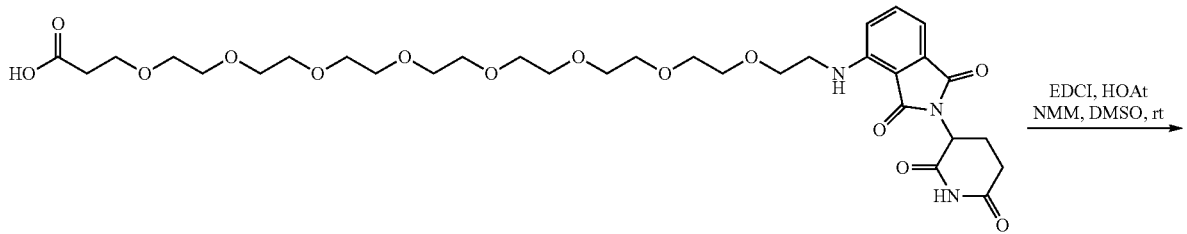

PML-26

-continued

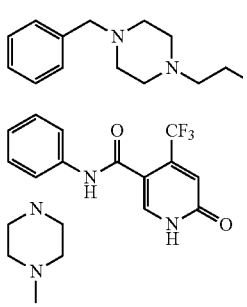
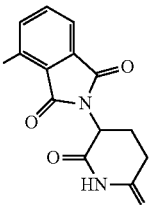

XF056-25

XF056-25 was synthesized following the standard procedures for preparing XF048-117 from intermediate 2 (8.4 mg, 0.014 mmol), PML-26 (9.8 mg, 0.014 mmol, 1.0 equiv), EDCI (4.1 mg, 0.021 mmol, 1.5 equiv), HOAt (2.9 mg, 0.021 mmol, 1.5 equiv), and NMM (4.2 mg, 0.042 mmol, 3.0 equiv) in DMSO (1 mL). XF056-25 was obtained as yellow solid in TFA salt form (9.3 mg, yield 52%). $^1$H NMR (600 MHz, CD$_3$OD) δ 8.25 (d, J=2.1 Hz, 1H), 8.03 (s, 1H), 7.73 (s, 1H), 7.69 (d, J=8.0 Hz, 1H), 7.51 (t, J=7.9 Hz, 3H), 7.43 (d, J=7.7 Hz, 1H), 7.36 (d, J=8.4 Hz, 1H), 7.03 (dd, J=13.6, 7.8 Hz, 2H), 6.93 (s, 1H), 5.04 (dd, J=12.8, 5.5 Hz, 1H), 4.19 (s, 2H), 3.86-3.05 (m, 54H), 2.96 (s, 3H), 2.90-2.79 (m, 1H), 2.76-2.64 (m, 2H), 2.46 (t, J=5.8 Hz, 2H), 2.12-2.04 (m, 1H). HRMS (m/z) for $C_{63}H_{84}F_3N_{10}O_{15}{}^+$ [M+H]$^+$: calculated 1277.6064. found 1277.6087.

Example 47: Synthesis of XF056-26

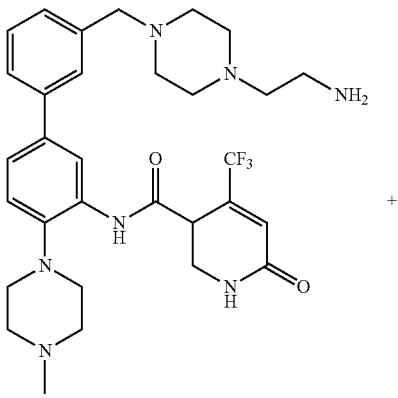

Intermediate 2

+

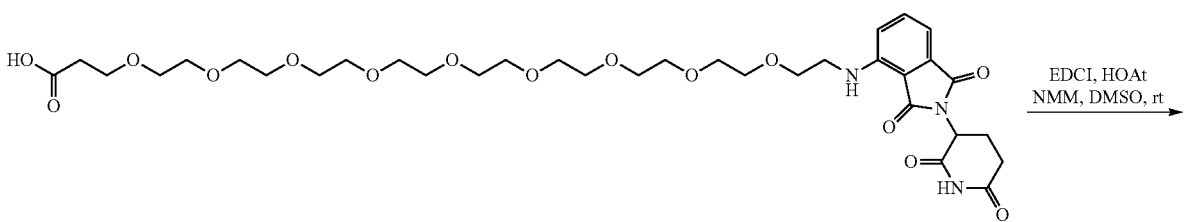

PML-27

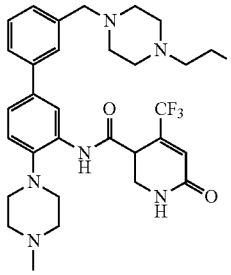
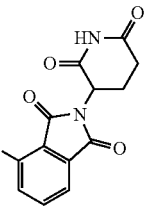

XF056-26

XF056-26 was synthesized following the standard procedures for preparing XF048-117 from intermediate 2 (8.4 mg, 0.014 mmol), PML-27 (10.4 mg, 0.014 mmol, 1.0 equiv), EDCI (4.1 mg, 0.021 mmol, 1.5 equiv), HOAt (2.9 mg, 0.021 mmol, 1.5 equiv), and NMM (4.2 mg, 0.042 mmol, 3.0 equiv) in DMSO (1 mL). XF056-26 was obtained as yellow solid in TFA salt form (6.5 mg, yield 35%). $^1$H NMR (600 MHz, CD$_3$OD) δ 8.25 (s, 1H), 8.03 (s, 1H), 7.72 (s, 1H), 7.67 (d, J=7.9 Hz, 1H), 7.59-7.47 (m, 3H), 7.42 (d, J=7.7 Hz, 1H), 7.36 (d, J=8.4 Hz, 1H), 7.04 (dd, J=17.0, 7.8 Hz, 2H), 6.94 (s, 1H), 5.04 (dd, J=12.9, 5.5 Hz, 1H), 4.11 (s, 2H), 3.77-3.15 (m, 38H), 3.37-2.99 (m, 20H), 2.96 (s, 3H), 2.89-2.78 (m, 1H), 2.77-2.62 (m, 2H), 2.45 (t, J=5.9 Hz, 2H), 2.14-2.01 (m, 1H). HRMS (m/z) for $C_{65}H_{88}F_3N_{10}O_{16}^+$ [M+H]$^+$: calculated 1321.6326. found 1321.6352.

Example 48: Synthesis of XF056-24

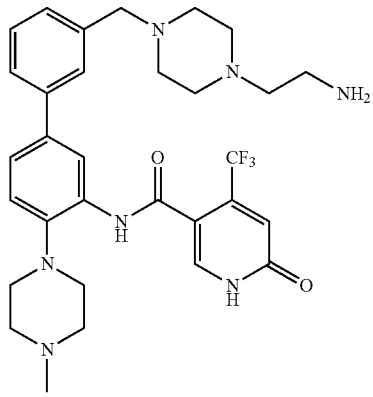

Intermediate 2

+

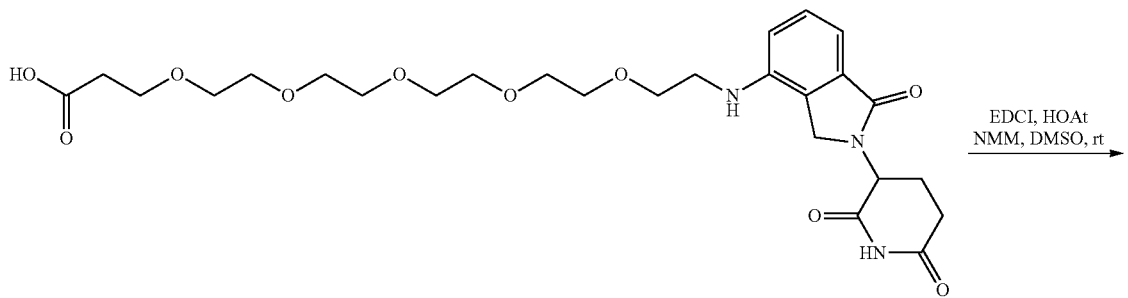

LML-1

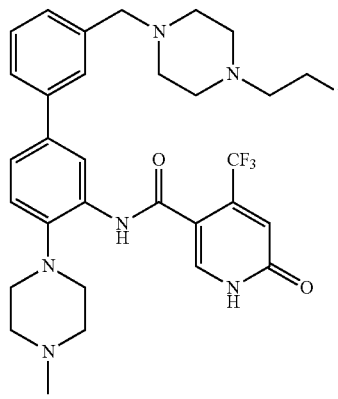

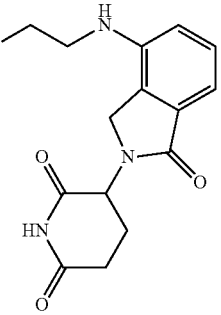

XF056-24

XF056-24 was synthesized following the standard procedures for preparing XF048-117 from intermediate 2 (8.4 mg, 0.014 mmol), LML-1 (7.7 mg, 0.014 mmol, 1.0 equiv), EDCI (4.1 mg, 0.021 mmol, 1.5 equiv), HOAt (2.9 mg, 0.021 mmol, 1.5 equiv), and NMM (4.2 mg, 0.042 mmol, 3.0 equiv) in DMSO (1 mL). XF056-24 was obtained as yellow solid in TFA salt form (10.9 mg, yield 69%). $^1$H NMR (600 MHz, CD$_3$OD) δ 8.26 (s, 1H), 8.02 (s, 1H), 7.81-7.63 (m, 2H), 7.53 (t, J=8.0 Hz, 3H), 7.44 (d, J=7.6 Hz, 1H), 7.37 (d, J=8.3 Hz, 1H), 7.23 (d, J=7.5 Hz, 1H), 7.03 (d, J=8.0 Hz, 1H), 6.93 (s, 1H), 5.28-5.11 (m, 1H), 4.58-4.24 (m, 2H), 4.21 (s, 2H), 4.11-3.77 (m, 3H), 3.75-3.04 (m, 19H), 3.01-2.81 (m, 5H), 2.71-2.63 (m, 1H), 2.50-2.39 (m, 2H), 2.21-2.13 (m, 1H). HRMS (m/z) for $C_{57}H_{74}F_3N_{10}O_{11}^+$ [M+H]$^+$: calculated 1131.5485. found 1131.5467.

Example 49: Synthesis of XF056-32

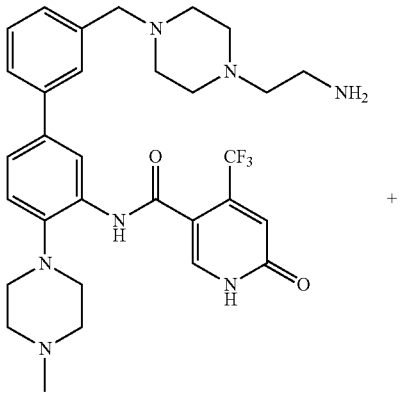

Intermediate 2

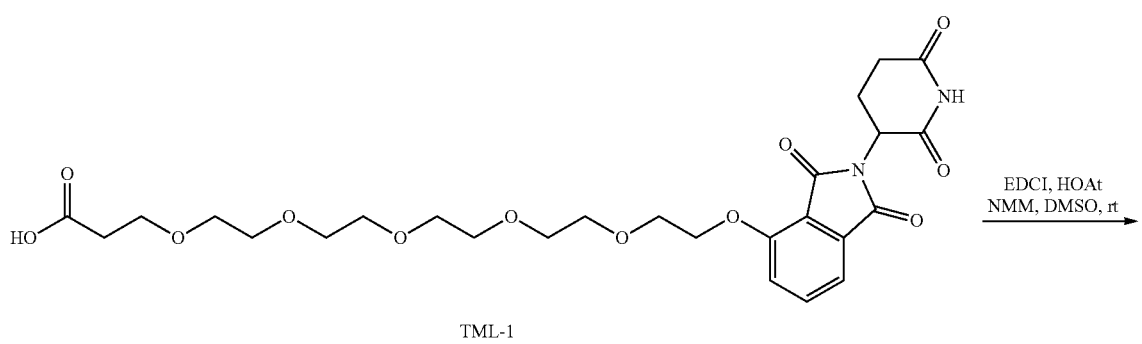

TML-1

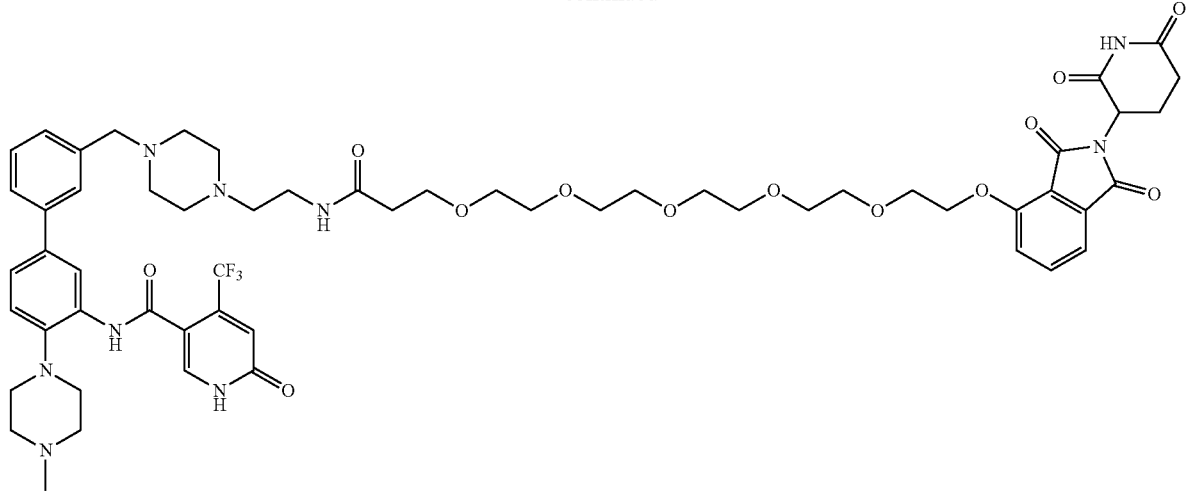

XF056-32

XF056-32 was synthesized following the standard procedures for preparing XF048-117 from intermediate 2 (10 mg, 0.017 mmol), TML-1 (9.5 mg, 0.017 mmol, 1.0 equiv), EDCI (4.9 mg, 0.026 mmol, 1.5 equiv), HOAt (3.5 mg, 0.026 mmol, 1.5 equiv), and NMM (5.3 mg, 0.052 mmol, 3.0 equiv) in DMSO (1 mL). XF056-32 was obtained as white solid in TFA salt form (14.2 mg, yield 69%). $^1$H NMR (600 MHz, CD$_3$OD) δ 8.24 (d, J=11.4 Hz, 1H), 8.04 (d, J=5.4 Hz, 1H), 7.73-7.69 (m, 3H), 7.61-7.29 (m, 6H), 6.94 (s, 1H), 5.10-5.01 (m, 1H), 4.39 (t, J=4.5 Hz, 1H), 4.31 (t, J=4.1 Hz, 1H), 4.21 (d, J=8.3 Hz, 2H), 3.99-3.83 (m, 3H), 3.81-3.46 (m, 27H), 3.45-3.07 (m, 9H), 2.97 (s, 3H), 2.91-2.80 (m, 1H), 2.78-2.63 (m, 2H), 2.54 (t, J=6.2 Hz, 1H), 2.50-2.42 (m, 2H), 2.12-2.01 (m, 1H). HRMS (m/z) for C$_{57}$H$_{72}$F$_3$N$_9$O$_{13}^+$ [M+H]$^+$: calculated 1146.5118. found 1146.5151.

Example 50: Synthesis of XF056-72

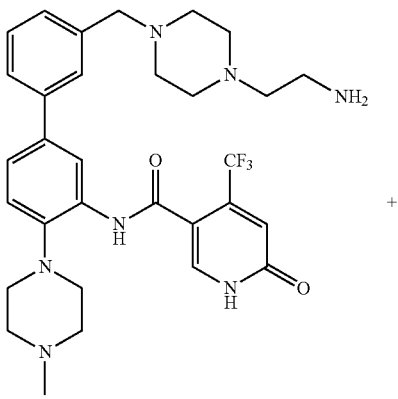

Intermediate 2

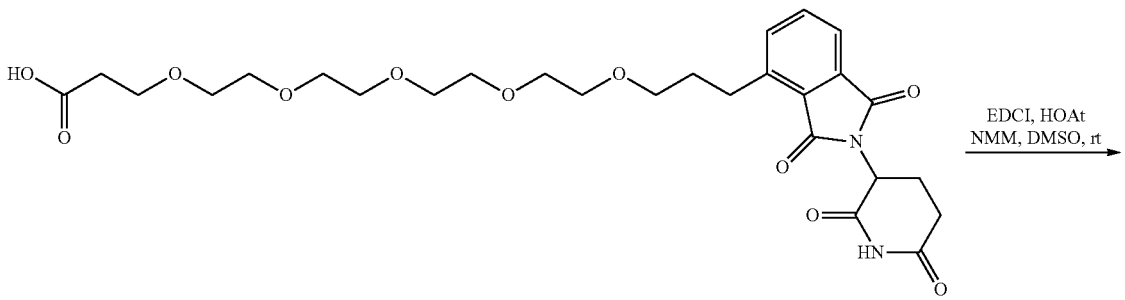

TML-2

-continued

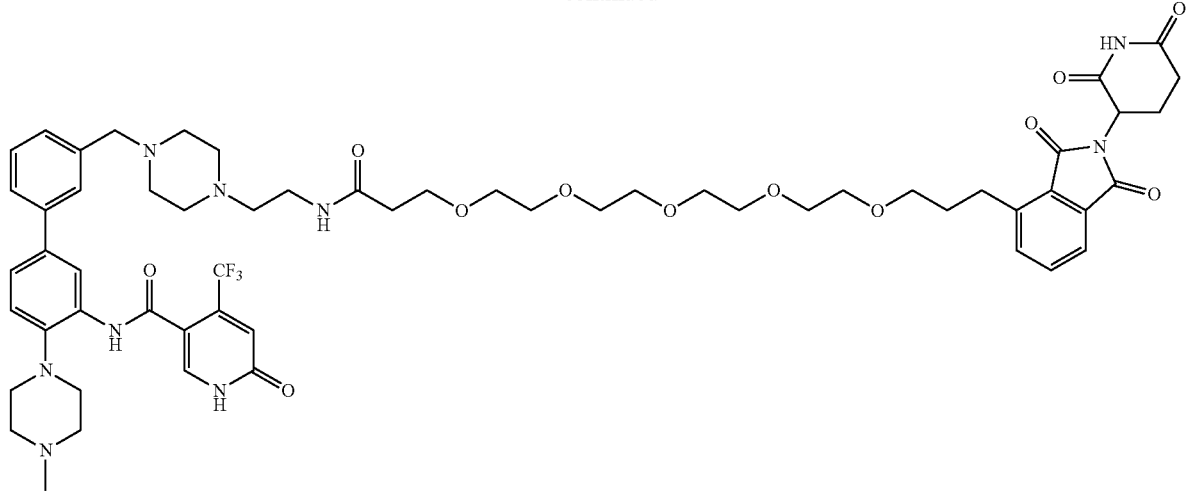

XF056-72

XF056-72 was synthesized following the standard procedures for preparing XF048-117 from intermediate 2 (11.7 mg, 0.02 mmol), TML-2 (12 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF056-72 was obtained as white solid in TFA salt form (17.7 mg, yield 77%). $^1$H NMR (600 MHz, CD$_3$OD) δ 8.24 (s, 1H), 8.02 (d, J=2.5 Hz, 1H), 7.79-7.57 (m, 5H), 7.57-7.49 (m, 2H), 7.45 (d, J=7.7 Hz, 1H), 7.41-7.32 (m, 1H), 6.93 (s, 1H), 5.17-5.05 (m, 1H), 4.24 (s, 2H), 3.78-3.20 (m, 36H), 3.19-3.09 (m, 6H), 2.95 (s, 3H), 2.91-2.81 (m, 1H), 2.78-2.64 (m, 2H), 2.50-2.40 (m, 2H), 2.17-2.07 (m, 1H), 1.97-1.81 (m, 2H). HRMS (m/z) for C$_{58}$H$_{73}$F$_3$N$_9$O$_{12}$$^+$ [M+H]$^+$: calculated 1144.5325. found 1144.5369.

Example 51: Synthesis of XF056-38

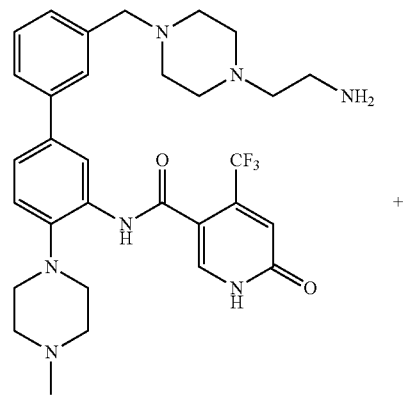

Intermediate 2

+

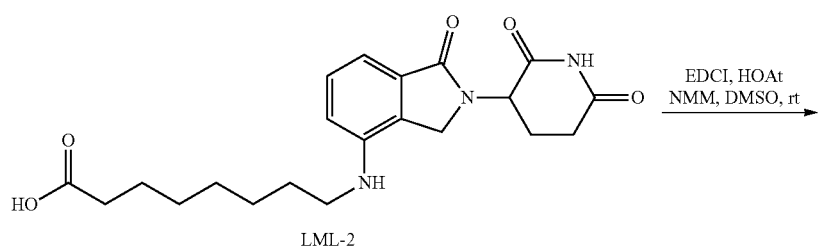

LML-2

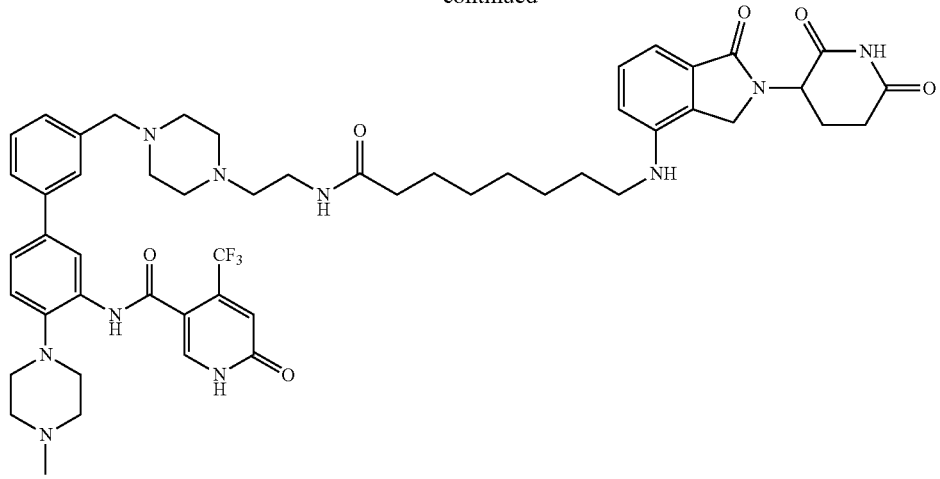

XF056-38

XF056-38 was synthesized following the standard procedures for preparing XF048-117 from intermediate 2 (10 mg, 0.017 mmol), LML-2 (6.8 mg, 0.017 mmol, 1.0 equiv), EDCI (4.9 mg, 0.026 mmol, 1.5 equiv), HOAt (3.5 mg, 0.026 mmol, 1.5 equiv), and NMM (5.3 mg, 0.052 mmol, 3.0 equiv) in DMSO (1 mL). XF056-38 was obtained as yellow solid in TFA salt form (9.4 mg, yield 56%). $^1$H NMR (600 MHz, CD$_3$OD) δ 8.27 (s, 1H), 8.03 (s, 1H), 7.82-7.63 (m, 2H), 7.60-7.50 (m, 2H), 7.44 (d, J=7.6 Hz, 1H), 7.38 (d, J=8.3 Hz, 1H), 7.31 (t, J=7.8 Hz, 1H), 7.21 (d, J=7.5 Hz, 1H), 7.01 (d, J=8.0 Hz, 1H), 6.94 (s, 1H), 5.13 (dd, J=13.6, 5.1 Hz, 1H), 4.37 (d, J=16.5 Hz, 1H), 4.28 (d, J=16.7 Hz, 1H), 4.24-4.10 (m, 2H), 3.80-3.55 (m, 4H), 3.47-3.40 (m, 2H), 3.38-2.78 (m, 23H), 2.20 (t, J=7.4 Hz, 2H), 1.68-1.43 (m, 4H), 1.40-1.15 (m, 6H). HRMS (m/z) for C$_{52}$H$_{64}$F$_3$N$_{10}$O$_6{}^+$ [M+H]$^+$: calculated 981.4957. found 981.4977.

Example 52: Synthesis of XF056-39

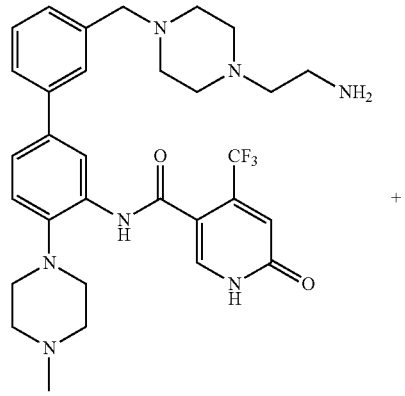

Intermediate 2

+

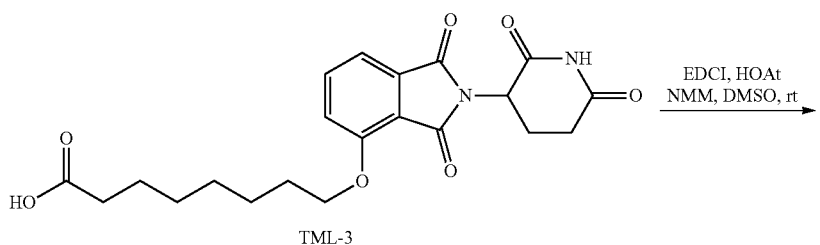

TML-3

EDCI, HOAt
NMM, DMSO, rt
→

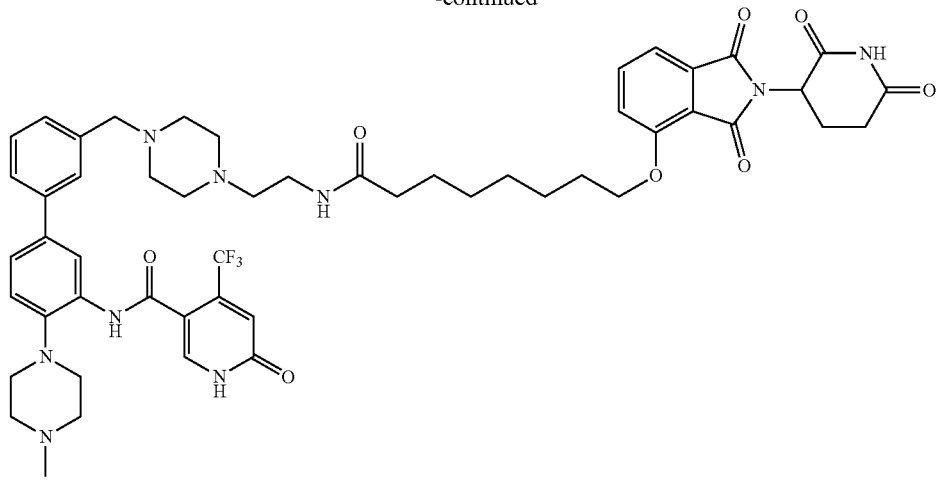

XF056-39

XF056-39 was synthesized following the standard procedures for preparing XF048-117 from intermediate 2 (10 mg, 0.017 mmol), TML-3 (7.1 mg, 0.017 mmol, 1.0 equiv), EDCI (4.9 mg, 0.026 mmol, 1.5 equiv), HOAt (3.5 mg, 0.026 mmol, 1.5 equiv), and NMM (5.3 mg, 0.052 mmol, 3.0 equiv) in DMSO (1 mL). XF056-39 was obtained as white solid in TFA salt form (11.2 mg, yield 66%). $^1$H NMR (600 MHz, CD$_3$OD) δ 8.25 (s, 1H), 8.04 (s, 1H), 7.79-7.71 (m, 2H), 7.69 (d, J=7.8 Hz, 1H), 7.56-7.48 (m, 2H), 7.48-7.36 (m, 4H), 6.95 (s, 1H), 5.08 (dd, J=12.8, 5.4 Hz, 1H), 4.31-4.09 (m, 4H), 3.62 (d, J=11.8 Hz, 2H), 3.45 (t, J=6.1 Hz, 2H), 3.37-3.06 (m, 14H), 3.00-2.92 (m, 5H), 2.91-2.79 (m, 1H), 2.77-2.61 (m, 2H), 2.22 (t, J=7.4 Hz, 2H), 2.17-2.05 (m, 1H), 1.83 (t, J=7.5 Hz, 2H), 1.73-1.58 (m, 2H), 1.58-1.49 (m, 2H), 1.47-1.26 (m, 4H). HRMS (m/z) for $C_{52}H_{61}F_3N_9O_8^+$ [M+H]$^+$: calculated 996.4596. found 996.4562.

Example 53: Synthesis of XF056-104

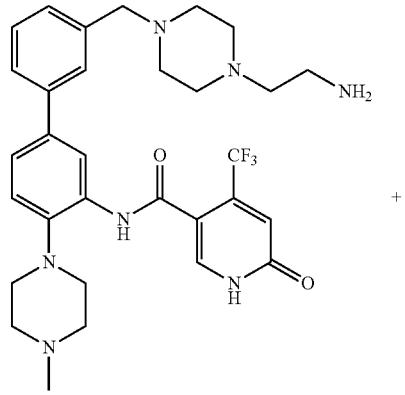

Intermediate 2

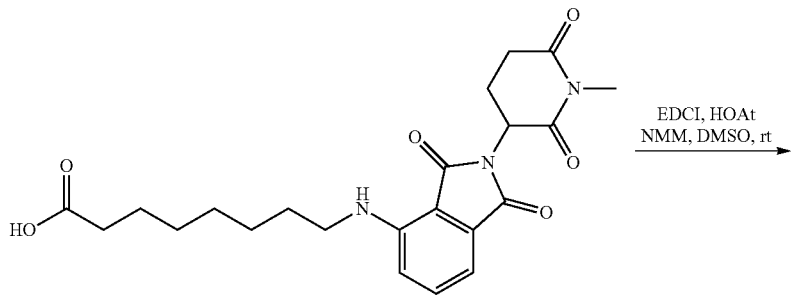

PML-28

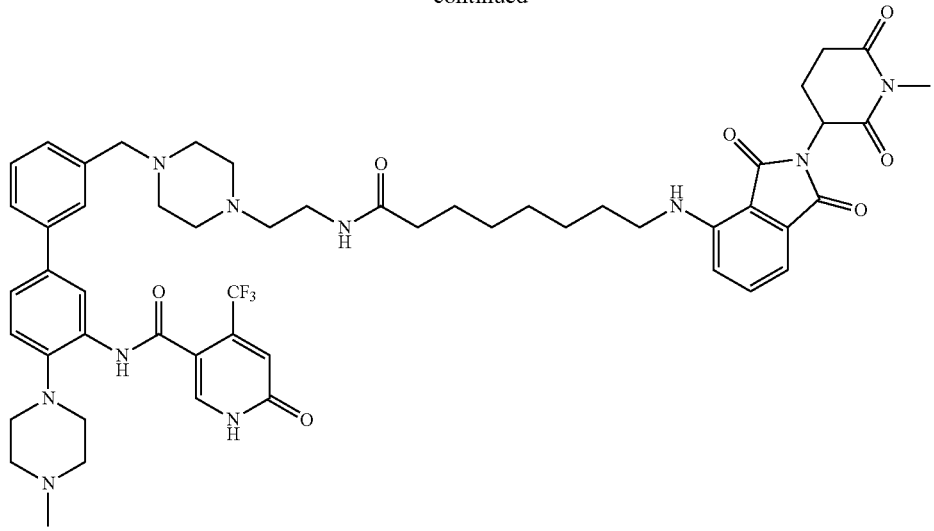

XF056-104

XF056-104 was synthesized following the standard procedures for preparing XF048-117 from intermediate 2 (12 mg, 0.02 mmol), PML-28 (8.6 mg, 0.02 mmol, 1.0 equiv), EDCI (5.8 mg, 0.026 mmol, 1.5 equiv), HOAt (4.2 mg, 0.03 mmol, 1.5 equiv), and NMM (6.1 mg, 0.06 mmol, 3.0 equiv) in DMSO (1 mL). XF056-104 was obtained as yellow solid in TFA salt form (17.7 mg, yield 88%). $^1$H NMR (600 MHz, CD$_3$OD) δ 8.25 (d, J=2.1 Hz, 1H), 8.03 (s, 1H), 7.75 (s, 1H), 7.70 (d, J=7.7 Hz, 1H), 7.57-7.50 (m, 3H), 7.44 (d, J=7.6 Hz, 1H), 7.37 (d, J=8.3 Hz, 1H), 7.01 (d, J=7.7 Hz, 2H), 6.93 (s, 1H), 5.05 (dd, J=13.0, 5.4 Hz, 1H), 4.20 (s, 2H), 3.61 (d, J=11.7 Hz, 2H), 3.45 (t, J=6.0 Hz, 2H), 3.35-3.07 (m, 19H), 3.01 (t, J=6.0 Hz, 2H), 2.96 (s, 3H), 2.89-2.81 (m, 2H), 2.71-2.62 (m, 1H), 2.20 (t, J=7.5 Hz, 2H), 2.08-2.03 (m, 1H), 1.69-1.54 (m, 4H), 1.47-1.27 (m, 6H). HRMS (m/z) for C$_{53}$H$_{64}$F$_3$N$_{10}$O$_7^+$ [M+H]$^+$: calculated 1009.4906. found 1009.4885.

Example 54: Synthesis of XF056-118

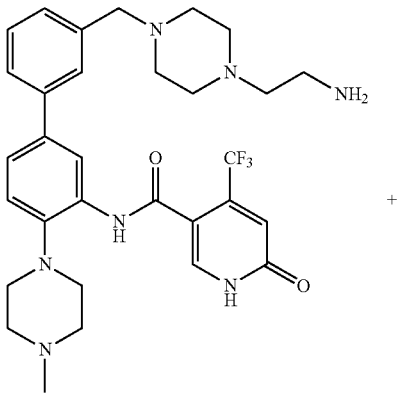

Intermediate 2

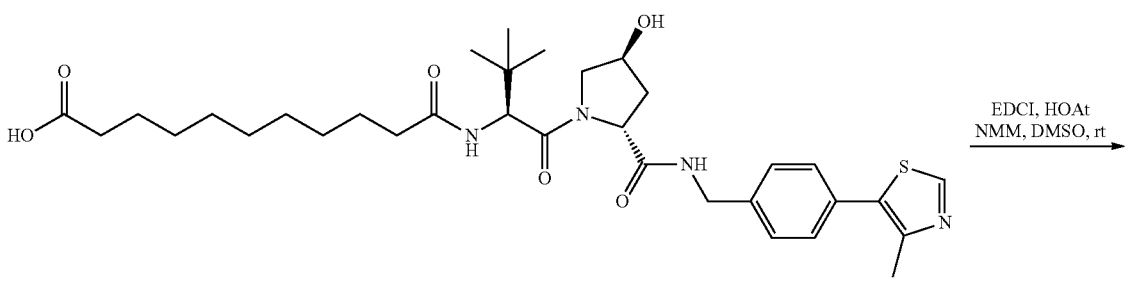

VHL—C9—COOH Negative control 1

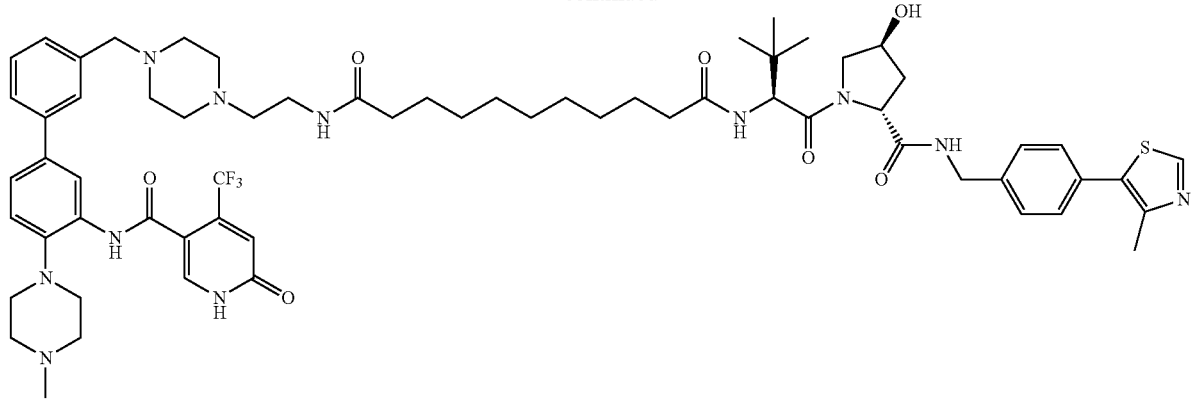

XF056-118

XF056-118 was synthesized following the standard procedures for preparing XF048-117 from intermediate 2 (12 mg, 0.02 mmol), VHL-C9-COOH Negative control 1 (12.5 mg, 0.02 mmol, 1.0 equiv), EDCI (5.8 mg, 0.026 mmol, 1.5 equiv), HOAt (4.2 mg, 0.03 mmol, 1.5 equiv), and NMM (6.1 mg, 0.06 mmol, 3.0 equiv) in DMSO (1 mL). XF056-118 was obtained as white solid in TFA salt form (20.5 mg, yield 85%). $^1$H NMR (600 MHz, CD$_3$OD) δ 8.99 (s, 1H), 8.26 (d, J=2.1 Hz, 1H), 8.02 (s, 1H), 7.76 (s, 1H), 7.71 (d, J=7.8 Hz, 1H), 7.57-7.49 (m, 3H), 7.48-7.41 (m, 3H), 7.41-7.30 (m, 3H), 6.93 (s, 1H), 4.61-4.55 (m, 1H), 4.55-4.46 (m, 2H), 4.45-4.40 (m, 1H), 4.34 (d, J=15.7 Hz, 1H), 4.26 (s, 2H), 4.03-3.96 (m, 2H), 3.73 (dd, J=10.9, 3.4 Hz, 1H), 3.61 (d, J=11.8 Hz, 2H), 3.48 (t, J=6.0 Hz, 2H), 3.45-3.20 (m, 11H), 3.20-3.03 (m, 4H), 2.96 (s, 3H), 2.49 (s, 3H), 2.30-2.23 (m, 1H), 2.21-2.12 (m, 4H), 2.07-1.98 (m, 1H), 1.59-1.49 (m, 2H), 1.46-1.30 (m, 2H), 1.28-1.13 (m, 10H), 1.07 (s, 9H). HRMS (m/z) for C$_{64}$H$_{85}$F$_3$N$^{11}$O$_7$S$^+$ [M+H]$^+$: calculated 1208.6301. found 1208.6293.

Example 55: Synthesis of Intermediates 6 and 7

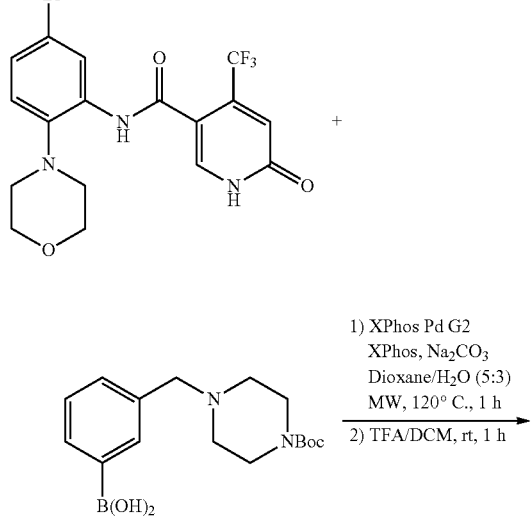

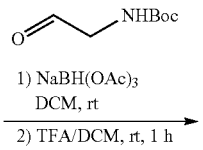

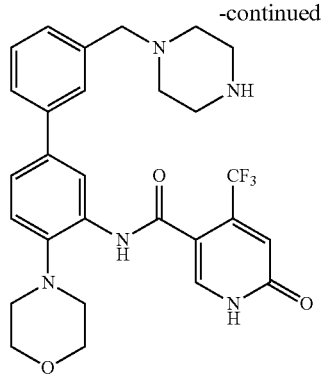

Intermediate 6

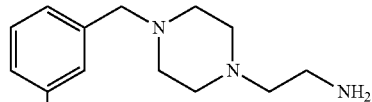

Intermediate 7

To a solution of N-(5-bromo-2-morpholinophenyl)-6-oxo-4-(trifluoromethyl)-1,6-dihydropyridine-3-carboxamide (Getlik et al., 2016) (380 mg, 0.85 mmol) and (3-((4-(tert-butoxycarbonyl)piperazin-1-yl)methyl)phenyl)boronic acid (820 mg, 2.6 mmol, 3.0 euqiv) in 8 mL of 1,4-dioxane/H$_2$O (5:3) were added sodium carbonate (901 mg, 8.6 mmol, 10 equiv), XPhos (81 mg, 0.17 mmol, 0.2 equiv), and XPhos Pd G2 (134 mg, 0.17 mmol, 0.2 equiv). The reaction was heated to 120° C. for 1 h under Microwave. The solvent was removed and purified by reverse phase ISCO (10%-100% methanol/0.1% TFA in H$_2$O) to afford product (108 mg, yield 20%). This product was dissolved in DCM (5 mL) and TFA (5 mL). The resulting mixture was stirring for 30 minutes. Then, it was concentrated and purified by reverse phase ISCO (10%-100% methanol/0.1% TFA in H₂O) to afford Intermediate 6 as white solid in TFA salt form (78 mg, yield 86%). ESI-MS m z 542.5; To a solution of intermediate 6 (78 mg, 0.14 mmol), and tert-butyl (2-oxoethyl)carbamate (46 mg, 0.28 mmol, 2.0 equiv) in dichloromethane (3 mL) was added sodium triacetoxyborohydride (61 mg, 0.28 mmol). After stirring overnight, saturated sodium bicarbonate was added to quench reaction. The mixture was extracted with DCM (3×10 mL), dried over Na₂SO₄, filtered and concentrated. The crude product was purified by reverse phase ISCO (10%-100% methanol/0.1% TFA in H₂O) to afford white solid. This product was dissolved in DCM (5 mL) and TFA (5 mL). The resulting mixture was stirring for 30 minutes. Then, it was concentrated and purified by preparative HPLC (10%-100% methanol/0.1% TFA in H₂O) to afford Intermediate 7 (XF061-109) as white solid in TFA salt form (32.9 mg, yield 40%). ¹H NMR (600 MHz, CD₃OD) δ 8.27 (d, J=2.2 Hz, 1H), 7.98 (s, 1H), 7.81-7.74 (m, 2H), 7.58 (t, J=7.7 Hz, 1H), 7.52 (dd, J=8.3, 2.2 Hz, 1H), 7.49 (d, J=7.6 Hz, 1H), 7.36 (d, J=8.3 Hz, 1H), 6.93 (s, 1H), 4.43 (s, 2H), 3.89-3.73 (m, 4H), 3.50-3.17 (m, 8H), 3.07 (dd, J=6.7, 4.8 Hz, 2H), 3.03-2.89 (m, 4H), 2.72 (dd, J=6.7, 4.9 Hz, 2H). HRMS (m/z) for $C_{30}H_{36}F_3N_6O_3^+$ [M+H]⁺: calculated 585.2796. found 585.2777.

Example 56: Synthesis of XF061-111

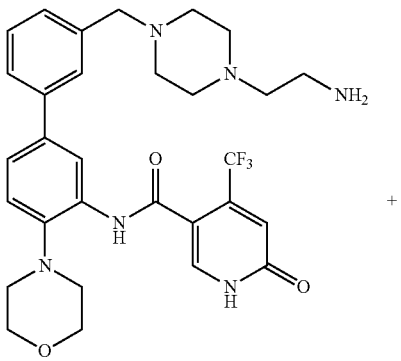

Intermediate 7

+

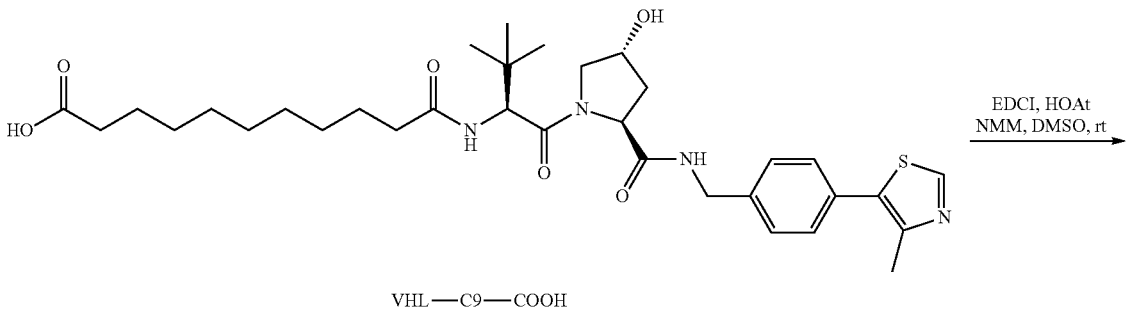

VHL—C9—COOH

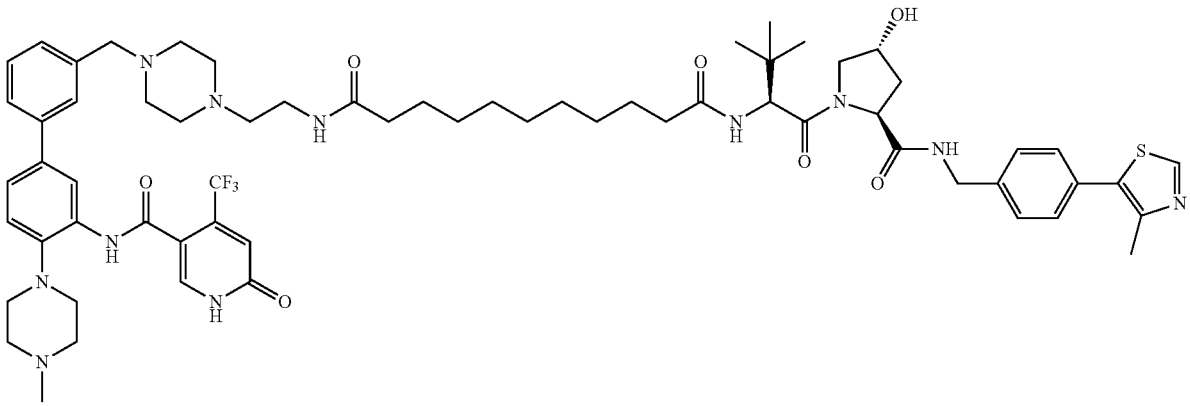

XF061-111

XF061-111 was synthesized following the standard procedures for preparing XF048-117 from intermediate 7 (11.7 mg, 0.02 mmol), VHL-C9-COOH (12.6 mg, 0.02 mmol, 1.0 equiv), EDCI (5.8 mg, 0.026 mmol, 1.5 equiv), HOAt (4.2 mg, 0.03 mmol, 1.5 equiv), and NMM (6.1 mg, 0.06 mmol, 3.0 equiv) in DMSO (1 mL). XF056-118 was obtained as white solid in TFA salt form (7.4 mg, yield 31%). $^1$H NMR (600 MHz, CD$_3$OD) δ 9.01 (s, 1H), 8.28 (d, J=2.2 Hz, 1H), 7.97 (s, 1H), 7.82 (d, J=9.0 Hz, 1H), 7.79-7.67 (m, 2H), 7.65-7.26 (m, 7H), 6.94 (s, 1H), 4.68-4.45 (m, 4H), 4.36 (dd, J=15.3, 5.1 Hz, 1H), 4.20 (s, 2H), 3.94-3.74 (m, 4H), 3.45 (t, J=6.1 Hz, 2H), 3.39-3.08 (m, 10H), 3.06-2.85 (m, 6H), 2.48 (s, 3H), 2.37-2.14 (m, 5H), 2.07 (ddd, J=13.3, 9.2, 4.5 Hz, 1H), 1.69-1.48 (m, 4H), 1.39-1.25 (m, 10H), 1.03 (s, 9H). HRMS (m/z) for C$_{63}$H$_{82}$F$_3$N$_{10}$O$_8$S$^+$ [M+H]$^+$: calculated 1195.5984. found 1195.5995.

Example 57: Synthesis of XF067-66

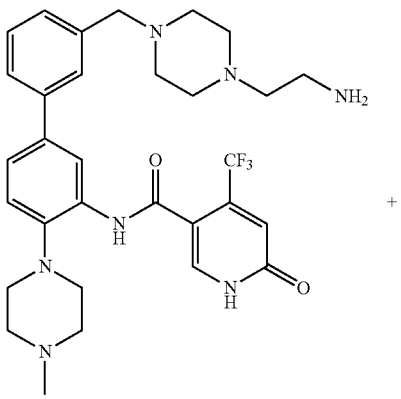

Intermediate 2

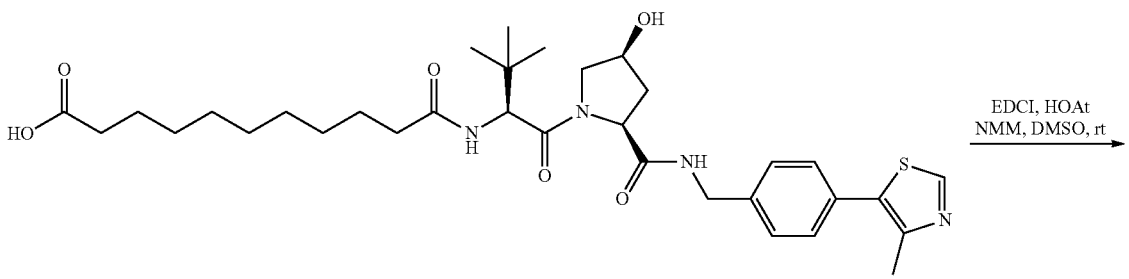

VHL—C9—COOH   Negative control 2

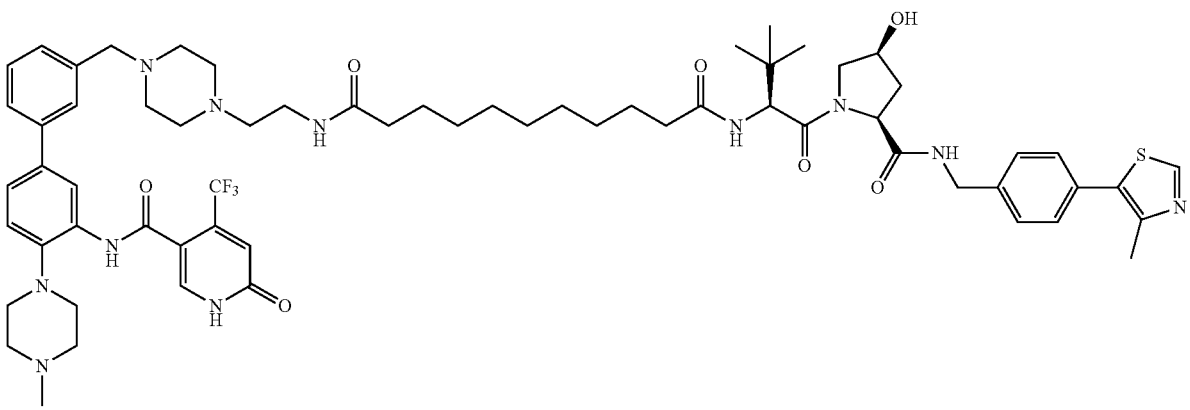

XF067-66

XF067-66 was synthesized following the standard procedures for preparing XF048-117 from intermediate 2 (12 mg, 0.02 mmol), VHL-C9-COOH Negative control 2 (12.5 mg, 0.02 mmol, 1.0 equiv), EDCI (5.8 mg, 0.026 mmol, 1.5 equiv), HOAt (4.2 mg, 0.03 mmol, 1.5 equiv), and NMM (6.1 mg, 0.06 mmol, 3.0 equiv) in DMSO (1 mL). XF067-66 was obtained as white solid in TFA salt form (9.3 mg, yield 39%). $^1$H NMR (600 MHz, CD$_3$OD) δ 9.00 (s, 1H), 8.29 (d, J=2.1 Hz, 1H), 8.05 (s, 1H), 7.80-7.70 (m, 2H), 7.58-7.52 (m, 2H), 7.51-7.39 (m, 6H), 6.97 (s, 1H), 4.58-4.47 (m, 2H), 4.44-4.37 (m, 2H), 4.18 (s, 2H), 4.09-3.96 (m, 1H), 3.72 (dd, J=10.4, 3.8 Hz, 1H), 3.64 (d, J=11.7 Hz, 2H), 3.47 (t, J=6.0 Hz, 2H), 3.40-3.07 (m, 16H), 3.06-2.97 (m, 5H), 2.60-2.41 (m, 4H), 2.39-2.16 (m, 3H), 2.07-1.96 (m, 1H), 1.68-1.51 (m, 4H), 1.45-1.20 (m, 10H), 1.05 (s, 9H). HRMS (m/z) for C$_{64}$H$_{85}$F$_3$N$^{11}$O$_7$S$^+$ [M+H]$^+$: calculated 1208.6301, found 1208.6288.

Example 58: Synthesis of Intermediate 8

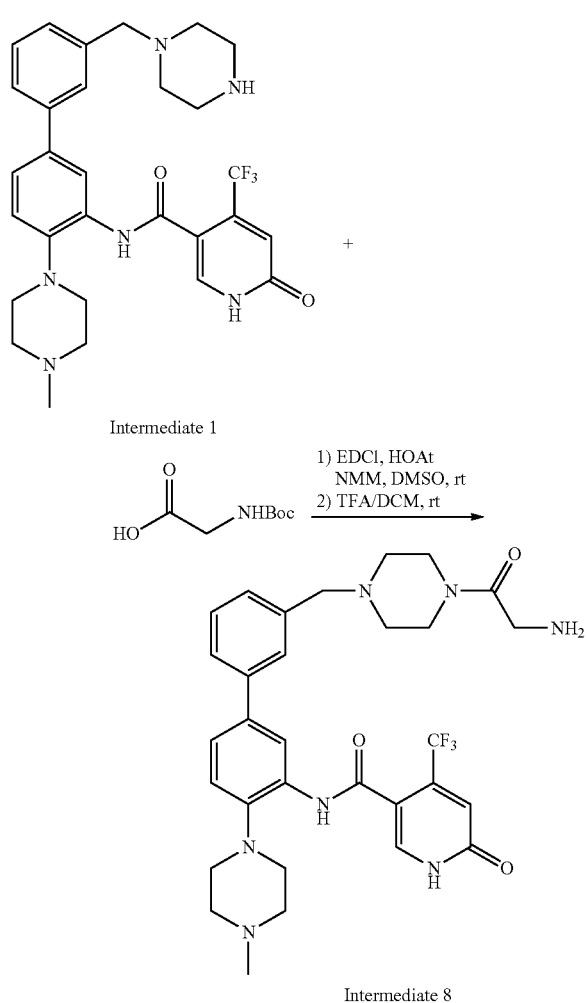 [SMILES: CN1CCN(c2ccc(-c3cccc(CN4CCNCC4)c3)cc2NC(=O)c2c[nH]c(=O)cc2C(F)(F)F)CC1 ; CC(C)(C)OC(=O)NCC(=O)O ; CN1CCN(c2ccc(-c3cccc(CN4CCN(C(=O)CN)CC4)c3)cc2NC(=O)c2c[nH]c(=O)cc2C(F)(F)F)CC1]

Intermediate 8

To the solution of intermediate 1 (22.2 mg, 0.04 mmol) in DMSO (1 mL) were added (tert-butoxycarbonyl)glycine (7 mg, 0.04 mmol, 1.0 equiv), EDCI (1-ethyl-3-(3-dimethyl-aminopropyl)carbodiimide) (11.6 mg, 0.06 mmol, 1.5 equiv), HOAt (1-hydroxy-7-azabenzo-triazole) (8.2 mg, 0.06 mmol, 1.5 equiv), and NMM (N-Methylmorpholine) (12.2 mg, 0.12 mmol, 3.0 equiv). After being stirring overnight at room temperature, the resulting mixture was purified by preparative HPLC (10%-100% methanol/0.1% TFA in H$_2$O) to afford white solid. This This product was dissolved in DCM (1 mL) and TFA (1 mL). The resulting mixture was stirring for 30 minutes. Then, it was concentrated and purified by preparative HPLC (10%-100% methanol/0.1% TFA in H$_2$O) to afford Intermediate 8 (XF078-162) as white solid in TFA salt form (20.4 mg, yield 83%). $^1$H NMR (500 MHz, CD$_3$OD) δ 8.30 (d, J=2.2 Hz, 1H), 8.06 (s, 1H), 7.85-7.78 (m, 2H), 7.64-7.56 (m, 2H), 7.56-7.51 (m, 1H), 7.42 (d, J=8.3 Hz, 1H), 6.96 (s, 1H), 4.50 (d, J=4.3 Hz, 2H), 4.03 (d, J=4.3 Hz, 2H), 3.79 (s, 2H), 3.64 (d, J=11.8 Hz, 2H), 3.48-3.35 (m, 8H), 3.21 (t, J=13.1 Hz, 4H), 2.99 (d, J=4.3 Hz, 3H). HRMS (m/z) for C$_{31}$H$_{37}$F$_3$N$_7$O$_3$$^+$ [M+H]$^+$: calculated 612.2904. found 612.2911.

Example 59: Synthesis of Intermediate 9

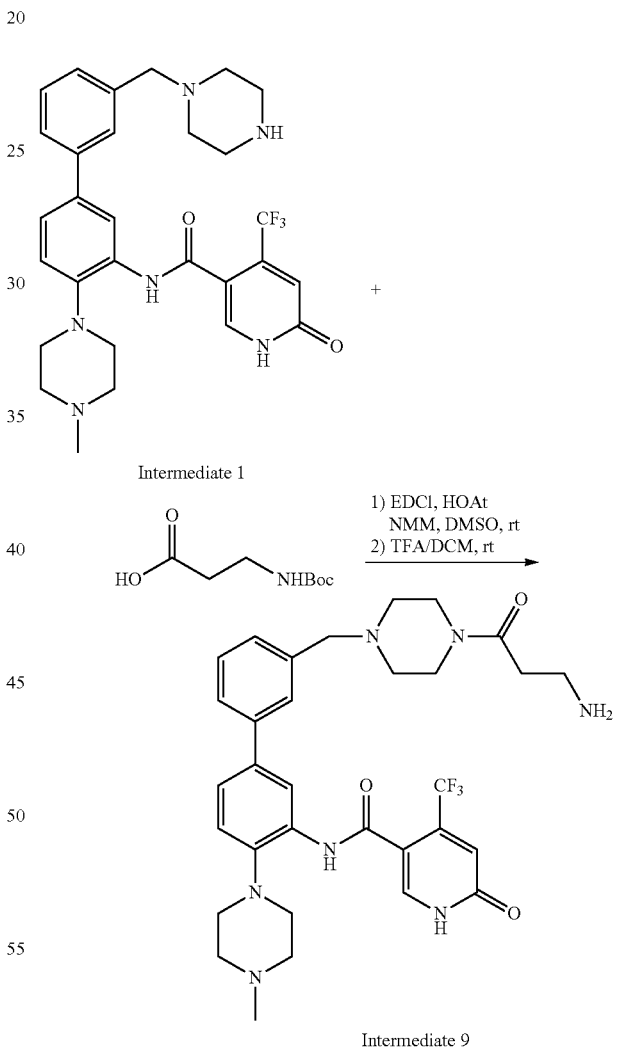

Intermediate 9

Intermediate 9 was synthesized following the standard procedures for preparing Intermediate 8 from intermediate 1 (22.2 mg, 0.04 mmol), 3-((tert-butoxycarbonyl)amino)propanoic acid (7.6 mg, 0.04 mmol, 1.0 equiv), EDCI (11.6 mg, 0.06 mmol, 1.5 equiv), HOAt (8.2 mg, 0.06 mmol, 1.5 equiv), and NMM (12.2 mg, 0.12 mmol, 3.0 equiv) in DMSO (1 mL). Intermediate 9 (XF078-163) was obtained as white solid in TFA salt form (28.9 mg, yield 77%). $^1$H NMR (500 MHz, CD$_3$OD) δ 8.29 (d, J=2.2 Hz, 1H), 8.06 (s, 1H), 7.84 (q, J=2.5, 1.9 Hz, 1H), 7.80 (d, J=7.6 Hz, 1H), 7.64-7.55 (m, 2H), 7.53 (d, J=7.5 Hz, 1H), 7.42 (dd, J=8.4, 4.4 Hz, 1H), 6.95 (s, 1H), 4.48 (d, J=4.4 Hz, 2H), 3.63 (d, J=11.8 Hz, 2H), 3.47-3.33 (m, 9H), 3.21 (dd, J=15.0, 9.5 Hz, 3H), 3.05-2.93 (m, 5H), 2.61 (t, J=6.7 Hz, 2H), 1.97 (p, J=7.0 Hz, 2H). HRMS (m/z) for C$_{32}$H$_{39}$F$_3$N$_7$O$_3^+$ [M+H]$^+$: calculated 626.3061. found 626.3078.

Example 60: Synthesis of Intermediate 10

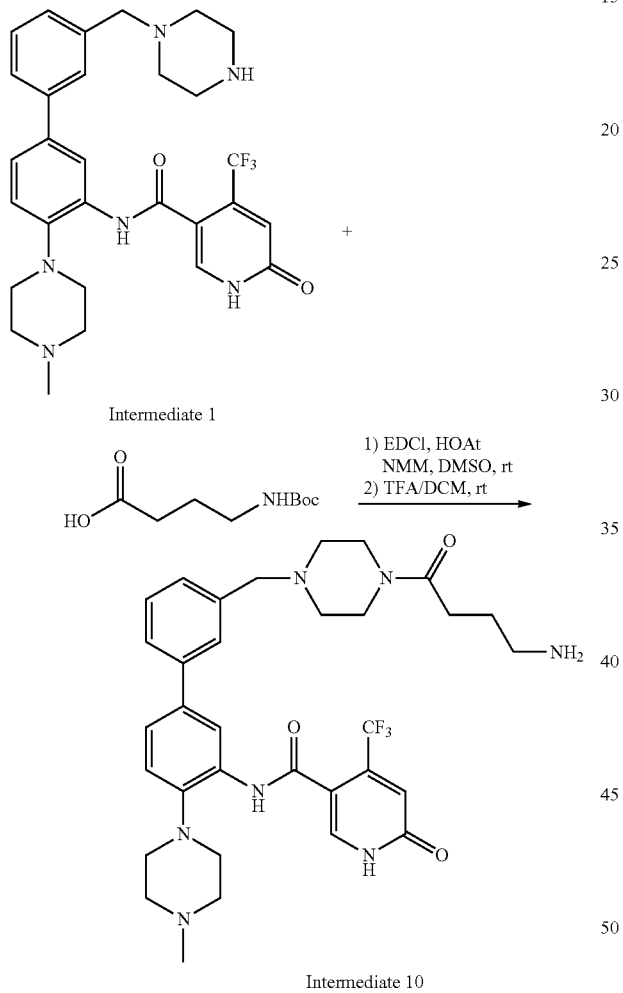

Intermediate 10

Intermediate 10 was synthesized following the standard procedures for preparing Intermediate 8 from intermediate 1 (22.2 mg, 0.04 mmol), 4-((tert-butoxycarbonyl)amino)butanoic acid (8.2 mg, 0.04 mmol, 1.0 equiv), EDCI (11.6 mg, 0.06 mmol, 1.5 equiv), HOAt (8.2 mg, 0.06 mmol, 1.5 equiv), and NMM (12.2 mg, 0.12 mmol, 3.0 equiv) in DMSO (1 mL). Intermediate 10 (XF078-164) was obtained as white solid in TFA salt form (18 mg, yield 70%). $^1$H NMR (500 MHz, CD$_3$OD) δ 8.30 (d, J=2.2 Hz, 1H), 8.06 (s, 1H), 7.86-7.78 (m, 2H), 7.65-7.56 (m, 2H), 7.56-7.50 (m, 1H), 7.42 (d, J=8.3 Hz, 1H), 6.96 (s, 1H), 4.49 (d, J=4.6 Hz, 2H), 3.64 (d, J=11.7 Hz, 2H), 3.33 (tt, J=4.8, 2.9 Hz, 12H), 3.26-3.14 (m, 2H), 3.04-2.95 (m, 5H), 2.62 (q, J=6.8, 6.0 Hz, 2H), 1.97 (p, J=6.8 Hz, 2H). HRMS (m/z) for C$_{33}$H$_{41}$F$_3$N$_7$O$_3^+$ [M+H]$^+$: calculated 640.3217. found 640.3198.

Example 61: Synthesis of Intermediate 11

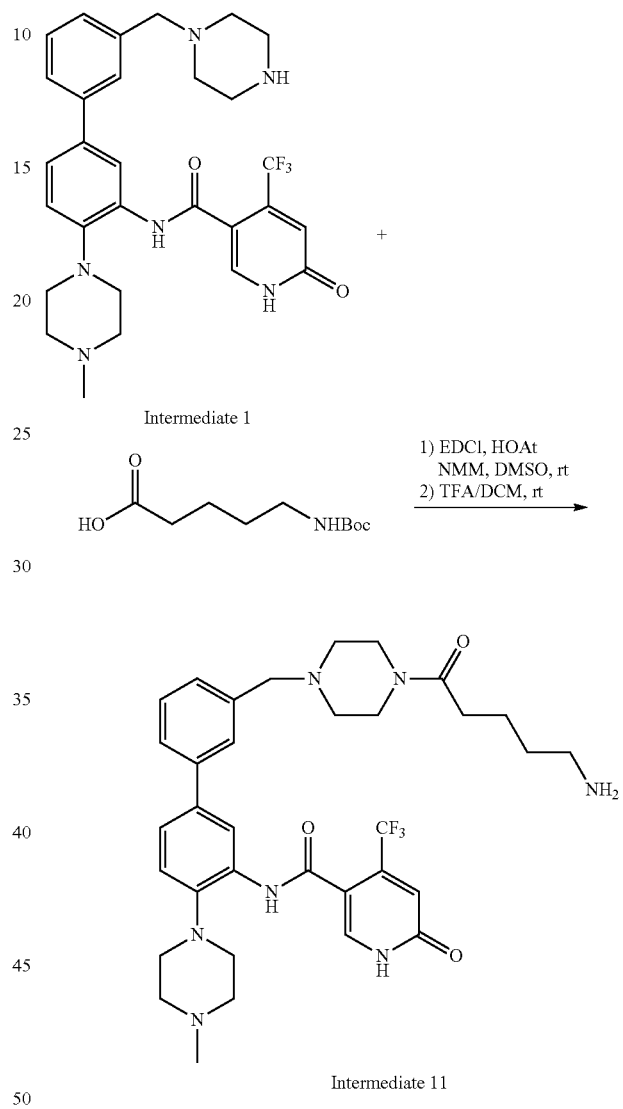

Intermediate 11

Intermediate 11 was synthesized following the standard procedures for preparing Intermediate 8 from intermediate 1 (33.3 mg, 0.06 mmol), 5-((tert-butoxycarbonyl)amino)pentanoic acid (13 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 11 (XF078-166) was obtained as white solid in TFA salt form (40.2 mg, yield 98%). $^1$H NMR (500 MHz, CD$_3$OD) δ 8.30 (d, J=2.3 Hz, 1H), 8.06 (s, 1H), 7.86-7.78 (m, 2H), 7.64-7.56 (m, 2H), 7.56-7.51 (m, 1H), 7.41 (d, J=8.4 Hz, 1H), 6.95 (s, 1H), 4.48 (s, 2H), 3.64 (d, J=11.7 Hz, 2H), 3.49-3.29 (m, 12H), 3.26-3.14 (m, 2H), 2.97 (d, J=8.6 Hz, 5H), 2.53 (d, J=5.9 Hz, 2H), 1.72 (tt, J=7.2, 3.7 Hz, 4H). HRMS (m/z) for C$_{34}$H$_{43}$F$_3$N$_7$O$_3^+$ [M+H]$^+$: calculated 654.3374, found 654.3401.

Example 62: Synthesis of Intermediate 12

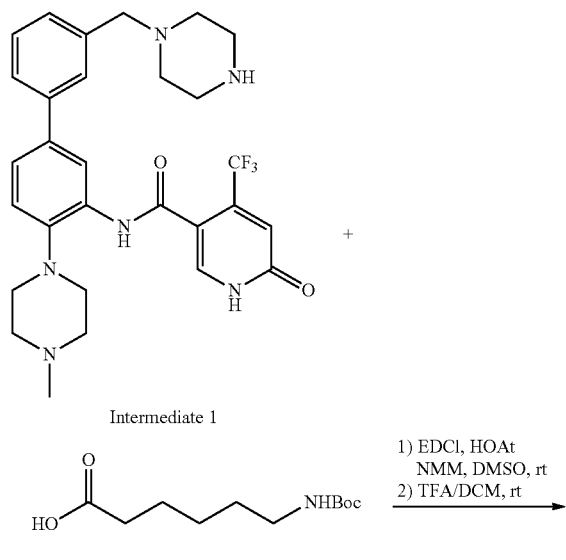

Intermediate 12

Example 63: Synthesis of Intermediate 13

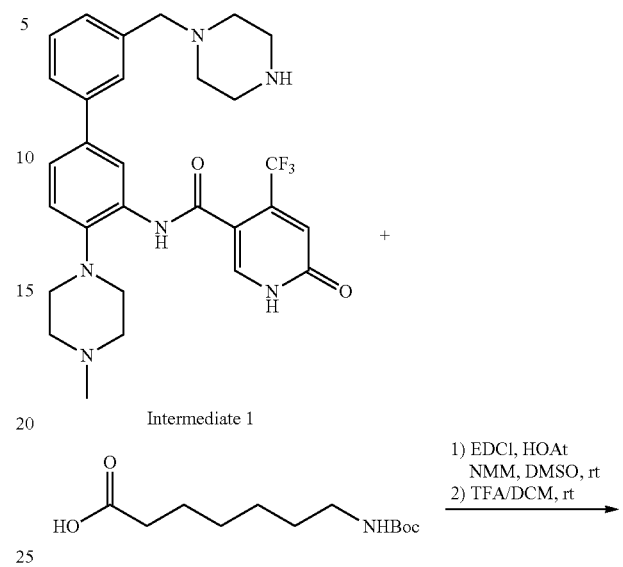

Intermediate 13

Intermediate 12 was synthesized following the standard procedures for preparing Intermediate 8 from intermediate 1 (33.3 mg, 0.06 mmol), 6-((tert-butoxycarbonyl)amino) hexanoic acid (13.9 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 12 (XF078-167) was obtained as white solid in TFA salt form (26.7 mg, yield 67%). $^1$H NMR (500 MHz, CD$_3$OD) δ 8.30 (d, J=2.2 Hz, 1H), 8.06 (s, 1H), 7.87-7.77 (m, 2H), 7.64-7.56 (m, 2H), 7.55-7.50 (m, 1H), 7.42 (d, J=8.4 Hz, 1H), 6.95 (s, 1H), 4.48 (d, J=4.4 Hz, 2H), 3.64 (d, J=11.8 Hz, 2H), 3.53-3.30 (m, 12H), 3.21 (t, J=13.2 Hz, 2H), 2.99 (s, 3H), 2.95 (t, J=7.6 Hz, 2H), 2.49 (t, J=7.3 Hz, 2H), 1.76-1.57 (m, 4H), 1.45 (tq, J=9.9, 7.1, 6.0 Hz, 2H). HRMS (m/z) for C$_{35}$H$_{45}$F$_3$N$_7$O$_3$$^+$ [M+H]$^+$: calculated 668.3530. found 668.3554.

Intermediate 13 was synthesized following the standard procedures for preparing Intermediate 8 from intermediate 1 (33.3 mg, 0.06 mmol), 7-((tert-butoxycarbonyl)amino)heptanoic acid (14.7 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 13 (XF078-168) was obtained as white solid in TFA salt form (35.6 mg, yield 87%). $^1$H NMR (500 MHz, CD$_3$OD) δ 8.30 (d, J=2.3 Hz, 1H), 8.07 (d, J=4.5 Hz, 1H), 7.84 (q, J=2.4, 1.9 Hz, 1H), 7.82-7.78 (m, 1H), 7.59 (ddd, J=13.0, 8.0, 2.9 Hz, 2H), 7.53 (d, J=7.5 Hz, 1H), 7.41 (d, J=8.4 Hz, 1H), 6.95 (d, J=4.5 Hz, 1H), 4.48 (s, 2H), 3.64 (d, J=11.7 Hz, 2H), 3.52-3.26 (m, 12H), 3.27-3.14 (m, 2H), 2.99 (s, 3H), 2.94 (q, J=7.8, 6.3 Hz, 2H), 2.47 (q, J=7.5, 6.1 Hz, 2H), 1.76-1.55 (m, 4H), 1.43 (tq, J=10.2, 6.0, 4.6 Hz, 4H). HRMS (m/z) for C$_{36}$H$_{47}$F$_3$N$_7$O$_3$$^+$ [M+H]$^+$: calculated 682.3687. found 682.3666.

Example 64: Synthesis of Intermediate 14

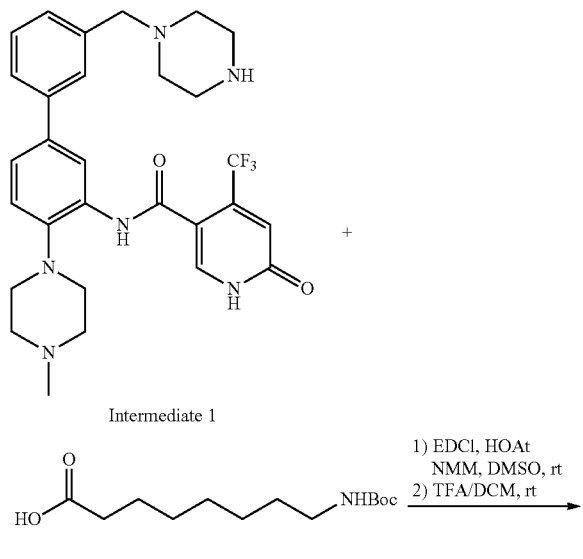

Example 65: Synthesis of Intermediate 15

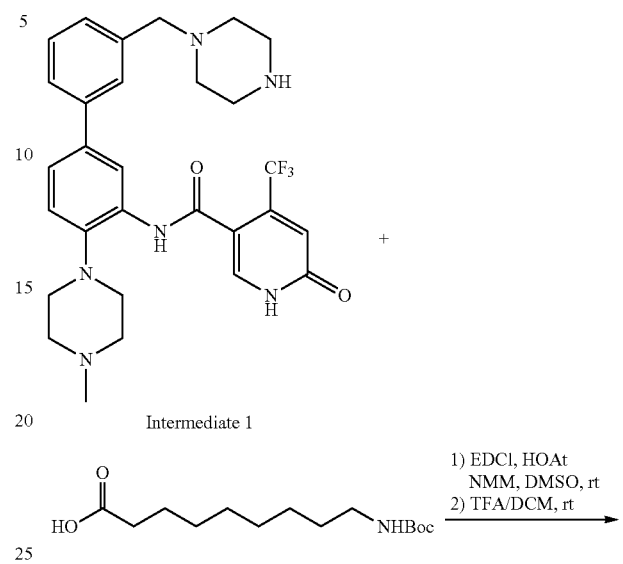

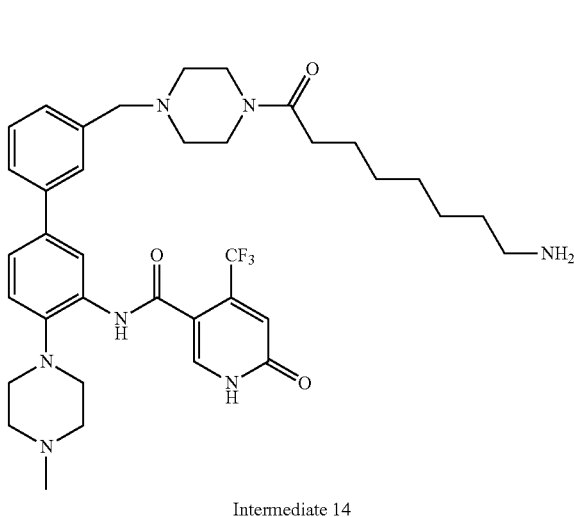

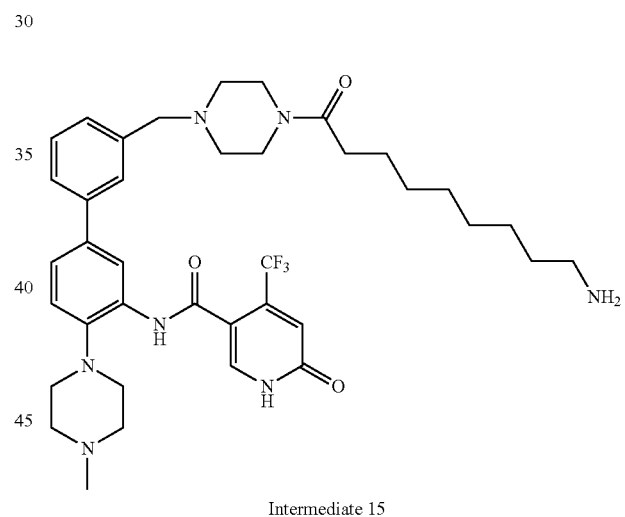

Intermediate 14 was synthesized following the standard procedures for preparing Intermediate 8 from intermediate 1 (33.3 mg, 0.06 mmol), 8-((tert-butoxycarbonyl)amino)octanoic acid (15.5 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 14 (XF078-169) was obtained as white solid in TFA salt form (36.2 mg, yield 87%). $^1$H NMR (500 MHz, CD$_3$OD) δ 8.30 (d, J=2.2 Hz, 1H), 8.07 (d, J=4.8 Hz, 1H), 7.86-7.77 (m, 2H), 7.65-7.55 (m, 2H), 7.55-7.50 (m, 1H), 7.42 (d, J=8.4 Hz, 1H), 6.95 (s, 1H), 4.48 (s, 2H), 3.64 (d, J=11.8 Hz, 2H), 3.46-3.28 (m, 12H), 3.21 (t, J=13.2 Hz, 2H), 2.99 (s, 3H), 2.93 (t, J=7.6 Hz, 2H), 2.46 (q, J=7.6, 6.4 Hz, 2H), 1.72-1.57 (m, 4H), 1.42 (q, J=4.6 Hz, 6H). HRMS (m/z) for $C_{37}H_{49}F_3N_7O_3^+$ [M+H]$^+$: calculated 696.3843. found 696.3825.

Intermediate 66 was synthesized following the standard procedures for preparing Intermediate 8 from intermediate 1 (33.3 mg, 0.06 mmol), 9-((tert-butoxycarbonyl)amino) nonanoic acid (16.4 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 15 (XF078-170) was obtained as white solid in TFA salt form (38.5 mg, yield 91%). $^1$H NMR (500 MHz, CD$_3$OD) δ 8.30 (d, J=2.2 Hz, 1H), 8.06 (s, 1H), 7.87-7.78 (m, 2H), 7.60 (ddd, J=13.6, 8.0, 2.7 Hz, 2H), 7.53 (d, J=7.5 Hz, 1H), 7.41 (d, J=8.4 Hz, 1H), 6.95 (s, 1H), 4.48 (d, J=5.0 Hz, 2H), 3.64 (d, J=11.6 Hz, 2H), 3.47-3.28 (m, 12H), 3.26-3.16 (m, 2H), 2.99 (s, 3H), 2.94 (q, J=7.8, 6.5 Hz, 2H), 2.46 (q, J=7.5, 6.5 Hz, 2H), 1.74-1.53 (m, 4H), 1.47-1.30 (m, 8H). HRMS (m/z) for $C_{38}H_{51}F_3N_7O_3^+$ [M+H]$^+$: calculated 710.4000. found 710.3978.

Example 66: Synthesis of Intermediate 16

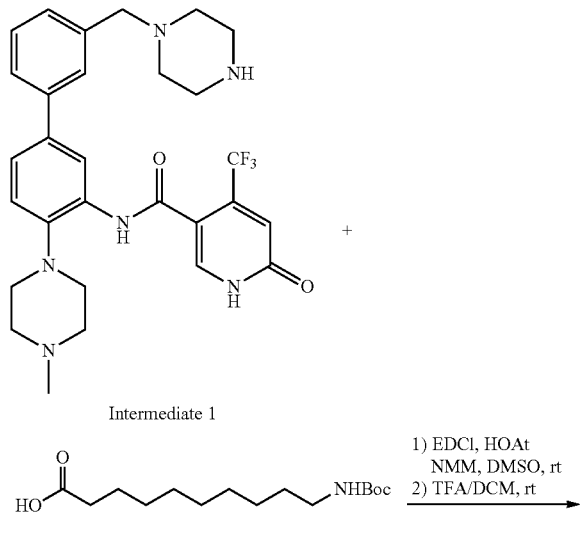

Example 67: Synthesis of Intermediate 17

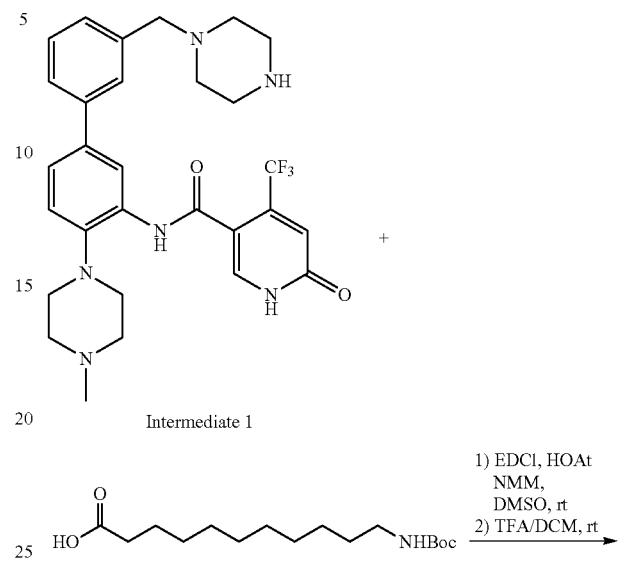

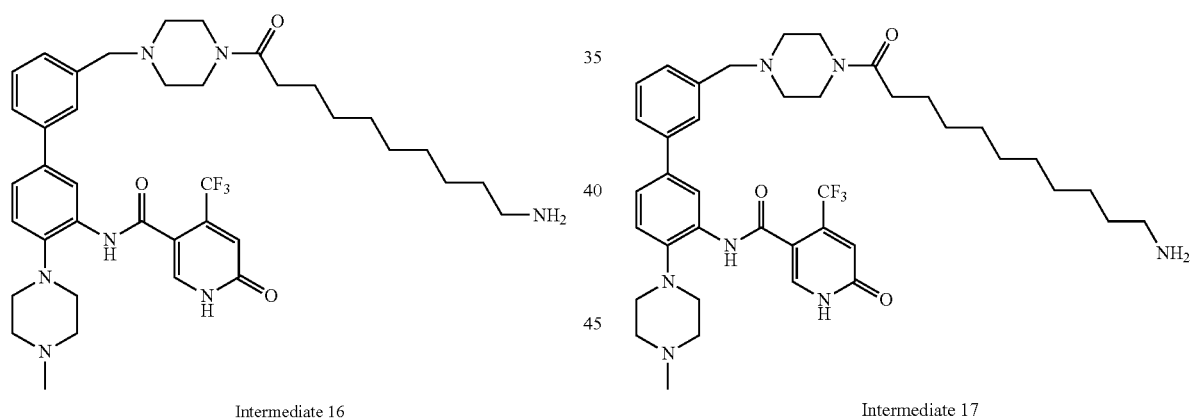

Intermediate 16 was synthesized following the standard procedures for preparing Intermediate 8 from intermediate 1 (33.3 mg, 0.06 mmol), 10-((tert-butoxycarbonyl)amino)decanoic acid (17.2 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 16 (XF078-171) was obtained as white solid in TFA salt form (35.5 mg, yield 82%). $^1$H NMR (500 MHz, CD$_3$OD) δ 8.30 (d, J=2.1 Hz, 1H), 8.07 (d, J=4.9 Hz, 1H), 7.86-7.77 (m, 2H), 7.65-7.56 (m, 2H), 7.53 (d, J=7.4 Hz, 1H), 7.42 (d, J=8.4 Hz, 1H), 6.95 (s, 1H), 4.47 (s, 2H), 3.64 (d, J=11.7 Hz, 2H), 3.49-3.28 (m, 12H), 3.23 (d, J=13.7 Hz, 2H), 2.99 (s, 3H), 2.94 (q, J=7.7, 6.4 Hz, 2H), 2.45 (q, J=7.5, 6.3 Hz, 2H), 1.71-1.57 (m, 4H), 1.48-1.27 (m, 10H). HRMS (m/z) for C$_{39}$H$_{53}$F$_3$N$_7$O$_3$$^+$ [M+H]$^+$: calculated 724.4156. found 724.4119.

Intermediate 17 was synthesized following the standard procedures for preparing Intermediate 8 from intermediate 1 (33.3 mg, 0.06 mmol), 11-((tert-butoxycarbonyl)amino)undecanoic acid (18.2 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 17 (XF078-172) was obtained as white solid in TFA salt form (39.7 mg, yield 91%). $^1$H NMR (500 MHz, CD$_3$OD) δ 8.30 (d, J=2.1 Hz, 1H), 8.07 (d, J=4.9 Hz, 1H), 7.86-7.77 (m, 2H), 7.65-7.56 (m, 2H), 7.53 (d, J=7.4 Hz, 1H), 7.42 (d, J=8.4 Hz, 1H), 6.95 (s, 1H), 4.47 (s, 2H), 3.64 (d, J=11.7 Hz, 2H), 3.49-3.28 (m, 12H), 3.23 (d, J=13.7 Hz, 2H), 2.99 (s, 3H), 2.94 (q, J=7.7, 6.4 Hz, 2H), 2.45 (q, J=7.5, 6.3 Hz, 2H), 1.71-1.57 (m, 4H), 1.48-1.27 (m, 10H). HRMS (m/z) for C$_{40}$H$_{55}$F$_3$N$_7$O$_3$$^+$ [M+H]$^+$: calculated 738.4313. found 738.4324.

Example 68: Synthesis of Intermediate 19

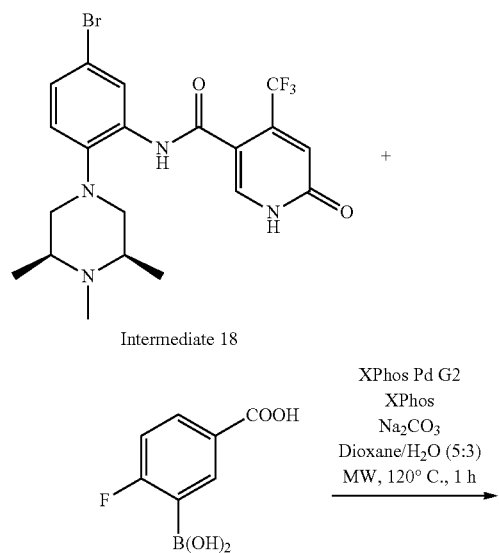

Intermediate 19

Example 69: Synthesis of Intermediate 20

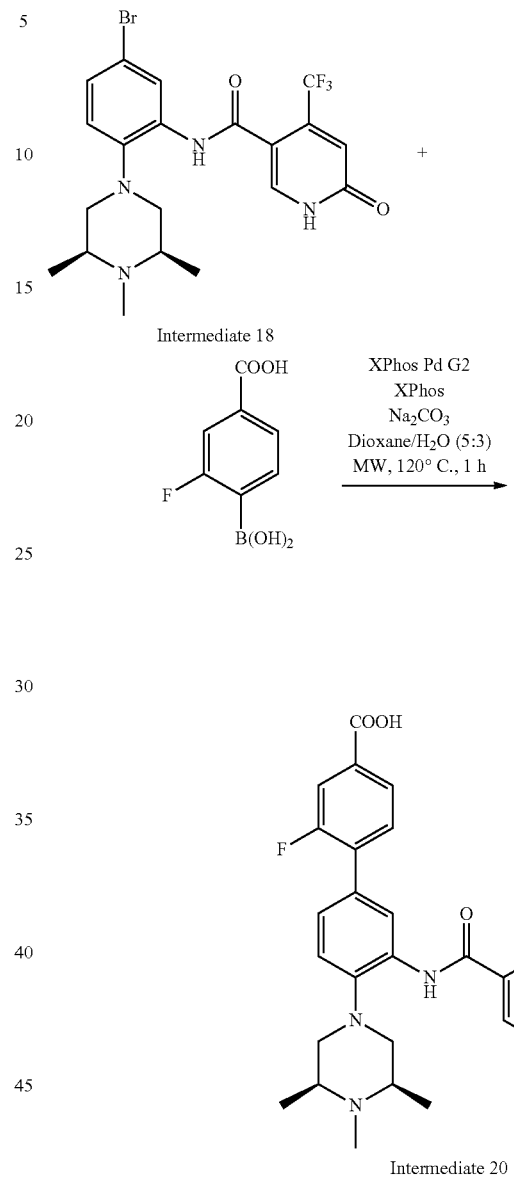

Intermediate 20

To a solution of Intermediate 18 (WO2017147701A1) (294 mg, 0.6 mmol) and 3-borono-4-fluorobenzoic acid (333 mg, 1.8 mmol, 3.0 euqiv) in 8 mL of 1,4-dioxane/H$_2$O (5:3) were added sodium carbonate (636 mg, 6 mmol, 10 equiv), XPhos (58 mg, 0.12 mmol, 0.2 equiv), and XPhos Pd G2 (95 mg, 0.12 mmol, 0.2 equiv). The reaction was heated to 120° C. for 1 h under Microwave. The solvent was removed and purified by reverse phase ISCO (10%-100% methanol/0.1% TFA in H$_2$O) to afford the Intermediate 19 (XF056-121) as white solid in TFA salt form (161.3 mg, yield 63%). $^1$H NMR (600 MHz, CD$_3$OD) δ 8.15 (dd, J=7.7, 2.3 Hz, 2H), 8.07-7.99 (m, 2H), 7.45 (dt, J=8.4, 1.8 Hz, 1H), 7.38 (d, J=8.3 Hz, 1H), 7.30 (dd, J=10.3, 8.6 Hz, 1H), 6.91 (s, 1H), 3.54 (ddp, J=13.0, 6.5, 3.2 Hz, 2H), 3.36-3.31 (m, 2H), 3.03-2.99 (m, 2H), 2.98 (s, 3H), 1.44 (d, J=6.5 Hz, 6H). HRMS (m/z) for C$_{27}$H$_{27}$F$_4$N$_4$O$_4^+$ [M+H]$^+$: calculated 547.1963, found 547.1938.

To a solution of Intermediate 18 (204 mg, 0.42 mmol) and 4-borono-4-fluorobenzoic acid (231 mg, 1.26 mmol, 3.0 euqiv) in 8 mL of 1,4-dioxane/H$_2$O (5:3) were added sodium carbonate (445 mg, 4.2 mmol, 10 equiv), XPhos (40 mg, 0.084 mmol, 0.2 equiv), and XPhos Pd G2 (66 mg, 0.084 mmol, 0.2 equiv). The reaction was heated to 120° C. for 1 h under Microwave. The solvent was removed and purified by reverse phase ISCO (10%-100% methanol/0.1% TFA in H$_2$O) to afford the Intermediate 20 (XF056-155) as white solid in TFA salt form (161.3 mg, yield 70%). $^1$H NMR (600 MHz, CD$_3$OD) δ 8.16 (s, 1H), 8.01 (s, 1H), 7.92 (dd, J=8.0, 1.6 Hz, 1H), 7.80 (d, J=10.9 Hz, 1H), 7.62 (t, J=7.9 Hz, 1H), 7.51 (d, J=8.7 Hz, 1H), 7.38 (d, J=8.4 Hz, 1H), 6.94 (s, 1H), 3.56-3.48 (m, 2H), 3.39-3.33 (m, 2H), 2.99 (s, 3H), 2.98-2.91 (m, 2H), 1.45 (d, J=6.5 Hz, 6H). HRMS (m/z) for C$_{27}$H$_{27}$F$_4$N$_4$O$_4^+$ [M+H]$^+$: calculated 547.1963. found 547.1966.

Example 70: Synthesis of XF056-124

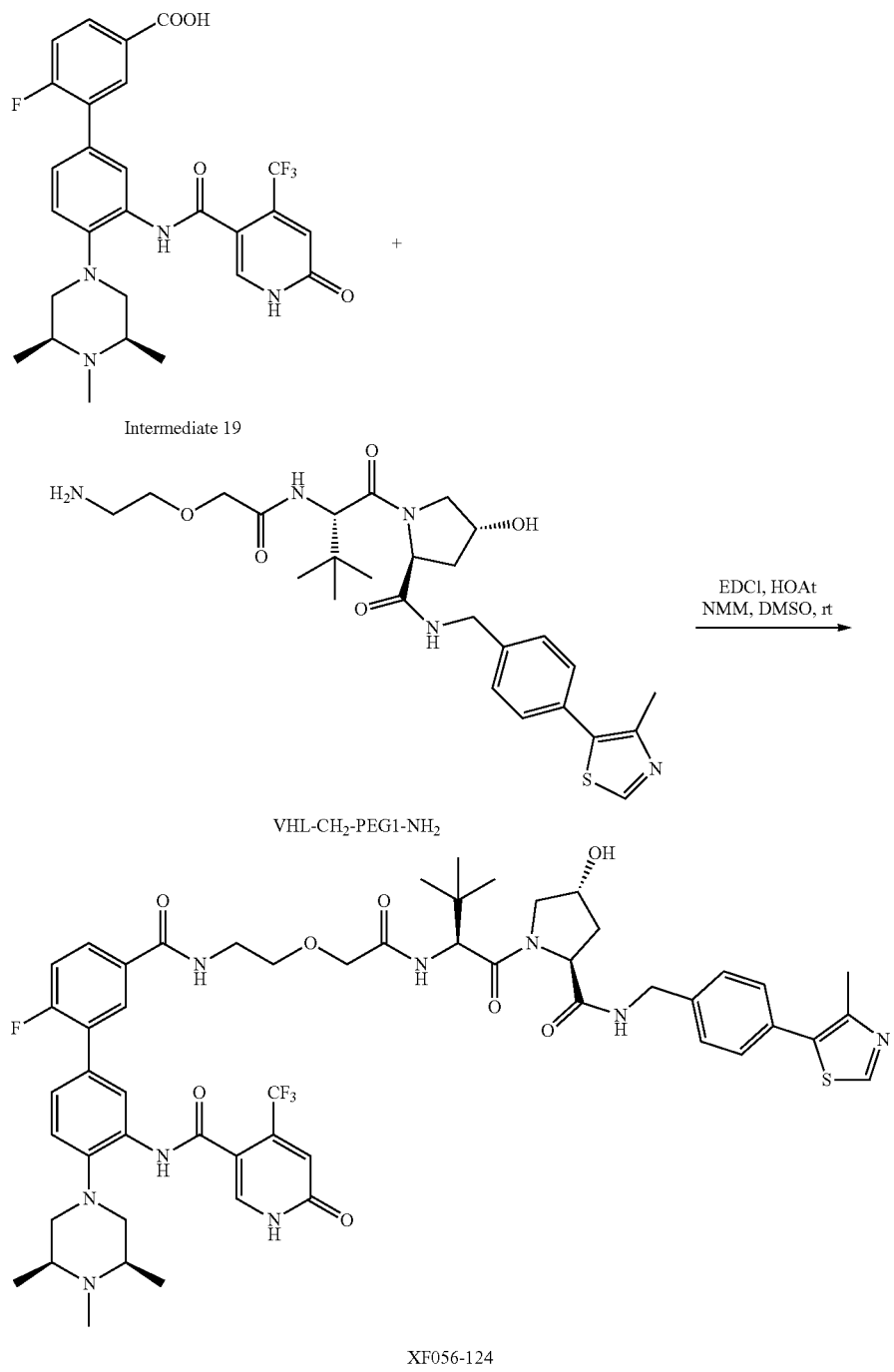 [SMILES: C[C@@H]1CN(c2ccc(-c3cc(C(=O)O)ccc3F)cc2NC(=O)c2c[nH]c(=O)cc2C(F)(F)F)C[C@H](C)N1C ; Cc1ncsc1-c1ccc(CNC(=O)[C@@H]2C[C@@H](O)CN2C(=O)[C@@H](NC(=O)COCCN)C(C)(C)C)cc1 ; Cc1ncsc1-c1ccc(CNC(=O)[C@@H]2C[C@@H](O)CN2C(=O)[C@@H](NC(=O)COCCNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1]

To the solution of intermediate 19 (11.9 mg, 0.022 mmol) in DMSO (1 mL) were added VHL-CH$_2$-PEG1-NH$_2$ (12.4 mg, 0.022 mmol, 1.0 equiv), EDCI (1-ethyl-3-(3-dimethyl-aminopropyl)carbodiimide) (6.3 mg, 0.033 mmol, 1.5 equiv), HOAt (1-hydroxy-7-azabenzo-triazole) (4.5 mg, 0.033 mmol, 1.5 equiv), and NMM (N-Methylmorpholine) (6.7 mg, 0.066 mmol, 3.0 equiv). After being stirring overnight at room temperature, the resulting mixture was purified by preparative HPLC (10%-100% methanol/0.1% TFA in H$_2$O) to afford XF056-124 as white solid in TFA salt form (15.1 mg, yield 65%). $^1$H NMR (600 MHz, CD$_3$OD) δ 8.93 (s, 1H), 8.14 (s, 1H), 8.05-7.99 (m, 2H), 7.94-7.87 (m, 1H), 7.49-7.34 (m, 6H), 7.28-7.18 (m, 1H), 6.92 (d, J=3.2 Hz, 1H), 4.68 (s, 1H), 4.59-4.47 (m, 3H), 4.36-4.30 (m, 1H), 4.13-4.00 (m, 2H), 3.88-3.82 (m, 1H), 3.79-3.67 (m, 5H), 3.64-3.57 (m, 2H), 3.55-3.46 (m, 2H), 3.38-3.30 (m, 2H), 2.98 (d, J=3.4 Hz, 3H), 2.44 (s, 3H), 2.24-2.18 (m, 1H), 2.07 (ddd, J=13.4, 9.4, 4.4 Hz, 1H), 1.47-1.39 (m, 6H), 0.97 (s, 9H). HRMS (m/z) for C$_{53}$H$_{62}$F$_4$N$_9$O$_8$S$^+$ [M+H]$^+$: calculated 1060.4373. found 1060.4389.

Example 71: Synthesis of XF056-125

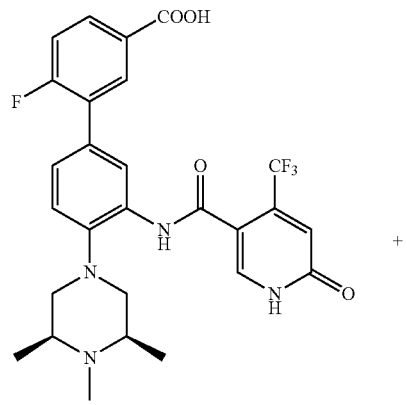

Intermediate 19

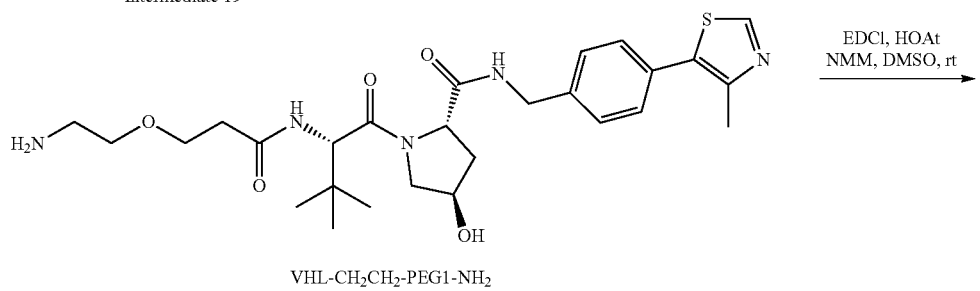

VHL-CH₂CH₂-PEG1-NH₂

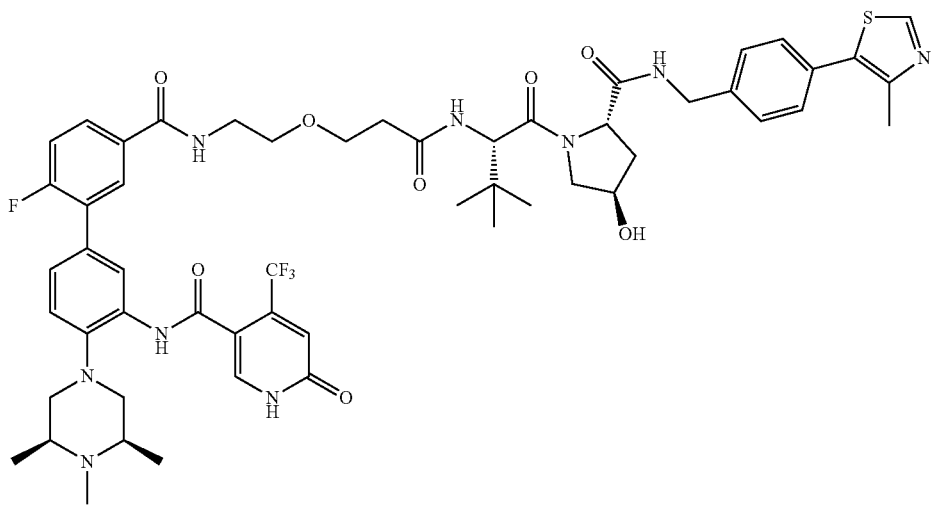

XF056-125

XF056-125 was synthesized following the standard procedures for preparing XF056-124 from intermediate 19 (11.9 mg, 0.022 mmol), VHL-CH₂CH₂-PEG1-NH₂ (17 mg, 0.022 mmol, 1.0 equiv), EDCI (6.3 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). XF056-125 was obtained as white solid in TFA salt form (17.7 mg, yield 75%). $^1$H NMR (600 MHz, CD$_3$OD) δ 8.94 (d, J=1.2 Hz, 1H), 8.15 (s, 1H), 8.00 (d, J=7.3 Hz, 2H), 7.91-7.82 (m, 1H), 7.52-7.33 (m, 6H), 7.26 (dd, J=10.3, 8.6 Hz, 1H), 6.92 (s, 1H), 4.62 (s, 1H), 4.56 (dd, J=9.4, 7.3 Hz, 1H), 4.50-4.41 (m, 2H), 4.32 (d, J=15.5 Hz, 1H), 3.86 (d, J=10.9 Hz, 1H), 3.81-3.74 (m, 2H), 3.74-3.69 (m, 1H), 3.69-3.59 (m, 3H), 3.58-3.49 (m, 3H), 3.37-3.32 (m, 2H), 2.98 (s, 5H), 2.56-2.49 (m, 2H), 2.44 (d, J=1.2 Hz, 3H), 2.21 (dd, J=13.1, 7.7 Hz, 1H), 2.11-2.03 (m, 1H), 1.44 (d, J=6.5 Hz, 6H), 0.97 (s, 9H). HRMS (m/z) for $C_{54}H_{64}F_4N_9O_8S^+$ [M+H]$^+$: calculated 1074.4529. found 1074.4576.

Example 72: Synthesis of XF056-126

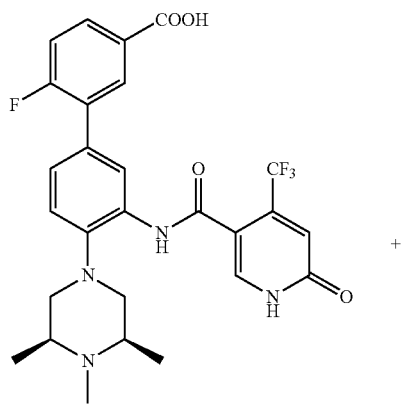

Intermediate 19

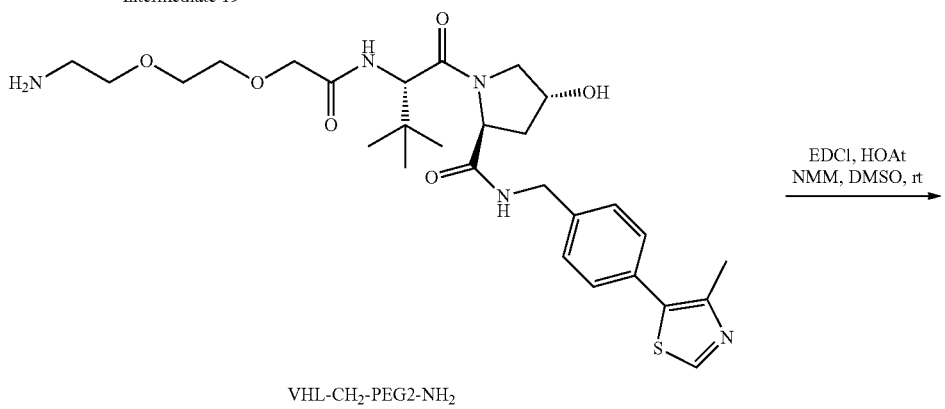

VHL-CH$_2$-PEG2-NH$_2$

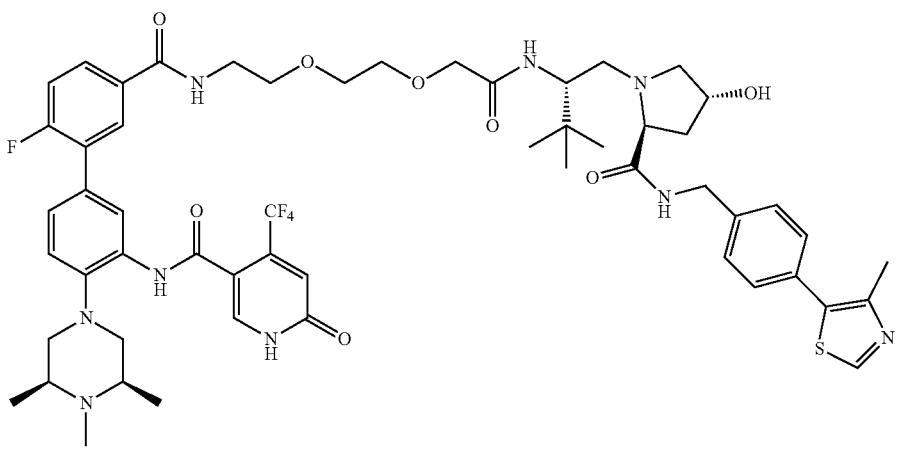

XF056-126

XF056-126 was synthesized following the standard procedures for preparing XF056-124 from intermediate 19 (11.9 mg, 0.022 mmol), VHL-CH$_2$-PEG2-NH$_2$ (13.5 mg, 0.022 mmol, 1.0 equiv), EDCI (6.3 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). XF056-126 was obtained as white solid in TFA salt form (21.8 mg, yield 90%). $^1$H NMR (600 MHz, CD$_3$OD) δ 8.95 (s, 1H), 8.14 (s, 1H), 8.01 (s, 1H), 7.94 (dd, J=7.5, 2.4 Hz, 1H), 7.88-7.79 (m, 1H), 7.54-7.33 (m, 6H), 7.32-7.19 (m, 1H), 6.92 (s, 1H), 4.72 (s, 1H), 4.54-4.45 (m, 3H), 4.28 (d, J=15.5 Hz, 1H), 4.05-3.88 (m, 2H), 3.84-3.77 (m, 1H), 3.73-3.63 (m, 6H), 3.61-3.50 (m, 5H), 3.36-3.32 (m, 4H), 2.98 (s, 3H), 2.46 (s, 3H), 2.26-2.15 (m, 1H), 2.13-1.99 (m, 1H), 1.44 (d, J=6.4 Hz, 6H), 1.01 (s, 9H). HRMS (m/z) for C$_{55}$H$_{66}$F$_4$N$_9$O$_9$S$^+$ [M+H]$^+$: calculated 1104.4635. found 1104.4599.

Example 73: Synthesis of XF056-127

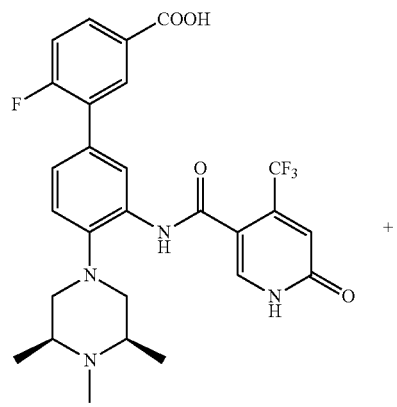

Intermediate 19

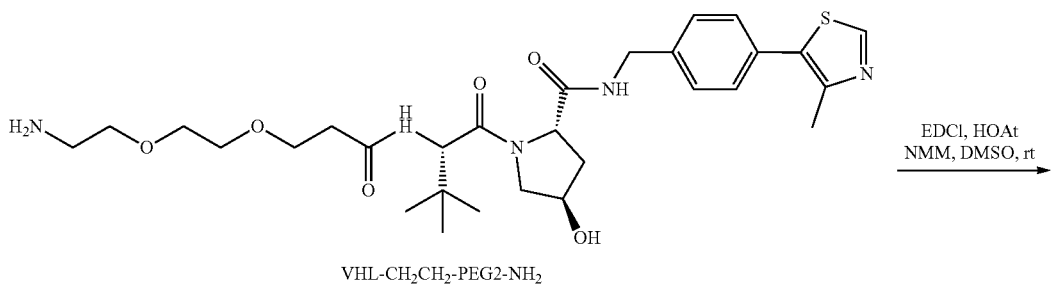

VHL-CH₂CH₂-PEG2-NH₂

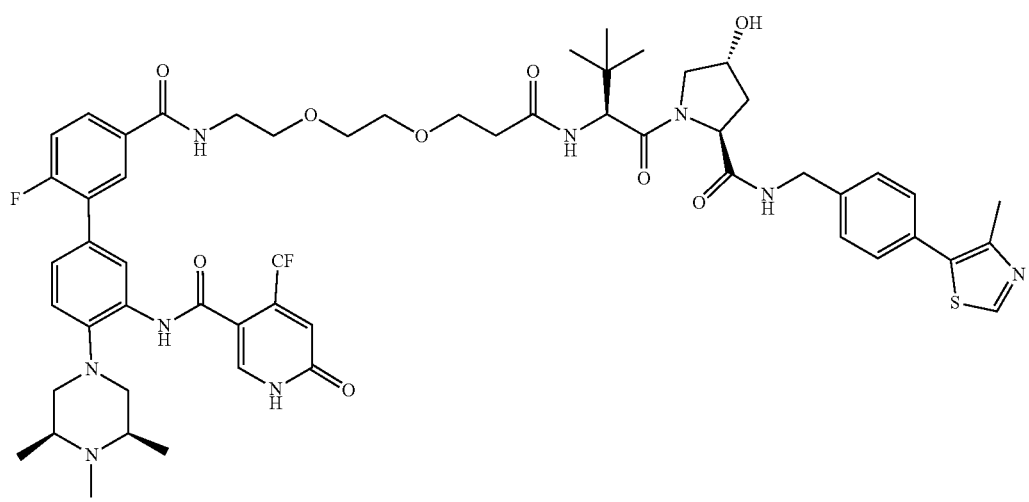

XF056-127

XF056-127 was synthesized following the standard procedures for preparing XF056-124 from intermediate 19 (11.9 mg, 0.022 mmol), VHL-CH₂CH₂-PEG2-NH₂ (17.9 mg, 0.022 mmol, 1.0 equiv), EDCI (6.3 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). XF056-127 was obtained as white solid in TFA salt form (22.8 mg, yield 92%). $^1$H NMR (600 MHz, CD$_3$OD) δ 8.97 (s, 1H), 8.15 (d, J=2.0 Hz, 1H), 8.06-7.90 (m, 2H), 7.84 (ddd, J=8.5, 4.5, 2.3 Hz, 1H), 7.51-7.40 (m, 3H), 7.40-7.32 (m, 3H), 7.27 (dd, J=10.3, 8.6 Hz, 1H), 6.92 (s, 1H), 4.63 (s, 1H), 4.59-4.45 (m, 3H), 4.33 (d, J=15.5 Hz, 1H), 3.91-3.83 (m, 1H), 3.78 (dd, J=10.9, 3.9 Hz, 1H), 3.74-3.47 (m, 12H), 3.36-3.30 (m, 2H), 3.02-2.92 (m, 5H), 2.53-2.38 (m, 5H), 2.23-2.17 (m, 1H), 2.10-2.01 (m, 1H), 1.44 (d, J=6.5 Hz, 6H), 1.00 (s, 9H). HRMS (m/z) for $C_{56}H_{68}F_4N_9O_9S^+$ [M+H]$^+$: calculated 1118.4791. found 1118.4823.

Example 74: Synthesis of XF056-128

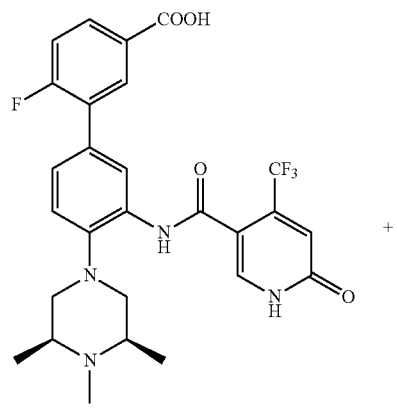

Intermediate 19

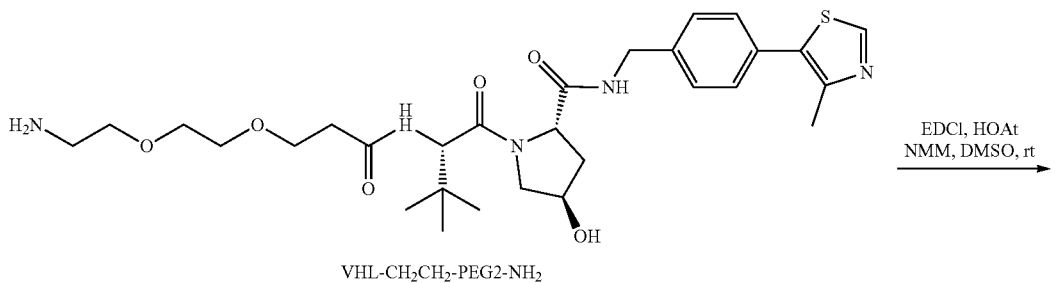

VHL-CH₂CH₂-PEG2-NH₂

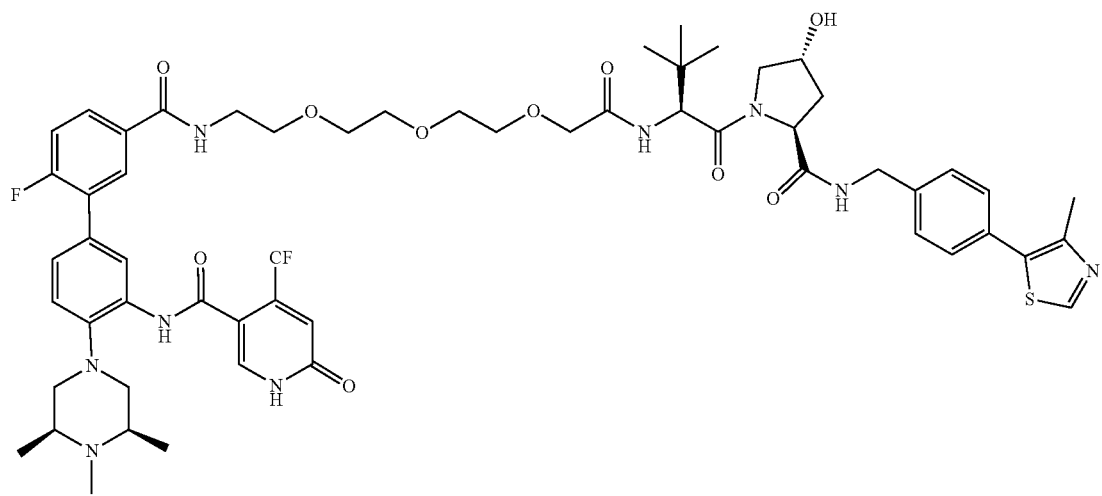

XF056-127

XF056-128 was synthesized following the standard procedures for preparing XF056-124 from intermediate 19 (13 mg, 0.024 mmol), VHL-CH$_2$-PEG3-NH$_2$ (20.3 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-128 was obtained as white solid in TFA salt form (17.4 mg, yield 63%). $^1$H NMR (600 MHz, CD$_3$OD) δ 8.95 (s, 1H), 8.15 (d, J=2.1 Hz, 1H), 8.06-7.93 (m, 2H), 7.89-7.76 (m, 1H), 7.52-7.32 (m, 6H), 7.31-7.23 (m, 1H), 6.92 (s, 1H), 4.67 (s, 1H), 4.61-4.45 (m, 3H), 4.34 (d, J=15.5 Hz, 1H), 4.01-3.89 (m, 2H), 3.88-3.74 (m, 2H), 3.69-3.47 (m, 14H), 3.36-3.34 (m, 1H), 3.33-3.32 (m, 1H), 3.09-2.92 (m, 5H), 2.46 (s, 3H), 2.28-2.16 (m, 1H), 2.13-2.02 (m, 1H), 1.44 (d, J=6.5 Hz, 6H), 1.01 (s, 9H). HRMS (m/z) for $C_{57}H_{70}F_4N_9O_{10}S^+$ [M+H]$^+$: calculated 1148.4897. found 1148.4917.

Example 75: Synthesis of XF056-129

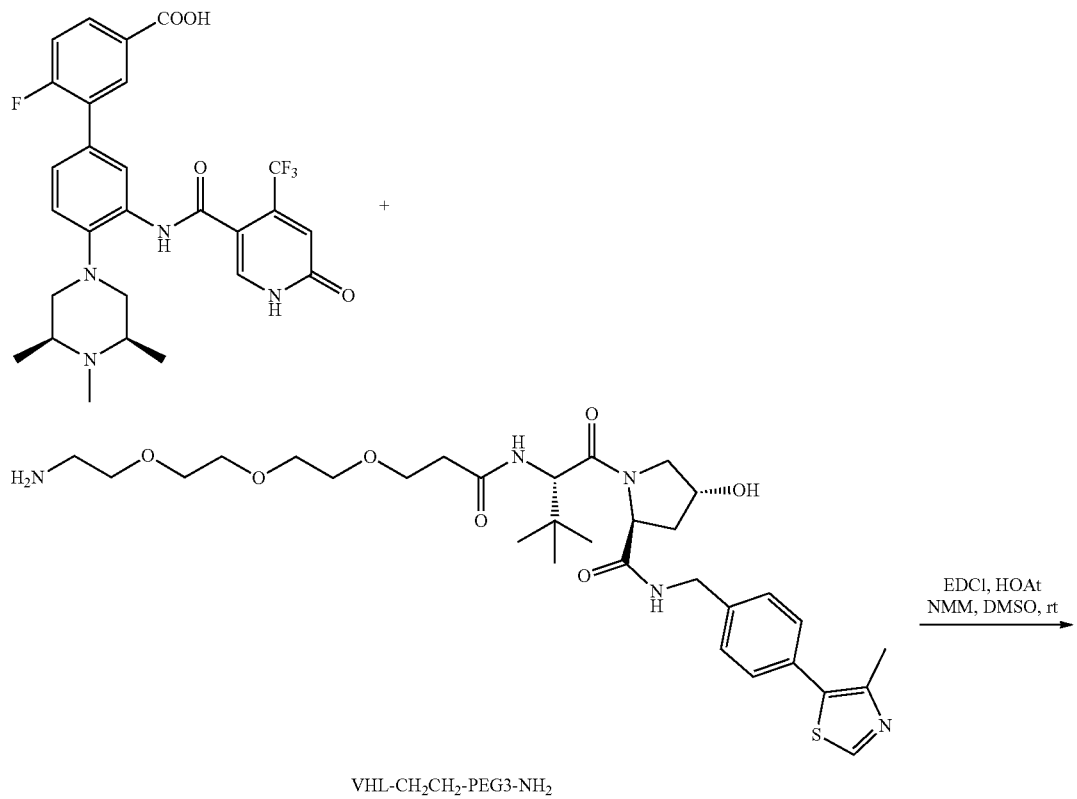

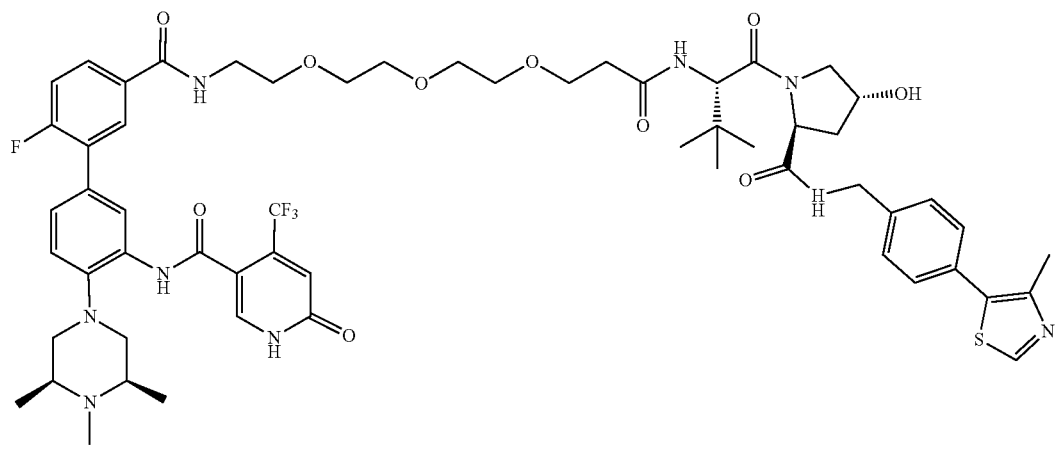

XF056-129

XF056-129 was synthesized following the standard procedures for preparing XF056-124 from intermediate 19 (13 mg, 0.024 mmol), VHL-CH$_2$CH$_2$-PEG3-NH$_2$ (20.7 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-129 was obtained as white solid in TFA salt form (11.7 mg, yield 42%). $^1$H NMR (600 MHz, CD$_3$OD) δ 8.97 (s, 1H), 8.15 (s, 1H), 8.07-7.94 (m, 2H), 7.85 (ddd, J=8.5, 4.5, 2.4 Hz, 1H), 7.53-7.32 (m, 6H), 7.28 (dd, J=10.3, 8.6 Hz, 1H), 6.92 (s, 1H), 4.62 (s, 1H), 4.58-4.45 (m, 3H), 4.34 (d, J=15.5 Hz, 1H), 3.86 (d, J=11.0 Hz, 1H), 3.77 (dd, J=11.0, 3.9 Hz, 1H), 3.71-3.49 (m, 16H), 3.37-3.31 (m, 2H), 2.98 (s, 5H), 2.54-2.38 (m, 5H), 2.24-2.17 (m, 1H), 2.09-2.03 (m, 1H), 1.43 (d, J=6.5 Hz, 6H), 1.00 (s, 9H). HRMS (m/z) for C$_{58}$H$_{72}$F$_4$N$_9$O$_{10}$S$^+$ [M+H]$^+$: calculated 1162.5053. found 1162.5043.

Example 76: Synthesis of XF056-130

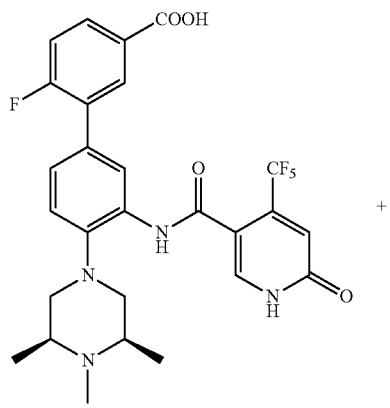

Intermediate 19

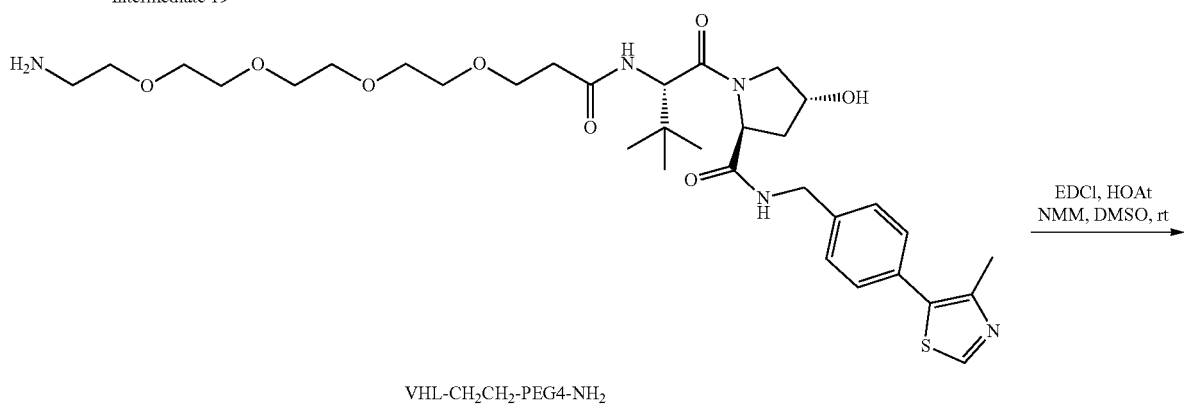

VHL-CH₂CH₂-PEG4-NH₂

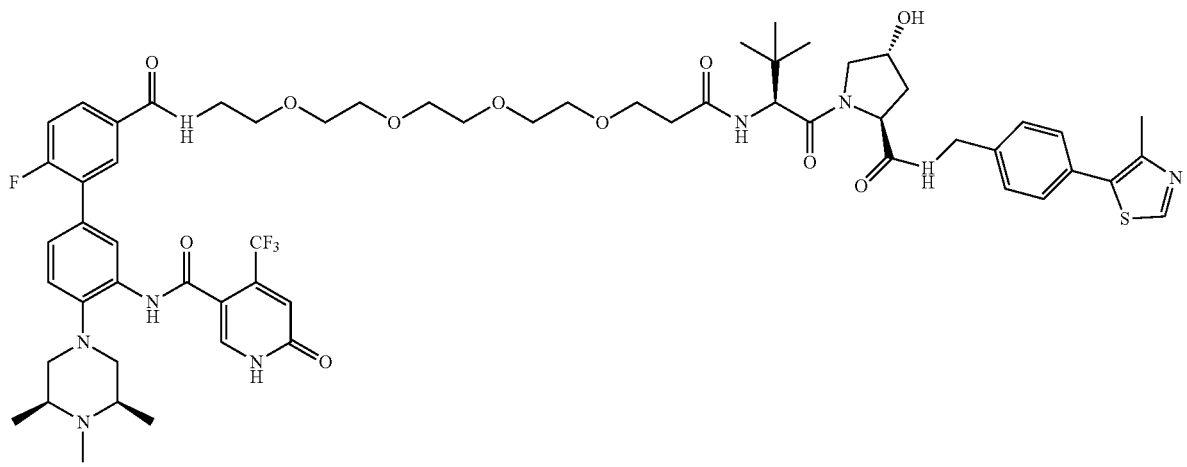

XF056-130

XF056-130 was synthesized following the standard procedures for preparing XF056-124 from intermediate 19 (13 mg, 0.024 mmol), VHL-CH₂CH₂-PEG4-NH₂ (17.1 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-130 was obtained as white solid in TFA salt form (22.6 mg, yield 78%). $^1$H NMR (600 MHz, CD$_3$OD) δ 9.03 (s, 1H), 8.16 (d, J=1.9 Hz, 1H), 8.05-7.94 (m, 2H), 7.93-7.80 (m, 1H), 7.54-7.35 (m, 6H), 7.29 (dd, J=10.3, 8.6 Hz, 1H), 6.92 (s, 1H), 4.63 (s, 1H), 4.60-4.46 (m, 3H), 4.35 (d, J=15.5 Hz, 1H), 3.92-3.84 (m, 1H), 3.78 (dd, J=11.0, 3.9 Hz, 1H), 3.74-3.47 (m, 20H), 3.38-3.30 (m, 2H), 3.05-2.91 (m, 5H), 2.58-2.50 (m, 1H), 2.50-2.39 (m, 4H), 2.21 (ddt, J=13.0, 7.5, 1.9 Hz, 1H), 2.07 (ddd, J=13.3, 9.2, 4.4 Hz, 1H), 1.44 (d, J=6.5 Hz, 6H), 1.01 (s, 9H). HRMS (m/z) for C$_{60}$H$_{76}$F$_4$N$_9$O$^{11}$S$^+$ [M+H]$^+$: calculated 1206.5316. found 1206.5287.

Example 77: Synthesis of XF056-131

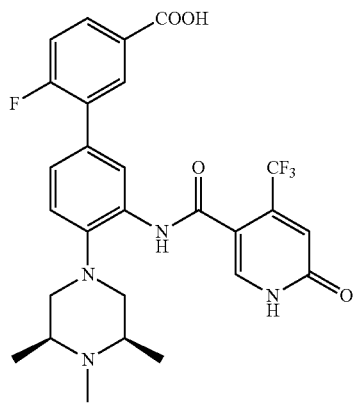

Intermediate 19

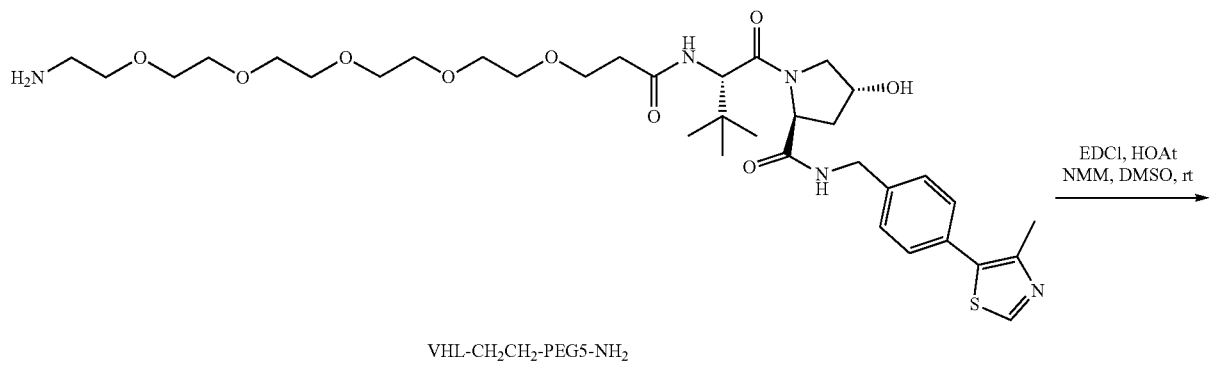

VHL-CH₂CH₂-PEG5-NH₂

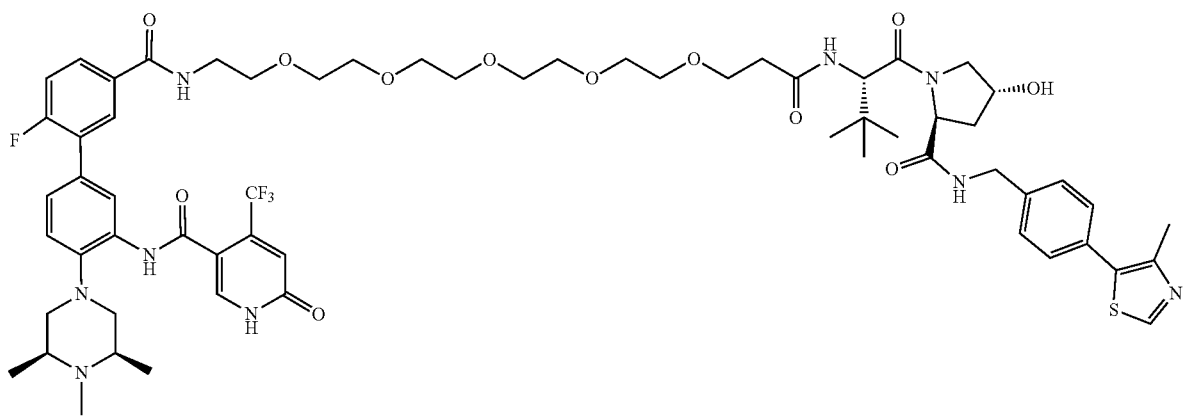

XF056-131

XF056-131 was synthesized following the standard procedures for preparing XF056-124 from intermediate 19 (13 mg, 0.022 mmol), VHL-CH₂CH₂-PEG5-NH₂ (22.8 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-131 was obtained as white solid in TFA salt form (15.3 mg, yield 51%). $^1$H NMR (600 MHz, CD$_3$OD) δ 9.02 (s, 1H), 8.16 (d, J=1.9 Hz, 1H), 8.06-7.97 (m, 2H), 7.93-7.82 (m, 1H), 7.54-7.36 (m, 6H), 7.29 (dd, J=10.3, 8.6 Hz, 1H), 6.93 (s, 1H), 4.63 (s, 1H), 4.60-4.45 (m, 3H), 4.35 (d, J=15.5 Hz, 1H), 3.87 (d, J=11.2 Hz, 1H), 3.78 (dd, J=11.0, 3.9 Hz, 1H), 3.74-3.48 (m, 24H), 3.38-3.32 (m, 2H), 2.98 (d, J=3.0 Hz, 5H), 2.59-2.51 (m, 1H), 2.51-2.41 (m, 4H), 2.24-2.16 (m, 1H), 2.11-2.03 (m, 1H), 1.44 (d, J=6.5 Hz, 6H), 1.02 (s, 9H). HRMS (m/z) for $C_{62}H_{80}F_4N_9O_{12}S^+$ [M+H]$^+$: calculated 1250.5578. found 1250.5534.

Example 78: Synthesis of XF056-132

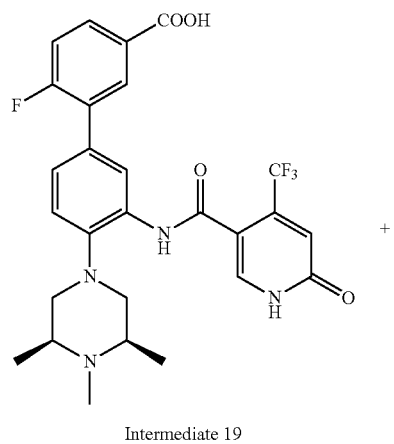

Intermediate 19

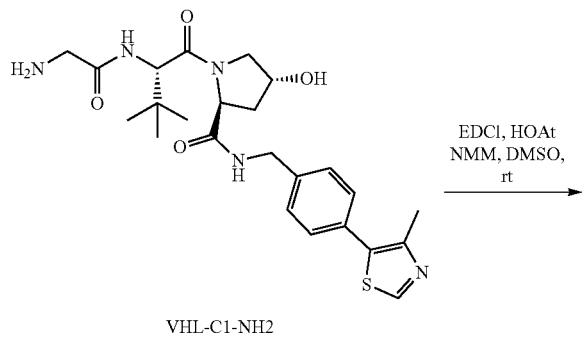

VHL-C1-NH2

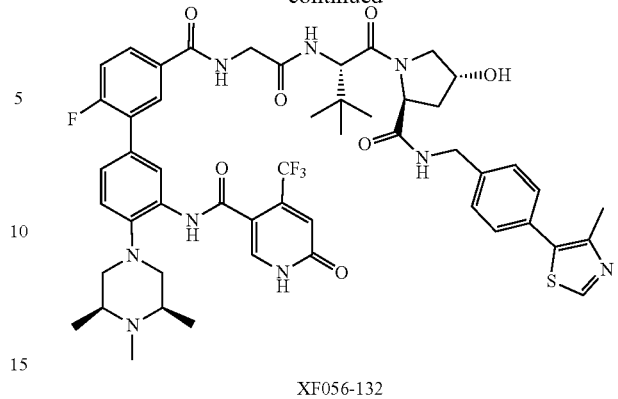

XF056-132

XF056-132 was synthesized following the standard procedures for preparing XF056-124 from intermediate 19 (13 mg, 0.024 mmol), VHL-C1-NH$_2$ (17.2 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-132 was obtained as white solid in TFA salt form (21.2 mg, yield 89%). $^1$H NMR (600 MHz, CD$_3$OD) δ 8.99 (s, 1H), 8.15 (s, 1H), 8.09-7.97 (m, 2H), 7.96-7.83 (m, 1H), 7.53-7.22 (m, 7H), 6.91 (s, 1H), 4.66 (s, 1H), 4.62-4.45 (m, 3H), 4.34 (d, J=15.5 Hz, 1H), 4.18-4.03 (m, 2H), 3.89 (d, J=11.2 Hz, 1H), 3.79 (dd, J=11.0, 3.8 Hz, 1H), 3.58-3.48 (m, 2H), 3.37-3.30 (m, 2H), 3.03-2.93 (m, 5H), 2.46 (s, 3H), 2.26-2.18 (m, 1H), 2.12-2.01 (m, 1H), 1.44 (d, J=6.5 Hz, 6H), 1.04 (s, 9H). HRMS (m/z) for C$_{51}$H$_{58}$F$_4$N$_9$O$_7$S$^+$ [M+H]$^+$: calculated 1016.4111. found 1016.4156.

Example 79: Synthesis of XF056-133

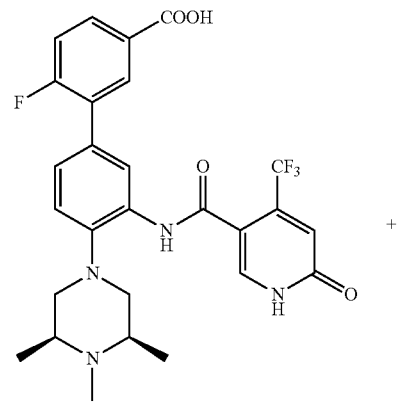

Intermediate 19

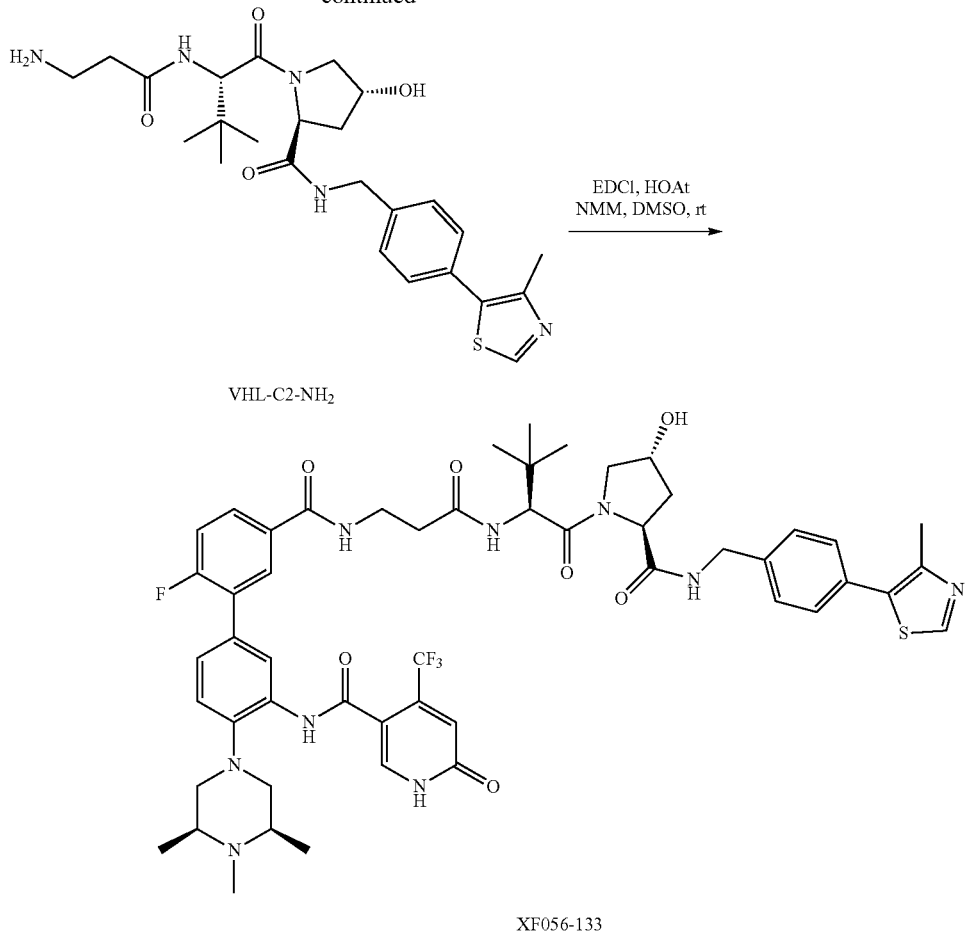

VHL-C2-NH₂

XF056-133

XF056-133 was synthesized following the standard procedures for preparing XF056-124 from intermediate 19 (13 mg, 0.024 mmol), VHL-C2-NH₂ (17.5 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-133 was obtained as white solid in TFA salt form (19 mg, yield 77%). ¹H NMR (600 MHz, CD₃OD) δ 8.96 (s, 1H), 8.14 (s, 1H), 8.07-7.93 (m, 2H), 7.89-7.77 (m, 1H), 7.50-7.24 (m, 7H), 6.92 (s, 1H), 4.61 (s, 1H), 4.58-4.46 (m, 3H), 4.33 (d, J=15.5 Hz, 1H), 3.92 (d, J=11.2 Hz, 1H), 3.78 (dd, J=10.9, 3.9 Hz, 1H), 3.68 (dt, J=13.6, 6.8 Hz, 1H), 3.65-3.58 (m, 1H), 3.53 (q, J=7.6, 5.4 Hz, 2H), 3.37-3.32 (m, 2H), 2.98 (d, J=5.2 Hz, 5H), 2.67-2.54 (m, 2H), 2.46 (s, 3H), 2.23-2.16 (m, 1H), 2.09-2.02 (m, 1H), 1.44 (d, J=6.5 Hz, 6H), 1.00 (s, 9H). HRMS (m/z) for $C_{52}H_{60}F_4N_9O_7S^+$ [M+H]⁺: calculated 1030.4267, found 1030.4276.

Example 80: Synthesis of XF056-134

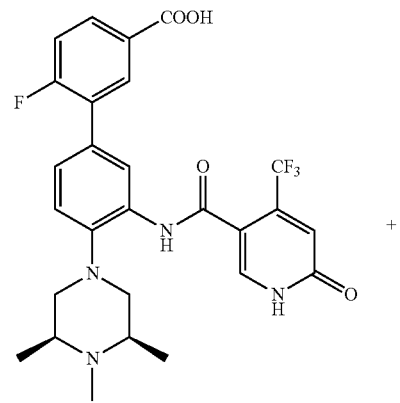

Intermediate 19

+

-continued

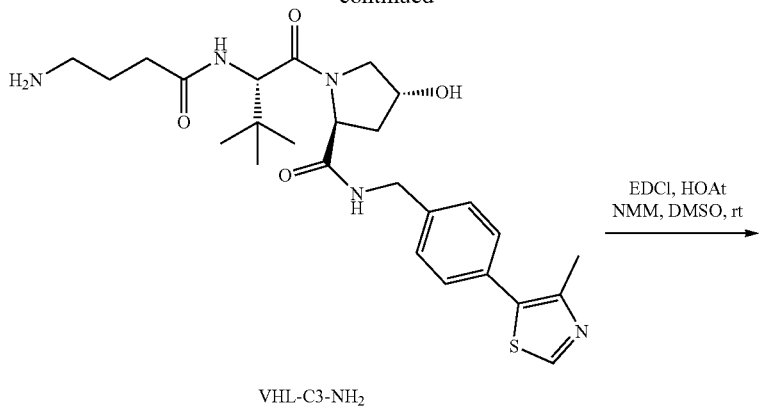

VHL-C3-NH₂

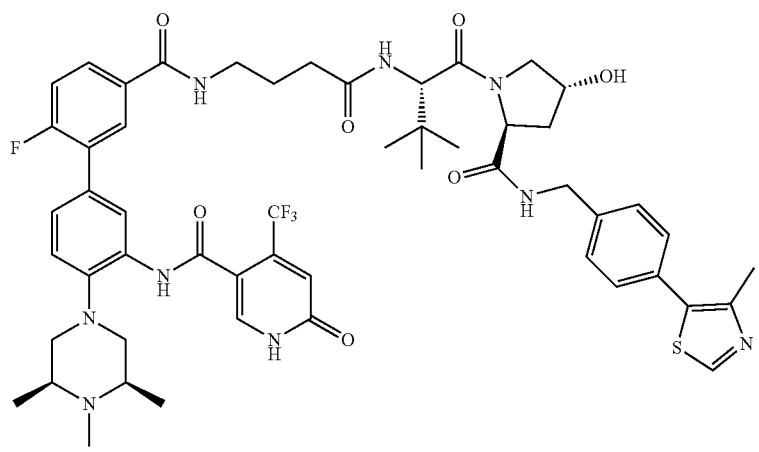

XF056-134

XF056-134 was synthesized following the standard procedures for preparing XF056-124 from intermediate 19 (13 mg, 0.024 mmol), VHL-C3-NH₂ (17.8 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-134 was obtained as white solid in TFA salt form (18.7 mg, yield 75%). $^1$H NMR (600 MHz, CD₃OD) δ 9.02 (s, 1H), 8.25-8.09 (m, 1H), 8.09-7.92 (m, 2H), 7.86 (ddd, J=8.5, 4.5, 2.4 Hz, 1H), 7.55-7.34 (m, 6H), 7.29 (dd, J=10.2, 8.6 Hz, 1H), 6.92 (s, 1H), 4.64-4.43 (m, 4H), 4.35 (d, J=15.5 Hz, 1H), 3.90 (d, J=11.0 Hz, 1H), 3.78 (dd, J=11.0, 4.0 Hz, 1H), 3.60-3.50 (m, 2H), 3.41 (h, J=6.7 Hz, 2H), 3.35-3.32 (m, 2H), 2.98 (s, 5H), 2.47 (s, 3H), 2.43-2.31 (m, 2H), 2.23-2.16 (m, 1H), 2.12-2.03 (m, 1H), 1.99-1.85 (m, 2H), 1.44 (d, J=6.5 Hz, 6H), 1.03 (s, 9H). HRMS (m/z) for $C_{53}H_{62}F_4N_9O_7S^+$ [M+H]$^+$: calculated 1044.4424. found 1044.4445.

Example 81: Synthesis of XF056-135

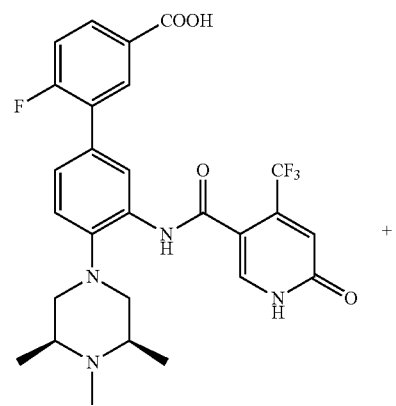

Intermediate 19

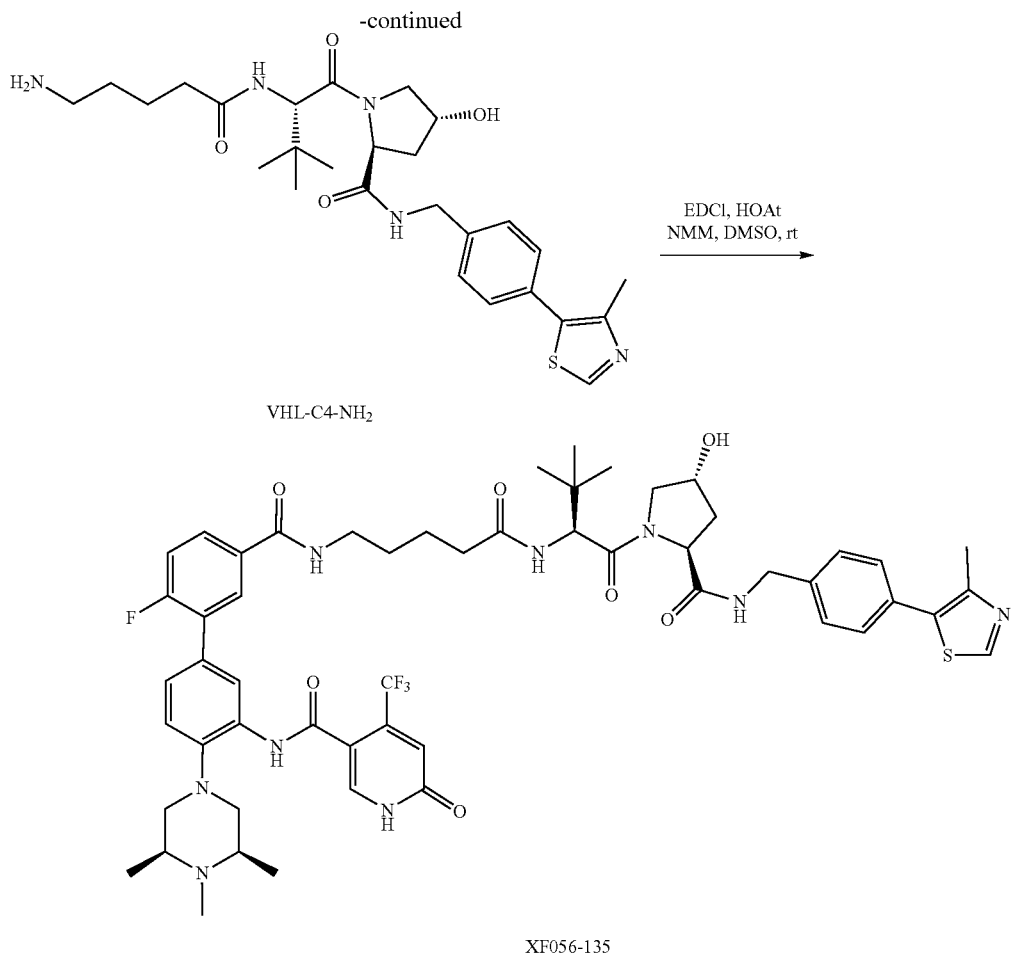

VHL-C4-NH₂

XF056-135

XF056-135 was synthesized following the standard procedures for preparing XF056-124 from intermediate 19 (13 mg, 0.024 mmol), VHL-C4-NH₂ (13.6 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-135 was obtained as white solid in TFA salt form (8.1 mg, yield 32%). ¹H NMR (600 MHz, CD₃OD) δ 8.96 (s, 1H), 8.15 (s, 1H), 8.05-7.93 (m, 2H), 7.88-7.82 (m, 1H), 7.55-7.22 (m, 7H), 6.93 (s, 1H), 4.63-4.41 (m, 4H), 4.34 (d, J=15.5 Hz, 1H), 3.89 (d, J=11.0 Hz, 1H), 3.78 (dd, J=10.9, 3.9 Hz, 1H), 3.52 (d, J=6.9 Hz, 2H), 3.40 (t, J=6.7 Hz, 2H), 3.33 (t, J=10.9 Hz, 2H), 2.98 (d, J=7.6 Hz, 5H), 2.47 (s, 3H), 2.39-2.27 (m, 2H), 2.20 (dd, J=13.2, 7.5 Hz, 1H), 2.13-2.03 (m, 1H), 1.75-1.60 (m, 4H), 1.44 (d, J=6.5 Hz, 6H), 1.02 (s, 9H). HRMS (m/z) for C₅₄H₆₄F₄N₉O₇S⁺ [M+H]⁺: calculated 1058.4580. found 1058.4565.

Example 82: Synthesis of XF056-136

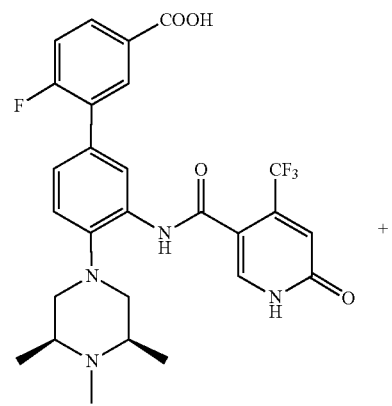

Intermediate 19

-continued

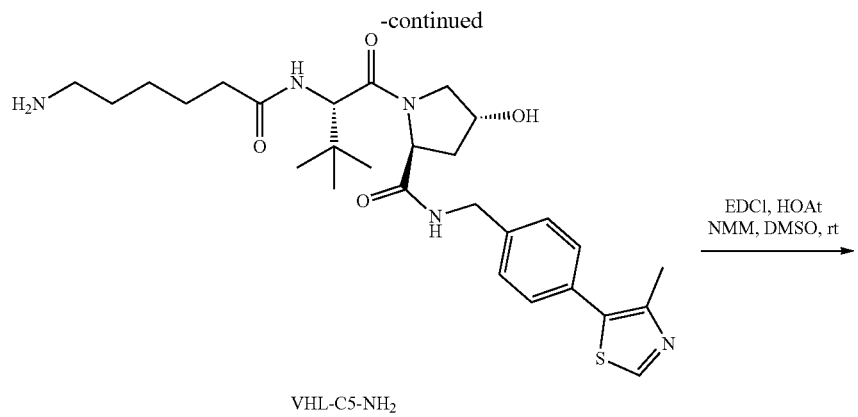

VHL-C5-NH₂

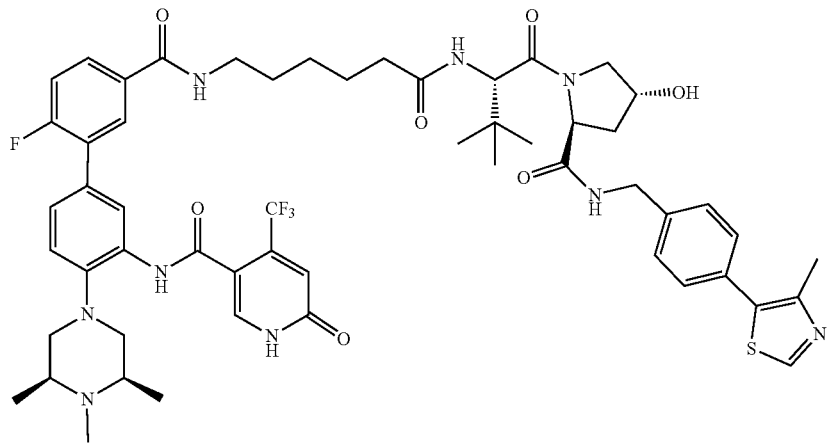

XF056-136 was synthesized following the standard procedures for preparing XF056-124 from intermediate 19 (13 mg, 0.024 mmol), VHL-C5-NH₂ (13.9 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-136 was obtained as white solid in TFA salt form (15.9 mg, yield 63%). ¹H NMR (600 MHz, CD₃OD) δ 8.99 (s, 1H), 8.15 (s, 1H), 8.03-7.95 (m, 2H), 7.88-7.70 (m, 1H), 7.64-7.35 (m, 6H), 7.28 (dd, J=10.2, 8.6 Hz, 1H), 6.92 (s, 1H), 4.63-4.44 (m, 4H), 4.34 (d, J=15.5 Hz, 1H), 3.89 (dd, J=11.1, 2.1 Hz, 1H), 3.78 (dd, J=11.0, 3.9 Hz, 1H), 3.60-3.48 (m, 2H), 3.42-3.37 (m, 2H), 3.34-3.30 (m, 2H), 3.06-2.93 (m, 5H), 2.47 (s, 3H), 2.36-2.25 (m, 2H), 2.21 (ddt, J=13.2, 7.7, 2.0 Hz, 1H), 2.13-2.02 (m, 1H), 1.72-1.56 (m, 4H), 1.48-1.34 (m, 8H), 1.00 (s, 9H). HRMS (m/z) for $C_{55}H_{66}F_4N_9O_7S^+$ [M+H]⁺: calculated 1072.4737. found 1072.4713.

Example 83: Synthesis of XF056-137

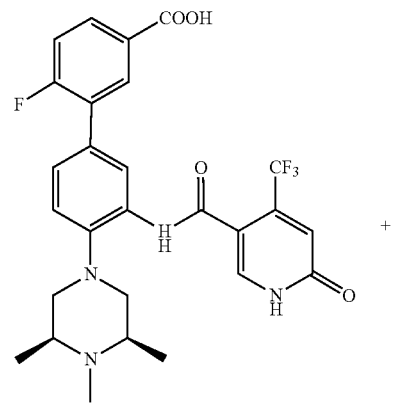

Intermediate 19

+

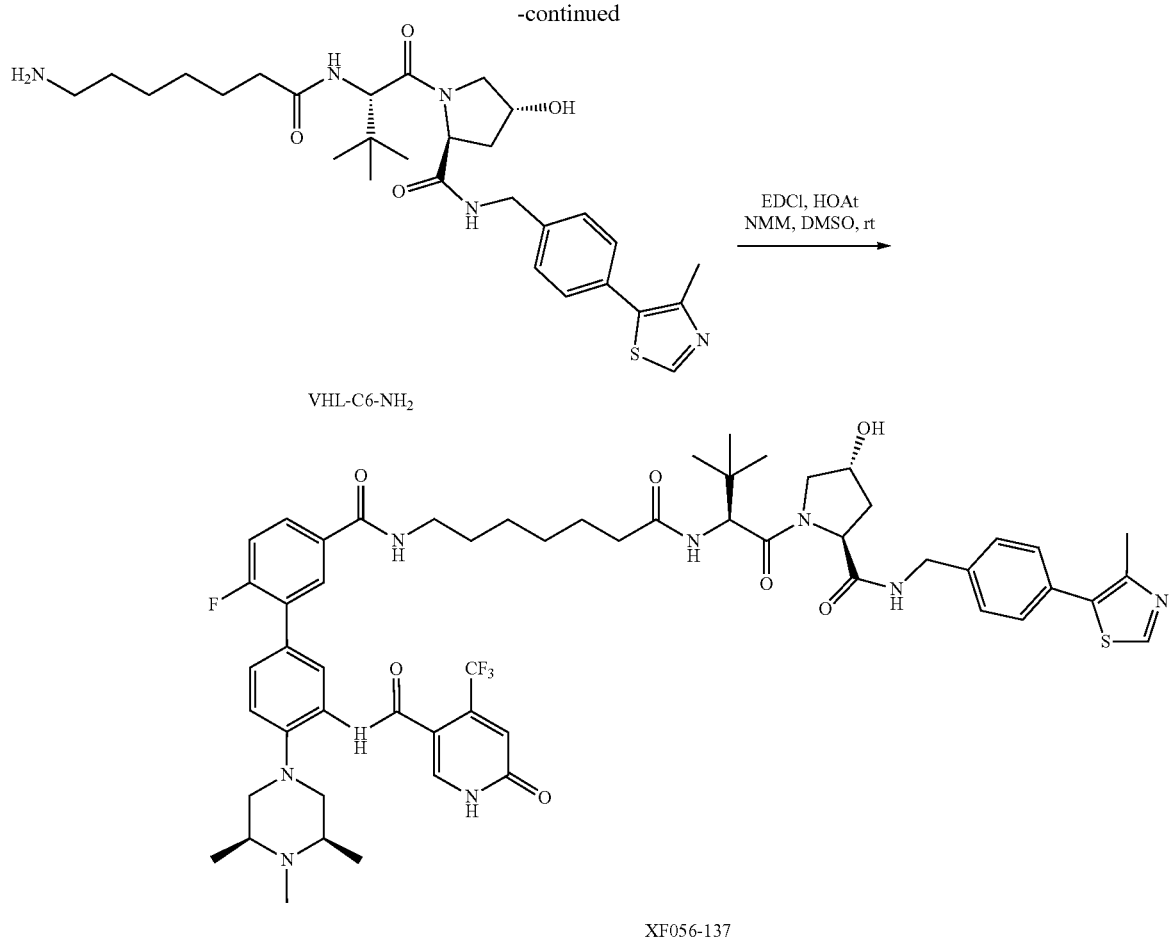

VHL-C6-NH₂

XF056-137

XF056-137 was synthesized following the standard procedures for preparing XF056-124 from intermediate 19 (13 mg, 0.024 mmol), VHL-C6-NH₂ (14.3 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-137 was obtained as white solid in TFA salt form (12.6 mg, yield 48%). ¹H NMR (600 MHz, CD₃OD) δ 8.97 (s, 1H), 8.14 (s, 1H), 8.01 (s, 1H), 7.96 (dd, J=7.4, 2.4 Hz, 1H), 7.86-7.80 (m, 1H), 7.49-7.41 (m, 3H), 7.43-7.35 (m, 3H), 7.27 (dd, J=10.3, 8.5 Hz, 1H), 6.93 (s, 1H), 4.62 (s, 1H), 4.60-4.46 (m, 3H), 4.34 (d, J=15.5 Hz, 1H), 3.90 (d, J=11.0 Hz, 1H), 3.79 (dd, J=11.0, 3.9 Hz, 1H), 3.53-3.50 (m, 2H), 3.42-3.30 (m, 4H), 3.04-2.93 (m, 5H), 2.47 (s, 3H), 2.33-2.17 (m, 3H), 2.07 (ddd, J=13.2, 9.2, 4.4 Hz, 1H), 1.66-1.60 (m, 4H), 1.55-1.30 (m, 10H), 1.00 (s, 9H). HRMS (m/z) for $C_{56}H_{68}F_4N_9O_7S^+$ [M+H]⁺: calculated 1086.4893. found 1086.4910.

Example 84: Synthesis of XF056-138

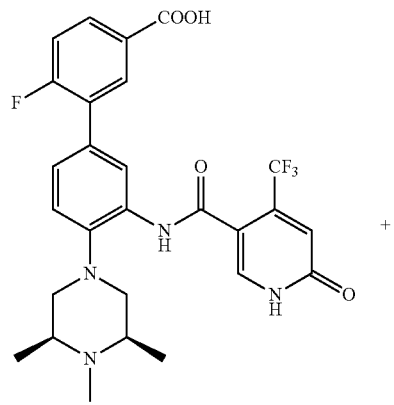

Intermediate 19

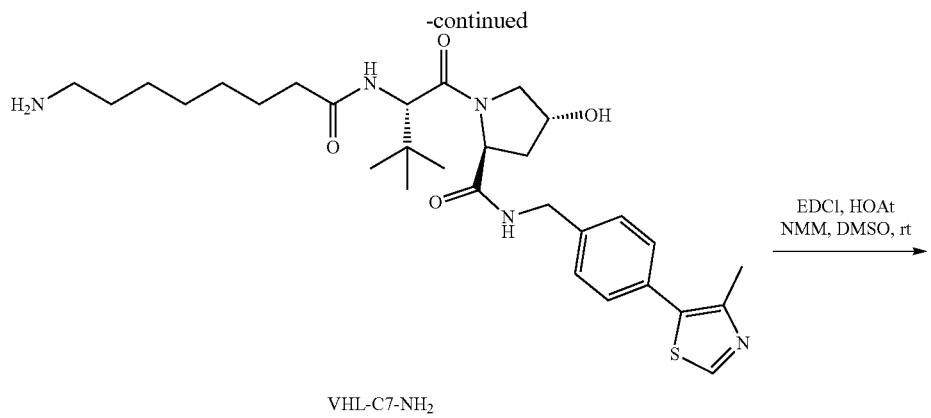

VHL-C7-NH₂

EDCl, HOAt
NMM, DMSO, rt

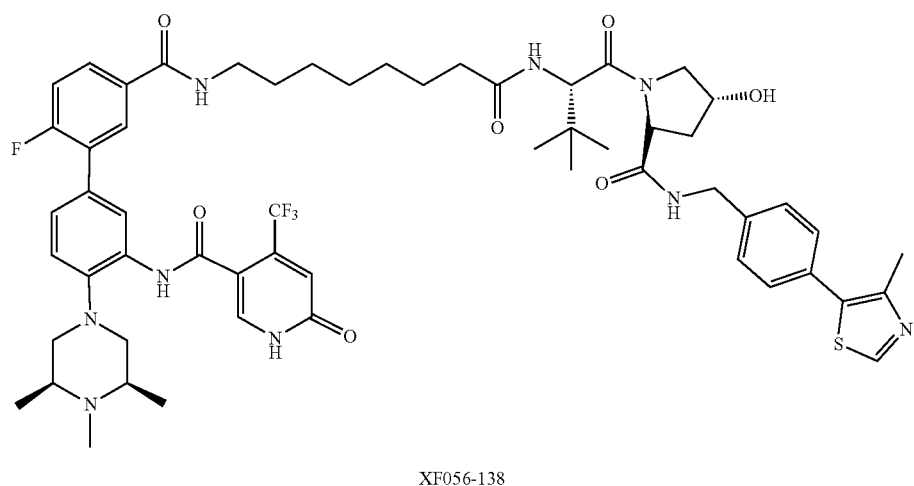

XF056-138

XF056-138 was synthesized following the standard procedures for preparing XF056-124 from intermediate 19 (13 mg, 0.024 mmol), VHL-C7-NH₂ (19.2 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-138 was obtained as white solid in TFA salt form (16.7 mg, yield 63%). ¹H NMR (600 MHz, CD₃OD) δ 8.96 (s, 1H), 8.15 (s, 1H), 8.02-7.93 (m, 2H), 7.86-7.80 (m, 1H), 7.50-7.34 (m, 6H), 7.27 (dd, J=10.3, 8.6 Hz, 1H), 6.92 (s, 1H), 4.62 (s, 1H), 4.59-4.46 (m, 3H), 4.35 (d, J=15.4 Hz, 1H), 3.89 (d, J=11.0 Hz, 1H), 3.79 (dd, J=10.9, 3.9 Hz, 1H), 3.53 (ddd, J=10.1, 6.8, 3.0 Hz, 2H), 3.40-3.33 (m, 4H), 2.98 (d, J=5.5 Hz, 5H), 2.47 (s, 3H), 2.33-2.16 (m, 3H), 2.10-2.02 (m, 1H), 1.70-1.52 (m, 4H), 1.44 (d, J=6.5 Hz, 6H), 1.42-1.30 (m, 6H), 1.01 (s, 9H). HRMS (m/z) for $C_{57}H_{70}F_4N_9O_7S^+$ [M+H]⁺: calculated 1100.5050. found 1100.5076.

Example 85: Synthesis of XF056-139

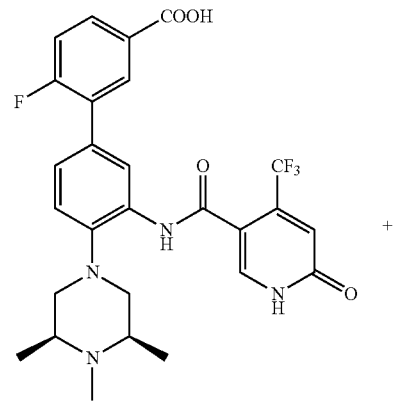

Intermediate 19

+

-continued

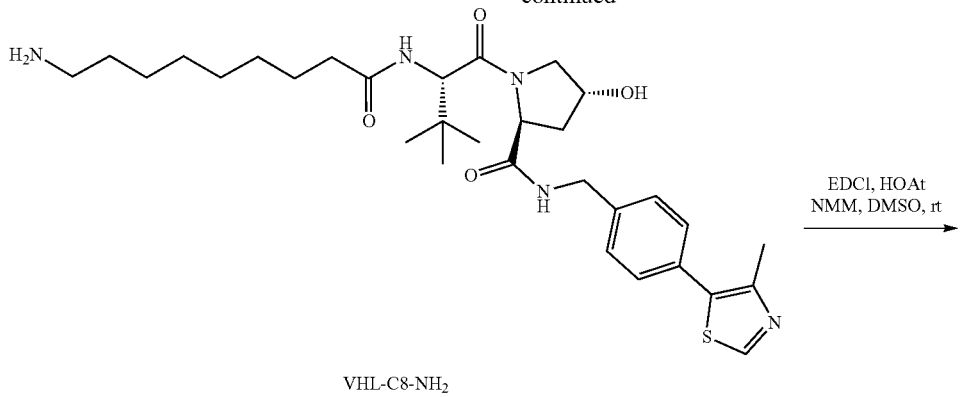

VHL-C8-NH2

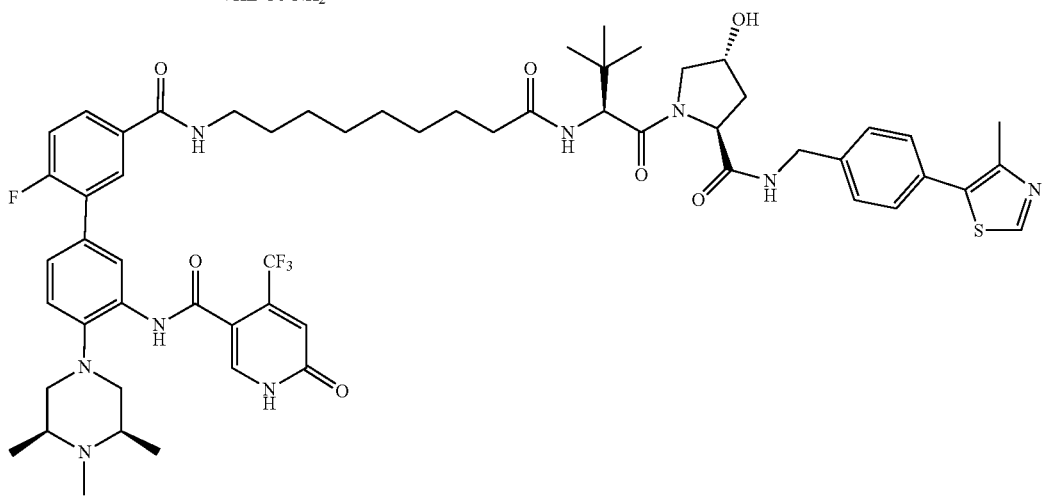

XF056-139

XF056-139 was synthesized following the standard procedures for preparing XF056-124 from intermediate 19 (13 mg, 0.024 mmol), VHL-C8-NH$_2$ (14.9 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-139 was obtained as white solid in TFA salt form (19.1 mg, yield 71%). $^1$H NMR (600 MHz, CD$_3$OD) δ 8.99 (s, 1H), 8.16-8.13 (m, 1H), 8.01 (s, 1H), 7.97 (dd, J=7.4, 2.4 Hz, 1H), 7.86-7.80 (m, 1H), 7.52-7.34 (m, 6H), 7.31-7.24 (m, 1H), 6.93 (s, 1H), 4.62 (s, 1H), 4.60-4.46 (m, 3H), 4.35 (d, J=15.5 Hz, 1H), 3.92-3.87 (m, 1H), 3.79 (dd, J=11.0, 3.9 Hz, 1H), 3.57-3.47 (m, 2H), 3.40-3.31 (m, 4H), 2.98 (d, J=3.9 Hz, 5H), 2.47 (s, 3H), 2.33-2.17 (m, 3H), 2.11-2.03 (m, 1H), 1.66-1.55 (m, 4H), 1.44 (d, J=6.5 Hz, 6H), 1.39-1.32 (m, 8H), 1.02 (s, 9H). HRMS (m/z) for C$_{58}$H$_{72}$F$_4$N$_9$O$_7$S$^+$ [M+H]$^+$: calculated 1114.5206. found 1114.5243.

Example 86: Synthesis of XF056-140

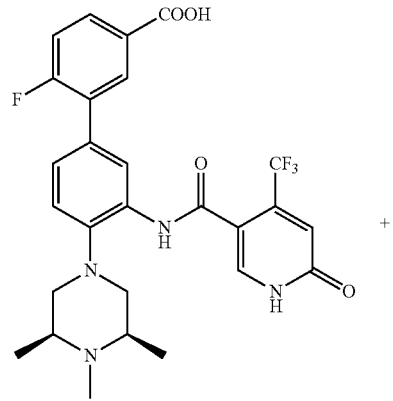

Intermediate 19

+

-continued

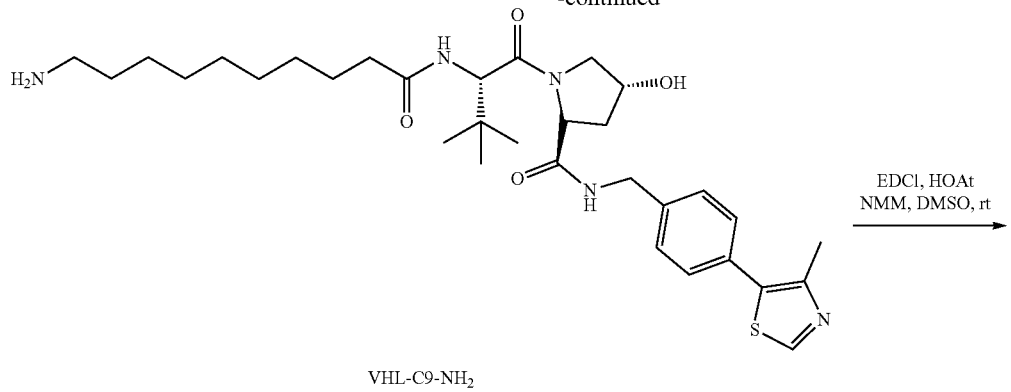

VHL-C9-NH$_2$

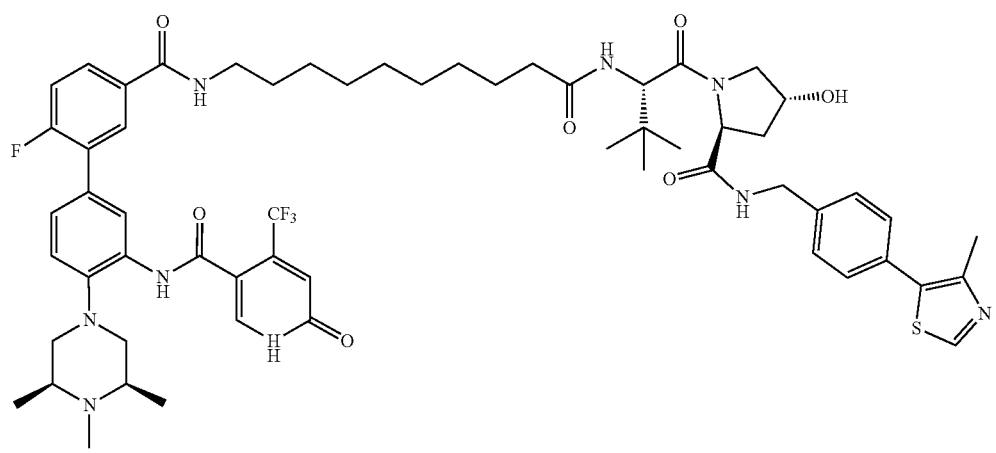

XF056-140

XF056-140 was synthesized following the standard procedures for preparing XF056-124 from intermediate 19 (13 mg, 0.024 mmol), VHL-C9-NH$_2$ (19.8 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-140 was obtained as white solid in TFA salt form (12.6 mg, yield 33%). $^1$H NMR (600 MHz, CD$_3$OD) δ 8.99 (s, 1H), 8.15 (s, 1H), 8.03-7.94 (m, 2H), 7.83 (ddd, J=8.7, 4.6, 2.4 Hz, 1H), 7.51-7.45 (m, 2H), 7.48-7.35 (m, 4H), 7.31-7.25 (m, 1H), 6.93 (s, 1H), 4.62 (s, 1H), 4.60-4.47 (m, 3H), 4.35 (d, J=15.4 Hz, 1H), 3.89 (d, J=11.0 Hz, 1H), 3.79 (dd, J=10.9, 3.9 Hz, 1H), 3.54-3.51 (m, 2H), 3.40-3.30 (m, 4H), 3.06-2.90 (m, 5H), 2.48 (s, 3H), 2.32-2.17 (m, 3H), 2.11-2.03 (m, 1H), 1.61 (dd, J=16.1, 8.9 Hz, 4H), 1.44 (d, J=6.5 Hz, 6H), 1.41-1.22 (m, 10H), 1.02 (s, 9H). HRMS (m/z) for C$_{59}$H$_{74}$F$_4$N$_9$O$_7$S$^+$ [M+H]$^+$: calculated 1128.5363. found 1128.5341.

Example 87: Synthesis of XF056-141

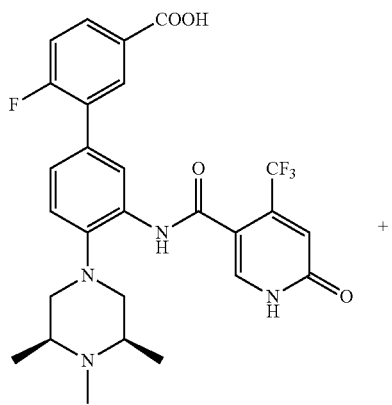

Intermediate 19

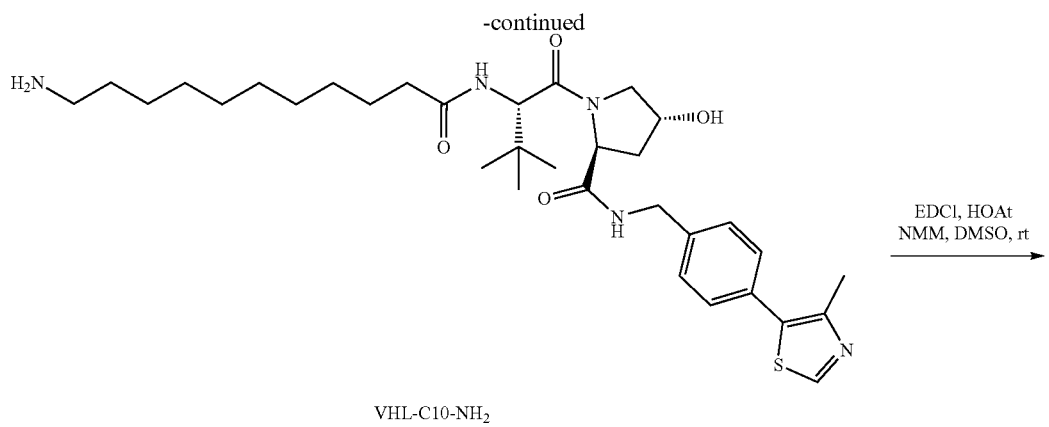

VHL-C10-NH₂

EDCl, HOAt
NMM, DMSO, rt
→

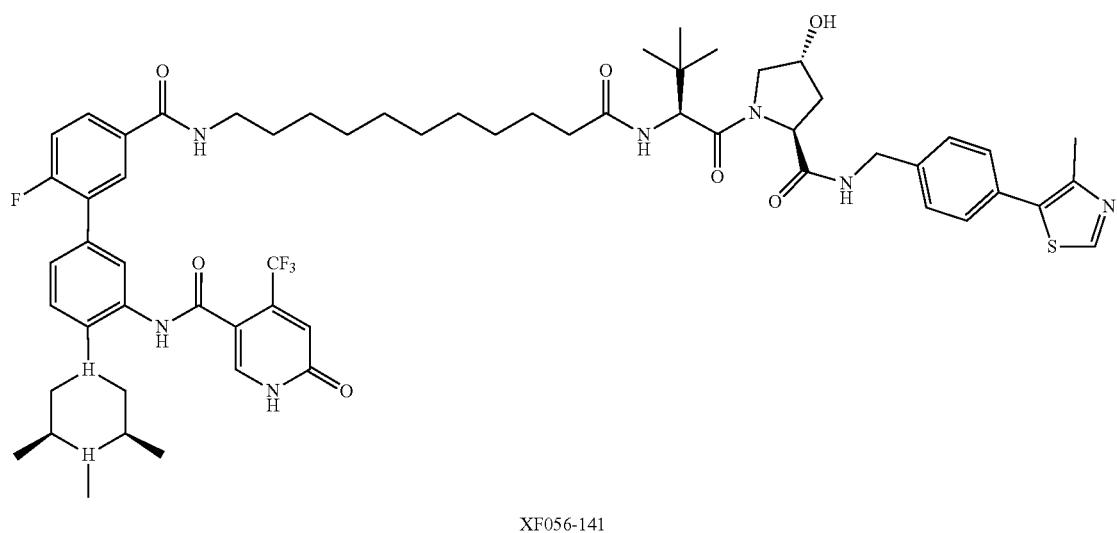

XF056-141

XF056-141 was synthesized following the standard procedures for preparing XF056-124 from intermediate 19 (13 mg, 0.024 mmol), VHL-C10-NH₂ (15.6 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-141 was obtained as white solid in TFA salt form (16 mg, yield 58%). ¹H NMR (600 MHz, CD₃OD) δ 8.94 (s, 1H), 8.17-8.13 (m, 1H), 8.03-7.94 (m, 2H), 7.84 (ddd, J=8.5, 4.6, 2.4 Hz, 1H), 7.51-7.35 (m, 6H), 7.28 (dd, J=10.3, 8.6 Hz, 1H), 6.93 (s, 1H), 4.62 (s, 1H), 4.59-4.47 (m, 3H), 4.35 (d, J=15.5 Hz, 1H), 3.89 (d, J=11.0 Hz, 1H), 3.79 (dd, J=11.0, 3.9 Hz, 1H), 3.52 (s, 2H), 3.40-3.30 (m, 4H), 2.98 (s, 5H), 2.47 (s, 3H), 2.32-2.17 (m, 3H), 2.07 (ddd, J=13.2, 9.0, 4.5 Hz, 1H), 1.65-1.56 (m, 4H), 1.44 (d, J=6.5 Hz, 6H), 1.33 (d, J=35.2 Hz, 12H), 1.02 (s, 9H). HRMS (m/z) for $C_{60}H_{76}F_4N_9O_7S^+$ [M+H]⁺: calculated 1142.5519. found 1142.5487.

Example 88: Synthesis of XF056-142

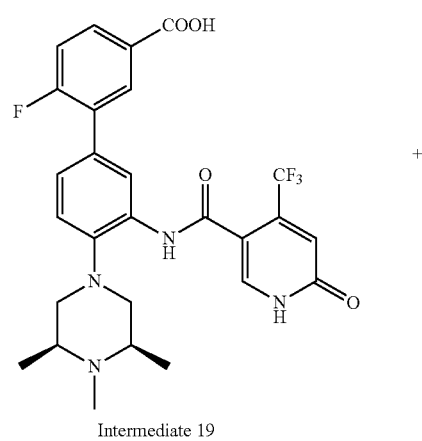

Intermediate 19

+

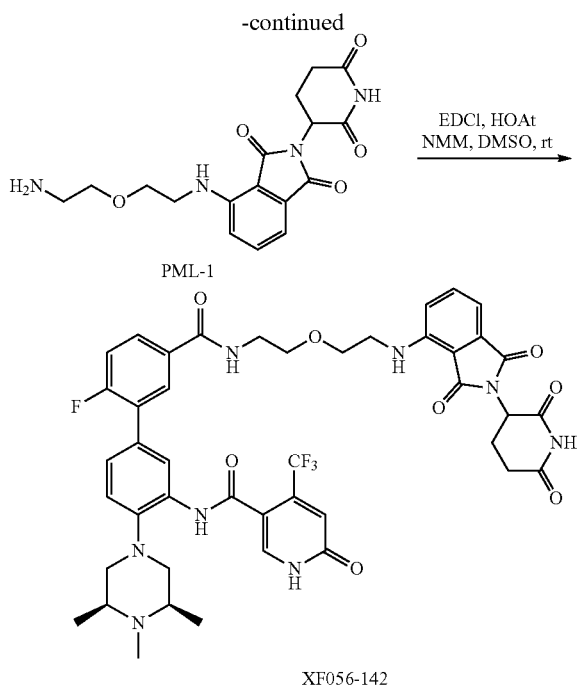

XF056-142 was synthesized following the standard procedures for preparing XF056-124 from intermediate 19 (13 mg, 0.024 mmol), PML-1 (9.5 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-142 was obtained as yellow solid in TFA salt form (5.1 mg, yield 24%). $^1$H NMR (600 MHz, CD$_3$OD) δ 8.13 (d, J=2.1 Hz, 1H), 8.02-7.95 (m, 2H), 7.80 (ddd, J=8.6, 4.5, 2.4 Hz, 1H), 7.51-7.45 (m, 1H), 7.45-7.41 (m, 1H), 7.33 (d, J=8.4 Hz, 1H), 7.25 (dd, J=10.3, 8.6 Hz, 1H), 7.02 (d, J=8.6 Hz, 1H), 6.91 (d, J=7.1 Hz, 1H), 6.88 (s, 1H), 4.96-4.92 (m, 1H), 3.76-3.68 (m, 4H), 3.60 (t, J=5.3 Hz, 2H), 3.55-3.45 (m, 4H), 3.36-3.32 (m, 2H), 3.01-2.91 (m, 5H), 2.72-2.47 (m, 3H), 1.96-1.88 (m, 1H), 1.44 (dd, J=6.5, 2.4 Hz, 6H). HRMS (m/z) for $C_{44}H_{45}F_4N_8O_8^+$ [M+H]$^+$: calculated 889.3291. found 889.3305.

Example 89: Synthesis of XF056-143

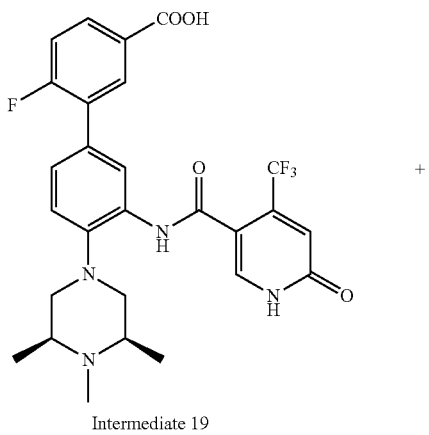

Intermediate 19

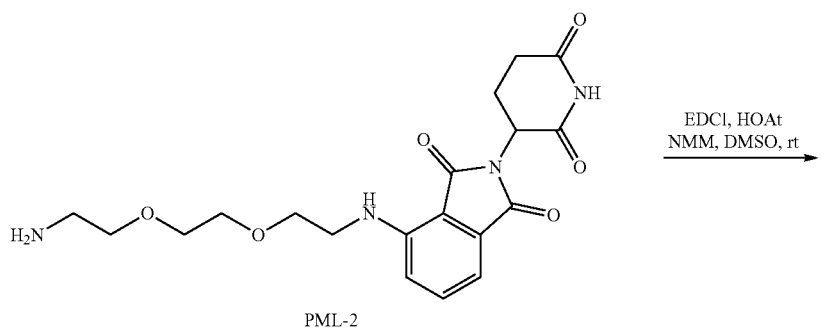

PML-2

-continued

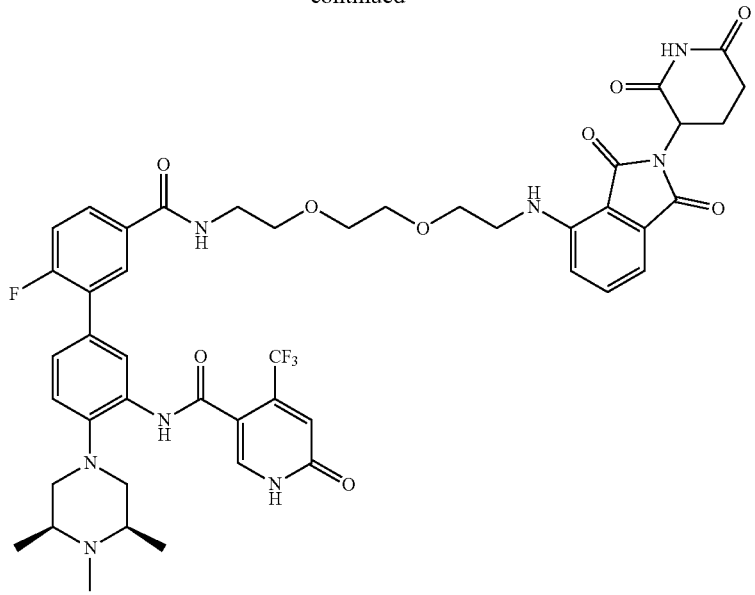

XF056-143

XF056-143 was synthesized following the standard procedures for preparing XF056-124 from intermediate 19 (13 mg, 0.024 mmol), PML-2 (12.4 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-143 was obtained as yellow solid in TFA salt form (16.3 mg, yield 73%). $^1$H NMR (600 MHz, CD$_3$OD) δ 8.07 (d, J=2.1 Hz, 1H), 8.02-7.94 (m, 2H), 7.81 (ddd, J=8.6, 4.6, 2.4 Hz, 1H), 7.46-7.38 (m, 2H), 7.29 (d, J=8.4 Hz, 1H), 7.19 (dd, J=10.4, 8.6 Hz, 1H), 6.96-6.88 (m, 3H), 4.97 (dd, J=12.7, 5.5 Hz, 1H), 3.74-3.63 (m, 8H), 3.59 (dd, J=6.2, 4.5 Hz, 2H), 3.49 (s, 2H), 3.37-3.30 (m, 2H), 3.31-3.26 (m, 2H), 2.99-2.90 (m, 5H), 2.82-2.73 (m, 1H), 2.70-2.56 (m, 2H), 2.08-2.01 (m, 1H), 1.45-1.40 (m, 6H). HRMS (m/z) for C$_{46}$H$_{49}$F$_4$N$_8$O$_9^+$ [M+H]$^+$: calculated 933.3553. found 933.3571.

Example 90: Synthesis of XF056-144

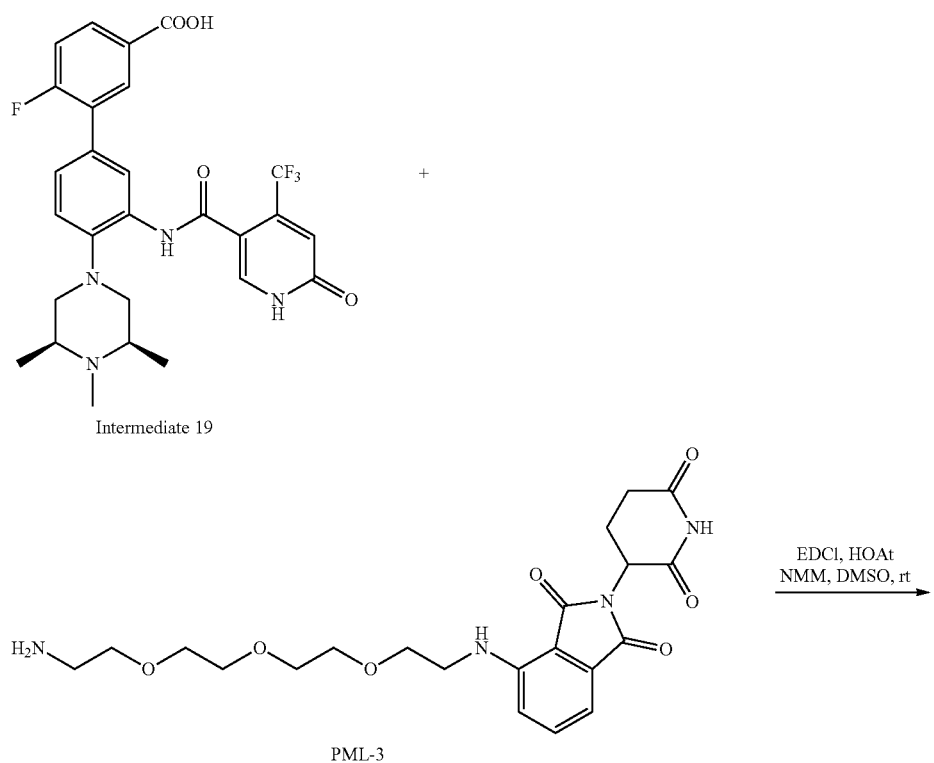

Intermediate 19

PML-3

EDCI, HOAt
NMM, DMSO, rt

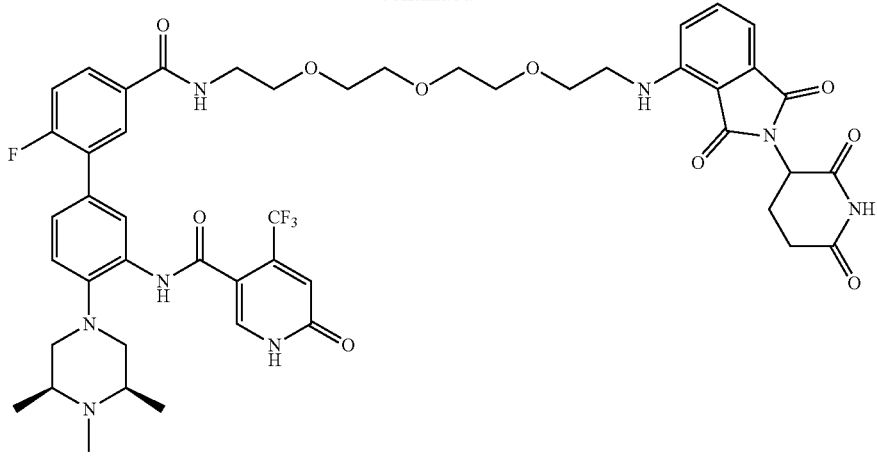

XF056-144

XF056-144 was synthesized following the standard procedures for preparing XF056-124 from intermediate 19 (13 mg, 0.024 mmol), PML-3 (13.5 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-144 was obtained as yellow solid in TFA salt form (15 mg, yield 64%). $^1$H NMR (600 MHz, CD$_3$OD) δ 8.09 (d, J=1.9 Hz, 1H), 8.04-7.94 (m, 2H), 7.84 (ddd, J=8.6, 4.6, 2.4 Hz, 1H), 7.50-7.41 (m, 2H), 7.36-7.14 (m, 2H), 7.05-6.85 (m, 3H), 5.02 (dd, J=12.8, 5.4 Hz, 1H), 3.68-3.44 (m, 16H), 3.36-3.24 (m, 4H), 3.01-2.88 (m, 5H), 2.87-2.78 (m, 2H), 2.75-2.60 (m, 1H), 2.10-2.05 (m, 1H), 1.43 (dd, J=6.5, 3.9 Hz, 6H). HRMS (m/z) for C$_{48}$H$_{53}$F$_4$N$_8$O$_{10}$$^+$ [M+H]$^+$: calculated 977.3815. found 977.3795.

Example 91: Synthesis of XF056-145

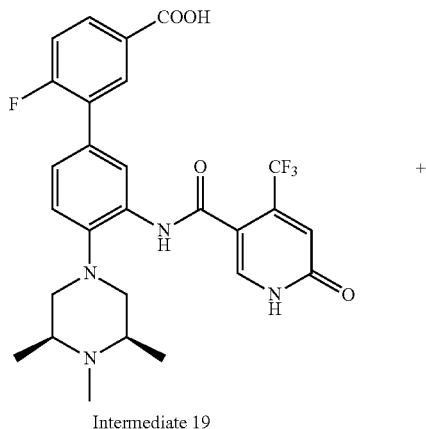

Intermediate 19

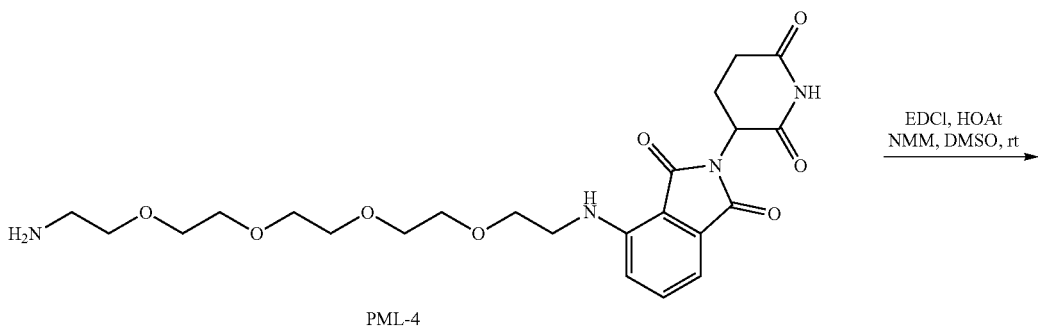

PML-4

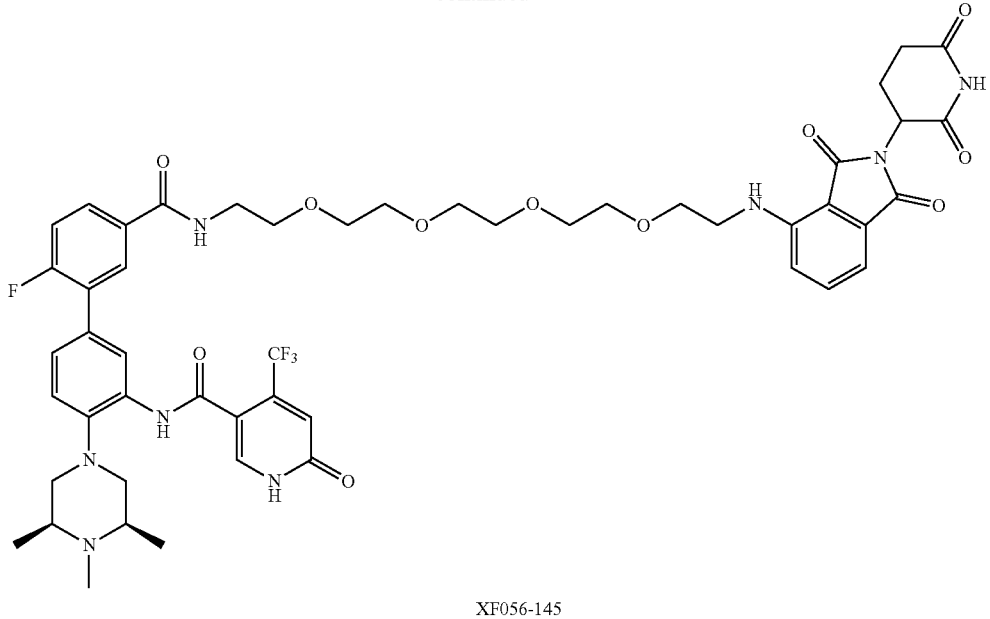

XF056-145

XF056-145 was synthesized following the standard procedures for preparing XF056-124 from intermediate 19 (13 mg, 0.024 mmol), PML-4 (13.6 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-145 was obtained as yellow solid in TFA salt form (9.5 mg, yield 39%). $^1$H NMR (600 MHz, CD$_3$OD) δ 8.11 (d, J=1.9 Hz, 1H), 8.02-7.94 (m, 2H), 7.85 (ddd, J=8.5, 4.5, 2.4 Hz, 1H), 7.52-7.37 (m, 2H), 7.35-7.20 (m, 2H), 6.98 (t, J=7.6 Hz, 2H), 6.92 (s, 1H), 5.02 (dd, J=12.8, 5.5 Hz, 1H), 3.76-3.44 (m, 20H), 3.40 (t, J=5.3 Hz, 2H), 3.34-3.30 (m, 2H), 3.00-2.89 (m, 5H), 2.82 (ddd, J=17.5, 13.9, 5.4 Hz, 1H), 2.75-2.62 (m, 2H), 2.10-2.03 (m, 1H), 1.43 (dd, J=6.5, 3.2 Hz, 6H). HRMS (m/z) for $C_{50}H_{57}F_4N_8O_{11}^+$ [M+H]$^+$: calculated 1021.4077. found 1021.4054.

Example 92: Synthesis of XF056-146

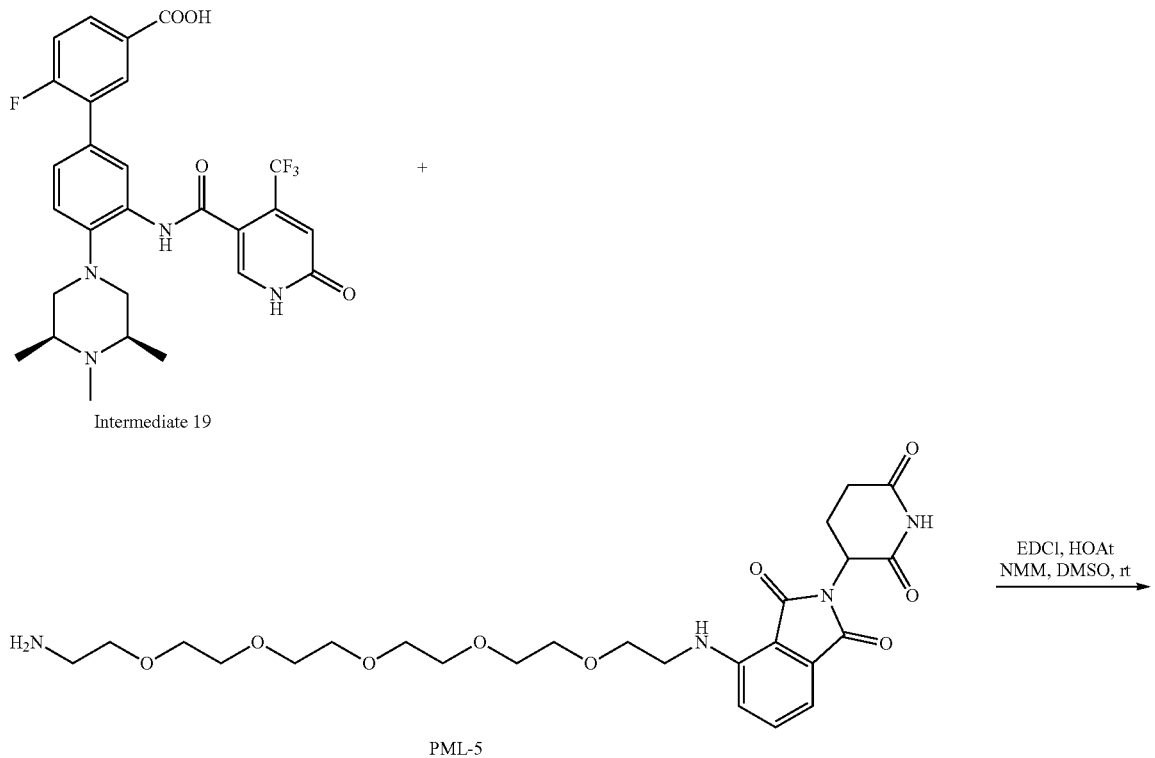

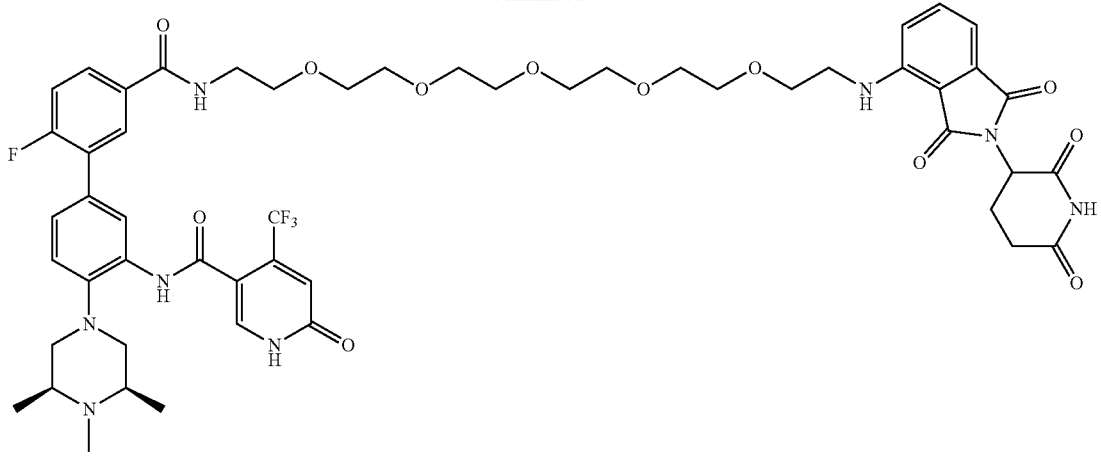

XF056-146

XF056-146 was synthesized following the standard procedures for preparing XF056-124 from intermediate 19 (13 mg, 0.024 mmol), PML-5 (14.6 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-146 was obtained as yellow solid in TFA salt form (16.3 mg, yield 64%). $^1$H NMR (600 MHz, CD$_3$OD) δ 8.13 (d, J=1.9 Hz, 1H), 8.07-7.92 (m, 2H), 7.91-7.81 (m, 1H), 7.56-7.43 (m, 2H), 7.37-7.22 (m, 2H), 7.00 (dd, J=14.4, 7.8 Hz, 2H), 6.91 (s, 1H), 5.02 (dd, J=12.8, 5.5 Hz, 1H), 3.72-3.45 (m, 24H), 3.42 (t, J=5.3 Hz, 2H), 3.35-3.29 (m, 2H), 3.02-2.89 (m, 5H), 2.83 (ddd, J=17.5, 14.0, 5.3 Hz, 1H), 2.75-2.62 (m, 2H), 2.13-2.04 (m, 1H), 1.43 (dd, J=6.5, 2.2 Hz, 6H). HRMS (m/z) for C$_{52}$H$_{61}$F$_4$N$_8$O$_{12}^+$ [M+H]$^+$: calculated 1065.4340. found 1065.4334.

Example 93: Synthesis of XF056-147

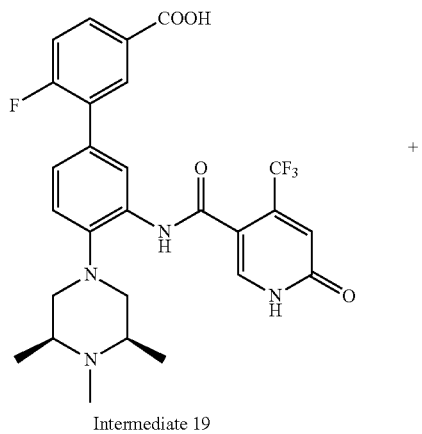

Intermediate 19

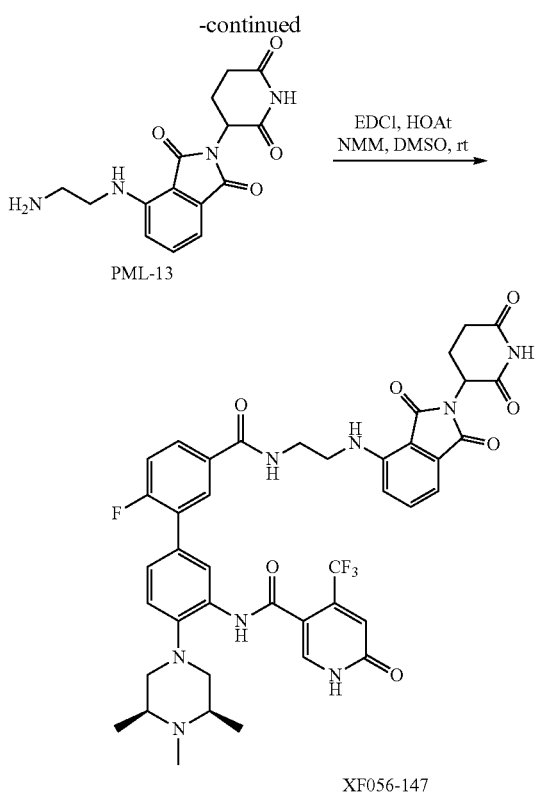

XF056-147

XF056-147 was synthesized following the standard procedures for preparing XF056-124 from intermediate 19 (13 mg, 0.024 mmol), PML-13 (10.3 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-147 was obtained as yellow solid in TFA salt form (17.5 mg, yield 86%). $^1$H NMR (600 MHz, CD$_3$OD) δ 8.09 (d, J=1.8 Hz, 1H), 7.99 (s, 1H), 7.84 (dd, J=7.4, 2.4 Hz, 1H), 7.83-7.76 (m, 1H), 7.51-7.37 (m, 2H), 7.33 (d, J=8.4 Hz, 1H), 7.25 (dd, J=10.3, 8.5 Hz, 1H), 7.11 (d, J=8.6 Hz, 1H), 6.96-6.83 (m, 2H), 5.00 (dd, J=12.8, 5.4 Hz, 1H), 3.68-3.47 (m, 6H), 3.37-3.32 (m, 2H), 3.01-2.94 (m, 5H), 2.88-2.75 (m, 1H), 2.71-2.55 (m, 2H), 2.06-1.98 (m, 1H), 1.44 (dd, J=6.5, 2.8 Hz, 6H). HRMS (m/z) for $C_{42}H_{41}F_4N_8O_7^+$ [M+H]$^+$: calculated 845.3029. found 845.3014.

Example 94: Synthesis of XF056-148

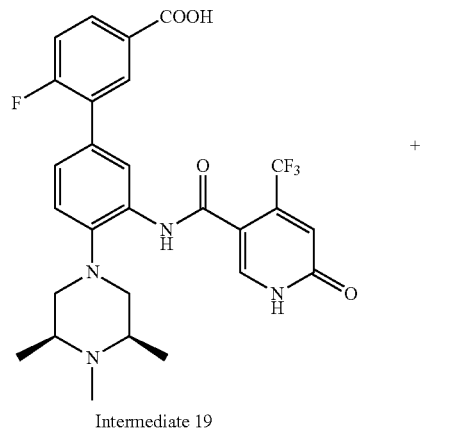

Intermediate 19

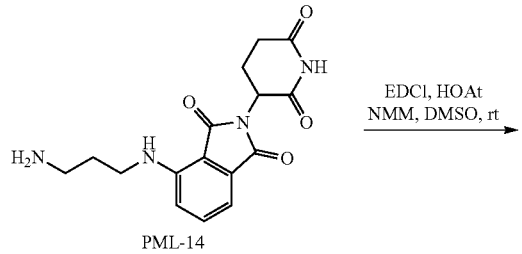

PML-14

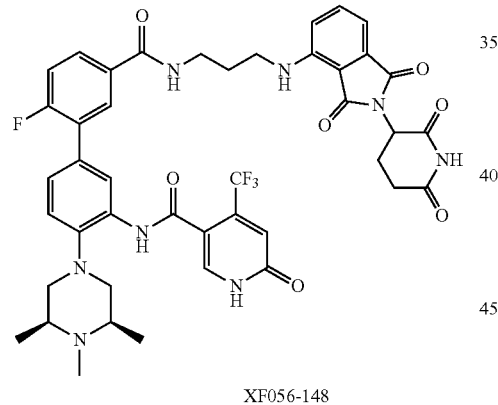

XF056-148

XF056-148 was synthesized following the standard procedures for preparing XF056-124 from intermediate 19 (13 mg, 0.024 mmol), PML-14 (10.7 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-148 was obtained as yellow solid in TFA salt form (17.4 mg, yield 84%). $^1$H NMR (600 MHz, CD$_3$OD) δ 8.16-8.12 (m, 1H), 8.02 (s, 1H), 7.96 (dd, J=7.4, 2.4 Hz, 1H), 7.81 (ddd, J=8.5, 4.5, 2.4 Hz, 1H), 7.52-7.44 (m, 2H), 7.35 (d, J=8.3 Hz, 1H), 7.26 (dd, J=10.3, 8.5 Hz, 1H), 7.03 (d, J=8.7 Hz, 1H), 6.97 (d, J=7.1 Hz, 1H), 6.92 (s, 1H), 4.99 (dd, J=12.7, 5.5 Hz, 1H), 3.55-3.49 (m, 4H), 3.43 (t, J=6.6 Hz, 2H), 3.36-3.31 (m, 2H), 2.98 (d, J=7.0 Hz, 5H), 2.84-2.74 (m, 1H), 2.72-2.57 (m, 2H), 2.05-1.92 (m, 3H), 1.44 (dd, J=6.6, 1.3 Hz, 6H). HRMS (m/z) for $C_{43}H_{43}F_4N_8O_7^+$ [M+H]$^+$: calculated 859.3185, found 859.3202.

Example 95: Synthesis of XF056-149

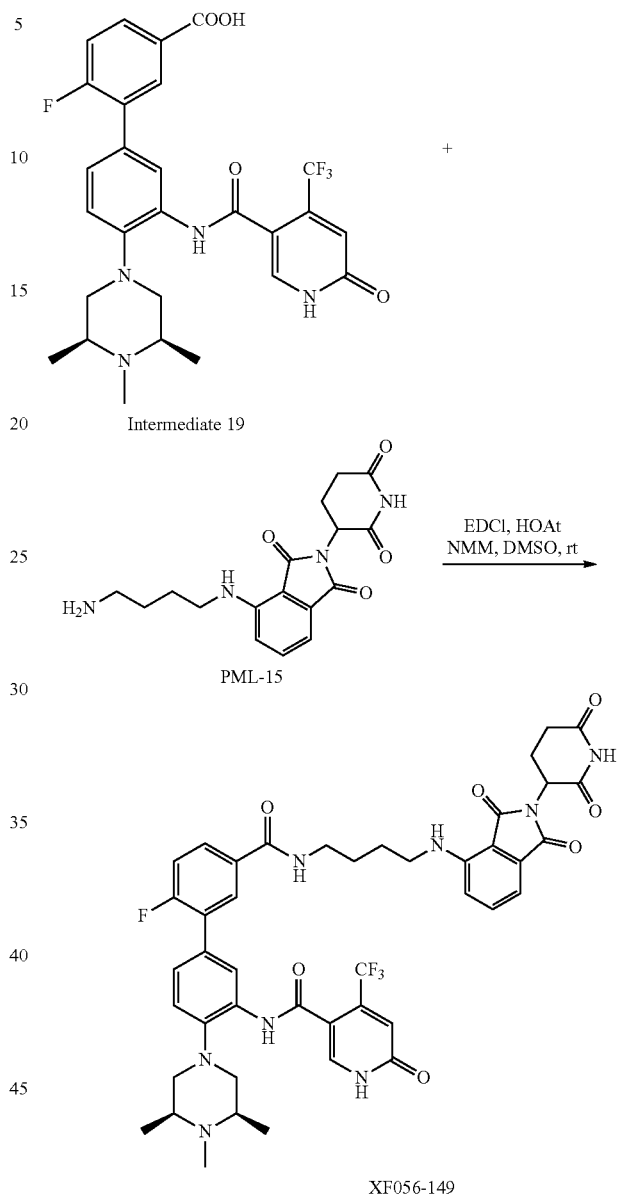

XF056-149 was synthesized following the standard procedures for preparing XF056-124 from intermediate 19 (13 mg, 0.024 mmol), PML-15 (11 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-149 was obtained as yellow solid in TFA salt form (11.5 mg, yield 55%). $^1$H NMR (600 MHz, CD$_3$OD) δ 8.16-8.10 (m, 1H), 7.99 (s, 1H), 7.93 (dd, J=7.4, 2.4 Hz, 1H), 7.81 (ddd, J=8.5, 4.6, 2.4 Hz, 1H), 7.48-7.41 (m, 2H), 7.35 (d, J=8.4 Hz, 1H), 7.26 (dd, J=10.3, 8.6 Hz, 1H), 6.99 (d, J=8.6 Hz, 1H), 6.95-6.89 (m, 2H), 5.01 (dd, J=12.8, 5.5 Hz, 1H), 3.60-3.32 (m, 8H), 3.06-2.92 (m, 5H), 2.87-2.77 (m, 1H), 2.74-2.60 (m, 2H), 2.10-2.02 (m, 1H), 1.77-1.71 (m, 4H), 1.44 (dd, J=6.5, 2.1 Hz, 6H). HRMS (m/z) for $C_{44}H_{45}F_4N_8O_7^+$ [M+H]$^+$: calculated 873.3342. found 873.3351.

Example 96: Synthesis of XF056-150

Example 97: Synthesis of XF056-151

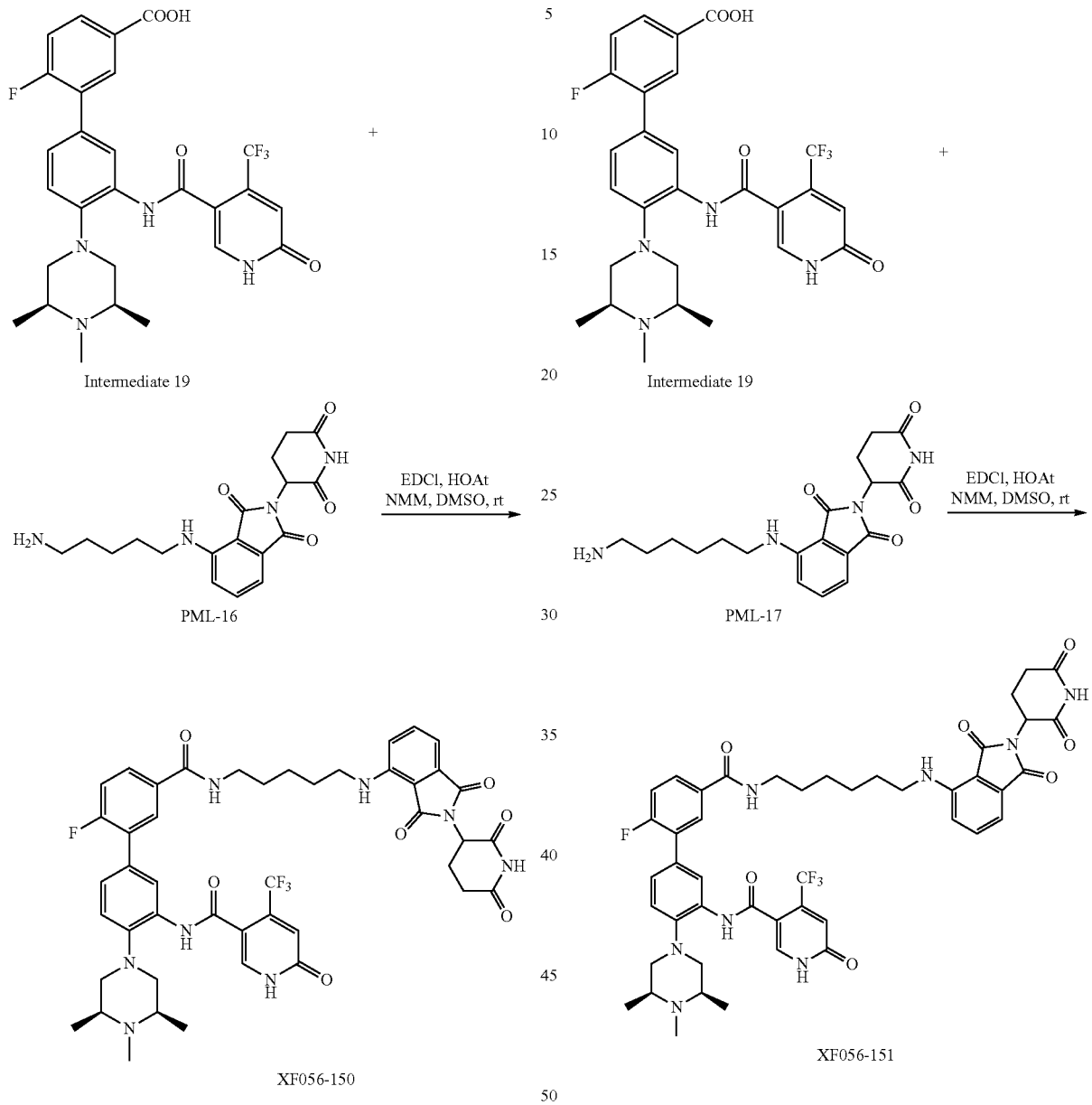

XF056-150 was synthesized following the standard procedures for preparing XF056-124 from intermediate 19 (13 mg, 0.024 mmol), PML-16 (11.3 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-150 was obtained as yellow solid in TFA salt form (17.3 mg, yield 81%). $^1$H NMR (600 MHz, CD$_3$OD) δ 8.14 (d, J=8.4 Hz, 1H), 8.02-7.93 (m, 2H), 7.81 (s, 1H), 7.50-7.43 (m, 2H), 7.35 (t, J=9.1 Hz, 1H), 7.26 (q, J=9.6 Hz, 1H), 7.02-6.87 (m, 3H), 4.98-4.91 (m, 5.3 Hz, 1H), 3.52-3.45 (m, 2H), 3.44-3.37 (m, 2H), 3.36-3.27 (m, 4H), 3.01-2.94 (m, 5H), 2.80 (s, 1H), 2.71-2.60 (m, 2H), 2.03 (d, J=8.0 Hz, 1H), 1.74-1.64 (m, 4H), 1.57-1.38 (m, 8H). HRMS (m/z) for C$_{45}$H$_{47}$F$_4$N$_8$O$_7$$^+$ [M+H]$^+$: calculated 887.3498. found 887.3516.

XF056-151 was synthesized following the standard procedures for preparing XF056-124 from intermediate 19 (13 mg, 0.024 mmol), PML-17 (9.8 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-151 was obtained as yellow solid in TFA salt form (10.1 mg, yield 47%). $^1$H NMR (600 MHz, CD$_3$OD) δ 8.13 (d, J=1.8 Hz, 1H), 8.04-7.94 (m, 2H), 7.91-7.81 (m, 1H), 7.54-7.44 (m, 2H), 7.35 (d, J=8.4 Hz, 1H), 7.28 (dd, J=10.4, 8.6 Hz, 1H), 6.97 (d, J=7.8 Hz, 2H), 6.91 (s, 1H), 5.02 (dd, J=12.8, 5.4 Hz, 1H), 3.55-3.47 (m, 2H), 3.42-3.37 (m, 2H), 3.35-3.30 (m, 4H), 3.01-2.92 (m, 5H), 2.88-2.76 (m, 1H), 2.74-2.61 (m, 2H), 2.11-2.03 (m, 1H), 1.72-1.59 (m, 4H), 1.51-1.40 (m, 10H). HRMS (m/z) for C$_{46}$H$_{49}$F$_4$N$_8$O$_7$$^+$ [M+H]$^+$: calculated 901.3665. found 901.3687.

Example 98: Synthesis of XF056-152

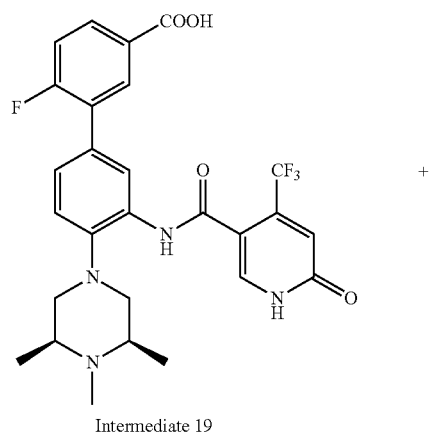
Intermediate 19

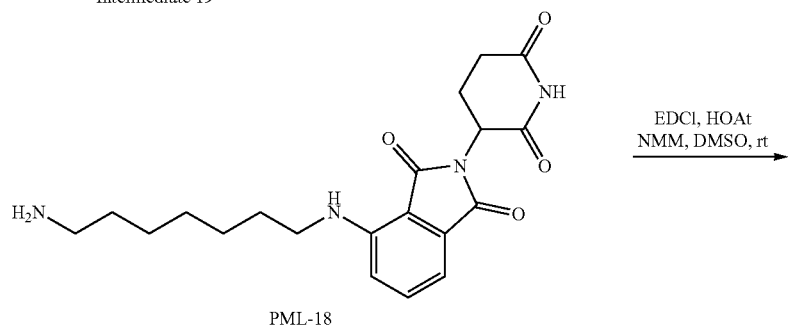
PML-18

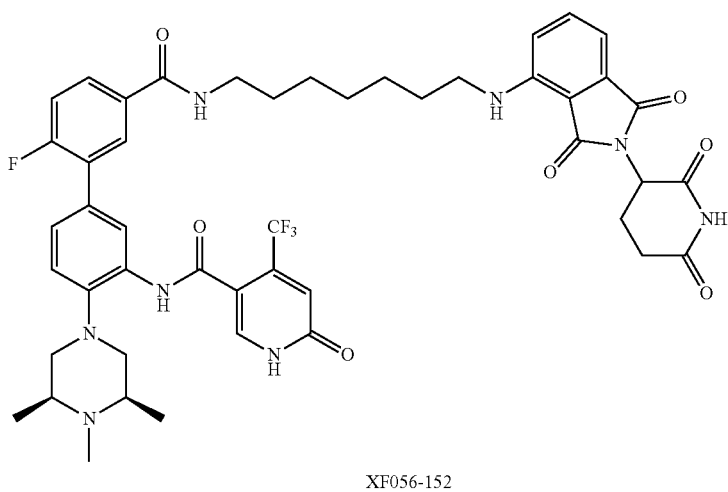
XF056-152

XF056-152 was synthesized following the standard procedures for preparing XF056-124 from intermediate 19 (13 mg, 0.024 mmol), PML-18 (12 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-152 was obtained as yellow solid in TFA salt form (16.2 mg, yield 74%). $^1$H NMR (600 MHz, CD$_3$OD) δ 8.18-8.08 (m, 1H), 8.03-7.92 (m, 2H), 7.83 (ddd, J=8.6, 4.6, 2.4 Hz, 1H), 7.55-7.41 (m, 2H), 7.34 (d, J=8.4 Hz, 1H), 7.27 (dd, J=10.3, 8.6 Hz, 1H), 6.96 (d, J=7.8 Hz, 2H), 6.91 (s, 1H), 5.01 (dd, J=12.8, 5.5 Hz, 1H), 3.56-3.48 (m, 2H), 3.41-3.22 (m, 6H), 3.00-2.92 (m, 5H), 2.87-2.77 (m, 1H), 2.76-2.61 (m, 2H), 2.06 (ddt, J=10.5, 5.5, 3.0 Hz, 1H), 1.66-1.58 (m, 4H), 1.42 (s, 12H). HRMS (m/z) for C$_{47}$H$_{51}$F$_4$N$_8$O$_7^+$ [M+H]$^+$: calculated 915.3811. found 915.3787.

Example 99: Synthesis of XF056-153

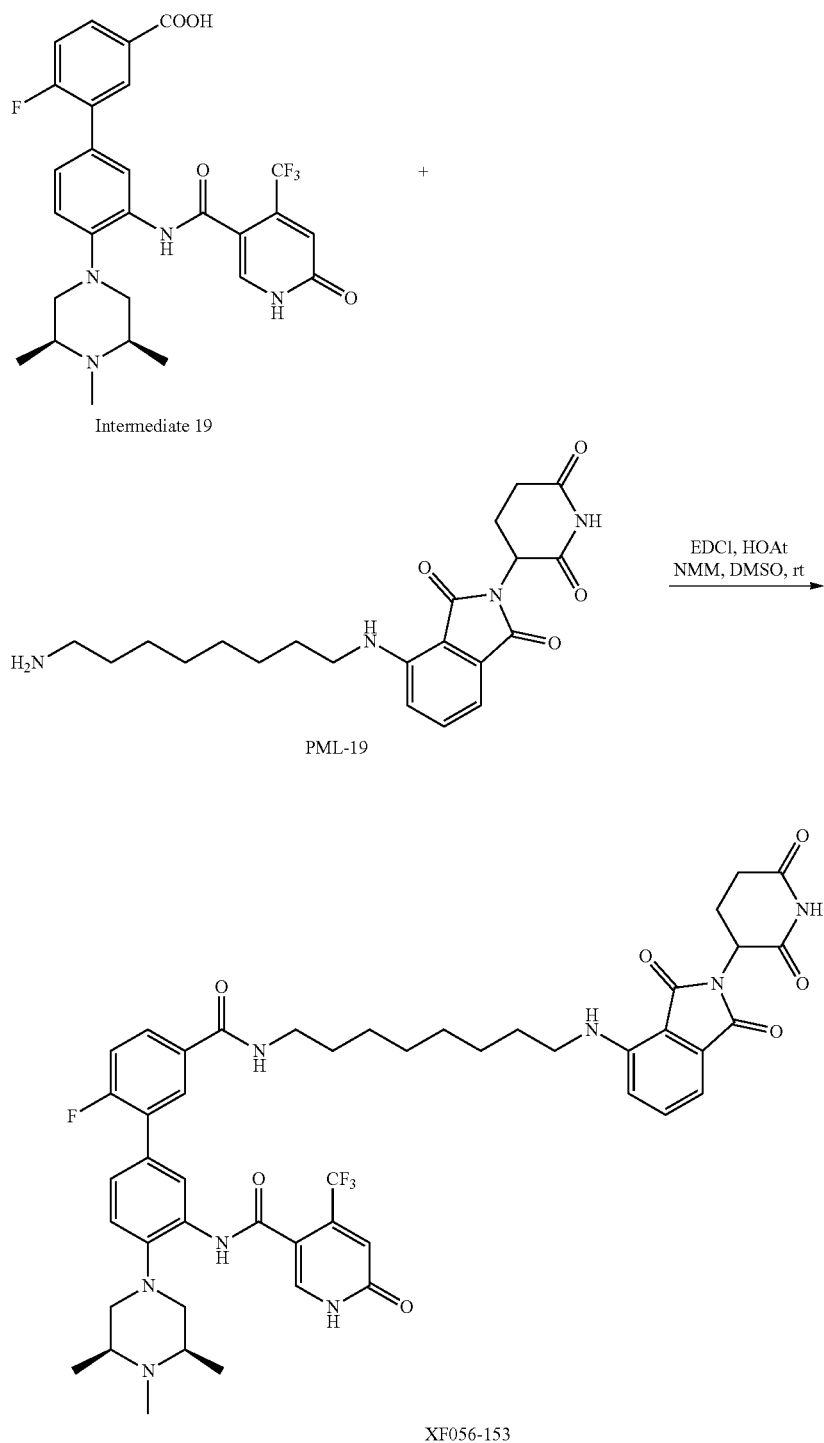

XF056-153 was synthesized following the standard procedures for preparing XF056-124 from intermediate 19 (13 mg, 0.024 mmol), PML-19 (12.3 mg, 0.024 mmol, 1.0 equiv), EDCI (6.8 mg, 0.04 mmol, 1.5 equiv), HOAt (4.8 mg, 0.04 mmol, 1.5 equiv), and NMM (8.1 mg, 0.08 mmol, 3.0 equiv) in DMSO (1 mL). XF056-153 was obtained as yellow solid in TFA salt form (10.5 mg, yield 47%). $^1$H NMR (600 MHz, CD$_3$OD) δ 8.29-8.06 (m, 1H), 8.05-7.91 (m, 2H), 7.87-7.74 (m, 1H), 7.58-7.39 (m, 2H), 7.37-7.24 (m, 2H), 7.03-6.82 (m, 3H), 5.02 (dd, J=12.5, 5.5 Hz, 1H), 3.56-3.48 (m, 2H), 3.37 (t, J=7.1 Hz, 2H), 3.32-3.29 (m, 2H), 3.23 (t, J=7.0 Hz, 2H), 3.04-2.90 (m, 5H), 2.87-2.78 (m, 1H), 2.77-2.63 (m, 2H), 2.13-1.99 (m, 1H), 1.69-1.55 (m, 4H), 1.47-1.30 (m, 14H). HRMS (m/z) for $C_{48}H_{53}F_4N_8O_7^+$ [M+H]$^+$: calculated 929.3968. found 929.3974.

Example 100: Synthesis of XF056-157

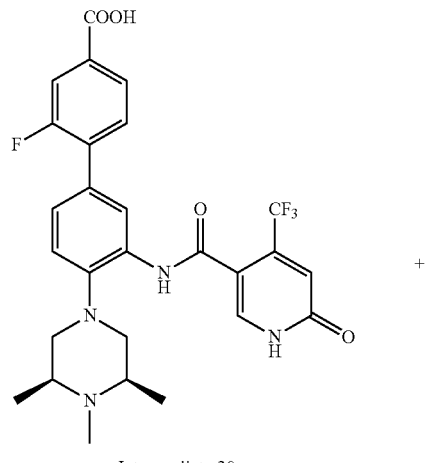

Intermediate 20

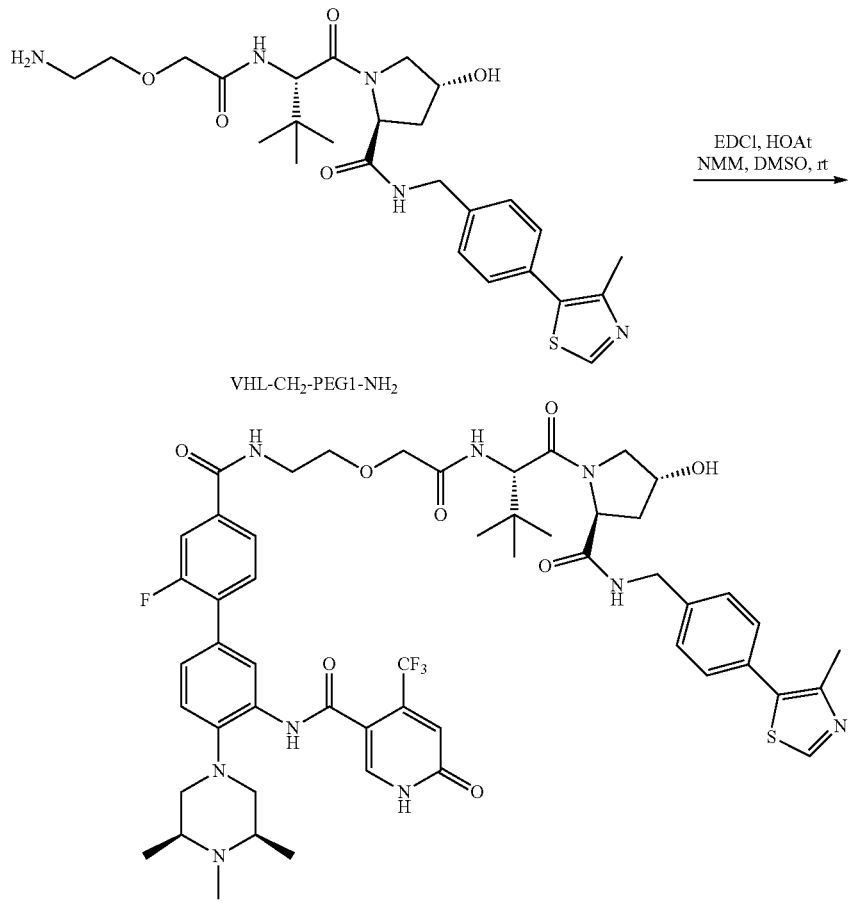

To the solution of intermediate 20 (10.6 mg, 0.019 mmol) in DMSO (1 mL) were added VHL-CH$_2$-PEG1-NH$_2$ (10.8 mg, 0.019 mmol, 1.0 equiv), EDCI (1-ethyl-3-(3-dimethyl-aminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv). After being stirring overnight at room temperature, the resulting mixture was purified by preparative HPLC (10%-100% methanol/0.1% TFA in H$_2$O) to afford XF056-157 as white solid in TFA salt form (10.4 mg, yield 52%). $^1$H NMR (600 MHz, CD$_3$OD) δ 9.01 (s, 1H), 8.12 (d, J=1.7 Hz, 1H), 8.00 (s, 1H), 7.79 (dd, J=8.0, 1.7 Hz, 1H), 7.74-7.70 (m, 1H), 7.55 (t, J=8.0 Hz, 1H), 7.46-7.41 (m, 4H), 7.40-7.32 (m, 2H), 6.92 (d, J=5.6 Hz, 1H), 4.71 (s, 1H), 4.60-4.55 (m, 1H), 4.56-4.46 (m, 2H), 4.31 (d, J=15.6 Hz, 1H), 4.14-4.00 (m, 2H), 3.88 (d, J=11.1 Hz, 1H), 3.82-3.66 (m, 3H), 3.65-3.56 (m, 2H), 3.56-3.47 (m, 2H), 3.36-3.32 (m, 2H), 3.01-2.92 (m, 5H), 2.44 (s, 3H), 2.27-2.18 (m, 1H), 2.11-2.02 (m, 1H), 1.46-1.41 (m, 6H), 1.00 (s, 9H). HRMS (m/z) for C$_{53}$H$_{62}$F$_4$N$_9$O$_8$S$^+$ [M+H]$^+$: calculated 1060.4373. found 1060.4377.

Example 101: Synthesis of XF056-158

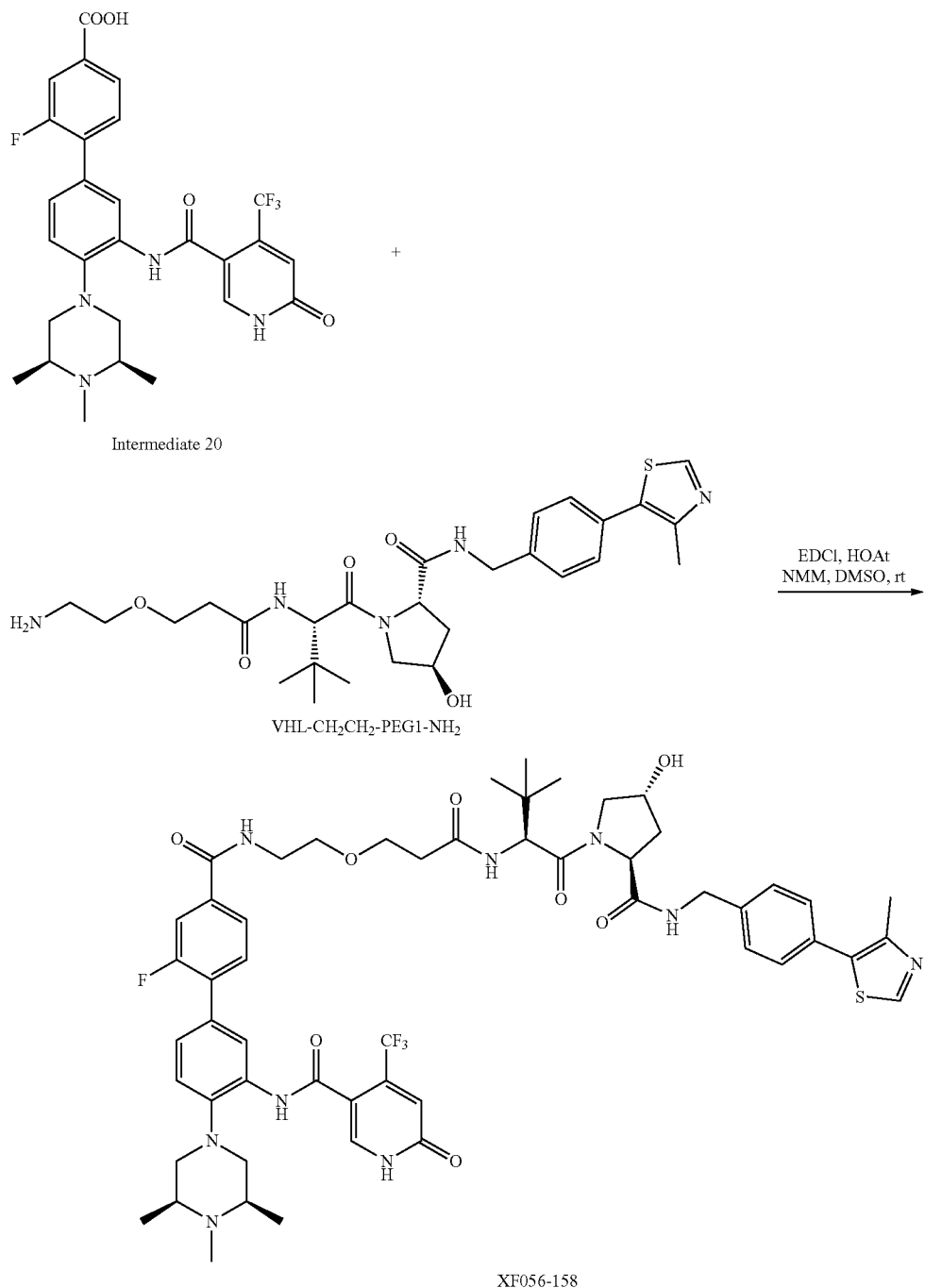

XF056-158 was synthesized following the standard procedures for preparing XF056-157 from intermediate 20 (10.6 mg, 0.019 mmol), VHL-CH$_2$CH$_2$-PEG1-NH$_2$ (14.7 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-158 was obtained as white solid in TFA salt form (17.7 mg, 75%). $^1$H NMR (600 MHz, CD$_3$OD) δ 8.93 (s, 1H), 8.15 (s, 1H), 8.00 (s, 1H), 7.76 (dd, J=8.1, 1.7 Hz, 1H), 7.71 (dd, J=11.5, 1.7 Hz, 1H), 7.58 (t, J=7.9 Hz, 1H), 7.48-7.45 (m, 1H), 7.42 (d, J=8.1 Hz, 2H), 7.39-7.33 (m, 3H), 6.92 (s, 1H), 4.65 (s, 1H), 4.57 (dd, J=9.2, 7.6 Hz, 1H), 4.49 (d, J=15.5 Hz, 2H), 4.33 (d, J=15.5 Hz, 1H), 3.89 (d, J=11.0 Hz, 1H), 3.82-3.70 (m, 3H), 3.70-3.51 (m, 6H), 3.39-3.31 (m, 2H), 2.98 (d, J=6.7 Hz, 5H), 2.61-2.48 (m, 2H), 2.44 (s, 3H), 2.25-2.17 (m, 1H), 2.10-2.02 (m, 1H), 1.44 (d, J=6.4 Hz, 6H), 0.99 (s, 9H). HRMS (m/z) for C$_{54}$H$_{64}$F$_4$N$_9$O$_8$S$^+$ [M+H]$^+$: calculated 1074.4529. found 1074.4519.

Example 102: Synthesis of XF056-159

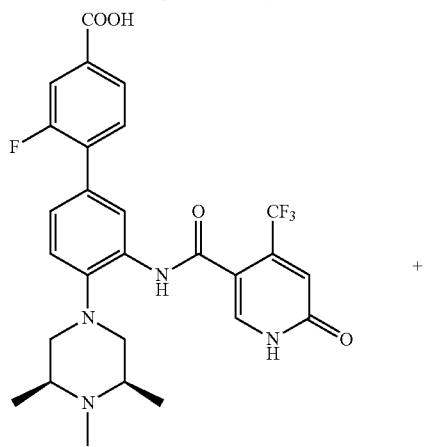

Intermediate 20

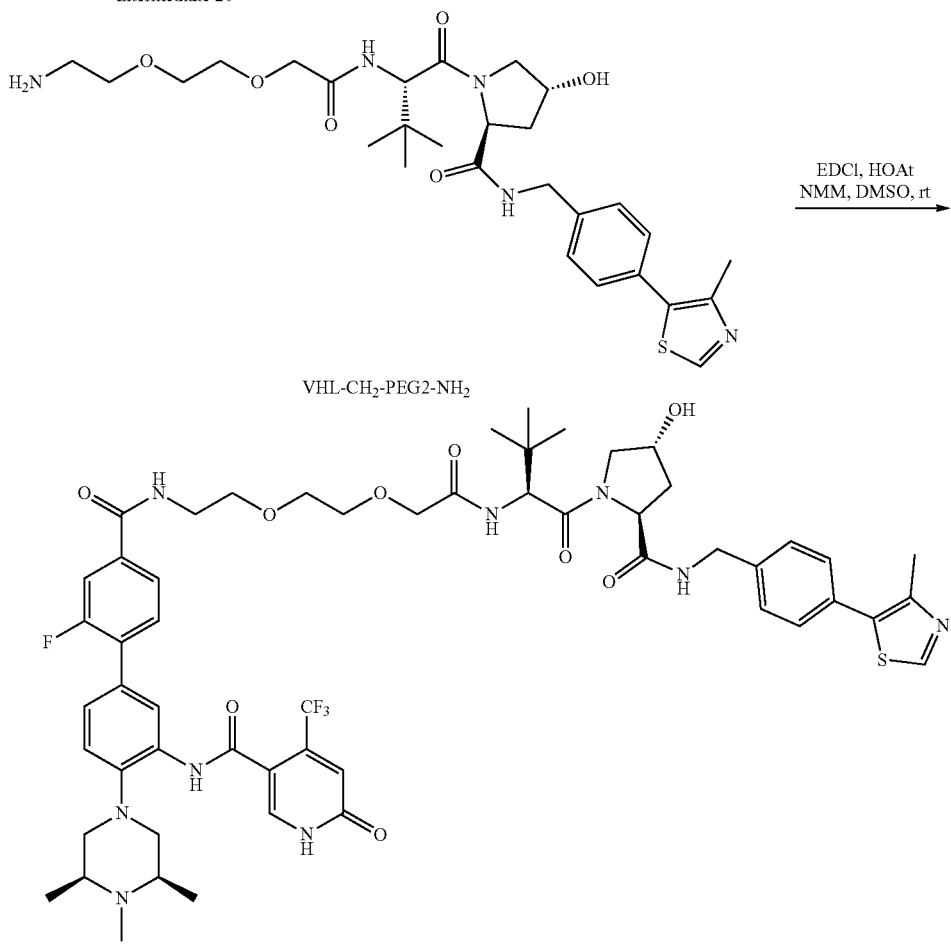

XF056-159 was synthesized following the standard procedures for preparing XF056-157 from intermediate 20 (10.6 mg, 0.019 mmol), VHL-CH$_2$CH$_2$-PEG1-NH$_2$ (11.6 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-159 was obtained as white solid in TFA salt form (11.1 mg, yield 53%). $^1$H NMR (600 MHz, CD$_3$OD) δ 8.97 (s, 1H), 8.14 (d, J=1.9 Hz, 1H), 8.01 (s, 1H), 7.70 (dd, J=8.0, 1.7 Hz, 1H), 7.64 (dd, J=11.4, 1.8 Hz, 1H), 7.60-7.54 (m, 1H), 7.50-7.31 (m, 6H), 6.93 (s, 1H), 4.76-4.71 (m, 1H), 4.62-4.55 (m, 1H), 4.53-4.44 (m, 2H), 4.30 (d, J=15.4 Hz, 1H), 4.10-3.97 (m, 2H), 3.87 (d, J=11.0 Hz, 1H), 3.80 (dd, J=11.0, 3.8 Hz, 1H), 3.76-3.48 (m, 10H), 3.36-3.32 (m, 2H), 3.02-2.94 (m, 5H), 2.45 (s, 3H), 2.28-2.20 (m, 1H), 2.10-2.04 (m, 1H), 1.44 (dd, J=6.5, 1.9 Hz, 6H), 1.02 (s, 9H). HRMS (m/z) for C$_{55}$H$_{66}$F$_4$N$_9$O$_9$S$^+$ [M+H]$^+$: calculated 1104.4635. found 1104.4612.

Example 103: Synthesis of XF056-160

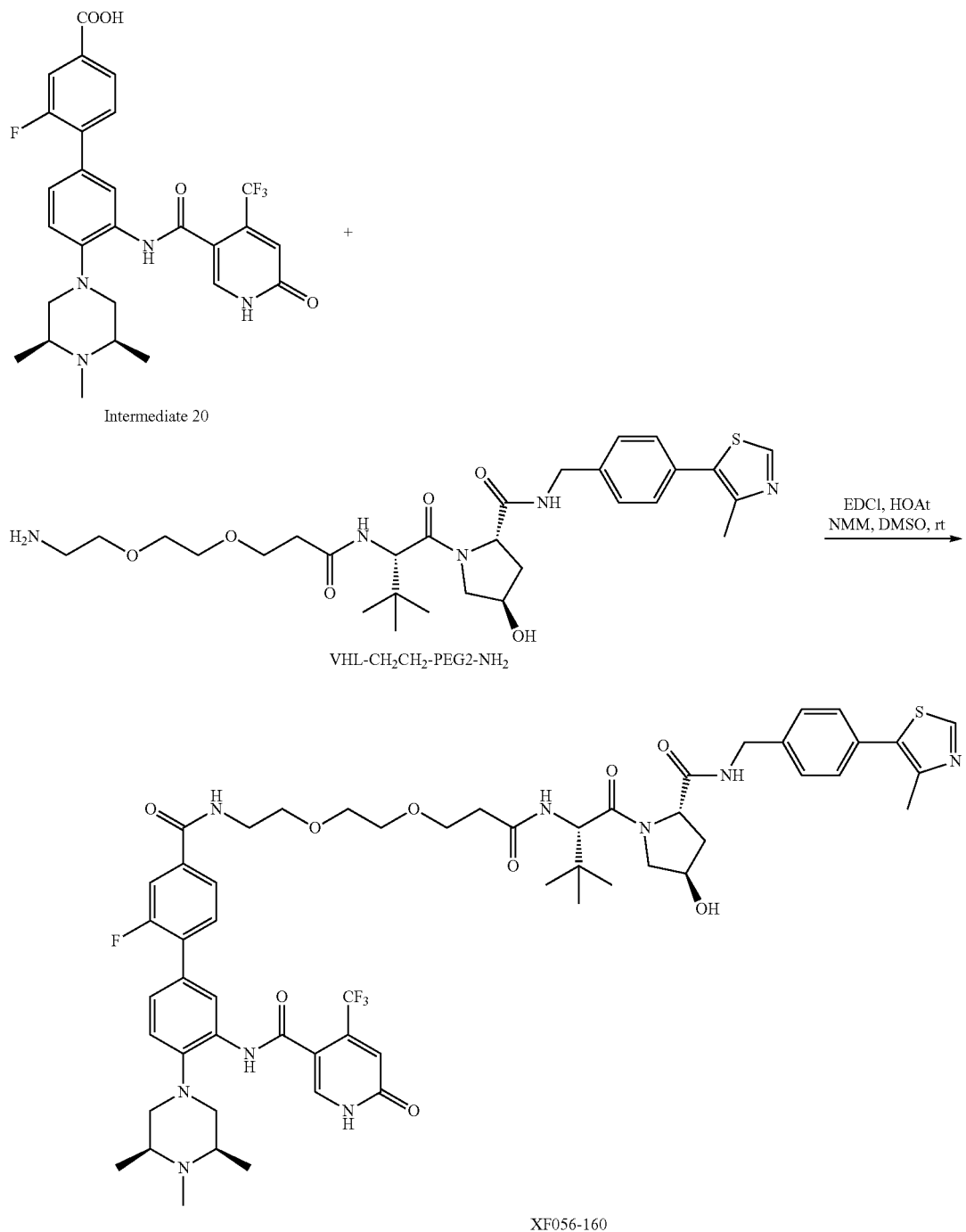

XF056-160 was synthesized following the standard procedures for preparing XF056-157 from intermediate 20 (10.6 mg, 0.019 mmol), VHL-CH$_2$CH$_2$-PEG2-NH$_2$ (15.5 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-160 was obtained as white solid in TFA salt form (15 mg, yield 71%). $^1$H NMR (600 MHz, CD$_3$OD) δ 8.99 (s, 1H), 8.15 (s, 1H), 8.01 (s, 1H), 7.72 (dd, J=8.0, 1.7 Hz, 1H), 7.66 (dd, J=11.5, 1.8 Hz, 1H), 7.59 (t, J=7.9 Hz, 1H), 7.50-7.35 (m, 6H), 6.92 (s, 1H), 4.65 (s, 1H), 4.60-4.54 (m, 1H), 4.53-4.46 (m, 2H), 4.34 (d, J=15.5 Hz, 1H), 3.88 (dd, J=11.1, 1.9 Hz, 1H), 3.81-3.49 (m, 13H), 3.37-3.32 (m, 2H), 3.02-2.91 (m, 5H), 2.58-2.38 (m, 5H), 2.26-2.16 (m, 1H), 2.12-2.01 (m, 1H), 1.44 (dd, J=6.4, 1.2 Hz, 6H), 1.02 (s, 9H). HRMS (m/z) for C$_{56}$H$_{68}$F$_4$N$_9$O$_9$S$^+$ [M+H]$^+$: calculated 1118.4791. found 1118.4769.

Example 104: Synthesis of XF056-161

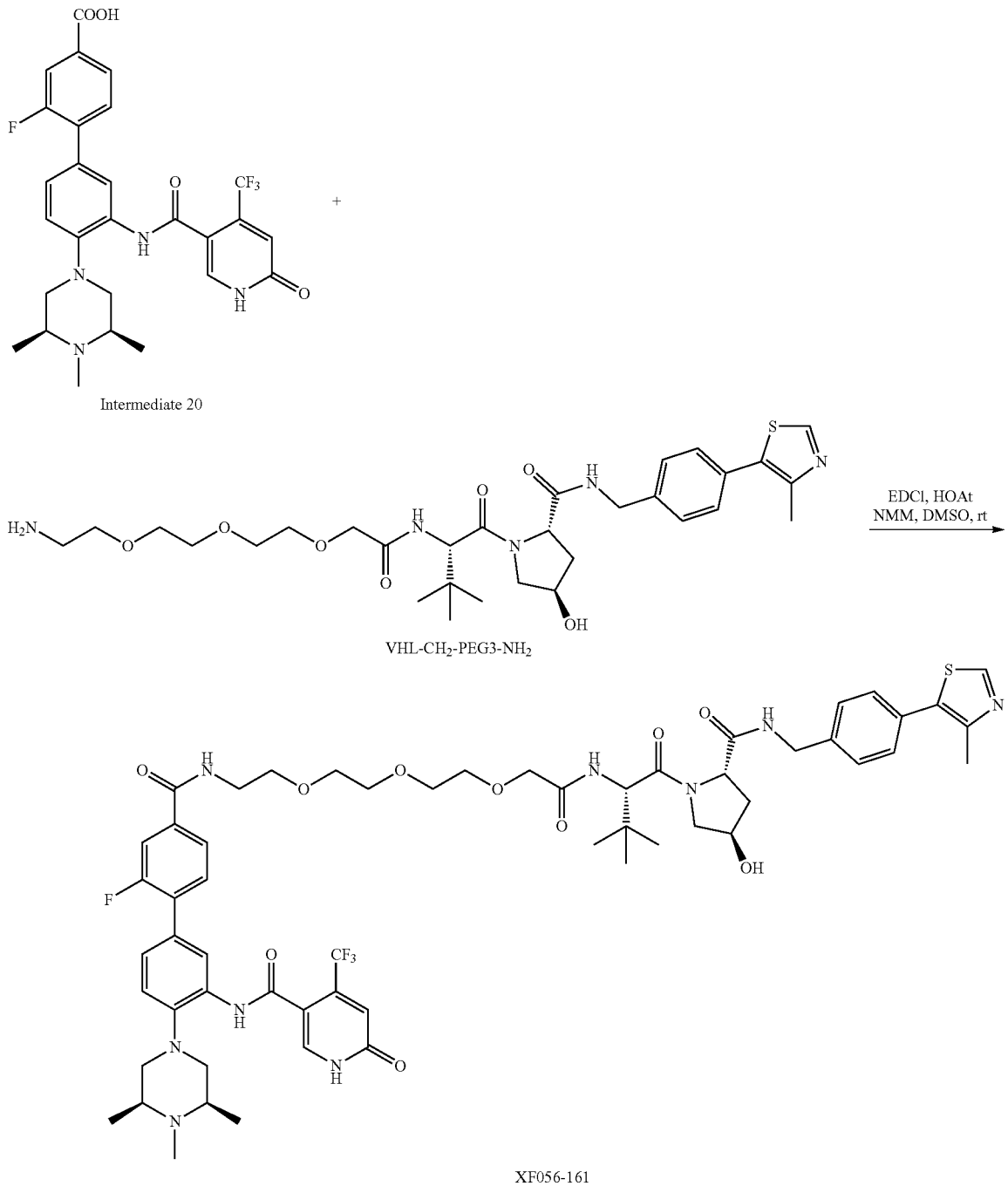

XF056-161 was synthesized following the standard procedures for preparing XF056-157 from intermediate 20 (10.6 mg, 0.019 mmol), VHL-CH$_2$-PEG3-NH$_2$ (16.1 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-161 was obtained as white solid in TFA salt form (17.6 mg, yield 81%). $^1$H NMR (600 MHz, CD$_3$OD) δ 8.97 (s, 1H), 8.15 (s, 1H), 8.01 (s, 1H), 7.71 (dd, J=8.0, 1.7 Hz, 1H), 7.66 (dd, J=11.4, 1.7 Hz, 1H), 7.58 (t, J=7.9 Hz, 1H), 7.51-7.27 (m, 6H), 6.93 (s, 1H), 4.69 (s, 1H), 4.60-4.54 (m, 1H), 4.53-4.46 (m, 2H), 4.34 (d, J=15.5 Hz, 1H), 4.08-3.92 (m, 2H), 3.86 (d, J=11.0 Hz, 1H), 3.79 (dd, J=11.0, 3.8 Hz, 1H), 3.74-3.48 (m, 14H), 3.38-3.32 (m, 2H), 3.01-2.93 (m, 5H), 2.47 (s, 3H), 2.25-2.18 (m, 1H), 2.12-2.03 (m, 1H), 1.44 (dd, J=6.6, 1.8 Hz, 6H), 1.02 (s, 9H). HRMS (m/z) for C$_{57}$H$_{70}$F$_4$N$_9$O$_{10}$S$^+$ [M+H]$^+$: calculated 1148.4897. found 1148.4876.

Example 105: Synthesis of XF056-162

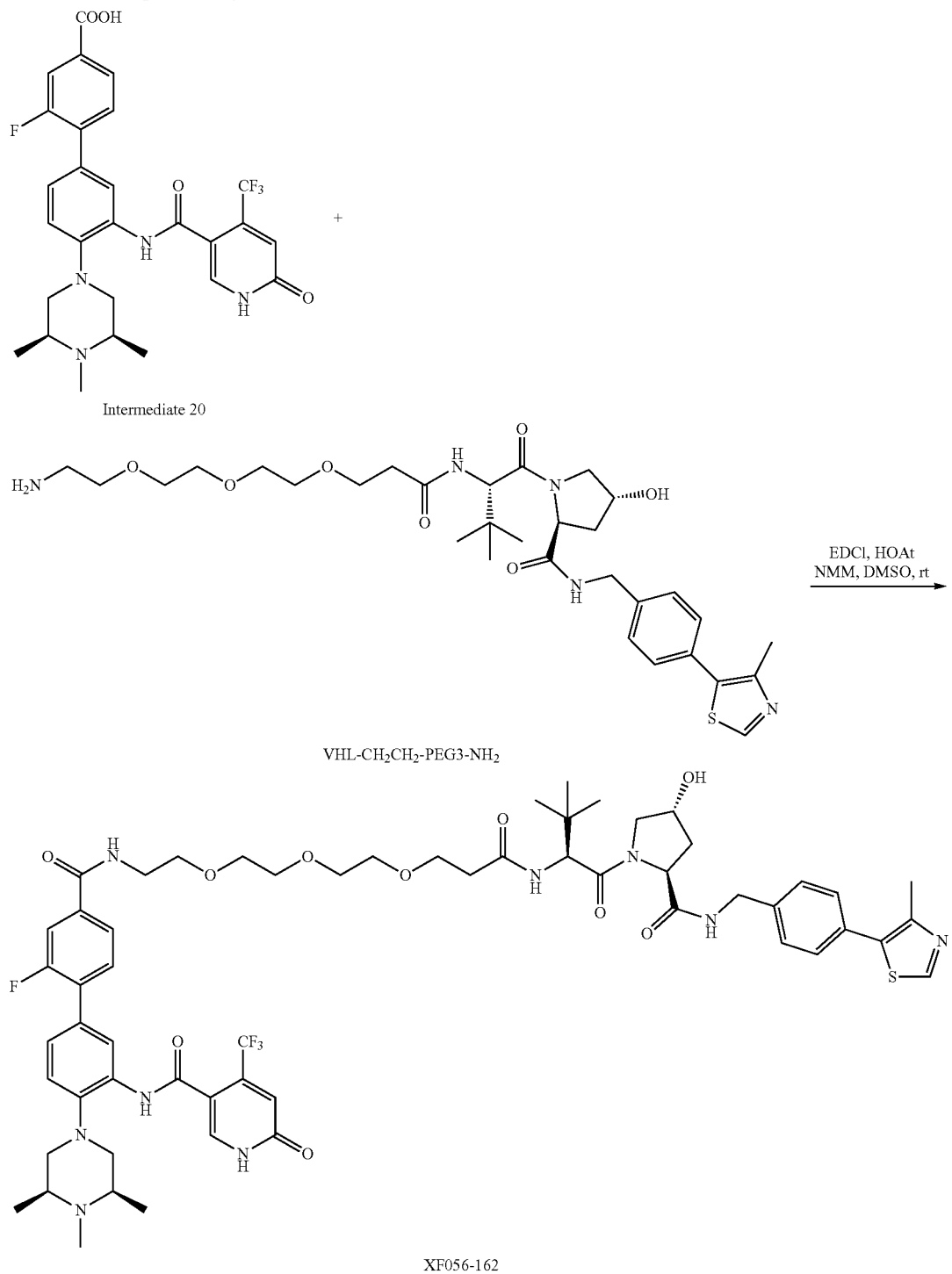

XF056-162 was synthesized following the standard procedures for preparing XF056-157 from intermediate 20 (10.6 mg, 0.019 mmol), VHL-CH$_2$CH$_2$-PEG3-NH$_2$ (16.4 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-162 was obtained as white solid in TFA salt form (13.3 mg, yield 60%). $^1$H NMR (600 MHz, CD$_3$OD) δ 8.97 (s, 1H), 8.16 (s, 1H), 8.01 (s, 1H), 7.73 (dd, J=8.0, 1.7 Hz, 1H), 7.68 (dd, J=11.4, 1.7 Hz, 1H), 7.59 (t, J=7.9 Hz, 1H), 7.50-7.43 (m, 3H), 7.40 (d, J=8.3 Hz, 2H), 7.37 (d, J=8.4 Hz, 1H), 6.92 (s, 1H), 4.63 (s, 1H), 4.59-4.46 (m, 3H), 4.34 (d, J=15.4 Hz, 1H), 3.87 (d, J=11.0 Hz, 1H), 3.78 (dd, J=11.0, 3.9 Hz, 1H), 3.74-3.48 (m, 16H), 3.34 (d, J=13.4 Hz, 2H), 3.03-2.93 (m, 5H), 2.60-2.51 (m, 1H), 2.51-2.40 (m, 4H), 2.25-2.17 (m, 1H), 2.12-1.99 (m, 1H), 1.44 (d, J=6.5 Hz, 6H), 1.01 (s, 9H). HRMS (m/z) for C$_{58}$H$_{72}$F$_4$N$_9$O$_{10}$S$^+$ [M+H]$^+$: calculated 1162.5053. found 1162.5067.

Example 106: Synthesis of XF056-163

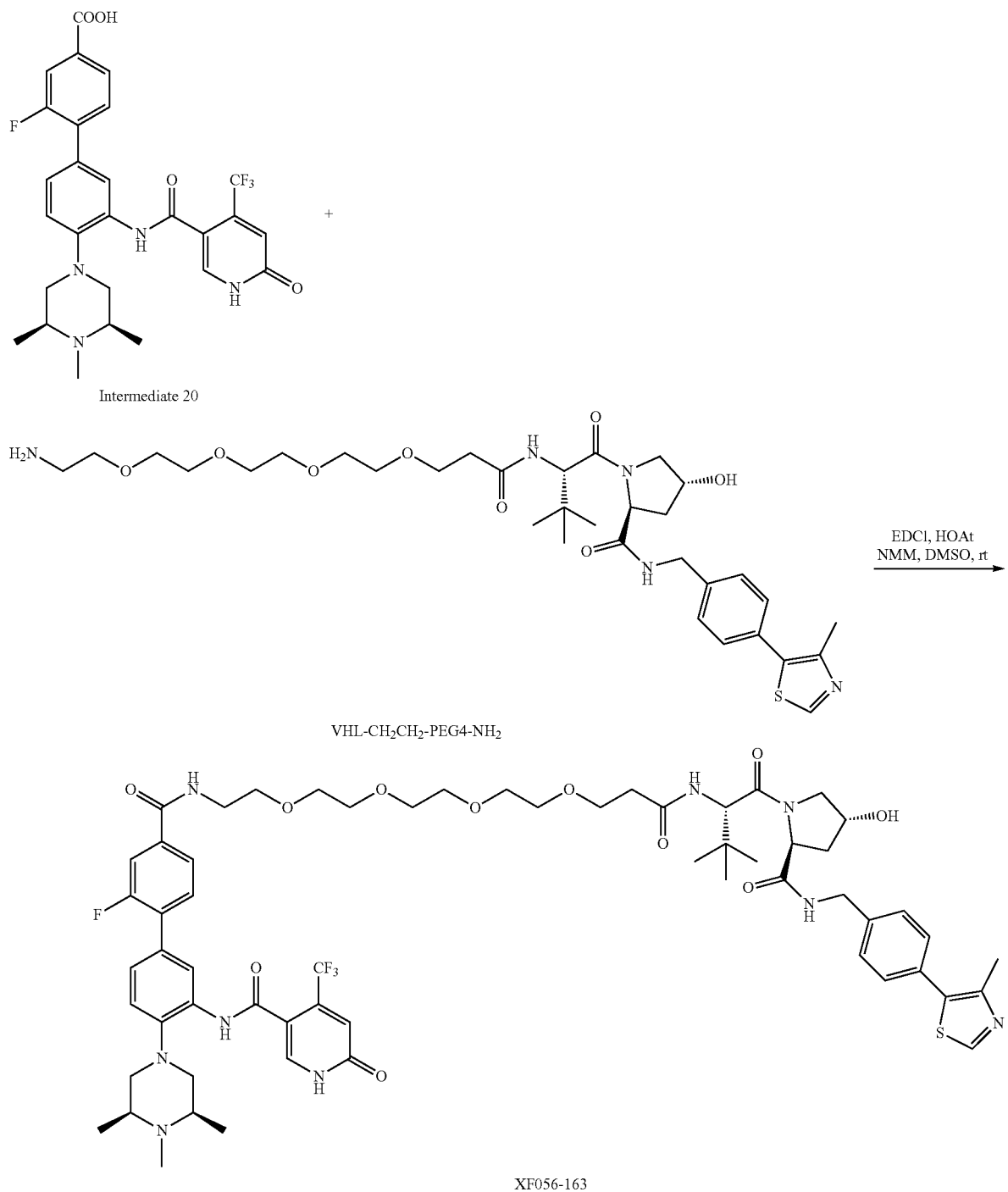

XF056-163 was synthesized following the standard procedures for preparing XF056-157 from intermediate 20 (10.6 mg, 0.019 mmol), VHL-CH$_2$CH$_2$-PEG4-NH$_2$ (13.6 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-163 was obtained as white solid in TFA salt form (12.4 mg, yield 54%). $^1$H NMR (600 MHz, CD$_3$OD) δ 8.97 (s, 1H), 8.16 (s, 1H), 8.01 (s, 1H), 7.74 (dd, J=8.0, 1.7 Hz, 1H), 7.69 (dd, J=11.5, 1.7 Hz, 1H), 7.60 (t, J=7.9 Hz, 1H), 7.50-7.30 (m, 6H), 6.93 (s, 1H), 4.63 (s, 1H), 4.59-4.45 (m, 3H), 4.34 (d, J=15.5 Hz, 1H), 3.90-3.86 (m, 1H), 3.78 (dd, J=11.0, 3.9 Hz, 1H), 3.72-3.49 (m, 20H), 3.35 (d, J=13.1 Hz, 2H), 2.98 (d, J=7.7 Hz, 5H), 2.60-2.36 (m, 5H), 2.28-2.17 (m, 1H), 2.12-2.03 (m, 1H), 1.44 (d, J=6.5 Hz, 6H), 1.01 (s, 9H). HRMS (m/z) for C$_{60}$H$_{76}$F$_4$N$_9$O$_{11}$S$^+$ [M+H]$^+$: calculated 1206.5316. found 1206.5345.

Example 107: Synthesis of XF056-164

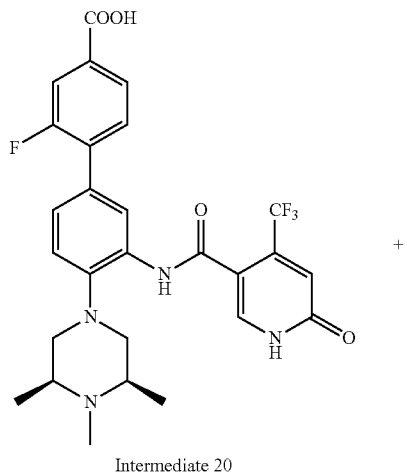

Intermediate 20

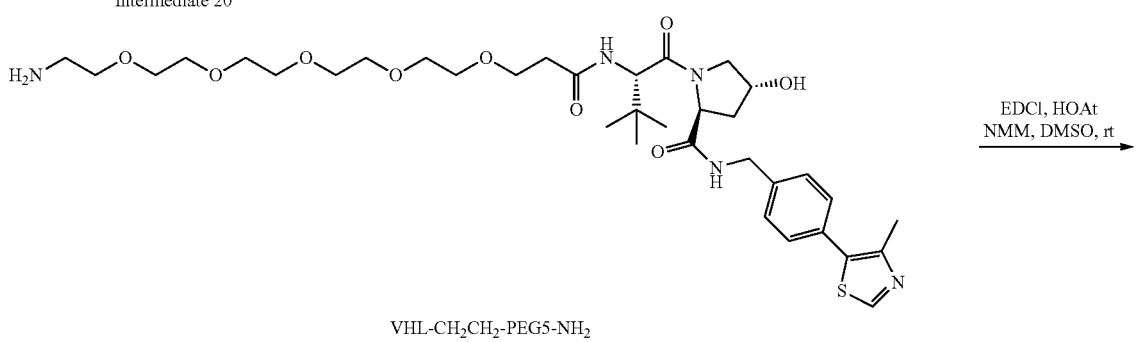

VHL-CH₂CH₂-PEG5-NH₂

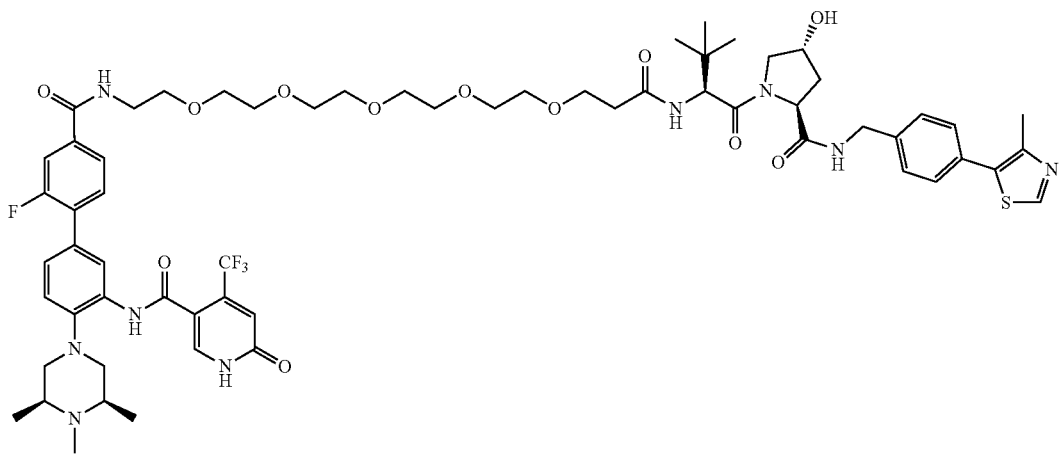

XF056-164

XF056-164 was synthesized following the standard procedures for preparing XF056-157 from intermediate 20 (10.6 mg, 0.019 mmol), VHL-CH₂CH₂-PEG5-NH₂ (18 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-164 was obtained as white solid in TFA salt form (12.4 mg, yield 52%). $^1$H NMR (600 MHz, CD$_3$OD) δ 8.98 (s, 1H), 8.16 (d, J=1.6 Hz, 1H), 8.01 (s, 1H), 7.75 (dd, J=8.0, 1.7 Hz, 1H), 7.69 (dd, J=11.5, 1.7 Hz, 1H), 7.60 (t, J=7.9 Hz, 1H), 7.54-7.32 (m, 6H), 6.93 (s, 1H), 4.63 (s, 1H), 4.60-4.43 (m, 3H), 4.34 (d, J=15.6 Hz, 1H), 3.88 (d, J=10.9 Hz, 1H), 3.78 (dd, J=11.0, 3.9 Hz, 1H), 3.73-3.50 (m, 24H), 3.35 (d, J=13.0 Hz, 2H), 3.01-2.92 (m, 5H), 2.58-2.51 (m, 1H), 2.50-2.41 (m, 4H), 2.25-2.17 (m, 1H), 2.11-2.02 (m, 1H), 1.44 (d, J=6.4 Hz, 6H), 1.02 (s, 9H). HRMS (m/z) for $C_{62}H_{80}F_4N_9O_{12}S^+$ [M+H]$^+$: calculated 1250.5578. found 1250.5589.

Example 108: Synthesis of XF056-165

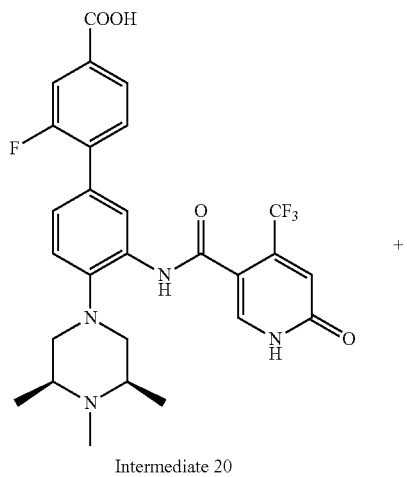

Intermediate 20

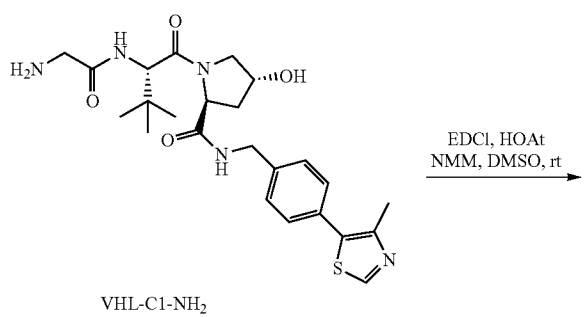

VHL-C1-NH₂

→ EDCl, HOAt, NMM, DMSO, rt

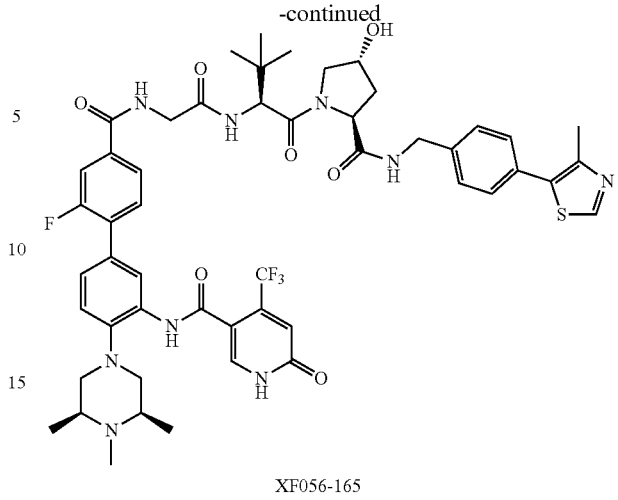

XF056-165

XF056-165 was synthesized following the standard procedures for preparing XF056-157 from intermediate 20 (10.6 mg, 0.019 mmol), VTIL-C1-NH$_2$ (13.6 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-165 was obtained as white solid in TFA salt form (13.8 mg, yield 71%). $^1$H NMR (600 MHz, CD$_3$OD) δ 8.95 (s, 1H), 8.15 (d, J=1.9 Hz, 1H), 8.01 (s, 1H), 7.79 (d, J=1.7 Hz, 1H), 7.72 (dd, J=11.3, 1.7 Hz, 1H), 7.61 (t, J=7.9 Hz, 1H), 7.53-7.45 (m, 3H), 7.43-7.34 (m, 3H), 6.93 (s, 1H), 4.67 (s, 1H), 4.61-4.47 (m, 3H), 4.34 (d, J=15.5 Hz, 1H), 4.16-4.04 (m, 2H), 3.90 (d, J=11.1 Hz, 1H), 3.80 (dd, J=11.0, 3.8 Hz, 1H), 3.56-3.48 (m, 2H), 3.40-3.33 (m, 2H), 2.98 (d, J=11.4 Hz, 5H), 2.46 (s, 3H), 2.25-2.19 (m, 1H), 2.10-2.01 (m, 1H), 1.45 (d, J=6.5 Hz, 6H), 1.05 (s, 9H). HRMS (m/z) for C$_{51}$H$_{58}$F$_4$N$_9$O$_7$S$^+$ [M+H]$^+$: calculated 1016.4111. found 1016.4123.

Example 109: Synthesis of XF056-166

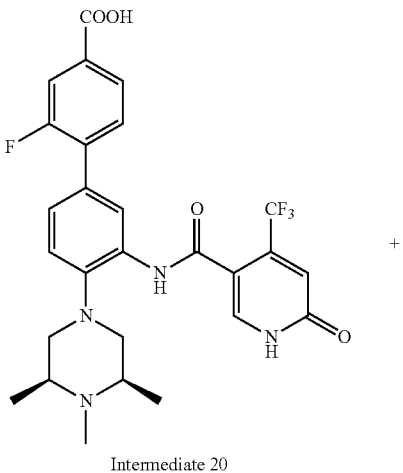

Intermediate 20

-continued

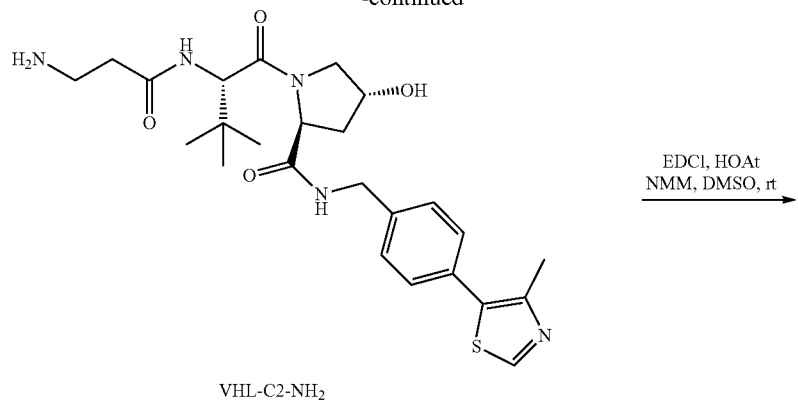

VHL-C2-NH₂

EDCl, HOAt
NMM, DMSO, rt
→

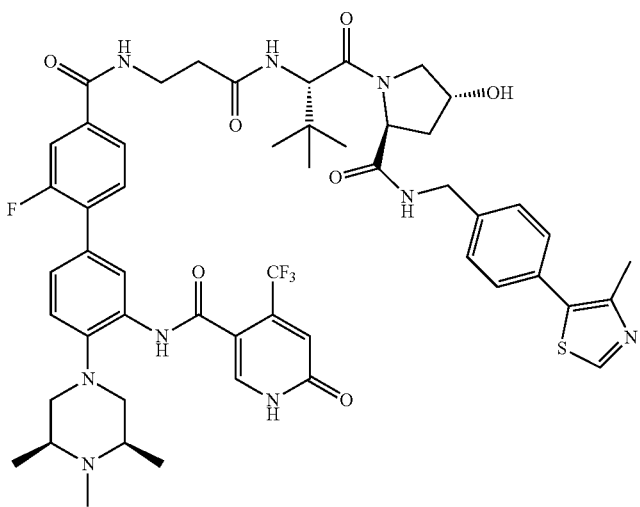

XF056-166

XF056-166 was synthesized following the standard procedures for preparing XF056-157 from intermediate 20 (10.6 mg, 0.019 mmol), VHL-C2-NH₂ (13.9 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-166 was obtained as white solid in TFA salt form (13.2 mg, yield 67%). $^1$H NMR (600 MHz, CD₃OD) δ 8.96 (s, 1H), 8.14 (d, J=1.8 Hz, 1H), 8.00 (s, 1H), 7.78-7.63 (m, 2H), 7.58 (t, J=7.9 Hz, 1H), 7.51-7.42 (m, 3H), 7.42-7.30 (m, 3H), 6.92 (s, 1H), 4.62 (s, 1H), 4.60-4.47 (m, 3H), 4.34 (d, J=15.5 Hz, 1H), 3.94 (d, J=11.0 Hz, 1H), 3.80 (dd, J=11.0, 3.9 Hz, 1H), 3.71 (dt, J=13.4, 6.6 Hz, 1H), 3.63-3.49 (m, 3H), 3.37-3.32 (m, 2H), 3.02-2.92 (m, 5H), 2.67-2.56 (m, 2H), 2.45 (s, 3H), 2.24-2.20 (m, 1H), 2.11-2.02 (m, 1H), 1.44 (dd, J=6.5, 2.9 Hz, 6H), 1.03 (s, 9H). HRMS (m/z) for $C_{52}H_{60}F_4N_9O_7S^+$ [M+H]⁺: calculated 1030.4267. found 1030.4256.

Example 110: Synthesis of XF056-167
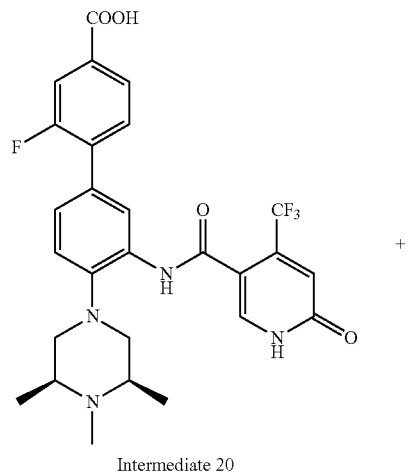
Intermediate 20
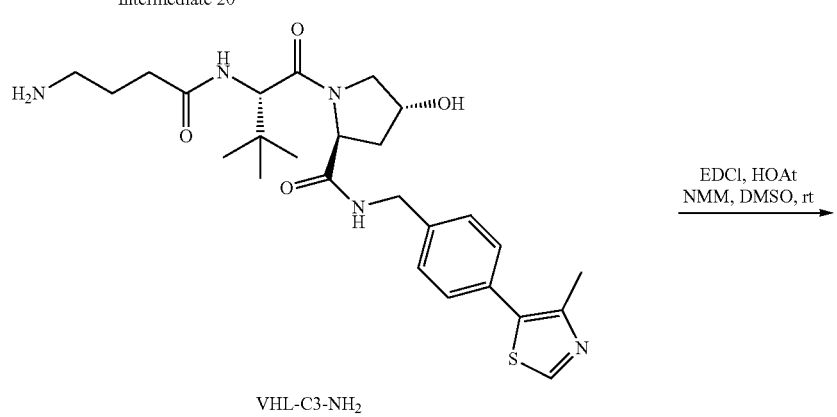
VHL-C3-NH₂
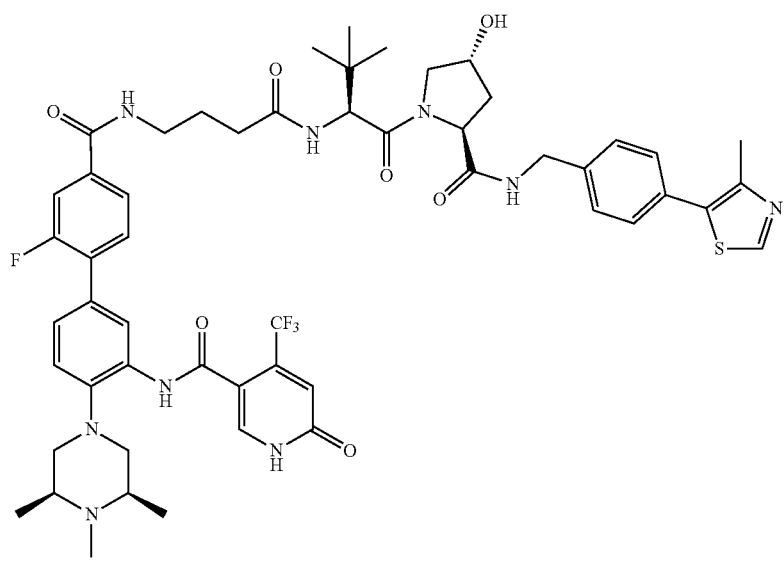
XF056-167

XF056-167 was synthesized following the standard procedures for preparing XF056-157 from intermediate 20 (10.6 mg, 0.019 mmol), VHL-C3-NH$_2$ (14.1 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-167 was obtained as white solid in TFA salt form (11 mg, yield 59%). $^1$H NMR (600 MHz, CD$_3$OD) δ 8.96 (s, 1H), 8.16 (s, 1H), 8.01 (s, 1H), 7.74 (dd, J=8.0, 1.8 Hz, 1H), 7.73-7.66 (m, 1H), 7.60 (t, J=7.9 Hz, 1H), 7.47 (dd, J=9.2, 7.4 Hz, 3H), 7.43-7.33 (m, 3H), 6.93 (s, 1H), 4.64-4.46 (m, 4H), 4.34 (d, J=15.4 Hz, 1H), 3.92 (d, J=11.0 Hz, 1H), 3.81 (dd, J=10.9, 4.0 Hz, 1H), 3.53 (ddd, J=9.9, 6.4, 3.0 Hz, 2H), 3.48-3.36 (m, 2H), 3.35 (d, J=12.7 Hz, 2H), 3.04-2.93 (m, 5H), 2.47 (s, 3H), 2.44-2.35 (m, 2H), 2.25-2.18 (m, 1H), 2.08 (ddd, J=13.3, 9.1, 4.4 Hz, 1H), 1.98-1.86 (m, 2H), 1.45 (d, J=6.5 Hz, 6H), 1.05 (s, 9H). HRMS (m/z) for C$_{53}$H$_{62}$F$_4$N$_9$O$_7$S$^+$ [M+H]$^+$: calculated 1044.4424, found 1044.4413.

Example 111: Synthesis of XF056-168

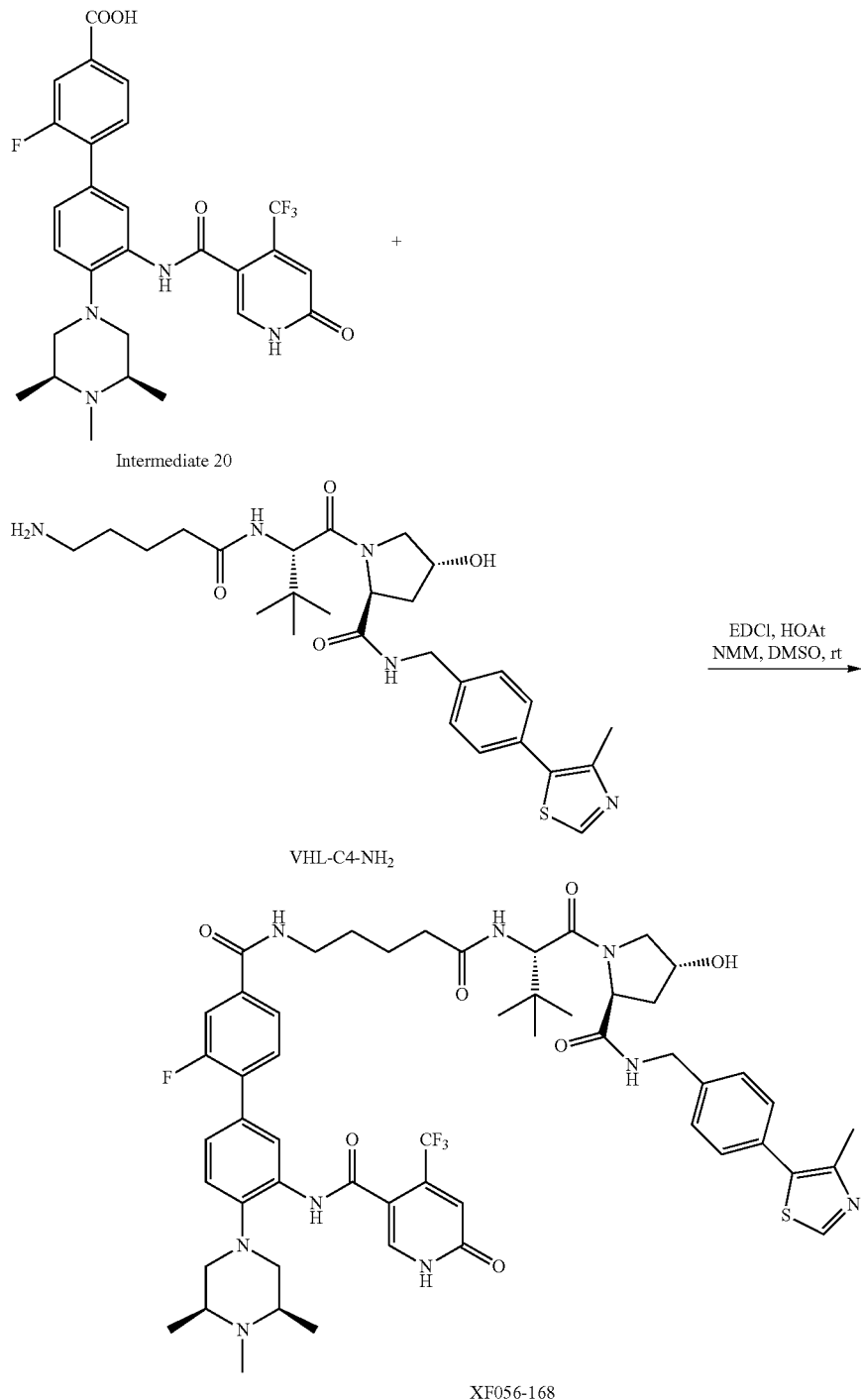

XF056-168 was synthesized following the standard procedures for preparing XF056-157 from intermediate 20 (10.6 mg, 0.019 mmol), VHL-C4-NH$_2$ (10.8 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-168 was obtained as white solid in TFA salt form (10.8 mg, yield 54%). $^1$H NMR (600 MHz, CD$_3$OD) δ 8.96 (s, 1H), 8.15 (s, 1H), 8.01 (s, 1H), 7.73 (dd, J=8.0, 1.8 Hz, 1H), 7.67 (dd, J=11.5, 1.8 Hz, 1H), 7.59 (t, J=7.9 Hz, 1H), 7.52-7.44 (m, 3H), 7.46-7.35 (m, 3H), 6.93 (s, 1H), 4.62 (s, 1H), 4.59-4.46 (m, 3H), 4.38-4.27 (m, 1H), 3.91 (d, J=11.0 Hz, 1H), 3.80 (dd, J=11.0, 3.9 Hz, 1H), 3.52-3.49 (m, 2H), 3.41 (t, J=6.7 Hz, 2H), 3.35 (d, J=12.7 Hz, 2H), 3.02-2.93 (m, 5H), 2.47 (s, 3H), 2.42-2.29 (m, 2H), 2.21-2.17 (m, 1H), 2.07 (ddd, J=13.2, 9.1, 4.5 Hz, 1H), 1.72-1.62 (m, 4H), 1.44 (d, J=6.5 Hz, 6H), 1.03 (s, 9H). HRMS (m/z) for $C_{54}H_{64}F_4N_9O_7S^+$ [M+H]$^+$: calculated 1058.4580, found 1058.4597.

Example 112: Synthesis of XF056-169

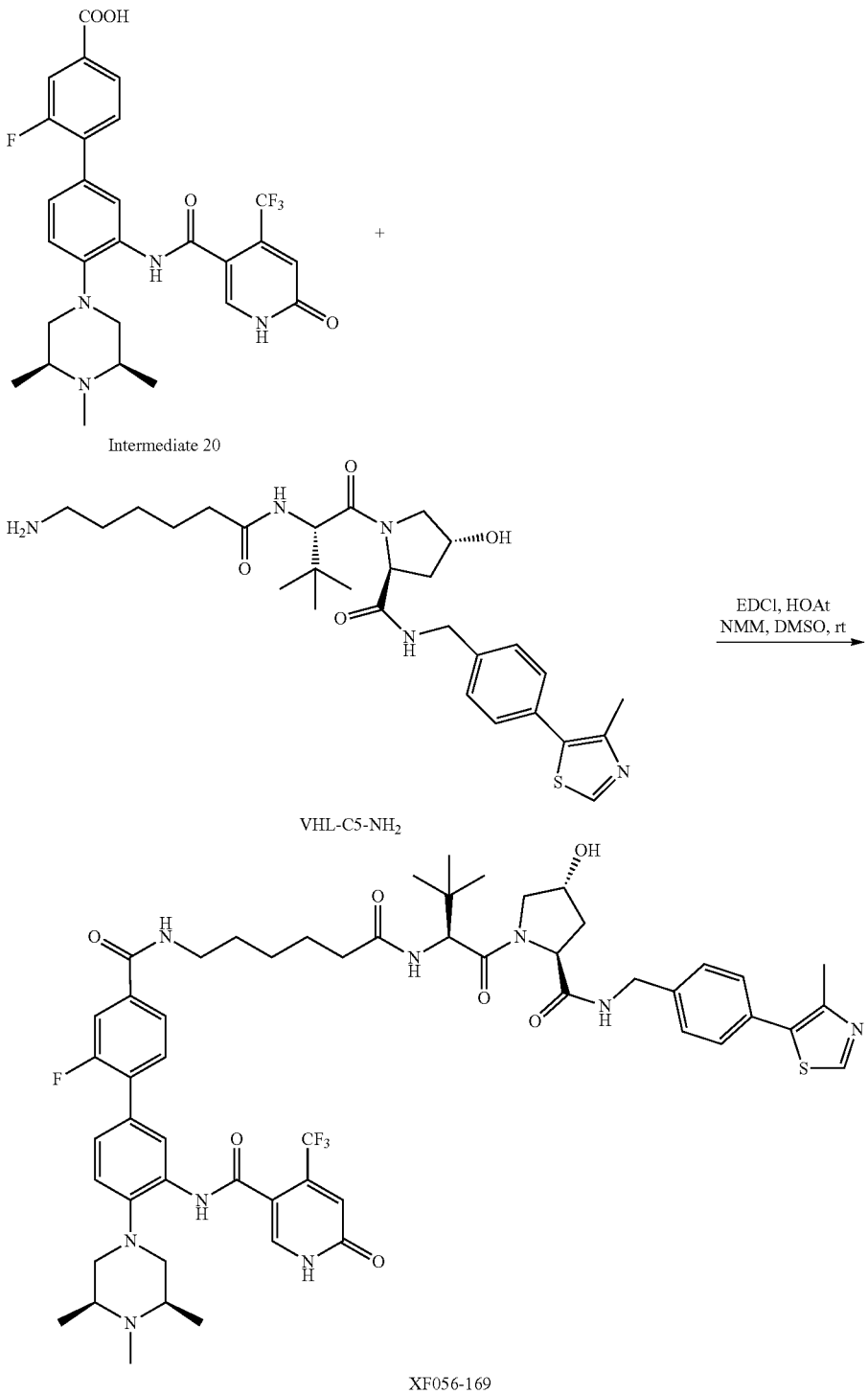

XF056-169 was synthesized following the standard procedures for preparing XF056-157 from intermediate 20 (10.6 mg, 0.019 mmol), VHL-C5-NH$_2$ (11 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-169 was obtained as white solid in TFA salt form (13.2 mg, yield 65%). $^1$H NMR (600 MHz, CD$_3$OD) δ 9.00 (s, 1H), 8.15 (s, 1H), 8.00 (s, 1H), 7.72 (dd, J=8.1, 1.7 Hz, 1H), 7.66 (dd, J=11.4, 1.7 Hz, 1H), 7.58 (t, J=8.0 Hz, 1H), 7.47 (s, 2H), 7.47-7.33 (m, 4H), 6.93 (s, 1H), 4.64-4.54 (m, 2H), 4.56-4.46 (m, 2H), 4.34 (d, J=15.4 Hz, 1H), 3.90 (d, J=11.0 Hz, 1H), 3.79 (dd, J=11.0, 4.0 Hz, 1H), 3.53 (td, J=9.8, 5.0 Hz, 2H), 3.43-3.32 (m, 4H), 3.02-2.90 (m, 5H), 2.47 (s, 3H), 2.37-2.17 (m, 3H), 2.07 (ddd, J=13.3, 9.1, 4.4 Hz, 1H), 1.72-1.60 (m, 4H), 1.47-1.33 (m, 8H), 1.02 (s, 9H). HRMS (m/z) for C$_{55}$H$_{66}$F$_4$N$_9$O$_7$S$^+$ [M+H]$^+$: calculated 1072.4737. found 1072.4734.

Example 113: Synthesis of XF056-170

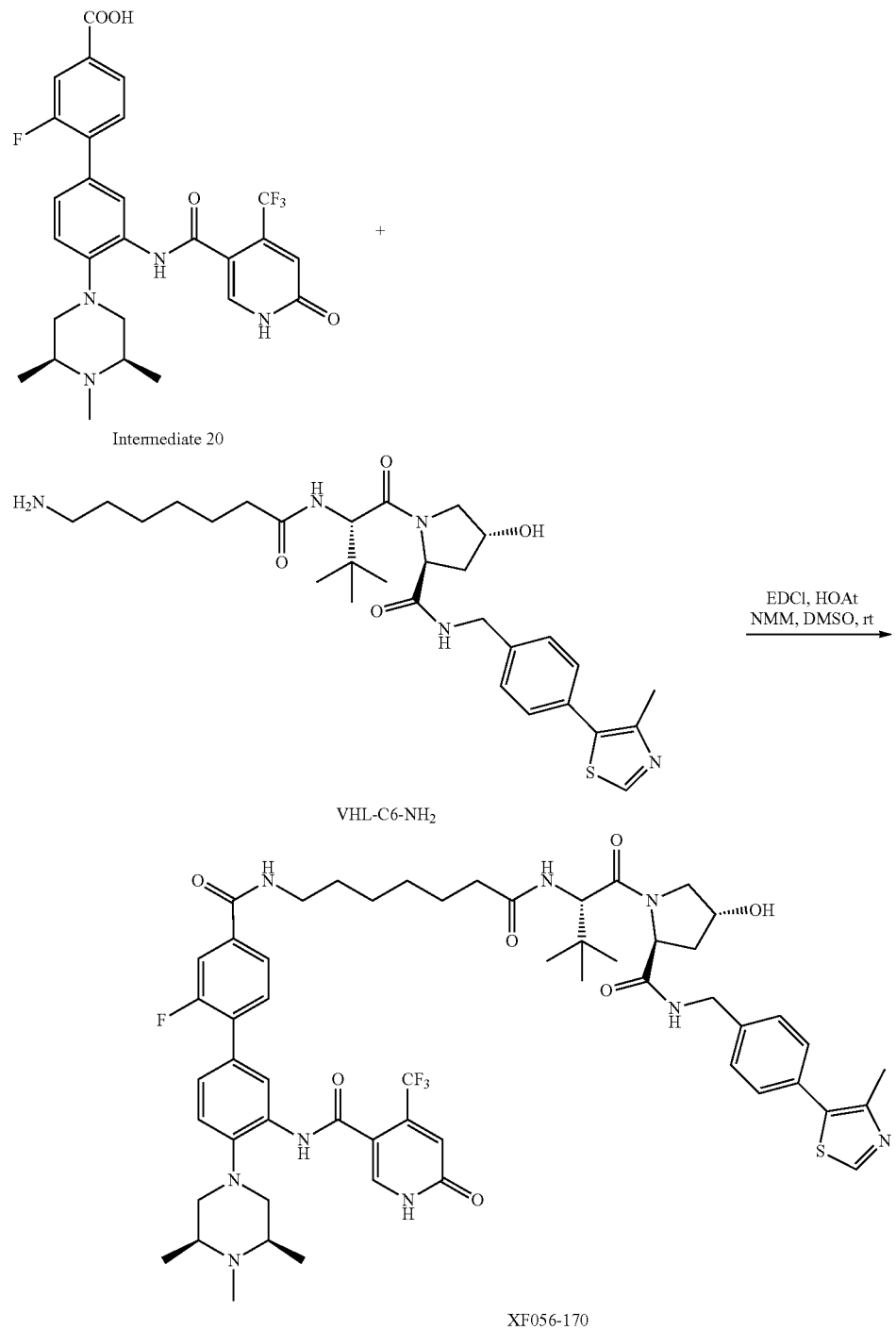

XF056-170 was synthesized following the standard procedures for preparing XF056-157 from intermediate 20 (10.6 mg, 0.019 mmol), VHL-C6-NH$_2$ (11.3 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-170 was obtained as white solid in TFA salt form (13.2 mg, yield 65%). $^1$H NMR (600 MHz, CD$_3$OD) δ 8.91 (s, 1H), 8.15 (s, 1H), 8.01 (s, 1H), 7.71 (dd, J=8.0, 1.7 Hz, 1H), 7.69-7.55 (m, 2H), 7.50-7.43 (m, 3H), 7.43-7.34 (m, 3H), 6.93 (s, 1H), 4.66-4.61 (m, 1H), 4.61-4.54 (m, 1H), 4.54-4.47 (m, 2H), 4.35 (d, J=15.5 Hz, 1H), 3.91 (d, J=11.0 Hz, 1H), 3.80 (dd, J=11.0, 3.9 Hz, 1H), 3.53 (s, 2H), 3.42-3.33 (m, 4H), 3.01-2.93 (m, 5H), 2.46 (s, 3H), 2.28 (hept, J=7.1 Hz, 2H), 2.21 (dd, J=13.2, 7.7 Hz, 1H), 2.11-2.01 (m, 1H), 1.66-1.61 (m, 4H), 1.48-1.34 (m, 10H), 1.03 (s, 9H). HRMS (m/z) for C$_{56}$H$_{68}$F$_4$N$_9$O$_7$S$^+$ [M+H]$^+$: calculated 1086.4893. found 1086.4875.

Example 114: Synthesis of XF056-171

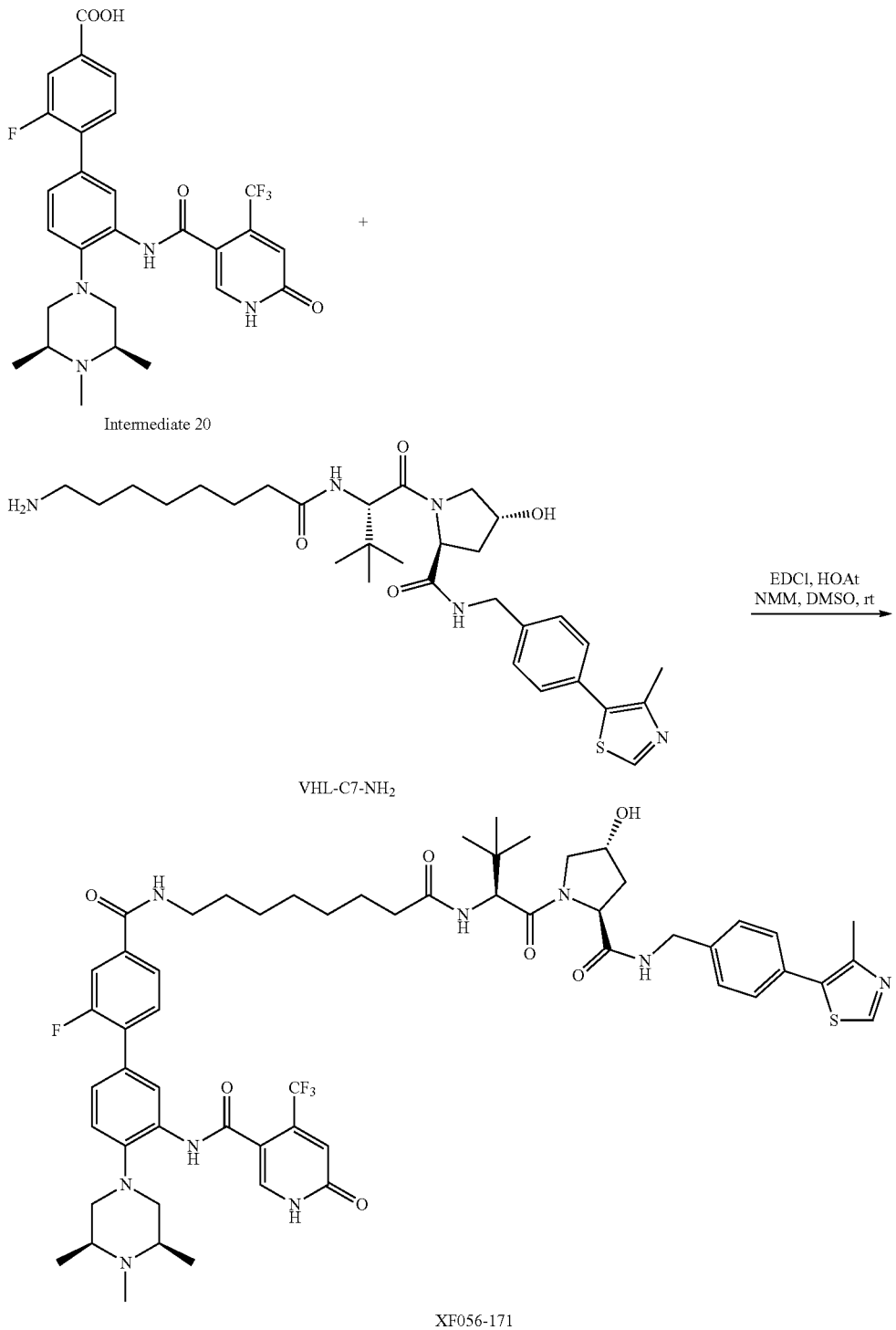

XF056-171

XF056-171 was synthesized following the standard procedures for preparing XF056-157 from intermediate 20 (10.6 mg, 0.019 mmol), VHL-C7-NH$_2$ (15.2 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-171 was obtained as white solid in TFA salt form (13.2 mg, yield 65%). $^1$H NMR (600 MHz, CD$_3$OD) δ 8.95 (s, 1H), 8.15 (s, 1H), 8.01 (s, 1H), 7.70 (dd, J=8.1, 1.7 Hz, 1H), 7.64 (dd, J=11.5, 1.7 Hz, 1H), 7.58 (t, J=7.9 Hz, 1H), 7.48-7.45 (m, 2H), 7.47-7.34 (m, 4H), 6.93 (s, 1H), 4.63 (s, 1H), 4.60-4.46 (m, 3H), 4.35 (d, J=15.5 Hz, 1H), 3.90 (d, J=11.1 Hz, 1H), 3.79 (dd, J=10.9, 3.9 Hz, 1H), 3.56-3.49 (m, 2H), 3.42-3.30 (m, 4H), 2.98 (d, J=7.8 Hz, 5H), 2.46 (s, 3H), 2.34-2.16 (m, 3H), 2.07 (ddd, J=13.3, 9.1, 4.5 Hz, 1H), 1.66-1.58 (m, 4H), 1.48-1.29 (m, 12H), 1.02 (s, 9H). HRMS (m/z) for C$_{57}$H$_{70}$F$_4$N$_9$O$_7$S$^+$ [M+H]$^+$: calculated 1100.5050. found 1100.5034.

Example 115: Synthesis of XF056-172

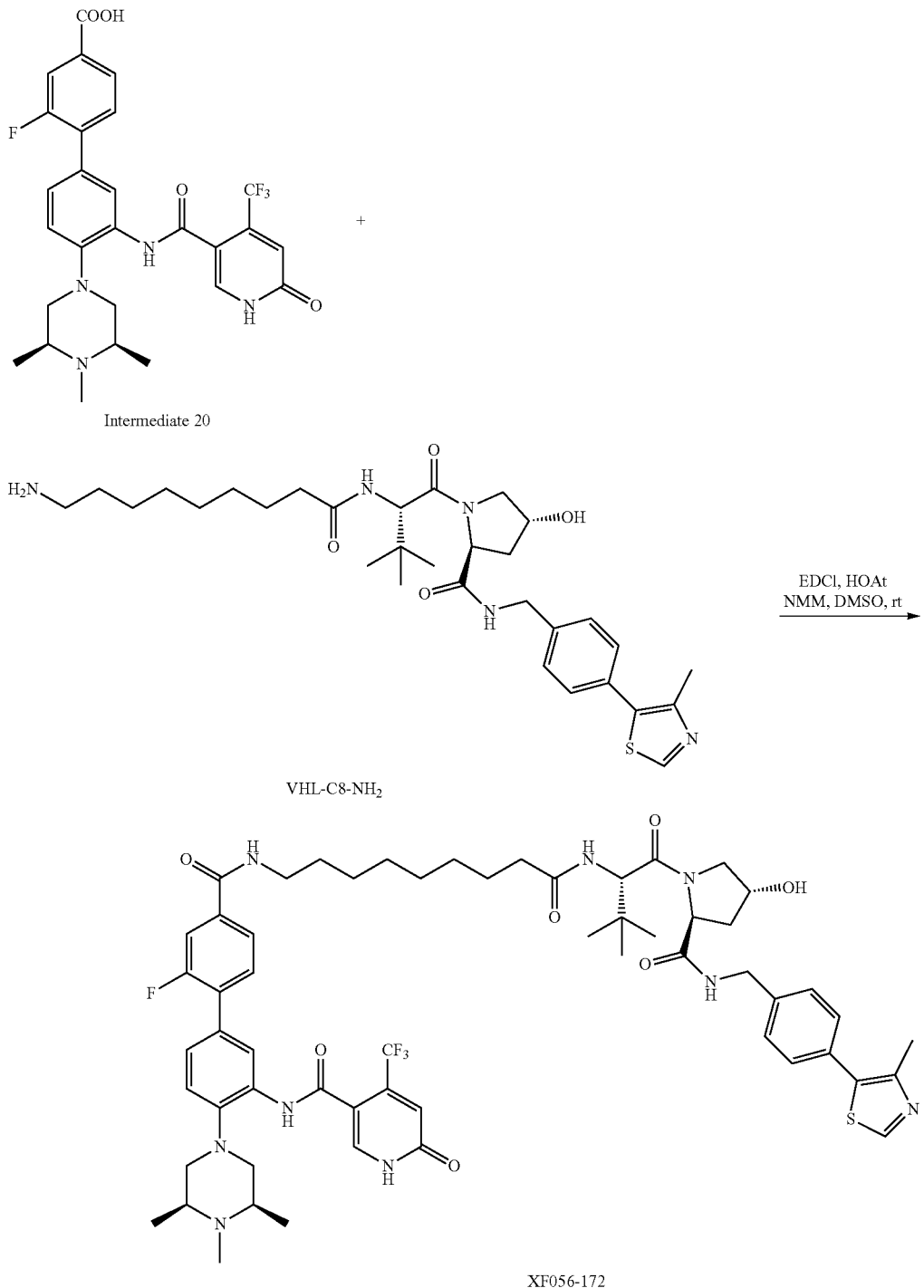

XF056-172

XF056-172 was synthesized following the standard procedures for preparing XF056-157 from intermediate 20 (10.6 mg, 0.019 mmol), VHL-C8-NH$_2$ (11.8 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-172 was obtained as white solid in TFA salt form (10.3 mg, yield 49%). $^1$H NMR (600 MHz, CD$_3$OD) δ 8.93 (s, 1H), 8.15 (s, 1H), 8.01 (s, 1H), 7.71 (dd, J=8.0, 1.7 Hz, 1H), 7.65 (dd, J=11.4, 1.8 Hz, 1H), 7.58 (t, J=7.9 Hz, 1H), 7.50-7.44 (m, 2H), 7.47-7.34 (m, 4H), 6.93 (s, 1H), 4.63 (s, 1H), 4.60-4.46 (m, 3H), 4.35 (d, J=15.5 Hz, 1H), 3.90 (d, J=10.9 Hz, 1H), 3.79 (dd, J=11.0, 3.9 Hz, 1H), 3.53 (s, 2H), 3.41-3.31 (m, 4H), 2.98 (d, J=6.5 Hz, 5H), 2.46 (s, 3H), 2.34-2.18 (m, 3H), 2.07 (ddd, J=13.3, 9.1, 4.5 Hz, 1H), 1.69-1.55 (m, 4H), 1.44 (d, J=6.4 Hz, 6H), 1.36 (s, 8H), 1.02 (s, 9H). HRMS (m/z) for C$_{58}$H$_{72}$F$_4$N$_9$O$_7$S$^+$ [M+H]$^+$: calculated 1114.5206. found 1114.5218.

Example 116: Synthesis of XF056-173

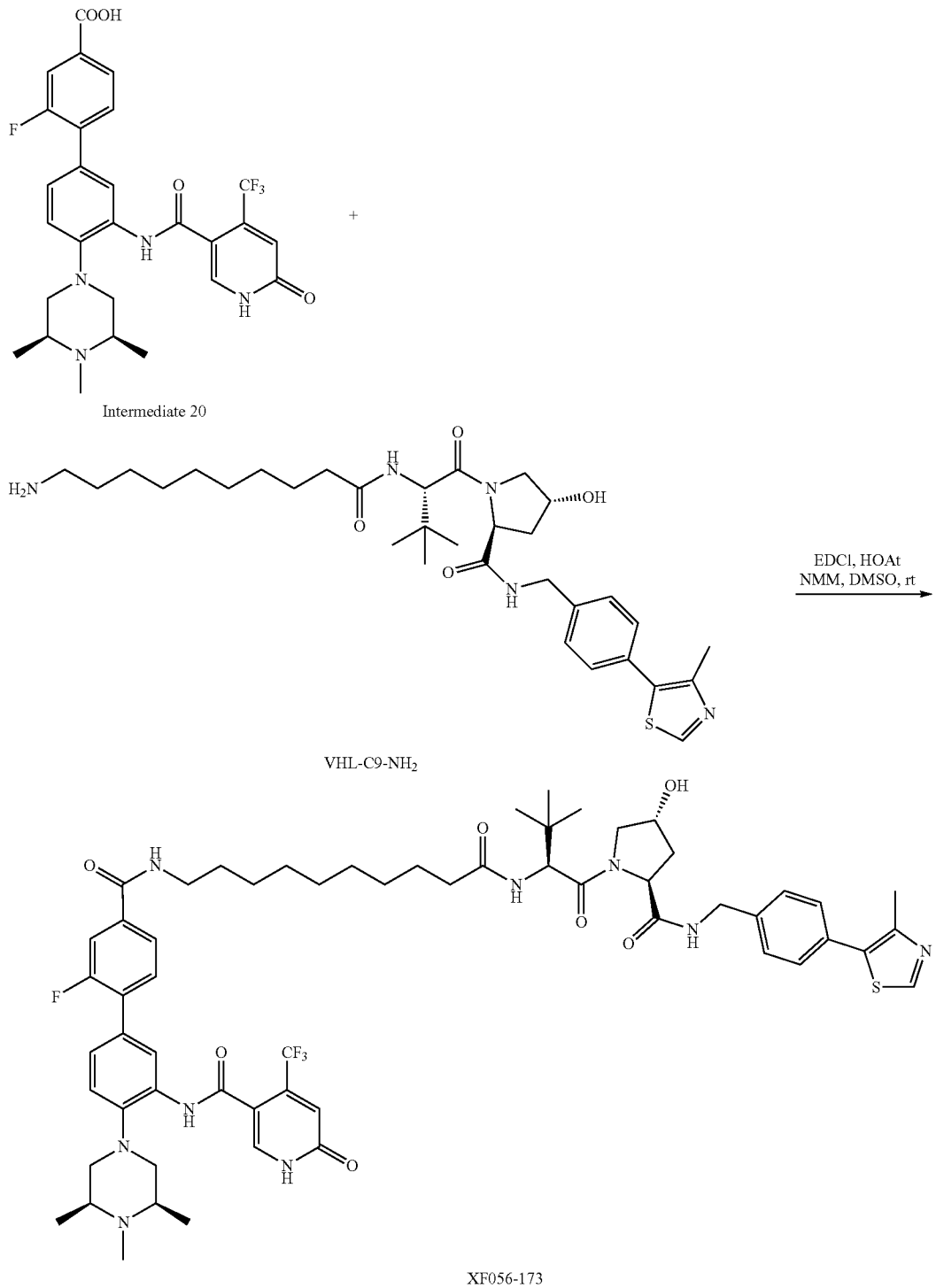

XF056-173 was synthesized following the standard procedures for preparing XF056-157 from intermediate 20 (10.6 mg, 0.019 mmol), VHL-C9-NH$_2$ (15.7 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-173 was obtained as white solid in TFA salt form (11.8 mg, yield 55%). $^1$H NMR (600 MHz, CD$_3$OD) δ 8.99 (s, 1H), 8.15 (s, 1H), 8.01 (s, 1H), 7.75-7.68 (m, 1H), 7.66 (dt, J=11.4, 3.2 Hz, 1H), 7.63-7.56 (m, 1H), 7.51-7.35 (m, 6H), 6.93 (s, 1H), 4.63 (s, 1H), 4.60-4.46 (m, 3H), 4.35 (d, J=15.5 Hz, 1H), 3.93-3.87 (m, 1H), 3.79 (dd, J=11.0, 3.9 Hz, 1H), 3.53 (s, 2H), 3.41-3.32 (m, 4H), 2.98 (d, J=6.2 Hz, 5H), 2.47 (s, 3H), 2.33-2.17 (m, 3H), 2.07 (ddd, J=13.3, 9.1, 4.5 Hz, 1H), 1.65-1.58 (m, 4H), 1.44 (d, J=6.4 Hz, 6H), 1.39-1.32 (m, 10H), 1.02 (s, 9H). HRMS (m/z) for C$_{59}$H$_{74}$F$_4$N$_9$O$_7$S$^+$ [M+H]$^+$: calculated 1128.5363. found 1128.5354.

Example 117: Synthesis of XF056-174

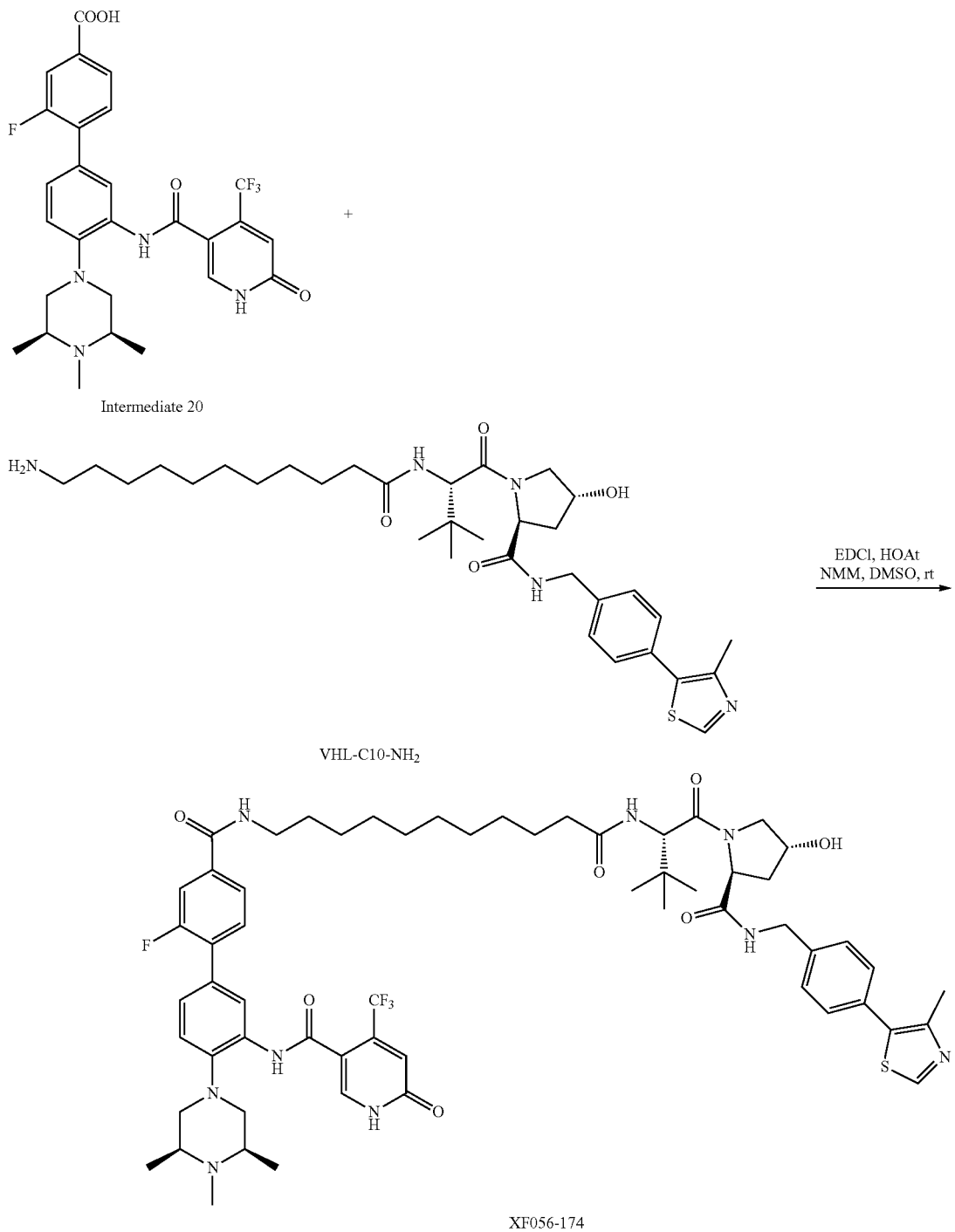

XF056-174 was synthesized following the standard procedures for preparing XF056-157 from intermediate 20 (10.6 mg, 0.019 mmol), VHL-C10-NH$_2$ (12.4 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-174 was obtained as white solid in TFA salt form (19.2 mg, yield 88%). $^1$H NMR (600 MHz, CD$_3$OD) δ 9.00 (s, 1H), 8.17-8.14 (m, 1H), 8.01 (s, 1H), 7.72 (dd, J=8.1, 1.7 Hz, 1H), 7.68-7.62 (m, 1H), 7.59 (t, J=7.9 Hz, 1H), 7.51-7.35 (m, 6H), 6.93 (s, 1H), 4.63 (s, 1H), 4.60-4.46 (m, 3H), 4.35 (d, J=15.5 Hz, 1H), 3.90 (dt, J=11.4, 1.8 Hz, 1H), 3.79 (dd, J=11.0, 3.9 Hz, 1H), 3.53 (ddd, J=10.0, 6.7, 3.1 Hz, 2H), 3.40-3.31 (m, 4H), 3.02-2.94 (m, 5H), 2.48 (s, 3H), 2.33-2.17 (m, 3H), 2.07 (ddd, J=13.3, 9.1, 4.5 Hz, 1H), 1.66-1.57 (m, 4H), 1.44 (d, J=6.5 Hz, 6H), 1.39-1.35 (m, 12H), 1.02 (s, 9H). HRMS (m/z) for C$_{60}$H$_{76}$F$_4$N$_9$O$_7$S$^+$ [M+H]$^+$: calculated 1142.5519. found 1142.5523.

Example 118: Synthesis of XF056-175

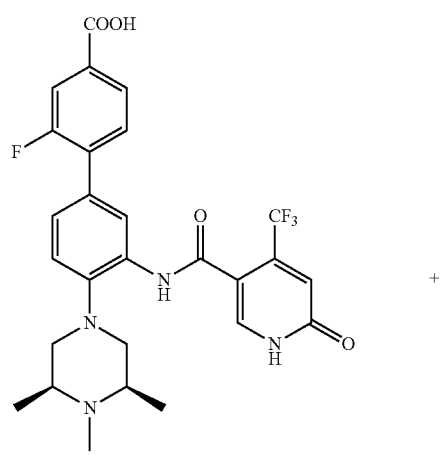

Intermediate 20

+

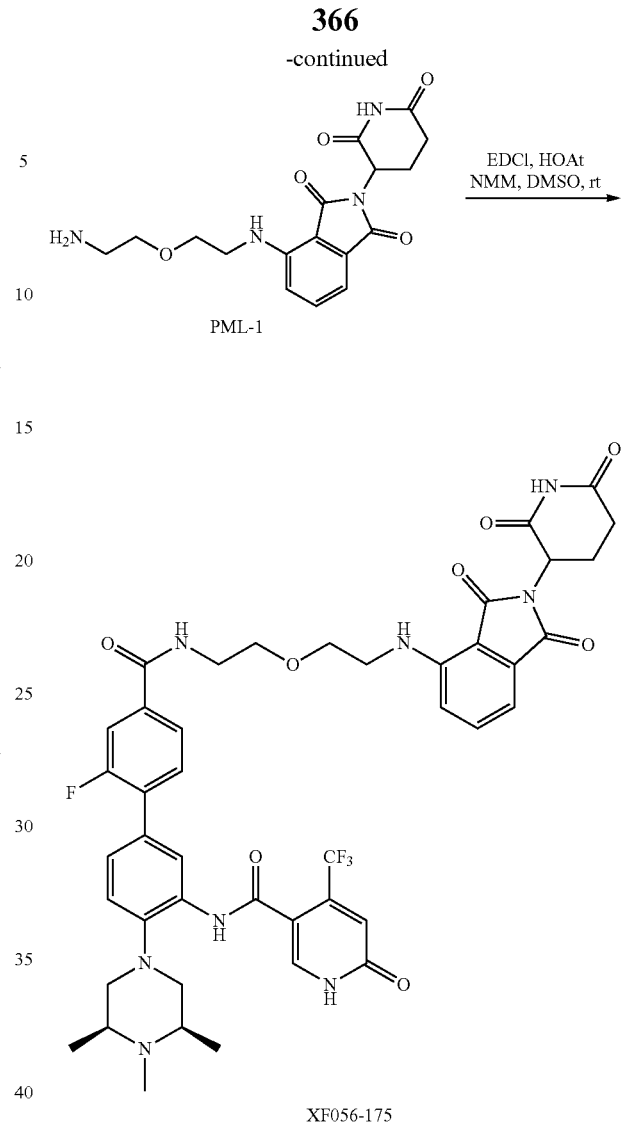

XF056-175

XF056-175 was synthesized following the standard procedures for preparing XF056-157 from intermediate 20 (10.6 mg, 0.019 mmol), PML-1 (9 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-175 was obtained as yellow solid in TFA salt form (7.2 mg, yield 43%). $^1$H NMR (600 MHz, CD$_3$OD) δ 8.12 (s, 1H), 8.06 (s, 1H), 7.66-7.59 (m, 2H), 7.56-7.44 (m, 3H), 7.36 (d, J=8.4 Hz, 1H), 7.06 (d, J=8.6 Hz, 1H), 6.96-6.91 (m, 2H), 4.97-4.83 (m, 1H), 3.77-3.69 (m, 4H), 3.65-3.55 (m, 2H), 3.55-3.48 (m, 4H), 3.40-3.34 (m, 2H), 3.04-2.92 (m, 5H), 2.67-2.53 (m, 3H), 2.00-1.94 (m, 1H), 1.45 (dd, J=6.4, 1.2 Hz, 6H). HRMS (m/z) for C$_{44}$H$_{45}$F$_4$N$_8$O$_8$$^+$ [M+H]$^+$: calculated 889.3291. found 889.3277.

Example 119: Synthesis of XF056-176

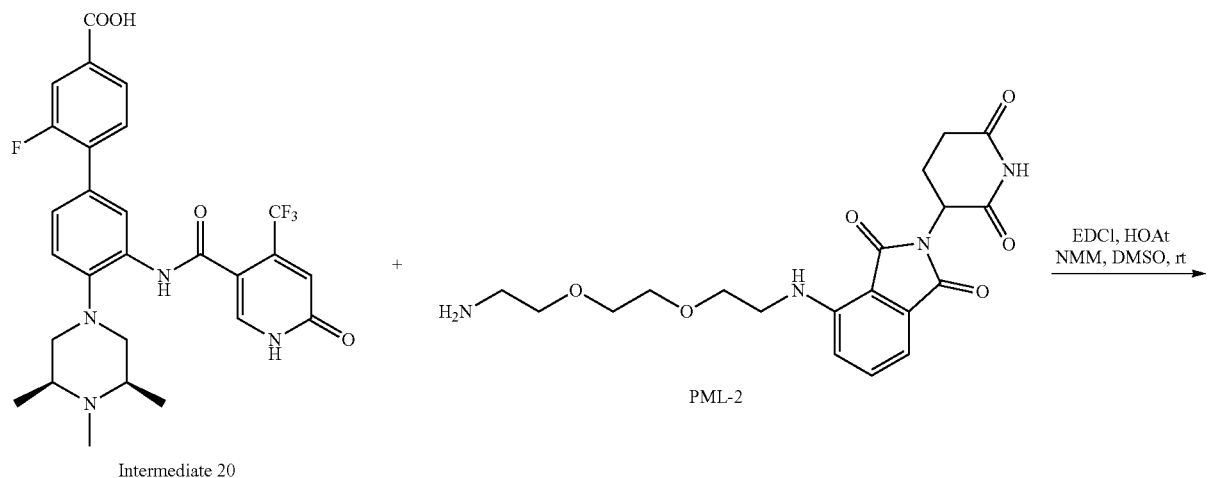

Intermediate 20

PML-2

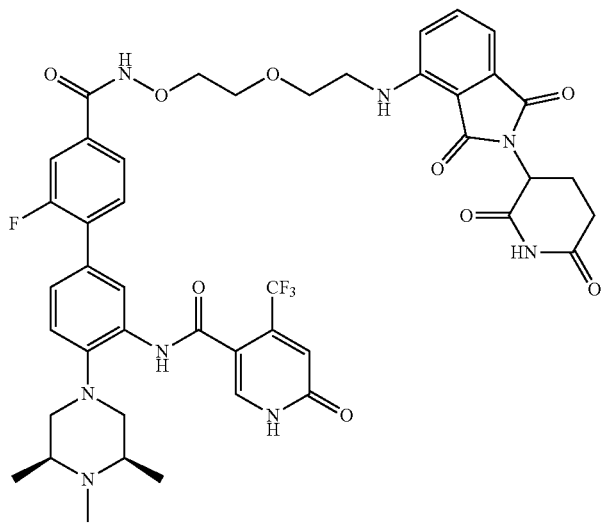

XF056-176

XF056-176 was synthesized following the standard procedures for preparing XF056-157 from intermediate 20 (10.6 mg, 0.019 mmol), PML-2 (9.8 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-176 was obtained as yellow solid in TFA salt form (12.2 mg, yield 68%). $^1$H NMR (600 MHz, CD$_3$OD) δ 8.08 (s, 1H), 8.03 (s, 1H), 7.66 (dd, J=8.0, 1.7 Hz, 1H), 7.60 (dd, J=11.5, 1.7 Hz, 1H), 7.49-7.38 (m, 3H), 7.33 (d, J=8.4 Hz, 1H), 6.98-6.89 (m, 3H), 5.00 (dd, J=12.7, 5.5 Hz, 1H), 3.77-3.66 (m, 8H), 3.59 (q, J=5.3 Hz, 2H), 3.52 (d, J=9.2 Hz, 2H), 3.41 (t, J=5.2 Hz, 2H), 3.34 (dd, J=12.5, 2.2 Hz, 2H), 3.01-2.92 (m, 5H), 2.85-2.76 (m, 1H), 2.73-2.59 (m, 2H), 2.09-2.02 (m, 1H), 1.44 (dd, J=6.5, 1.9 Hz, 6H). HRMS (m/z) for C$_{46}$H$_{49}$F$_4$N$_8$O$_9{}^+$ [M+H]$^+$: calculated 933.3553. found 933.3521.

Example 120: Synthesis of XF056-177
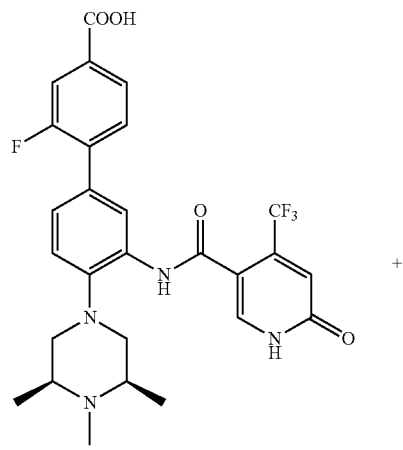
Intermediate 20
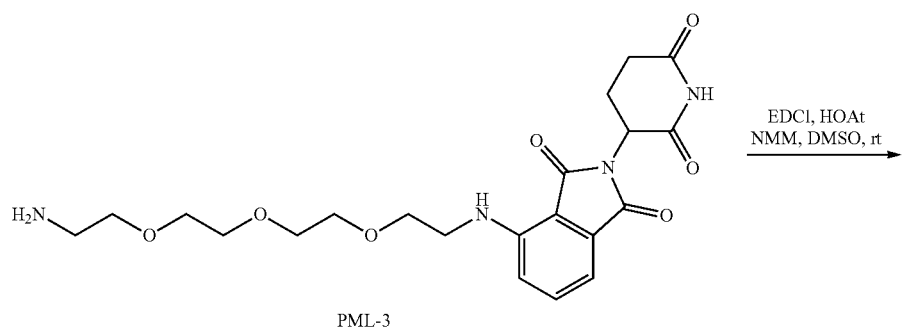
PML-3
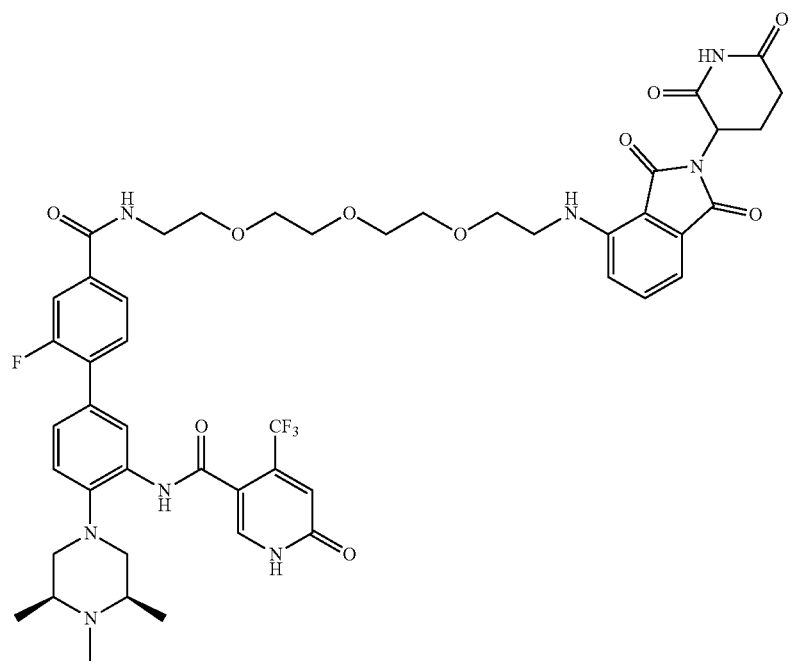
XF056-177

XF056-177 was synthesized following the standard procedures for preparing XF056-157 from intermediate 20 (10.6 mg, 0.019 mmol), PML-3 (10.7 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-177 was obtained as yellow solid in TFA salt form (11.7 mg, yield 63%). $^1$H NMR (600 MHz, CD$_3$OD) δ 8.09 (d, J=1.9 Hz, 1H), 8.00 (s, 1H), 7.72 (dd, J=8.1, 1.8 Hz, 1H), 7.66 (dd, J=11.6, 1.8 Hz, 1H), 7.56 (t, J=7.9 Hz, 1H), 7.46-7.38 (m, 2H), 7.29 (d, J=8.4 Hz, 1H), 6.96-6.90 (m, 3H), 5.02 (dd, J=12.7, 5.5 Hz, 1H), 3.68-3.58 (m, 12H), 3.58 (t, J=5.2 Hz, 2H), 3.54-3.44 (m, 2H), 3.40-3.33 (m, 2H), 3.33-3.27 (m, 2H), 3.00-2.89 (m, 5H), 2.88-2.78 (m, 1H), 2.75-2.62 (m, 2H), 2.10-2.02 (m, 1H), 1.47-1.41 (m, 6H). HRMS (m/z) for $C_{48}H_{53}F_4N_8O_{10}^+$ [M+H]$^+$: calculated 977.3815. found 977.3803.

Example 121: Synthesis of XF056-178

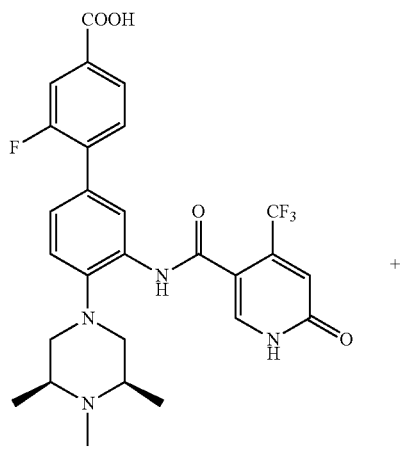

Intermediate 20

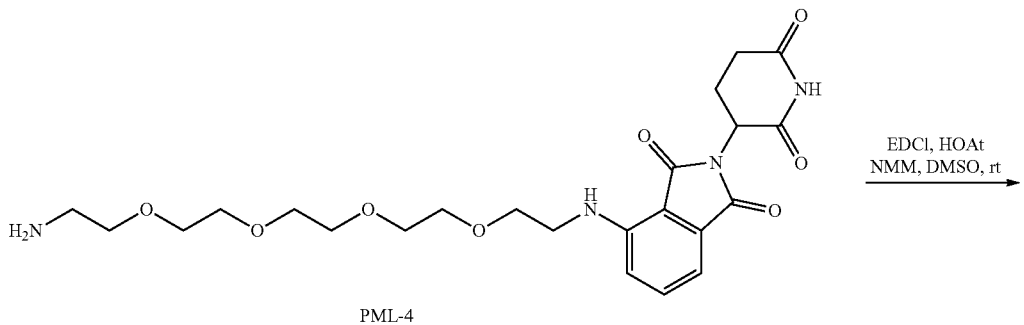

PML-4

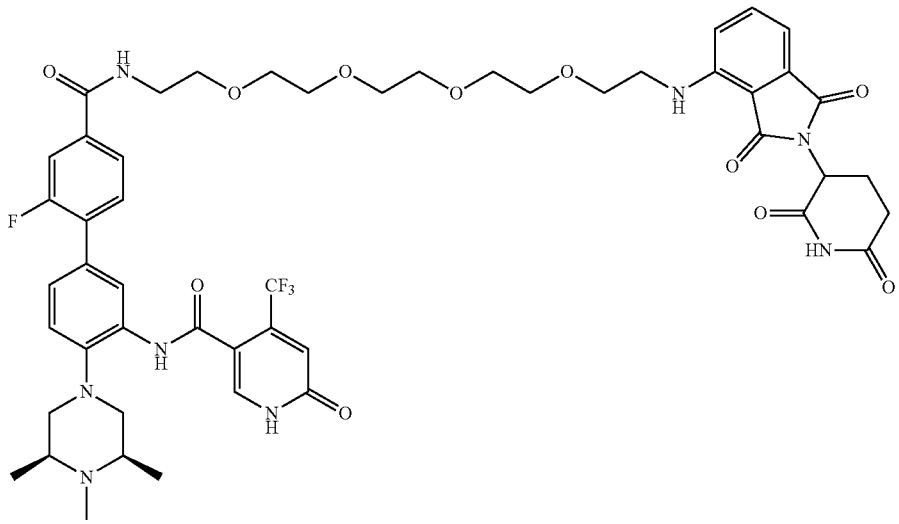

XF056-178

XF056-178 was synthesized following the standard procedures for preparing XF056-157 from intermediate 20 (10.6 mg, 0.019 mmol), PML-4 (10.7 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-178 was obtained as yellow solid in TFA salt form (7 mg, yield 36%). $^1$H NMR (600 MHz, CD$_3$OD) δ 8.12 (d, J=1.7 Hz, 1H), 8.00 (s, 1H), 7.74 (dd, J=8.0, 1.7 Hz, 1H), 7.68 (dd, J=11.5, 1.7 Hz, 1H), 7.59 (t, J=7.9 Hz, 1H), 7.49-7.40 (m, 2H), 7.31 (d, J=8.4 Hz, 1H), 6.98 (dd, J=7.8, 2.4 Hz, 2H), 6.92 (s, 1H), 5.02 (dd, J=12.8, 5.4 Hz, 1H), 3.69-3.55 (m, 18H), 3.50 (s, 2H), 3.39 (t, J=5.4 Hz, 2H), 3.36-3.28 (m, 2H), 3.01-2.89 (m, 5H), 2.87-2.78 (m, 1H), 2.75-2.62 (m, 2H), 2.10-2.02 (m, 1H), 1.44 (dd, J=6.5, 3.4 Hz, 6H). HRMS (m/z) for $C_{50}H_{57}F_4N_8O_{11}^+$ [M+H]$^+$: calculated 1021.4077. found 1021.4082.

Example 122: Synthesis of XF056-179

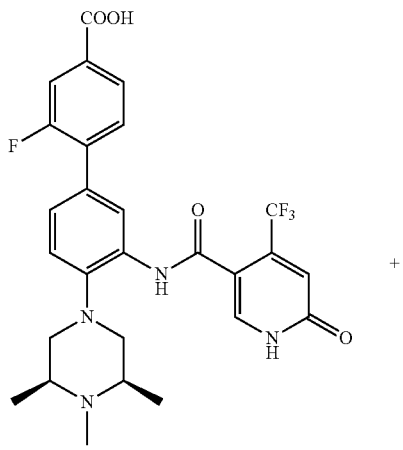

Intermediate 20

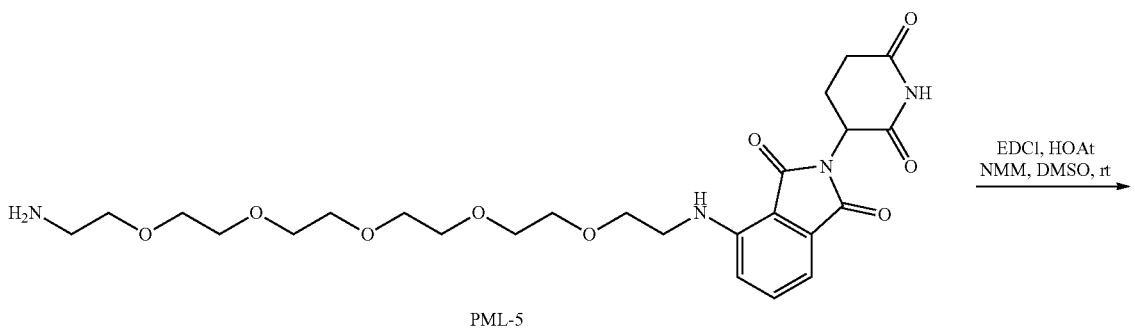

PML-5

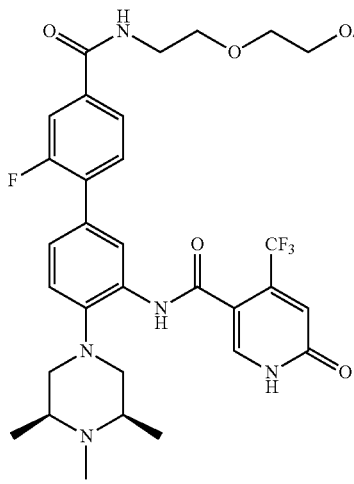

XF056-179

XF056-179 was synthesized following the standard procedures for preparing XF056-157 from intermediate 20 (10.6 mg, 0.019 mmol), PML-5 (11.6 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-179 was obtained as yellow solid in TFA salt form (10.2 mg, yield 50%). $^1$H NMR (600 MHz, CD$_3$OD) δ 8.13 (d, J=1.8 Hz, 1H), 8.00 (s, 1H), 7.74 (dd, J=8.0, 1.7 Hz, 1H), 7.68 (dd, J=11.5, 1.7 Hz, 1H), 7.59 (t, J=7.9 Hz, 1H), 7.51-7.41 (m, 2H), 7.32 (d, J=8.4 Hz, 1H), 6.99 (t, J=7.9 Hz, 2H), 6.92 (s, 1H), 5.02 (dd, J=12.8, 5.4 Hz, 1H), 3.70-3.54 (m, 20H), 3.55-3.46 (m, 2H), 3.53-3.47 (m, 2H), 3.41 (t, J=5.3 Hz, 2H), 3.35-3.29 (m, 2H), 2.99-2.90 (m, 5H), 2.87-2.78 (m, 1H), 2.75-2.63 (m, 2H), 2.11-2.03 (m, 1H), 1.43 (dd, J=6.5, 2.2 Hz, 6H). HRMS (m/z) for C$_{52}$H$_{61}$F$_4$N$_8$O$_{12}$$^+$ [M+H]$^+$: calculated 1065.4340. found 1065.4358.

Example 123: Synthesis of XF056-180

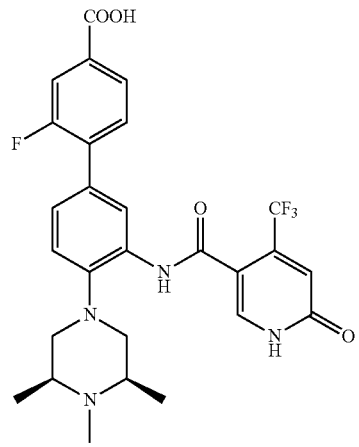

Intermediate 20

+

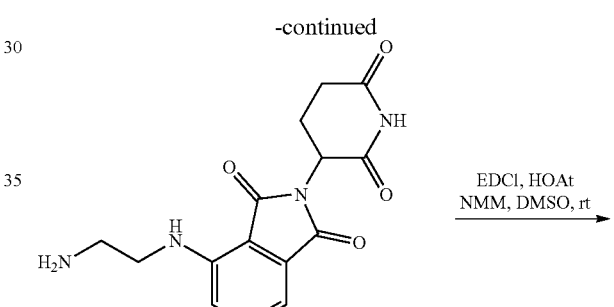

PML-13

$\xrightarrow{\text{EDCl, HOAt}}_{\text{NMM, DMSO, rt}}$

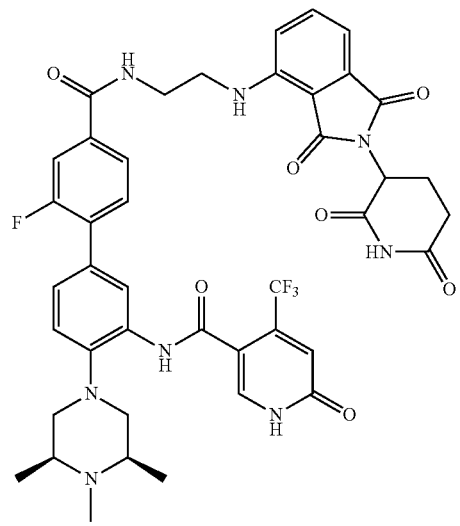

XF056-180

XF056-180 was synthesized following the standard procedures for preparing XF056-157 from intermediate 20 (10.6 mg, 0.019 mmol), PML-13 (8.2 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-180 was obtained as yellow solid in TFA salt form (6.3 mg, yield 39%). $^1$H NMR (600 MHz, CD$_3$OD) δ 8.14 (s, 1H), 8.01 (s, 1H), 7.68 (dd, J=8.0, 1.7 Hz, 1H), 7.63 (dd, J=11.4, 1.8 Hz, 1H), 7.58 (t, J=7.9 Hz, 1H), 7.53 (dd, J=8.6, 7.1 Hz, 1H), 7.48 (dt, J=8.3, 1.9 Hz, 1H), 7.36 (d, J=8.4 Hz, 1H), 7.19 (d, J=8.6 Hz, 1H), 7.04 (d, J=7.0 Hz, 1H), 6.93 (s, 1H), 5.05 (dd, J=12.5, 5.5 Hz, 1H), 3.66-3.58 (m, 4H), 3.51 (q, J=5.3, 3.1 Hz, 2H), 3.34 (d, J=13.0 Hz, 2H), 3.02-2.93 (m, 5H), 2.88-2.80 (m, 1H), 2.75-2.64 (m, 2H), 2.09 (dd, J=10.5, 5.2 Hz, 1H), 1.44 (d, J=6.5 Hz, 6H). HRMS (m/z) for $C_{42}H_{41}F_4N_8O_7^+$ [M+H]$^+$: calculated 845.3029. found 845.3045.

Example 124: Synthesis of XF056-181

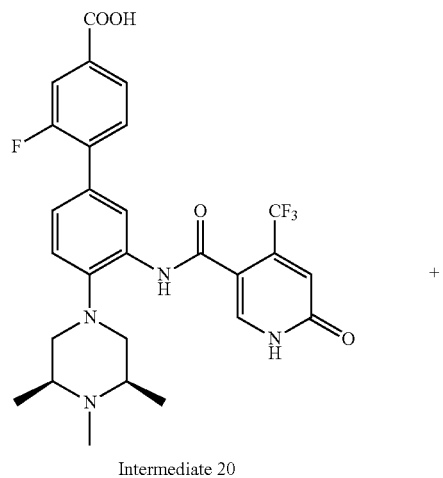

Intermediate 20

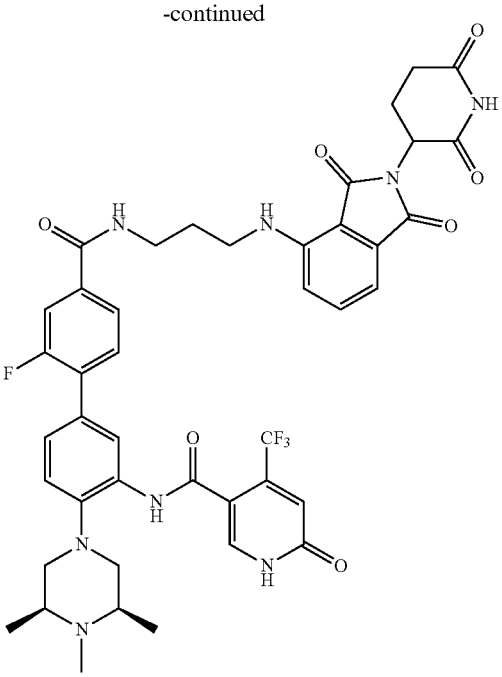

XF056-181

XF056-181 was synthesized following the standard procedures for preparing XF056-157 from intermediate 20 (10.6 mg, 0.019 mmol), PML-14 (8.4 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-181 was obtained as yellow solid in TFA salt form (11.5 mg, yield 70%). $^1$H NMR (600 MHz, CD$_3$OD) δ 8.14 (s, 1H), 8.03 (s, 1H), 7.71-7.60 (m, 2H), 7.60-7.45 (m, 3H), 7.36 (d, J=8.4 Hz, 1H), 7.03 (dd, J=27.7, 7.8 Hz, 2H), 6.92 (s, 1H), 5.00 (dd, J=12.5, 5.5 Hz, 1H), 3.56-3.48 (m, 4H), 3.44 (t, J=6.6 Hz, 2H), 3.37-3.31 (m, 2H), 3.01-2.93 (m, 5H), 2.84-2.75 (m, 1H), 2.71-2.60 (m, 2H), 2.08-1.92 (m, 3H), 1.44 (dd, J=6.6, 1.1 Hz, 6H). HRMS (m/z) for $C_{43}H_{43}F_4N_8O_7^+$ [M+H]$^+$: calculated 859.3185, found 859.3167.

Example 125: Synthesis of XF056-182

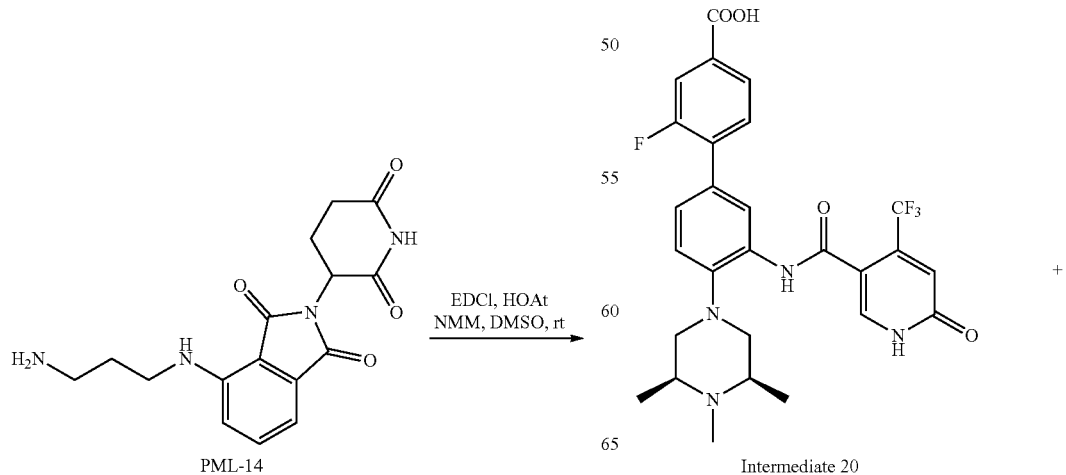

PML-14    Intermediate 20

Example 126: Synthesis of XF056-183

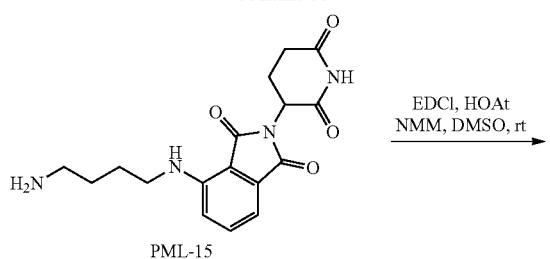

PML-15

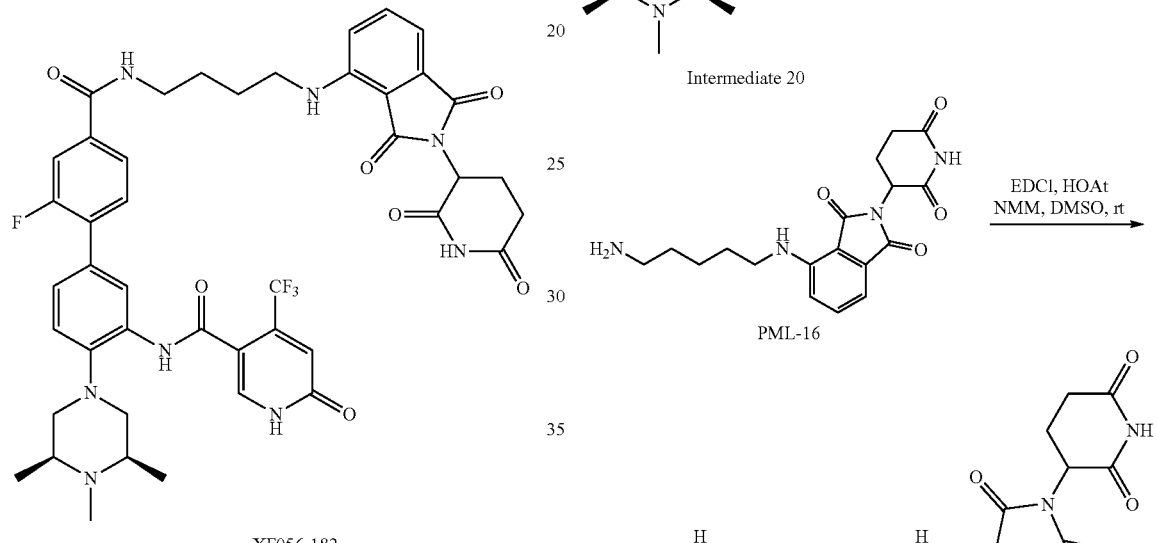

XF056-182

XF056-182 was synthesized following the standard procedures for preparing XF056-157 from intermediate 20 (10.6 mg, 0.019 mmol), PML-15 (8.7 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-182 was obtained as yellow solid in TFA salt form (13.4 mg, yield 81%). $^1$H NMR (600 MHz, CD$_3$OD) δ 8.14 (s, 1H), 8.01 (s, 1H), 7.68 (dd, J=8.1, 1.7 Hz, 1H), 7.63 (dd, J=11.4, 1.8 Hz, 1H), 7.57 (t, J=7.9 Hz, 1H), 7.53-7.45 (m, 2H), 7.36 (d, J=8.4 Hz, 1H), 7.01 (dd, J=26.6, 7.8 Hz, 2H), 6.92 (s, 1H), 5.03 (dd, J=12.5, 5.5 Hz, 1H), 3.57-3.48 (m, 2H), 3.44 (q, J=5.7, 4.7 Hz, 2H), 3.40-3.31 (m, 4H), 3.04-2.90 (m, 5H), 2.88-2.77 (m, 1H), 2.76-2.64 (m, 2H), 2.12-2.01 (m, 1H), 1.78-1.72 (m, 4H), 1.44 (d, J=6.5 Hz, 6H). HRMS (m/z) for C$_{44}$H$_{45}$F$_4$N$_8$O$_7^+$ [M+H]$^+$: calculated 873.3342. found 873.3314.

XF056-183 was synthesized following the standard procedures for preparing XF056-157 from intermediate 20 (10.6 mg, 0.019 mmol), PML-16 (9 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-183 was obtained as yellow solid in TFA salt form (13.1 mg, yield 78%). ¹H NMR (600 MHz, CD₃OD) δ 8.14 (s, 1H), 8.03 (s, 1H), 7.69-7.53 (m, 3H), 7.53-7.45 (m, 2H), 7.36 (d, J=8.4 Hz, 1H), 7.00 (dd, J=27.0, 7.8 Hz, 2H), 6.93 (s, 1H), 4.99 (dd, J=12.6, 5.5 Hz, 1H), 3.53 (s, 2H), 3.48-3.38 (m, 2H), 3.40-3.32 (m, 4H), 3.02-2.94 (m, 5H), 2.84-2.71 (m, 1H), 2.70-2.59 (m, 2H), 2.06-1.99 (m, 1H), 1.77-1.66 (m, 4H), 1.57-1.49 (m, 2H), 1.44 (d, J=6.5 Hz, 6H). HRMS (m/z) for $C_{45}H_{47}F_4N_8O_7^+$ [M+H]⁺: calculated 887.3498. found 887.3507.

Example 127: Synthesis of XF056-184

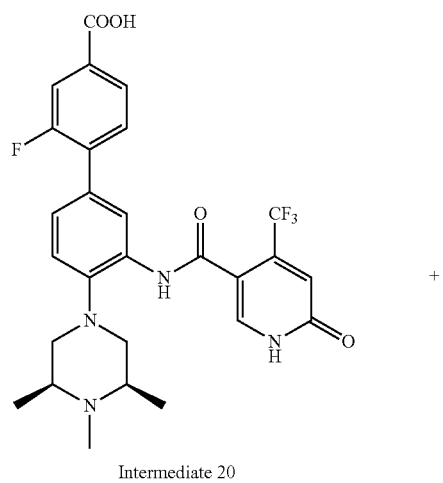

Intermediate 20

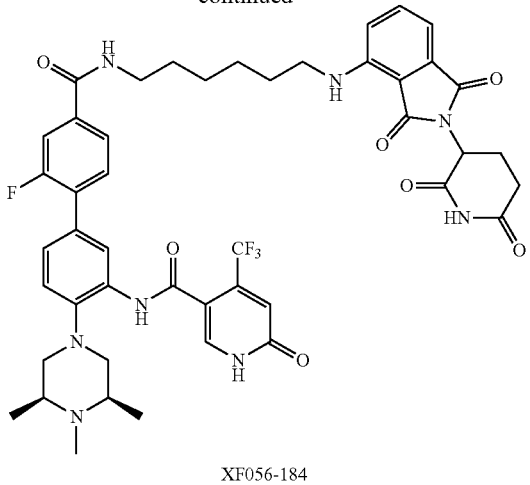

XF056-184

XF056-184 was synthesized following the standard procedures for preparing XF056-157 from intermediate 20 (10.6 mg, 0.019 mmol), PML-17 (7.8 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-184 was obtained as yellow solid in TFA salt form (9.5 mg, yield 55%). ¹H NMR (600 MHz, CD₃OD) δ 8.14 (s, 1H), 8.01 (s, 1H), 7.70 (dd, J=8.0, 1.7 Hz, 1H), 7.64 (dd, J=11.5, 1.7 Hz, 1H), 7.57 (t, J=7.9 Hz, 1H), 7.54-7.45 (m, 2H), 7.36 (d, J=8.4 Hz, 1H), 7.03-6.97 (m, 2H), 6.93 (s, 1H), 5.06-5.00 (m, 1H), 3.52 (dd, J=9.9, 3.1 Hz, 2H), 3.42-3.27 (m, 6H), 3.05-2.92 (m, 5H), 2.88-2.78 (m, 1H), 2.76-2.64 (m, 2H), 2.12-2.04 (m, 1H), 1.77-1.68 (m, 4H), 1.54-1.40 (m, 10H). HRMS (m/z) for $C_{46}H_{49}F_4N_8O_7^+$ [M+H]⁺: calculated 901.3665. found 901.3642.

Example 128: Synthesis of XF056-185

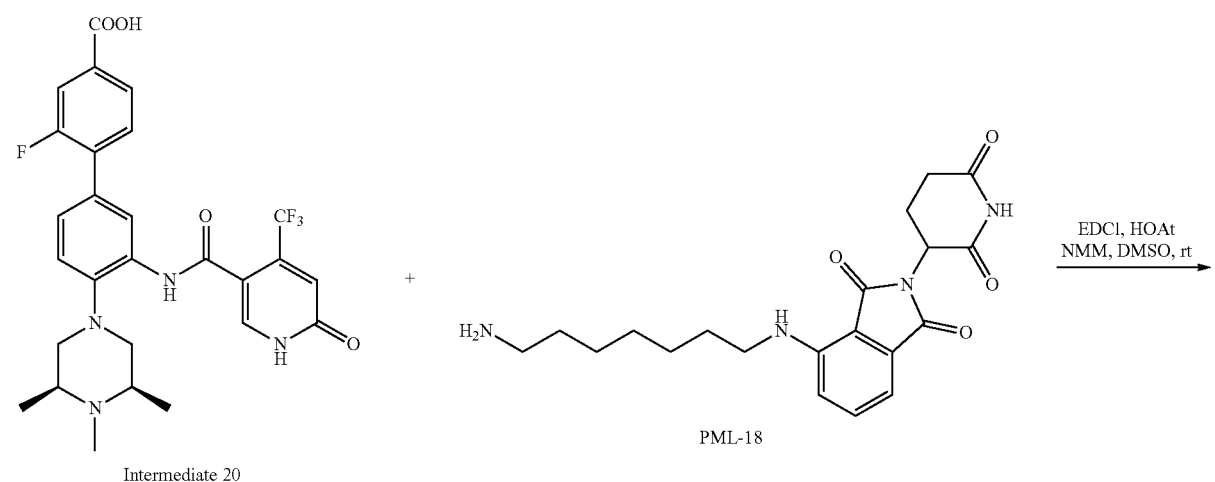

Intermediate 20     PML-18

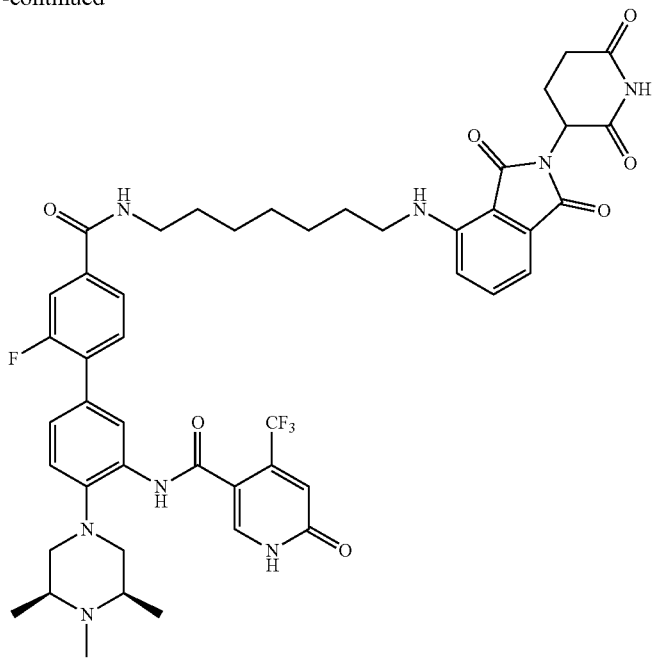

XF056-185

XF056-185 was synthesized following the standard procedures for preparing XF056-157 from intermediate 20 (10.6 mg, 0.019 mmol), PML-18 (9.5 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-185 was obtained as yellow solid in TFA salt form (9.3 mg, yield 53%). $^1$H NMR (600 MHz, CD$_3$OD) δ 8.14 (d, J=1.8 Hz, 1H), 8.01 (s, 1H), 7.70 (dd, J=8.0, 1.7 Hz, 1H), 7.65 (dd, J=11.5, 1.8 Hz, 1H), 7.58 (t, J=7.9 Hz, 1H), 7.54-7.45 (m, 2H), 7.36 (d, J=8.4 Hz, 1H), 7.00 (t, J=7.4 Hz, 2H), 6.93 (s, 1H), 5.02 (dd, J=12.4, 5.5 Hz, 1H), 3.54-3.51 (m, 2H), 3.42-3.28 (m, 6H), 2.98-2.89 (m, 5H), 2.82 (ddd, J=18.2, 14.4, 5.4 Hz, 1H), 2.75-2.63 (m, 2H), 2.11-2.03 (m, 1H), 1.66-160 (m, 7.2 Hz, 4H), 1.47-1.42 (m, 12H). HRMS (m/z) for $C_{47}H_{51}F_4N_8O_7^+$ [M+H]$^+$: calculated 915.3811. found 915.3836.

Example 129: Synthesis of XF056-186

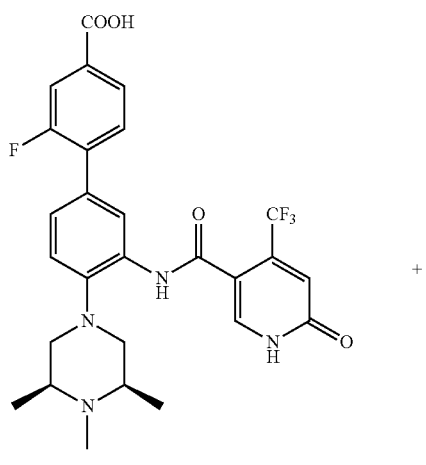

Intermediate 20

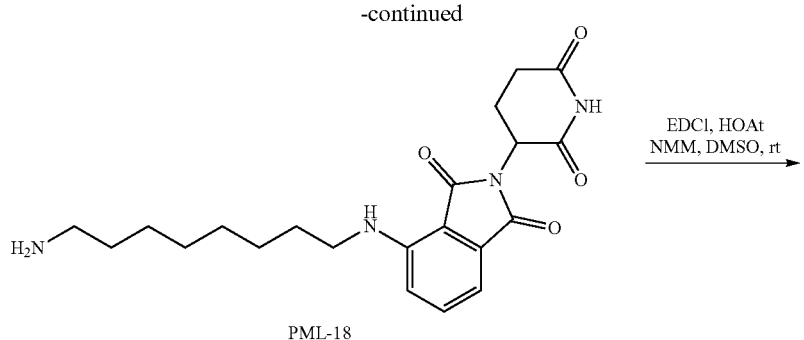

PML-18

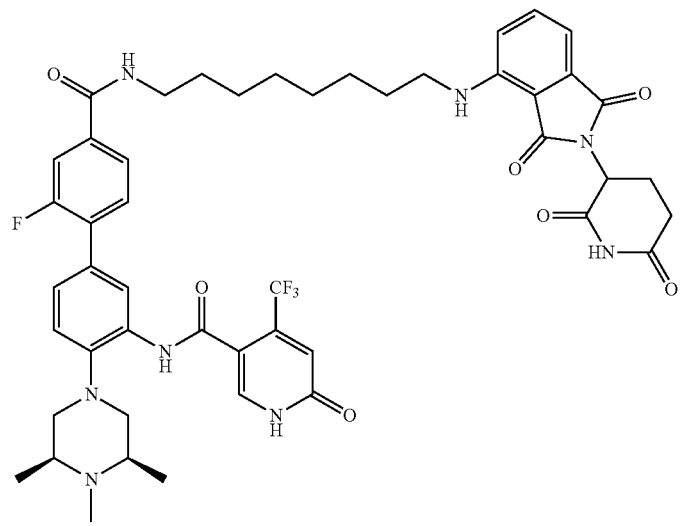

XF056-186

XF056-186 was synthesized following the standard procedures for preparing XF056-157 from intermediate 20 (10.6 mg, 0.019 mmol), PML-19 (9.8 mg, 0.019 mmol, 1.0 equiv), EDCI (1-ethyl-3-(3-dimethylaminopropyl)carbodiimide) (5.6 mg, 0.029 mmol, 1.5 equiv), HOAt (1-hydroxy-7-azabenzo-triazole) (4 mg, 0.029 mmol, 1.5 equiv), and NMM (N-Methylmorpholine) (5.9 mg, 0.058 mmol, 3.0 equiv) in DMSO (1 mL). XF056-186 was obtained as yellow solid in TFA salt form (13.9 mg, yield 79%). $^1$H NMR (600 MHz, CD$_3$OD) δ 8.14 (s, 1H), 8.01 (s, 1H), 7.71 (dd, J=8.1, 1.7 Hz, 1H), 7.65 (dd, J=11.5, 1.7 Hz, 1H), 7.58 (t, J=7.9 Hz, 1H), 7.53-7.44 (m, 2H), 7.35 (d, J=8.4 Hz, 1H), 7.01-6.96 (m, 2H), 6.92 (s, 1H), 5.03 (dd, J=12.5, 5.5 Hz, 1H), 3.55-3.48 (m, 2H), 3.38 (t, J=7.1 Hz, 2H), 3.37-3.31 (m, 2H), 3.27 (t, J=7.0 Hz, 2H), 2.98 (d, J=9.8 Hz, 5H), 2.88-2.78 (m, 1H), 2.76-2.64 (m, 2H), 2.12-2.04 (m, 1H), 1.64 (p, J=7.3 Hz, 4H), 1.49-1.31 (m, 14H). HRMS (m/z) for C$_{48}$H$_{53}$F$_4$N$_8$O$_7^+$ [M+H]$^+$: calculated 929.3968, found 929.3944.

Example 130: Synthesis of XF061-104

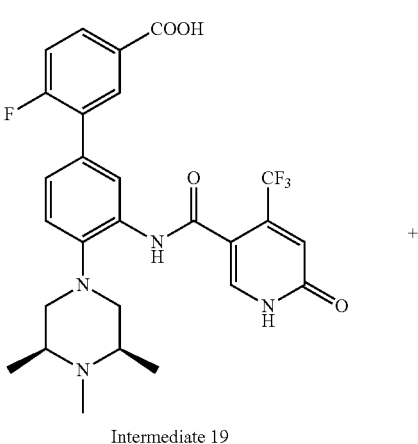

Intermediate 19

387
-continued

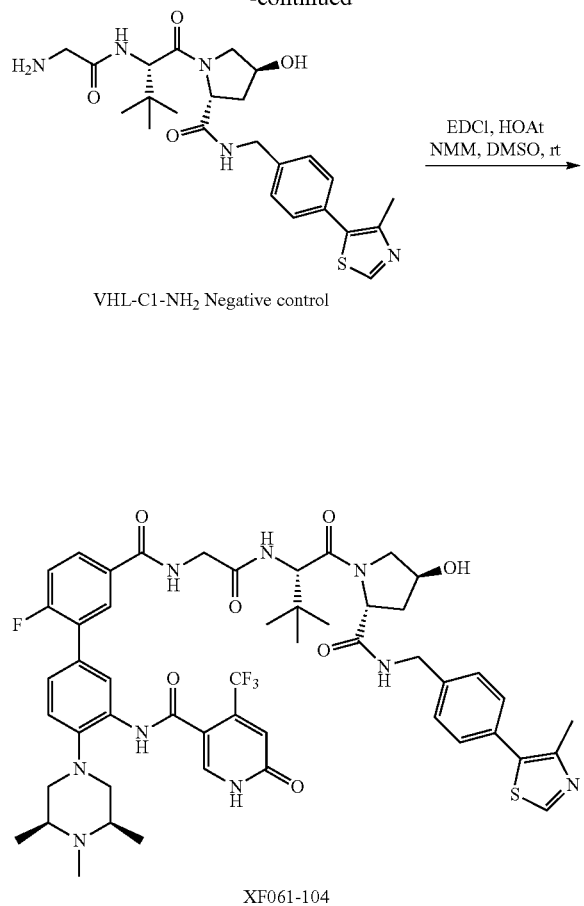

VHL-C1-NH₂ Negative control

XF061-104

XF061-104 was synthesized following the standard procedures for preparing XF056-124 from intermediate 19 (18.3 mg, 0.033 mmol), VHL-C1-NH₂ Negative control (16.3 mg, 0.02 mmol, 1.0 equiv), EDCI (1-ethyl-3-(3-dimethylaminopropyl)carbodiimide) (9.6 mg, 0.05 mmol, 1.5 equiv), HOAt (1-hydroxy-7-azabenzo-triazole) (6.8 mg, 0.05 mmol, 1.5 equiv), and NMM (N-Methylmorpholine) (10.1 mg, 0.1 mmol, 3.0 equiv) in DMSO (1 mL). XF061-104 was obtained as white solid in TFA salt form (29.2 mg, yield 89%). ¹H NMR (600 MHz, CD₃OD) δ 9.13 (s, 1H), 8.12 (s, 1H), 8.01 (d, J=8.1 Hz, 1H), 7.94 (dd, J=7.4, 2.4 Hz, 1H), 7.81 (ddd, J=8.9, 4.6, 2.3 Hz, 1H), 7.39 (dt, J=8.6, 2.8 Hz, 1H), 7.33 (d, J=8.3 Hz, 1H), 7.30 (s, 4H), 7.23 (dd, J=10.3, 8.5 Hz, 1H), 6.92 (s, 1H), 4.54 (t, J=7.5 Hz, 1H), 4.52-4.48 (m, 1H), 4.47-4.39 (m, 2H), 4.29 (d, J=15.5 Hz, 1H), 4.08 (s, 2H), 3.97 (q, J=5.5, 5.1 Hz, 2H), 3.72 (dd, J=10.9, 3.3 Hz, 1H), 3.56-3.46 (m, 2H), 3.02-2.92 (m, 6H), 2.43 (s, 3H), 2.24 (ddd, J=13.2, 8.5, 4.5 Hz, 1H), 2.10 (dt, J=12.4, 6.1 Hz, 1H), 1.44 (dd, J=6.2, 4.1 Hz, 6H), 1.09 (s, 9H). HRMS (m/z) for $C_{51}H_{58}F_4N_9O_7S^+$ [M+H]⁺: calculated 1016.4111. found 1016.4115.

388

Example 131: Synthesis of XF067-67

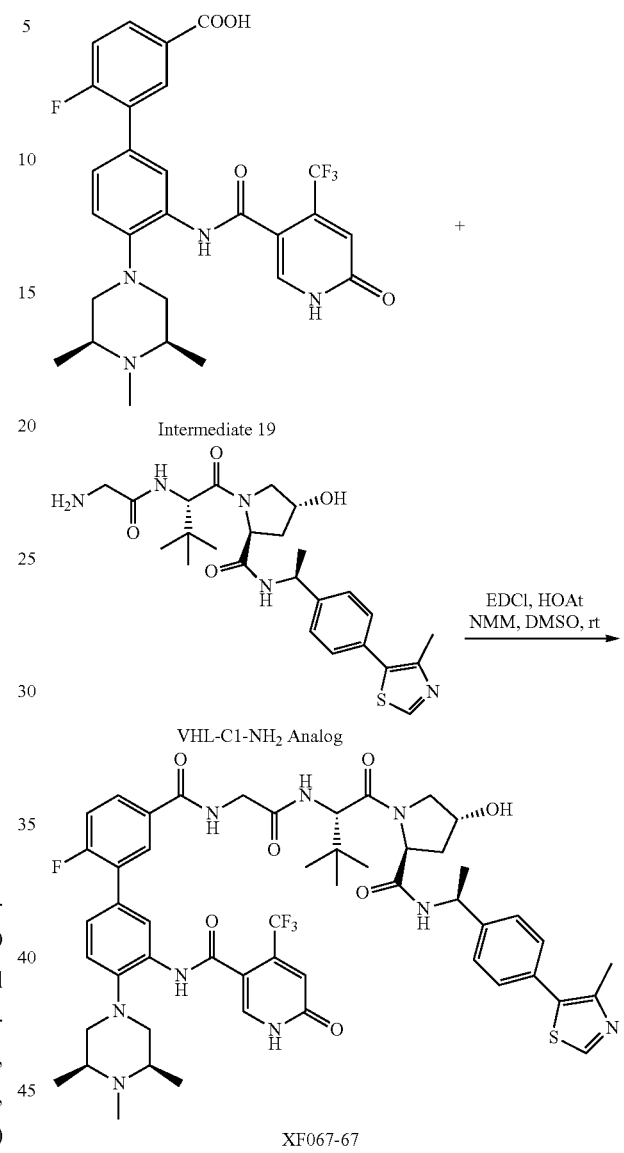

Intermediate 19

VHL-C1-NH₂ Analog

XF067-67

XF067-67 was synthesized following the standard procedures for preparing XF056-124 from intermediate 19 (11 mg, 0.02 mmol), VHL-C1-NH₂ Analog (10 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF067-67 was obtained as white solid in TFA salt form (12.8 mg, yield 62%). ¹H NMR (500 MHz, CD₃OD) δ 8.96 (s, 1H), 8.19 (s, 1H), 8.14-7.99 (m, 3H), 7.99-7.87 (m, 1H), 7.56-7.28 (m, 6H), 6.95 (d, J=2.3 Hz, 1H), 5.09-4.94 (m, 1H), 4.68 (d, J=2.6 Hz, 1H), 4.58 (td, J=8.6, 8.1, 2.4 Hz, 1H), 4.48-4.35 (m, 1H), 4.22-4.03 (m, 2H), 3.89 (d, J=11.0 Hz, 1H), 3.82-3.69 (m, 1H), 3.55 (tt, J=6.8, 3.3 Hz, 2H), 3.44-3.35 (m, 2H), 3.09-2.95 (m, 5H), 2.50 (d, J=2.3 Hz, 3H), 2.21 (ddt, J=11.7, 7.5, 2.0 Hz, 1H), 1.97 (ddd, J=13.3, 9.2, 4.4 Hz, 1H), 1.63-1.28 (m, 9H), 1.07 (d, J=2.4 Hz, 9H). HRMS (m/z) for $C_{52}H_{60}F_4N_9O_7S^+$ [M+H]⁺: calculated 1030.4267. found 1030.4244.

Example 132: Synthesis of XF067-68

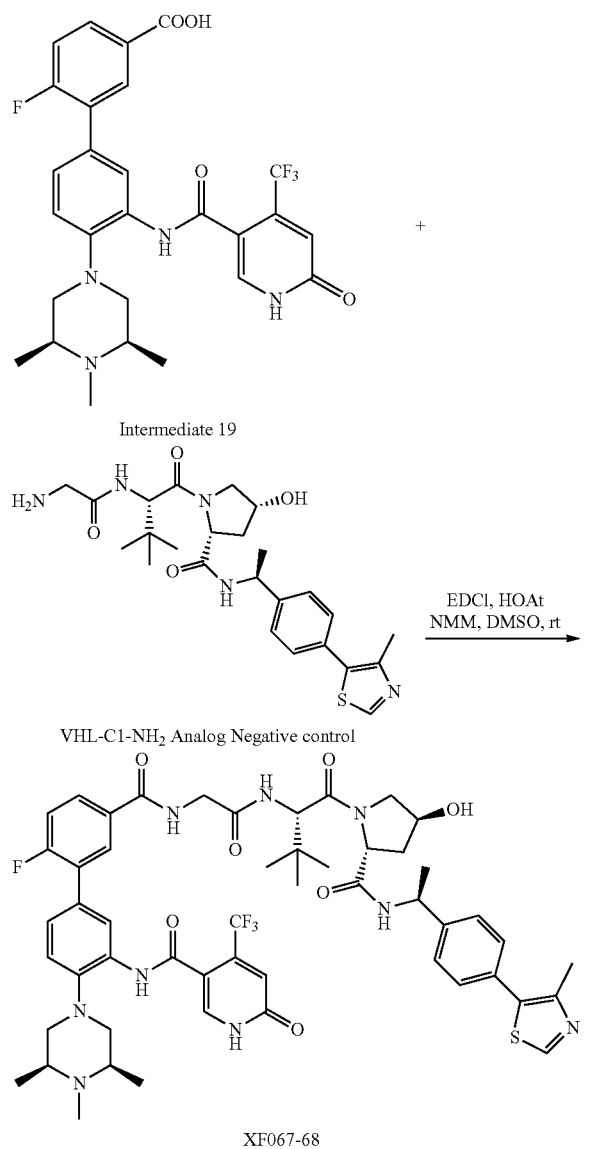

Intermediate 19

VHL-C1-NH$_2$ Analog Negative control

XF067-68

XF067-68 was synthesized following the standard procedures for preparing XF056-124 from intermediate 19 (11 mg, 0.02 mmol), VHL-C1-NH$_2$ Analog Negative control (10 mg, 0.02 mmol, 1.0 equiv), EDCI (1-ethyl-3-(3-dimethyl-aminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF067-68 was obtained as white solid in TFA salt form (15.4 mg, yield 75%). $^1$H NMR (600 MHz, CD$_3$OD) δ 9.05 (s, 1H), 8.10 (d, J=7.1 Hz, 2H), 8.01-7.95 (m, 2H), 7.87-7.83 (m, 1H), 7.49-7.45 (m, 2H), 7.37-7.26 (m, 3H), 7.22 (dd, J=10.3, 8.5 Hz, 1H), 6.92 (s, 1H), 5.00 (q, J=8.6, 7.6 Hz, 1H), 4.54 (dd, J=8.3, 6.5 Hz, 1H), 4.49 (d, J=6.9 Hz, 1H), 4.42-4.36 (m, 1H), 4.11 (q, J=16.6 Hz, 2H), 3.97 (d, J=1.6 Hz, 2H), 3.68 (dd, J=10.8, 3.5 Hz, 1H), 3.51 (d, J=10.9 Hz, 2H), 3.37-3.31 (m, 2H), 3.02-2.91 (m, 4H), 2.42 (s, 3H), 2.24-2.15 (m, 1H), 2.12-2.04 (m, 1H), 1.42 (dd, J=17.1, 6.8 Hz, 9H), 1.08 (s, 9H).

HRMS (m/z) for C$_{52}$H$_{60}$F$_4$N$_9$O$_7$S$^+$ [M+H]$^+$: calculated 1030.4267, found 1030.4277.

Example 133: Synthesis of Intermediate 21

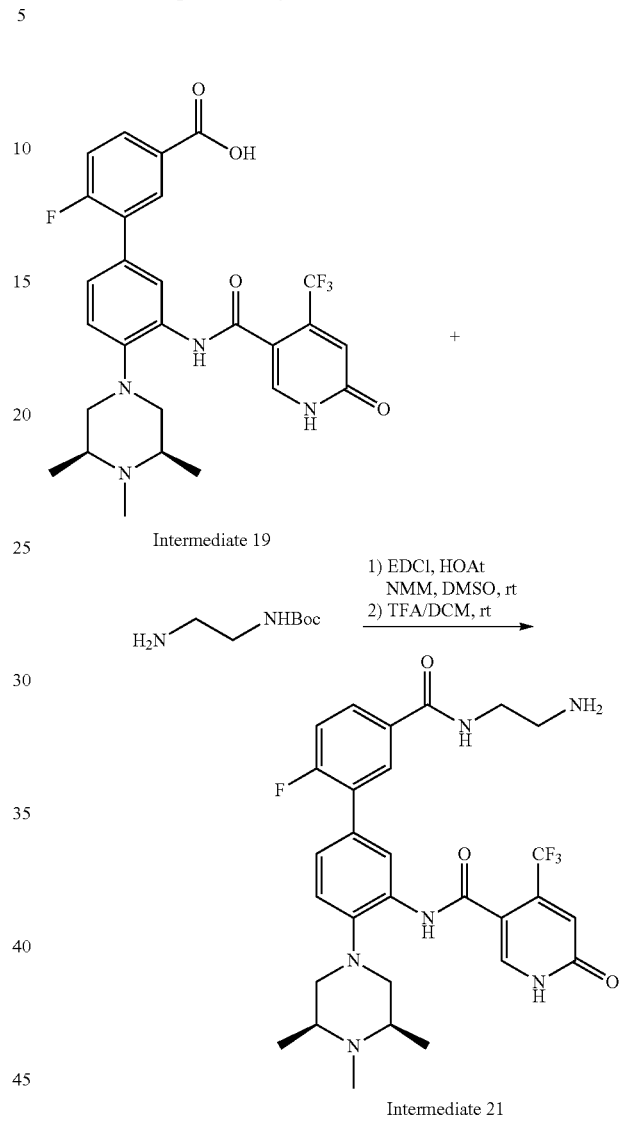

Intermediate 19

Intermediate 21

To the solution of intermediate 19 (32.8 mg, 0.06 mmol) in DMSO (1 mL) were added tert-butyl (2-aminoethyl) carbamate (9.6 mg, 0.06 mmol, 1.0 equiv), EDCI (1-ethyl-3-(3-dimethylaminopropyl)carbodiimide) (17.3 mg, 0.09 mmol, 1.5 equiv), HOAt (1-hydroxy-7-azabenzo-triazole) (12.2 mg, 0.09 mmol, 1.5 equiv), and NMM (N-Methylmorpholine) (18.2 mg, 0.12 mmol, 3.0 equiv). After being stirring overnight at room temperature, the resulting mixture was purified by preparative HPLC (10%-100% methanol/0.1% TFA in H$_2$O) to afford white solid.

This This product was dissolved in DCM (1 mL) and TFA (1 mL). The resulting mixture was stirring for 30 minutes. Then, it was concentrated and purified by preparative HPLC (10%-100% methanol/0.1% TFA in H$_2$O) to afford Intermediate 21 (XF078-175) as white solid in TFA salt form (34.2 mg, yield 97%). $^1$H NMR (500 MHz, CD$_3$OD) δ 8.20 (t, J=2.9 Hz, 1H), 8.08 (dd, J=7.4, 2.4 Hz, 1H), 8.05 (d, J=4.7 Hz, 1H), 7.93 (ddd, J=8.6, 4.6, 2.4 Hz, 1H), 7.51 (dq, J=6.2, 1.9 Hz, 1H), 7.42 (d, J=8.4 Hz, 1H), 7.37-7.29 (m, 1H), 6.93

(s, 1H), 3.71 (q, J=5.9, 5.4 Hz, 2H), 3.64-3.55 (m, 2H), 3.33 (dt, J=3.4, 1.7 Hz, 2H), 3.22 (t, J=5.8 Hz, 2H), 3.13-2.92 (m, 5H), 1.47 (t, J=5.6 Hz, 6H). HRMS (m/z) for $C_{29}H_{33}F_3N_6O_3^+$ [M+H]$^+$: calculated 589.2545. found 589.2533.

Example 134: Synthesis of Intermediate 22

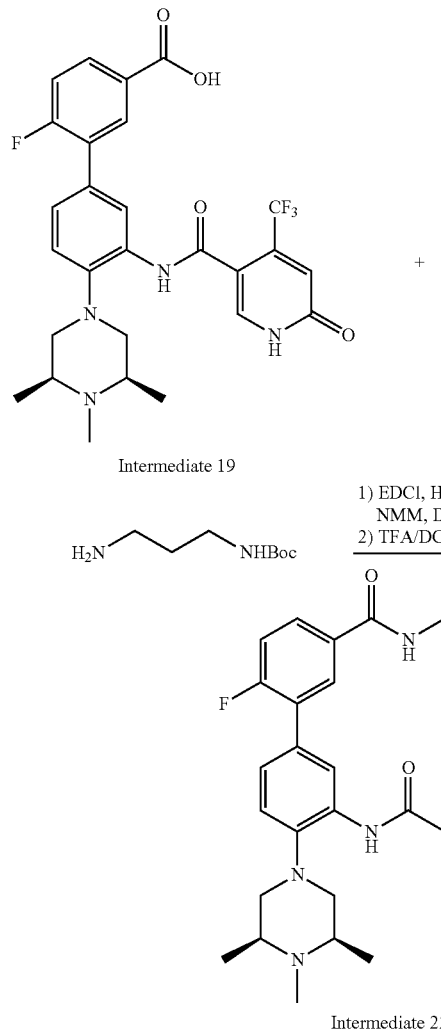

Intermediate 22

Intermediate 22 was synthesized following the standard procedures for preparing Intermediate 21 from intermediate 19 (32.8 mg, 0.06 mmol), tert-butyl (3-aminopropyl)carbamate (10.4 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 22 (XF078-176) was obtained as white solid in TFA salt form (28.2 mg, yield 78%). $^1$H NMR (500 MHz, CD$_3$OD) δ 8.19 (t, J=3.0 Hz, 1H), 8.07-8.01 (m, 2H), 7.91 (ddd, J=8.5, 4.6, 2.4 Hz, 1H), 7.51 (dq, J=7.9, 2.6, 1.9 Hz, 1H), 7.42 (d, J=8.4 Hz, 1H), 7.34 (dd, J=10.3, 8.6 Hz, 1H), 6.95 (s, 1H), 3.67-3.46 (m, 4H), 3.41-3.35 (m, 2H), 3.13-2.92 (m, 7H), 2.00 (q, J=6.9 Hz, 2H), 1.47 (t, J=5.8 Hz, 6H). HRMS (m/z) for $C_{30}H_{35}F_4N_6O_3^+$ [M+H]$^+$: calculated 603.2701, found 603.2698.

Example 135: Synthesis of Intermediate 23

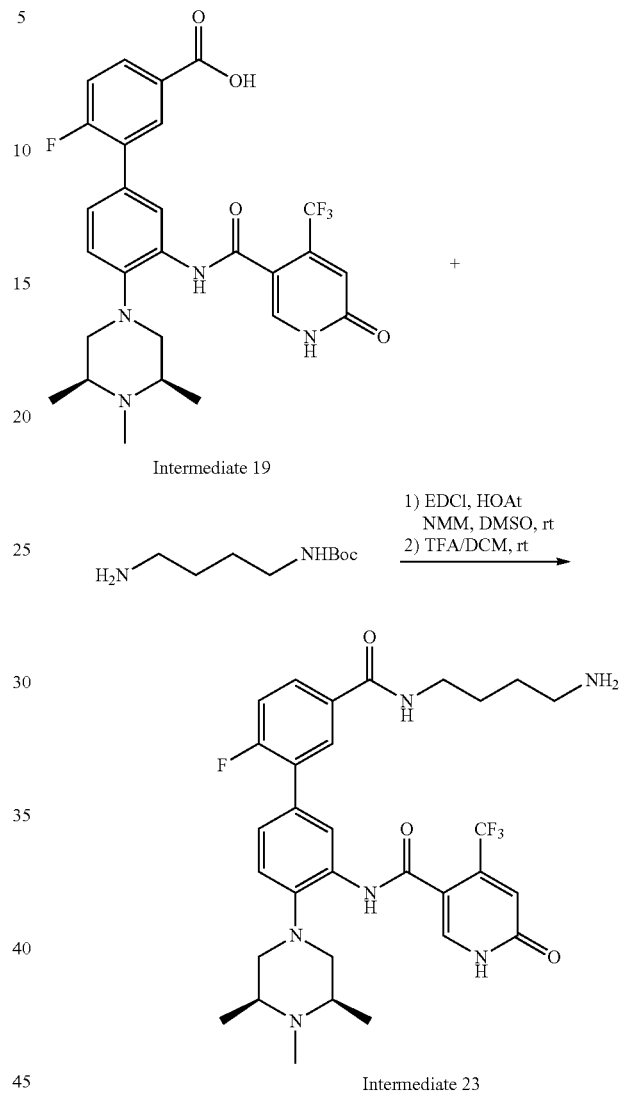

Intermediate 23

Intermediate 23 was synthesized following the standard procedures for preparing Intermediate 21 from intermediate 19 (32.8 mg, 0.06 mmol), tert-butyl (4-aminobutyl)carbamate (11.3 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 23 (XF078-177) was obtained as white solid in TFA salt form (33.9 mg, yield 92%). $^1$H NMR (500 MHz, CD$_3$OD) δ 8.18 (t, J=3.1 Hz, 1H), 8.06-7.99 (m, 2H), 7.88 (dtd, J=9.2, 4.6, 2.2 Hz, 1H), 7.53-7.47 (m, 1H), 7.41 (dd, J=8.5, 4.2 Hz, 1H), 7.33 (dd, J=10.3, 8.6 Hz, 1H), 6.95 (s, 1H), 3.62-3.51 (m, 2H), 3.49-3.42 (m, 2H), 3.36 (s, 1H), 3.09-2.93 (m, 8H), 1.75 (dq, J=8.0, 5.2, 4.6 Hz, 4H), 1.46 (t, J=5.5 Hz, 6H). HRMS (m/z) for $C_{31}H_{37}F_4N_6O_3^+$ [M+H]$^+$: calculated 617.2858, found 617.2881.

Example 136: Synthesis of Intermediate 24

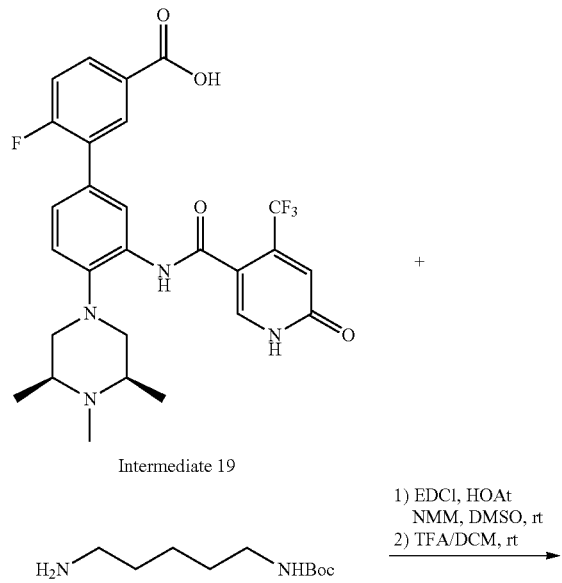

Example 137: Synthesis of Intermediate 25

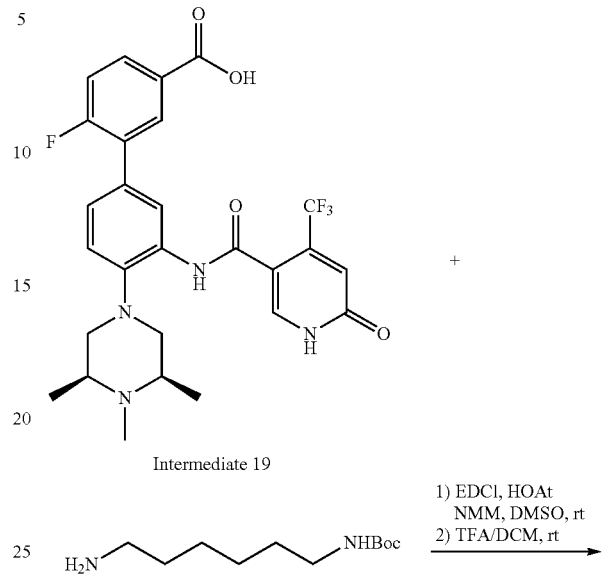

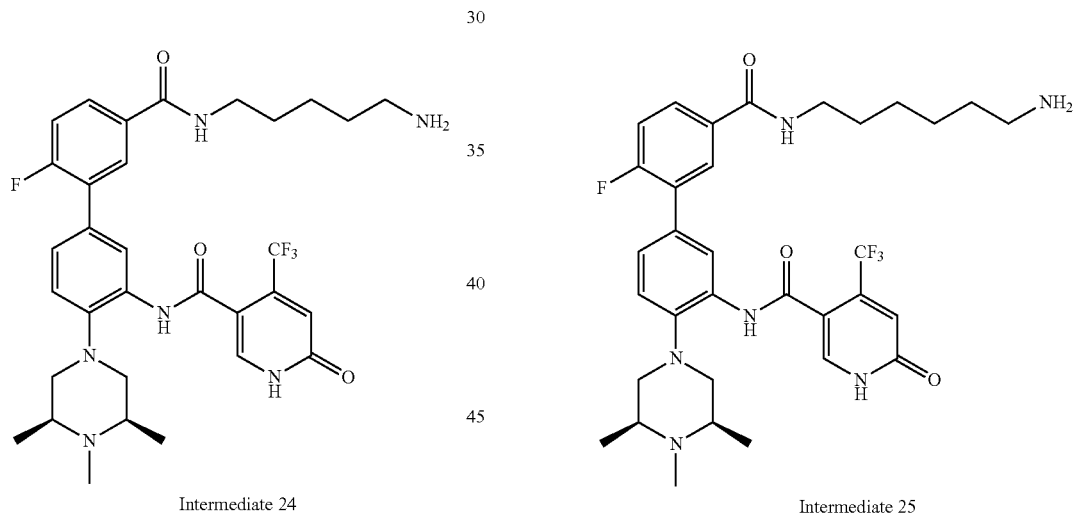

Intermediate 24 was synthesized following the standard procedures for preparing Intermediate 21 from intermediate 19 (32.8 mg, 0.06 mmol), tert-butyl (5-aminopentyl)carbamate (12.1 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 24 (XF078-178) was obtained as white solid in TFA salt form (31.7 mg, yield 84%). $^1$H NMR (500 MHz, CD$_3$OD) δ 8.19 (d, J=2.2 Hz, 1H), 8.06-7.99 (m, 2H), 7.91-7.83 (m, 1H), 7.50 (dt, J=8.7, 2.3 Hz, 1H), 7.41 (dd, J=8.4, 3.6 Hz, 1H), 7.32 (dd, J=10.4, 8.5 Hz, 1H), 6.94 (d, J=3.7 Hz, 1H), 3.58 (ddt, J=10.1, 6.8, 3.4 Hz, 2H), 3.44 (t, J=7.0 Hz, 2H), 3.38-3.26 (m, 1H), 3.12-2.89 (m, 8H), 1.79-1.64 (m, 6H), 1.47 (d, J=6.3 Hz, 6H). HRMS (m/z) for C$_{32}$H$_{39}$F$_4$N$_6$O$_3$$^+$ [M+H]$^+$: calculated 631.3014. found 631.3005.

Intermediate 25 was synthesized following the standard procedures for preparing Intermediate 21 from intermediate 19 (32.8 mg, 0.06 mmol), tert-butyl (6-aminohexyl)carbamate (13 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 25 (XF078-179) was obtained as white solid in TFA salt form (36.4 mg, yield 94%). $^1$H NMR (500 MHz, CD$_3$OD) 8.21-8.15 (m, 1H), 8.06-7.97 (m, 2H), 7.87 (ddd, J=8.6, 4.7, 2.4 Hz, 1H), 7.50 (dt, J=8.2, 2.0 Hz, 1H), 7.41 (dd, J=8.5, 2.8 Hz, 1H), 7.31 (ddd, J=11.4, 8.5, 2.8 Hz, 1H), 6.93 (d, J=2.9 Hz, 1H), 3.58 (ddt, J=9.9, 6.5, 3.2 Hz, 2H), 3.42 (td, J=7.2, 2.7 Hz, 2H), 3.38-3.34 (m, 1H), 3.11-2.85 (m, 8H), 1.68 (p, J=6.7 Hz, 4H), 1.47 (dq, J=6.5, 3.1 Hz, 10H). HRMS (m/z) for C$_{33}$H$_{41}$F$_4$N$_6$O$_3$$^+$ [M+H]$^+$: calculated 645.3171. found 645.3174.

Example 138: Synthesis of Intermediate 26

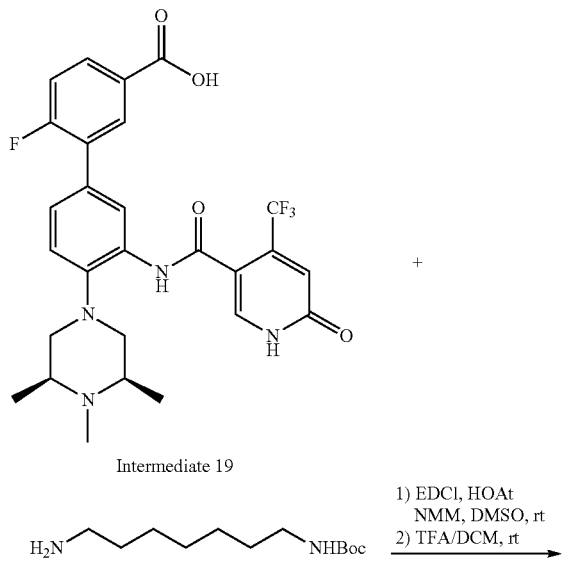

Intermediate 26

Example 139: Synthesis of Intermediate 27

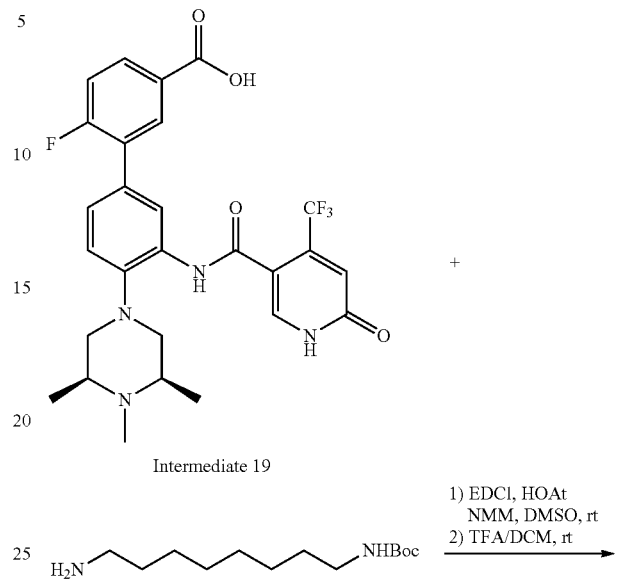

Intermediate 27

Intermediate 26 was synthesized following the standard procedures for preparing Intermediate 21 from intermediate 19 (32.8 mg, 0.06 mmol), tert-butyl (7-aminoheptyl)carbamate (13.8 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 26 (XF078-180) was obtained as white solid in TFA salt form (31.8 mg, yield 81%). $^1$H NMR (500 MHz, CD$_3$OD) 8.18 (d, J=2.6 Hz, 1H), 8.06-7.97 (m, 2H), 7.86 (ddt, J=7.7, 5.4, 2.7 Hz, 1H), 7.50 (dt, J=8.6, 2.3 Hz, 1H), 7.40 (dd, J=8.4, 3.1 Hz, 1H), 7.30 (ddd, J=11.3, 8.5, 3.1 Hz, 1H), 6.93 (d, J=3.0 Hz, 1H), 3.63-3.52 (m, 2H), 3.41 (td, J=7.2, 3.0 Hz, 2H), 3.36-3.33 (m, 1H), 3.12-2.78 (m, 8H), 1.67 (q, J=7.1 Hz, 4H), 1.52-1.32 (m, 12H). HRMS (m/z) for C$_{34}$H$_{43}$F$_4$N$_6$O$_3^+$ [M+H]$^+$: calculated 659.3327. found 659.3343.

Intermediate 27 was synthesized following the standard procedures for preparing Intermediate 21 from intermediate 19 (32.8 mg, 0.06 mmol), tert-butyl (8-aminooctyl)carbamate (14.6 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 27 (XF078-181) was obtained as white solid in TFA salt form (32.6 mg, yield 81%). $^1$H NMR (500 MHz, CD$_3$OD) 8.18 (t, J=2.7 Hz, 1H), 8.07-7.96 (m, 2H), 7.86 (ddt, J=8.2, 6.1, 2.9 Hz, 1H), 7.54-7.44 (m, 1H), 7.40 (dd, J=8.4, 3.5 Hz, 1H), 7.31 (ddd, J=12.1, 8.5, 3.6 Hz, 1H), 6.93 (d, J=3.6 Hz, 1H), 3.63-3.51 (m, 2H), 3.40 (td, J=7.2, 3.5 Hz, 2H), 3.37-3.34 (m, 1H), 3.10-2.80 (m, 8H), 1.71-1.61 (m, 4H), 1.51-1.36 (m, 14H). HRMS (m/z) for C$_{35}$H$_{45}$F$_4$N$_6$O$_3^+$ [M+H]$^+$: calculated 673.3484. found 673.3467.

Example 140: Synthesis of Intermediate 28

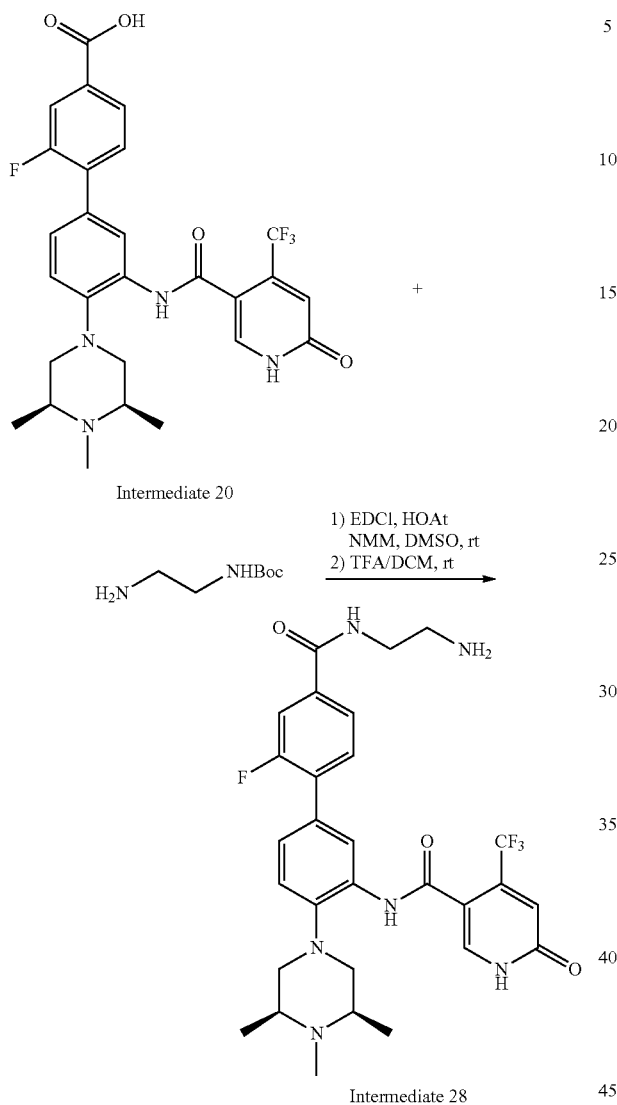

Intermediate 28

To the solution of intermediate 20 (32.8 mg, 0.06 mmol) in DMSO (1 mL) were added tert-butyl (2-aminoethyl) carbamate (9.6 mg, 0.06 mmol, 1.0 equiv), EDCI (1-ethyl-3-(3-dimethylaminopropyl)carbodiimide) (17.3 mg, 0.09 mmol, 1.5 equiv), HOAt (1-hydroxy-7-azabenzo-triazole) (12.2 mg, 0.09 mmol, 1.5 equiv), and NMM (N-Methyl-morpholine) (18.2 mg, 0.12 mmol, 3.0 equiv). After being stirring overnight at room temperature, the resulting mixture was purified by preparative HPLC (10%-100% methanol/0.1% TFA in H$_2$O) to afford white solid. This This product was dissolved in DCM (1 mL) and TFA (1 mL). The resulting mixture was stirring for 30 minutes. Then, it was concentrated and purified by preparative HPLC (10%-100% methanol/0.1% TFA in H$_2$O) to afford Intermediate 28 (XF078-182) as white solid in TFA salt form (33 mg, yield 94%). $^1$H NMR (600 MHz, CD$_3$OD) δ 8.17 (s, 1H), 8.02 (s, 1H), 7.78 (dd, J=8.0, 1.8 Hz, 1H), 7.72 (dd, J=11.5, 1.7 Hz, 1H), 7.62 (t, J=7.9 Hz, 1H), 7.52-7.44 (m, 1H), 7.38 (d, J=8.3 Hz, 1H), 6.91 (s, 1H), 3.69 (t, J=5.9 Hz, 2H), 3.56 (ddd, J=10.7, 6.8, 3.2 Hz, 2H), 3.34 (s, 1H), 3.19 (t, J=5.9 Hz, 3H), 3.05-2.94 (m, 5H), 1.44 (d, J=6.5 Hz, 6H). HRMS (m/z) for C$_{29}$H$_{33}$F$_3$N$_6$O$_3$$^+$ [M+H]$^+$: calculated 589.2545. found 589.2553.

Example 141: Synthesis of Intermediate 29

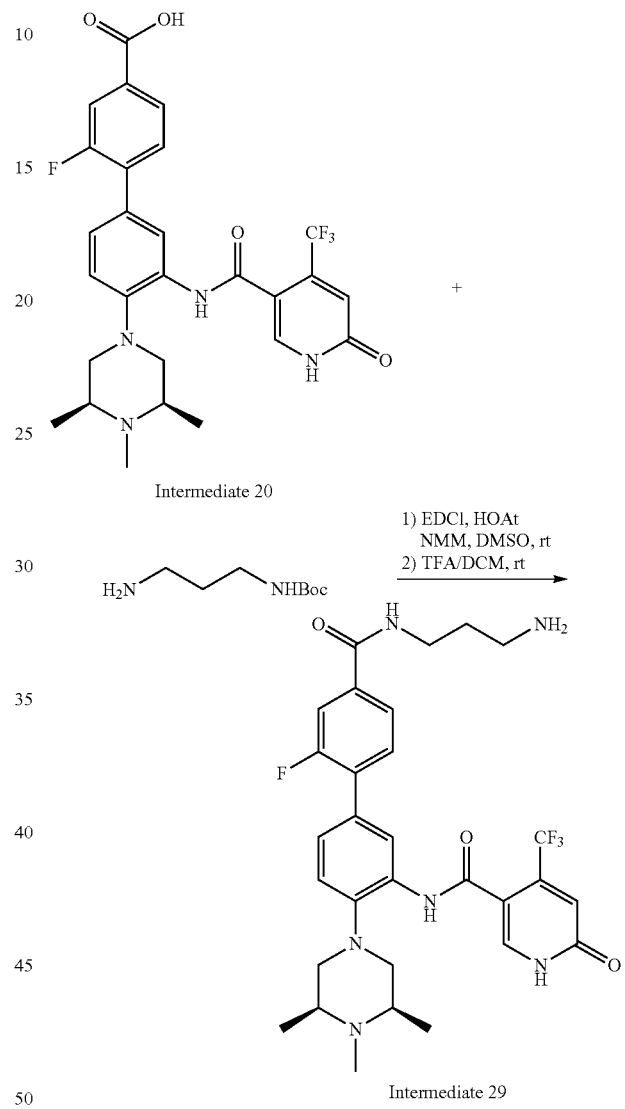

Intermediate 29

Intermediate 29 was synthesized following the standard procedures for preparing Intermediate 21 from intermediate 20 (32.8 mg, 0.06 mmol), tert-butyl (3-aminopropyl)carbamate (10.4 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 29 (XF078-183) was obtained as white solid in TFA salt form (33 mg, yield 91%). $^1$H NMR (600 MHz, CD$_3$OD) δ 8.17 (s, 1H), 8.02 (s, 1H), 7.75 (dd, J=8.1, 1.8 Hz, 1H), 7.69 (dd, J=11.4, 1.8 Hz, 1H), 7.62 (t, J=7.9 Hz, 1H), 7.49 (dt, J=8.3, 1.9 Hz, 1H), 7.38 (d, J=8.4 Hz, 1H), 6.92 (s, 1H), 3.60-3.47 (m, 4H), 3.37-3.32 (m, 2H), 3.05-2.94 (m, 7H), 1.98 (p, J=7.0 Hz, 2H), 1.44 (d, J=6.6 Hz, 6H). HRMS (m/z) for C$_{30}$H$_{35}$F$_4$N$_6$O$_3$$^+$ [M+H]$^+$: calculated 603.2701. found 603.2716.

Example 142: Synthesis of Intermediate 30

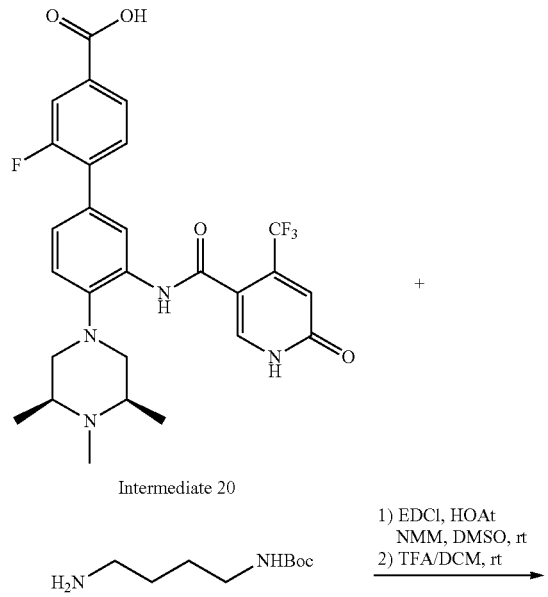

Example 143: Synthesis of Intermediate 31

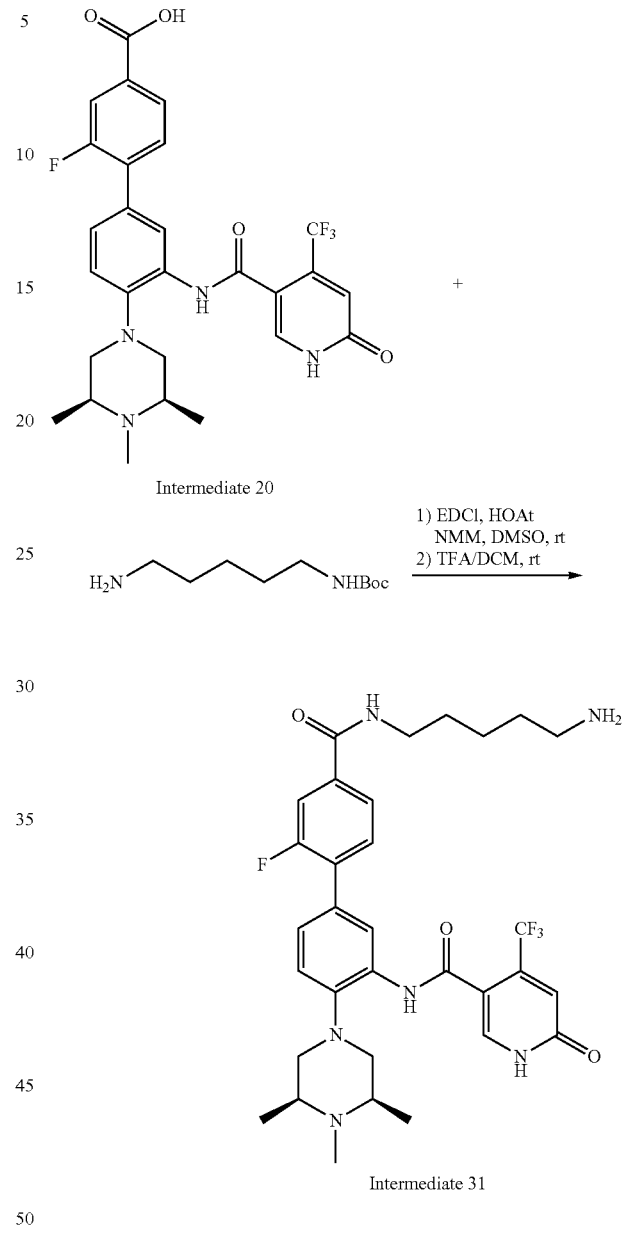

Intermediate 30 was synthesized following the standard procedures for preparing Intermediate 21 from intermediate 20 (32.8 mg, 0.06 mmol), tert-butyl (4-aminobutyl)carbamate (11.3 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 30 (XF078-184) was obtained as white solid in TFA salt form (30 mg, yield 81%). $^1$H NMR (600 MHz, CD$_3$OD) δ 8.16 (s, 1H), 8.01 (s, 1H), 7.73 (dd, J=8.0, 1.7 Hz, 1H), 7.67 (dd, J=11.4, 1.7 Hz, 1H), 7.61 (t, J=7.9 Hz, 1H), 7.48 (dt, J=8.3, 1.9 Hz, 1H), 7.38 (d, J=8.4 Hz, 1H), 6.92 (s, 1H), 3.59-3.50 (m, 2H), 3.45 (t, J=6.2 Hz, 2H), 3.36-3.31 (m, 2H), 3.04-2.93 (m, 7H), 1.73 (tq, J=9.5, 6.5, 4.9 Hz, 4H), 1.44 (d, J=6.5 Hz, 6H). HRMS (m/z) for $C_{31}H_{37}F_4N_6O_3^+$ [M+H]$^+$: calculated 617.2858. found 617.2841.

Intermediate 31 was synthesized following the standard procedures for preparing Intermediate 21 from intermediate 20 (32.8 mg, 0.06 mmol), tert-butyl (5-aminopentyl)carbamate (12.1 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 31 (XF078-185) was obtained as white solid in TFA salt form (34.3 mg, yield 91%). $^1$H NMR (600 MHz, CD$_3$OD) δ 8.16 (s, 1H), 8.01 (s, 1H), 7.73 (dd, J=8.0, 1.7 Hz, 1H), 7.67 (dd, J=11.4, 1.7 Hz, 1H), 7.60 (t, J=7.9 Hz, 1H), 7.48 (dt, J=8.3, 1.9 Hz, 1H), 7.38 (d, J=8.4 Hz, 1H), 6.92 (s, 1H), 3.59-3.50 (m, 2H), 3.42 (t, J=7.1 Hz, 2H), 3.36-3.31 (m, 2H), 3.07-2.89 (m, 7H), 1.70 (dp, J=17.3, 7.5 Hz, 4H), 1.53-1.40 (m, 8H). HRMS (m/z) for $C_{32}H_{39}F_4N_6O_3^+$ [M+H]$^+$: calculated 631.3014. found 631.3025.

Example 144: Synthesis of Intermediate 32

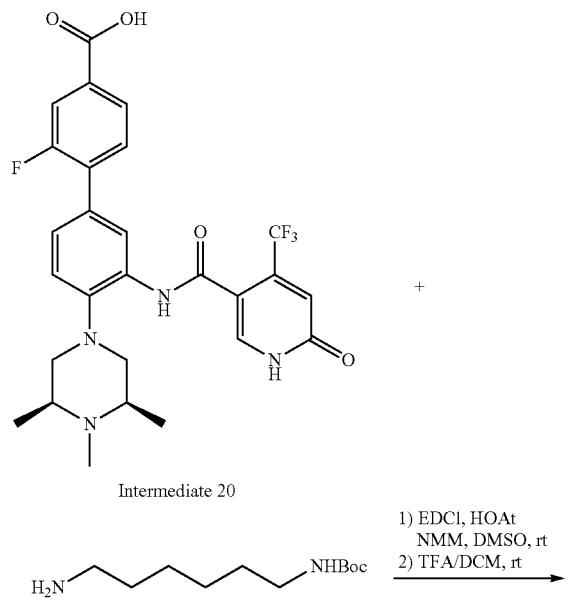

Example 145: Synthesis of Intermediate 33

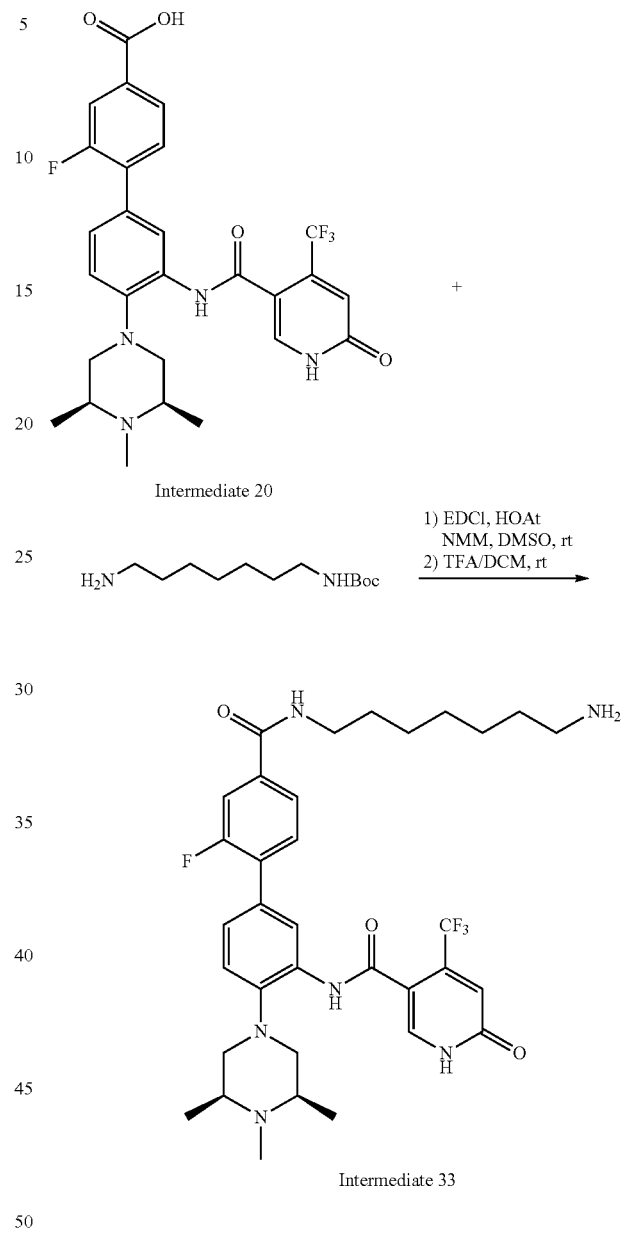

Intermediate 32 was synthesized following the standard procedures for preparing Intermediate 21 from intermediate 20 (32.8 mg, 0.06 mmol), tert-butyl (6-aminohexyl)carbamate (13 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 32 (XF078-186) was obtained as white solid in TFA salt form (17.8 mg, yield 46%). $^1$H NMR (600 MHz, CD$_3$OD) 8.16 (s, 1H), 8.01 (s, 1H), 7.72 (dd, J=8.0, 1.7 Hz, 1H), 7.66 (dd, J=11.4, 1.7 Hz, 1H), 7.60 (t, J=7.9 Hz, 1H), 7.49-7.45 (m, 1H), 7.38 (d, J=8.4 Hz, 1H), 6.92 (s, 1H), 3.55 (ddd, J=10.4, 6.7, 3.2 Hz, 2H), 3.40 (t, J=7.2 Hz, 2H), 3.36-3.32 (m, 2H), 3.04-2.96 (m, 5H), 2.93 (t, J=7.6 Hz, 2H), 1.71-1.63 (m, 4H), 1.51-1.40 (m, 10H). HRMS (m/z) for $C_{33}H_{41}F_4N_6O_3^+$ [M+H]$^+$: calculated 645.3171. found 645.3167.

Intermediate 33 was synthesized following the standard procedures for preparing Intermediate 21 from intermediate 20 (32.8 mg, 0.06 mmol), tert-butyl (7-aminoheptyl)carbamate (13.8 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 33 (XF082-1) was obtained as white solid in TFA salt form (34 mg, yield 86%). $^1$H NMR (600 MHz, CD$_3$OD) 8.16 (s, 1H), 8.02 (s, 1H), 7.72 (dd, J=8.0, 1.7 Hz, 1H), 7.66 (dd, J=11.5, 1.7 Hz, 1H), 7.60 (t, J=7.9 Hz, 1H), 7.48 (dt, J=8.2, 2.0 Hz, 1H), 7.38 (d, J=8.4 Hz, 1H), 6.91 (s, 1H), 3.61-3.50 (m, 2H), 3.39 (t, J=7.2 Hz, 2H), 3.36-3.31 (m, 2H), 3.04-2.95 (m, 5H), 2.92 (t, J=7.7 Hz, 2H), 1.66 (h, J=6.9 Hz, 4H), 1.48-1.38 (m, 12H). HRMS (m/z) for $C_{34}H_{43}F_4N_6O_3^+$ [M+H]$^+$: calculated 659.3327. found 659.3317.

Example 146: Synthesis of Intermediate 34

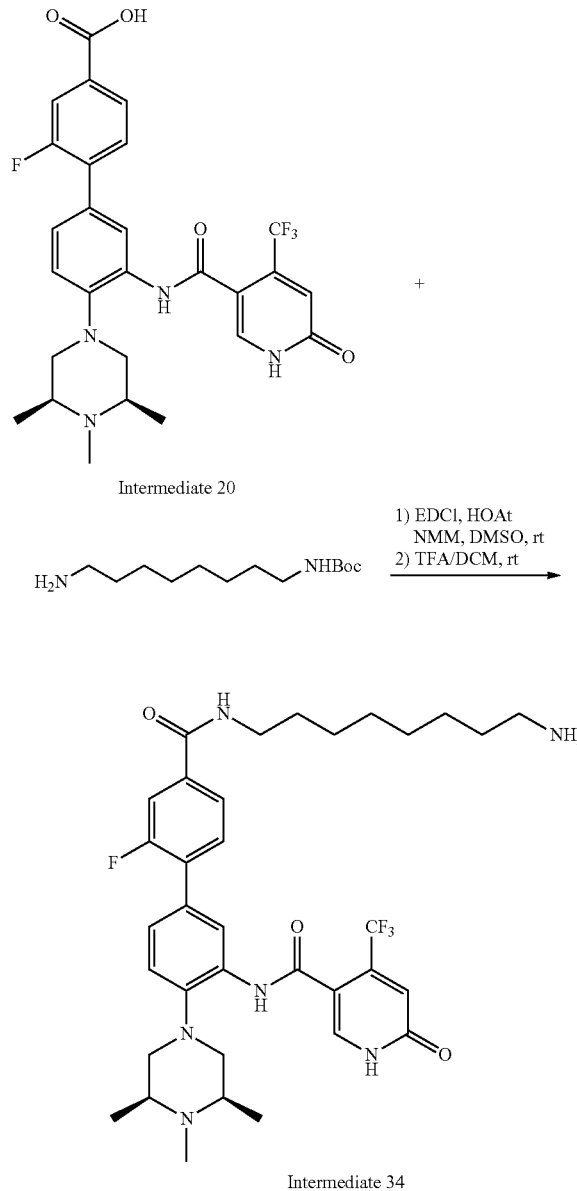

Example 147: Synthesis of Intermediate 36

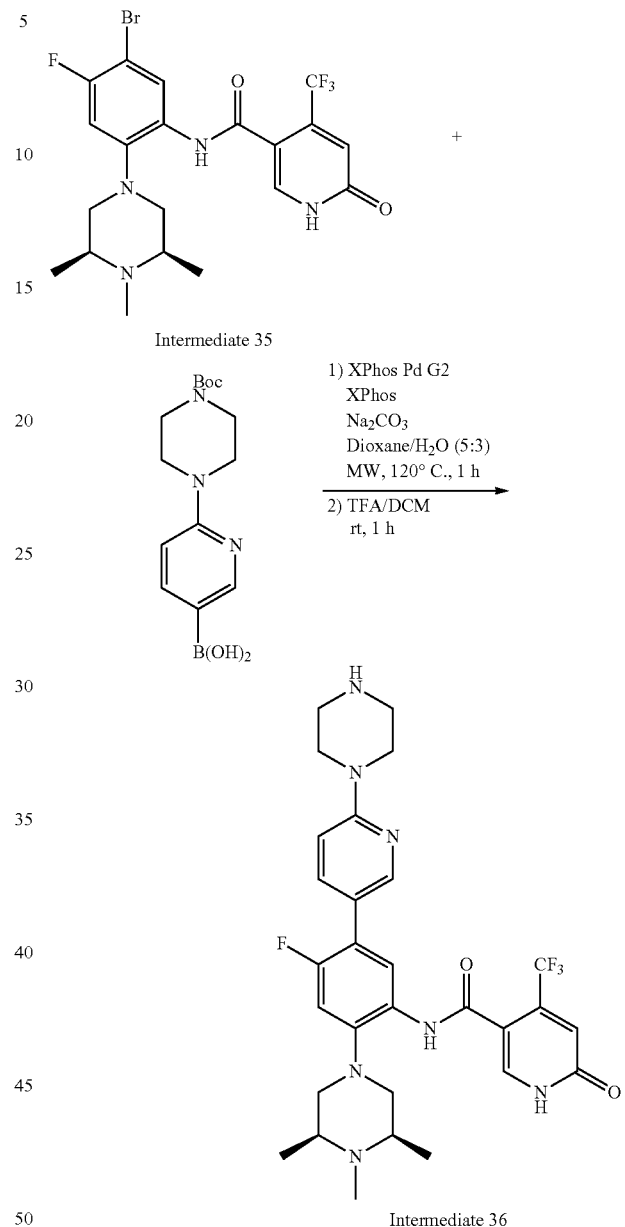

Intermediate 34 was synthesized following the standard procedures for preparing Intermediate 21 from intermediate 19 (32.8 mg, 0.06 mmol), tert-butyl (8-aminooctyl)carbamate (14.6 mg, 0.06 mmol, 1.0 equiv), EDCI (17.3 mg, 0.09 mmol, 1.5 equiv), HOAt (12.2 mg, 0.09 mmol, 1.5 equiv), and NMM (18.2 mg, 0.18 mmol, 3.0 equiv) in DMSO (1 mL). Intermediate 34 (XF082-2) was obtained as white solid in TFA salt form (27 mg, yield 67%). $^1$H NMR (600 MHz, CD$_3$OD) 8.16 (s, 1H), 8.02 (s, 1H), 7.72 (dd, J=8.1, 1.7 Hz, 1H), 7.65 (dd, J=11.4, 1.7 Hz, 1H), 7.60 (t, J=7.9 Hz, 1H), 7.48 (dt, J=8.3, 1.9 Hz, 1H), 7.38 (d, J=8.3 Hz, 1H), 6.91 (s, 1H), 3.55 (ddd, J=10.5, 6.6, 3.1 Hz, 2H), 3.38 (t, J=7.2 Hz, 2H), 3.36-3.32 (m, 2H), 3.06-2.95 (m, 5H), 2.91 (t, J=7.7 Hz, 2H), 1.64 (p, J=7.2 Hz, 4H), 1.42 (dd, J=22.5, 5.2 Hz, 14H). HRMS (m/z) for C$_{35}$H$_{45}$F$_4$N$_6$O$_3{}^+$ [M+H]$^+$: calculated 673.3484. found 673.3499.

To a solution of Intermediate 35 (WO2017147700A1) (505 mg, 1 mmol) and (6-(4-(tert-butoxycarbonyl)piperazin-1-yl)pyridin-3-yl)boronic acid (924 mg, 3 mmol, 3.0 euqiv) in 8 mL of 1,4-dioxane/H$_2$O (5:3) were added sodium carbonate (1060 mg, 10 mmol, 10 equiv), XPhos (95.2 mg, 0.2 mmol, 0.2 equiv), and XPhos Pd G2 (157.4 mg, 0.2 mmol, 0.2 equiv). The reaction was heated to 120° C. for 1 h under Microwave. The solvent was removed and purified by reverse phase ISCO (10%-100% methanol/0.1% TFA in H$_2$O) to afford product as white solid. This product was dissolved in DCM (10 mL) and TFA (10 mL). The resulting mixture was stirring for 1 h. Then, it was concentrated and purified by reverse phase ISCO (10%-100% methanol/0.1% TFA in H$_2$O) to afford Intermediate 36 as white solid in TFA salt form (463.4 mg, yield 79%). $^1$H NMR (600 MHz, CD$_3$OD) δ 8.32 (d, J=2.2 Hz, 1H), 8.19 (dd, J=9.2, 2.3 Hz, 1H), 8.07-7.92 (m, 2H), 7.40 (d, J=9.4 Hz, 1H), 7.20 (d, J=11.8 Hz, 1H), 6.89 (s, 1H), 4.01 (t, J=5.3 Hz, 4H), 3.62-3.53 (m, 2H), 3.49-3.39 (m, 4H), 3.35 (d, J=12.7 Hz, 2H), 3.01 (dd, J=13.4, 11.0 Hz, 2H), 2.97 (s, 3H), 1.43 (d, J=6.4 Hz, 6H). HRMS (m/z) for C$_{29}$H$_{34}$F$_4$N$_7$O$_2{}^+$ [M+H]$^+$: calculated 588.2705. found 588.2732.
Example 148: Synthesis of XF067-131
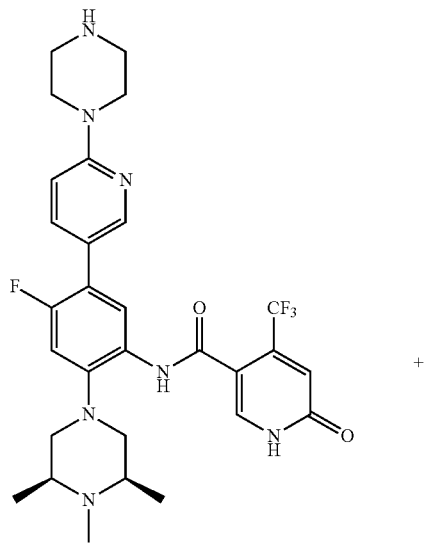
Intermediate 36
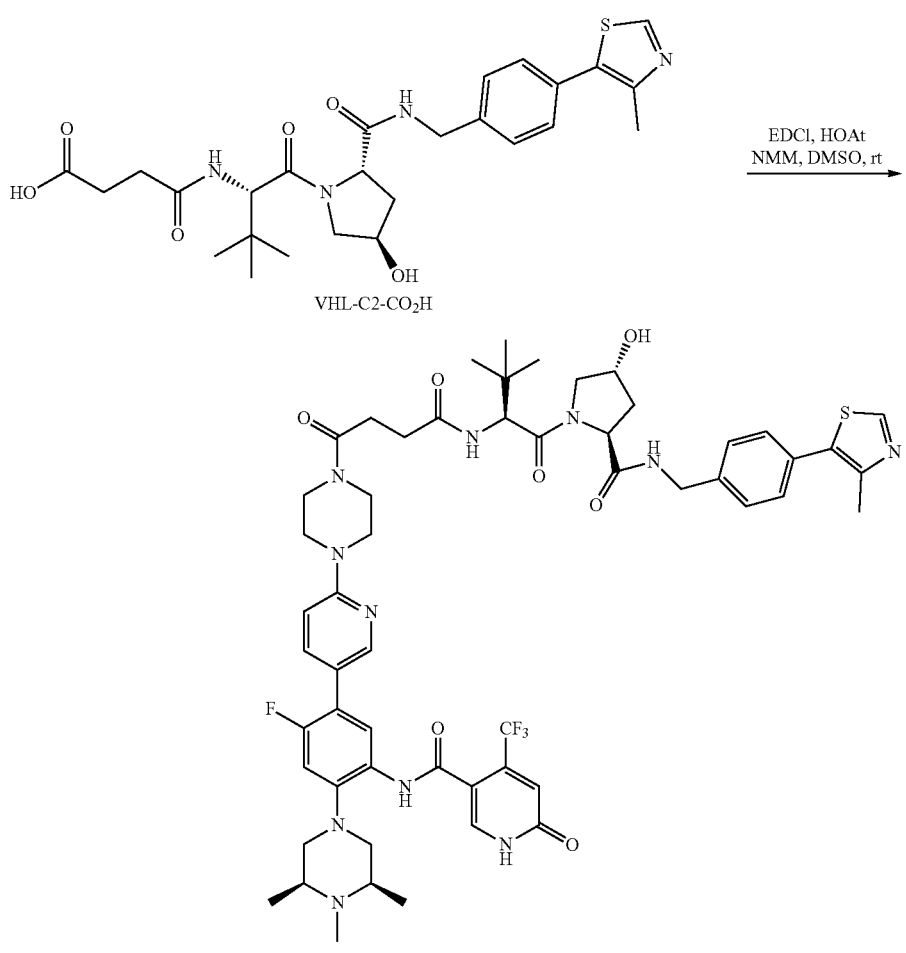
XF067-131

To the solution of intermediate 36 (14.6 mg, 0.025 mmol) in DMSO (1 mL) were added VHL-C2-COOH (12.2 mg, 0.025 mmol, 1.0 equiv), EDCI (1-ethyl-3-(3-dimethylaminopropyl)carbodiimide) (7.1 mg, 0.037 mmol, 1.5 equiv), HOAt (1-hydroxy-7-azabenzo-triazole) (5 mg, 0.037 mmol, 1.5 equiv), and NMM (N-Methylmorpholine) (7.5 mg, 0.074 mmol, 3.0 equiv). After being stirring overnight at room temperature, the resulting mixture was purified by preparative HPLC (10%-100% methanol/0.1% TFA in $H_2O$) to afford XF067-131 as white solid in TFA salt form (10.8 mg, yield 39%). $^1$H NMR (600 MHz, $CD_3OD$) δ 9.01 (s, 1H), 8.27-8.13 (m, 2H), 8.00 (d, J=8.7 Hz, 2H), 7.53-7.33 (m, 5H), 7.22 (d, J=11.7 Hz, 1H), 6.93 (s, 1H), 4.60 (s, 1H), 4.58-4.45 (m, 4H), 4.36 (d, J=15.5 Hz, 1H), 3.90-3.75 (m, 10H), 3.55-3.46 (m, 2H), 3.37 (d, J=13.2 Hz, 2H), 3.00-2.91 (m, 5H), 2.77-2.55 (m, 3H), 2.48 (s, 3H), 2.25-2.16 (m, 1H), 2.07 (ddd, J=13.3, 9.1, 4.5 Hz, 1H), 1.44 (d, J=6.5 Hz, 6H), 1.04 (s, 9H). HRMS (m/z) for $C_{55}H_{66}F_4N^{11}O_7S^+$ [M+H]$^+$: calculated 1100.4798, found 1100.4768.

Example 149: Synthesis of XF067-133

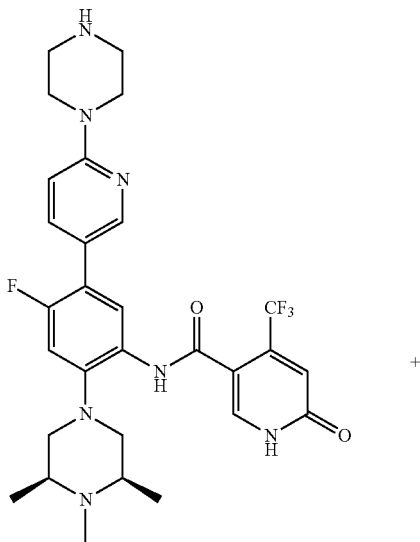

Intermediate 36

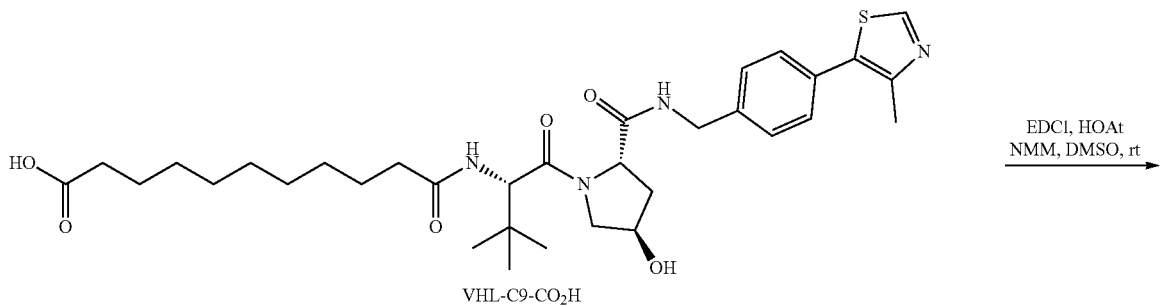

VHL-C9-CO$_2$H

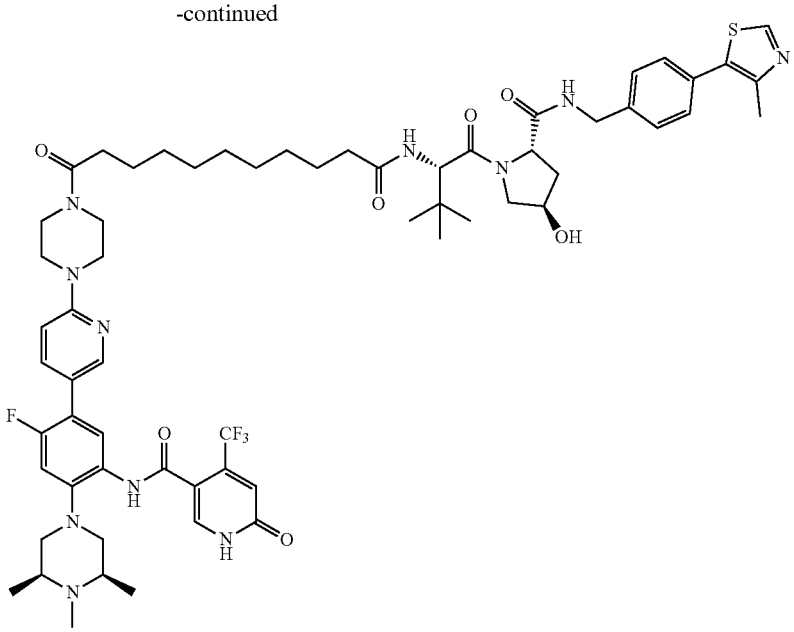

XF067-133

XF067-133 was synthesized following the standard procedures for preparing XF067-131 from intermediate 36 (14.6 mg, 0.025 mmol), VHL-C9-COOH (15.7 mg, 0.025 mmol, 1.0 equiv), EDCI (7.1 mg, 0.037 mmol, 1.5 equiv), HOAt (5 mg, 0.037 mmol, 1.5 equiv), and NMM (7.5 mg, 0.074 mmol, 3.0 equiv) in DMSO (1 mL). XF067-133 was obtained as white solid in TFA salt form (20.8 mg, yield 69%). $^1$H NMR (600 MHz, CD$_3$OD) δ 9.02 (s, 1H), 8.27-8.15 (m, 2H), 8.04-7.96 (m, 2H), 7.49-7.38 (m, 5H), 7.22 (d, J=11.8 Hz, 1H), 6.93 (s, 1H), 4.63 (s, 1H), 4.60-4.46 (m, 3H), 4.36 (d, J=15.5 Hz, 1H), 3.90 (d, J=11.0 Hz, 1H), 3.86-3.75 (m, 9H), 3.57-3.49 (m, 2H), 3.37 (d, J=13.0 Hz, 2H), 3.01-2.91 (m, 5H), 2.48 (s, 3H), 2.45 (t, J=7.5 Hz, 2H), 2.35-2.17 (m, 3H), 2.11-2.03 (m, 1H), 1.62 (dt, J=15.1, 7.3 Hz, 2H), 1.44 (d, J=6.5 Hz, 6H), 1.35 (d, J=20.8 Hz, 12H), 1.03 (s, 9H). HRMS (m/z) for $C_{62}H_{80}F_4N^{11}O_7S^+$ [M+H]$^+$: calculated 1198.5894. found 1198.5904.

Example 150: Synthesis of XF067-134

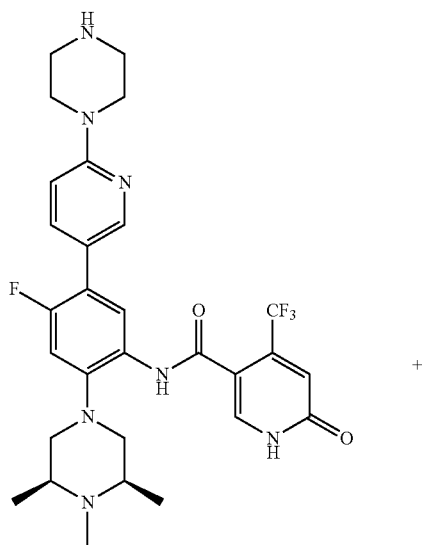

Intermediate 36

+

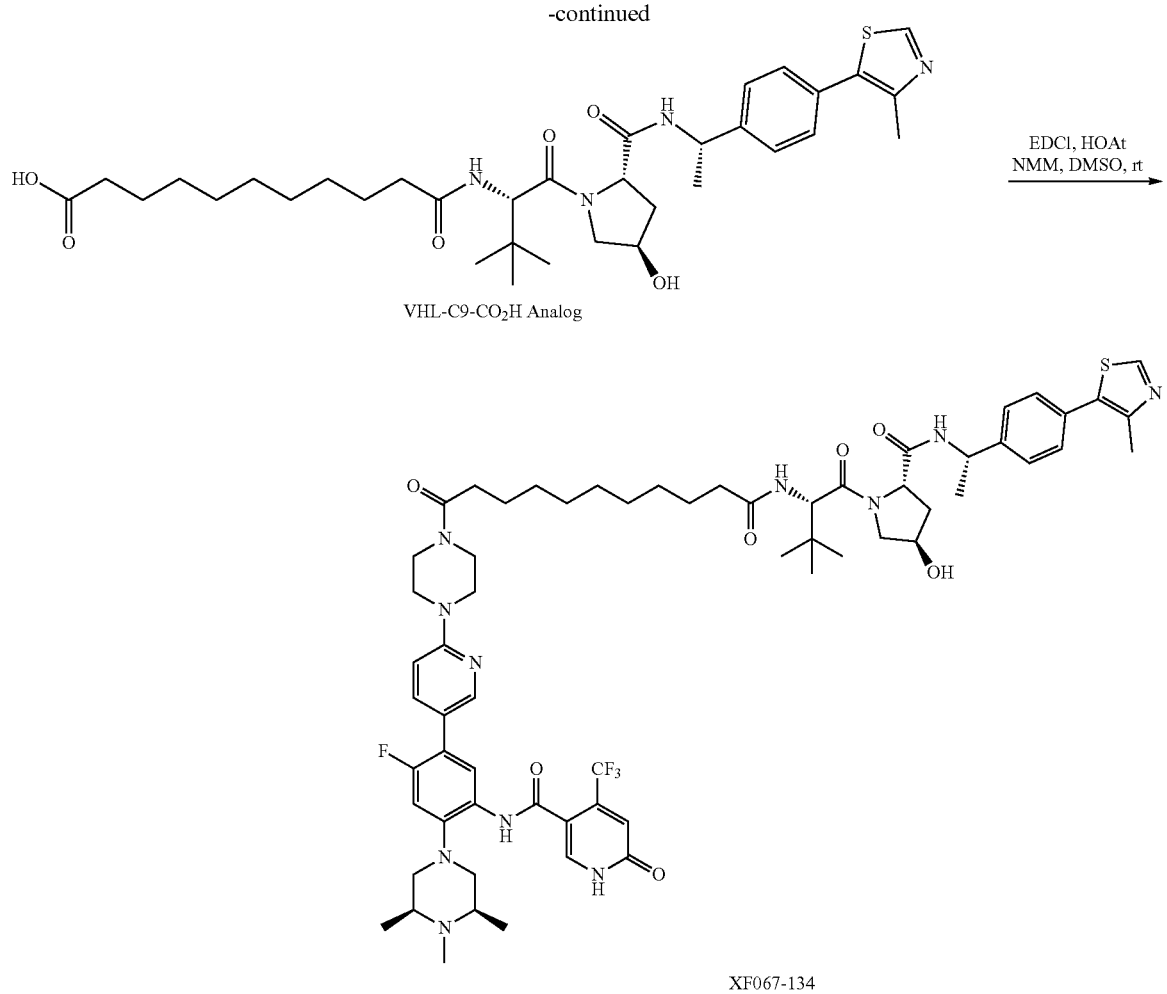

VHL-C9-CO₂H Analog

XF067-134

XF067-134 was synthesized following the standard procedures for preparing XF067-131 from intermediate 36 (14.6 mg, 0.025 mmol), VHL-C9-COOH Analog (16.1 mg, 0.025 mmol, 1.0 equiv), EDCI (7.1 mg, 0.037 mmol, 1.5 equiv), HOAt (5 mg, 0.037 mmol, 1.5 equiv), and NMM (7.5 mg, 0.074 mmol, 3.0 equiv) in DMSO (1 mL). XF067-134 was obtained as white solid in TFA salt form (21.8 mg, yield 72%). $^1$H NMR (600 MHz, CD$_3$OD) δ 9.05 (s, 1H), 8.24 (dd, J=9.4, 2.4 Hz, 1H), 8.19 (d, J=2.3 Hz, 1H), 8.03-7.97 (m, 2H), 7.49-7.38 (m, 5H), 7.22 (d, J=11.9 Hz, 1H), 6.93 (s, 1H), 4.98 (dd, J=16.4, 9.4 Hz, 2H), 4.62 (s, 1H), 4.57 (dd, J=9.3, 7.3 Hz, 1H), 4.43 (dq, J=5.7, 3.2, 2.5 Hz, 1H), 3.90-3.72 (m, 10H), 3.57-3.49 (m, 2H), 3.37 (d, J=12.9 Hz, 2H), 3.03-2.93 (m, 5H), 2.49 (s, 3H), 2.46 (t, J=7.6 Hz, 2H), 2.34-2.14 (m, 3H), 1.99-1.90 (m, 1H), 1.67-1.55 (m, 4H), 1.50 (d, J=7.0 Hz, 3H), 1.44 (d, J=6.5 Hz, 6H), 1.38-1.30 (m, 9H), 1.04 (s, 9H). HRMS (m/z) for $C_{63}H_{82}F_4N_{11}O_7S^+$ [M+H]$^+$: calculated 1212.6050, found 1212.6033.

Example 151: Synthesis of Intermediate 37

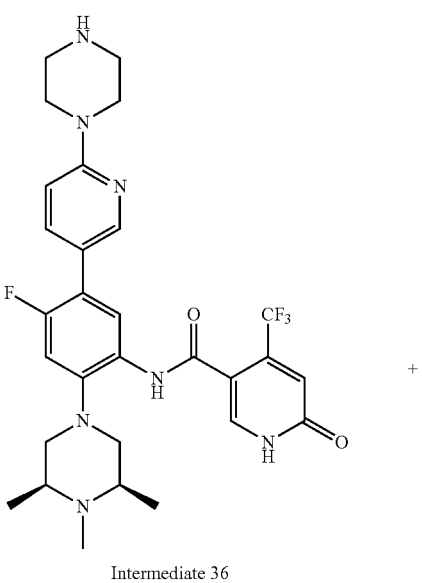

Intermediate 36

-continued

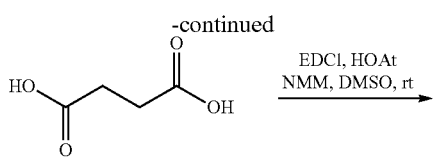

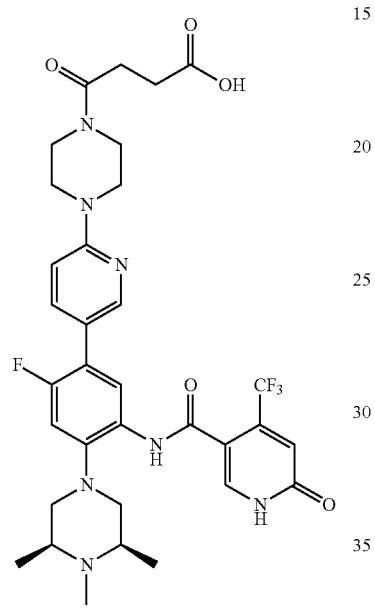

Intermediate 37

To the solution of intermediate 36 (400 mg, 0.68 mmol) in DMSO (5 mL) were added succinic acid (161 mg, 1.36 mmol, 2.0 equiv), EDCI (1-ethyl-3-(3-dimethylaminopropyl)carbodiimide) (196 mg, 1.02 mmol, 1.5 equiv), HOAt (1-hydroxy-7-azabenzo-triazole) (139 mg, 1.02 mmol, 1.5 equiv), and NMM (N-Methylmorpholine) (139 mg, 2.04 mmol, 3.0 equiv). After being stirring overnight at room temperature, the resulting mixture was purified by reverse phase ISCO (10%-100% methanol/0.1% TFA in $H_2O$) to afford Intermediate 37 (XF067-130) as white solid in TFA salt form (346.9 mg, yield 74%). $^1$H NMR (600 MHz, $CD_3OD$) δ 8.26 (dd, J=9.4, 2.2 Hz, 1H), 8.20 (d, J=2.2 Hz, 1H), 8.05-7.98 (m, 2H), 7.48 (d, J=9.6 Hz, 1H), 7.22 (d, J=11.9 Hz, 1H), 6.90 (s, 1H), 3.94-3.86 (m, 4H), 3.86-3.79 (m, 4H), 3.56 (dtd, J=9.7, 6.6, 3.1 Hz, 2H), 3.40-3.33 (m, 2H), 3.05-2.94 (m, 5H), 2.72 (dd, J=7.5, 5.2 Hz, 2H), 2.64 (dd, J=7.4, 5.1 Hz, 2H), 1.44 (d, J=6.5 Hz, 6H). HRMS (m/z) for $C_{33}H_{38}F_4N_7O_5^+$ [M+H]$^+$: calculated 688.2865, found 688.2834.

Example 152: Synthesis of XF067-140

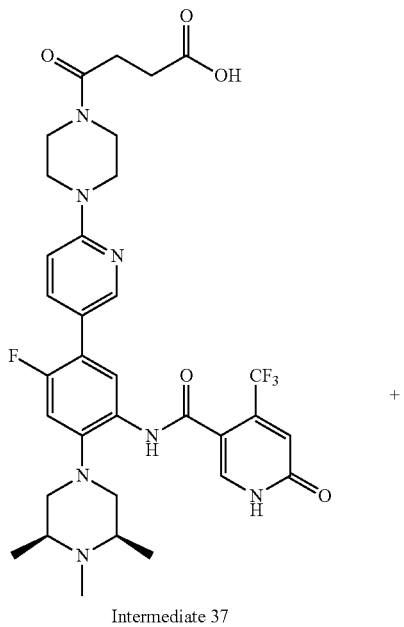

Intermediate 37

+

-continued

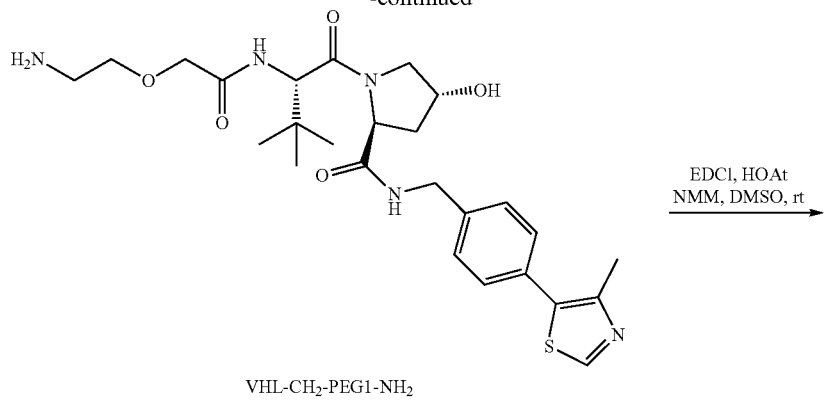

VHL-CH₂-PEG1-NH₂

EDCI, HOAt
NMM, DMSO, rt
→

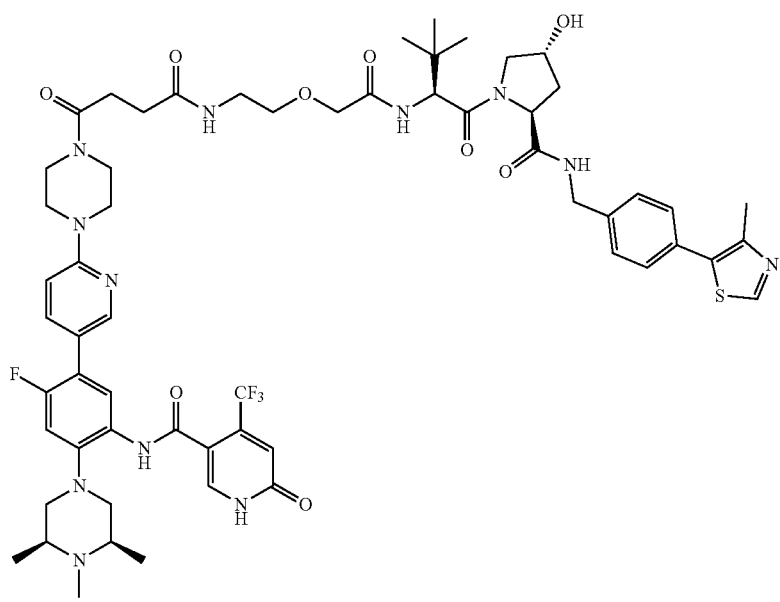

XF067-140

To the solution of intermediate 37 (10 mg, 0.015 mmol) in DMSO (1 mL) were added VHL-CH₂-PEG1-NH₂ (8.3 mg, 0.015 mmol, 1.0 equiv), EDCI (1-ethyl-3-(3-dimethyl-aminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv). After being stirring overnight at room temperature, the resulting mixture was purified by preparative HPLC (10%-100% methanol/0.1% TFA in H₂O) to afford XF067-140 as white solid in TFA salt form (5.3 mg, yield 29%). ¹H NMR (600 MHz, CD₃OD) δ 8.92 (s, 1H), 8.20 (s, 1H), 8.17-8.11 (m, 1H), 8.04-7.96 (m, 2H), 7.49-7.39 (m, 4H), 7.35 (t, J=9.6 Hz, 1H), 7.21 (d, J=12.0 Hz, 1H), 6.94 (s, 1H), 4.71 (s, 1H), 4.64-4.47 (m, 3H), 4.35 (dd, J=15.5, 7.9 Hz, 1H), 4.08 (d, J=15.2 Hz, 1H), 3.97 (d, J=15.3 Hz, 1H), 3.90-3.71 (m, 12H), 3.68-3.62 (m, 1H), 3.61-3.56 (m, 1H), 3.54-3.47 (m, 2H), 3.46-3.33 (m, 2H), 3.06-2.89 (m, 5H), 2.73-2.65 (m, 2H), 2.64-2.56 (m, 2H), 2.47 (s, 3H), 2.27-2.20 (m, 1H), 2.13-2.05 (m, 1H), 1.44 (d, J=6.5 Hz, 6H), 1.04 (s, 9H). HRMS (m/z) for $C_{59}H_{73}F_4N_{12}O_9S^+$ [M+H]⁺: calculated 1201.5275. found 1201.5246.

Example 153: Synthesis of XF067-141
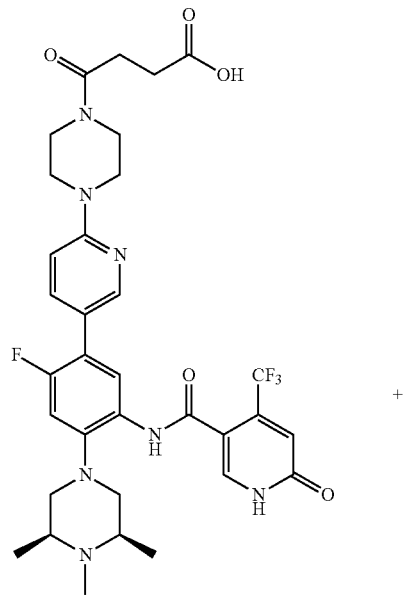
Intermediate 37
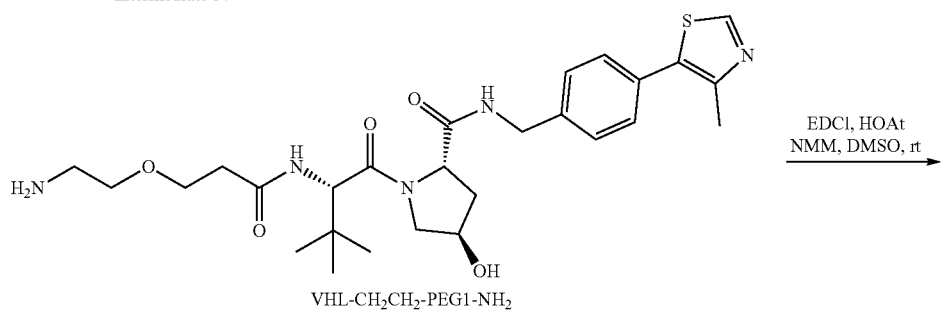
VHL-CH₂CH₂-PEG1-NH₂
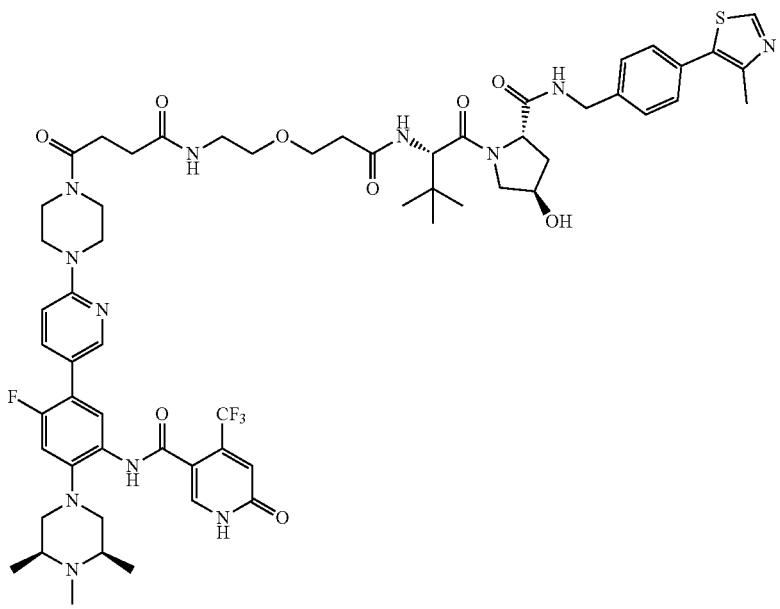
XF067-141

XF067-141 was synthesized following the standard procedures for preparing XF067-140 from intermediate 37 (10 mg, 0.015 mmol), VHL-CH₂CH₂-PEG1-NH₂ (11.6 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-141 was obtained as white solid in TFA salt form (4.4 mg, yield 24%). $^1$H NMR (600 MHz, CD$_3$OD) δ 8.92 (s, 1H), 8.20 (s, 1H), 8.14 (d, J=9.2 Hz, 1H), 8.03-7.94 (m, 2H), 7.47-7.39 (m, 4H), 7.33 (d, J=9.5 Hz, 1H), 7.21 (d, J=11.7 Hz, 1H), 6.93 (s, 1H), 4.68 (s, 1H), 4.62-4.53 (m, 2H), 4.51-4.48 (m, 1H), 4.33 (d, J=15.5 Hz, 1H), 3.91 (d, J=11.2 Hz, 1H), 3.85-3.64 (m, 13H), 3.58-3.44 (m, 4H), 3.44-3.33 (m, 2H), 2.97 (d, J=17.4 Hz, 5H), 2.72-2.41 (m, 9H), 2.27-2.19 (m, 1H), 2.13-2.08 (m, 1H), 1.44 (d, J=6.4 Hz, 6H), 1.05 (s, 9H). HRMS (m/z) for C$_{60}$H$_{75}$F$_4$N$_{12}$O$_9$S$^+$ [M+H]$^+$: calculated 1215.5431. found 1215.5455.

Example 154: Synthesis of XF067-142

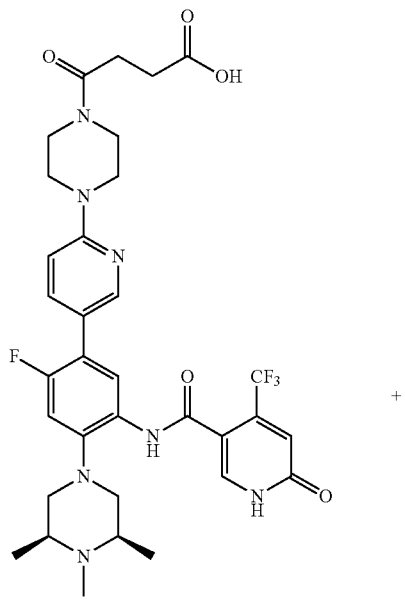

Intermediate 37

+

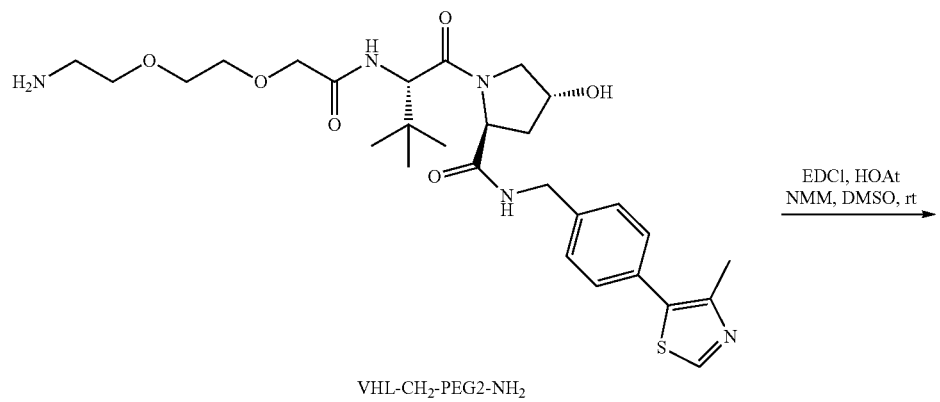

VHL-CH₂-PEG2-NH₂

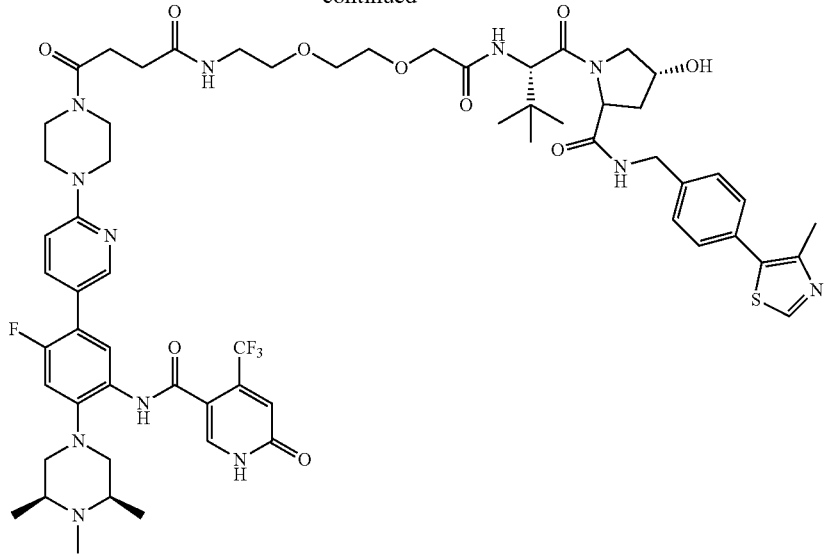

XF067-142

XF067-142 was synthesized following the standard procedures for preparing XF067-140 from intermediate 37 (10 mg, 0.015 mmol), VHL-CH$_2$-PEG2-NH$_2$ (9.2 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-142 was obtained as white solid in TFA salt form (11.7 mg, yield 63%). $^1$H NMR (600 MHz, CD$_3$OD) δ 8.99 (s, 1H), 8.23-8.12 (m, 2H), 8.05-7.90 (m, 2H), 7.51-7.32 (m, 5H), 7.22 (d, J=11.8 Hz, 1H), 6.93 (d, J=2.9 Hz, 1H), 4.79 (s, 1H), 4.63-4.53 (m, 2H), 4.53-4.41 (m, 1H), 4.39-4.23 (m, 1H), 4.13-3.97 (m, 2H), 3.92-3.47 (m, 20H), 3.37 (d, J=13.3 Hz, 2H), 3.02-2.91 (m, 5H), 2.67-2.44 (m, 7H), 2.29-2.20 (m, 1H), 2.13-2.02 (m, 1H), 1.44 (d, J=6.2 Hz, 6H), 1.07 (s, 9H). HRMS (m/z) for C$_{61}$H$_{77}$F$_4$N$_{12}$O$_{10}$S$^+$ [M+H]$^+$: calculated 1245.5537. found 1245.5562.

Example 155: Synthesis of XF067-143

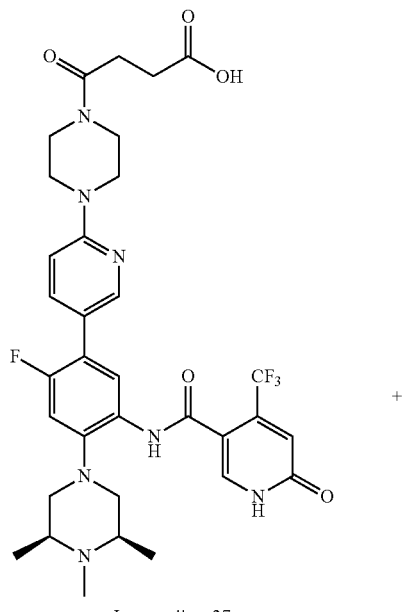

Intermediate 37

-continued

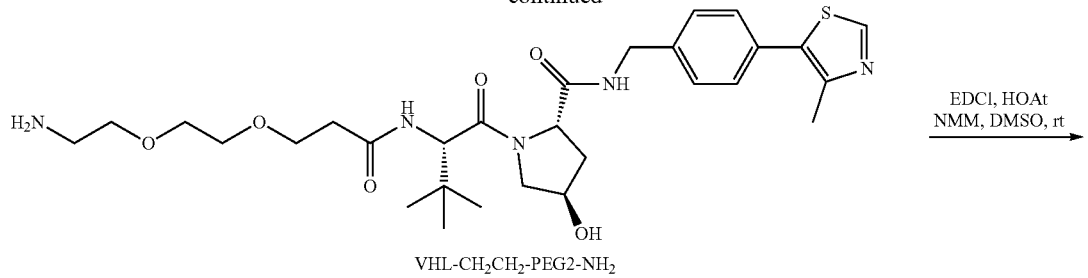

VHL-CH₂CH₂-PEG2-NH₂

→ EDCl, HOAt
NMM, DMSO, rt

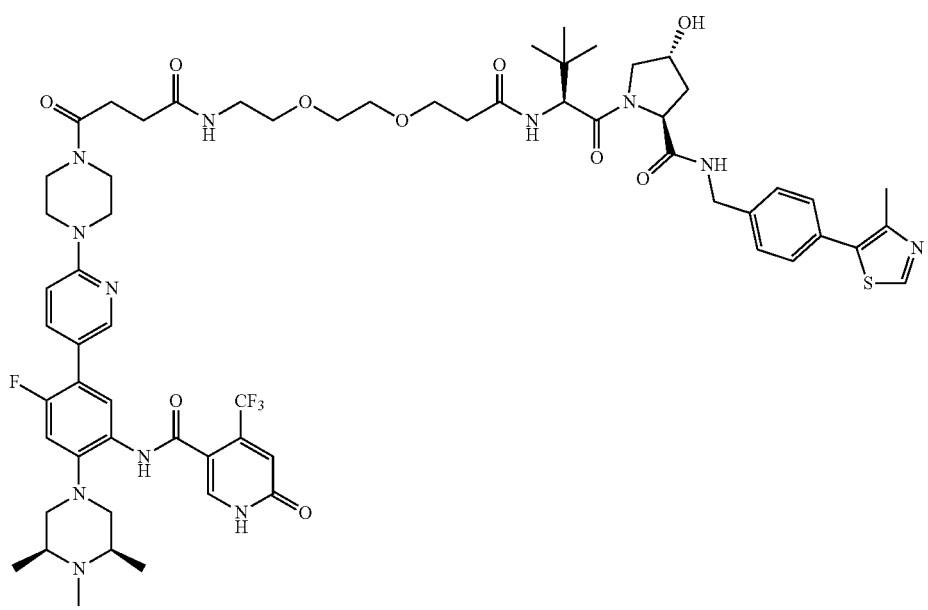

XF067-143

XF067-143 was synthesized following the standard procedures for preparing XF067-140 from intermediate 37 (10 mg, 0.015 mmol), VHL-CH₂CH₂-PEG2-NH₂ (12.3 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-143 was obtained as white solid in TFA salt form (6.4 mg, yield 34%). $^1$H NMR (600 MHz, CD$_3$OD) δ 8.96 (s, 1H), 8.25-8.10 (m, 2H), 8.08-7.96 (m, 2H), 7.55-7.36 (m, 5H), 7.22 (d, J=11.7 Hz, 1H), 6.93 (s, 1H), 4.67 (s, 1H), 4.60-4.46 (m, 3H), 4.36 (d, J=15.5 Hz, 1H), 3.94-3.69 (m, 16H), 3.67-3.57 (m, 4H), 3.55-3.49 (m, 2H), 3.42-3.33 (m, 2H), 3.02-2.91 (m, 5H), 2.71 (t, J=6.7 Hz, 2H), 2.62-2.52 (m, 2H), 2.52-2.45 (m, 5H), 2.27-2.19 (m, 1H), 2.11-2.04 (m, 1H), 1.44 (d, J=6.4 Hz, 6H), 1.04 (s, 9H). HRMS (m/z) for $C_{62}H_{79}F_4N_{12}O_{10}S^+$ [M+H]$^+$: calculated 1259.5693, found 1259.5719.

Example 156: Synthesis of XF067-144
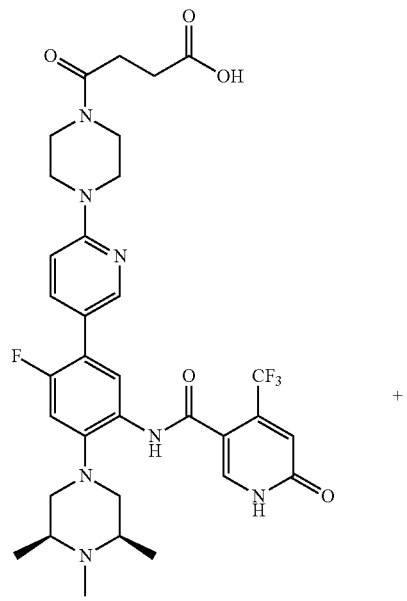
Intermediate 37
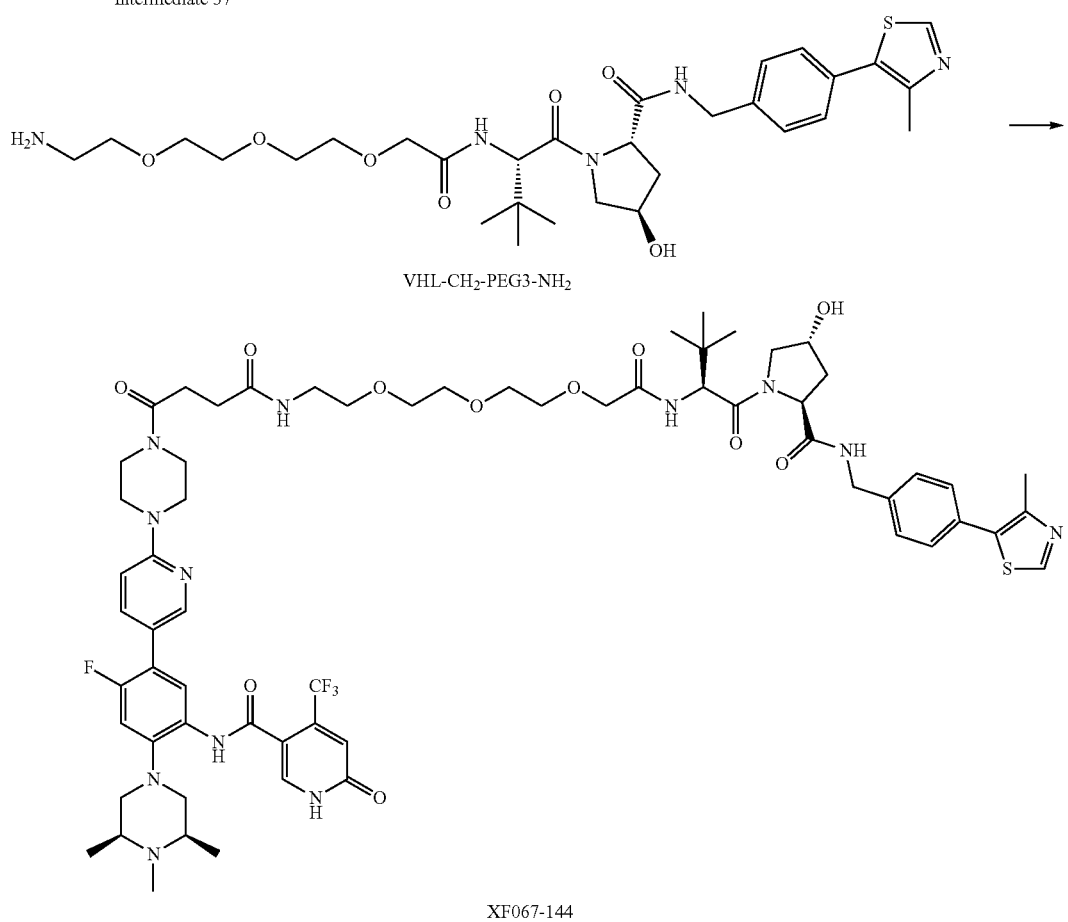
XF067-144 was synthesized following the standard procedures for preparing XF067-140 from intermediate 37 (10 mg, 0.015 mmol), VHL-CH$_2$-PEG3-NH$_{12}$ (12.7 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-144 was obtained as white solid in TFA salt form (14.8 mg, yield 76%). $^1$H NMR (600 MHz, CD$_3$OD) δ 8.98 (s, 1H), 8.20 (d, J=13.1 Hz, 2H), 8.08-7.94 (m, 2H), 7.55-7.35 (m, 5H), 7.22 (d, J=11.7 Hz, 1H), 6.93 (s, 1H), 4.70 (d, J=2.7 Hz, 1H), 4.63-4.42 (m, 3H), 4.37 (d, J=15.5 Hz, 1H), 4.06 (t, J=3.0 Hz, 2H), 3.92-3.47 (m, 24H), 3.39-3.31 (m, 2H), 2.97 (d, J=9.9 Hz, 5H), 2.71 (t, J=6.7 Hz, 2H), 2.54 (t, J=6.9 Hz, 2H), 2.48 (s, 3H), 2.29-2.19 (m, 1H), 2.16-1.98 (m, 1H), 1.44 (d, J=6.4 Hz, 6H), 1.04 (t, J=2.9 Hz, 9H). HRMS (m/z) for $C_{63}H_{81}F_4N_{12}O_{11}S^+$ [M+H]$^+$: calculated 1289.5799, found 1289.5812.
Example 157: Synthesis of XF067-145
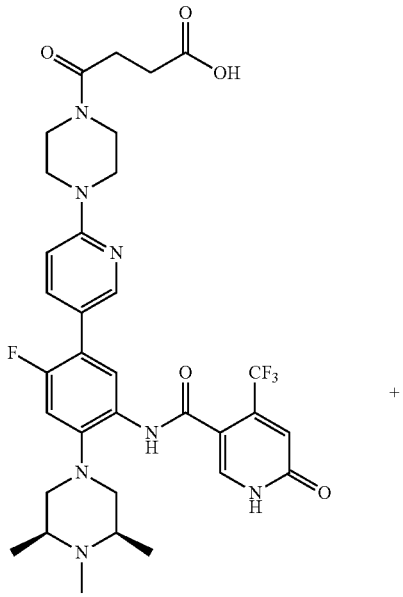
Intermediate 37
+
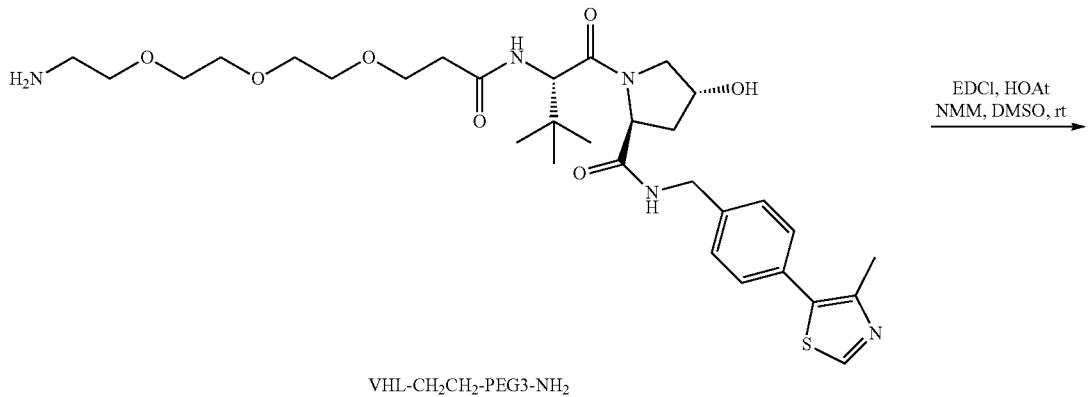
VHL-CH$_2$CH$_2$-PEG3-NH$_2$
EDCl, HOAt
NMM, DMSO, rt
→

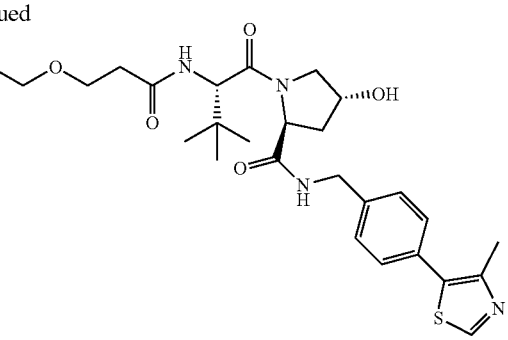
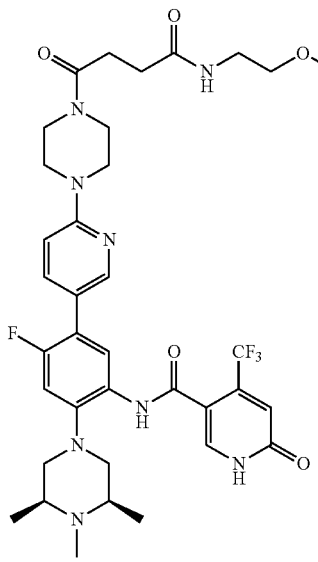

XF067-145

XF067-145 was synthesized following the standard procedures for preparing XF067-140 from intermediate 37 (10 mg, 0.015 mmol), VHL-CH$_2$CH$_2$-PEG3-NH$_2$ (12.2 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-145 was obtained as white solid in TFA salt form (9.4 mg, yield 48%). $^1$H NMR (600 MHz, CD$_3$OD) δ 8.99 (s, 1H), 8.24-8.08 (m, 2H), 8.00 (d, J=10.1 Hz, 2H), 7.56-7.29 (m, 5H), 7.22 (d, J=11.8 Hz, 1H), 6.93 (s, 1H), 4.65 (s, 1H), 4.61-4.45 (m, 3H), 4.36 (d, J=15.5 Hz, 1H), 3.93-3.68 (m, 14H), 3.66-3.57 (m, 8H), 3.56-3.49 (m, 4H), 3.40-3.34 (m, 2H), 3.02-2.91 (m, 5H), 2.72 (t, J=6.8 Hz, 2H), 2.65-2.54 (m, 2H), 2.51-2.43 (m, 5H), 2.29-2.15 (m, 1H), 2.12-2.01 (m, 1H), 1.44 (d, J=6.4 Hz, 6H), 1.03 (s, 9H). HRMS (m/z) for C$_{64}$H$_{83}$F$_4$N$_{12}$O$_{11}$S$^+$ [M+H]$^+$: calculated 1303.5956, found 1303.5913.

Example 158: Synthesis of XF067-146

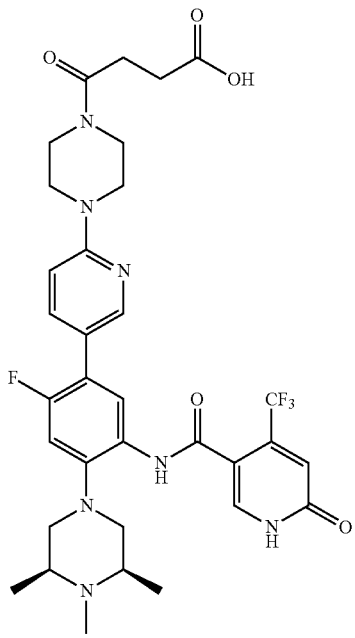

Intermediate 37

-continued

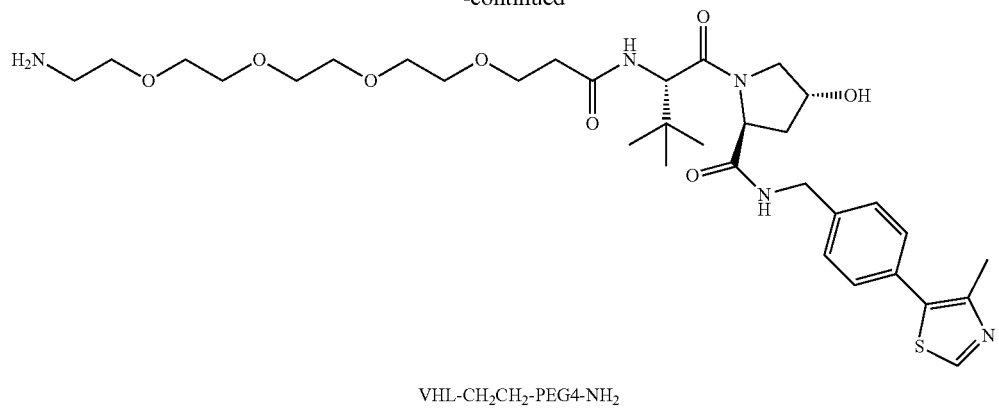

VHL-CH$_2$CH$_2$-PEG4-NH$_2$

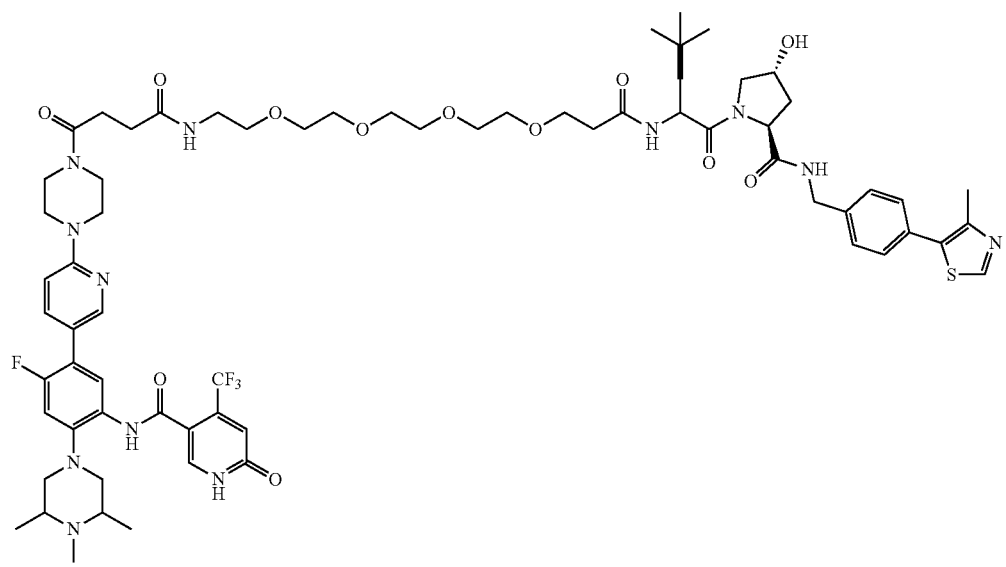

XF067-146

XF067-146 was synthesized following the standard procedures for preparing XF067-140 from intermediate 37 (10 mg, 0.015 mmol), VHL-CH$_2$CH$_2$-PEG4-NH$_2$ (10.7 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-146 was obtained as white solid in TFA salt form (9.5 mg, yield 47%). $^1$H NMR (600 MHz, CD$_3$OD) δ 8.97 (s, 1H), 8.20 (d, J=10.7 Hz, 2H), 8.09-7.97 (m, 2H), 7.65-7.31 (m, 5H), 7.22 (d, J=11.8 Hz, 1H), 6.93 (s, 1H), 4.64 (s, 1H), 4.61-4.44 (m, 3H), 4.36 (d, J=15.5 Hz, 1H), 3.90-3.69 (m, 16H), 3.67-3.58 (m, 12H), 3.56-3.48 (m, 2H), 3.41-3.34 (m, 2H), 3.06-2.92 (m, 5H), 2.72 (t, J=6.7 Hz, 2H), 2.61-2.51 (m, 2H), 2.48-2.44 (m, 5H), 2.24-2.18 (m, 1H), 2.07 (ddd, J=13.3, 9.2, 4.4 Hz, 1H), 1.44 (d, J=6.5 Hz, 6H), 1.03 (s, 9H). HRMS (m/z) for C$_{66}$H$_{87}$F$_4$N$_{12}$O$_{12}$S$^+$ [M+H]$^+$: calculated 1347.6218. found 1347.6245.

Example 159: Synthesis of XF067-147
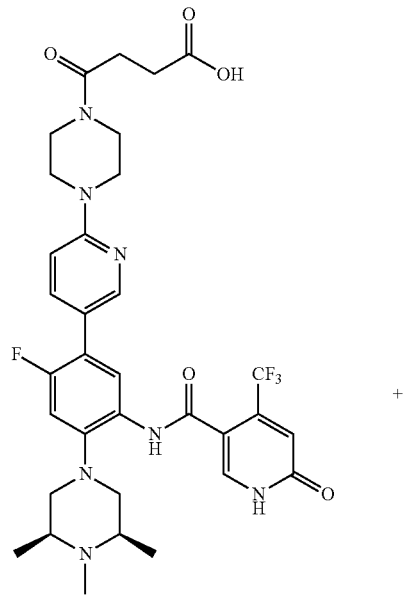
Intermediate 37
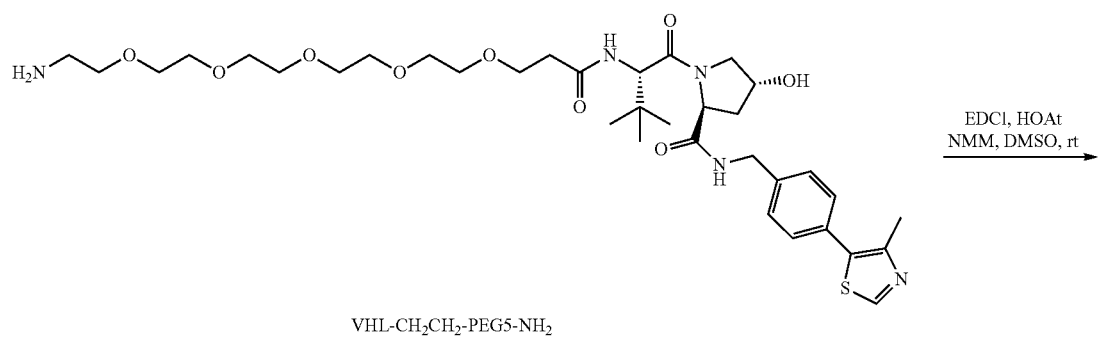
VHL-CH₂CH₂-PEG5-NH₂
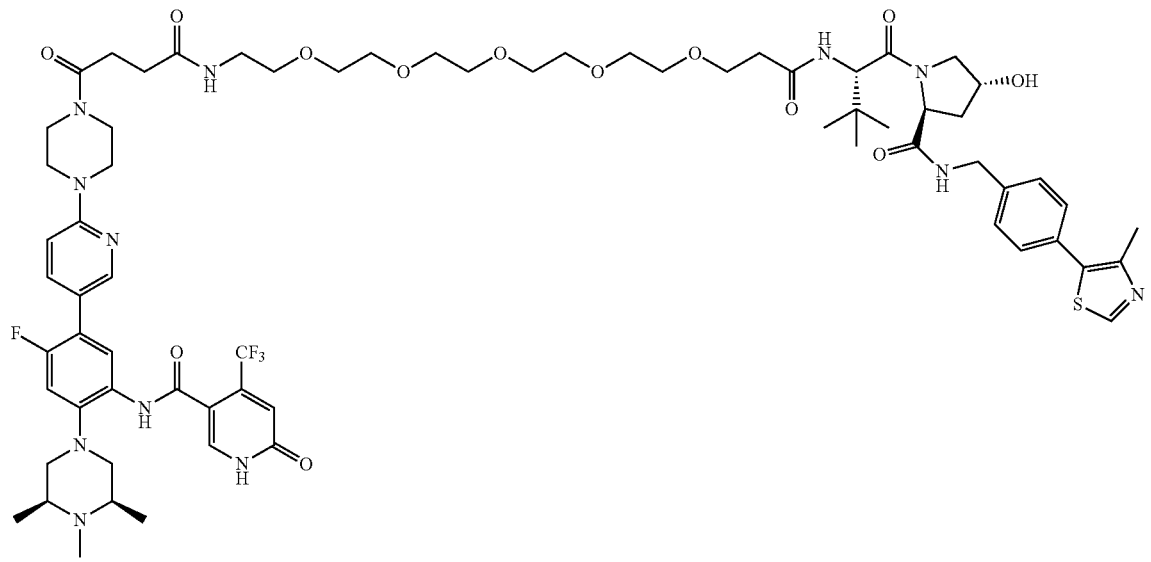
XF067-147

XF067-147 was synthesized following the standard procedures for preparing XF067-140 from intermediate 37 (10 mg, 0.015 mmol), VHL-CH$_2$CH$_2$-PEG5-NH$_2$ (14.2 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-147 was obtained as white solid in TFA salt form (7.3 mg, yield 35%). $^1$H NMR (600 MHz, CD$_3$OD) δ 8.98 (s, 1H), 8.26-8.09 (m, 2H), 8.08-7.88 (m, 2H), 7.54-7.32 (m, 5H), 7.21 (d, J=11.7 Hz, 1H), 6.93 (s, 1H), 4.64 (s, 1H), 4.57-4.42 (m, 3H), 4.35 (d, J=15.5 Hz, 1H), 3.91-3.68 (m, 16H), 3.67-3.57 (m, 16H), 3.53 (t, J=5.5 Hz, 2H), 3.40-3.34 (m, 2H), 2.97 (d, J=11.3 Hz, 5H), 2.72 (t, J=6.7 Hz, 2H), 2.59-2.53 (m, 2H), 2.48-2.44 (m, 5H), 2.29-2.16 (m, 1H), 2.14-2.03 (m, 1H), 1.44 (d, J=6.5 Hz, 6H), 1.03 (s, 9H). HRMS (m/z) for C$_{68}$H$_{91}$F$_4$N$_{12}$O$_{13}$S$^+$ [M+H]$^+$: calculated 1391.6480, found 1391.6502.

Example 160: Synthesis of XF067-148

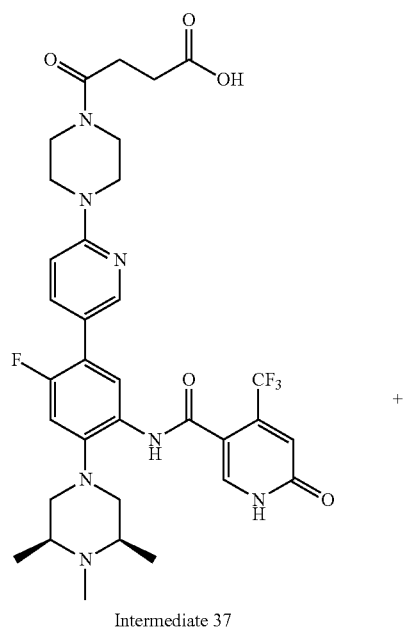

Intermediate 37

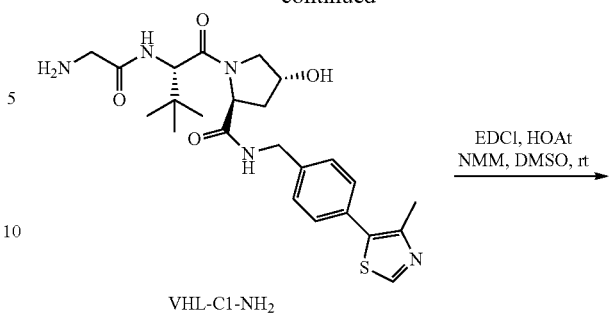

VHL-C1-NH$_2$

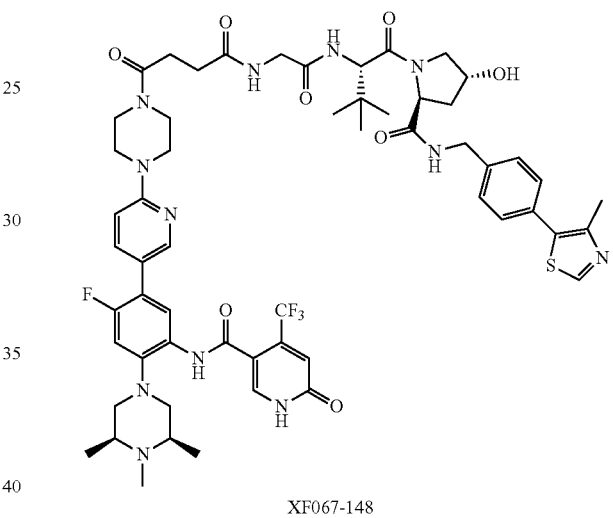

XF067-148

XF067-148 was synthesized following the standard procedures for preparing XF067-140 from intermediate 37 (10 mg, 0.015 mmol), VHL-C1-NH$_2$ (10.7 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-148 was obtained as white solid in TFA salt form (12.8 mg, yield 74%). $^1$H NMR (600 MHz, CD$_3$OD) δ 8.92 (s, 1H), 8.20 (d, J=2.4 Hz, 1H), 8.17-8.07 (m, 1H), 8.07-7.96 (m, 2H), 7.58-7.26 (m, 5H), 7.20 (d, J=11.7 Hz, 1H), 6.93 (s, 1H), 4.65 (s, 1H), 4.59-4.44 (m, 2H), 4.40-4.33 (m, 4H), 3.95-3.64 (m, 10H), 3.52-3.46 (m, 2H), 3.40-3.34 (m, 2H), 2.97-2.91 (m, 5H), 2.77 (t, J=6.8 Hz, 2H), 2.60 (t, J=6.6 Hz, 2H), 2.46 (s, 3H), 2.25-2.19 (m, 1H), 2.12-2.03 (m, 1H), 1.53-1.39 (m, 6H), 1.04 (s, 9H). HRMS (m/z) for C$_{57}$H$_{69}$F$_4$N$_{12}$O$_8$S$^+$ [M+H]$^+$: calculated 1157.5013, found 1157.5017.

Example 161: Synthesis of XF067-149

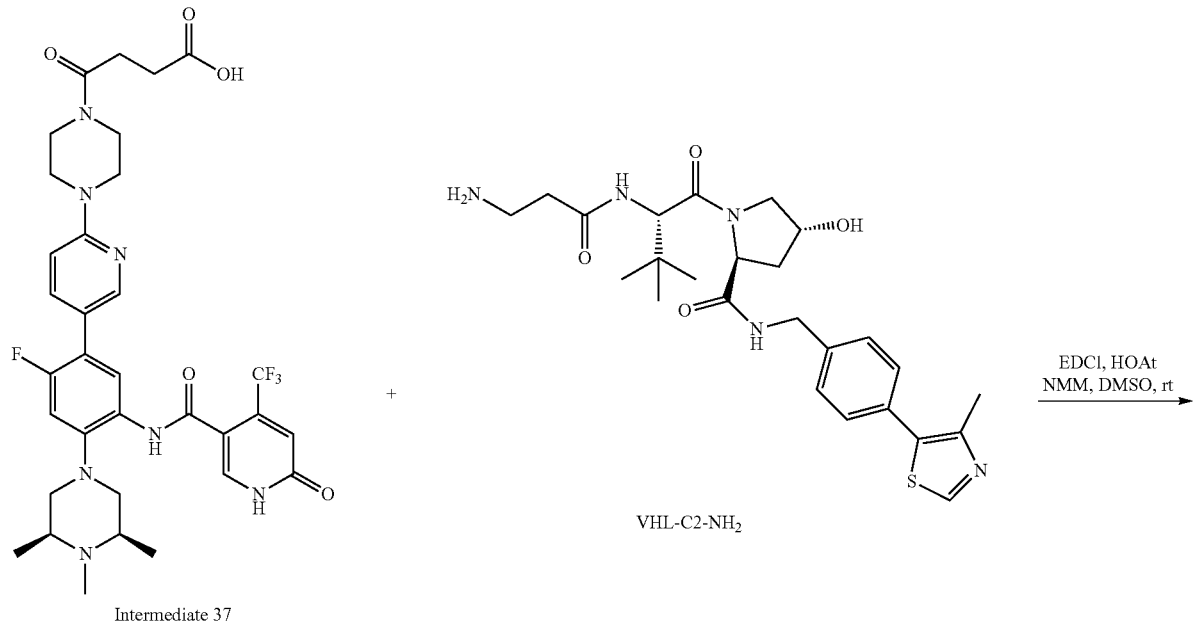

Intermediate 37

VHL-C2-NH₂

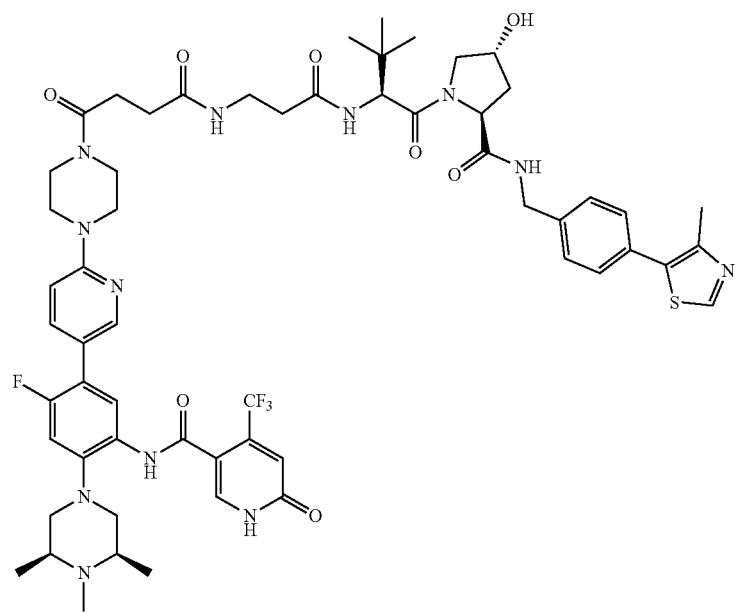

XF067-149

XF067-149 was synthesized following the standard procedures for preparing XF067-140 from intermediate 37 (10 mg, 0.015 mmol), VHL-C2-NH₂ (10.9 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-149 was obtained as white solid in TFA salt form (9.6 mg, yield 55%). $^1$H NMR (600 MHz, CD$_3$OD) δ 8.95 (s, 1H), 8.18 (d, J=11.0 Hz, 2H), 8.09-7.91 (m, 2H), 7.47 (d, J=8.0 Hz, 2H), 7.44-7.32 (m, 3H), 7.22 (d, J=11.8 Hz, 1H), 6.93 (s, 1H), 4.63-4.47 (m, 4H), 4.34 (dd, J=15.3, 7.1 Hz, 1H), 3.94 (d, J=11.1 Hz, 1H), 3.86-3.70 (m, 11H), 3.51 (dd, J=11.7, 5.5 Hz, 2H), 3.40-3.34 (m, 2H), 2.97 (d, J=13.8 Hz, 5H), 2.74-2.67 (m, 2H), 2.56-2.41 (m, 7H), 2.27-2.20 (m, 1H), 2.12-2.04 (m, 1H), 1.44 (d, J=6.4 Hz, 6H), 1.04 (s, 9H). HRMS (m/z) for $C_{58}H_{71}F_4N_{12}O_8S^+$ [M+H]$^+$: calculated 1171.5169, found 1171.5187.

Example 162: Synthesis of XF067-150
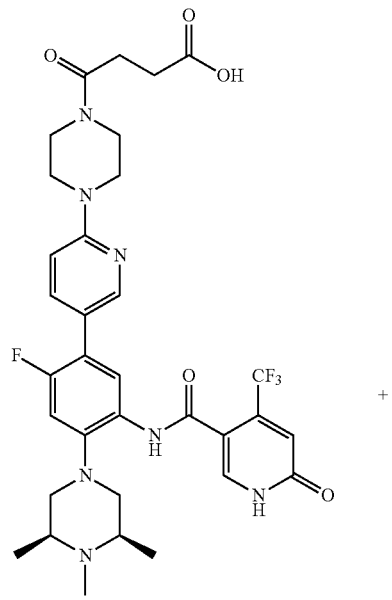
Intermediate 37
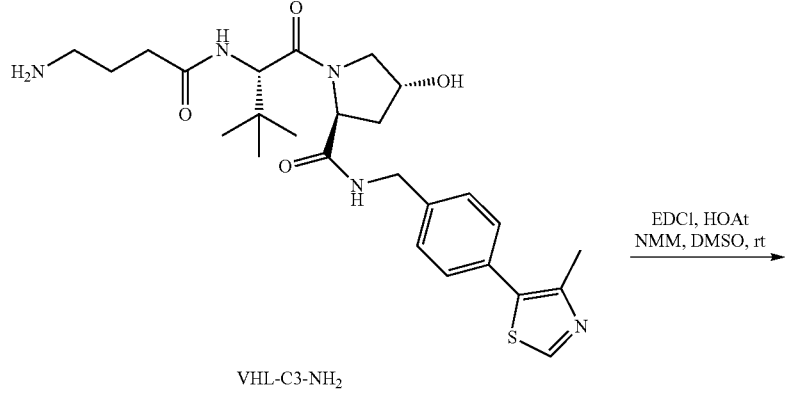
VHL-C3-NH₂
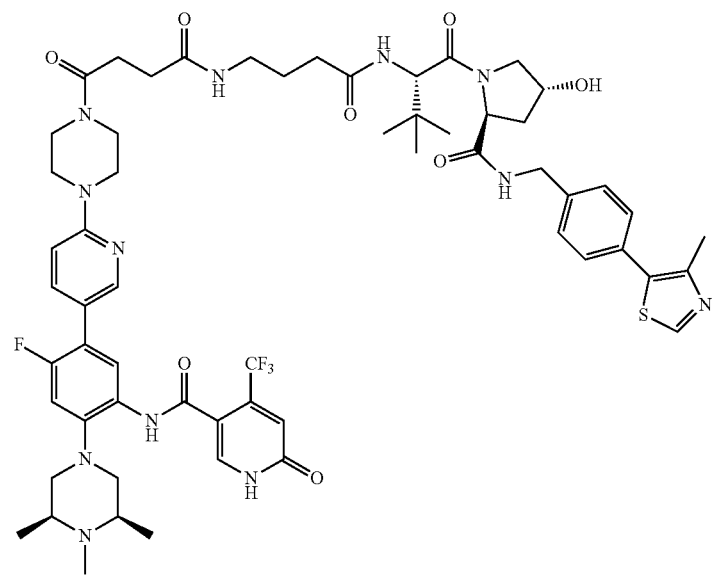
XF067-150

XF067-150 was synthesized following the standard procedures for preparing XF067-140 from intermediate 37 (10 mg, 0.015 mmol), VHL-C3-NH$_2$ (11.1 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-150 was obtained as white solid in TFA salt form (8.5 mg, yield 48%). $^1$H NMR (600 MHz, CD$_3$OD) δ 8.93 (s, 1H), 8.21-8.10 (m, 2H), 8.05-7.94 (m, 2H), 7.54-7.42 (m, 2H), 7.42-7.38 (m, 2H), 7.34 (d, J=9.5 Hz, 1H), 7.21 (d, J=11.8 Hz, 1H), 6.93 (s, 1H), 4.61 (s, 1H), 4.59-4.45 (m, 3H), 4.36 (d, J=15.5 Hz, 1H), 3.99-3.71 (m, 10H), 3.52 (s, 2H), 3.37 (d, J=13.1 Hz, 2H), 3.20-3.17 (m, 2H), 2.97 (d, J=14.0 Hz, 5H), 2.73 (t, J=6.8 Hz, 2H), 2.52 (t, J=6.6 Hz, 2H), 2.46 (s, 3H), 2.36-2.24 (m, 2H), 2.24-2.18 (m, 1H), 2.08 (ddd, J=13.4, 9.3, 4.5 Hz, 1H), 1.79 (p, J=6.9 Hz, 2H), 1.44 (d, J=6.5 Hz, 6H), 1.04 (s, 9H). HRMS (m/z) for C$_{59}$H$_{73}$F$_4$N$_{12}$O$_8$S$^+$ [M+H]$^+$: calculated 1185.5326. found 1185.5351.

Example 163: Synthesis of XF067-151

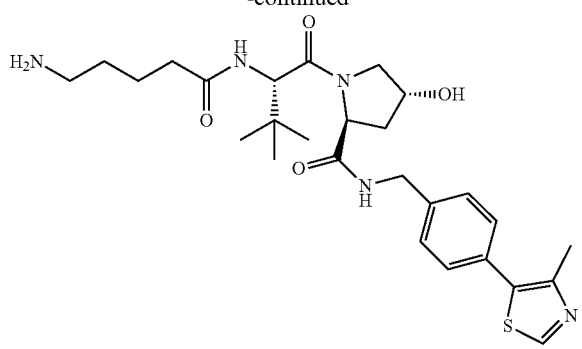

VHL-C4-NH$_2$

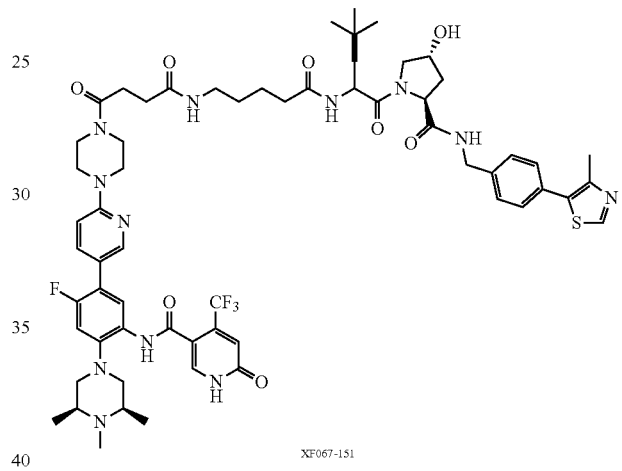

XF067-151

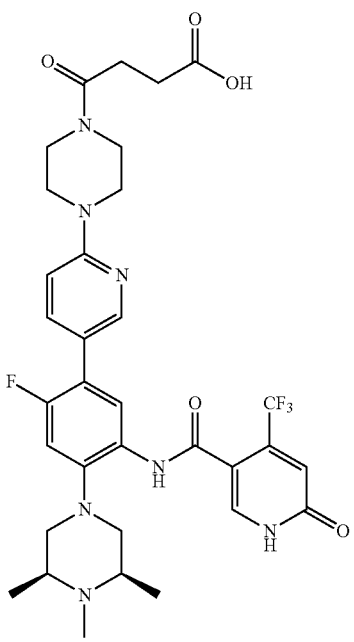

Intermediate 37

XF067-151 was synthesized following the standard procedures for preparing XF067-140 from intermediate 37 (10 mg, 0.015 mmol), VHL-C4-NH$_2$ (8.5 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-151 was obtained as white solid in TFA salt form (6.2 mg, yield 34%). $^1$H NMR (600 MHz, CD$_3$OD) δ 8.93 (s, 1H), 8.21-8.09 (m, 2H), 8.07-7.92 (m, 2H), 7.60-7.25 (m, 5H), 7.27-7.09 (m, 1H), 6.93 (s, 1H), 4.69-4.46 (m, 4H), 4.36 (d, J=15.3 Hz, 1H), 3.85-3.77 (m, 10H), 3.54-3.45 (m, 2H), 3.43-3.36 (m, 2H), 3.18 (t, J=6.8 Hz, 2H), 3.07-2.89 (m, 5H), 2.82-2.65 (m, 2H), 2.53-2.49 (m, 2H), 2.47 (s, 3H), 2.35-2.27 (m, 2H), 2.27-2.15 (m, 1H), 2.13-2.01 (m, 1H), 1.71-1.55 (m, 2H), 1.52 (q, J=7.5 Hz, 2H), 1.44 (d, J=6.5 Hz, 6H), 1.03 (s, 9H). HRMS (m/z) for C$_{60}$H$_{75}$F$_4$N$_{12}$O$_8$S$^+$ [M+H]$^+$: calculated 1199.5428. found 1199.5413.

Example 164: Synthesis of XF067-152
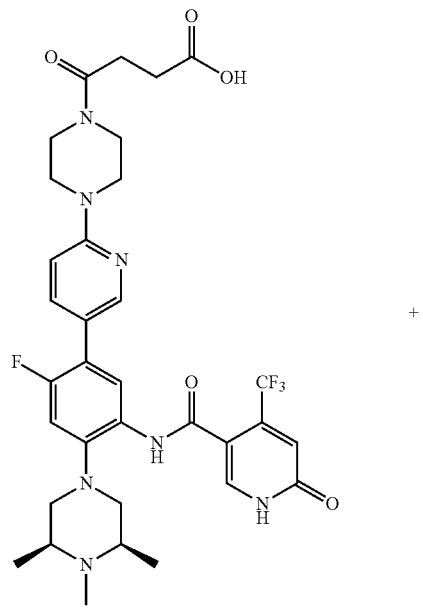
Intermediate 37
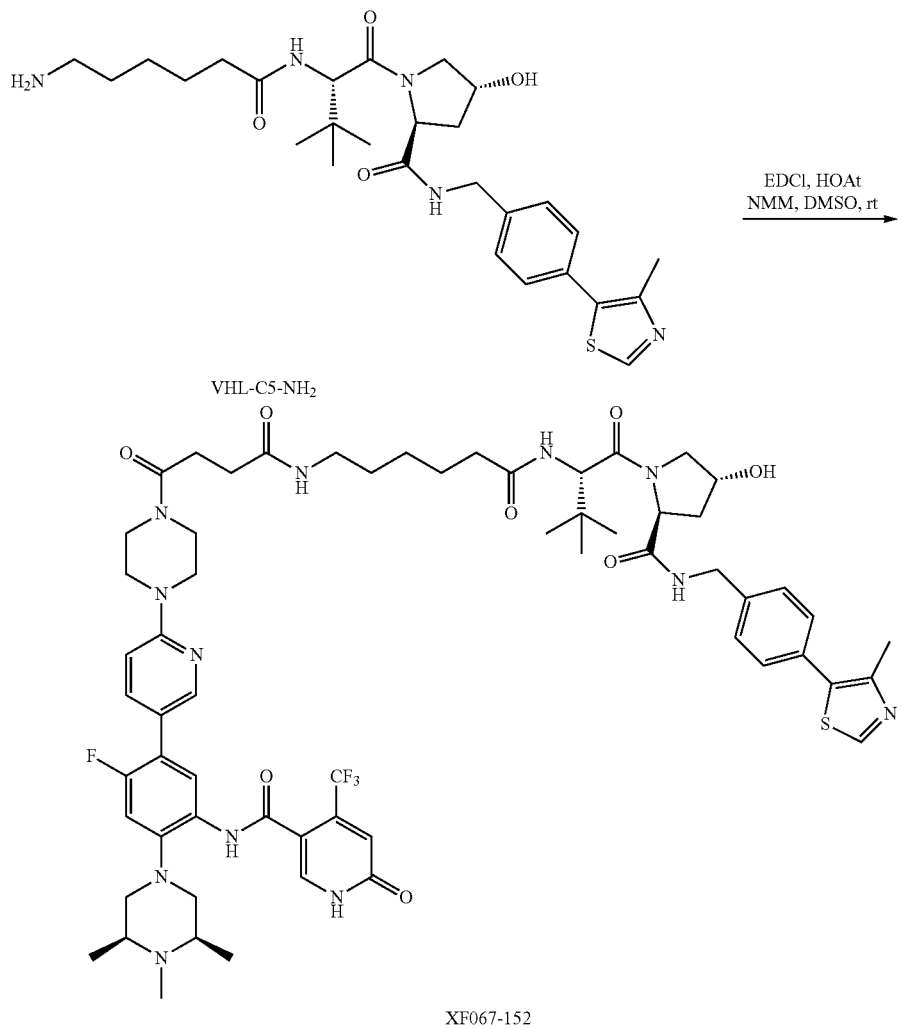

XF067-152 was synthesized following the standard procedures for preparing XF067-140 from intermediate 37 (10 mg, 0.015 mmol), VHL-C5-NH$_2$ (8.7 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-152 was obtained as white solid in TFA salt form (9.1 mg, yield 50%). $^1$H NMR (600 MHz, CD$_3$OD) δ 8.98 (s, 1H), 8.27-8.13 (m, 2H), 8.09-7.94 (m, 2H), 7.61-7.34 (m, 5H), 7.22 (d, J=11.9 Hz, 1H), 6.93 (s, 1H), 4.63 (s, 1H), 4.60-4.45 (m, 3H), 4.36 (d, J=15.4 Hz, 1H), 3.96-3.70 (m, 10H), 3.58-3.48 (m, 2H), 3.38 (d, J=13.0 Hz, 2H), 3.16 (t, J=7.1 Hz, 2H), 2.97-2.92 (m, 5H), 2.71 (t, J=6.7 Hz, 2H), 2.59-2.36 (m, 5H), 2.40-2.15 (m, 3H), 2.13-2.02 (m, 1H), 1.62 (p, J=7.5 Hz, 2H), 1.55-1.48 (m, 2H), 1.48-1.42 (m, 6H), 1.42-1.32 (m, 2H), 1.03 (s, 9H). HRMS (m/z) for C$_{61}$H$_{77}$F$_4$N$_{12}$O$_8$S$^+$ [M+H]$^+$: calculated 1213.5639. found 1213.5664.

Example 165: Synthesis of XF067-153

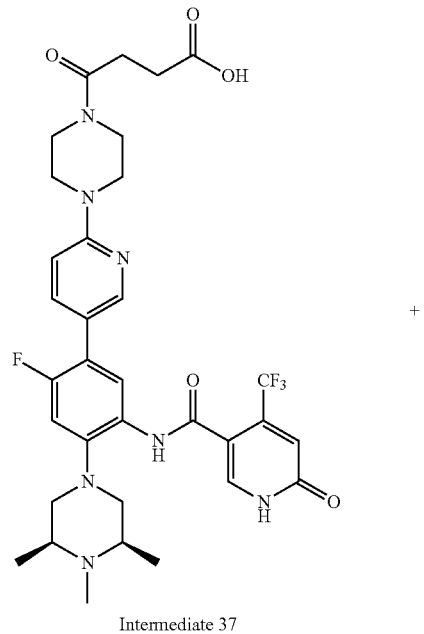

Intermediate 37

+

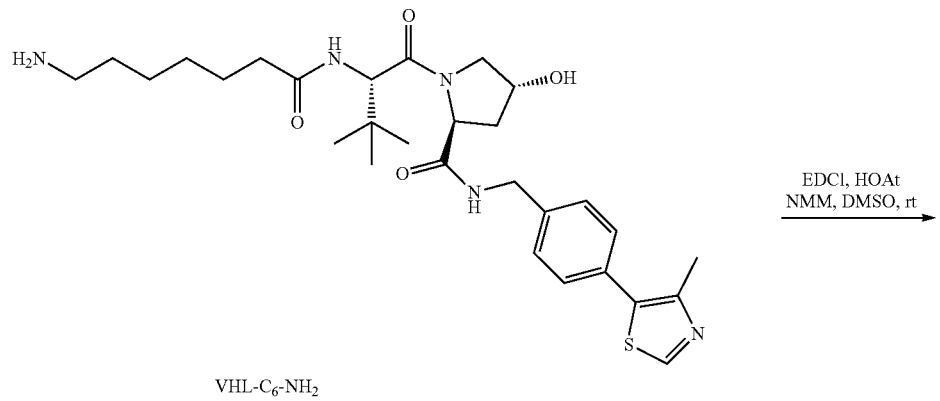

VHL-C$_6$-NH$_2$

-continued

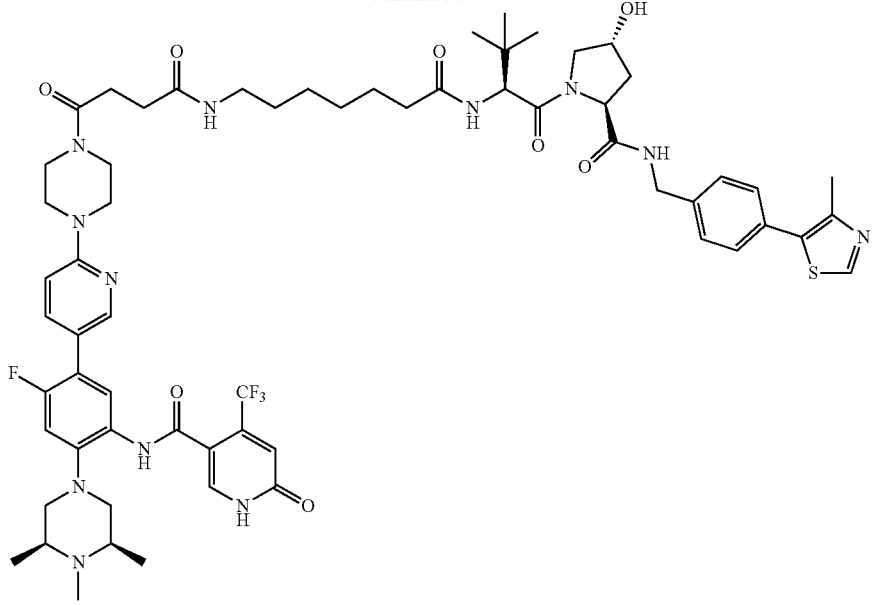

XF067-153

XF067-153 was synthesized following the standard procedures for preparing XF067-140 from intermediate 37 (10 mg, 0.015 mmol), VHL-C6-NH$_2$ (8.9 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-153 was obtained as white solid in TFA salt form (3.9 mg, yield 21%). $^1$H NMR (600 MHz, CD$_3$OD) δ 8.92 (s, 1H), 8.26-8.08 (m, 2H), 7.99 (d, J=12.7 Hz, 2H), 7.48-7.31 (m, 5H), 7.21 (d, J=11.4 Hz, 1H), 6.93 (s, 1H), 4.64 (s, 1H), 4.61-4.40 (m, 3H), 4.35 (d, J=15.3 Hz, 1H), 3.97-3.66 (m, 10H), 3.55-3.48 (m, 2H), 3.44-3.34 (m, 2H), 3.21-3.11 (m, 2H), 2.97 (d, J=21.8 Hz, 5H), 2.73-2.69 (m, 2H), 2.58-2.51 (m, 2H), 2.47 (d, J=2.9 Hz, 3H), 2.36-2.14 (m, 3H), 2.13-2.01 (m, 1H), 1.72-1.55 (m, 2H), 1.52-1.47 (m, 2H), 1.44 (d, J=6.4 Hz, 6H), 1.34-130 (m, 4H), 1.03 (s, 9H). HRMS (m/z) for C$_{62}$H$_{79}$F$_4$N$_{12}$O$_8$S$^+$ [M+H]$^+$: calculated 1227.5795. found 1227.5804.

Example 166: Synthesis of XF067-154

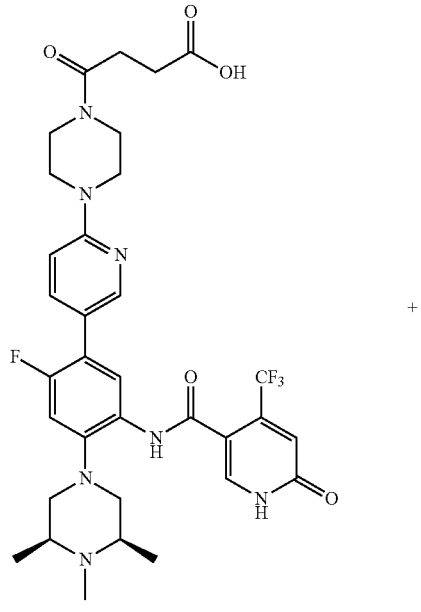

Intermediate 37

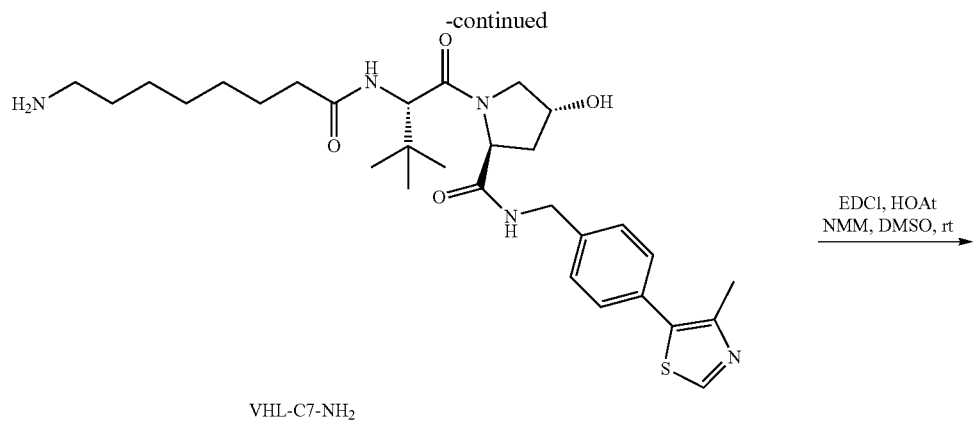

VHL-C7-NH₂

EDCI, HOAt
NMM, DMSO, rt

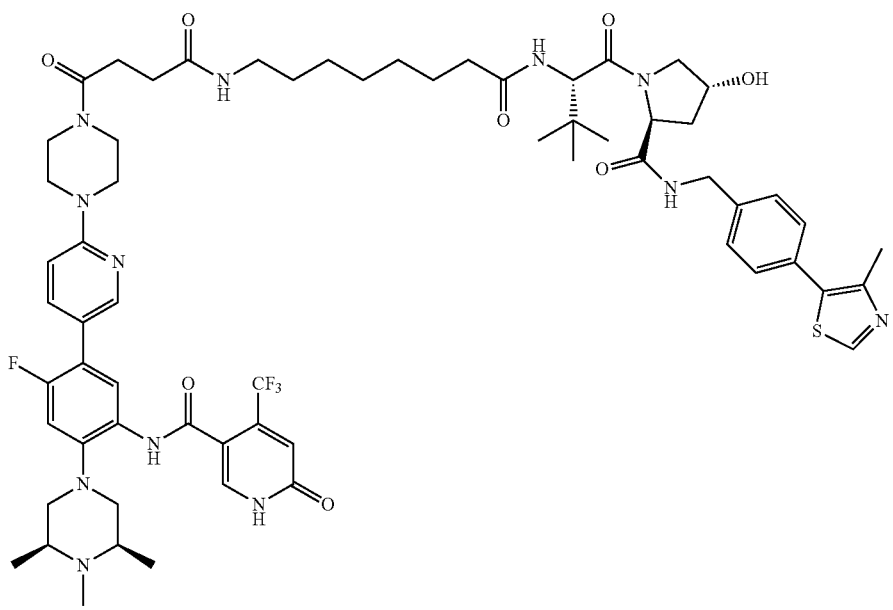

XF067-154

XF067-154 was synthesized following the standard procedures for preparing XF067-140 from intermediate 37 (10 mg, 0.015 mmol), VHL-C7-NH₂ (12 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-154 was obtained as white solid in TFA salt form (6.6 mg, yield 35%). $^1$H NMR (600 MHz, CD$_3$OD) δ 8.94 (s, 1H), 8.27-8.05 (m, 2H), 8.00 (d, J=10.6 Hz, 2H), 7.56-7.32 (m, 5H), 7.31-7.11 (m, 1H), 6.93 (s, 1H), 4.63 (s, 1H), 4.61-4.47 (m, 3H), 4.36 (d, J=15.5 Hz, 1H), 4.04-3.72 (m, 10H), 3.58-3.48 (m, 2H), 3.42-3.34 (m, 2H), 3.15 (t, J=7.1 Hz, 2H), 3.04-2.90 (m, 5H), 2.71 (t, J=6.7 Hz, 2H), 2.58-2.45 (m, 5H), 2.34-2.17 (m, 3H), 2.11-2.01 (m, 1H), 1.72-1.55 (m, 2H), 1.52-1.39 (m, 8H), 1.39-1.24 (m, 6H), 1.03 (s, 9H). HRMS (m/z) for $C_{63}H_{81}F_4N_{12}O_8S^+$ [M+H]$^+$: calculated 1241.5952, found 1241.5918.

Example 167: Synthesis of XF067-
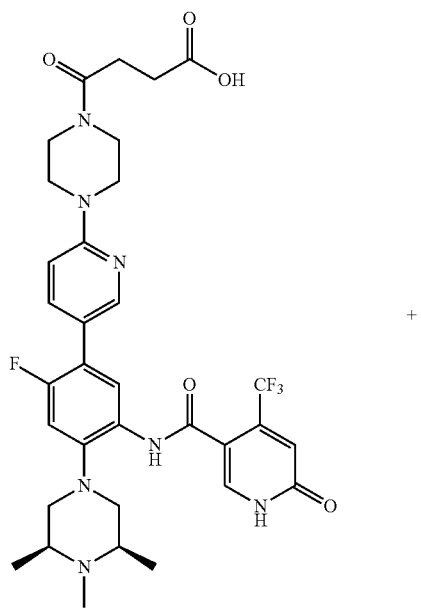
Intermediate 37
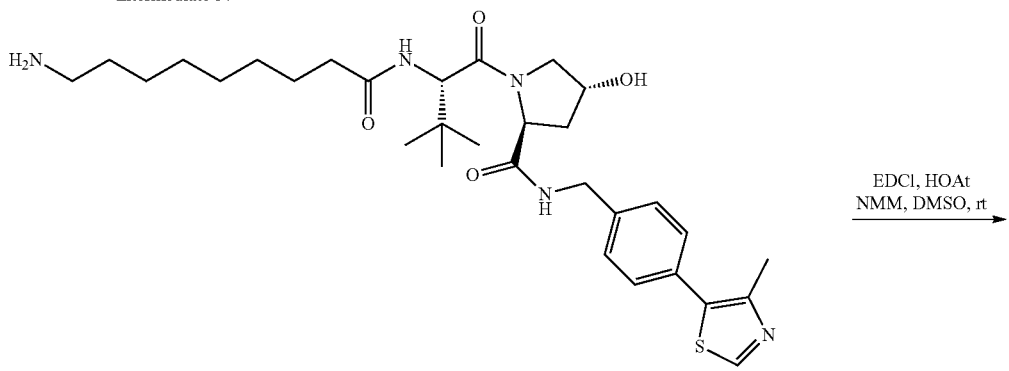
VHL-C8-NH2
EDCl, HOAt
NMM, DMSO, rt
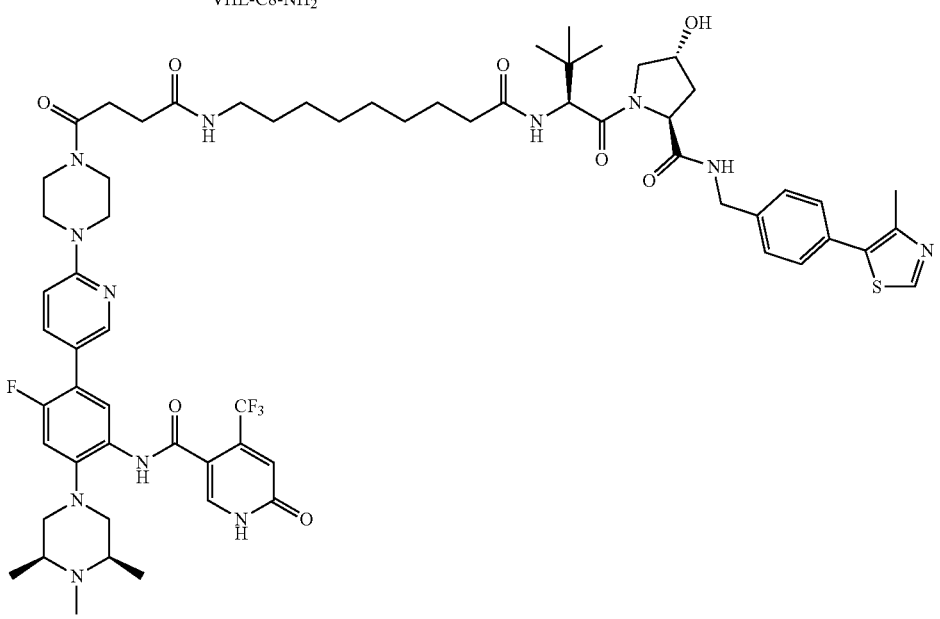
XF067-155

XF067-155 was synthesized following the standard procedures for preparing XF067-140 from intermediate 37 (10 mg, 0.015 mmol), VHL-C8-NH$_2$ (9.3 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-155 was obtained as white solid in TFA salt form (6.2 mg, yield 33%). $^1$H NMR (600 MHz, CD$_3$OD) δ 8.94 (s, 1H), 8.21 (d, J=2.2 Hz, 1H), 8.14 (d, J=9.3 Hz, 1H), 8.07-7.90 (m, 2H), 7.50-7.39 (m, 4H), 7.34 (d, J=9.4 Hz, 1H), 7.21 (d, J=11.8 Hz, 1H), 6.93 (s, 1H), 4.63 (s, 1H), 4.61-4.44 (m, 3H), 4.35 (d, J=15.5 Hz, 1H), 3.99-3.69 (m, 10H), 3.56-3.48 (m, 2H), 3.37 (d, J=13.0 Hz, 2H), 3.15 (t, J=7.1 Hz, 2H), 3.02-2.89 (m, 5H), 2.71 (t, J=6.7 Hz, 2H), 2.53 (t, J=6.7 Hz, 2H), 2.47 (s, 3H), 2.32-2.15 (m, 3H), 2.07 (s, 1H), 1.63-1.54 (m, 2H), 1.53-1.38 (m, 8H), 1.32-1.26 (m, 8H), 1.03 (s, 9H). HRMS (m/z) for C$_{64}$H$_{83}$F$_4$N$_{12}$O$_8$S$^+$ [M+H]$^+$: calculated 1255.6108. found 1255.6097.

Example 168: Synthesis of XF067-156

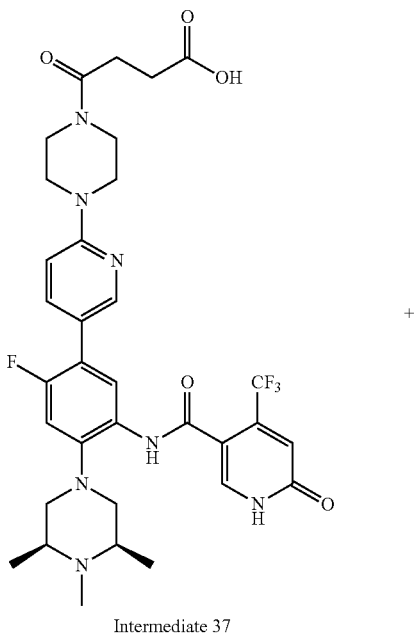

Intermediate 37

+

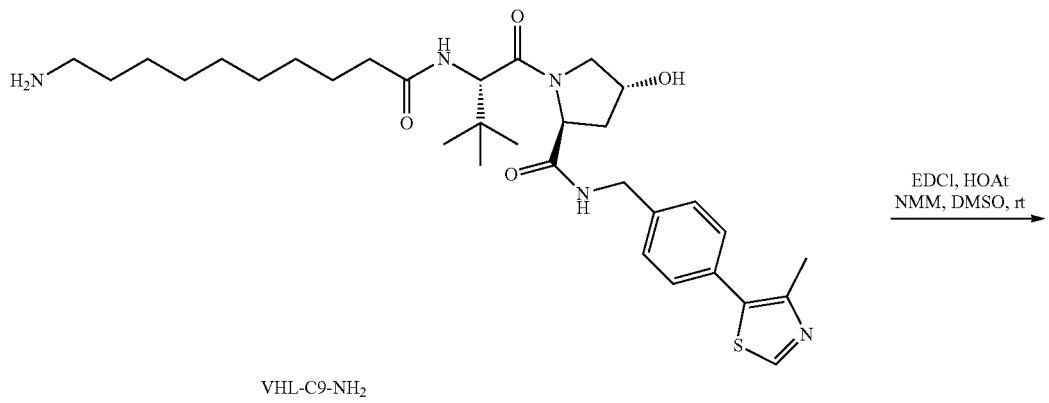

VHL-C9-NH$_2$

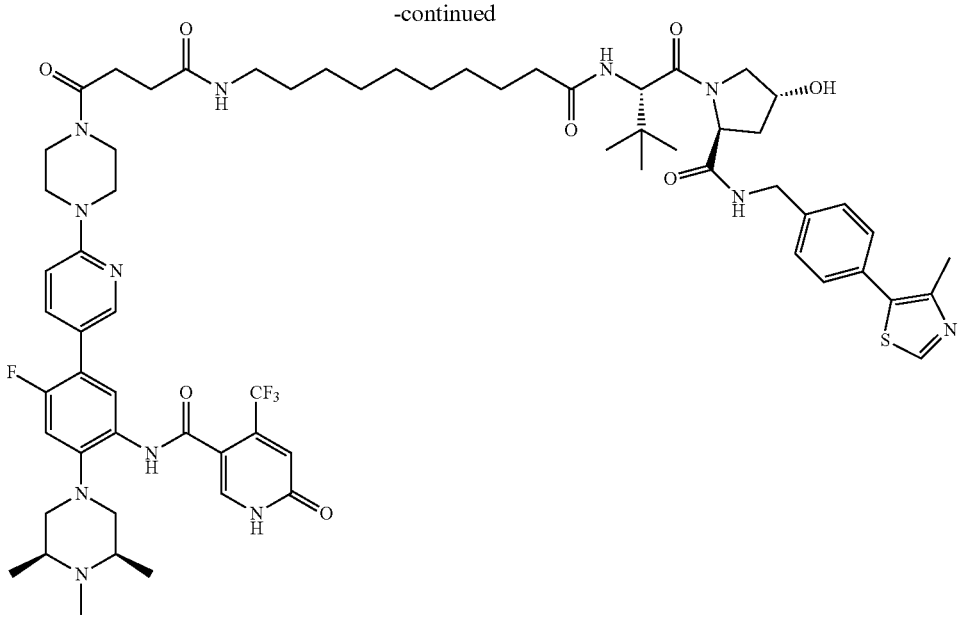

XF067-156

XF067-156 was synthesized following the standard procedures for preparing XF067-140 from intermediate 37 (10 mg, 0.015 mmol), VHL-C9-NH$_2$ (12.4 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-156 was obtained as white solid in TFA salt form (13.6 mg, yield 71%). $^1$H NMR (600 MHz, CD$_3$OD) δ 8.93 (s, 1H), 8.22 (d, J=2.2 Hz, 1H), 8.14 (d, J=9.3 Hz, 1H), 8.06-7.89 (m, 2H), 7.51-7.38 (m, 4H), 7.33 (d, J=9.4 Hz, 1H), 7.22 (d, J=11.8 Hz, 1H), 6.93 (s, 1H), 4.64 (s, 1H), 4.61-4.45 (m, 3H), 4.35 (d, J=15.5 Hz, 1H), 3.98-3.66 (m, 10H), 3.55-3.49 (m, 2H), 3.37 (d, J=13.0 Hz, 2H), 3.15 (t, J=7.1 Hz, 2H), 3.02-2.89 (m, 5H), 2.71 (t, J=6.7 Hz, 2H), 2.53 (t, J=6.7 Hz, 2H), 2.46 (s, 3H), 2.312-2.13 (m, 3H), 2.06 (s, 1H), 1.63-1.54 (m, 2H), 1.53-1.38 (m, 8H), 1.32-1.21 (m, 10H), 1.03 (s, 9H). HRMS (m/z) for C$_{65}$H$_{85}$F$_4$N$_{12}$O$_8$S$^+$ [M+H]$^+$: calculated 1269.6265. found 1269.6246.

Example 169: Synthesis of XF067-157

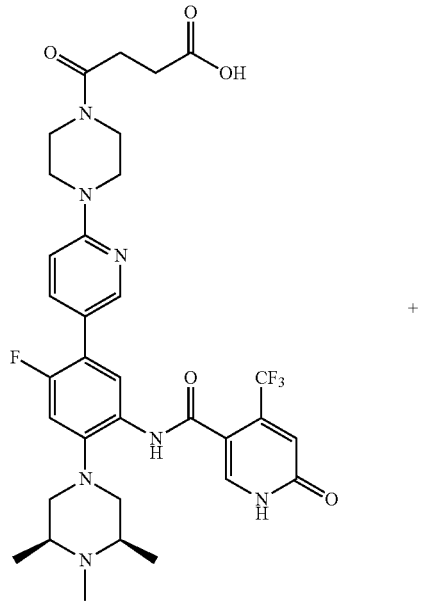

Intermediate 37

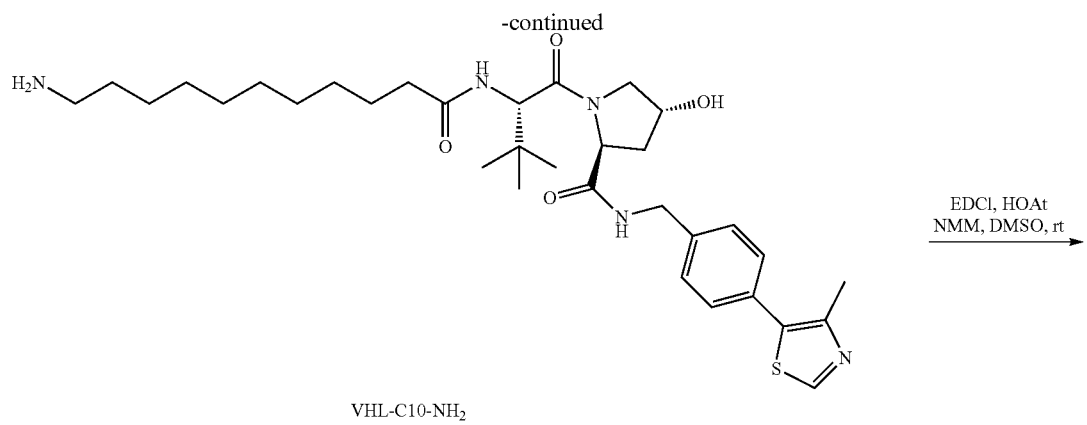

VHL-C10-NH₂

EDCl, HOAt
NMM, DMSO, rt

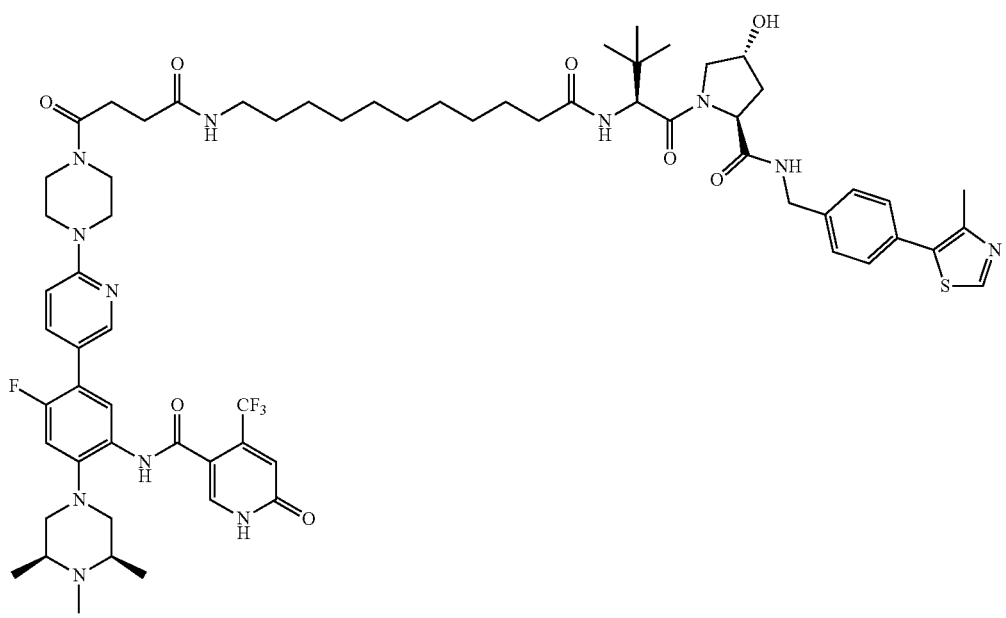

XF067-157

XF067-157 was synthesized following the standard procedures for preparing XF067-140 from intermediate 37 (10 mg, 0.015 mmol), VHL-C10-NH₂ (9.8 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-157 was obtained as white solid in TFA salt form (4.1 mg, yield 21%). ¹H NMR (600 MHz, CD₃OD) δ 8.92 (s, 1H), 8.21 (d, J=2.4 Hz, 1H), 8.12 (d, J=9.2 Hz, 1H), 8.03-7.94 (m, 2H), 7.53-7.37 (m, 4H), 7.32 (d, J=9.5 Hz, 1H), 7.20 (d, J=11.7 Hz, 1H), 6.93 (s, 1H), 4.63 (s, 1H), 4.61-4.42 (m, 3H), 4.35 (d, J=15.5 Hz, 1H), 4.00-3.68 (m, 10H), 3.57-3.48 (m, 2H), 3.44-3.35 (m, 2H), 3.22-3.10 (m, 2H), 3.06-2.82 (m, 5H), 2.72 (t, J=6.7 Hz, 2H), 2.53 (t, J=6.7 Hz, 2H), 2.47 (s, 3H), 2.34-2.18 (m, 3H), 2.13-2.02 (m, 1H), 1.67-1.54 (m, 2H), 1.51-1.40 (m, 8H), 1.40-1.24 (m, 12H), 1.03 (s, 9H). HRMS (m/z) for $C_{66}H_{87}F_4N_{12}O_8S^+$ [M+H]⁺: calculated 1283.6421. found 1283.6445.

Example 170: Synthesis of XF067-158

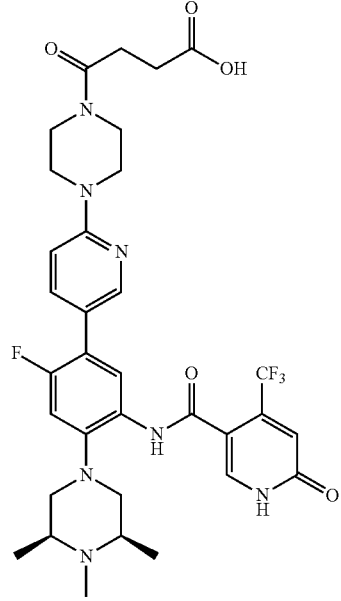

Intermediate 37

+

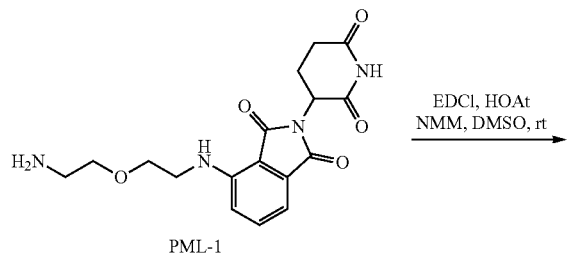

PML-1

→ (EDCl, HOAt, NMM, DMSO, rt)

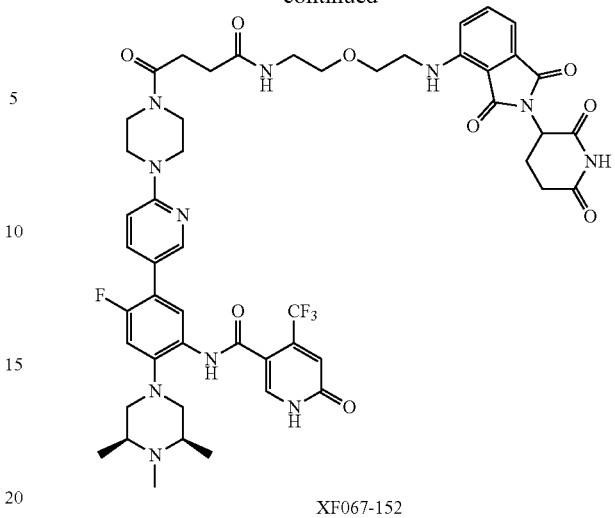

XF067-152

XF067-158 was synthesized following the standard procedures for preparing XF067-140 from intermediate 37 (10 mg, 0.015 mmol), PML-1 (7.1 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-158 was obtained as yellow solid in TFA salt form (7.9 mg, yield 51%). $^1$H NMR (600 MHz, CD$_3$OD) δ 8.25-8.08 (m, 2H), 8.06-7.96 (m, 2H), 7.55 (t, J=7.8 Hz, 1H), 7.33 (d, J=9.7 Hz, 1H), 7.21 (d, J=11.8 Hz, 1H), 7.06 (dd, J=25.6, 7.8 Hz, 2H), 6.93 (s, 1H), 5.09 (dd, J=12.6, 5.5 Hz, 1H), 3.88-3.64 (m, 10H), 3.64-3.47 (m, 6H), 3.43-3.35 (m, 4H), 3.05-2.92 (m, 5H), 2.92-2.45 (m, 7H), 2.14-2.04 (m, 1H), 1.44 (d, J=6.4 Hz, 6H). HRMS (m/z) for $C_{50}H_{56}F_4N_{11}O_9^+$ [M+H]$^+$: calculated 1030.4193. found 1030.4178.

Example 171: Synthesis of XF067-159

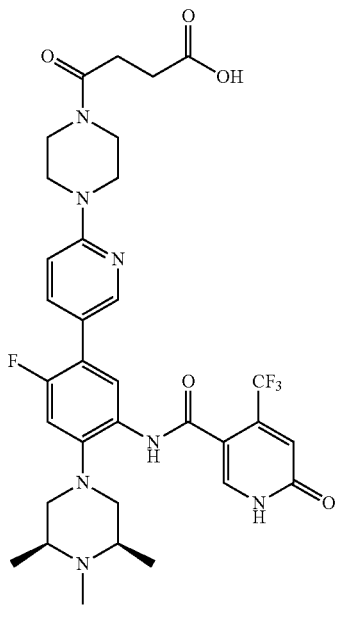

Intermediate 37

+

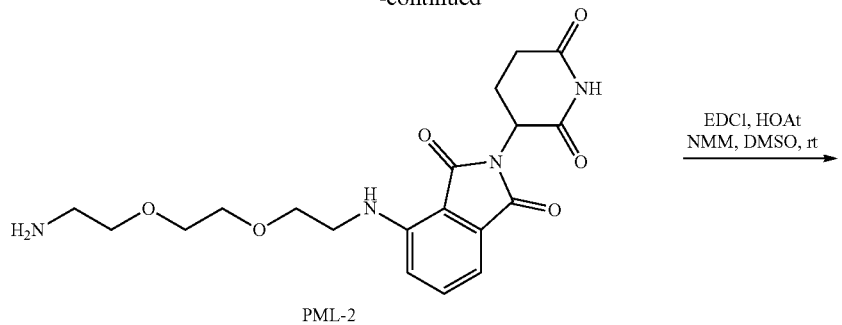

PML-2

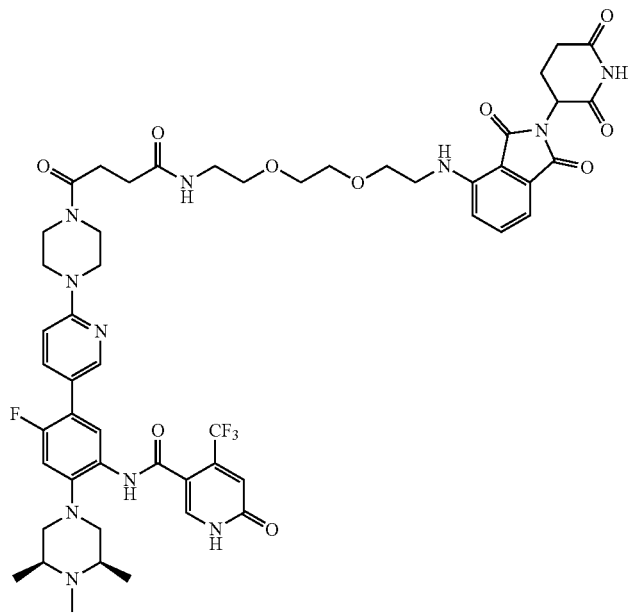

XF067-159

XF067-159 was synthesized following the standard procedures for preparing XF067-140 from intermediate 37 (10 mg, 0.015 mmol), PML-2 (7.8 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-159 was obtained as yellow solid in TFA salt form (9.4 mg, yield 58%). $^1$H NMR (600 MHz, CD$_3$OD) δ 8.20 (d, J=2.3 Hz, 1H), 8.10 (d, J=9.0 Hz, 1H), 8.02 (s, 1H), 7.97 (d, J=8.1 Hz, 1H), 7.54 (dd, J=8.6, 7.1 Hz, 1H), 7.29 (d, J=9.4 Hz, 1H), 7.20 (d, J=11.9 Hz, 1H), 7.08 (d, J=8.6 Hz, 1H), 7.03 (d, J=7.0 Hz, 1H), 6.93 (s, 1H), 5.06 (dd, J=12.7, 5.4 Hz, 1H), 3.83-3.71 (m, 12H), 3.72-3.60 (m, 4H), 3.55 (t, J=5.5 Hz, 2H), 3.50 (t, J=5.3 Hz, 2H), 3.36 (q, J=6.5, 5.4 Hz, 4H), 3.00-2.92 (m, 5H), 2.90-2.79 (m, 1H), 2.77-2.64 (m, 4H), 2.52 (t, J=6.7 Hz, 2H), 2.10 (ddt, J=10.9, 5.7, 3.3 Hz, 1H), 1.44 (d, J=6.5 Hz, 6H). HRMS (m/z) for $C_{52}H_{60}F_4N_{11}O_{10}^+$ [M+H]$^+$: calculated 1074.4455. found 1074.4421.

Example 172: Synthesis of XF067-160
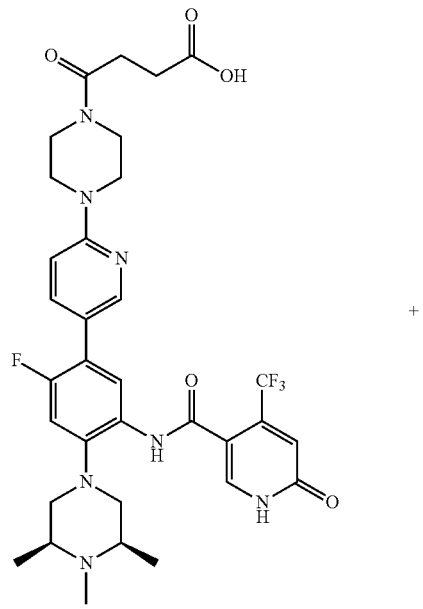
Intermediate 37
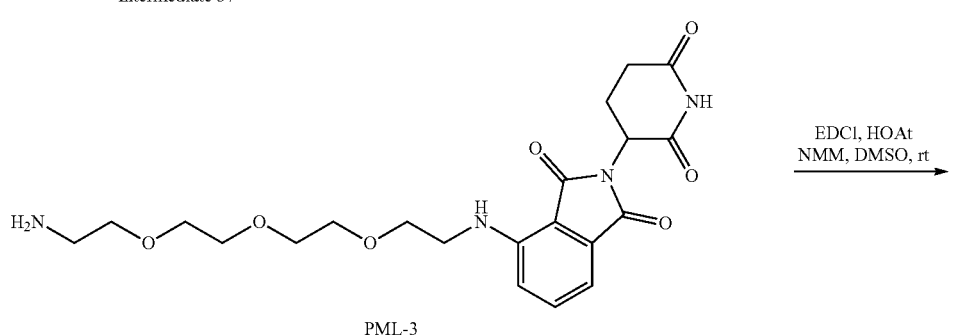
PML-3
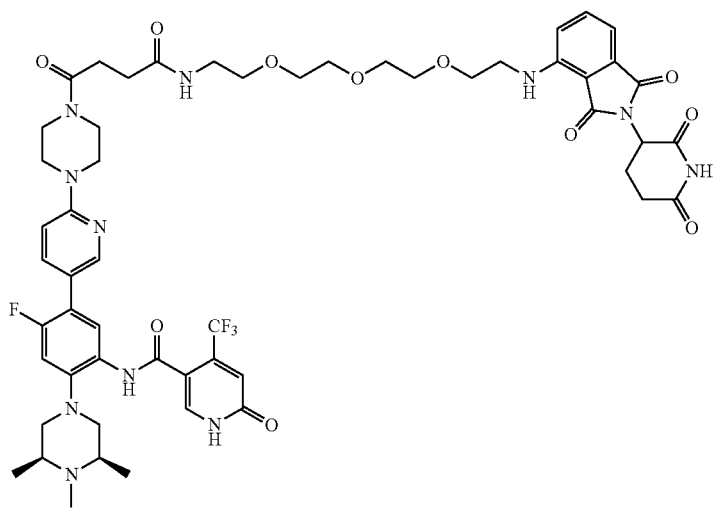
XF067-160

XF067-160 was synthesized following the standard procedures for preparing XF067-140 from intermediate 37 (10 mg, 0.015 mmol), PML-3 (8.4 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-160 was obtained as yellow solid in TFA salt form (11 mg, yield 66%). $^1$H NMR (600 MHz, CD$_3$OD) δ 8.19 (d, J=2.3 Hz, 1H), 8.10 (d, J=8.8 Hz, 1H), 8.02 (s, 1H), 7.97 (d, J=8.1 Hz, 1H), 7.53 (dd, J=8.6, 7.1 Hz, 1H), 7.30 (d, J=9.4 Hz, 1H), 7.19 (d, J=11.8 Hz, 1H), 7.07 (d, J=8.5 Hz, 1H), 7.01 (d, J=7.1 Hz, 1H), 6.93 (s, 1H), 5.04 (dd, J=12.9, 5.5 Hz, 1H), 3.86-3.76 (m, 8H), 3.75-3.69 (m, 4H), 3.68-3.61 (m, 6H), 3.62-3.57 (m, 2H), 3.54-3.47 (m, 4H), 3.40-3.32 (m, 4H), 3.00-2.92 (m, 5H), 2.90-2.79 (m, 1H), 2.77-2.64 (m, 4H), 2.54 (t, J=6.7 Hz, 2H), 2.10 (ddt, J=11.0, 6.0, 3.3 Hz, 1H), 1.44 (d, J=6.5 Hz, 6H). HRMS (m/z) for $C_{54}H_{64}F_4N_{11}O_{11}^+$ [M+H]$^+$: calculated 1118.4717. found 1118.4736.

Example 173: Synthesis of XF067-161

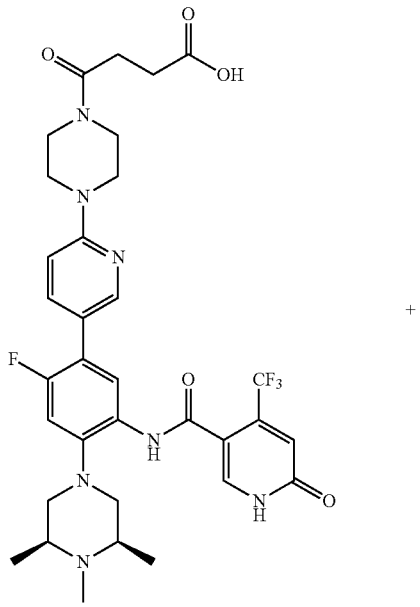

Intermediate 37

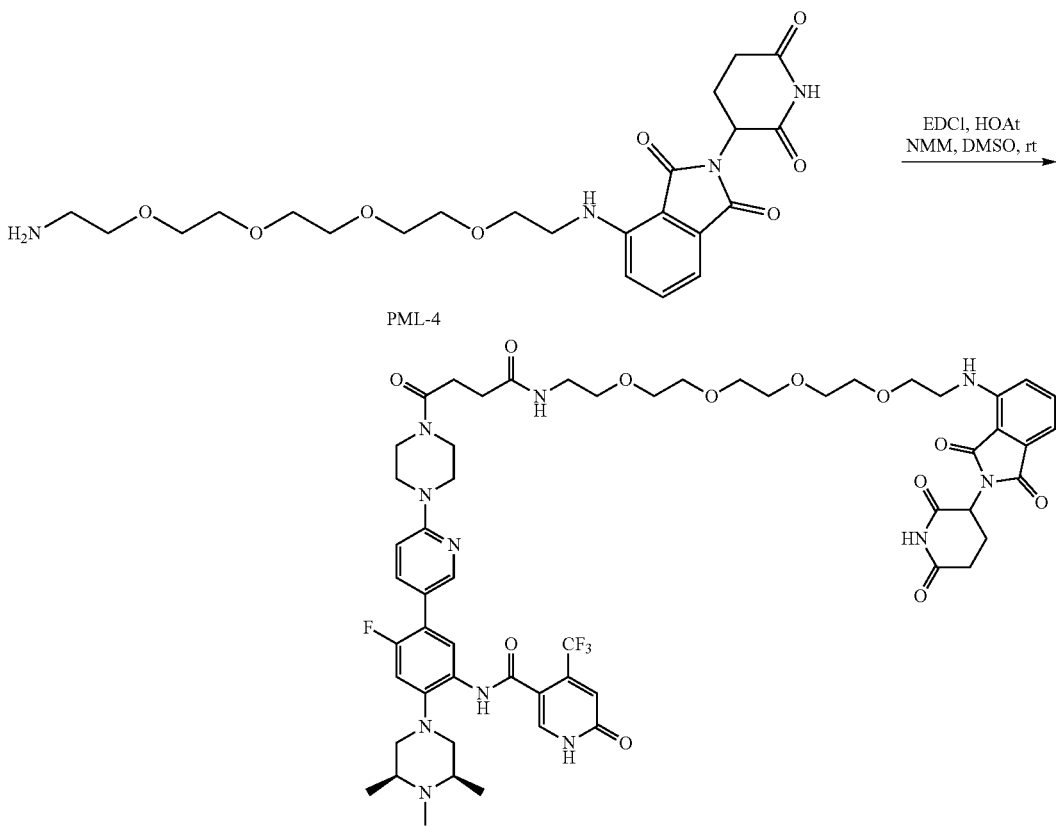

PML-4

XF067-161

XF067-161 was synthesized following the standard procedures for preparing XF067-140 from intermediate 37 (10 mg, 0.015 mmol), PML-4 (8.4 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-161 was obtained as yellow solid in TFA salt form (4.6 mg, yield 26%). $^1$H NMR (600 MHz, CD$_3$OD) δ 8.22 (d, J=2.2 Hz, 1H), 8.02 (d, J=7.1 Hz, 2H), 7.96 (d, J=8.1 Hz, 1H), 7.57-7.49 (m, 1H), 7.23-7.12 (m, 2H), 7.07 (d, J=8.5 Hz, 1H), 7.02 (d, J=7.0 Hz, 1H), 6.93 (s, 1H), 5.04 (dd, J=12.8, 5.5 Hz, 1H), 3.83-3.73 (m, 6H), 3.55-3.45 (m, 18H), 3.55-3.45 (m, 4H), 3.39-3.32 (m, 4H), 3.02-2.89 (m, 5H), 2.89-2.79 (m, 1H), 2.78-2.64 (m, 4H), 2.54 (t, J=6.8 Hz, 2H), 2.14-2.05 (m, 1H), 1.44 (d, J=6.4 Hz, 6H). HRMS (m/z) for $C_{57}H_{68}F_4N_1O_{12}{}^+$ [M+H]$^+$: calculated 1162.4980. found 1162.4965.

Example 174: Synthesis of XF067-162

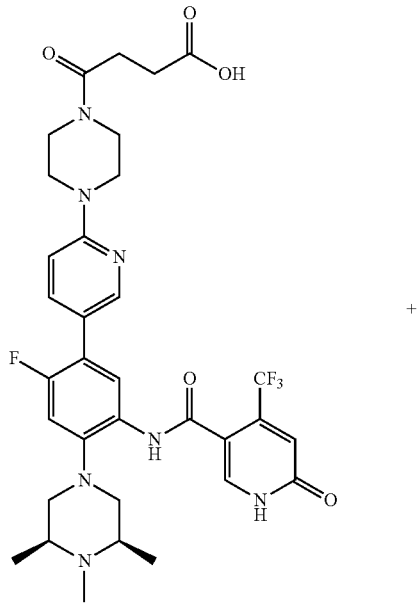

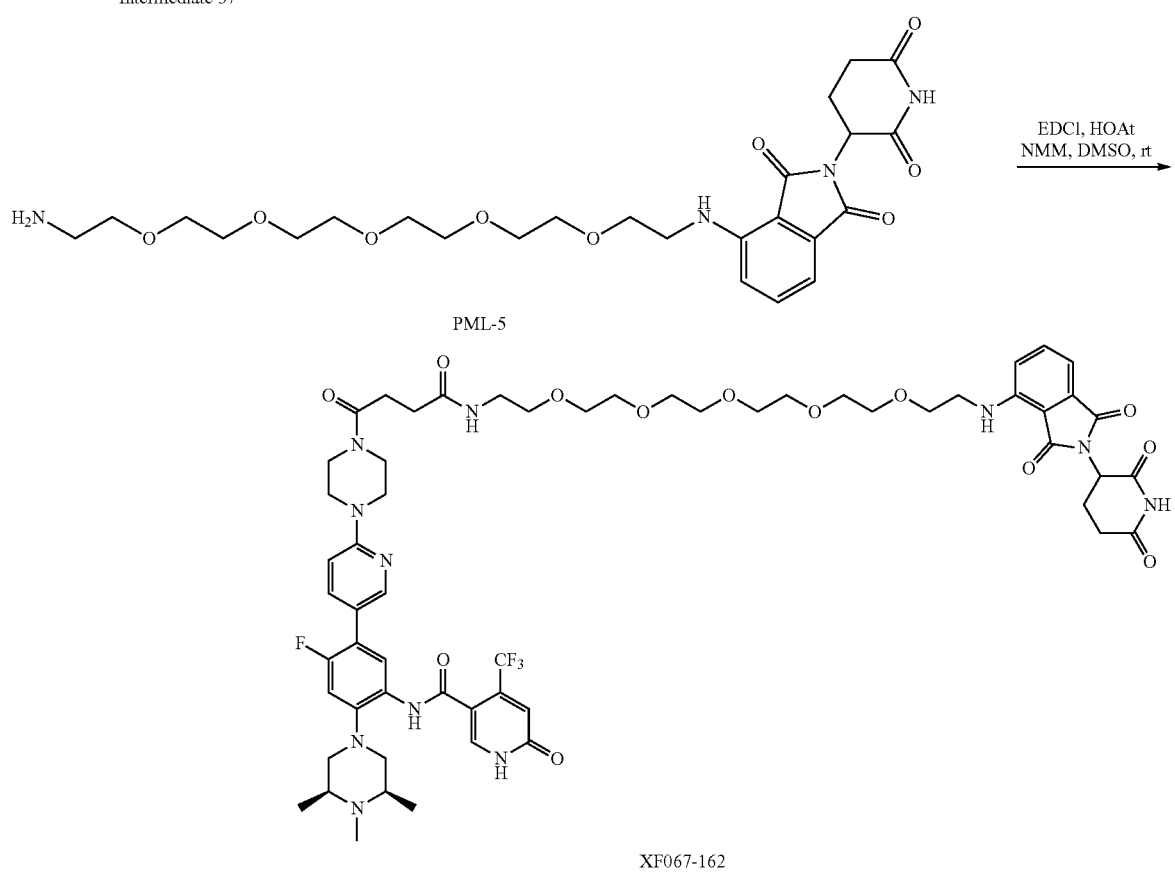

XF067-162 was synthesized following the standard procedures for preparing XF067-140 from intermediate 37 (10 mg, 0.015 mmol), PML-5 (9.1 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-162 was obtained as yellow solid in TFA salt form (10.3 mg, yield 57%). $^1$H NMR (600 MHz, CD$_3$OD) δ 8.20 (d, J=2.3 Hz, 1H), 8.11 (d, J=9.5 Hz, 1H), 8.06-7.83 (m, 2H), 7.63-7.45 (m, 1H), 7.31 (d, J=9.4 Hz, 1H), 7.19 (d, J=11.8 Hz, 1H), 7.07 (d, J=8.6 Hz, 1H), 7.02 (d, J=7.1 Hz, 1H), 6.93 (s, 1H), 5.04 (dd, J=12.8, 5.5 Hz, 1H), 3.86-3.69 (m, 10H), 3.67-3.57 (m, 18H), 3.55-3.44 (m, 4H), 3.41-3.33 (m, 4H), 3.02-2.91 (m, 5H), 2.90-2.79 (m, 1H), 2.78-2.63 (m, 4H), 2.55 (t, J=6.8 Hz, 2H), 2.15-2.06 (m, 1H), 1.44 (d, J=6.5 Hz, 6H). HRMS (m/z) for $C_{59}H_{72}F_4N_{11}O_{13}^+$ [M+H]$^+$: calculated 1206.5242, found 1206.5278.

Example 175: Synthesis of XF067-163

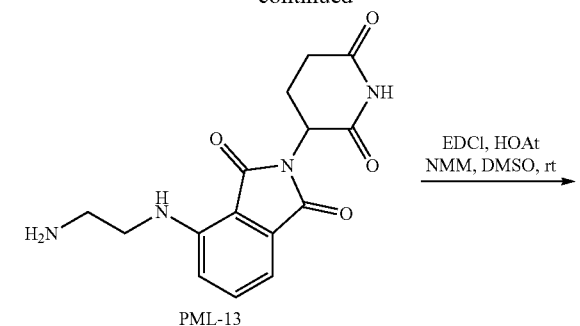

PML-13

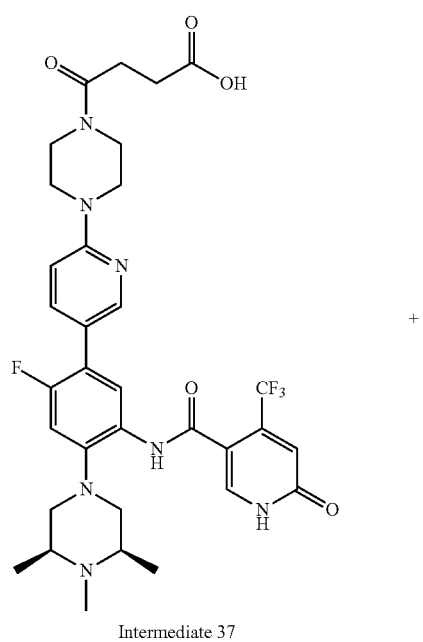

Intermediate 37

+

XF067-163

XF067-163 was synthesized following the standard procedures for preparing XF067-140 from intermediate 37 (10 mg, 0.015 mmol), PML-13 (6.5 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-163 was obtained as yellow solid in TFA salt form (9.5 mg, yield 64%). $^1$H NMR (600 MHz, CD$_3$OD) δ 8.26-8.12 (m, 2H), 8.08-7.93 (m, 2H), 7.54 (dd, J=8.6, 7.1 Hz, 1H), 7.35 (d, J=9.5 Hz, 1H), 7.21 (dd, J=11.9, 3.3 Hz, 1H), 7.12 (d, J=8.5 Hz, 1H), 7.02 (d, J=7.0 Hz, 1H), 6.93 (s, 1H), 5.04 (dd, J=12.6, 5.4 Hz, 1H), 3.88-3.66 (m, 10H), 3.57-3.32 (m, 6H), 2.97 (d, J=10.2 Hz, 5H), 2.92-2.75 (m, 1H), 2.76-2.60 (m, 4H), 2.52 (t, J=6.7 Hz, 2H), 2.20-1.89 (m, 1H), 1.44 (d, J=6.5 Hz, 6H). HRMS (m/z) for $C_{48}H_{52}F_4N_1O_8^+$ [M+H]$^+$: calculated 986.3931. found 986.3957.

Example 176: Synthesis of XF067-164

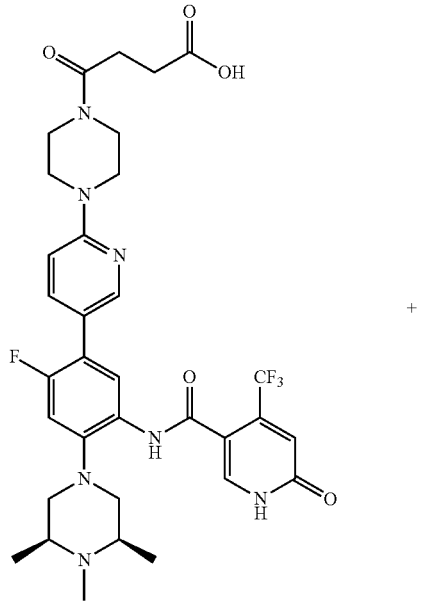

Intermediate 37

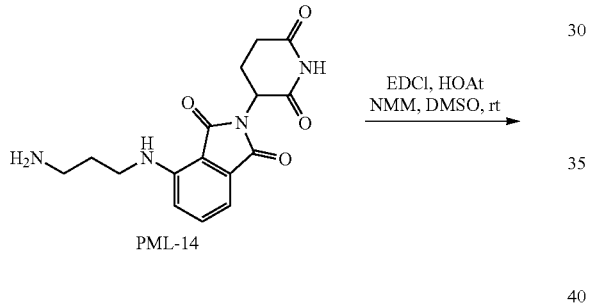

PML-14

XF067-164 was synthesized following the standard procedures for preparing XF067-140 from intermediate 37 (10 mg, 0.015 mmol), PML-14 (6.7 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-164 was obtained as yellow solid in TFA salt form (9.5 mg, yield 63%). $^1$H NMR (600 MHz, CD$_3$OD) δ 8.21-8.10 (m, 2H), 8.08-7.82 (m, 2H), 7.52 (dd, J=8.5, 7.0 Hz, 1H), 7.33 (d, J=9.4 Hz, 1H), 7.20 (d, J=11.9 Hz, 1H), 7.06 (d, J=8.6 Hz, 1H), 7.03-6.86 (m, 2H), 5.03 (dd, J=12.6, 5.5 Hz, 1H), 3.83 (dd, J=29.7, 8.8 Hz, 8H), 3.71 (t, J=5.4 Hz, 2H), 3.59-3.42 (m, 3H), 3.37 (s, 4H), 3.03-2.92 (m, 5H), 2.88-2.78 (m, 1H), 2.77-2.63 (m, 4H), 2.57 (t, J=6.5 Hz, 2H), 2.08 (ddd, J=10.5, 5.4, 2.8 Hz, 1H), 1.80 (p, J=6.6 Hz, 2H), 1.44 (d, J=6.4 Hz, 6H). HRMS (m/z) for C$_{49}$H$_{54}$F$_4$N$_{11}$O$_8$$^+$ [M+H]$^+$: calculated 1000.4087. found 1000.4068.

Example 177: Synthesis of XF067-165

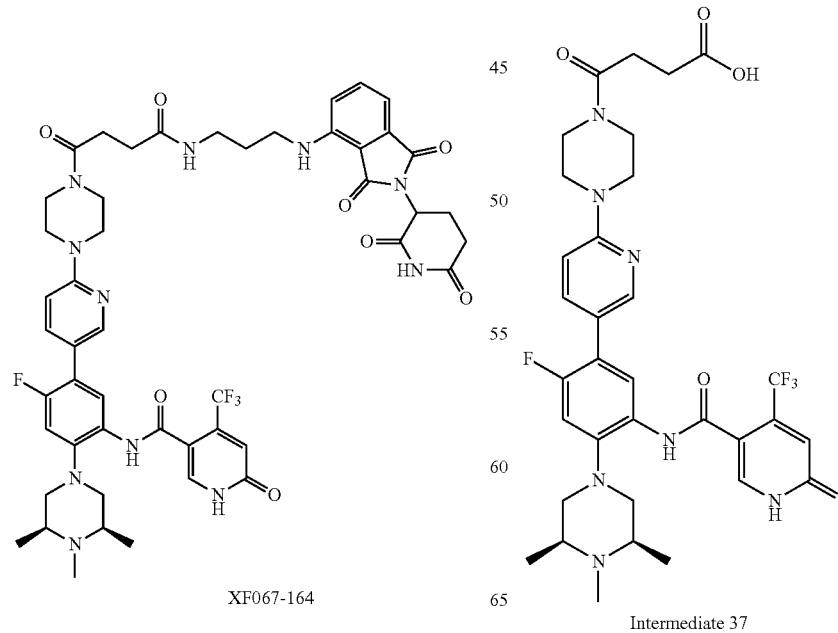

XF067-164

Intermediate 37

Example 178: Synthesis of XF067-166

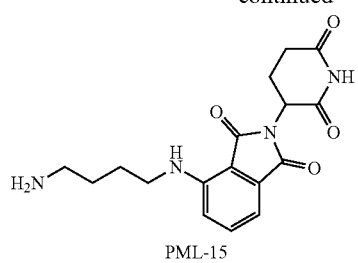

PML-15

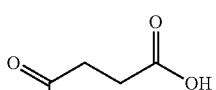

EDCl, HOAt
NMM, DMSO, rt

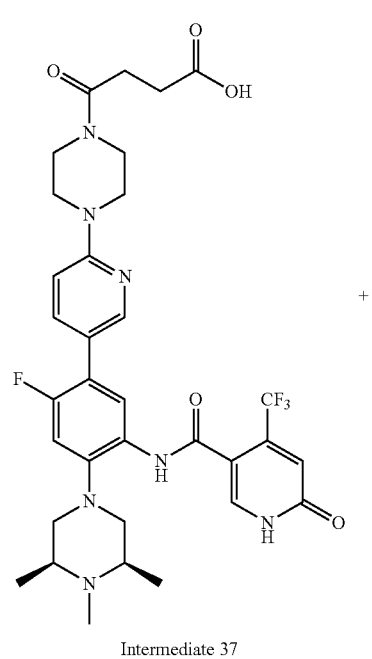

Intermediate 37

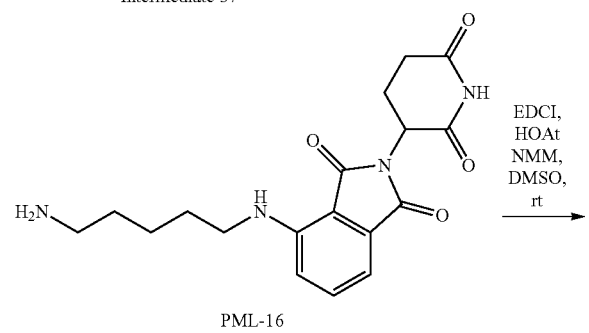

PML-16

EDCl, HOAt NMM, DMSO, rt

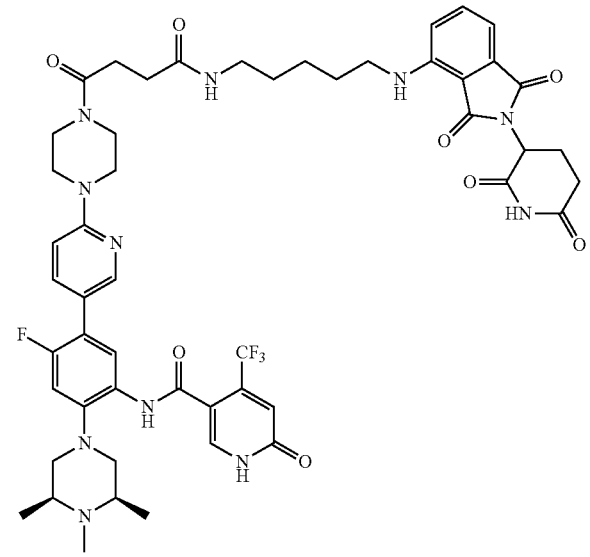

XF067-166

XF067-165 was synthesized following the standard procedures for preparing XF067-140 from intermediate 37 (10 mg, 0.015 mmol), PML-15 (6.9 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-165 was obtained as yellow solid in TFA salt form (8.8 mg, yield 58%). $^1$H NMR (600 MHz, CD$_3$OD) δ 8.19 (d, J=2.3 Hz, 1H), 8.12 (d, J=9.3 Hz, 1H), 8.05-7.89 (m, 2H), 7.53 (dd, J=8.6, 7.0 Hz, 1H), 7.30 (d, J=9.5 Hz, 1H), 7.19 (d, J=11.9 Hz, 1H), 7.04 (d, J=8.6 Hz, 1H), 6.99 (d, J=7.0 Hz, 1H), 6.93 (s, 1H), 5.04 (dd, J=12.5, 5.5 Hz, 1H), 3.90-3.63 (m, 10H), 3.51 (s, 2H), 3.36 (d, J=13.1 Hz, 2H), 3.24 (t, J=6.7 Hz, 2H), 2.97 (d, J=17.1 Hz, 5H), 2.89-2.79 (m, 1H), 2.77-2.64 (m, 4H), 2.53 (t, J=6.5 Hz, 2H), 2.15-2.03 (m, 1H), 1.73-1.56 (m, 4H), 1.44 (dd, J=6.5, 2.0 Hz, 6H). HRMS (m/z) for $C_{50}H_{56}F_4N_{11}O_8^+$ [M+H]$^+$: calculated 1014.4244. found 1014.4227.

XF067-166 was synthesized following the standard procedures for preparing XF067-140 from intermediate 37 (10 mg, 0.015 mmol), PML-16 (7.1 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-166 was obtained as yellow solid in TFA salt form (8.1 mg, yield 52%). $^1$H NMR (600 MHz, CD$_3$OD) δ 8.20 (s, 1H), 8.10 (d, J=9.7 Hz, 1H), 8.06-7.89 (m, 2H), 7.68-7.47 (m, 1H), 7.27 (d, J=9.3 Hz, 1H), 7.19 (d, J=11.7 Hz, 1H), 7.01 (ddd, J=17.4, 7.8, 2.8 Hz, 2H), 6.93 (s, 1H), 5.04 (dd, J=12.8, 5.4 Hz, 1H), 3.86-3.63 (m, 10H), 3.57-3.44 (m, 2H), 3.40-3.33 (m, 2H), 3.24-3.14 (m, 2H), 3.02-2.90 (m, 5H), 2.90-2.77 (m, 1H), 2.77-2.66 (m, 4H), 2.66-2.37 (m, 2H), 2.16-1.94 (m, 1H), 1.71-1.62 (m, 2H), 1.61-1.51 (m, 2H), 1.51-1.40 (m, 8H). HRMS (m/z) for C$_{51}$H$_{58}$F$_4$N$_{11}$O$_8{}^+$ [M+H]$^+$: calculated 1028.4400, found 1028.4379.

Example 179: Synthesis of XF067-167

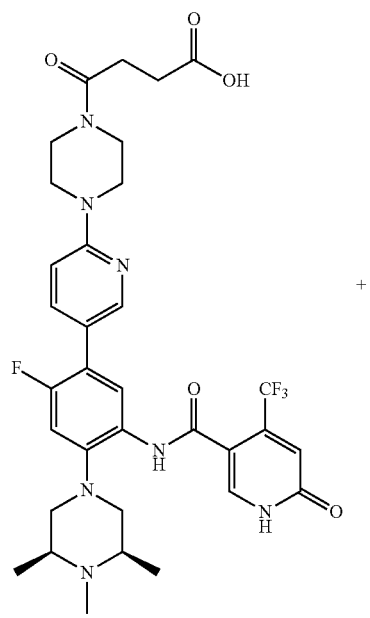

Intermediate 37

+

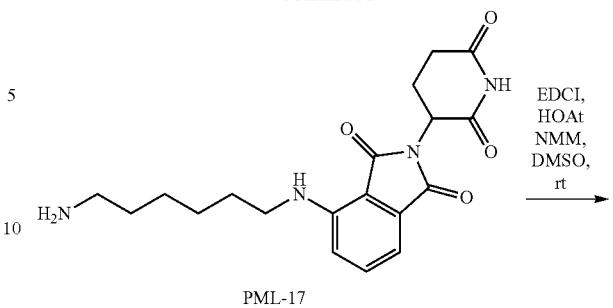

PML-17

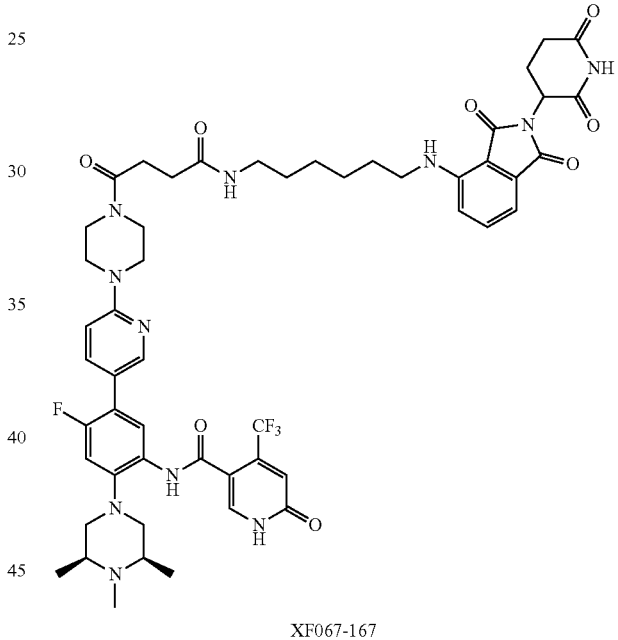

XF067-167

XF067-167 was synthesized following the standard procedures for preparing XF067-140 from intermediate 37 (10 mg, 0.015 mmol), PML-17 (6.1 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-167 was obtained as yellow solid in TFA salt form (9 mg, yield 58%). $^1$H NMR (600 MHz, CD$_3$OD) δ 8.40-8.10 (m, 2H), 8.10-7.87 (m, 2H), 7.53 (dd, J=8.6, 7.1 Hz, 1H), 7.34 (d, J=9.4 Hz, 1H), 7.19 (d, J=11.9 Hz, 1H), 7.00 (dd, J=13.2, 7.8 Hz, 2H), 6.93 (s, 1H), 5.04 (dd, J=12.4, 5.5 Hz, 1H), 3.88-3.66 (m, 10H), 3.51 (s, 2H), 3.40-3.34 (m, 2H), 3.17 (dt, J=10.9, 6.9 Hz, 2H), 2.98-2.93 (m, 5H), 2.84 (ddd, J=19.1, 14.7, 6.0 Hz, 1H), 2.76-2.65 (m, 4H), 2.53 (t, J=6.6 Hz, 2H), 2.15-2.05 (m, 1H), 1.65 (p, J=7.2 Hz, 2H), 1.56-1.28 (m, 12H). HRMS (m/z) for C$_{52}$H$_{60}$F$_4$N$_{11}$O$_8{}^+$ [M+H]$^+$: calculated 1042.4557, found 1042.4578.

Example 180: Synthesis of XF067-168

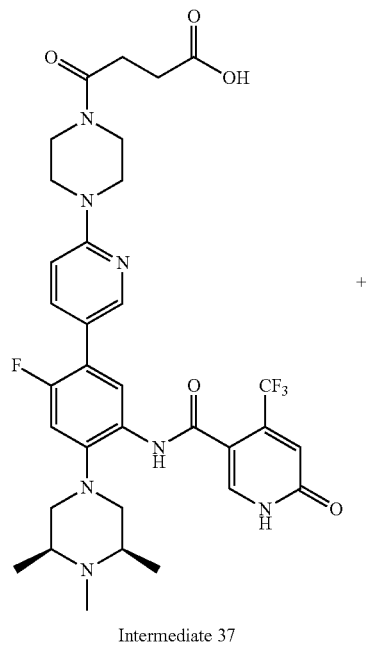

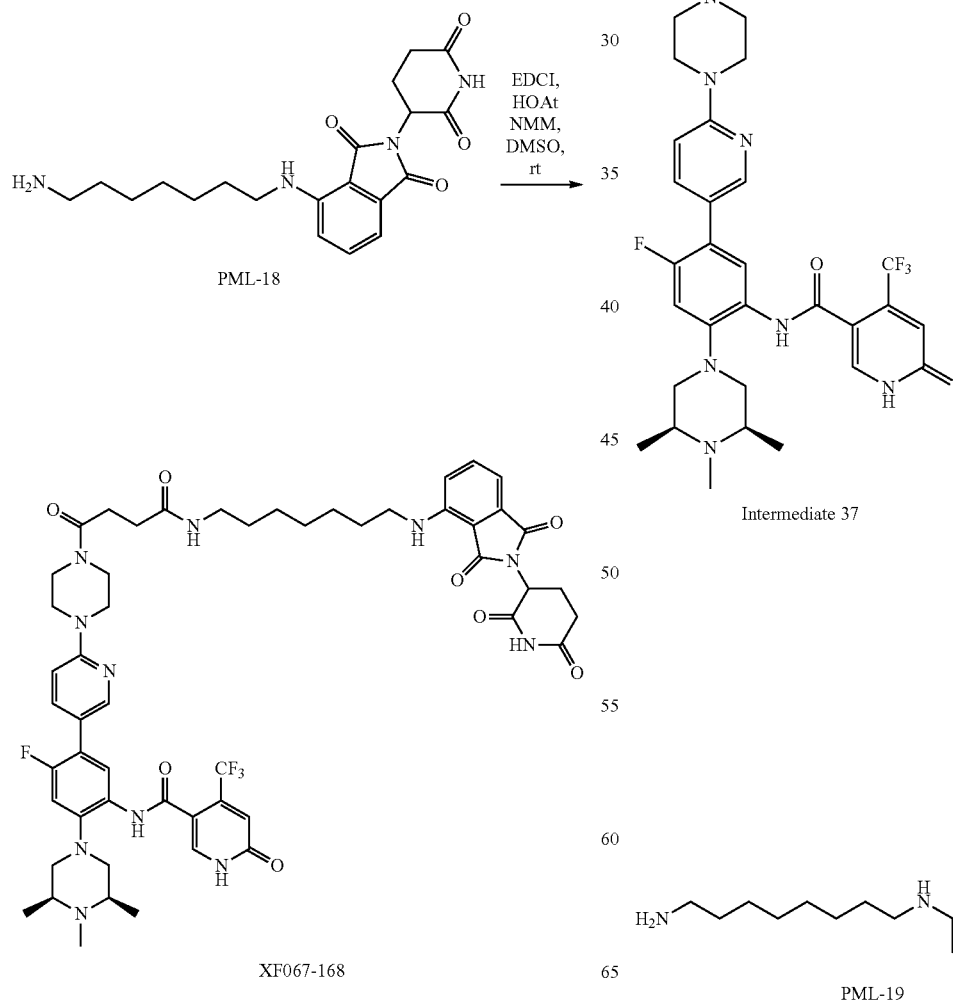

XF067-168 was synthesized following the standard procedures for preparing XF067-140 from intermediate 37 (10 mg, 0.015 mmol), PML-18 (7.5 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-168 was obtained as yellow solid in TFA salt form (9.7 mg, yield 61%). $^1$H NMR (600 MHz, CD$_3$OD) δ 8.22-8.12 (m, 2H), 8.04-7.90 (m, 2H), 7.53 (dd, J=8.6, 7.0 Hz, 1H), 7.37 (d, J=9.4 Hz, 1H), 7.19 (d, J=11.8 Hz, 1H), 7.00 (t, J=8.1 Hz, 2H), 6.93 (s, 1H), 5.04 (dd, J=12.7, 5.4 Hz, 1H), 3.94-3.69 (m, 10H), 3.55-3.48 (m, 2H), 3.41-3.33 (m, 2H), 3.17 (t, J=6.9 Hz, 2H), 3.01-2.90 (m, 5H), 2.88-2.78 (m, 1H), 2.77-2.66 (m, 4H), 2.53 (t, J=6.6 Hz, 2H), 2.09 (ddt, J=10.5, 5.4, 3.2 Hz, 1H), 1.64 (q, J=7.3 Hz, 2H), 1.55-1.47 (m, 2H), 1.47-1.32 (m, 12H). HRMS (m/z) for $C_{53}H_{62}F_4N_{11}O_8^+$ [M+H]$^+$: calculated 1056.4713. found 1056.4689.

Example 181: Synthesis of XF067-169

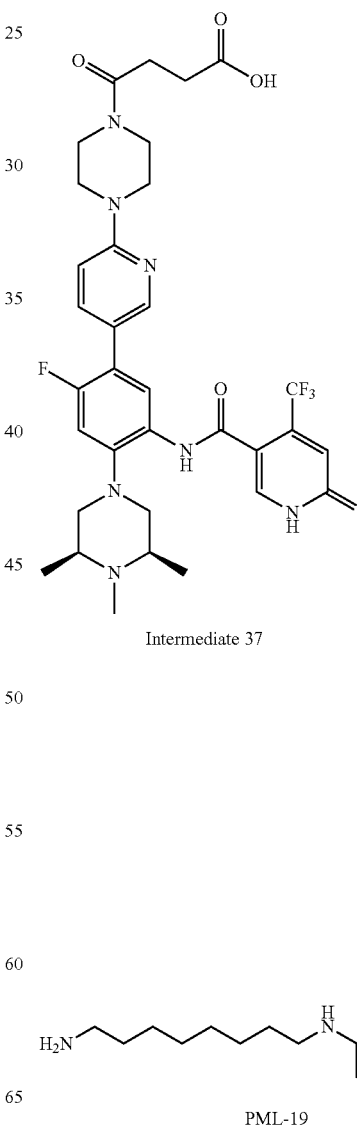

477

-continued

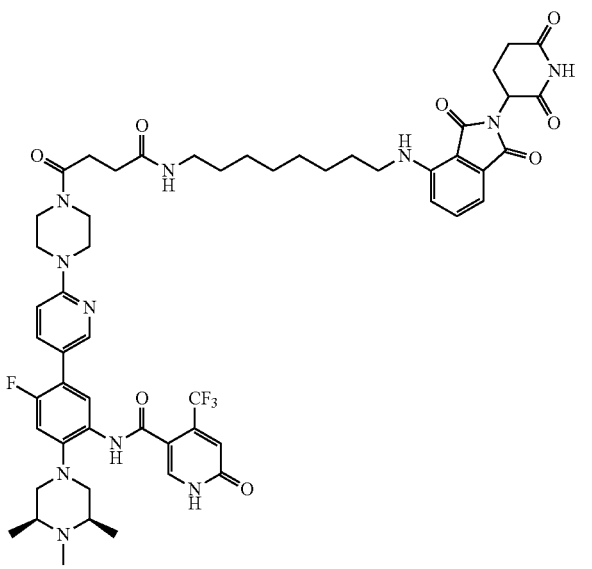

XF067-169

XF067-169 was synthesized following the standard procedures for preparing XF067-140 from intermediate 37 (10 mg, 0.015 mmol), PML-19 (7.7 mg, 0.015 mmol, 1.0 equiv), EDCI (4.3 mg, 0.023 mmol, 1.5 equiv), HOAt (3.2 mg, 0.023 mmol, 1.5 equiv), and NMM (4.6 mg, 0.046 mmol, 3.0 equiv) in DMSO (1 mL). XF067-169 was obtained as yellow solid in TFA salt form (10.4 mg, yield 65%). $^1$H NMR (600 MHz, CD$_3$OD) δ 8.42-8.13 (m, 2H), 8.07-7.96 (m, 2H), 7.58-7.43 (m, 1H), 7.36 (d, J=9.5 Hz, 1H), 7.19 (d, J=11.9 Hz, 1H), 7.00 (t, J=8.0 Hz, 2H), 6.93 (s, 1H), 5.04 (dd, J=12.6, 5.5 Hz, 1H), 3.97-3.69 (m, 10H), 3.52 (td, J=7.0, 3.4 Hz, 2H), 3.38-3.32 (m, 2H), 3.16 (t, J=7.0 Hz, 2H), 3.00-2.91 (m, 5H), 2.89-2.77 (m, 1H), 2.76-2.65 (m, 4H), 2.53 (t, J=6.7 Hz, 2H), 2.13-2.06 (m, 1H), 1.64 (p, J=7.1 Hz, 2H), 1.55-1.28 (m, 16H). HRMS (m/z) for C$_{54}$H$_{64}$F$_4$N$_{11}$O$_8$$^+$ [M+H]$^+$: calculated 1070.4870. found 1070.4861.

Example 182: Synthesis of Intermediate 39

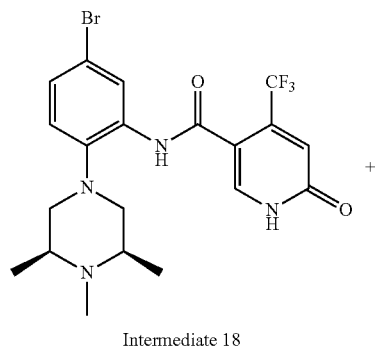

Intermediate 18

478

-continued

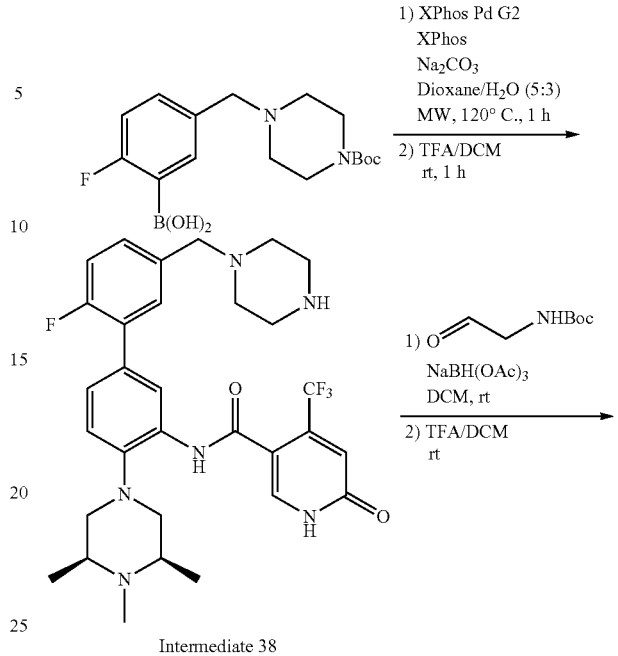

Intermediate 38

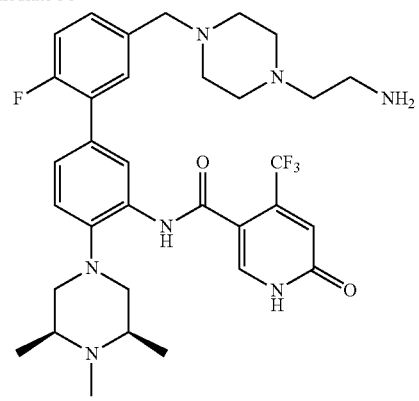

Intermediate 39

To a solution of Intermediate 18 (WO2017147701A1) (731 mg, 1.5 mmol) and (5-((4-(tert-butoxycarbonyl)piperazin-1-yl)methyl)-2-fluorophenyl)boronic acid (Journal of Organic Chemistry, 74(19), 7364-7369; 2009) (1 g, 3 mmol, 3.0 euqiv) in 8 mL of 1,4-dioxane/H$_2$O (5:3) were added sodium carbonate (1.5 g, 15 mmol, 10 equiv), XPhos (143 mg, 0.3 mmol, 0.2 equiv), and XPhos Pd G2 (143 mg, 0.3 mmol, 0.2 equiv). The reaction was heated to 120° C. for 1 h under Microwave. The solvent was removed and purified by reverse phase ISCO (10%-100% methanol/0.1% TFA in H$_2$O) to afford the product (690 mg, yield 66%). The product was dissolved in DCM (15 mL) and TFA (15 mL). The resulting mixture was stirring for 30 minutes. Then, it was concentrated and purified by reverse phase ISCO (10%-100% methanol/0.1% TFA in H$_2$O) to afford Intermediate 38 (XF067-172A) as white solid in TFA salt form (586.2 mg, yield 97%). To a solution of intermediate 38 (586 mg, 0.97 mmol), and tert-butyl (2-oxoethyl)carbamate (311 mg, 1.95 mmol, 2.0 equiv) in dichloromethane (10 mL) was added sodium triacetoxyborohydride (412 mg, 1.95 mmol). After stirring overnight, saturated sodium bicarbonate was added to quench reaction. The mixture was extracted with DCM (3×10 mL), dried over Na$_2$SO$_4$, filtered and concentrated.

The crude product was purified by reverse phase ISCO (10%-100% methanol/0.1% TFA in H₂O) to afford white solid. This product was dissolved in DCM (5 mL) and TFA (5 mL). The resulting mixture was stirring for 30 minutes. Then, it was concentrated and purified by preparative HPLC (10%-100% methanol/0.1% TFA in H₂O) to afford Intermediate 39 (XF067-172) as white solid in TFA salt form (524.5 mg, yield 84%). $^1$H NMR (600 MHz, CD$_3$OD) δ 8.16 (d, J=2.0 Hz, 1H), 8.02 (s, 1H), 7.71 (dd, J=7.3, 2.4 Hz, 1H), 7.53 (ddd, J=8.5, 4.5, 2.3 Hz, 1H), 7.47 (dt, J=8.1, 1.8 Hz, 1H), 7.38 (d, J=8.4 Hz, 1H), 7.32 (dd, J=10.3, 8.4 Hz, 1H), 6.90 (s, 1H), 4.40 (s, 2H), 3.61-3.53 (m, 2H), 3.49-3.20 (m, 9H), 3.12-2.93 (m, 7H), 2.93-2.75 (m, 1H), 2.73 (dd, J=6.7, 4.8 Hz, 2H), 1.44 (d, J=6.5 Hz, 6H). HRMS (m/z) for C$_{33}$H$_{42}$F$_4$N$_7$O$_2$$^+$ [M+H]$^+$: calculated 644.3331. found 644.3317.

Example 183: Synthesis of XF078-1

To the solution of intermediate 39 (12.9 mg, 0.02 mmol) in DMSO (1 mL) were added VHL-PEG1-CH$_2$—COOH (10.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirring overnight at room temperature, the resulting mixture was purified by preparative HPLC (10%-100% methanol/0.1% TFA in H₂O) to afford XF078-1 as white solid in TFA salt form (17.5 mg, yield 75%). $^1$H NMR (600 MHz, CD$_3$OD) δ 9.05 (s, 1H), 8.15 (s, 1H), 8.00 (s, 1H), 7.65 (dd, J=7.3, 2.3 Hz, 1H), 7.54-7.39 (m, 6H), 7.37 (d, J=8.4 Hz, 1H), 7.28 (dd, J=10.3, 8.3 Hz, 1H), 6.92 (s, 1H), 4.69 (s, 1H), 4.61-4.43 (m, 3H), 4.36 (d, J=15.5 Hz, 1H), 4.21 (d, J=12.6 Hz, 2H), 4.19-4.03 (m, 4H), 3.89 (d, J=11.0 Hz, 1H), 3.80 (dd, J=11.0, 3.8 Hz, 1H), 3.62-3.48 (m, 4H), 3.46-3.31 (m, 10H), 3.15 (t, J=5.8 Hz, 2H), 3.07-2.92 (m, 5H), 2.48 (d, J=2.6 Hz, 3H), 2.27-2.19 (m, 1H), 2.15-1.99 (m, 1H), 1.44 (d, J=6.5 Hz, 6H), 1.04 (s, 9H). HRMS (m/z) for C$_{59}$H$_{74}$F$_4$N$_{11}$O$_8$S$^+$ [M+H]$^+$: calculated 1172.5373. found 1172.5367.

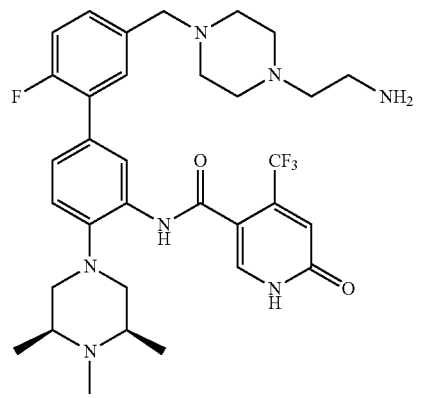

Intermediate 39

+

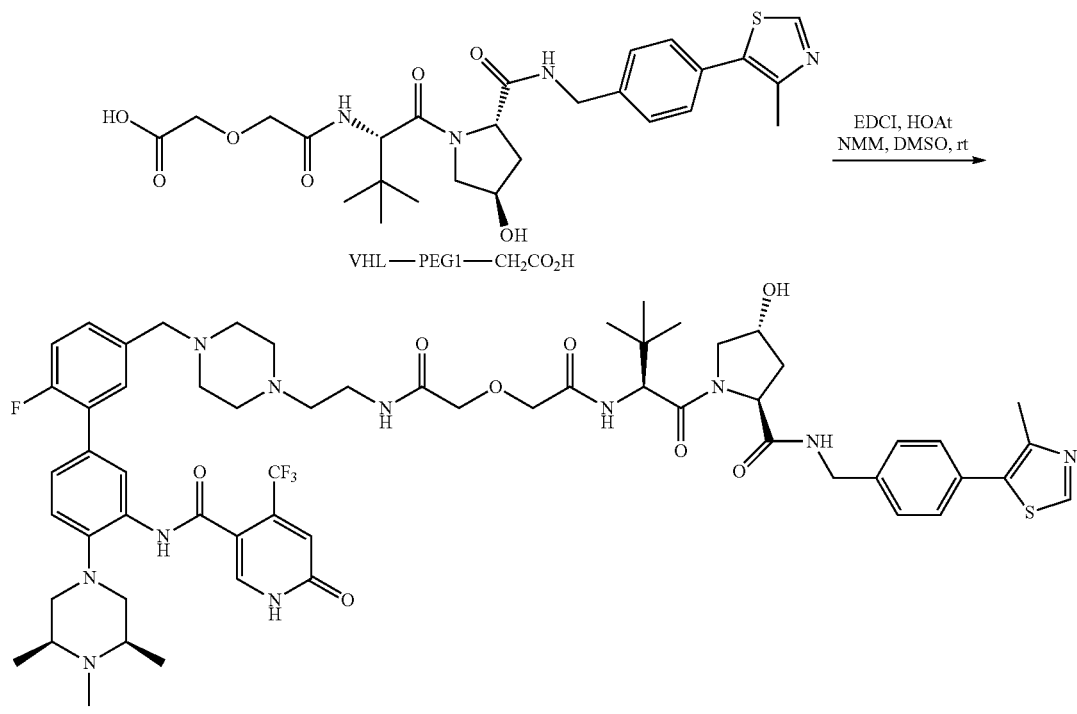

XF078-1

Example 184: Synthesis of XF078-2

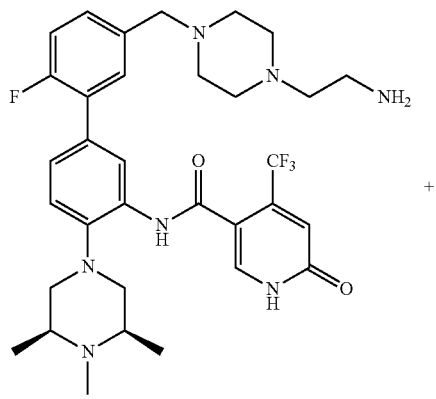

Intermediate 39

+

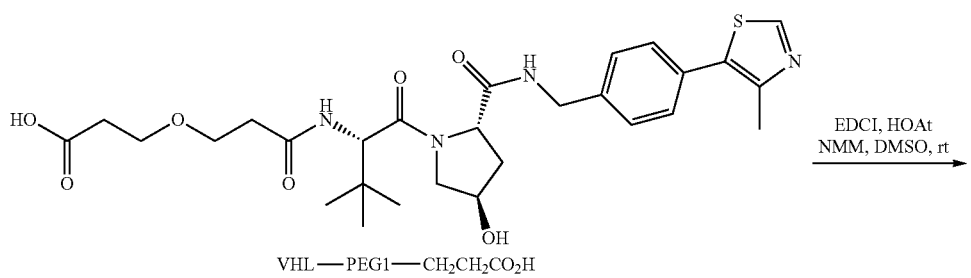

VHL—PEG1—CH₂CH₂CO₂H

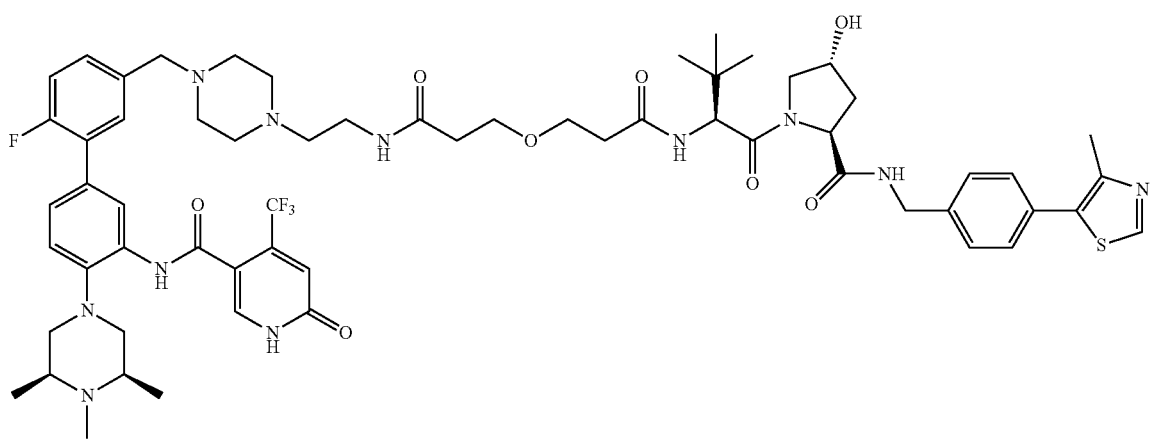

XF078-2

XF078-2 was synthesized following the standard procedures for preparing XF078-1 from intermediate 39 (12.9 mg, 0.02 mmol), VHL-PEG1-CH$_2$CH$_2$COOH (11.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-2 was obtained as white solid in TFA salt form (23.3 mg, yield 76%). $^1$H NMR (600 MHz, CD$_3$OD) δ 9.06 (s, 1H), 8.15 (s, 1H), 8.00 (s, 1H), 7.74-7.56 (m, 1H), 7.50-7.33 (m, 7H), 7.27 (dd, J=10.3, 8.3 Hz, 1H), 6.93 (s, 1H), 4.62 (s, 1H), 4.59-4.44 (m, 3H), 4.36 (d, J=15.5 Hz, 1H), 4.20 (s, 2H), 3.87 (d, J=11.0 Hz, 1H), 3.79 (dd, J=10.9, 3.9 Hz, 1H), 3.75-3.65 (m, 4H), 3.57-3.31 (m, 14H), 3.17 (t, J=5.9 Hz, 2H), 3.05-2.96 (m, 5H), 2.58-2.40 (m, 7H), 2.29-2.16 (m, 1H), 2.11-1.98 (m, 1H), 1.44 (d, J=6.4 Hz, 6H), 1.03 (s, 9H). HRMS (m/z) for C$_{61}$H$_{78}$F$_4$N$_{11}$O$_8$S$^+$ [M+H]$^+$: calculated 1200.5686. found 1200.5654.

Example 185: Synthesis of XF078-3

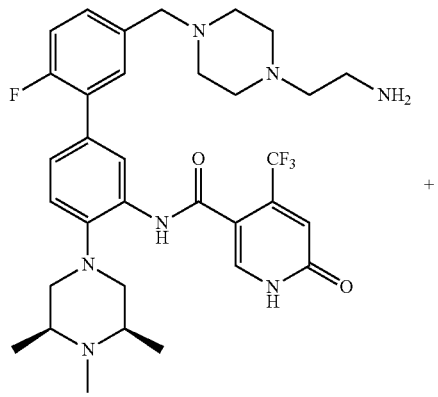

Intermediate 39

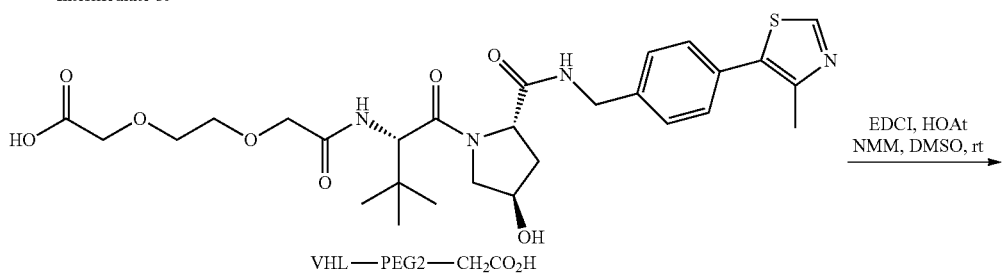

VHL—PEG2—CH₂CO₂H

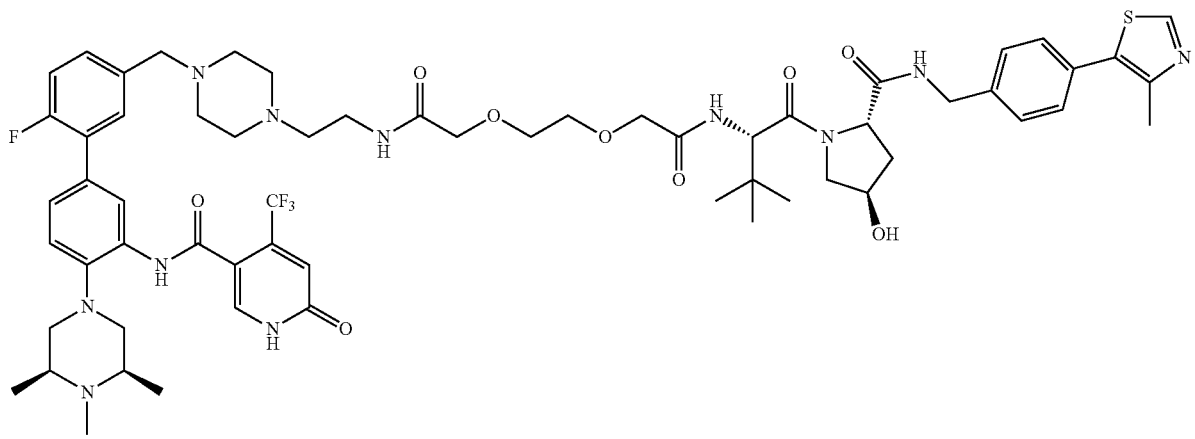

XF078-3

XF078-3 was synthesized following the standard procedures for preparing XF078-1 from intermediate 39 (12.9 mg, 0.02 mmol), VHL-PEG2-CH₂COOH (11.8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NM (N-Methylmorpholine) (6.1 mg, 0.06 mmol, 3.0 equiv) in DMSO (1 mL). XF078-3 was obtained as white solid in TFA salt form (25.7 mg, yield 82%). ¹H NMR (600 MHz, CD₃OD) δ 9.02 (s, 1H), 8.15 (s, 1H), 8.00 (s, 1H), 7.63 (dd, J=7.4, 2.3 Hz, 1H), 7.50-7.39 (m, 6H), 7.37-7.34 (m, 1H), 7.29-7.20 (m, 1H), 6.92 (s, 1H), 4.69 (s, 1H), 4.59-4.51 (m, 1H), 4.50-4.35 (m, 3H), 4.16 (d, J=8.1 Hz, 2H), 4.14-3.92 (m, 4H), 3.86 (d, J=11.1 Hz, 1H), 3.82-3.68 (m, 5H), 3.54 (dt, J=9.8, 3.7 Hz, 4H), 3.43-3.19 (m, 10H), 3.16-3.08 (m, 2H), 3.04-2.91 (m, 5H), 2.48 (s, 3H), 2.27-2.17 (m, 1H), 2.14-2.01 (m, 1H), 1.44 (d, J=6.4 Hz, 6H), 1.03 (s, 9H). HRMS (m/z) for $C_{61}H_{78}F_4N_{11}O_9S^+$ [M+H]⁺: calculated 1216.5639. found 1216.5658.

Example 186: Synthesis of XF078-4

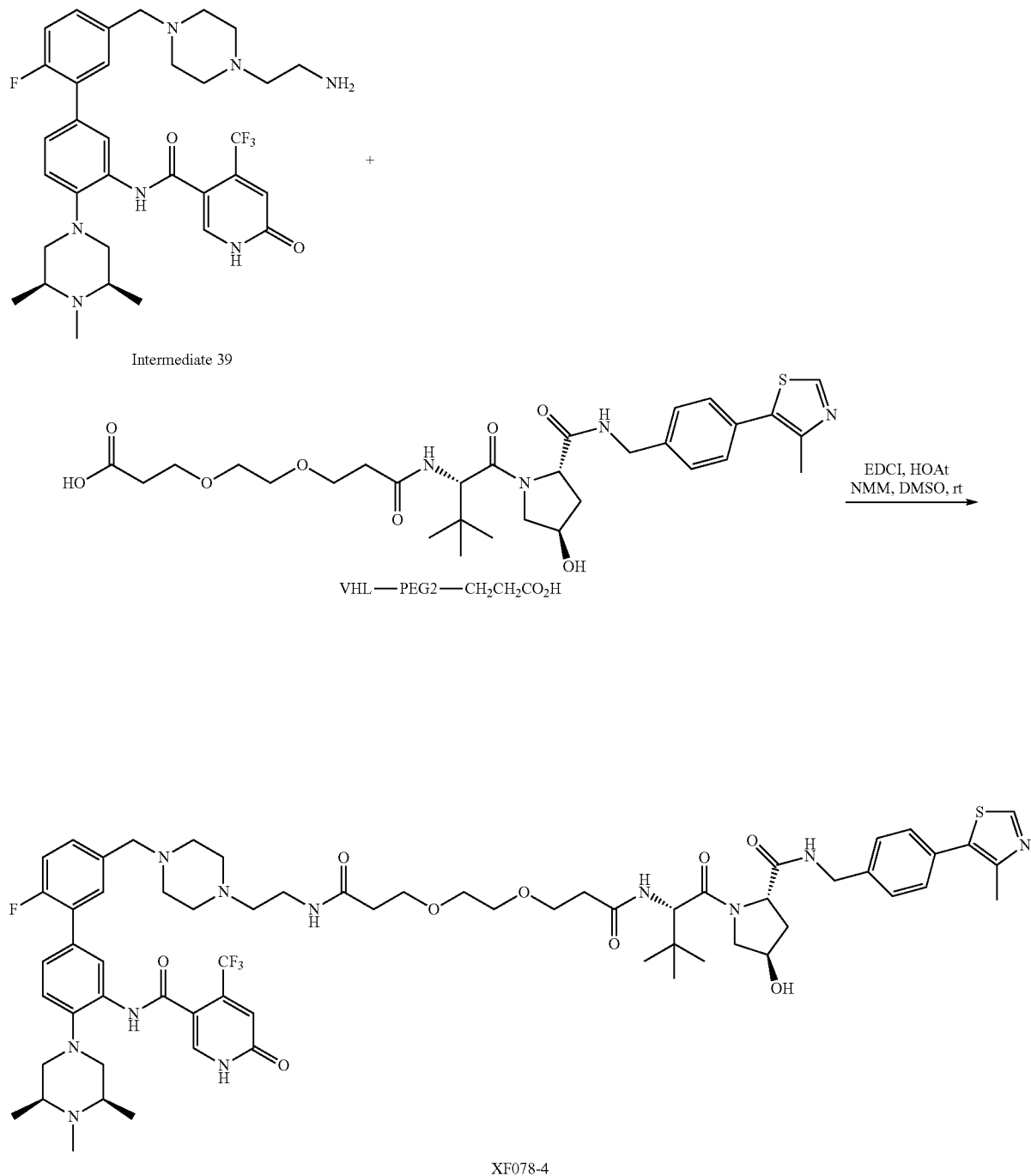

XF078-4 was synthesized following the standard procedures for preparing XF078-1 from intermediate 39 (12.9 mg, 0.02 mmol), VHL-PEG2-CH$_2$CH$_2$COOH (12.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-4 was obtained as white solid in TFA salt form (20.2 mg, yield 64%). $^1$H NMR (600 MHz, CD$_3$OD) δ 9.00 (s, 1H), 8.15 (s, 1H), 8.00 (s, 1H), 7.62 (dd, J=7.4, 2.3 Hz, 1H), 7.50-7.43 (m, 4H), 7.41 (d, J=8.0 Hz, 2H), 7.37 (d, J=8.4 Hz, 1H), 7.27 (dd, J=10.4, 8.4 Hz, 1H), 6.93 (s, 1H), 4.63 (s, 1H), 4.60-4.45 (m, 3H), 4.36 (d, J=15.5 Hz, 1H), 4.14 (s, 2H), 3.88 (d, J=11.0 Hz, 1H), 3.79 (dd, J=11.0, 3.9 Hz, 1H), 3.74-3.68 (m, 4H), 3.62-3.46 (m, 6H), 3.45-3.19 (m, 12H), 3.13 (t, J=5.9 Hz, 2H), 3.04-2.96 (m, 5H), 2.59-2.51 (m, 1H), 2.50-2.41 (m, 6H), 2.25-2.16 (m, 1H), 2.12-2.03 (m, 1H), 1.44 (d, J=6.5 Hz, 6H), 1.02 (s, 9H). HRMS (m/z) for C$_{63}$H$_{82}$F$_4$N$_{11}$O$_9$S$^+$ [M+H]$^+$: calculated 1244.5948. found 1244.5912.

Example 187: Synthesis of XF078-5

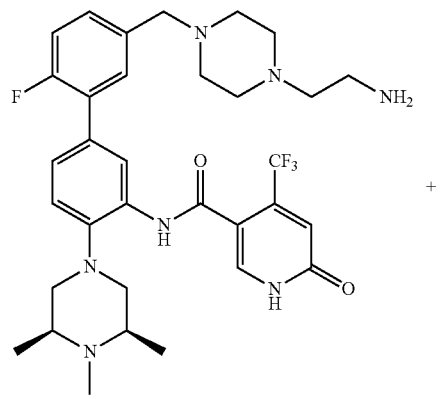

Intermediate 39

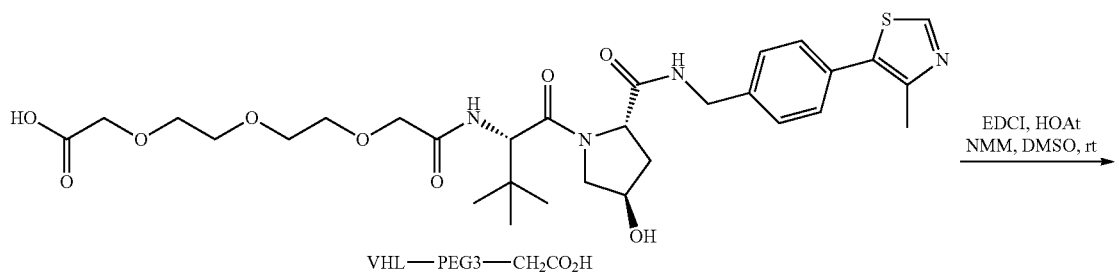

VHL—PEG3—CH$_2$CO$_2$H

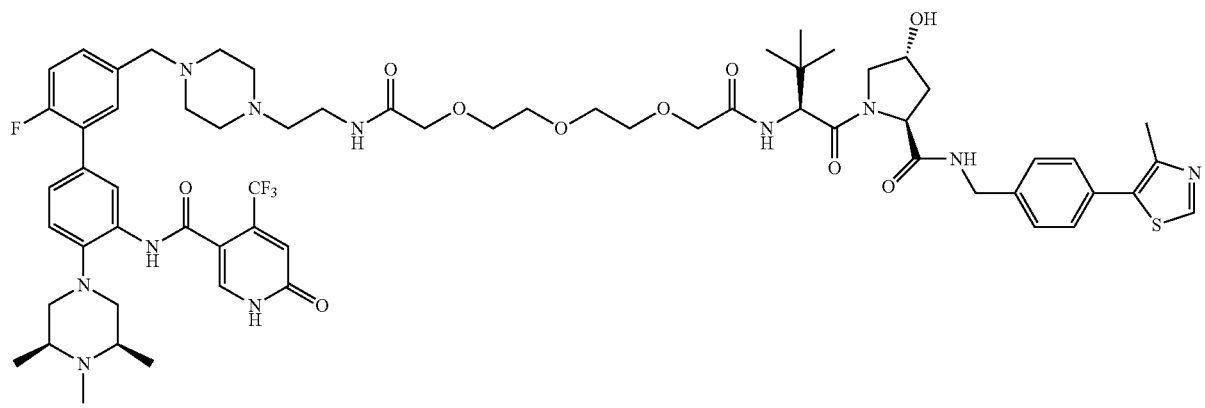

XF078-5

XF078-5 was synthesized following the standard procedures for preparing XF078-1 from intermediate 39 (12.9 mg, 0.02 mmol), VHL-PEG3-CH$_2$COOH (12.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-5 was obtained as white solid in TFA salt form (18.8 mg, yield 59%). $^1$H NMR (600 MHz, CD$_3$OD) δ 8.96 (s, 1H), 8.15 (s, 1H), 8.00 (s, 1H), 7.82-7.34 (m, 8H), 7.26 (dd, J=10.5, 8.5 Hz, 1H), 6.93 (s, 1H), 4.66 (s, 1H), 4.59-4.44 (m, 3H), 4.40-4.27 (m, 1H), 4.13-3.91 (m, 6H), 3.89-3.62 (m, 8H), 3.58-2.88 (m, 23H), 2.47 (s, 3H), 2.32-2.18 (m, 1H), 2.15-2.01 (m, 1H), 1.59-1.29 (m, 6H), 1.03 (s, 9H). HRMS (m/z) for C$_{63}$H$_{82}$F$_4$N$_{11}$O$_{10}$S$^+$ [M+H]$^+$: calculated 1260.5897. found 1260.5906.

Example 188: Synthesis of XF078-6

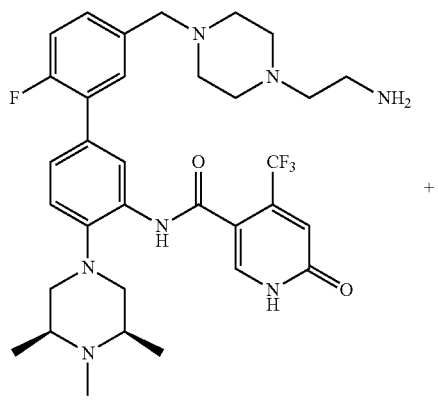

Intermediate 39

+

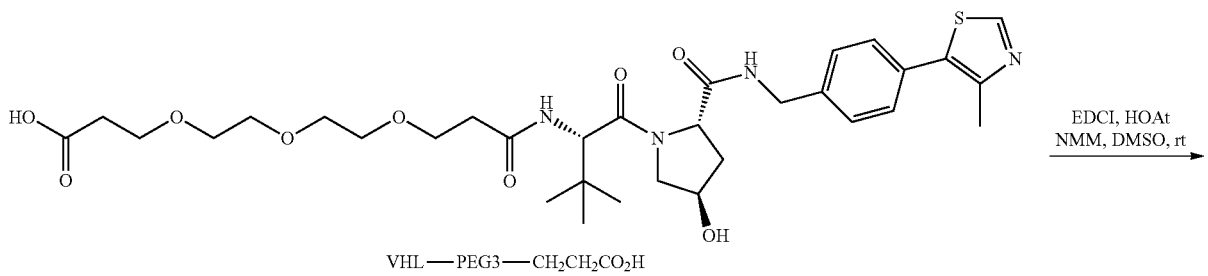

VHL—PEG3—CH₂CH₂CO₂H

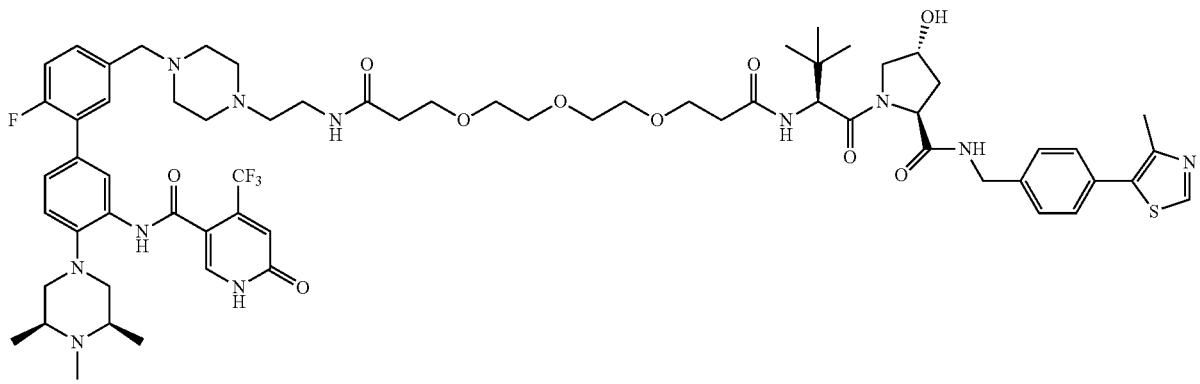

XF078-6

XF078-6 was synthesized following the standard procedures for preparing XF078-1 from intermediate 39 (12.9 mg, 0.02 mmol), VHL-PEG3-CH₂CH₂COOH (13.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-6 was obtained as white solid in TFA salt form (23.5 mg, yield 72%). $^1$H NMR (600 MHz, CD$_3$OD) δ 9.03 (s, 1H), 8.31-8.04 (m, 1H), 8.00 (s, 1H), 7.63 (dd, J=7.4, 2.3 Hz, 1H), 7.51-7.38 (m, 6H), 7.37 (d, J=8.3 Hz, 1H), 7.27 (dd, J=10.4, 8.4 Hz, 1H), 6.93 (s, 1H), 4.63 (s, 1H), 4.59-4.44 (m, 3H), 4.36 (d, J=15.5 Hz, 1H), 4.17 (s, 2H), 3.88 (d, J=11.0 Hz, 1H), 3.79 (dd, J=11.0, 3.8 Hz, 1H), 3.71 (q, J=5.9, 5.3 Hz, 4H), 3.62-3.48 (m, 12H), 3.48-3.20 (m, 10H), 3.16 (t, J=5.9 Hz, 2H), 3.04-2.95 (m, 5H), 2.56 (ddd, J=15.0, 7.1, 5.3 Hz, 1H), 2.51-2.39 (m, 6H), 2.27-2.15 (m, 1H), 2.13-2.00 (m, 1H), 1.44 (d, J=6.5 Hz, 6H), 1.03 (s, 9H). HRMS (m/z) for C$_{65}$H$_{86}$F$_4$N$_{11}$O$_{10}$S$^+$ [M+H]$^+$: calculated 1288.6210. found 1288.6234.

Example 189: Synthesis of XF078-7

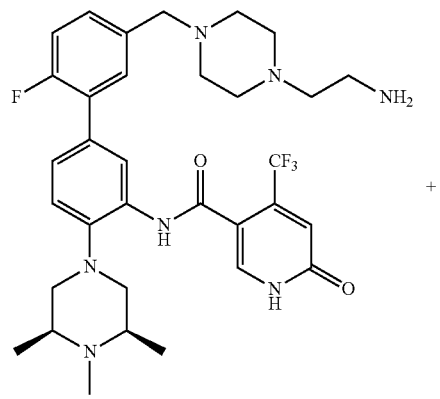

Intermediate 39

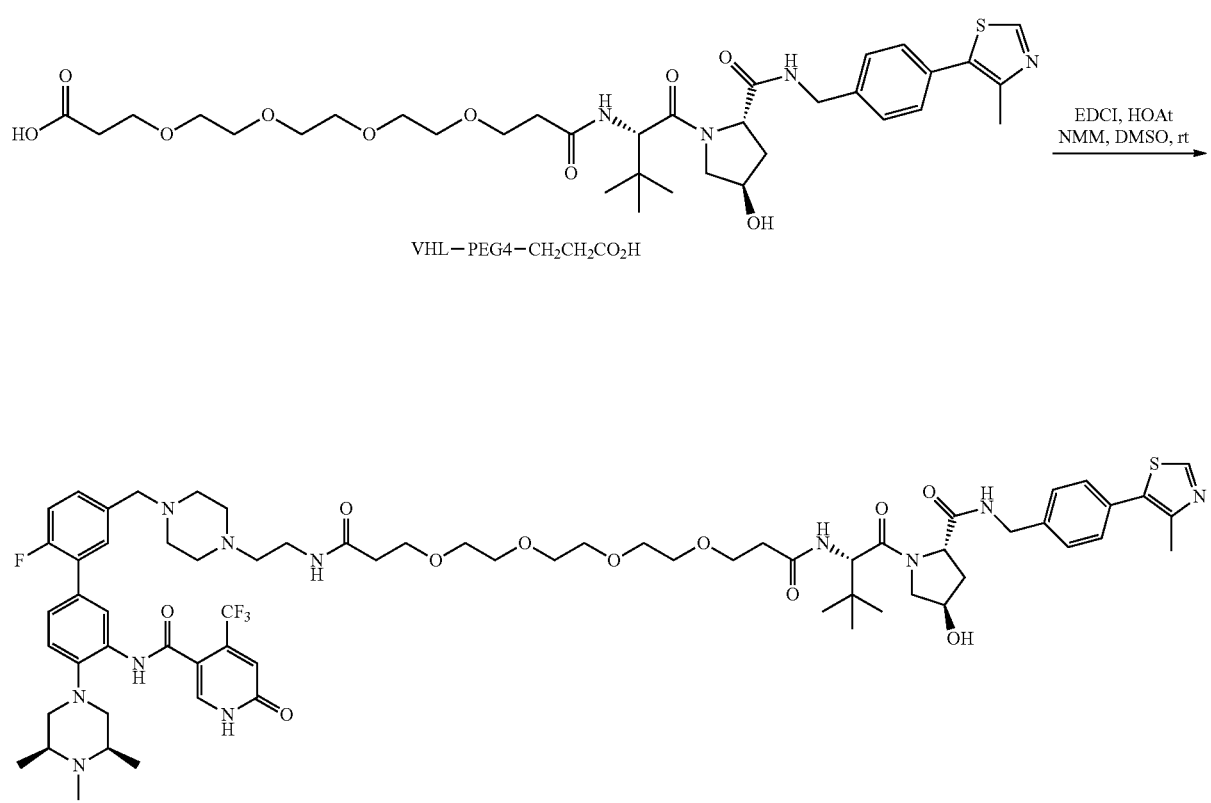

XF078-7 was synthesized following the standard procedures for preparing XF078-1 from intermediate 39 (12.9 mg, 0.02 mmol), VHL-PEG4-CH$_2$CH$_2$COOH (13.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-7 was obtained as white solid in TFA salt form (19.5 mg, yield 58%). $^1$H NMR (600 MHz, CD$_3$OD) δ 9.00 (s, 1H), 8.15 (s, 1H), 8.00 (s, 1H), 7.62 (dd, J=7.4, 2.4 Hz, 1H), 7.52-7.39 (m, 6H), 7.37 (d, J=8.4 Hz, 1H), 7.31-7.16 (m, 1H), 6.93 (s, 1H), 4.63 (s, 1H), 4.59-4.45 (m, 3H), 4.36 (d, J=15.5 Hz, 1H), 4.12 (s, 2H), 3.87 (d, J=11.0 Hz, 1H), 3.84-3.78 (m, 1H), 3.77-3.66 (m, 4H), 3.65-3.49 (m, 16H), 3.45-3.10 (m, 12H), 3.03-2.94 (m, 5H), 2.56 (ddd, J=15.0, 7.4, 5.2 Hz, 1H), 2.52-2.41 (m, 6H), 2.24-2.16 (m, 1H), 2.11-1.97 (m, 1H), 1.44 (d, J=6.5 Hz, 6H), 1.03 (s, 9H). HRMS (m/z) for C$_{67}$H$_{90}$F$_4$N$_{11}$O$_{11}$S$^+$ [M+H]$^+$: calculated 1332.6473. found 1332.6456.

Example 190: Synthesis of XF078-8

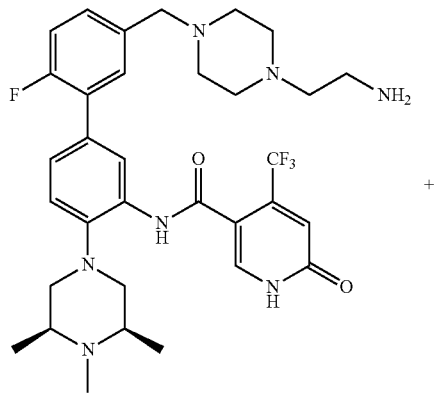

Intermediate 39

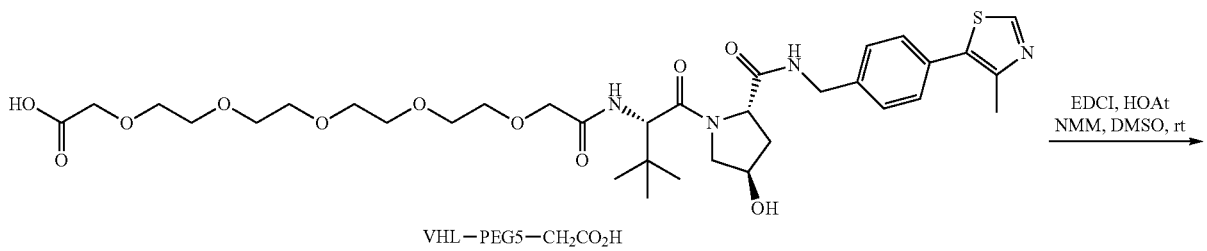

VHL—PEG5—CH$_2$CO$_2$H

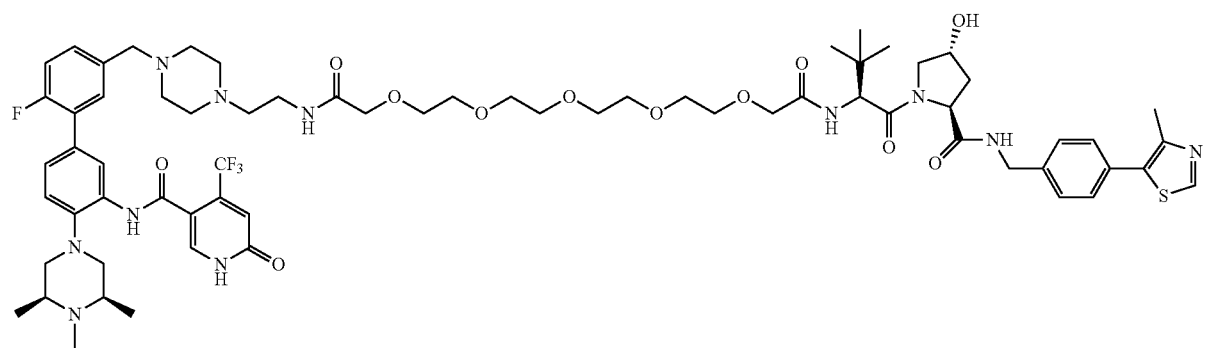

XF078-8

XF078-8 was synthesized following the standard procedures for preparing XF078-1 from intermediate 39 (12.9 mg, 0.02 mmol), VHL-PEG5-CH$_2$COOH (14.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-8 was obtained as white solid in TFA salt form (18 mg, yield 53%). $^1$H NMR (600 MHz, CD$_3$OD) δ 8.99 (s, 1H), 8.15 (s, 1H), 8.01 (s, 1H), 7.63 (dd, J=7.4, 2.3 Hz, 1H), 7.53-7.39 (m, 6H), 7.37 (d, J=8.3 Hz, 1H), 7.27 (dd, J=10.4, 8.4 Hz, 1H), 6.93 (s, 1H), 4.63 (s, 1H), 4.60-4.44 (m, 3H), 4.35 (d, J=15.5 Hz, 1H), 4.16 (s, 2H), 4.14-3.92 (m, 4H), 3.87 (d, J=11.0 Hz, 1H), 3.78 (dd, J=11.0, 3.8 Hz, 1H), 3.73-3.48 (m, 20H), 3.46-3.07 (m, 12H), 3.07-2.90 (m, 5H), 2.48 (s, 3H), 2.29-2.18 (m, 1H), 2.16-1.99 (m, 1H), 1.44 (d, J=6.5 Hz, 6H), 1.04 (s, 9H). HRMS (m/z) for C$_{67}$H$_{90}$F$_4$N$_{11}$O$_{12}$S$^+$ [M+H]$^+$: calculated 1348.6422. found 1348.6478.

Example 191: Synthesis of XF078-9
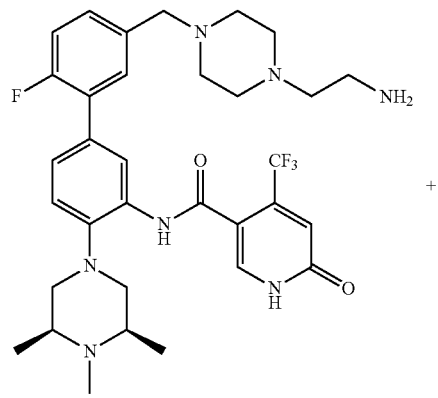
Intermediate 39
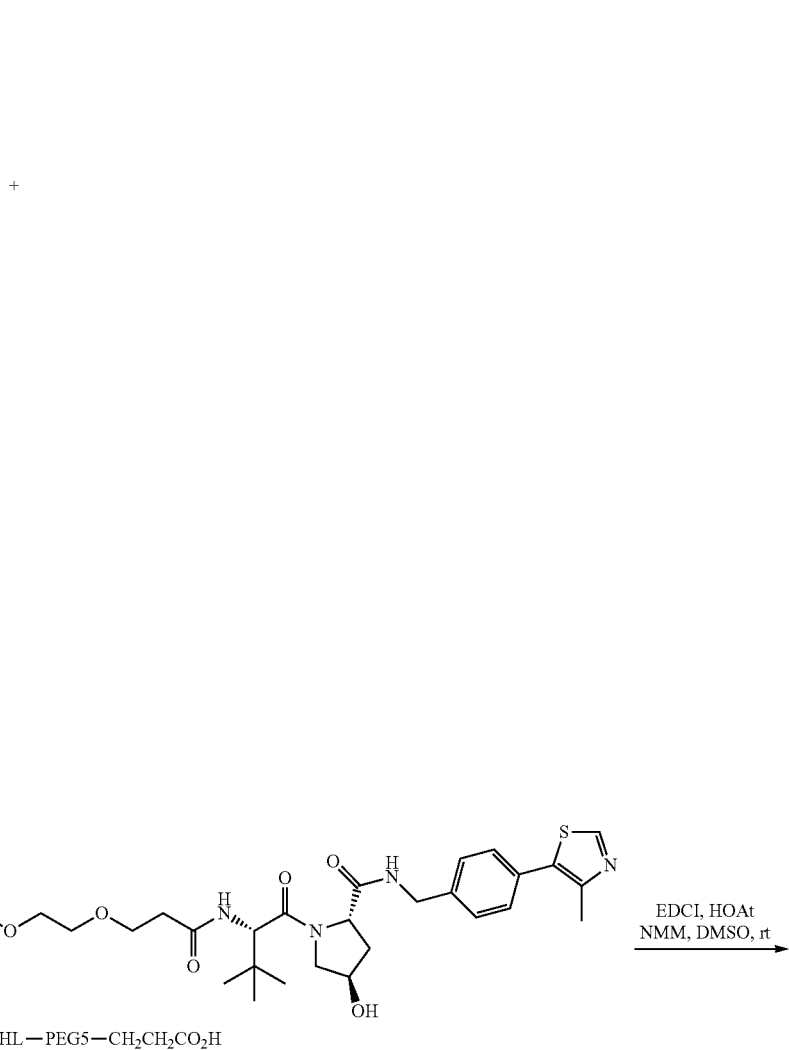
VHL—PEG5—CH₂CH₂CO₂H
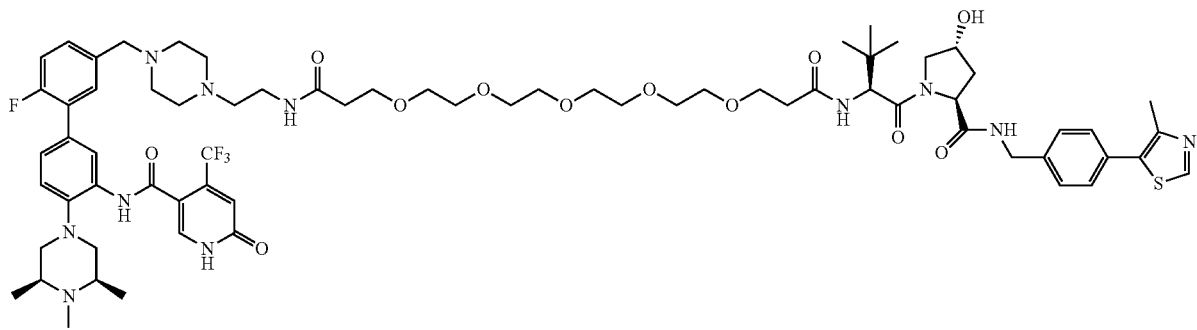
XF078-9

XF078-9 was synthesized following the standard procedures for preparing XF078-1 from intermediate 39 (12.9 mg, 0.02 mmol), VHL-PEG5-CH$_2$CH$_2$COOH (15 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-9 was obtained as white solid in TFA salt form (21.4 mg, yield 62%). $^1$H NMR (600 MHz, CD$_3$OD) δ 8.98 (s, 1H), 8.15 (s, 1H), 8.01 (s, 1H), 7.62 (d, J=7.2 Hz, 1H), 7.57-7.34 (m, 7H), 7.27 (dd, J=10.5, 8.3 Hz, 1H), 6.92 (s, 1H), 4.63 (d, J=2.3 Hz, 1H), 4.59-4.46 (m, 3H), 4.37-4.30 (m, 1H), 4.13 (s, 2H), 3.87 (d, J=10.9 Hz, 1H), 3.79 (dd, J=10.9, 3.8 Hz, 1H), 3.76-3.67 (m, 4H), 3.64-2.91 (m, 37H), 2.62-2.51 (m, 1H), 2.52-2.40 (m, 6H), 2.25-2.17 (m, 1H), 2.12-1.96 (m, 1H), 1.45-1.38 (m, 6H), 1.02 (s, 9H). HRMS (m/z) for C$_{69}$H$_{94}$F$_4$N$_{11}$O$_{13}$S$^+$ [M+H]$^+$: calculated 1376.6735. found 1376.6711.

Example 192: Synthesis of XF078-10

XF078-10 was synthesized following the standard procedures for preparing XF078-1 from intermediate 39 (12.9 mg, 0.02 mmol), VHL-C2-COOH (10.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-10 was obtained as white solid in TFA salt form (19.9 mg, yield 66%). $^1$H NMR (600 MHz, CD$_3$OD) δ 9.01 (s, 1H), 8.15 (s, 1H), 8.00 (s, 1H), 7.61 (dd, J=7.4, 2.3 Hz, 1H), 7.49-7.42 (m, 4H), 7.41 (d, J=8.2 Hz, 2H), 7.36 (d, J=8.4 Hz, 1H), 7.26 (dd, J=10.4, 8.5 Hz, 1H), 6.93 (s, 1H), 4.58-4.48 (m, 3H), 4.48-4.43 (m, 1H), 4.35 (d, J=15.5 Hz, 1H), 4.10 (q, J=13.0 Hz, 2H), 3.82 (d, J=11.0 Hz, 1H), 3.74 (dd, J=10.9, 3.9 Hz, 1H), 3.64-3.38 (m, 4H), 3.35-3.16 (m, 12H), 3.07-2.92 (m, 5H), 2.67-2.59 (m, 2H), 2.51-2.41 (m, 5H), 2.21 (dd, J=13.2, 7.6 Hz, 1H), 2.09-2.02 (m, 1H), 1.44 (d, J=6.5 Hz, 6H), 1.03 (s, 9H). HRMS (m/z) for C$_{59}$H$_{74}$F$_4$N$_{11}$O$_7$S$^+$ [M+H]$^+$: calculated 1156.5424, found 1156.5478.

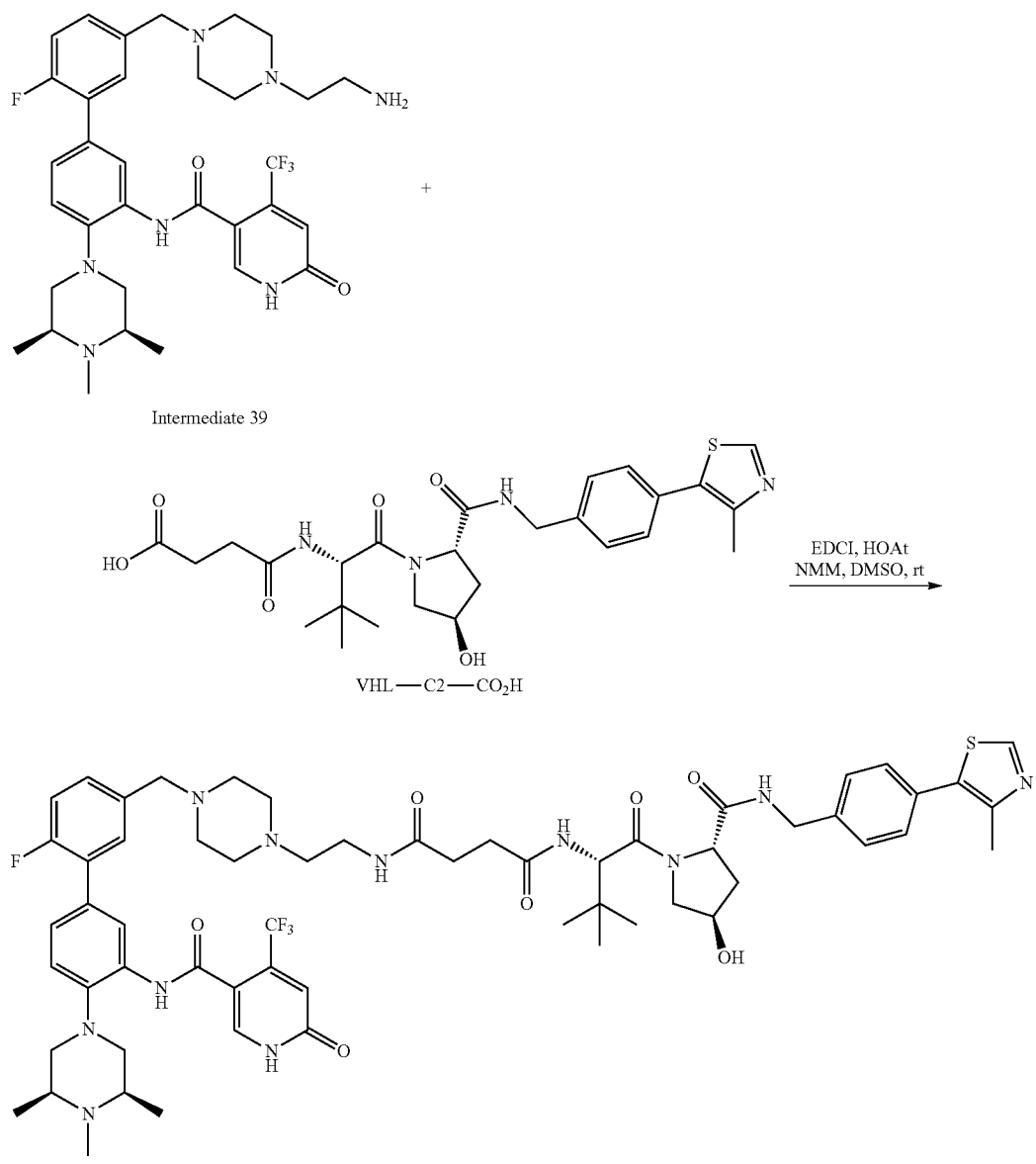

Intermediate 39

VHL—C2—CO$_2$H

EDCI, HOAt
NMM, DMSO, rt

XF078-10

Example 193: Synthesis of XF078-11
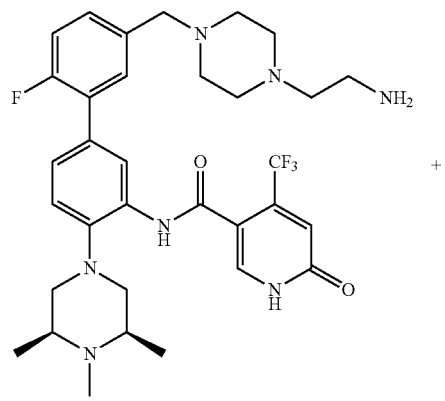
Intermediate 39
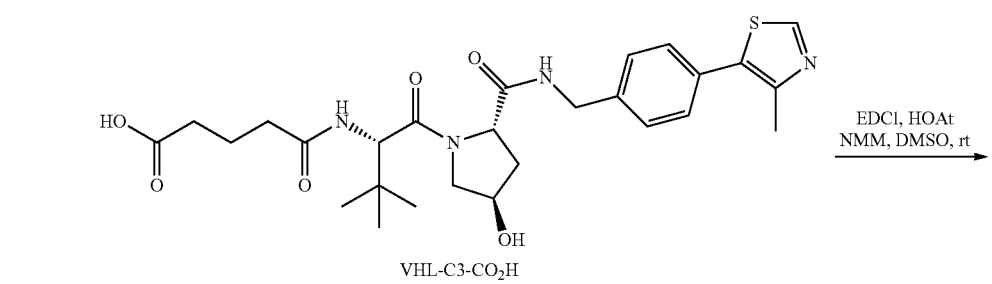
VHL-C3-CO₂H
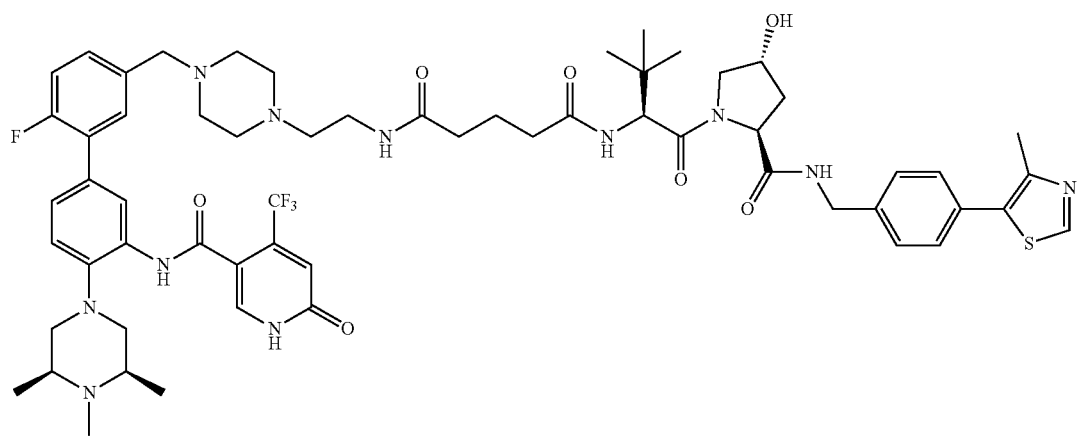
XF078-11

XF078-11 was synthesized following the standard procedures for preparing XF078-1 from intermediate 39 (12.9 mg, 0.02 mmol), VHL-C3-COOH (10.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-11 was obtained as white solid in TFA salt form (18.8 mg, yield 62%). $^1$H NMR (600 MHz, CD$_3$OD) δ 9.02 (s, 1H), 8.15 (s, 1H), 8.00 (s, 1H), 7.62 (dd, J=7.4, 2.3 Hz, 1H), 7.54-7.31 (m, 7H), 7.26 (dd, J=10.4, 8.4 Hz, 1H), 6.92 (s, 1H), 4.66-4.46 (m, 4H), 4.36 (d, J=15.5 Hz, 1H), 4.15 (s, 2H), 3.91 (d, J=11.0 Hz, 1H), 3.79 (dd, J=10.9, 3.8 Hz, 1H), 3.59-3.44 (m, 4H), 3.44-3.15 (m, 10H), 3.11 (t, J=6.0 Hz, 2H), 3.05-2.93 (m, 5H), 2.47 (s, 3H), 2.37-2.17 (m, 5H), 2.11-2.03 (m, 1H), 1.89 (p, J=7.4 Hz, 2H), 1.44 (d, J=6.5 Hz, 6H), 1.03 (s, 9H). HRMS (m/z) for C$_{60}$H$_{76}$F$_4$N$_{11}$O$_7$S$^+$ [M+H]$^+$: calculated 1170.5581. found 1170.5545.

Example 194: Synthesis of XF078-12

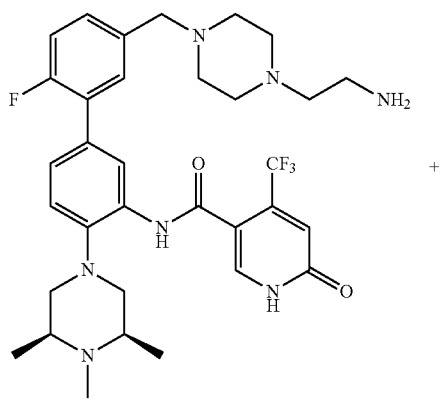

Intermediate 39

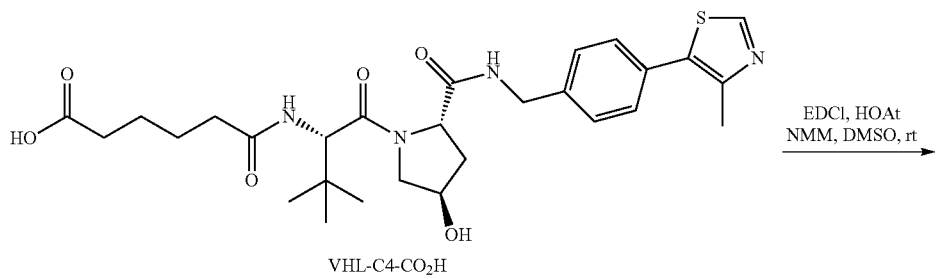

VHL-C4-CO$_2$H

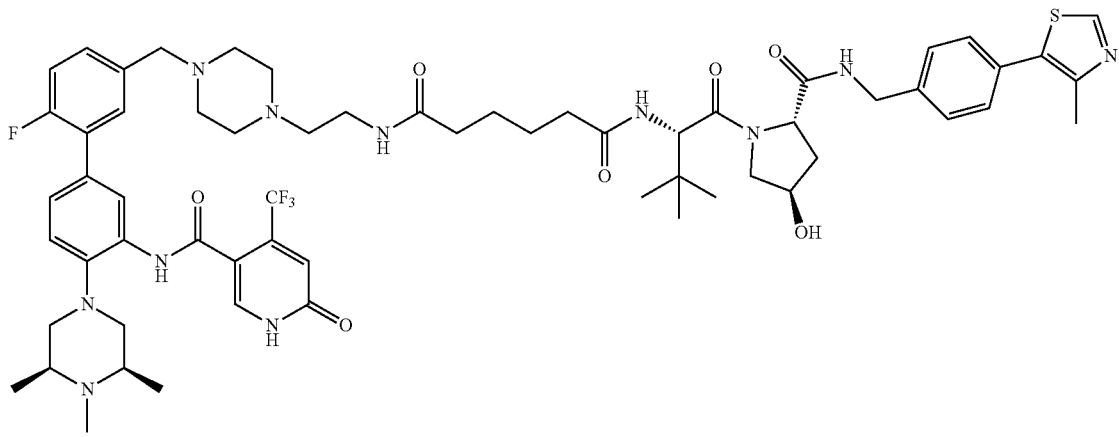

XF078-12

XF078-12 was synthesized following the standard procedures for preparing XF078-1 from intermediate 39 (12.9 mg, 0.02 mmol), VHL-C4-COOH (11.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-12 was obtained as white solid in TFA salt form (11.9 mg, yield 39%). $^1$H NMR (600 MHz, CD$_3$OD) δ 8.96 (s, 1H), 8.22-8.12 (m, 1H), 8.00 (s, 1H), 7.61 (dd, J=7.5, 2.3 Hz, 1H), 7.49-7.39 (m, 6H), 7.37 (d, J=8.4 Hz, 1H), 7.26 (dd, J=10.4, 8.4 Hz, 1H), 6.93 (s, 1H), 4.61 (s, 1H), 4.57-4.45 (m, 3H), 4.36 (d, J=15.5 Hz, 1H), 4.08 (s, 2H), 3.88 (d, J=10.9 Hz, 1H), 3.77 (dd, J=10.9, 3.9 Hz, 1H), 3.58-3.40 (m, 4H), 3.38-3.06 (m, 10H), 3.04-2.94 (m, 7H), 2.47 (s, 3H), 2.33-2.16 (m, 5H), 2.07 (ddd, J=13.4, 9.2, 4.5 Hz, 1H), 1.61 (dd, J=7.4, 4.3 Hz, 4H), 1.44 (d, J=6.5 Hz, 6H), 1.02 (s, 9H). HRMS (m/z) for C$_{61}$H$_{78}$F$_4$N$_1$O$_7$S$^+$ [M+H]$^+$: calculated 1184.5737. found 1184.5712.

Example 195: Synthesis of XF078-13

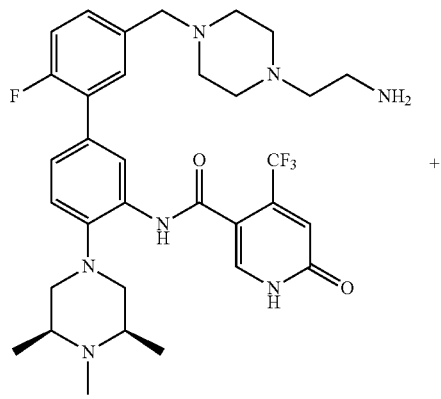

Intermediate 39

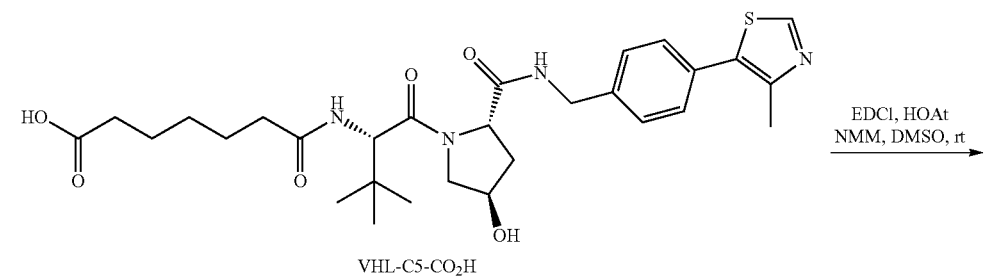

VHL-C5-CO$_2$H

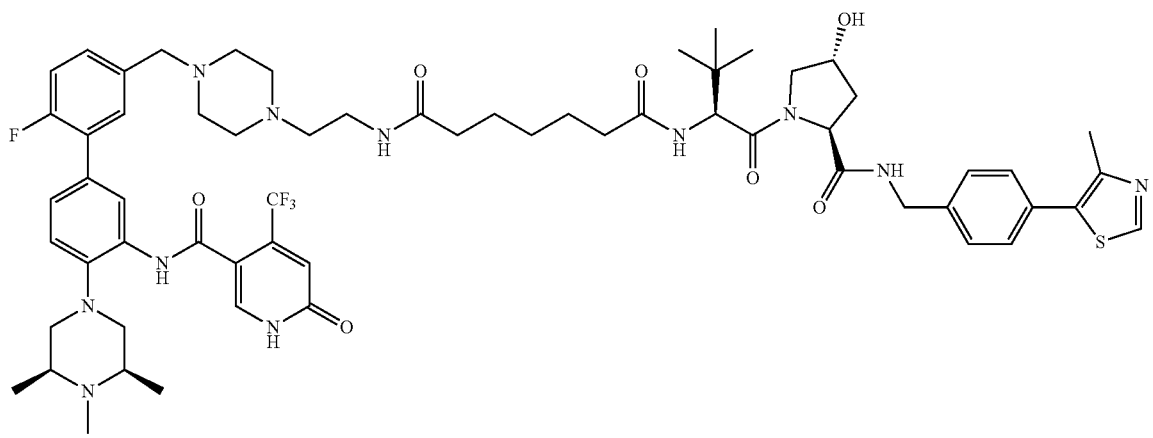

XF078-13

XF078-13 was synthesized following the standard procedures for preparing XF078-1 from intermediate 39 (12.9 mg, 0.02 mmol), VHL-C5-COOH (11.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-13 was obtained as white solid in TFA salt form (17.9 mg, yield 58%). $^1$H NMR (600 MHz, CD$_3$OD) δ 9.00 (s, 1H), 8.15 (s, 1H), 8.00 (s, 1H), 7.62 (dd, J=7.3, 2.4 Hz, 1H), 7.51-7.44 (m, 4H), 7.43-7.39 (m, 2H), 7.37 (d, J=8.4 Hz, 1H), 7.27 (dd, J=10.4, 8.4 Hz, 1H), 6.93 (s, 1H), 4.62 (s, 1H), 4.60-4.43 (m, 3H), 4.36 (d, J=15.6 Hz, 1H), 4.12 (s, 2H), 3.89 (d, J=10.9 Hz, 1H), 3.79 (dd, J=10.9, 3.9 Hz, 1H), 3.58-3.45 (m, 4H), 3.43-3.12 (m, 10H), 3.08 (t, J=6.1 Hz, 2H), 2.99 (d, J=7.3 Hz, 5H), 2.48 (d, J=3.0 Hz, 3H), 2.34-2.16 (m, 5H), 2.07 (ddd, J=13.4, 9.1, 4.5 Hz, 1H), 1.68-1.55 (m, 4H), 1.44 (d, J=6.5 Hz, 6H), 1.40-1.30 (m, 2H), 1.03 (s, 9H). HRMS (m/z) for C$_{62}$H$_{80}$F$_4$N$_{11}$O$_7$S$^+$ [M+H]$^+$: calculated 1198.5894. found 1198.5906.

Example 196: Synthesis of XF078-14

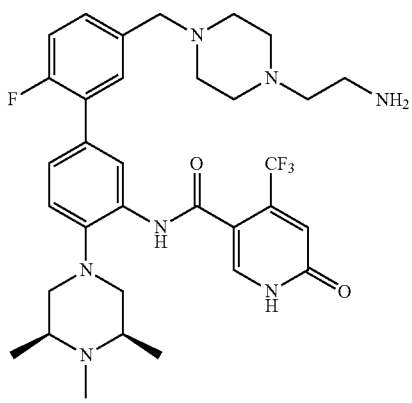

Intermediate 39

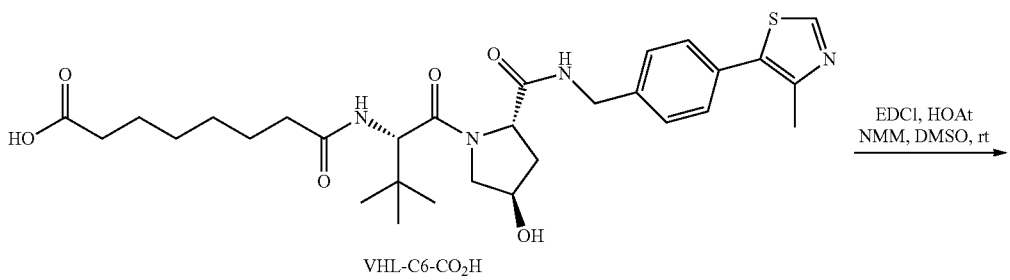

VHL-C6-CO$_2$H

EDCI, HOAt
NMM, DMSO, rt

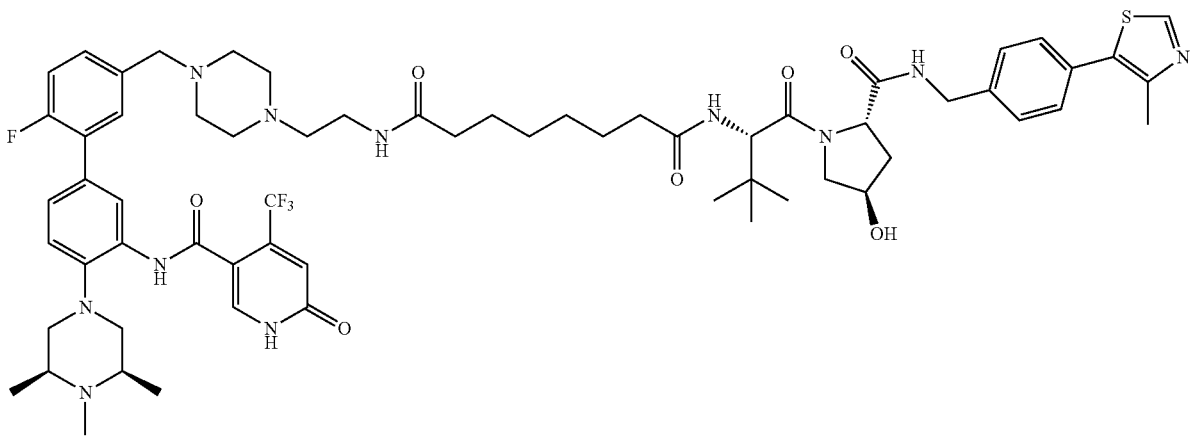

XF078-14

XF078-14 was synthesized following the standard procedures for preparing XF078-1 from intermediate 39 (12.9 mg, 0.02 mmol), VHL-C6-COOH (11.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-14 was obtained as white solid in TFA salt form (20.1 mg, yield 65%). $^1$H NMR (600 MHz, CD$_3$OD) δ 9.00 (s, 1H), 8.15 (s, 1H), 8.00 (s, 1H), 7.62 (dd, J=7.4, 2.5 Hz, 1H), 7.50-7.40 (m, 6H), 7.37 (d, J=8.5 Hz, 1H), 7.27 (dd, J=10.5, 8.3 Hz, 1H), 6.93 (s, 1H), 4.63 (s, 1H), 4.60-4.46 (m, 3H), 4.36 (d, J=15.4 Hz, 1H), 4.14 (s, 2H), 3.89 (d, J=11.0 Hz, 1H), 3.79 (dd, J=11.0, 3.9 Hz, 1H), 3.59-3.51 (m, 2H), 3.48 (t, J=6.0 Hz, 2H), 3.41-3.11 (m, 10H), 3.08 (t, J=6.2 Hz, 2H), 2.99-2.90 (m, 5H), 2.48 (d, J=3.0 Hz, 3H), 2.35-2.15 (m, 5H), 2.07 (ddd, J=13.2, 9.1, 4.4 Hz, 1H), 1.65-1.53 (m, 4H), 1.44 (d, J=6.4 Hz, 6H), 1.39-1.29 (m, 4H), 1.03 (s, 9H). HRMS (m/z) for C$_{63}$H$_{82}$F$_4$N$_1$O$_7$S$^+$ [M+H]$^+$: calculated 1212.6050. found 1212.6077.

Example 197: Synthesis of XF078-15

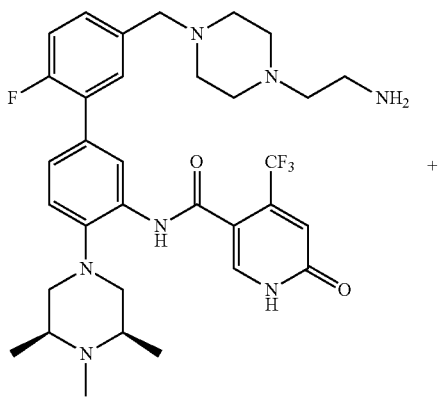

Intermediate 39

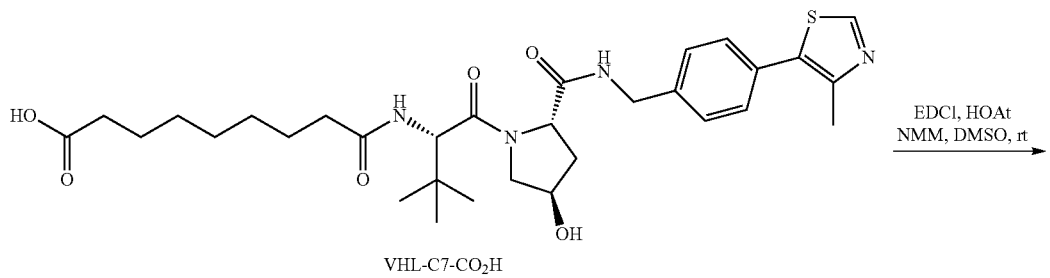

VHL-C7-CO$_2$H

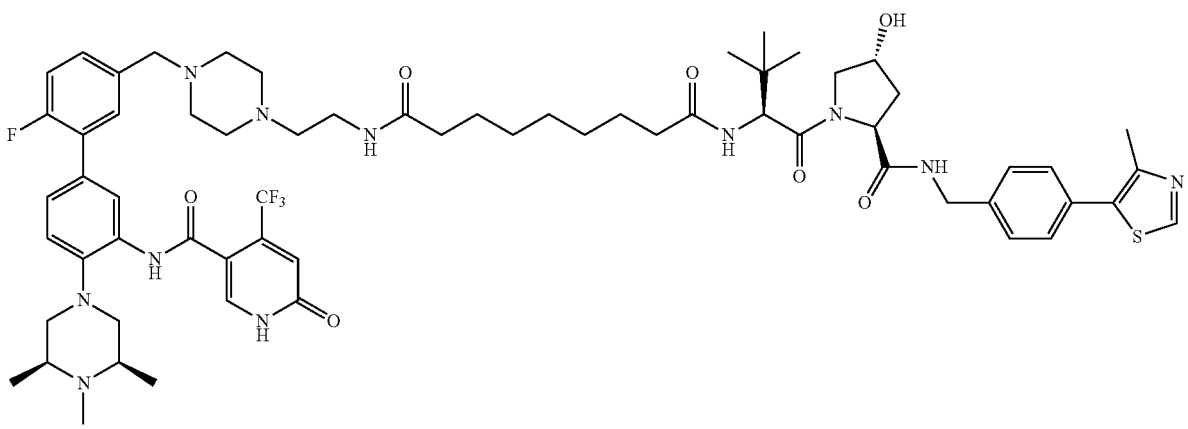

XF078-15

XF078-15 was synthesized following the standard procedures for preparing XF078-1 from intermediate 39 (12.9 mg, 0.02 mmol), VHL-C7-COOH (12 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-15 was obtained as white solid in TFA salt form (17.7 mg, yield 56%). $^1$H NMR (600 MHz, CD$_3$OD) δ 8.98 (s, 1H), 8.15 (s, 1H), 8.00 (s, 1H), 7.62 (dd, J=7.5, 2.4 Hz, 1H), 7.49-7.39 (m, 6H), 7.37 (d, J=8.4 Hz, 1H), 7.27 (dd, J=10.4, 8.4 Hz, 1H), 6.93 (s, 1H), 4.63 (s, 1H), 4.61-4.45 (m, 3H), 4.36 (d, J=15.5 Hz, 1H), 4.10 (s, 2H), 3.89 (d, J=11.0 Hz, 1H), 3.79 (dd, J=11.0, 4.0 Hz, 1H), 3.54 (td, J=8.3, 6.4, 3.1 Hz, 2H), 3.47 (t, J=6.0 Hz, 2H), 3.36-3.10 (m, 10H), 3.06 (t, J=6.1 Hz, 2H), 3.03-2.93 (m, 5H), 2.48 (s, 3H), 2.35-2.16 (m, 5H), 2.13-2.06 (m, 1H), 1.67-1.51 (m, 4H), 1.44 (d, J=6.5 Hz, 6H), 1.38-1.26 (m, 6H), 1.03 (s, 9H). HRMS (m/z) for $C_{64}H_{84}F_4N^{11}O_7S^+$ [M+H]$^+$: calculated 1226.6207. found 1226.6219.

Example 198: Synthesis of XF078-16

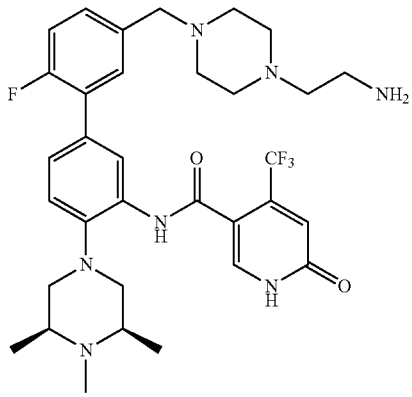

Intermediate 39

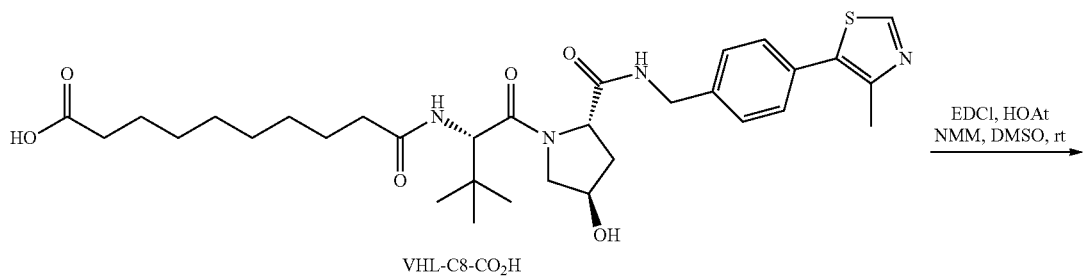

VHL-C8-CO$_2$H

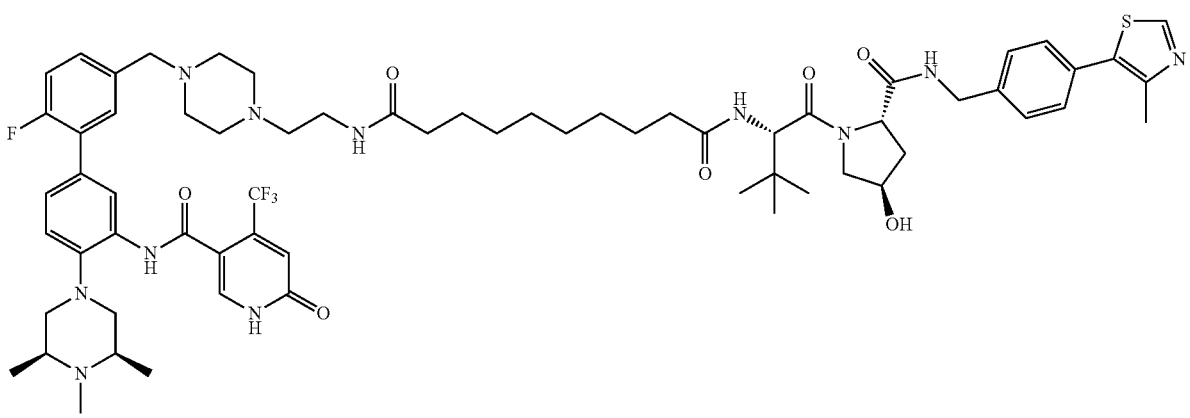

XF078-16

XF078-16 was synthesized following the standard procedures for preparing XF078-1 from intermediate 39 (12.9 mg, 0.02 mmol), VHL-C8-COOH (12.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-16 was obtained as white solid in TFA salt form (18.5 mg, yield 58%). $^1$H NMR (600 MHz, CD$_3$OD) δ 8.99 (s, 1H), 8.15 (s, 1H), 8.00 (s, 1H), 7.61 (dd, J=7.5, 2.4 Hz, 1H), 7.50-7.32 (m, 7H), 7.26 (dd, J=10.4, 8.4 Hz, 1H), 6.93 (s, 1H), 4.63 (s, 1H), 4.60-4.47 (m, 3H), 4.36 (d, J=15.5 Hz, 1H), 4.09 (s, 2H), 3.89 (d, J=11.0 Hz, 1H), 3.80 (dd, J=10.9, 3.9 Hz, 1H), 3.59-3.50 (m, 2H), 3.47 (t, J=6.0 Hz, 2H), 3.35-3.10 (m, 10H), 3.06-2.96 (m, 7H), 2.48 (s, 3H), 2.35-2.12 (m, 5H), 2.07 (ddd, J=13.3, 9.2, 4.5 Hz, 1H), 1.71-1.51 (m, 4H), 1.44 (d, J=6.5 Hz, 6H), 1.31 (d, J=2.6 Hz, 8H), 1.03 (s, 9H). HRMS (m/z) for C$_{65}$H$_{86}$F$_4$N$_{11}$O$_7$S$^+$ [M+H]$^+$: calculated 1240.6363. found 1240.6341.

Example 199: Synthesis of XF078-17

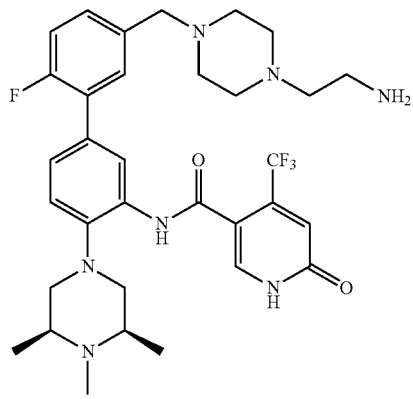

Intermediate 39

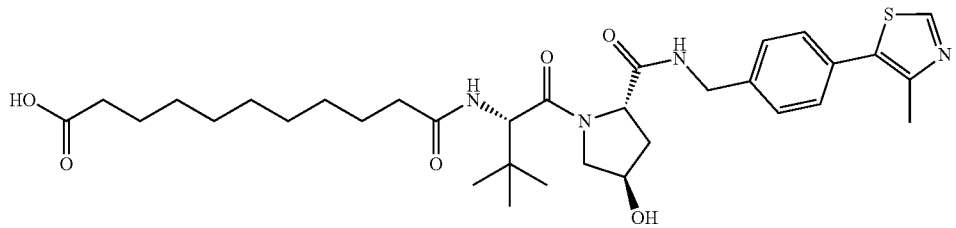

VHL-C9-CO$_2$H

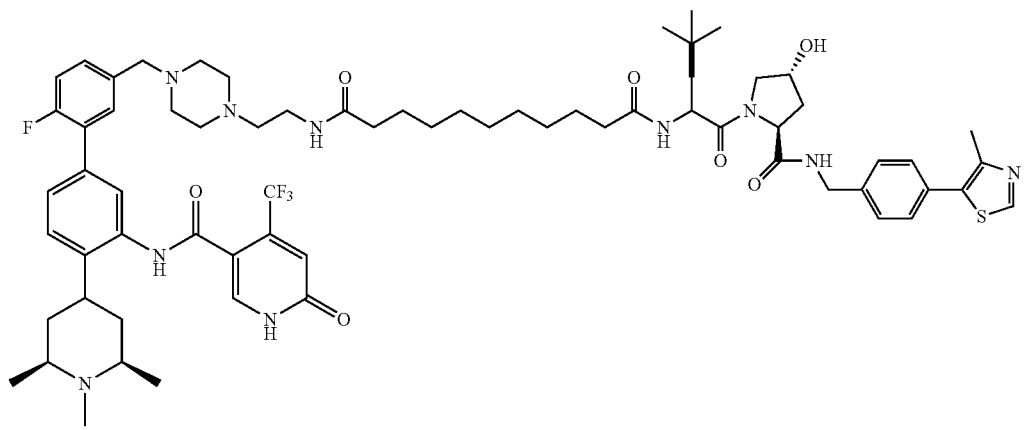

XF078-17

XF078-17 was synthesized following the standard procedures for preparing XF078-1 from intermediate 39 (12.9 mg, 0.02 mmol), VHL-C9-COOH (12.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-17 was obtained as white solid in TFA salt form (26.5 mg, yield 83%). $^1$H NMR (600 MHz, CD$_3$OD) δ 8.99 (s, 1H), 8.15 (s, 1H), 8.00 (s, 1H), 7.62 (d, J=7.2 Hz, 1H), 7.49-7.34 (m, 7H), 7.27 (t, J=9.4 Hz, 1H), 6.93 (s, 1H), 4.62 (d, J=3.6 Hz, 1H), 4.60-4.43 (m, 3H), 4.36 (d, J=15.4 Hz, 1H), 4.11 (s, 2H), 3.89 (d, J=11.1 Hz, 1H), 3.80 (dd, J=11.1, 4.1 Hz, 1H), 3.58-3.42 (m, 4H), 3.30 (s, 10H), 3.09-2.92 (m, 7H), 2.48 (d, J=3.5 Hz, 3H), 2.35-2.13 (m, 5H), 2.07 (ddd, J=13.3, 9.1, 4.5 Hz, 1H), 1.64-1.50 (m, 4H), 1.44 (d, J=6.3 Hz, 6H), 1.38-1.25 (m, 10H), 1.02 (s, 9H). HRMS (m/z) for C$_{66}$H$_{88}$F$_4$N$_{11}$O$_7$S$^+$ [M+H]$^+$: calculated 1254.6250. found 1254.6276.

Example 200: Synthesis of XF078-18

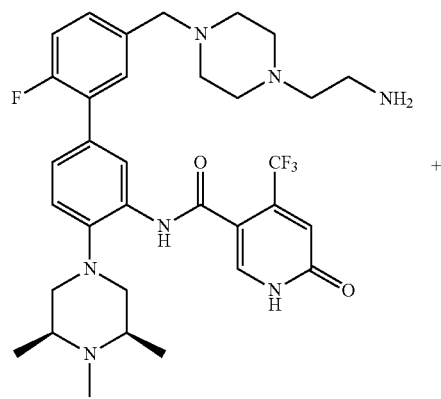

Intermediate 39

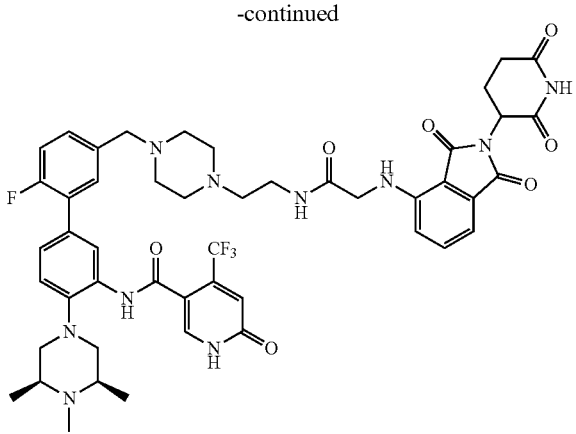

XF078-18

XF078-18 was synthesized following the standard procedures for preparing XF078-1 from intermediate 39 (12.9 mg, 0.02 mmol), PML-6 (6.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-18 was obtained as yellow solid in TFA salt form (12.6 mg, yield 48%). $^1$H NMR (600 MHz, CD$_3$OD) δ 8.14 (s, 1H), 7.99 (d, J=3.1 Hz, 1H), 7.68-7.51 (m, 2H), 7.47 (d, J=7.9 Hz, 2H), 7.36 (dd, J=8.4, 2.9 Hz, 1H), 7.32-7.20 (m, 1H), 7.09 (dd, J=7.1, 3.0 Hz, 1H), 7.02-6.80 (m, 2H), 5.08 (dd, J=12.4, 5.3 Hz, 1H), 4.19-3.96 (m, 4H), 3.59-3.38 (m, 4H), 3.25-2.79 (m, 18H), 2.78-2.67 (m, 2H), 2.20-2.02 (m, 1H), 1.50-1.38 (m, 6H). HRMS (m/z) for C$_{48}$H$_{53}$F$_4$N$_{10}$O$_7$$^+$ [M+H]$^+$: calculated 957.4029. found 957.4064.

Example 201: Synthesis of XF078-19

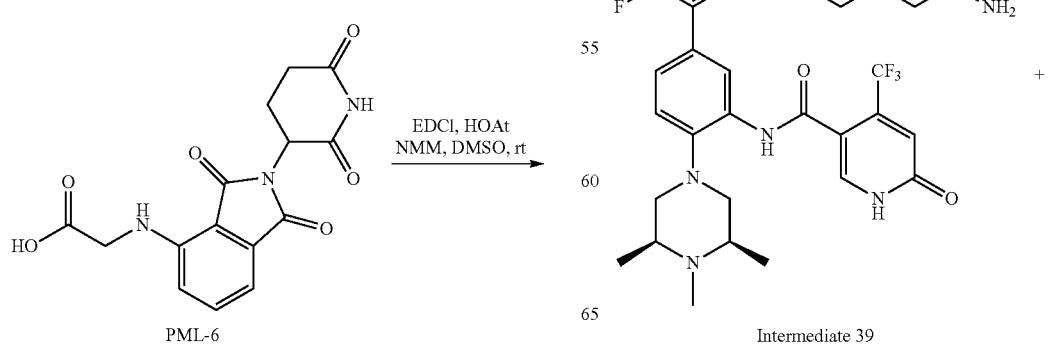

PML-6      Intermediate 39

-continued

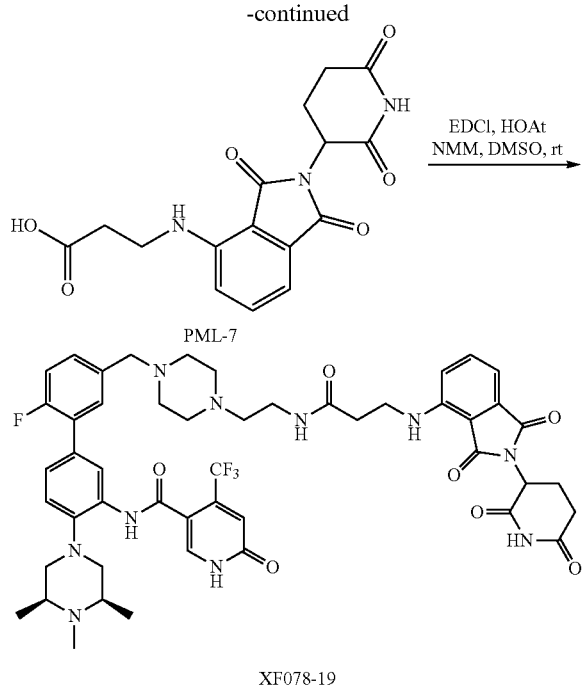

PML-7

XF078-19

XF078-19 was synthesized following the standard procedures for preparing XF078-1 from intermediate 39 (12.9 mg, 0.02 mmol), PML-7 (6.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-19 was obtained as yellow solid in TFA salt form (15.1 mg, yield 48%). $^1$H NMR (600 MHz, CD$_3$OD) δ 8.13 (d, J=2.0 Hz, 1H), 7.99 (s, 1H), 7.61 (dd, J=7.4, 2.3 Hz, 1H), 7.54 (dd, J=8.6, 7.1 Hz, 1H), 7.48-7.41 (m, 2H), 7.35 (d, J=8.4 Hz, 1H), 7.26 (dd, J=10.4, 8.4 Hz, 1H), 7.09 (d, J=8.6 Hz, 1H), 7.04 (d, J=7.1 Hz, 1H), 6.90 (s, 1H), 5.01 (dd, J=12.8, 5.5 Hz, 1H), 4.12 (d, J=2.4 Hz, 2H), 3.63 (t, J=6.3 Hz, 2H), 3.58-3.42 (m, 4H), 3.36-3.11 (m, 10H), 3.09-2.94 (m, 7H), 2.85-2.74 (m, 1H), 2.71-2.59 (m, 2H), 2.55 (td, J=5.9, 2.3 Hz, 2H), 2.19-2.03 (m, 1H), 1.44 (d, J=6.5 Hz, 6H). HRMS (m/z) for $C_{49}H_{55}F_4N_{10}O_7^+$ [M+H]$^+$: calculated 971.4186. found 971.4213.

Example 202: Synthesis of XF078-20

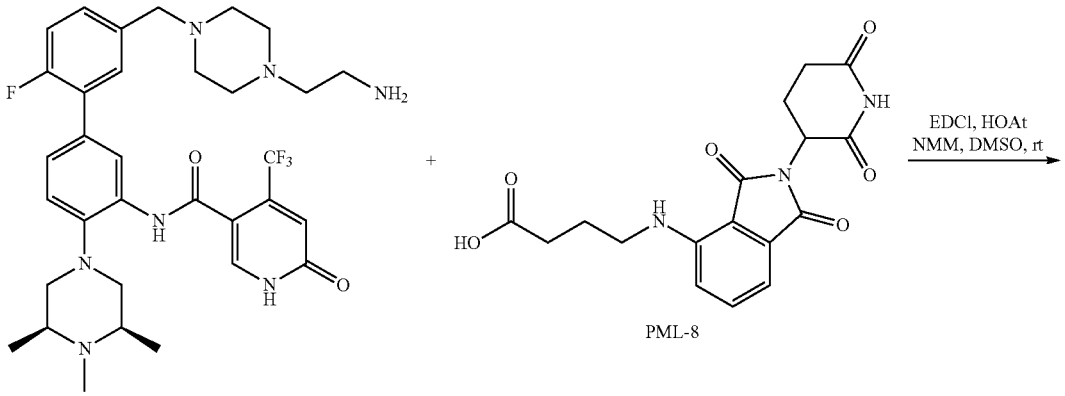

Intermediate 39

PML-8

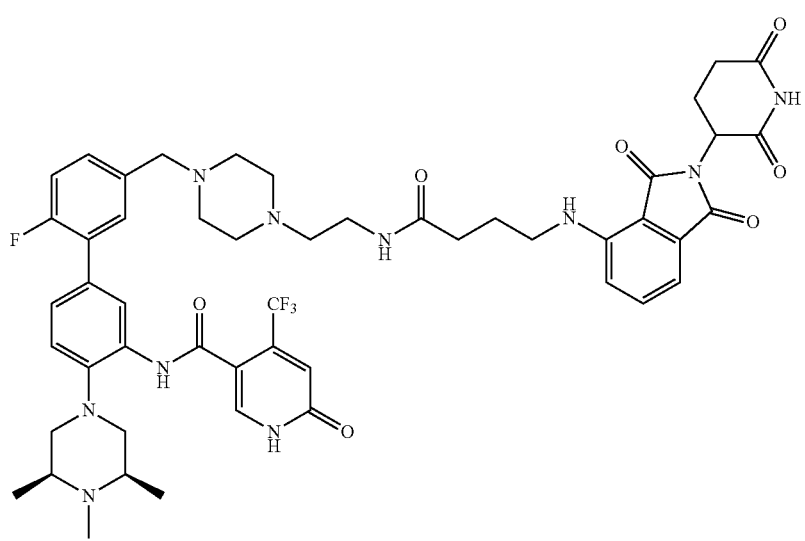

XF078-20

XF078-20 was synthesized following the standard procedures for preparing XF078-1 from intermediate 39 (12.9 mg, 0.02 mmol), PML-8 (7.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-20 was obtained as yellow solid in TFA salt form (14.8 mg, yield 56%). $^1$H NMR (600 MHz, CD$_3$OD) δ 8.13 (s, 1H), 7.99 (d, J=3.4 Hz, 1H), 7.58 (d, J=7.2 Hz, 1H), 7.52 (d, J=6.7 Hz, 1H), 7.48-7.42 (m, 2H), 7.35 (d, J=8.2 Hz, 1H), 7.30-7.19 (m, 1H), 7.12-7.01 (m, 2H), 6.91 (d, J=3.0 Hz, 1H), 5.03 (dd, J=13.0, 5.3 Hz, 1H), 4.13-3.99 (m, 2H), 3.60-3.49 (m, 2H), 3.47-2.93 (m, 21H), 2.90-2.76 (m, 1H), 2.68 (dd, J=30.2, 15.2 Hz, 2H), 2.37-2.30 (m, 2H), 2.14-2.04 (m, 1H), 2.03-1.90 (m, 2H), 1.50-1.34 (m, 6H). HRMS (m/z) for $C_{50}H_{57}F_4N_{10}O_7^+$ [M+H]$^+$: calculated 985.4342. found 985.4319.

Example 203: Synthesis of XF078-21

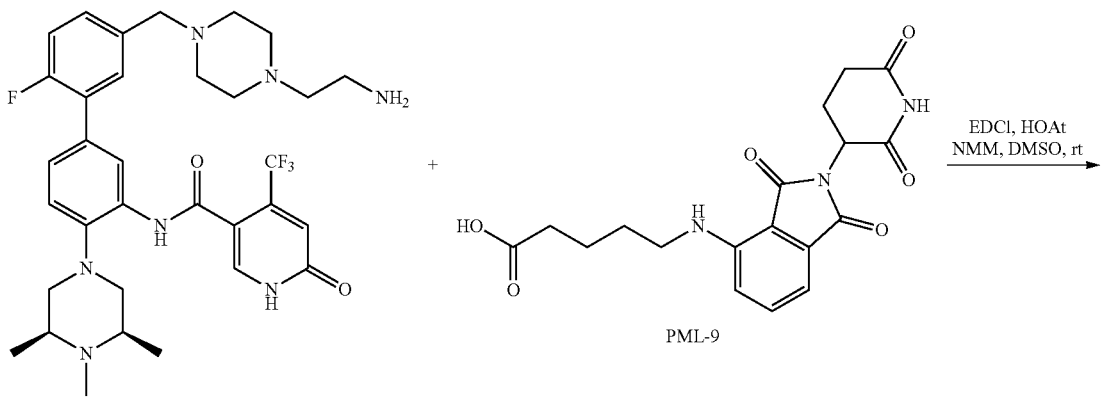

Intermediate 39

PML-9

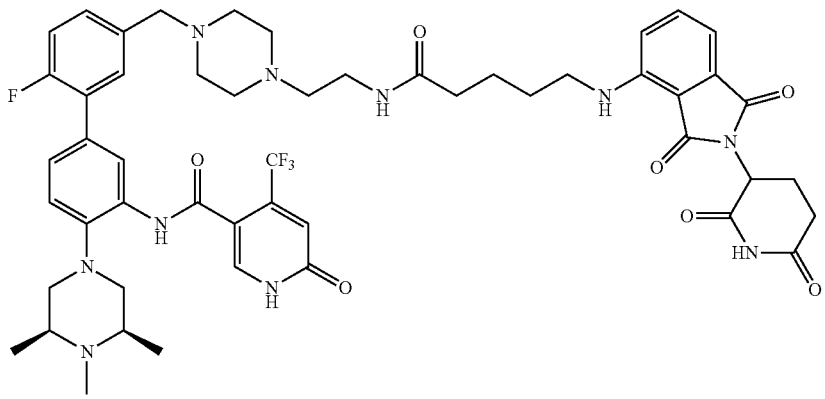

XF078-21

XF078-21 was synthesized following the standard procedures for preparing XF078-1 from intermediate 39 (12.9 mg, 0.02 mmol), PML-9 (7.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-21 was obtained as yellow solid in TFA salt form (15.5 mg, yield 58%). $^1$H NMR (600 MHz, CD$_3$OD) δ 8.14 (s, 1H), 7.99 (s, 1H), 7.61 (dd, J=7.3, 2.3 Hz, 1H), 7.52 (dd, J=8.6, 7.1 Hz, 1H), 7.49-7.39 (m, 2H), 7.35 (d, J=8.4 Hz, 1H), 7.26 (dd, J=10.4, 8.4 Hz, 1H), 7.09-6.94 (m, 2H), 6.91 (s, 1H), 5.02 (dd, J=12.7, 5.4 Hz, 1H), 4.11 (s, 2H), 3.59-3.49 (m, 2H), 3.46 (t, J=6.0 Hz, 2H), 3.37-3.07 (m, 12H), 3.03-2.90 (m, 7H), 2.86-2.78 (m, 1H), 2.75-2.61 (m, 2H), 2.27 (t, J=7.1 Hz, 2H), 2.12-2.01 (m, 1H), 1.76-1.60 (m, 4H), 1.44 (d, J=6.4 Hz, 6H). HRMS (m/z) for C$_{51}$H$_{59}$F$_4$N$_{10}$O$_7{}^+$ [M+H]$^+$: calculated 999.4499. found 999.4523.

Example 204: Synthesis of XF078-22

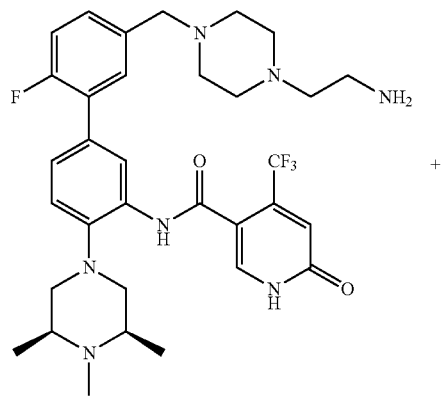

Intermediate 39

+

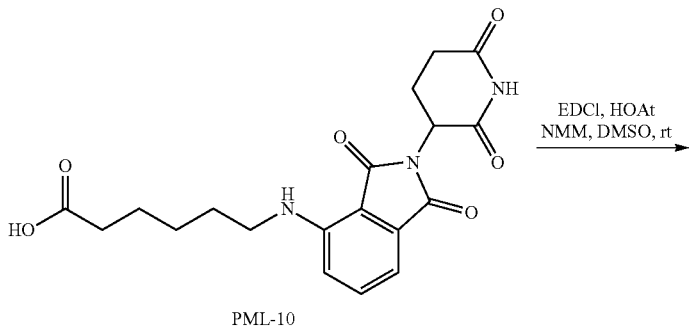

PML-10

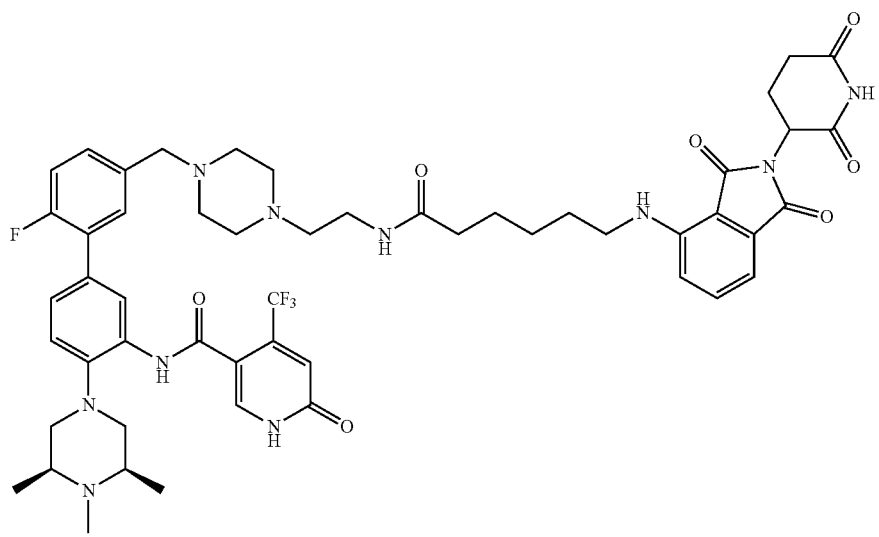

XF078-22

XF078-22 was synthesized following the standard procedures for preparing XF078-1 from intermediate 39 (12.9 mg, 0.02 mmol), PML-10 (7.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-22 was obtained as yellow solid in TFA salt form (12 mg, yield 44%). $^1$H NMR (600 MHz, CD$_3$OD) δ 8.13 (s, 1H), 7.99 (s, 1H), 7.60 (d, J=7.2 Hz, 1H), 7.55-7.48 (m, 1H), 7.48-7.39 (m, 2H), 7.35 (dd, J=8.5, 2.4 Hz, 1H), 7.26 (t, J=9.0 Hz, 1H), 7.05-6.96 (m, 2H), 6.92 (s, 1H), 5.03 (ddd, J=12.8, 5.6, 2.3 Hz, 1H), 4.07 (s, 2H), 3.53 (s, 2H), 3.45 (d, J=6.2 Hz, 2H), 3.37-2.94 (m, 19H), 2.88-2.76 (m, 1H), 2.76-2.63 (m, 2H), 2.28-2.19 (m, 2H), 2.14-2.05 (m, 1H), 1.72-1.60 (m, 4H), 1.48-1.38 (m, 8H). HRMS (m/z) for $C_{52}H_{61}F_4N_{10}O_7^+$ [M+H]$^+$: calculated 1013.4655. found 1013.4664.

Example 205: Synthesis of XF078-23

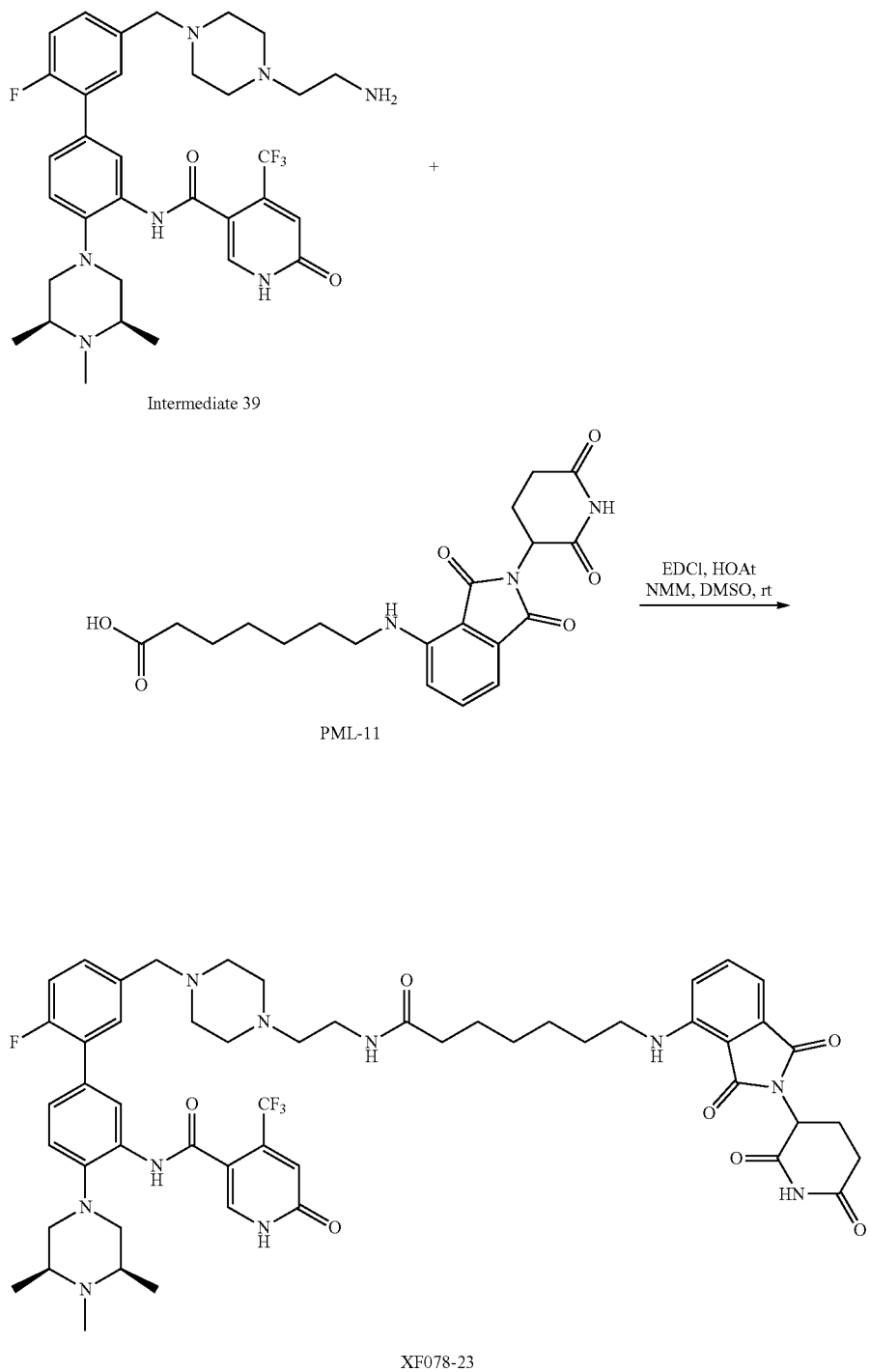

XF078-23 was synthesized following the standard procedures for preparing XF078-1 from intermediate 39 (12.9 mg, 0.02 mmol), PML-11 (8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-23 was obtained as yellow solid in TFA salt form (16.4 mg, yield 60%). $^1$H NMR (600 MHz, CD$_3$OD) δ 8.14 (s, 1H), 8.00 (s, 1H), 7.61 (dd, J=7.4, 2.3 Hz, 1H), 7.52 (dd, J=8.5, 7.2 Hz, 1H), 7.49-7.42 (m, 2H), 7.35 (d, J=8.3 Hz, 1H), 7.26 (dd, J=10.4, 8.4 Hz, 1H), 7.05-6.98 (m, 2H), 6.92 (s, 1H), 5.03 (dd, J=12.7, 5.5 Hz, 1H), 4.08 (s, 2H), 3.59-3.50 (m, 2H), 3.46 (t, J=6.0 Hz, 2H), 3.36-3.06 (m, 12H), 3.06-2.95 (m, 7H), 2.90-2.79 (m, 1H), 2.76-2.59 (m, 2H), 2.21 (t, J=7.5 Hz, 2H), 2.11-2.03 (m, 1H), 1.69-1.57 (m, 4H), 1.47-1.30 (m, 10H). HRMS (m/z) for C$_{53}$H$_{63}$F$_4$N$_{10}$O$_7{}^+$ [M+H]$^+$: calculated 1027.4812. found 1027.4788.

Example 206: Synthesis of XF078-24

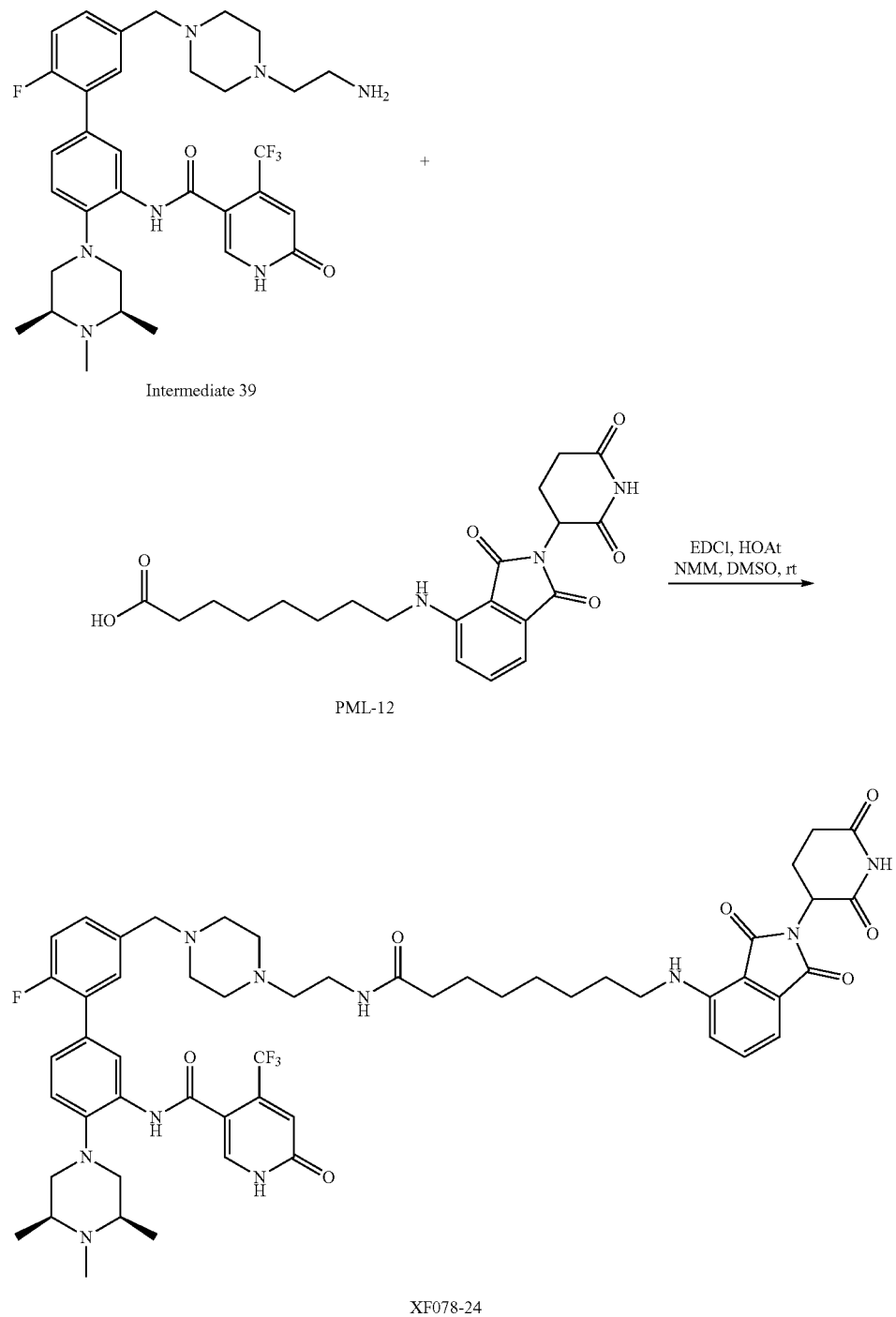

Intermediate 39

PML-12

XF078-24

XF078-24 was synthesized following the standard procedures for preparing XF078-1 from intermediate 39 (12.9 mg, 0.02 mmol), PML-12 (8.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-24 was obtained as yellow solid in TFA salt form (20.2 mg, yield 73%). $^1$H NMR (600 MHz, CD$_3$OD) δ 8.14 (s, 1H), 8.00 (s, 1H), 7.63 (dd, J=7.3, 2.3 Hz, 1H), 7.57-7.49 (m, 1H), 7.49-7.42 (m, 2H), 7.35 (d, J=8.4 Hz, 1H), 7.27 (dd, J=10.4, 8.4 Hz, 1H), 7.05-6.96 (m, 2H), 6.92 (s, 1H), 5.03 (dd, J=12.7, 5.4 Hz, 1H), 4.15 (s, 2H), 3.62-3.45 (m, 4H), 3.41-3.14 (m, 12H), 3.11-2.96 (m, 7H), 2.88-2.77 (m, 1H), 2.77-2.65 (m, 2H), 2.20 (t, J=7.5 Hz, 2H), 2.11-2.04 (m, 1H), 1.71-1.55 (m, 4H), 1.50-1.20 (m, 12H). HRMS (m/z) for C$_{54}$H$_{65}$F$_4$N$_{10}$O$_7^+$ [M+H]$^+$: calculated 1041.4968. found 1041.4975.

Example 207: Synthesis of XF078-25

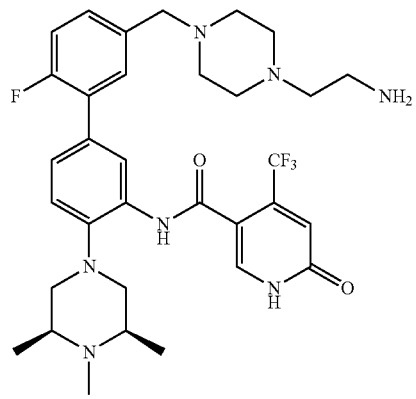

Intermediate 39

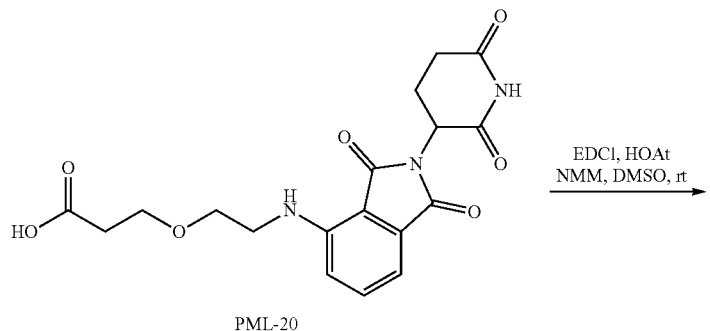

PML-20

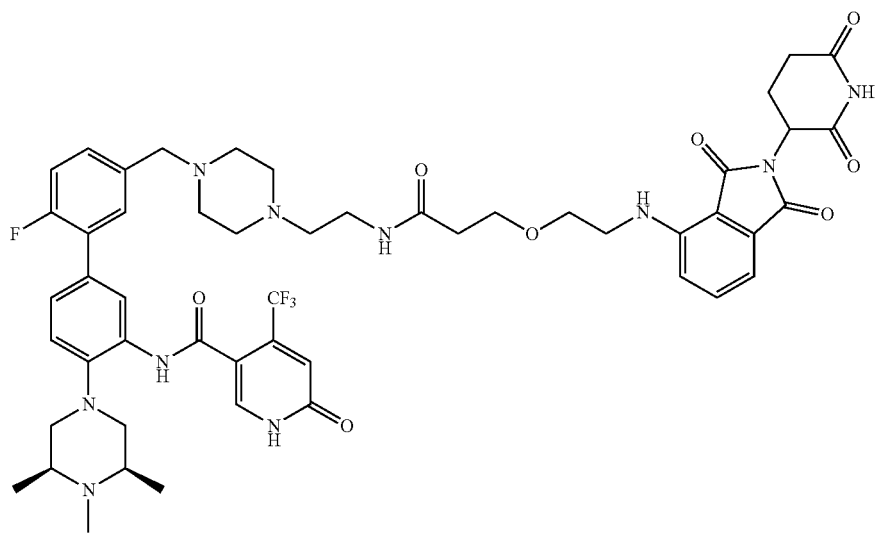

XF078-25

XF078-25 was synthesized following the standard procedures for preparing XF078-1 from intermediate 39 (12.9 mg, 0.02 mmol), PML-20 (8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-25 was obtained as yellow solid in TFA salt form (16.2 mg, yield 60%). $^1$H NMR (600 MHz, CD$_3$OD) δ 8.12 (s, 1H), 8.00 (s, 1H), 7.57 (d, J=7.3 Hz, 1H), 7.51 (t, J=7.7 Hz, 1H), 7.49-7.39 (m, 2H), 7.34 (d, J=8.4 Hz, 1H), 7.23 (t, J=9.3 Hz, 1H), 7.08-6.99 (m, 2H), 6.92 (s, 1H), 5.03 (dd, J=12.6, 5.7 Hz, 1H), 4.00 (s, 2H), 3.75 (t, J=5.7 Hz, 2H), 3.66 (t, J=5.2 Hz, 2H), 3.53 (s, 2H), 3.49-3.41 (m, 4H), 3.37-2.92 (m, 17H), 2.88-2.76 (m, 1H), 2.76-2.62 (m, 2H), 2.47 (t, J=5.8 Hz, 2H), 2.18-2.01 (m, 1H), 1.44 (d, J=6.5 Hz, 6H). HRMS (m/z) for C$_{51}$H$_{59}$F$_4$N$_{10}$O$_8$$^+$ [M+H]$^+$: calculated 1015.4448, found 1015.4467.

Example 208: Synthesis of XF078-26

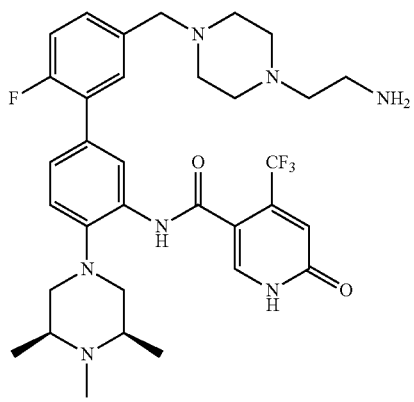

Intermediate 39

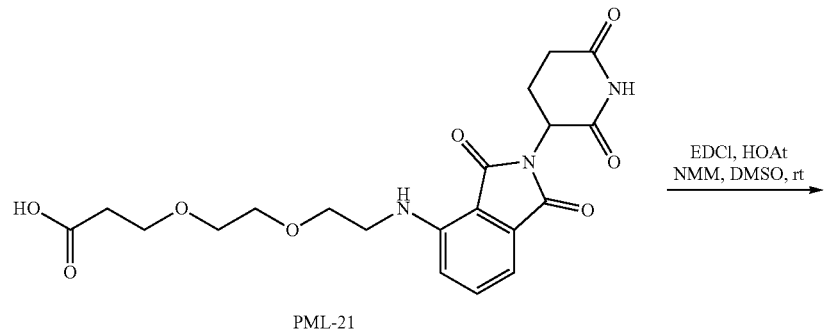

PML-21

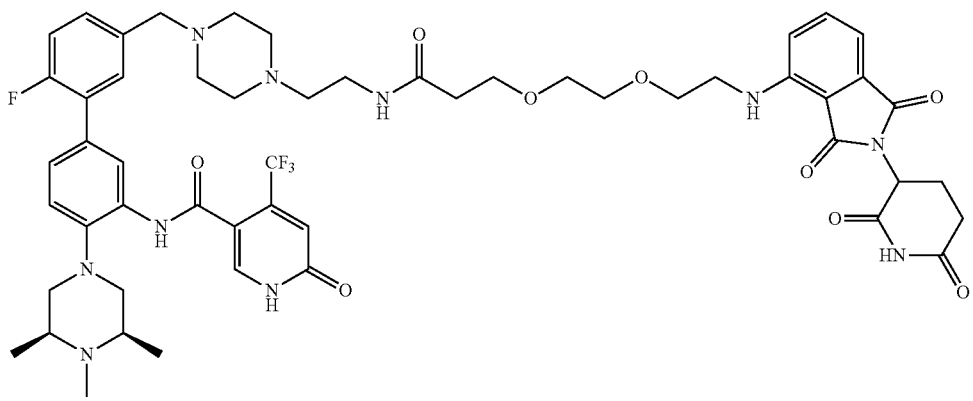

XF078-26

XF078-26 was synthesized following the standard procedures for preparing XF078-1 from intermediate 39 (12.9 mg, 0.02 mmol), PML-21 (8.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-26 was obtained as yellow solid in TFA salt form (22.9 mg, yield 82%). $^1$H NMR (600 MHz, CD$_3$OD) δ 8.13 (d, J=2.1 Hz, 1H), 8.00 (s, 1H), 7.60 (dd, J=7.3, 2.3 Hz, 1H), 7.51 (dd, J=8.6, 7.1 Hz, 1H), 7.48-7.38 (m, 2H), 7.34 (d, J=8.4 Hz, 1H), 7.25 (dd, J=10.4, 8.4 Hz, 1H), 7.05-6.98 (m, 2H), 6.91 (s, 1H), 5.03 (dd, J=12.8, 5.5 Hz, 1H), 4.10 (s, 2H), 3.72 (t, J=5.9 Hz, 2H), 3.67 (t, J=5.2 Hz, 2H), 3.60-3.51 (m, 4H), 3.57-3.50 (m, 2H), 3.50-3.40 (m, 4H), 3.38-3.13 (m, 10H), 3.09 (t, J=5.8 Hz, 2H), 3.02-2.92 (m, 5H), 2.82 (ddd, J=14.1, 10.7, 7.1 Hz, 1H), 2.75-2.58 (m, 2H), 2.45 (t, J=5.9 Hz, 2H), 2.15-2.00 (m, 1H), 1.43 (dd, J=6.5, 1.7 Hz, 6H). HRMS (m/z) for $C_{53}H_{63}F_4N_{10}O_9^+$ [M+H]$^+$: calculated 1059.4710. found 1059.4689.

Example 209: Synthesis of XF078-27

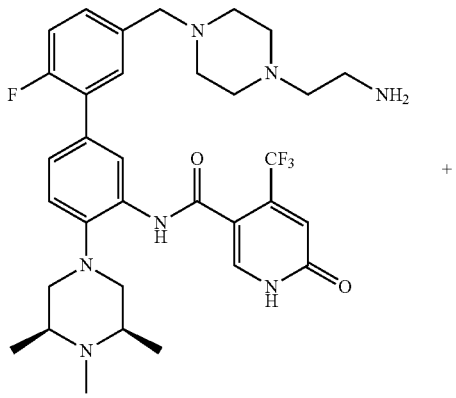

Intermediate 39

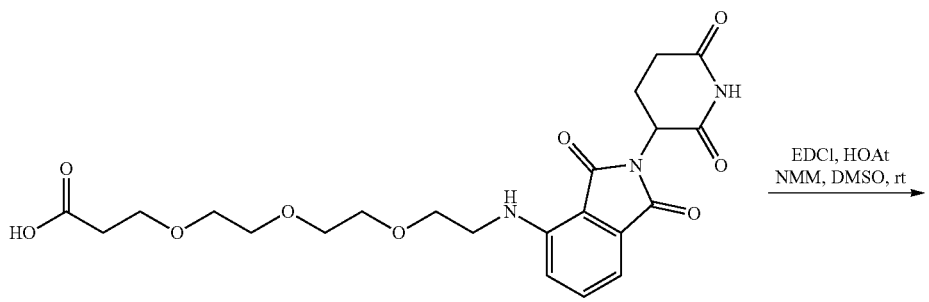

PML-22

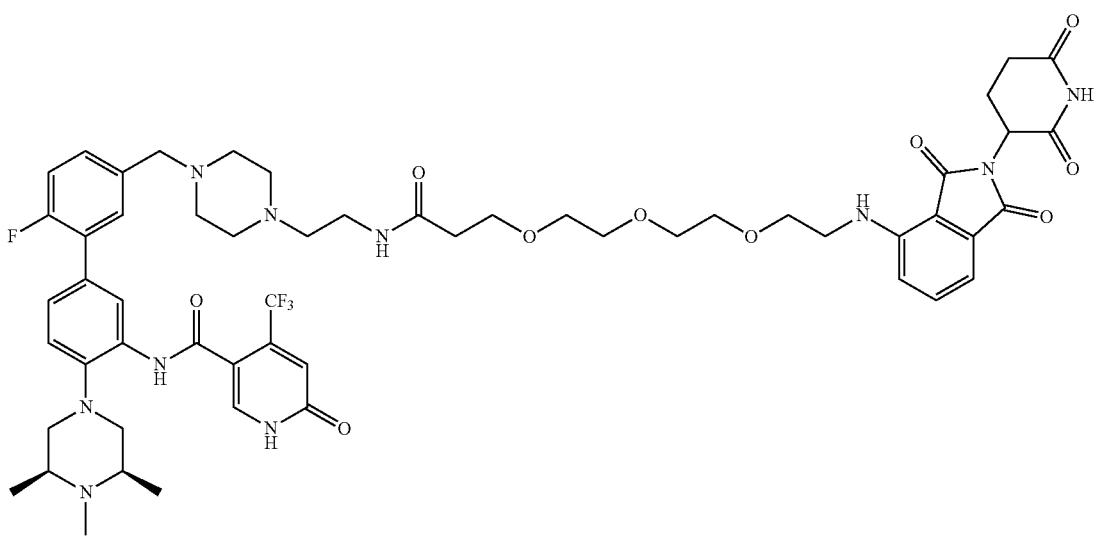

XF078-27

XF078-27 was synthesized following the standard procedures for preparing XF078-1 from intermediate 39 (12.9 mg, 0.02 mmol), PML-22 (9.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-27 was obtained as yellow solid in TFA salt form (17.6 mg, yield 61%). $^1$H NMR (600 MHz, CD$_3$OD) δ 8.17-8.09 (m, 1H), 8.00 (s, 1H), 7.57 (dd, J=7.5, 2.3 Hz, 1H), 7.50 (dd, J=8.6, 7.1 Hz, 1H), 7.46-7.38 (m, 2H), 7.34 (d, J=8.4 Hz, 1H), 7.23 (dd, J=10.5, 8.4 Hz, 1H), 7.10-6.96 (m, 2H), 6.92 (s, 1H), 5.04 (dd, J=12.8, 5.5 Hz, 1H), 4.02 (s, 2H), 3.73-3.39 (m, 16H), 3.38-3.03 (m, 14H), 3.02-2.94 (m, 5H), 2.91-2.77 (m, 1H), 2.76-2.63 (m, 2H), 2.44 (t, J=5.9 Hz, 2H), 2.12-2.03 (m, 1H), 1.44 (d, J=6.4 Hz, 6H). HRMS (m/z) for C$_{55}$H$_{67}$F$_4$N$_{10}$O$_{10}{}^+$ [M+H]$^+$: calculated 1103.4972. found 1103.4956.

Example 210: Synthesis of XF078-28

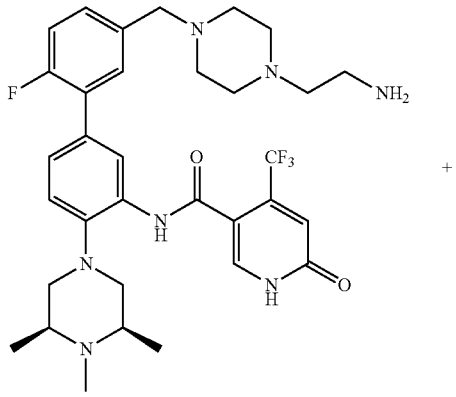

Intermediate 39

+

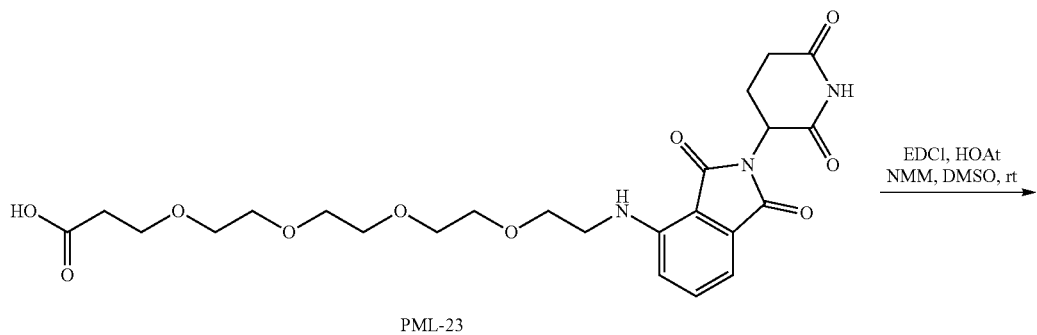

PML-23

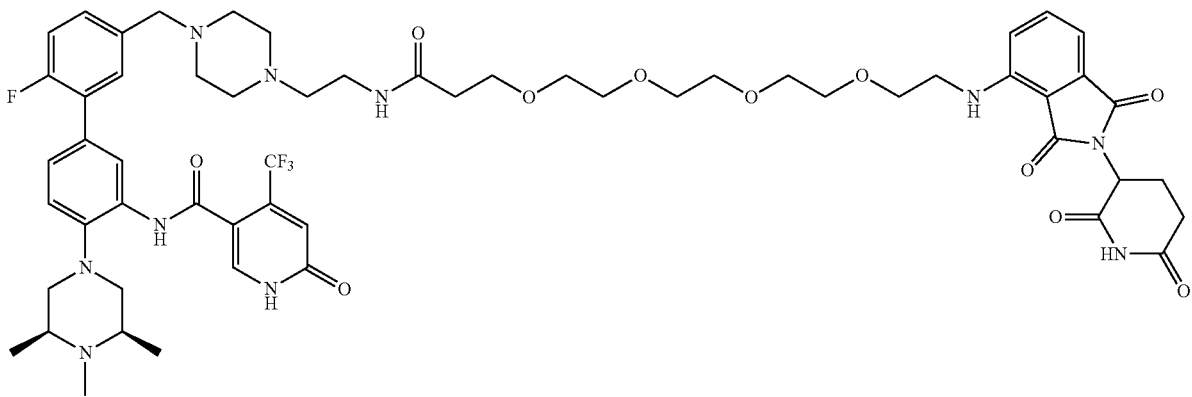

XF078-28

XF078-28 was synthesized following the standard procedures for preparing XF078-1 from intermediate 39 (12.9 mg, 0.02 mmol), PML-23 (10.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-28 was obtained as yellow solid in TFA salt form (17.1 mg, yield 57%). $^1$H NMR (600 MHz, CD$_3$OD) δ 8.12 (s, 1H), 8.00 (s, 1H), 7.58 (dd, J=7.6, 2.3 Hz, 1H), 7.50 (dd, J=8.5, 7.1 Hz, 1H), 7.47-7.40 (m, 2H), 7.34 (d, J=8.3 Hz, 1H), 7.23 (dd, J=10.4, 8.4 Hz, 1H), 7.12-6.99 (m, 2H), 6.92 (s, 1H), 5.04 (dd, J=12.8, 5.5 Hz, 1H), 4.02 (s, 2H), 3.77-3.40 (m, 20H), 3.40-2.92 (m, 19H), 2.90-2.76 (m, 1H), 2.75-2.63 (m, 2H), 2.45 (t, J=5.8 Hz, 2H), 2.15-2.01 (m, 1H), 1.44 (d, J=6.4 Hz, 6H). HRMS (m/z) for C$_{57}$H$_{71}$F$_4$N$_{10}$O$_{11}$$^+$ [M+H]$^+$: calculated 1147.5234. found 1147.5251.

Example 211: Synthesis of XF078-29

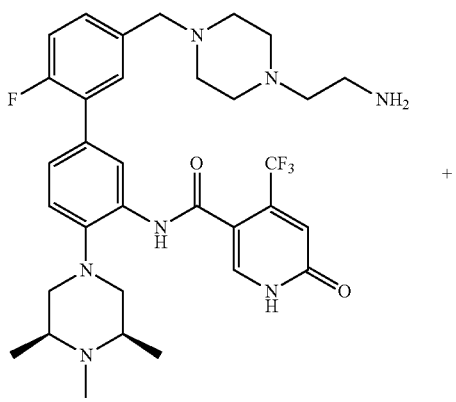

Intermediate 39

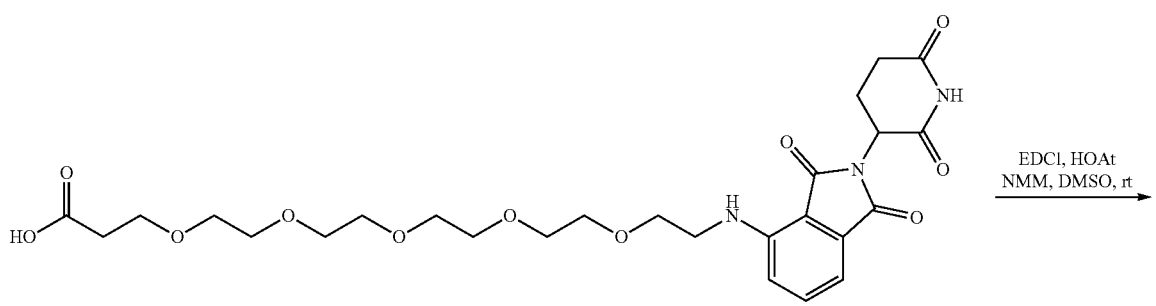

PML-24

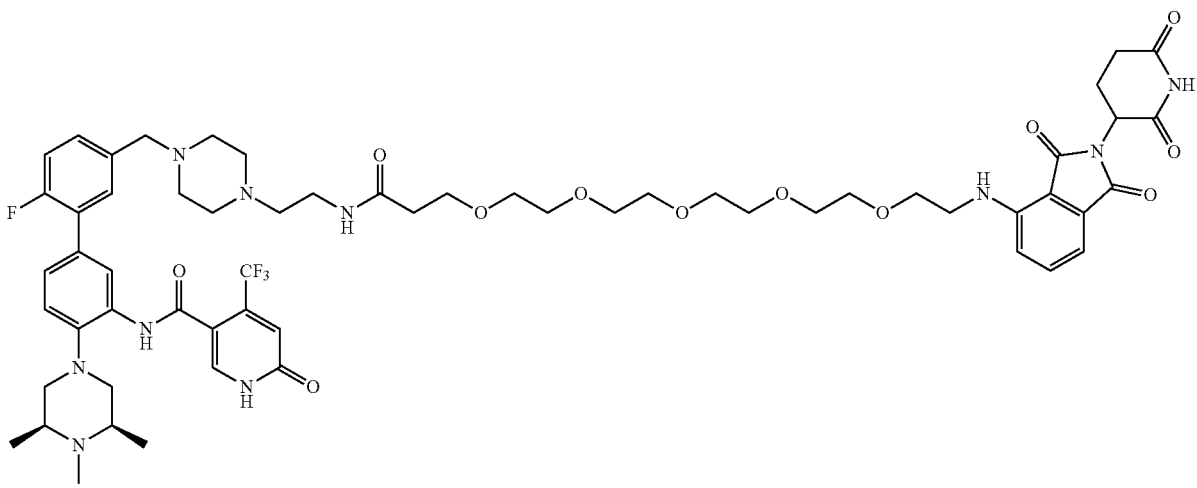

XF078-28

XF078-29 was synthesized following the standard procedures for preparing XF078-1 from intermediate 39 (12.9 mg, 0.02 mmol), PML-24 (11.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-29 was obtained as yellow solid in TFA salt form (15.8 mg, yield 52%). $^1$H NMR (600 MHz, CD$_3$OD) δ 8.13 (s, 1H), 8.00 (s, 1H), 7.59 (dd, J=7.4, 2.3 Hz, 1H), 7.51 (dd, J=8.6, 7.2 Hz, 1H), 7.47-7.37 (m, 2H), 7.34 (d, J=8.4 Hz, 1H), 7.28-7.19 (m, 1H), 7.07-6.98 (m, 2H), 6.92 (s, 1H), 5.04 (dd, J=12.8, 5.5 Hz, 1H), 4.05 (s, 2H), 3.75-3.66 (m, 4H), 3.66-3.47 (m, 18H), 3.44 (t, J=5.2 Hz, 2H), 3.39-3.06 (m, 14H), 3.05-2.94 (m, 5H), 2.88-2.80 (m, 1H), 2.76-2.60 (m, 2H), 2.45 (t, J=5.9 Hz, 2H), 2.16-2.02 (m, 1H), 1.46-1.38 (m, 6H). HRMS (m/z) for C$_{59}$H$_{75}$F$_4$N$_{10}$O$_{12}$$^+$ [M+H]$^+$: calculated 1191.5497, found 1191.5512.

Example 212: Synthesis of Intermediate 40

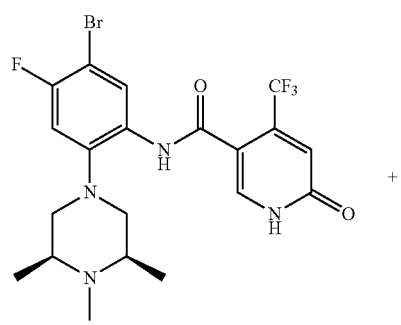

Intermediate 35

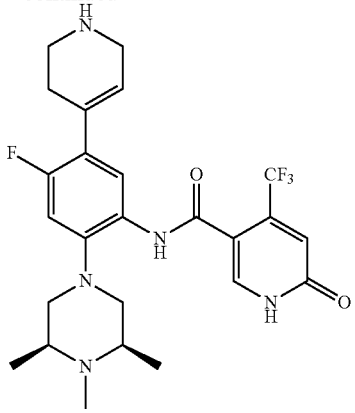

Intermediate 40

To a solution of Intermediate 35 (600 mg, 1.23 mmol) and (1-(tert-butoxycarbonyl)-1,2,3,6-tetrahydropyridin-4-yl)boronic acid (560 mg, 2.46 mmol, 2.0 euqiv) in 8 mL of 1,4-dioxane/H$_2$O (5:3) were added sodium carbonate (1300 mg, 10 mmol, 10 equiv), XPhos (117 mg, 0.25 mmol, 0.2 equiv), and XPhos Pd G2 (194 mg, 0.25 mmol, 0.2 equiv). The reaction was heated to 120° C. for 1 h under Microwave. The solvent was removed and purified by reverse phase ISCO (10%-100% methanol/0.1% TFA in H$_2$O) to afford product as white solid. This product was dissolved in DCM (10 mL) and TFA (10 mL). The resulting mixture was stirring for 1 h. Then, it was concentrated and purified by reverse phase ISCO (10%-100% methanol/0.1% TFA in H$_2$O) to afford Intermediate 40 (XF067-171) as white solid in TFA salt form (404.8 mg, yield 65%). $^1$H NMR (600 MHz, CD$_3$OD) δ 8.00 (s, 1H), 7.81 (d, J=7.7 Hz, 1H), 7.07 (d, J=12.0 Hz, 1H), 6.88 (s, 1H), 6.05 (d, J=3.7 Hz, 1H), 3.87 (d, J=3.4 Hz, 2H), 3.56 (ddd, J=10.5, 6.7, 3.4 Hz, 2H), 3.45 (t, J=6.1 Hz, 2H), 3.34 (s, 2H), 2.97 (d, J=14.5 Hz, 5H), 2.77 (d, J=6.4 Hz, 2H), 1.42 (d, J=6.4 Hz, 6H). HRMS (m/z) for C$_{25}$H$_{30}$F$_4$N$_5$O$_2$$^+$ [M+H]$^+$: calculated 508.2330. found 508.2337.

Example 213: Synthesis of XF078-30

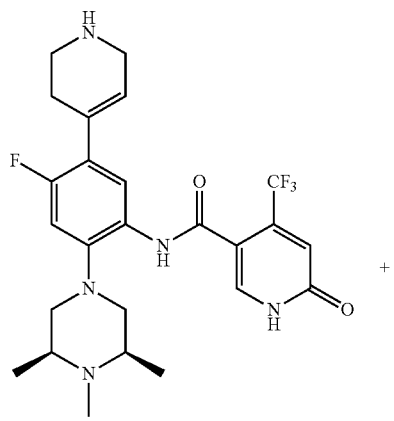

Intermediate 40

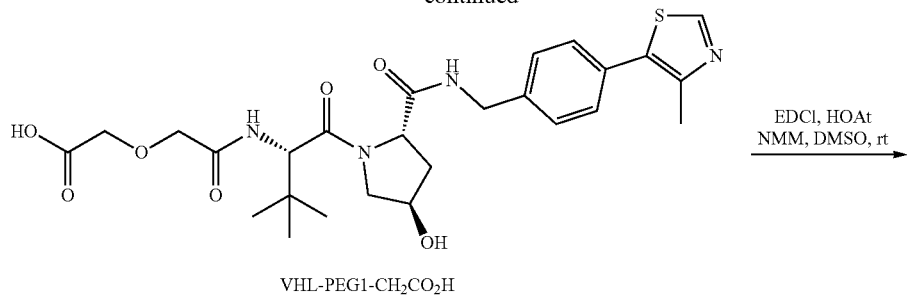

VHL-PEG1-CH2CO2H

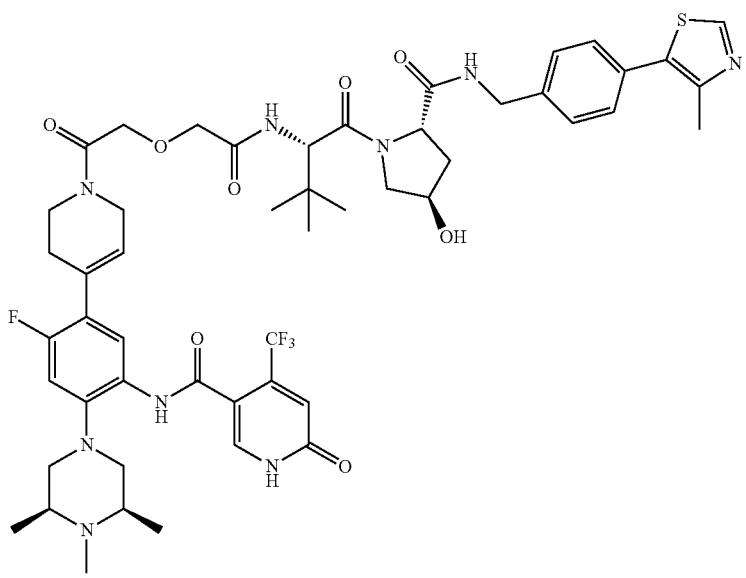

XF078-30

To the solution of Intermediate 40 (12.9 mg, 0.02 mmol) in DMSO (1 mL) were added VHL-PEG1-CH₂—COOH (10.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirring overnight at room temperature, the resulting mixture was purified by preparative HPLC (10%-100% methanol/0.1% TFA in H₂O) to afford XF078-30 as white solid in TFA salt form (14.5 mg, yield 70%). ¹H NMR (600 MHz, CD₃OD) δ 8.95 (s, 1H), 7.98 (s, 1H), 7.77 (d, J=8.0 Hz, 1H), 7.55-7.23 (m, 4H), 7.03 (dd, J=11.9, 2.5 Hz, 1H), 6.92 (s, 1H), 6.08-5.89 (m, 1H), 4.68 (d, J=2.7 Hz, 1H), 4.61-4.39 (m, 5H), 4.33 (dd, J=15.5, 3.7 Hz, 1H), 4.24-4.06 (m, 4H), 3.89 (d, J=11.0 Hz, 1H), 3.85-3.74 (m, 2H), 3.63 (t, J=5.7 Hz, 1H), 3.51-3.44 (m, 2H), 2.97 (s, 3H), 2.92-2.85 (m, 2H), 2.64-2.55 (m, 2H), 2.55-2.41 (m, 5H), 2.27-2.18 (m, 1H), 2.10-2.03 (m, 1H), 1.42 (d, J=6.5, 1.7 Hz, 6H), 1.05 (s, 9H). HRMS (m/z) for $C_{51}H_{62}F_4N_9O_8S^+$ [M+H]⁺: calculated 1036.4373. found 1036.4379.

Example 214: Synthesis of XF078-31

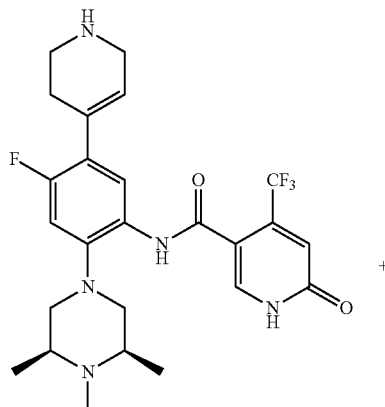

Intermediate 40

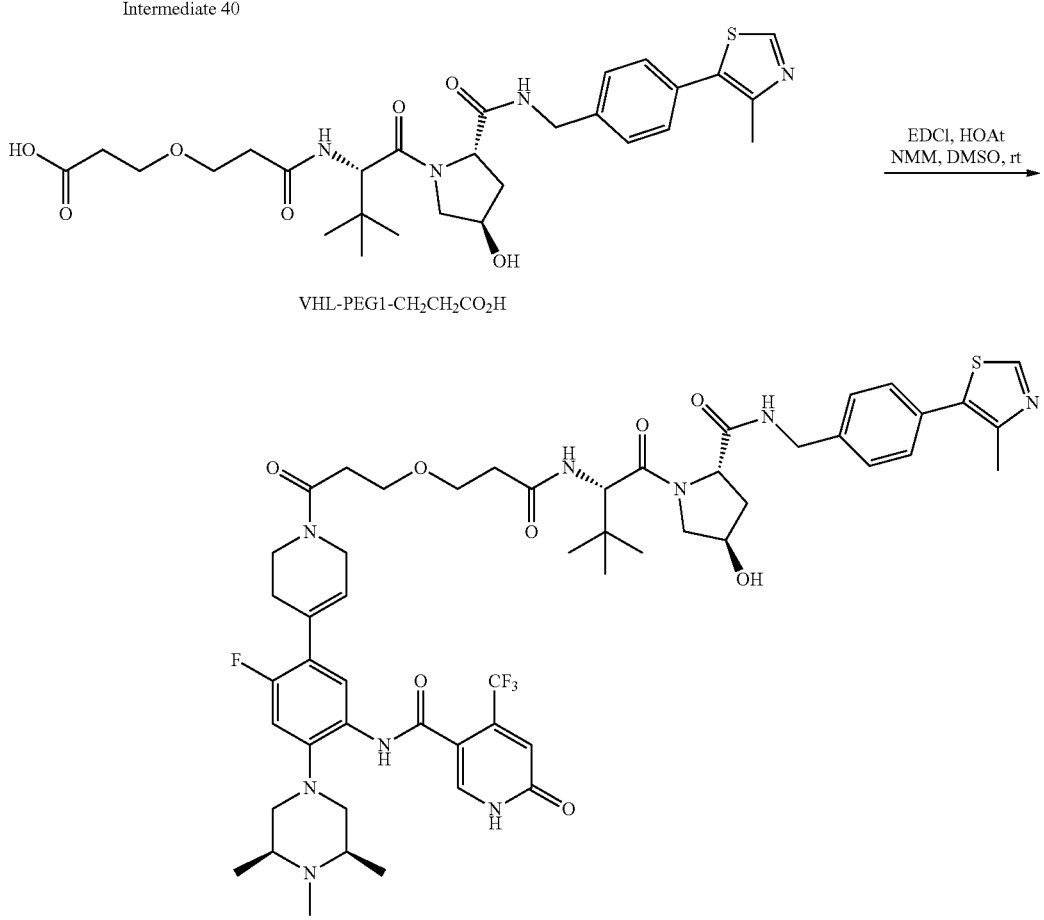

XF078-31 was synthesized following the standard procedures for preparing XF078-30 from intermediate 40 (12.9 mg, 0.02 mmol), VHL-PEG1-CH$_2$CH$_2$COOH (11.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-31 was obtained as white solid in TFA salt form (14.6 mg, yield 69%). $^1$H NMR (600 MHz, CD$_3$OD) δ 8.96 (s, 1H), 7.98 (s, 1H), 7.77 (dd, J=8.1, 3.3 Hz, 1H), 7.58-7.25 (m, 4H), 7.02 (d, J=12.0 Hz, 1H), 6.91 (s, 1H), 6.16-5.61 (m, 1H), 4.64 (d, J=2.7 Hz, 1H), 4.60-4.46 (m, 3H), 4.39-4.29 (m, 1H), 4.26-4.15 (m, 2H), 3.88 (d, J=11.1 Hz, 1H), 3.83-3.66 (m, 7H), 3.47 (s, 2H), 3.30-3.26 (m, 2H), 2.97 (s, 3H), 2.93-2.85 (m, 2H), 2.82-2.68 (m, 2H), 2.60-2.41 (m, 7H), 2.27-2.18 (m, 1H), 2.13-2.02 (m, 1H), 1.41 (s, 6H), 1.02 (s, 9H). HRMS (m/z) for C$_{53}$H$_{66}$F$_4$N$_9$O$_8$S$^+$ [M+H]$^+$: calculated 1064.4686. found 1064.4653.

Example 215: Synthesis of XF078-32

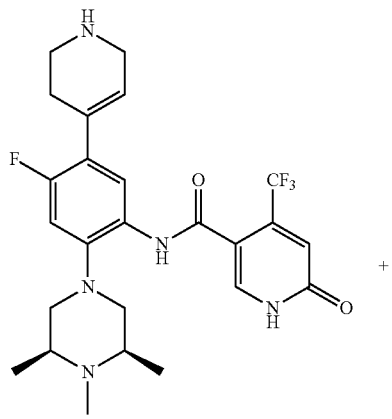

Intermediate 40

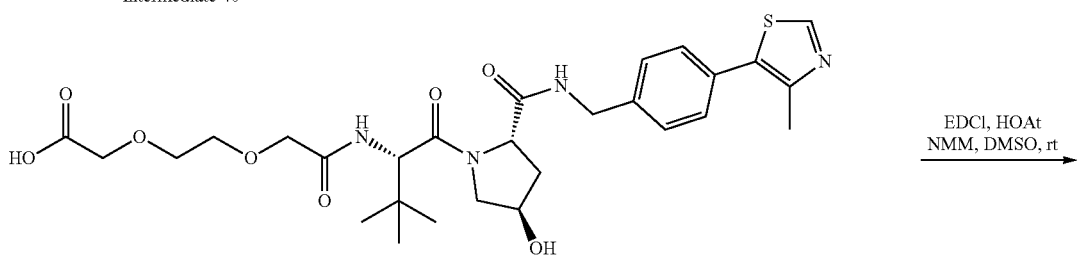

VHL-PEG2-CH₂CO₂H

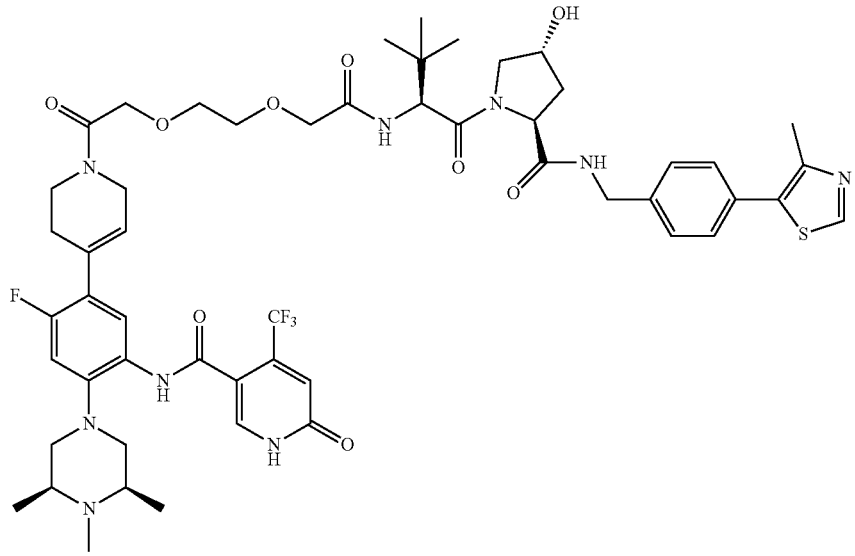

XF078-32

XF078-32 was synthesized following the standard procedures for preparing XF078-30 from intermediate 40 (12.9 mg, 0.02 mmol), VHL-PEG2-CH₂COOH (11.8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-32 was obtained as white solid in TFA salt form (12.9 mg, yield 60%). $^1$H NMR (600 MHz, CD₃OD) δ 9.00 (d, J=2.8 Hz, 1H), 7.98 (s, 1H), 7.75 (dd, J=12.5, 8.0 Hz, 1H), 7.57-7.31 (m, 4H), 7.02 (dd, J=11.9, 6.9 Hz, 1H), 6.91 (s, 1H), 6.12-5.89 (m, 1H), 4.71 (d, J=8.1 Hz, 1H), 4.57 (dt, J=12.1, 8.3 Hz, 1H), 4.53-4.45 (m, 2H), 4.44-3.99 (m, 7H), 3.96-3.58 (m, 8H), 3.54-3.42 (m, 2H), 3.30-3.22 (m, 2H), 3.01-2.78 (m, 5H), 2.62-2.39 (m, 5H), 2.28-2.18 (m, 1H), 2.13-2.01 (m, 1H), 1.49-1.21 (m, 6H), 1.04 (s, 9H). HRMS (m/z) for $C_{53}H_{66}F_4N_9O_9S^+$ [M+H]⁺: calculated 1080.4635. found 1080.4674.

Example 216: Synthesis of XF078-33

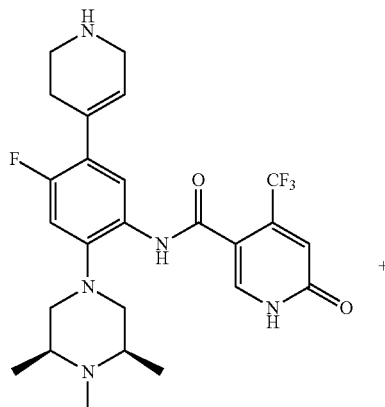

Intermediate 40

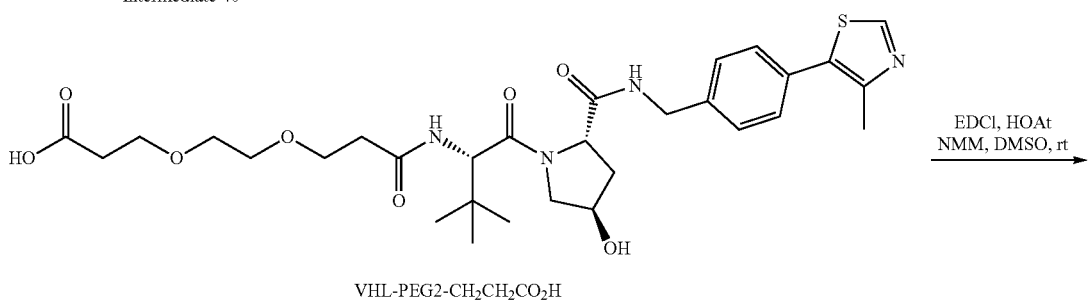

VHL-PEG2-CH₂CH₂CO₂H

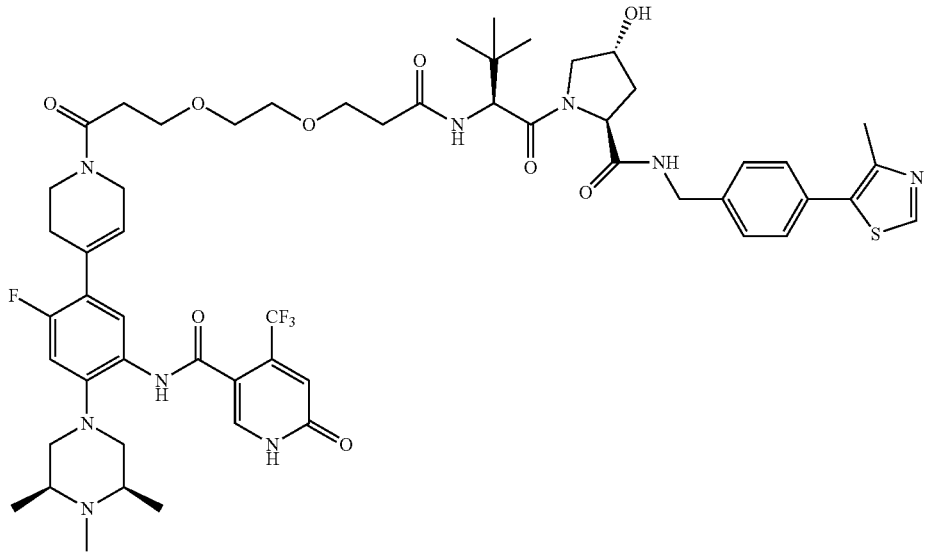

XF078-33

XF078-33 was synthesized following the standard procedures for preparing XF078-30 from intermediate 40 (12.9 mg, 0.02 mmol), VHL-PEG2-CH₂CH₂COOH (12.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-33 was obtained as white solid in TFA salt form (14.9 mg, yield 67%). $^1$H NMR (600 MHz, CD$_3$OD) δ 8.99 (s, 1H), 7.98 (s, 1H), 7.78 (d, J=7.8 Hz, 1H), 7.57-7.34 (m, 4H), 7.03 (d, J=12.0 Hz, 1H), 6.92 (s, 1H), 6.08-5.90 (m, 1H), 4.64 (s, 1H), 4.59-4.45 (m, 3H), 4.35 (d, J=15.5 Hz, 1H), 4.24 (d, J=3.4 Hz, 1H), 4.21-4.14 (m, 1H), 3.88 (d, J=11.0 Hz, 1H), 3.82-3.65 (m, 6H), 3.65-3.55 (m, 4H), 3.53-3.44 (m, 2H), 3.31-3.25 (m, 2H), 2.97 (s, 3H), 2.94-2.85 (m, 2H), 2.71 (dt, J=24.2, 6.3 Hz, 2H), 2.60-2.41 (m, 8H), 2.25-2.17 (m, 1H), 2.12-1.99 (m, 1H), 1.42 (dd, J=6.5, 1.6 Hz, 6H), 1.03 (s, 9H). HRMS (m/z) for C$_{55}$H$_{70}$F$_4$N$_9$O$_9$S$^+$ [M+H]$^+$: calculated 1108.4948, found 1108.4930.

Example 217: Synthesis of XF078-34

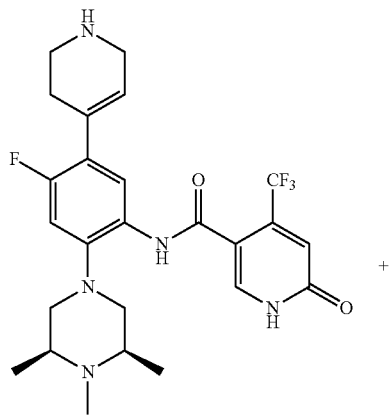

Intermediate 40

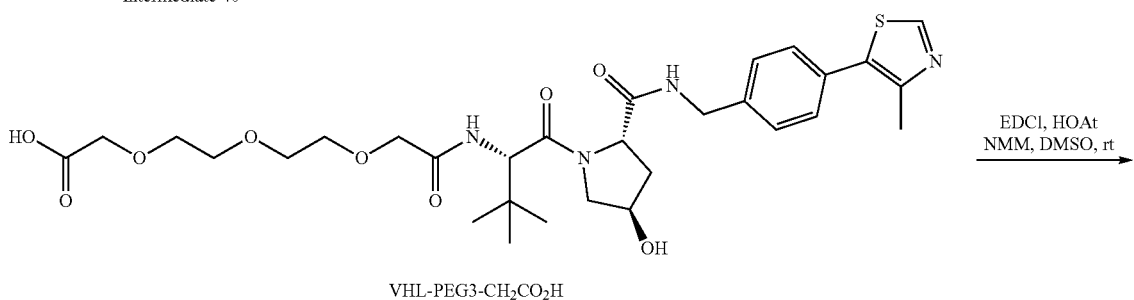

VHL-PEG3-CH2CO2H

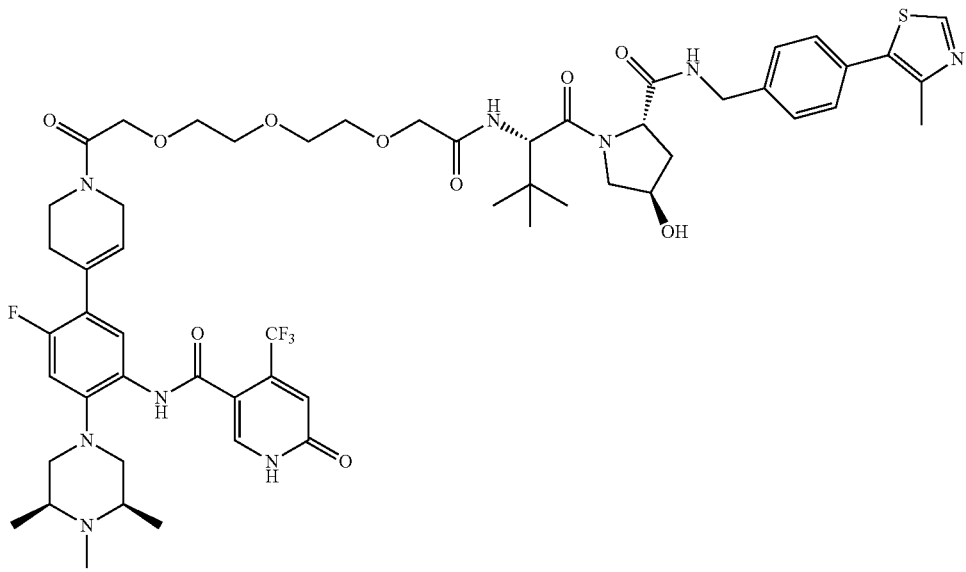

XF078-34

XF078-34 was synthesized following the standard procedures for preparing XF078-30 from intermediate 40 (12.9 mg, 0.02 mmol), VHL-PEG3-CH2COOH (12.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-34 was obtained as white solid in TFA salt form (12.6 mg, yield 56%). $^1$H NMR (600 MHz, CD$_3$OD) δ 9.00 (s, 1H), 7.99 (d, J=7.8 Hz, 1H), 7.77 (dd, J=8.2, 3.8 Hz, 1H), 7.53-7.32 (m, 4H), 7.03 (d, J=12.0 Hz, 1H), 6.92 (s, 1H), 6.08-5.89 (m, 1H), 4.68 (s, 1H), 4.59-4.44 (m, 3H), 4.45-4.25 (m, 3H), 4.16 (s, 2H), 4.09-3.95 (m, 2H), 3.86 (d, J=11.0 Hz, 1H), 3.82-3.59 (m, 11H), 3.53-3.43 (m, 2H), 3.32 (s, 2H), 2.97 (s, 3H), 2.93-2.86 (m, 2H), 2.62-2.43 (m, 5H), 2.22 (dd, J=13.1, 7.6 Hz, 1H), 2.18-2.01 (m, 1H), 1.53-1.27 (m, 6H), 1.03 (s, 9H). HRMS (m/z) for $C_{55}H_{70}F_4N_9O_{10}S^+$ [M+H]$^+$: calculated 1124.4897. found 1124.4865.

Example 218: Synthesis of XF078-35

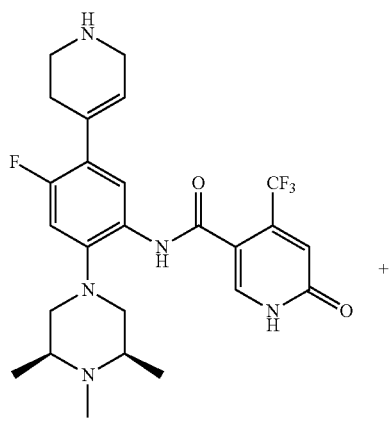

Intermediate 40

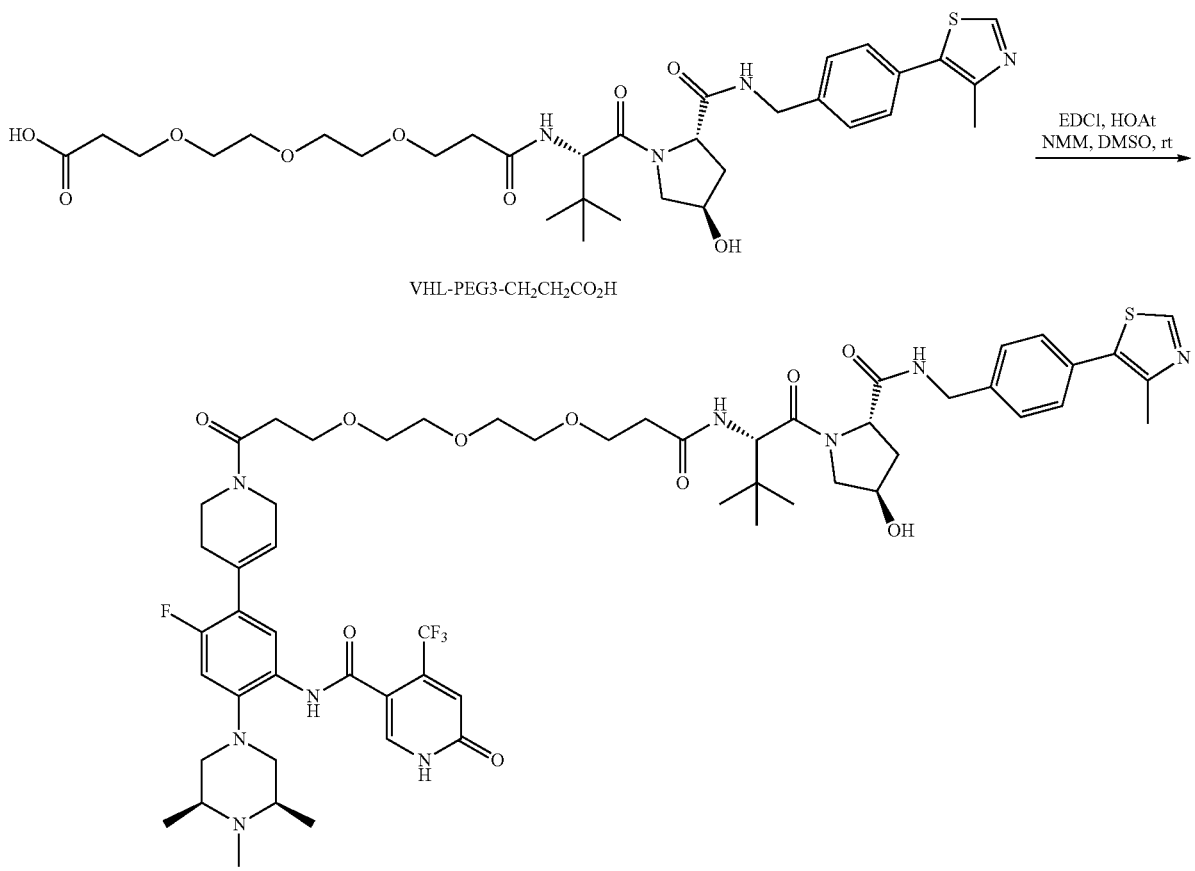

XF078-35 was synthesized following the standard procedures for preparing XF078-30 from intermediate 40 (12.9 mg, 0.02 mmol), VHL-PEG3-CH$_2$CH$_2$COOH (13.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-35 was obtained as white solid in TFA salt form (16.1 mg, yield 70%). $^1$H NMR (600 MHz, CD$_3$OD) δ 8.98 (s, 1H), 7.98 (s, 1H), 7.78 (d, J=8.0 Hz, 1H), 7.51-7.35 (m, 4H), 7.03 (d, J=12.0 Hz, 1H), 6.92 (s, 1H), 6.02 (d, J=3.8 Hz, 1H), 4.64 (s, 1H), 4.62-4.46 (m, 3H), 4.35 (d, J=15.5 Hz, 1H), 4.25 (d, J=3.3 Hz, 1H), 4.19 (d, J=3.3 Hz, 1H), 3.88 (d, J=11.1 Hz, 1H), 3.80-3.65 (m, 7H), 3.64-3.54 (m, 8H), 3.52-3.41 (m, 2H), 3.34-3.30 (m, 2H), 2.97 (s, 3H), 2.95-2.84 (m, 2H), 2.75-2.66 (m, 2H), 2.61-2.52 (m, 2H), 2.48-2.41 (m, 5H), 2.21 (dd, J=13.2, 7.7 Hz, 1H), 2.11-1.98 (m, 1H), 1.42 (d, J=6.4 Hz, 6H), 1.03 (s, 9H). HRMS (m/z) for C$_{57}$H$_{74}$F$_4$N$_9$O$_{10}$S$^+$ [M+H]$^+$: calculated 1152.5210. found 1152.5234.

Example 219: Synthesis of XF078-36

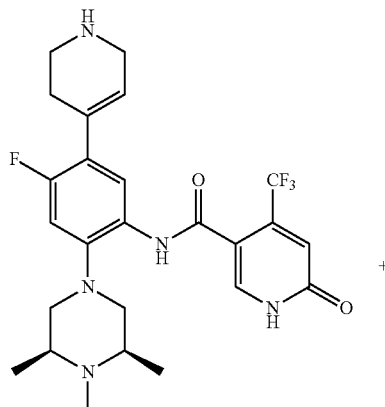

Intermediate 40

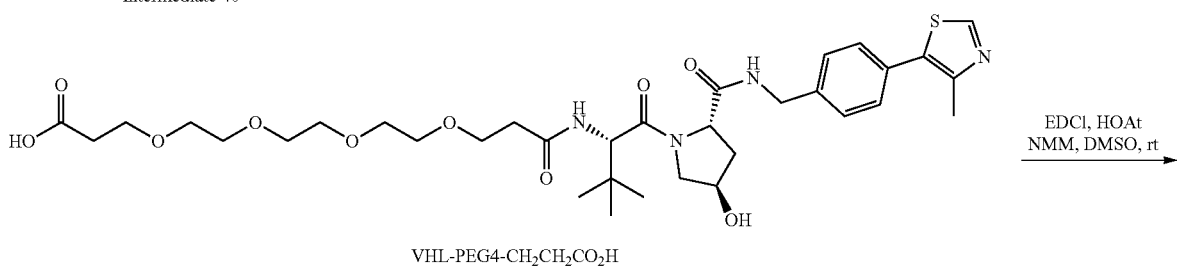

VHL-PEG4-CH₂CH₂CO₂H

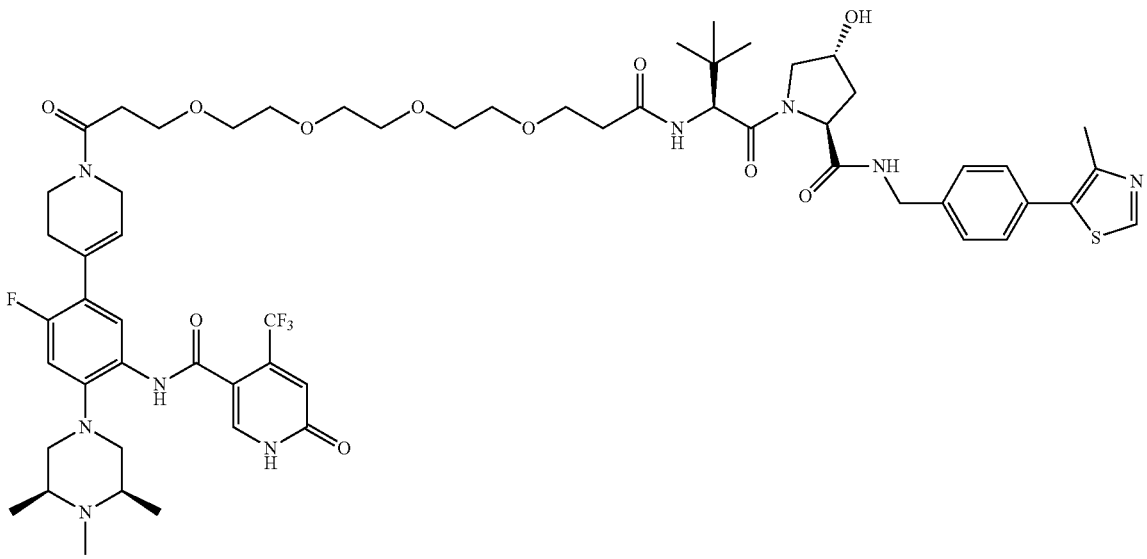

XF078-36

XF078-36 was synthesized following the standard procedures for preparing XF078-30 from intermediate 40 (12.9 mg, 0.02 mmol), VHL-PEG4-CH₂CH₂COOH (14.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-36 was obtained as white solid in TFA salt form (15.1 mg, yield 63%). $^1$H NMR (600 MHz, CD$_3$OD) δ 9.01 (d, J=1.9 Hz, 1H), 7.98 (s, 1H), 7.79 (d, J=7.9 Hz, 1H), 7.60-7.35 (m, 4H), 7.04 (d, J=12.2 Hz, 1H), 6.92 (s, 1H), 6.12-5.88 (m, 1H), 4.64 (d, J=2.0 Hz, 1H), 4.59-4.47 (m, 3H), 4.35 (d, J=15.4 Hz, 1H), 4.29-4.15 (m, 2H), 3.89-3.83 (m, 1H), 3.84-3.66 (m, 7H), 3.60-3.53 (m, 12H), 3.48 (s, 2H), 3.35-3.30 (m, 2H), 2.97 (s, 3H), 2.90 (t, J=12.4 Hz, 2H), 2.82-2.64 (m, 2H), 2.61-2.51 (m, 2H), 2.52-2.41 (m, 5H), 2.21 (t, J=10.5 Hz, 1H), 2.12-2.05 (m, 1H), 1.42 (d, J=6.3 Hz, 6H), 1.03 (s, 9H). HRMS (m/z) for C$_{59}$H$_{78}$F$_4$N$_9$O$_{11}$S$^+$ [M+H]$^+$: calculated 1196.5472, found 1196.5452.

Example 220: Synthesis of XF078-37

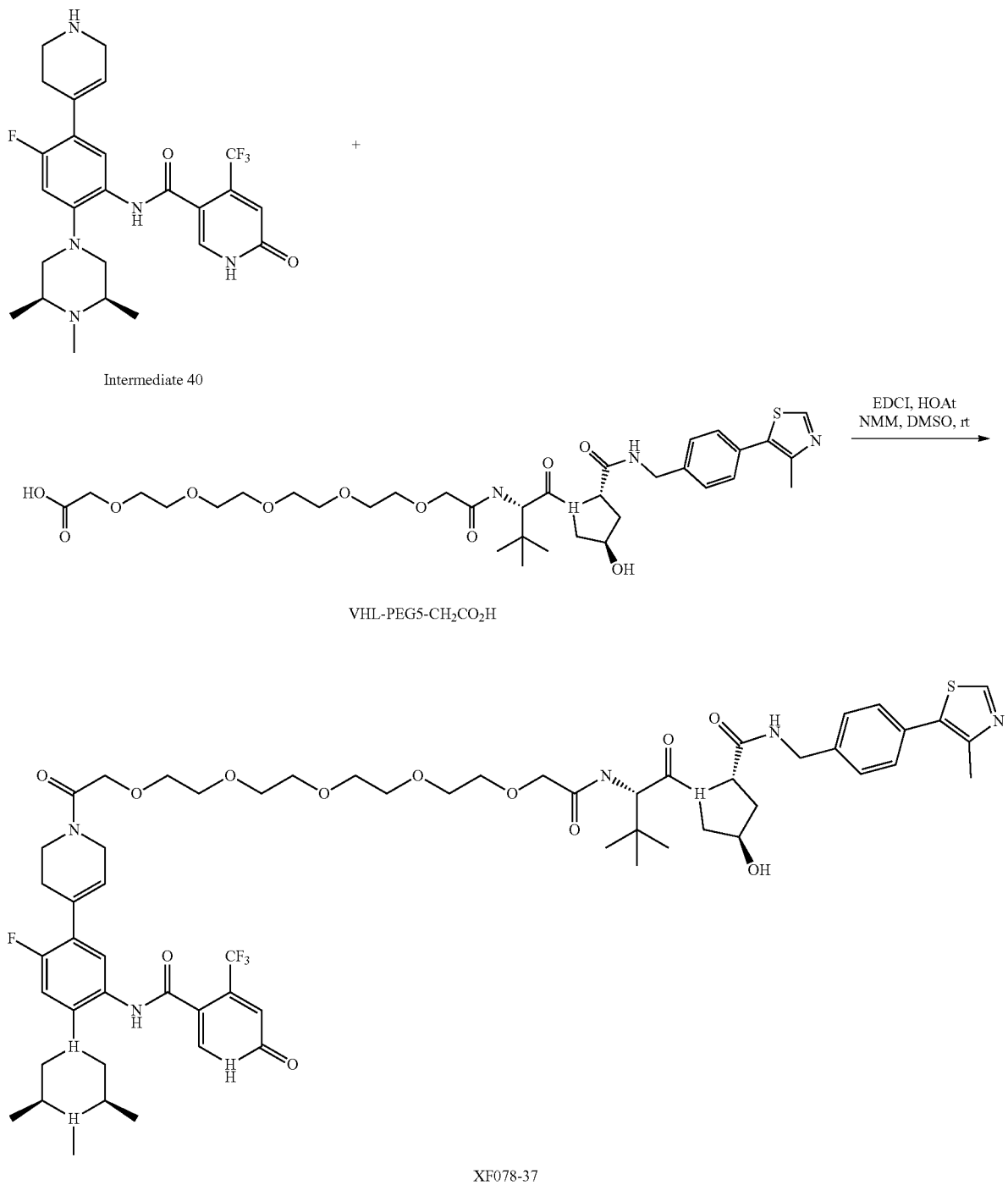

XF078-37 was synthesized following the standard procedures for preparing XF078-30 from intermediate 40 (12.9 mg, 0.02 mmol), VHL-PEG5-CH₂COOH (14.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-37 was obtained as white solid in TFA salt form (15.2 mg, yield 63%). $^1$H NMR (600 MHz, CD$_3$OD) δ 9.04 (d, J=2.5 Hz, 1H), 7.98 (s, 1H), 7.79 (d, J=8.0 Hz, 1H), 7.55-7.38 (m, 4H), 7.04 (d, J=12.0 Hz, 1H), 6.92 (s, 1H), 6.14-5.89 (m, 1H), 4.69 (s, 1H), 4.61-4.45 (m, 3H), 4.39-4.27 (m, 3H), 4.17 (s, 2H), 4.11-3.99 (m, 2H), 3.86 (d, J=11.0 Hz, 1H), 3.82-3.74 (m, 2H), 3.74-3.52 (m, 17H), 3.52-3.41 (m, 2H), 3.34-3.29 (m, 2H), 2.97 (s, 3H), 2.95-2.84 (m, 2H), 2.62-2.55 (m, 2H), 2.49 (s, 3H), 2.23 (dd, J=13.2, 7.6 Hz, 1H), 2.13-2.00 (m, 1H), 1.42 (d, J=6.4 Hz, 6H), 1.03 (s, 9H). HRMS (m/z) for C$_{59}$H$_{78}$F$_4$N$_9$O$_{12}$S$^+$ [M+H]$^+$: calculated 1212.5421. found 1212.5407.

Example 221: Synthesis of XF078-38

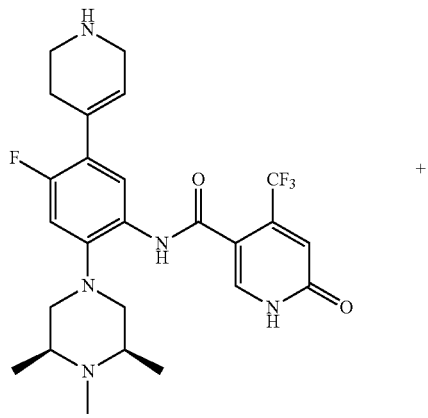

Intermediate 40

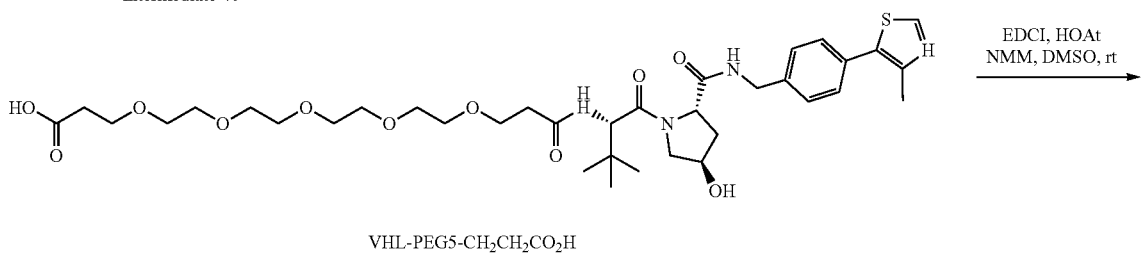

VHL-PEG5-CH₂CH₂CO₂H

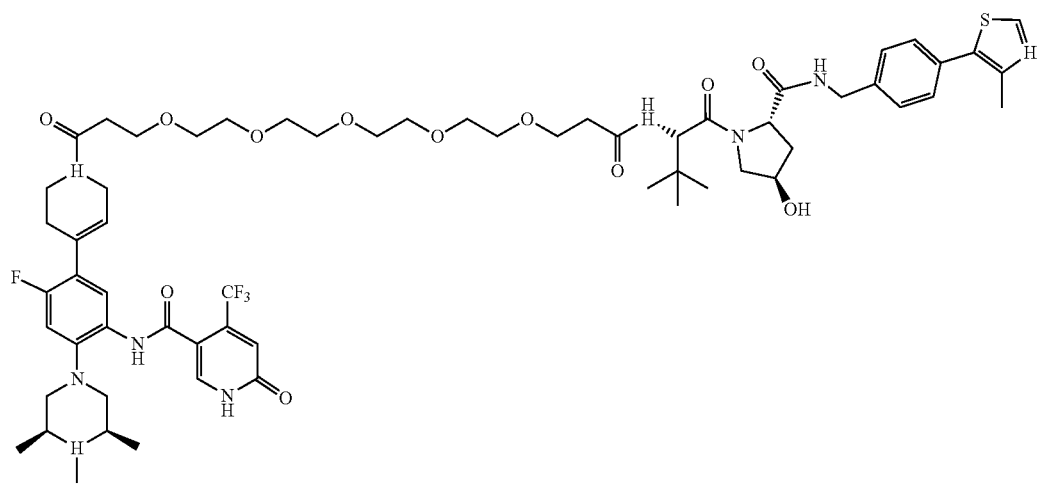

XF078-38

XF078-38 was synthesized following the standard procedures for preparing XF078-30 from intermediate 40 (12.9 mg, 0.02 mmol), VHL-PEG5-CH₂CH₂COOH (15 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-38 was obtained as white solid in TFA salt form (13.9 mg, yield 56%). $^1$H NMR (600 MHz, CD₃OD) δ 9.02 (s, 1H), 7.98 (s, 1H), 7.79 (d, J=8.1 Hz, 1H), 7.57-7.30 (m, 4H), 7.04 (d, J=11.9 Hz, 1H), 6.92 (s, 1H), 6.13-5.96 (m, 1H), 4.64 (d, J=4.1 Hz, 1H), 4.63-4.43 (m, 3H), 4.35 (d, J=15.6 Hz, 1H), 4.30-4.16 (m, 2H), 3.88 (d, J=10.8 Hz, 1H), 3.83-3.67 (m, 7H), 3.67-3.55 (m, 16H), 3.51-3.44 (m, 2H), 3.34-3.32 (m, 2H), 2.97 (s, 3H), 2.89 (t, J=12.1 Hz, 2H), 2.83-2.67 (m, 2H), 2.64-2.41 (m, 7H), 2.21 (t, J=10.6 Hz, 1H), 2.12-1.98 (m, 1H), 1.42 (d, J=6.5 Hz, 6H), 1.03 (s, 9H). HRMS (m/z) for $C_{61}H_{82}F_4N_9O_{12}S^+$ [M+H]⁺: calculated 1240.5734. found 1240.5754.

Example 222: Synthesis of XF078-39

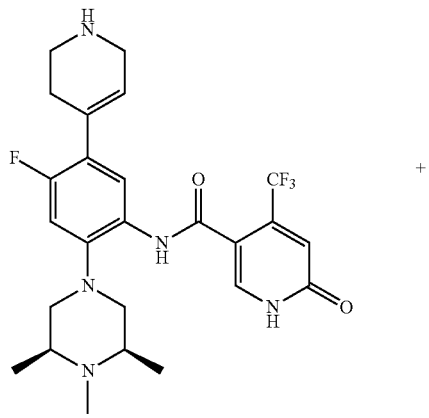

Intermediate 40

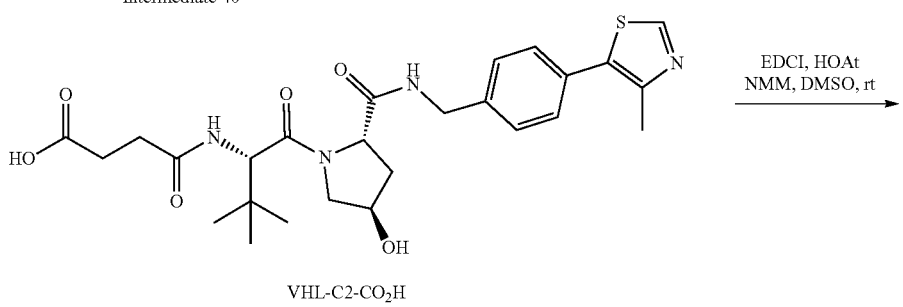

VHL-C2-CO$_2$H

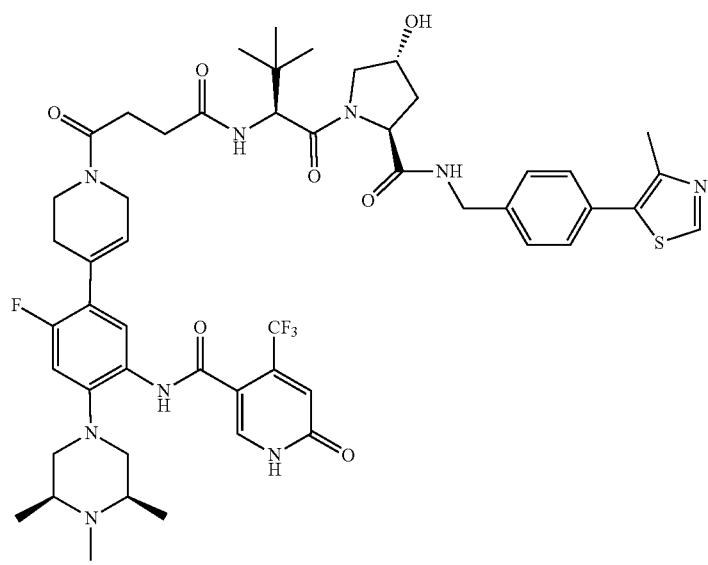

XF078-39 was synthesized following the standard procedures for preparing XF078-30 from intermediate 40 (12.9 mg, 0.02 mmol), VHL-C2-COOH (10.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-39 was obtained as white solid in TFA salt form (18.7 mg, yield 92%). $^1$H NMR (600 MHz, CD$_3$OD) δ 9.05 (d, J=9.3 Hz, 1H), 7.98 (s, 1H), 7.78 (d, J=8.1 Hz, 1H), 7.65-7.36 (m, 4H), 7.04 (d, J=12.0 Hz, 1H), 6.92 (s, 1H), 6.11-5.93 (m, 1H), 4.66-4.45 (m, 4H), 4.36 (d, J=15.5 Hz, 1H), 4.30-4.07 (m, 2H), 3.89 (d, J=11.1 Hz, 1H), 3.83-3.68 (m, 3H), 3.53-3.42 (m, 2H), 3.37-3.29 (m, 2H), 2.97 (s, 3H), 2.94-2.84 (m, 2H), 2.83-2.42 (m, 9H), 2.21 (dd, J=13.1, 7.8 Hz, 1H), 2.12-2.03 (m, 1H), 1.42 (d, J=6.5 Hz, 6H), 1.03 (s, 9H). HRMS (m/z) for C$_{51}$H$_{62}$F$_4$N$_9$O$_7$S$^+$ [M+H]$^+$: calculated 1020.4424, found 1020.4435.

Example 223: Synthesis of XF078-40

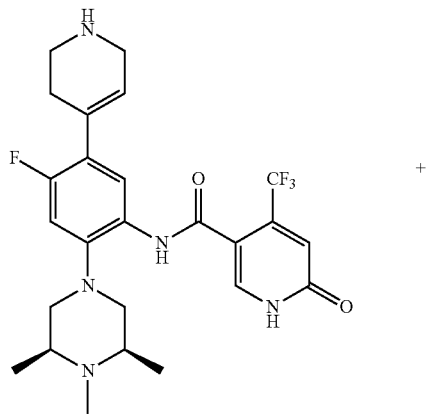

Intermediate 40

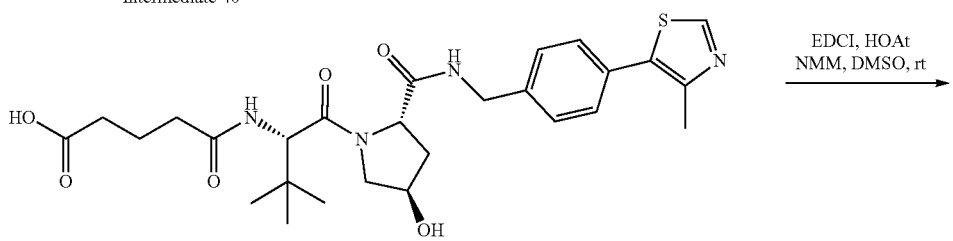

VHL-C3-CO₂H

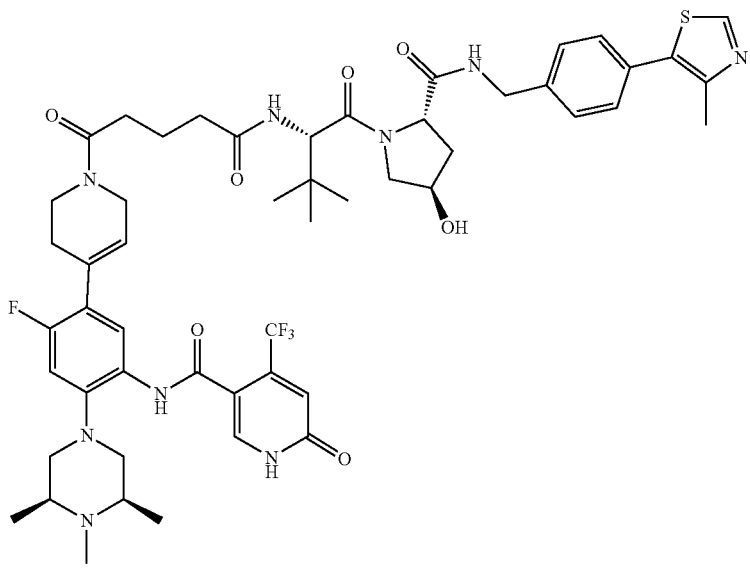

XF078-40

XF078-40 was synthesized following the standard procedures for preparing XF078-30 from intermediate 40 (12.9 mg, 0.02 mmol), VHL-C3-COOH (10.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-40 was obtained as white solid in TFA salt form (10.9 mg, yield 53%). $^1$H NMR (600 MHz, CD$_3$OD) δ 8.94 (s, 1H), 7.97 (s, 1H), 7.78 (d, J=8.0 Hz, 1H), 7.50-7.34 (m, 4H), 7.03 (d, J=12.0 Hz, 1H), 6.91 (s, 1H), 6.14-5.87 (m, 1H), 4.66-4.44 (m, 4H), 4.34 (d, J=15.5 Hz, 1H), 4.19 (d, J=10.2 Hz, 2H), 3.92 (d, J=11.0 Hz, 1H), 3.85-3.78 (m, 1H), 3.78-3.69 (m, 2H), 3.52-3.44 (m, 2H), 3.35-3.30 (m, 2H), 2.97 (s, 3H), 2.88 (t, J=12.1 Hz, 2H), 2.62-2.54 (m, 2H), 2.52-2.40 (m, 5H), 2.36 (dp, J=12.4, 7.0 Hz, 2H), 2.21 (t, J=10.5 Hz, 1H), 2.11-2.02 (m, 1H), 1.93 (p, J=7.2 Hz, 2H), 1.42 (d, J=6.4 Hz, 6H), 1.04 (s, 9H). HRMS (m/z) for $C_{52}H_{64}F_4N_9O_7S^+$ [M+H]$^+$: calculated 1034.4580, found 1034.4559.

Example 224: Synthesis of XF078-41

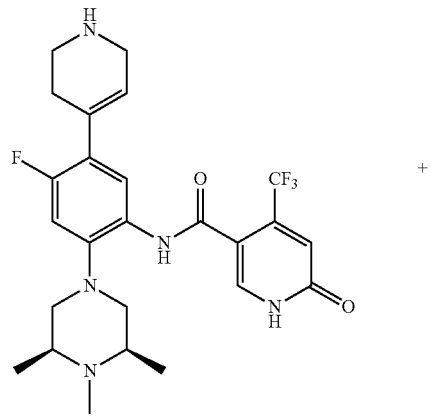

Intermediate 40

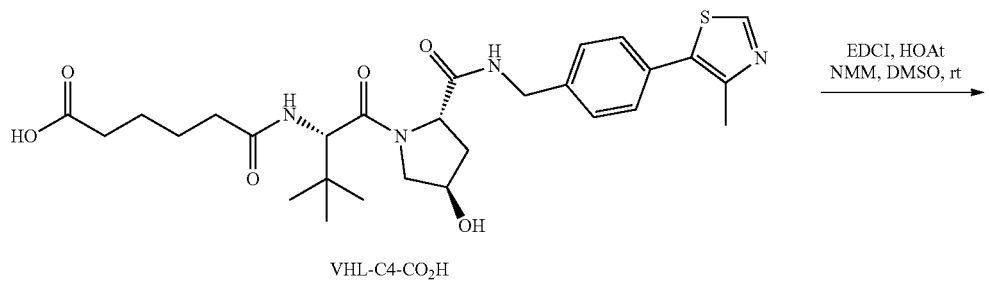

VHL-C4-CO$_2$H

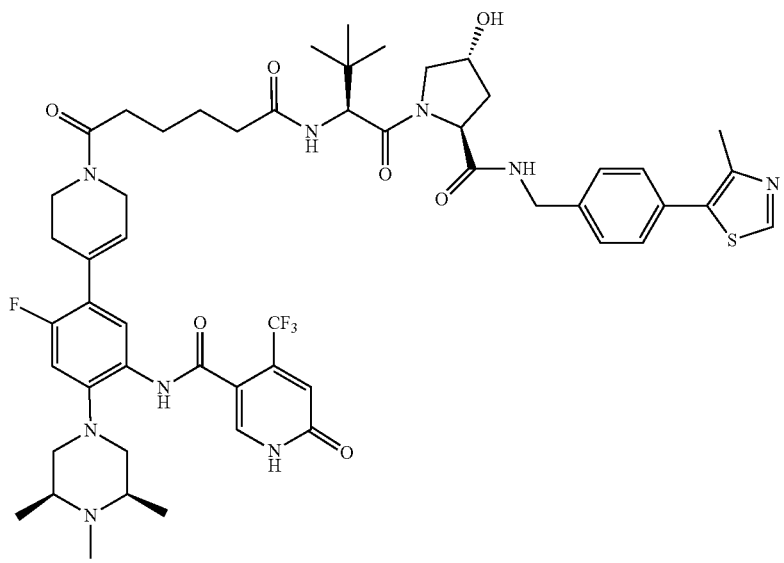

XF078-41

XF078-41 was synthesized following the standard procedures for preparing XF078-30 from intermediate 40 (12.9 mg, 0.02 mmol), VHL-C4-COOH (11.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-41 was obtained as white solid in TFA salt form (17.4 mg, yield 83%). $^1$H NMR (600 MHz, CD$_3$OD) δ 9.05 (s, 1H), 7.98 (s, 1H), 7.78 (d, J=8.0 Hz, 1H), 7.53-7.39 (m, 4H), 7.03 (d, J=12.0 Hz, 1H), 6.92 (s, 1H), 6.06-5.99 (m, 1H), 4.62 (d, J=3.0 Hz, 1H), 4.59-4.45 (m, 3H), 4.35 (d, J=15.5 Hz, 1H), 4.29-4.16 (m, 2H), 3.90 (d, J=10.8 Hz, 1H), 3.85-3.68 (m, 3H), 3.52-3.45 (m, 2H), 3.35-3.30 (m, 2H), 2.97 (s, 3H), 2.89 (t, J=12.3 Hz, 2H), 2.63-2.55 (m, 1H), 2.52-2.41 (m, 6H), 2.39-2.26 (m, 2H), 2.25-2.17 (m, 1H), 2.11-2.01 (m, 1H), 1.75-1.59 (m, 4H), 1.42 (d, J=6.4 Hz, 6H), 1.03 (d, J=3.5 Hz, 9H). HRMS (m/z) for C$_{53}$H$_{66}$F$_4$N$_9$O$_7$S$^+$ [M+H]$^+$: calculated 1048.4737. found 1048.4714.

Example 225: Synthesis of XF078-42

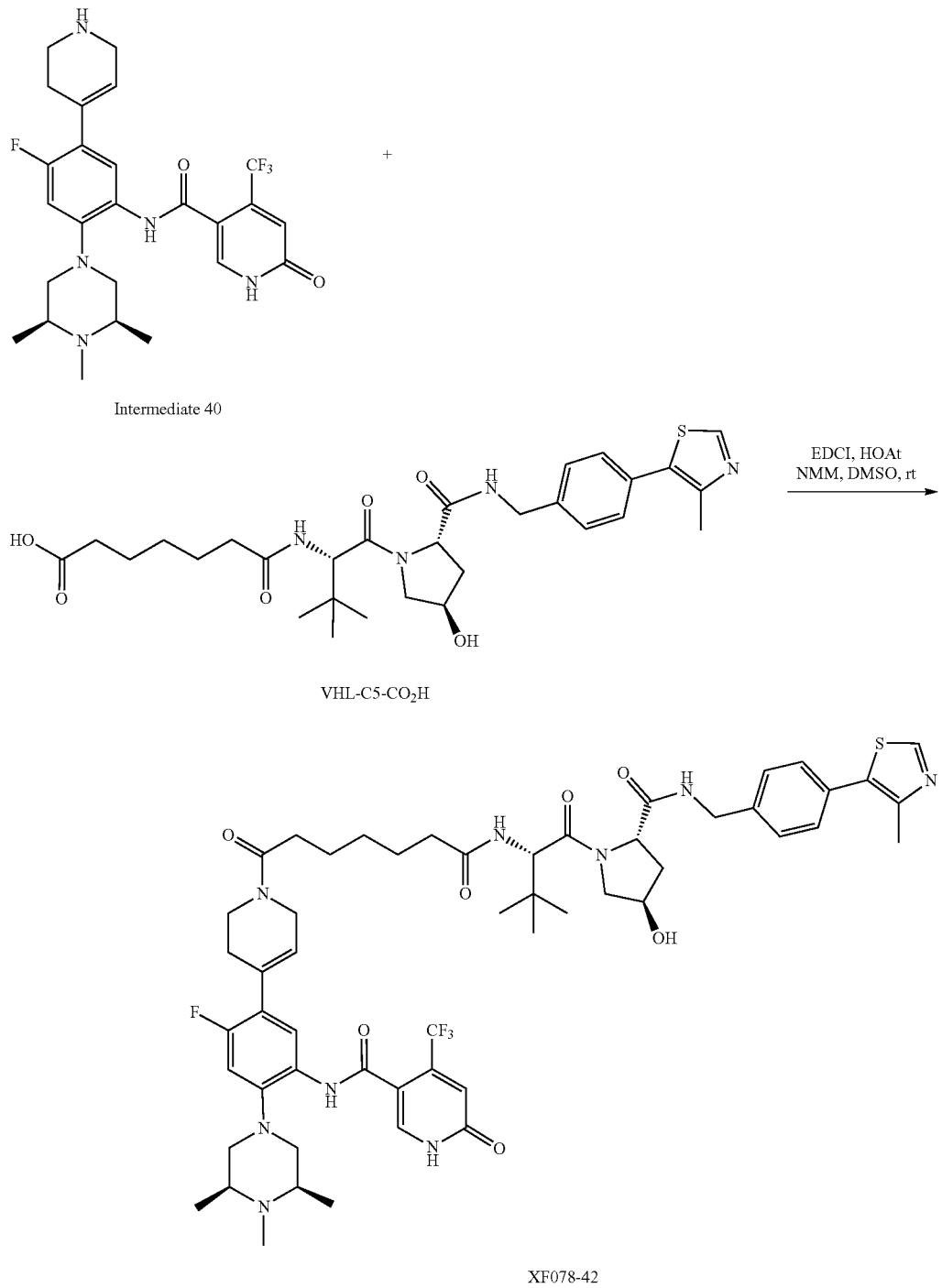

XF078-42 was synthesized following the standard procedures for preparing XF078-30 from intermediate 40 (12.9 mg, 0.02 mmol), VHL-C5-COOH (11.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-42 was obtained as white solid in TFA salt form (16.1 mg, yield 76%). $^1$H NMR (600 MHz, CD$_3$OD) δ 9.02 (s, 1H), 7.98 (s, 1H), 7.78 (d, J=8.3 Hz, 1H), 7.57-7.38 (m, 4H), 7.03 (d, J=12.0 Hz, 1H), 6.92 (s, 1H), 6.09-5.98 (m, 1H), 4.67-4.45 (m, 4H), 4.35 (d, J=15.6 Hz, 1H), 4.27-4.13 (m, 2H), 3.99-3.88 (m, 1H), 3.84-3.71 (m, 3H), 3.56-3.42 (m, 2H), 3.32-3.29 (m, 2H), 2.93-2.90 (m, 5H), 2.61-2.41 (m, 7H), 2.36-2.18 (m, 3H), 2.07 (ddd, J=13.2, 9.0, 4.5 Hz, 1H), 1.64 (s, 4H), 1.51-1.28 (m, 8H), 1.03 (s, 9H). HRMS (m/z) for $C_{54}H_{68}F_4N_9O_7S^+$ [M+H]$^+$: calculated 1062.4893. found 1062.4876.

Example 226: Synthesis of XF078-43

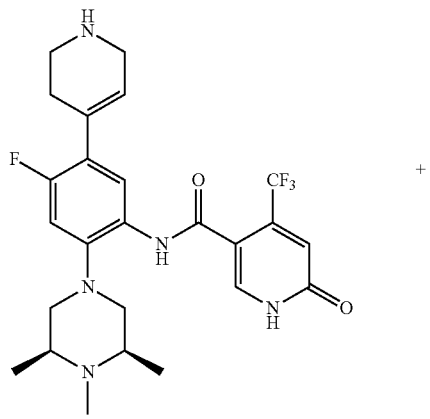

Intermediate 40

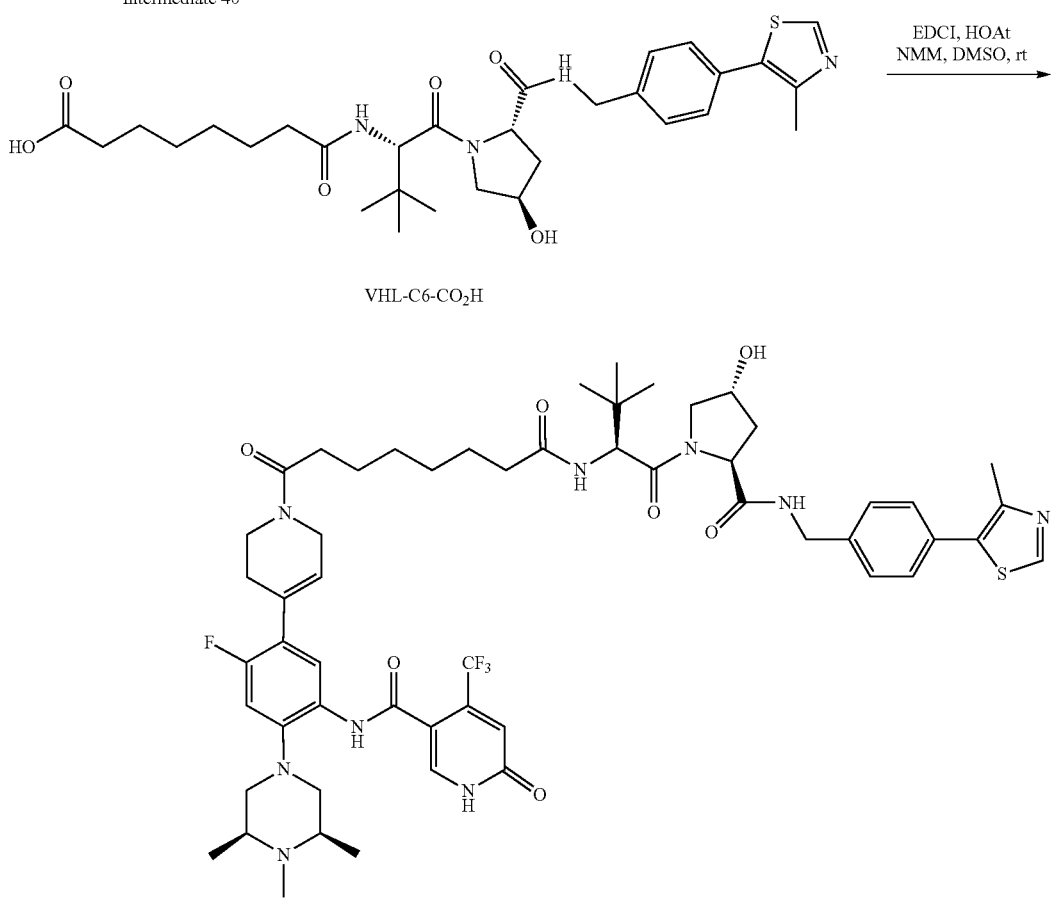

XF078-43

XF078-43 was synthesized following the standard procedures for preparing XF078-30 from intermediate 40 (12.9 mg, 0.02 mmol), VHL-C6-COOH (11.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-43 was obtained as white solid in TFA salt form (15.5 mg, yield 72%). $^1$H NMR (600 MHz, CD$_3$OD) δ 8.95 (s, 1H), 7.98 (s, 1H), 7.78 (d, J=8.0 Hz, 1H), 7.59-7.33 (m, 4H), 7.04 (d, J=12.0 Hz, 1H), 6.92 (s, 1H), 6.02 (d, J=4.1 Hz, 1H), 4.68-4.43 (m, 4H), 4.35 (d, J=15.4 Hz, 1H), 4.23-4.11 (m, 2H), 3.90 (d, J=10.9 Hz, 1H), 3.86-3.70 (m, 3H), 3.55-3.44 (m, 2H), 3.35-3.29 (m, 2H), 2.97 (s, 3H), 2.89 (t, J=12.2 Hz, 2H), 2.59-2.40 (m, 7H), 2.36-2.18 (m, 3H), 2.07 (ddd, J=13.3, 9.2, 4.5 Hz, 1H), 1.69-1.55 (m, 4H), 1.49-1.29 (m, 10H), 1.03 (s, 9H). HRMS (m/z) for $C_{55}H_{70}F_4N_9O_7S^+$ [M+H]$^+$: calculated 1076.5050. found 1076.5042.

Example 227: Synthesis of XF078-44

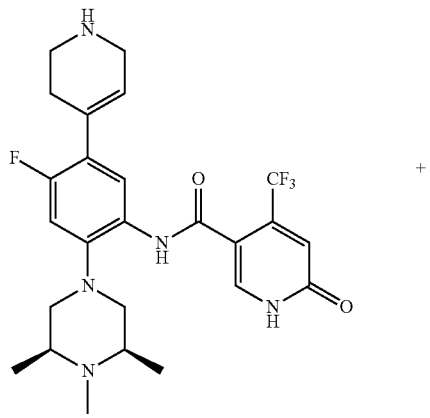

Intermediate 40

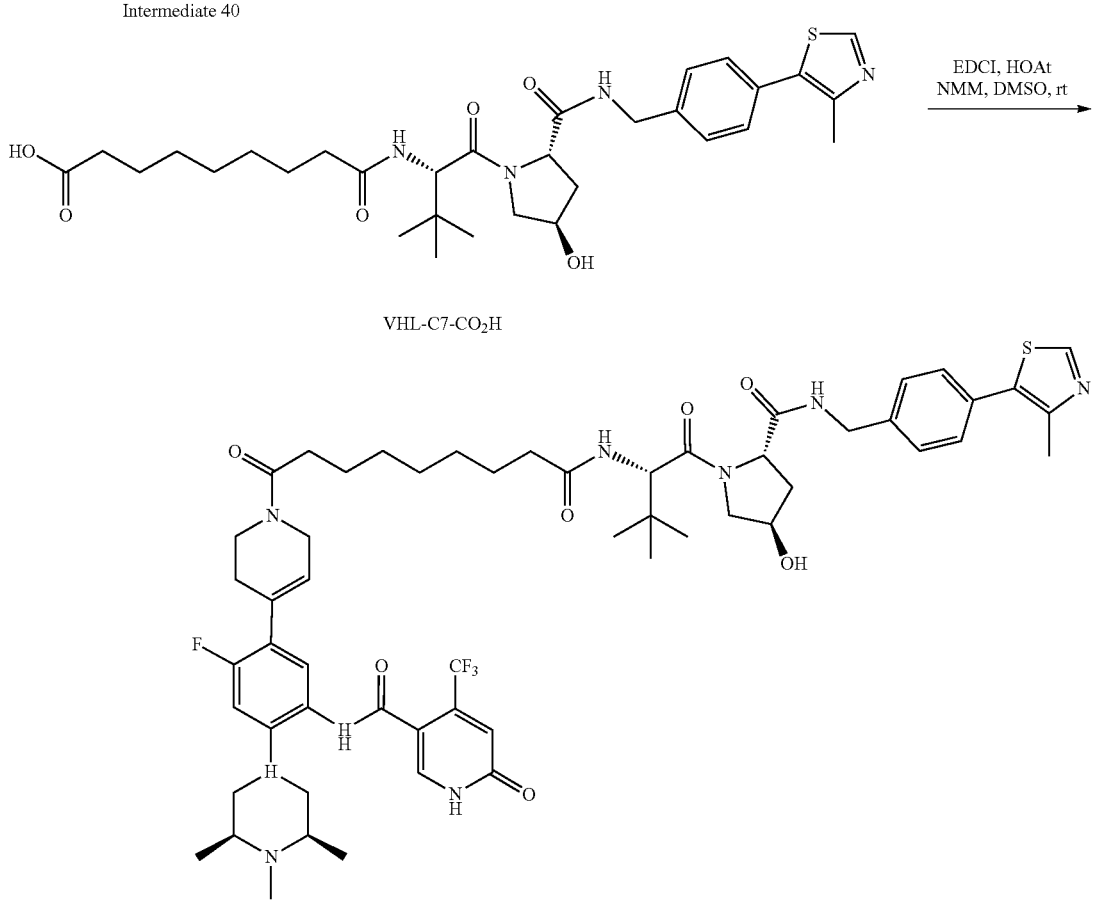

XF078-44

XF078-44 was synthesized following the standard procedures for preparing XF078-30 from intermediate 40 (12.9 mg, 0.02 mmol), VHL-C7-COOH (12 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-44 was obtained as white solid in TFA salt form (8.6 mg, yield 39%). $^1$H NMR (600 MHz, CD$_3$OD) δ 8.93 (s, 1H), 7.98 (s, 1H), 7.78 (d, J=8.0 Hz, 1H), 7.53-7.35 (m, 4H), 7.03 (d, J=12.0 Hz, 1H), 6.92 (s, 1H), 6.02 (s, 1H), 4.63 (s, 1H), 4.60-4.48 (m, 3H), 4.36 (d, J=15.4 Hz, 1H), 4.27-4.13 (m, 2H), 3.90 (d, J=11.1 Hz, 1H), 3.83-3.71 (m, 3H), 3.54-3.44 (m, 2H), 3.37-3.29 (m, 2H), 2.97 (s, 3H), 2.88 (t, J=12.2 Hz, 2H), 2.61-2.38 (m, 7H), 2.35-2.17 (m, 3H), 2.11-2.05 (m, 1H), 1.67-1.57 (m, 4H), 1.39 (s, 12H), 1.03 (s, 9H). HRMS (m/z) for $C_{56}H_{72}F_4N_9O_7S^+$ [M+H]$^+$: calculated 1090.5206, found 1090.5186.

Example 228: Synthesis of XF078-45

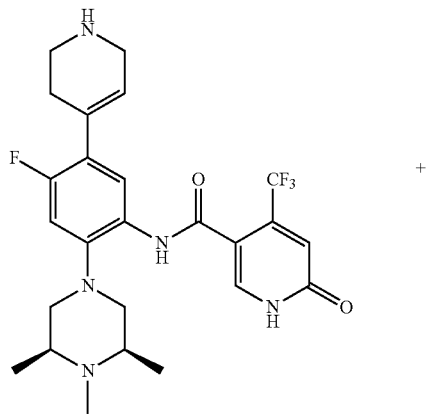

Intermediate 40

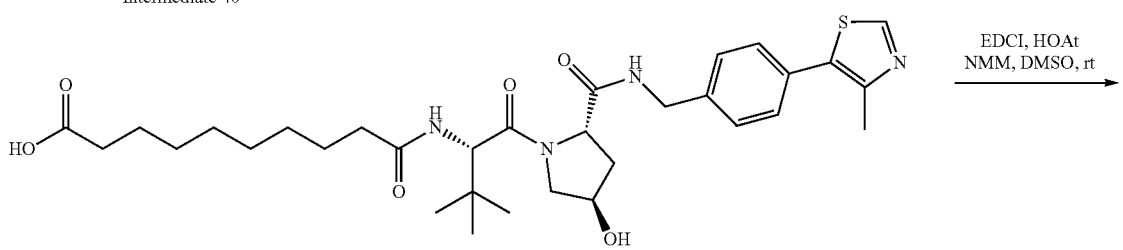

VHL-C8-CO₂H

EDCI, HOAt
NMM, DMSO, rt

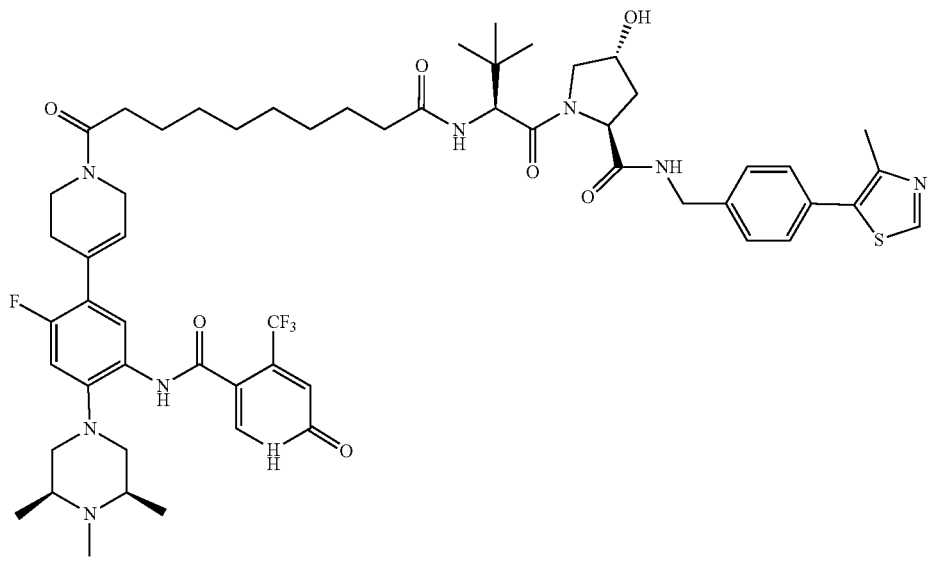

XF078-45

XF078-45 was synthesized following the standard procedures for preparing XF078-30 from intermediate 40 (12.9 mg, 0.02 mmol), VHL-C8-COOH (12.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-45 was obtained as white solid in TFA salt form (12.5 mg, yield 57%). $^1$H NMR (600 MHz, CD₃OD) δ 8.99 (s, 1H), 7.98 (s, 1H), 7.78 (d, J=8.0 Hz, 1H), 7.51-7.39 (m, 4H), 7.04 (d, J=12.0 Hz, 1H), 6.92 (s, 1H), 6.02 (s, 1H), 4.63 (s, 1H), 4.60-4.46 (m, 3H), 4.35 (d, J=15.5 Hz, 1H), 4.24-4.13 (m, 2H), 3.90 (d, J=11.0 Hz, 1H), 3.83-3.70 (m, 3H), 3.52-3.42 (m, 2H), 3.36-3.30 (m, 2H), 2.97 (s, 3H), 2.89 (t, J=12.2 Hz, 2H), 2.60-2.37 (m, 7H), 2.32-2.18 (m, 3H), 2.07 (ddd, J=13.3, 9.1, 4.5 Hz, 1H), 1.67-1.55 (m, 4H), 1.45-1.27 (m, 14H), 1.03 (s, 9H). HRMS (m/z) for $C_{57}H_{74}F_4N_9O_7S^+$ [M+H]$^+$: calculated 1104.5303. found 1104.5285.

Example 229: Synthesis of XF078-46

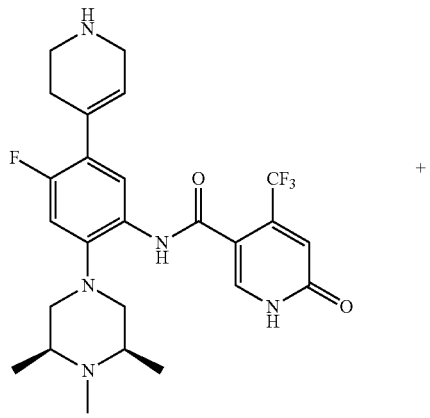

Intermediate 40

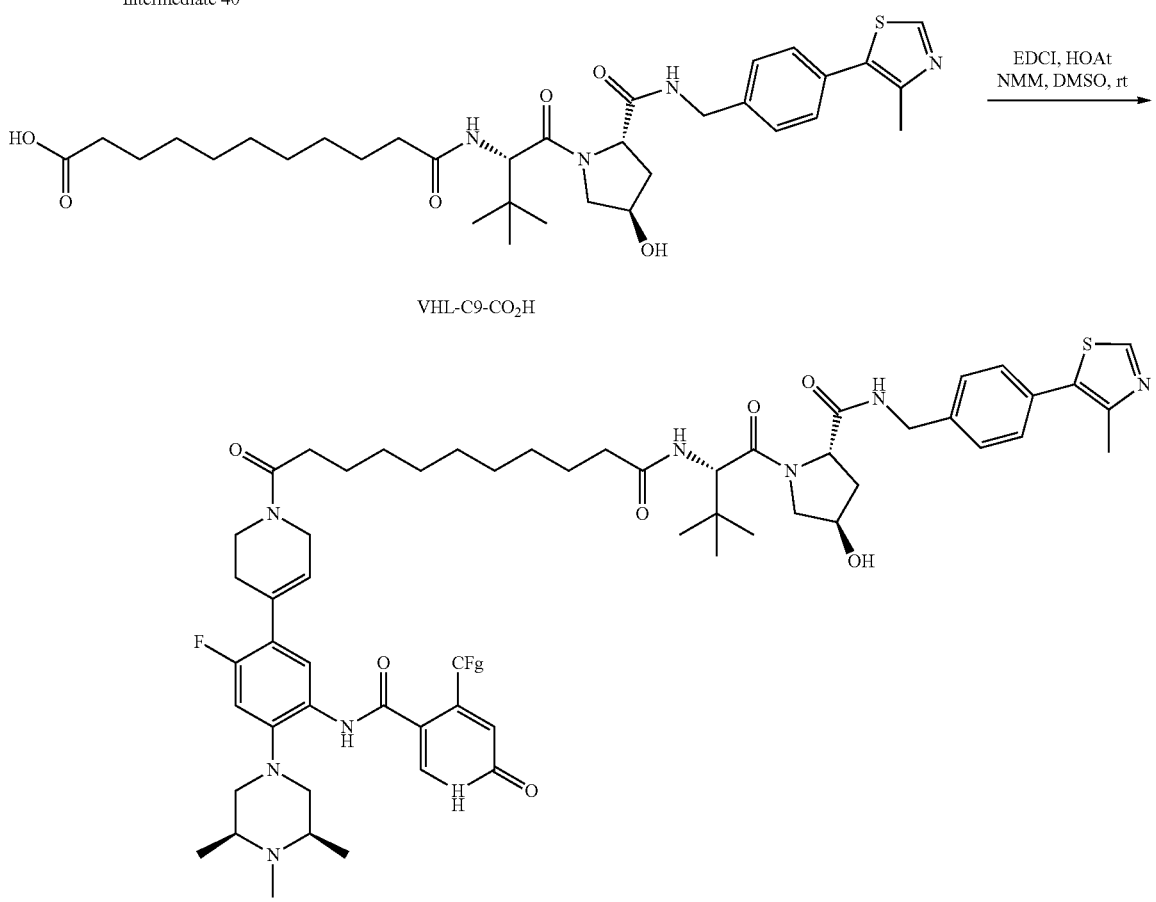

XF078-46 was synthesized following the standard procedures for preparing XF078-30 from intermediate 40 (12.9 mg, 0.02 mmol), VHL-C9-COOH (12.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-46 was obtained as white solid in TFA salt form (11.7 mg, yield 52%). $^1$H NMR (600 MHz, CD$_3$OD) δ 8.94 (s, 1H), 7.98 (s, 1H), 7.78 (d, J=7.9 Hz, 1H), 7.47 (d, J=8.0 Hz, 2H), 7.42 (d, J=8.2 Hz, 2H), 7.04 (d, J=11.9 Hz, 1H), 6.92 (s, 1H), 6.04-5.97 (m, 1H), 4.63 (s, 1H), 4.60-4.48 (m, 3H), 4.36 (d, J=15.4 Hz, 1H), 4.26-4.16 (m, 2H), 3.90 (d, J=11.0 Hz, 1H), 3.82-3.70 (m, 3H), 3.47 (s, 2H), 3.35-3.31 (m, 2H), 2.97 (s, 3H), 2.92-2.85 (m, 2H), 2.60-2.53 (m, 1H), 2.51-2.39 (m, 6H), 2.33-2.16 (m, 3H), 2.11-2.05 (m, 1H), 1.67-1.55 (m, 4H), 1.37 (s, 16H), 1.03 (s, 9H). HRMS (m/z) for $C_{58}H_{76}F_4N_9O_7S^+$ [M+H]$^+$: calculated 1118.5519. found 1118.5487.

Example 230: Synthesis of XF078-47

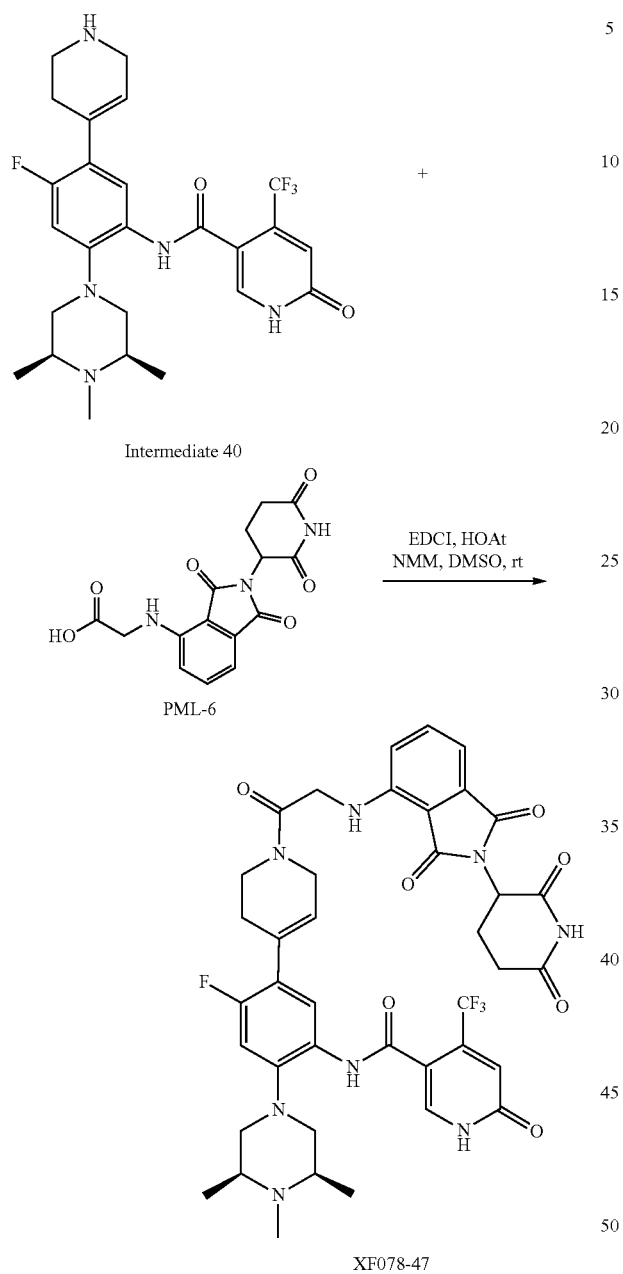

Intermediate 40

PML-6

XF078-47

XF078-47 was synthesized following the standard procedures for preparing XF078-30 from intermediate 40 (12.9 mg, 0.02 mmol), PML-6 (6.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-47 was obtained as yellow solid in TFA salt form (10.8 mg, yield 66%). $^1$H NMR (600 MHz, CD$_3$OD) δ 7.99 (d, J=1.8 Hz, 1H), 7.80 (d, J=8.1 Hz, 1H), 7.52 (dd, J=8.5, 7.1 Hz, 1H), 7.07-6.94 (m, 3H), 6.90 (s, 1H), 6.08-6.02 (m, 1H), 5.05 (ddd, J=12.5, 5.5, 3.1 Hz, 1H), 4.27-4.15 (m, 4H), 3.84-3.79 (m, 1H), 3.73 (t, J=5.9 Hz, 1H), 3.48 (d, J=11.3 Hz, 2H), 3.30-3.25 (m, 2H), 2.96 (s, 3H), 2.92-2.60 (m, 6H), 2.56-2.49 (m, 1H), 2.18-2.06 (m, 1H), 1.41 (d, J=6.4 Hz, 6H). HRMS (m/z) for C$_{40}$H$_{41}$F$_4$N$_8$O$_7^+$ [M+H]$^+$: calculated 821.3029. found 821.3013.

Example 231: Synthesis of XF078-48

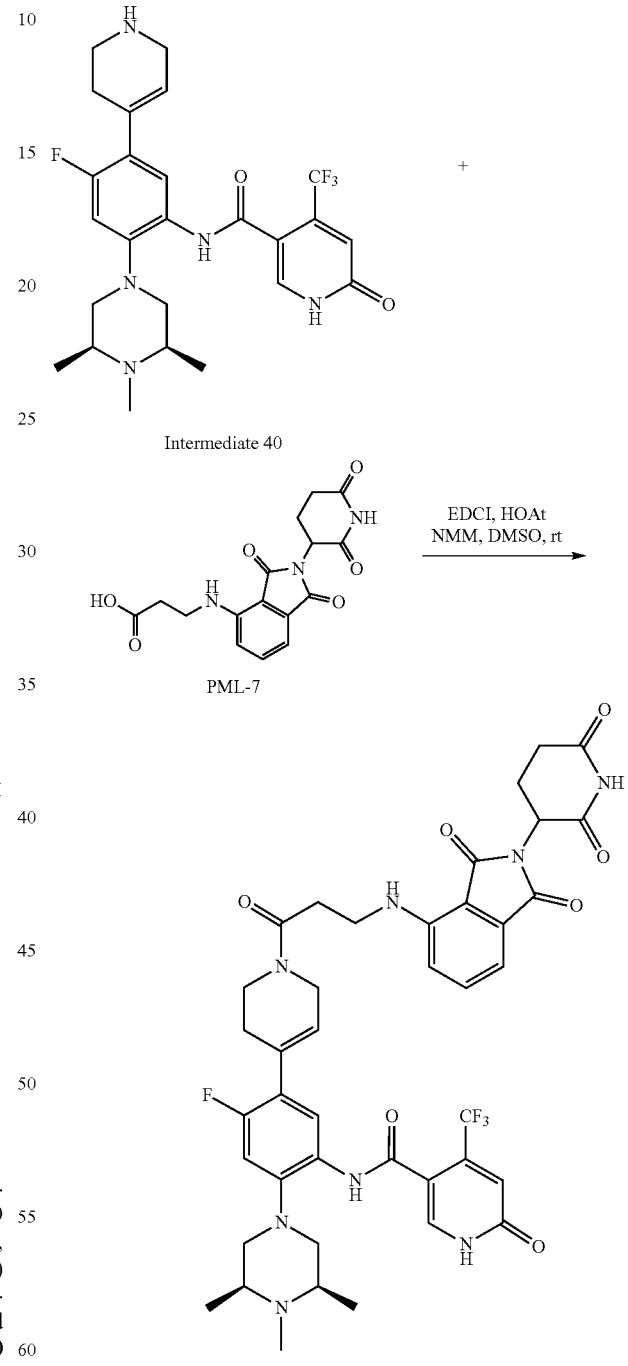

Intermediate 40

PML-7

XF078-48

XF078-48 was synthesized following the standard procedures for preparing XF078-30 from intermediate 40 (12.9 mg, 0.02 mmol), PML-7 (6.9 mg, 0.02 mmol, 1.0 equiv), EDCI (1-ethyl-3-(3-dimethylaminopropyl)carbodiimide)

(5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-48 was obtained as yellow solid in TFA salt form (12.5 mg, yield 75%). $^1$H NMR (600 MHz, CD$_3$OD) δ 8.05 (s, 1H), 7.73-7.61 (m, 1H), 7.58-7.49 (m, 1H), 7.15-7.08 (m, 1H), 7.05-6.97 (m, 2H), 6.92 (s, 1H), 6.05-5.90 (m, 1H), 5.06-4.92 (m, 1H), 4.29-4.16 (m, 2H), 3.83-3.61 (m, 4H), 3.53-3.44 (m, 2H), 3.31-3.26 (m, 2H), 2.97 (s, 3H), 2.93-2.57 (m, 5H), 2.51-2.45 (m, 2H), 2.33-2.23 (m, 2H), 2.05-1.85 (m, 1H), 1.47-1.38 (m, 6H). HRMS (m/z) for C$_{41}$H$_{43}$F$_4$N$_8$O$_7$$^+$ [M+H]$^+$: calculated 835.3185, found 835.3164.

Example 232: Synthesis of XF078-49

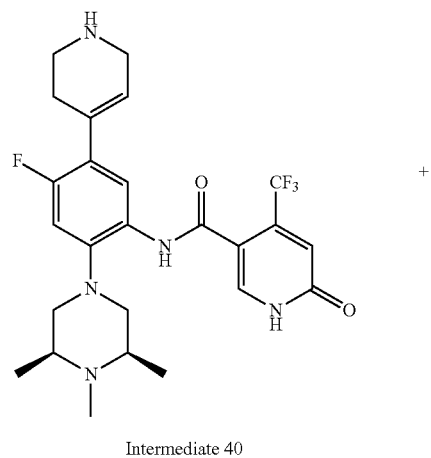
Intermediate 40

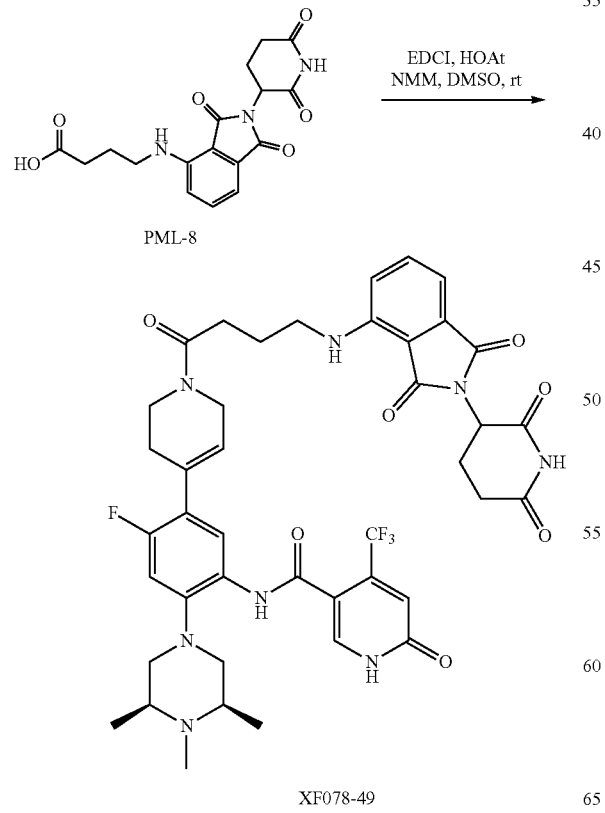

XF078-49 was synthesized following the standard procedures for preparing XF078-30 from intermediate 40 (12.9 mg, 0.02 mmol), PML-8 (7.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-49 was obtained as yellow solid in TFA salt form (12.7 mg, yield 75%). $^1$H NMR (600 MHz, CD$_3$OD) δ 8.02 (s, 1H), 7.69 (d, J=8.0 Hz, 1H), 7.56-7.44 (m, 1H), 7.08 (dd, J=8.6, 2.0 Hz, 2H), 7.04-6.90 (m, 2H), 6.08-6.01 (m, 1H), 5.08-4.96 (m, 1H), 4.24-4.14 (m, 2H), 3.79-3.74 (m, 1H), 3.72-3.65 (m, 1H), 3.54-3.38 (m, 6H), 2.97 (s, 3H), 2.92-2.78 (m, 3H), 2.75-2.62 (m, 2H), 2.60-2.52 (m, 2H), 2.51-2.38 (m, 2H), 2.12-1.94 (m, 3H), 1.42 (s, 6H). HRMS (m/z) for C$_{42}$H$_{45}$F$_4$N$_8$O$_7$$^+$ [M+H]$^+$: calculated 849.3342, found 849.3331.

Example 233: Synthesis of XF078-50

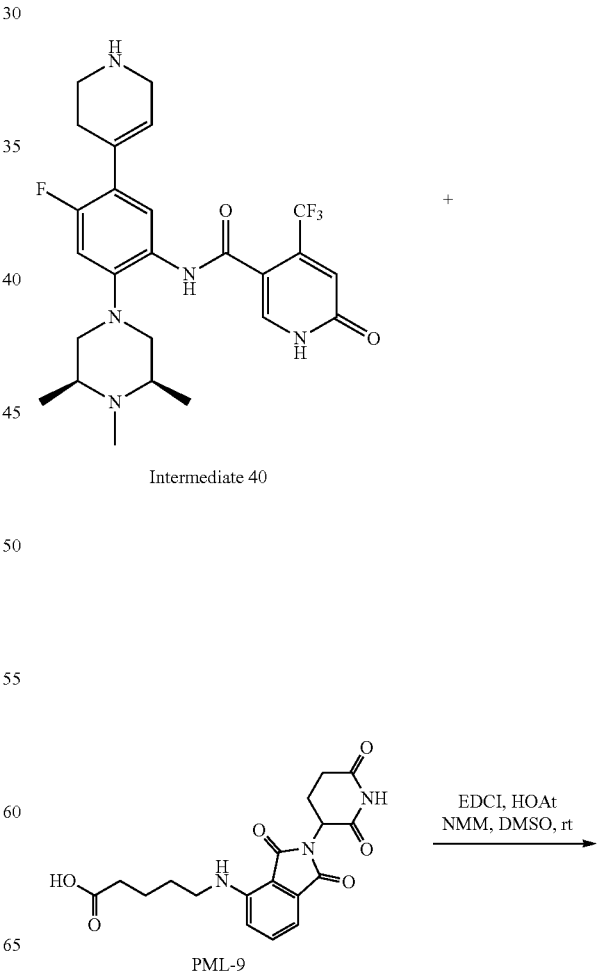

-continued

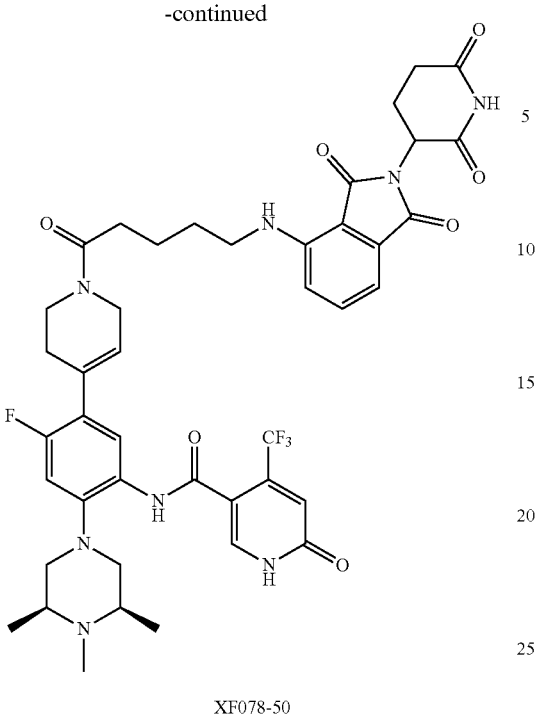

XF078-50

XF078-50 was synthesized following the standard procedures for preparing XF078-30 from intermediate 40 (12.9 mg, 0.02 mmol), PML-9 (7.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-50 was obtained as yellow solid in TFA salt form (6.5 mg, yield 38%). $^1$H NMR (600 MHz, CD$_3$OD) δ 7.98 (d, J=8.0 Hz, 1H), 7.73 (t, J=7.1 Hz, 1H), 7.56-7.48 (m, 1H), 7.08-6.97 (m, 3H), 6.92 (s, 1H), 6.02 (d, J=11.8 Hz, 1H), 5.03 (dt, J=12.2, 4.8 Hz, 1H), 4.24-4.16 (m, 2H), 3.82-3.69 (m, 2H), 3.52-3.43 (m, 2H), 3.40-3.31 (m, 4H), 2.97 (s, 3H), 2.92-2.76 (m, 2H), 2.76-2.62 (m, 2H), 2.57-2.45 (m, 5H), 2.13-2.03 (m, 1H), 1.85-1.64 (m, 4H), 1.42 (d, 6H). HRMS (m/z) for $C_{43}H_{47}F_4N_8O_7^+$ [M+H]$^+$: calculated 863.3498. found 863.3513.

Example 234: Synthesis of XF078-51

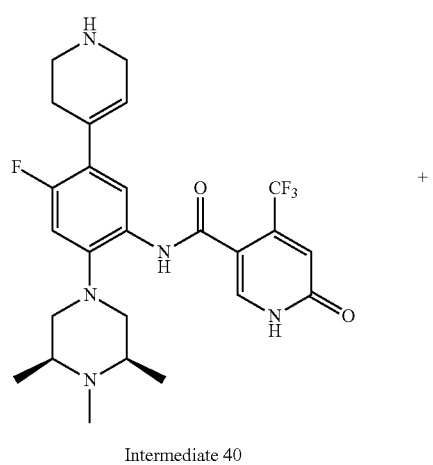

Intermediate 40

+

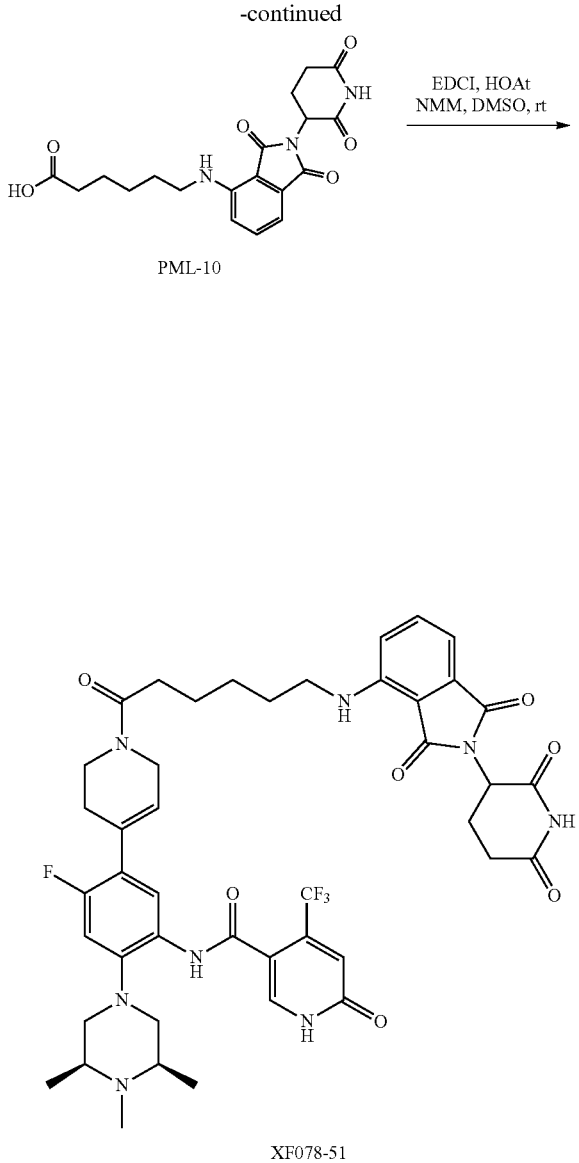

PML-10

$\xrightarrow{\text{EDCI, HOAt}}_{\text{NMM, DMSO, rt}}$

XF078-51

XF078-51 was synthesized following the standard procedures for preparing XF078-30 from intermediate 40 (12.9 mg, 0.02 mmol), PML-10 (7.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-51 was obtained as yellow solid in TFA salt form (10.6 mg, yield 61%). $^1$H NMR (600 MHz, CD$_3$OD) δ 7.97 (d, J=2.3 Hz, 1H), 7.73 (t, J=8.7 Hz, 1H), 7.49 (dt, J=13.3, 7.9 Hz, 1H), 7.05-6.85 (m, 4H), 6.04 (d, J=14.4 Hz, 1H), 5.04 (dt, J=12.7, 5.1 Hz, 1H), 4.28-4.10 (m, 2H), 3.83-3.67 (m, 2H), 3.52-3.39 (m, 2H), 3.29-3.20 (m, 1H), 2.96 (d, J=6.1 Hz, 3H), 2.92-2.62 (m, 5H), 2.61-

2.41 (m, 4H), 2.13-2.00 (m, 1H), 1.67 (q, J=6.4, 5.9 Hz, 5H), 1.55-1.19 (m, 10H). HRMS (m/z) for $C_{44}H_{49}F_4N_8O_7^+$ [M+H]$^+$: calculated 877.3655. found 877.3634.

Example 235: Synthesis of XF078-52

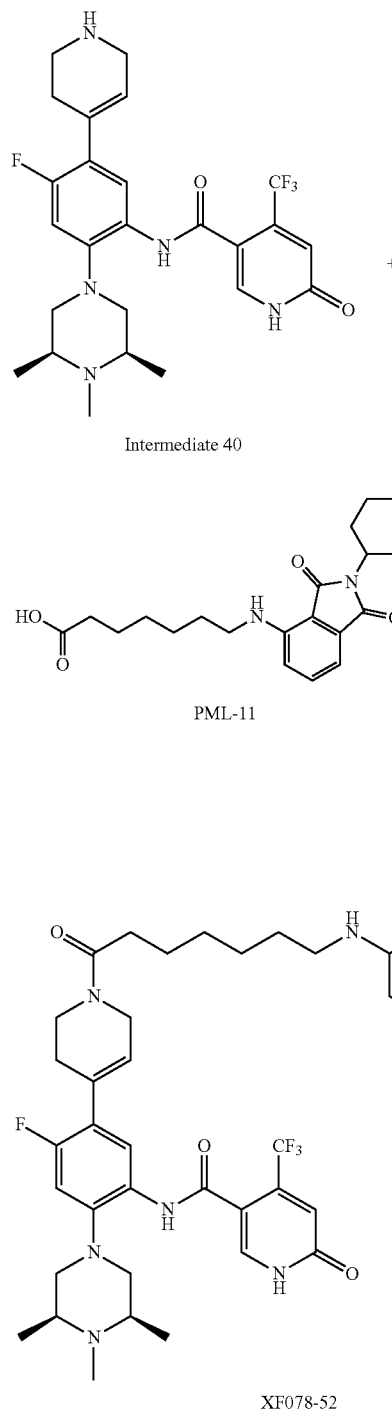

XF078-52

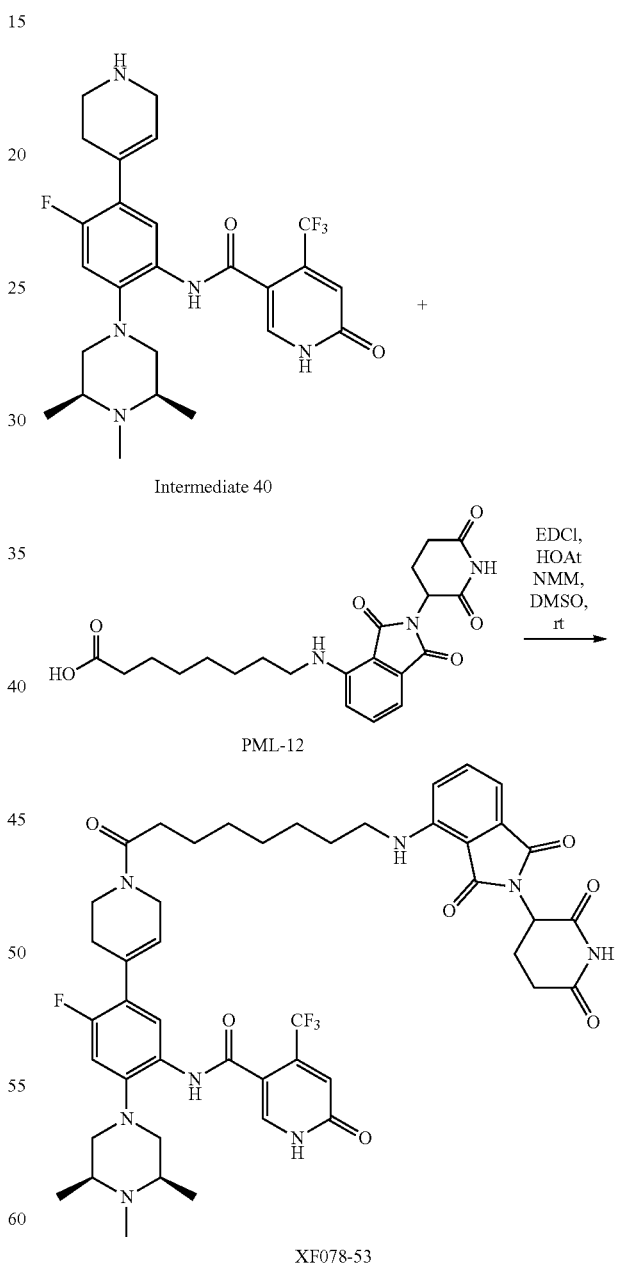

XF078-52 was synthesized following the standard procedures for preparing XF078-30 from intermediate 40 (12.9 mg, 0.02 mmol), PML-11 (8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-52 was obtained as yellow solid in TFA salt form (12 mg, yield 70%). $^1$H NMR (600 MHz, CD$_3$OD) δ 7.97 (d, J=2.3 Hz, 1H), 7.74 (d, J=8.9 Hz, 1H), 7.61-7.39 (m, 1H), 7.08-6.76 (m, 4H), 6.17-5.90 (m, 1H), 5.20-4.99 (m, 1H), 4.35-4.02 (m, 2H), 3.89-3.66 (m, 2H), 3.56-3.37 (m, 2H), 3.31-3.20 (m, 2H), 3.00-2.64 (m, 10H), 2.62-2.40 (m, 4H), 2.13-2.05 (m, 1H), 1.74-1.61 (m, 4H), 1.52-1.29 (m, 10H). HRMS (m/z) for $C_{45}H_{51}F_4N_8O_7^+$ [M+H]$^+$: calculated 891.3811. found 891.3825.

Example 236: Synthesis of XF078-53

XF078-53 was synthesized following the standard procedures for preparing XF078-30 from intermediate 40 (12.9 mg, 0.02 mmol), PML-12 (8.3 mg, 0.02 mmol, 1.0 equiv), EDCI (1-ethyl-3-(3-dimethylaminopropyl)carbodiimide)

(5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-53 was obtained as yellow solid in TFA salt form (13.6 mg, yield 75%). $^1$H NMR (600 MHz, CD$_3$OD) δ 7.97 (d, J=1.8 Hz, 1H), 7.76 (d, J=8.0 Hz, 1H), 7.51 (dd, J=8.5, 7.1 Hz, 1H), 7.02-6.96 (m, 3H), 6.91 (s, 1H), 6.03 (d, J=15.1 Hz, 1H), 5.03 (ddd, J=12.5, 5.6, 2.0 Hz, 1H), 4.25-4.15 (m, 2H), 3.80-3.70 (m, 2H), 3.52-3.43 (m, 2H), 3.30-3.25 (m, 4H), 2.96 (s, 3H), 2.91-2.64 (m, 4H), 2.59-2.54 (m, 1H), 2.45 (s, 4H), 2.14-2.04 (m, 1H), 1.70-1.59 (m, 4H), 1.51-1.36 (m, 12H). HRMS (m/z) for C$_{46}$H$_{53}$F$_4$N$_8$O$_7^+$ [M+H]$^+$: calculated 905.3968. found 905.3943.

Example 237: Synthesis of XF078-54

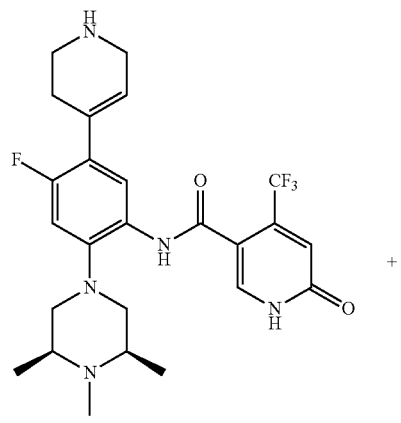

Intermediate 40

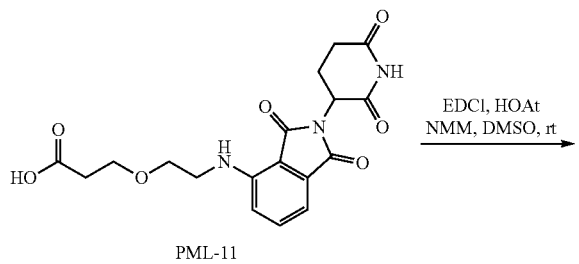

PML-11

EDCl, HOAt
NMM, DMSO, rt
→

-continued

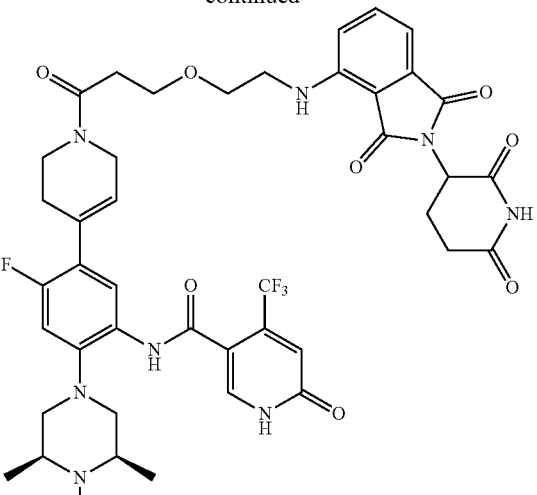

XF078-54

XF078-54 was synthesized following the standard procedures for preparing XF078-30 from intermediate 40 (12.9 mg, 0.02 mmol), PML-20 (8 mg, 0.02 mmol, 1.0 equiv), EDCl (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-54 was obtained as yellow solid in TFA salt form (9.2 mg, yield 52%). $^1$H NMR (600 MHz, CD$_3$OD) δ 7.99 (d, J=6.9 Hz, 1H), 7.79-7.65 (m, 1H), 7.48 (ddd, J=18.9, 8.6, 7.1 Hz, 1H), 7.12-6.82 (m, 4H), 5.98 (d, J=39.1 Hz, 1H), 5.00 (ddd, J=18.0, 12.6, 5.5 Hz, 1H), 4.33-4.09 (m, 2H), 3.96-3.60 (m, 6H), 3.54-3.38 (m, 3H), 3.34-3.29 (m, 2H), 2.97 (s, 3H), 2.93-2.59 (m, 8H), 2.57-2.41 (m, 2H), 2.05 (dd, J=20.3, 11.2 Hz, 1H), 1.42 (t, J=6.4 Hz, 6H). HRMS (m/z) for C$_{43}$H$_{47}$F$_4$N$_8$O$_8^+$ [M+H]$^+$: calculated 879.3447. found 879.3412.

Example 238: Synthesis of XF078-55

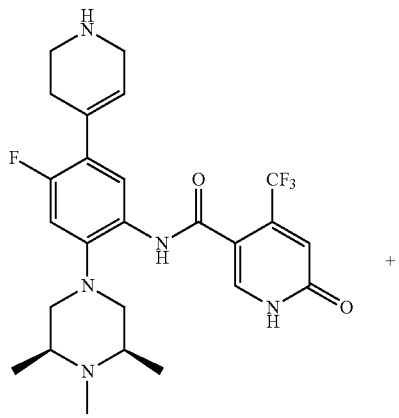

Intermediate 40

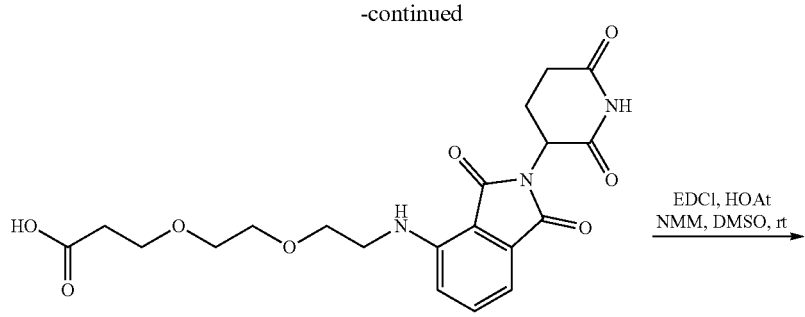

PML-21

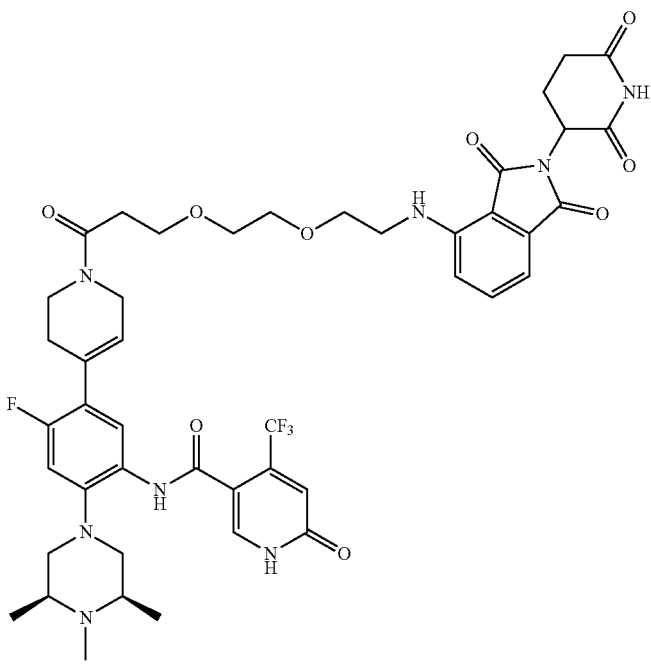

XF078-55

XF078-55 was synthesized following the standard procedures for preparing XF078-30 from intermediate 40 (12.9 mg, 0.02 mmol), PML-21 (8.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-55 was obtained as yellow solid in TFA salt form (14.8 mg, yield 80%). $^1$H NMR (600 MHz, CD$_3$OD) δ 7.98 (d, J=2.1 Hz, 1H), 7.72 (t, J=7.0 Hz, 1H), 7.47 (td, J=8.6, 6.9 Hz, 1H), 7.05-6.88 (m, 4H), 6.00 (d, J=51.2 Hz, 1H), 5.03 (dd, J=12.5, 5.5 Hz, 1H), 4.29-4.12 (m, 2H), 3.82-3.56 (m, 9H), 3.52-3.38 (m, 4H), 3.24 (t, J=13.4 Hz, 2H), 2.95 (s, 3H), 2.92-2.62 (m, 8H), 2.62-2.44 (m, 2H), 2.14-2.04 (m, 1H), 1.45-1.38 (m, 6H). HRMS (m/z) for $C_{45}H_{51}F_4N_8O_9^+$ [M+H]$^+$: calculated 923.3710. found 923.3723.

Example 239: Synthesis of XF078-56

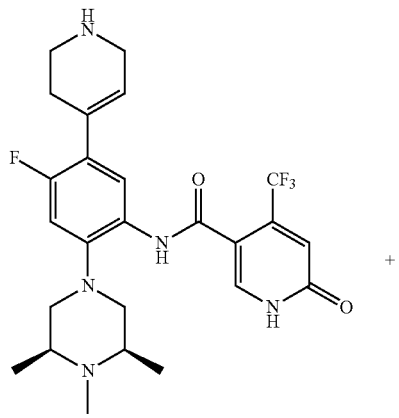

Intermediate 40

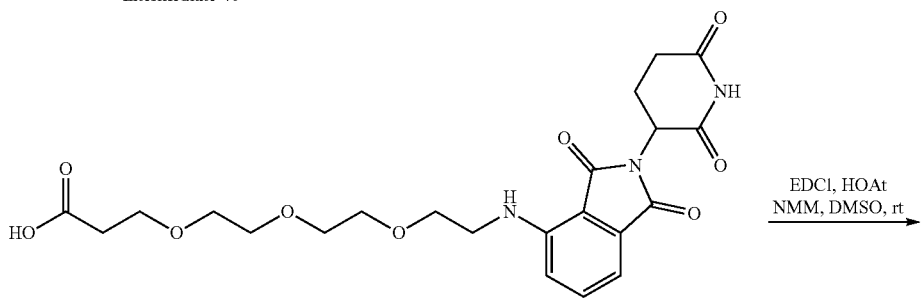

PML-22

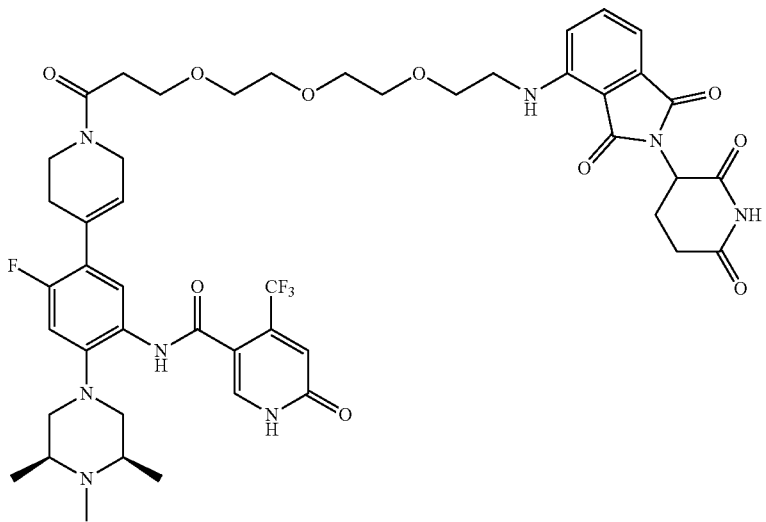

XF078-56

XF078-56 was synthesized following the standard procedures for preparing XF078-30 from intermediate 40 (12.9 mg, 0.02 mmol), PML-22 (9.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-56 was obtained as yellow solid in TFA salt form (16.4 mg, yield 85%). $^1$H NMR (600 MHz, CD$_3$OD) δ 7.97 (s, 1H), 7.74 (d, J=7.9 Hz, 1H), 7.58-7.43 (m, 1H), 7.11-6.86 (m, 4H), 6.02 (d, J=19.3 Hz, 1H), 5.04 (dd, J=12.6, 5.5 Hz, 1H), 4.32-4.13 (m, 2H), 3.83-3.35 (m, 17H), 3.32-3.19 (m, 2H), 2.96 (s, 3H), 2.92-2.59 (m, 8H), 2.59-2.42 (m, 2H), 2.22-1.98 (m, 1H), 1.52-1.32 (m, 6H). HRMS (m/z) for C$_{47}$H$_{55}$F$_4$N$_8$O$_{10}$$^+$ [M+H]$^+$: calculated 967.3972. found 967.3988.

Example 240: Synthesis of XF078-57
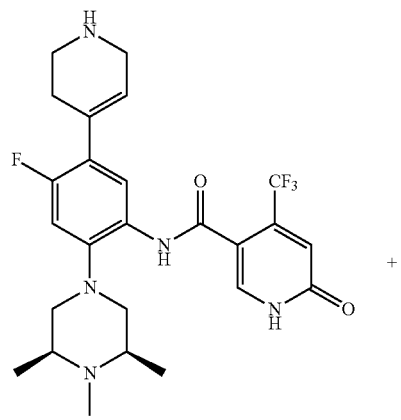
Intermediate 40
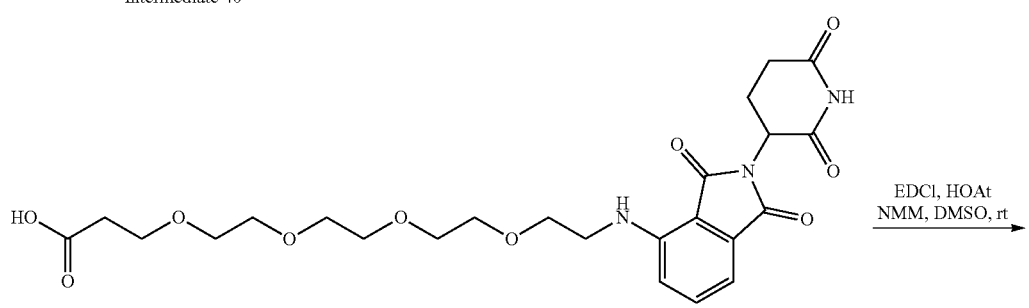
PML-21
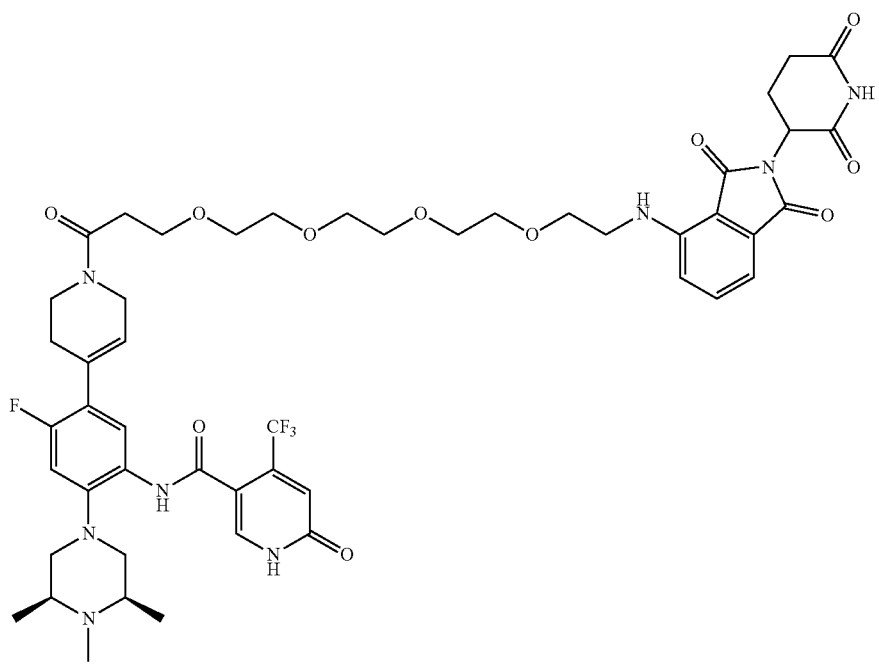
XF078-57

XF078-57 was synthesized following the standard procedures for preparing XF078-30 from intermediate 40 (12.9 mg, 0.02 mmol), PML-23 (10.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-57 was obtained as yellow solid in TFA salt form (15.5 mg, yield 77%). $^1$H NMR (600 MHz, CD$_3$OD) δ 7.98 (s, 1H), 7.75 (dd, J=8.1, 2.4 Hz, 1H), 7.50 (ddd, J=8.7, 7.0, 1.7 Hz, 1H), 7.21-6.84 (m, 4H), 6.08-5.96 (m, 1H), 5.09-5.03 (m, 1H), 4.33-4.13 (m, 2H), 3.81-3.52 (m, 17H), 3.52-3.37 (m, 4H), 3.30-3.23 (m, 2H), 2.96 (d, J=1.5 Hz, 3H), 2.90-2.64 (m, 8H), 2.61-2.41 (m, 2H), 2.15-2.02 (m, 1H), 1.41 (dd, J=6.5, 3.0 Hz, 6H). HRMS (m/z) for C$_{49}$H$_{59}$F$_4$N$_8$O$_{11}^+$ [M+H]$^+$: calculated 1011.4234. found 1011.4216.

Example 241: Synthesis of XF078-58

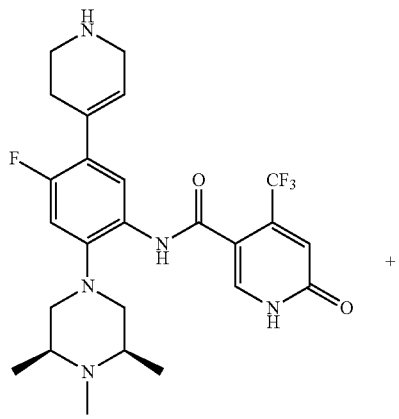

Intermediate 40

+

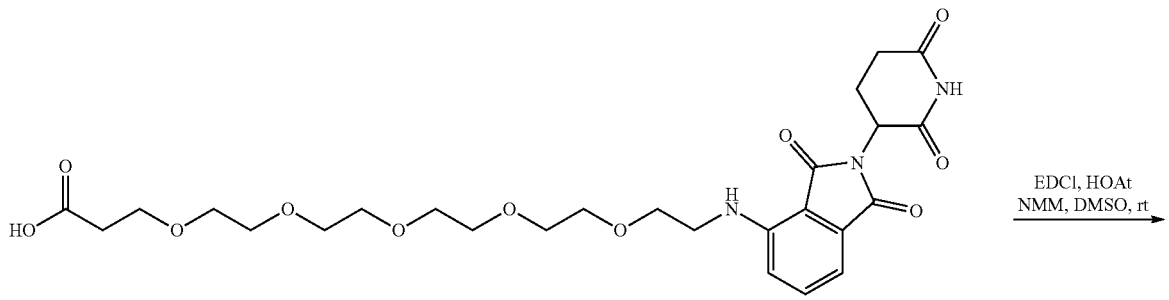

PML-24

EDCl, HOAt
NMM, DMSO, rt

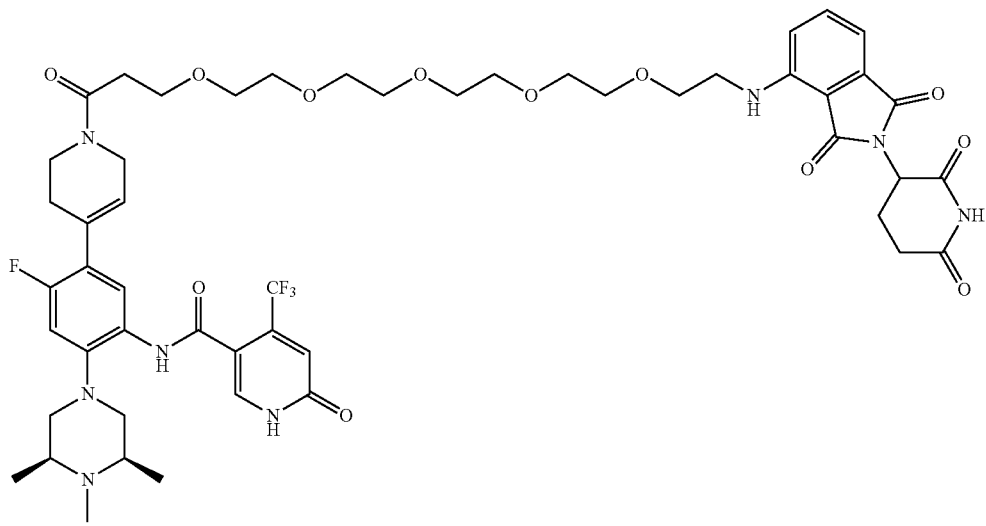

XF078-58

XF078-58 was synthesized following the standard procedures for preparing XF078-30 from intermediate 40 (12.9 mg, 0.02 mmol), PML-24 (11.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-58 was obtained as yellow solid in TFA salt form (9.2 mg, yield 44%). $^1$H NMR (600 MHz, CD$_3$OD) δ 7.98 (s, 1H), 7.75 (d, J=8.1 Hz, 1H), 7.51 (t, J=7.9 Hz, 1H), 7.09-6.93 (m, 3H), 6.91 (s, 1H), 6.03 (d, J=10.9 Hz, 1H), 5.04 (dd, J=12.6, 5.6 Hz, 1H), 4.22 (d, J=33.6 Hz, 2H), 3.82-3.69 (m, 6H), 3.67-3.53 (m, 15H), 3.51-3.41 (m, 4H), 3.30-3.22 (m, 2H), 2.96 (s, 3H), 2.91-2.81 (m, 3H), 2.81-2.65 (m, 5H), 2.60-2.54 (m, 1H), 2.49-2.43 (m, 1H), 2.15-2.01 (m, 1H), 1.41 (dd, J=6.6, 2.7 Hz, 6H). HRMS (m/z) for $C_{51}H_{63}F_4N_8O_{12}^+$ [M+H]$^+$: calculated 1055.4496. found 1055.4413.

Example 242: Synthesis of Intermediate 42

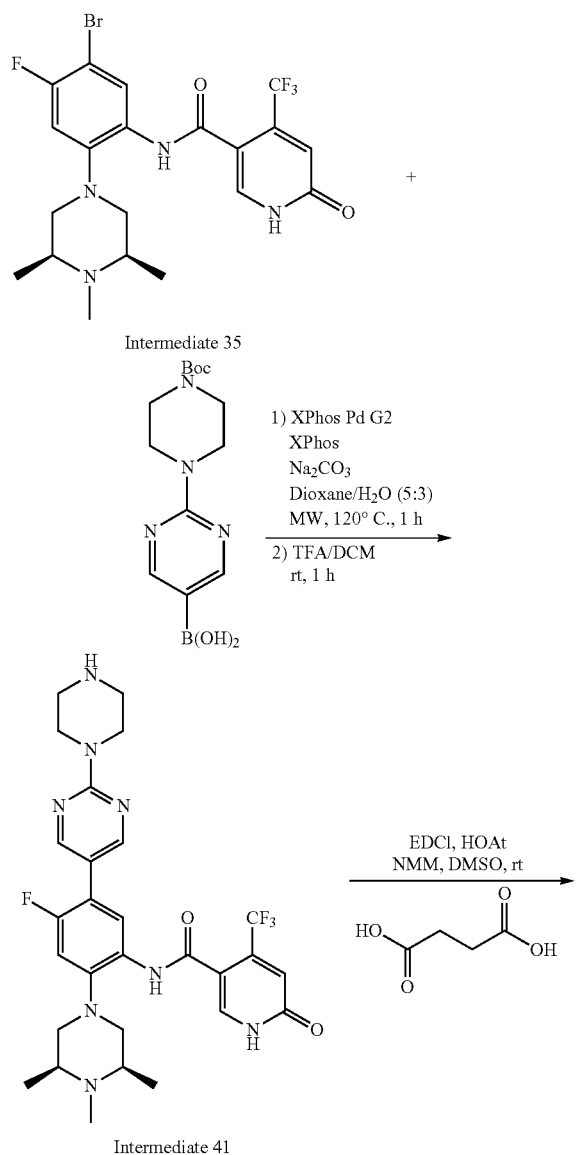

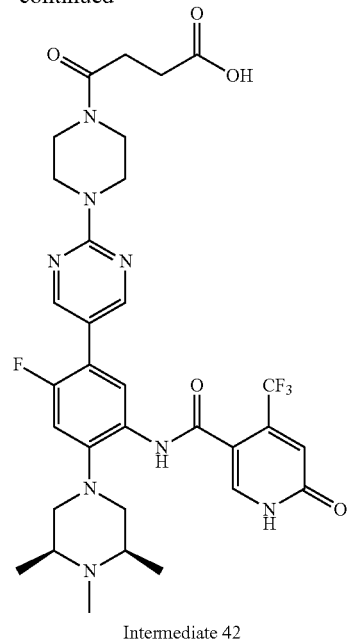

Intermediate 42

To a solution of Intermediate 35 (WO2017147700A1) (505 mg, 1 mmol) and (2-(4-(tert-butoxycarbonyl)piperazin-1-yl)pyrimidin-5-yl)boronic acid (924 mg, 3 mmol, 3.0 euqiv) in 8 mL of 1,4-dioxane/H$_2$O (5:3) were added sodium carbonate (1060 mg, 10 mmol, 10 equiv), XPhos (95.2 mg, 0.2 mmol, 0.2 equiv), and XPhos Pd G2 (157 mg, 0.2 mmol, 0.2 equiv). The reaction was heated to 120° C. for 1 h under Microwave. The solvent was removed and purified by reverse phase ISCO (10%-100% methanol/0.1% TFA in H$_2$O) to afford product as white solid. This product was dissolved in DCM (10 mL) and TFA (10 mL). The resulting mixture was stirring for 1 h. Then, it was concentrated and purified by reverse phase ISCO (10%-100% methanol/0.1% TFA in H$_2$O) to afford Intermediate 41 as white solid in TFA salt form (461 mg, yield 78%). HRMS (m/z) for $C_{28}H_{33}F_4N_8O_2^+$ [M+H]$^+$: calculated 589.2657. found 589.2614. To the solution of intermediate 41 (461 mg, 0.78 mmol) in DMSO (5 mL) were added succinic acid (185 mg, 1.56 mmol, 2.0 equiv), EDCI (1-ethyl-3-(3-dimethylamino-propyl)carbodiimide) (225 mg, 1.17 mmol, 1.5 equiv), HOAt (1-hydroxy-7-azabenzo-triazole) (159 mg, 1.17 mmol, 1.5 equiv), and NMM (N-Methylmorpholine) (236 mg, 2.34 mmol, 3.0 equiv). After being stirring overnight at room temperature, the resulting mixture was purified by reverse phase ISCO (10%-100% methanol/0.1% TFA in H$_2$O) to afford Intermediate 42 (XF078-60) as white solid in TFA salt form (318 mg, yield 59%). $^1$H NMR (600 MHz, CD$_3$OD) δ 8.57 (s, 2H), 8.02 (s, 1H), 7.96 (d, J=8.1 Hz, 1H), 7.17 (d, J=11.6 Hz, 1H), 6.89 (s, 1H), 3.91 (dd, J=6.7, 3.9 Hz, 2H), 3.80 (dd, J=6.7, 4.0 Hz, 2H), 3.64 (dt, J=19.4, 5.4 Hz, 4H), 3.56 (ddd, J=10.3, 6.6, 3.3 Hz, 2H), 3.34 (s, 2H), 3.03-2.89 (m, 5H), 2.70 (dd, J=7.5, 5.4 Hz, 2H), 2.60 (dd, J=7.4, 5.3 Hz, 2H), 1.43 (d, J=6.4 Hz, 6H). HRMS (m/z) for $C_{32}H_{37}F_4N_8O_5^+$ [M+H]$^+$: calculated 689.2818. found 689.2833.

Example 243: Synthesis of XF078-61
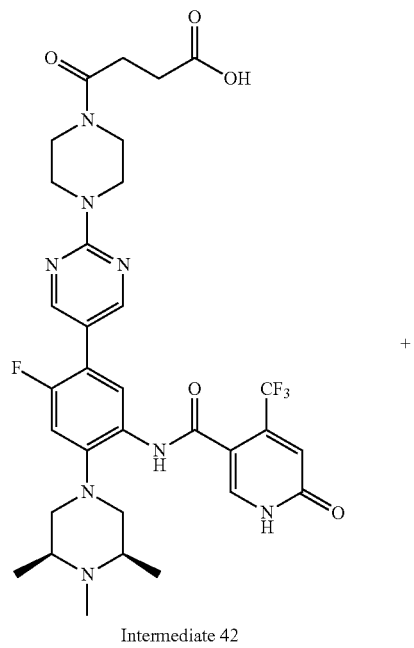
Intermediate 42
+
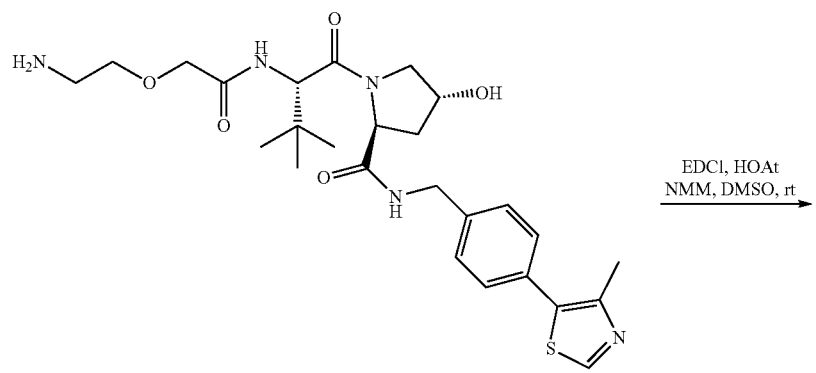
VHL-CH₂-PEG1-NH₂

-continued

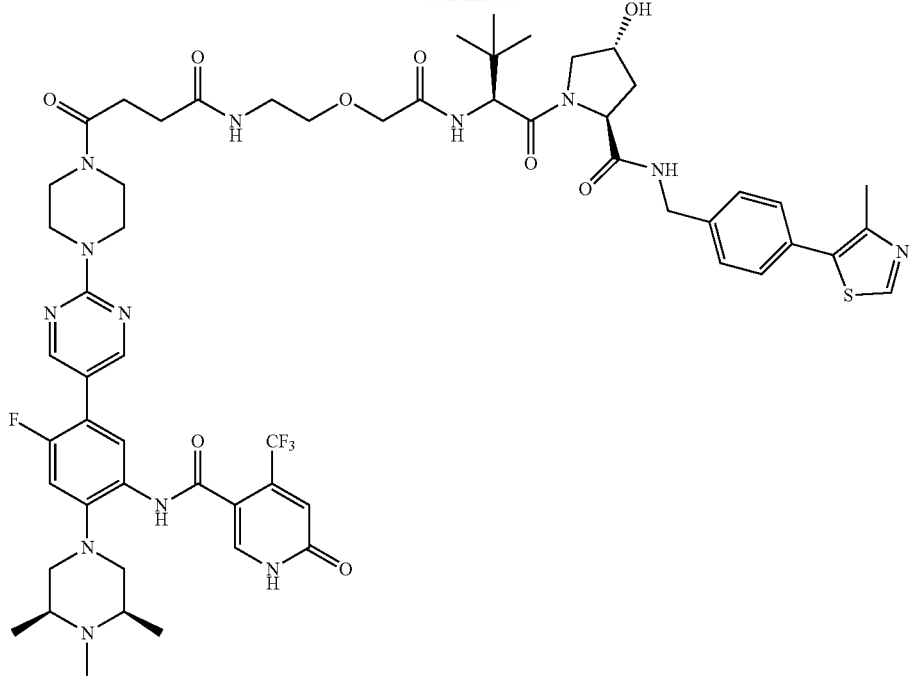

XF078-61

To the solution of intermediate 42 (10.4 mg, 0.015 mmol) in DMSO (1 mL) were added VHL-CH2-PEG1-NH$_2$ (8.3 mg, 0.015 mmol, 1.0 equiv), EDCI (1-ethyl-3-(3-dimethyl-aminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv). After being stirring overnight at room temperature, the resulting mixture was purified by preparative HPLC (10%-100% methanol/0.1% TFA in H$_2$O) to afford XF078-61 as white solid in TFA salt form (7.8 mg, yield 43%). $^1$H NMR (800 MHz, CD$_3$OD) δ 8.96 (s, 1H), 8.58 (s, 2H), 8.04 (s, 1H), 7.95 (d, J=8.0 Hz, 1H), 7.53-7.38 (m, 4H), 7.20 (d, J=11.5 Hz, 1H), 6.96 (s, 1H), 4.74 (s, 1H), 4.67-4.48 (m, 3H), 4.38 (d, J=15.5 Hz, 1H), 4.17-4.07 (m, 1H), 4.00 (d, J=15.3 Hz, 1H), 3.97-3.78 (m, 6H), 3.75-3.58 (m, 6H), 3.56-3.49 (m, 2H), 3.45 (t, J=5.2 Hz, 2H), 3.39 (d, J=13.1 Hz, 2H), 3.07-2.90 (m, 5H), 2.81-2.67 (m, 2H), 2.67-2.53 (m, 2H), 2.50 (s, 3H), 2.29-2.16 (m, 1H), 2.13 (ddd, J=13.3, 9.2, 4.3 Hz, 1H), 1.47 (d, J=6.5 Hz, 6H), 1.22-0.82 (m, 9H). HRMS (m/z) for C$_{58}$H$_{72}$F$_4$N$_{13}$O$_9$S$^+$ [M+H]$^+$: calculated 1202.5227. found 1202.5233.

Example 244: Synthesis of XF078-62

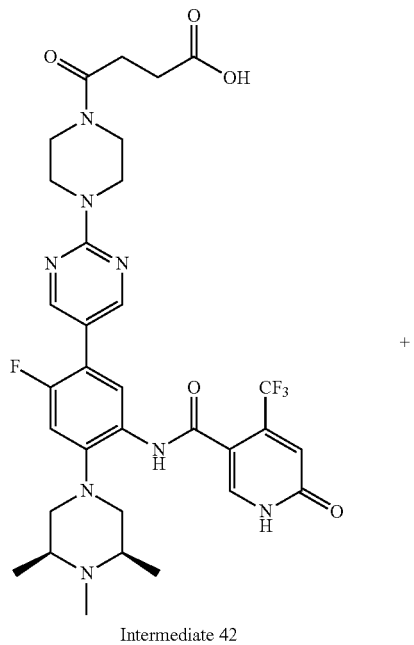

Intermediate 42

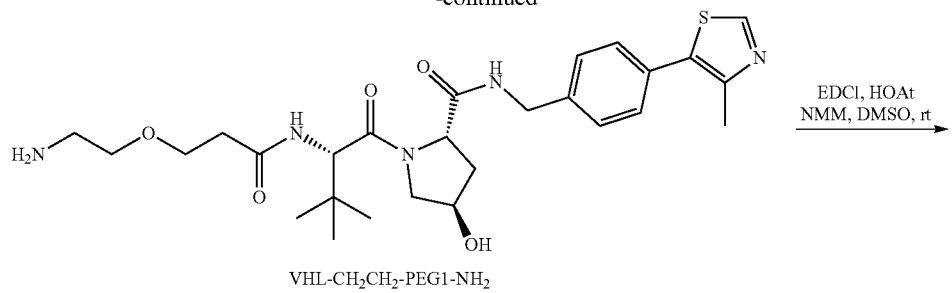

VHL-CH₂CH₂-PEG1-NH₂

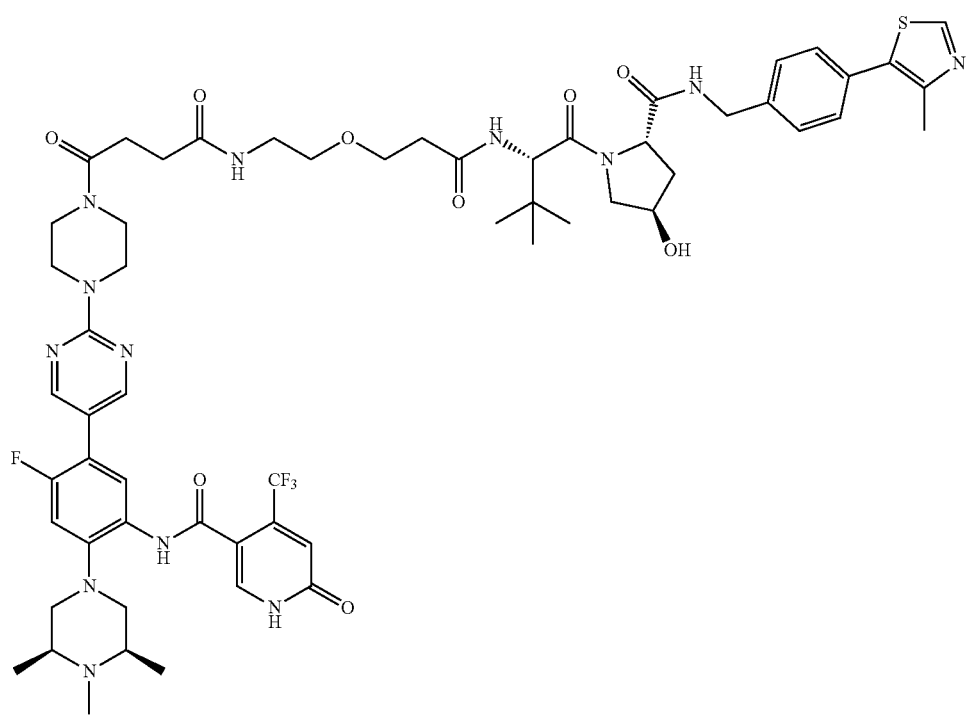

XF078-62

XF078-62 was synthesized following the standard procedures for preparing XF078-61 from intermediate 42 (10.4 mg, 0.015 mmol), VHL-CH₂CH₂-PEG1-NH₂ (11.3 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-62 was obtained as white solid in TFA salt form (11.7 mg, yield 64%). ¹H NMR (800 MHz, CD₃OD) δ 8.99 (s, 1H), 8.57 (s, 2H), 8.04 (d, J=6.8 Hz, 1H), 7.95 (d, J=8.0 Hz, 1H), 7.62-7.36 (m, 4H), 7.20 (d, J=11.5 Hz, 1H), 6.96 (s, 1H), 4.72 (s, 1H), 4.68-4.51 (m, 3H), 4.36 (d, J=15.3 Hz, 1H), 4.03-3.89 (m, 3H), 3.84 (q, J=4.4, 3.9 Hz, 3H), 3.74 (t, J=5.8 Hz, 2H), 3.71-3.46 (m, 9H), 3.46-3.35 (m, 5H), 3.04-2.91 (m, 5H), 2.75-2.45 (m, 7H), 2.27 (dd, J=13.2, 7.6 Hz, 1H), 2.12 (ddd, J=13.3, 9.2, 4.4 Hz, 1H), 1.47 (d, J=6.5 Hz, 6H), 1.08 (s, 9H). HRMS (m/z) for $C_{59}H_{74}F_4N_{13}O_9S^+$ [M+H]⁺: calculated 1216.5384. found 1216.5404.

Example 245: Synthesis of XF078-63
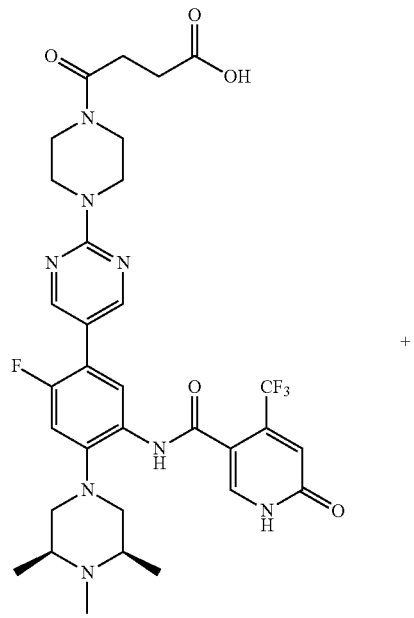
Intermediate 42
+
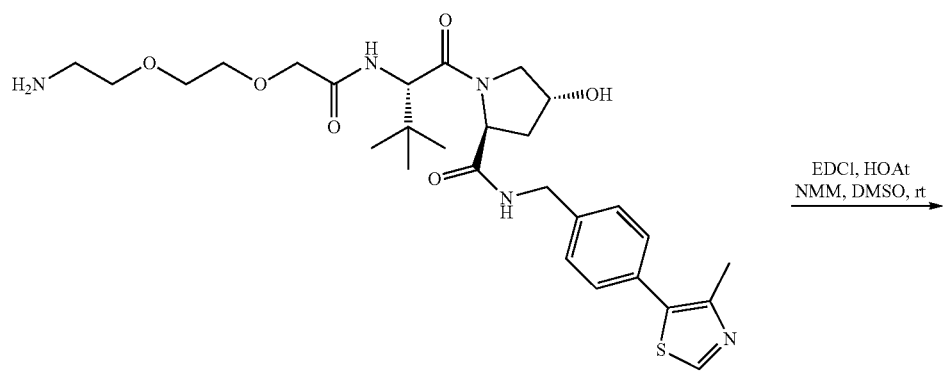
VHL-CH$_2$-PEG2-NH$_2$

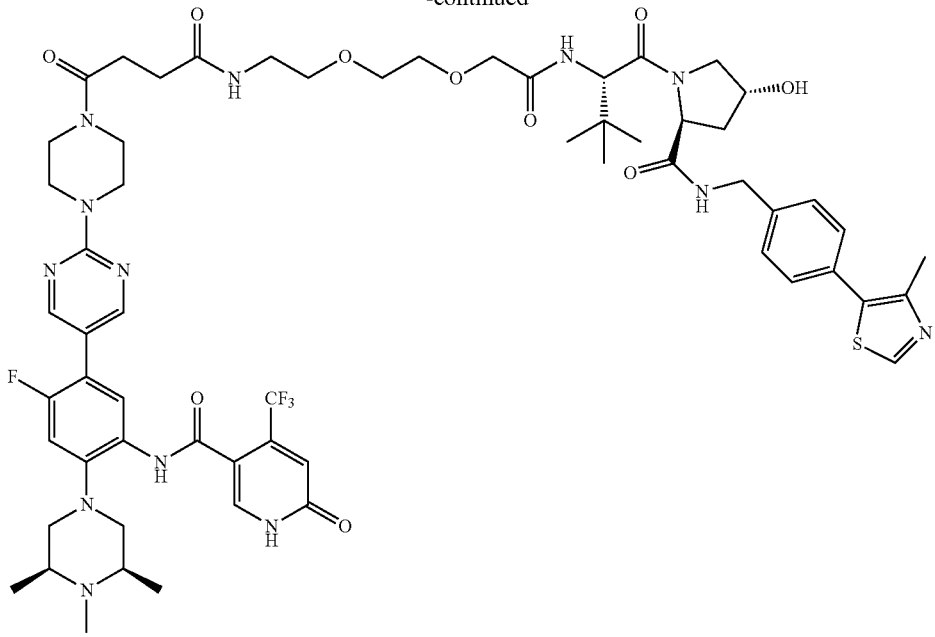

XF078-63

XF078-63 was synthesized following the standard procedures for preparing XF078-61 from intermediate 42 (10.4 mg, 0.015 mmol), VHL-CH$_2$-PEG2-NH$_2$ (9.2 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-63 was obtained as white solid in TFA salt form (8.5 mg, yield 45%). $^1$H NMR (800 MHz, CD$_3$OD) δ 8.98 (s, 1H), 8.57 (s, 2H), 8.04 (d, J=3.2 Hz, 1H), 7.95 (d, J=8.0 Hz, 1H), 7.52-7.36 (m, 4H), 7.20 (d, J=11.5 Hz, 1H), 6.96 (s, 1H), 4.69-4.50 (m, 4H), 4.41-4.32 (m, 1H), 4.15-4.01 (m, 2H), 3.99-3.79 (m, 6H), 3.78-3.48 (m, 12H), 3.42-3.36 (m, 4H), 2.99-2.94 (m, 5H), 2.73-2.45 (m, 7H), 2.29 (dd, J=13.2, 7.7 Hz, 1H), 2.13 (ddd, J=13.3, 9.2, 4.3 Hz, 1H), 1.47 (d, J=6.5 Hz, 6H), 1.10 (s, 9H). HRMS (m/z) for C$_{60}$H$_{76}$F$_4$N$_{13}$O$_{10}$S$^+$ [M+H]$^+$: calculated 1246.5489. found 1246.5502.

Example 246: Synthesis of XF078-64

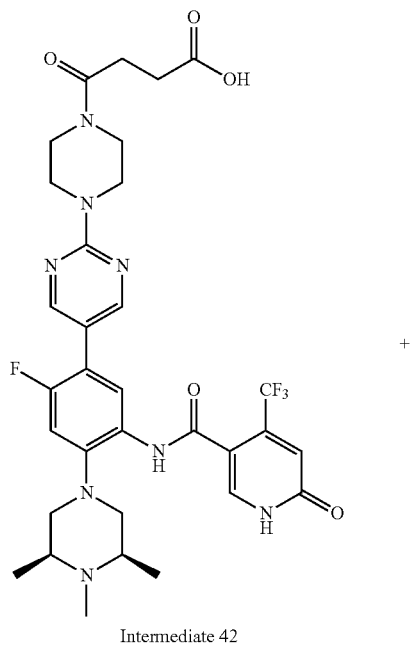

Intermediate 42

+

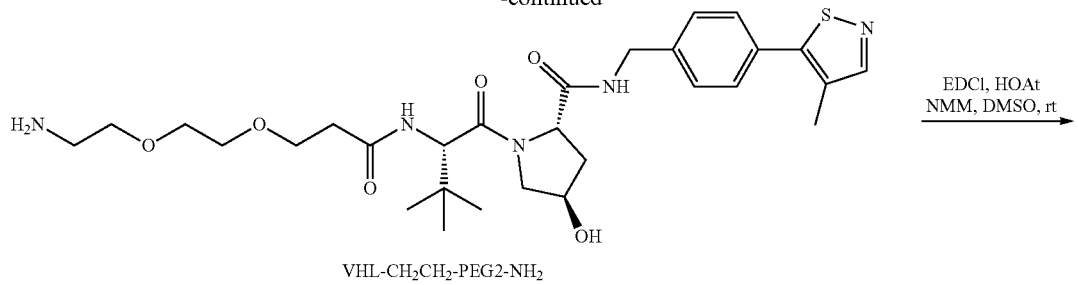

VHL-CH₂CH₂-PEG2-NH₂

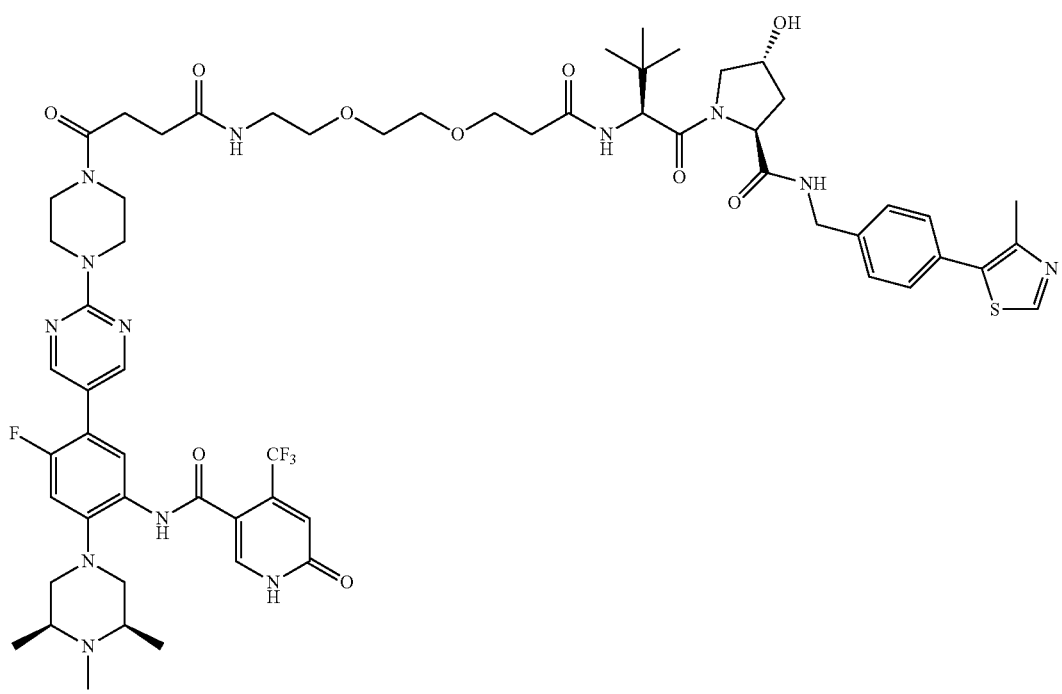

XF078-64

XF078-64 was synthesized following the standard procedures for preparing XF078-61 from intermediate 42 (10.4 mg, 0.015 mmol), VHL-CH₂CH₂-PEG2-NH₂ (12.3 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-64 was obtained as white solid in TFA salt form (9 mg, yield 48%). ¹H NMR (800 MHz, CD₃OD) δ 8.97 (s, 1H), 8.57 (s, 2H), 8.04 (s, 1H), 7.95 (d, J=8.1 Hz, 1H), 7.55-7.39 (m, 4H), 7.20 (d, J=11.5 Hz, 1H), 6.96 (s, 1H), 4.70 (s, 1H), 4.61 (t, J=8.5 Hz, 1H), 4.58-4.48 (m, 2H), 4.40 (d, J=15.4 Hz, 1H), 4.04-3.90 (m, 3H), 3.90-3.80 (m, 3H), 3.80-3.74 (m, 2H), 3.72-3.60 (m, 8H), 3.58-3.50 (m, 4H), 3.43-3.34 (m, 4H), 2.99 (d, J=36.9 Hz, 5H), 2.75 (t, J=7.0 Hz, 2H), 2.67-2.46 (m, 7H), 2.25 (dd, J=13.2, 7.6 Hz, 1H), 2.11 (ddd, J=13.2, 9.1, 4.5 Hz, 1H), 1.47 (d, J=6.5 Hz, 6H), 1.07 (s, 9H). HRMS (m/z) for $C_{61}H_{78}F_4N_{13}O_{10}S^+$ [M+H]⁺: calculated 1260.5646, found 1260.5615.

Example 247: Synthesis of XF078-65
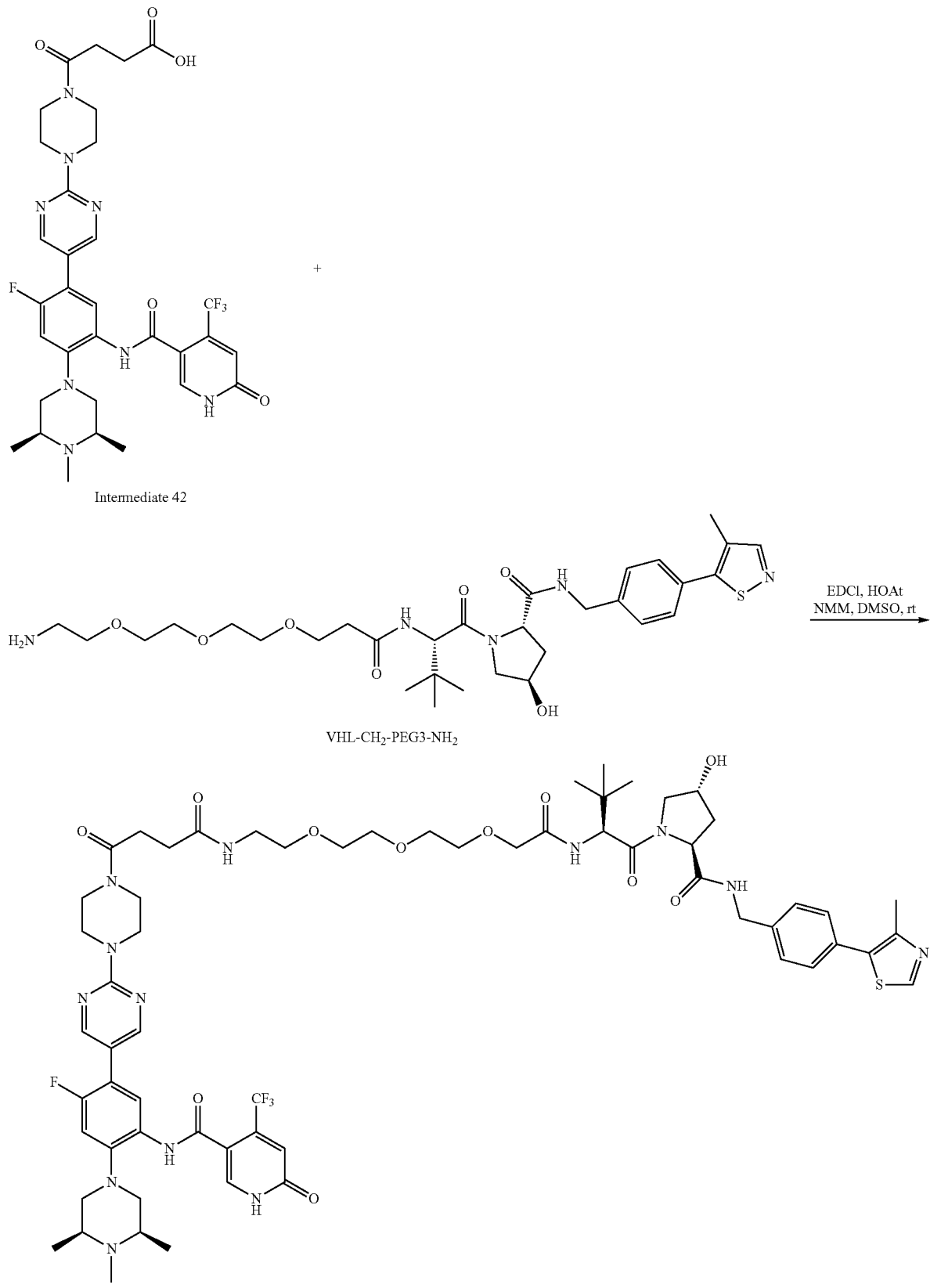

XF078-65 was synthesized following the standard procedures for preparing XF078-61 from intermediate 42 (10.4 mg, 0.015 mmol), VHL-CH$_2$-PEG3-NH$_2$ (12.7 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-65 was obtained as white solid in TFA salt form (8.5 mg, yield 44%). $^1$H NMR (800 MHz, CD$_3$OD) δ 8.98 (s, 1H), 8.58 (s, 2H), 8.04 (d, J=6.5 Hz, 1H), 7.95 (d, J=8.1 Hz, 1H), 7.56-7.36 (m, 4H), 7.20 (d, J=11.6 Hz, 1H), 6.96 (s, 1H), 4.73 (s, 1H), 4.67-4.49 (m, 3H), 4.41 (d, J=15.4 Hz, 1H), 4.15-4.04 (m, 2H), 4.01-3.80 (m, 6H), 3.80-3.61 (m, 12H), 3.60-3.48 (m, 4H), 3.44-3.34 (m, 4H), 2.99 (d, J=39.9 Hz, 5H), 2.75 (t, J=6.9 Hz, 2H), 2.61-2.44 (m, 5H), 2.35-2.22 (m, 1H), 2.19-2.00 (m, 1H), 1.47 (d, J=6.5 Hz, 6H), 1.07 (s, 9H). HRMS (m/z) for C$_{62}$H$_{80}$F$_4$N$_{13}$O$_{11}$S$^+$ [M+H]$^+$: calculated 1290.5752. found 1290.5724.

Example 248: Synthesis of XF078-66

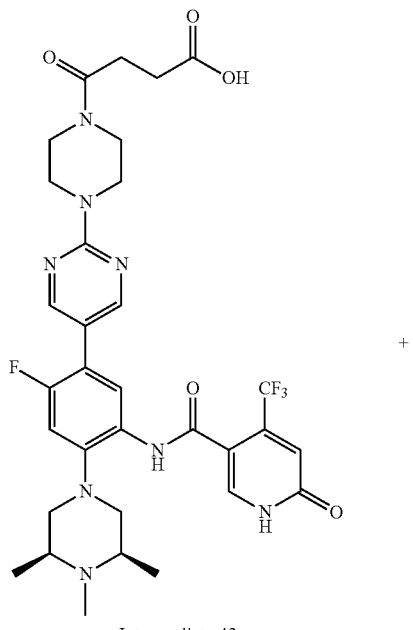

Intermediate 42

+

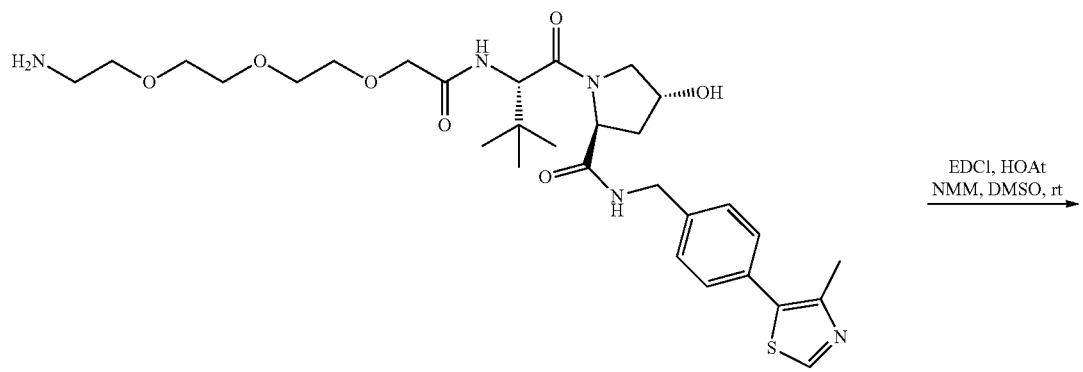

VHL-CH$_2$CH$_2$-PEG3-NH$_2$

-continued

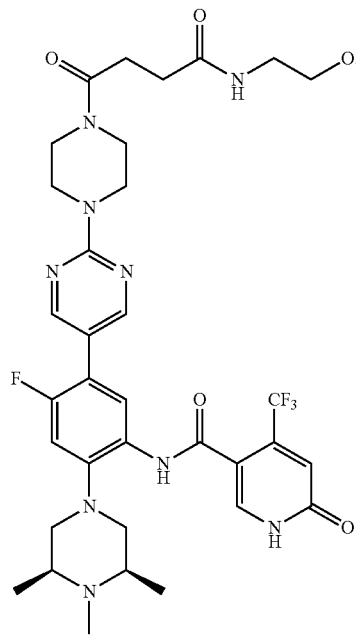
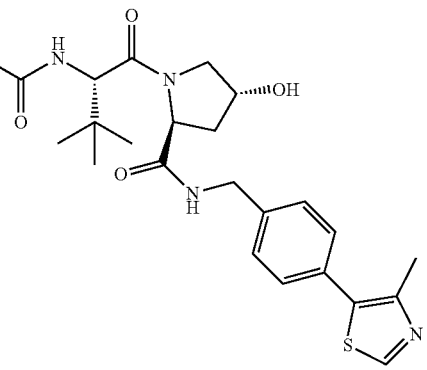

XF078-66

XF078-66 was synthesized following the standard procedures for preparing XF078-61 from intermediate 42 (10.4 mg, 0.015 mmol), VHL-CH$_2$CH$_2$-PEG3-NH$_2$ (12.2 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-66 was obtained as white solid in TFA salt form (10.9 mg, yield 56%). $^1$H NMR (800 MHz, CD$_3$OD) δ 8.99 (s, 1H), 8.58 (s, 2H), 8.04 (s, 1H), 7.95 (d, J=8.0 Hz, 1H), 7.53-7.38 (m, 4H), 7.20 (d, J=11.5 Hz, 1H), 6.96 (s, 1H), 4.68 (s, 1H), 4.63-4.49 (m, 3H), 4.39 (d, J=15.4 Hz, 1H), 4.01-3.72 (m, 8H), 3.72-3.58 (m, 12H), 3.59-3.49 (m, 4H), 3.44-3.34 (m, 4H), 3.13-2.88 (m, 5H), 2.76 (t, J=6.9 Hz, 2H), 2.68-2.43 (m, 7H), 2.24 (dd, J=13.3, 7.6 Hz, 1H), 2.11 (ddd, J=13.3, 9.1, 4.4 Hz, 1H), 1.47 (d, J=6.5 Hz, 6H), 1.06 (s, 9H). HRMS (m/z) for C$_{63}$H$_{82}$F$_4$N$_{13}$O$_{11}$S$^+$ [M+H]$^+$: calculated 1304.5908. found 1304.5888.

Example 249: Synthesis of XF078-67

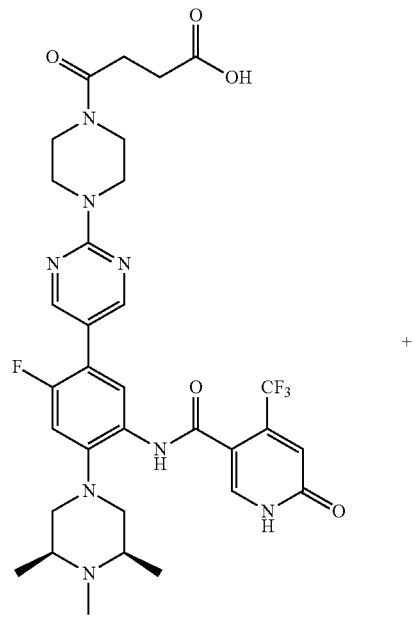

Intermediate 42

-continued

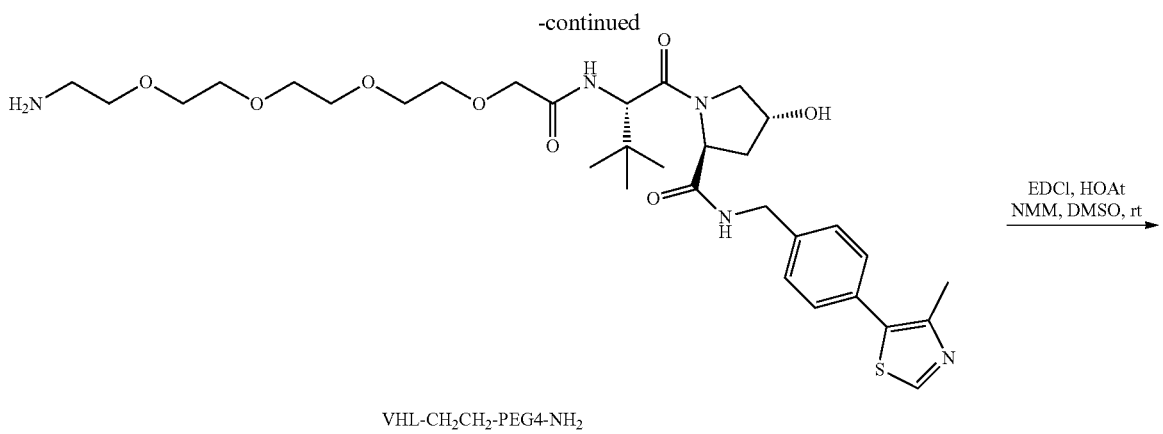

VHL-CH₂CH₂-PEG4-NH₂

EDCl, HOAt
NMM, DMSO, rt
→

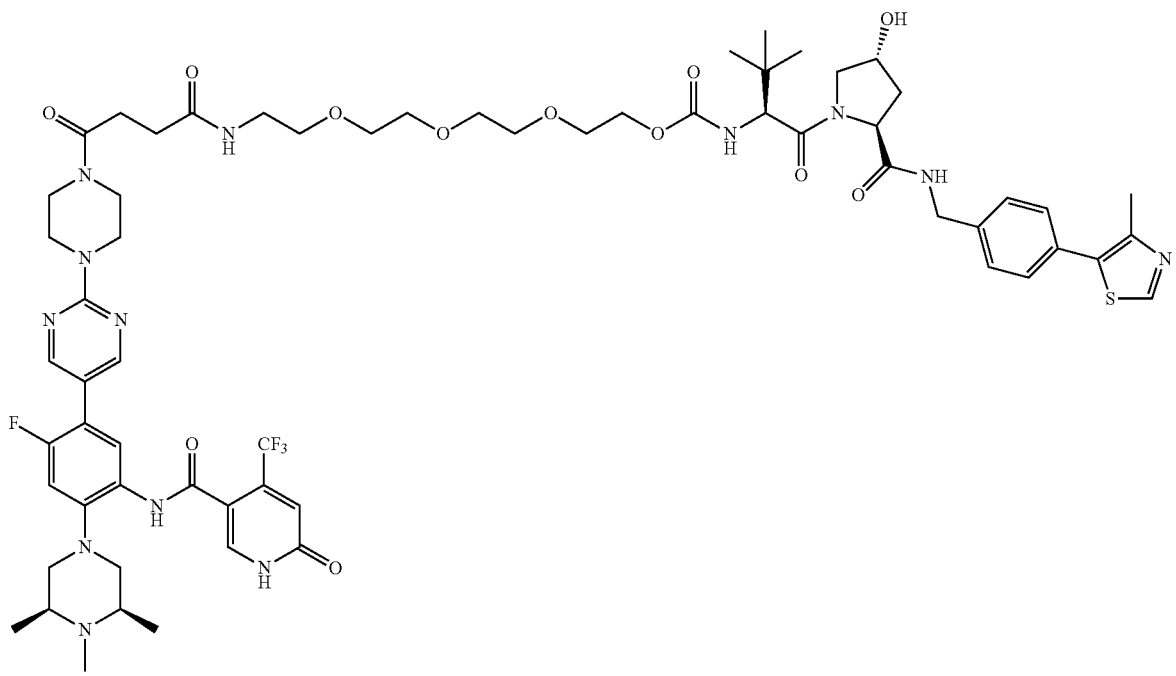

XF078-67

XF078-67 was synthesized following the standard procedures for preparing XF078-61 from intermediate 42 (10.4 mg, 0.015 mmol), VHL-CH₂CH₂-PEG4-NH₂ (10.7 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-67 was obtained as white solid in TFA salt form (13.8 mg, yield 68%). $^1$H NMR (800 MHz, CD$_3$OD) δ 9.00 (s, 1H), 8.58 (s, 2H), 8.04 (d, J=6.7 Hz, 1H), 7.95 (d, J=8.1 Hz, 1H), 7.55-7.39 (m, 4H), 7.20 (d, J=11.5 Hz, 1H), 6.96 (s, 1H), 4.68 (s, 1H), 4.62-4.49 (m, 3H), 4.38 (d, J=15.5 Hz, 1H), 4.02-3.84 (m, 5H), 3.86-3.59 (m, 19H), 3.55 (dt, J=28.6, 5.4 Hz, 4H), 3.41-3.35 (m, 4H), 2.99 (d, J=35.9 Hz, 5H), 2.76 (t, J=6.9 Hz, 2H), 2.64-2.45 (m, 7H), 2.24 (dd, J=13.3, 7.6 Hz, 1H), 2.11 (ddd, J=13.3, 9.1, 4.5 Hz, 1H), 1.47 (d, J=6.5 Hz, 6H), 1.06 (s, 9H). HRMS (m/z) for C$_{65}$H$_{86}$F$_4$N$_{13}$O$_{12}$S$^+$ [M+H]$^+$: calculated 1348.6170. found 1348.6153.

Example 250: Synthesis of XF078-68
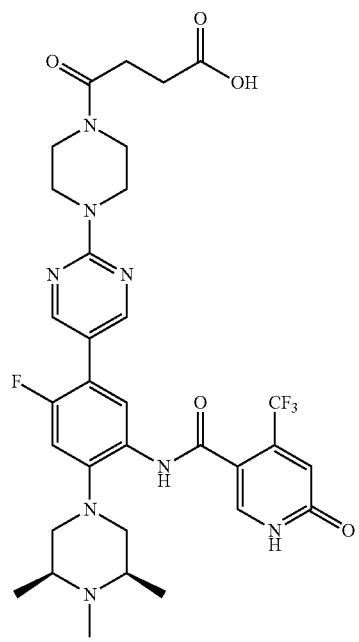
Intermediate 42
+
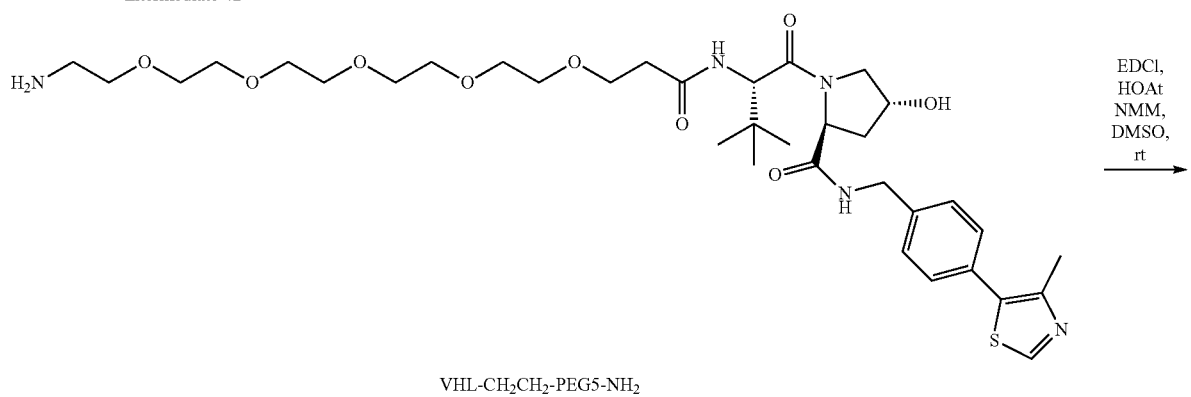
VHL-CH$_2$CH$_2$-PEG5-NH$_2$
EDCl, HOAt NMM, DMSO, rt
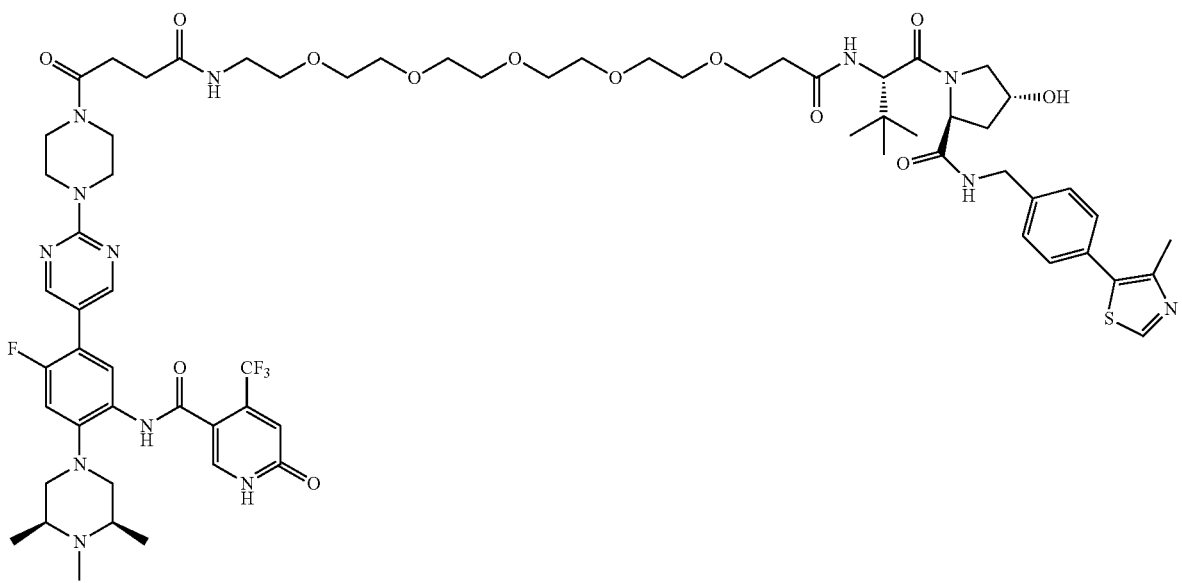
XF078-68 le;5qXF078-68 was synthesized following the standard procedures for preparing XF078-61 from intermediate 42 (10.4 mg, 0.015 mmol), VHL-CH$_2$CH$_2$-PEG5-NH$_2$ (14.2 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-68 was obtained as white solid in TFA salt form (9.9 mg, yield 47%). $^1$H NMR (800 MHz, CD$_3$OD) δ 8.99 (s, 1H), 8.58 (s, 2H), 8.04 (d, J=6.4 Hz, 1H), 7.95 (d, J=8.0 Hz, 1H), 7.51-7.39 (m, 4H), 7.20 (d, J=11.5 Hz, 1H), 6.96 (s, 1H), 4.67 (s, 1H), 4.63-4.49 (m, 3H), 4.38 (d, J=15.5 Hz, 1H), 4.02-3.86 (m, 5H), 3.82 (dd, J=10.8, 3.9 Hz, 1H), 3.78-3.50 (m, 26H), 3.44-3.37 (m, 4H), 3.10-2.89 (m, 5H), 2.76 (t, J=6.9 Hz, 2H), 2.65-2.46 (m, 7H), 2.24 (dd, J=13.3, 7.7 Hz, 1H), 2.11 (ddd, J=13.3, 9.1, 4.5 Hz, 1H), 1.47 (d, J=6.5 Hz, 6H), 1.06 (s, 9H). HRMS (m/z) for C$_{67}$H$_{90}$F$_4$N$_{13}$O$_{13}$S$^+$ [M+H]$^+$: calculated 1392.6432. found 1392.6411.

Example 251: Synthesis of XF078-69

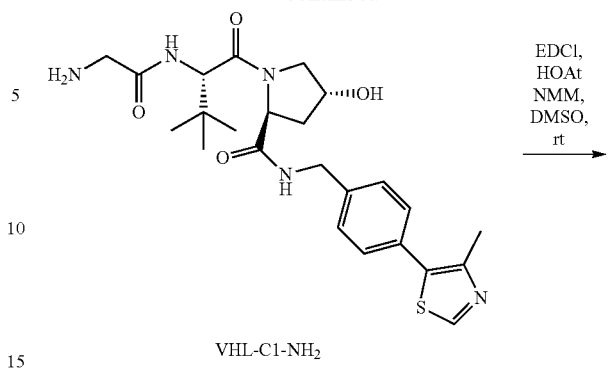

VHL-C1-NH$_2$

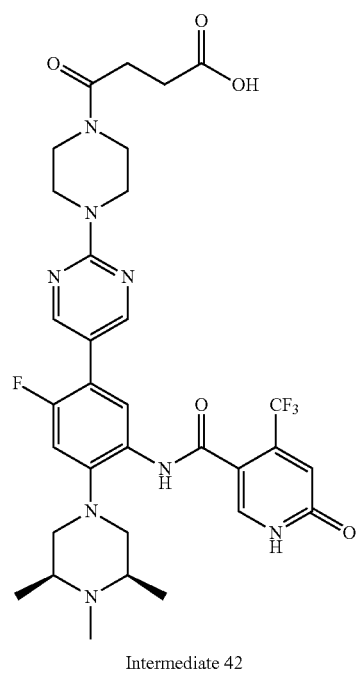

Intermediate 42

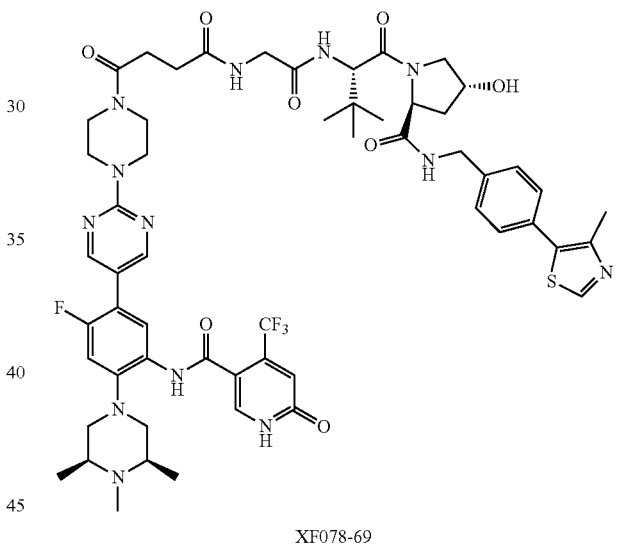

XF078-69

XF078-69 was synthesized following the standard procedures for preparing XF078-61 from intermediate 42 (10.4 mg, 0.015 mmol), VHL-C1-NH$_2$ (10.7 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-69 was obtained as white solid in TFA salt form (9.9 mg, yield 57%). $^1$H NMR (800 MHz, CD$_3$OD) δ 8.97 (s, 1H), 8.56 (s, 2H), 8.04 (s, 1H), 7.95 (d, J=8.0 Hz, 1H), 7.53-7.38 (m, 4H), 7.20 (d, J=11.6 Hz, 1H), 6.96 (s, 1H), 4.68 (s, 1H), 4.61-4.47 (m, 3H), 4.39 (d, J=15.4 Hz, 1H), 4.02-3.61 (m, 12H), 3.56-3.48 (m, 2H), 3.42-3.34 (m, 2H), 3.05-2.90 (m, 5H), 2.81 (t, J=6.8 Hz, 2H), 2.65-2.56 (m, 2H), 2.48 (s, 3H), 2.24 (t, J=10.5 Hz, 1H), 2.10 (ddd, J=13.3, 9.1, 4.5 Hz, 1H), 1.47 (d, J=6.5 Hz, 6H), 1.07 (s, 9H). HRMS (m/z) for C$_{56}$H$_{68}$F$_4$N$_{13}$O$_8$S$^+$ [M+H]$^+$: calculated 1158.4965. found 1158.4968.

Example 252: Synthesis of XF078-70

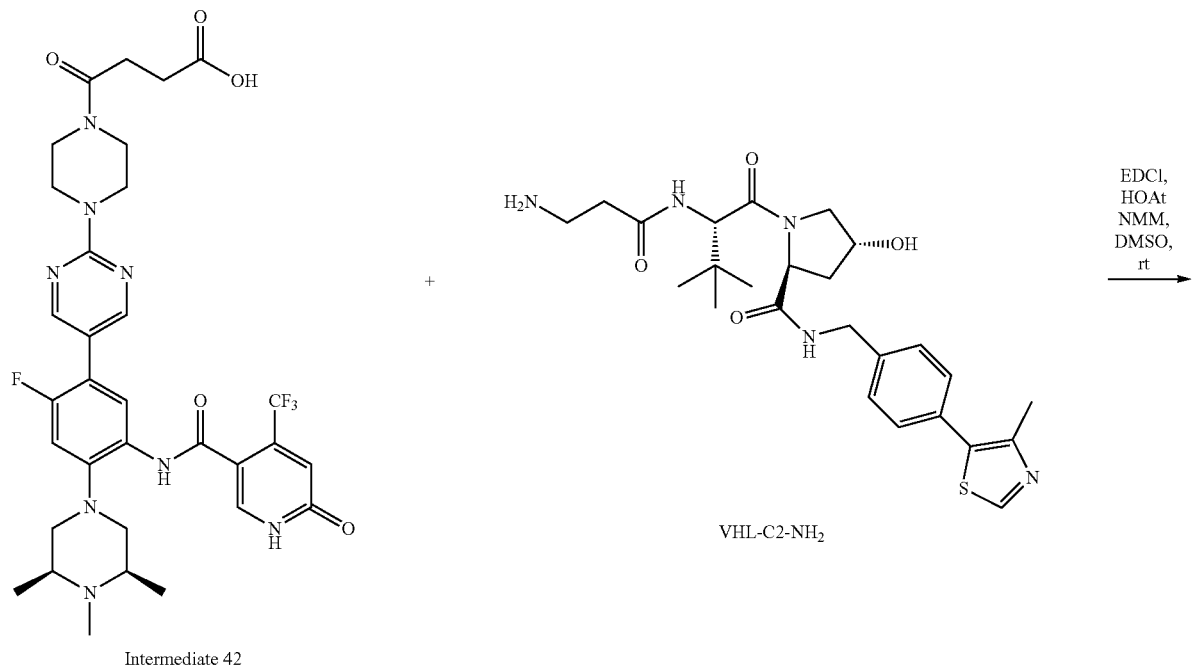

Intermediate 42

VHL-C2-NH₂

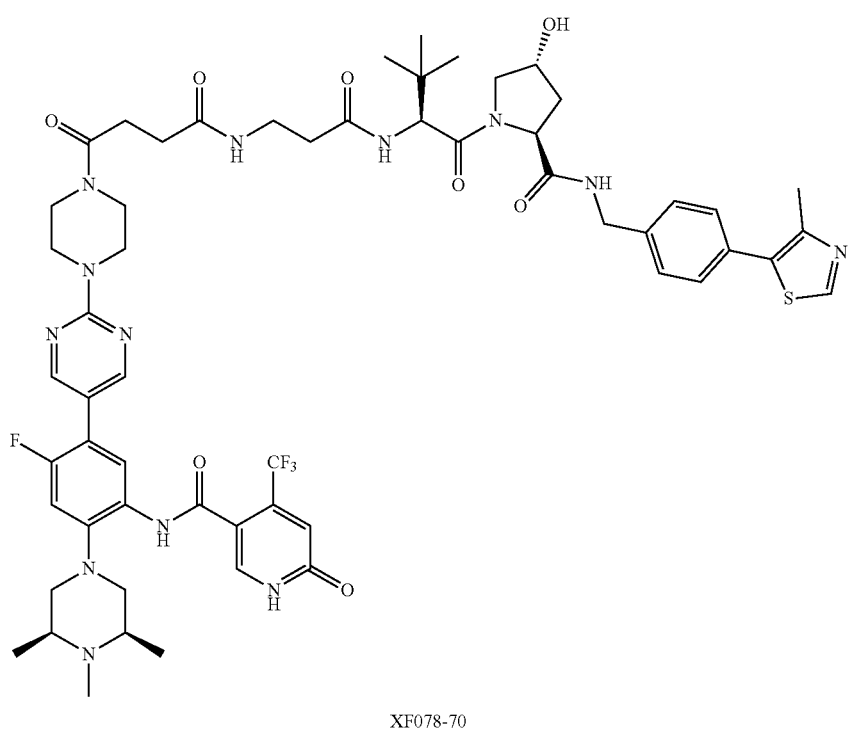

XF078-70

XF078-70 was synthesized following the standard procedures for preparing XF078-61 from intermediate 42 (10.4 mg, 0.015 mmol), VHL-C2-NH₂ (10.9 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-70 was obtained as white solid in TFA salt form (15.6 mg, yield 89%). $^1$H NMR (800 MHz, CD$_3$OD) δ 8.98 (s, 1H), 8.57 (s, 2H), 8.05 (s, 1H), 7.95 (d, J=8.0 Hz, 1H), 7.56-7.37 (m, 4H), 7.20 (d, J=11.5 Hz, 1H), 6.96 (s, 1H), 4.69-4.49 (m, 4H), 4.37 (d, J=15.4 Hz, 1H), 3.99-3.89 (m, 3H), 3.89-3.79 (m, 3H), 3.70-3.59 (m, 6H), 3.58-3.48 (m, 2H), 3.45-3.38 (m, 2H), 2.99-2.93 (m, 5H), 2.75 (h, J=9.2 Hz, 2H), 2.59-2.43 (m, 7H), 2.26 (dd, J=13.1, 7.6 Hz, 1H), 2.12 (ddd, J=13.3, 9.2, 4.4 Hz, 1H), 1.47 (d, J=6.5 Hz, 6H), 1.07 (s, 9H). HRMS (m/z) for $C_{57}H_{70}F_4N_{13}O_8S^+$ [M+H]$^+$: calculated 1172.5122. found 1172.5134.

Example 253: Synthesis of XF078-71

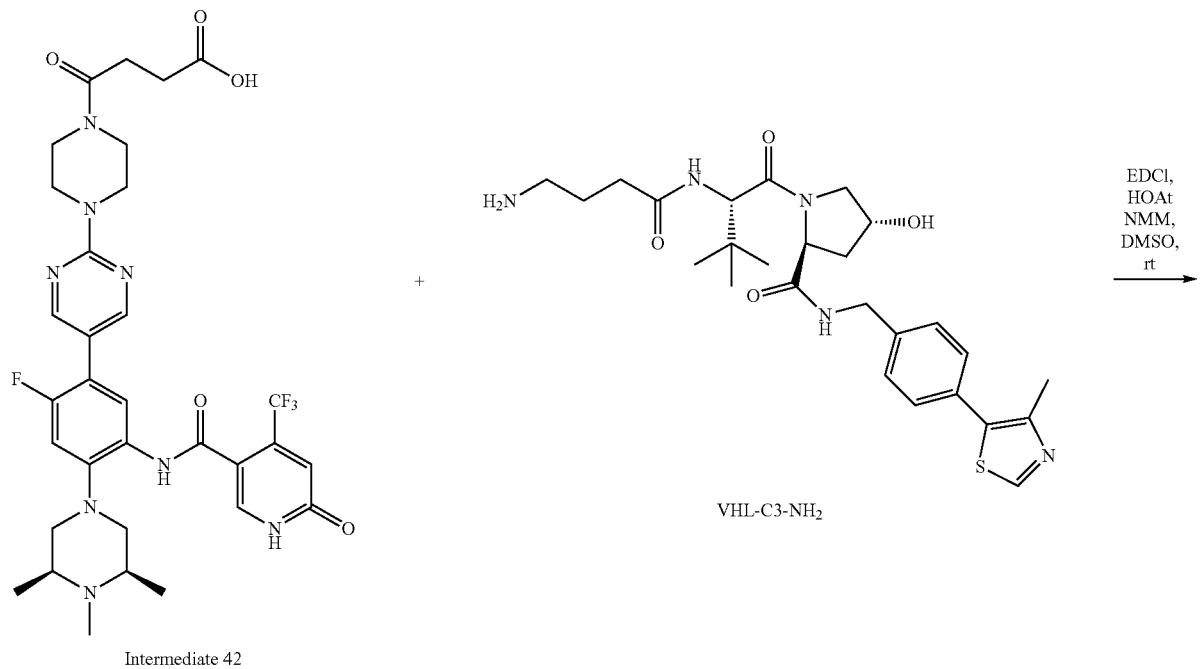

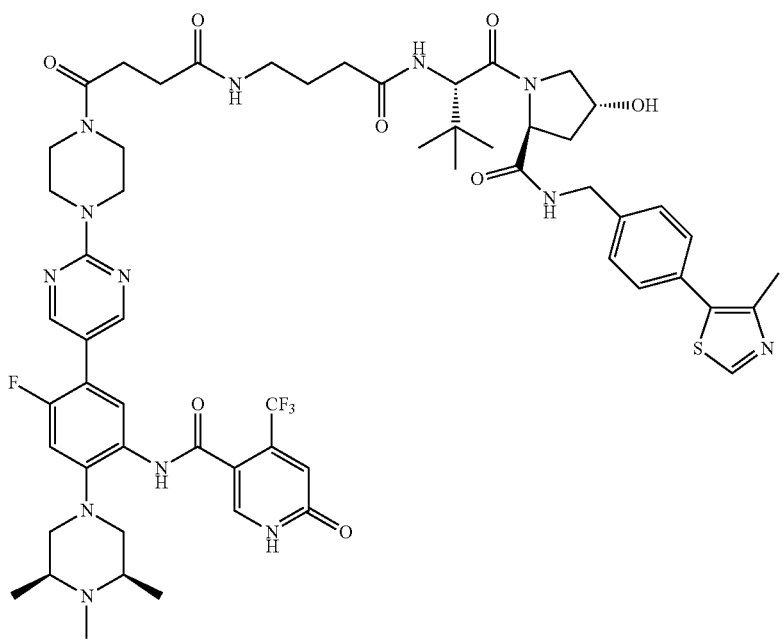

XF078-71 was synthesized following the standard procedures for preparing XF078-61 from intermediate 42 (10.4 mg, 0.015 mmol), VHL-C3-NH$_2$ (11.1 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-71 was obtained as white solid in TFA salt form (11.5 mg, yield 65%). $^1$H NMR (800 MHz, CD$_3$OD) δ 8.97 (s, 1H), 8.55 (s, 2H), 8.04 (s, 1H), 7.95 (d, J=8.1 Hz, 1H), 7.56-7.39 (m, 4H), 7.20 (d, J=11.5 Hz, 1H), 6.96 (s, 1H), 4.67-4.55 (m, 3H), 4.52 (s, 1H), 4.38 (d, J=15.4 Hz, 1H), 4.03-3.78 (m, 6H), 3.77-3.62 (m, 4H), 3.58-3.50 (m, 2H), 3.39 (d, J=13.1 Hz, 2H), 3.23-3.19 (m, 2H), 3.05-2.92 (m, 5H), 2.81-2.73 (m, 2H), 2.57-2.44 (m, 5H), 2.40-2.30 (m, 2H), 2.24 (dd, J=13.2, 7.6 Hz, 1H), 2.11 (ddd, J=13.3, 9.1, 4.5 Hz, 1H), 1.88-1.75 (m, 2H), 1.47 (d, J=6.5 Hz, 6H), 1.07 (s, 9H). HRMS (m/z) for C$_{58}$H$_{72}$F$_4$N$_{13}$O$_8$S$^+$ [M+H]$^+$: calculated 1186.5278. found 1186.5266.

Example 254: Synthesis of XF078-72

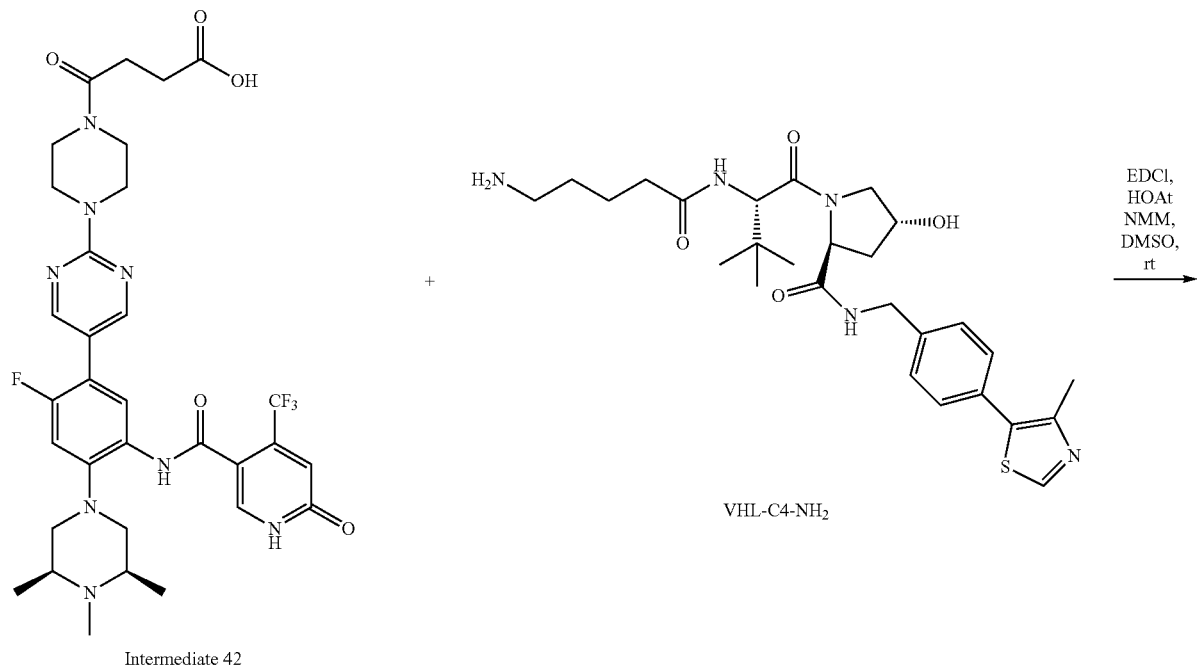

Intermediate 42

VHL-C4-NH₂

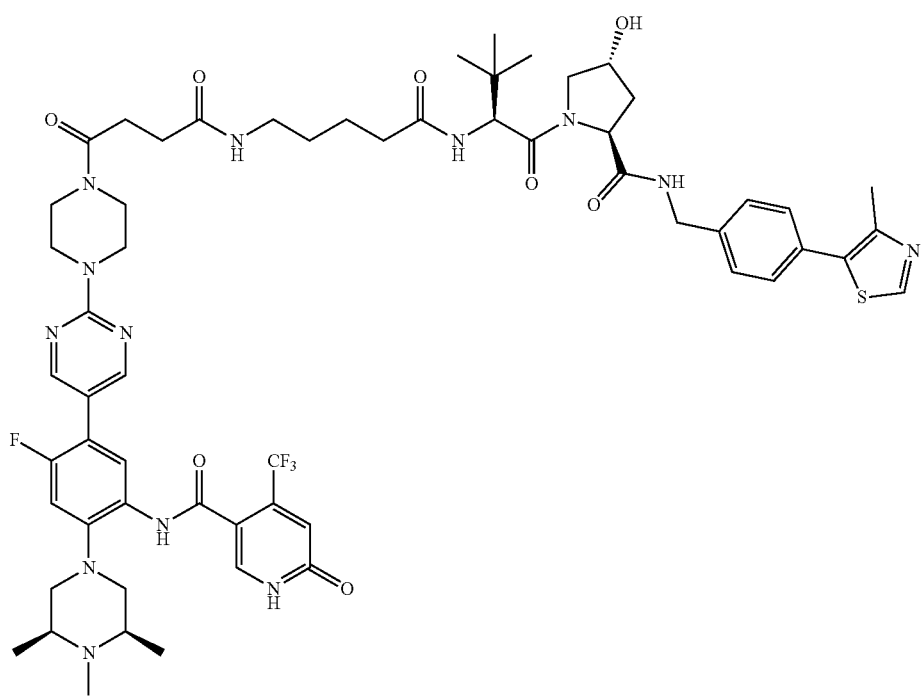

XF078-72

XF078-72 was synthesized following the standard procedures for preparing XF078-61 from intermediate 42 (10.4 mg, 0.015 mmol), VHL-C4-NH₂ (8.5 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-72 was obtained as white solid in TFA salt form (9 mg, yield 50%). $^1$H NMR (800 MHz, CD$_3$OD) δ 9.00 (s, 1H), 8.58 (s, 2H), 8.04 (s, 1H), 7.95 (d, J=8.0 Hz, 1H), 7.56-7.37 (m, 4H), 7.20 (d, J=11.5 Hz, 1H), 6.96 (s, 1H), 4.65 (s, 1H), 4.64-4.52 (m, 3H), 4.39 (d, J=15.4 Hz, 1H), 4.02-3.80 (m, 6H), 3.73-3.62 (m, 4H), 3.53 (s, 2H), 3.39 (d, J=13.1 Hz, 2H), 3.21 (t, J=7.0 Hz, 2H), 3.04-2.92 (m, 5H), 2.76 (t, J=6.9 Hz, 2H), 2.59-2.44 (m, 5H), 2.33 (h, J=6.8 Hz, 2H), 2.25 (t, J=10.4 Hz, 1H), 2.11 (ddd, J=13.3, 9.1, 4.5 Hz, 1H), 1.70-1.62 (m, 2H), 1.57-1.52 (m, 2H), 1.47 (d, J=6.5 Hz, 6H), 1.07 (s, 9H). HRMS (m/z) for $C_{59}H_{74}F_4N_{13}O_8S^+$ [M+H]$^+$: calculated 1200.5435. found 1200.5454.

Example 255: Synthesis of XF078-73
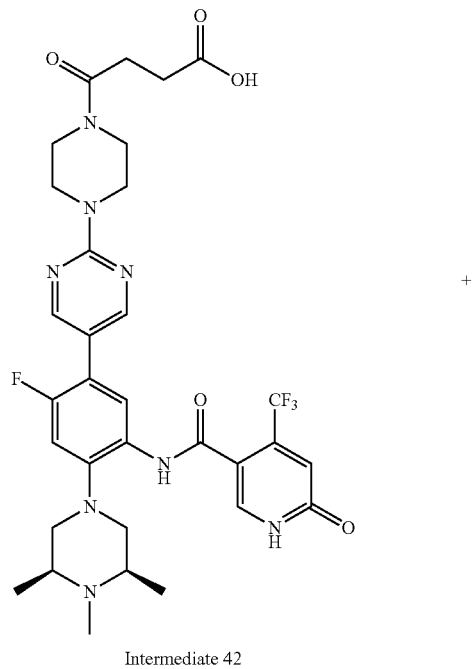
Intermediate 42
+
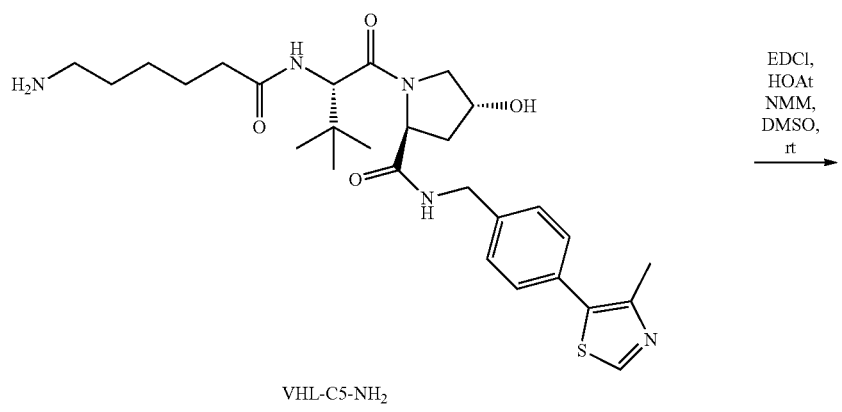
VHL-C5-NH$_2$
EDCl, HOAt NMM, DMSO, rt →

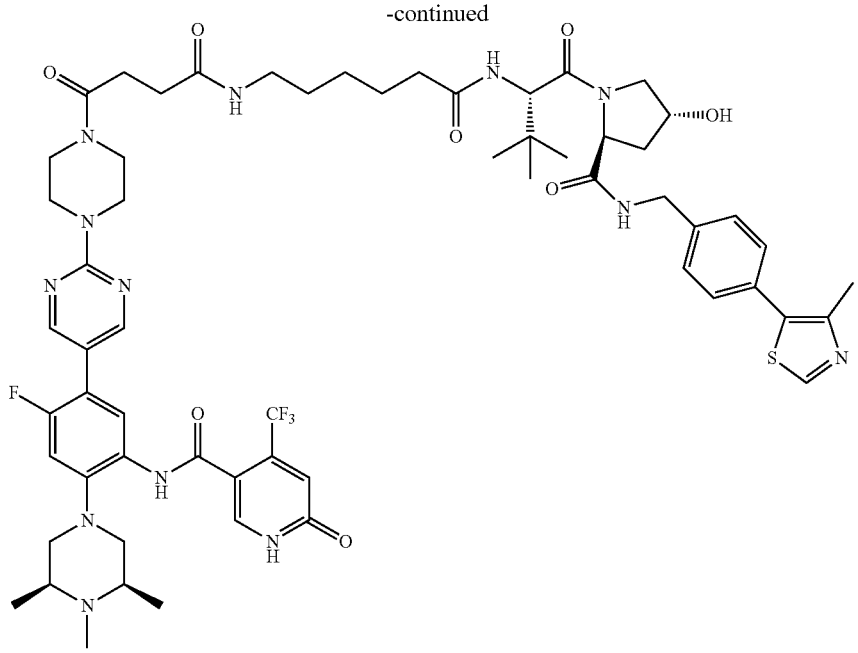

XF078-73

XF078-73 was synthesized following the standard procedures for preparing XF078-61 from intermediate 42 (10.4 mg, 0.015 mmol), VHL-C5-NH$_2$ (8.7 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-73 was obtained as white solid in TFA salt form (12.6 mg, yield 69%). $^1$H NMR (800 MHz, CD$_3$OD) δ 8.99 (s, 1H), 8.58 (s, 2H), 8.04 (d, J=7.0 Hz, 1H), 7.95 (d, J=8.0 Hz, 1H), 7.49 (d, J=7.8 Hz, 2H), 7.44 (d, J=7.9 Hz, 2H), 7.20 (d, J=11.5 Hz, 1H), 6.96 (s, 1H), 4.67 (s, 1H), 4.64-4.55 (m, 2H), 4.52 (s, 1H), 4.39 (d, J=15.5 Hz, 1H), 3.98-3.92 (m, 4H), 3.89-3.80 (m, 2H), 3.70-3.63 (m, 4H), 3.53 (d, J=9.8 Hz, 2H), 3.39 (d, J=13.1 Hz, 2H), 3.19 (t, J=7.0 Hz, 2H), 2.99-2.94 (m, 5H), 2.75 (t, J=6.9 Hz, 2H), 2.57-2.46 (m, 5H), 2.36-2.22 (m, 3H), 2.11 (ddd, J=13.4, 9.2, 4.5 Hz, 1H), 1.68-1.63 (m, 2H), 1.56-1.50 (m, 2H), 1.47 (d, J=6.5 Hz, 6H), 1.41-1.34 (m, 2H), 1.06 (s, 9H). HRMS (m/z) for C$_{60}$H$_{76}$F$_4$N$_{13}$O$_8$S$^+$ [M+H]$^+$: calculated 1214.5591. found 1214.5586.

Example 256: Synthesis of XF078-74

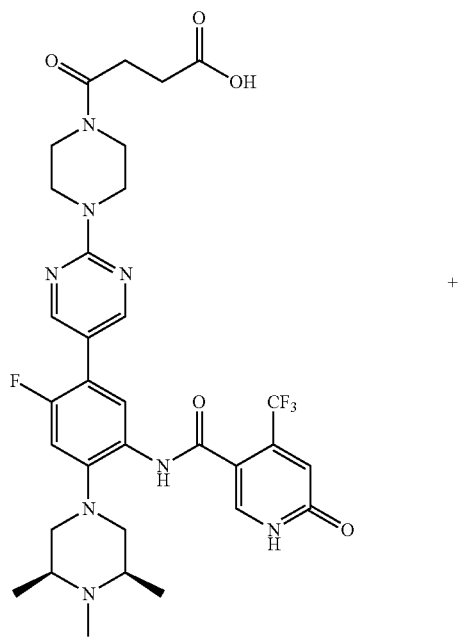

Intermediate 42

+

-continued

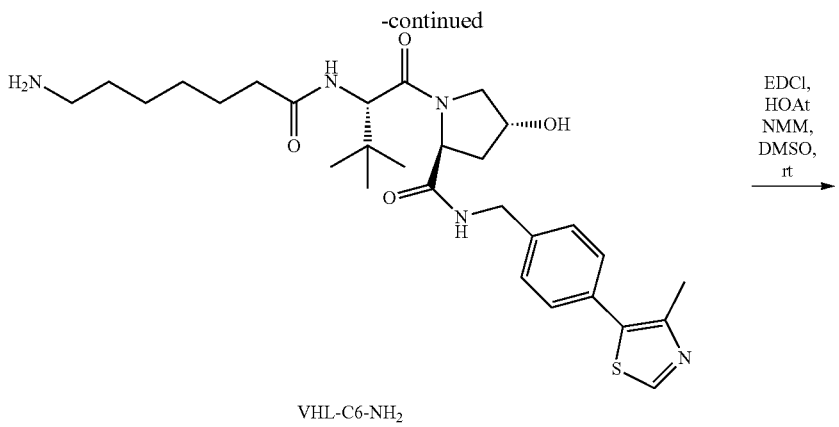

VHL-C6-NH₂

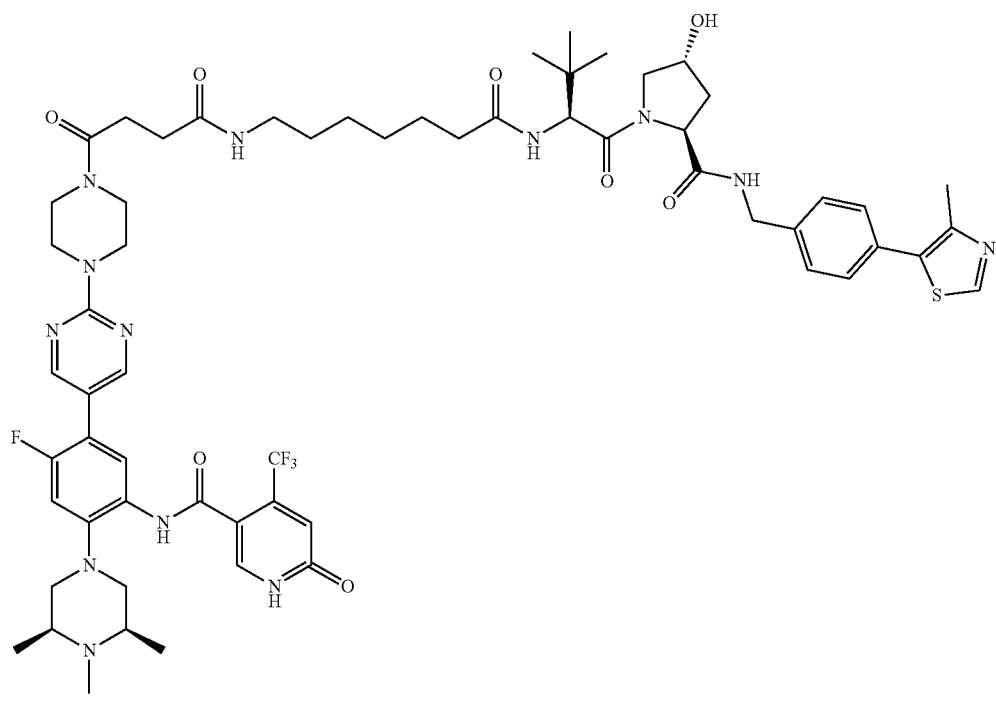

XF078-74

XF078-74 was synthesized following the standard procedures for preparing XF078-61 from intermediate 42 (10.4 mg, 0.015 mmol), VHL-C6-NH₂ (8.9 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-74 was obtained as white solid in TFA salt form (7.6 mg, yield 41%). $^1$H NMR (800 MHz, CD₃OD) δ 8.95 (s, 1H), 8.58 (s, 2H), 8.04 (s, 1H), 7.95 (d, J=8.0 Hz, 1H), 7.53-7.37 (m, 4H), 7.20 (d, J=11.5 Hz, 1H), 6.96 (s, 1H), 4.70-4.63 (m, 1H), 4.62-4.48 (m, 3H), 4.38 (d, J=15.4 Hz, 1H), 4.01-3.78 (m, 6H), 3.75-3.60 (m, 4H), 3.52 (s, 2H), 3.39 (d, J=13.2 Hz, 2H), 3.19 (t, J=7.1 Hz, 2H), 3.07-2.91 (m, 5H), 2.75 (t, J=6.8 Hz, 2H), 2.59-2.42 (m, 5H), 2.39-2.20 (m, 3H), 2.11 (ddd, J=13.2, 9.1, 4.5 Hz, 1H), 1.70-1.57 (m, 2H), 1.38 (d, J=24.9 Hz, 12H), 1.06 (s, 9H). HRMS (m/z) for $C_{61}H_{78}F_4N_{13}O_8S^+$ [M+H]⁺: calculated 1228.5748. found 1228.5756.

Example 257: Synthesis of XF078-75
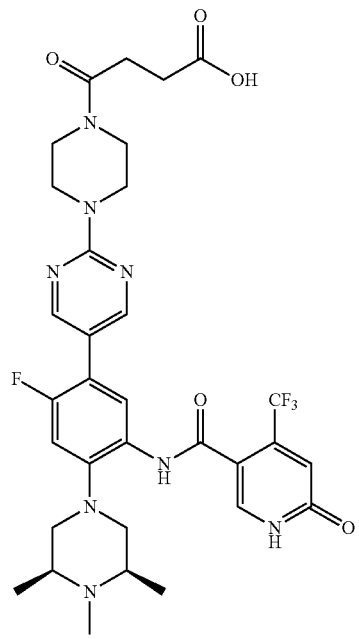
Intermediate 42
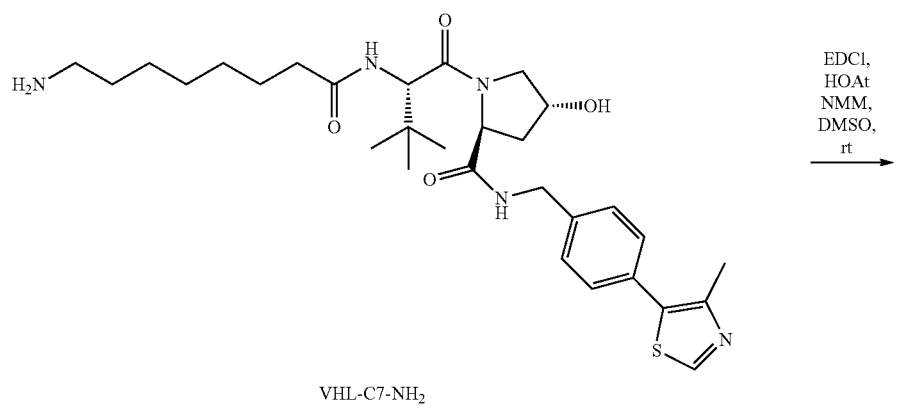
VHL-C7-NH₂

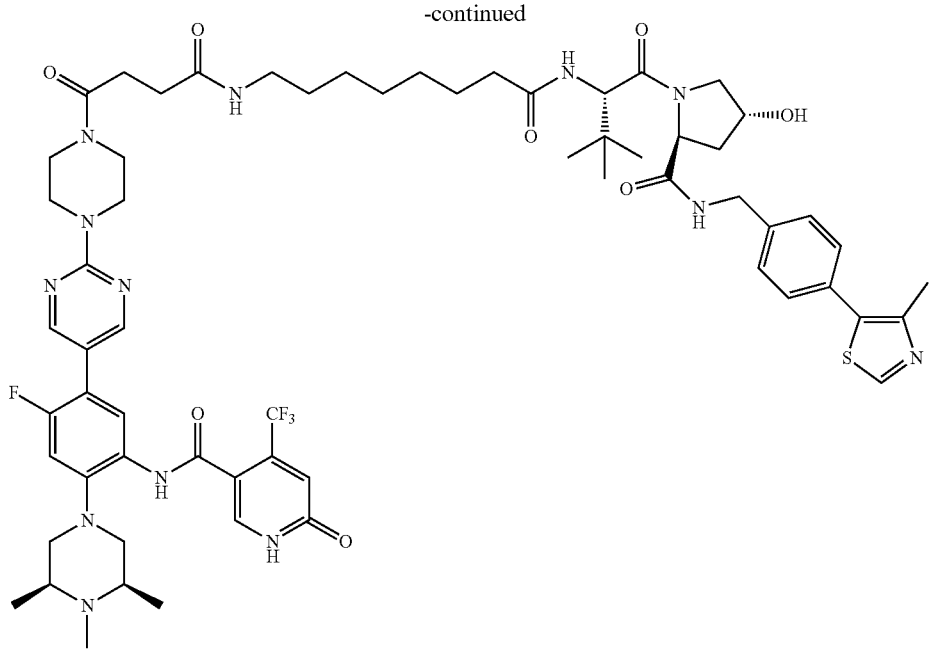

XF078-75

XF078-75 was synthesized following the standard procedures for preparing XF078-61 from intermediate 42 (10.4 mg, 0.015 mmol), VHL-C7-NH$_2$ (12 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-75 was obtained as white solid in TFA salt form (9.8 mg, yield 53%). $^1$H NMR (800 MHz, CD$_3$OD) δ 8.99 (s, 1H), 8.58 (s, 2H), 8.04 (s, 1H), 7.95 (d, J=8.1 Hz, 1H), 7.55-7.35 (m, 4H), 7.20 (d, J=11.5 Hz, 1H), 6.96 (s, 1H), 4.67 (s, 1H), 4.64-4.48 (m, 3H), 4.39 (d, J=15.3 Hz, 1H), 4.02-3.76 (m, 6H), 3.69 (t, J=5.4 Hz, 4H), 3.58-3.48 (m, 2H), 3.39 (d, J=13.1 Hz, 2H), 3.18 (t, J=7.2 Hz, 2H), 3.08-2.91 (m, 5H), 2.75 (t, J=6.8 Hz, 2H), 2.58-2.45 (m, 5H), 2.35-2.05 (m, 4H), 1.69-1.57 (m, 2H), 1.56-1.27 (m, 14H), 1.06 (s, 9H). HRMS (m/z) for C$_{62}$H$_{80}$F$_4$N$_{13}$O$_8$S$^+$ [M+H]$^+$: calculated 1242.5904, found 1242.5879.

Example 258: Synthesis of XF078-76

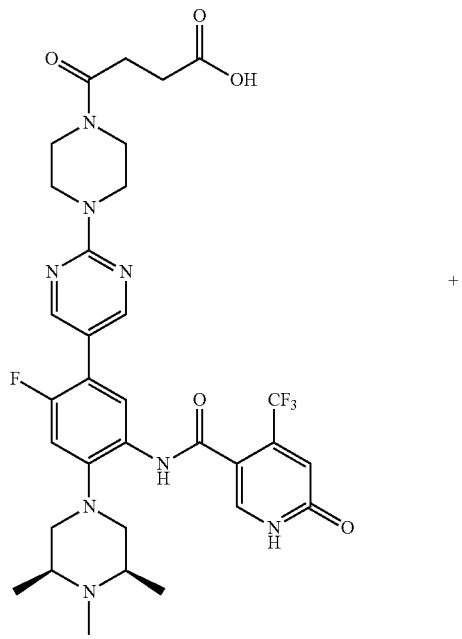

Intermediate 42

+

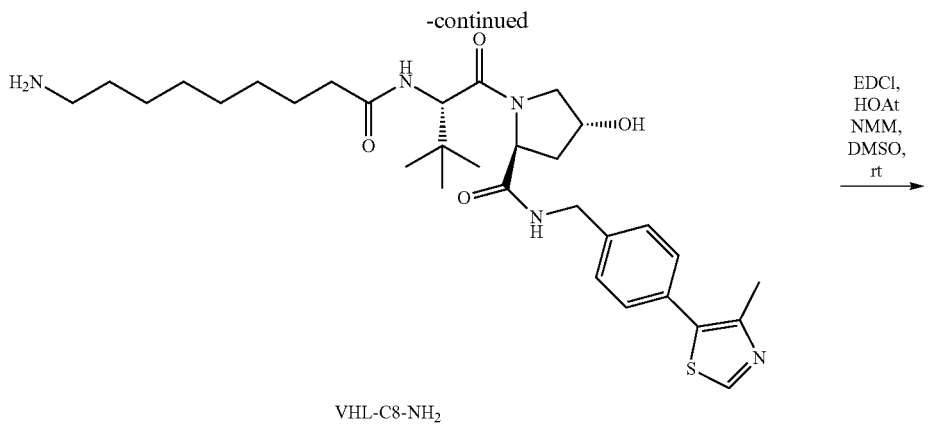

VHL-C8-NH₂

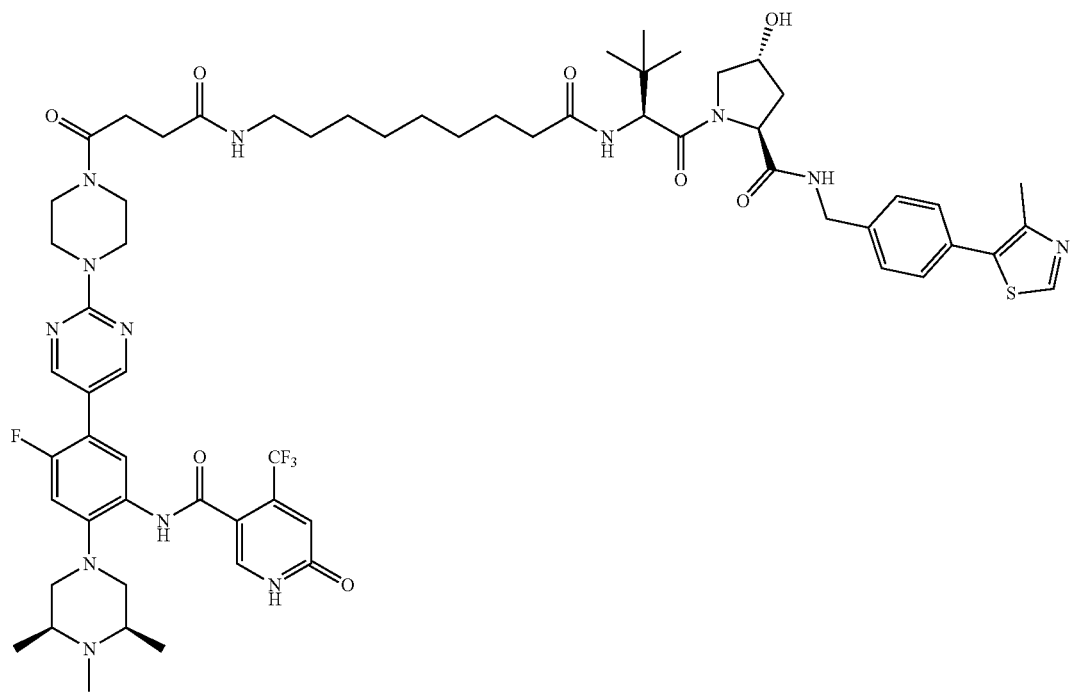

XF078-76

XF078-76 was synthesized following the standard procedures for preparing XF078-61 from intermediate 42 (10.4 mg, 0.015 mmol), VHL-C8-NH₂ (9.3 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-76 was obtained as white solid in TFA salt form (9.6 mg, yield 51%). $^1$H NMR (800 MHz, CD$_3$OD) δ 8.99 (s, 1H), 8.59 (s, 2H), 8.04 (d, J=6.4 Hz, 1H), 7.95 (d, J=8.0 Hz, 1H), 7.55-7.35 (m, 4H), 7.20 (d, J=11.5 Hz, 1H), 6.96 (s, 1H), 4.66 (s, 1H), 4.63-4.48 (m, 3H), 4.38 (d, J=15.4 Hz, 1H), 4.00-3.79 (m, 6H), 3.69 (t, J=5.4 Hz, 4H), 3.57-3.50 (m, 2H), 3.43-3.37 (m, 2H), 3.21-3.15 (m, 2H), 3.04-2.92 (m, 5H), 2.75 (t, J=6.9 Hz, 2H), 2.57-2.45 (m, 5H), 2.36-2.05 (m, 4H), 1.72-1.58 (m, 2H), 1.56-1.27 (m, 16H), 1.06 (s, 9H). HRMS (m/z) for C$_{63}$H$_{82}$F$_4$N$_{13}$O$_8$S$^+$ [M+H]$^+$: calculated 1256.6061, found 1256.6042.

Example 259: Synthesis of XF078-77
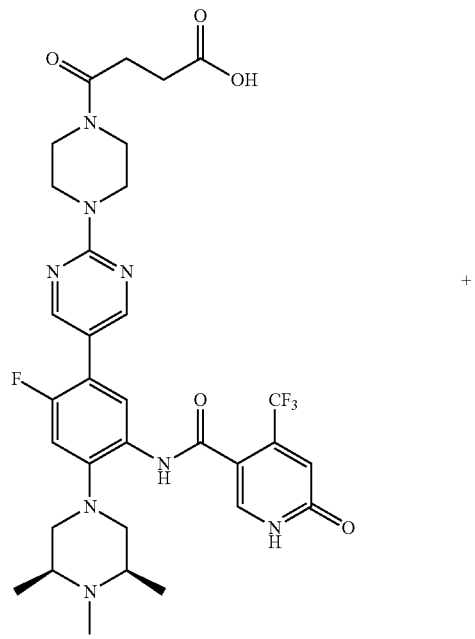
Intermediate 42
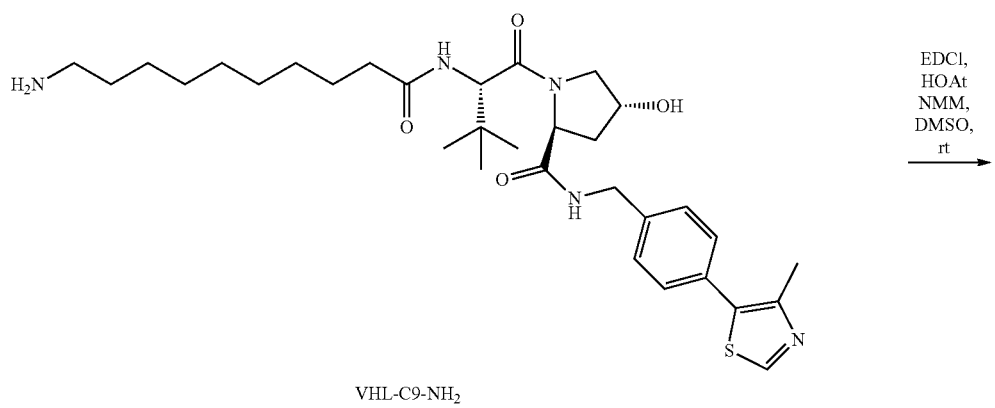
VHL-C9-NH₂

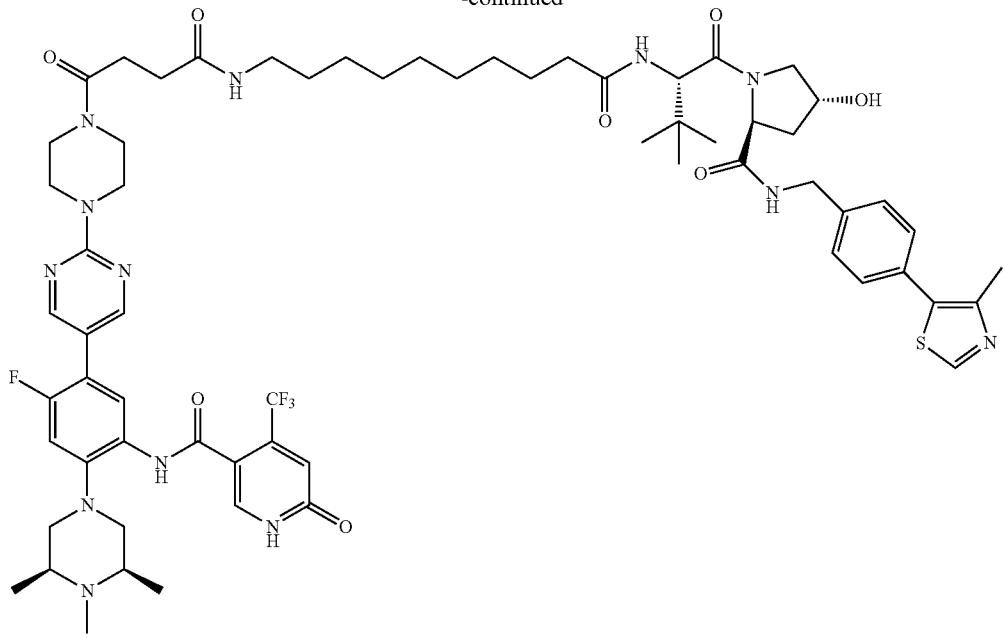

XF078-77

XF078-77 was synthesized following the standard procedures for preparing XF078-61 from intermediate 42 (10.4 mg, 0.015 mmol), VHL-C9-NH$_2$ (12.4 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-77 was obtained as white solid in TFA salt form (12 mg, yield 63%). $^1$H NMR (800 MHz, CD$_3$OD) δ 9.01 (s, 1H), 8.59 (s, 2H), 8.04 (s, 1H), 7.95 (d, J=8.0 Hz, 1H), 7.68-7.39 (m, 4H), 7.20 (d, J=11.5 Hz, 1H), 6.96 (s, 1H), 4.74-4.64 (m, 1H), 4.62-4.47 (m, 3H), 4.38 (d, J=15.4 Hz, 1H), 4.01-3.80 (m, 6H), 3.75-3.66 (m, 4H), 3.57-3.48 (m, 2H), 3.42-3.36 (m, 2H), 3.18 (t, J=7.1 Hz, 2H), 3.04-2.89 (m, 5H), 2.79-2.71 (m, 2H), 2.59-2.46 (m, 5H), 2.35-2.19 (m, 3H), 2.11 (ddd, J=13.3, 9.0, 4.5 Hz, 1H), 1.72-1.57 (m, 2H), 1.56-1.29 (m, 18H), 1.06 (s, 9H). HRMS (m/z) for C$_{64}$H$_{84}$F$_4$N$_{13}$O$_8$S$^+$ [M+H]$^+$: calculated 1270.6217. found 1270.6243.

Example 260: Synthesis of XF078-78

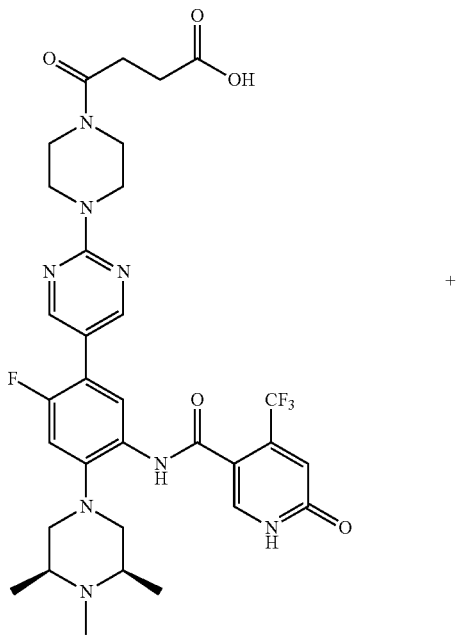

Intermediate 42

+

637
638
-continued
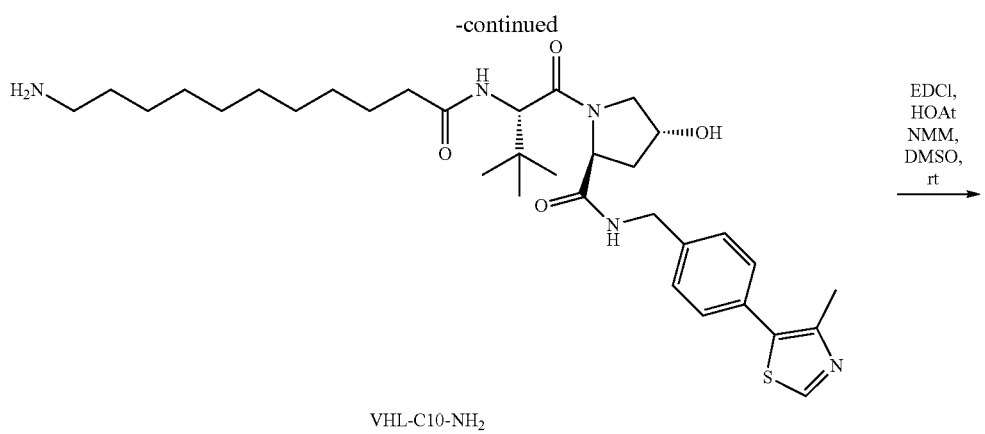
VHL-C10-NH₂
EDCl, HOAt NMM, DMSO, rt
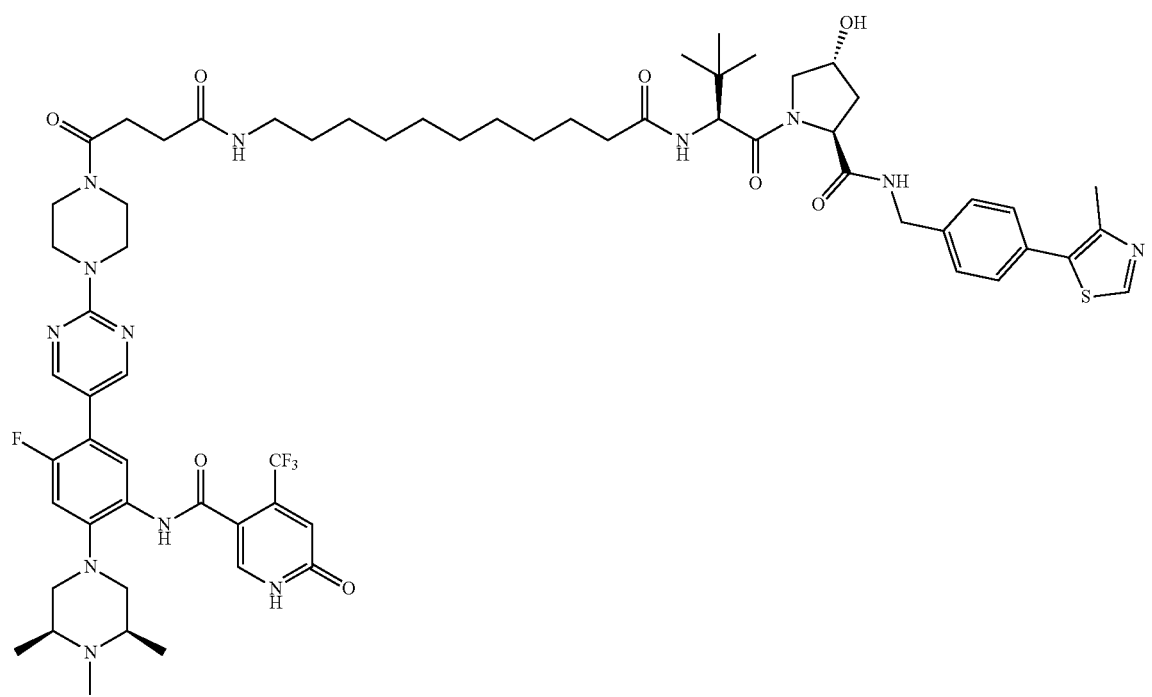
XF078-78

XF078-78 was synthesized following the standard procedures for preparing XF078-61 from intermediate 42 (10.4 mg, 0.015 mmol), VHL-C10-NH$_2$ (9.8 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-78 was obtained as white solid in TFA salt form (6.9 mg, yield 36%). $^1$H NMR (800 MHz, CD$_3$OD) δ 8.96 (s, 1H), 8.59 (s, 2H), 8.04 (s, 1H), 7.95 (d, J=8.0 Hz, 1H), 7.55-7.40 (m, 4H), 7.20 (d, J=11.5 Hz, 1H), 6.96 (s, 1H), 4.66 (s, 1H), 4.63-4.46 (m, 3H), 4.38 (d, J=15.4 Hz, 1H), 4.05-3.80 (m, 6H), 3.78-3.59 (m, 4H), 3.53 (t, J=8.4 Hz, 2H), 3.39 (d, J=13.0 Hz, 2H), 3.18 (q, J=6.9 Hz, 2H), 3.05-2.90 (m, 5H), 2.76 (t, J=6.9 Hz, 2H), 2.58-2.44 (m, 5H), 2.37-2.21 (m, 3H), 2.11 (ddd, J=13.3, 9.1, 4.5 Hz, 1H), 1.62 (d, 2H), 1.54-1.27 (m, 20H), 1.06 (s, 9H). HRMS (m/z) for C$_{65}$H$_{86}$F$_4$N$_{13}$O$_8$S$^+$ [M+H]$^+$: calculated 1284.6374. found 1284.6355.

Example 261: Synthesis of XF078-79

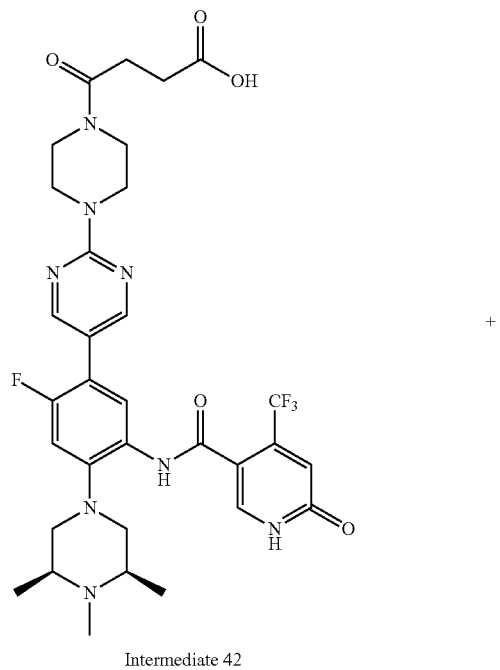

Intermediate 42

+

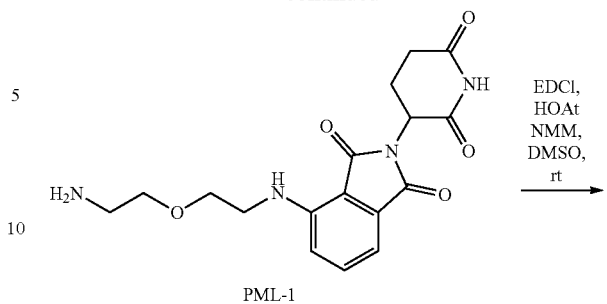

PML-1

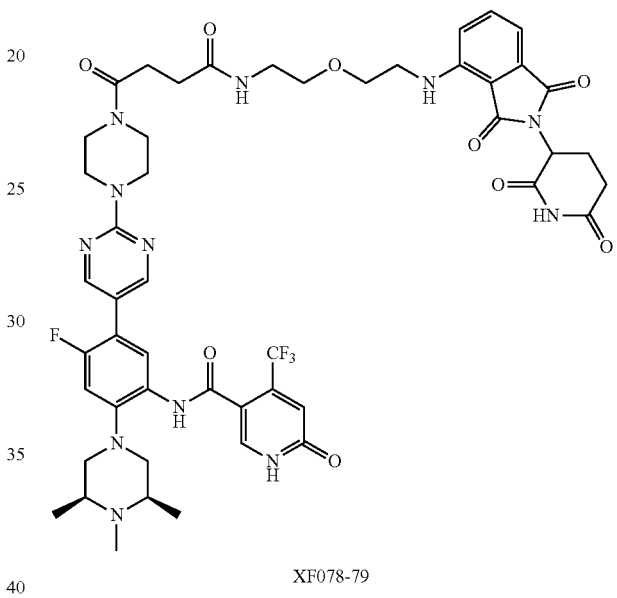

XF078-79

XF078-79 was synthesized following the standard procedures for preparing XF078-61 from intermediate 42 (10.4 mg, 0.015 mmol), PML-1 (7.1 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-79 was obtained as yellow solid in TFA salt form (9.1 mg, yield 59%). $^1$H NMR (800 MHz, CD$_3$OD) δ 8.57 (s, 2H), 8.04 (d, J=6.2 Hz, 1H), 7.95 (d, J=8.1 Hz, 1H), 7.57 (t, J=7.8 Hz, 1H), 7.19 (d, J=11.5 Hz, 1H), 7.08 (dd, J=27.3, 7.8 Hz, 2H), 6.95 (s, 1H), 5.20-5.08 (m, 1H), 4.01-3.80 (m, 4H), 3.78-3.45 (m, 12H), 3.44-3.26 (m, 4H), 3.06-2.80 (m, 6H), 2.80-2.69 (m, 4H), 2.65-2.53 (m, 2H), 2.18-2.10 (m, 1H), 1.46 (d, J=6.5 Hz, 6H). HRMS (m/z) for C$_{49}$H$_{55}$F$_4$N$_2$O$_9$$^+$ [M+H]$^+$: calculated 1031.4146, found 1031.4174.

Example 262: Synthesis of XF078-80
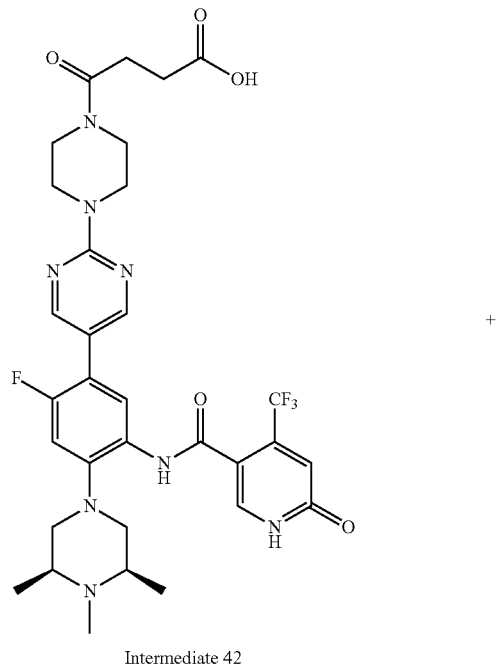
Intermediate 42
+
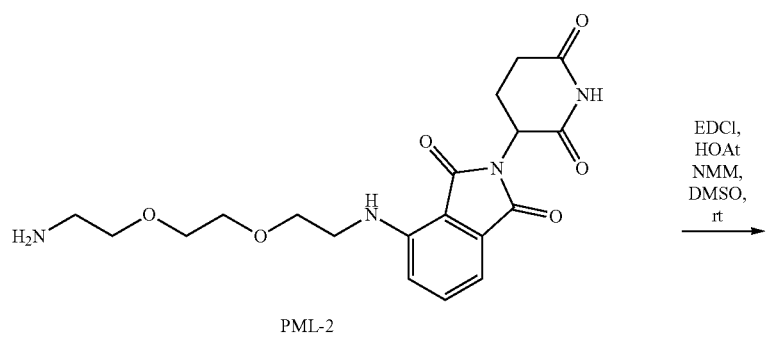
PML-2

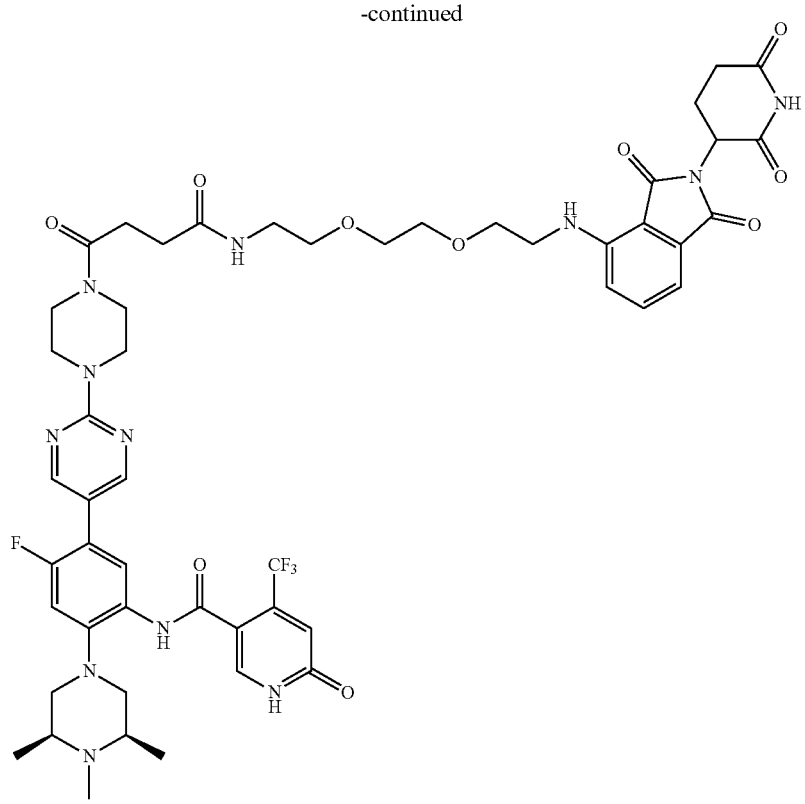

XF078-80

XF078-80 was synthesized following the standard procedures for preparing XF078-61 from intermediate 42 (10.4 mg, 0.015 mmol), PML-2 (7.8 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-80 was obtained as yellow solid in TFA salt form (10.4 mg, yield 64%). $^1$H NMR (800 MHz, CD$_3$OD) δ 8.57 (s, 2H), 8.04 (s, 1H), 7.94 (d, J=8.0 Hz, 1H), 7.61-7.48 (m, 1H), 7.19 (d, J=11.5 Hz, 1H), 7.13-6.99 (m, 2H), 6.95 (s, 1H), 5.17-5.04 (m, 1H), 4.04-3.80 (m, 4H), 3.76-3.48 (m, 16H), 3.41-3.35 (m, 4H), 3.06-2.79 (m, 6H), 2.79-2.66 (m, 4H), 2.58-2.41 (m, 2H), 2.22-2.06 (m, 1H), 1.46 (d, J=6.5 Hz, 6H). HRMS (m/z) for $C_{51}H_{59}F_4N_{12}O_{10}^+$ [M+H]$^+$: calculated 1075.4408. found 1075.4414.

Example 263: Synthesis of XF078-81
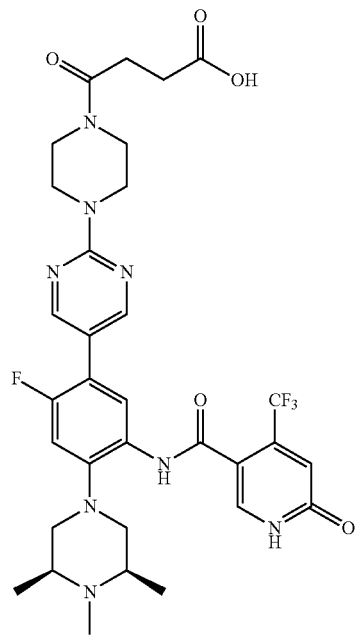
Intermediate 42
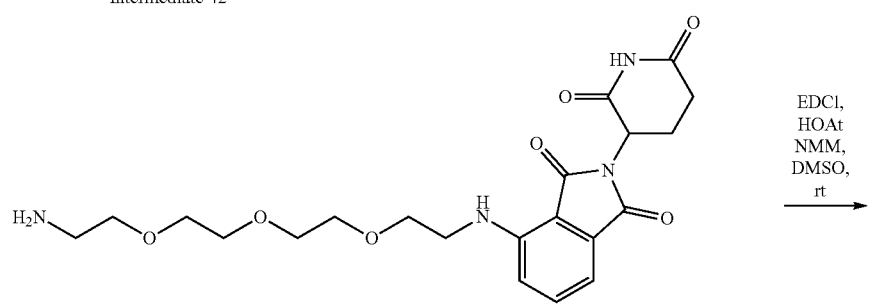
PML-3
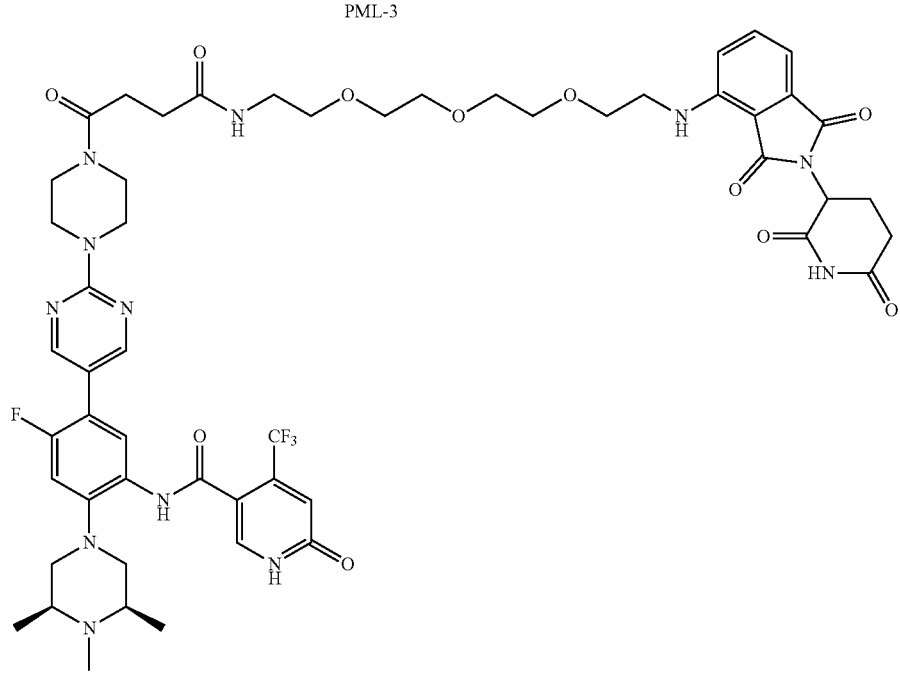
XF078-81

XF078-81 was synthesized following the standard procedures for preparing XF078-61 from intermediate 42 (10.4 mg, 0.015 mmol), PML-3 (8.4 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-81 was obtained as yellow solid in TFA salt form (11.8 mg, yield 70%). $^1$H NMR (800 MHz, CD$_3$OD) δ 8.57 (s, 2H), 8.04 (d, J=6.4 Hz, 1H), 7.94 (d, J=8.1 Hz, 1H), 7.55 (t, J=7.8 Hz, 1H), 7.19 (d, J=11.5 Hz, 1H), 7.09 (d, J=8.5 Hz, 1H), 7.04 (d, J=7.1 Hz, 1H), 6.95 (s, 1H), 5.11-5.08 (m, 1H), 4.00-3.80 (m, 4H), 3.77-3.57 (m, 16H), 3.56-3.48 (m, 4H), 3.40-3.35 (m, 4H), 3.04-2.79 (m, 6H), 2.80-2.65 (m, 4H), 2.55 (t, J=6.9 Hz, 2H), 2.13 (ddt, J=13.2, 8.3, 4.6 Hz, 1H), 1.46 (d, J=6.5 Hz, 6H). HRMS (m/z) for $C_{53}H_{63}F_4N_{12}O_{11}^+$ [M+H]$^+$: calculated 1119.4670. found 1119.4689.

Example 264: Synthesis of XF078-82

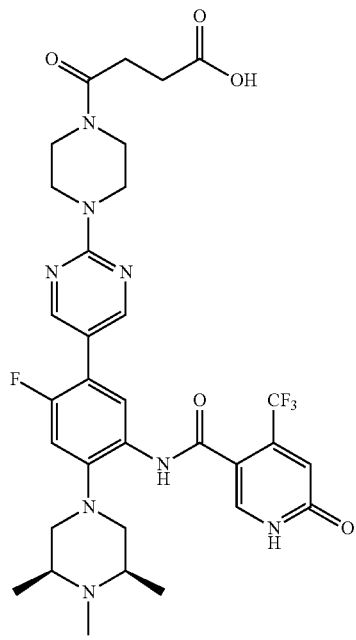

Intermediate 42

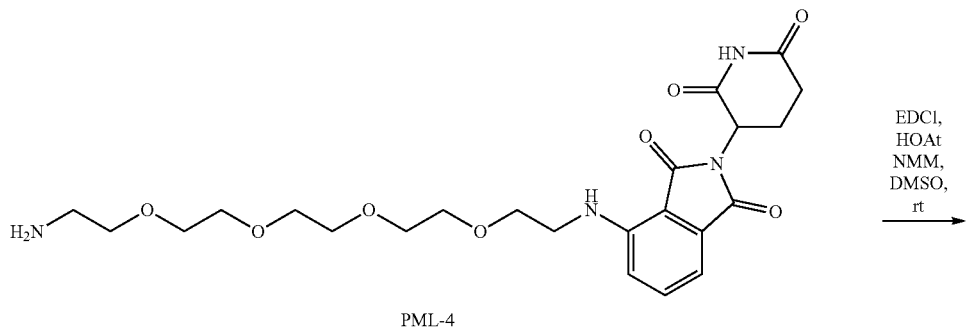

PML-4

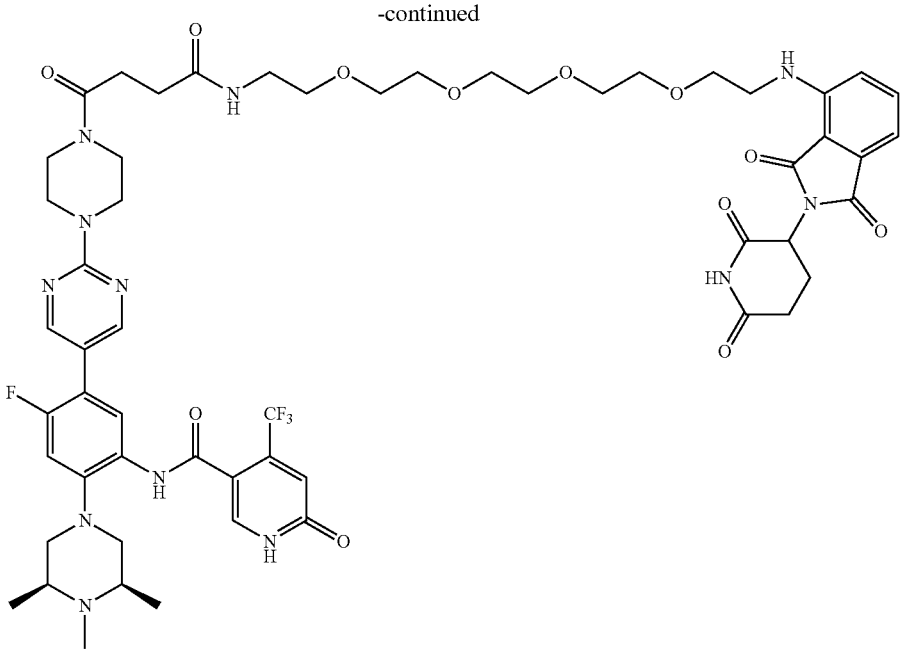

XF078-82

XF078-82 was synthesized following the standard procedures for preparing XF078-61 from intermediate 42 (10.4 mg, 0.015 mmol), PML-4 (8.5 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-82 was obtained as yellow solid in TFA salt form (7 mg, yield 40%). $^1$H NMR (800 MHz, CD$_3$OD) δ 8.57 (s, 2H), 8.04 (d, J=6.3 Hz, 1H), 7.94 (d, J=8.1 Hz, 1H), 7.55 (t, J=7.8 Hz, 1H), 7.19 (d, J=11.5 Hz, 1H), 7.07 (dd, J=36.7, 7.8 Hz, 2H), 6.95 (s, 1H), 5.12-5.06 (m, 1H), 3.98-3.82 (m, 4H), 3.80-3.56 (m, 20H), 3.57-3.48 (m, 4H), 3.42-3.36 (m, 4H), 3.04-2.80 (m, 6H), 2.80-2.67 (m, 4H), 2.56 (t, J=6.9 Hz, 2H), 2.23-2.09 (m, 1H), 1.46 (d, J=6.4 Hz, 6H). HRMS (m/z) for $C_{55}H_{67}F_4N_{12}O_{12}^+$[M+H]$^+$: calculated 1163.4932. found 1163.4913.

Example 265: Synthesis of XF078-83

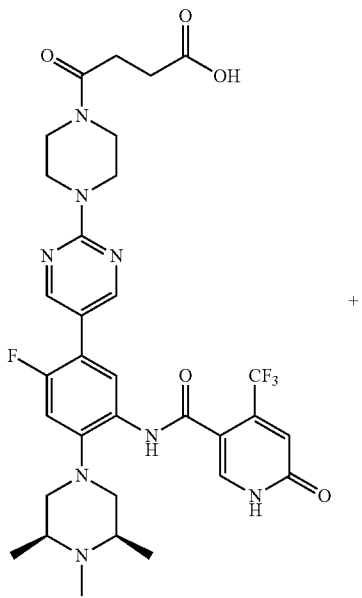

Intermediate 42

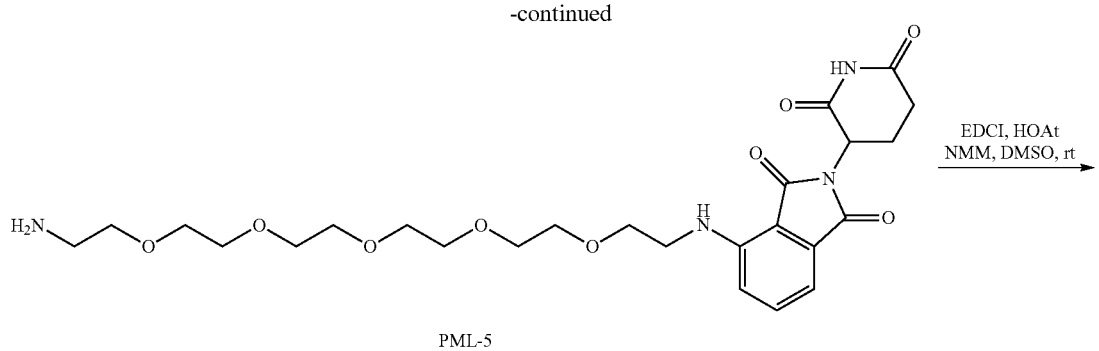

PML-5

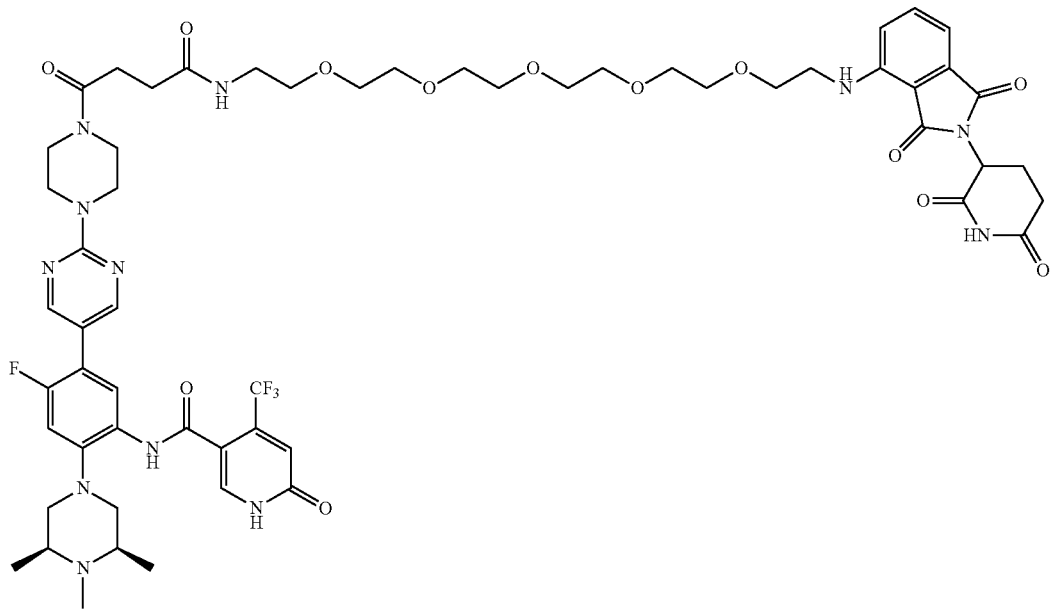

XF078-83

XF078-83 was synthesized following the standard procedures for preparing XF078-61 from intermediate 42 (10.4 mg, 0.015 mmol), PML-5 (9.1 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-83 was obtained as yellow solid in TFA salt form (11.3 mg, yield 62%). $^1$H NMR (800 MHz, CD$_3$OD) δ 8.57 (s, 2H), 8.04 (d, J=6.2 Hz, 1H), 7.94 (d, J=8.0 Hz, 1H), 7.59-7.48 (m, 1H), 7.18 (d, J=11.6 Hz, 1H), 7.07 (dd, J=34.5, 7.8 Hz, 2H), 6.95 (s, 1H), 5.11-5.02 (m, 1H), 3.99-3.83 (m, 4H), 3.80-3.45 (m, 28H), 3.40-3.34 (m, 4H), 3.03-2.80 (m, 6H), 2.81-2.66 (m, 4H), 2.56 (t, J=6.8 Hz, 2H), 2.19-2.09 (m, 1H), 1.46 (d, J=6.5 Hz, 6H). HRMS (m/z) for C$_{57}$H$_{71}$F$_4$N$_{12}$O$_{13}^+$ [M+H]$^+$: calculated 1207.5194, found 1207.5214.

Example 266: Synthesis of XF078-84

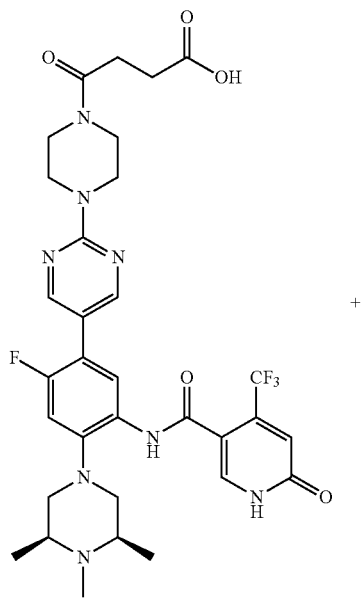

Intermediate 42

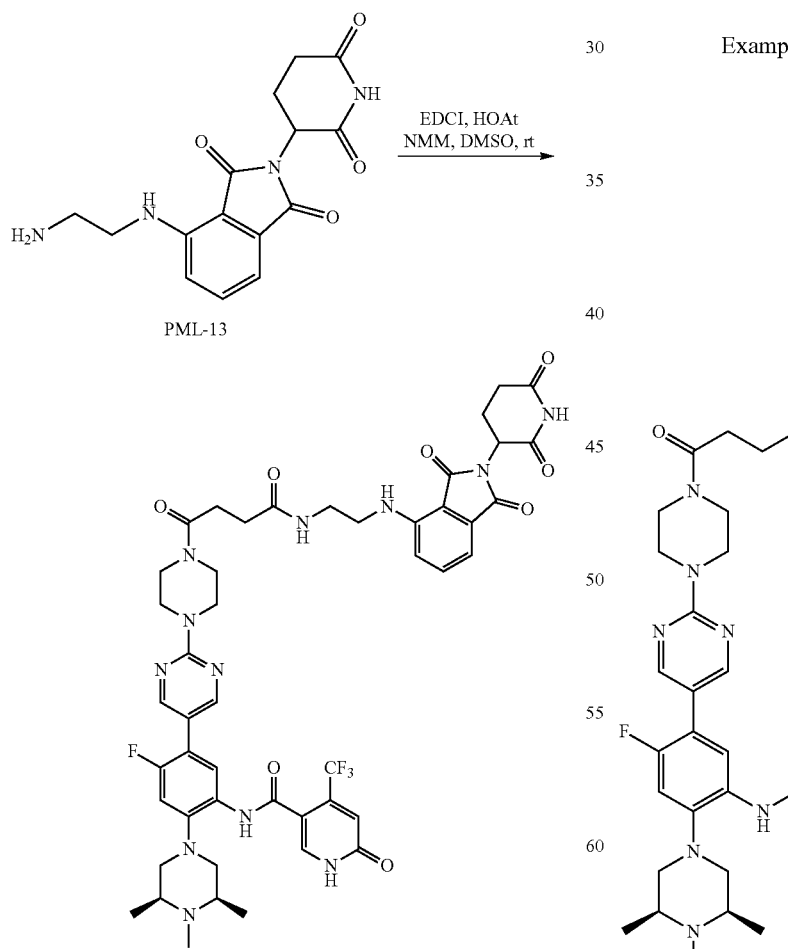

PML-13

XF078-84

XF078-84 was synthesized following the standard procedures for preparing XF078-61 from intermediate 42 (10.4 mg, 0.015 mmol), PML-13 (6.5 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-84 was obtained as yellow solid in TFA salt form (7.1 mg, yield 48%). $^1$H NMR (800 MHz, CD$_3$OD) δ 8.58 (s, 2H), 8.04 (d, J=6.0 Hz, 1H), 7.95 (d, J=8.1 Hz, 1H), 7.56 (t, J=7.8 Hz, 1H), 7.25-7.11 (m, 2H), 7.05 (d, J=7.0 Hz, 1H), 6.96 (s, 1H), 5.12-5.03 (m, 1H), 3.97-3.79 (m, 4H), 3.72-3.63 (m, 4H), 3.56-3.42 (m, 6H), 3.42-3.36 (m, 2H), 3.06-2.91 (m, 5H), 2.91-2.80 (m, 1H), 2.79-2.69 (m, 4H), 2.53 (t, J=6.9 Hz, 2H), 2.18-2.09 (m, 1H), 1.47 (d, J=6.5 Hz, 6H). HRMS (m/z) for C$_{47}$H$_{51}$F$_4$N$_{12}$O$_8^+$ [M+H]$^+$: calculated 987.3883. found 987.3867.

Example 267: Synthesis of XF078-85

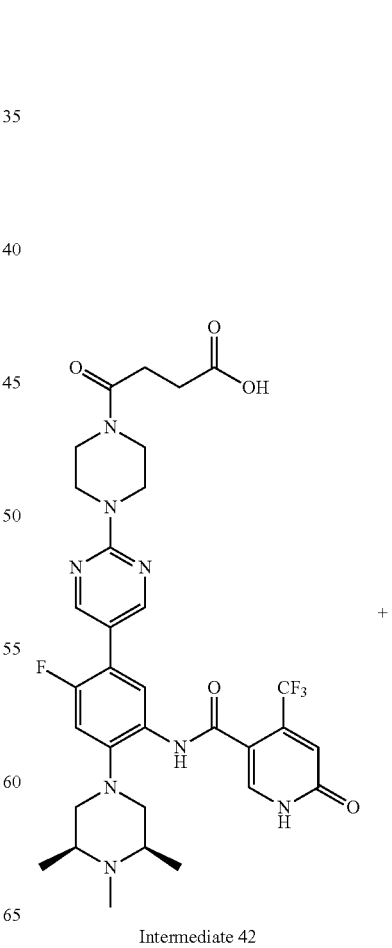

Intermediate 42

655

-continued

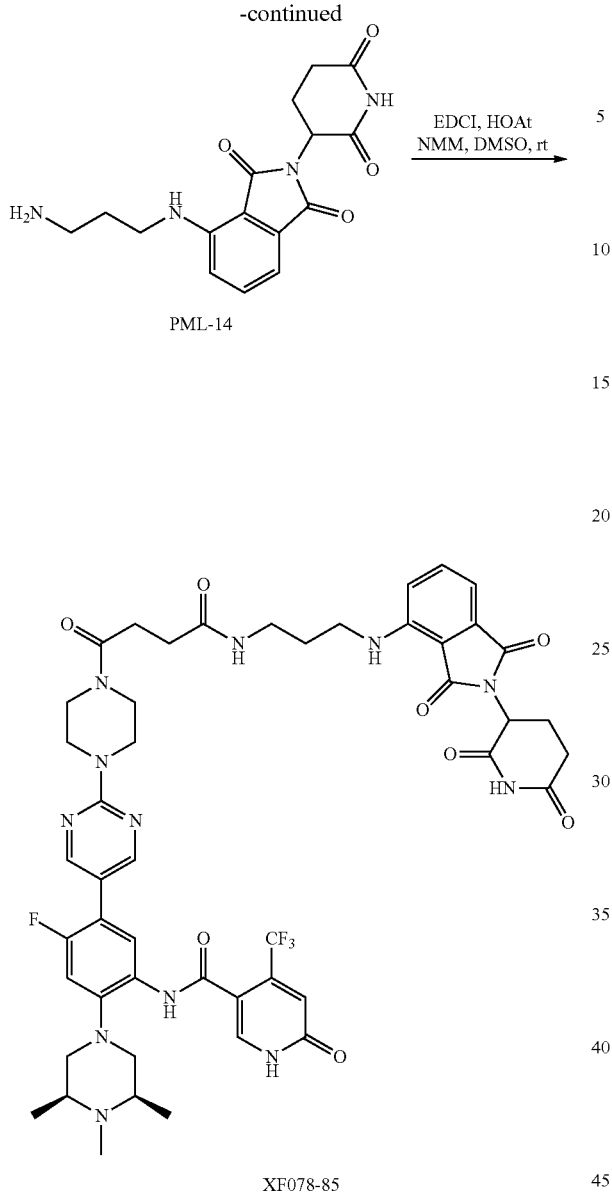

PML-14

XF078-85

XF078-85 was synthesized following the standard procedures for preparing XF078-61 from intermediate 42 (10.4 mg, 0.015 mmol), PML-14 (6.7 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-85 was obtained as yellow solid in TFA salt form (12.5 mg, yield 830%). $^1$H NMR (800 MHz, CD$_3$OD) δ 8.57 (s, 2H), 8.05 (s, 1H), 7.95 (d, J=8.0 Hz, 1H), 7.56 (t, J=7.8 Hz, 1H), 7.20 (d, J=11.5 Hz, 1H), 7.10 (d, J=8.6 Hz, 1H), 7.03 (d, J=7.0 Hz, 1H), 6.96 (s, 1H), 5.10-5.02 (m, 1H), 3.99-3.92 (m, 2H), 3.90-3.81 (m, 2H), 3.75-3.64 (m, 4H), 3.56-3.46 (m, 2H), 3.44-3.36 (m, 6H), 3.04-2.91 (m, 5H), 2.90-2.81 (m, 1H), 2.81-2.68 (m, 4H), 2.60-2.54 (m, 2H), 2.16-2.07 (m, 1H), 1.86 (p, J=6.7 Hz, 2H), 1.47 (d, J=6.5 Hz, 6H). HRMS (m/z) for C$_{48}$H$_{53}$F$_4$N$_{12}$O$_8{}^+$ [M+H]$^+$: calculated 1001.4040, found 1001.4013.

656

Example 268: Synthesis of XF078-86

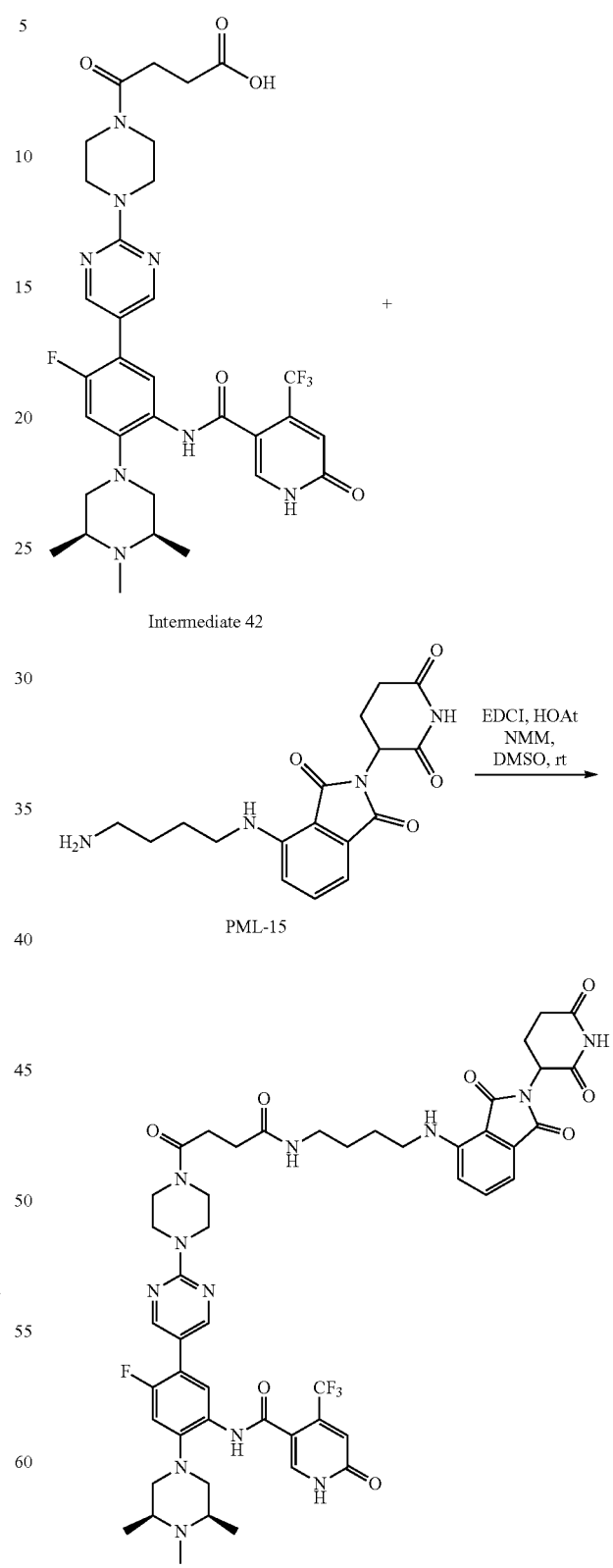

Intermediate 42

PML-15

XF078-86

XF078-86 was synthesized following the standard procedures for preparing XF078-61 from intermediate 42 (10.4 mg, 0.015 mmol), PML-15 (6.9 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-86 was obtained as yellow solid in TFA salt form (14.1 mg, yield 93%). $^1$H NMR (800 MHz, CD$_3$OD) δ 8.58 (s, 2H), 8.04 (d, J=5.7 Hz, 1H), 7.94 (d, J=8.0 Hz, 1H), 7.55 (t, J=7.8 Hz, 1H), 7.18 (d, J=11.6 Hz, 1H), 7.11-6.99 (m, 2H), 6.95 (s, 1H), 5.11-5.03 (m, 1H), 3.97-3.89 (m, 2H), 3.88-3.78 (m, 2H), 3.72-3.63 (m, 4H), 3.57-3.47 (m, 2H), 3.40-3.25 (m, 6H), 3.04-2.80 (m, 6H), 2.80-2.70 (m, 4H), 2.58-2.49 (m, 2H), 2.15-2.09 (m, 1H), 1.73-1.60 (m, 4H), 1.51-1.44 (m, 6H). HRMS (m/z) for $C_{49}H_5F_4N_{12}O_8^+$ [M+H]$^+$: calculated 1015.4196. found 1015.4207.

Example 269: Synthesis of XF078-87

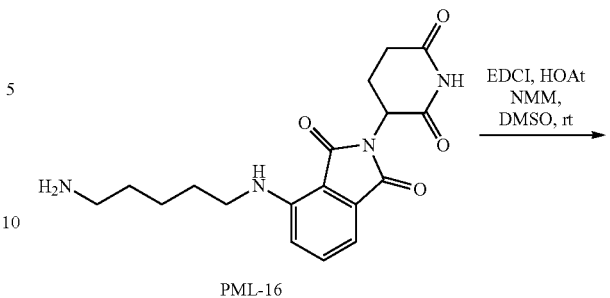

PML-16

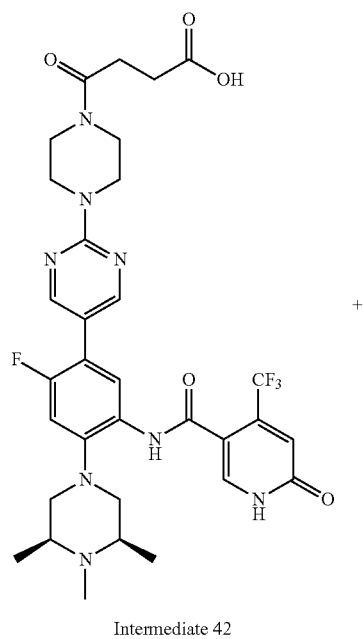

Intermediate 42

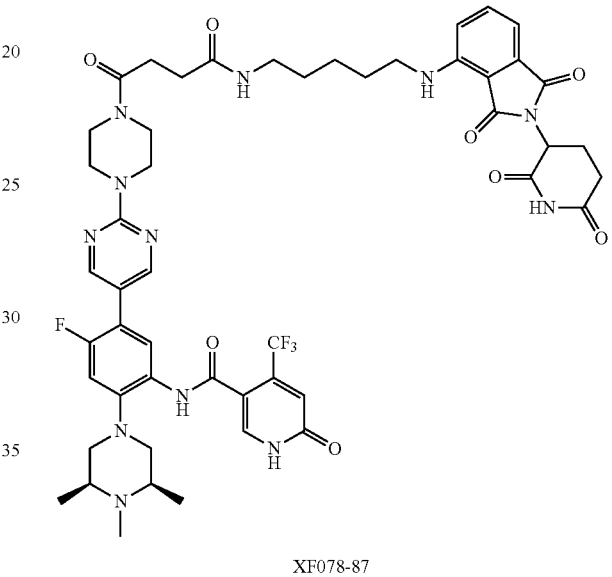

XF078-87

XF078-87 was synthesized following the standard procedures for preparing XF078-61 from intermediate 42 (10.4 mg, 0.015 mmol), PML-16 (7.1 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-87 was obtained as yellow solid in TFA salt form (7.9 mg, yield 51%). $^1$H NMR (800 MHz, CD$_3$OD) δ 8.58 (s, 2H), 8.04 (d, J=5.7 Hz, 1H), 7.94 (d, J=8.0 Hz, 1H), 7.55 (t, J=7.8 Hz, 1H), 7.19 (d, J=11.5 Hz, 1H), 7.08-6.97 (m, 2H), 6.96 (s, 1H), 5.12-5.04 (m, 1H), 4.00-3.89 (m, 2H), 3.90-3.83 (m, 2H), 3.75-3.63 (m, 4H), 3.59-3.49 (m, 2H), 3.43-3.18 (m, 6H), 3.04-2.81 (m, 6H), 2.80-2.68 (m, 4H), 2.54 (t, J=6.8 Hz, 2H), 2.12 (ddt, J=13.2, 8.0, 4.2 Hz, 1H), 1.70 (p, J=7.2 Hz, 2H), 1.59 (p, J=7.0 Hz, 2H), 1.52-1.42 (m, 8H). HRMS (m/z) for $C_{50}H_{57}F_4N_{12}O_8^+$ [M+H]$^+$: calculated 1029.4353, found 1029.4366.

Example 270: Synthesis of XF078-88

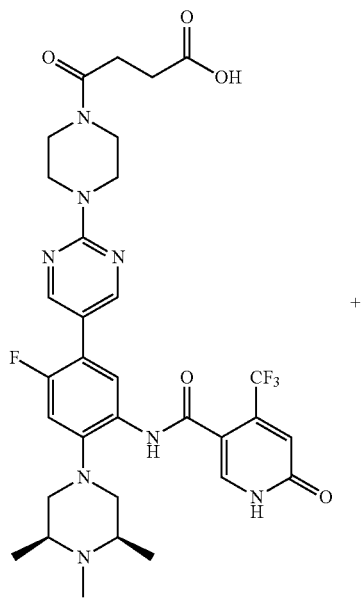

Intermediate 42

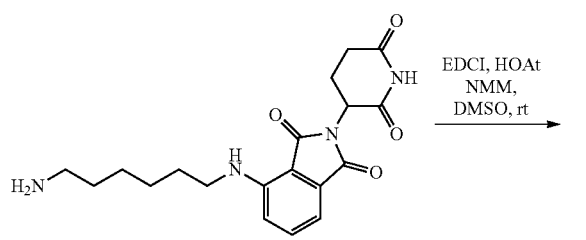

PML-17

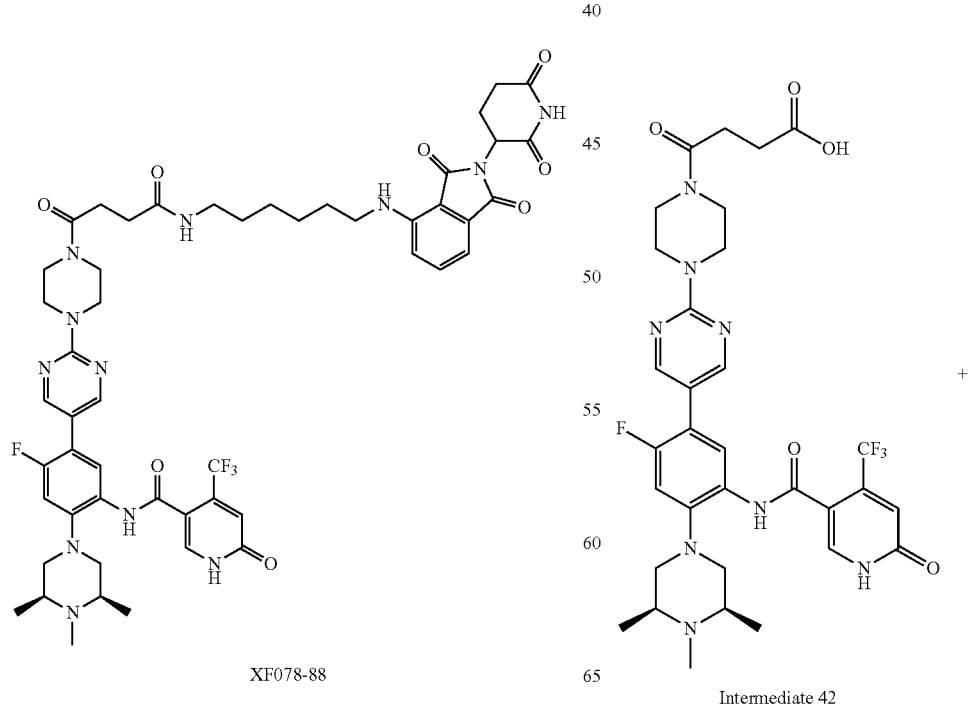

XF078-88

XF078-88 was synthesized following the standard procedures for preparing XF078-61 from intermediate 42 (10.4 mg, 0.015 mmol), PML-17 (6.1 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-88 was obtained as yellow solid in TFA salt form (10.9 mg, yield 70%). $^1$H NMR (800 MHz, CD$_3$OD) δ 8.58 (s, 2H), 8.04 (d, J=6.8 Hz, 1H), 7.93 (d, J=8.0 Hz, 1H), 7.61-7.50 (m, 1H), 7.17 (d, J=11.5 Hz, 1H), 7.05-6.97 (m, 2H), 6.95 (s, 1H), 5.07 (dd, J=12.9, 5.5 Hz, 1H), 4.00-3.90 (m, 2H), 3.90-3.80 (m, 2H), 3.74-3.60 (m, 4H), 3.58-3.47 (m, 2H), 3.40-3.14 (m, 6H), 3.05-2.81 (m, 6H), 2.79-2.70 (m, 4H), 2.54 (t, J=6.7 Hz, 2H), 2.15-1.93 (m, 1H), 1.67 (p, J=7.1 Hz, 2H), 1.54 (p, J=7.1 Hz, 2H), 1.49-1.33 (m, 10H). HRMS (m/z) for $C_{51}H_{59}F_4N_2O_8^+$ [M+H]$^+$: calculated 1043.4509, found 1043.4532.

Example 271: Synthesis of XF078-89

Intermediate 42

Example 272: Synthesis of XF078-90

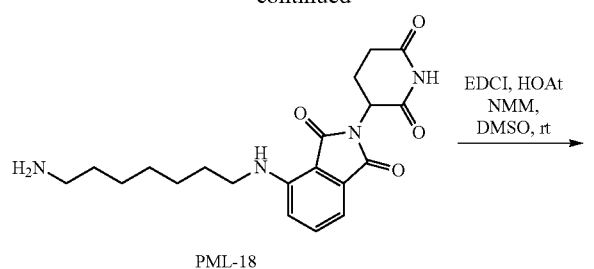

PML-18

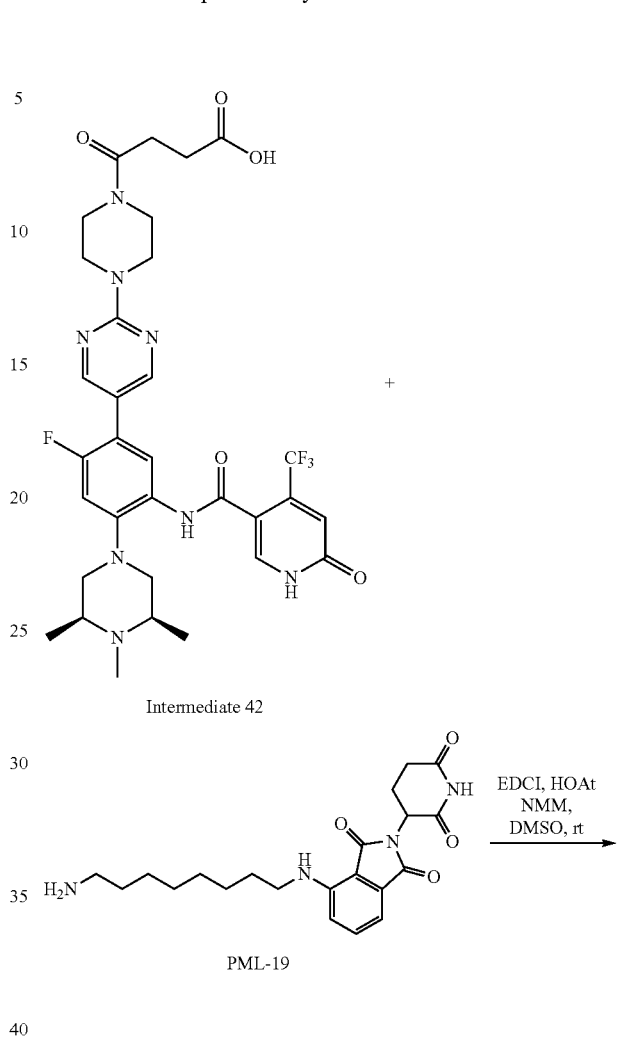

Intermediate 42

PML-19

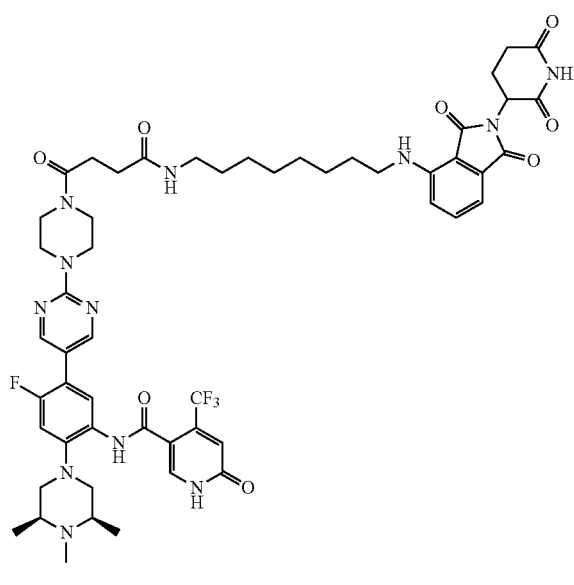

XF078-89

XF078-89 was synthesized following the standard procedures for preparing XF078-61 from intermediate 42 (10.4 mg, 0.015 mmol), PML-18 (7.5 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-89 was obtained as yellow solid in TFA salt form (12.4 mg, yield 78%). $^1$H NMR (800 MHz, CD$_3$OD) δ 8.58 (s, 2H), 8.03 (d, J=7.5 Hz, 1H), 7.96-7.88 (m, 1H), 7.61-7.45 (m, 1H), 7.16 (d, J=11.6 Hz, 1H), 7.00 (dd, J=7.9, 3.9 Hz, 2H), 6.95 (s, 1H), 5.13-5.02 (m, 1H), 3.91 (s, 4H), 3.73-3.64 (m, 4H), 3.56-3.49 (m, 2H), 3.40-3.15 (m, 6H), 3.04-2.81 (m, 6H), 2.80-2.69 (m, 4H), 2.54 (t, J=6.7 Hz, 2H), 2.16-2.05 (m, 1H), 1.65 (h, J=6.5, 5.9 Hz, 2H), 1.55-1.32 (m, 14H). HRMS (m/z) for $C_{52}H_{61}F_4N_{12}O_8^+$ [M+H]$^+$: calculated 1057.4666. found 1057.4654.

XF078-90

XF078-90 was synthesized following the standard procedures for preparing XF078-61 from intermediate 42 (10.4 mg, 0.015 mmol), PML-19 (7.7 mg, 0.015 mmol, 1.0 equiv), EDCI (1-ethyl-3-(3-dimethylaminopropyl)carbodiimide) (4.3 mg, 0.023 mmol, 1.5 equiv), HOAt (1-hydroxy-7-azabenzo-triazole) (3.2 mg, 0.023 mmol, 1.5 equiv), and NMM (N-Methylmorpholine) (4.6 mg, 0.046 mmol, 3.0 equiv) in DMSO (1 mL). XF078-90 was obtained as yellow solid in TFA salt form (14 mg, yield 87%). $^1$H NMR (800 MHz, CD$_3$OD) δ 8.58 (s, 2H), 8.03 (d, J=7.3 Hz, 1H), 7.98-7.85 (m, 1H), 7.54 (t, J=7.8 Hz, 1H), 7.16 (d, J=11.6 Hz, 1H), 7.01 (d, J=7.8 Hz, 2H), 6.95 (s, 1H), 5.09-5.03 (m, 1H), 3.97-3.84 (m, 4H), 3.74-3.65 (m, 4H), 3.53 (ddd, J=15.5, 9.6, 5.2 Hz, 2H), 3.41-3.15 (m, 6H), 3.04-2.80 (m, 6H), 2.79-2.68 (m, 4H), 2.53-2.43 (m, 2H), 2.15-2.08 (m, 1H), 1.69-1.61 (m, 2H), 1.56-1.31 (m, 16H). HRMS (m/z) for C$_{53}$H$_{63}$F$_4$N$_{12}$O$_8{}^+$ [M+H]$^+$: calculated 1071.4822. found 1071.4865.

Example 273: Synthesis of Intermediate 44

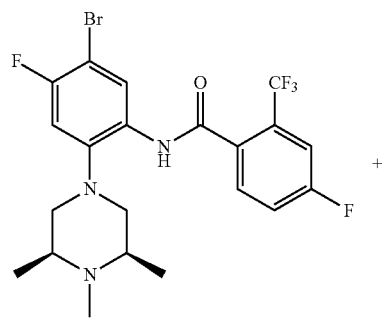

Intermediate 43

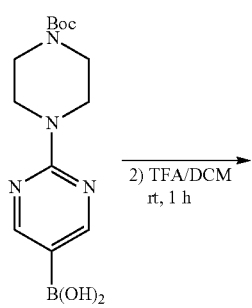

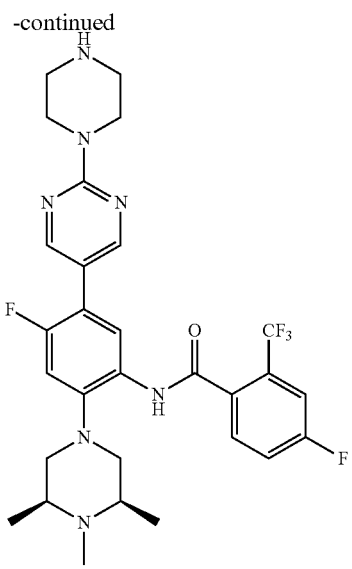

Intermediate 44

To a solution of Intermediate 43 (WO2017147700A1) (412 mg, 0.81 mmol) and (2-(4-(tert-butoxycarbonyl)piperazin-1-yl)pyrimidin-5-yl)boronic acid (752 mg, 2.44 mmol, 3.0 euqiv) in 8 mL of 1,4-dioxane/H$_2$O (5:3) were added sodium carbonate (858 mg, 8.1 mmol, 10 equiv), XPhos (77 mg, 0.16 mmol, 0.2 equiv), and XPhos Pd G2 (127 mg, 0.16 mmol, 0.2 equiv). The reaction was heated to 120° C. for 1 h under Microwave. The solvent was removed and purified by reverse phase ISCO (10%-100% methanol/0.1% TFA in H$_2$O) to afford product as white solid.

This product was dissolved in DCM (10 mL) and TFA (10 mL). The resulting mixture was stirring for 1 h. Then, it was concentrated and purified by reverse phase ISCO (10%-100% methanol/0.1% TFA in H$_2$O) to afford Intermediate 44 (XF078-94) as white solid in TFA salt form (410.4 mg, yield 86%). $^1$H NMR (500 MHz, CD$_3$OD) δ 8.63 (s, 2H), 8.08 (dd, J=8.6, 2.8 Hz, 1H), 7.80 (dd, J=8.6, 5.2 Hz, 1H), 7.62 (dd, J=9.0, 2.7 Hz, 1H), 7.58-7.52 (m, 1H), 7.21 (d, J=11.6 Hz, 1H), 4.17 (q, J=5.4, 5.0 Hz, 6H), 3.59-3.47 (m, 3H), 3.42-3.37 (m, 2H), 3.13-3.01 (m, 3H), 2.97 (s, 3H), 1.46 (d, J=6.5 Hz, 6H). HRMS (m/z) for C$_{29}$H$_{33}$F$_5$N$_7$O$^+$ [M+H]$^+$: calculated 590.2661. found 590.2676.

Example 274: Synthesis of XF078-99

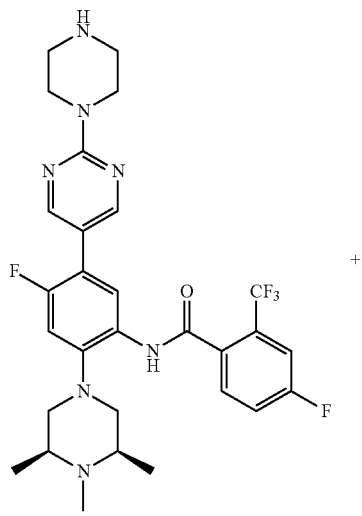

Intermediate 44

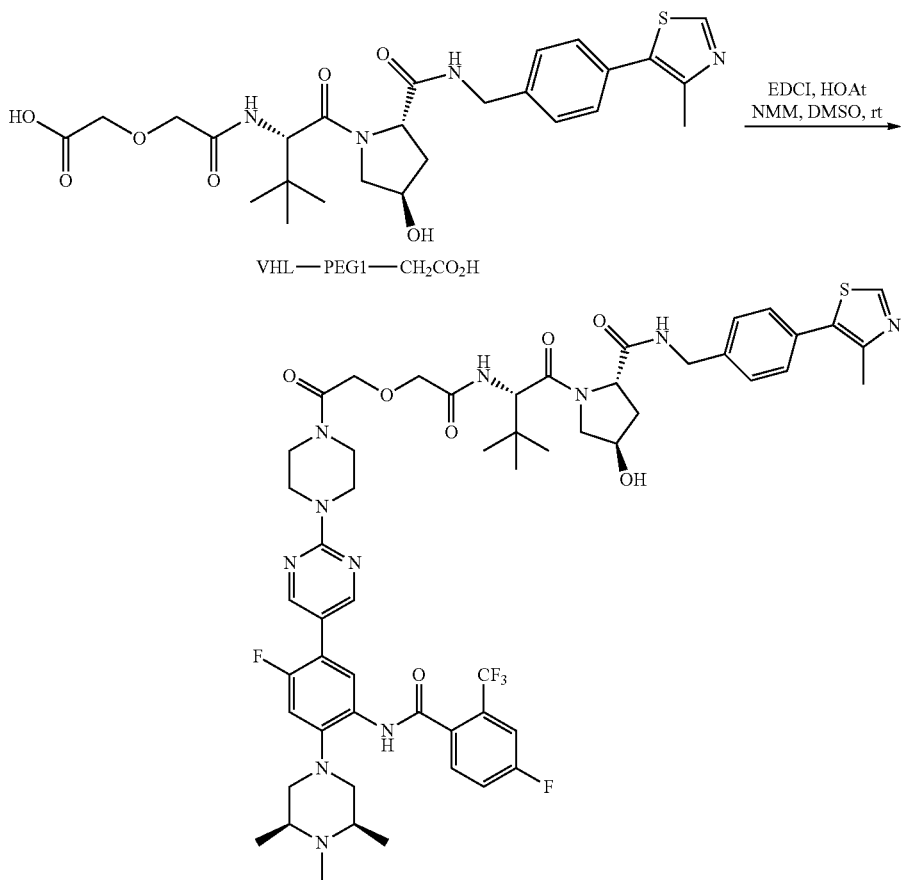

To the solution of intermediate 44 (11.8 mg, 0.02 mmol) in DMSO (1 mL) were added VHL-PEG1-CH₂COOH (10.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirring overnight at room temperature, the resulting mixture was purified by preparative HPLC (10%-100% methanol/0.1% TFA in H₂O) to afford XF078-99 as white solid in TFA salt form (17.5 mg, yield 78%). $^1$H NMR (800 MHz, CD$_3$OD) δ 8.97 (s, 1H), 8.56 (d, J=6.8 Hz, 2H), 8.07 (d, J=8.1 Hz, 1H), 7.83 (dd, J=8.5, 5.1 Hz, 1H), 7.68 (dd, J=9.2, 2.6 Hz, 1H), 7.59 (t, J=7.8 Hz, 1H), 7.50-7.40 (m, 4H), 7.22 (d, J=11.5 Hz, 1H), 4.75-4.67 (m, 1H), 4.64-4.42 (m, 5H), 4.36 (d, J=15.5 Hz, 1H), 4.21 (d, J=15.2 Hz, 1H), 4.18-4.08 (m, 1H), 4.04-3.87 (m, 5H), 3.83 (dd, J=10.9, 3.9 Hz, 1H), 3.79-3.66 (m, 2H), 3.63-3.56 (m, 2H), 3.56-3.47 (m, 2H), 3.46-3.35 (m, 2H), 3.06-2.96 (m, 5H), 2.49 (s, 3H), 2.31-2.20 (m, 1H), 2.17- 2.07 (m, 1H), 1.47 (d, J=6.5 Hz, 6H), 1.09 (s, 9H). HRMS (m/z) for $C_{55}H_{65}F_5N^{11}O_7S^+$ [M+H]$^+$: calculated 1118.4704. found 1118.4687.
Example 275: Synthesis of XF078-100
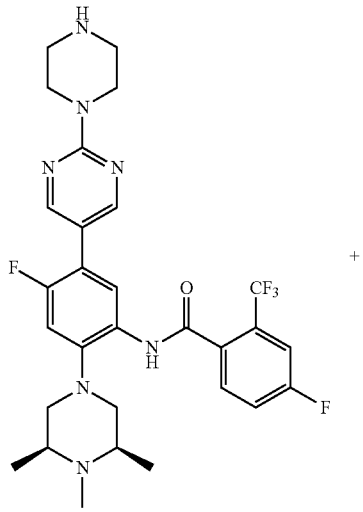
Intermediate 44
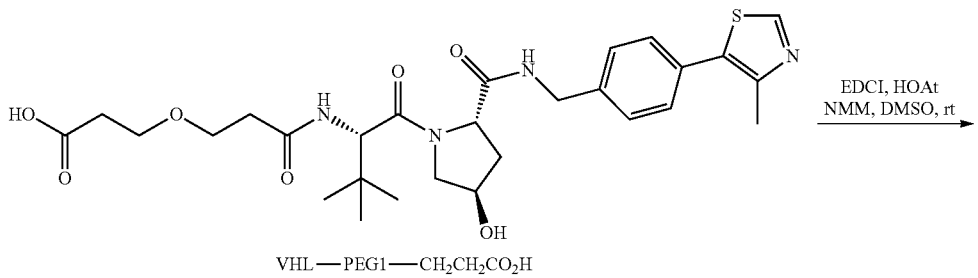
VHL—PEG1—CH$_2$CH$_2$CO$_2$H
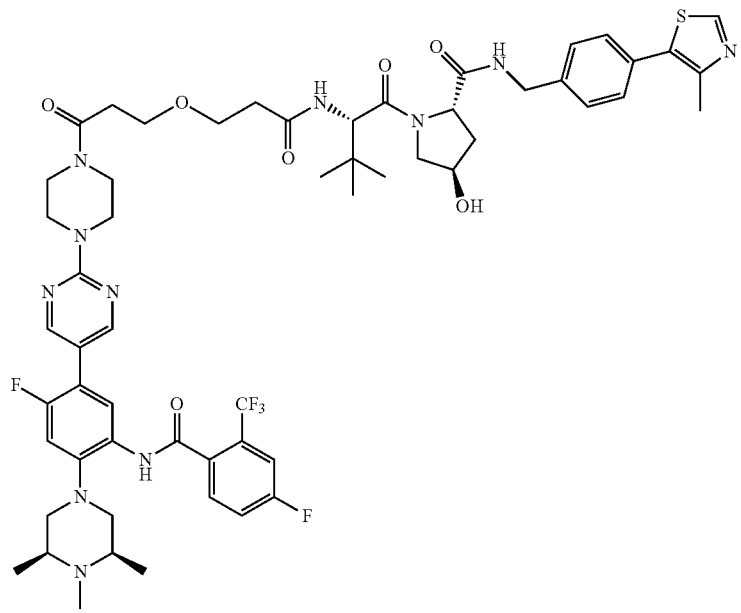
XF078-100

XF078-100 was synthesized following the standard procedures for preparing XF078-99 from intermediate 44 (11.8 mg, 0.02 mmol), VHL-PEG1-CH$_2$CH$_2$COOH (11.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-100 was obtained as white solid in TFA salt form (15.1 mg, yield 66%). $^1$H NMR (800 MHz, CD$_3$OD) δ 8.97 (s, 1H), 8.56 (s, 2H), 8.08 (d, J=8.1 Hz, 1H), 7.82 (dd, J=8.5, 5.1 Hz, 1H), 7.74-7.61 (m, 1H), 7.59 (t, J=7.4 Hz, 1H), 7.53-7.38 (m, 4H), 7.21 (d, J=11.5 Hz, 1H), 4.73-4.64 (m, 1H), 4.63-4.50 (m, 3H), 4.38 (d, J=15.4 Hz, 1H), 3.99-3.85 (m, 5H), 3.85-3.63 (m, 9H), 3.54-3.47 (m, 2H), 3.44-3.37 (m, 2H), 3.04-2.95 (m, 5H), 2.81-2.73 (m, 2H), 2.61-2.41 (m, 5H), 2.28-2.22 (m, 1H), 2.11 (ddd, J=13.3, 9.1, 4.4 Hz, 1H), 1.47 (d, J=6.5 Hz, 6H), 1.06 (s, 9H). HRMS (m/z) for C$_{57}$H$_{69}$F$_5$N$^{11}$O$_7$S$^+$ [M+H]$^+$: calculated 1146.5017. found 1146.4988.

Example 276: Synthesis of XF078-101

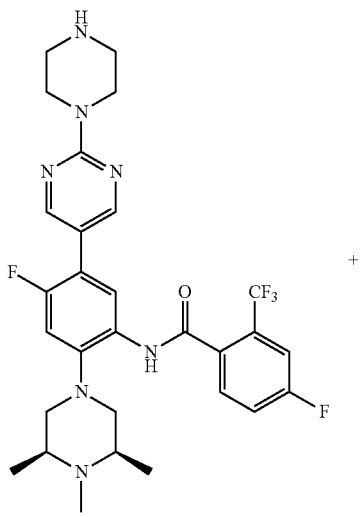

Intermediate 44

+

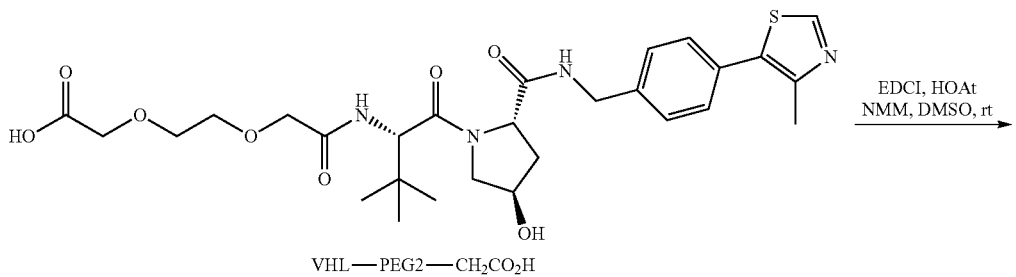

VHL—PEG2—CH$_2$CO$_2$H

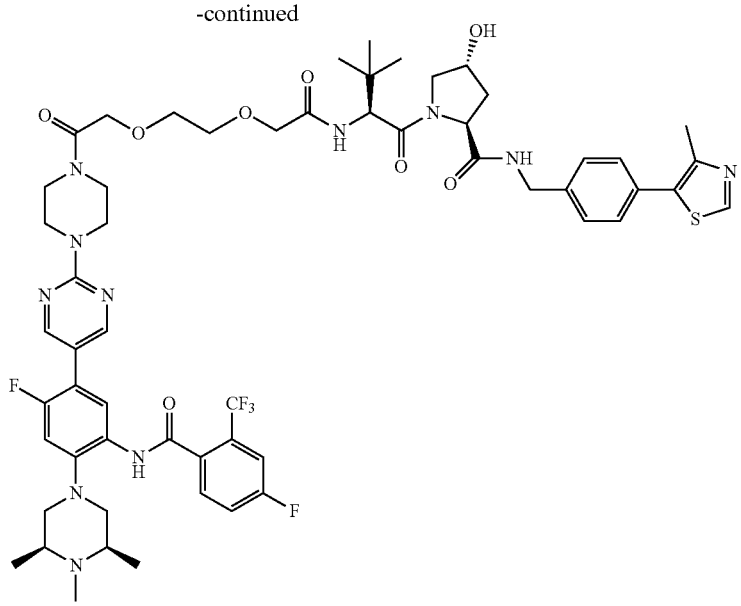

XF078-101

XF078-101 was synthesized following the standard procedures for preparing XF078-99 from intermediate 44 (11.8 mg, 0.02 mmol), VHL-PEG2-CH₂COOH (11.8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-101 was obtained as white solid in TFA salt form (14.1 mg, yield 61%). $^1$H NMR (800 MHz, CD$_3$OD) δ 9.01 (s, 1H), 8.56 (s, 2H), 8.08 (d, J=8.1 Hz, 1H), 7.82 (dd, J=8.6, 5.0 Hz, 1H), 7.72-7.65 (m, 1H), 7.59 (t, J=8.4 Hz, 1H), 7.48-7.39 (m, 4H), 7.21 (d, J=11.5 Hz, 1H), 4.81-4.71 (m, 1H), 4.63-4.48 (m, 3H), 4.47-4.35 (m, 3H), 4.13-4.04 (m, 2H), 4.02-3.73 (m, 10H), 3.72-3.60 (m, 4H), 3.54-3.48 (m, 2H), 3.40 (d, J=13.1 Hz, 2H), 3.03-2.94 (m, 5H), 2.48 (s, 3H), 2.31-2.22 (m, 1H), 2.16-2.06 (m, 1H), 1.47 (d, J=6.5 Hz, 6H), 1.08 (s, 9H). HRMS (m/z) for C$_{57}$H$_{69}$F$_5$N$_1$O$_8$S$^+$ [M+H]$^+$: calculated 1162.4966. found 1162.5012.

Example 277: Synthesis of XF078-102

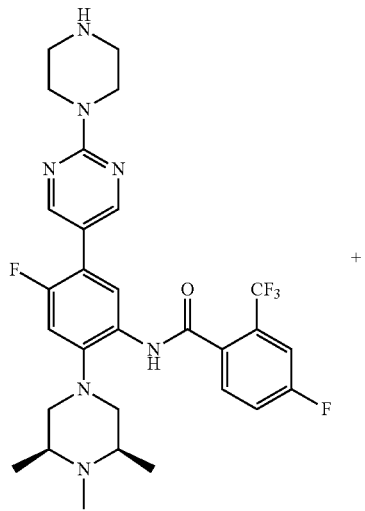

Intermediate 44

-continued

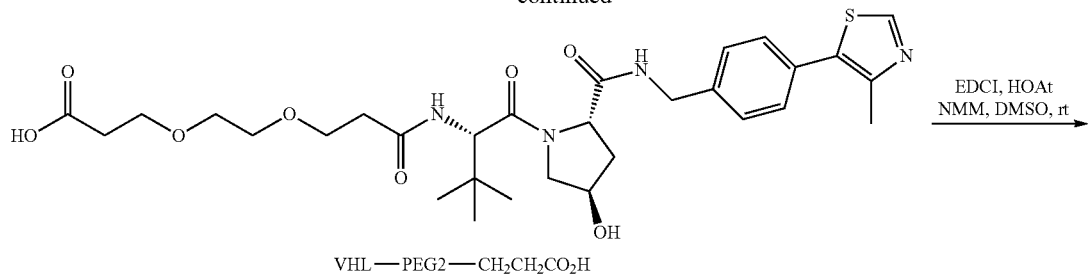

VHL—PEG2—CH₂CH₂CO₂H

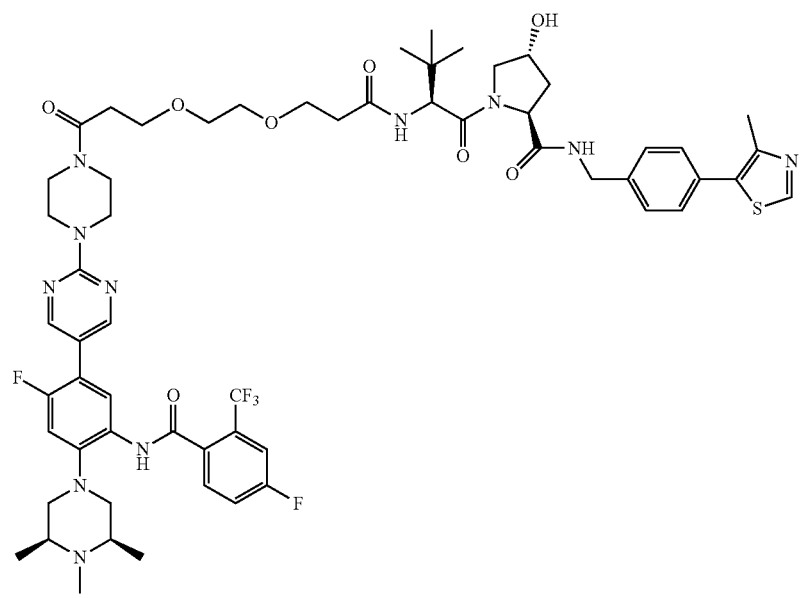

XF078-102

XF078-102 was synthesized following the standard procedures for preparing XF078-99 from intermediate 44 (11.8 mg, 0.02 mmol), VHL-PEG2-CH₂CH₂COOH (12.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-102 was obtained as white solid in TFA salt form (14.1 mg, yield 61%). ¹H NMR (800 MHz, CD₃OD) δ 9.01 (s, 1H), 8.59 (s, 2H), 8.08 (d, J=8.1 Hz, 1H), 7.83 (dd, J=8.6, 5.1 Hz, 1H), 7.68 (dd, J=9.2, 2.6 Hz, 1H), 7.59 (t, J=7.5 Hz, 1H), 7.54-7.38 (m, 4H), 7.22 (d, J=11.5 Hz, 1H), 4.73-4.63 (m, 1H), 4.63-4.48 (m, 3H), 4.42-4.34 (m, 1H), 3.99-3.85 (m, 6H), 3.84-3.55 (m, 12H), 3.54-3.46 (m, 2H), 3.40 (d, J=13.1 Hz, 2H), 3.03-2.93 (m, 5H), 2.79-2.70 (m, 2H), 2.61-2.46 (m, 5H), 2.23 (dd, J=13.5, 7.4 Hz, 1H), 2.16-2.05 (m, 1H), 1.47 (d, J=6.5 Hz, 6H), 1.06 (s, 9H). HRMS (m/z) for $C_{59}H_{73}F_5N_{11}O_8S^+$ [M+H]⁺: calculated 1190.5279. found 1190.5253.

Example 278: Synthesis of XF078-103

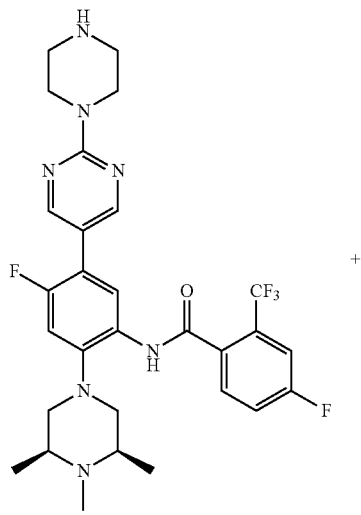

Intermediate 44

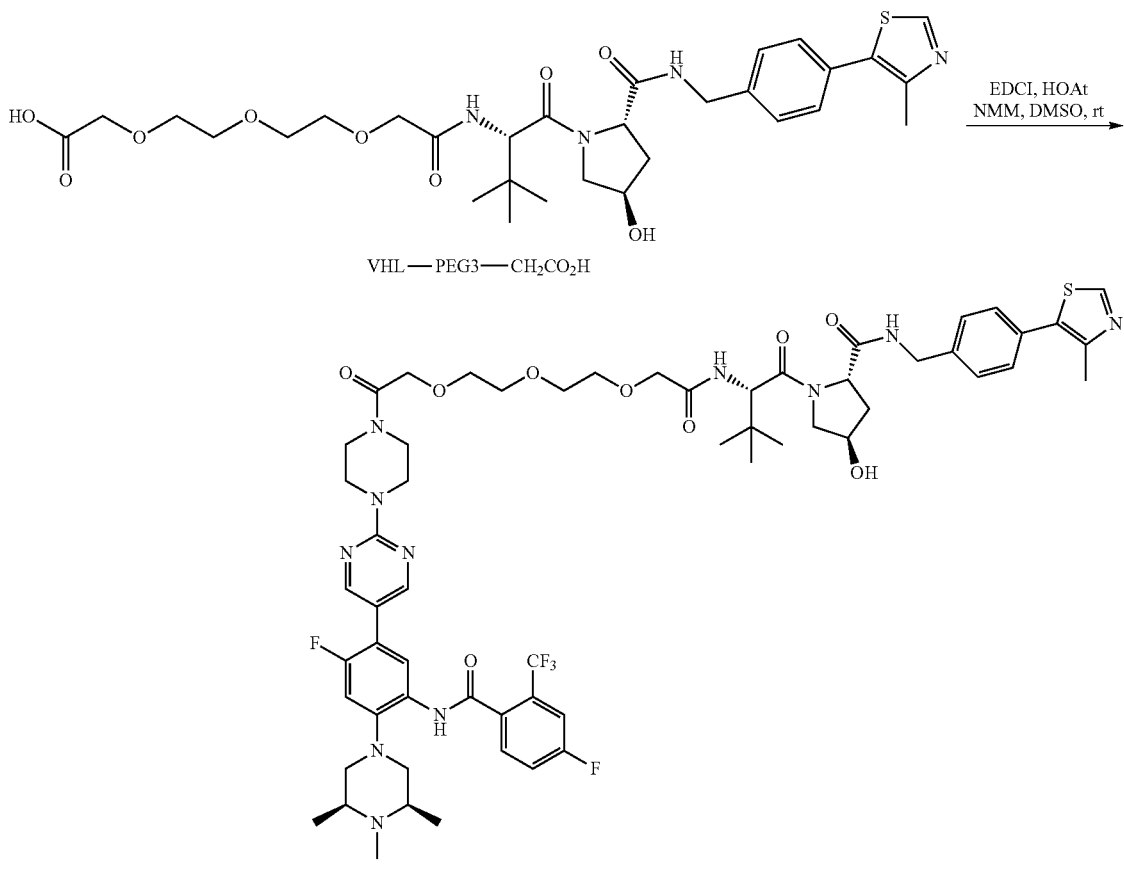

XF078-103 was synthesized following the standard procedures for preparing XF078-99 from intermediate 44 (11.8 mg, 0.02 mmol), VHL-PEG3-CH$_2$COOH (12.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-103 was obtained as white solid in TFA salt form (16.8 mg, yield 70%). $^1$H NMR (800 MHz, CD$_3$OD) δ 9.01 (s, 1H), 8.58 (s, 2H), 8.08 (d, J=8.0 Hz, 1H), 7.83 (dd, J=8.6, 5.2 Hz, 1H), 7.71-7.65 (m, 1H), 7.64-7.56 (m, 1H), 7.53-7.41 (m, 4H), 7.22 (dd, J=13.9, 6.9 Hz, 1H), 4.75-4.69 (m, 1H), 4.62-4.47 (m, 3H), 4.42-4.30 (m, 3H), 4.08-3.98 (m, 2H), 4.00-3.86 (m, 5H), 3.86-3.60 (m, 13H), 3.50-3.43 (m, 2H), 3.40 (d, J=13.0 Hz, 2H), 2.99-2.87 (m, 5H), 2.50 (s, 3H), 2.24 (dd, J=13.3, 7.6 Hz, 1H), 2.11 (ddd, J=13.3, 9.2, 4.5 Hz, 1H), 1.47 (d, J=6.5 Hz, 6H), 1.06 (s, 9H). HRMS (m/z) for C$_{59}$H$_{73}$F$_5$N$_{11}$O$_9$S$^+$ [M+H]$^+$: calculated 1206.5228. found 1206.5246.

Example 279: Synthesis of XF078-104

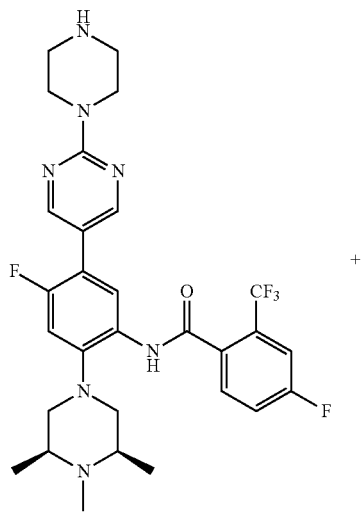

Intermediate 44

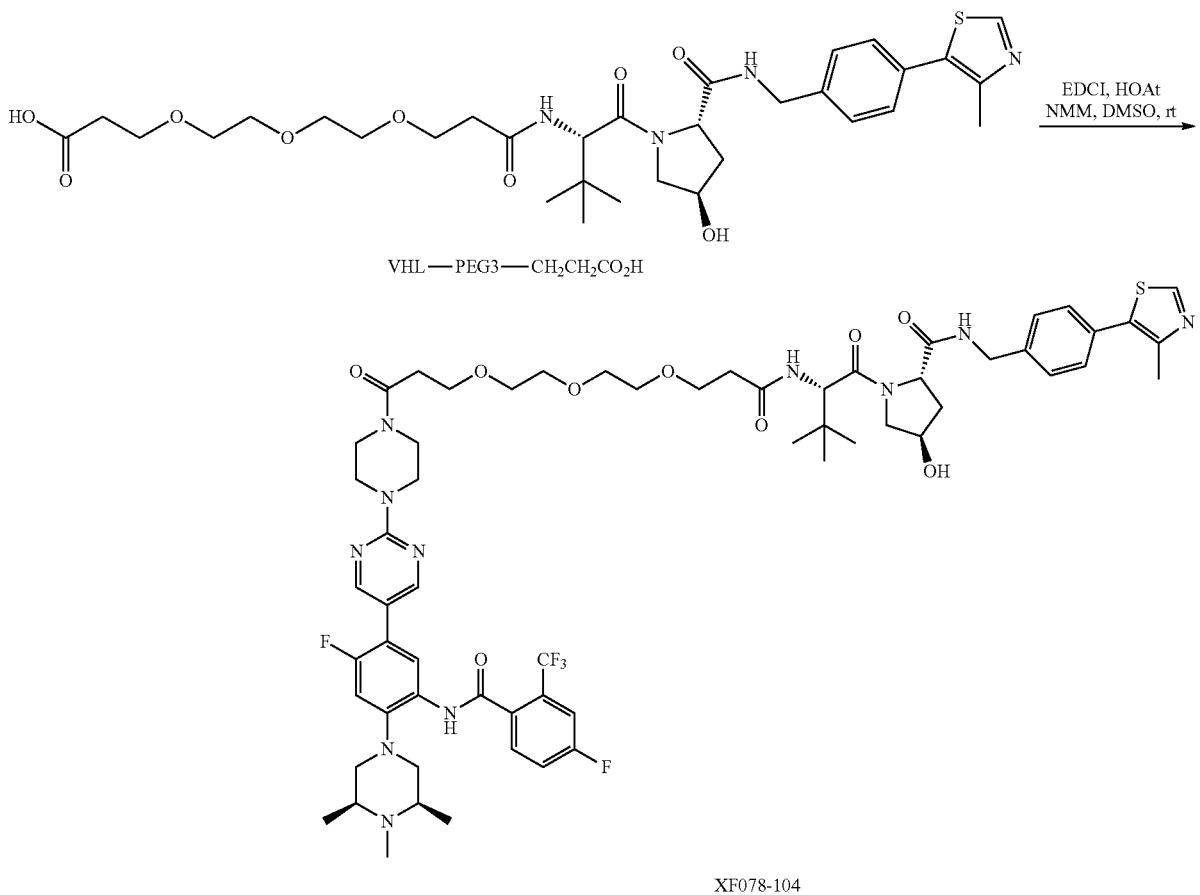

XF078-104 was synthesized following the standard procedures for preparing XF078-99 from intermediate 44 (11.8 mg, 0.02 mmol), VHL-PEG3-CH$_2$CH$_2$COOH (13.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-104 was obtained as white solid in TFA salt form (18.8 mg, yield 76%). $^1$H NMR (800 MHz, CD$_3$OD) δ 9.01 (s, 1H), 8.59 (d, J=4.0 Hz, 2H), 8.08 (d, J=8.1 Hz, 1H), 7.83 (dd, J=8.6, 5.1 Hz, 1H), 7.68 (dd, J=9.2, 2.6 Hz, 1H), 7.66-7.53 (m, 1H), 7.53-7.40 (m, 4H), 7.22 (d, J=11.5 Hz, 1H), 4.67 (d, J=6.2 Hz, 1H), 4.62-4.48 (m, 3H), 4.38 (t, J=14.0 Hz, 1H), 4.03-3.85 (m, 6H), 3.85-3.55 (m, 16H), 3.54-3.46 (m, 2H), 3.39 (d, J=13.0 Hz, 2H), 2.99 (d, J=9.8 Hz, 5H), 2.74 (t, J=6.3 Hz, 2H), 2.62-2.55 (m, 2H), 2.50 (s, 3H), 2.23 (dd, J=13.5, 7.5 Hz, 1H), 2.10 (ddd, J=13.2, 9.1, 4.6 Hz, 1H), 1.47 (d, J=6.5 Hz, 6H), 1.06 (s, 9H). HRMS (m/z) for C$_{61}$H$_{77}$F$_5$N$_{11}$O$_9$S$^+$ [M+H]$^+$: calculated 1234.5541. found 1234.5517.

Example 280: Synthesis of XF078-105
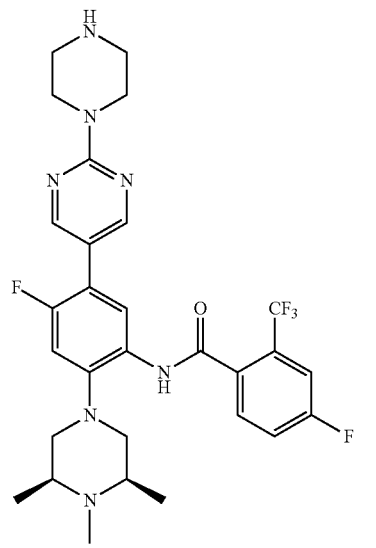
Intermediate 44
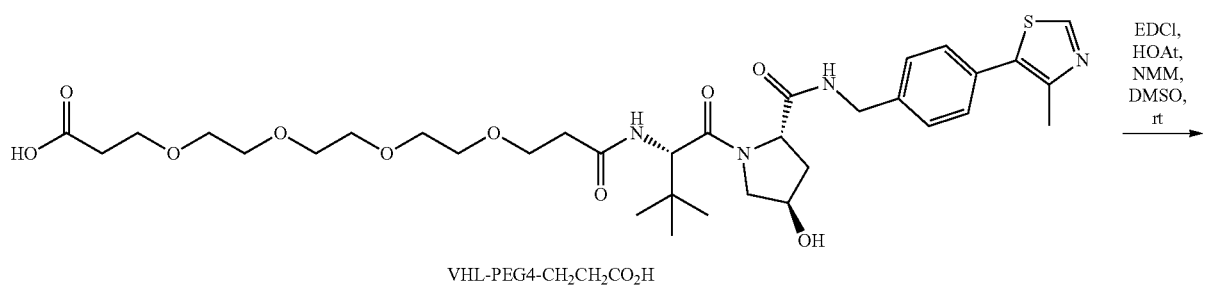
VHL-PEG4-CH$_2$CH$_2$CO$_2$H
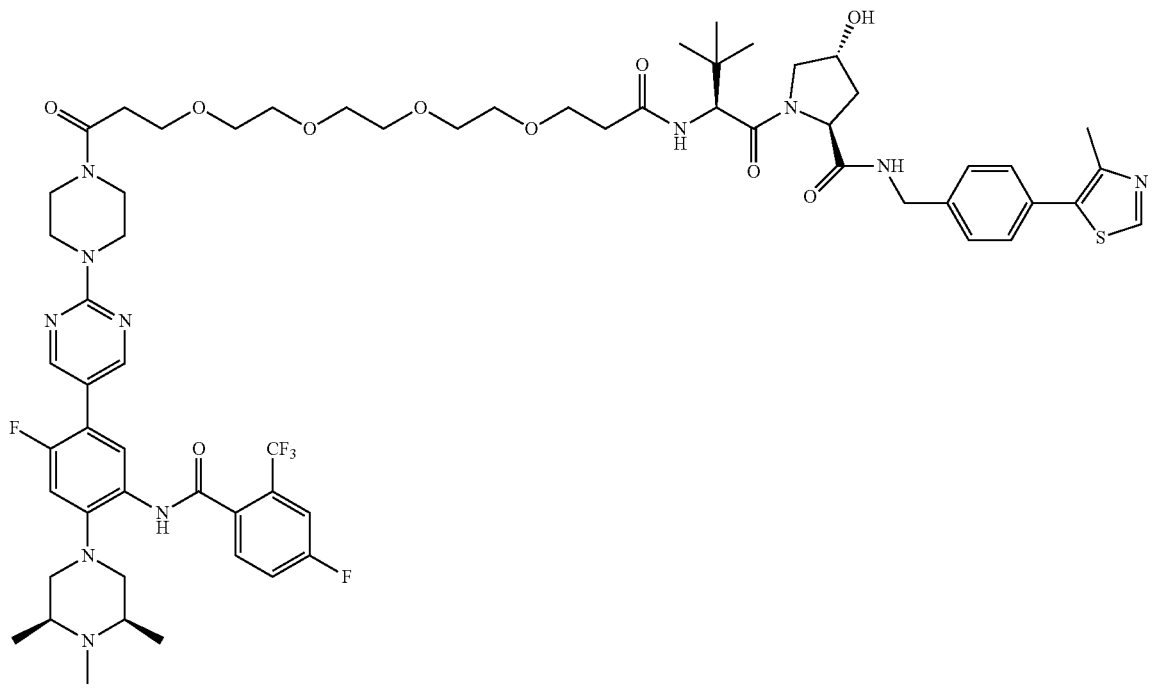
XF078-105

XF078-105 was synthesized following the standard procedures for preparing XF078-99 from intermediate 44 (11.8 mg, 0.02 mmol), VHL-PEG4-CH$_2$CH$_2$COOH (14.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-105 was obtained as white solid in TFA salt form (14.1 mg, yield 55%). $^1$H NMR (800 MHz, CD$_3$OD) δ 9.01 (s, 1H), 8.60 (s, 2H), 8.08 (d, J=8.1 Hz, 1H), 7.83 (dd, J=8.6, 5.1 Hz, 1H), 7.71-7.67 (m, 1H), 7.65-7.56 (m, 1H), 7.52-7.38 (m, 4H), 7.22 (d, J=11.5 Hz, 1H), 4.73-4.66 (m, 1H), 4.64-4.45 (m, 3H), 4.38 (t, J=13.1 Hz, 1H), 4.00-3.94 (m, 2H), 3.93-3.85 (m, 4H), 3.84-3.78 (m, 4H), 3.78-3.69 (m, 6H), 3.67-3.53 (m, 10H), 3.54-3.46 (m, 2H), 3.40 (d, J=13.1 Hz, 2H), 3.04-2.94 (m, 5H), 2.75 (t, J=6.3 Hz, 2H), 2.63-2.55 (m, 1H), 2.54-2.47 (m, 4H), 2.23 (dd, J=13.4, 7.6 Hz, 1H), 2.10 (ddd, J=13.3, 9.1, 4.5 Hz, 1H), 1.47 (d, J=6.5 Hz, 6H), 1.05 (s, 9H). HRMS (m/z) for C$_{63}$H$_{81}$F$_5$N$_{11}$O$_{10}$S$^+$ [M+H]$^+$: calculated 1278.5803. found 1278.5786.

Example 281: Synthesis of XF078-106

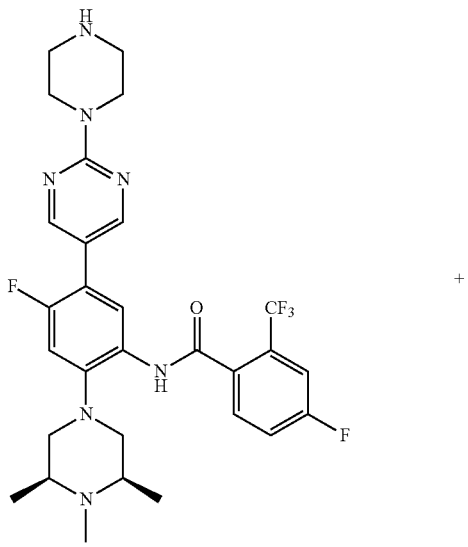

Intermediate 44

+

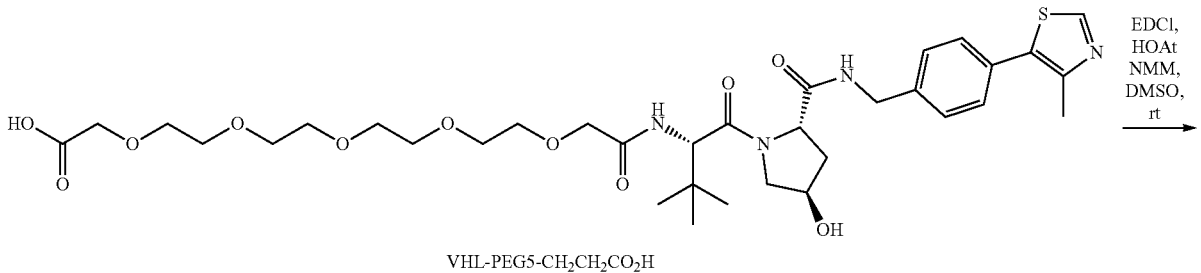

VHL-PEG5-CH$_2$CH$_2$CO$_2$H

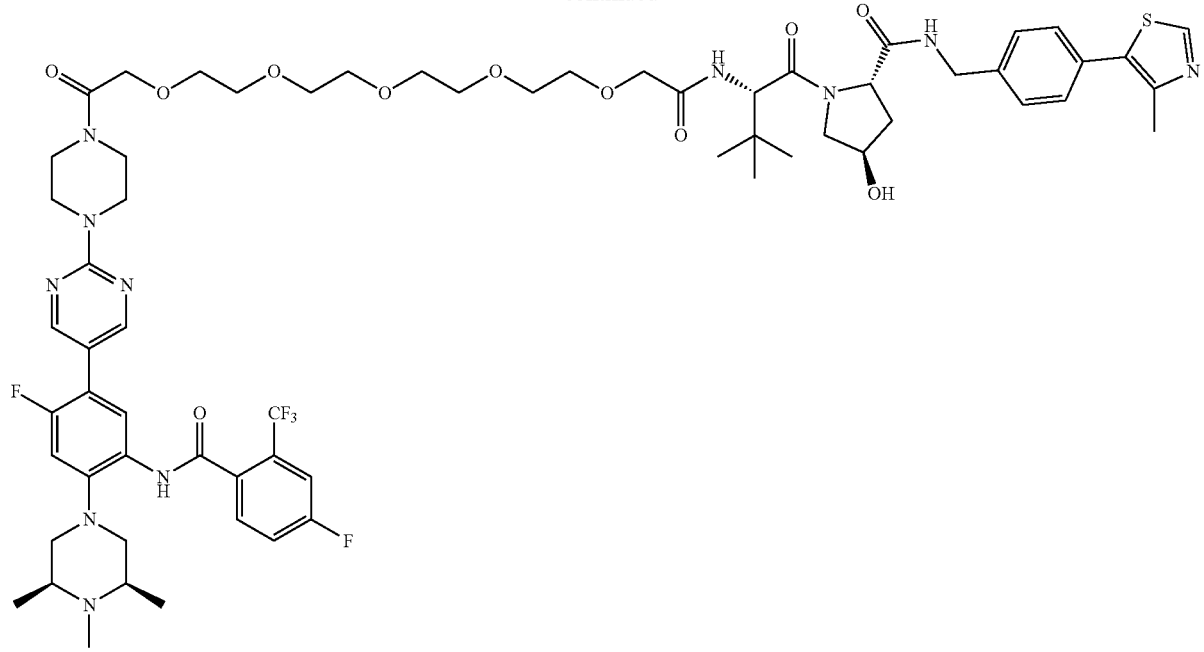

XF078-106

XF078-106 was synthesized following the standard procedures for preparing XF078-99 from intermediate 44 (11.8 mg, 0.02 mmol), VHL-PEG5-CH$_2$COOH (14.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-106 was obtained as white solid in TFA salt form (13.3 mg, yield 51%). $^1$H NMR (800 MHz, CD$_3$OD) δ 9.02 (s, 1H), 8.59 (s, 2H), 8.08 (d, J=8.2 Hz, 1H), 7.83 (dd, J=8.6, 5.1 Hz, 1H), 7.75-7.65 (m, 1H), 7.59 (t, J=7.7 Hz, 1H), 7.50-7.43 (m, 4H), 7.22 (d, J=11.6 Hz, 1H), 4.71 (s, 1H), 4.62-4.50 (m, 3H), 4.41-4.29 (m, 3H), 4.12-4.03 (m, 2H), 4.00-3.86 (m, 6H), 3.76-3.56 (m, 20H), 3.53-3.47 (m, 2H), 3.43-3.35 (m, 2H), 3.05-2.94 (m, 5H), 2.57-2.43 (m, 3H), 2.25 (dd, J=13.2, 7.5 Hz, 1H), 2.11 (ddd, J=13.3, 9.1, 4.4 Hz, 1H), 1.47 (d, 6H), 1.06 (s, 9H). HRMS (m/z) for C$_{63}$H$_{81}$F$_5$N$_{11}$O$_{11}$S$^+$ [M+H]$^+$: calculated 1294.5752. found 1294.5789.

Example 282: Synthesis of XF078-107

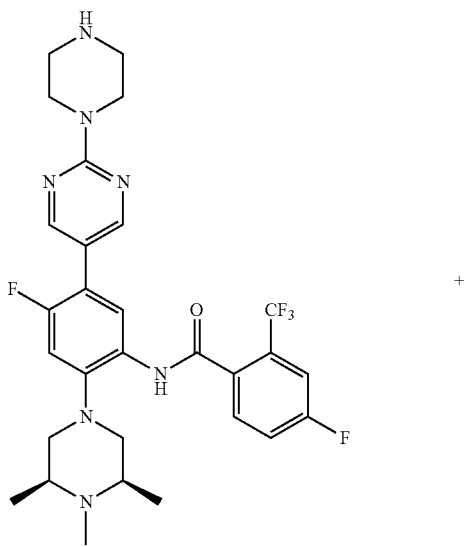

Intermediate 44

+

-continued

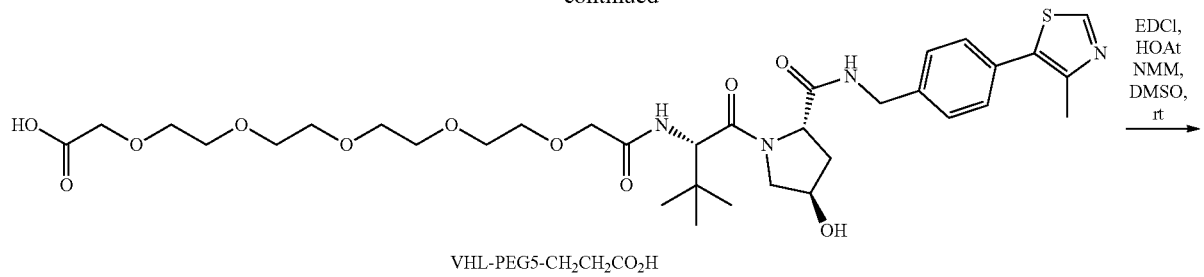

VHL-PEG5-CH₂CH₂CO₂H

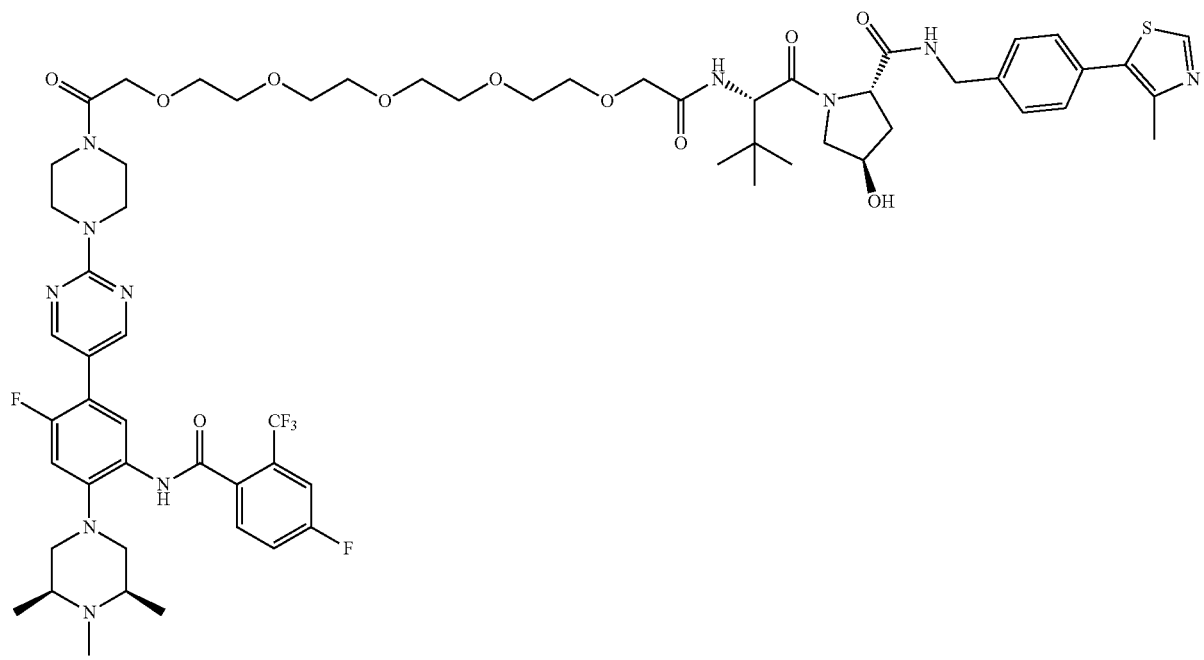

XF078-107

XF078-107 was synthesized following the standard procedures for preparing XF078-99 from intermediate 44 (11.8 mg, 0.02 mmol), VHL-PEG5-CH₂CH₂COOH (15 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-107 was obtained as white solid in TFA salt form (12.1 mg, yield 46%). ¹H NMR (800 MHz, CD₃OD) δ 9.01 (s, 1H), 8.60 (s, 2H), 8.08 (d, J=8.1 Hz, 1H), 7.83 (dd, J=8.6, 5.1 Hz, 1H), 7.75-7.64 (m, 1H), 7.59 (t, J=7.6 Hz, 1H), 7.57-7.38 (m, 4H), 7.22 (d, J=11.5 Hz, 1H), 4.73-4.64 (m, 1H), 4.63-4.49 (m, 3H), 4.43-4.29 (m, 1H), 4.02-3.95 (m, 2H), 3.94-3.86 (m, 3H), 3.85-3.79 (m, 3H), 3.78-3.67 (m, 6H), 3.67-3.54 (m, 16H), 3.54-3.47 (m, 2H), 3.40 (d, J=13.1 Hz, 2H), 3.04-2.95 (m, 5H), 2.75 (t, J=6.2 Hz, 2H), 2.62-2.55 (m, 1H), 2.54-2.44 (m, 4H), 2.23 (dd, J=13.3, 7.6 Hz, 1H), 2.10 (ddd, J=13.3, 9.1, 4.5 Hz, 1H), 1.47 (d, J=6.5 Hz, 6H), 1.05 (s, 9H). HRMS (m/z) for $C_{65}H_{85}F_5N_{11}O_{11}S^+$ [M+H]⁺: calculated 1322.6065. found 1322.6034.

Example 283: Synthesis of XF078-108
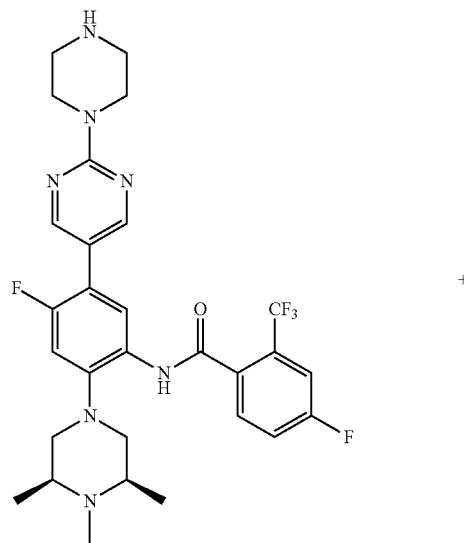
Intermediate 44
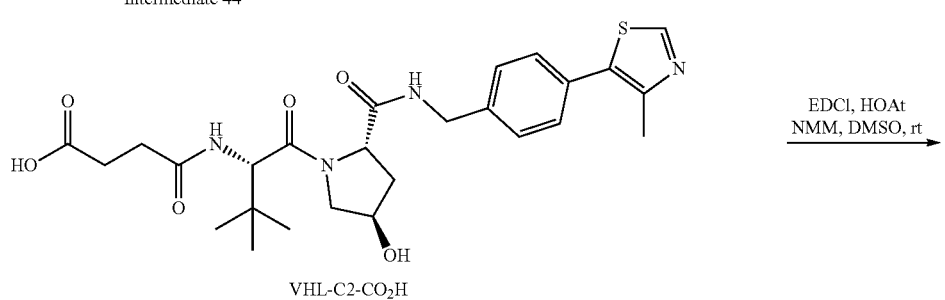
VHL-C2-CO₂H
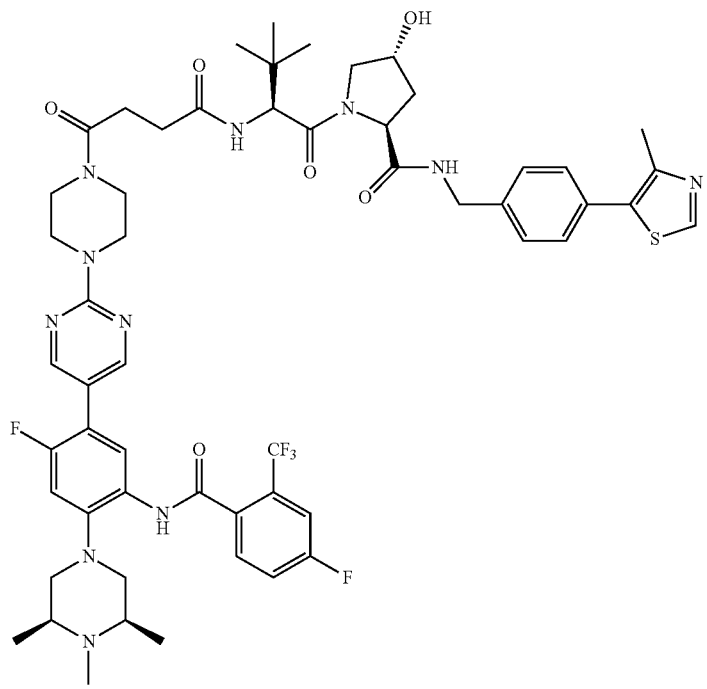
XF078-108

XF078-108 was synthesized following the standard procedures for preparing XF078-99 from intermediate 44 (11.8 mg, 0.02 mmol), VHL-C2-COOH (10.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-108 was obtained as white solid in TFA salt form (12.5 mg, yield 57%). $^1$H NMR (800 MHz, CD$_3$OD) δ 9.01 (s, 1H), 8.59 (s, 2H), 8.08 (d, J=8.1 Hz, 1H), 7.83 (dd, J=8.6, 5.1 Hz, 1H), 7.77-7.64 (m, 1H), 7.59 (t, J=7.5 Hz, 1H), 7.57-7.41 (m, 4H), 7.22 (t, J=11.0 Hz, 1H), 4.66-4.50 (m, 4H), 4.39 (d, J=15.5 Hz, 1H), 4.01-3.87 (m, 5H), 3.82 (dd, J=10.9, 3.9 Hz, 1H), 3.76-3.66 (m, 4H), 3.51 (d, J=10.3 Hz, 2H), 3.40 (d, J=13.0 Hz, 2H), 3.05-2.92 (m, 5H), 2.88-2.73 (m, 2H), 2.68 (dt, J=14.2, 6.8 Hz, 1H), 2.65-2.59 (m, 1H), 2.51 (s, 3H), 2.27-2.22 (m, 1H), 2.10 (ddd, J=13.3, 9.1, 4.5 Hz, 1H), 1.47 (d, J=6.5 Hz, 6H), 1.07 (s, 9H). HRMS (m/z) for C$_{55}$H$_{65}$F$_5$N$^{11}$O$_6$S$^+$ [M+H]$^+$: calculated 1102.4755. found 1102.4764.

Example 284: Synthesis of XF078-109

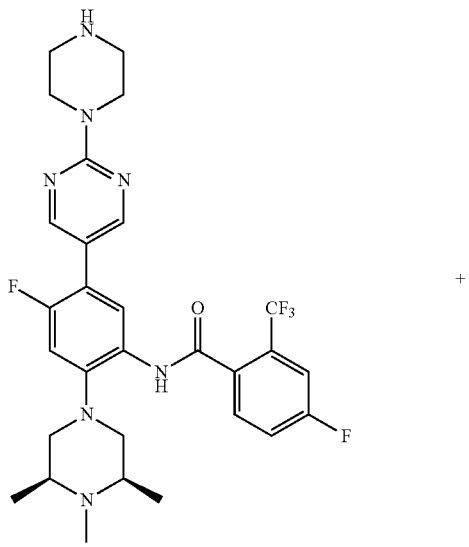

Intermediate 44

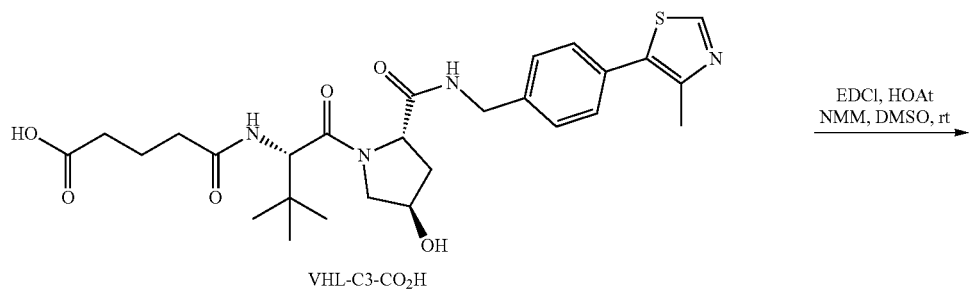

VHL-C3-CO$_2$H

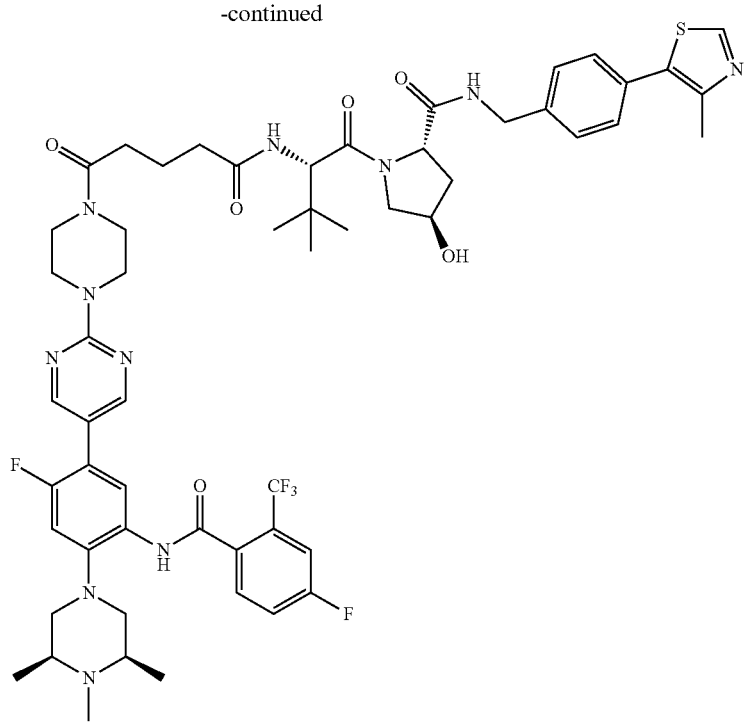

XF078-109

XF078-109 was synthesized following the standard procedures for preparing XF078-99 from intermediate 44 (11.8 mg, 0.02 mmol), VHL-C3-COOH (10.8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-109 was obtained as white solid in TFA salt form (15.9 mg, yield 710%). $^1$H NMR (800 MHz, CD$_3$OD) δ 8.96 (s, 1H), 8.57 (s, 2H), 8.07 (d, J=8.1 Hz, 1H), 7.83 (t, J=6.9 Hz, 1H), 7.73-7.64 (m, 1H), 7.59 (t, J=8.1 Hz, 1H), 7.55-7.38 (m, 4H), 7.21 (d, J=11.5 Hz, 1H), 4.71-4.47 (m, 4H), 4.38 (d, J=15.4 Hz, 1H), 4.02-3.78 (m, 6H), 3.78-3.58 (m, 4H), 3.54-3.46 (m, 2H), 3.40 (d, J=13.0 Hz, 2H), 3.04-2.93 (m, 5H), 2.54-2.44 (m, 5H), 2.39 (t, J=7.1 Hz, 2H), 2.28-2.23 (m, 1H), 2.11 (ddd, J=13.3, 9.1, 4.4 Hz, 1H), 1.99-1.93 (m, 2H), 1.47 (d, J=6.5 Hz, 6H), 1.06 (d, J=29.7 Hz, 9H). HRMS (m/z) for $C_{56}H_{67}F_5N^{11}O_6S^+$ [M+H]$^+$: calculated 1116.4911. found 1116.4934.

Example 285: Synthesis of XF078-110

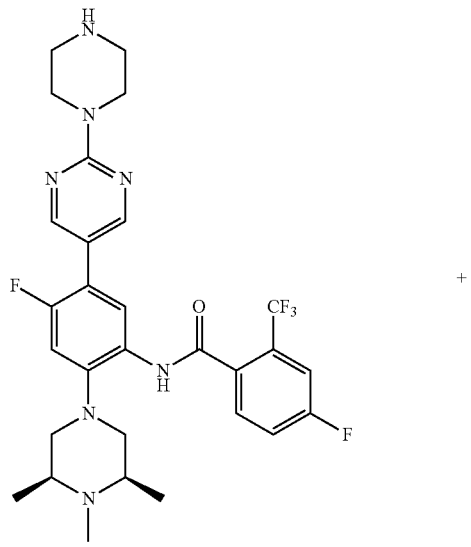

Intermediate 44

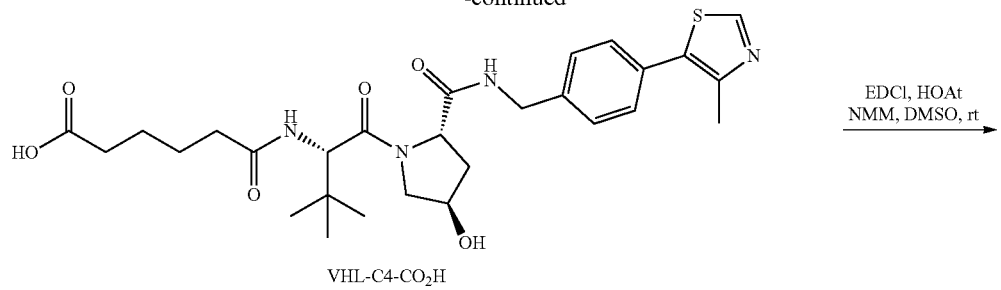

VHL-C4-CO₂H

EDCl, HOAt
NMM, DMSO, rt

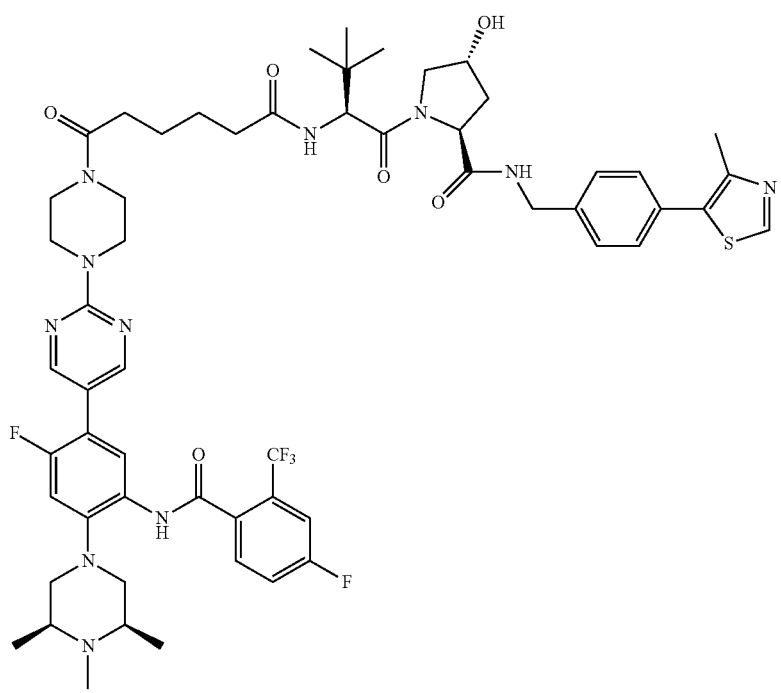

XF078-110

XF078-110 was synthesized following the standard procedures for preparing XF078-99 from intermediate 44 (11.8 mg, 0.02 mmol), VHL-C4-COOH (11.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-110 was obtained as white solid in TFA salt form (13.5 mg, yield 60%). $^1$H NMR (800 MHz, CD$_3$OD) δ 8.94 (s, 1H), 8.58 (s, 2H), 8.08 (d, J=8.1 Hz, 1H), 7.91-7.77 (m, 1H), 7.69 (d, J=8.9 Hz, 1H), 7.59 (t, J=8.4 Hz, 1H), 7.56-7.36 (m, 4H), 7.22 (d, J=11.4 Hz, 1H), 4.71-4.47 (m, 4H), 4.38 (d, J=15.3 Hz, 1H), 4.03-3.75 (m, 6H), 3.69 (td, J=13.4, 6.8 Hz, 4H), 3.57-3.46 (m, 2H), 3.40 (d, J=13.2 Hz, 2H), 3.09-2.87 (m, 5H), 2.62-2.42 (m, 5H), 2.41-2.27 (m, 2H), 2.27-2.18 (m, 1H), 2.15-1.99 (m, 1H), 1.75-1.62 (m, 4H), 1.47 (d, J=6.5 Hz, 6H), 1.07 (s, 9H). HRMS (m/z) for C57H$_{69}$F$_5$N$^{11}$O$_6$S$^+$ [M+H]$^+$: calculated 1130.5068. found 1130.5042.

Example 286: Synthesis of XF078-111
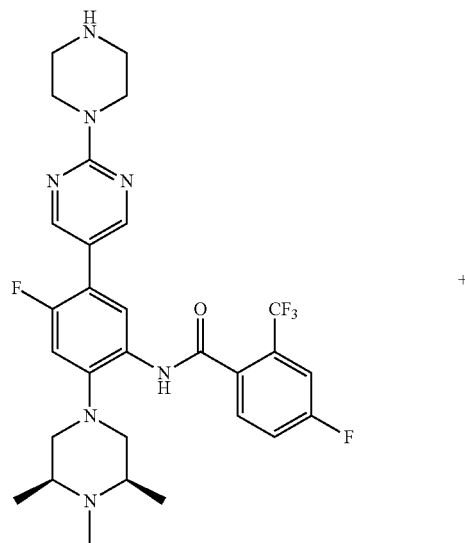
Intermediate 44
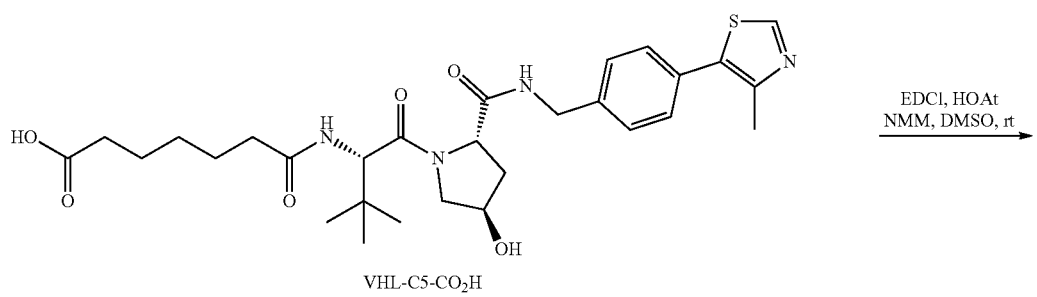
VHL-C5-CO$_2$H
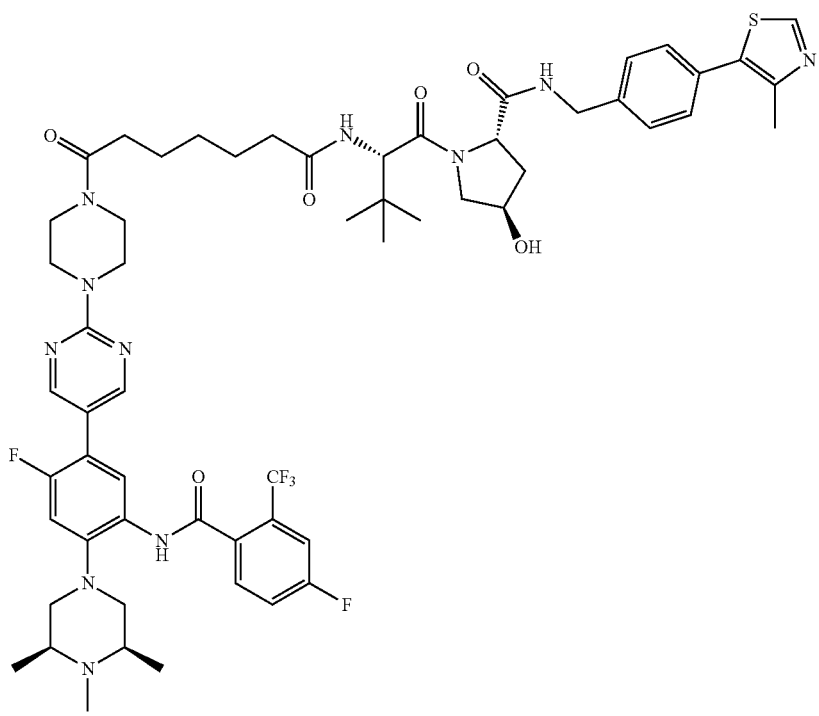
XF078-111

XF078-111 was synthesized following the standard procedures for preparing XF078-99 from intermediate 44 (11.8 mg, 0.02 mmol), VHL-C5-COOH (11.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-111 was obtained as white solid in TFA salt form (16.8 mg, yield 73%). $^1$H NMR (800 MHz, CD$_3$OD) δ 8.99 (s, 1H), 8.59 (s, 2H), 8.22-7.94 (m, 1H), 7.94-7.76 (m, 1H), 7.76-7.64 (m, 1H), 7.64-7.55 (m, 1H), 7.55-7.39 (m, 4H), 7.29-7.18 (m, 1H), 4.67-4.48 (m, 4H), 4.38 (d, J=15.3 Hz, 1H), 4.00-3.73 (m, 6H), 3.75-3.60 (m, 4H), 3.56-3.47 (m, 2H), 3.40 (d, J=13.1 Hz, 2H), 3.04-2.93 (m, 5H), 2.54-2.44 (m, 5H), 2.42-2.21 (m, 3H), 2.14-2.06 (m, 1H), 1.73-1.63 (m, 4H), 1.55-1.23 (m, 8H), 1.07 (s, 9H). HRMS (m/z) for $C_{58}H_{71}F_5N^{11}O_6S^+$ [M+H]$^+$: calculated 1144.5224. found 1144.5245.

Example 287: Synthesis of XF078-112

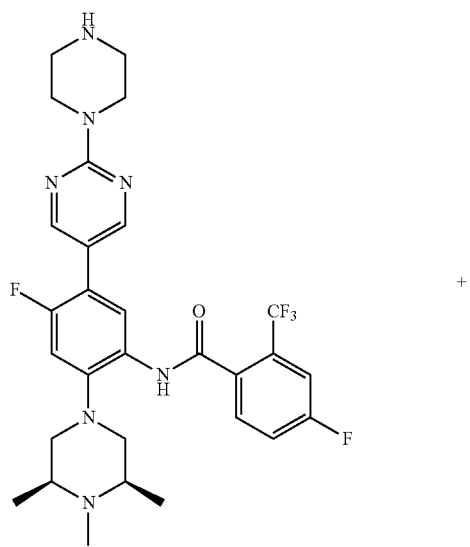

Intermediate 44

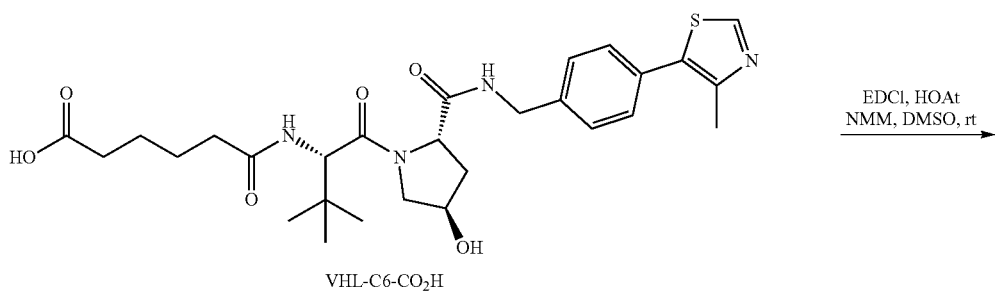

VHL-C6-CO$_2$H

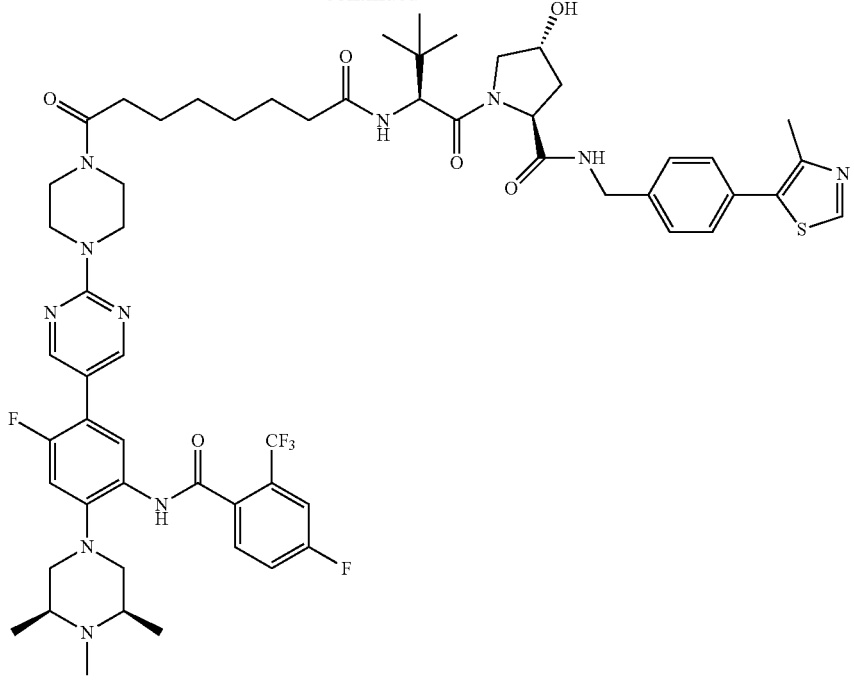

XF078-112

XF078-112 was synthesized following the standard procedures for preparing XF078-99 from intermediate 44 (11.8 mg, 0.02 mmol), VHL-C6-COOH (11.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-112 was obtained as white solid in TFA salt form (13.5 mg, yield 58%). $^1$H NMR (800 MHz, CD$_3$OD) δ 8.97 (s, 1H), 8.59 (s, 2H), 8.08 (d, J=8.0 Hz, 1H), 7.83 (t, J=6.9 Hz, 1H), 7.69 (d, J=8.8 Hz, 1H), 7.59 (t, J=8.3 Hz, 1H), 7.53-7.36 (m, 4H), 7.22 (d, J=11.5 Hz, 1H), 4.67 (s, 1H), 4.64-4.48 (m, 3H), 4.38 (d, J=15.5 Hz, 1H), 4.04-3.80 (m, 6H), 3.74-3.64 (m, 4H), 3.55-3.47 (m, 2H), 3.45-3.37 (m, 2H), 3.03-2.91 (m, 5H), 2.57-2.42 (m, 5H), 2.42-2.21 (m, 3H), 2.15-2.06 (m, 1H), 1.80-1.59 (m, 4H), 1.53-1.30 (m, 10H), 1.06 (s, 9H). HRMS (m/z) for C$_{59}$H$_{73}$F$_5$N$_{11}$O$_6$S$^+$ [M+H]$^+$: calculated 1158.5381. found 1158.5397.

Example 288: Synthesis of XF078-113

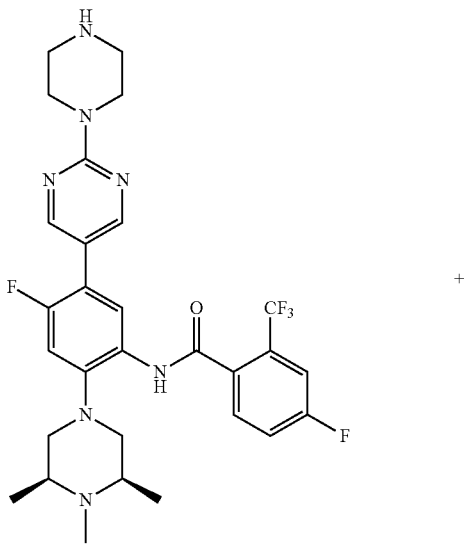

Intermediate 44

+

701
702
-continued
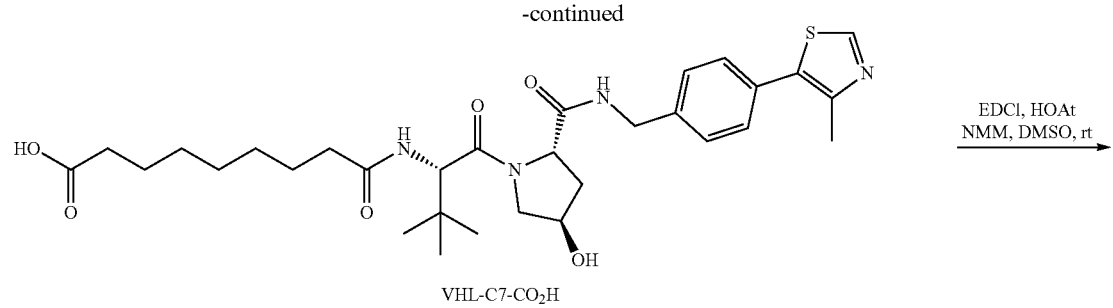
VHL-C7-CO₂H
EDCl, HOAt
NMM, DMSO, rt
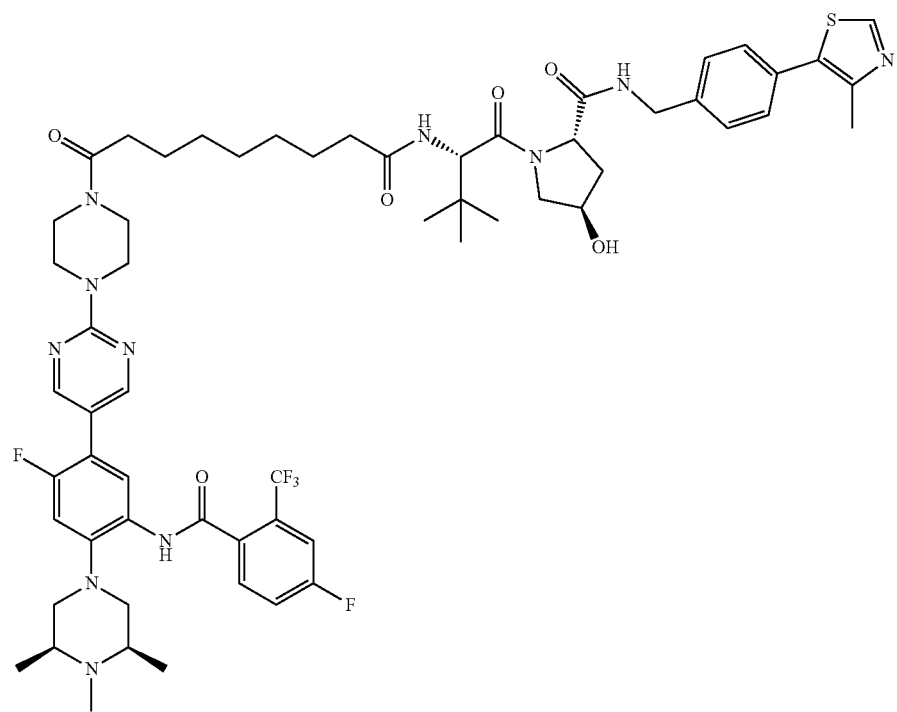
XF078-113

XF078-113 was synthesized following the standard procedures for preparing XF078-99 from intermediate 44 (11.8 mg, 0.02 mmol), VHL-C7-COOH (12 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-113 was obtained as white solid in TFA salt form (14.3 mg, yield 59%). $^1$H NMR (800 MHz, CD$_3$OD) δ 8.99 (s, 1H), 8.59 (s, 2H), 8.08 (d, J=8.1 Hz, 1H), 7.83 (dd, J=8.5, 5.2 Hz, 1H), 7.68 (dd, J=9.2, 2.5 Hz, 1H), 7.59 (t, J=8.2 Hz, 1H), 7.53-7.40 (m, 4H), 7.22 (d, J=11.5 Hz, 1H), 4.66 (s, 1H), 4.64-4.45 (m, 3H), 4.39 (d, J=15.3 Hz, 1H), 4.00-3.80 (m, 6H), 3.75-3.61 (m, 4H), 3.58-3.49 (m, 2H), 3.40 (d, J=13.2 Hz, 2H), 2.99 (d, J=16.7 Hz, 5H), 2.54-2.46 (m, 5H), 2.37-2.19 (m, 3H), 2.10 (s, 1H), 1.70-1.59 (m, 4H), 1.53-1.30 (m, 12H), 1.06 (s, 9H). HRMS (m/z) for $C_{60}H_{75}F_5N^{11}O_6S^+$ [M+H]$^+$: calculated 1172.5537. found 1172.5545.

Example 289: Synthesis of XF078-114

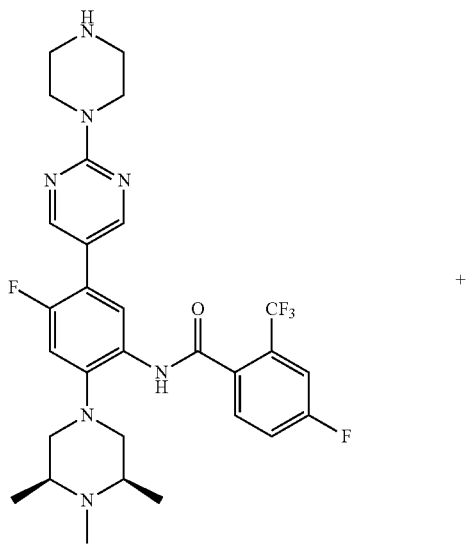

Intermediate 44

+

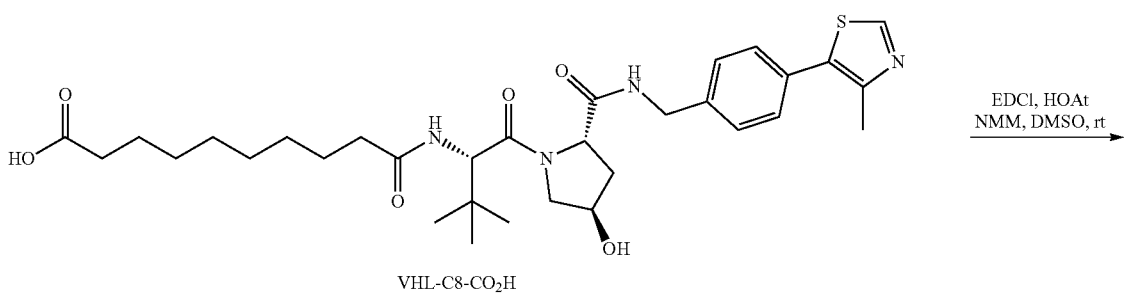

VHL-C8-CO$_2$H

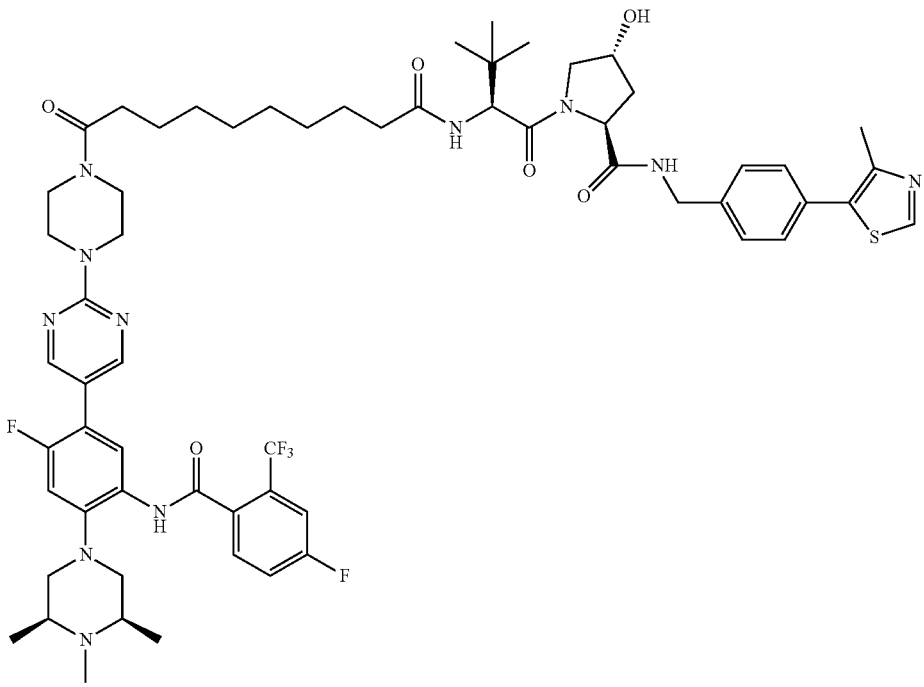

XF078-114

XF078-114 was synthesized following the standard procedures for preparing XF078-99 from intermediate 44 (11.8 mg, 0.02 mmol), VHL-C8-COOH (12.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-114 was obtained as white solid in TFA salt form (11.6 mg, yield 49%). $^1$H NMR (800 MHz, CD$_3$OD) δ 8.96 (s, 1H), 8.59 (s, 2H), 8.08 (d, J=8.1 Hz, 1H), 7.83 (dd, J=8.6, 5.1 Hz, 1H), 7.74-7.65 (m, 1H), 7.63-7.57 (m, 1H), 7.54-7.39 (m, 4H), 7.22 (d, J=11.5 Hz, 1H), 4.70-4.47 (m, 4H), 4.38 (d, J=15.4 Hz, 1H), 4.04-3.78 (m, 6H), 3.69 (dt, J=11.3, 5.6 Hz, 4H), 3.56-3.48 (m, 2H), 3.46-3.38 (m, 2H), 3.05-2.93 (m, 5H), 2.59-2.41 (m, 5H), 2.37-2.21 (m, 3H), 2.11 (ddd, J=13.3, 9.1, 4.5 Hz, 1H), 1.71-1.59 (m, 4H), 1.51-1.30 (m, 14H), 1.06 (s, 9H). HRMS (m/z) for C$_{61}$H$_{77}$F$_5$N$^{11}$O$_6$S$^+$ [M+H]$^+$: calculated 1186.5694. found 1186.5706.

Example 290: Synthesis of XF078-115

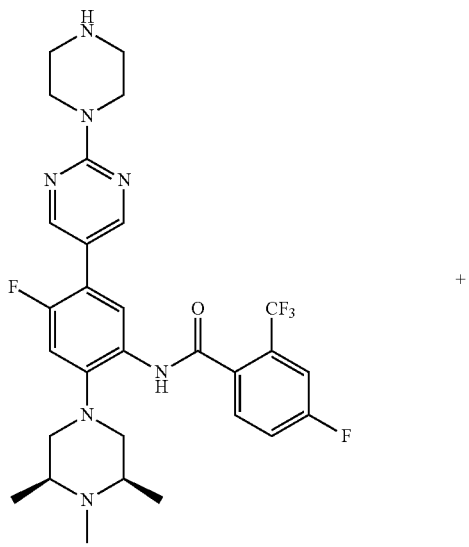

Intermediate 44

+

-continued

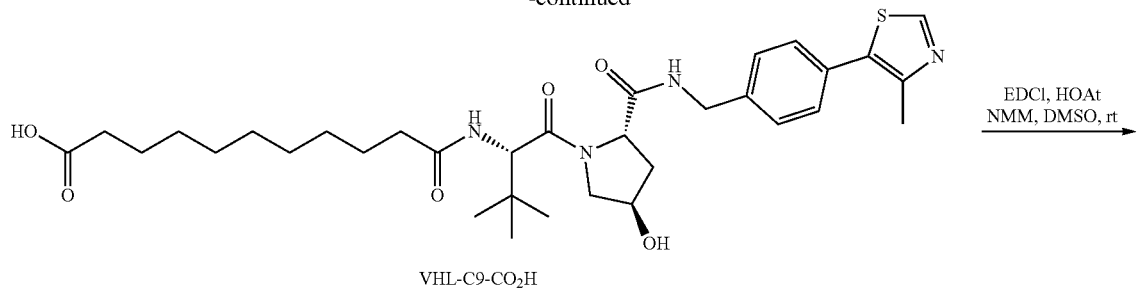

VHL-C9-CO₂H

EDCl, HOAt
NMM, DMSO, rt

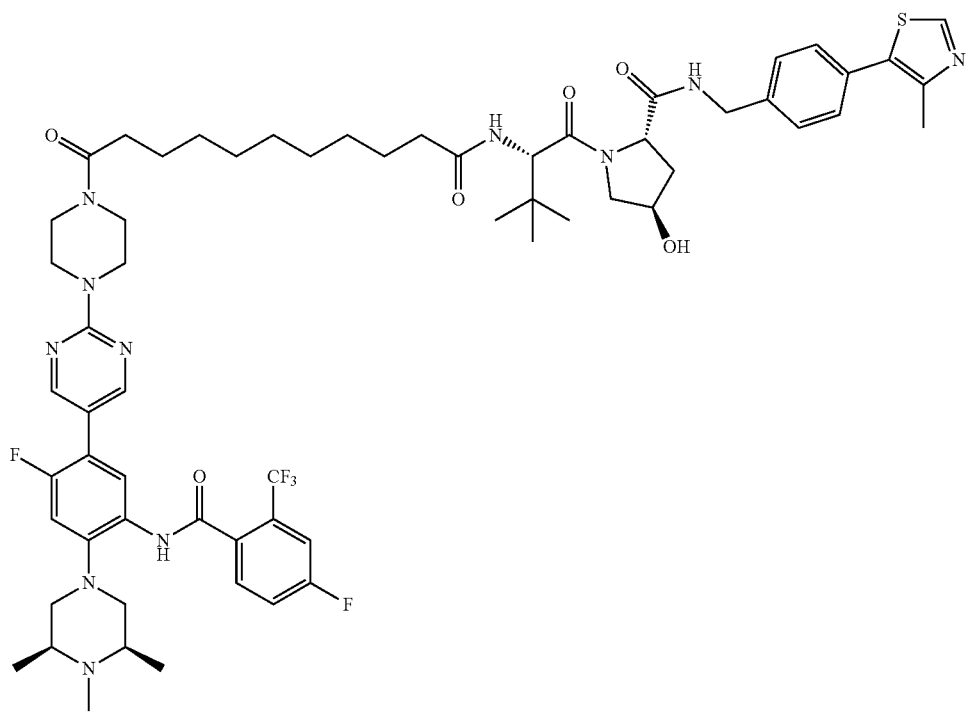

XF078-115

XF078-115 was synthesized following the standard procedures for preparing XF078-99 from intermediate 44 (11.8 mg, 0.02 mmol), VHL-C9-COOH (12.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-115 was obtained as white solid in TFA salt form (7.8 mg, yield 33%). ¹H NMR (800 MHz, CD₃OD) δ 8.97 (s, 1H), 8.59 (s, 2H), 8.08 (d, J=8.1 Hz, 1H), 7.83 (dd, J=8.6, 5.1 Hz, 1H), 7.68 (dd, J=9.2, 2.7 Hz, 1H), 7.59 (t, J=7.8 Hz, 1H), 7.52-7.40 (m, 4H), 7.22 (d, J=11.5 Hz, 1H), 4.66 (s, 1H), 4.62-4.54 (m, 2H), 4.52 (s, 1H), 4.38 (d, J=15.4 Hz, 1H), 3.99-3.78 (m, 6H), 3.69-3.60 (m, 4H), 3.54-3.48 (m, 2H), 3.40 (d, J=13.0 Hz, 2H), 3.01-2.95 (m, 5H), 2.52-2.43 (m, 5H), 2.35-2.21 (m, 3H), 2.13-2.08 (m, 1H), 1.68-1.60 (m, 4H), 1.53-1.27 (m, 16H), 1.06 (s, 9H). HRMS (m/z) for $C_{62}H_{79}F_5N^{11}O_6S^+$ [M+H]⁺: calculated 1200.5850. found 1200.5876.

Example 291: Synthesis of XF078-116

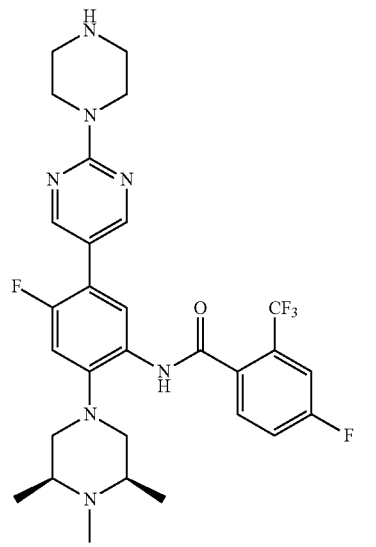

XF078-116 was synthesized following the standard procedures for preparing XF078-99 from intermediate 44 (11.8 mg, 0.02 mmol), PML-6 (6.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-116 was obtained as yellow solid in TFA salt form (11.6 mg, yield 64%). $^1$H NMR (800 MHz, CD$_3$OD) δ 8.62 (s, 2H), 8.08 (d, J=8.0 Hz, 1H), 7.84 (d, J=5.6 Hz, 1H), 7.68 (d, J=8.7 Hz, 1H), 7.66-7.54 (m, 2H), 7.21 (d, J=11.5 Hz, 1H), 7.13 (d, J=7.0 Hz, 1H), 7.06 (d, J=8.6 Hz, 1H), 5.19-5.07 (m, 1H), 4.30 (s, 2H), 4.11-3.91 (m, 4H), 3.85-3.65 (m, 4H), 3.59-3.46 (m, 2H), 3.40 (d, J=12.8 Hz, 2H), 3.09-2.70 (m, 8H), 2.23-2.10 (m, 1H), 1.47 (d, J=6.5 Hz, 6H). HRMS (m/z) for C$_{44}$H$_{44}$F$_5$N$_{10}$O$_6$$^+$ [M+H]$^+$: calculated 903.3360. found 903.3378.

Example 292: Synthesis of XF078-117

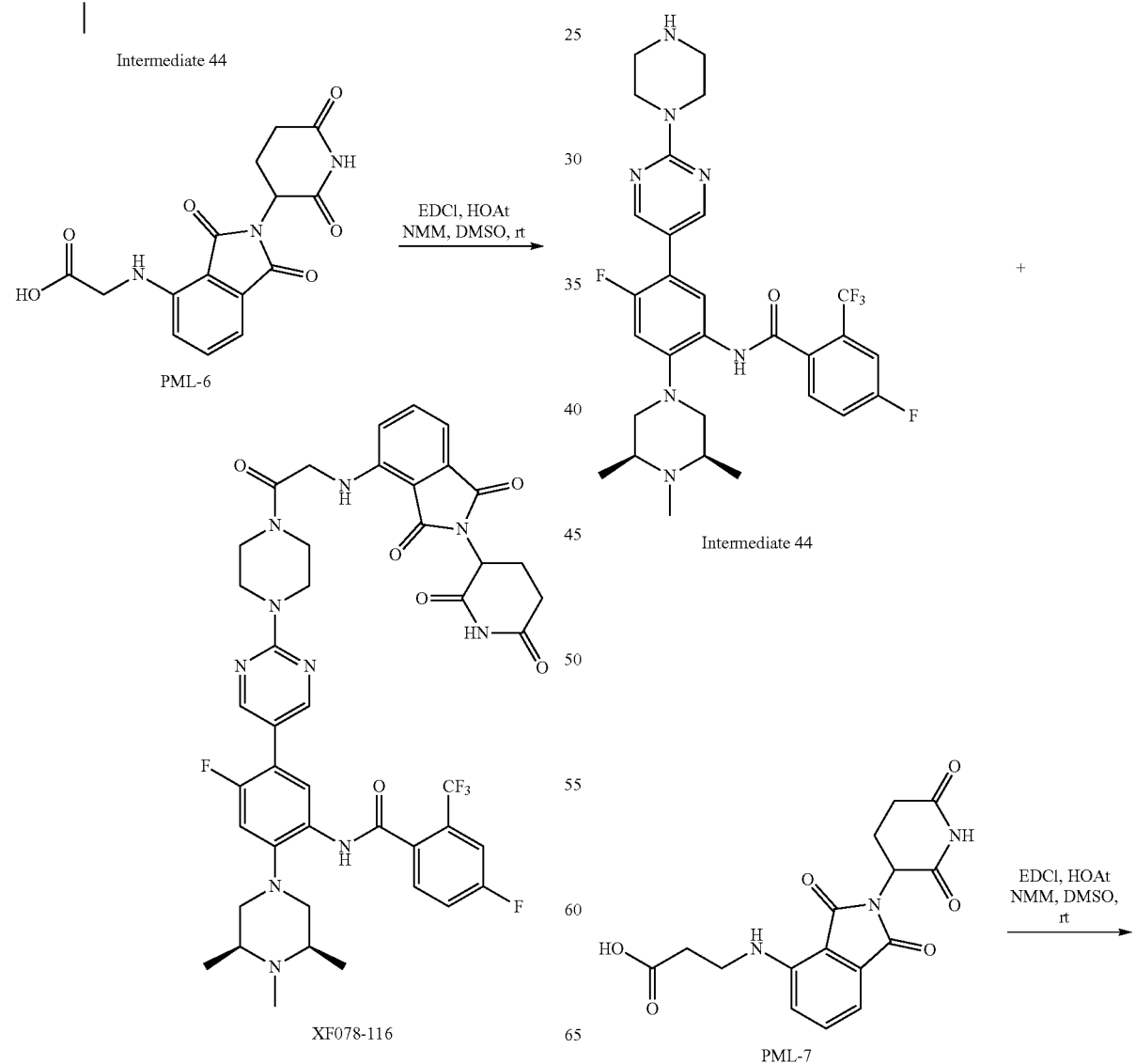

711
-continued

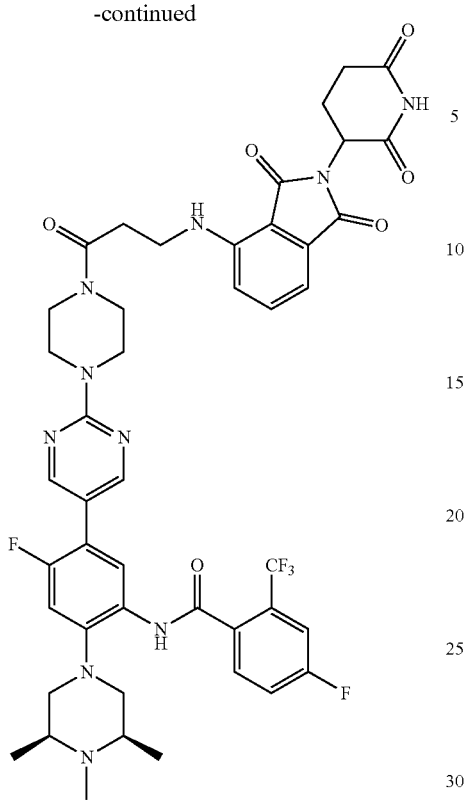

XF078-117

XF078-117 was synthesized following the standard procedures for preparing XF078-99 from intermediate 44 (11.8 mg, 0.02 mmol), PML-7 (6.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-117 was obtained as yellow solid in TFA salt form (12.8 mg, yield 70%). $^1$H NMR (800 MHz, CD$_3$OD) δ 8.58 (s, 2H), 8.07 (d, J=8.1 Hz, 1H), 7.83 (dd, J=8.6, 5.1 Hz, 1H), 7.67 (dd, J=9.3, 2.6 Hz, 1H), 7.61-7.54 (m, 2H), 7.21 (d, J=11.5 Hz, 1H), 7.14 (d, J=8.5 Hz, 1H), 7.05 (d, J=7.0 Hz, 1H), 5.04-4.90 (m, 1H), 3.87-3.81 (m, 4H), 3.77-3.61 (m, 6H), 3.52-3.47 (m, 2H), 3.39 (d, J=12.9 Hz, 2H), 3.00-2.94 (m, 5H), 2.89-2.79 (m, 3H), 2.76-2.66 (m, 2H), 2.12-2.06 (m, 1H), 1.47 (d, J=6.5 Hz, 6H). HRMS (m/z) for C$_{45}$H$_{46}$F$_5$N$_{10}$O$_6$$^+$ [M+H]$^+$: calculated 917.3516. found 917.3523.

Example 293: Synthesis of XF078-118

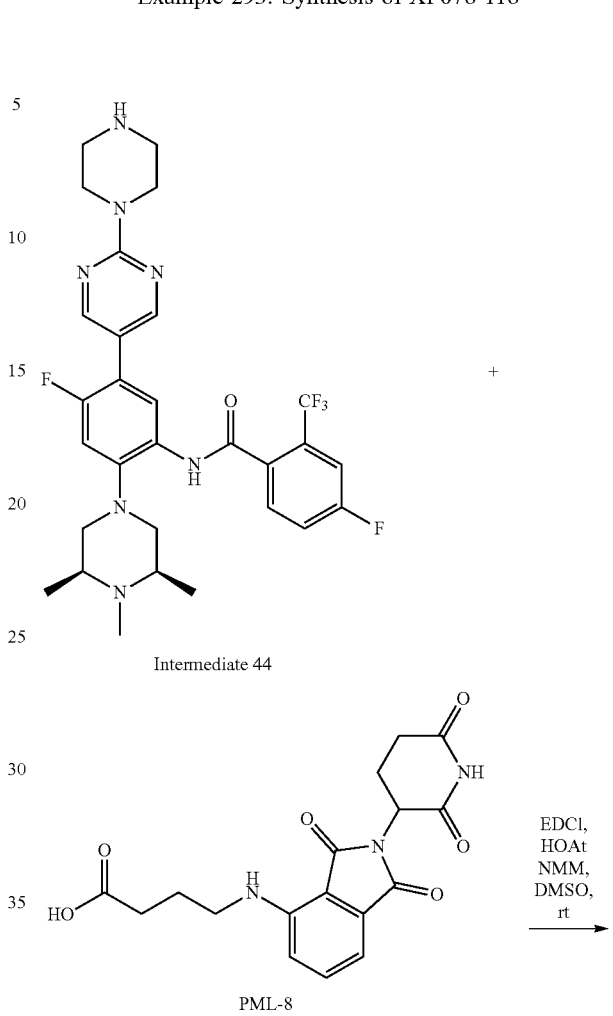

XF078-118 was synthesized following the standard procedures for preparing XF078-99 from intermediate 44 (11.8 mg, 0.02 mmol), PML-8 (7.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-118 was obtained as yellow solid in TFA salt form (12.8 mg, yield 69%). $^1$H NMR (800 MHz, CD$_3$OD) δ 8.59 (s, 2H), 8.08 (d, J=8.1 Hz, 1H), 7.88-7.79 (m, 1H), 7.75-7.64 (m, 1H), 7.63-7.53 (m, 2H), 7.21 (d, J=11.4 Hz, 1H), 7.18-7.10 (m, 1H), 7.09-6.99 (m, 1H), 5.12-4.98 (m, 1H), 4.01-3.82 (m, 4H), 3.78-3.61 (m, 4H), 3.54-3.48 (m, 2H), 3.46-3.36 (m, 4H), 3.03-2.91 (m, 5H), 2.91-2.80 (m, 1H), 2.80-2.69 (m, 2H), 2.60 (t, J=7.0 Hz, 2H), 2.18-2.08 (m, 1H), 2.06-1.93 (m, 2H), 1.47 (d, J=6.5 Hz, 6H). HRMS (m/z) for C$_{46}$H$_{48}$F$_5$N$_{10}$O$_6^+$ [M+H]$^+$: calculated 931.3673. found 931.3625.

Example 294: Synthesis of XF078-119

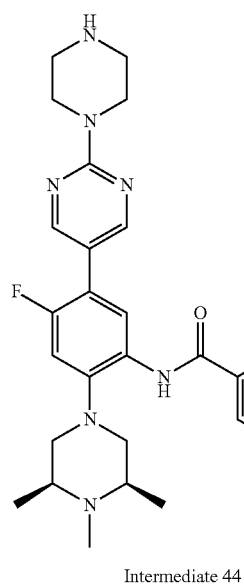

Intermediate 44

+

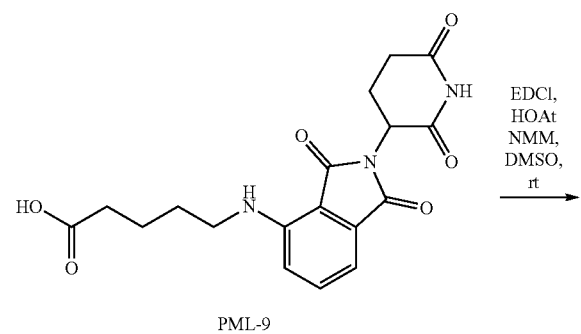

PML-9

EDCl, HOAt NMM, DMSO, rt

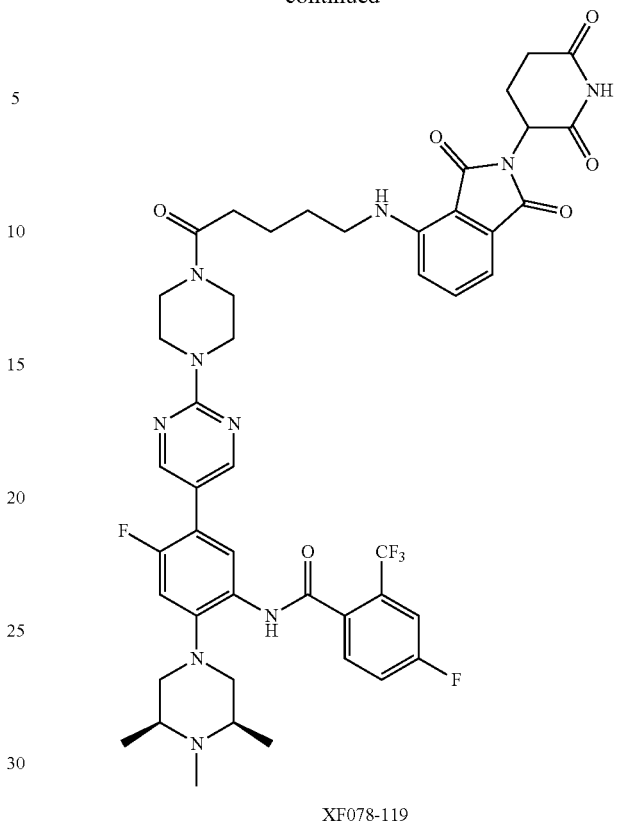

XF078-119

XF078-119 was synthesized following the standard procedures for preparing XF078-99 from intermediate 44 (11.8 mg, 0.02 mmol), PML-9 (7.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-119 was obtained as yellow solid in TFA salt form (10.4 mg, yield 55%). $^1$H NMR (800 MHz, CD$_3$OD) δ 8.59 (s, 2H), 8.09 (d, J=8.1 Hz, 1H), 7.83 (dd, J=8.6, 5.1 Hz, 1H), 7.68 (dd, J=9.1, 2.6 Hz, 1H), 7.61-7.54 (m, 2H), 7.21 (d, J=11.5 Hz, 1H), 7.08 (d, J=8.6 Hz, 1H), 7.03 (d, J=7.0 Hz, 1H), 5.09-5.02 (m, 1H), 3.92-3.87 (m, 2H), 3.87-3.83 (m, 2H), 3.71-3.64 (m, 4H), 3.52-3.48 (m, 2H), 3.42-3.36 (m, 4H), 2.98-2.89 (m, 5H), 2.90-2.82 (m, 1H), 2.77-2.70 (m, 2H), 2.58-2.54 (m, 2H), 2.15-2.09 (m, 1H), 1.80-1.75 (m, 4H), 1.47 (d, J=6.5 Hz, 6H). HRMS (m/z) for C$_{47}$H$_{50}$F$_5$N$_{10}$O$_6^+$ [M+H]$^+$: calculated 945.3829. found 945.3866.

Example 295: Synthesis of XF078-120

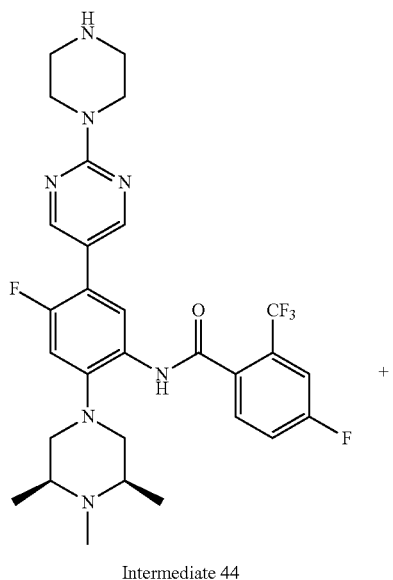

Intermediate 44

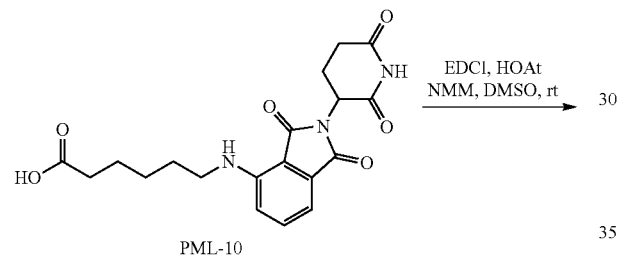

PML-10

XF078-120 was synthesized following the standard procedures for preparing XF078-99 from intermediate 44 (11.8 mg, 0.02 mmol), PML-10 (7.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-120 was obtained as yellow solid in TFA salt form (7.8 mg, yield 41%). $^1$H NMR (800 MHz, CD$_3$OD) δ 8.59 (s, 2H), 8.09 (d, J=8.1 Hz, 1H), 7.84 (t, J=6.9 Hz, 1H), 7.75-7.65 (m, 1H), 7.57-7.49 (m, 2H), 7.22 (d, J=11.5 Hz, 1H), 7.07 (d, J=8.5 Hz, 1H), 7.02 (d, J=7.1 Hz, 1H), 5.15-5.03 (m, 1H), 3.99-3.80 (m, 4H), 3.68-3.57 (m, 4H), 3.57-3.49 (m, 2H), 3.43-3.35 (m, 4H), 2.98-2.90 (m, 5H), 2.91-2.82 (m, 1H), 2.79-2.68 (m, 2H), 2.60-2.42 (m, 2H), 2.18-2.09 (m, 1H), 1.74-1.69 (m, 4H), 1.58-1.42 (m, 8H). HRMS (m/z) for $C_{48}H_{52}F_5N_{10}O_6^+$ [M+H]$^+$: calculated 959.3986. found 959.4005.

Example 296: Synthesis of XF078-121

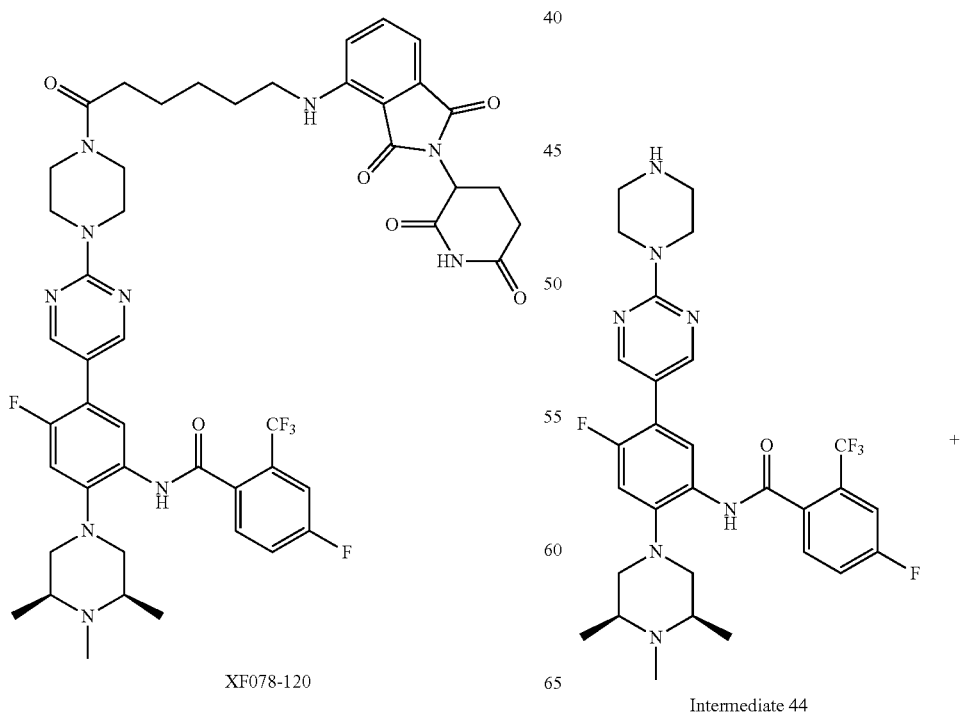

XF078-120

Intermediate 44

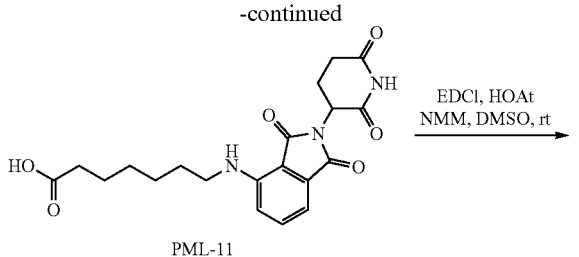

PML-11

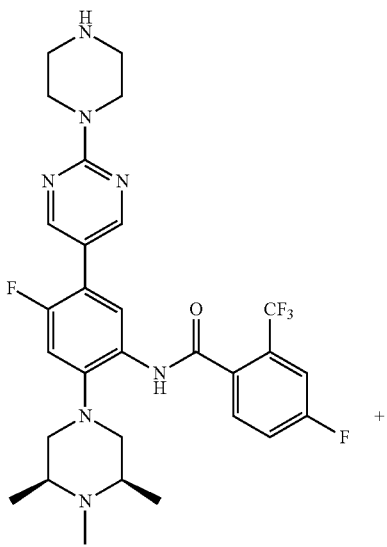

XF078-121

XF078-121 was synthesized following the standard procedures for preparing XF078-99 from intermediate 44 (11.8 mg, 0.02 mmol), PML-11 (8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-121 was obtained as yellow solid in TFA salt form (11.9 mg, yield 61%). $^1$H NMR (800 MHz, CD$_3$OD) δ 8.59 (s, 2H), 8.08 (d, J=8.1 Hz, 1H), 7.83 (dd, J=8.6, 5.1 Hz, 1H), 7.68 (dd, J=9.3, 2.6 Hz, 1H), 7.61-7.53 (m, 2H), 7.21 (d, J=11.5 Hz, 1H), 7.07-7.01 (m, 2H), 5.08-5.03 (m, 1H), 3.93 (t, J=5.3 Hz, 2H), 3.88 (t, J=5.4 Hz, 2H), 3.72-3.65 (m, 4H), 3.52-3.49 (m, 2H), 3.39 (d, J=13.0 Hz, 2H), 3.37-3.33 (m, 2H), 3.01-2.95 (m, 5H), 2.90-2.82 (m, 1H), 2.78-2.69 (m, 2H), 2.49 (t, J=7.5 Hz, 2H), 2.15-2.10 (m, 1H), 1.74-1.66 (m, 4H), 1.53-1.43 (m, 10H). HRMS (m/z) for C$_{49}$H$_{54}$F$_5$N$_{10}$O$_6$$^+$ [M+H]$^+$: calculated 973.4142. found 973.4167.

Example 297: Synthesis of XF078-122

Intermediate 44

-continued
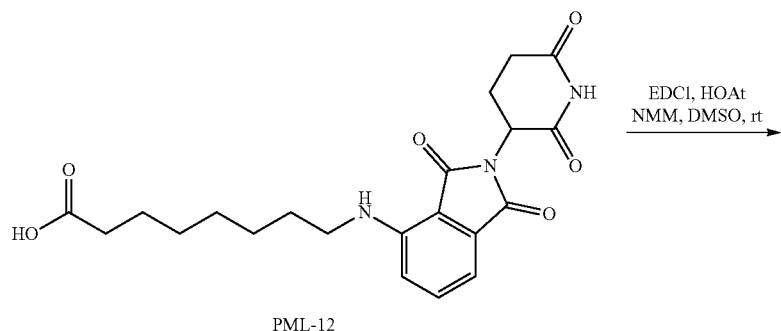
PML-12
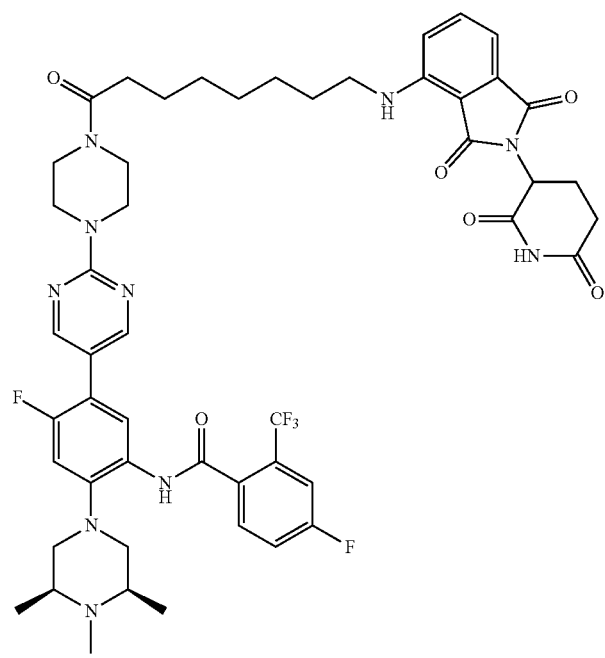
XF078-122

XF078-122 was synthesized following the standard procedures for preparing XF078-99 from intermediate 44 (11.8 mg, 0.02 mmol), PML-12 (8.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-122 was obtained as yellow solid in TFA salt form (13.9 mg, yield 70%). $^1$H NMR (800 MHz, CD$_3$OD) δ 8.59 (s, 2H), 8.08 (d, J=8.1 Hz, 1H), 7.83 (dd, J=8.6, 5.1 Hz, 1H), 7.68 (dd, J=9.3, 2.6 Hz, 1H), 7.61-7.51 (m, 2H), 7.21 (d, J=11.5 Hz, 1H), 7.06-7.00 (m, 2H), 5.09-5.02 (m, 1H), 3.96-3.91 (m, 2H), 3.88 (t, J=5.4 Hz, 2H), 3.72-3.65 (m, 4H), 3.53-3.48 (m, 2H), 3.39 (d, J=13.0 Hz, 2H), 3.32 (s, 2H), 2.98-2.91 (m, 5H), 2.90-2.82 (m, 1H), 2.78-2.69 (m, 2H), 2.48 (t, J=7.6 Hz, 2H), 2.15-2.09 (m, 1H), 1.72-1.61 (m, 4H), 1.51-1.42 (m, 12H). HRMS (m/z) for $C_{50}H_{56}F_5N_{10}O_6^+$ [M+H]$^+$: calculated 987.4299. found 987.4295.

Example 298: Synthesis of XF078-123

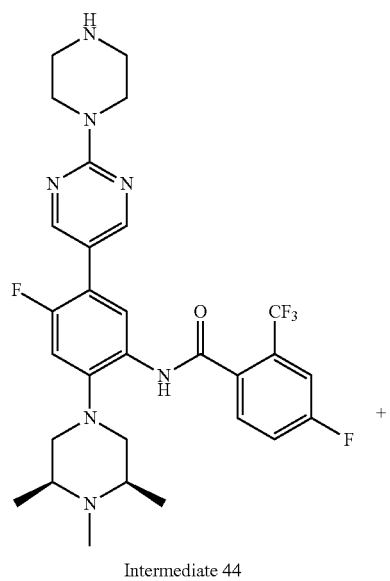

Intermediate 44

+

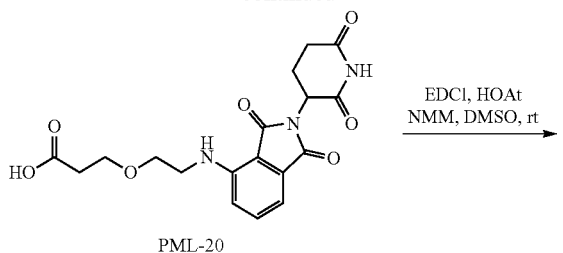

PML-20

EDCl, HOAt
NMM, DMSO, rt

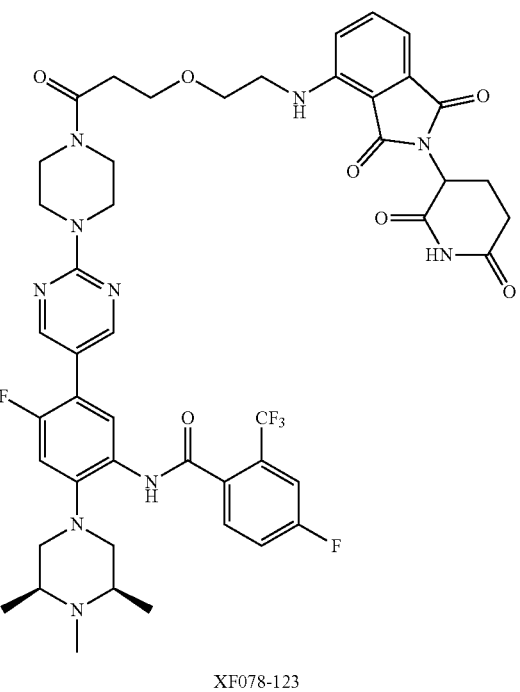

XF078-123

XF078-123 was synthesized following the standard procedures for preparing XF078-99 from intermediate 44 (11.8 mg, 0.02 mmol), PML-20 (8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-123 was obtained as yellow solid in TFA salt form (9.8 mg, yield 51%). $^1$H NMR (800 MHz, CD$_3$OD) δ 8.52 (s, 2H), 8.09 (d, J=8.2 Hz, 1H), 7.86 (t, J=6.8 Hz, 1H), 7.69 (d, J=8.8 Hz, 1H), 7.63-7.48 (m, 2H), 7.21 (d, J=11.5 Hz, 1H), 7.08 (d, J=8.6 Hz, 1H), 6.99 (d, J=7.0 Hz, 1H), 5.09-5.00 (m, 1H), 3.89-3.82 (m, 6H), 3.77-3.70 (m, 6H), 3.56-3.47 (m, 2H), 3.42-3.35 (m, 4H), 3.03-2.92 (m, 5H), 2.90-2.64 (m, 5H), 2.17-2.07 (m, 1H), 1.48 (d, J=6.5 Hz, 6H). HRMS (m/z) for $C_{47}H_{50}F_5N_{10}O_7^+$ [M+H]$^+$: calculated 961.3779. found 961.3754.

Example 299: Synthesis of XF078-124
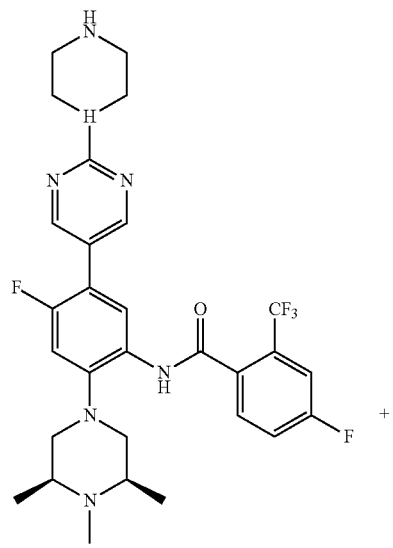
Intermediate 44
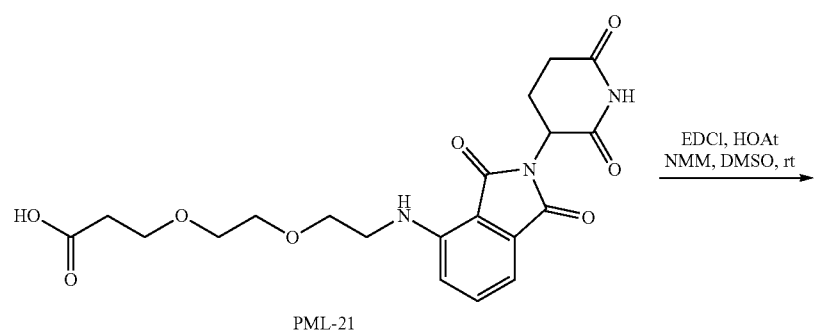
PML-21

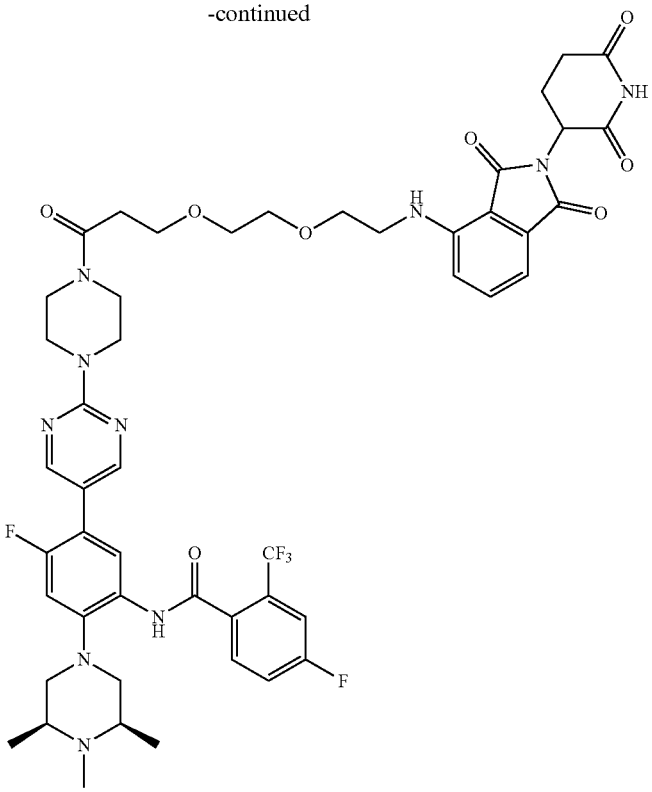

XF078-124

XF078-124 was synthesized following the standard procedures for preparing XF078-99 from intermediate 44 (11.8 mg, 0.02 mmol), PML-21 (8.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-124 was obtained as yellow solid in TFA salt form (14.6 mg, yield 73%). $^1$H NMR (800 MHz, CD$_3$OD) δ 8.51 (s, 2H), 8.06 (d, J=8.1 Hz, 1H), 7.85 (dd, J=8.5, 5.1 Hz, 1H), 7.67 (dd, J=9.2, 2.6 Hz, 1H), 7.60 (dd, J=8.1, 2.5 Hz, 1H), 7.49 (t, J=7.8 Hz, 1H), 7.18 (d, J=11.6 Hz, 1H), 7.02 (d, J=8.5 Hz, 1H), 6.96 (d, J=7.0 Hz, 1H), 5.05 (dd, J=12.9, 5.5 Hz, 1H), 3.91 (t, J=5.2 Hz, 2H), 3.87-3.76 (m, 4H), 3.75-3.60 (m, 10H), 3.53-3.47 (m, 2H), 3.45 (t, J=5.4 Hz, 2H), 3.41-3.36 (m, 2H), 3.02-2.91 (m, 5H), 2.91-2.82 (m, 1H), 2.78-2.67 (m, 4H), 2.21-2.09 (m, 1H), 1.53-1.42 (m, 6H). HRMS (m/z) for C$_{49}$H$_{54}$F$_5$N$_{10}$O$_8$$^+$ [M+H]$^+$: calculated 1005.4041. found 1005.4015.

Example 300: Synthesis of XF078-125

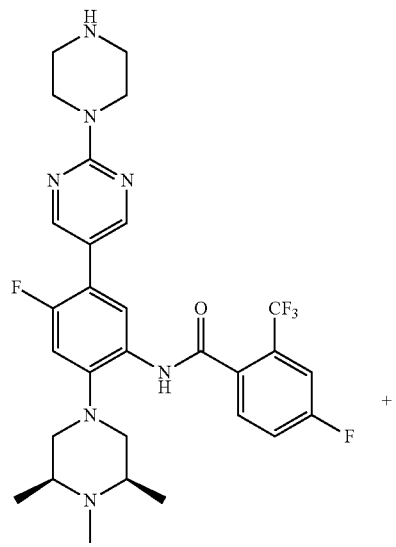

Intermediate 44

+

-continued

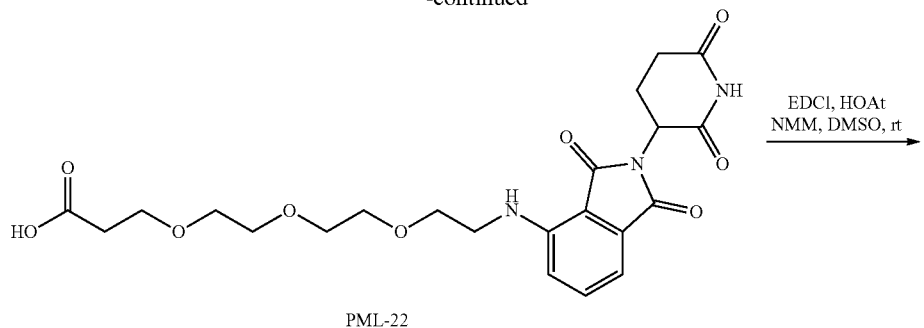

PML-22

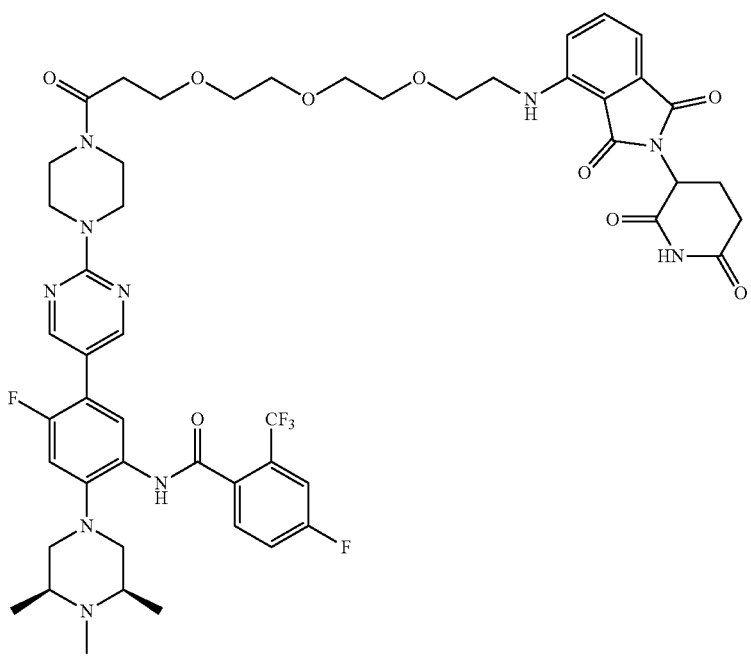

XF078-125

XF078-125 was synthesized following the standard procedures for preparing XF078-99 from intermediate 44 (11.8 mg, 0.02 mmol), PML-22 (9.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-125 was obtained as yellow solid in TFA salt form (9.8 mg, yield 47%). $^1$H NMR (800 MHz, CD$_3$OD) δ 8.55 (s, 2H), 8.05 (d, J=8.1 Hz, 1H), 7.84 (t, J=6.9 Hz, 1H), 7.73-7.64 (m, 1H), 7.62-7.58 (m, 1H), 7.51 (t, J=7.8 Hz, 1H), 7.17 (d, J=11.5 Hz, 1H), 7.03 (d, J=8.6 Hz, 1H), 7.00 (d, J=7.1 Hz, 1H), 5.11-5.04 (m, 1H), 3.95 (t, J=5.2 Hz, 2H), 3.90-3.82 (m, 2H), 3.83-3.74 (m, 2H), 3.75-3.58 (m, 14H), 3.54-3.42 (m, 4H), 3.38 (d, J=13.0 Hz, 2H), 3.04-2.81 (m, 6H), 2.78-2.66 (m, 4H), 2.18-2.06 (m, 1H), 1.68-1.38 (m, 6H). HRMS (m/z) for $C_{51}H_{58}F_5N_{10}O_9^+$ [M+H]$^+$: calculated 1049.4303, found 1049.4334.

Example 301: Synthesis of XF078-126
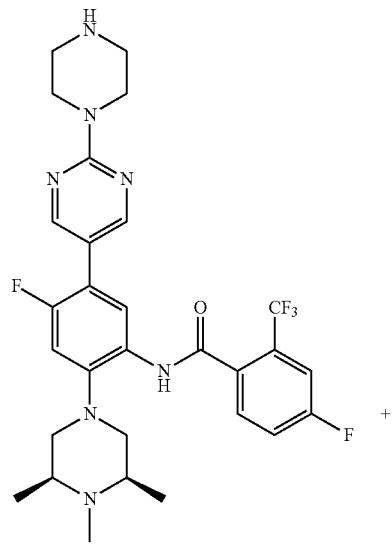
Intermediate 44 +
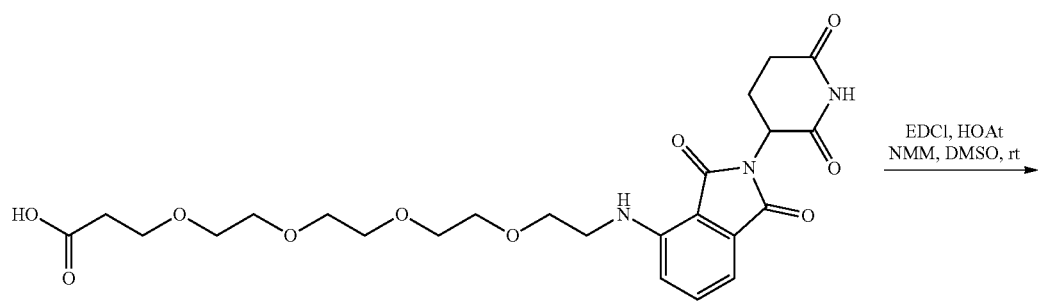
PML-23
EDCl, HOAt
NMM, DMSO, rt -continued

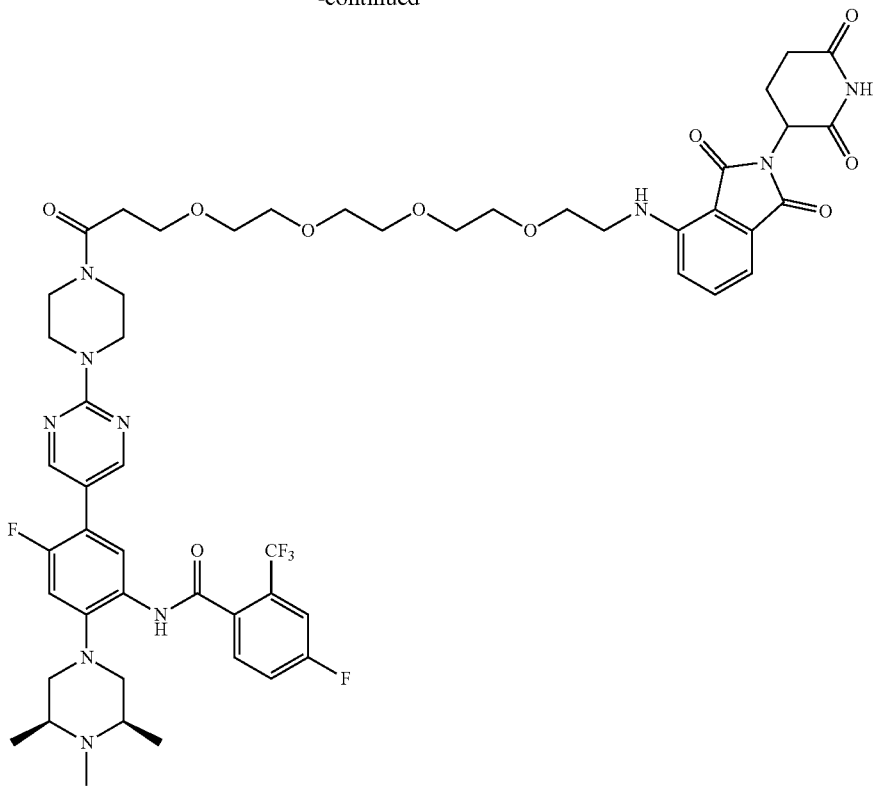

XF078-126

XF078-126 was synthesized following the standard procedures for preparing XF078-99 from intermediate 44 (11.8 mg, 0.02 mmol), PML-23 (10.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-126 was obtained as yellow solid in TFA salt form (12.5 mg, yield 57%). $^1$H NMR (800 MHz, CD$_3$OD) δ 8.57 (s, 2H), 8.07 (d, J=8.1 Hz, 1H), 7.83 (dd, J=8.6, 5.1 Hz, 1H), 7.67 (dt, J=10.4, 5.1 Hz, 1H), 7.59 (dq, J=8.3, 2.5 Hz, 1H), 7.52 (t, J=7.8 Hz, 1H), 7.18 (d, J=11.5 Hz, 1H), 7.10-6.91 (m, 2H), 5.05 (dd, J=13.0, 5.5 Hz, 1H), 4.04-3.85 (m, 4H), 3.83-3.34 (m, 26H), 3.01-2.94 (m, 5H), 2.90-2.78 (m, 1H), 2.79-2.61 (m, 4H), 2.16-2.05 (m, 1H), 1.47 (dd, J=6.5, 4.2 Hz, 6H). HRMS (m/z) for C$_{53}$H$_{62}$F$_5$N$_{10}$O$_{10}$$^+$ [M+H]$^+$: calculated 1093.4565. found 1093.4543.

Example 302: Synthesis of XF078-127

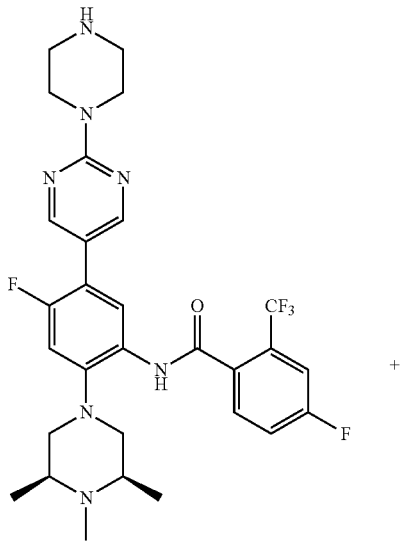

Intermediate 44

+

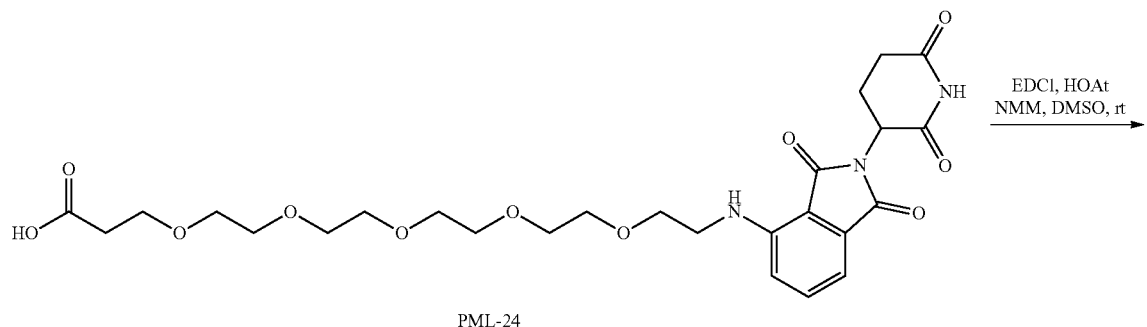
PML-24
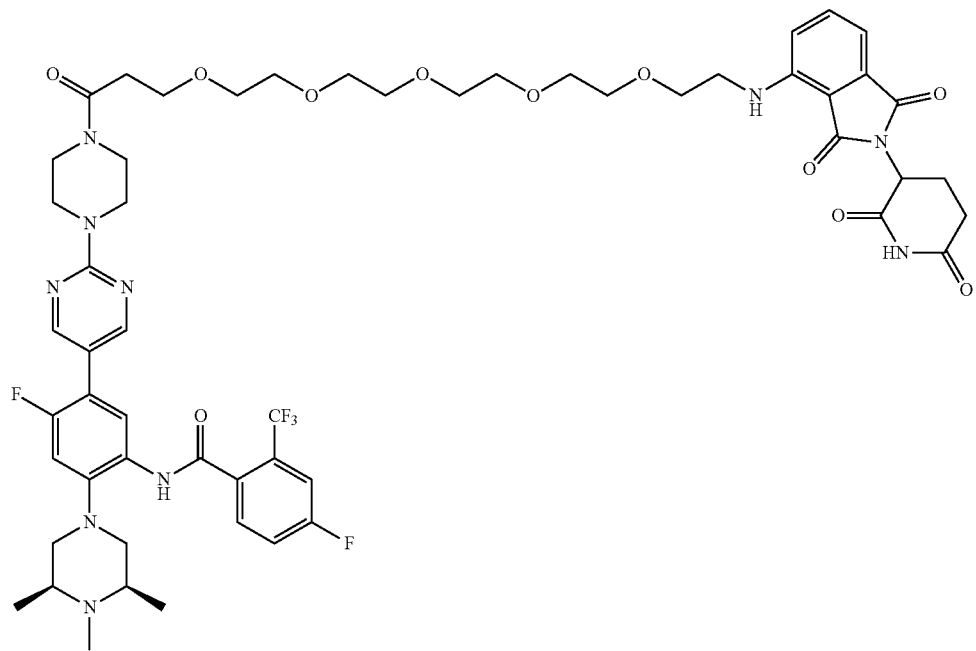
XF078-127

XF078-127 was synthesized following the standard procedures for preparing XF078-99 from intermediate 44 (11.8 mg, 0.02 mmol), PML-24 (11.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-127 was obtained as yellow solid in TFA salt form (13.9 mg, yield 61%). $^1$H NMR (800 MHz, CD$_3$OD) δ 8.58 (s, 2H), 8.07 (d, J=8.2 Hz, 1H), 7.83 (dd, J=8.6, 5.1 Hz, 1H), 7.77-7.63 (m, 1H), 7.63-7.57 (m, 1H), 7.53 (t, J=7.8 Hz, 1H), 7.19 (d, J=11.5 Hz, 1H), 7.07 (d, J=8.6 Hz, 1H), 7.03 (d, J=7.0 Hz, 1H), 5.19-5.01 (m, 1H), 4.04-3.83 (m, 4H), 3.82-3.56 (m, 24H), 3.54-3.43 (m, 4H), 3.38 (d, J=13.0 Hz, 2H), 3.04-2.93 (m, 5H), 2.92-2.80 (m, 1H), 2.80-2.67 (m, 4H), 2.23-2.00 (m, 1H), 1.56-1.42 (m, 6H). HRMS (m/z) for $C_{55}H_{66}F_5N_{10}O_{11}^+$ [M+H]$^+$: calculated 1137.4827. found 1137.4846.

Example 303: Synthesis of Intermediate 45

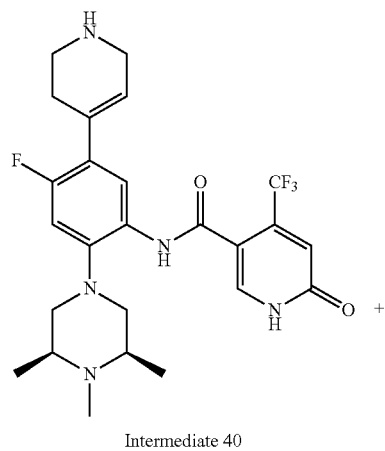

Intermediate 40

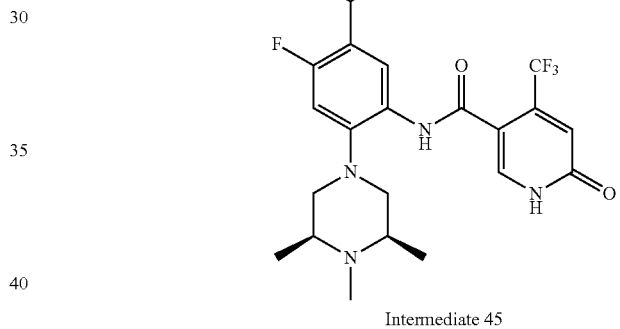

Intermediate 45

To a solution of Intermediate 40 (463.4 mg, 0.91 mmol) and tert-butyl 4-((2-chloropyrimidin-5-yl)methyl)piperazine-1-carboxylate (WO2015101293A1) (428 mg, 1.37 mmol, 1.5 euqiv) in 5 mL of dimethylacetamide were added potassium carbonate (378 mg, 2.73 mmol, 3 equiv). The reaction was heated to 70° C. overnight. Water was added and the reaction mixture was extracted with EtOAc (3×20 mL). combined organic layer was dried over Na$_2$SO$_4$, filtered and the solvent was removed and purified by reverse phase ISCO (10%-100% methanol/0.1% TFA in H$_2$O) to afford product as white solid. This product was dissolved in DCM (10 mL) and TFA (10 mL). The resulting mixture was stirring for 1 h. Then, it was concentrated and purified by reverse phase ISCO (10%-100% methanol/0.1% TFA in H$_2$O) to afford Intermediate 45 (XF078-96) as white solid in TFA salt form (415.2 mg, yield 56%). $^1$H NMR (500 MHz, CD$_3$OD) δ 8.52 (d, J=15.1 Hz, 2H), 8.03 (d, J=15.1 Hz, 1H), 7.84 (dd, J=15.3, 7.8 Hz, 1H), 7.08 (dd, J=15.2, 11.9 Hz, 1H), 6.94 (d, J=15.1 Hz, 1H), 6.22-6.06 (m, 1H), 4.51-4.37 (m, 2H), 4.30-4.02 (m, 4H), 3.67-3.44 (m, 12H), 3.08-2.88 (m, 5H), 2.72-2.49 (m, 2H), 1.46 (dd, J=15.1, 6.5 Hz, 6H). HRMS (m/z) for $C_{34}H_{42}F_4N_9O_2^+$ [M+H]$^+$: calculated 684.3392. found 684.3413.

Example 304: Synthesis of XF078-132
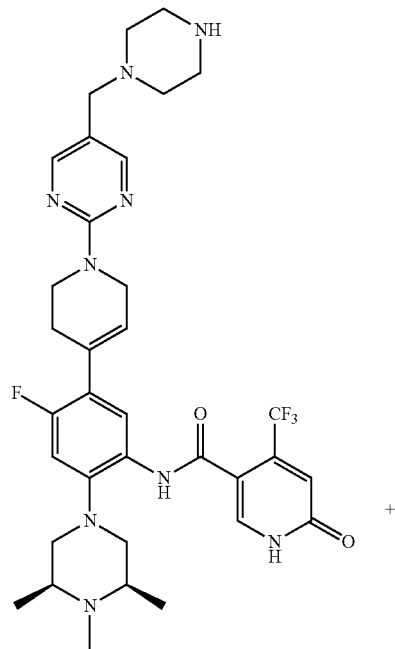
Intermediate 45
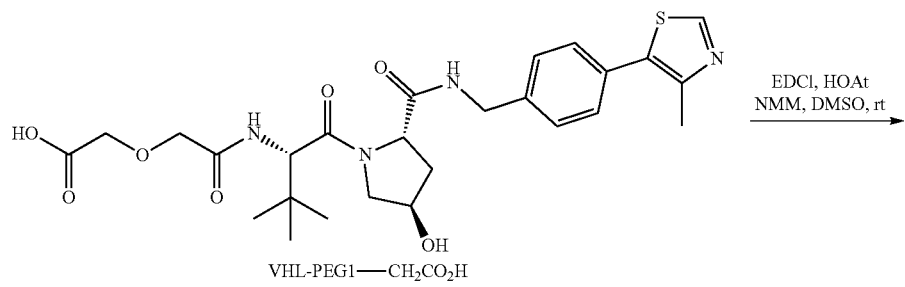
VHL-PEG1—CH₂CO₂H -continued

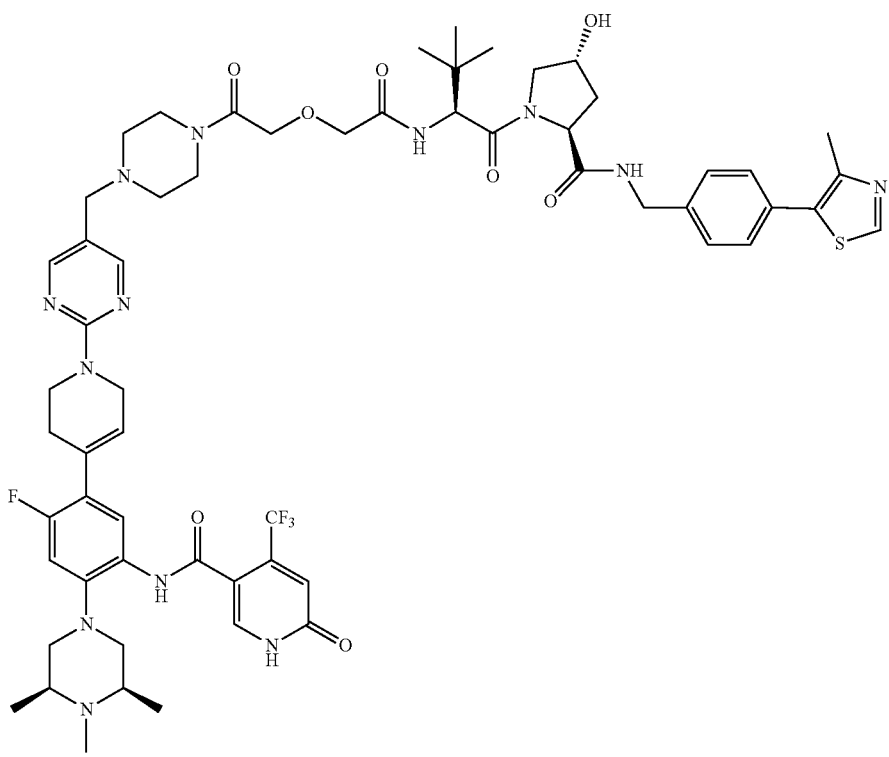

XF078-132

To the solution of intermediate 45 (13.6 mg, 0.02 mmol) in DMSO (1 mL) were added VHL-PEG1-CH$_2$COOH (10.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirring overnight at room temperature, the resulting mixture was purified by preparative HPLC (10%-100% methanol/0.1% TFA in H$_2$O) to afford XF078-132 as white solid in TFA salt form (16.3 mg, yield 67%). $^1$H NMR (800 MHz, CD$_3$OD) δ 9.00 (s, 1H), 8.48 (s, 2H), 8.01 (d, J=8.4 Hz, 1H), 7.83 (d, J=7.9 Hz, 1H), 7.57-7.39 (m, 4H), 7.07 (d, J=12.0 Hz, 1H), 6.95 (s, 1H), 6.14 (s, 1H), 4.72 (s, 1H), 4.64-4.57 (m, 1H), 4.56-4.35 (m, 7H), 4.34-4.23 (m, 2H), 4.18 (d, J=15.1 Hz, 1H), 4.15-4.06 (m, 3H), 3.93 (d, J=11.0 Hz, 1H), 3.84 (dd, J=11.0, 3.8 Hz, 1H), 3.55-3.46 (m, 2H), 3.43-3.28 (m, 10H), 3.04-2.88 (m, 5H), 2.66-2.56 (m, 2H), 2.50 (s, 3H), 2.30-2.22 (m, 1H), 2.14-2.06 (m, 1H), 1.45 (d, J=6.5 Hz, 6H), 1.09 (s, 9H). HRMS (m/z) for C$_{60}$H$_{74}$F$_4$N$_{13}$O$_8$S$^+$ [M+H]$^+$: calculated 1212.5435, found 1212.5412.

Example 305: Synthesis of XF078-133
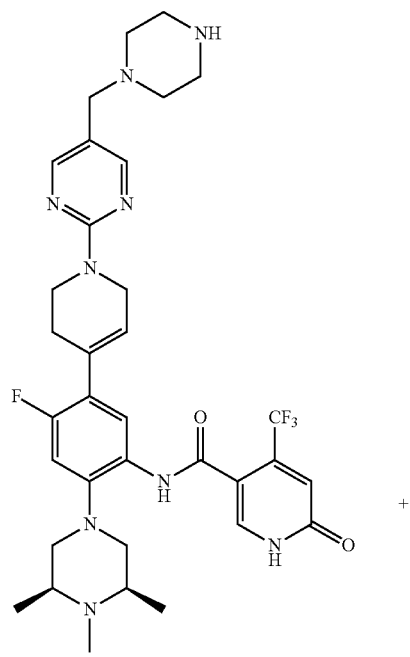
Intermediate 45
+
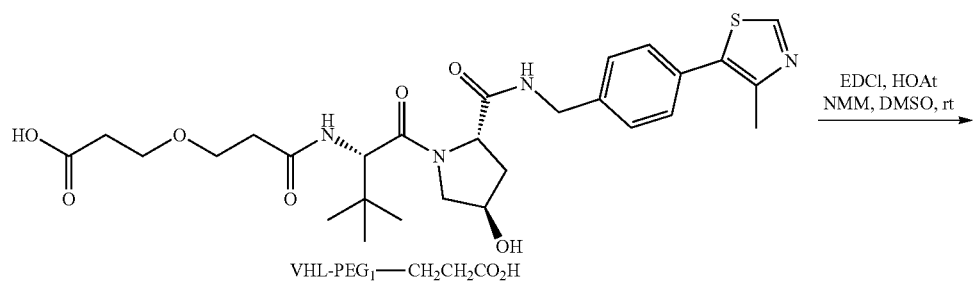
VHL-PEG₁—CH₂CH₂CO₂H
$\xrightarrow{\text{EDCl, HOAt} \atop \text{NMM, DMSO, rt}}$ -continued

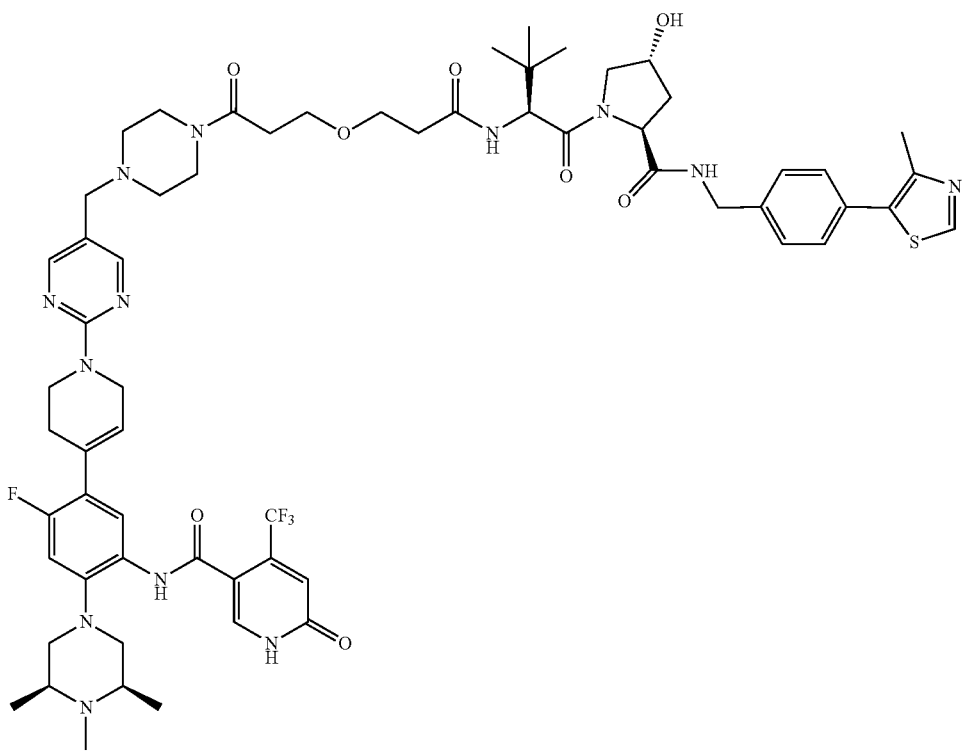

XF078-133

XF078-133 was synthesized following the standard procedures for preparing XF078-132 from intermediate 45 (13.6 mg, 0.02 mmol), VHL-PEG1-CH$_2$CH$_2$COOH (11.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-133 was obtained as white solid in TFA salt form (15.6 mg, yield 63%). $^1$H NMR (800 MHz, CD$_3$OD) δ 9.03 (s, 1H), 8.48 (s, 2H), 8.00 (d, J=7.5 Hz, 1H), 7.83 (d, J=7.9 Hz, 1H), 7.56-7.36 (m, 4H), 7.07 (d, J=11.9 Hz, 1H), 6.95 (s, 1H), 6.13 (d, J=3.7 Hz, 1H), 4.69 (s, 1H), 4.60-4.48 (m, 3H), 4.48-4.37 (m, 3H), 4.35-4.25 (m, 2H), 4.21-4.07 (m, 2H), 3.91 (d, J=11.1 Hz, 1H), 3.83 (dd, J=10.9, 3.9 Hz, 1H), 3.81-3.68 (m, 4H), 3.56-3.48 (m, 2H), 3.46-3.22 (m, 10H), 3.00 (s, 3H), 2.97-2.90 (m, 2H), 2.78-2.43 (m, 9H), 2.30-2.22 (m, 1H), 2.15-2.00 (m, 1H), 1.45 (d, J=6.5 Hz, 6H), 1.06 (s, 9H). HRMS (m/z) for C$_{62}$H$_{78}$F$_4$N$_{13}$O$_8$S$^+$ [M+H]$^+$: calculated 1240.5748. found 1240.5756.

Example 306: Synthesis of XF078-134
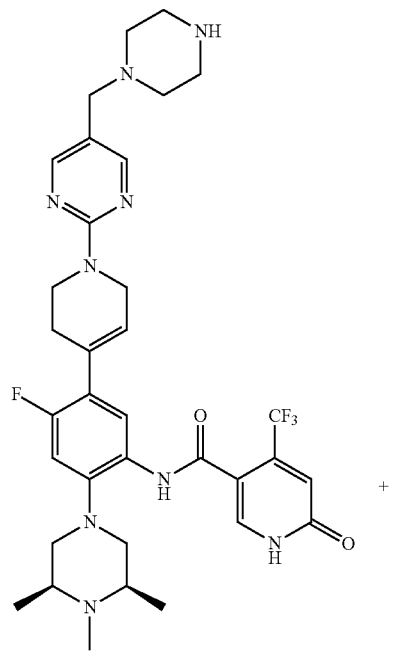
Intermediate 45
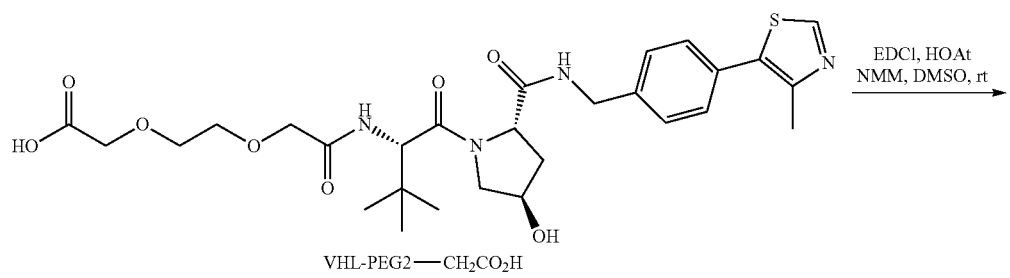
VHL-PEG2—CH₂CO₂H

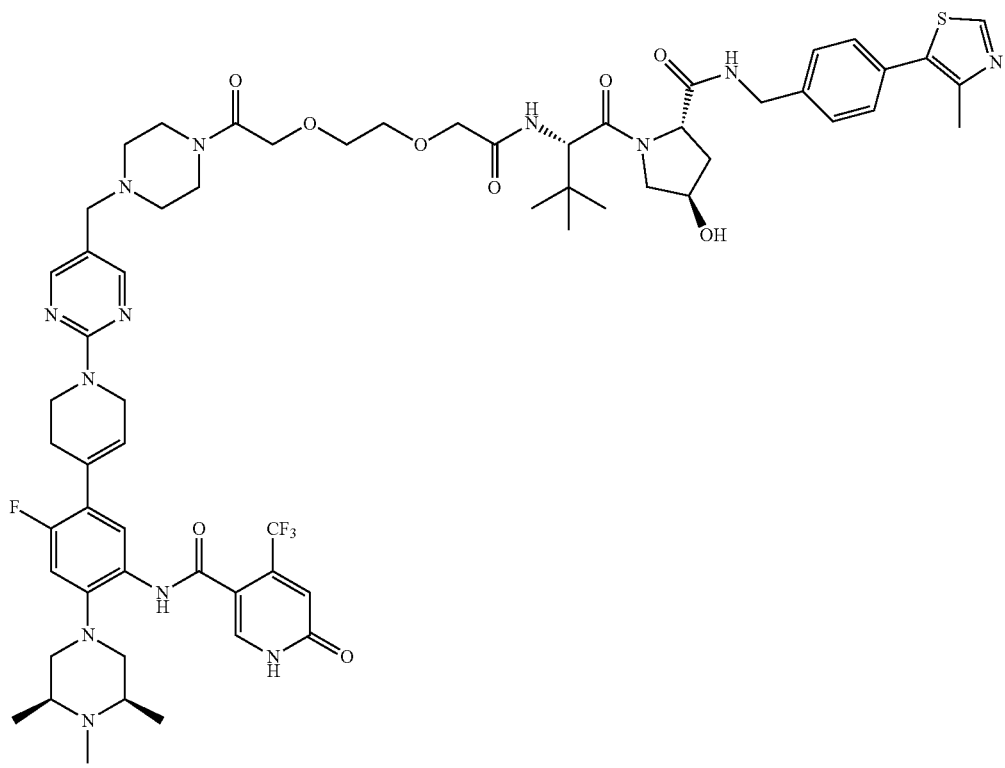

XF078-134

XF078-134 was synthesized following the standard procedures for preparing XF078-132 from intermediate 45 (13.6 mg, 0.02 mmol), VHL-PEG2-CH$_2$COOH (11.8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-134 was obtained as white solid in TFA salt form (15.4 mg, yield 61%). $^1$H NMR (800 MHz, CD$_3$OD) δ 9.01 (d, J=11.4 Hz, 1H), 8.48 (s, 2H), 8.01 (s, 1H), 7.83 (d, J=7.8 Hz, 1H), 7.54-7.38 (m, 4H), 7.07 (d, J=11.9 Hz, 1H), 6.95 (s, 1H), 6.13 (d, J=3.8 Hz, 1H), 4.79-4.65 (m, 1H), 4.63-4.22 (m, 10H), 4.17-4.05 (m, 4H), 3.95-3.70 (m, 6H), 3.59-3.37 (m, 12H), 3.06-2.87 (m, 5H), 2.67-2.56 (m, 2H), 2.49 (s, 3H), 2.37-2.22 (m, 1H), 2.17-2.05 (m, 1H), 1.45 (d, J=6.5 Hz, 6H), 1.06 (s, 9H). HRMS (m/z) for C$_{62}$H$_{78}$F$_4$N$_{13}$O$_9$S$^+$ [M+H]$^+$: calculated 1256.5697. found 1256.5712.

Example 307: Synthesis of XF078-135
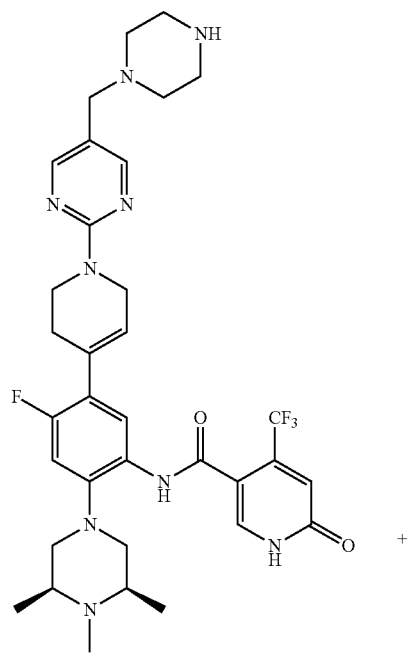
Intermediate 45
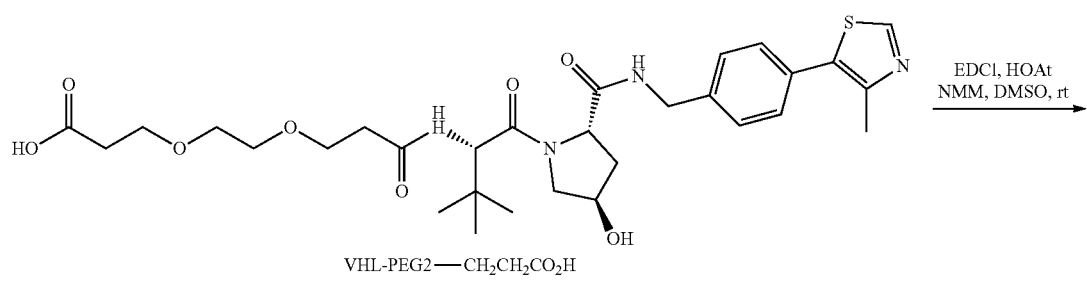
VHL-PEG2—CH₂CH₂CO₂H

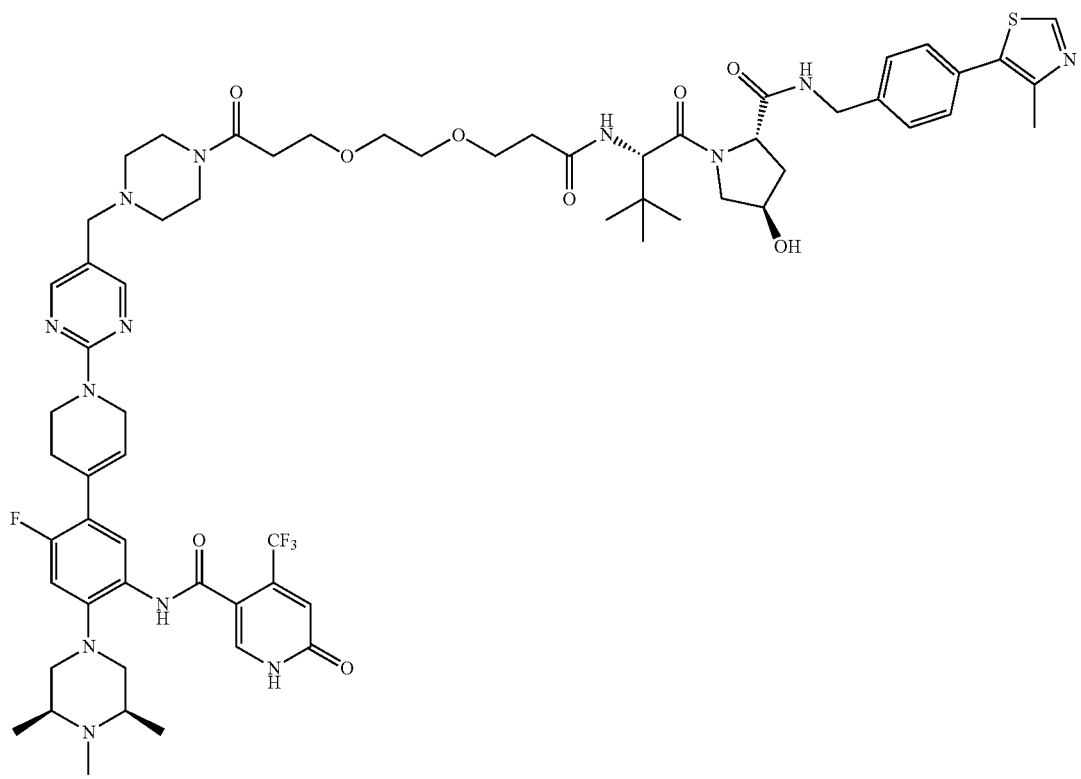

XF078-135

XF078-135 was synthesized following the standard procedures for preparing XF078-132 from intermediate 45 (13.6 mg, 0.02 mmol), VHL-PEG2-CH$_2$CH$_2$COOH (12.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-135 was obtained as white solid in TFA salt form (16.2 mg, yield 63%). $^1$H NMR (800 MHz, CD$_3$OD) δ 9.02 (s, 1H), 8.61-8.38 (m, 2H), 8.01 (s, 1H), 7.83 (d, J=8.0 Hz, 1H), 7.57-7.36 (m, 4H), 7.13-7.05 (m, 1H), 6.95 (s, 1H), 6.14 (d, J=3.7 Hz, 1H), 4.67 (s, 1H), 4.63-4.35 (m, 6H), 4.30 (s, 2H), 4.17-4.06 (m, 2H), 3.94-3.71 (m, 6H), 3.68-3.57 (m, 4H), 3.54-3.36 (m, 12H), 3.00 (s, 3H), 2.96-2.91 (m, 2H), 2.76-2.66 (m, 1H), 2.66-2.41 (m, 8H), 2.25 (dd, J=13.2, 7.6 Hz, 1H), 2.11 (ddd, J=13.3, 9.2, 4.4 Hz, 1H), 1.45 (d, J=6.5 Hz, 6H), 1.06 (s, 9H). HRMS (m/z) for C$_{64}$H$_{82}$F$_4$N$_{13}$O$_9$S$^+$ [M+H]$^+$: calculated 1284.6010. found 1284.6032.

Example 308: Synthesis of XF078-136
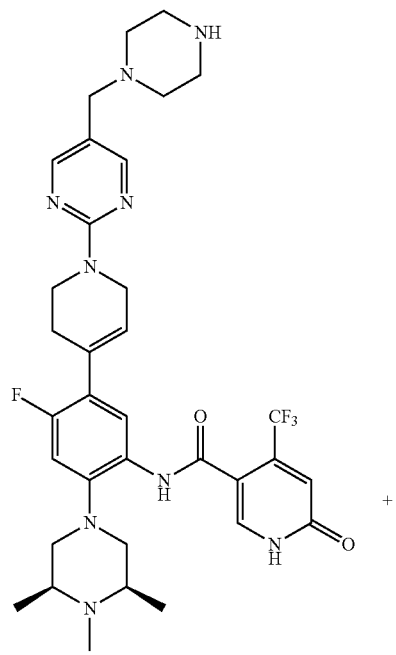
Intermediate 45
+
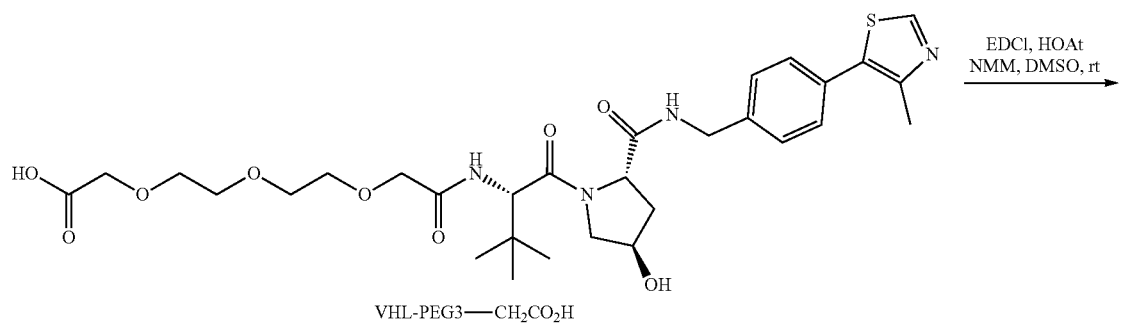
VHL-PEG3—CH₂CO₂H

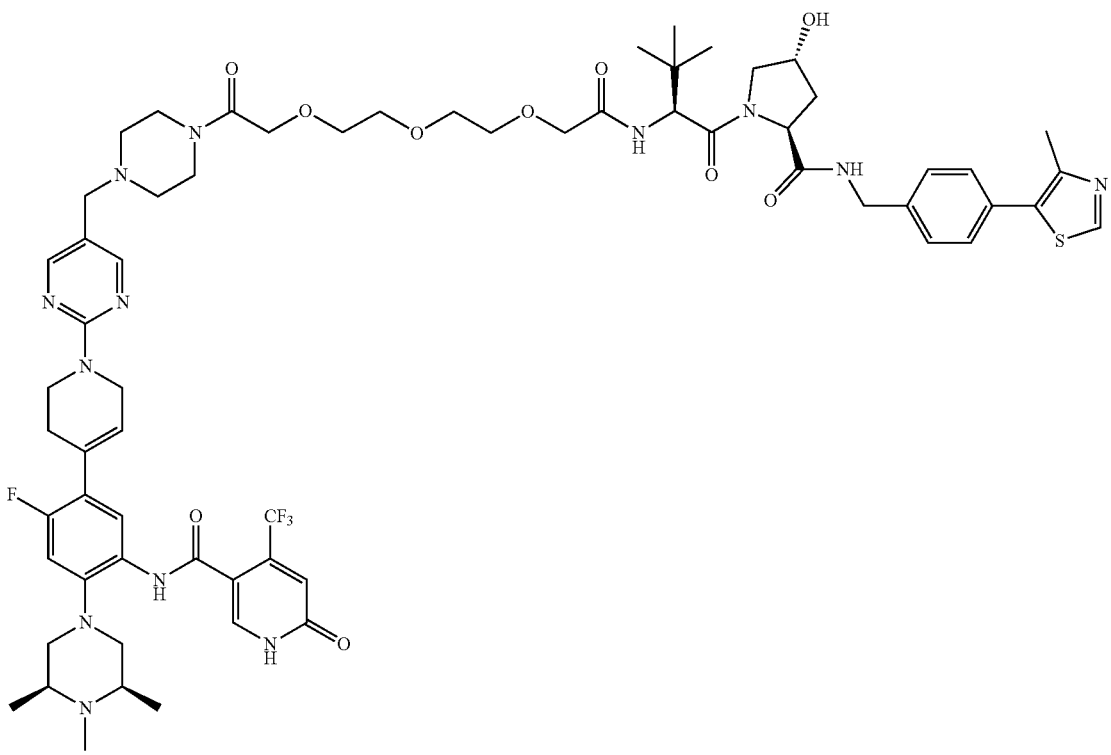

XF078-136

XF078-136 was synthesized following the standard procedures for preparing XF078-132 from intermediate 45 (13.6 mg, 0.02 mmol), VHL-PEG3-CH$_2$COOH (12.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-136 was obtained as white solid in TFA salt form (16.1 mg, yield 62%). $^1$H NMR (800 MHz, CD$_3$OD) δ 9.00 (d, J=16.1 Hz, 1H), 8.47 (d, J=21.6 Hz, 2H), 8.01 (s, 1H), 7.83 (d, J=8.0 Hz, 1H), 7.54-7.39 (m, 4H), 7.07 (dd, J=11.9, 4.6 Hz, 1H), 6.95 (s, 1H), 6.44-5.93 (m, 1H), 4.74-4.67 (m, 1H), 4.62-4.50 (m, 3H), 4.50-4.38 (m, 3H), 4.33-4.19 (m, 4H), 4.17-4.00 (m, 4H), 3.90-3.63 (m, 10H), 3.55-3.39 (m, 12H), 3.02-2.88 (m, 5H), 2.67-2.54 (m, 2H), 2.50 (s, 3H), 2.29-2.23 (m, 1H), 2.15-2.07 (m, 1H), 1.45 (d, J=6.5 Hz, 6H), 1.06 (s, 9H). HRMS (m/z) for C$_{64}$H$_{82}$F$_4$N$_{13}$O$_{10}$S$^+$ [M+H]$^+$: calculated 1300.5959. found 1300.5968.

Example 309: Synthesis of XF078-137
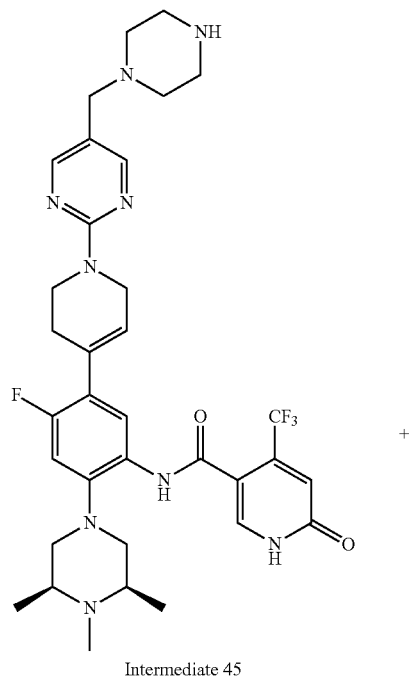
Intermediate 45
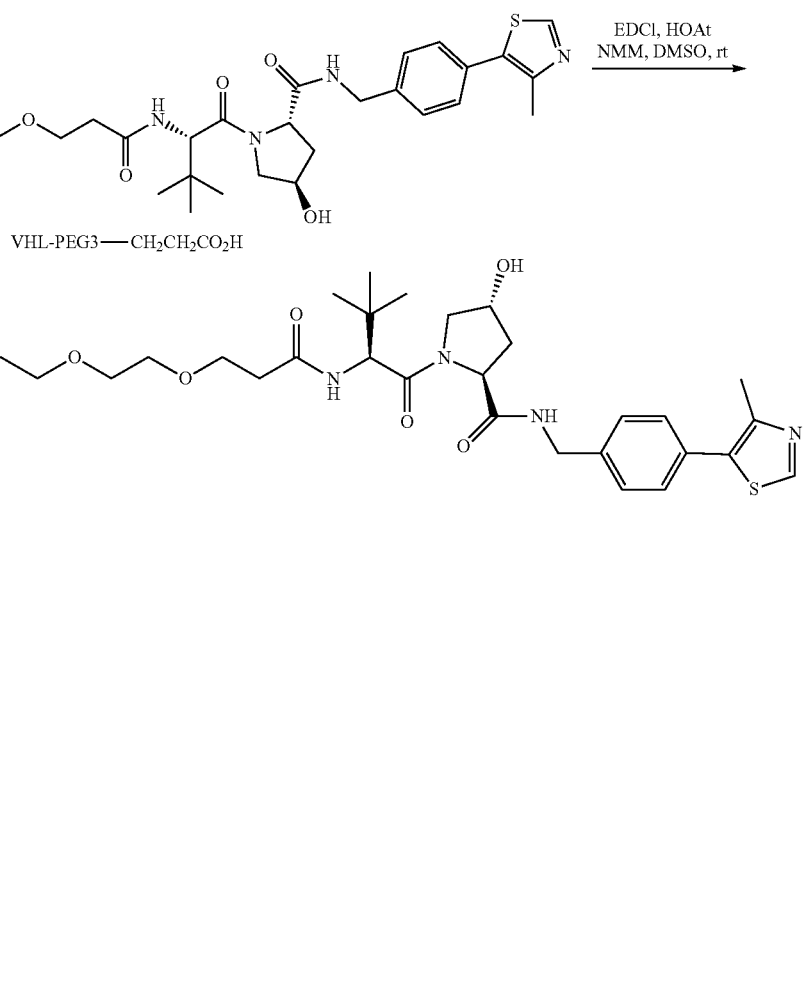
VHL-PEG3—CH₂CH₂CO₂H
XF078-137

XF078-137 was synthesized following the standard procedures for preparing XF078-132 from intermediate 45 (13.6 mg, 0.02 mmol), VHL-PEG3-CH$_2$CH$_2$COOH (13.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-137 was obtained as white solid in TFA salt form (18.1 mg, yield 68%). $^1$H NMR (800 MHz, CD$_3$OD) δ 9.00 (s, 1H), 8.56-8.43 (m, 2H), 8.00 (d, J=8.2 Hz, 1H), 7.83 (d, J=7.9 Hz, 1H), 7.56-7.37 (m, 4H), 7.07 (d, J=11.9 Hz, 1H), 6.95 (s, 1H), 6.14 (d, J=3.8 Hz, 1H), 4.66 (s, 1H), 4.62-4.35 (m, 6H), 4.29 (d, J=3.0 Hz, 2H), 4.13 (t, J=5.7 Hz, 2H), 3.98-3.72 (m, 6H), 3.72-3.57 (m, 8H), 3.57-3.33 (m, 12H), 3.07-2.90 (m, 5H), 2.78-2.46 (m, 9H), 2.25 (dd, J=13.2, 7.6 Hz, 1H), 2.11 (ddd, J=13.4, 9.2, 4.5 Hz, 1H), 1.45 (d, J=6.5 Hz, 6H), 1.06 (s, 9H). HRMS (m/z) for C$_{66}$H$_{86}$F$_4$N$_{13}$O$_{10}$S$^+$ [M+H]$^+$: calculated 1328.6272. found 1328.6246.

Example 310: Synthesis of XF078-138

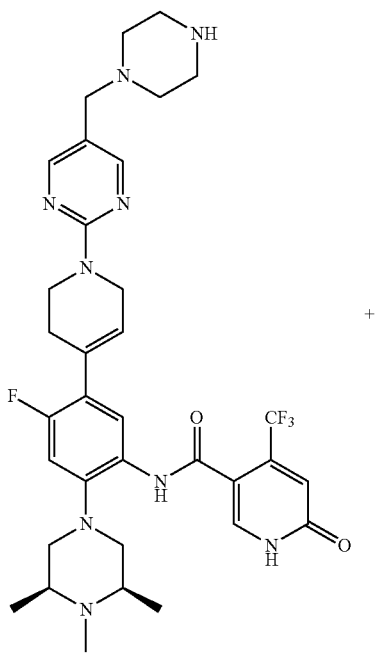

Intermediate 45

+

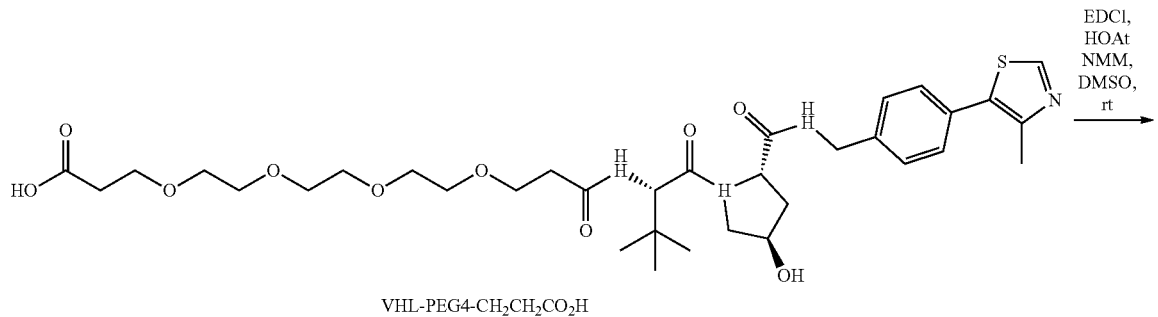

VHL-PEG4-CH$_2$CH$_2$CO$_2$H

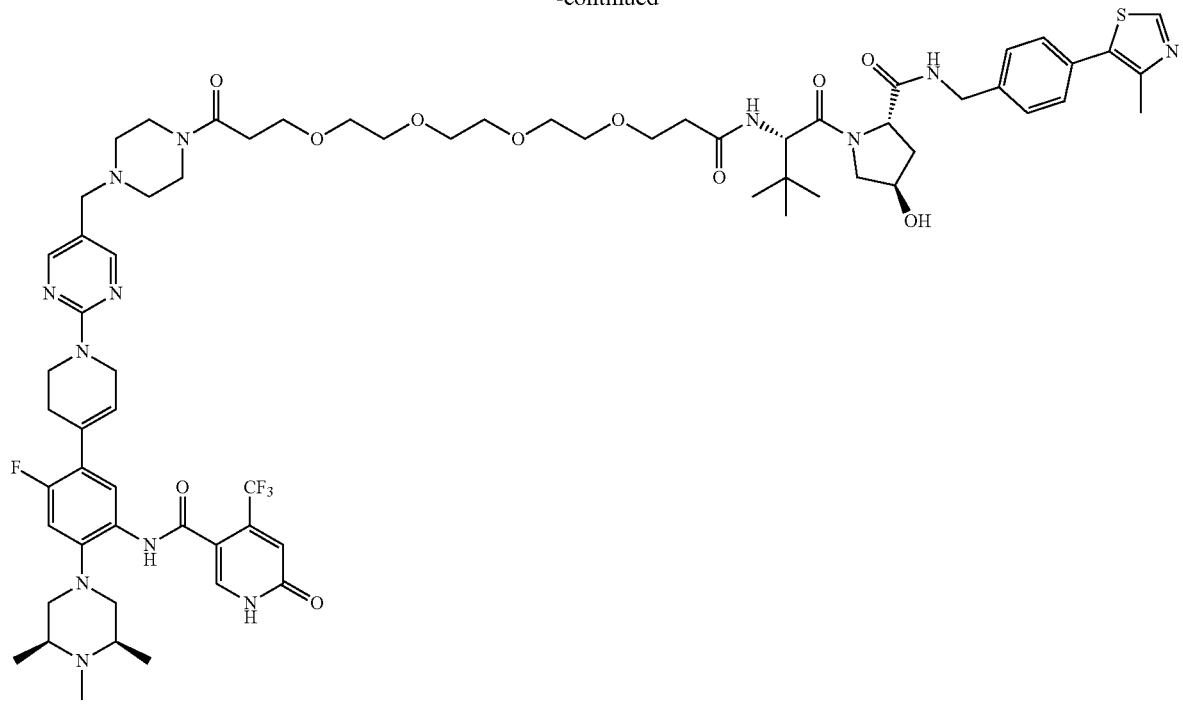

XF078-138

XF078-138 was synthesized following the standard procedures for preparing XF078-132 from intermediate 45 (13.6 mg, 0.02 mmol), VHL-PEG4-CH₂CH₂COOH (14.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-138 was obtained as white solid in TFA salt form (19 mg, yield 69%). ¹H NMR (800 MHz, CD₃OD) δ 9.02 (s, 1H), 8.49 (s, 2H), 8.00 (d, J=8.7 Hz, 1H), 7.83 (d, J=8.0 Hz, 1H), 7.63-7.33 (m, 4H), 7.07 (d, J=11.9 Hz, 1H), 6.95 (s, 1H), 6.15 (d, J=4.0 Hz, 1H), 4.72-4.22 (m, 9H), 4.13-3.99 (m, 2H), 3.99-3.58 (m, 20H), 3.55-3.30 (m, 12H), 2.97 (d, J=46.8 Hz, 5H), 2.68-2.43 (m, 9H), 2.24 (dd, J=13.2, 7.3 Hz, 1H), 2.10 (ddd, J=13.3, 9.1, 4.5 Hz, 1H), 1.45 (d, J=6.5 Hz, 6H), 1.06 (s, 9H). HRMS (m/z) for $C_{68}H_{90}F_4N_{13}O_{11}S^+$ [M+H]⁺: calculated 1372.6534. found 1372.6556.

Example 311: Synthesis of XF078-139

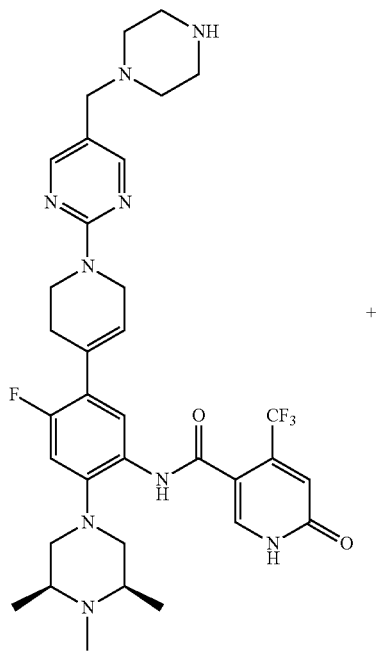

Intermediate 45

-continued

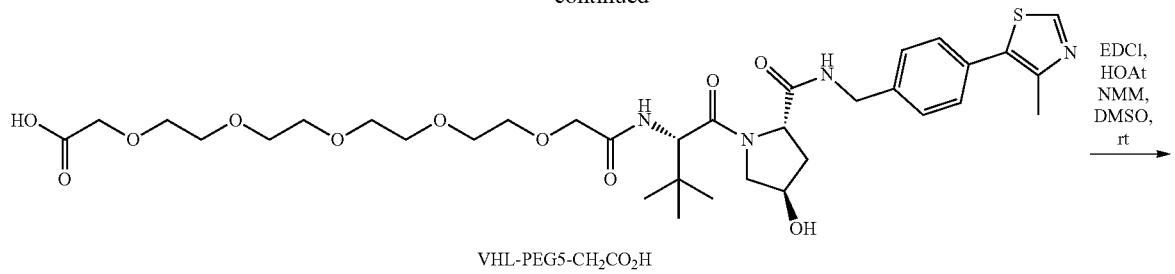

VHL-PEG5-CH₂CO₂H

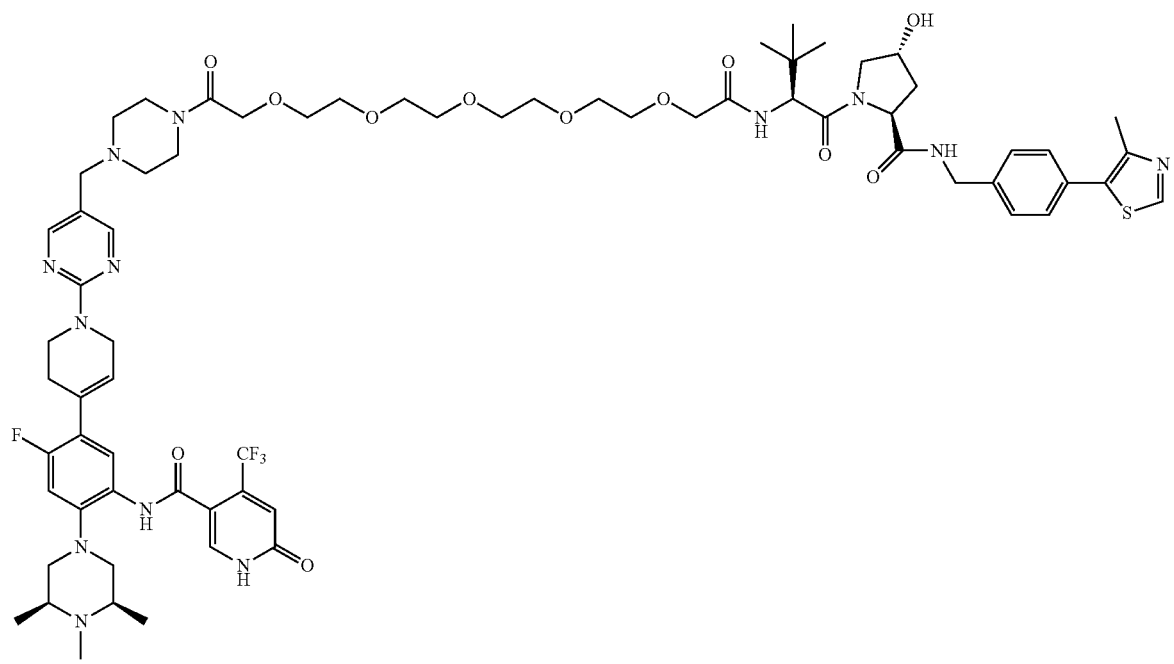

XF078-139

XF078-139 was synthesized following the standard procedures for preparing XF078-132 from intermediate 45 (13.6 mg, 0.02 mmol), VHL-PEG5-CH₂COOH (14.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-139 was obtained as white solid in TFA salt form (14.6 mg, yield 53%). $^1$H NMR (800 MHz, CD$_3$OD) δ 9.01 (d, J=6.7 Hz, 1H), 8.48 (s, 2H), 8.00 (d, J=9.3 Hz, 1H), 7.84 (d, J=8.0 Hz, 1H), 7.57-7.39 (m, 4H), 7.07 (d, J=11.9 Hz, 1H), 6.95 (s, 1H), 6.15 (s, 1H), 4.66-4.03 (m, 15H), 3.98-3.57 (m, 18H), 3.55-3.38 (m, 12H), 3.03-2.91 (m, 5H), 2.64-2.59 (m, 2H), 2.50 (s, 3H), 2.32-2.22 (m, 1H), 2.18-2.02 (m, 1H), 1.45 (d, J=6.5 Hz, 6H), 1.07 (s, 9H). HRMS (m/z) for C$_{68}$H$_{90}$F$_4$N$_{13}$O$_{12}$S$^+$ [M+H]$^+$: calculated 1388.6483. found 1388.6502.

Example 312: Synthesis of XF078-140
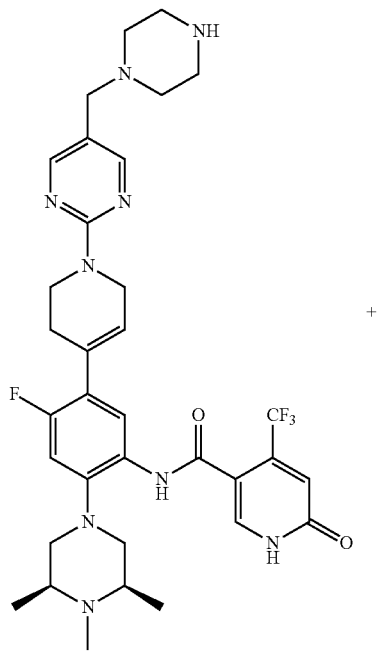
Intermediate 45
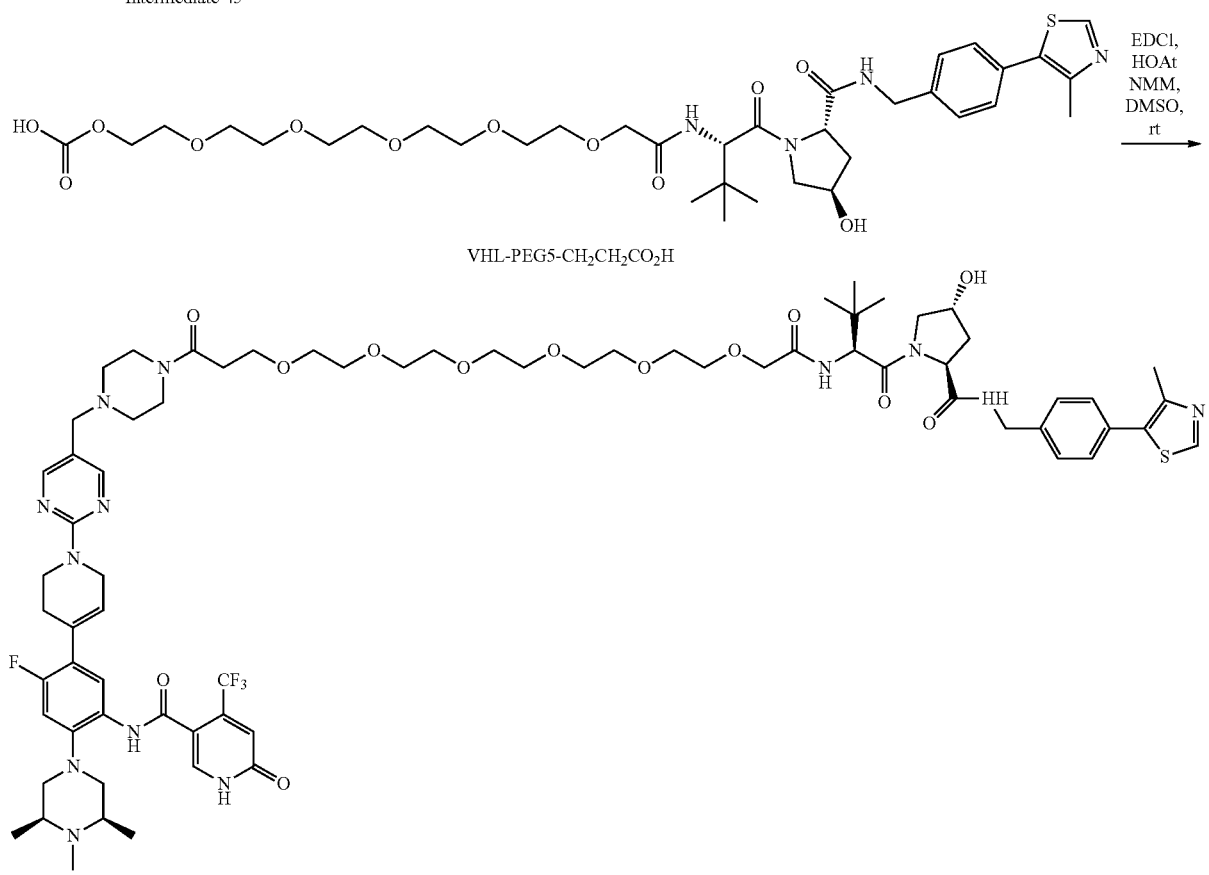
XF078-140
XF078-140 was synthesized following the standard procedures for preparing XF078-132 from intermediate 45 (13.6 mg, 0.02 mmol), VHL-PEG5-CH$_2$CH$_2$COOH (15 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-140 was obtained as white solid in TFA salt form (10.3 mg, yield 36%). $^1$H NMR (800 MHz, CD$_3$OD) δ 8.99 (s, 1H), 8.49 (s, 2H), 8.01 (s, 1H), 7.83 (d, J=8.0 Hz, 1H), 7.61-7.38 (m, 4H), 7.07 (d, J=11.9 Hz, 1H), 6.95 (s, 1H), 6.15 (s, 1H), 4.71-4.25 (m, 9H), 4.13-4.04 (m, 2H), 3.94-3.55 (m, 22H), 3.55-3.38 (m, 12H), 3.09-2.88 (m, 5H), 2.67-2.44 (m, 9H), 2.29-2.17 (m, 1H), 2.14-2.02 (m, 1H), 1.45 (d, J=6.5 Hz, 6H), 1.06 (s, 9H). HRMS (m/z) for C$_{70}$H$_{94}$F$_4$N$_{13}$O$_{12}$S$^+$ [M+H]$^+$: calculated 1416.6796. found 1416.6778.
Example 313: Synthesis of XF078-141
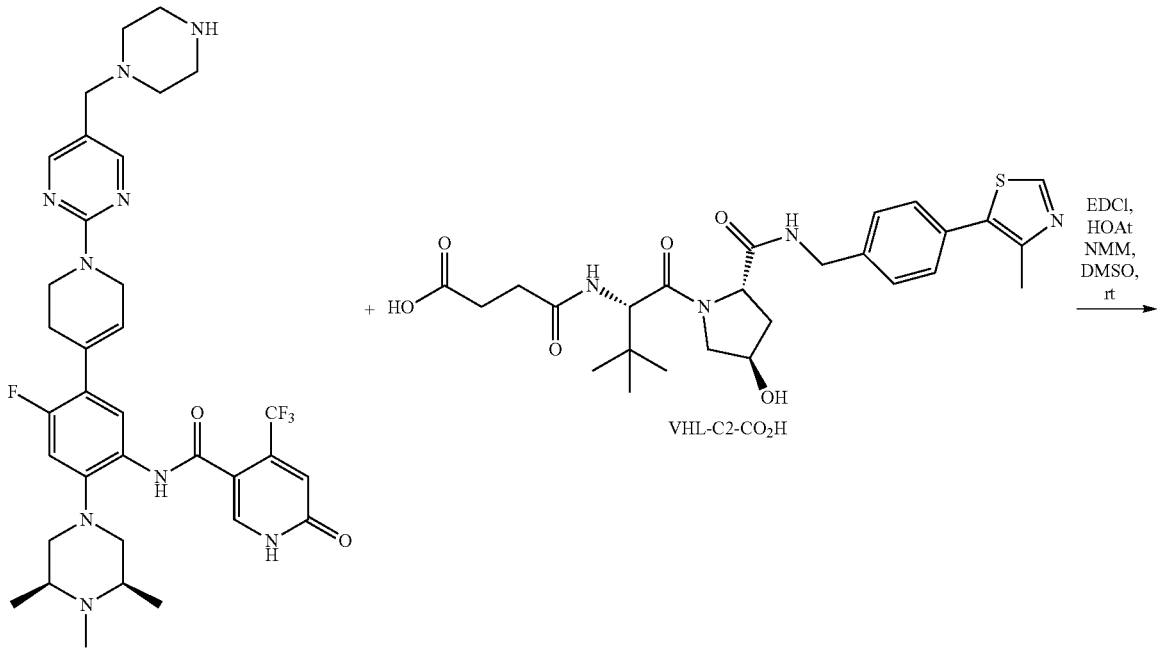
Intermediate 45
VHL-C2-CO$_2$H
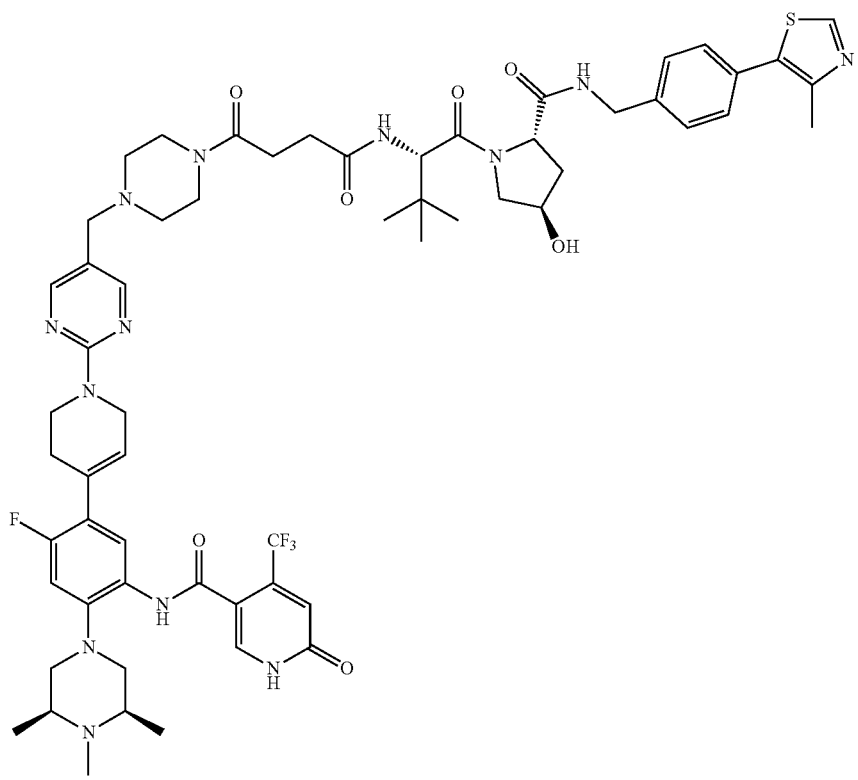
XF078-141

XF078-141 was synthesized following the standard procedures for preparing XF078-132 from intermediate 45 (13.6 mg, 0.02 mmol), VHL-C2-COOH (10.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-141 was obtained as white solid in TFA salt form (20.1 mg, yield 84%). $^1$H NMR (800 MHz, CD$_3$OD) δ 9.09 (s, 1H), 8.49 (s, 2H), 8.01 (s, 1H), 7.83 (d, J=8.0 Hz, 1H), 7.57-7.39 (m, 4H), 7.07 (d, J=11.9 Hz, 1H), 6.95 (s, 1H), 6.15 (d, J=3.5 Hz, 1H), 4.67-4.50 (m, 4H), 4.46 (d, J=3.4 Hz, 2H), 4.40 (d, J=15.4 Hz, 1H), 4.30 (s, 2H), 4.14 (t, J=5.7 Hz, 2H), 3.91 (d, J=10.9 Hz, 1H), 3.82 (dd, J=10.9, 4.0 Hz, 1H), 3.55-3.38 (m, 12H), 3.03-2.91 (m, 5H), 2.79-2.56 (m, 6H), 2.52 (s, 3H), 2.30-2.19 (m, 1H), 2.13-2.08 (m, 1H), 1.45 (d, J=6.5 Hz, 6H), 1.06 (s, 9H). HRMS (m/z) for C$_{60}$H$_{74}$F$_4$N$_{13}$O$_7$S$^+$ [M+H]$^+$: calculated 1196.5486. found 1196.5454.

Example 314: Synthesis of XF078-142

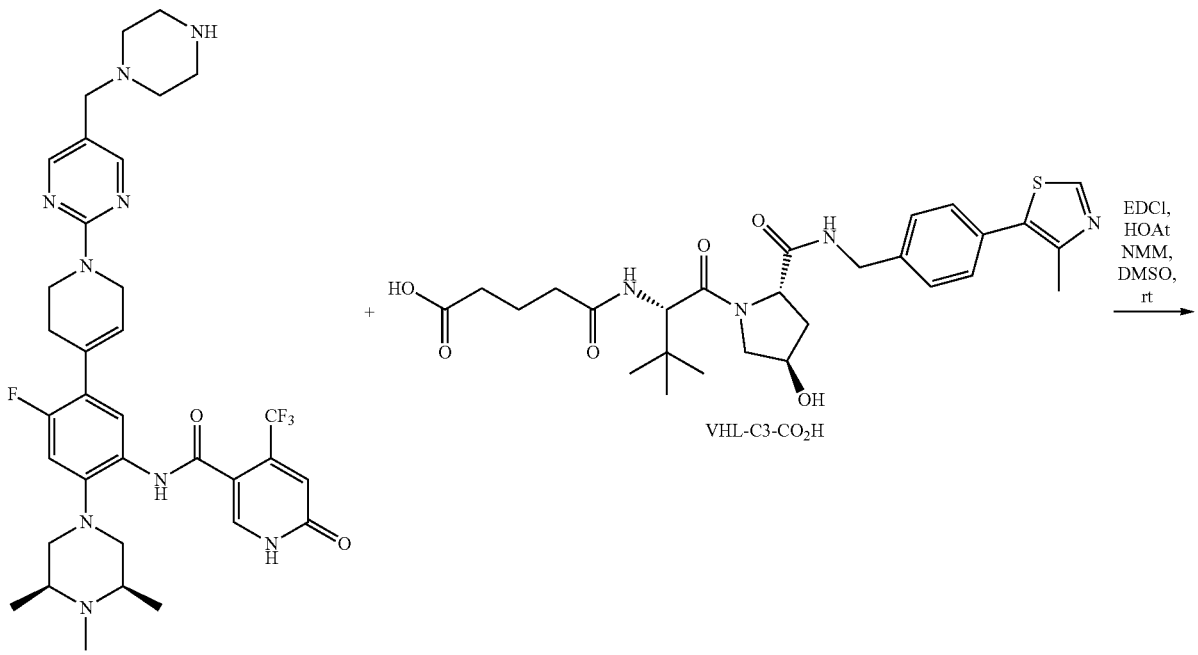

Intermediate 45

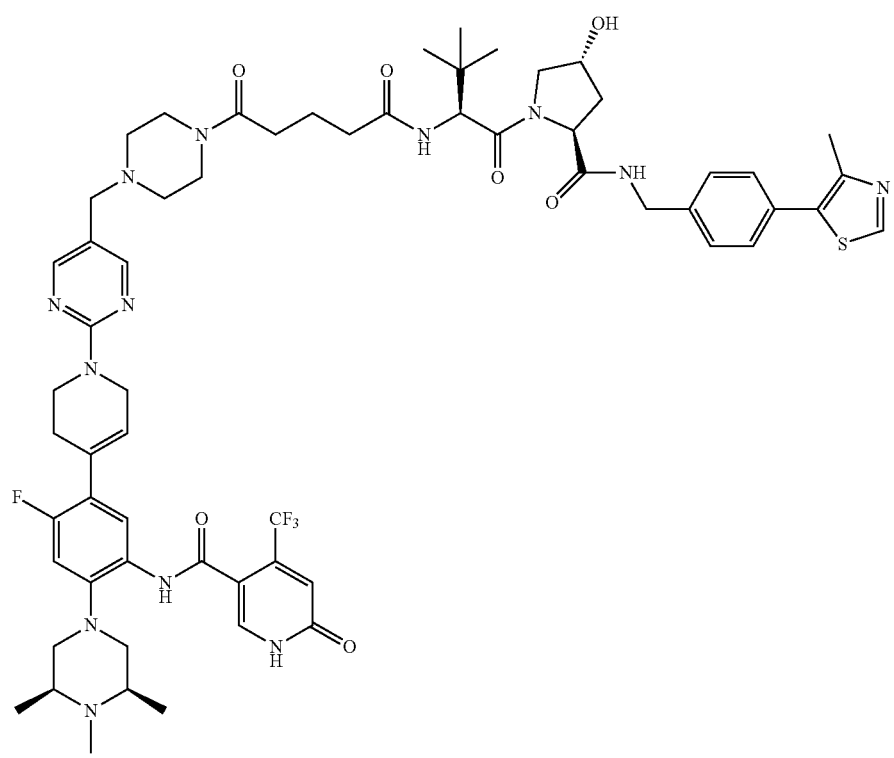

XF078-142

XF078-142 was synthesized following the standard procedures for preparing XF078-132 from intermediate 45 (13.6 mg, 0.02 mmol), VHL-C3-COOH (10.8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-142 was obtained as white solid in TFA salt form (17.6 mg, yield 73%). $^1$H NMR (800 MHz, CD$_3$OD) δ 9.04 (s, 1H), 8.49 (s, 2H), 8.01 (d, J=9.3 Hz, 1H), 7.83 (d, J=7.9 Hz, 1H), 7.54-7.39 (m, 4H), 7.07 (d, J=11.9 Hz, 1H), 6.95 (s, 1H), 6.13 (s, 1H), 4.69-4.35 (m, 7H), 4.27 (s, 2H), 4.12 (t, J=5.8 Hz, 2H), 3.96 (d, J=10.9 Hz, 1H), 3.82 (dd, J=10.9, 4.0 Hz, 1H), 3.64-3.33 (m, 12H), 3.04-2.90 (m, 5H), 2.66-2.56 (m, 2H), 2.54-2.41 (m, 5H), 2.41-2.30 (m, 2H), 2.25 (dd, J=13.2, 7.6 Hz, 1H), 2.10 (ddd, J=13.3, 9.3, 4.4 Hz, 1H), 1.99-1.88 (m, 2H), 1.45 (d, J=6.5 Hz, 6H), 1.07 (s, 9H). HRMS (m/z) for $C_{61}H_{76}F_4N_{13}O_7S^+$ [M+H]$^+$: calculated 1210.5642. found 1210.5659.

Example 315: Synthesis of XF078-143

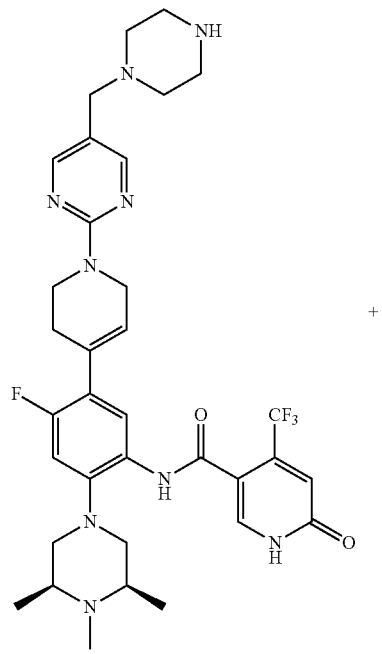

Intermediate 45

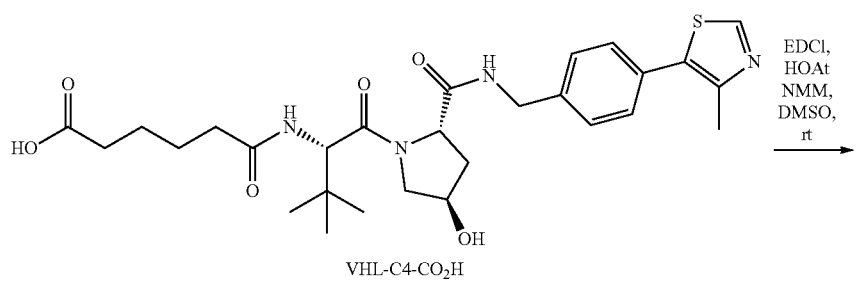

VHL-C4-CO$_2$H

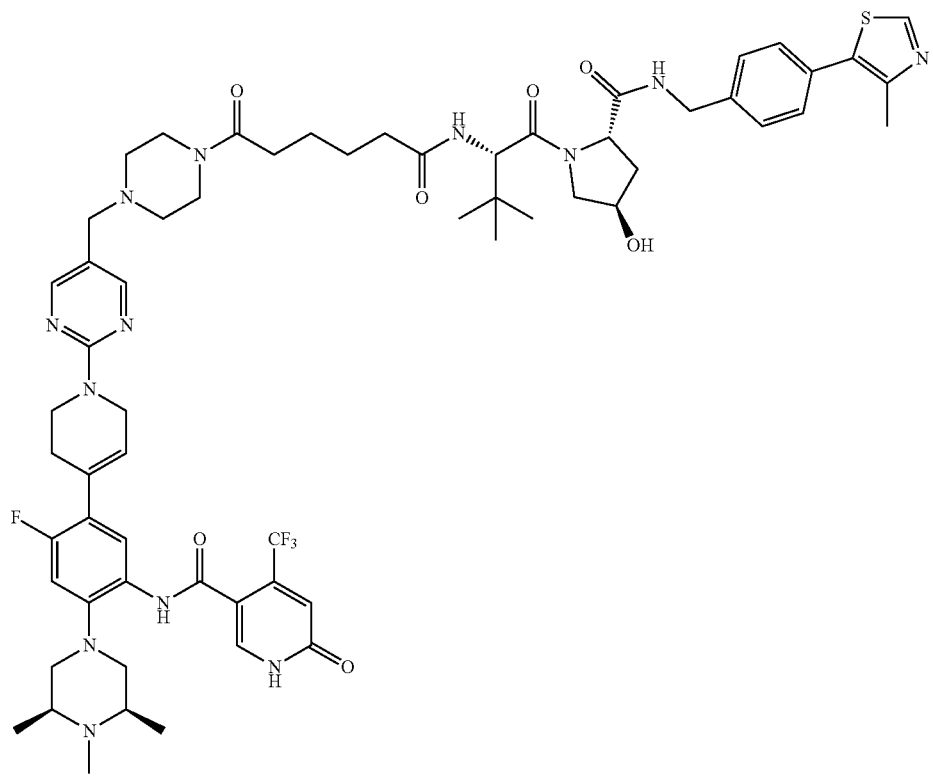

XF078-143

XF078-143 was synthesized following the standard procedures for preparing XF078-132 from intermediate 45 (13.6 mg, 0.02 mmol), VHL-C4-COOH (11.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-143 was obtained as white solid in TFA salt form (23.6 mg, yield 96%). $^1$H NMR (800 MHz, CD$_3$OD) δ 9.11 (s, 1H), 8.48 (s, 2H), 8.01 (s, 1H), 7.83 (d, J=8.0 Hz, 1H), 7.57-7.38 (m, 4H), 7.07 (d, J=11.9 Hz, 1H), 6.95 (s, 1H), 6.14 (d, J=3.7 Hz, 1H), 4.73-4.36 (m, 7H), 4.32-4.22 (m, 2H), 4.19-4.08 (m, 2H), 3.99-3.78 (m, 2H), 3.59-3.43 (m, 12H), 3.07-2.90 (m, 5H), 2.64-2.58 (m, 2H), 2.56-2.43 (m, 5H), 2.40-2.29 (m, 2H), 2.27-2.22 (m, 1H), 2.14-2.07 (m, 1H), 1.75-1.60 (m, 4H), 1.45 (d, J=6.5 Hz, 6H), 1.06 (s, 9H). HRMS (m/z) for C$_{62}$H$_{78}$F$_4$N$_{13}$O$_7$S$^+$ [M+H]$^+$: calculated 1224.5799, found 1224.5819.

Example 316: Synthesis of XF078-144
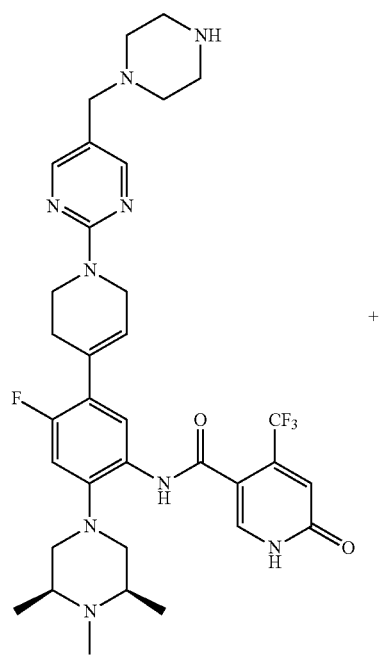
Intermediate 45
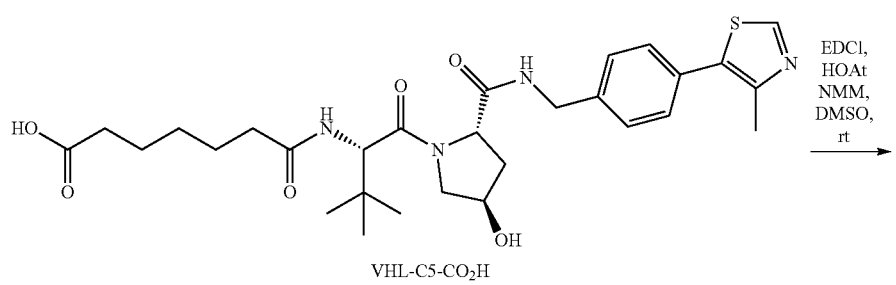
VHL-C5-CO₂H -continued

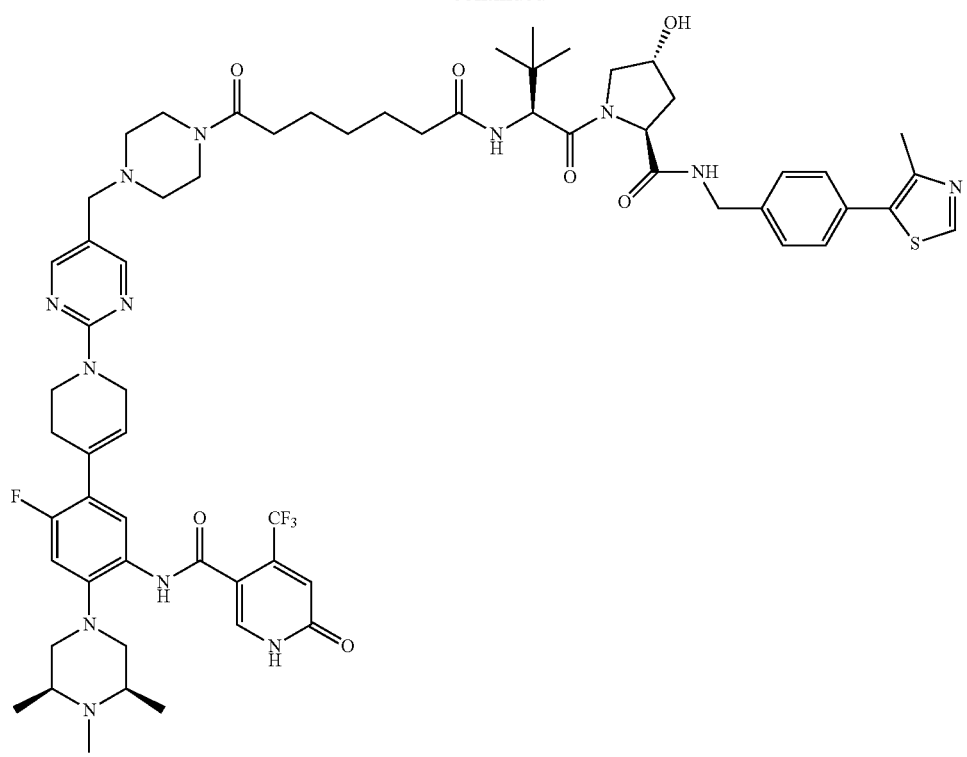

XF078-144

XF078-144 was synthesized following the standard procedures for preparing XF078-132 from intermediate 45 (13.6 mg, 0.02 mmol), VHL-C5-COOH (11.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-144 was obtained as white solid in TFA salt form (23.1 mg, yield 93%). $^1$H NMR (800 MHz, CD$_3$OD) δ 9.07 (s, 1H), 8.49 (s, 2H), 8.01 (s, 1H), 7.84 (dd, J=15.6, 7.8 Hz, 1H), 7.63-7.36 (m, 4H), 7.07 (d, J=11.9 Hz, 1H), 6.95 (s, 1H), 6.14 (d, J=4.0 Hz, 1H), 4.66 (s, 1H), 4.63-4.34 (m, 6H), 4.29 (s, 2H), 4.13 (t, J=5.7 Hz, 2H), 3.99-3.79 (m, 2H), 3.58-3.38 (m, 12H), 3.03-2.92 (m, 5H), 2.61 (h, J=6.1, 4.8 Hz, 2H), 2.55-2.40 (m, 5H), 2.37-2.21 (m, 3H), 2.15-2.09 (m, 1H), 1.65 (h, J=7.7 Hz, 4H), 1.53-1.31 (m, 8H), 1.06 (s, 9H). HRMS (m/z) for $C_{63}H_{80}F_4N_{13}O_7S^+$ [M+H]$^+$: calculated 1238.5955, found 1238.5971.

Example 317: Synthesis of XF078-145
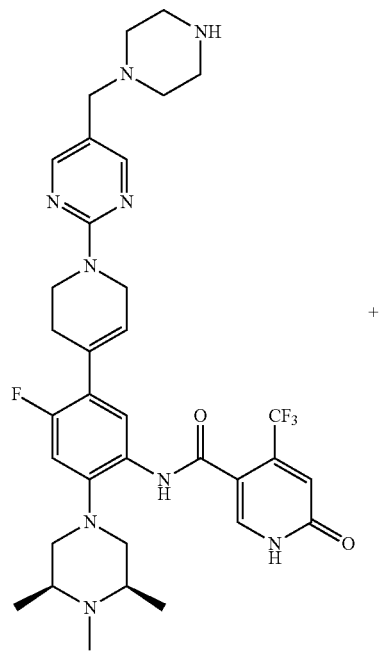
Intermediate 45
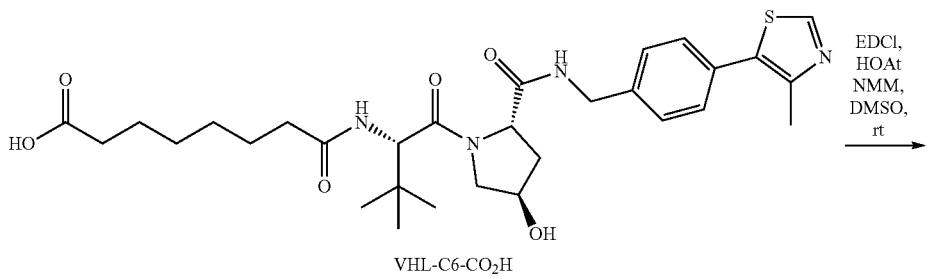
VHL-C6-CO₂H

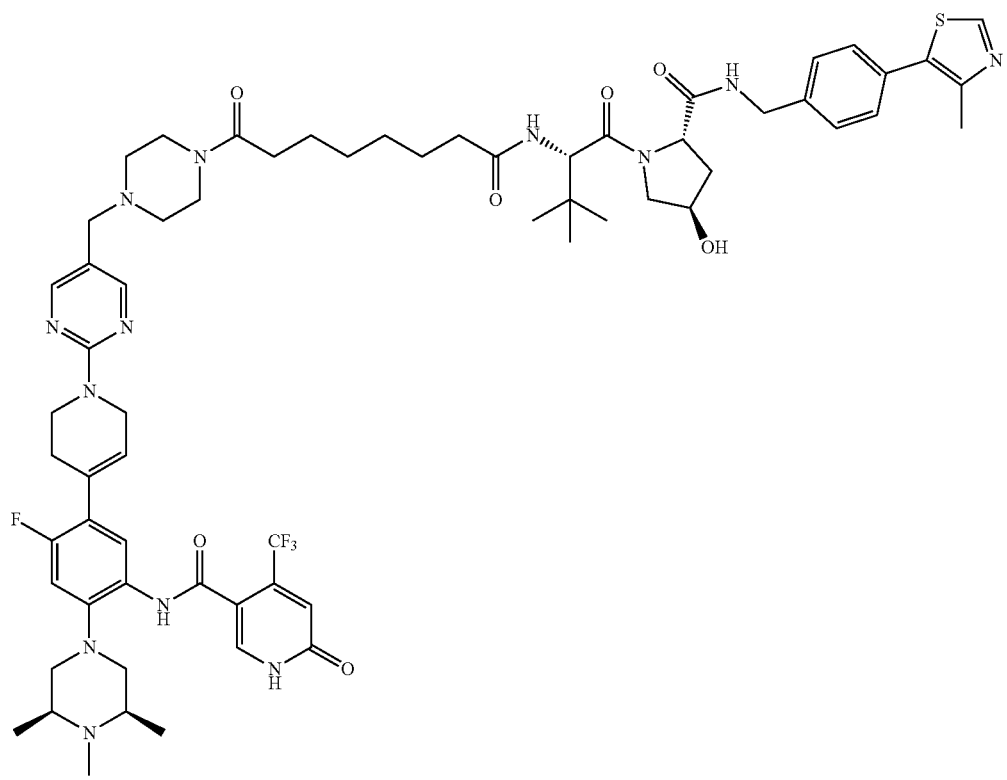

XF078-145

XF078-145 was synthesized following the standard procedures for preparing XF078-132 from intermediate 45 (13.6 mg, 0.02 mmol), VHL-C6-COOH (11.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-145 was obtained as white solid in TFA salt form (19.6 mg, yield 930%). $^1$H NMR (800 MHz, CD$_3$OD) δ 9.05 (s, 1H), 8.55-8.42 (m, 2H), 8.01 (d, J=9.6 Hz, 1H), 7.83 (d, J=7.9 Hz, 1H), 7.60-7.35 (m, 4H), 7.07 (d, J=11.9 Hz, 1H), 6.95 (s, 1H), 6.14 (d, J=4.0 Hz, 1H), 4.70-4.35 (m, 7H), 4.29 (s, 2H), 4.13 (t, J=5.7 Hz, 2H), 4.02-3.80 (m, 2H), 3.56-3.37 (m, 12H), 3.03-2.91 (m, 5H), 2.63-2.57 (m, 2H), 2.55-2.41 (m, 5H), 2.36-2.21 (m, 3H), 2.18-2.08 (m, 1H), 1.71-1.58 (m, 4H), 1.50-1.35 (m, 10H), 1.06 (s, 9H). HRMS (m/z) for C$_{64}$H$_{82}$F$_4$N$_{13}$O$_7$S$^+$ [M+H]$^+$: calculated 1252.6112. found 1252.6157.

Example 318: Synthesis of XF078-146
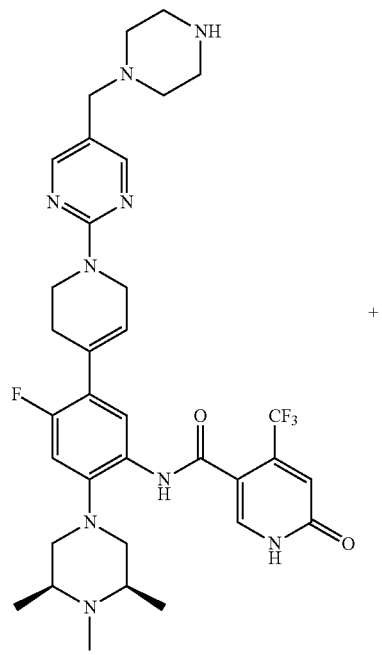
Intermediate 45
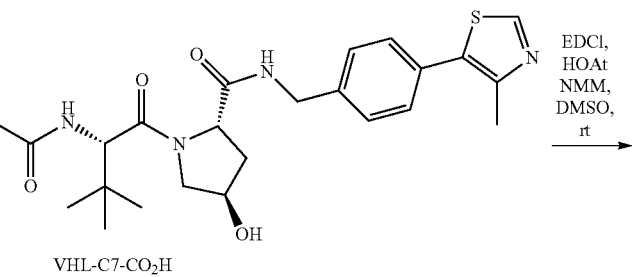
VHL-C7-CO₂H

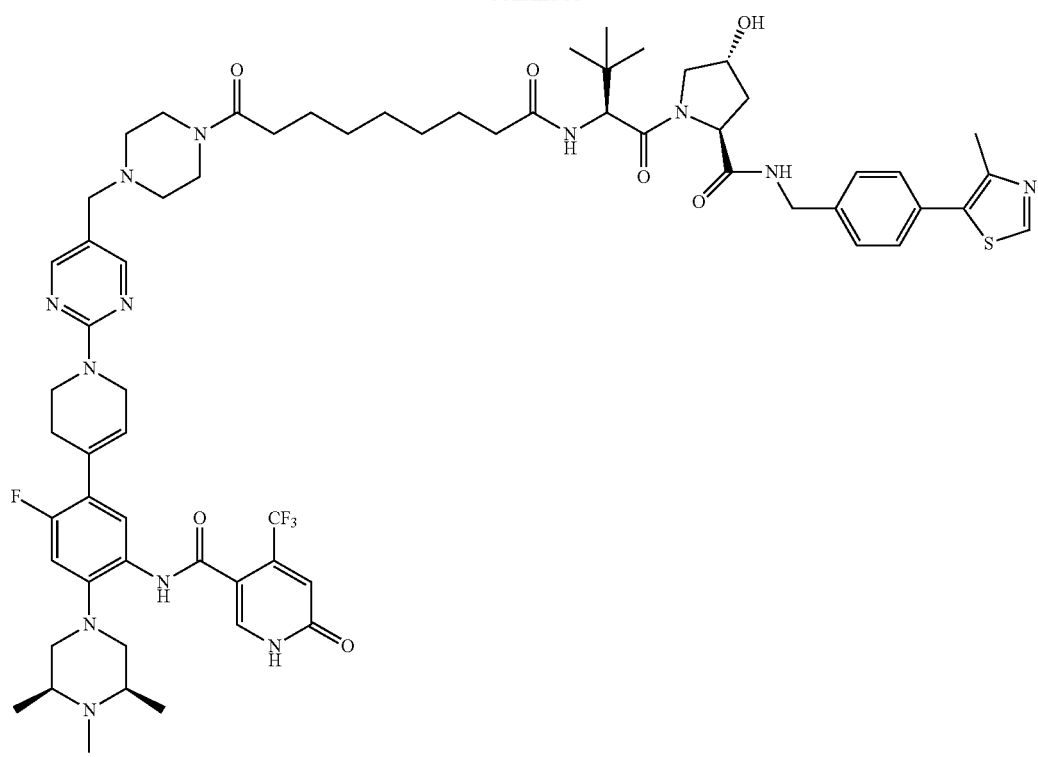

XF078-146

XF078-146 was synthesized following the standard procedures for preparing XF078-132 from intermediate 45 (13.6 mg, 0.02 mmol), VHL-C7-COOH (12 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-146 was obtained as white solid in TFA salt form (14.5 mg, yield 57%). $^1$H NMR (800 MHz, CD$_3$OD) δ 9.00 (s, 1H), 8.48 (s, 2H), 8.01 (s, 1H), 7.83 (d, J=8.0 Hz, 1H), 7.56-7.33 (m, 4H), 7.07 (d, J=11.9 Hz, 1H), 6.95 (s, 1H), 6.15 (d, J=3.6 Hz, 1H), 4.66 (s, 1H), 4.62-4.36 (m, 6H), 4.28 (s, 2H), 4.13 (t, J=5.7 Hz, 2H), 3.97-3.79 (m, 2H), 3.56-3.42 (m, 12H), 3.03-2.91 (m, 5H), 2.69-2.54 (m, 2H), 2.51-2.43 (m, 5H), 2.36-2.21 (m, 3H), 2.14-2.06 (m, 1H), 1.68-1.59 (m, 4H), 1.54-1.32 (m, 12H), 1.06 (s, 9H). HRMS (m/z) for $C_{65}H_{84}F_4N_{13}O_7S^+$ [M+H]$^+$: calculated 1266.6268. found 1266.6237.

Example 319: Synthesis of XF078-147
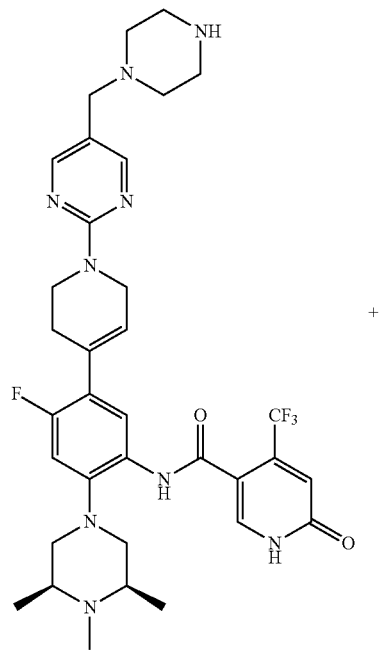
Intermediate 45
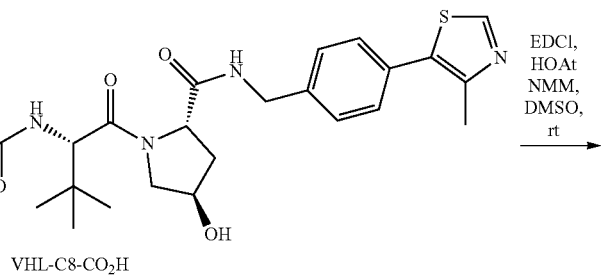
VHL-C8-CO₂H -continued

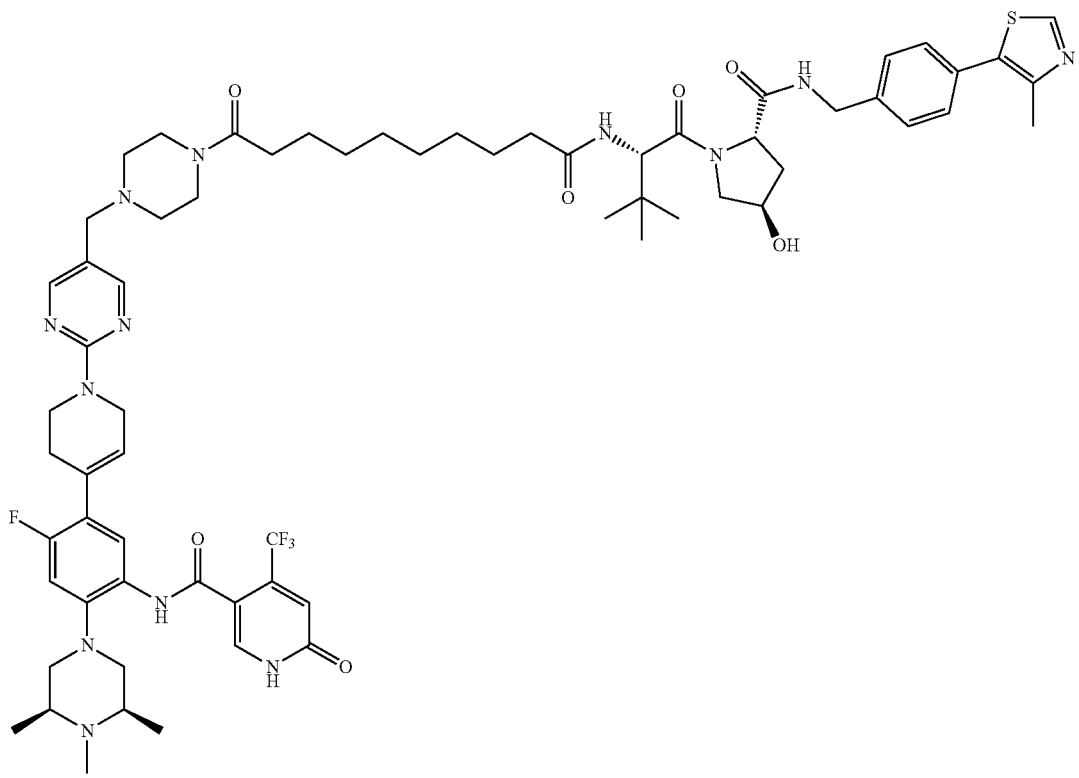

XF078-147

XF078-147 was synthesized following the standard procedures for preparing XF078-132 from intermediate 45 (13.6 mg, 0.02 mmol), VHL-C8-COOH (12.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-147 was obtained as white solid in TFA salt form (15.6 mg, yield 61%). $^1$H NMR (800 MHz, CD$_3$OD) δ 9.00 (s, 1H), 8.48 (s, 2H), 8.01 (s, 1H), 7.83 (d, J=7.9 Hz, 1H), 7.59-7.34 (m, 4H), 7.07 (d, J=11.9 Hz, 1H), 6.95 (s, 1H), 6.15 (s, 1H), 4.66 (s, 1H), 4.62-4.36 (m, 6H), 4.28 (s, 2H), 4.13 (t, J=5.6 Hz, 2H), 3.99-3.79 (m, 2H), 3.59-3.38 (m, 12H), 3.06-2.90 (m, 5H), 2.61 (s, 2H), 2.53-2.38 (m, 5H), 2.37-2.21 (m, 3H), 2.15-2.08 (m, 1H), 1.69-1.54 (m, 4H), 1.52-1.30 (m, 14H), 1.06 (s, 9H). HRMS (m/z) for $C_{66}H_{86}F_4N_{13}O_7S^+$ [M+H]$^+$: calculated 1280.6425. found 1280.6451.

Example 320: Synthesis of XF078-148
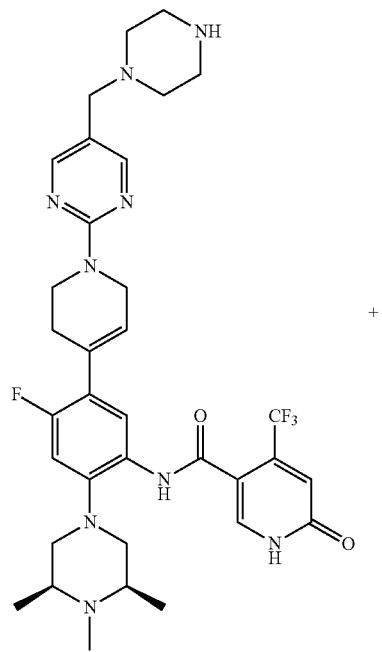
Intermediate 45
+
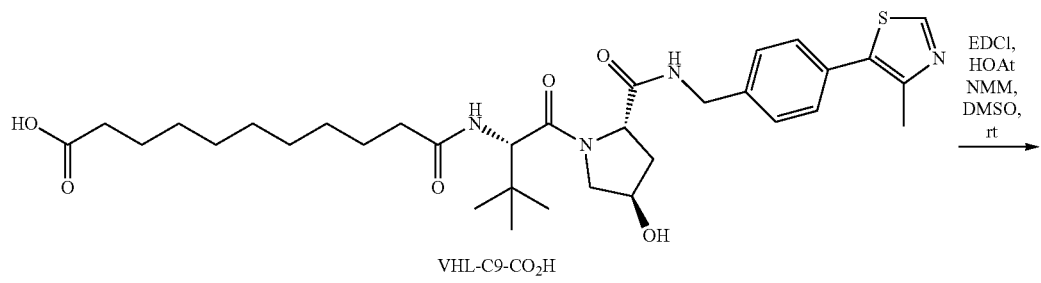
VHL-C9-CO₂H

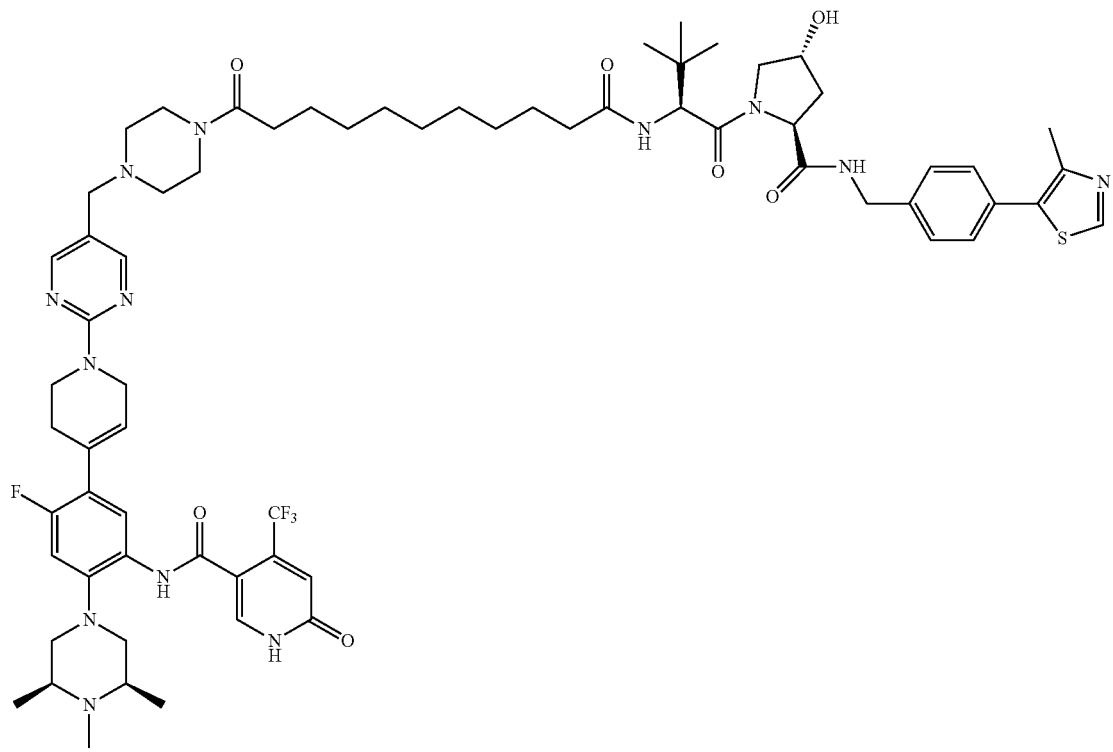

XF078-148

XF078-148 was synthesized following the standard procedures for preparing XF078-132 from intermediate 45 (13.6 mg, 0.02 mmol), VHL-C9-COOH (12.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-148 was obtained as white solid in TFA salt form (13.4 mg, yield 52%). $^1$H NMR (800 MHz, CD$_3$OD) δ 9.00 (s, 1H), 8.48 (s, 2H), 8.01 (s, 1H), 7.83 (d, J=7.9 Hz, 1H), 7.57-7.40 (m, 4H), 7.07 (d, J=11.9 Hz, 1H), 6.95 (s, 1H), 6.15 (d, J=3.8 Hz, 1H), 4.71-4.34 (m, 7H), 4.28 (s, 2H), 4.13 (t, J=5.7 Hz, 2H), 3.92 (d, J=11.0 Hz, 1H), 3.83 (dd, J=10.9, 4.0 Hz, 1H), 3.58-3.38 (m, 12H), 3.03-2.91 (m, 5H), 2.63-2.59 (m, 2H), 2.53-2.42 (m, 5H), 2.36-2.21 (m, 3H), 2.16-2.04 (m, 1H), 1.67-1.59 (m, 4H), 1.48-1.28 (m, 16H), 1.06 (s, 9H). HRMS (m/z) for $C_{67}H_{88}F_4N_{13}O_7S^+$ [M+H]$^+$: calculated 1294.6581. found 1294.6564.

Example 321: Synthesis of XF078-149

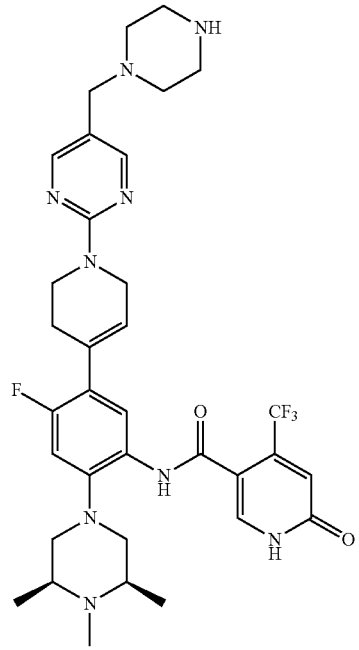

Intermediate 45

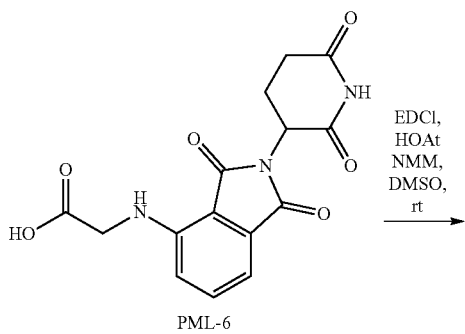

PML-6

EDCl, HOAt NMM, DMSO, rt →

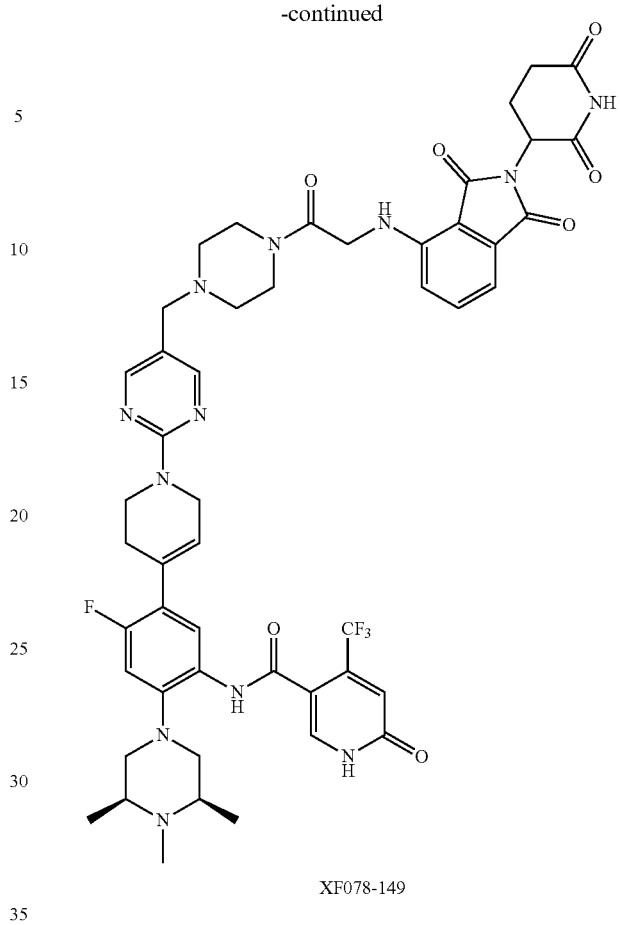

XF078-149

XF078-149 was synthesized following the standard procedures for preparing XF078-132 from intermediate 45 (13.6 mg, 0.02 mmol), PML-6 (6.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-149 was obtained as yellow solid in TFA salt form (9.8 mg, yield 49%). $^1$H NMR (800 MHz, CD$_3$OD) δ 8.49 (s, 2H), 8.01 (d, J=7.4 Hz, 1H), 7.81 (d, J=8.0 Hz, 1H), 7.45 (s, 1H), 7.10-7.00 (m, 2H), 6.97-6.85 (m, 2H), 6.13 (s, 1H), 5.13-5.06 (m, 1H), 4.47-4.39 (m, 2H), 4.40-4.26 (m, 2H), 4.22-4.05 (m, 4H), 3.57-3.37 (m, 12H), 3.05-2.84 (m, 5H), 2.84-2.67 (m, 3H), 2.58-2.44 (m, 2H), 2.17-2.05 (m, 1H), 1.45 (d, J=6.5 Hz, 6H). HRMS (m/z) for $C_{49}H_{53}F_4N_{12}O_7^+$ [M+H]$^+$: calculated 997.4097. found 997.4112.

Example 322: Synthesis of XF078-150

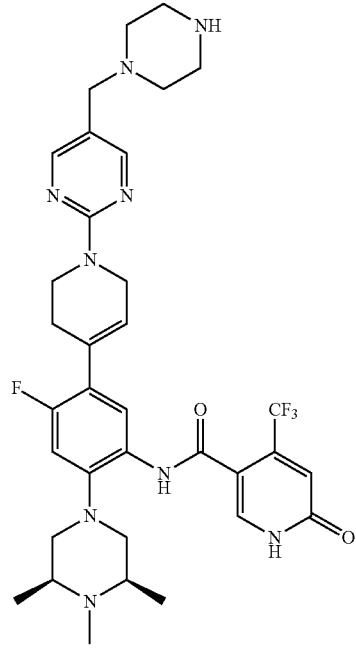

Intermediate 45

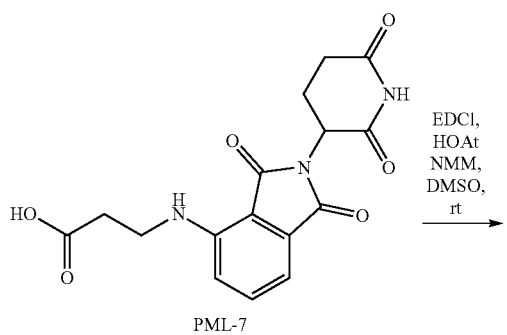

PML-7

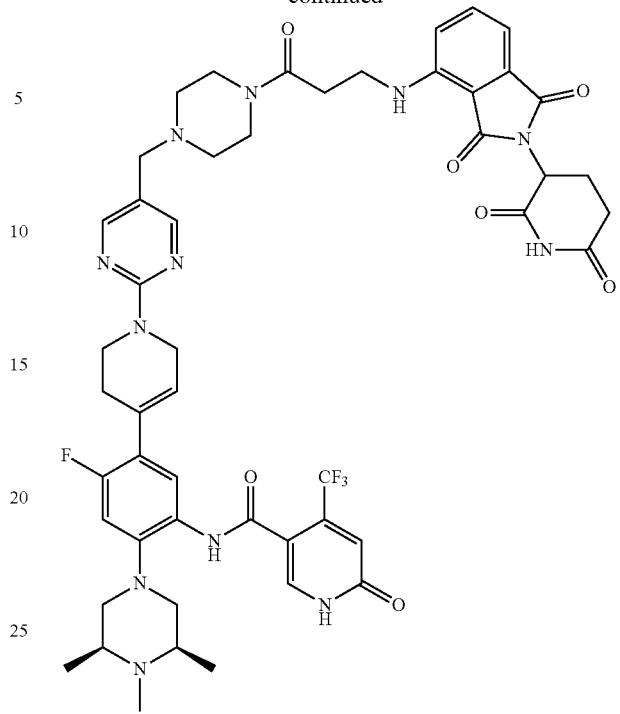

XF078-150

XF078-150 was synthesized following the standard procedures for preparing XF078-132 from intermediate 45 (13.6 mg, 0.02 mmol), PML-7 (6.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-150 was obtained as yellow solid in TFA salt form (7 mg, yield 35%). $^1$H NMR (800 MHz, CD$_3$OD) δ 8.46 (s, 2H), 8.01 (s, 1H), 7.83 (d, J=7.9 Hz, 1H), 7.72-7.52 (m, 1H), 7.25-7.03 (m, 3H), 6.95 (s, 1H), 6.15 (s, 1H), 5.08-4.99 (m, 1H), 4.49-4.37 (m, 2H), 4.29-4.20 (m, 2H), 4.13 (t, J=5.7 Hz, 2H), 3.76-3.67 (m, 2H), 3.56-3.40 (m, 12H), 3.05-2.69 (m, 10H), 2.63-2.59 (m, 2H), 2.17-2.10 (m, 1H), 1.50-1.41 (m, 6H). HRMS (m/z) for $C_{50}H_{55}F_4N_{12}O_7^+$ [M+H]$^+$: calculated 1011.4247. found 1011.4265.

Example 323: Synthesis of XF078-151

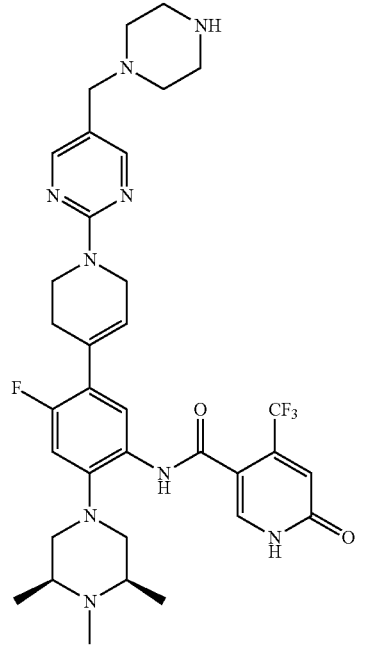

Intermediate 45

+

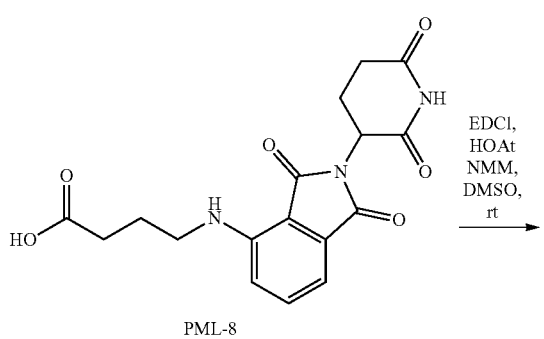

PML-8

EDCl, HOAt NMM, DMSO, rt

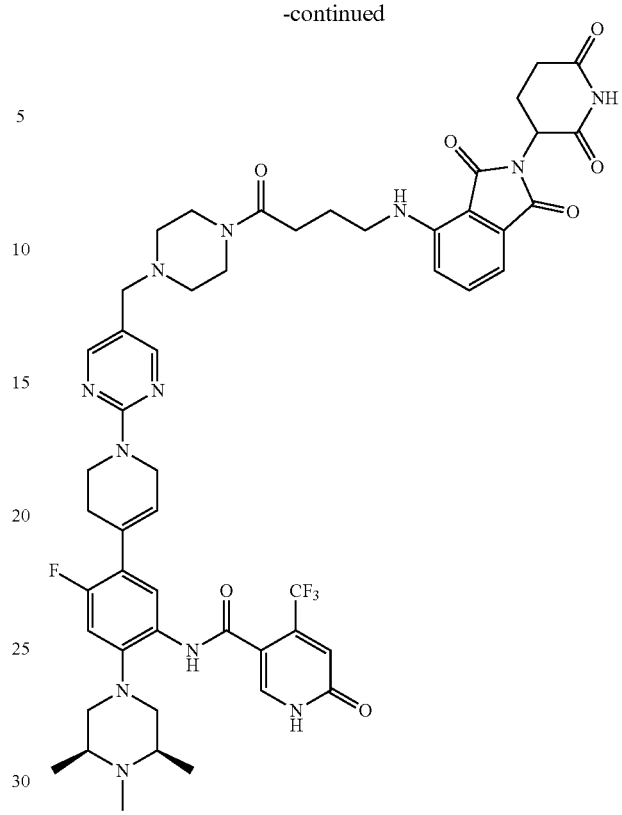

XF078-151

XF078-151 was synthesized following the standard procedures for preparing XF078-132 from intermediate 45 (13.6 mg, 0.02 mmol), PML-8 (7.2 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-151 was obtained as yellow solid in TFA salt form (12.5 mg, yield 61%). $^1$H NMR (800 MHz, CD$_3$OD) δ 8.46 (d, J=3.9 Hz, 2H), 8.00 (d, J=7.8 Hz, 1H), 7.82 (d, J=8.0 Hz, 1H), 7.65-7.55 (m, 1H), 7.18-7.04 (m, 3H), 6.95 (s, 1H), 6.15 (d, J=3.9 Hz, 1H), 5.08 (dd, J=13.0, 5.5 Hz, 1H), 4.52-4.39 (m, 2H), 4.25 (t, J=3.5 Hz, 2H), 4.18-4.08 (m, 2H), 3.56-3.35 (m, 14H), 3.06-2.69 (m, 8H), 2.65-2.51 (m, 4H), 2.17-2.12 (m, 1H), 2.08-1.90 (m, 2H), 1.45 (d, J=6.5 Hz, 6H). HRMS (m/z) for $C_{51}H_{57}F_4N_{12}O_7^+$ [M+H]$^+$: calculated 1025.4404. found 1025.4397.

Example 324: Synthesis of XF078-152

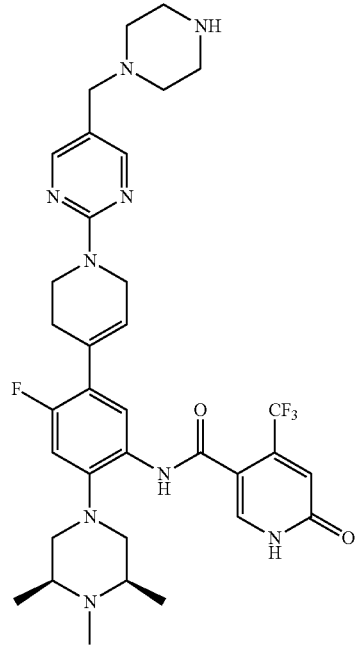

Intermediate 45

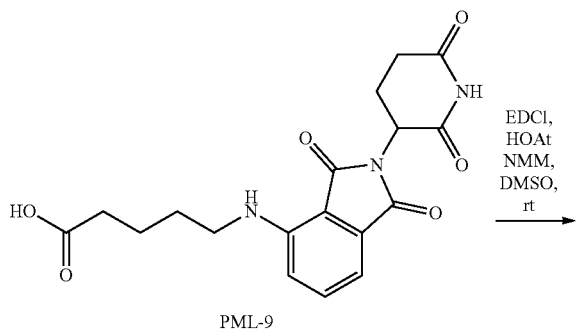

PML-9

→ EDCl, HOAt, NMM, DMSO, rt

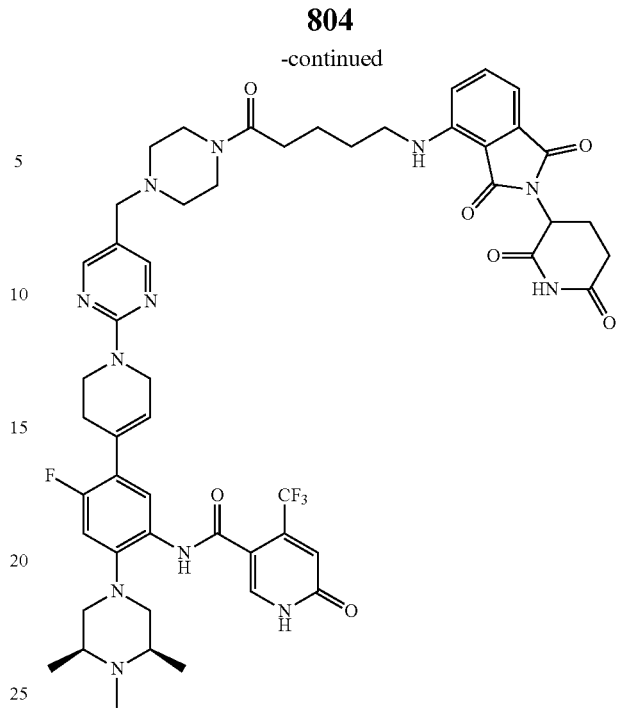

XF078-152

XF078-152 was synthesized following the standard procedures for preparing XF078-132 from intermediate 45 (13.6 mg, 0.02 mmol), PML-9 (7.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-152 was obtained as yellow solid in TFA salt form (10.7 mg, yield 51%). $^1$H NMR (800 MHz, CD$_3$OD) δ 8.47 (s, 2H), 8.01 (s, 1H), 7.83 (d, J=7.9 Hz, 1H), 7.64-7.49 (m, 1H), 7.13-7.03 (m, 3H), 6.95 (s, 1H), 6.15 (d, J=3.8 Hz, 1H), 5.11-5.04 (m, 1H), 4.46 (t, J=3.2 Hz, 2H), 4.27 (s, 2H), 4.17-4.07 (m, 2H), 3.40 (d, J=6.5 Hz, 14H), 3.04-2.68 (m, 8H), 2.66-2.58 (m, 2H), 2.55-2.49 (m, 2H), 2.16-2.09 (m, 1H), 1.79-1.72 (m, 4H), 1.45 (d, J=6.5 Hz, 6H). HRMS (m/z) for C$_{52}$H$_{59}$F$_4$N$_{12}$O$_7^+$ [M+H]$^+$: calculated 1039.4560. found 1039.4583.

Example 325: Synthesis of XF078-153

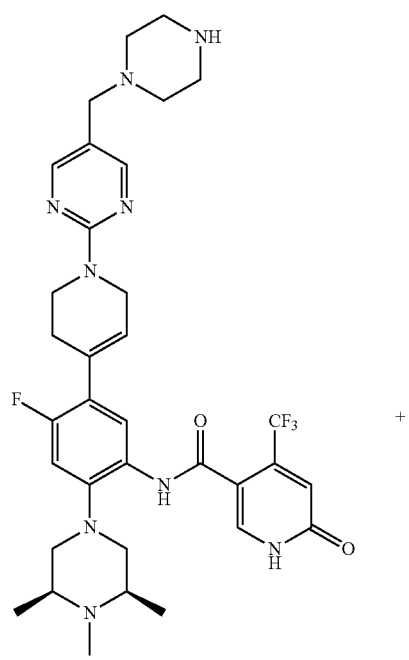

Intermediate 45

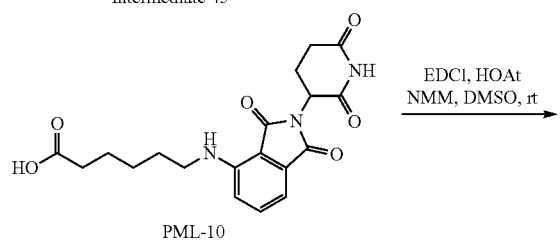

PML-10

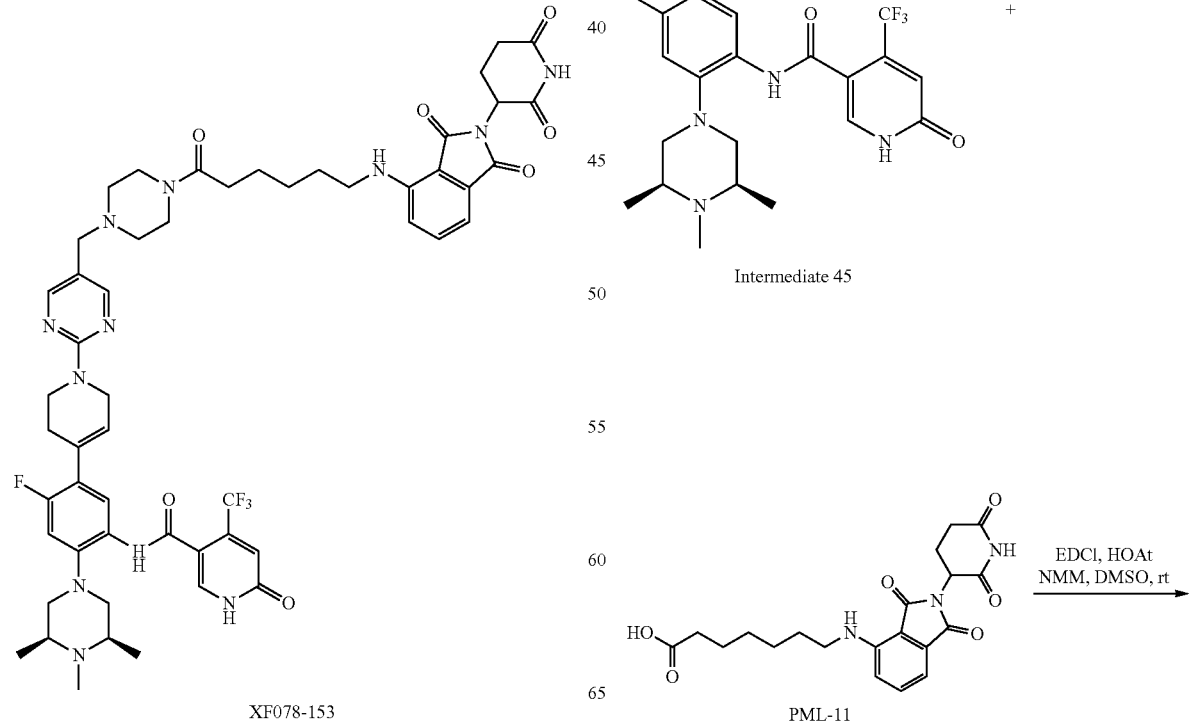

XF078-153

XF078-153 was synthesized following the standard procedures for preparing XF078-132 from intermediate 45 (13.6 mg, 0.02 mmol), PML-10 (7.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-153 was obtained as yellow solid in TFA salt form (12.8 mg, yield 61%). $^1$H NMR (800 MHz, CD$_3$OD) δ 8.61-8.35 (m, 2H), 8.01 (d, J=3.2 Hz, 1H), 7.87-7.79 (m, 1H), 7.65-7.48 (m, 1H), 7.22-7.03 (m, 3H), 6.95 (s, 1H), 6.30-6.03 (m, 1H), 5.07 (dd, J=12.6, 5.5 Hz, 1H), 4.55-4.38 (m, 2H), 4.35-4.22 (m, 2H), 4.20-4.08 (m, 2H), 3.57-3.32 (m, 14H), 3.08-2.64 (m, 8H), 2.64-2.56 (m, 2H), 2.51-2.42 (m, 2H), 2.19-2.09 (m, 1H), 1.76-1.63 (m, 4H), 1.54-1.41 (m, 8H). HRMS (m/z) for $C_{53}H_{61}F_4N_{12}O_7^+$ [M+H]$^+$: calculated 1053.4717. found 1053.4763.

Example 326: Synthesis of XF078-154

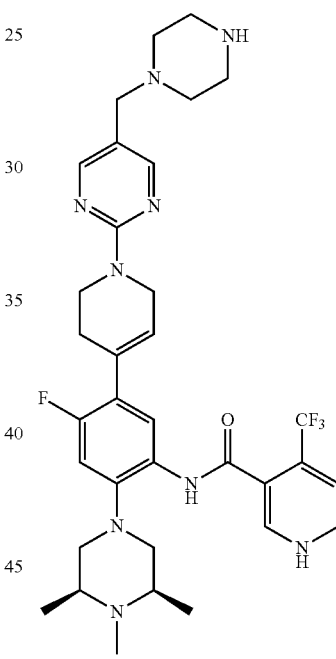

Intermediate 45

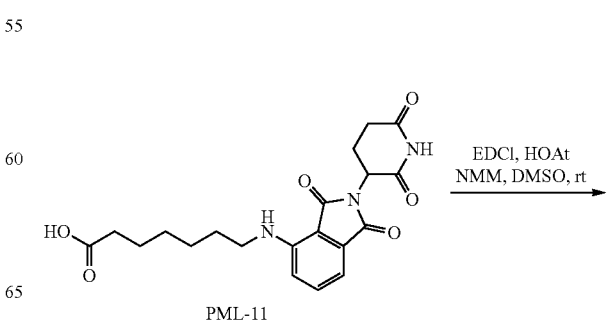

PML-11

-continued

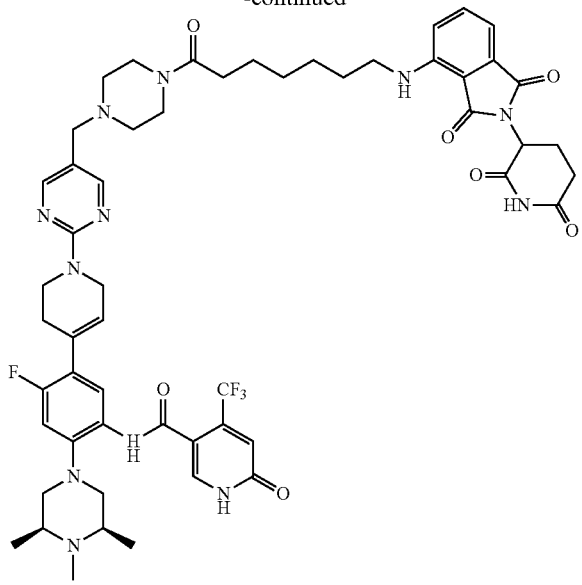

XF078-154

XF078-154 was synthesized following the standard procedures for preparing XF078-132 from intermediate 45 (13.6 mg, 0.02 mmol), PML-11 (8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-154 was obtained as yellow solid in TFA salt form (12.8 mg, yield 60%). $^1$H NMR (800 MHz, CD$_3$OD) δ 8.48 (s, 2H), 8.01 (s, 1H), 7.83 (d, J=8.0 Hz, 1H), 7.57 (dd, J=10.1, 5.4 Hz, 1H), 7.20-6.99 (m, 3H), 6.95 (s, 1H), 6.15 (s, 1H), 5.07 (dd, J=12.9, 5.6 Hz, 1H), 4.53-4.42 (m, 2H), 4.27 (s, 2H), 4.13 (t, J=5.7 Hz, 2H), 3.63-3.32 (m, 14H), 3.09-2.69 (m, 8H), 2.64-2.59 (m, 2H), 2.54-2.40 (m, 2H), 2.16-2.10 (m, 1H), 1.73-1.65 (m, 4H), 1.51-1.39 (m, 10H). HRMS (m/z) for $C_{54}H_{63}F_4N_{12}O_7^+$ [M+H]$^+$: calculated 1067.4873. found 1067.4888.

Example 327: Synthesis of XF078-155

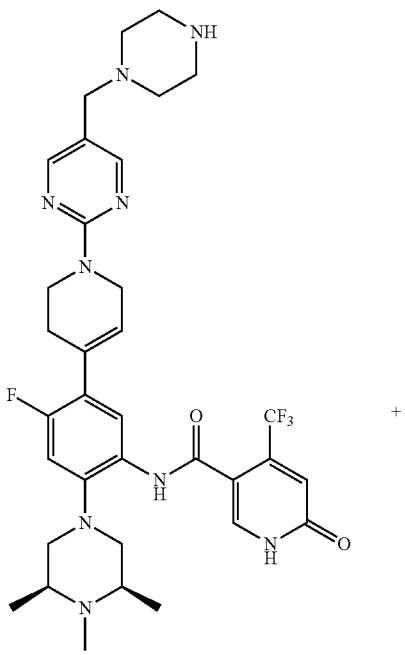

Intermediate 45

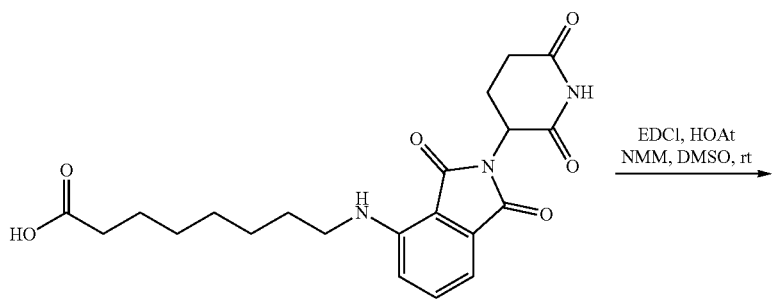

PML-12

-continued

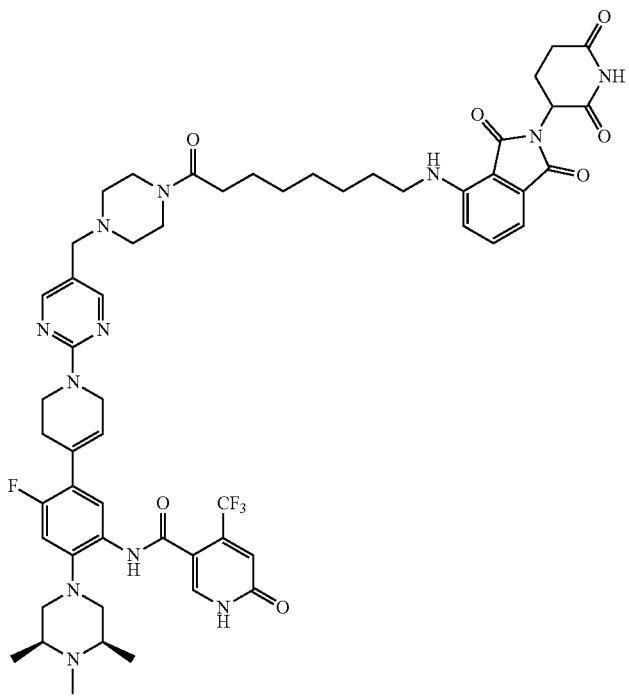

XF078-155

XF078-155 was synthesized following the standard procedures for preparing XF078-132 from intermediate 45 (13.6 mg, 0.02 mmol), PML-12 (8.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-155 was obtained as yellow solid in TFA salt form (14.1 mg, yield 66%). $^1$H NMR (800 MHz, CD$_3$OD) δ 8.48 (s, 2H), 8.00 (d, J=8.6 Hz, 1H), 7.82 (d, J=7.9 Hz, 1H), 7.66-7.51 (m, 1H), 7.12-6.99 (m, 3H), 6.95 (s, 1H), 6.15 (d, J=3.7 Hz, 1H), 5.07 (dd, J=12.8, 5.5 Hz, 1H), 4.54-4.38 (m, 2H), 4.28 (s, 2H), 4.13 (t, J=5.7 Hz, 2H), 3.59-3.32 (m, 14H), 3.09-2.69 (m, 8H), 2.65-2.56 (m, 2H), 2.44 (t, J=7.4 Hz, 2H), 2.18-2.09 (m, 1H), 1.85-1.53 (m, 4H), 1.50-1.34 (m, 12H). HRMS (m/z) for $C_{55}H_{65}F_4N_2O_7^+$ [M+H]$^+$: calculated 1081.5030. found 1081.5012.

Example 328: Synthesis of XF078-156

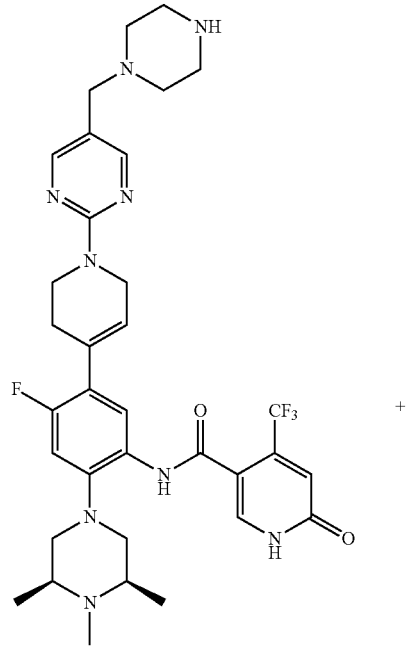

Intermediate 45

+

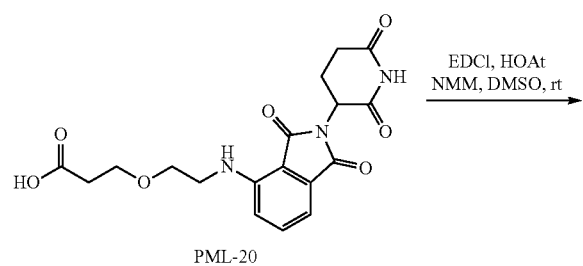

PML-20

EDCl, HOAt
NMM, DMSO, rt
→

-continued

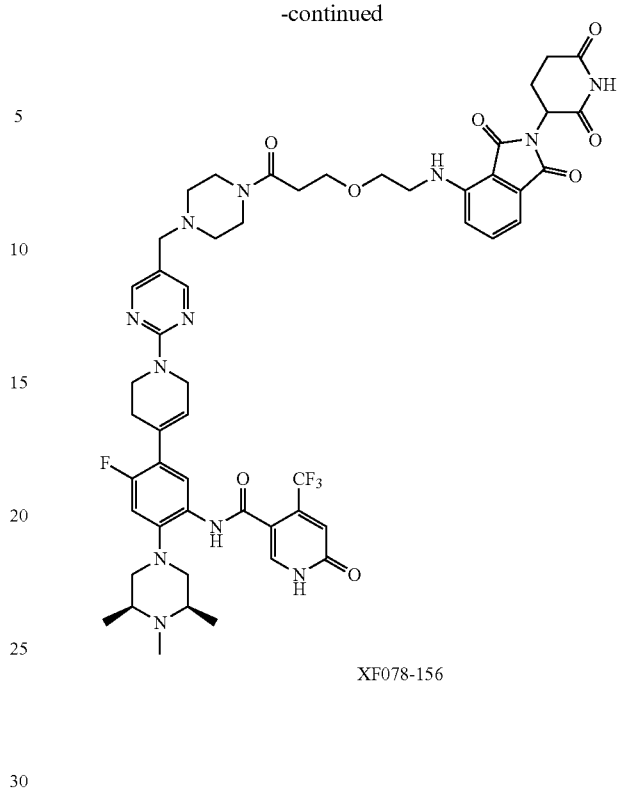

XF078-156

XF078-156 was synthesized following the standard procedures for preparing XF078-132 from intermediate 45 (13.6 mg, 0.02 mmol), PML-20 (8 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-156 was obtained as yellow solid in TFA salt form (13.4 mg, yield 63%). $^1$H NMR (800 MHz, CD$_3$OD) δ 8.52 (s, 1H), 8.37 (s, 2H), 8.01 (d, J=8.7 Hz, 1H), 7.90-7.75 (m, 1H), 7.17-7.03 (m, 3H), 6.95 (d, J=2.7 Hz, 1H), 6.14 (s, 1H), 5.07 (dd, J=12.8, 5.6 Hz, 1H), 4.48-4.38 (m, 2H), 4.29-4.17 (m, 2H), 4.16-4.08 (m, 2H), 3.92-3.78 (m, 4H), 3.76-3.67 (m, 6H), 3.58-3.40 (m, 8H), 2.97 (d, J=44.8 Hz, 5H), 2.89-2.45 (m, 7H), 2.16-2.11 (m, 1H), 1.45 (d, J=6.5 Hz, 6H). HRMS (m/z) for $C_{52}H_{59}F_4N_{12}O_8^+$ [M+H]$^+$: calculated 1055.4509. found 1055.4487.

Example 329: Synthesis of XF078-157
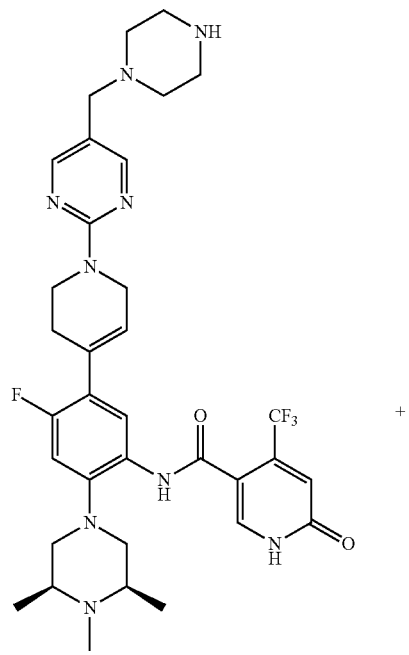
Intermediate 45
+
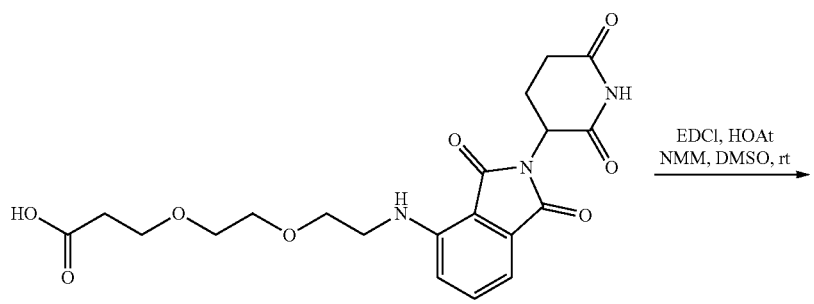
PML-21
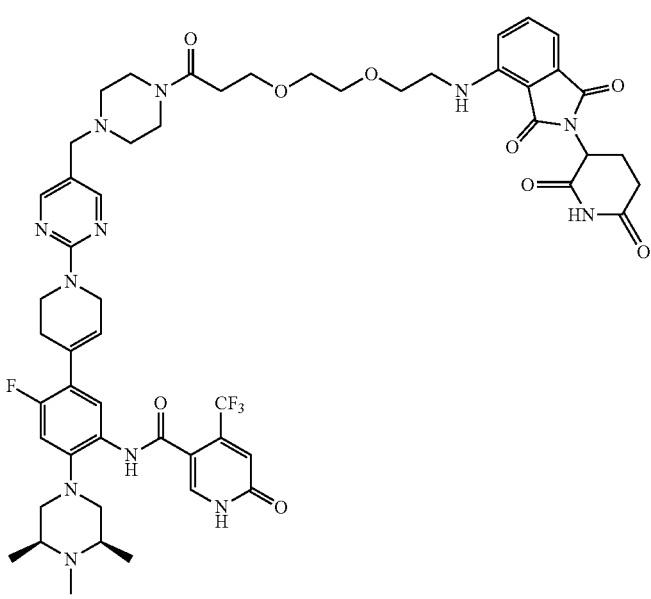
XF078-157

XF078-157 was synthesized following the standard procedures for preparing XF078-132 from intermediate 45 (13.6 mg, 0.02 mmol), PML-21 (8.7 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-157 was obtained as yellow solid in TFA salt form (15.9 mg, yield 71%). $^1$H NMR (800 MHz, CD$_3$OD) δ 8.43 (s, 2H), 8.00 (d, J=8.5 Hz, 1H), 7.82 (d, J=8.0 Hz, 1H), 7.56 (t, J=7.8 Hz, 1H), 7.17-7.04 (m, 3H), 6.94 (s, 1H), 6.13 (d, J=3.8 Hz, 1H), 5.06 (dd, J=12.8, 5.6 Hz, 1H), 4.48-4.38 (m, 2H), 4.22 (s, 2H), 4.10 (t, J=5.7 Hz, 2H), 3.82-3.45 (m, 21H), 3.03-2.54 (m, 12H), 2.19-2.05 (m, 2H), 1.45 (d, J=6.5 Hz, 6H). HRMS (m/z) for C$_{54}$H$_{63}$F$_4$N$_2$O$_9$$^+$ [M+H]$^+$: calculated 1099.4772. found 1099.4745.

Example 330: Synthesis of XF078-158

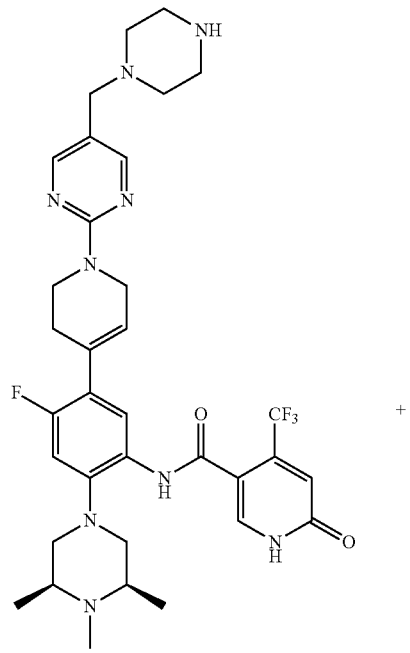

Intermediate 45

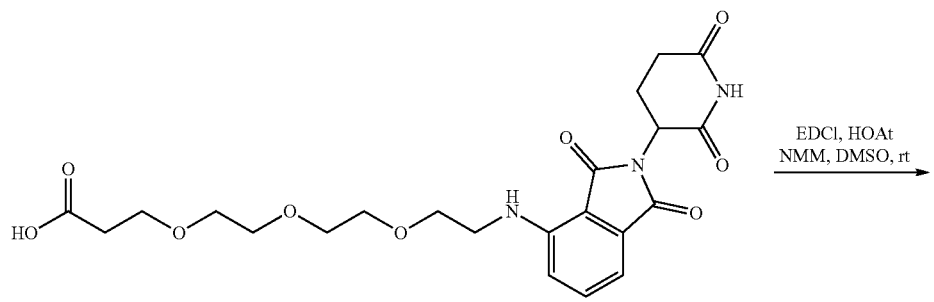

PML-22

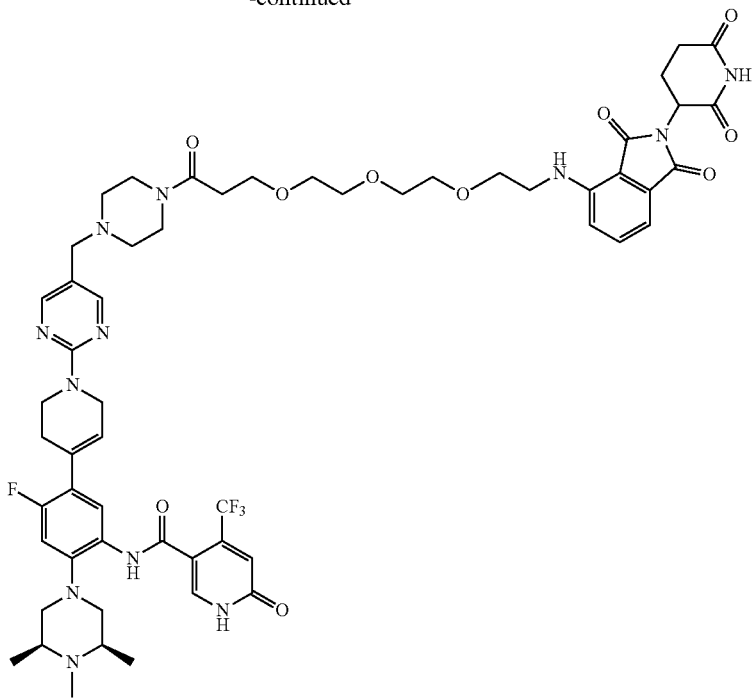

XF078-158

XF078-158 was synthesized following the standard procedures for preparing XF078-132 from intermediate 45 (13.6 mg, 0.02 mmol), PML-22 (9.5 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-158 was obtained as yellow solid in TFA salt form (17.7 mg, yield 77%). $^1$H NMR (800 MHz, CD$_3$OD) δ 8.43 (s, 2H), 8.01 (s, 1H), 7.83 (d, J=7.9 Hz, 1H), 7.52 (t, J=7.8 Hz, 1H), 7.16-6.81 (m, 4H), 6.14 (d, J=3.9 Hz, 1H), 5.08 (dt, J=12.5, 6.2 Hz, 1H), 4.39 (s, 2H), 4.28-4.17 (m, 2H), 4.15-4.02 (m, 2H), 3.84-3.39 (m, 26H), 3.03-2.50 (m, 12H), 2.25-2.06 (m, 1H), 1.45 (d, J=6.5 Hz, 6H). HRMS (m/z) for C$_{56}$H$_{67}$F$_4$N$_2$O$_{10}$$^+$ [M+H]$^+$: calculated 1043.5034. found 1043.5045.

Example 331: Synthesis of XF078-159

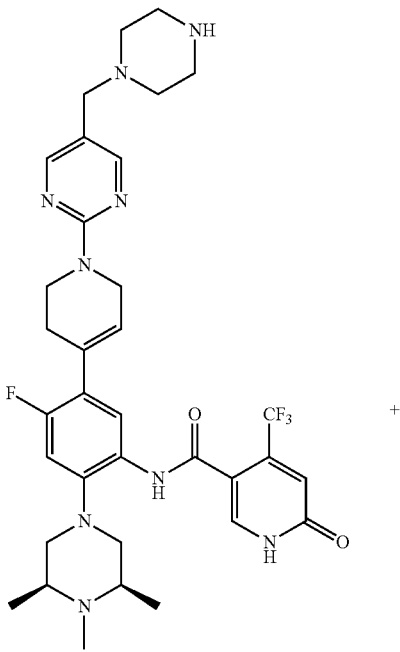

Intermediate 45

+

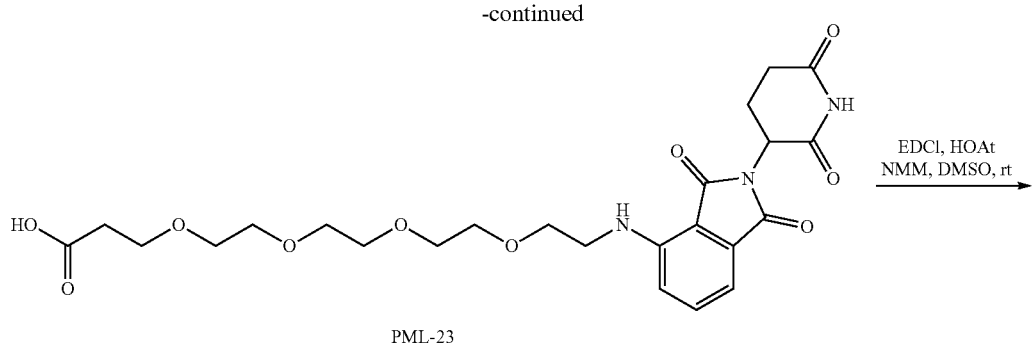

PML-23

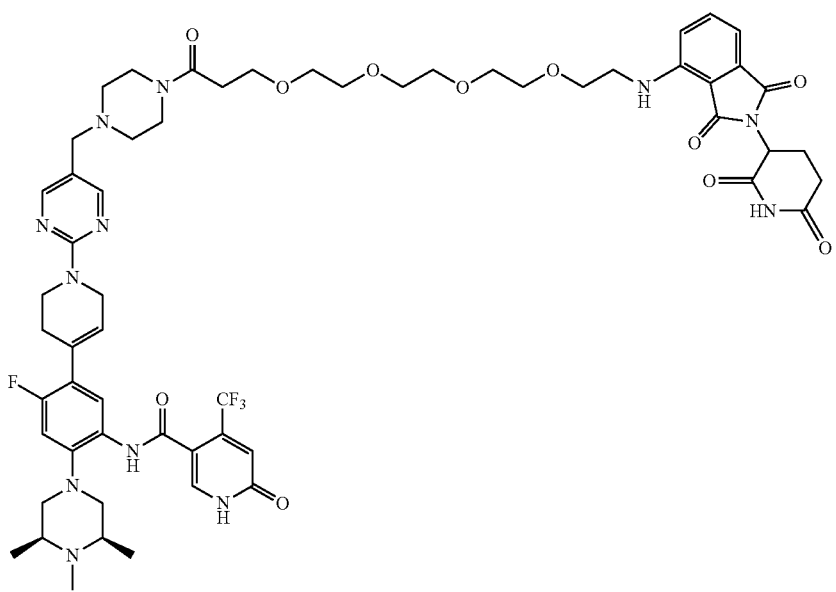

XF078-159

XF078-159 was synthesized following the standard procedures for preparing XF078-132 from intermediate 45 (13.6 mg, 0.02 mmol), PML-23 (10.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-159 was obtained as yellow solid in TFA salt form (18.8 mg, yield 79%). $^1$H NMR (800 MHz, CD$_3$OD) δ 8.45 (s, 2H), 8.01 (d, J=9.0 Hz, 1H), 7.83 (d, J=7.9 Hz, 1H), 7.56-7.44 (m, 1H), 7.12-6.88 (m, 4H), 6.14 (d, J=3.7 Hz, 1H), 5.08 (dd, J=12.8, 5.6 Hz, 1H), 4.39 (s, 2H), 4.35-4.17 (m, 2H), 4.13-4.00 (m, 2H), 3.88-3.40 (m, 30H), 3.03-2.56 (m, 12H), 2.20-2.05 (m, 1H), 1.45 (d, J=6.5 Hz, 6H). HRMS (m/z) for $C_{58}H_{71}F_4N_{12}O_{11}^+$ [M+H]$^+$: calculated 1087.5296. found 1087.5315.

Example 332: Synthesis of XF078-160
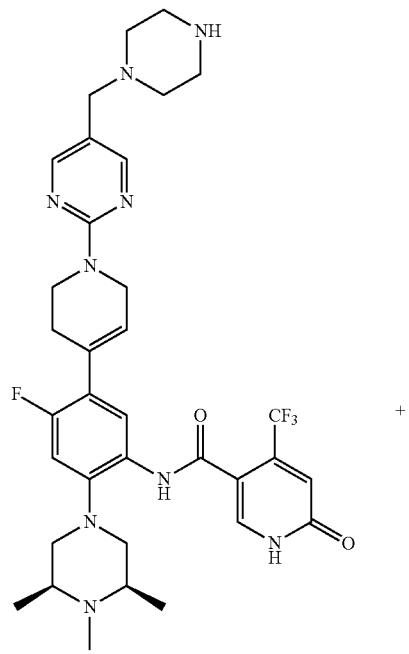
Intermediate 45
+
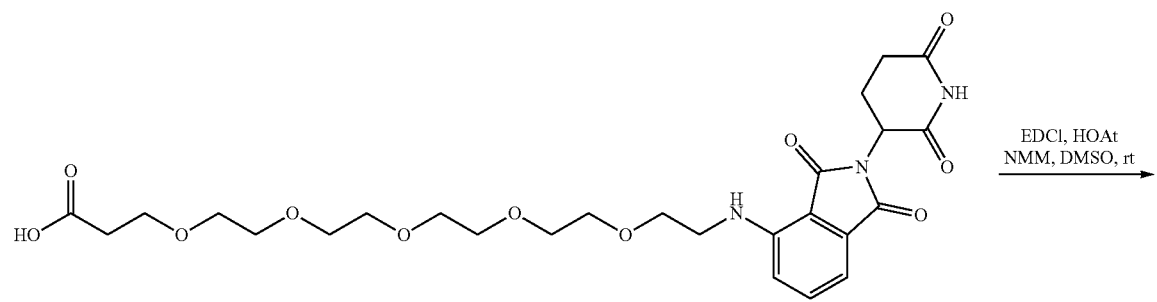
PML-24

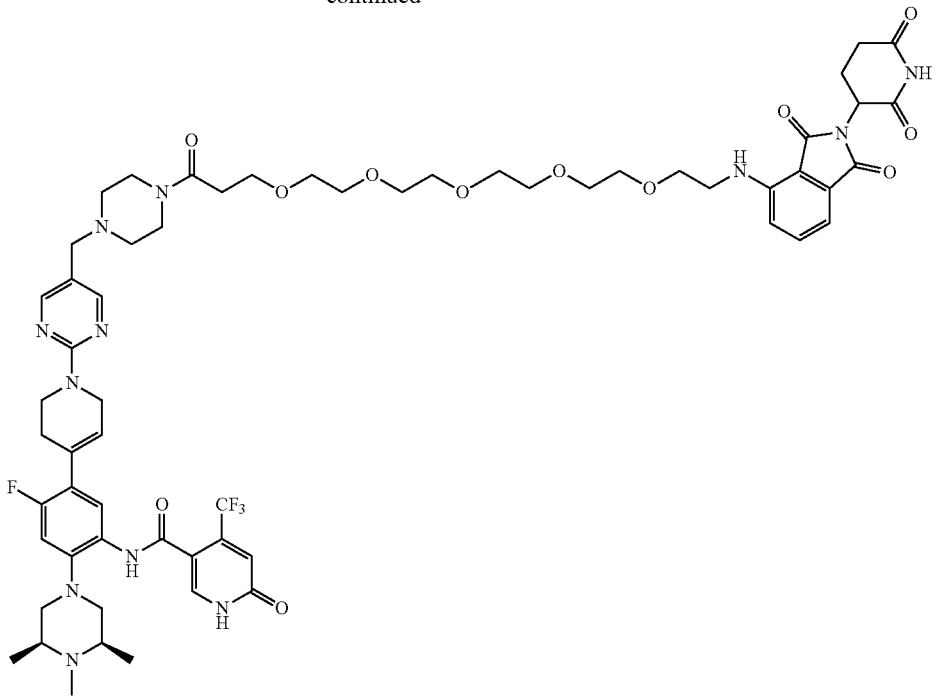

XF078-160

XF078-160 was synthesized following the standard procedures for preparing XF078-132 from intermediate 45 (13.6 mg, 0.02 mmol), PML-24 (11.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv) in DMSO (1 mL). XF078-160 was obtained as yellow solid in TFA salt form (19.5 mg, yield 79%). $^1$H NMR (800 MHz, CD$_3$OD) δ 8.48 (s, 2H), 8.01 (s, 1H), 7.89-7.73 (m, 1H), 7.54 (d, J=7.7 Hz, 1H), 7.18-7.01 (m, 3H), 7.00-6.89 (m, 1H), 6.22-5.99 (m, 1H), 5.07 (dd, J=12.8, 5.6 Hz, 1H), 4.43 (s, 2H), 4.37-4.20 (m, 2H), 4.20-3.98 (m, 2H), 3.87-3.39 (m, 34H), 3.03-2.50 (m, 12H), 2.17-2.09 (m, 1H), 1.53-1.43 (m, 6H). HRMS (m/z) for C$_{60}$H$_{75}$F$_4$N$_{12}$O$_{12}$$^+$ [M+H]$^+$: calculated 1231.5558. found 1231.5577.

Example 333: Synthesis of Intermediate 46

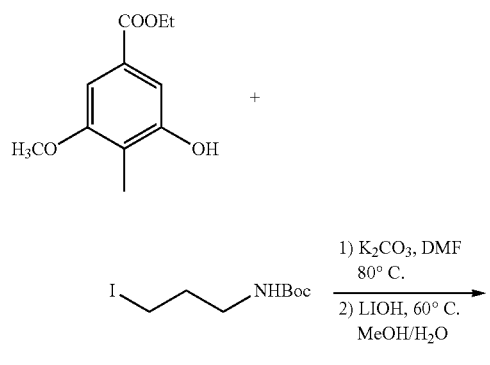

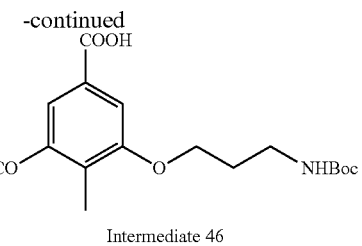

Intermediate 46

To a solution of ethyl 3-hydroxy-5-methoxy-4-methylbenzoate (805 mg, 3.83 mmol) in 10 mL of DMF were added potassium carbonate (1600 mg, 11.5 mmol, 3 equiv). The reaction was heated to 80° C. for 1 h. tert-butyl (3-iodopropyl)carbamate (1.64 g, 5.75 mmol, 1.75 equiv) was added slowly. The reaction stirred at 80° C. overnight. Water was added and the reaction mixture was extracted with EtOAc (3×20 mL). Combined organic layers were dried over Na$_2$SO$_4$, filtered and the solvent was removed and purified by ISCO (Hexane/EtOAc=4:1) to afford product as white solid (1.09 g, yield 78%). This product was dissolved in Methanol (30 mL) and H$_2$O (10 mL). LiOH (208 mg, 8.66 mmol, 3 equiv) was added. The resulting mixture was stirring at 80° C. overnight. Then, it was concentrated and purified by reverse phase ISCO (10%-100% methanol/0.1% TFA in H$_2$O) to afford Intermediate 46 (XF061-30) as white solid (923 mg, yield 94%). $^1$H NMR (600 MHz, DMSO-d$_6$) δ 7.18 (d, J=8.6 Hz, 2H), 6.89 (t, J=5.7 Hz, 1H), 3.93 (t, J=6.2 Hz, 2H), 3.74 (s, 3H), 3.08 (q, J=6.6 Hz, 2H), 1.97 (s, 3H), 1.82 (p, J=6.6 Hz, 2H), 1.34 (s, 9H).

Example 334: Synthesis of Intermediate 48

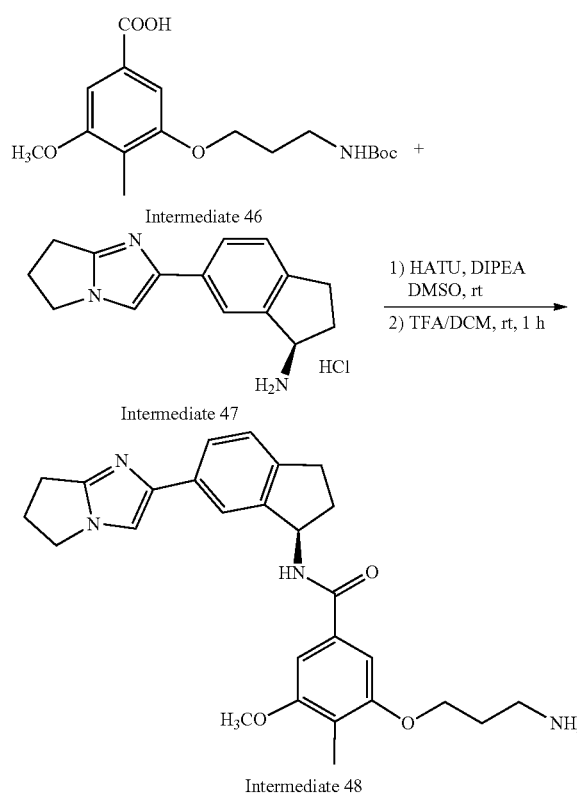

Intermediate 48

To the solution of intermediate 46 (571 mg, 1.68 mmol) in DMSO (5 mL) were added intermediate 47 (403 mg, 1.68 mmol, 1.0 equiv), HATU (1-[Bis(dimethylamino)methylene]-1H-1,2,3-triazolo[4,5-b]pyridinium 3-oxid hexafluorophosphate) (1.28 g, 3.76 mmol, 2 equiv), and DIPEA (N-Methylmorpholine) (650 mg, 5.04 mmol, 3.0 equiv). After being stirring for 1 h at room temperature, the resulting mixture was purified by reverse phase ISCO (10%-100% methanol/0.1% TFA in $H_2O$) to afford the crude product. This product was dissolved in DCM (10 mL) and TFA (10 mL). After being stirring for 1 h at room temperature, the resulting mixture was purified by reverse phase ISCO (10%-100% methanol/0.1% TFA in $H_2O$) to afford the Intermediate 42 (XF061-32) as white solid in TFA salt form (520 mg, yield 67%). $^1$H NMR (600 MHz, $CD_3OD$) δ 7.72 (s, 1H), 7.63-7.49 (m, 2H), 7.38 (d, J=7.9 Hz, 1H), 7.19 (d, J=8.0 Hz, 2H), 5.68 (t, J=7.8 Hz, 1H), 4.27 (t, J=7.3 Hz, 2H), 4.15 (t, J=5.8 Hz, 2H), 3.84 (s, 3H), 3.19 (q, J=7.5 Hz, 5H), 3.11 (ddd, J=16.4, 8.9, 3.4 Hz, 1H), 2.93 (dt, J=16.4, 8.4 Hz, 1H), 2.78 (p, J=7.5 Hz, 2H), 2.60 (dtd, J=11.8, 8.0, 3.4 Hz, 1H), 2.26-1.94 (m, 5H). HRMS (m/z) for $C_{27}H_{33}N_4O_3^+$ [M+H]$^+$: calculated 461.2547. found 461.2513.

Example 335: Synthesis of XF061-33

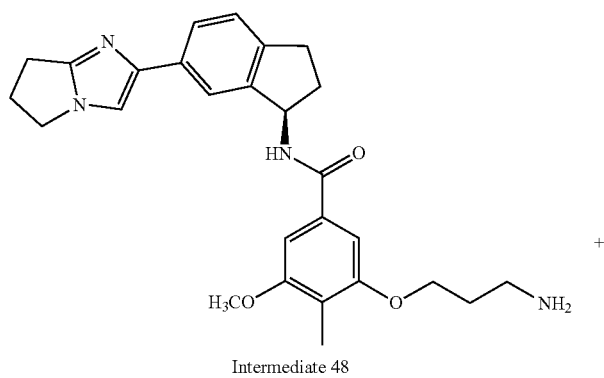

Intermediate 48

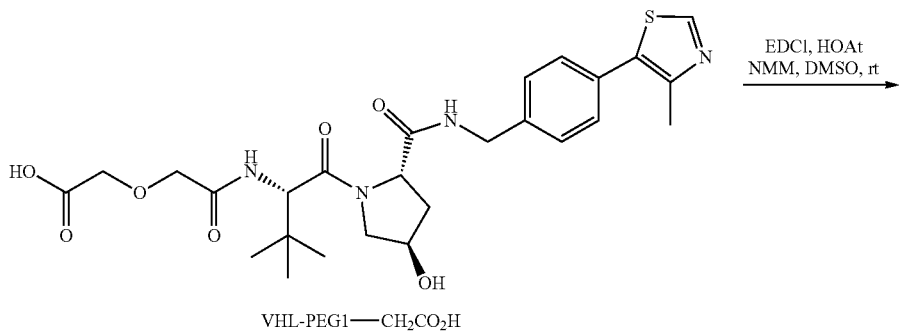

VHL-PEG1—$CH_2CO_2H$

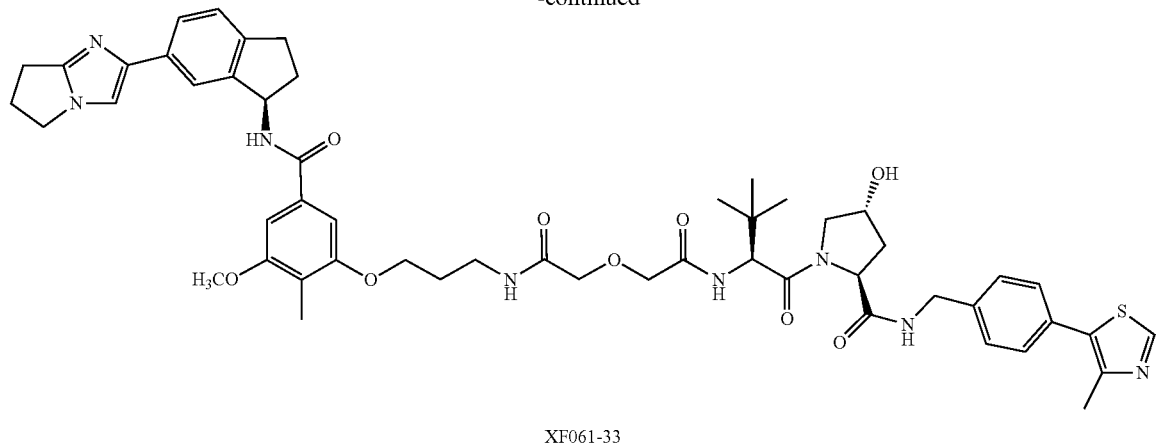

XF061-33

To the solution of intermediate 48 (13.8 mg, 0.024 mmol) in DMSO (1 mL) were added VHL-PEG1-CH$_2$COOH (13.1 mg, 0.024 mmol, 1.0 equiv), EDCI (1-ethyl-3-(3-dimethyl-aminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-33 as white solid in TFA salt form (19.7 mg, yield 83%). $^1$H NMR (600 MHz, CD$_3$OD) δ 8.94 (s, 1H), 7.75 (s, 1H), 7.58 (d, J=1.8 Hz, 1H), 7.54 (dd, J=7.9, 1.8 Hz, 1H), 7.48-7.44 (m, 2H), 7.43-7.38 (m, 3H), 7.18-7.13 (m, 2H), 5.71 (t, J=7.9 Hz, 1H), 4.68 (s, 1H), 4.60-4.54 (m, 2H), 4.51-4.48 (m, 1H), 4.35-4.30 (m, 1H), 4.29-4.25 (m, 2H), 4.10 (d, J=4.5 Hz, 2H), 4.07-4.03 (m, 4H), 3.89-3.82 (m, 4H), 3.82-3.77 (m, 1H), 3.47 (t, J=6.9 Hz, 2H), 3.22-3.18 (m, 2H), 3.16-3.08 (m, 1H), 3.00-2.92 (m, 1H), 2.81-2.75 (m, 2H), 2.66-2.58 (m, 1H), 2.40 (s, 3H), 2.25-2.20 (m, 1H), 2.17-1.99 (m, 7H), 1.02 (s, 9H). HRMS (m/z) for C$_{53}$H$_{65}$N$_8$O$_9$S$^+$ [M+H]$^+$: calculated 989.4590. found 989.4603.

Example 336: Synthesis of XF061-34

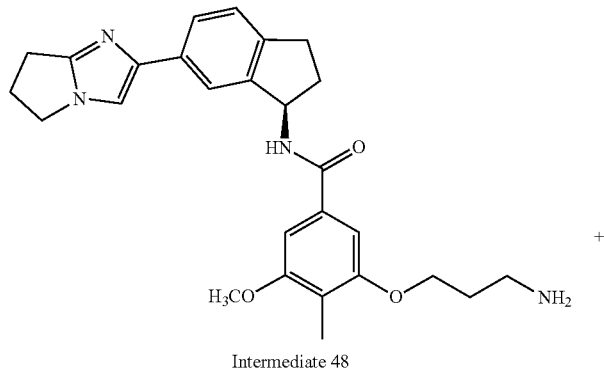

Intermediate 48

+

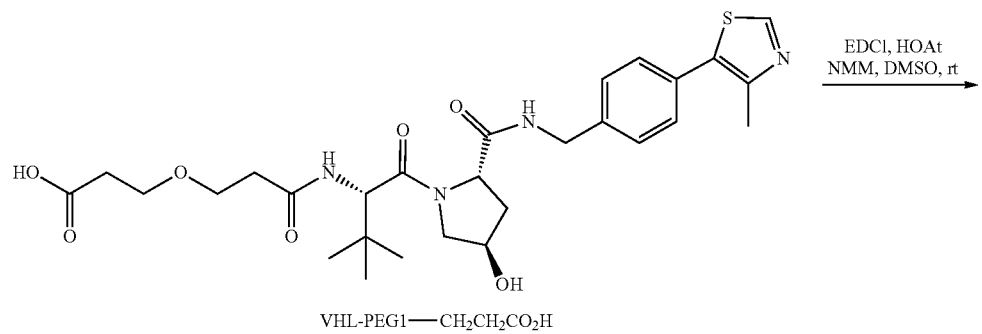

VHL-PEG1—CH$_2$CH$_2$CO$_2$H

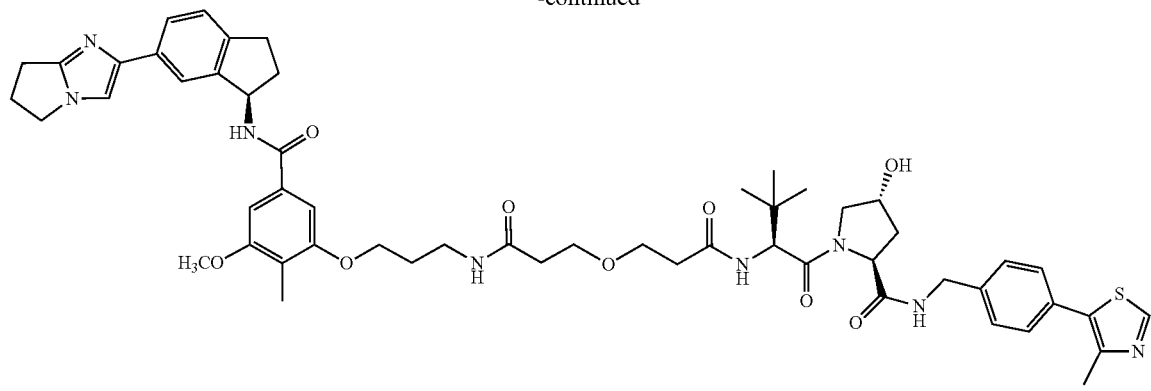

XF061-34

XF061-34 was synthesized following the standard procedures for preparing XF061-33 from intermediate 48 (13.8 mg, 0.024 mmol), VHL-PEG1-CH$_2$CH$_2$COOH (13.8 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-34 as white solid in TFA salt form (19.4 mg, yield 79%). $^1$H NMR (600 MHz, CD$_3$OD) δ 8.95 (s, 1H), 7.76 (s, 1H), 7.59 (d, J=1.8 Hz, 1H), 7.56-7.52 (m, 1H), 7.45-7.38 (m, 5H), 7.17-7.14 (m, 2H), 5.73 (t, J=7.9 Hz, 1H), 4.61 (s, 1H), 4.57-4.52 (m, 1H), 4.51 (d, J=15.4 Hz, 1H), 4.48-4.45 (m, 1H), 4.33 (d, J=15.6 Hz, 1H), 4.27 (t, J=7.3 Hz, 2H), 4.03 (t, J=6.2 Hz, 2H), 3.86-3.84 (m, 4H), 3.75 (dd, J=11.0, 3.8 Hz, 1H), 3.70-3.63 (m, 3H), 3.63-3.58 (m, 1H), 3.42-3.34 (m, 2H), 3.23-3.17 (m, 2H), 3.16-3.10 (m, 1H), 3.00-2.94 (m, 1H), 2.81-2.75 (m, 2H), 2.66-2.59 (m, 1H), 2.50-2.37 (m, 7H), 2.24-2.18 (m, 1H), 2.17-2.01 (m, 5H), 2.02-1.95 (m, 2H), 1.00 (s, 9H). HRMS (m/z) for C$_{55}$H$_{69}$N$_8$O$_9$S$^+$ [M+H]$^+$: calculated 1017.4903. found 1017.4886.

Example 337: Synthesis of XF061-35

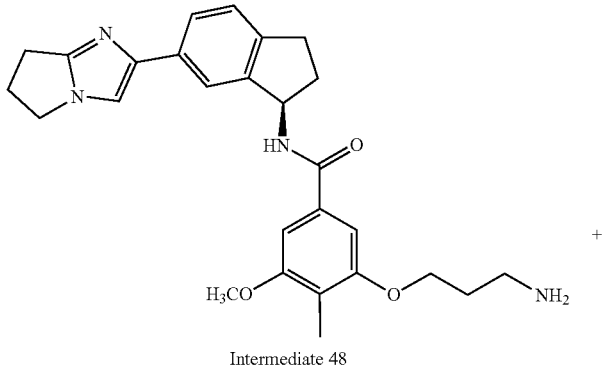

Intermediate 48

+

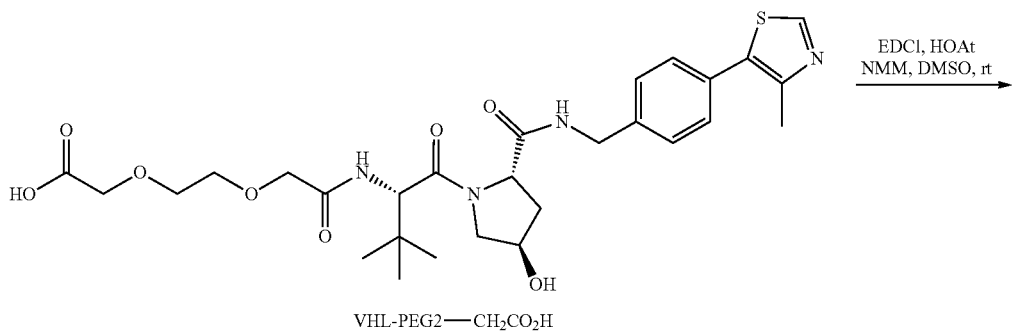

VHL-PEG2—CH$_2$CO$_2$H

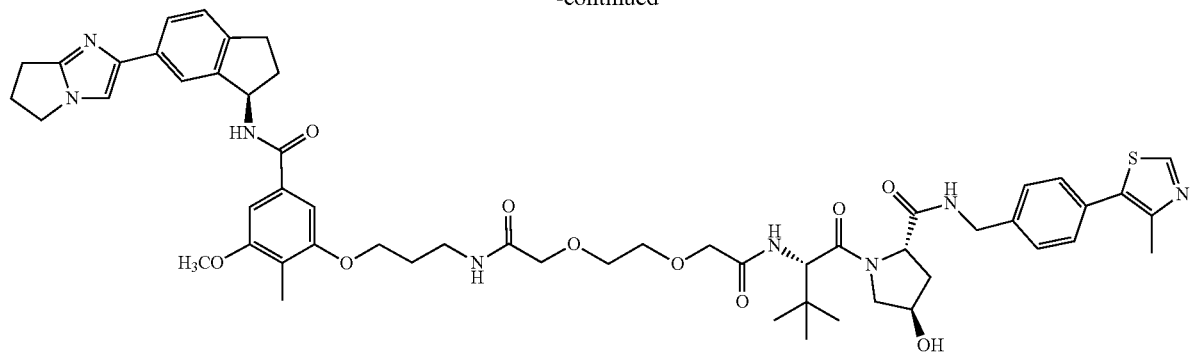

XF061-35

XF061-35 was synthesized following the standard procedures for preparing XF061-33 from intermediate 48 (13.8 mg, 0.024 mmol), VHL-PEG2-CH$_2$COOH (14.2 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-35 as white solid in TFA salt form (21.6 mg, yield 87%). $^1$H NMR (600 MHz, CD$_3$OD) δ 9.00 (s, 1H), 7.75 (s, 1H), 7.61-7.58 (m, 1H), 7.54 (dd, J=7.9, 1.8 Hz, 1H), 7.45-7.36 (m, 5H), 7.18-7.12 (m, 2H), 5.72 (t, J=7.9 Hz, 1H), 4.68 (s, 1H), 4.60-4.54 (m, 1H), 4.48-4.43 (m, 2H), 4.35 (d, J=15.5 Hz, 1H), 4.27 (t, J=7.3 Hz, 2H), 4.07-3.90 (m, 7H), 3.85 (s, 3H), 3.78-3.65 (m, 5H), 3.47-3.42 (m, 2H), 3.23-3.17 (m, 2H), 3.16-3.09 (m, 1H), 3.00-2.94 (m, 1H), 2.82-2.74 (m, 2H), 2.67-2.57 (m, 1H), 2.40 (s, 3H), 2.26-2.20 (m, 1H), 2.18-1.96 (m, 7H), 1.00 (s, 9H). HRMS (m/z) for C$_{55}$H$_{69}$N$_8$O$_{10}$S$^+$ [M+H]$^+$: calculated 1033.4852. found 1033.4875.

Example 338: Synthesis of XF061-36

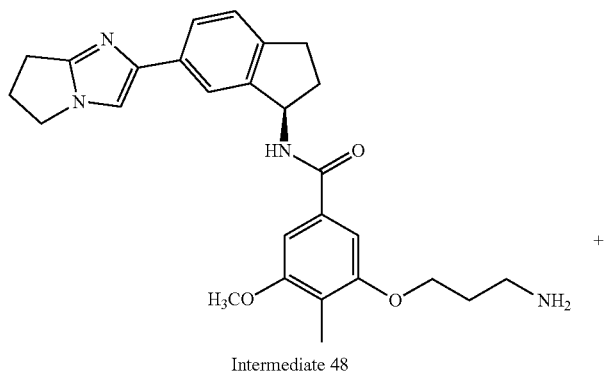

Intermediate 48

+

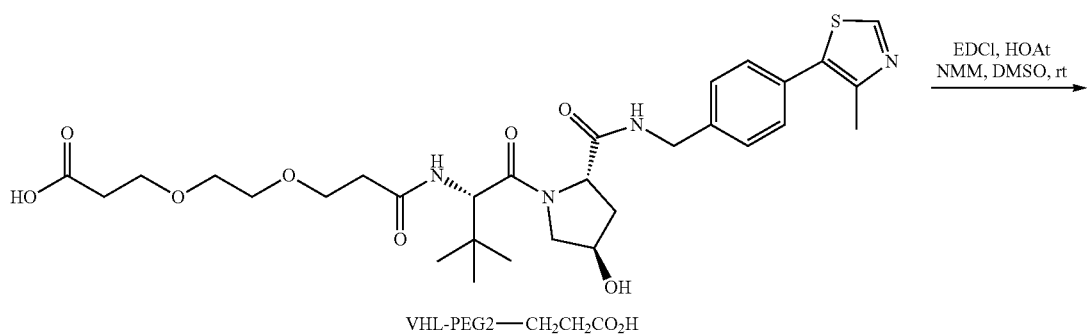

VHL-PEG2—CH$_2$CH$_2$CO$_2$H

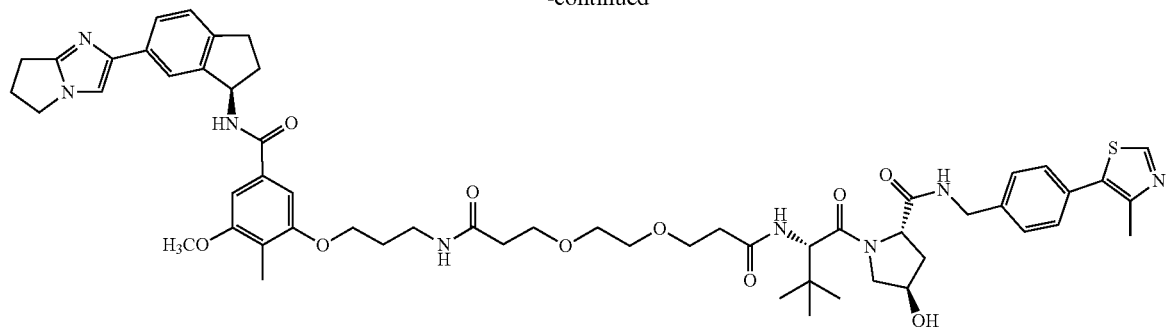

XF061-36

XF061-36 was synthesized following the standard procedures for preparing XF061-33 from intermediate 48 (13.8 mg, 0.024 mmol), VHL-PEG2-CH$_2$CH$_2$COOH (14.8 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-36 as white solid in TFA salt form (22.8 mg, yield 90%). $^1$H NMR (600 MHz, CD$_3$OD) δ 8.97 (s, 1H), 7.76 (s, 1H), 7.59 (d, J=1.8 Hz, 1H), 7.54 (dd, J=7.9, 1.7 Hz, 1H), 7.45 (d, J=8.1 Hz, 2H), 7.42-7.38 (m, 3H), 7.20-7.11 (m, 2H), 5.73 (t, J=7.9 Hz, 1H), 4.62 (s, 1H), 4.58-4.54 (m, 1H), 4.52 (d, J=15.5 Hz, 1H), 4.49-4.45 (m, 1H), 4.34 (d, J=15.5 Hz, 1H), 4.27 (t, J=7.3 Hz, 2H), 4.07-4.02 (m, 2H), 3.86-3.83 (m, 4H), 3.76 (dd, J=11.0, 3.8 Hz, 1H), 3.68-3.58 (m, 4H), 3.58-3.48 (m, 4H), 3.42-3.35 (m, 2H), 3.22-3.18 (m, 2H), 3.17-3.09 (m, 1H), 3.01-2.92 (m, 1H), 2.81-2.75 (m, 2H), 2.66-2.59 (m, 1H), 2.53-2.45 (m, 4H), 2.45-2.35 (m, 3H), 2.24-2.18 (m, 1H), 2.18-2.12 (m, 1H), 2.11-2.02 (m, 4H), 2.01-1.96 (m, 2H), 1.01 (s, 9H). HRMS (m/z) for C$_{57}$H$_{73}$N$_8$O$_{10}$S$^+$ [M+H]$^+$: calculated 1061.5165. found 1061.5144.

Example 339: Synthesis of XF061-37

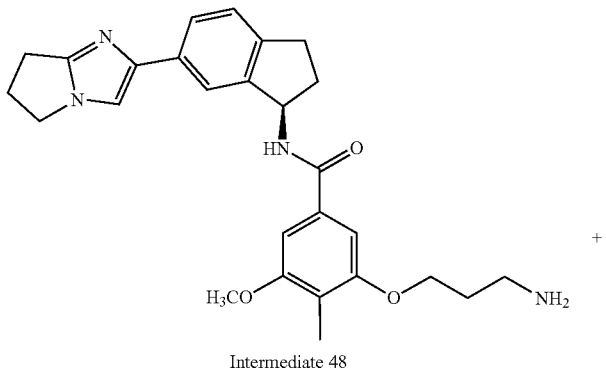

Intermediate 48

+

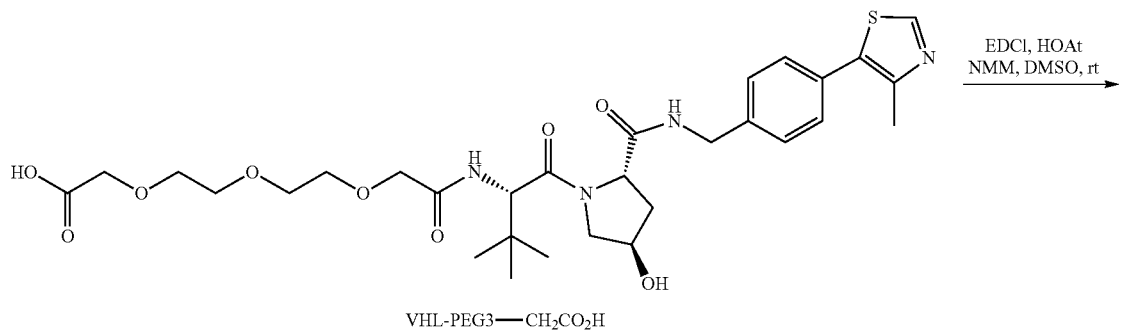

VHL-PEG3—CH$_2$CO$_2$H

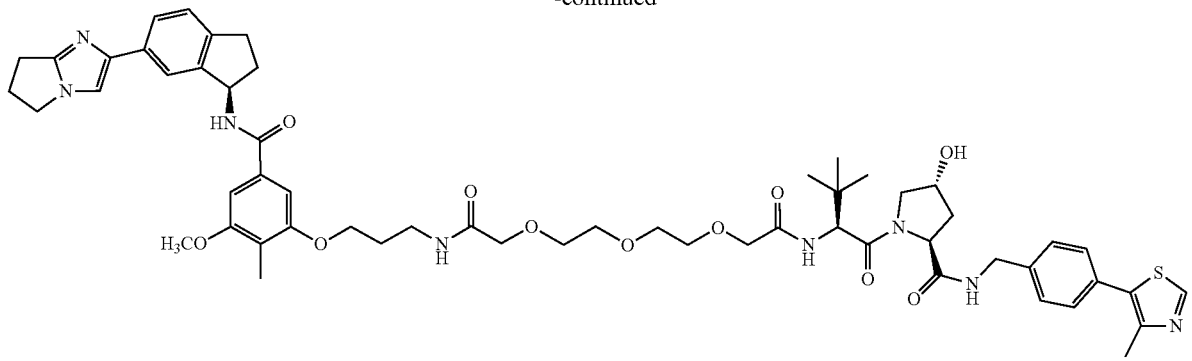

XF061-37

XF061-37 was synthesized following the standard procedures for preparing XF061-33 from intermediate 48 (13.8 mg, 0.024 mmol), VHL-PEG3-CH₂COOH (15.2 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H₂O) to afford XF061-37 as white solid in TFA salt form (24.1 mg, yield 93%). ¹H NMR (600 MHz, CD₃OD) δ 9.05 (s, 1H), 7.76 (s, 1H), 7.60-7.52 (m, 2H), 7.49-7.37 (m, 5H), 7.19-7.13 (m, 2H), 5.72 (t, J=7.9 Hz, 1H), 4.67 (s, 1H), 4.58-4.50 (m, 2H), 4.50-4.43 (m, 1H), 4.39-4.30 (m, 1H), 4.27 (t, J=7.3 Hz, 2H), 4.10-4.02 (m, 2H), 4.05-3.88 (m, 4H), 3.86-3.81 (m, 4H), 3.76 (dd, J=11.0, 3.8 Hz, 1H), 3.72-3.60 (m, 8H), 3.44 (t, J=6.9 Hz, 2H), 3.23-3.17 (m, 2H), 3.13 (ddd, J=16.5, 8.9, 3.3 Hz, 1H), 3.01-2.93 (m, 1H), 2.82-2.74 (m, 2H), 2.67-2.58 (m, 1H), 2.49 (s, 3H), 2.24-2.18 (m, 1H), 2.18-1.96 (m, 7H), 1.01 (s, 9H). HRMS (m/z) for $C_{57}H_{73}N_8O_{11}S^+$ [M+H]⁺: calculated 1077.5114. found 1077.5089.

Example 340: Synthesis of XF061-38

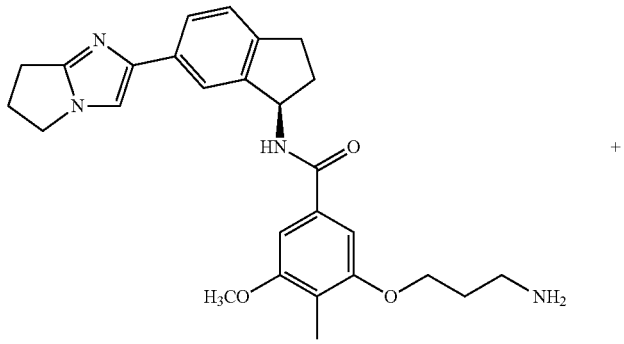

Intermediate 48

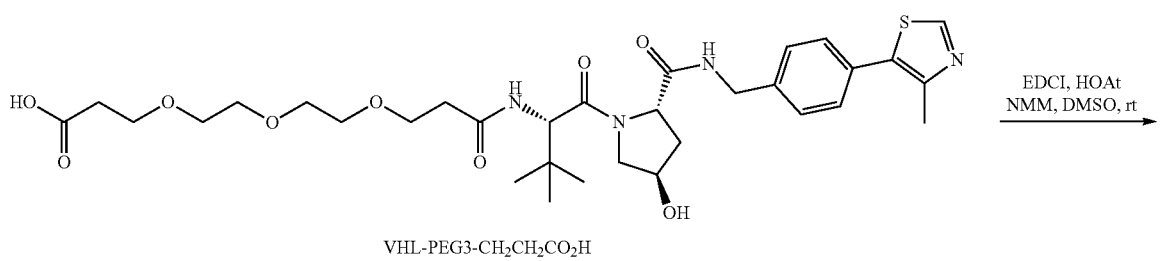

VHL-PEG3-CH₂CH₂CO₂H

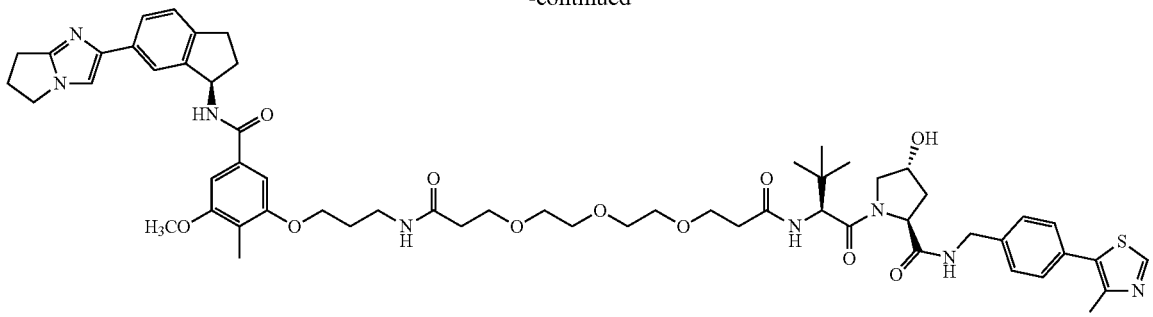

XF061-38

XF061-38 was synthesized following the standard procedures for preparing XF061-33 from intermediate 48 (13.8 mg, 0.024 mmol), VHL-PEG3-CH$_2$CH$_2$COOH (15.9 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-38 as white solid in TFA salt form (21.5 mg, yield 81%). $^1$H NMR (600 MHz, CD$_3$OD) δ 8.94 (s, 1H), 7.76 (s, 1H), 7.59-7.57 (m, 1H), 7.55 (dd, J=8.0, 1.8 Hz, 1H), 7.48-7.37 (m, 5H), 7.19-7.15 (m, 2H), 5.73 (t, J=7.9 Hz, 1H), 4.61 (s, 1H), 4.58-4.50 (m, 2H), 4.49-4.46 (m, 1H), 4.34 (d, J=15.5 Hz, 1H), 4.27 (t, J=7.3 Hz, 2H), 4.06 (t, J=6.2 Hz, 2H), 3.88-3.83 (m, 4H), 3.77 (dd, J=10.9, 3.9 Hz, 1H), 3.72-3.63 (m, 4H), 3.58-3.49 (m, 8H), 3.39 (t, J=6.8 Hz, 2H), 3.25-3.17 (m, 2H), 3.13 (ddd, J=16.4, 8.9, 3.4 Hz, 1H), 3.02-2.92 (m, 1H), 2.83-2.73 (m, 2H), 2.67-2.59 (m, 1H), 2.57-2.50 (m, 1H), 2.49-2.37 (m, 6H), 2.23-2.18 (m, 1H), 2.18-2.11 (m, 1H), 2.11-2.03 (m, 4H), 2.02-1.96 (m, 2H), 1.01 (s, 9H). HRMS (m/z) for C$_{59}$H$_{77}$N$_8$O$_{11}$S$^+$ [M+H]$^+$: calculated 1105.5427. found 1105.5456.

Example 341: Synthesis of XF061-39

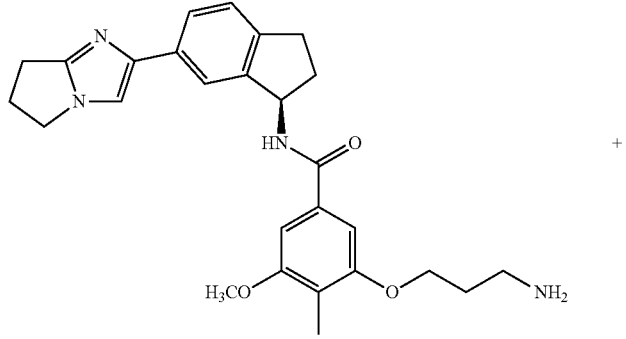

Intermediate 48

+

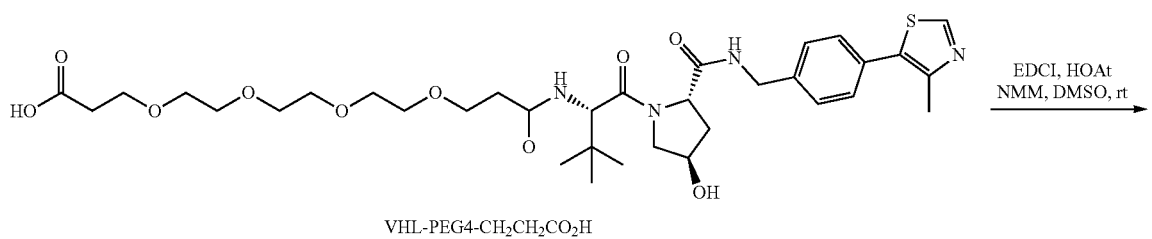

VHL-PEG4-CH$_2$CH$_2$CO$_2$H

EDCI, HOAt
NMM, DMSO, rt

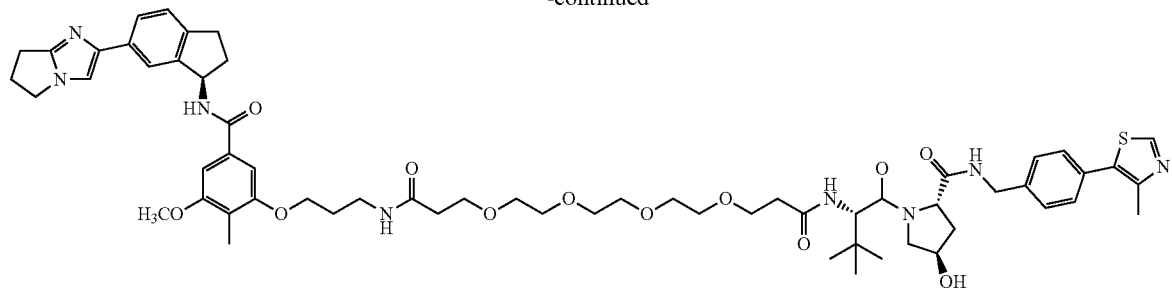

XF061-39

XF061-39 was synthesized following the standard procedures for preparing XF061-33 from intermediate 48 (13.8 mg, 0.024 mmol), VHL-PEG4-CH$_2$CH$_2$COOH (16.9 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-39 as white solid in TFA salt form (22 mg, yield 80%). $^1$H NMR (600 MHz, CD$_3$OD) δ 9.02 (s, 1H), 7.77 (s, 1H), 7.59 (d, J=1.8 Hz, 1H), 7.56-7.53 (m, 1H), 7.47 (d, J=8.1 Hz, 2H), 7.43-7.39 (m, 3H), 7.19-7.14 (m, 2H), 5.73 (t, J=8.0 Hz, 1H), 4.62 (s, 1H), 4.58-4.51 (m, 2H), 4.49-4.46 (m, 1H), 4.35 (d, J=15.5 Hz, 1H), 4.28 (t, J=7.3 Hz, 2H), 4.06 (t, J=6.3 Hz, 2H), 3.89-3.82 (m, 4H), 3.77 (dd, J=11.0, 3.9 Hz, 1H), 3.71-3.61 (m, 4H), 3.61-3.46 (m, 12H), 3.39 (t, J=6.8 Hz, 2H), 3.23-3.17 (m, 2H), 3.13 (ddd, J=16.4, 8.9, 3.4 Hz, 1H), 2.97 (dt, J=16.5, 8.4 Hz, 1H), 2.82-2.75 (m, 2H), 2.67-2.59 (m, 1H), 2.55-2.50 (m, 1H), 2.50-2.43 (m, 4H), 2.40 (t, J=6.1 Hz, 2H), 2.24-2.19 (m, 1H), 2.17-2.04 (m, 5H), 2.03-1.96 (m, 2H), 1.02 (s, 9H). HRMS (m/z) for C$_{61}$H$_{81}$N$_8$O$_{12}$S$^+$ [M+H]$^+$: calculated 1149.5689. found 1149.5702.

Example 342: Synthesis of XF061-40

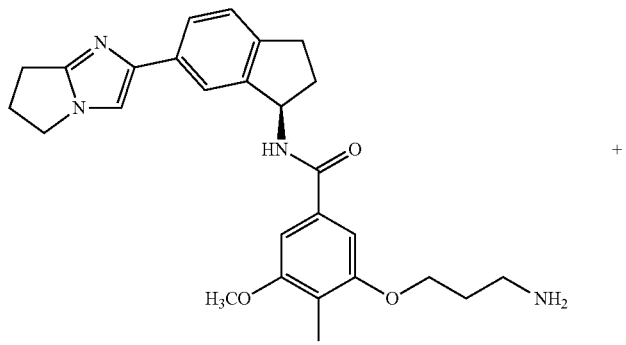

Intermediate 48

+

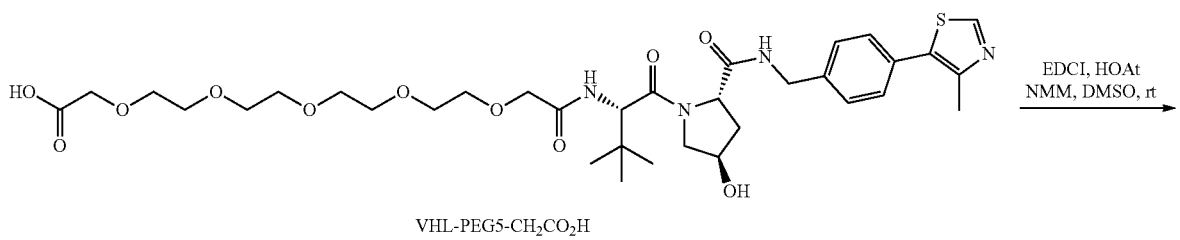

VHL-PEG5-CH$_2$CO$_2$H

EDCI, HOAt
NMM, DMSO, rt

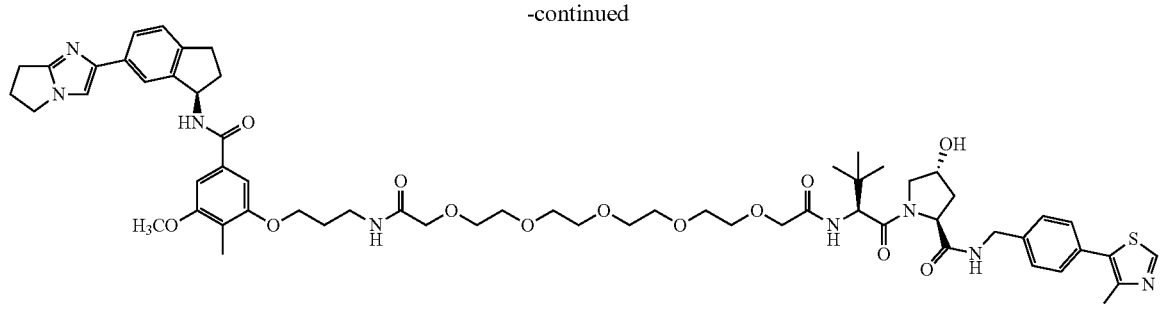

XF061-40

XF061-40 was synthesized following the standard procedures for preparing XF061-33 from intermediate 48 (13.8 mg, 0.024 mmol), VHL-PEG5-CH$_2$COOH (17.3 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-40 as white solid in TFA salt form (27.8 mg, yield 99%). $^1$H NMR (600 MHz, CD$_3$OD) δ 9.02 (s, 1H), 7.76 (s, 1H), 7.59-7.57 (m, 1H), 7.55 (dd, J=7.9, 1.8 Hz, 1H), 7.48-7.38 (m, 5H), 7.19-7.12 (m, 2H), 5.72 (t, J=8.0 Hz, 1H), 4.67 (s, 1H), 4.59-4.50 (m, 2H), 4.50-4.46 (m, 1H), 4.35 (d, J=15.5 Hz, 1H), 4.27 (t, J=7.3 Hz, 2H), 4.07 (t, J=6.1 Hz, 2H), 4.02-3.99 (m, 2H), 3.96-3.91 (m, 2H), 3.87-3.83 (m, 4H), 3.78 (dd, J=11.0, 3.8 Hz, 1H), 3.70-3.54 (m, 16H), 3.45 (t, J=6.8 Hz, 2H), 3.24-3.18 (m, 2H), 3.17-3.08 (m, 1H), 3.01-2.92 (m, 1H), 2.83-2.74 (m, 2H), 2.66-2.59 (m, 1H), 2.48 (s, 3H), 2.25-2.19 (m, 1H), 2.17-1.98 (m, 7H), 1.02 (s, 9H). HRMS (m/z) for C$_{61}$H$_{81}$N$_8$O$_{13}$S$^+$ [M+H]$^+$: calculated 1165.5638. found 1165.5612.

Example 343: Synthesis of XF061-41

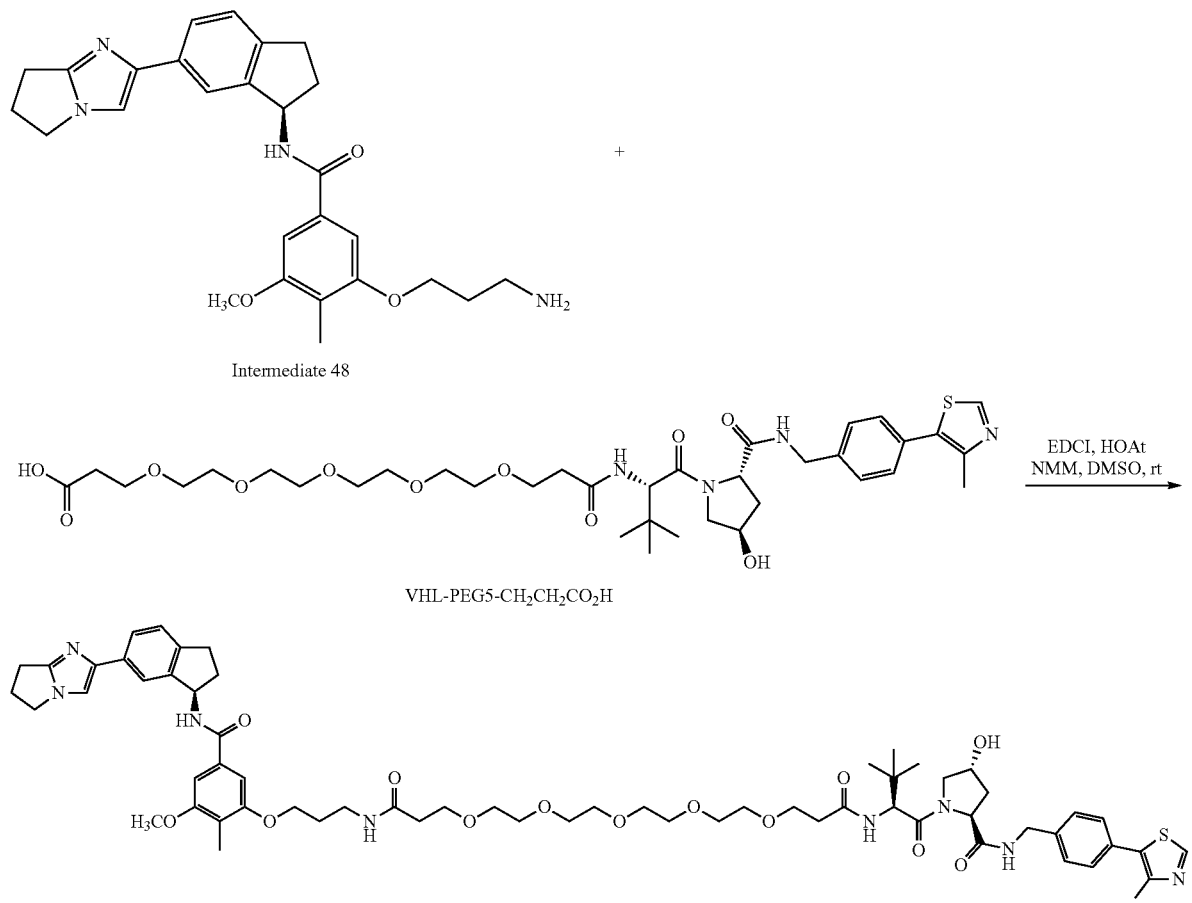

XF061-41 was synthesized following the standard procedures for preparing XF061-33 from intermediate 48 (13.8 mg, 0.024 mmol), VHL-PEG5-CH$_2$CH$_2$COOH (18 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-41 as white solid in TFA salt form (27.2 mg, yield 95%). $^1$H NMR (600 MHz, CD$_3$OD) δ 8.97 (s, 1H), 7.77 (s, 1H), 7.59 (d, J=1.9 Hz, 1H), 7.55 (dd, J=7.9, 1.8 Hz, 1H), 7.48-7.38 (m, 5H), 7.18-7.13 (m, 2H), 5.73 (t, J=8.0 Hz, 1H), 4.62 (s, 1H), 4.58-4.50 (m, 2H), 4.50-4.46 (m, 1H), 4.35 (d, J=15.5 Hz, 1H), 4.28 (t, J=7.3 Hz, 2H), 4.06 (t, J=6.3 Hz, 2H), 3.89-3.83 (m, 4H), 3.78 (dd, J=10.9, 3.9 Hz, 1H), 3.72-3.61 (m, 4H), 3.59-3.48 (m, 16H), 3.41-3.37 (m, 2H), 3.23-3.18 (m, 2H), 3.13 (ddd, J=16.4, 8.9, 3.4 Hz, 1H), 3.02-2.94 (m, 1H), 2.83-2.75 (m, 2H), 2.68-2.60 (m, 1H), 2.56-2.51 (m, 1H), 2.48-2.36 (m, 6H), 2.24-2.18 (m, 1H), 2.18-2.04 (m, 5H), 2.02-1.96 (m, 2H), 1.02 (s, 9H). HRMS (m/z) for C$_{63}$H$_{85}$N$_8$O$_{13}$S$^+$ [M+H]$^+$: calculated 1193.5591. found 1193.5607.

Example 344: Synthesis of XF061-42

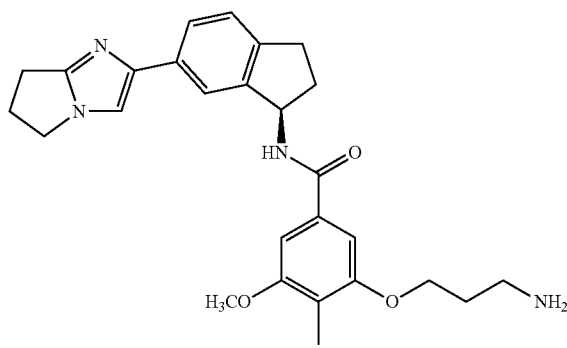

Intermediate 48

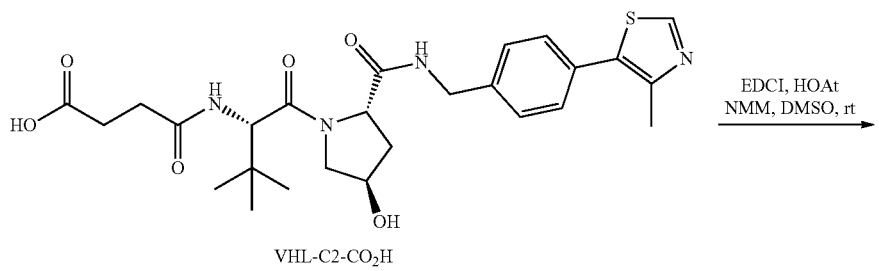

VHL-C2-CO$_2$H

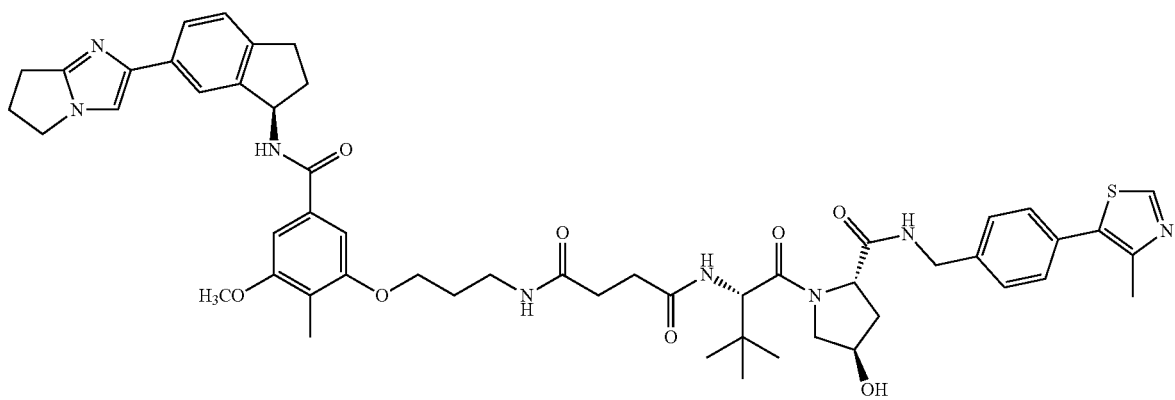

XF061-42

XF061-42 was synthesized following the standard procedures for preparing XF061-33 from intermediate 48 (13.8 mg, 0.024 mmol), VHL-C2-COOH (9.5 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-42 as white solid in TFA salt form (20.5 mg, yield 88%). $^1$H NMR (600 MHz, $CD_3OD$) δ 8.95 (s, 1H), 7.75 (s, 1H), 7.58 (d, J=1.9 Hz, 1H), 7.54 (dd, J=7.9, 1.8 Hz, 1H), 7.46 (d, J=8.2 Hz, 2H), 7.43-7.37 (m, 3H), 7.16 (s, 2H), 5.73 (t, J=7.9 Hz, 1H), 4.57-4.50 (m, 3H), 4.48-4.44 (m, 1H), 4.35 (d, J=15.4 Hz, 1H), 4.27 (t, J=7.3 Hz, 2H), 4.06 (t, J=6.1 Hz, 2H), 3.87-3.81 (m, 4H), 3.74 (dd, J=11.0, 3.9 Hz, 1H), 3.39-3.34 (m, 2H), 3.22-3.17 (m, 2H), 3.13 (ddd, J=16.5, 8.8, 3.4 Hz, 1H), 2.97 (dt, J=16.6, 8.5 Hz, 1H), 2.81-2.75 (m, 2H), 2.66-2.53 (m, 2H), 2.51-2.39 (m, 6H), 2.20 (ddt, J=13.2, 7.7, 2.0 Hz, 1H), 2.17-2.02 (m, 5H), 2.02-1.94 (m, 2H), 1.00 (s, 9H). HRMS (m/z) for $C_{53}H_{65}N_8O_8S^+$ $[M+H]^+$: calculated 973.4641, found 973.4665.

Example 345: Synthesis of XF061-43

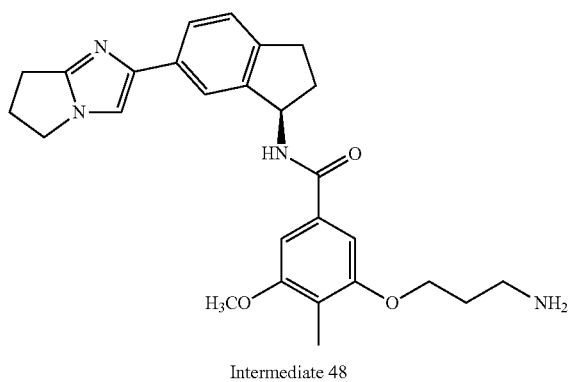

Intermediate 48

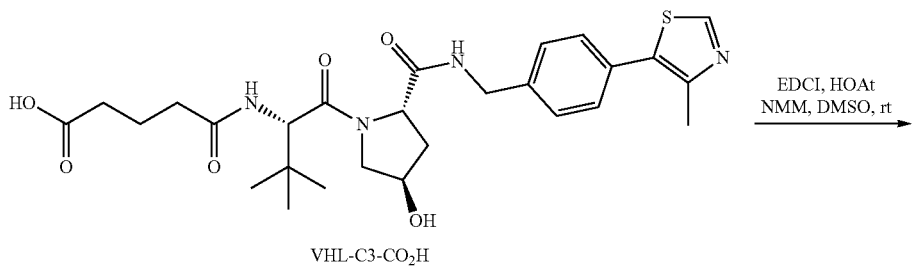

VHL-C3-CO$_2$H

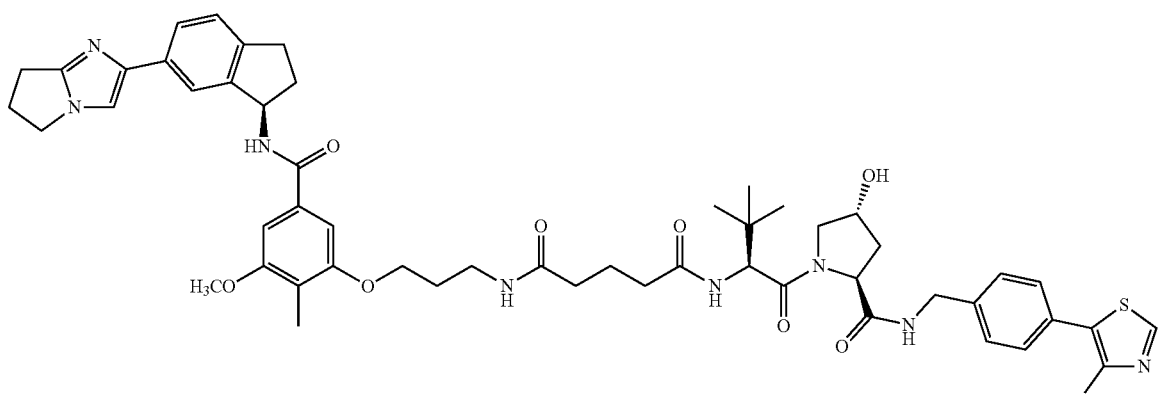

XF061-43

XF061-43 was synthesized following the standard procedures for preparing XF061-33 from intermediate 48 (13.8 mg, 0.024 mmol), VHL-C3-COOH (13.1 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-43 as white solid in TFA salt form (20.7 mg, yield 89%). $^1$H NMR (600 MHz, CD$_3$OD) δ 8.95 (s, 1H), 7.76 (d, J=1.7 Hz, 1H), 7.60-7.56 (m, 1H), 7.54 (dd, J=7.9, 1.8 Hz, 1H), 7.48-7.37 (m, 5H), 7.19-7.14 (m, 2H), 5.72 (t, J=8.0 Hz, 1H), 4.59-4.50 (m, 3H), 4.49-4.45 (m, 1H), 4.34 (d, J=15.5 Hz, 1H), 4.27 (t, J=7.3 Hz, 2H), 4.05 (t, J=6.1 Hz, 2H), 3.93-3.87 (m, 1H), 3.86-3.84 (m, 3H), 3.78 (dd, J=11.0, 3.9 Hz, 1H), 3.43-3.32 (m, 2H), 3.23-3.18 (m, 2H), 3.13 (ddd, J=16.4, 8.9, 3.4 Hz, 1H), 2.97 (dt, J=16.5, 8.3 Hz, 1H), 2.82-2.75 (m, 2H), 2.66-2.57 (m, 1H), 2.46 (s, 3H), 2.32-2.23 (m, 2H), 2.23-2.11 (m, 4H), 2.12-2.09 (m, 4H), 2.02-1.96 (m, 2H), 1.89-1.82 (m, 2H), 1.02 (s, 9H). HRMS (m/z) for C$_{54}$H$_{67}$N$_8$O$_8$S$^+$ [M+H]$^+$: calculated 987.4797. found 987.4768.

Example 346: Synthesis of XF061-44

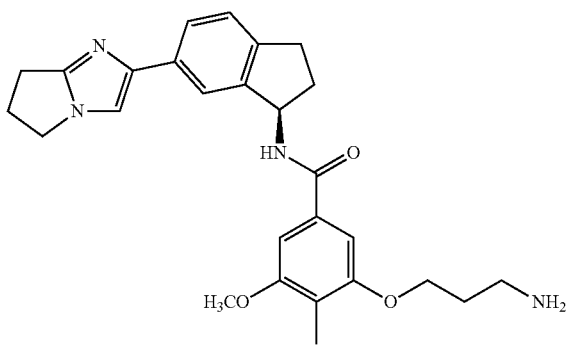

Intermediate 48

+

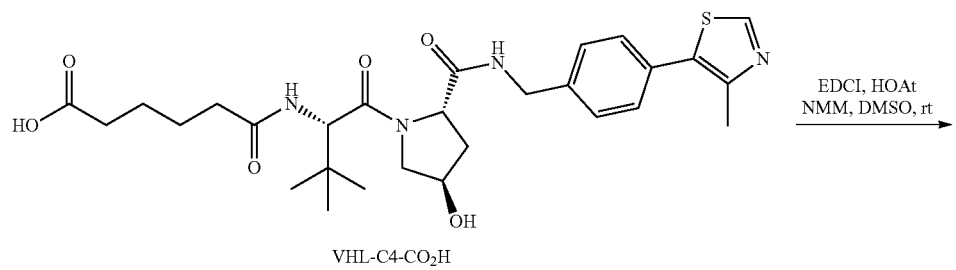

VHL-C4-CO$_2$H

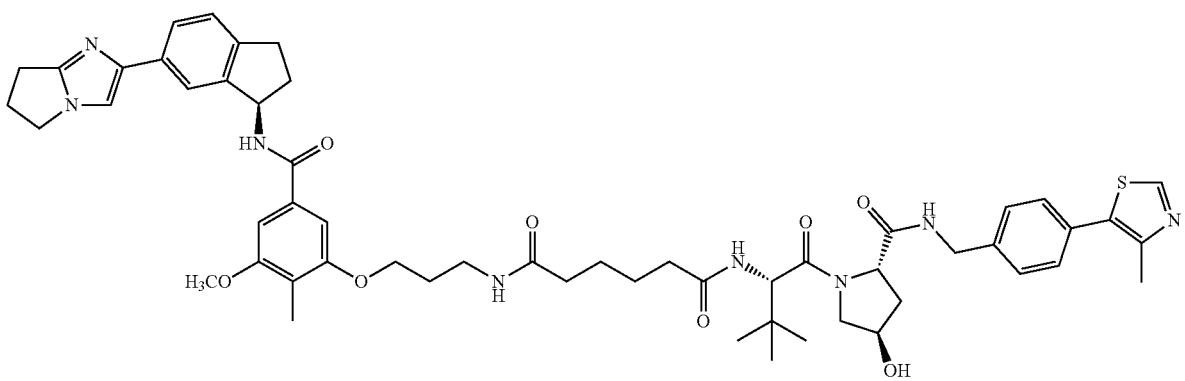

XF061-44

XF061-44 was synthesized following the standard procedures for preparing XF061-33 from intermediate 48 (13.8 mg, 0.024 mmol), VHL-C4-COOH (13.4 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-44 as white solid in TFA salt form (22.1 mg, yield 92%). $^1$H NMR (600 MHz, $CD_3OD$) δ 9.04 (s, 1H), 7.76 (s, 1H), 7.58 (d, J=1.8 Hz, 1H), 7.54 (dd, J=7.8, 1.7 Hz, 1H), 7.47 (d, J=8.2 Hz, 2H), 7.43-7.38 (m, 3H), 7.16 (d, J=1.6 Hz, 2H), 5.73 (t, J=8.0 Hz, 1H), 4.63-4.50 (m, 3H), 4.50-4.45 (m, 1H), 4.35 (d, J=15.5 Hz, 1H), 4.27 (t, J=7.3 Hz, 2H), 4.05 (t, J=6.2 Hz, 2H), 3.91-3.83 (m, 4H), 3.77 (dd, J=10.9, 4.0 Hz, 1H), 3.37 (t, J=6.9 Hz, 2H), 3.23-3.17 (m, 2H), 3.13 (ddd, J=16.4, 8.9, 3.4 Hz, 1H), 2.97 (dt, J=16.5, 8.4 Hz, 1H), 2.78 (p, J=7.5 Hz, 2H), 2.65-2.60 (m, 1H), 2.51 (s, 3H), 2.32-2.11 (m, 5H), 2.11-2.03 (m, 5H), 2.02-1.94 (m, 2H), 1.61-1.52 (m, 4H), 1.01 (s, 9H). HRMS (m/z) for $C_{55}H_{69}N_8O_8S^+$ $[M+H]^+$: calculated 1001.4954. found 1001.4966.

Example 347: Synthesis of XF061-45

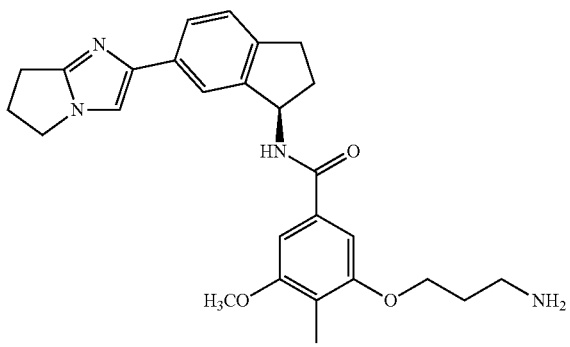

Intermediate 48

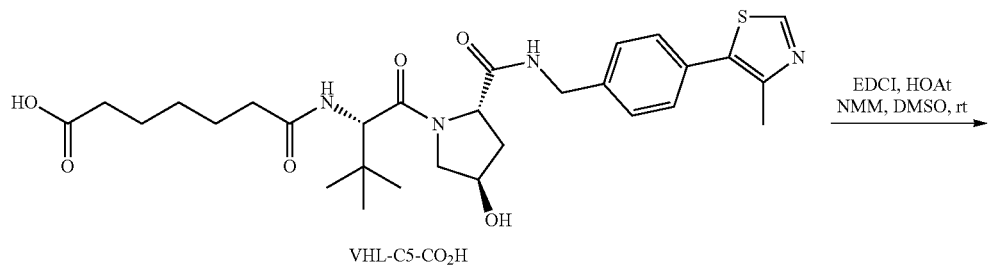

VHL-C5-$CO_2$H

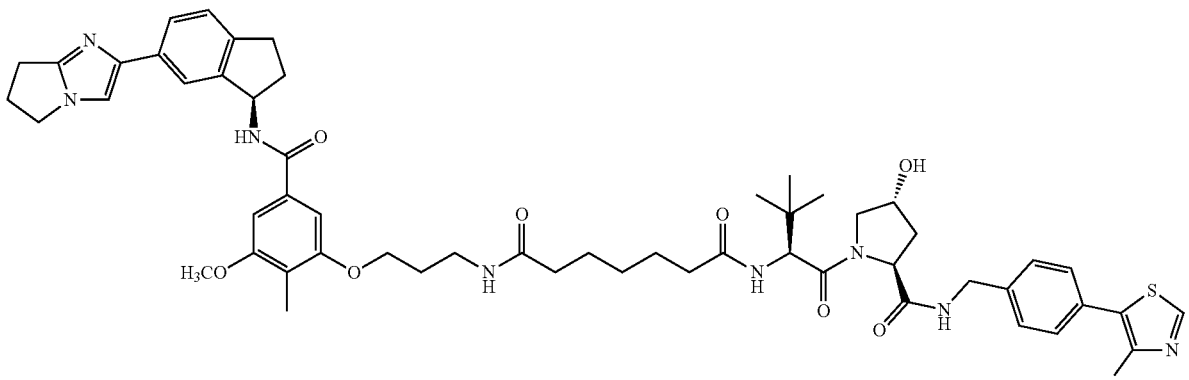

XF061-45

XF061-45 was synthesized following the standard procedures for preparing XF061-33 from intermediate 48 (13.8 mg, 0.024 mmol), VHL-C5-COOH (13.4 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-45 as white solid in TFA salt form (22.8 mg, yield 94%). $^1$H NMR (600 MHz, $CD_3OD$) δ 9.07 (s, 1H), 7.76 (s, 1H), 7.62-7.57 (m, 1H), 7.54 (dd, J=7.8, 1.8 Hz, 1H), 7.50-7.38 (m, 5H), 7.16 (s, 2H), 5.73 (t, J=7.9 Hz, 1H), 4.60 (s, 1H), 4.58-4.50 (m, 2H), 4.49-4.45 (m, 1H), 4.35 (d, J=15.5 Hz, 1H), 4.27 (t, J=7.3 Hz, 2H), 4.05 (t, J=6.1 Hz, 2H), 3.90-3.82 (m, 4H), 3.77 (dd, J=11.0, 3.9 Hz, 1H), 3.37 (t, J=6.9 Hz, 2H), 3.20 (dd, J=8.3, 6.9 Hz, 2H), 3.13 (ddd, J=16.4, 8.9, 3.3 Hz, 1H), 2.97 (dt, J=16.5, 8.4 Hz, 1H), 2.82-2.75 (m, 2H), 2.66-2.58 (m, 1H), 2.48 (s, 3H), 2.30-2.03 (m, 10H), 2.02-1.95 (m, 2H), 1.62-1.53 (m, 4H), 1.33-1.26 (m, 2H), 1.01 (s, 9H). HRMS (m/z) for $C_{56}H_{71}N_8O_8S^+$ [M+H]$^+$: calculated 1015.5110. found 1015.5145.

Example 348: Synthesis of XF061-46

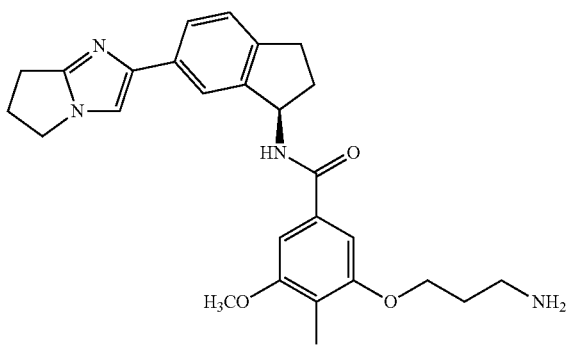

Intermediate 48

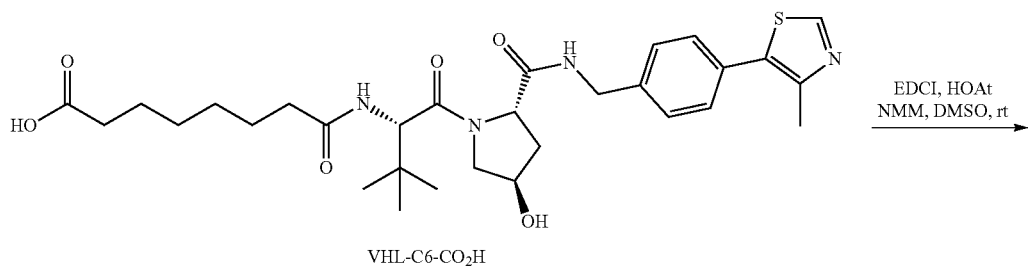

VHL-C6-CO$_2$H

+

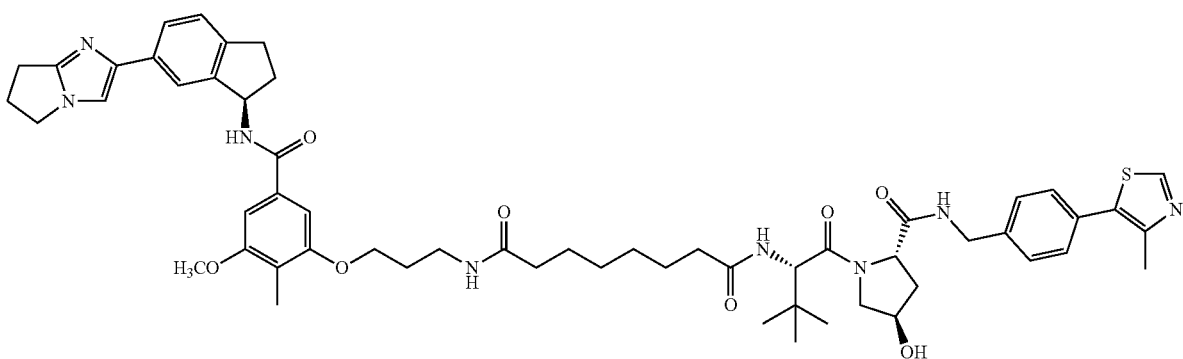

XF061-46

XF061-46 was synthesized following the standard procedures for preparing XF061-33 from intermediate 48 (13.8 mg, 0.024 mmol), VHL-C6-COOH (14.1 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-46 as white solid in TFA salt form (21.7 mg, yield 88%). $^1$H NMR (600 MHz, CD$_3$OD) δ 8.98 (s, 1H), 7.76 (s, 1H), 7.58 (d, J=1.9 Hz, 1H), 7.54 (dd, J=7.8, 1.8 Hz, 1H), 7.50-7.34 (m, 5H), 7.19-7.14 (m, 2H), 5.73 (t, J=8.0 Hz, 1H), 4.61 (s, 1H), 4.59-4.44 (m, 3H), 4.35 (d, J=15.5 Hz, 1H), 4.27 (t, J=7.3 Hz, 2H), 4.05 (t, J=6.1 Hz, 2H), 3.92-3.86 (m, 1H), 3.85 (s, 3H), 3.78 (dd, J=11.0, 3.9 Hz, 1H), 3.37 (t, J=6.9 Hz, 2H), 3.20 (dd, J=8.3, 6.9 Hz, 2H), 3.13 (ddd, J=16.5, 8.9, 3.4 Hz, 1H), 3.02-2.92 (m, 1H), 2.82-2.75 (m, 2H), 2.66-2.58 (m, 1H), 2.47 (s, 3H), 2.29-2.18 (m, 3H), 2.17-2.11 (m, 3H), 2.11-2.04 (m, 4H), 2.02-1.94 (m, 2H), 1.59-1.53 (m, 4H), 1.29 (p, J=3.6 Hz, 4H), 1.02 (s, 9H). HRMS (m/z) for $C_{57}H_{73}N_8O_8S^+$ [M+H]$^+$: calculated 1029.5267. found 1029.5276.

Example 349: Synthesis of XF061-47

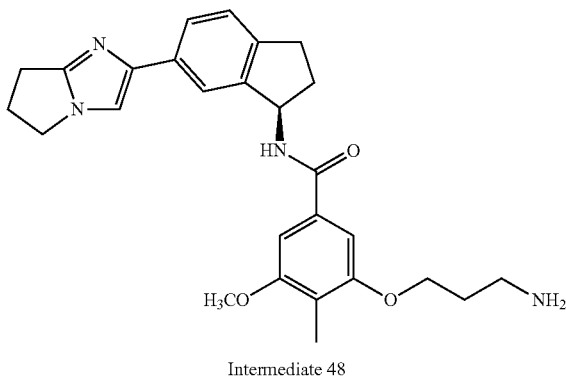

Intermediate 48

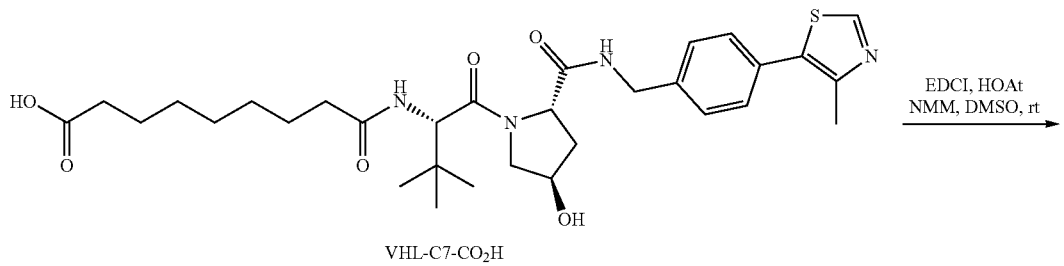

VHL-C7-CO$_2$H

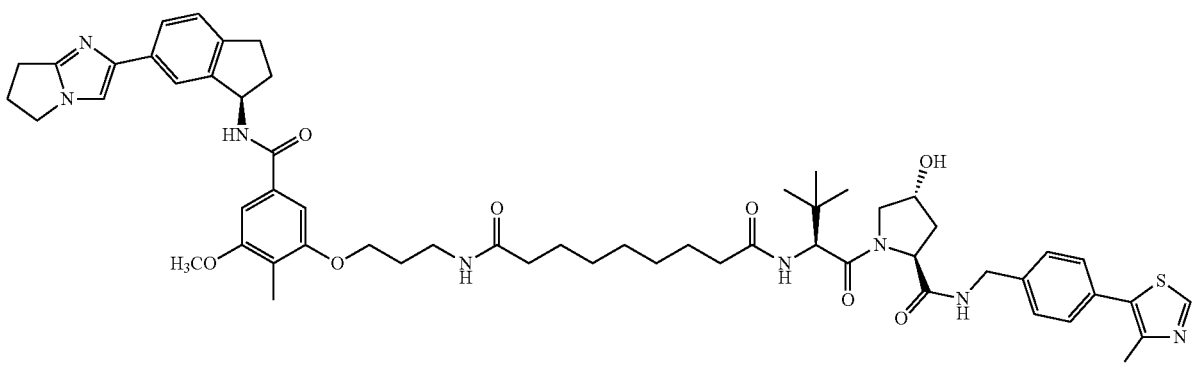

XF061-47

XF061-47 was synthesized following the standard procedures for preparing XF061-33 from intermediate 48 (13.8 mg, 0.024 mmol), VHL-C7-COOH (14.4 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-47 as white solid in TFA salt form (24.5 mg, yield 98%). $^1$H NMR (600 MHz, $CD_3OD$) δ 9.04 (s, 1H), 7.76 (s, 1H), 7.58 (s, 1H), 7.60-7.52 (m, 1H), 7.49-7.42 (m, 2H), 7.41 (d, J=8.3 Hz, 3H), 7.18-7.13 (m, 2H), 5.73 (t, J=7.9 Hz, 1H), 4.62 (s, 1H), 4.59-4.46 (m, 3H), 4.35 (d, J=15.5 Hz, 1H), 4.27 (t, J=7.3 Hz, 2H), 4.05 (t, J=6.1 Hz, 2H), 3.92-3.85 (m, 1H), 3.85 (s, 3H), 3.78 (dd, J=10.9, 3.9 Hz, 1H), 3.40-3.33 (m, 2H), 3.21 (dd, J=8.4, 6.9 Hz, 2H), 3.13 (ddd, J=16.4, 9.0, 3.4 Hz, 1H), 2.97 (dt, J=16.4, 8.5 Hz, 1H), 2.83-2.75 (m, 2H), 2.67-2.58 (m, 1H), 2.48 (s, 3H), 2.30-2.01 (m, 10H), 2.03-1.95 (m, 2H), 1.59-1.53 (m, 4H), 1.33-1.23 (m, 6H), 1.02 (s, 9H). HRMS (m/z) for $C_{58}H_{75}N_8O_8S^+$ $[M+H]^+$: calculated 1043.5423, found 1043.5467.

Example 350: Synthesis of XF061-48

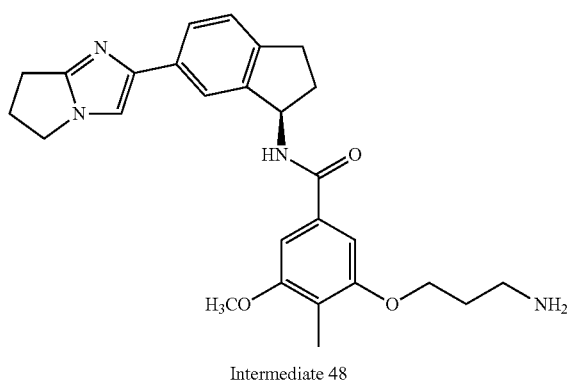

Intermediate 48

+

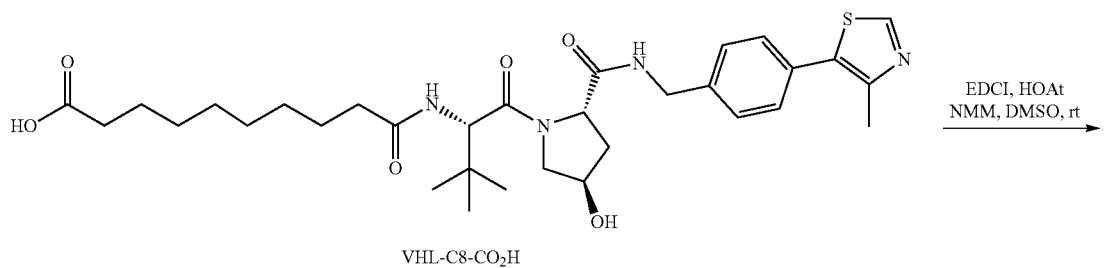

VHL-C8-CO$_2$H

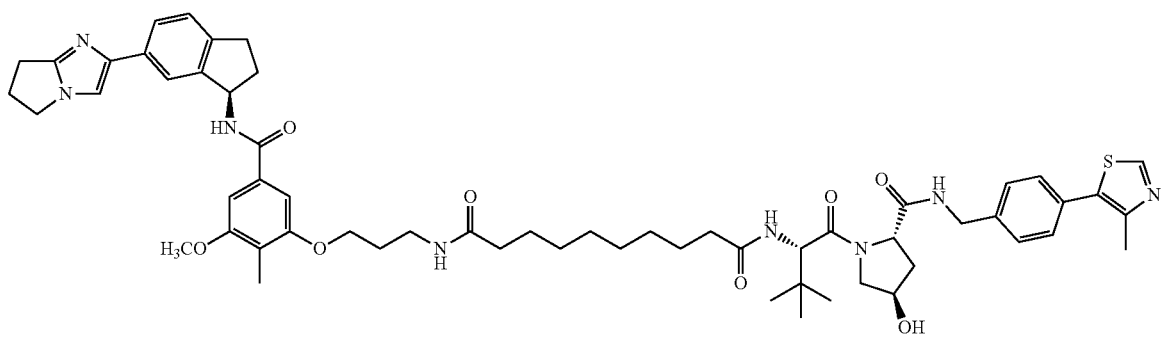

XF061-48

XF061-48 was synthesized following the standard procedures for preparing XF061-33 from intermediate 48 (13.8 mg, 0.024 mmol), VHL-C8-COOH (14.7 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-48 as white solid in TFA salt form (20 mg, yield 79%). $^1$H NMR (600 MHz, $CD_3OD$) δ 8.97 (s, 1H), 7.76 (s, 1H), 7.58 (s, 1H), 7.54 (dd, J=7.9, 1.8 Hz, 1H), 7.50-7.36 (m, 5H), 7.22-7.06 (m, 2H), 5.73 (t, J=7.9 Hz, 1H), 4.62 (s, 1H), 4.58-4.46 (m, 3H), 4.35 (dd, J=15.5, 4.3 Hz, 1H), 4.28 (t, J=7.3 Hz, 2H), 4.05 (t, J=6.1 Hz, 2H), 3.93-3.82 (m, 4H), 3.82-3.76 (m, 1H), 3.37 (t, J=6.8 Hz, 2H), 3.21 (dd, J=8.3, 6.9 Hz, 2H), 3.14 (ddd, J=16.4, 8.9, 3.4 Hz, 1H), 2.97 (dt, J=16.5, 8.5 Hz, 1H), 2.83-2.76 (m, 2H), 2.66-2.59 (m, 1H), 2.47 (s, 3H), 2.30-2.18 (m, 4H), 2.18-2.11 (m, 2H), 2.11-2.04 (m, 4H), 2.02-1.96 (m, 2H), 1.62-1.50 (m, 4H), 1.35-1.22 (m, 8H), 1.02 (s, 9H). HRMS (m/z) for $C_{59}H_{77}N_8O_8S^+$ $[M+H]^+$: calculated 1057.5580. found 1057.5612.

Example 351: Synthesis of XF061-49

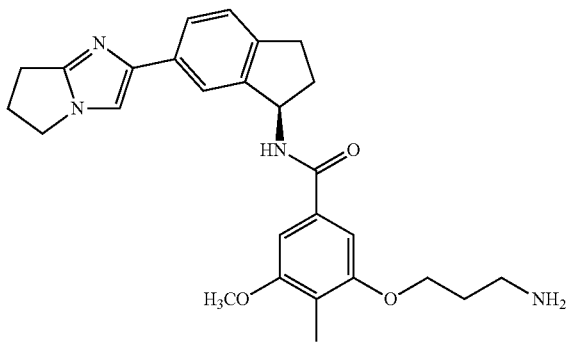

Intermediate 48

+

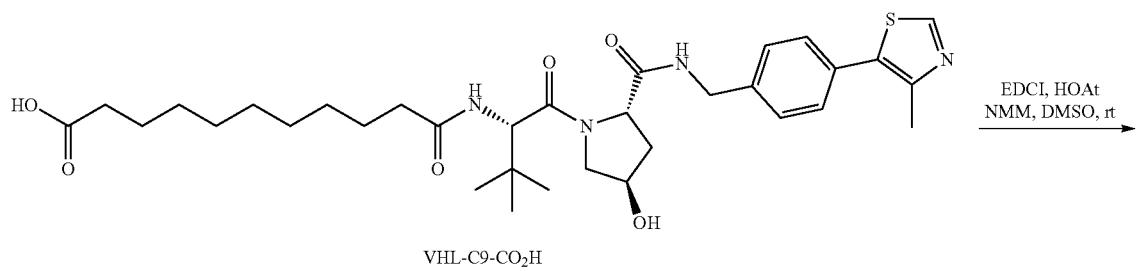

VHL-C9-CO$_2$H

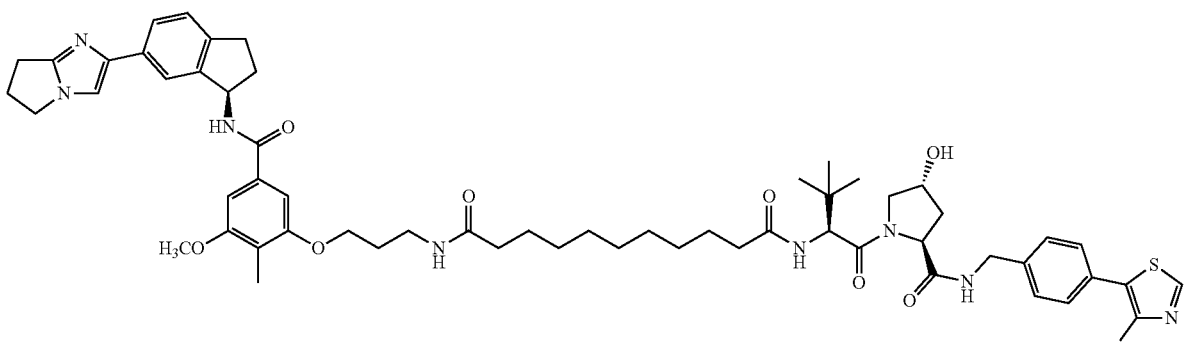

XF061-49

XF061-49 was synthesized following the standard procedures for preparing XF061-33 from intermediate 48 (13.8 mg, 0.024 mmol), VHL-C9-COOH (15.1 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-49 as white solid in TFA salt form (20.6 mg, yield 80%). $^1$H NMR (600 MHz, CD$_3$OD) δ 9.00 (s, 1H), 7.76 (s, 1H), 7.58 (s, 1H), 7.54 (dd, J=7.8, 1.8 Hz, 1H), 7.50-7.39 (m, 5H), 7.22-7.13 (m, 2H), 5.73 (t, J=7.9 Hz, 1H), 4.62 (s, 1H), 4.59-4.46 (m, 3H), 4.35 (d, J=15.5 Hz, 1H), 4.28 (t, J=7.3 Hz, 2H), 4.06 (t, J=6.1 Hz, 2H), 3.92-3.83 (m, 4H), 3.79 (dd, J=10.9, 3.9 Hz, 1H), 3.37 (t, J=6.9 Hz, 2H), 3.21 (dd, J=8.4, 6.9 Hz, 2H), 3.14 (ddd, J=16.4, 8.9, 3.4 Hz, 1H), 2.98 (dt, J=16.5, 8.6 Hz, 1H), 2.83-2.76 (m, 2H), 2.68-2.60 (m, 1H), 2.48 (s, 3H), 2.31-2.03 (m, 10H), 2.01-1.95 (m, 2H), 1.57 (s, 4H), 1.32-1.19 (m, 10H), 1.02 (s, 9H). HRMS (m/z) for C60H79N8O8S$^+$ [M+H]$^+$: calculated 1071.5736. found 1071.5766.

Example 352: Synthesis of XF061-50

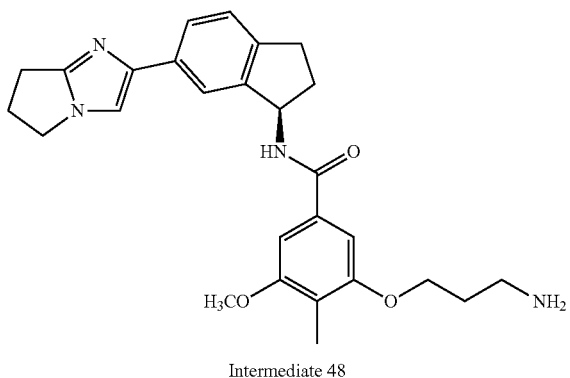

Intermediate 48

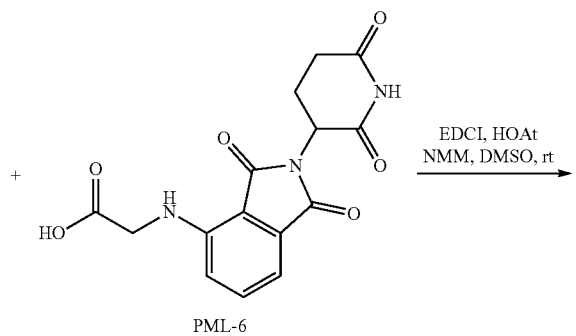

PML-6

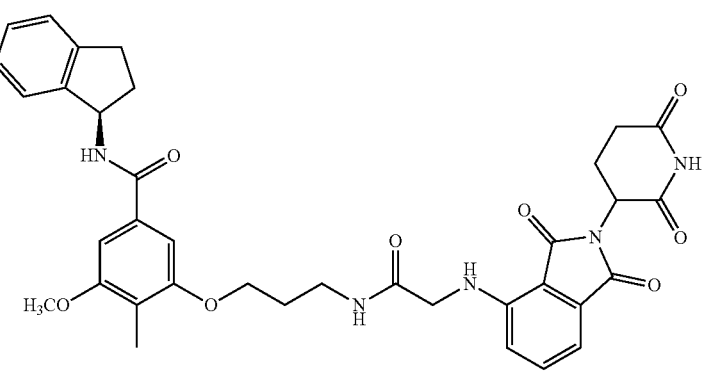

XF061-50

XF061-50 was synthesized following the standard procedures for preparing XF061-33 from intermediate 48 (13.8 mg, 0.024 mmol), PML-6 (7.9 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-50 as yellow solid in TFA salt form (13.5 mg, yield 73%). $^1$H NMR (600 MHz, CD$_3$OD) δ 7.72 (dd, J=6.4, 4.0 Hz, 1H), 7.55 (d, J=8.6 Hz, 1H), 7.53-7.45 (m, 1H), 7.42-7.34 (m, 2H), 7.14 (d, J=2.4 Hz, 1H), 7.10 (dd, J=5.0, 1.6 Hz, 1H), 6.94 (dd, J=9.3, 7.0 Hz, 1H), 6.79-6.71 (m, 1H), 5.72 (t, J=7.8 Hz, 1H), 5.00 (dd, J=12.7, 5.4 Hz, 1H), 4.24 (dt, J=7.8, 3.9 Hz, 2H), 4.04-3.88 (m, 4H), 3.84 (d, J=3.0 Hz, 3H), 3.51-3.36 (m, 2H), 3.21-3.07 (m, 3H), 2.97 (dtt, J=16.7, 8.6, 4.1 Hz, 1H), 2.84-2.58 (m, 6H), 2.13 (ddt, J=12.2, 8.4, 4.1 Hz, 1H), 2.08-1.93 (m, 6H). HRMS (m/z) for C$_{42}$H$_{44}$N$_7$O$_8^+$ [M+H]$^+$: calculated 774.3246. found 774.3234.

Example 353: Synthesis of XF061-51

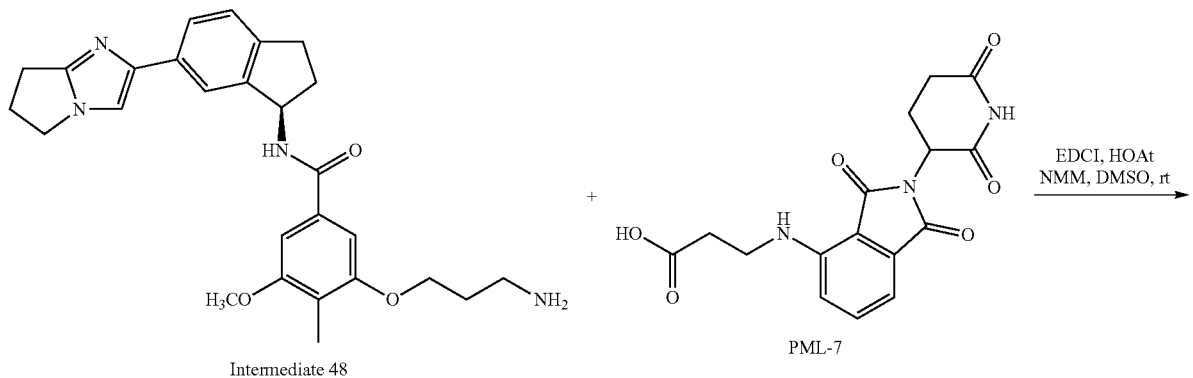

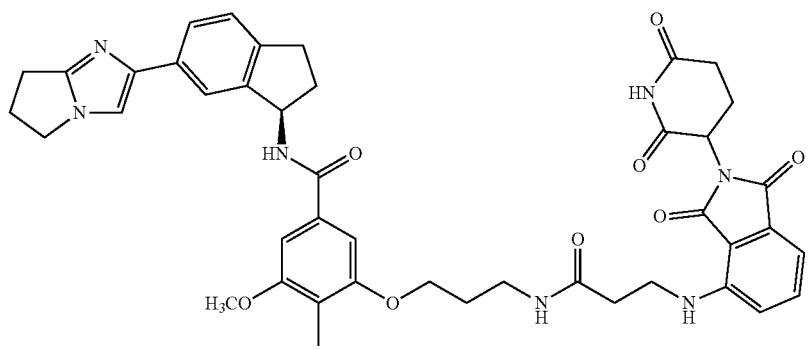

XF061-51

XF061-51 was synthesized following the standard procedures for preparing XF061-33 from intermediate 48 (13.8 mg, 0.024 mmol), PML-7 (8.3 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-51 as yellow solid in TFA salt form (16.8 mg, yield 89%). $^1$H NMR (600 MHz, CD$_3$OD) δ 7.72-7.67 (m, 1H), 7.58 (d, J=1.6 Hz, 1H), 7.54-7.47 (m, 3H), 7.40 (t, J=7.4 Hz, 1H), 7.17-7.14 (m, 1H), 7.02 (dd, J=9.8, 8.6 Hz, 1H), 6.99-6.93 (m, 1H), 5.74-5.67 (m, 1H), 4.90-4.82 (m, 1H), 4.19 (ddt, J=23.3, 11.2, 7.2 Hz, 2H), 4.03-3.93 (m, 2H), 3.85 (d, J=5.6 Hz, 3H), 3.65-3.51 (m, 2H), 3.50-3.26 (m, 2H), 3.20-3.11 (m, 3H), 3.01-2.92 (m, 1H), 2.81-2.66 (m, 3H), 2.67-2.54 (m, 3H), 2.53-2.39 (m, 2H), 2.20-2.09 (m, 1H), 2.06 (d, J=2.8 Hz, 3H), 1.96-1.88 (m, 3H). HRMS (m/z) for C$_{43}$H$_{46}$N$_7$O$_8{}^+$ [M+H]$^+$: calculated 788.3402. found 788.3379.

Example 354: Synthesis of XF061-52

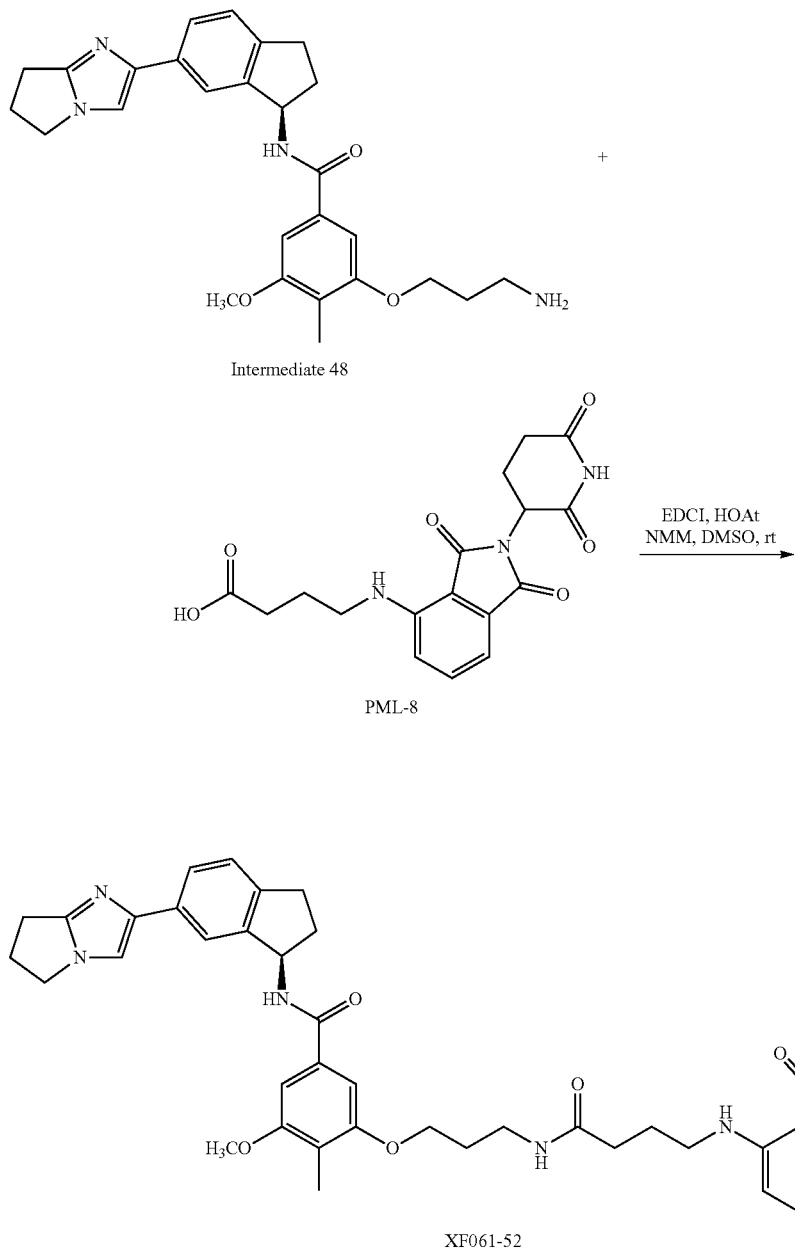

XF061-52 was synthesized following the standard procedures for preparing XF061-33 from intermediate 48 (13.8 mg, 0.024 mmol), PML-8 (8.6 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-52 as yellow solid in TFA salt form (13.1 mg, yield 68%). $^1$H NMR (600 MHz, CD$_3$OD) δ 7.72 (d, J=1.7 Hz, 1H), 7.58-7.55 (m, 1H), 7.53-7.49 (m, 1H), 7.49-7.44 (m, 1H), 7.40 (d, J=7.9 Hz, 1H), 7.20 (dd, J=24.5, 1.5 Hz, 1H), 7.15 (dd, J=5.6, 1.5 Hz, 1H), 6.99-6.93 (m, 2H), 5.72 (t, J=8.0 Hz, 1H), 4.98 (dd, J=12.8, 5.5 Hz, 1H), 4.28-4.21 (m, 2H), 4.08-3.99 (m, 2H), 3.84 (d, J=5.1 Hz, 3H), 3.45-3.30 (m, 2H), 3.31-3.21 (m, 2H), 3.22-3.09 (m, 3H), 3.01-2.92 (m, 1H), 2.81-2.71 (m, 3H), 2.71-2.57 (m, 3H), 2.28 (tdd, J=6.8, 4.4, 1.6 Hz, 2H), 2.20-2.08 (m, 1H), 2.08 (s, 3H), 2.05-1.99 (m, 1H), 1.99-1.94 (m, 2H), 1.96-1.84 (m, 2H). HRMS (m/z) for C$_{44}$H$_{48}$N$_7$O$_8$$^+$ [M+H]$^+$: calculated 802.3559. found 802.3575.

Example 355: Synthesis of XF061-53

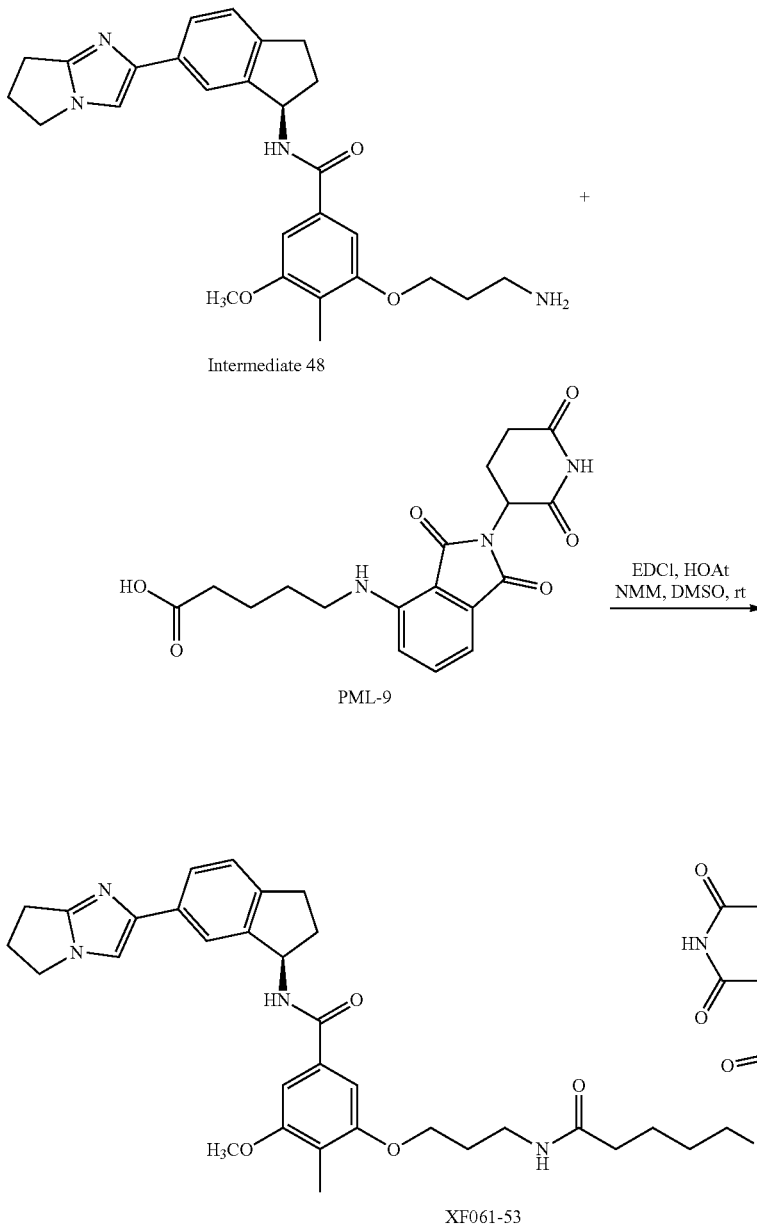

XF061-53 was synthesized following the standard procedures for preparing XF061-33 from intermediate 48 (13.8 mg, 0.024 mmol), PML-9 (8.9 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-53 as yellow solid in TFA salt form (17.1 mg, yield 87%). $^1$H NMR (600 MHz, CD$_3$OD) δ 7.72 (d, J=2.3 Hz, 1H), 7.57 (s, 1H), 7.54-7.46 (m, 2H), 7.40 (d, J=7.9 Hz, 1H), 7.15 (d, J=1.7 Hz, 2H), 6.98-6.93 (m, 2H), 5.76-5.68 (m, 1H), 5.02-4.92 (m, 1H), 4.24 (t, J=7.3 Hz, 2H), 4.07-4.02 (m, 2H), 3.87-3.81 (m, 3H), 3.43-3.33 (m, 2H), 3.28-3.23 (m, 2H), 3.18 (t, J=7.7 Hz, 2H), 3.16-3.09 (m, 1H), 3.00-2.91 (m, 1H), 2.83-2.73 (m, 3H), 2.72-2.58 (m, 3H), 2.26-2.20 (m, 2H), 2.17-2.10 (m, 1H), 2.09-2.02 (m, 4H), 2.01-1.94 (m, 2H), 1.72-1.64 (m, 2H), 1.64-1.56 (m, 2H). HRMS (m/z) for C$_{45}$H$_{50}$N$_7$O$_8^+$ [M+H]$^+$: calculated 816.3715. found 816.3732.

Example 356: Synthesis of XF061-54

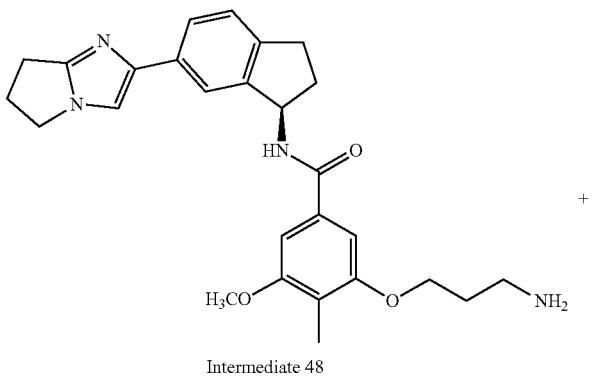

Intermediate 48

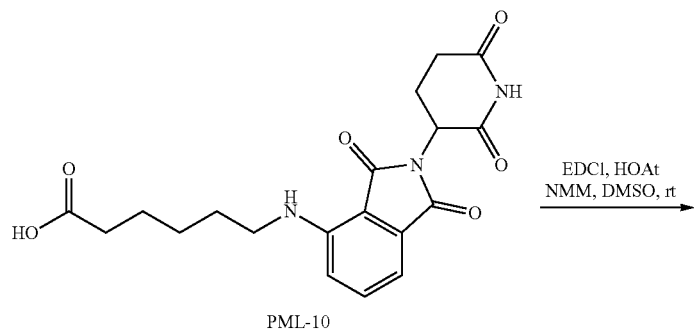

PML-10

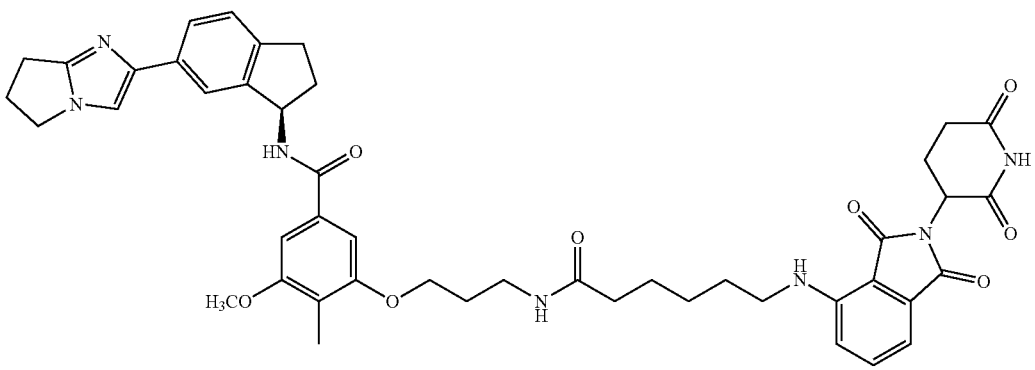

XF061-54

XF061-54 was synthesized following the standard procedures for preparing XF061-33 from intermediate 48 (13.8 mg, 0.024 mmol), PML-10 (9.3 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-54 as yellow solid in TFA salt form (17.8 mg, yield 89%). $^1$H NMR (600 MHz, $CD_3OD$) δ 7.72 (s, 1H), 7.57 (s, 1H), 7.54-7.45 (m, 2H), 7.40 (dd, J=8.0, 2.0 Hz, 1H), 7.21-7.10 (m, 2H), 6.99-6.94 (m, 2H), 5.72 (td, J=8.0, 3.0 Hz, 1H), 5.07-4.97 (m, 1H), 4.25 (t, J=7.3 Hz, 2H), 4.07-4.01 (m, 2H), 3.84 (s, 3H), 3.44-3.33 (m, 2H), 3.26-3.16 (m, 4H), 3.16-3.05 (m, 1H), 3.01-2.89 (m, 1H), 2.84-2.70 (m, 3H), 2.70-2.55 (m, 3H), 2.22-2.06 (m, 6H), 2.05-1.93 (m, 3H), 1.70-1.54 (m, 4H), 1.43-1.34 (m, 2H). HRMS (m/z) for $C_{46}H_{52}N_7O_8^+$ [M+H]$^+$: calculated 830.3872. found 830.3846.

Example 357: Synthesis of XF061-55

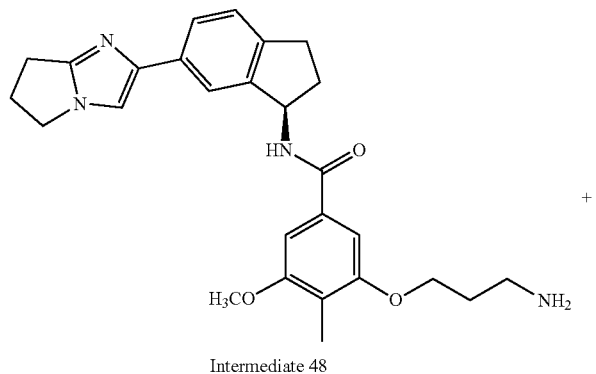

Intermediate 48

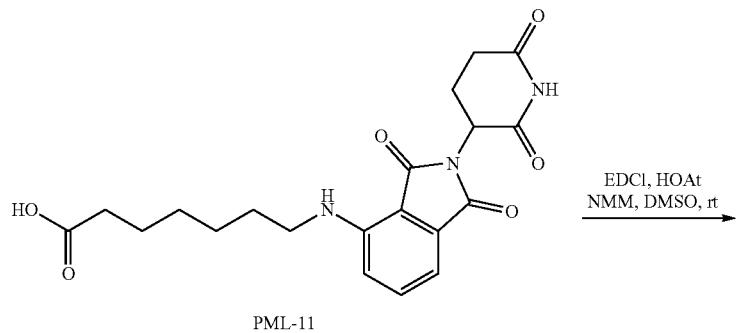

PML-11

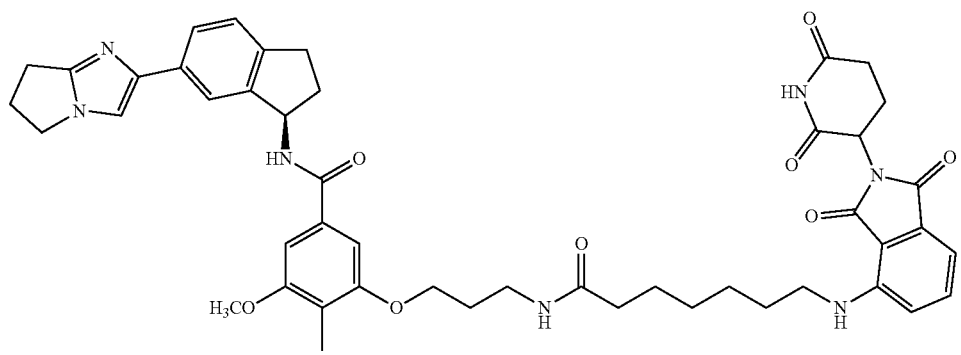

XF061-55

XF061-55 was synthesized following the standard procedures for preparing XF061-33 from intermediate 48 (13.8 mg, 0.024 mmol), PML-11 (9.6 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-55 as yellow solid in TFA salt form (13.5 mg, yield 67%).
$^1$H NMR (600 MHz, CD$_3$OD) δ 7.79-7.67 (m, 1H), 7.57 (d, J=1.7 Hz, 1H), 7.55-7.43 (m, 2H), 7.40 (d, J=7.9 Hz, 1H), 7.16 (d, J=1.3 Hz, 2H), 7.00-6.93 (m, 2H), 5.71 (t, J=7.8 Hz, 1H), 4.98 (ddd, J=14.8, 12.8, 5.5 Hz, 1H), 4.25 (t, J=7.3 Hz, 2H), 4.08-4.00 (m, 2H), 3.84 (s, 3H), 3.41-3.35 (m, 2H), 3.28-3.16 (m, 4H), 3.12 (ddd, J=16.4, 8.8, 3.3 Hz, 1H), 3.00-2.92 (m, 1H), 2.82-2.73 (m, 3H), 2.72-2.56 (m, 3H), 2.21-2.10 (m, 3H), 2.09-2.02 (m, 4H), 2.00-1.94 (m, 2H), 1.64-1.51 (m, 4H), 1.44-1.26 (m, 4H). HRMS (m/z) for C$_{47}$H$_{54}$N$_7$O$_8$$^+$ [M+H]$^+$: calculated 844.4028. found 844.4059.

Example 358: Synthesis of XF061-56

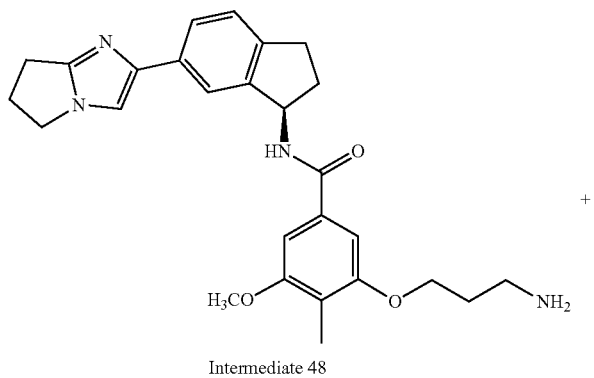

Intermediate 48

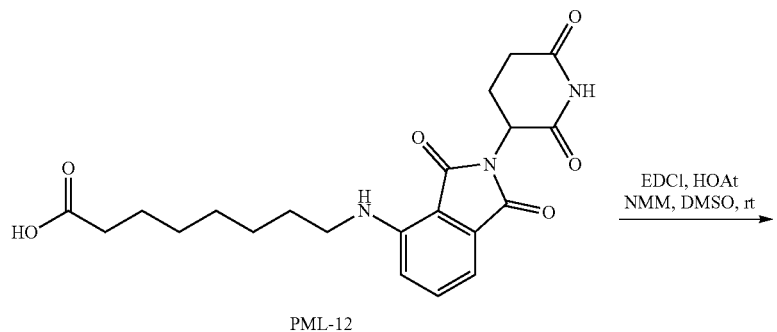

PML-12

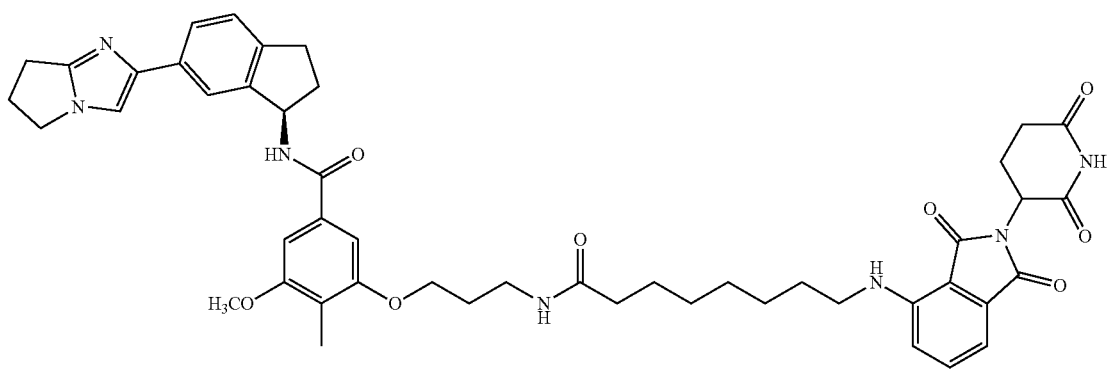

XF061-56

XF061-56 was synthesized following the standard procedures for preparing XF061-33 from intermediate 48 (13.8 mg, 0.024 mmol), PML-12 (10 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-56 as yellow solid in TFA salt form (13.1 mg, yield 64%). $^1$H NMR (600 MHz, CD$_3$OD) δ 7.73 (s, 1H), 7.57 (s, 1H), 7.55-7.44 (m, 2H), 7.40 (d, J=7.9 Hz, 1H), 7.16 (d, J=1.7 Hz, 2H), 6.97 (dd, J=7.8, 4.2 Hz, 2H), 5.72 (td, J=8.0, 3.1 Hz, 1H), 4.98 (ddd, J=18.5, 12.8, 5.5 Hz, 1H), 4.25 (t, J=7.3 Hz, 2H), 4.08-4.00 (m, 2H), 3.84 (s, 3H), 3.40-3.35 (m, 2H), 3.27-3.23 (m, 2H), 3.20 (d, J=7.4 Hz, 2H), 3.12 (ddd, J=16.4, 8.9, 3.3 Hz, 1H), 3.01-2.92 (m, 1H), 2.81-2.74 (m, 3H), 2.73-2.58 (m, 3H), 2.20-2.12 (m, 3H), 2.10-2.02 (m, 4H), 2.02-1.95 (m, 2H), 1.65-1.52 (m, 4H), 1.42-1.22 (m, 6H). HRMS (m/z) for C$_{48}$H$_{56}$N$_7$O$_8$$^+$ [M+H]$^+$: calculated 858.4185. found 858.4213.

Example 359: Synthesis of XF061-57

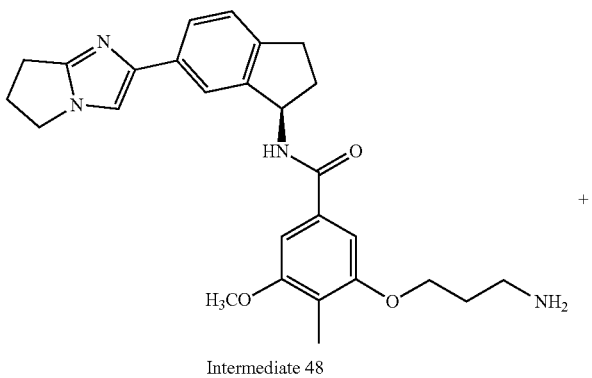

Intermediate 48

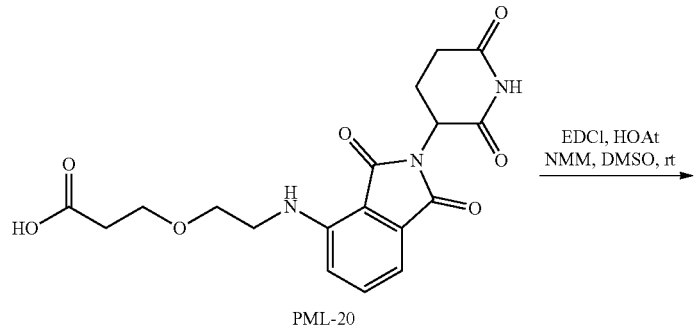

PML-20

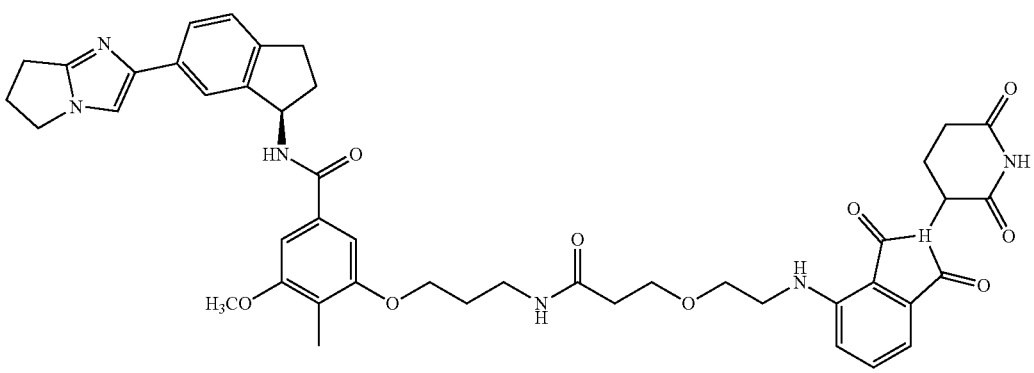

XF061-57

XF061-57 was synthesized following the standard procedures for preparing XF061-33 from intermediate 48 (13.8 mg, 0.024 mmol), PML-20 (9.3 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-57 as yellow solid in TFA salt form (17.1 mg, yield 95%).
$^1$H NMR (600 MHz, CD$_3$OD) δ 7.72 (s, 1H), 7.59 (d, J=3.6 Hz, 1H), 7.55-7.43 (m, 2H), 7.40 (t, J=7.4 Hz, 1H), 7.21-7.12 (m, 2H), 7.00-6.86 (m, 2H), 5.76-5.67 (m, 1H), 4.98-4.91 (m, 1H), 4.25 (dd, J=8.3, 6.2 Hz, 2H), 4.03-3.97 (m, 2H), 3.84 (s, 3H), 3.74-3.68 (m, 2H), 3.64-3.58 (m, 2H), 3.36 (ddt, J=9.5, 7.3, 3.4 Hz, 4H), 3.22-3.17 (m, 2H), 3.16-3.09 (m, 1H), 3.03-2.92 (m, 1H), 2.83-2.72 (m, 2H), 2.72-2.48 (m, 4H), 2.46-2.36 (m, 2H), 2.21-2.10 (m, 1H), 2.06 (s, 3H), 2.03-1.89 (m, 3H). HRMS (m/z) for C$_{45}$H$_{50}$N$_7$O$_9{}^+$ [M+H]$^+$: calculated 832.3665. found 832.3643.

Example 360: Synthesis of XF061-58

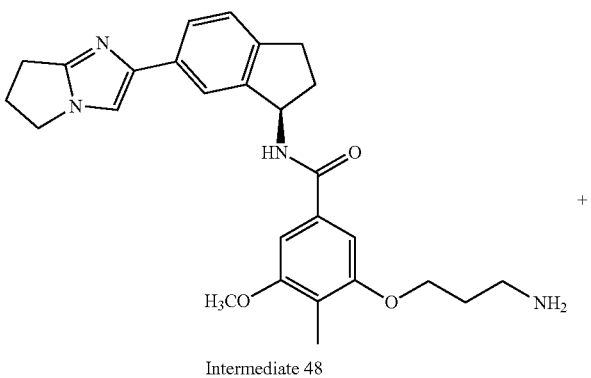

Intermediate 48

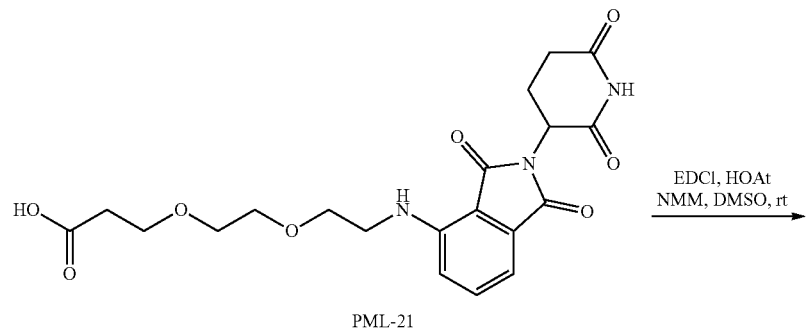

PML-21

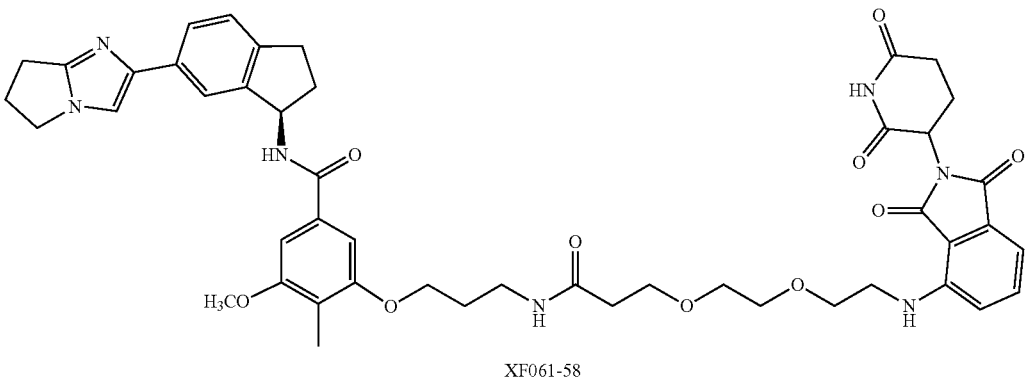

XF061-58

XF061-58 was synthesized following the standard procedures for preparing XF061-33 from intermediate 48 (13.8 mg, 0.024 mmol), PML-21 (10.4 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-58 as yellow solid in TFA salt form (17.9 mg, yield 85%). $^1$H NMR (600 MHz, CD$_3$OD) δ 7.73 (d, J=4.3 Hz, 1H), 7.59 (d, J=2.2 Hz, 1H), 7.53-7.44 (m, 2H), 7.40 (dd, J=7.9, 3.9 Hz, 1H), 7.17-7.11 (m, 2H), 7.01-6.92 (m, 2H), 5.75-5.68 (m, 1H), 4.92-4.85 (m, 1H), 4.29-4.21 (m, 2H), 4.03-3.96 (m, 2H), 3.84 (s, 3H), 3.70-3.59 (m, 4H), 3.62-3.52 (m, 4H), 3.42-3.31 (m, 5H), 3.22-3.09 (m, 3H), 3.01-2.92 (m, 1H), 2.81-2.53 (m, 6H), 2.41-2.36 (m, 2H), 2.19-2.09 (m, 1H), 2.07-1.98 (m, 4H), 1.98-1.91 (m, 2H). HRMS (m/z) for C$_{47}$H$_{54}$N$_7$O$_{10}$$^+$ [M+H]$^+$: calculated 876.3927. found 876.3945.

Example 361: Synthesis of XF061-59

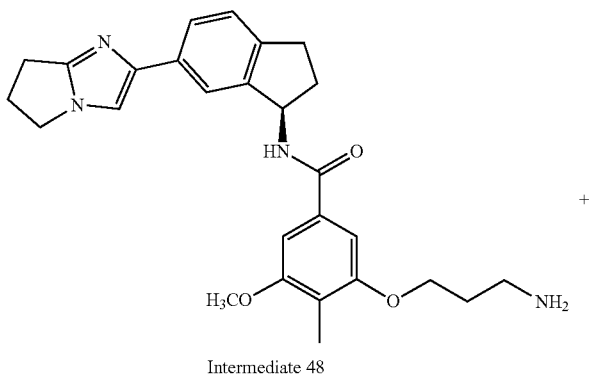

Intermediate 48

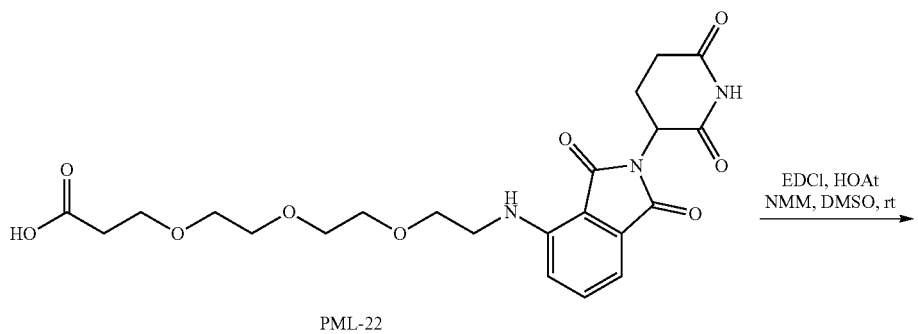

PML-22

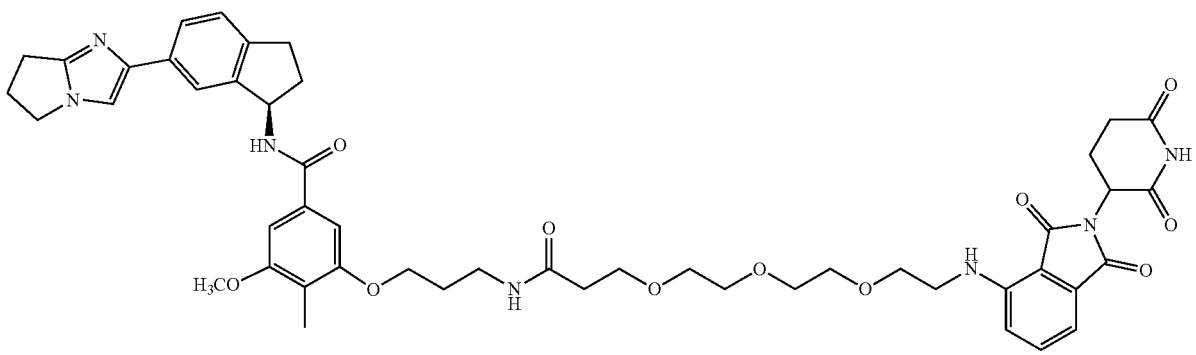

XF061-59

XF061-59 was synthesized following the standard procedures for preparing XF061-33 from intermediate 48 (13.8 mg, 0.024 mmol), PML-22 (11.4 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in $H_2O$) to afford XF061-59 as yellow solid in TFA salt form (17.8 mg, yield 81%). $^1$H NMR (600 MHz, $CD_3OD$) δ 7.73 (d, J=0.8 Hz, 1H), 7.58 (d, J=2.2 Hz, 1H), 7.53-7.44 (m, 2H), 7.39 (dd, J=7.9, 3.8 Hz, 1H), 7.18-7.13 (m, 2H), 7.02-6.94 (m, 2H), 5.72 (t, J=7.9 Hz, 1H), 5.03-4.94 (m, 1H), 4.25 (dd, J=8.4, 6.4 Hz, 2H), 4.06-4.00 (m, 2H), 3.85 (s, 3H), 3.69-3.46 (m, 12H), 3.46-3.39 (m, 2H), 3.42-3.32 (m, 2H), 3.22-3.09 (m, 3H), 3.01-2.92 (m, 1H), 2.83-2.57 (m, 6H), 2.40-2.33 (m, 2H), 2.20-2.09 (m, 1H), 2.08 (s, 4H), 2.07-1.93 (m, 2H). HRMS (m/z) for $C_{49}H_{58}N_7O_{11}^+$ [M+H]$^+$: calculated 920.4189. found 920.4216.

Example 362: Synthesis of XF061-60

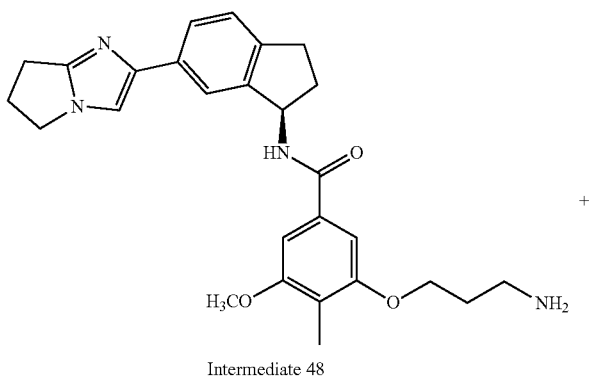

Intermediate 48

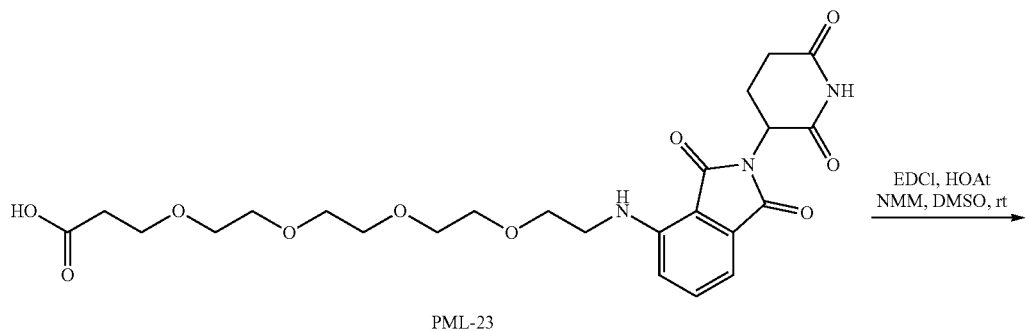

PML-23

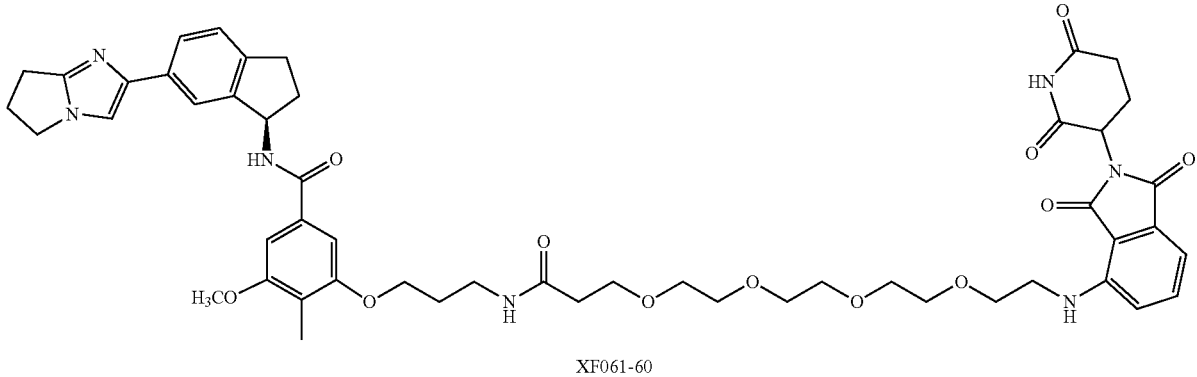

XF061-60

XF061-60 was synthesized following the standard procedures for preparing XF061-33 from intermediate 48 (13.8 mg, 0.024 mmol), PML-23 (12.8 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-60 as yellow solid in TFA salt form (20.1 mg, yield 87%). $^1$H NMR (600 MHz, CD$_3$OD) δ 7.73 (d, J=1.0 Hz, 1H), 7.58 (s, 1H), 7.53-7.43 (m, 2H), 7.39 (dd, J=8.0, 3.7 Hz, 1H), 7.18-7.13 (m, 2H), 7.03-6.92 (m, 2H), 5.72 (t, J=7.9 Hz, 1H), 5.02-4.91 (m, 1H), 4.25 (dd, J=8.2, 6.1 Hz, 2H), 4.07-4.00 (m, 2H), 3.85 (s, 3H), 3.69-3.62 (m, 2H), 3.63-3.58 (m, 6H), 3.57-3.54 (m, 2H), 3.53-3.44 (m, 6H), 3.44-3.40 (m, 2H), 3.38 (ddd, J=9.3, 5.6, 1.8 Hz, 2H), 3.22-3.08 (m, 3H), 2.96 (dt, J=16.6, 8.4 Hz, 1H), 2.84-2.58 (m, 6H), 2.37 (t, J=6.0 Hz, 2H), 2.20-2.09 (m, 1H), 2.10-2.07 (m, 4H), 2.00-1.94 (m, 2H). HRMS (m/z) for C$_{51}$H$_{62}$N$_7$O$_{12}$$^+$ [M+H]$^+$: calculated 964.4451. found 964.4428.

Example 363: Synthesis of XF061-61

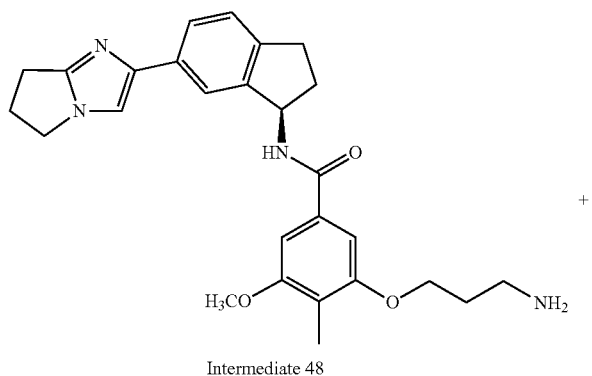

Intermediate 48

+

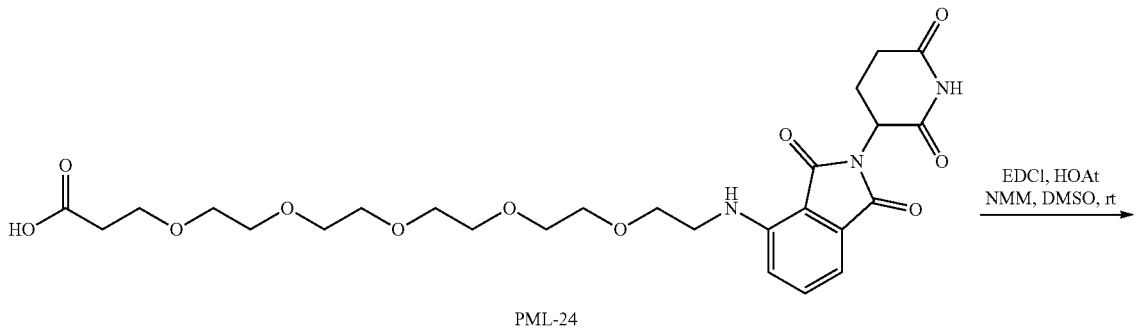

PML-24

EDCl, HOAt
NMM, DMSO, rt

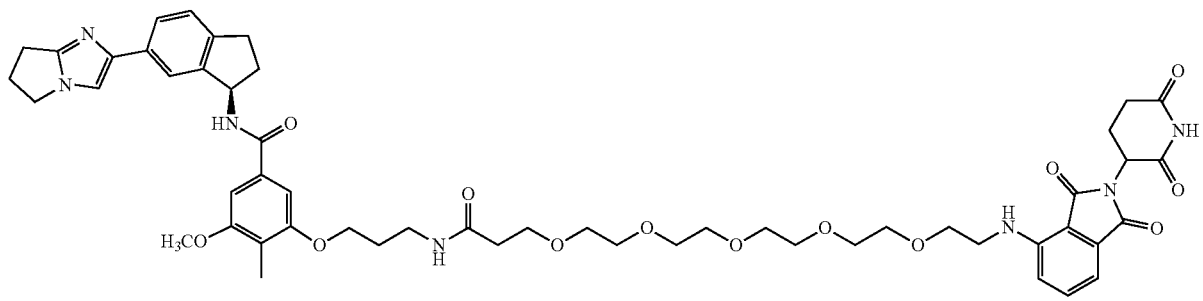

XF061-61

XF061-61 was synthesized following the standard procedures for preparing XF061-33 from intermediate 48 (13.8 mg, 0.024 mmol), PML-24 (13.6 mg, 0.024 mmol, 1.0 equiv), EDCI (1-ethyl-3-(3-dimethylaminopropyl)carbodiimide) (6.9 mg, 0.036 mmol, 1.5 equiv), HOAt (1-hydroxy-7-azabenzo-triazole) (4.9 mg, 0.036 mmol, 1.5 equiv), and NMM (N-Methylmorpholine) (7.3 mg, 0.072 mmol, 3.0 equiv). After being stirring overnight at room temperature, the resulting mixture was purified by preparative HPLC (10%-100% methanol/0.1% TFA in H$_2$O) to afford XF061-61 as yellow solid in TFA salt form (18.4 mg, yield 76%). $^1$H NMR (600 MHz, CD$_3$OD) δ 7.75 (s, 1H), 7.58 (s, 1H), 7.54-7.47 (m, 2H), 7.40 (dd, J=7.9, 3.2 Hz, 1H), 7.19-7.14 (m, 2H), 7.05-6.96 (m, 2H), 5.73 (t, J=8.0 Hz, 1H), 5.03-4.84 (m, 1H), 4.26 (t, J=7.3 Hz, 2H), 4.05 (dd, J=7.5, 5.1 Hz, 2H), 3.85 (s, 3H), 3.69-3.52 (m, 12H), 3.55-3.45 (m, 4H), 3.50-3.47 (m, 4H), 3.48-3.41 (m, 2H), 3.41-3.33 (m, 2H), 3.22-3.09 (m, 3H), 3.01-2.92 (m, 1H), 2.85-2.59 (m, 6H), 2.38 (t, J=6.0 Hz, 2H), 2.20-2.03 (m, 5H), 2.09-1.95 (m, 2H). HRMS (m/z) for $C_{53}H_{66}N_7O_{13}^+$ [M+H]$^+$: calculated 1008.4713. found 1008.4747.

Example 364: Synthesis of Intermediate 49

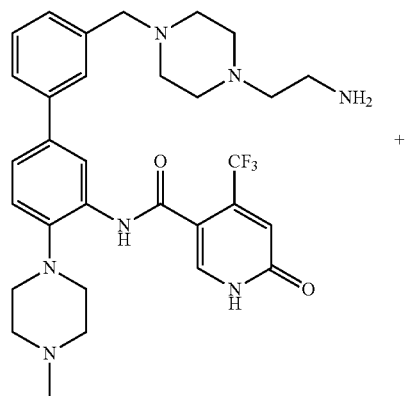

Intermediate 2

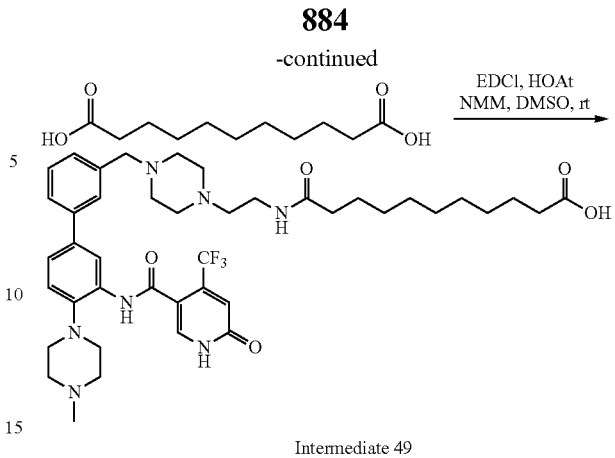

Intermediate 49

To the solution of intermediate 2 (179.1 mg, 0.3 mmol) in DMSO (1 mL) were added 1,9-undecanedioic acid (97.2 mg, 0.45 mmol, 1.5 equiv), EDCI (1-ethyl-3-(3-dimethylaminopropyl)carbodiimide) (86.4 mg, 0.45 mmol, 1.5 equiv), HOAt (1-hydroxy-7-azabenzo-triazole) (61.2 mg, 0.45 mmol, 1.5 equiv), and NMM (N-Methylmorpholine) (90.9 mg, 0.9 mmol, 3.0 equiv). After being stirring for 2 h at room temperature, the resulting mixture was purified by preparative HPLC (10%-100% methanol/0.1% TFA in H$_2$O) to afford intermediate 49 (XF082-4) as white solid in TFA salt form (123.8 mg, yield 52%). $^1$H NMR (500 MHz, CD$_3$OD) δ 8.29 (d, J=2.2 Hz, 1H), 8.05 (s, 1H), 7.81 (d, J=1.8 Hz, 1H), 7.76 (dt, J=7.9, 1.4 Hz, 1H), 7.57 (ddd, J=7.7, 4.6, 2.5 Hz, 2H), 7.53-7.47 (m, 1H), 7.40 (d, J=8.4 Hz, 1H), 6.95 (s, 1H), 4.37 (s, 2H), 3.63 (d, J=11.7 Hz, 2H), 3.56-3.42 (m, 8H), 3.40-3.25 (m, 6H), 2.98 (s, 3H), 2.26 (dt, J=28.7, 7.5 Hz, 4H), 2.05 (s, 3H), 1.70-1.47 (m, 4H), 1.33 (s, 11H). HRMS (m/z) for $C_{42}H_{57}F_3N_7O_5^+$ [M+H]$^+$: calculated 796.4368. found 796.4387.

Example 365: Synthesis of XF082-33

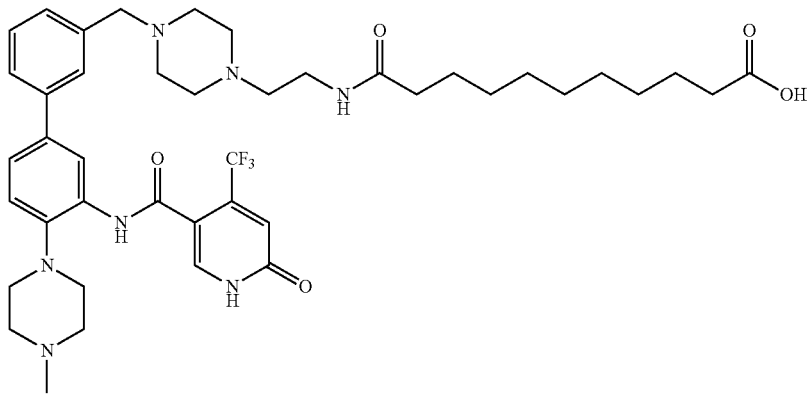

Intermediate 49

-continued

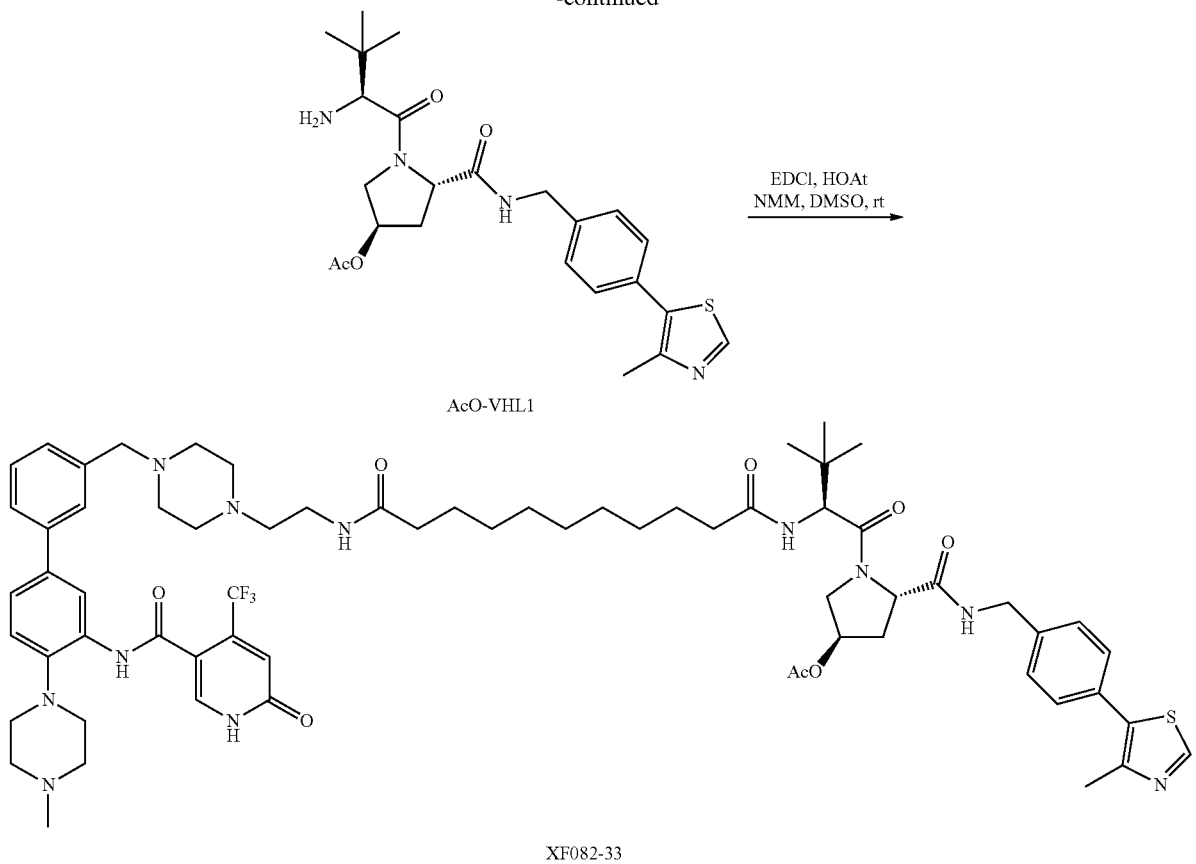

AcO-VHL1

XF082-33

To the solution of intermediate 49 (15.9 mg, 0.02 mmol) in DMSO (1 mL) were added AcO-VHL1 (9.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirring overnight at room temperature, the resulting mixture was purified by preparative HPLC (10%-100% methanol/0.1% TFA in $H_2O$) to afford XF082-33 as white solid in TFA salt form (22.3 mg, yield 89%). $^1$H NMR (600 MHz, $CD_3OD$) δ 9.09 (s, 1H), 8.26 (d, J=2.2 Hz, 1H), 8.03 (s, 1H), 7.78 (d, J=2.2 Hz, 1H), 7.73 (d, J=7.8 Hz, 1H), 7.57-7.51 (m, 2H), 7.50-7.44 (m, 3H), 7.43 (d, J=8.2 Hz, 2H), 7.38 (d, J=8.4 Hz, 1H), 6.94 (s, 1H), 5.36 (s, 1H), 4.55 (dd, J=15.9, 6.0 Hz, 2H), 4.50 (s, 1H), 4.36 (d, J=15.5 Hz, 1H), 4.30 (s, 2H), 4.16 (d, J=11.8 Hz, 1H), 4.09 (q, J=7.1 Hz, 1H), 3.98 (s, 1H), 3.90 (dd, J=11.7, 4.0 Hz, 1H), 3.61 (d, J=11.6 Hz, 2H), 3.49 (t, J=6.0 Hz, 2H), 3.39 (s, 4H), 3.34 (s, 2H), 3.28 (s, 2H), 3.20-3.09 (m, 4H), 2.96 (s, 3H), 2.49 (s, 3H), 2.42-2.34 (m, 1H), 2.33-2.16 (m, 5H), 2.04 (s, 3H), 2.00 (d, J=5.4 Hz, 1H), 1.58 (s, 1H), 1.30 (s, 13H), 1.23 (t, J=7.1 Hz, 1H), 1.03 (s, 9H). HRMS (m/z) for $C_{66}H_{87}F_3N_{11}O_8S^+$ [M+H]$^+$: calculated 1250.6406. found 1250.6379.

Example 366: Synthesis of XF082-34

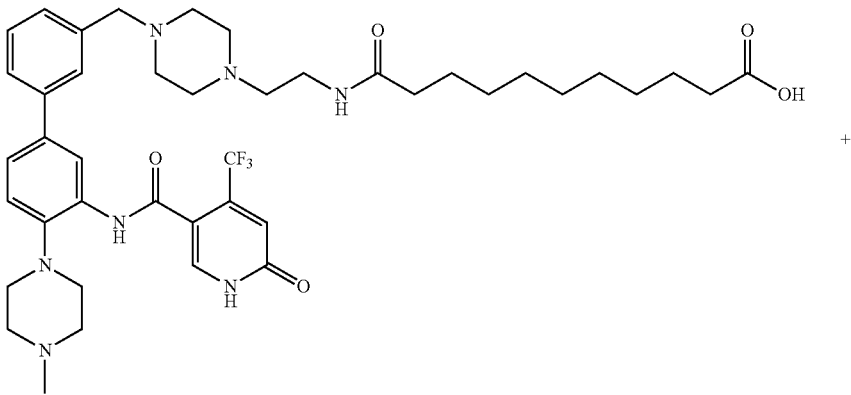

Intermediate 49

-continued

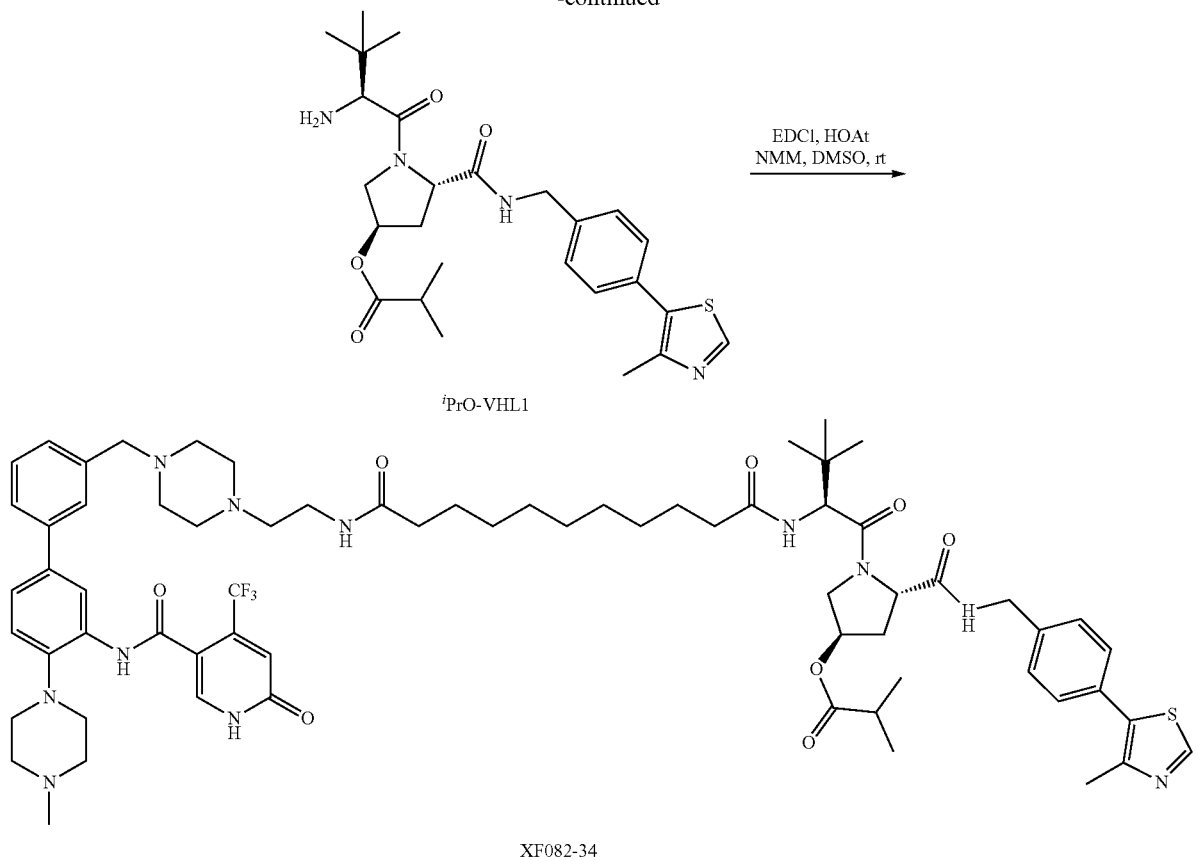

*iPrO-VHL1*

XF082-34

XF082-34 was synthesized following the standard procedures for preparing XF082-33 from intermediate 49 (15.9 mg, 0.02 mmol), *i*PrO-VHL1 (10 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirring overnight at room temperature, the resulting mixture was purified by preparative HPLC (10%-100% methanol/0.1% TFA in H$_2$O) to afford XF082-34 as white solid in TFA salt form (14.2 mg, yield 56%). $^1$H NMR (600 MHz, CD$_3$OD) δ 9.01 (s, 1H), 8.26 (d, J=2.2 Hz, 1H), 8.03 (s, 1H), 7.76 (s, 1H), 7.71 (d, J=7.8 Hz, 1H), 7.57-7.50 (m, 2H), 7.49-7.44 (m, 3H), 7.42 (d, J=8.1 Hz, 2H), 7.38 (d, J=8.3 Hz, 1H), 6.94 (s, 1H), 5.36 (s, 1H), 4.59-4.50 (m, 3H), 4.36 (d, J=15.4 Hz, 1H), 4.24 (s, 2H), 4.13 (d, J=11.8 Hz, 1H), 3.91 (dd, J=11.8, 4.0 Hz, 1H), 3.61 (d, J=11.8 Hz, 2H), 3.47 (t, J=6.0 Hz, 2H), 3.29-3.28 (m, 7H), 3.16 (t, J=12.7 Hz, 2H), 3.07 (t, J=6.0 Hz, 2H), 2.96 (s, 3H), 2.65 (s, 1H), 2.53 (p, J=6.9 Hz, 1H), 2.48 (s, 3H), 2.37 (dd, J=13.7, 7.7 Hz, 1H), 2.31-2.15 (m, 5H), 1.58 (s, 5H), 1.30 (s, 13H), 1.13 (d, J=7.0 Hz, 6H), 1.03 (s, 9H). HRMS (m/z) for C$_{68}$H$_{91}$F$_3$N$_{11}$O$_8$S$^+$ [M+H]$^+$: calculated 1278.6719. found 1278.6687.

Example 367: Synthesis of Intermediate 50

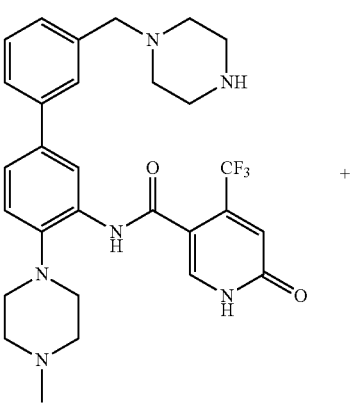

Intermediate 1

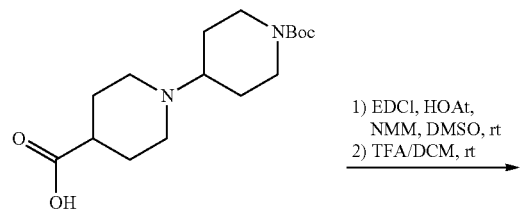

1) EDCI, HOAt, NMM, DMSO, rt
2) TFA/DCM, rt

889 -continued

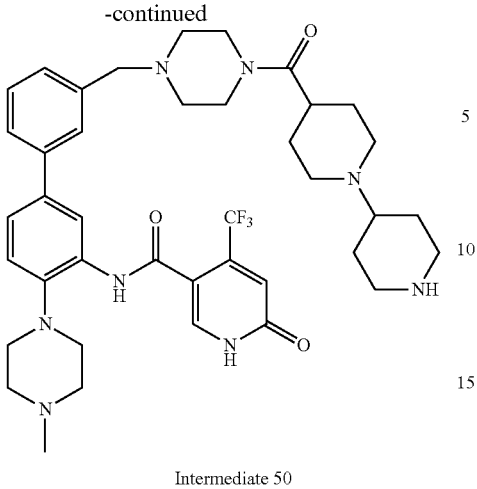

Intermediate 50

To the solution of intermediate 1 (33.3 mg, 0.06 mmol) in DMSO (1 mL) were added 1'-(tert-butoxycarbonyl)-[1,4'-bipiperidine]-4-carboxylic acid (18.7 mg, 0.06 mmol, 1.5 equiv), EDCI (1-ethyl-3-(3-dimethylaminopropyl)carbodiimide) (17.3 mg, 0.09 mmol, 1.5 equiv), HOAt (1-hydroxy-7-azabenzo-triazole) (12.2 mg, 0.09 mmol, 1.5 equiv), and NMM (N-Methylmorpholine) (18.2 mg, 0.18 mmol, 3.0 equiv). After being stirring for 3 h at room temperature, the resulting mixture was purified by preparative HPLC (10%-100% methanol/0.1% TFA in $H_2O$) to afford the crude product. This product was dissolved in DCM (2 mL) and TFA (2 mL). After being stirring for 1 h at room temperature, the resulting mixture was purified by preparative HPLC (10%-100% methanol/0.1% TFA in $H_2O$) to afford Intermediate 50 (XF061-32) as white solid in TFA salt form (28.6 mg, yield 64%). $^1$H NMR (600 MHz, $CD_3OD$) δ 8.27 (d, J=2.2 Hz, 1H), 8.04 (s, 1H), 7.81 (d, J=1.8 Hz, 1H), 7.78 (d, J=7.9 Hz, 1H), 7.62-7.53 (m, 2H), 7.51 (d, J=7.6 Hz, 1H), 7.39 (d, J=8.4 Hz, 1H), 6.93 (s, 1H), 4.46 (s, 2H), 3.68-3.53 (m, 7H), 3.52-3.32 (m, 7H), 3.28 (s, 2H), 3.22-3.02 (m, 8H), 2.96 (s, 3H), 2.36 (d, J=13.2 Hz, 2H), 2.03 (dt, J=21.2, 13.5 Hz, 8H). HRMS (m/z) for $C_{40}H_{52}F_3N_8O_3^+$ [M+H]$^+$: calculated 749.4109. found 749.4079.

Example 368: Synthesis of Intermediate 51

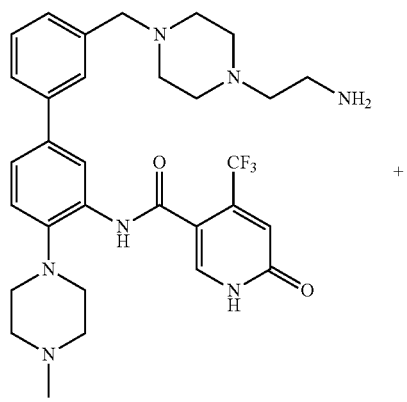

Intermediate 2

890 -continued

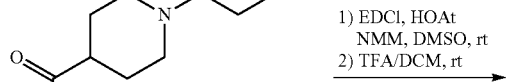

1) EDCl, HOAt NMM, DMSO, rt
2) TFA/DCM, rt

Intermediate 51

Intermediate 51 was synthesized following the standard procedures for preparing Intermediate 50 from intermediate 2 (35.8 mg, 0.06 mmol), 1'-(tert-butoxycarbonyl)-[1,4'-bipiperidine]-4-carboxylic acid (18.7 mg, 0.06 mmol, 1.5 equiv), EDCI (1-ethyl-3-(3-dimethylaminopropyl)carbodiimide) (17.3 mg, 0.09 mmol, 1.5 equiv), HOAt (1-hydroxy-7-azabenzo-triazole) (12.2 mg, 0.09 mmol, 1.5 equiv), and NMM (N-Methylmorpholine) (18.2 mg, 0.18 mmol, 3.0 equiv). Intermediate 51 was obtained by preparative HPLC (10%-100% methanol/0.1% TFA in $H_2O$) in yield of (24.8 mg, 52%). $^1$H NMR (600 MHz, $CD_3OD$) δ 8.25 (s, 1H), 8.03 (s, 1H), 7.78 (s, 1H), 7.73 (d, J=7.5 Hz, 1H), 7.54 (d, J=7.3 Hz, 2H), 7.47 (d, J=7.5 Hz, 1H), 7.38 (d, J=8.2 Hz, 1H), 6.94 (s, 1H), 4.31 (s, 2H), 3.72-3.53 (m, 6H), 3.51 (s, 2H), 3.46-3.37 (m, 6H), 3.32-3.28 (m, 4H), 3.21-3.02 (m, 8H), 2.96 (d, J=3.9 Hz, 3H), 2.37 (d, J=12.9 Hz, 2H), 2.12 (d, J=15.1 Hz, 2H), 2.06-2.01 (m, 8H). HRMS (m/z) for $C_{42}H_{57}F_3N_9O_3^+$ [M+H]$^+$: calculated 792.4531. found 792.4578.

Example compounds are set forth in Table 1, below.

In Table 1, the left portion of the structure of the WDR5 disruptors/degraders binds to WDR5 (as, e.g., OICR-9429 (Getlik et al., 2016), MM-589 (Karatas et al., 2017), compound B154 (US20180086767A1), and their derivatives), and the right portion of the structure recruits the ubiquitination machinery to WDR5, which induces poly-ubiquitination and degradation of WDR5 at the proteasome.

TABLE 1

| Examples | Compound ID | Structure | Chemical Name |
|---|---|---|---|
| 3 | XF048-117 | 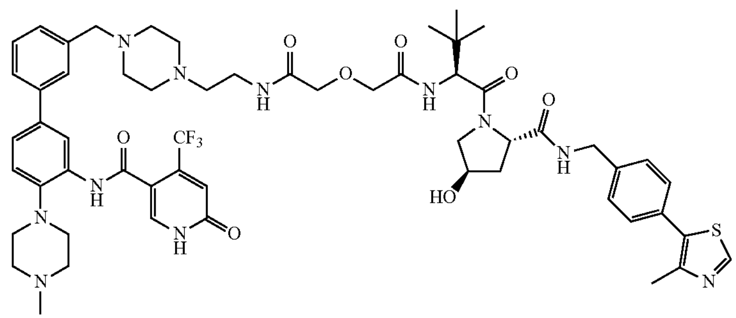 [SMILES: Cc1ncsc1-c1ccc(CNC(=O)[C@@H]2C[C@@H](O)CN2C(=O)[C@@H](NC(=O)COCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | N-(3'-((4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 4 | XF048-118 | 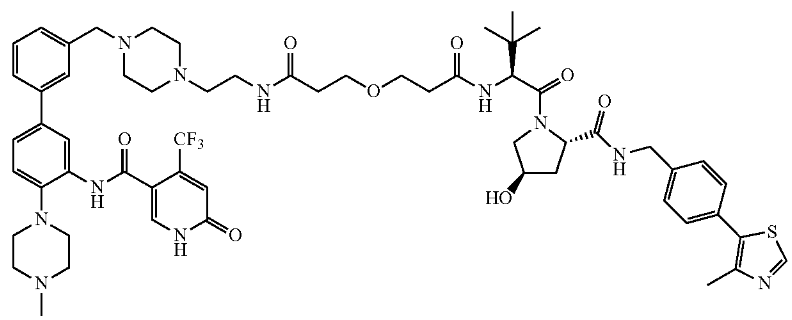 [SMILES: Cc1ncsc1-c1ccc(CNC(=O)[C@@H]2C[C@@H](O)CN2C(=O)[C@@H](NC(=O)CCOCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | N-(3'-((4-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 5 | XF048-119 | 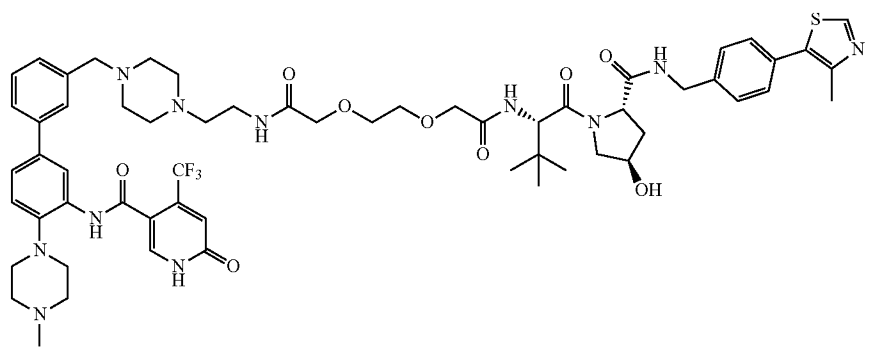 [SMILES: Cc1ncsc1-c1ccc(CNC(=O)[C@@H]2C[C@@H](O)CN2C(=O)[C@@H](NC(=O)COCCOCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | N-(3'-((4-((S)-13-((2S,4R)-4-hydroxy-2-((4-(4-methylthiazol-5-yl)benzyl)carbamoyl)pyrrolidine-1-carbonyl)-14,14-dimethyl-4,11-dioxo-6,9-dioxa-3,12-diazapentadecyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 6 | XF048-120 | 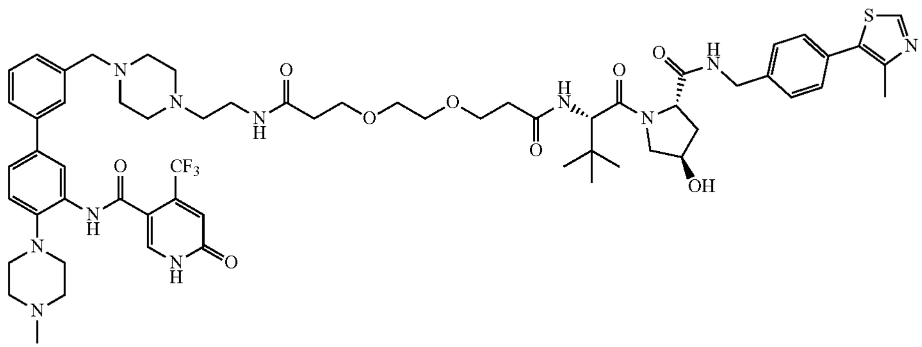 | N-(3'-((4-((S)-15-((2S,4R)-4-hydroxy-2-((4-(4-methylthiazol-5-yl)benzyl)carbamoyl)pyrrolidine-1-carbonyl)-16,16-dimethyl-4,13-dioxo-7,10-dioxa-3,14-diazaheptadecyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 7 | XF048-121 | 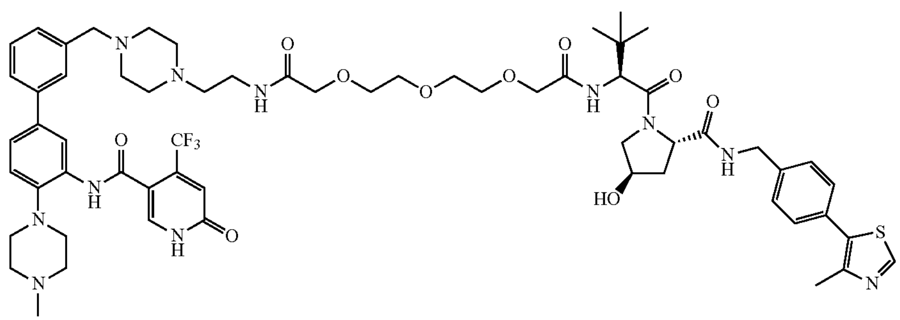 [SMILES: Cc1ncsc1-c1ccc(CNC(=O)[C@@H]2C[C@@H](O)CN2C(=O)[C@@H](NC(=O)COCCOCCOCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | N-(3'-((4-((S)-16-((2S,4R)-4-hydroxy-2-((4-(4-methylthiazol-5-yl)benzyl)carbamoyl)pyrrolidine-1-carbonyl)-17,17-dimethyl-4,14-dioxo-6,9,12-trioxa-3,15-diazaoctadecyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 8 | XF048-122 | 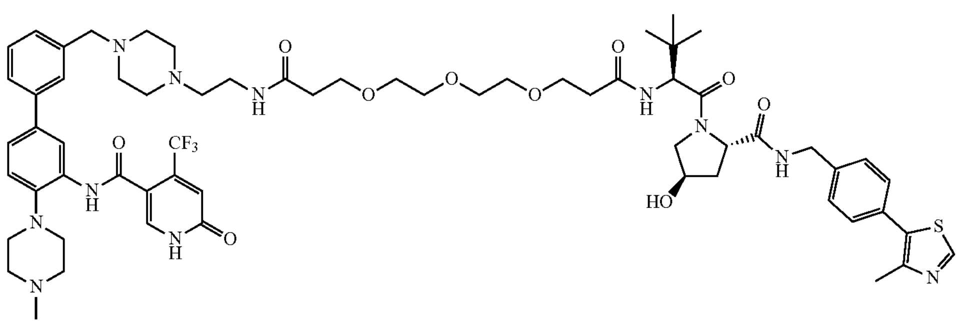 | N-(3'-((4-((S)-18-((2S,4R)-4-hydroxy-2-((4-(4-methylthiazol-5-yl)benzyl)carbamoyl)pyrrolidine-1-carbonyl)-19,19-dimethyl-4,16-dioxo-7,10,13-trioxa-3,17-diazaicosyl)piperazin-1-yl)methyl)-[1,1'-biphenyl]-4-(4-methylpiperazin-1-yl)-3-yl)-6-oxo-4-(trifluoromethyl)-1,6-dihydropyridine-3-carboxamide |

TABLE 1-continued

| Example | Compound ID | Structure | Chemical Name |
|---|---|---|---|
| 9 | XF048-123 | 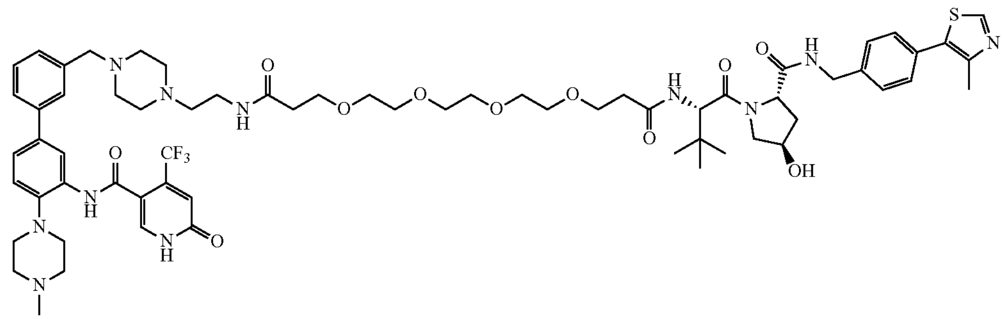 [SMILES: Cc1ncsc1-c1ccc(CNC(=O)[C@@H]2C[C@@H](O)CN2C(=O)[C@@H](NC(=O)CCOCCOCCOCCOCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | N1-(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N16-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)-4,7,10,13-tetraoxahexadecanediamide |
| 10 | XF048-124 | 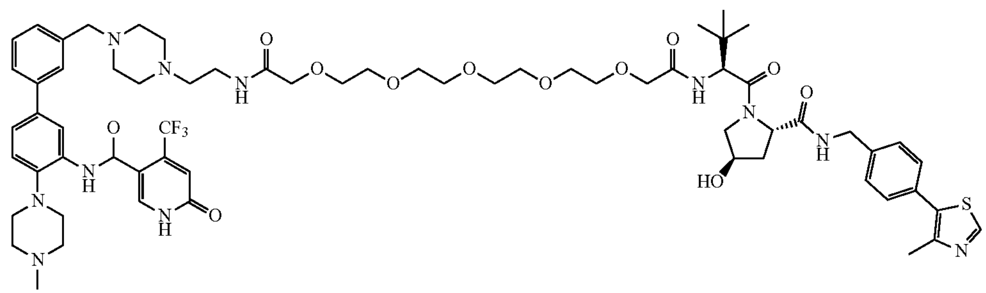 [SMILES: Cc1ncsc1-c1ccc(CNC(=O)[C@@H]2C[C@@H](O)CN2C(=O)[C@@H](NC(=O)COCCOCCOCCOCCOCC(=O)NCCN2CCN(Cc3cccc(-c4ccc(N5CCN(C)CC5)c(NC(O)c5c[nH]c(=O)cc5C(F)(F)F)c4)c3)CC2)C(C)(C)C)cc1] | N1-(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N17-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)-3,6,9,12,15-pentaoxaheptadecanediamide |
| 11 | XF048-125 | 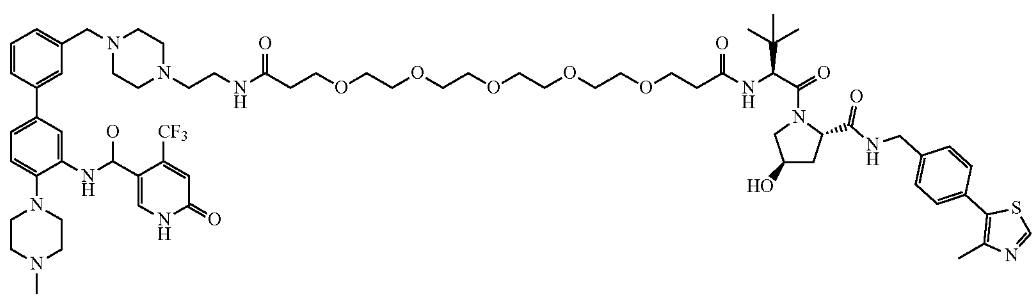 [SMILES: Cc1ncsc1-c1ccc(CNC(=O)[C@@H]2C[C@@H](O)CN2C(=O)[C@@H](NC(=O)CCOCCOCCOCCOCCOCCC(=O)NCCN2CCN(Cc3cccc(-c4ccc(N5CCN(C)CC5)c(NC(O)c5c[nH]c(=O)cc5C(F)(F)F)c4)c3)CC2)C(C)(C)C)cc1] | N1-(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N19-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)-4,7,10,13,16-pentaoxanonadecanediamide |

TABLE 1-continued

| Examples | Compound ID | Structure | Chemical Name |
|---|---|---|---|
| 12 | XF048-126 | 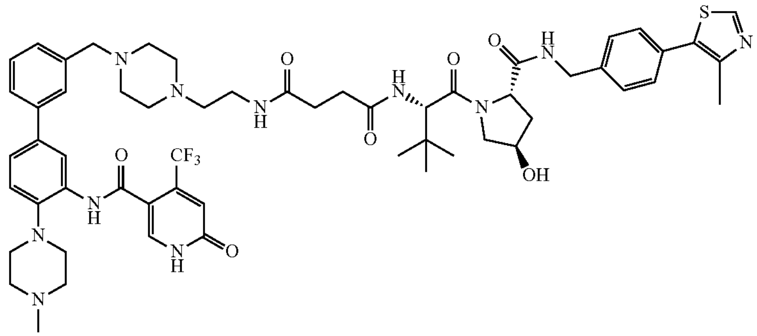 [SMILES: Cc1ncsc1-c1ccc(CNC(=O)[C@@H]2C[C@@H](O)CN2C(=O)[C@@H](NC(=O)CCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^4$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)succinamide |
| 13 | XF048-127 | 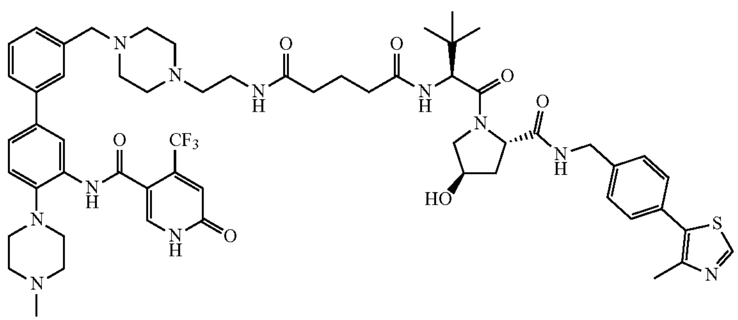 [SMILES: Cc1ncsc1-c1ccc(CNC(=O)[C@@H]2C[C@@H](O)CN2C(=O)[C@@H](NC(=O)CCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^5$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)glutaramide |
| 14 | XF048-128 | 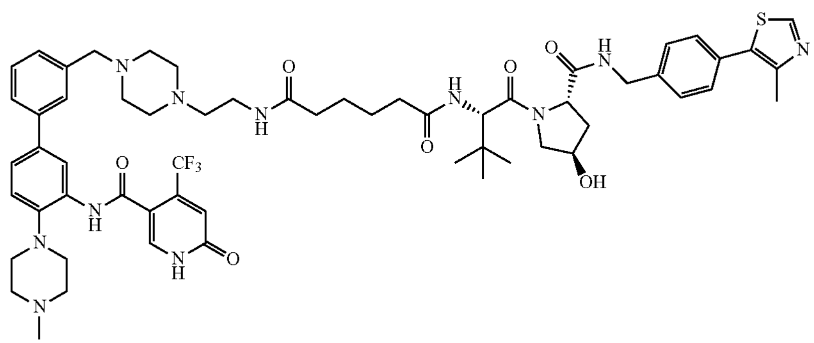 [SMILES: Cc1ncsc1-c1ccc(CNC(=O)[C@@H]2C[C@@H](O)CN2C(=O)[C@@H](NC(=O)CCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^6$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)adipamide |

TABLE 1-continued

| Examples | Compound ID | Structure | Chemical Name |
|---|---|---|---|
| 15 | XF048-129 | 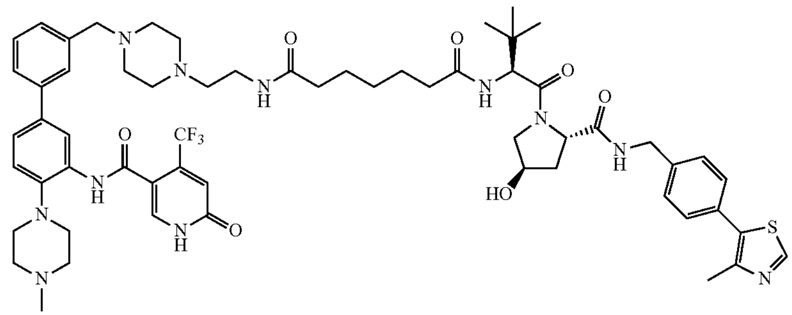 | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁷-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)heptanediamide |
| 16 | XF048-130 | 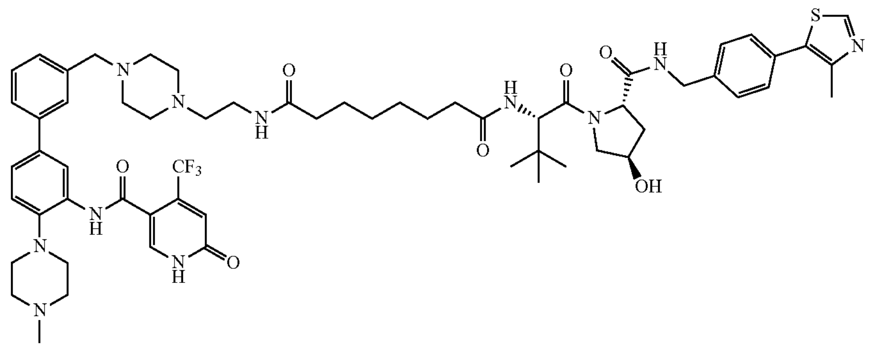 | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁸-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)octanediamide |
| 17 | XF048-131 | 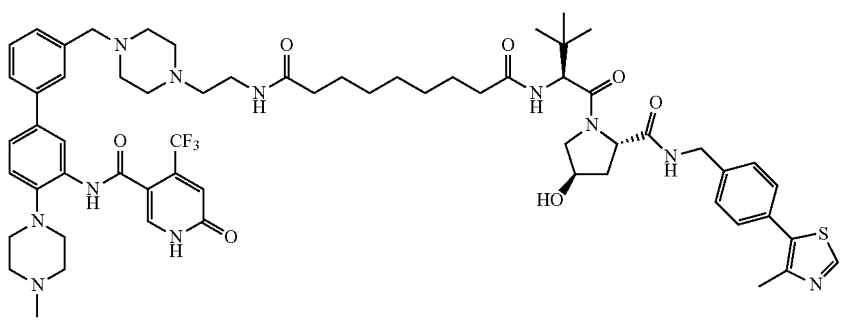 [SMILES: Cc1ncsc1-c1ccc(CNC(=O)[C@@H]2C[C@@H](O)CN2C(=O)[C@@H](NC(=O)CCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁹-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)nonanediamide |

TABLE 1-continued

| Examples | Compound ID | Structure | Chemical Name |
|---|---|---|---|
| 18 | XF048-132 | 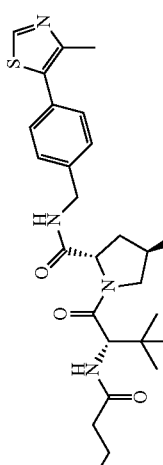 | N$^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N$^{10}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)decanediamide |
| 19 | XF048-133 | 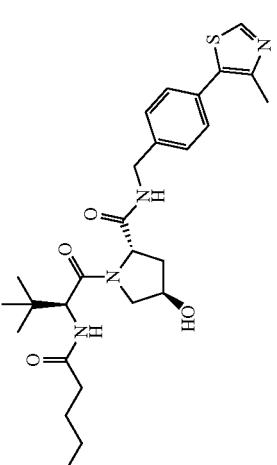 | N$^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N$^{11}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |

TABLE 1-continued

| Examples | Compound ID | Structure | Chemical Name |
|---|---|---|---|
| 20 | XF048-134 | 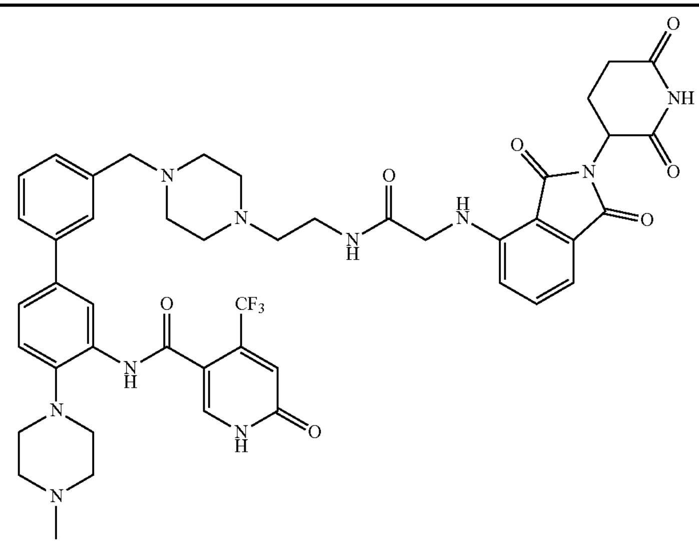 | N-(3'-((4-(2-(2-(2-(2,6-dioxopiperidin-3-yl)-1,3-dioxoisoindolin-4-yl)amino)acetamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 21 | XF048-135 | 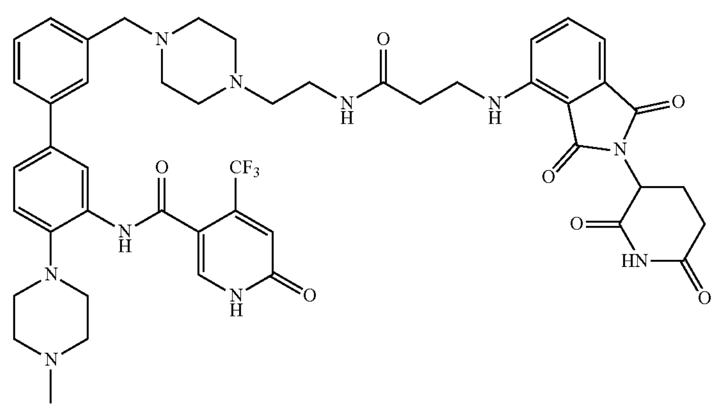 | N-(3'-((4-(2-(3-((2-(2,6-dioxopiperidin-3-yl)-1,3-dioxoisoindolin-4-yl)amino)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 22 | XF048-136 | 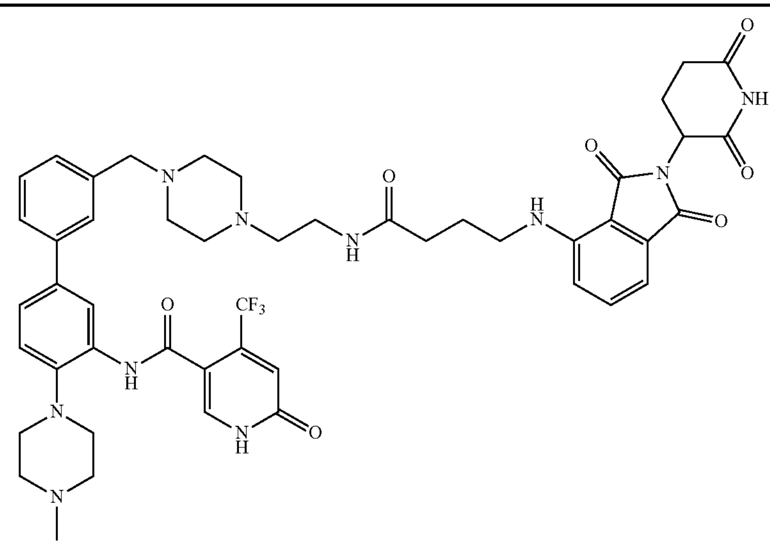 | N-(3'-((4-(2-(4-(2-(2,6-dioxopiperidin-3-yl)-1,3-dioxoisoindolin-4-yl)amino)butanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 23 | XF048-137 | 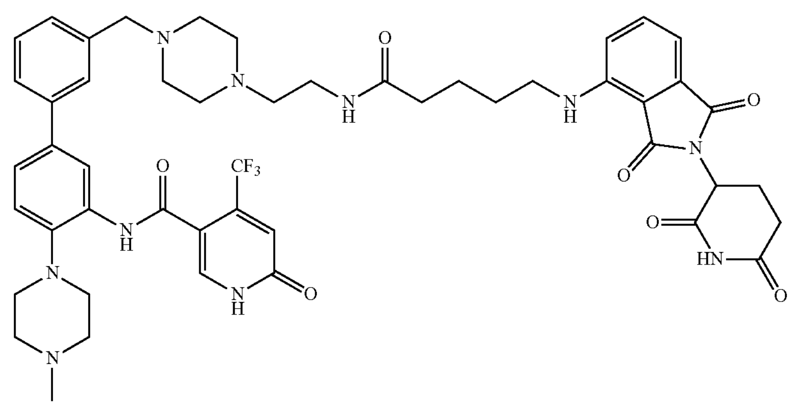 [SMILES: CN1CCN(c2ccc(-c3cccc(CN4CCN(CCNC(=O)CCCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(2-(5-((2-(2,6-dioxopiperidin-3-yl)-1,3-dioxoisoindolin-4-yl)amino)pentanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 24 | XF048-138 | 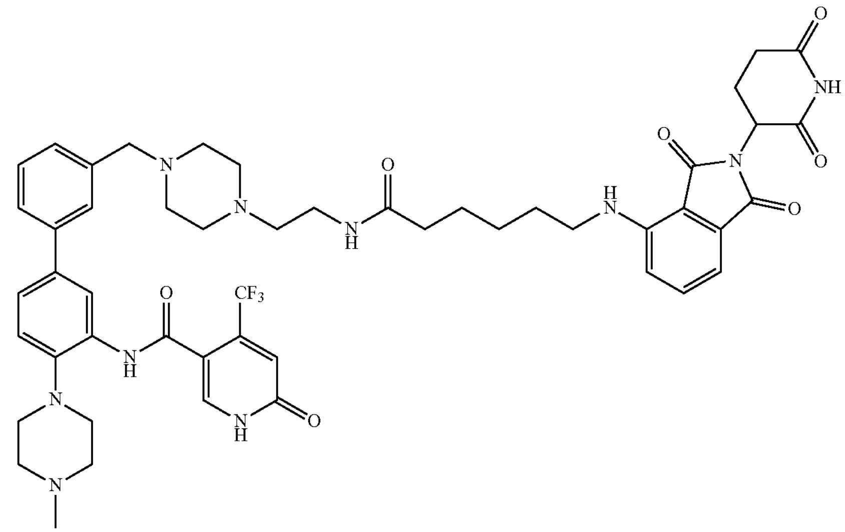 [SMILES: CN1CCN(c2ccc(-c3cccc(CN4CCN(CCNC(=O)CCCCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(2-(6-((2-(2,6-dioxopiperidin-3-yl)-1,3-dioxoisoindolin-4-yl)amino)hexanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 25 | XF048-139 | 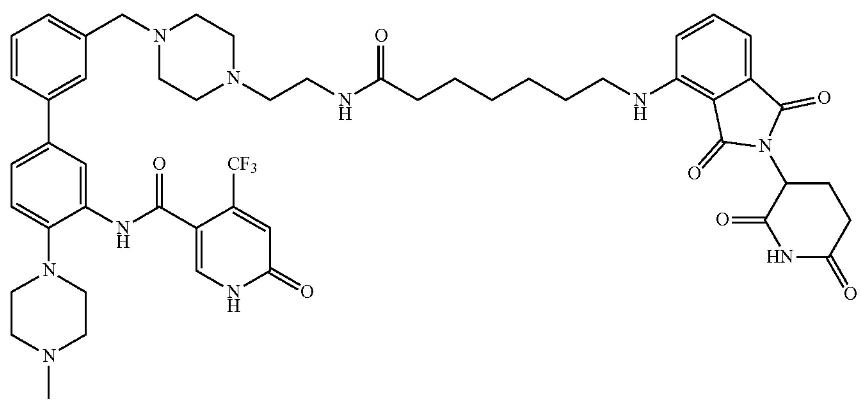 | N-(3'-((4-(2-(7-((2-(2,6-dioxopiperidin-3-yl)-1,3-dioxoisoindolin-4-yl)amino)heptanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 26 | XF048-140 | 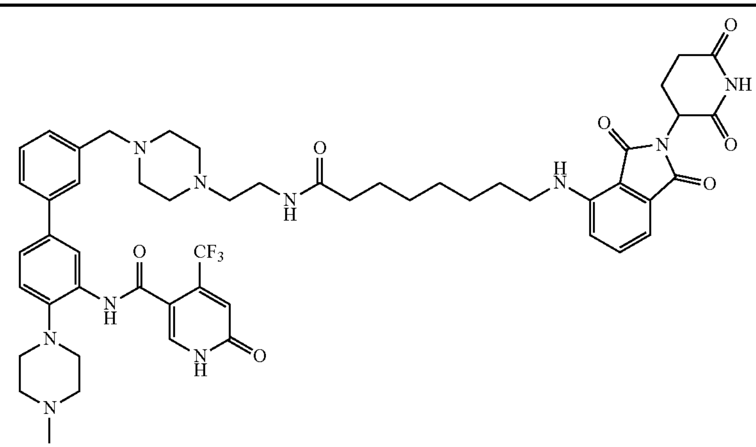 | N-(3'-((4-(2-(8-((2-(2,6-dioxopiperidin-3-yl)-1,3-dioxoisoindolin-4-yl)amino)octanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 27 | XF048-141 | 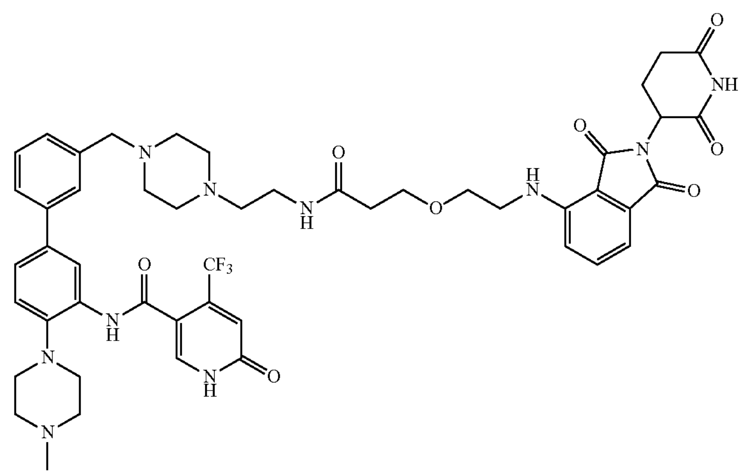 [SMILES: CN1CCN(c2ccc(-c3cccc(CN4CCN(CCNC(=O)CCOCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(2-(3-(2-(2-(2,6-dioxopiperidin-3-yl)-1,3-dioxoisoindolin-4-yl)amino)ethoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 28 | XF048-142 | 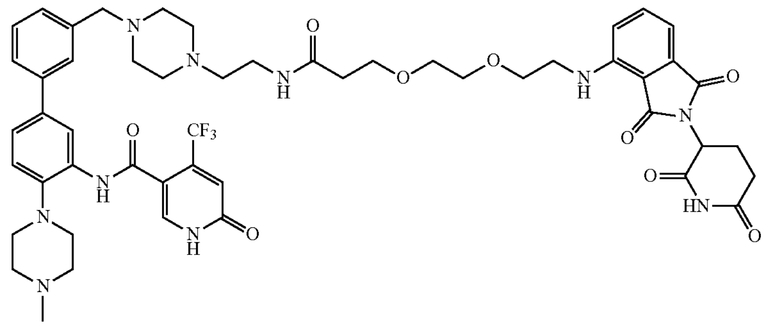 [SMILES: CN1CCN(c2ccc(-c3cccc(CN4CCN(CCNC(=O)CCOCCOCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(2-(3-(2-(2-((2-(2,6-dioxopiperidin-3-yl)-1,3-dioxoisoindolin-4-yl)amino)ethoxy)ethoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 29 | XF048-143 | 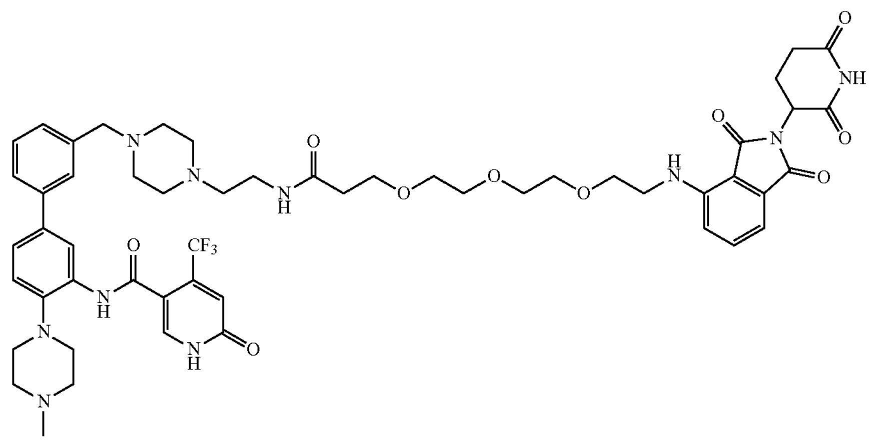 [SMILES: CN1CCN(c2ccc(-c3cccc(CN4CCN(CCNC(=O)CCOCCOCCOCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 30 | XF048-144 | 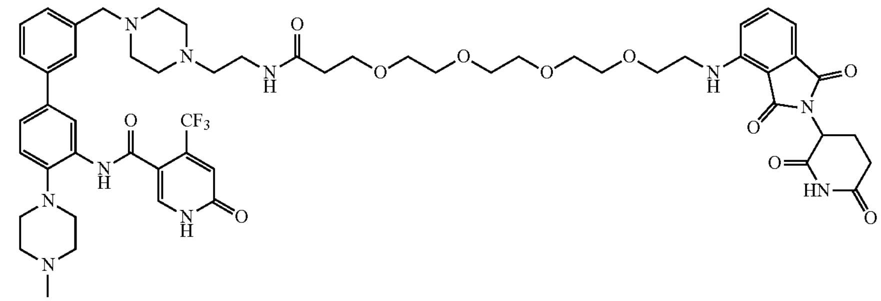 [SMILES: CN1CCN(c2ccc(-c3cccc(CN4CCN(CCNC(=O)CCOCCOCCOCCOCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(1-((2-(2,6-dioxopiperidin-3-yl)-1,3-dioxoisoindolin-4-yl)amino)-15-oxo-3,6,9,12-tetraoxa-16-azaoctadecan-18-yl)methyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 31 | XF048-145 | 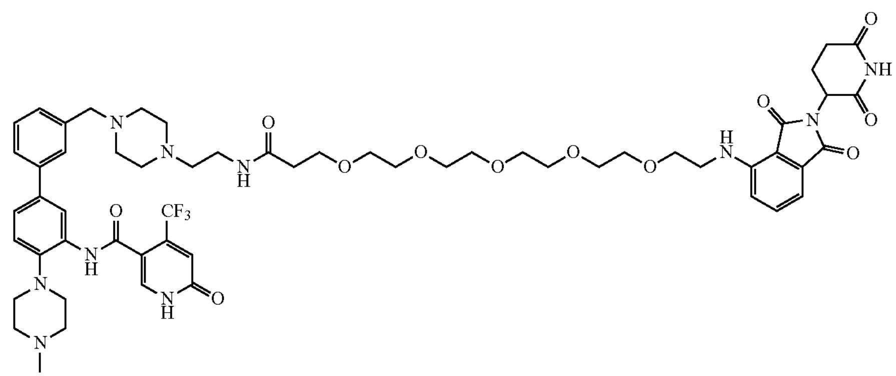 | N-(3'-((4-(1-((2-(2,6-dioxopiperidin-3-yl)-1,3-dioxoisoindolin-4-yl)amino)-18-oxo-3,6,9,12,15-pentaoxa-19-azahenicosan-21-yl)methyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 32 | XF050-166 | 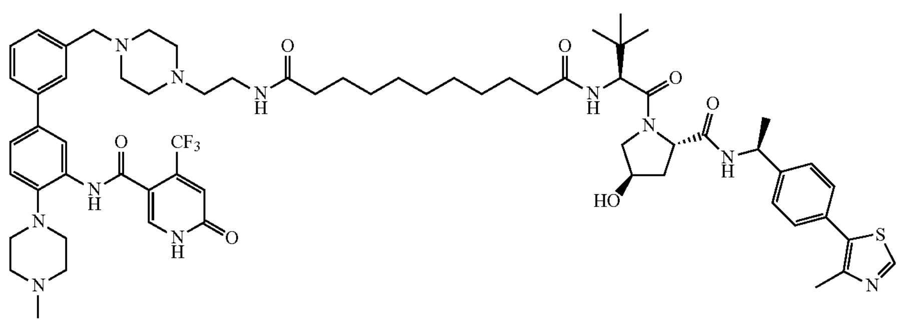 [SMILES: Cc1ncsc1-c1ccc([C@H](C)NC(=O)[C@@H]2C[C@@H](O)CN2C(=O)[C@@H](NC(=O)CCCCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | N¹-(S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-N¹¹-(2-(4-(4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |

TABLE 1-continued

| Examples | Compound ID | Structure | Chemical Name |
|---|---|---|---|
| 36 | XF050-169 | 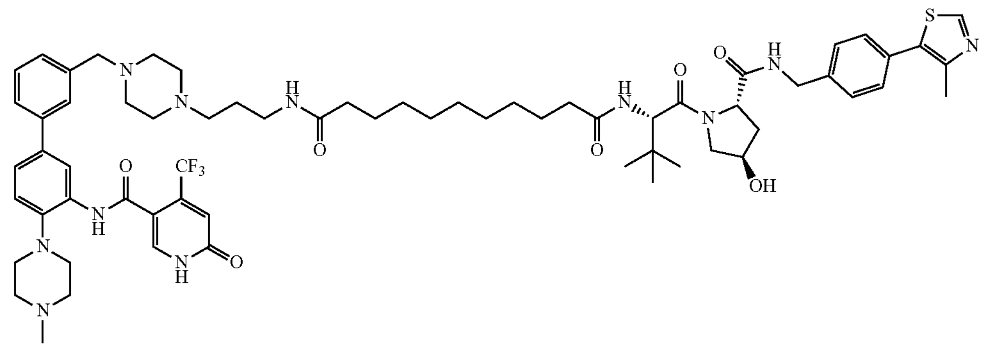 [SMILES: Cc1ncsc1-c1ccc(CNC(=O)[C@@H]2C[C@@H](O)CN2C(=O)[C@@H](NC(=O)CCCCCCCCCC(=O)NCCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{11}$-(3-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)propyl)undecanediamide |
| 37 | XF050-165 | 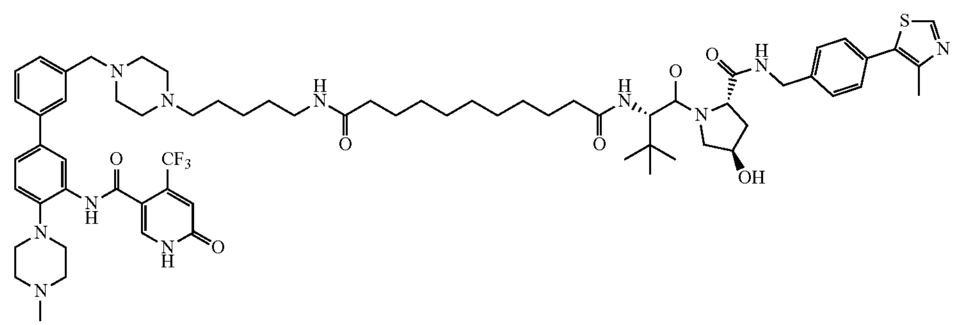 | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{11}$-(5-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)pentyl)undecanediamide |
| 38 | XF050-159 | 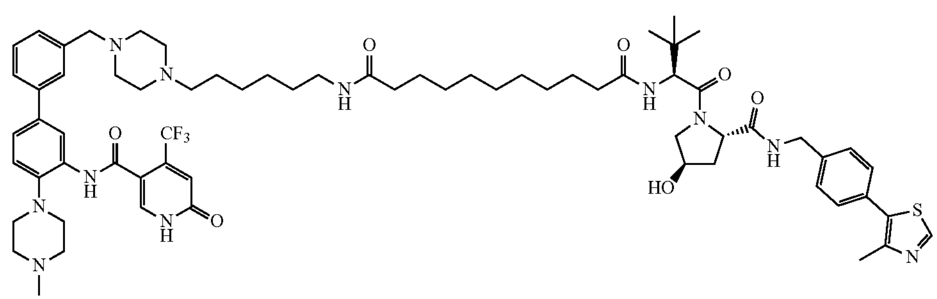 [SMILES: Cc1ncsc1-c1ccc(CNC(=O)[C@@H]2C[C@@H](O)CN2C(=O)[C@@H](NC(=O)CCCCCCCCCC(=O)NCCCCCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{11}$-(6-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)hexyl)undecanediamide |

TABLE 1-continued

| Examples | Compound ID | Structure | Chemical Name |
|---|---|---|---|
| 39 | XF050-160 | 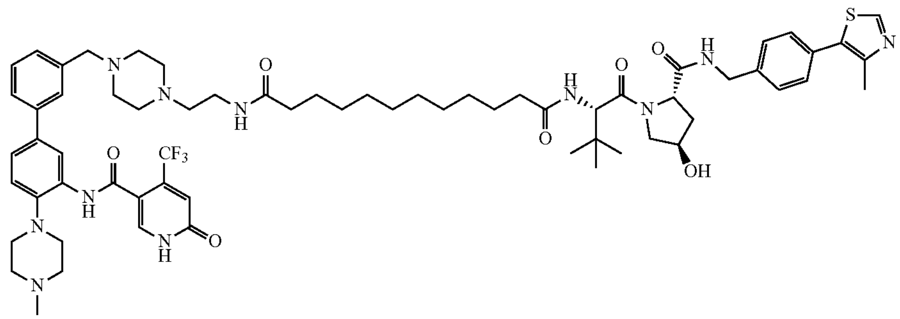 [SMILES: Cc1ncsc1-c1ccc(CNC(=O)[C@@H]2C[C@@H](O)CN2C(=O)[C@@H](NC(=O)CCCCCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{12}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)dodecanediamide |
| 40 | XF050-161 | 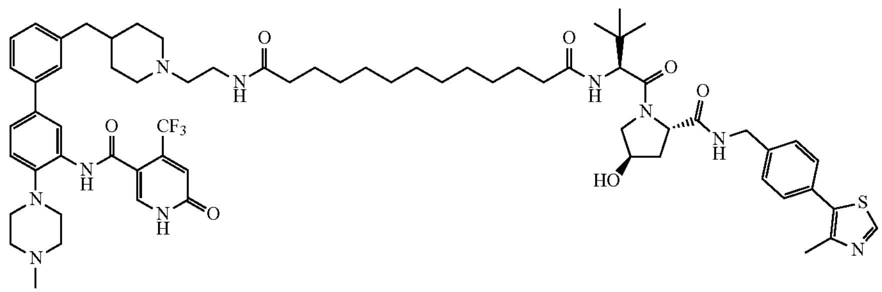 [SMILES: Cc1ncsc1-c1ccc(CNC(=O)[C@@H]2C[C@@H](O)CN2C(=O)[C@@H](NC(=O)CCCCCCCCCCCC(=O)NCCN2CCC(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{13}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)tridecanediamide |
| 41 | XF050-162 | 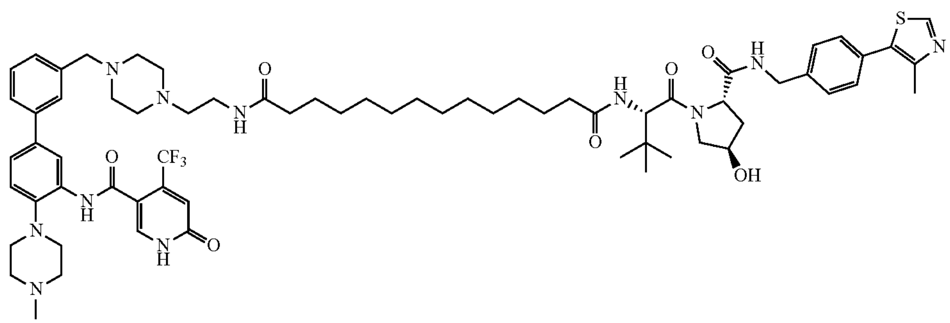 [SMILES: Cc1ncsc1-c1ccc(CNC(=O)[C@@H]2C[C@@H](O)CN2C(=O)[C@@H](NC(=O)CCCCCCCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{14}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)tetradecanediamide |

TABLE 1-continued

| Examples | Compound ID | Structure | Chemical Name |
|---|---|---|---|
| 42 | XF050-156 | 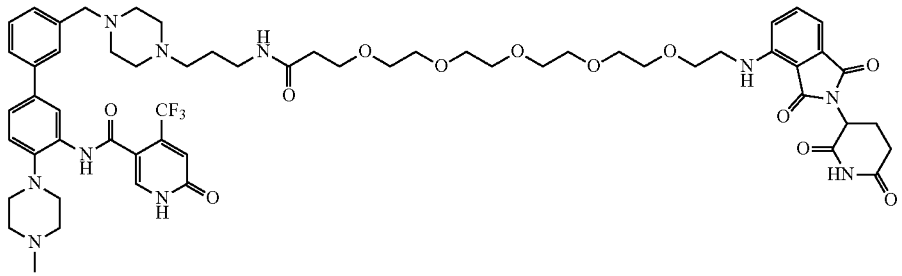 | N-(3'-((4-(1-((2-(2,6-dioxopiperidin-3-yl)-1,3-dioxoisoindolin-4-yl)amino)-18-oxo-3,6,9,12,15-pentaoxa-19-azadocosan-22-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 43 | XF050-164 | 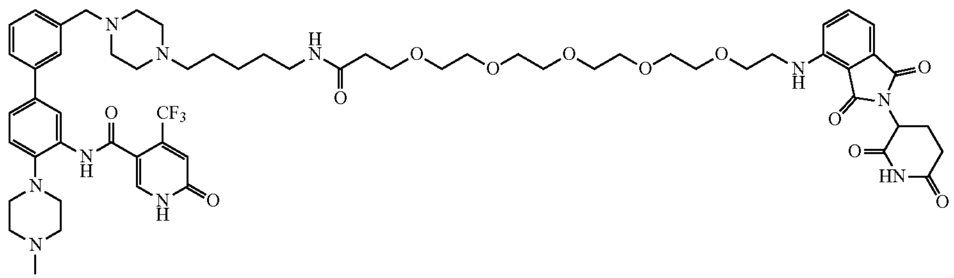 [SMILES: CN1CCN(c2ccc(-c3cccc(CN4CCN(CCCCCNC(=O)CCOCCOCCOCCOCCOCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(1-((2-(2,6-dioxopiperidin-3-yl)-1,3-dioxoisoindolin-4-yl)amino)-18-oxo-3,6,9,12,15-pentaoxa-19-azatetracosan-24-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 44 | XF050-158 | 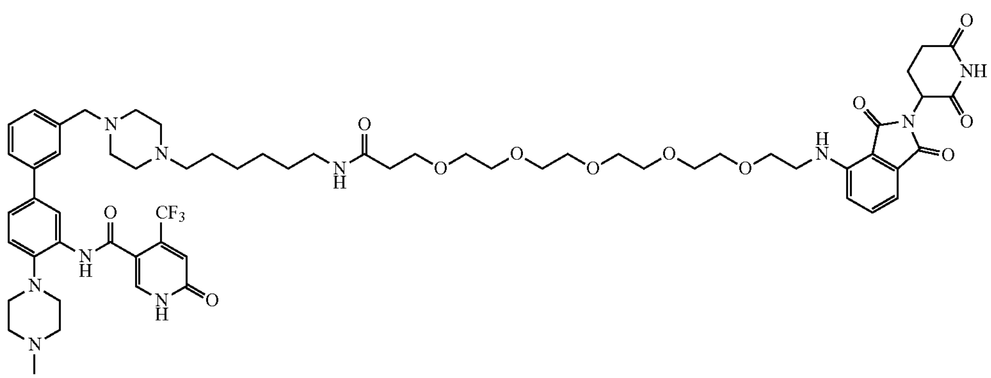 | N-(3'-((4-(1-((2-(2,6-dioxopiperidin-3-yl)-1,3-dioxoisoindolin-4-yl)amino)-18-oxo-3,6,9,12,15-pentaoxa-19-azapentacosan-25-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 45 | XF056-23 | 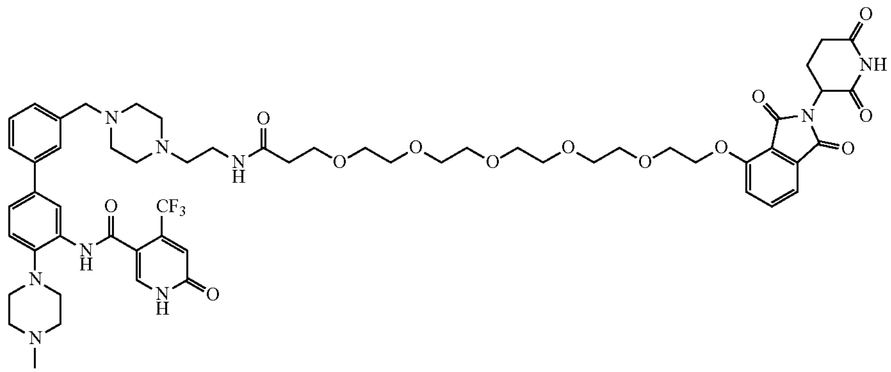 | N-(3'-((4-(1-((2-(2,6-dioxopiperidin-3-yl)-1,3-dioxoisoindolin-4-yl)oxy)-18-oxo-3,6,9,12,15-pentaoxa-19-azahenicosan-21-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 46 | XF056-25 | 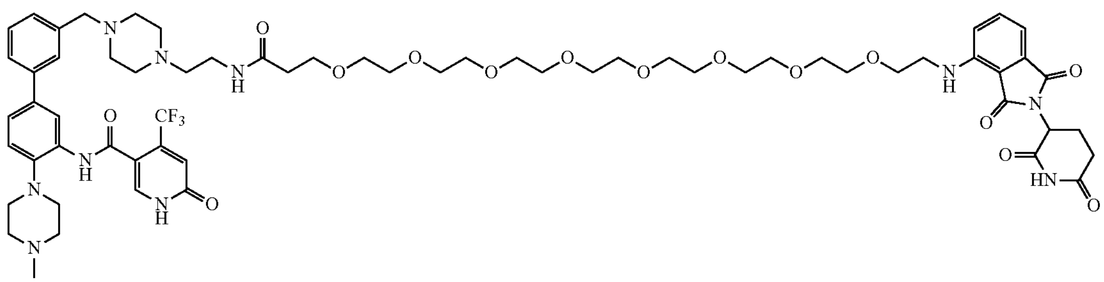 [SMILES: CN1CCN(c2ccc(-c3cccc(CN4CCN(CCNC(=O)CCOCCOCCOCCOCCOCCOCCOCCOCCNc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(1-(2-(2,6-dioxopiperidin-3-yl)-1,3-dioxoisoindolin-4-yl)amino)-27-oxo-3,6,9,12,15,18,21,24-octaoxa-28-azatriacontan-30-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 47 | XF056-26 | 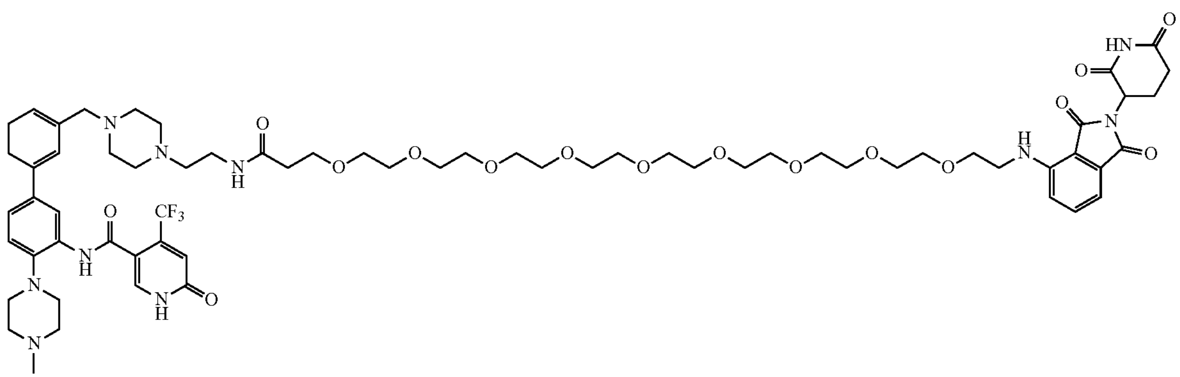 [SMILES: CN1CCN(c2ccc(C3=CC(CN4CCN(CCNC(=O)CCOCCOCCOCCOCCOCCOCCOCCOCCOCCNc5cccc6c5C(=O)N(C5CCC(=O)NC5=O)C6=O)CC4)=CCC3)cc2NC(=O)c2c[nH]c(=O)cc2C(F)(F)F)CC1] | N-(3'-((4-(1-((2-(2,6-dioxopiperidin-3-yl)-1,3-dioxoisoindolin-4-yl)amino)-30-oxo-3,6,9,12,15,18,21,24,27-nonaoxa-31-azatritriacontan-33-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 48 | XF056-24 | 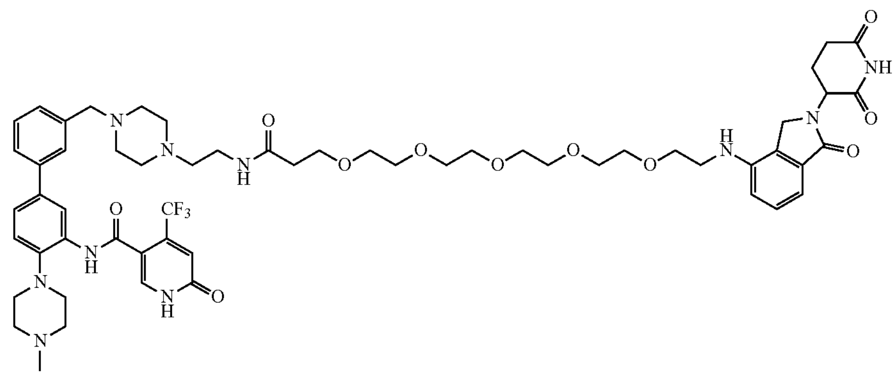 [SMILES: CN1CCN(c2ccc(-c3cccc(CN4CCN(CCNC(=O)CCOCCOCCOCCOCCOCCNc5cccc6c5CN(C5CCC(=O)NC5=O)C6=O)CC4)c3)cc2NC(=O)c2c[nH]c(=O)cc2C(F)(F)F)CC1] | N-(3'-((4-(1-((2-(2,6-dioxopiperidin-3-yl)-1-oxoisoindolin-4-yl)amino)-18-oxo-3,6,9,12,15-pentaoxa-19-azahenicosan-21-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 49 | XF056-32 | 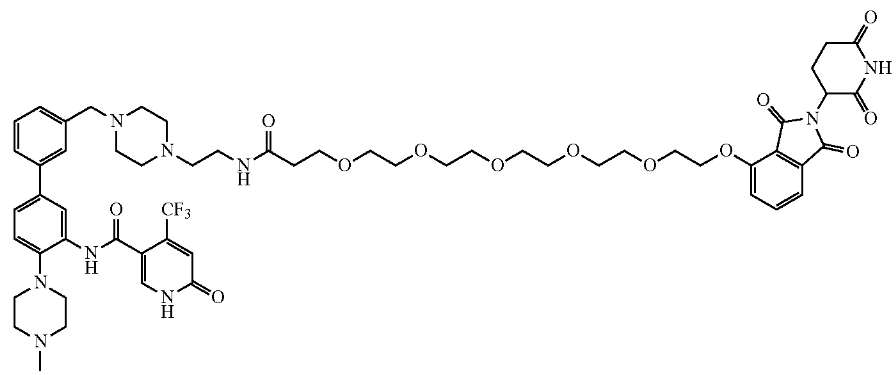 [SMILES: CN1CCN(c2ccc(-c3cccc(CN4CCN(CCNC(=O)CCOCCOCCOCCOCCOCCOc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(1-((2-(2,6-dioxopiperidin-3-yl)-1,3-dioxoisoindolin-4-yl)oxy)-18-oxo-3,6,9,12,15-pentaoxa-19-azahenicosan-21-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 50 | XF056-72 | 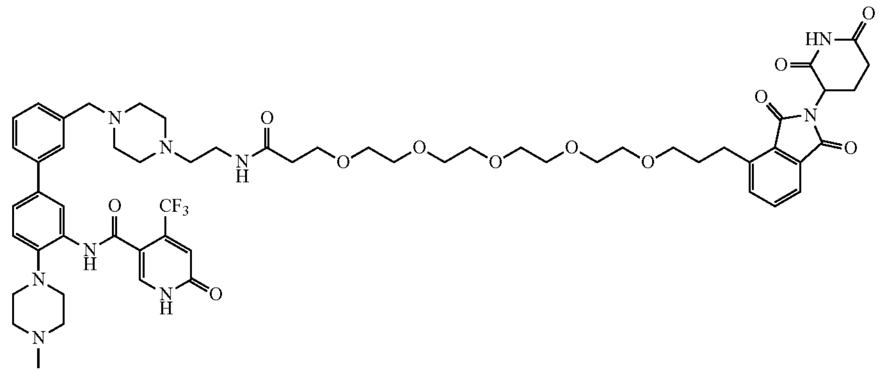 [SMILES: CN1CCN(c2ccc(-c3cccc(CN4CCN(CCNC(=O)CCOCCOCCOCCOCCOCCCc5cccc6c5C(=O)N(C5CCC(=O)NC5=O)C6=O)CC4)c3)cc2NC(=O)c2c[nH]c(=O)cc2C(F)(F)F)CC1] | N-(3'-((4-(22-(2-(2,6-dioxopiperidin-3-yl)-1,3-dioxoisoindolin-4-yl)-4-oxo-7,10,13,16,19-pentaoxa-3-azadocosyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 51 | XF056-38 | 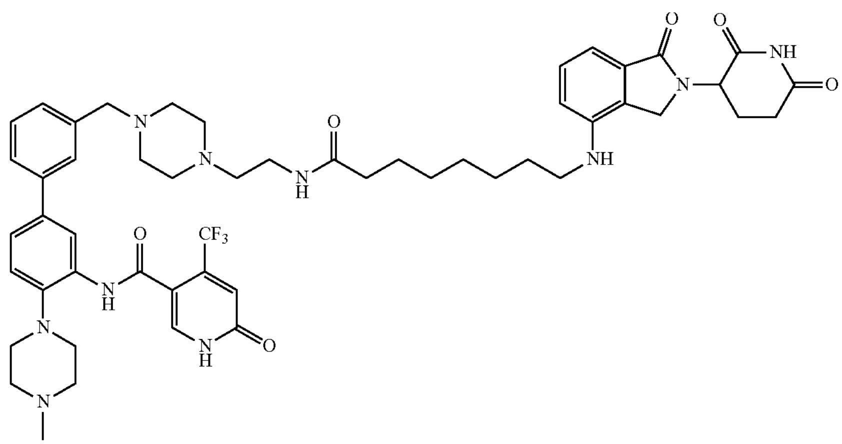 | N-(3'-((4-(2-(8-((2-(2,6-dioxopiperidin-3-yl)-1-oxoisoindolin-4-yl)amino)octanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 52 | XF056-39 | 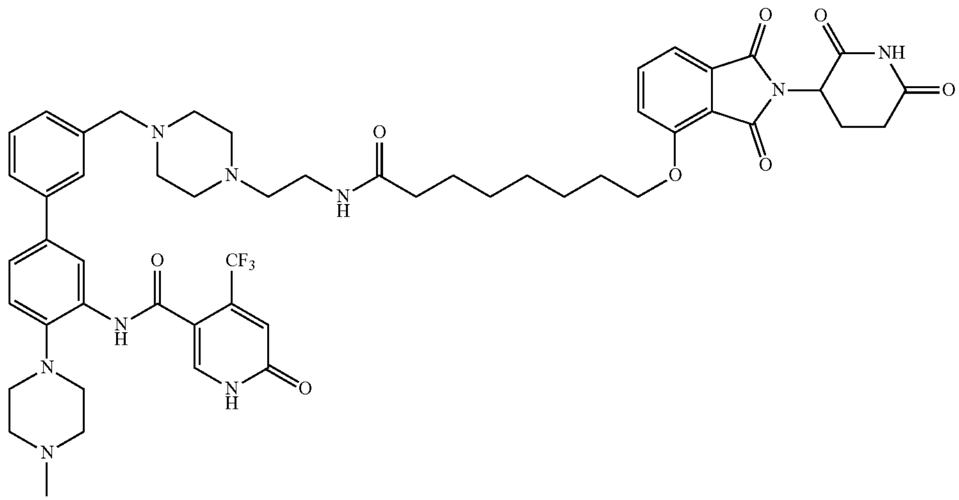 | N-(3'-((4-(2-(8-((2-(2,6-dioxopiperidin-3-yl)-1,3-dioxoisoindolin-4-yl)oxy)octanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 53 | XF056-104 | 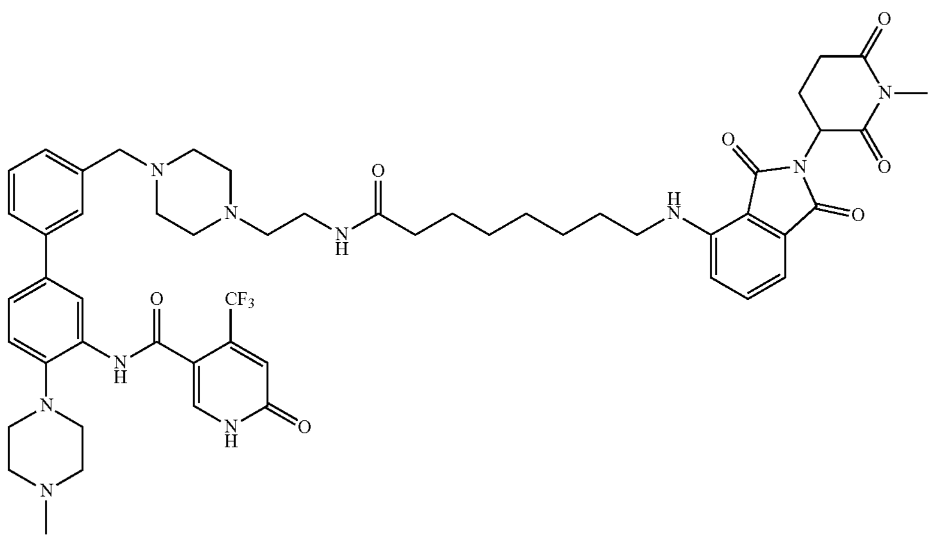 | N-(3'-((4-(2-(8-((2-(1-methyl-2,6-dioxopiperidin-3-yl)-1,3-dioxoisoindolin-4-yl)amino)octanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 54 | XF056-118 | 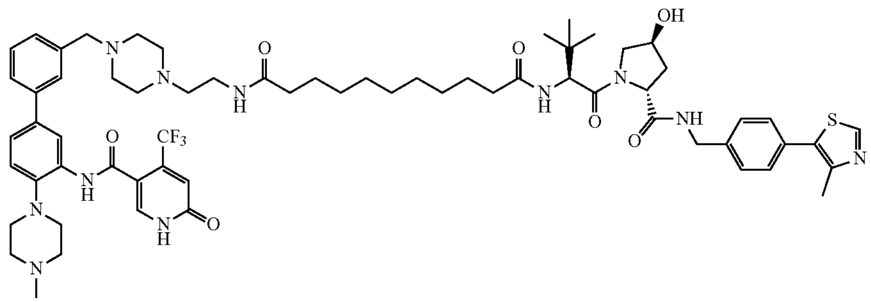 [SMILES: Cc1ncsc1-c1ccc(CNC(=O)[C@H]2C[C@H](O)CN2C(=O)[C@@H](NC(=O)CCCCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-(S)-1-((2R,4S)-4-hydroxy-2-((4-(4-methylthiazol-5-yl)benzyl)carbamoyl)pyrrolidin-1-yl)-3,3-dimethyl-1-oxobutan-2-yl)-$N^{11}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |
| 56 | XF061-111 | 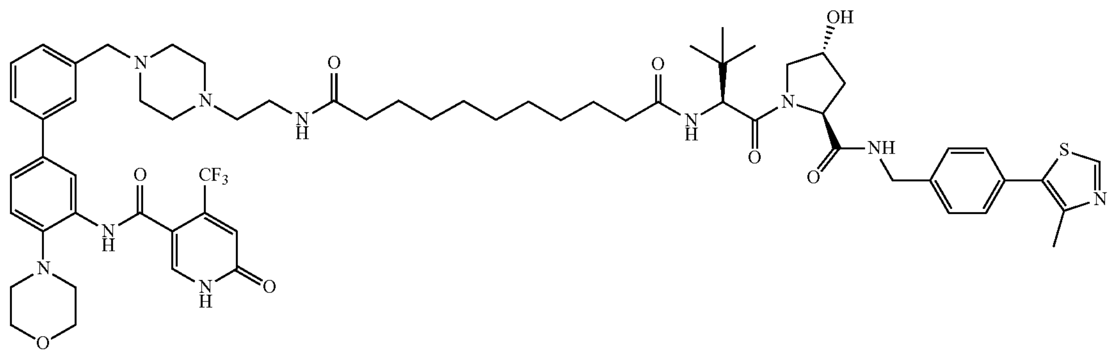 [SMILES: Cc1ncsc1-c1ccc(CNC(=O)[C@@H]2C[C@@H](O)CN2C(=O)[C@@H](NC(=O)CCCCCCCCCC(=O)NCCN2CCN(Cc3cccc(-c4ccc(N5CCOCC5)c(NC(=O)c5c[nH]c(=O)cc5C(F)(F)F)c4)c3)CC2)C(C)(C)C)cc1] | $N^1$-(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{11}$-(2-(4-(4'-morpholino-3'-(6-oxo-4-(trifluoromethyl)-1,6-dihydropyridine-3-carboxamido)-[1,1'-biphenyl]-3-yl)methyl)piperazin-1-yl)ethyl)undecanediamide |
| 57 | XF067-66 | 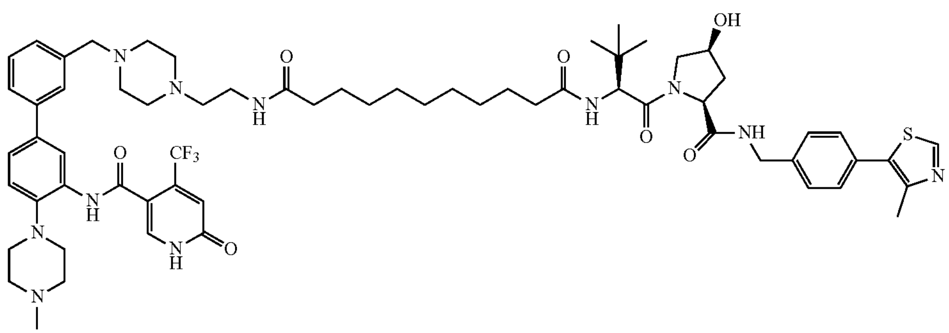 [SMILES: Cc1ncsc1-c1ccc(CNC(=O)[C@@H]2C[C@H](O)CN2C(=O)[C@@H](NC(=O)CCCCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | $N^1$-(S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)-$N^{11}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |

TABLE 1-continued

| Examples | Compound ID | Structure | Chemical Name |
|---|---|---|---|
| 70 | XF056-124 | 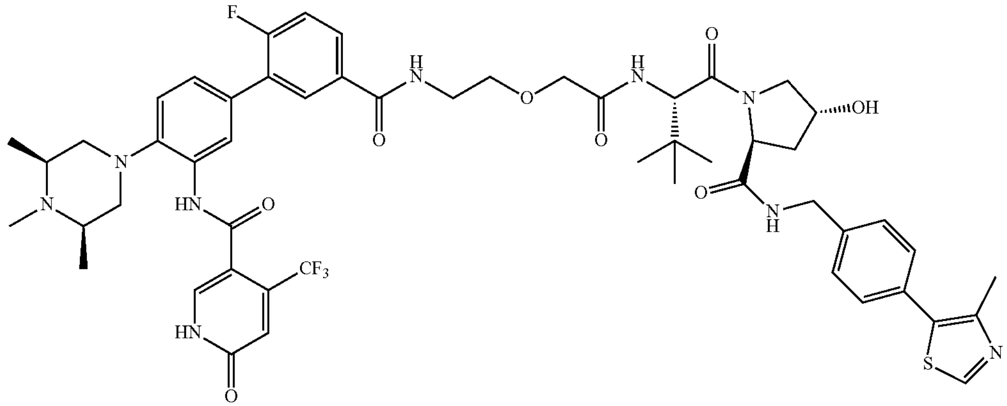 | N-(2'-fluoro-5'-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamoyl)-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 71 | XF056-125 | 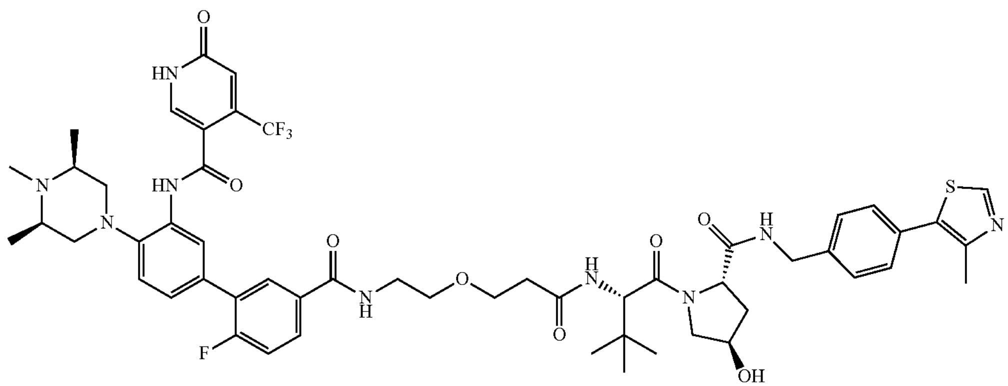 [SMILES: Cc1ncsc1-c1ccc(CNC(=O)[C@@H]2C[C@@H](O)CN2C(=O)[C@@H](NC(=O)CCOCCNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | N-(2'-fluoro-5'-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 72 | XF056-126 | 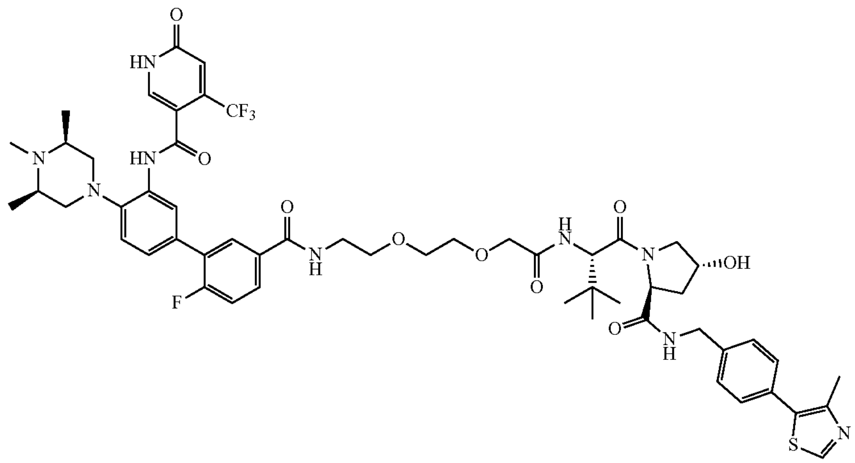 [SMILES: Cc1ncsc1-c1ccc(CNC(=O)[C@@H]2C[C@@H](O)CN2C(=O)[C@@H](NC(=O)COCCOCCNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | N-(2'-fluoro-5'-((2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 73 | XF056-127 | 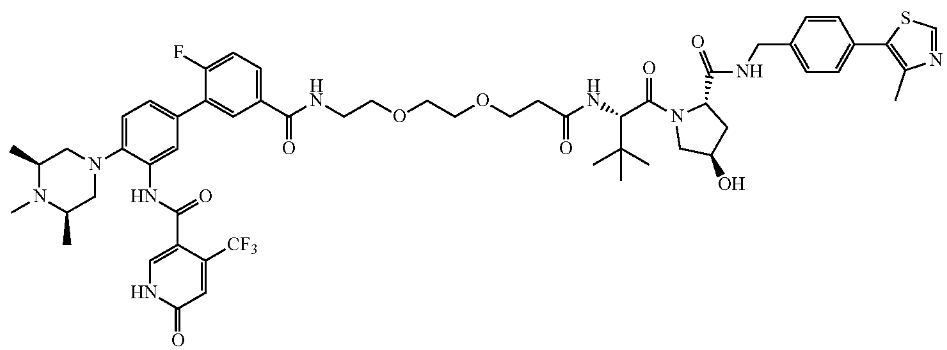 [SMILES: Cc1ncsc1-c1ccc(CNC(=O)[C@@H]2C[C@@H](O)CN2C(=O)[C@@H](NC(=O)CCOCCOCCNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | N-(2'-fluoro-5'-((2-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| Examples | Compound ID | Structure | Chemical Name |
|---|---|---|---|
| 74 | XF056-128 | 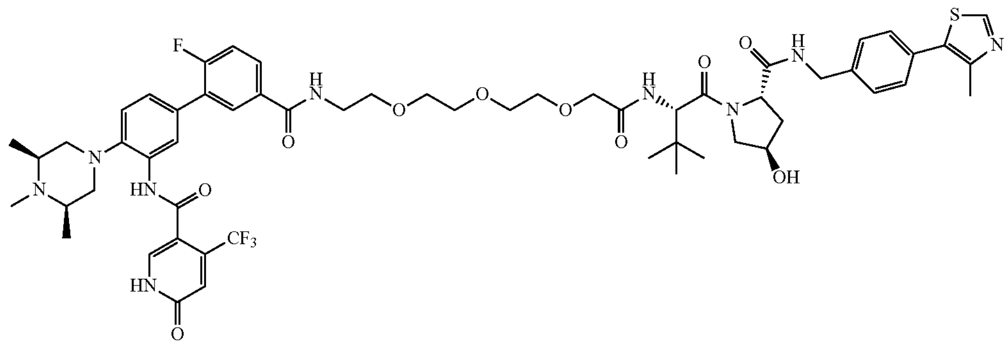 [SMILES: Cc1ncsc1-c1ccc(CNC(=O)[C@@H]2C[C@@H](O)CN2C(=O)[C@@H](NC(=O)COCCOCCOCCNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | N-(2'-fluoro-5'-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 75 | XF056-129 | 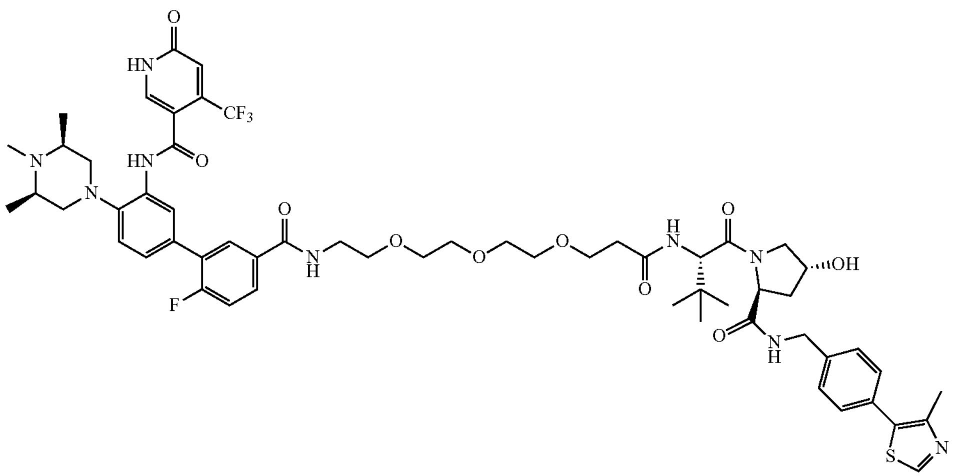 | N-(2'-fluoro-5'-(((S)-14-((2S,4R)-4-hydroxy-2-((4-(4-methylthiazol-5-yl)benzyl)carbamoyl)pyrrolidine-1-carbonyl)-15,15-dimethyl-12-oxo-3,6,9-trioxa-13-azahexadecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 76 | XF056-130 | 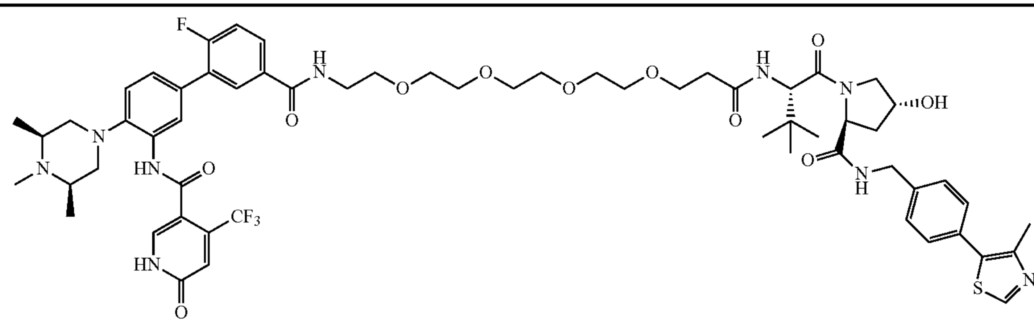 | N-(2'-fluoro-5'-(((S)-17-((2S,4R)-4-hydroxy-2-((4-(4-methylthiazol-5-yl)benzyl)carbamoyl)pyrrolidine-1-carbonyl)-18,18-dimethyl-15-oxo-3,6,9,12-tetraoxa-16-azanonadecyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 77 | XF056-131 | 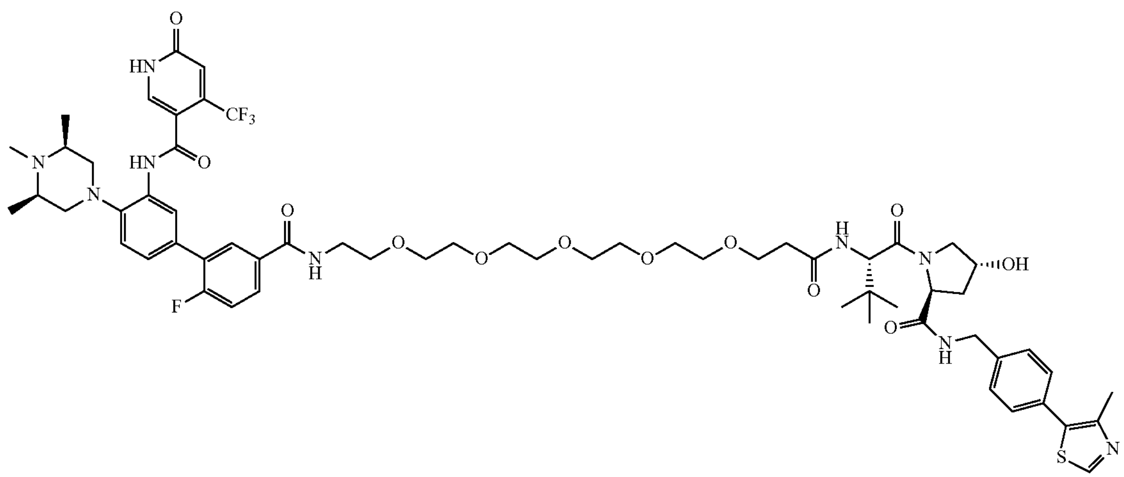 | N-(2'-fluoro-5'-(((S)-20-((2S,4R)-4-hydroxy-2-((4-(4-methylthiazol-5-yl)benzyl)carbamoyl)pyrrolidine-1-carbonyl)-21,21-dimethyl-18-oxo-3,6,9,12,15-pentaoxa-19-azadocosyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 78 | XF056-132 | 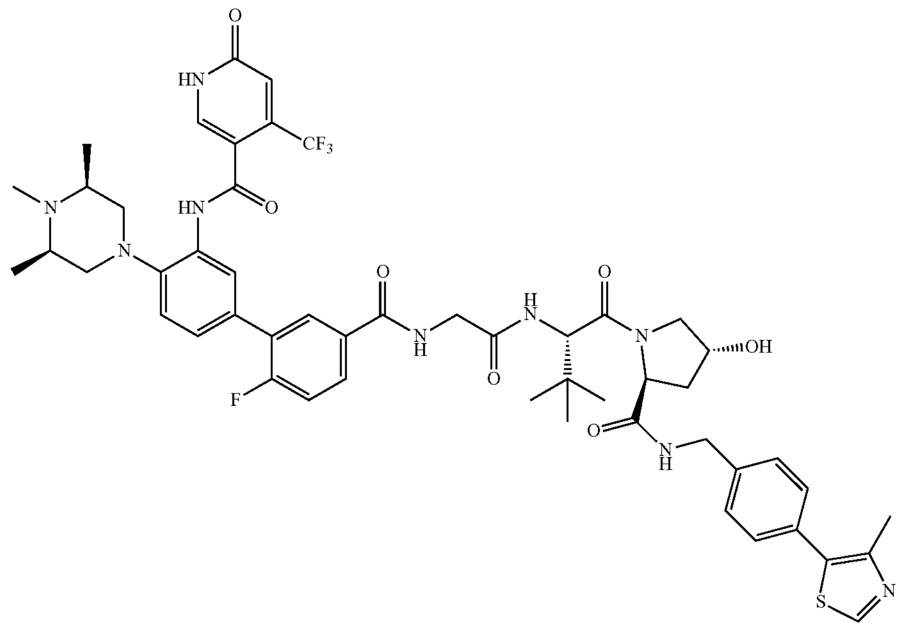 | N-(2'-fluoro-5'-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 79 | XF056-133 | 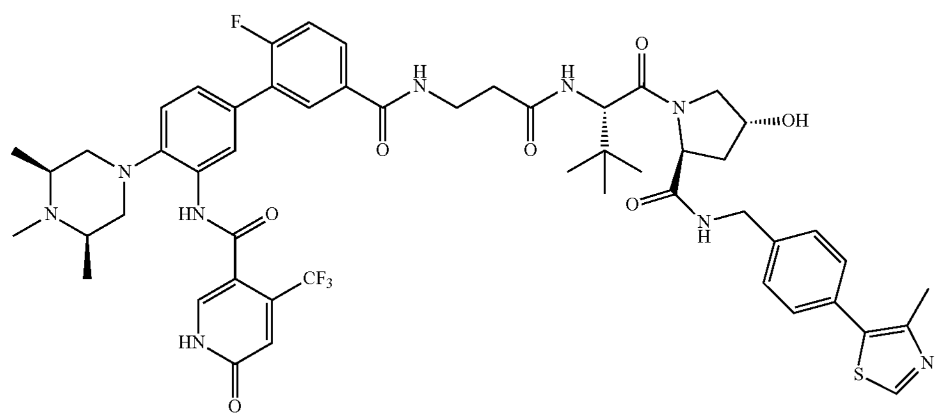 | N-(2'-fluoro-5'-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| 80 | XF056-134 | 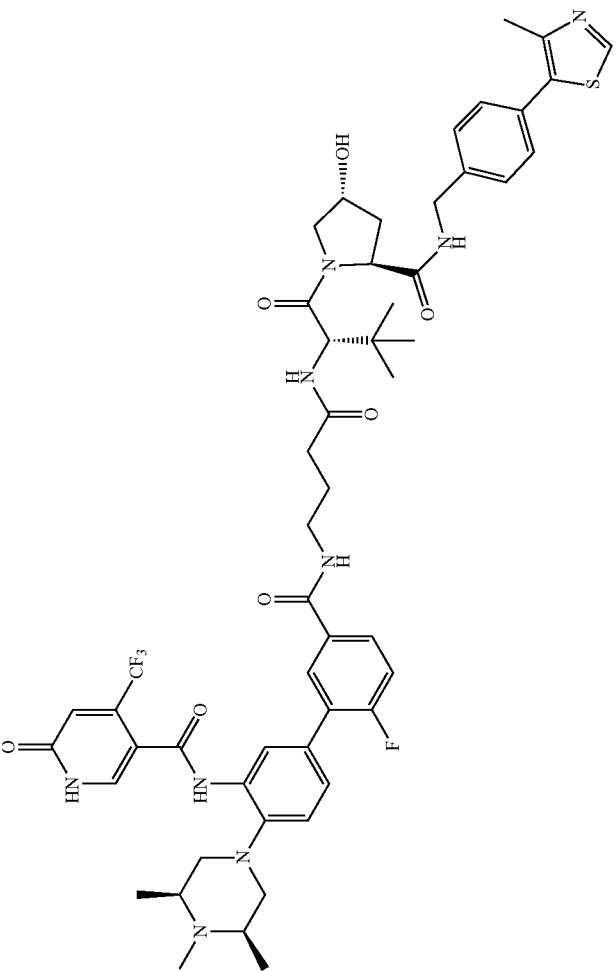 | N-(2'-fluoro-5'-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 81 | XF056-135 | 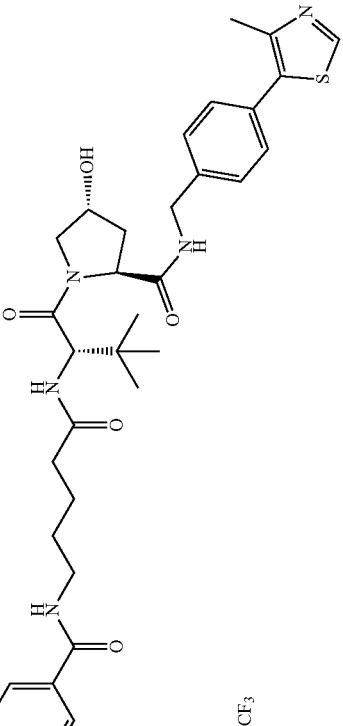 | N-(2'-fluoro-5'-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 82 | XF056-136 | 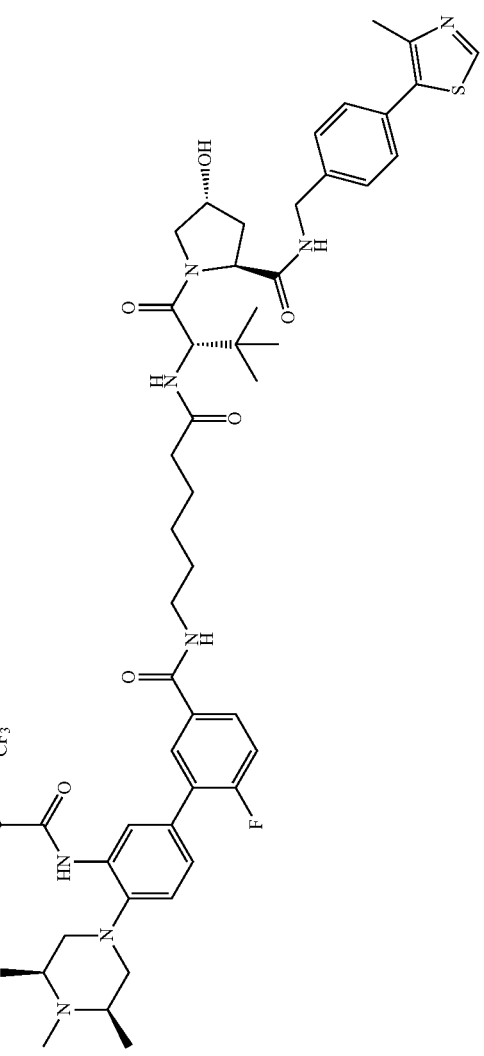 | N-(2'-fluoro-5'-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 83 | XF056- 137 | 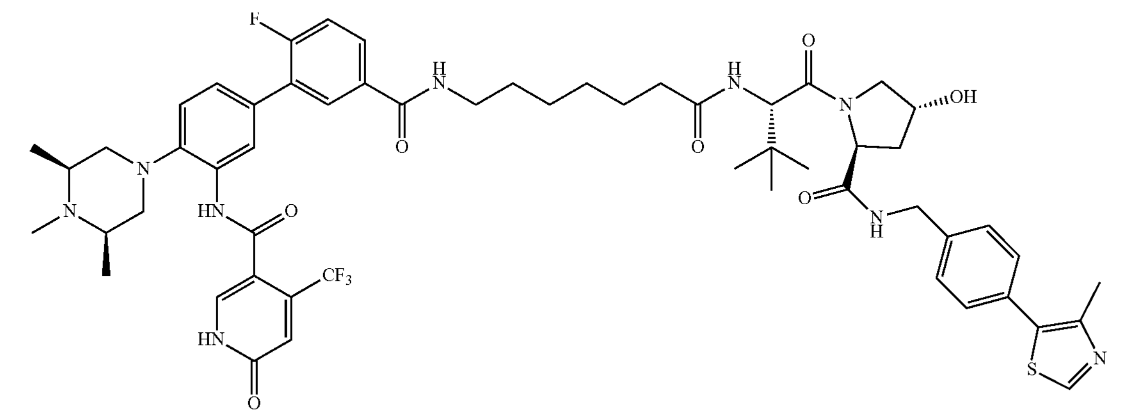 | N-(2'-fluoro-5'-((7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 84 | XF056- 138 | 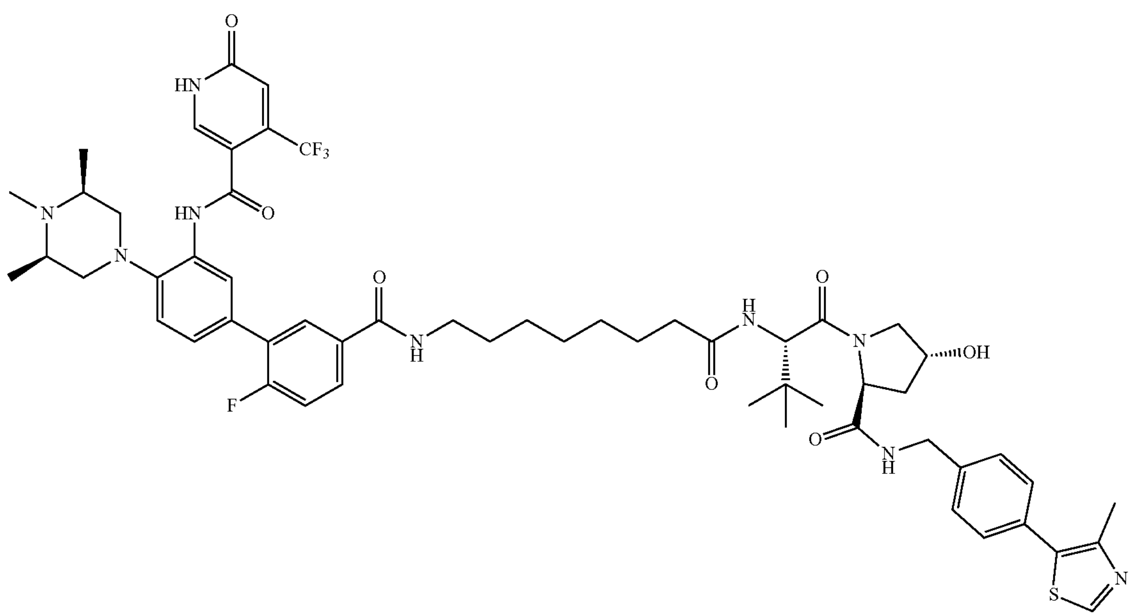 [SMILES: Cc1ncsc1-c1ccc(CNC(=O)[C@@H]2C[C@@H](O)CN2C(=O)[C@@H](NC(=O)CCCCCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | N-(2'-fluoro-5'-((8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 85 | XF056-139 | 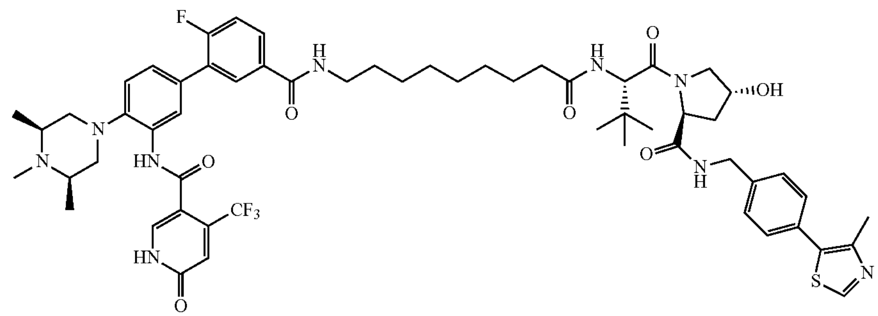 | N-(2'-fluoro-5'-((9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 86 | XF056-140 | 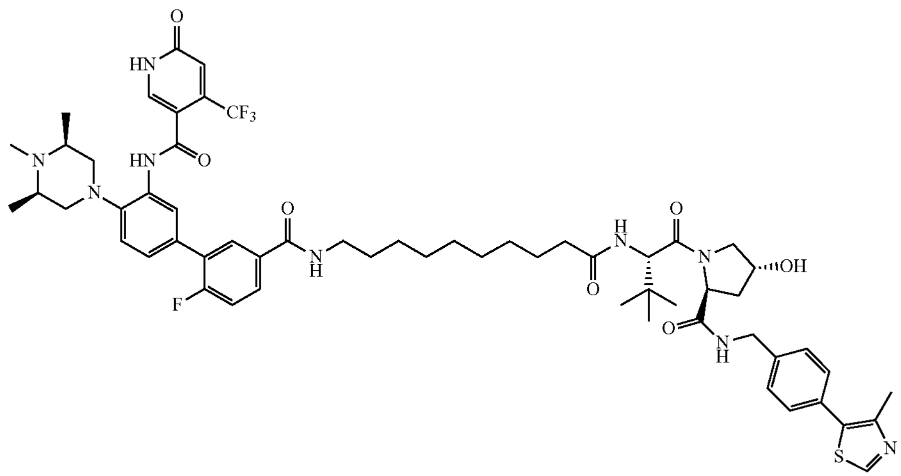 | N-(2'-fluoro-5'-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 87 | XF056-141 | 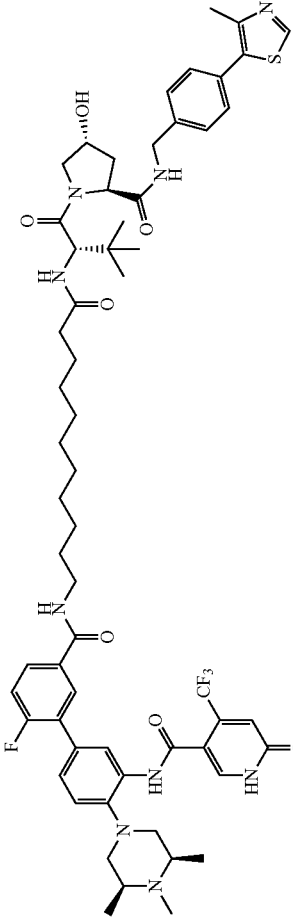 | N-(2'-fluoro-5'-((11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 88 | XF056-142 | 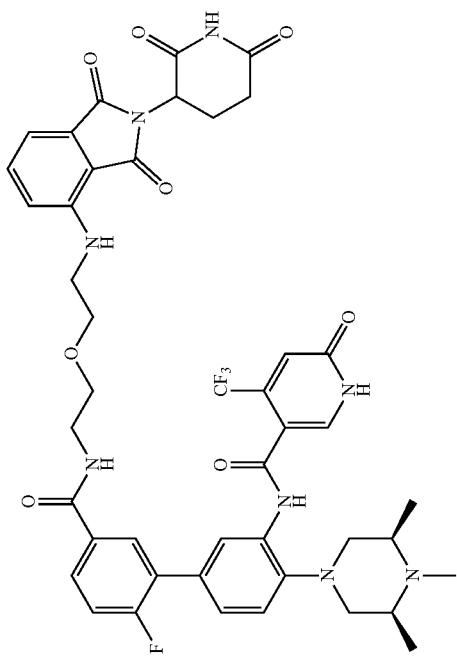 | N-(5'-((2-(2-((2-(2,6-dioxopiperidin-3-yl)-1,3-dioxoisoindolin-4-yl)amino)ethoxy)ethyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 89 | XF056-143 | 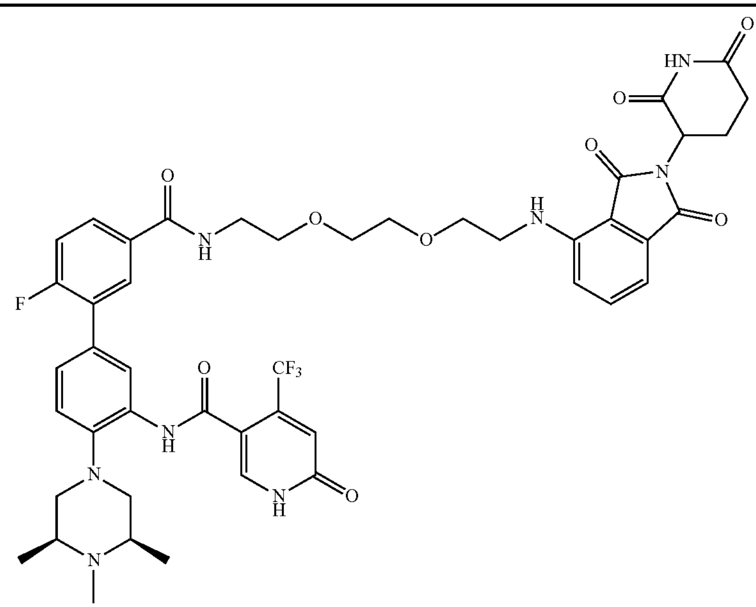 | N-(5'-((2-(2-(2-((2-(2,6-dioxopiperidin-3-yl)-1,3-dioxoisoindolin-4-yl)amino)ethoxy)ethoxy)ethyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 90 | XF056-144 | 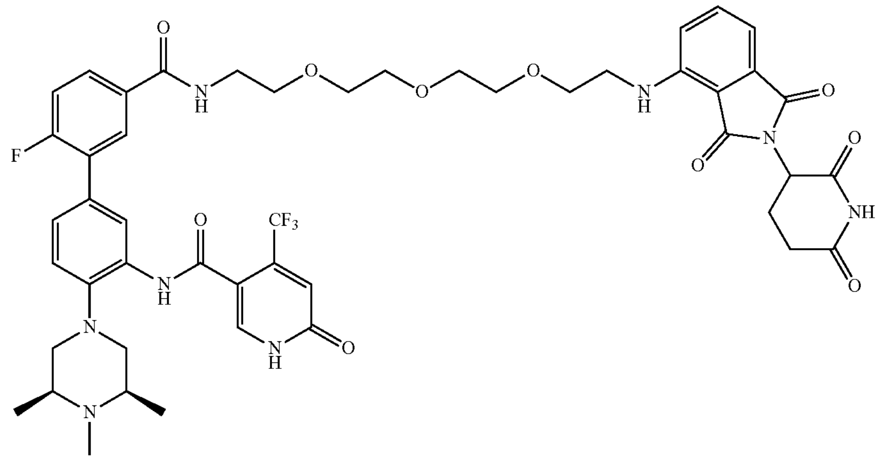 [SMILES: C[C@@H]1CN(c2ccc(-c3cc(C(=O)NCCOCCOCCOCCNc4cccc5c4C(=O)N(C4CCC(=O)NC4=O)C5=O)ccc3F)cc2NC(=O)c2c[nH]c(=O)cc2C(F)(F)F)C[C@H](C)N1C] | N-(5'-((2-(2-(2-(2-((2-(2,6-dioxopiperidin-3-yl)-1,3-dioxoisoindolin-4-yl)amino)ethoxy)ethoxy)ethyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 91 | XF056-145 | 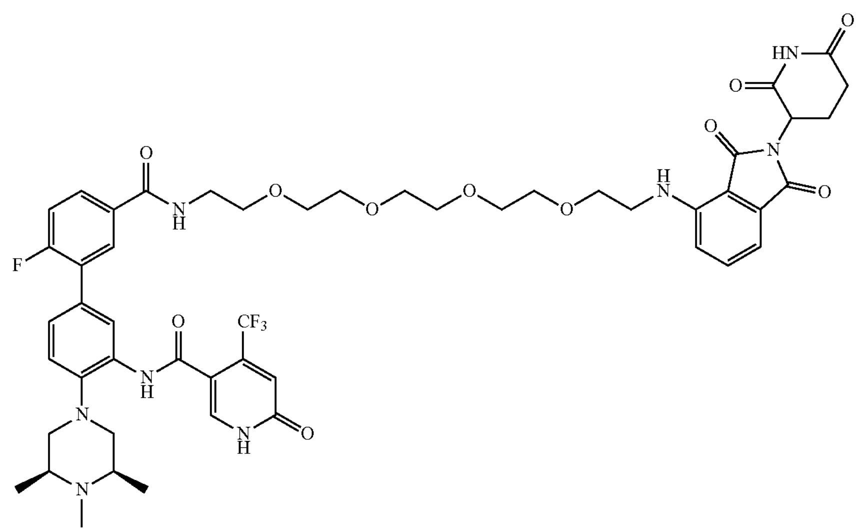 [SMILES: C[C@@H]1CN(c2ccc(-c3cc(C(=O)NCCOCCOCCOCCOCCNc4cccc5c4C(=O)N(C4CCC(=O)NC4=O)C5=O)ccc3F)cc2NC(=O)c2c[nH]c(=O)cc2C(F)(F)F)C[C@H](C)N1C] | N-(5'-((14-((2-(2,6-dioxopiperidin-3-yl)-1,3-dioxoisoindolin-4-yl)amino)-3,6,9,12-tetraoxatetradecyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

| Examples | Compound ID | Structure | Chemical Name |
|---|---|---|---|
| 92 | XF056-146 | 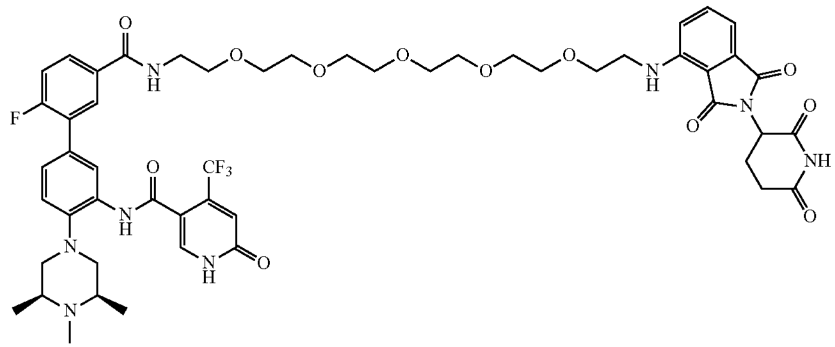 [SMILES: C[C@@H]1CN(c2ccc(-c3cc(C(=O)NCCOCCOCCOCCOCCOCCNc4cccc5c4C(=O)N(C4CCC(=O)NC4=O)C5=O)ccc3F)cc2NC(=O)c2c[nH]c(=O)cc2C(F)(F)F)C[C@H](C)N1C] | N-(5'-((17-((2-(2,6-dioxopiperidin-3-yl)-1,3-dioxoisoindolin-4-yl)amino)-3,6,9,12,15-pentaoxaheptadecyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 93 | XF056-147 | 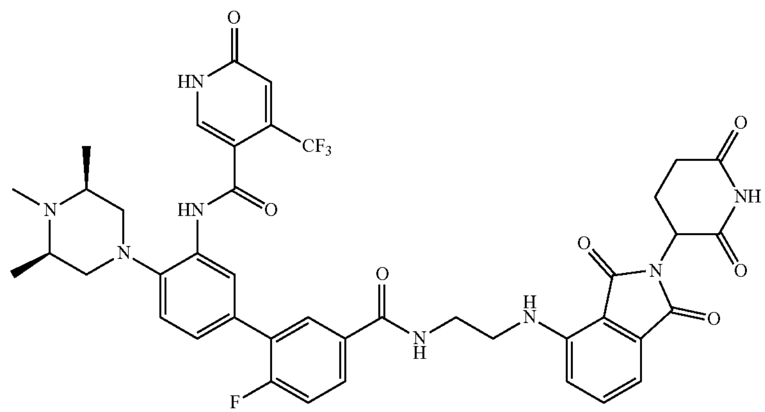 [SMILES: C[C@@H]1CN(c2ccc(-c3cc(C(=O)NCCNc4cccc5c4C(=O)N(C4CCC(=O)NC4=O)C5=O)ccc3F)cc2NC(=O)c2c[nH]c(=O)cc2C(F)(F)F)C[C@H](C)N1C] | N-(5'-((2-((2-(2,6-dioxopiperidin-3-yl)-1,3-dioxoisoindolin-4-yl)amino)ethyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 94 | XF056-148 | 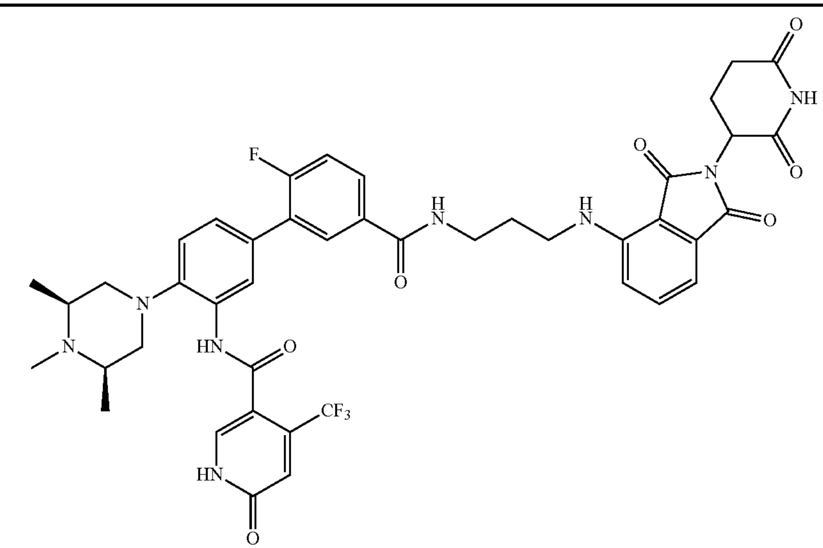 | N-(5'-((3-((2-(2,6-dioxopiperidin-3-yl)-1,3-dioxoisoindolin-4-yl)amino)propyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 95 | XF056-149 | 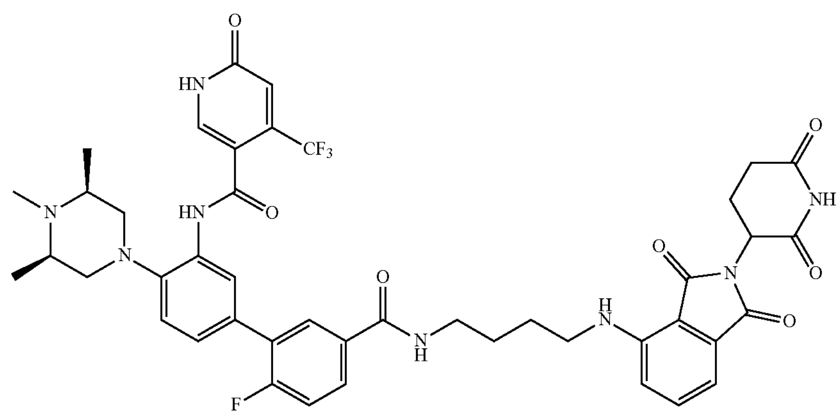 [SMILES: C[C@@H]1CN(c2ccc(-c3cc(C(=O)NCCCCNc4cccc5c4C(=O)N(C4CCC(=O)NC4=O)C5=O)ccc3F)cc2NC(=O)c2c[nH]c(=O)cc2C(F)(F)F)C[C@H](C)N1C] | N-(5'-((4-((2-(2,6-dioxopiperidin-3-yl)-1,3-dioxoisoindolin-4-yl)amino)butyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 96 | XF056-150 | 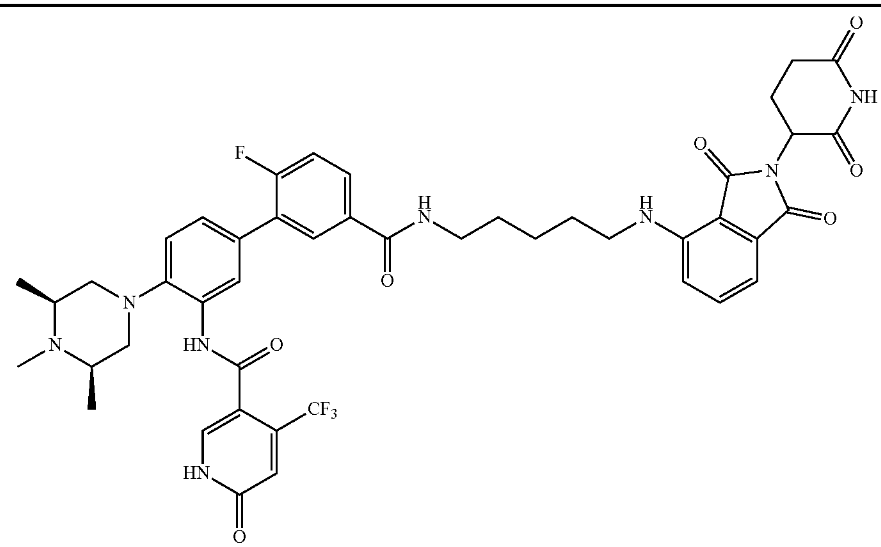 | N-(5'-((5-((2-(2,6-dioxopiperidin-3-yl)-1,3-dioxoisoindolin-4-yl)amino)pentyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 97 | XF056-151 | 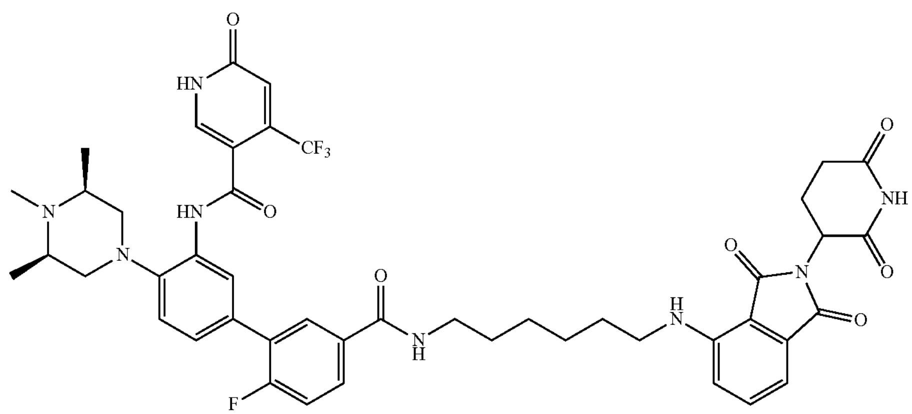 [SMILES: C[C@@H]1CN(c2ccc(-c3cc(C(=O)NCCCCCCNc4cccc5c4C(=O)N(C4CCC(=O)NC4=O)C5=O)ccc3F)cc2NC(=O)c2c[nH]c(=O)cc2C(F)(F)F)C[C@H](C)N1C] | N-(5'-((6-((2-(2,6-dioxopiperidin-3-yl)-1,3-dioxoisoindolin-4-yl)amino)hexyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 98 | XF056-152 | 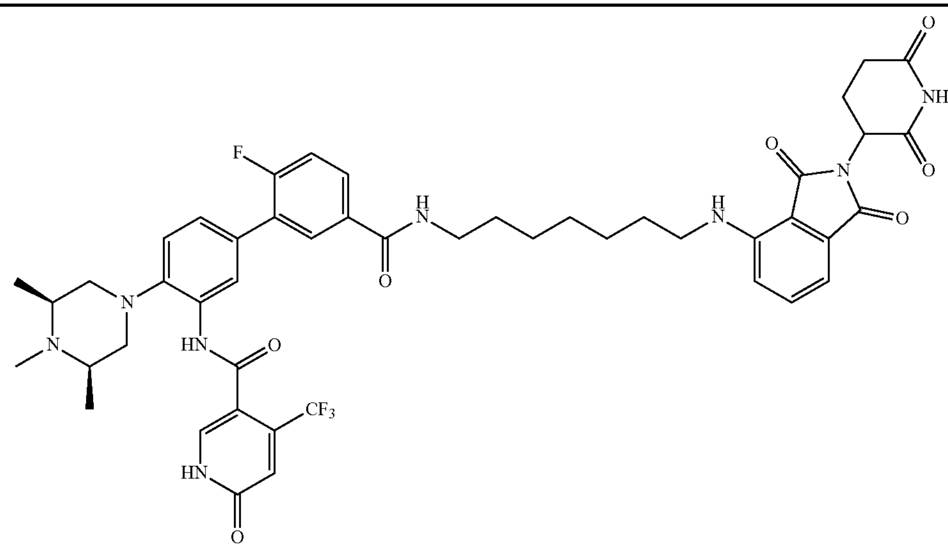 | N-(5'-((7-((2-(2,6-dioxopiperidin-3-yl)-1,3-dioxoisoindolin-4-yl)amino)heptyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 99 | XF056-153 | 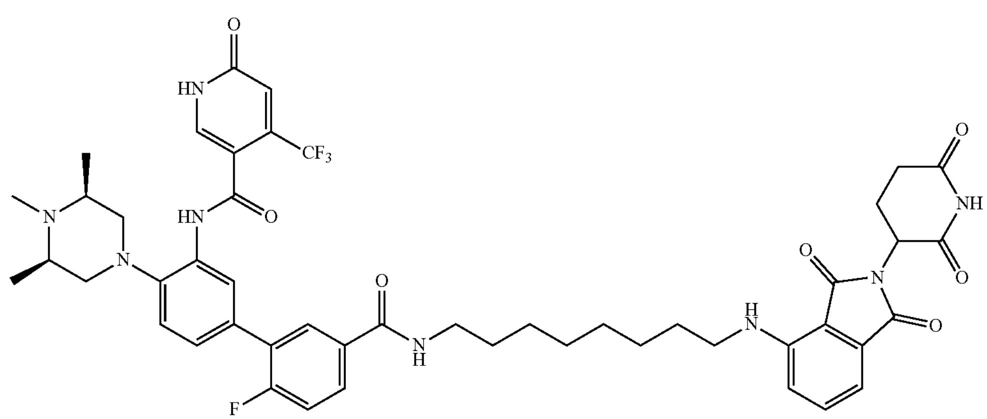 [SMILES: C[C@@H]1CN(c2ccc(-c3cc(C(=O)NCCCCCCCCNc4cccc5c4C(=O)N(C4CCC(=O)NC4=O)C5=O)ccc3F)cc2NC(=O)c2c[nH]c(=O)cc2C(F)(F)F)C[C@H](C)N1C] | N-(5'-((8-((2-(2,6-dioxopiperidin-3-yl)-1,3-dioxoisoindolin-4-yl)amino)octyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 100 | XF056-157 | 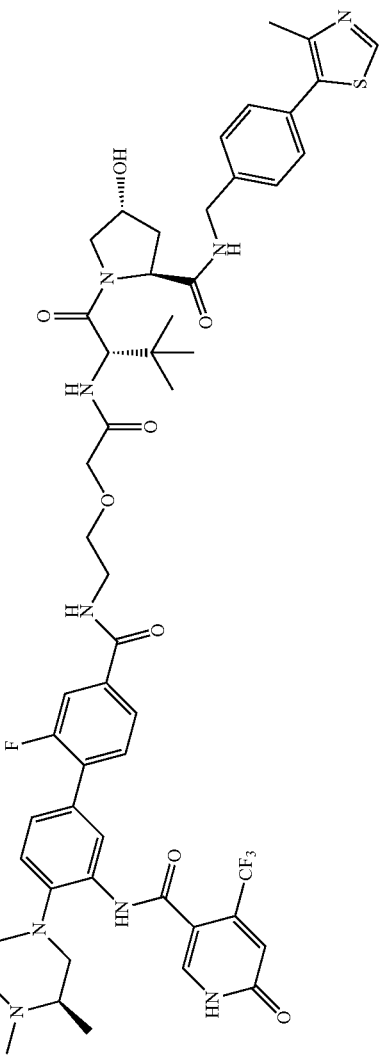 | N-(2'-fluoro-4'-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 101 | XF056-158 | 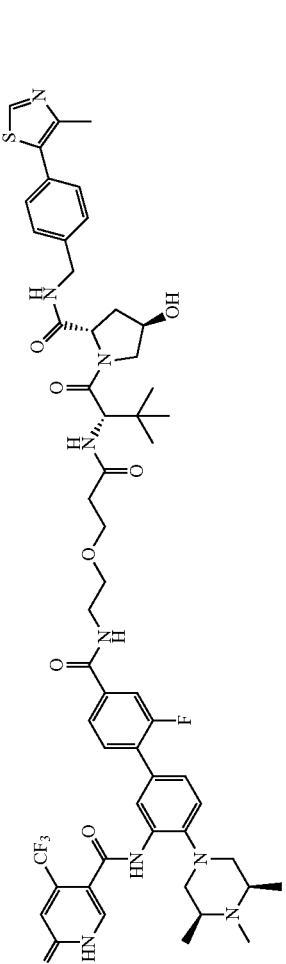 | N-(2'-fluoro-4'-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 102 | XF056-159 | 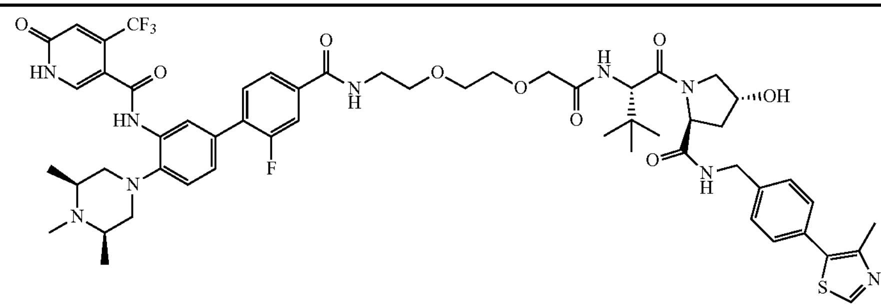 | N-(2'-fluoro-4'-((2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 103 | XF056-160 | 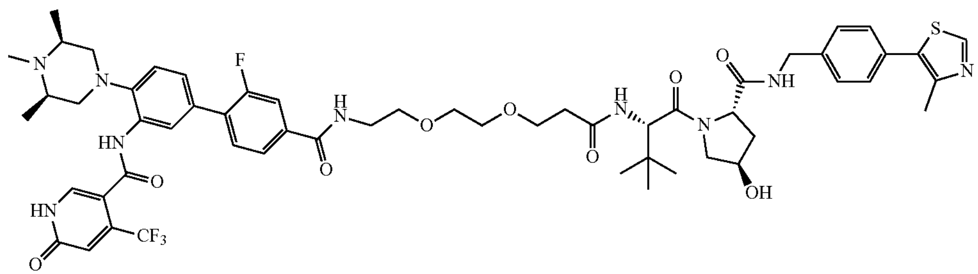 [SMILES: Cc1ncsc1-c1ccc(CNC(=O)[C@@H]2C[C@@H](O)CN2C(=O)[C@@H](NC(=O)CCOCCOCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 104 | XF056-161 | 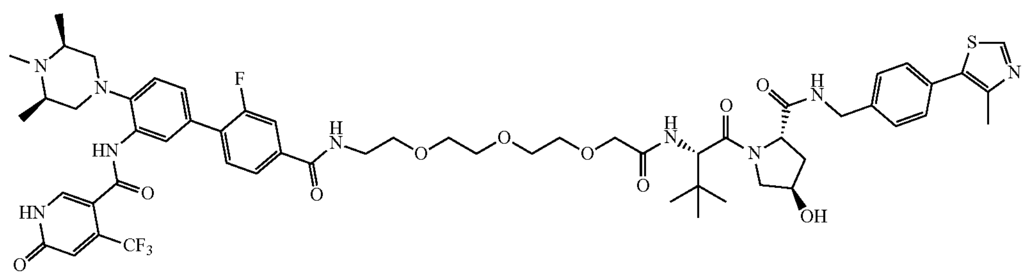 [SMILES: Cc1ncsc1-c1ccc(CNC(=O)[C@@H]2C[C@@H](O)CN2C(=O)[C@@H](NC(=O)COCCOCCOCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 105 | XF056-162 | 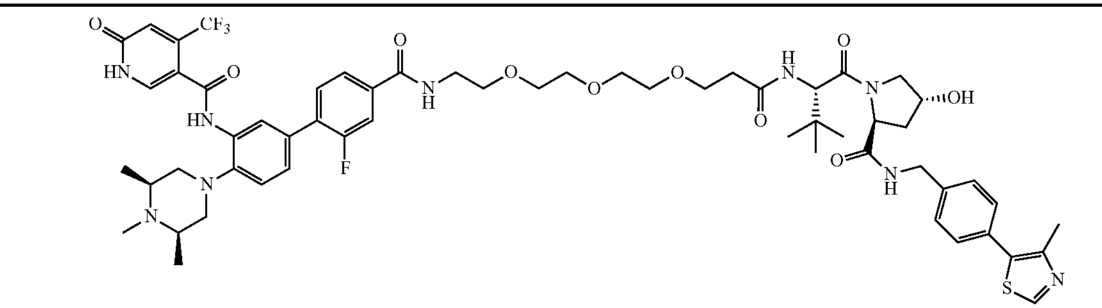 | N-(2'-fluoro-4'-(((S)-14-((2S,4R)-4-hydroxy-2-((4-(4-methylthiazol-5-yl)benzyl)carbamoyl)pyrrolidine-1-carbonyl)-15,15-dimethyl-12-oxo-3,6,9-trioxa-13-azahexadecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 106 | XF056-163 | 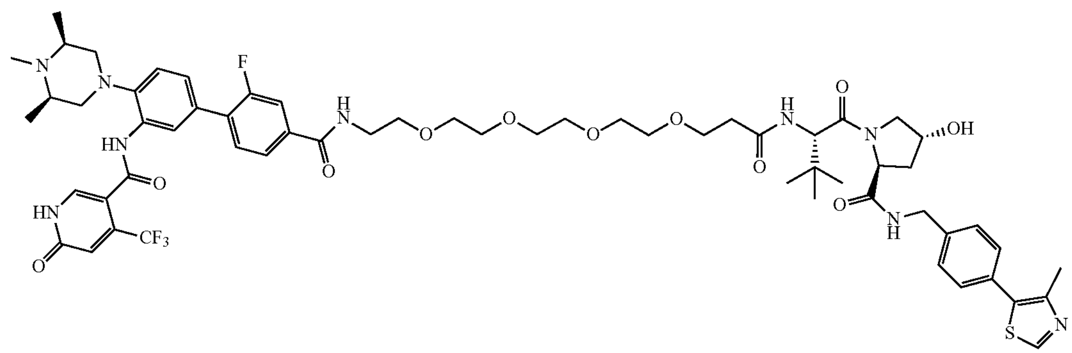 | N-(2'-fluoro-4'-(((S)-17-((2S,4R)-4-hydroxy-2-((4-(4-methylthiazol-5-yl)benzyl)carbamoyl)pyrrolidine-1-carbonyl)-18,18-dimethyl-15-oxo-3,6,9,12-tetraoxa-16-azanonadecyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 107 | XF056-164 | 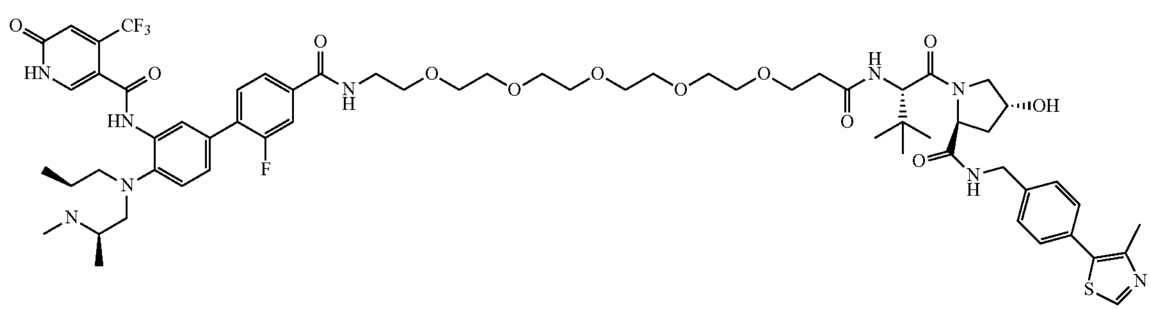 | N-(2'-fluoro-4'-(((S)-20-((2S,4R)-4-hydroxy-2-((4-(4-methylthiazol-5-yl)benzyl)carbamoyl)pyrrolidine-1-carbonyl)-21,21-dimethyl-18-oxo-3,6,9,12,15-pentaoxa-19-azadocosyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 108 | XF056-165 | 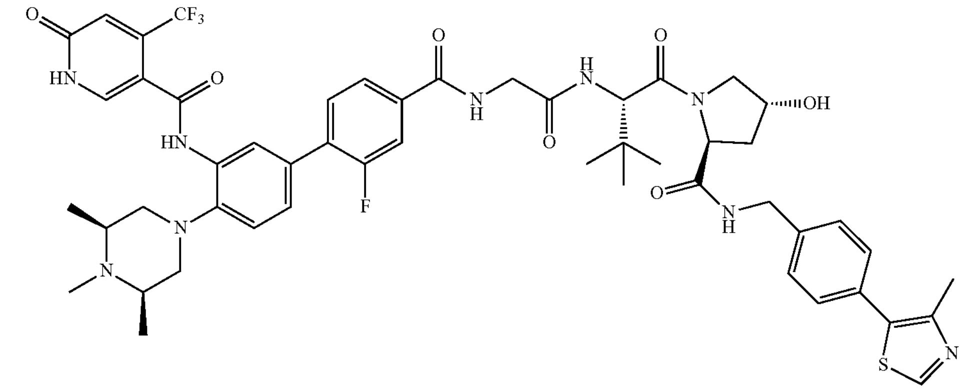 [SMILES: Cc1ncsc1-c1ccc(CNC(=O)[C@@H]2C[C@@H](O)CN2C(=O)[C@@H](NC(=O)CNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 109 | XF056-166 | 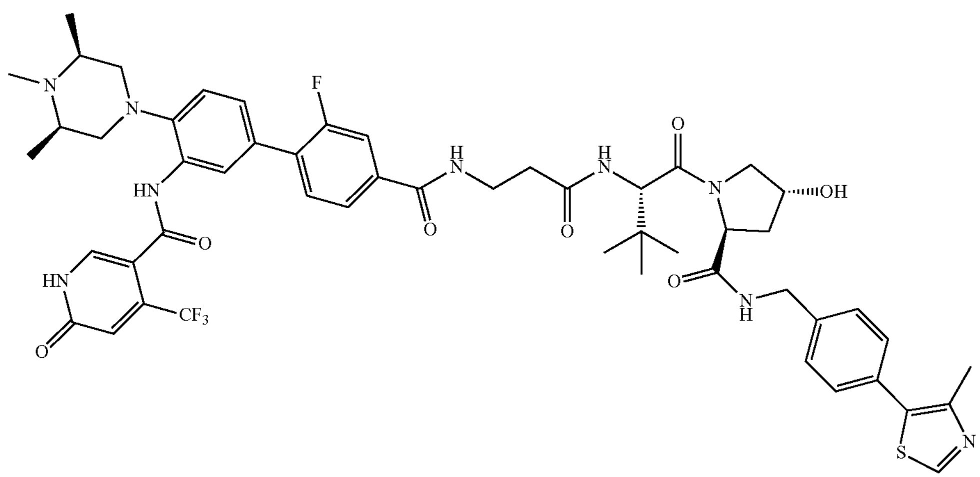 | N-(2'-fluoro-4'-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 110 | XF056-167 | 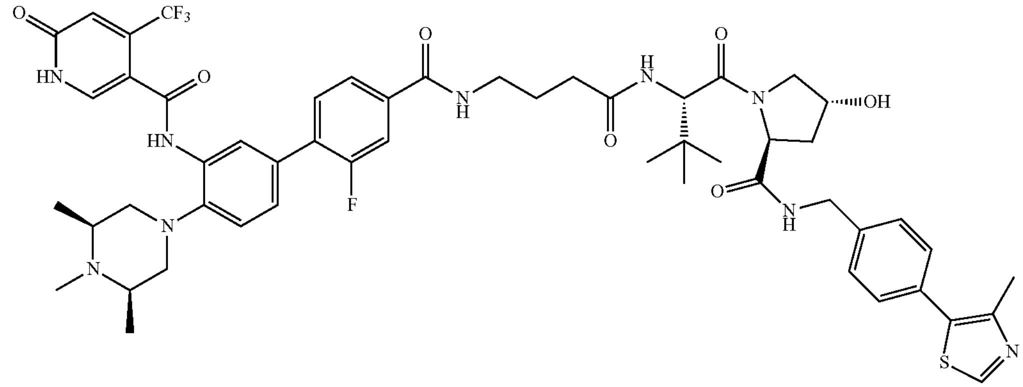 [SMILES: Cc1ncsc1-c1ccc(CNC(=O)[C@@H]2C[C@@H](O)CN2C(=O)[C@@H](NC(=O)CCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 111 | XF056-168 | 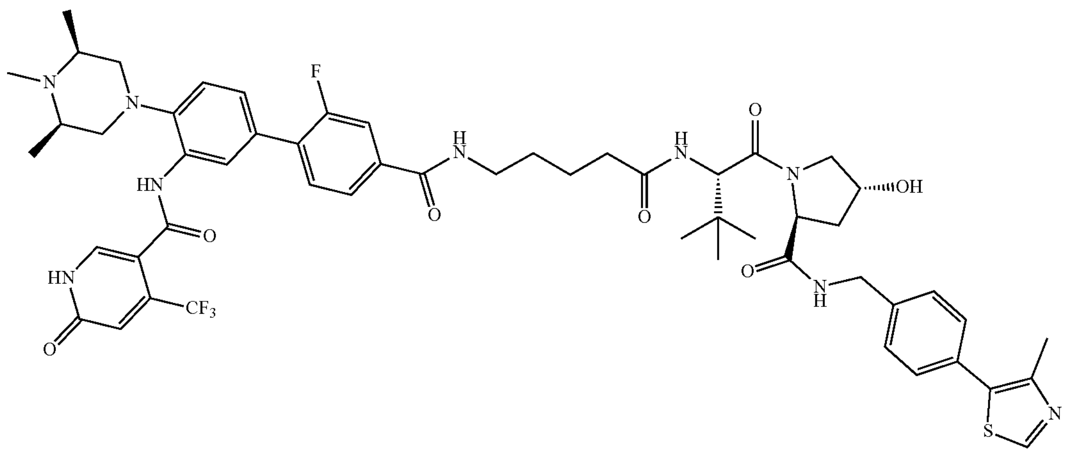 [SMILES: Cc1ncsc1-c1ccc(CNC(=O)[C@@H]2C[C@@H](O)CN2C(=O)[C@@H](NC(=O)CCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 112 | XF056-169 | 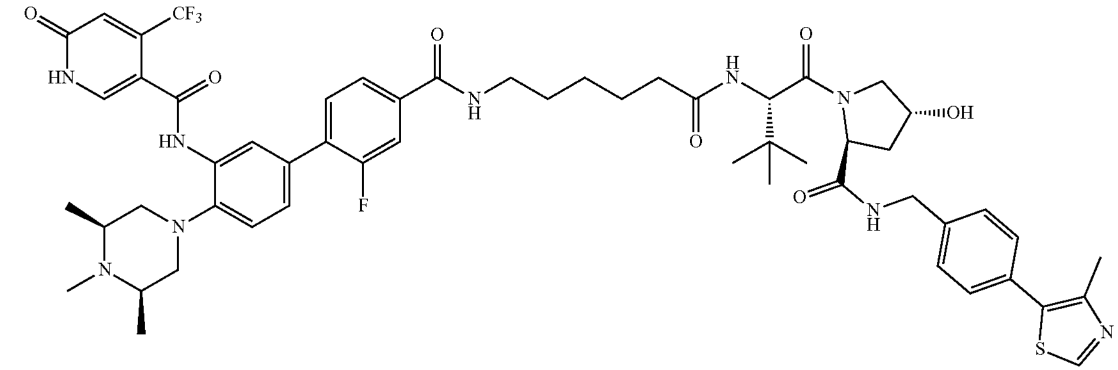 [SMILES: Cc1ncsc1-c1ccc(CNC(=O)[C@@H]2C[C@@H](O)CN2C(=O)[C@@H](NC(=O)CCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 113 | XF056-170 | 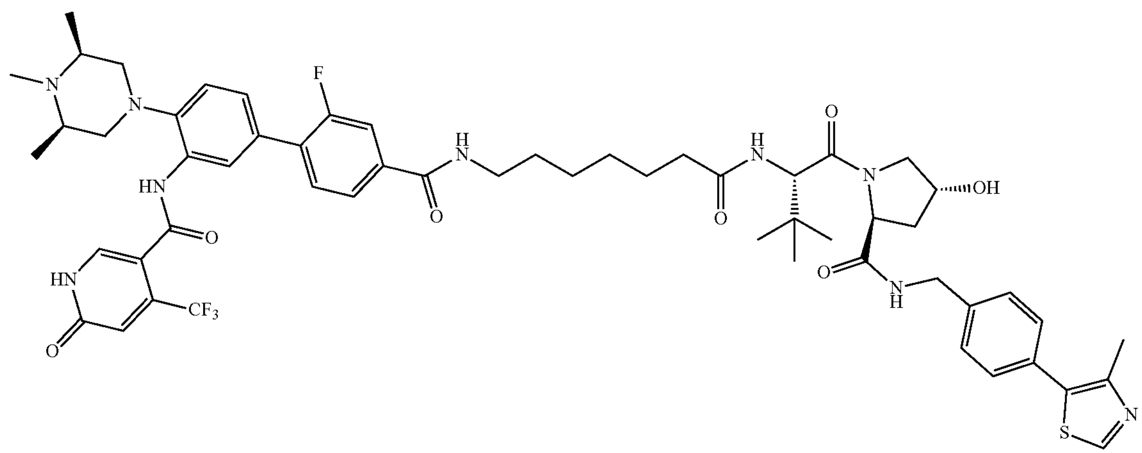 [SMILES: Cc1ncsc1-c1ccc(CNC(=O)[C@@H]2C[C@@H](O)CN2C(=O)[C@@H](NC(=O)CCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 114 | XF056-171 | 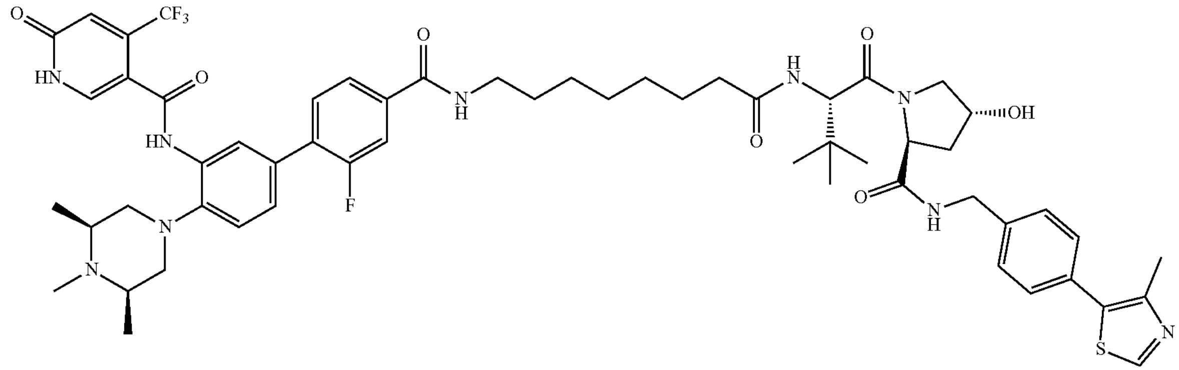 [SMILES: Cc1ncsc1-c1ccc(CNC(=O)[C@@H]2C[C@@H](O)CN2C(=O)[C@@H](NC(=O)CCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 115 | XF056-172 | 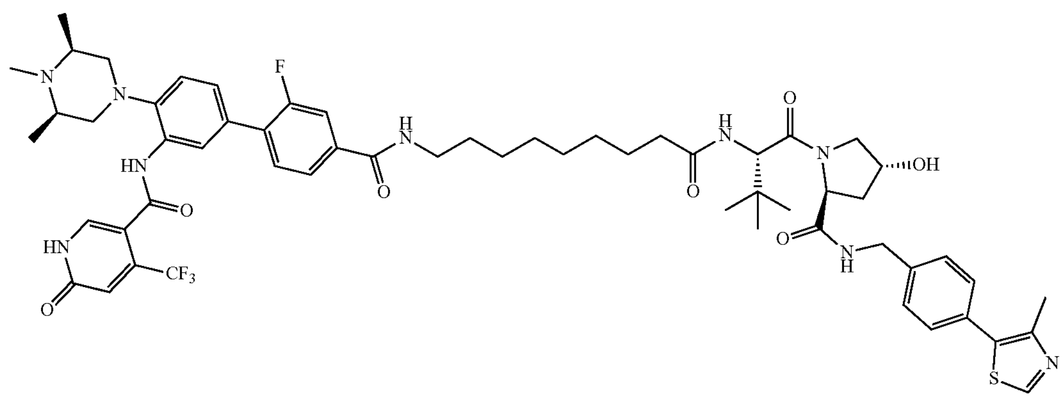 [SMILES: Cc1ncsc1-c1ccc(CNC(=O)[C@@H]2C[C@@H](O)CN2C(=O)[C@@H](NC(=O)CCCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 116 | XF056-173 | 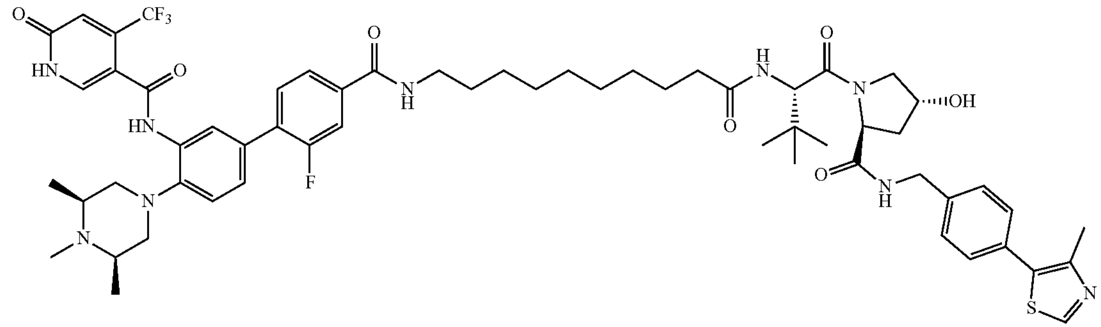 [SMILES: Cc1ncsc1-c1ccc(CNC(=O)[C@@H]2C[C@@H](O)CN2C(=O)[C@@H](NC(=O)CCCCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 117 | XF056-174 | 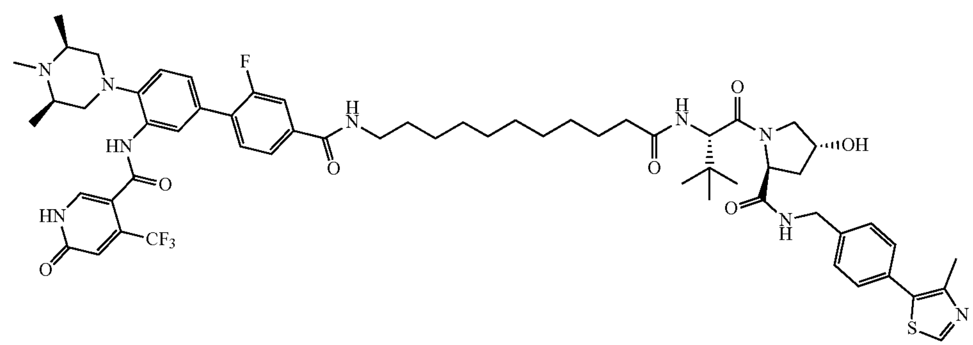 [SMILES: Cc1ncsc1-c1ccc(CNC(=O)[C@@H]2C[C@@H](O)CN2C(=O)[C@@H](NC(=O)CCCCCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)C(C)(C)C)cc1] | N-(2'-fluoro-4'-((11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| 118 | XF056-175 | 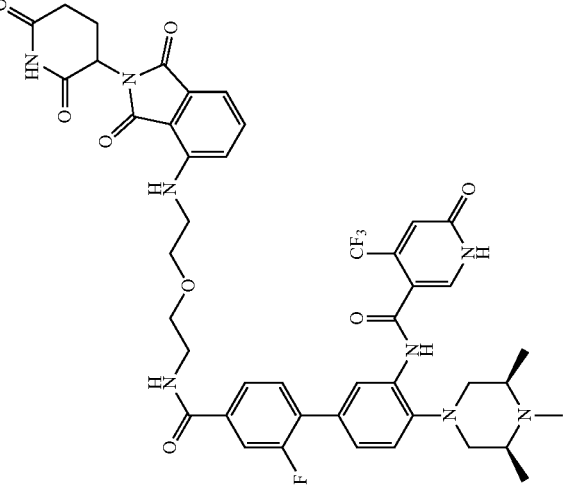 | N-(4'-((2-(2-((2-(2,6-dioxopiperidin-3-yl)-1,3-dioxoisoindolin-4-yl)amino)ethoxy)ethyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 119 | XF056-176 | 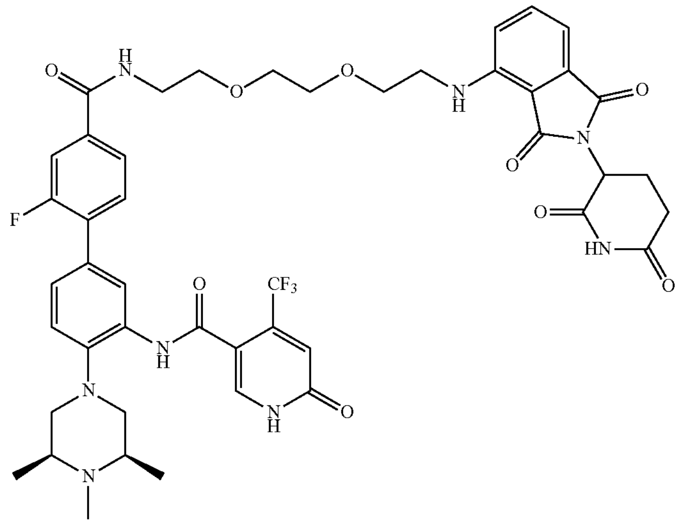 [SMILES: C[C@@H]1CN(c2ccc(-c3ccc(C(=O)NCCOCCOCCNc4cccc5c4C(=O)N(C4CCC(=O)NC4=O)C5=O)cc3F)cc2NC(=O)c2c[nH]c(=O)cc2C(F)(F)F)C[C@H](C)N1C] | N-(4'-((2-(2-(2-(2-(2,6-dioxopiperidin-3-yl)-1,3-dioxoisoindolin-4-yl)amino)ethoxy)ethoxy)ethyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 120 | XF056-177 | 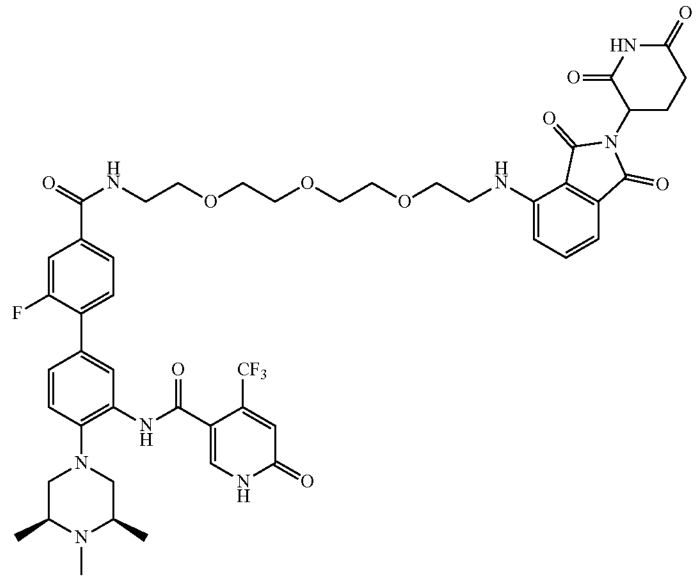 [SMILES: C[C@@H]1CN(c2ccc(-c3ccc(C(=O)NCCOCCOCCOCCNc4cccc5c4C(=O)N(C4CCC(=O)NC4=O)C5=O)cc3F)cc2NC(=O)c2c[nH]c(=O)cc2C(F)(F)F)C[C@H](C)N1C] | N-(4'-((2-(2-(2-(2-((2-(2,6-dioxopiperidin-3-yl)-1,3-dioxoisoindolin-4-yl)amino)ethoxy)ethoxy)ethoxy)ethyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 121 | XF056-178 | 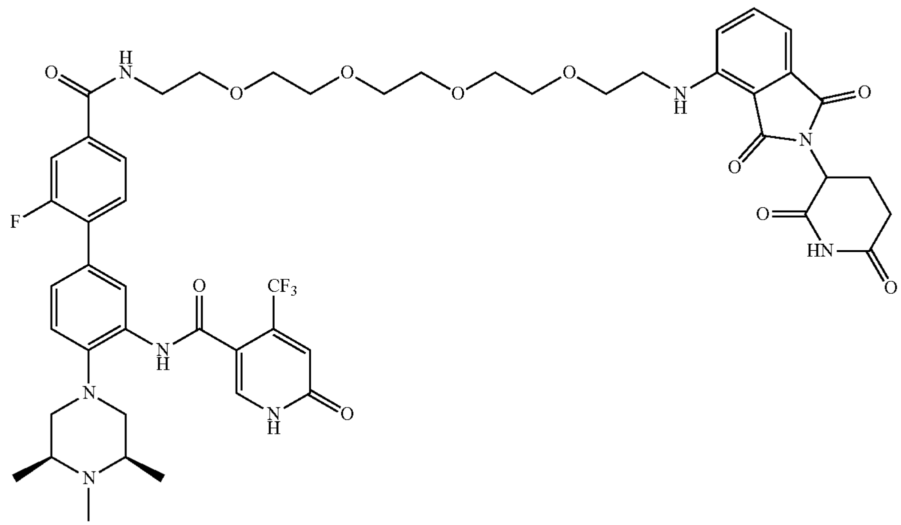 [SMILES: C[C@@H]1CN(c2ccc(-c3ccc(C(=O)NCCOCCOCCOCCOCCNc4cccc5c4C(=O)N(C4CCC(=O)NC4=O)C5=O)cc3F)cc2NC(=O)c2c[nH]c(=O)cc2C(F)(F)F)C[C@H](C)N1C] | N-(4'-((14-((2-(2,6-dioxopiperidin-3-yl)-1,3-dioxoisoindolin-4-yl)amino)-3,6,9,12-tetraoxatetradecyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| 122 | XF056-179 | 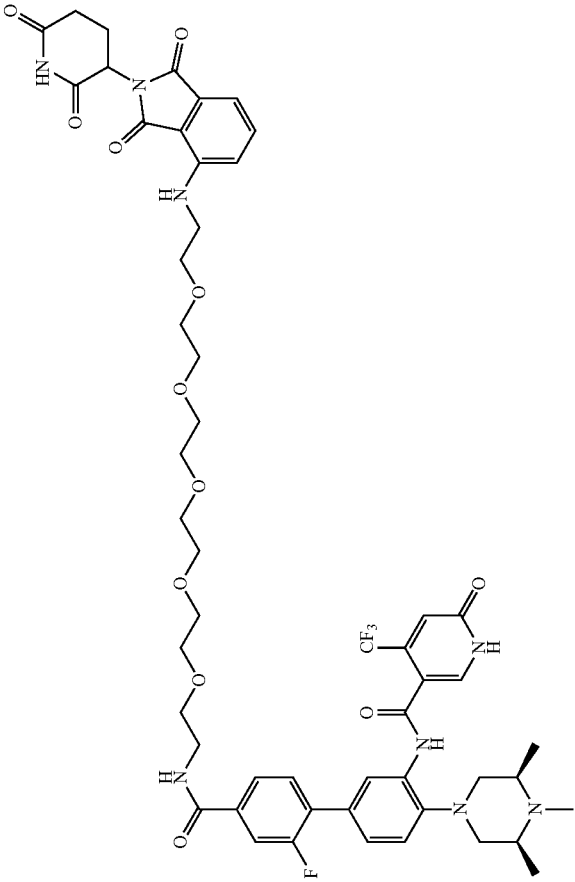 | N-(4'-((17-((2-(2,6-dioxopiperidin-3-yl)-1,3-dioxoisoindolin-4-yl)amino)-3,6,9,12,15-pentaoxaheptadecyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 123 | XF056-180 | 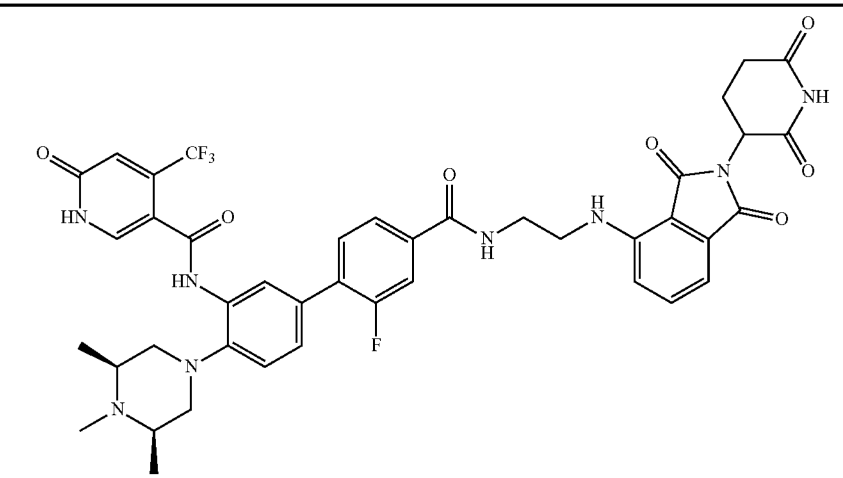 | N-(4'-((2-((2-(2,6-dioxopiperidin-3-yl)-1,3-dioxoisoindolin-4-yl)amino)ethyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 124 | XF056-181 | 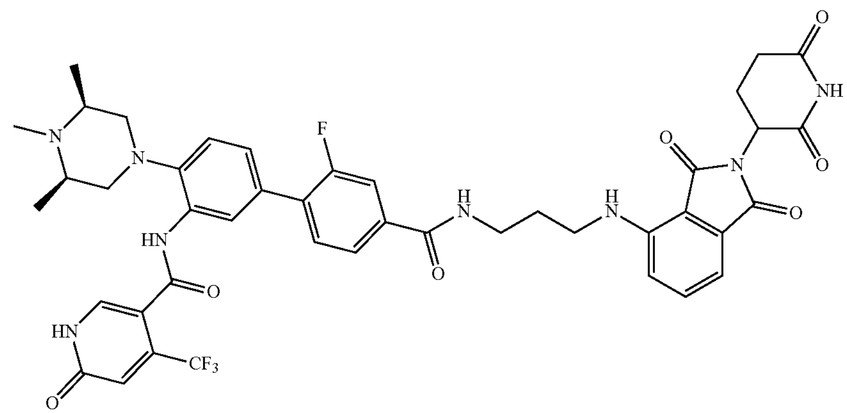 [SMILES: C[C@@H]1CN(c2ccc(-c3ccc(C(=O)NCCCNc4cccc5c4C(=O)N(C4CCC(=O)NC4=O)C5=O)cc3F)cc2NC(=O)c2c[nH]c(=O)cc2C(F)(F)F)C[C@H](C)N1C] | N-(4'-((3-((2-(2,6-dioxopiperidin-3-yl)-1,3-dioxoisoindolin-4-yl)amino)propyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 125 | XF056-182 | 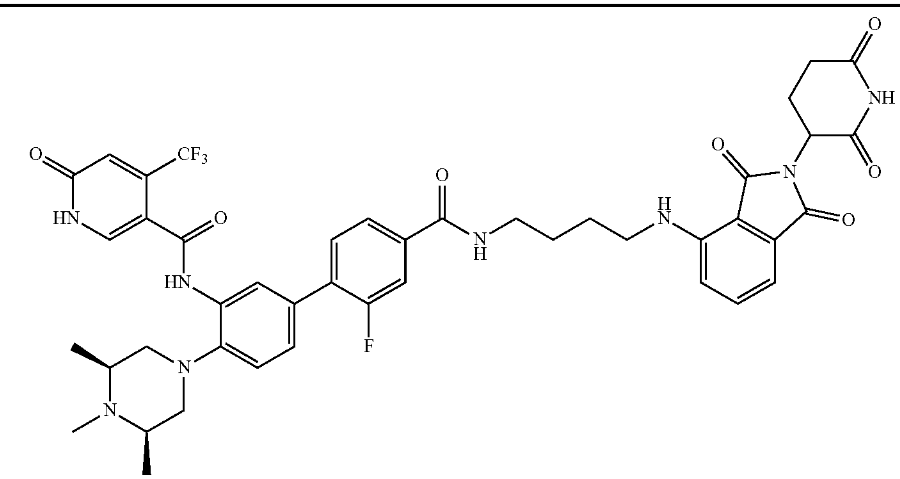 | N-(4'-((4-((2-(2,6-dioxopiperidin-3-yl)-1,3-dioxoisoindolin-4-yl)amino)butyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 126 | XF056-183 | 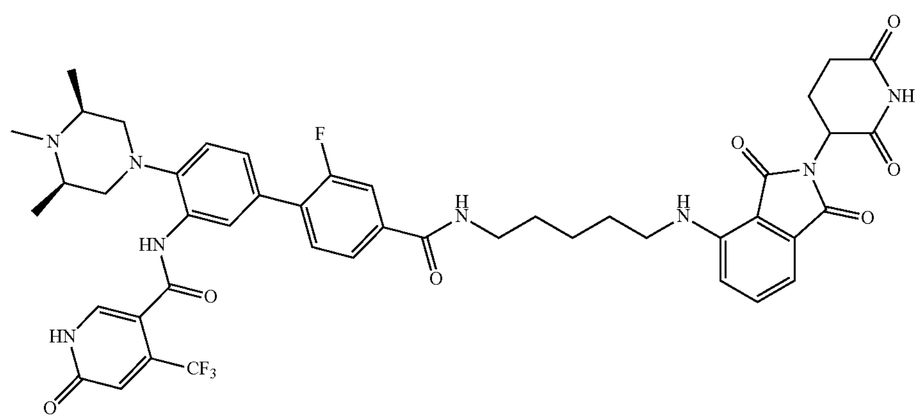 [SMILES: C[C@@H]1CN(c2ccc(-c3ccc(C(=O)NCCCCCNc4cccc5c4C(=O)N(C4CCC(=O)NC4=O)C5=O)cc3F)cc2NC(=O)c2c[nH]c(=O)cc2C(F)(F)F)C[C@H](C)N1C] | N-(4'-((5-((2-(2,6-dioxopiperidin-3-yl)-1,3-dioxoisoindolin-4-yl)amino)pentyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 127 | XF056-184 | 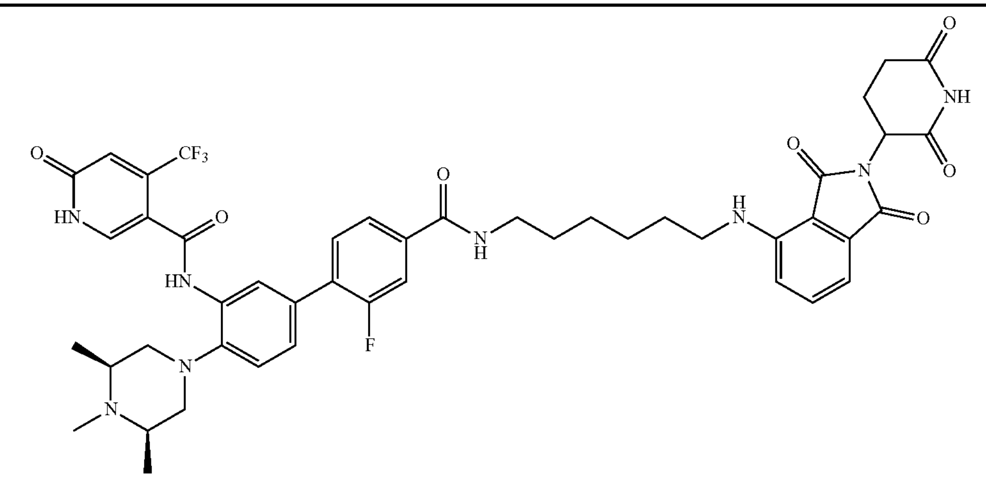 | N-(4'-((6-((2-(2,6-dioxopiperidin-3-yl)-1,3-dioxoisoindolin-4-yl)amino)hexyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 128 | XF056-185 | 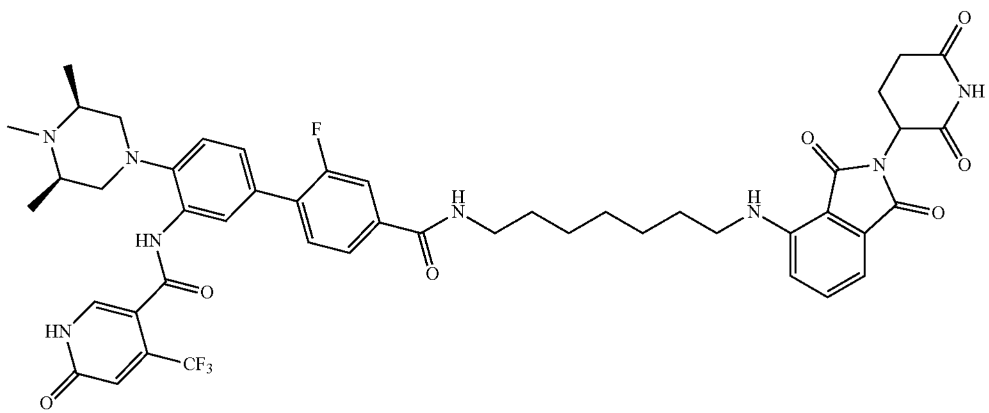 [SMILES: C[C@@H]1CN(c2ccc(-c3ccc(C(=O)NCCCCCCCNc4cccc5c4C(=O)N(C4CCC(=O)NC4=O)C5=O)cc3F)cc2NC(=O)c2c[nH]c(=O)cc2C(F)(F)F)C[C@H](C)N1C] | N-(4'-((7-((2-(2,6-dioxopiperidin-3-yl)-1,3-dioxoisoindolin-4-yl)amino)heptyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 129 | XF056-186 | 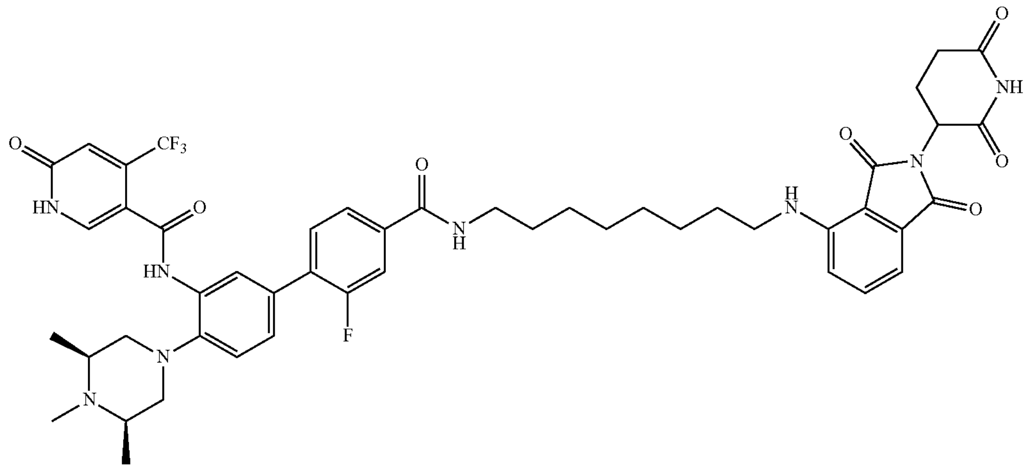 [SMILES: C[C@@H]1CN(c2ccc(-c3ccc(C(=O)NCCCCCCCCNc4cccc5c4C(=O)N(C4CCC(=O)NC4=O)C5=O)cc3F)cc2NC(=O)c2c[nH]c(=O)cc2C(F)(F)F)C[C@H](C)N1C] | N-(4'-((8-((2-(2,6-dioxopiperidin-3-yl)-1,3-dioxoisoindolin-4-yl)amino)octyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| 130 | XF061-104 | 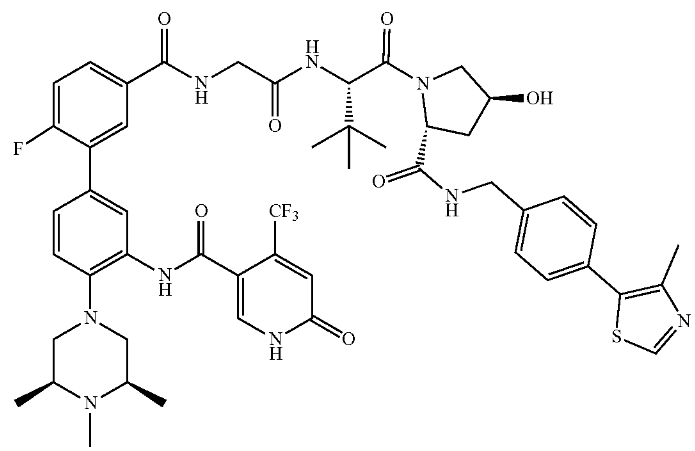 [SMILES: Cc1ncsc1-c1ccc(CNC(=O)[C@H]2C[C@H](O)CN2C(=O)[C@@H](NC(=O)CNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | N-(2'-fluoro-5'-((2-((S)-1-((2R,4S)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 131 | XF067-67 | 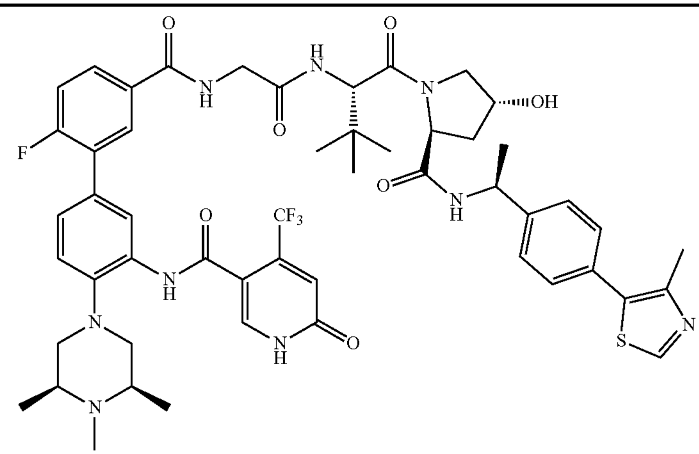 | N-(2'-fluoro-5'-((2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 132 | XF067-68 | 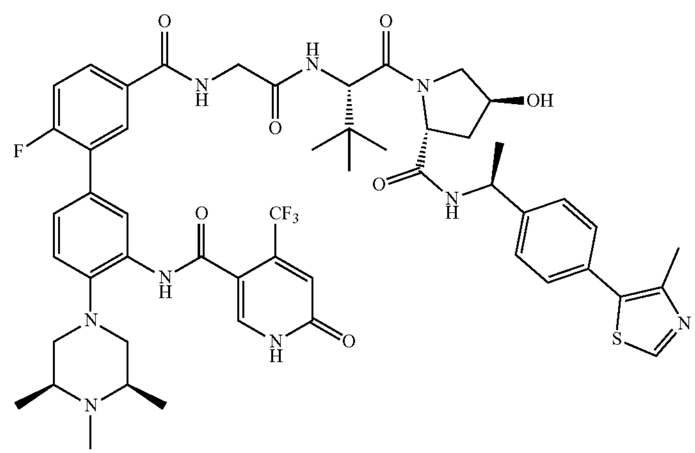 [SMILES: Cc1ncsc1-c1ccc([C@H](C)NC(=O)[C@H]2C[C@H](O)CN2C(=O)[C@@H](NC(=O)CNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | N-(2'-fluoro-5'-((2-(((S)-1-((2R,4S)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 148 | XF067-131 | 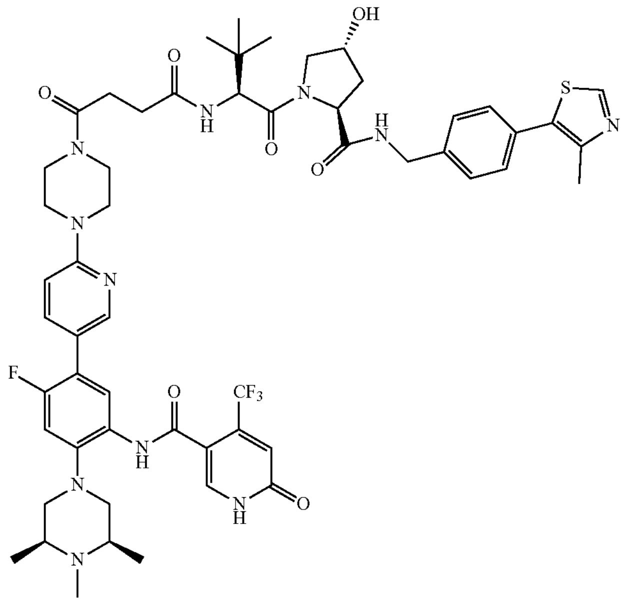 | N-(4-fluoro-5-(6-(4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Example | Compound ID | Structure | Chemical Name |
|---|---|---|---|
| 149 | XF067-133 | 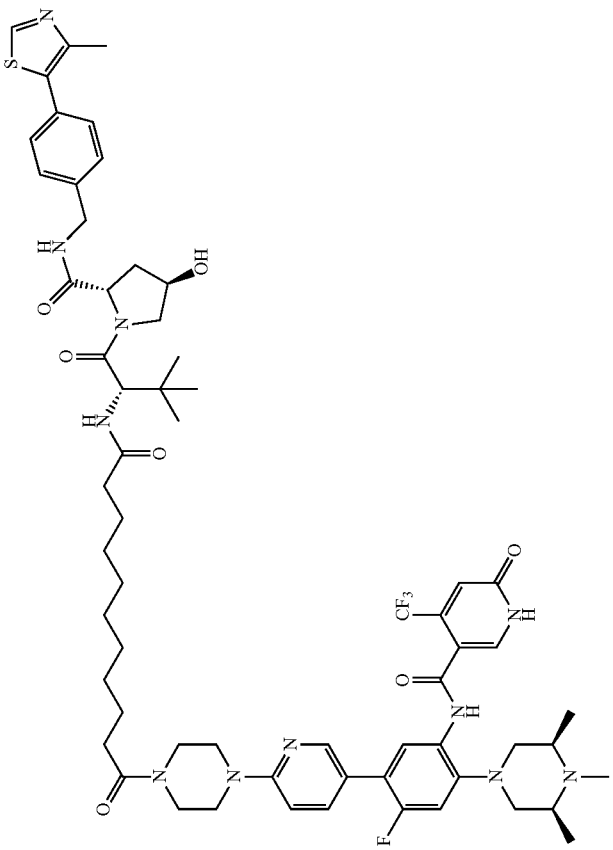 | N-(4-fluoro-5-(6-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 150 | XF067-134 | 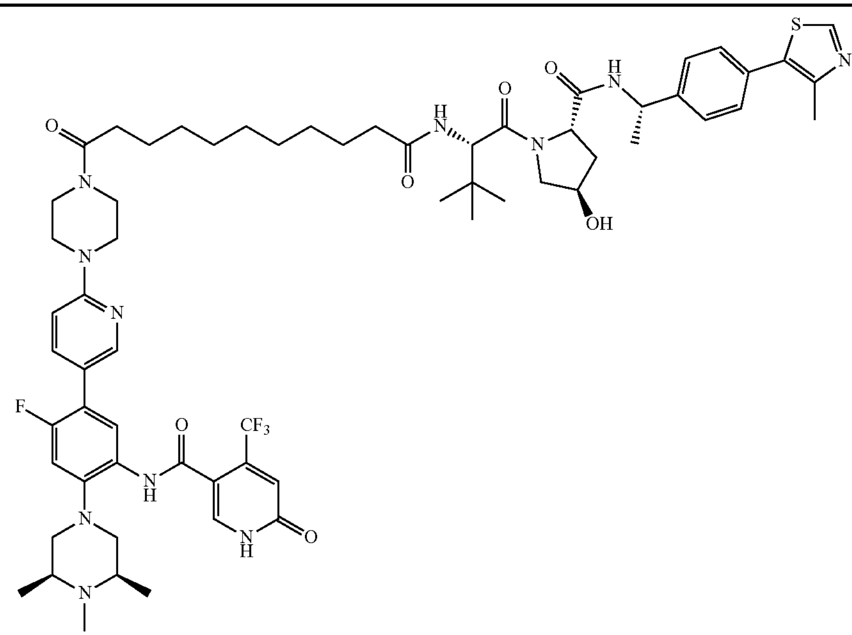 | N-(4-fluoro-5-(6-(4-(11-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-11-oxoundecanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex-am-ples | Com-pound ID | Structure | Chemical Name |
|---|---|---|---|
| 152 | XF067-140 | 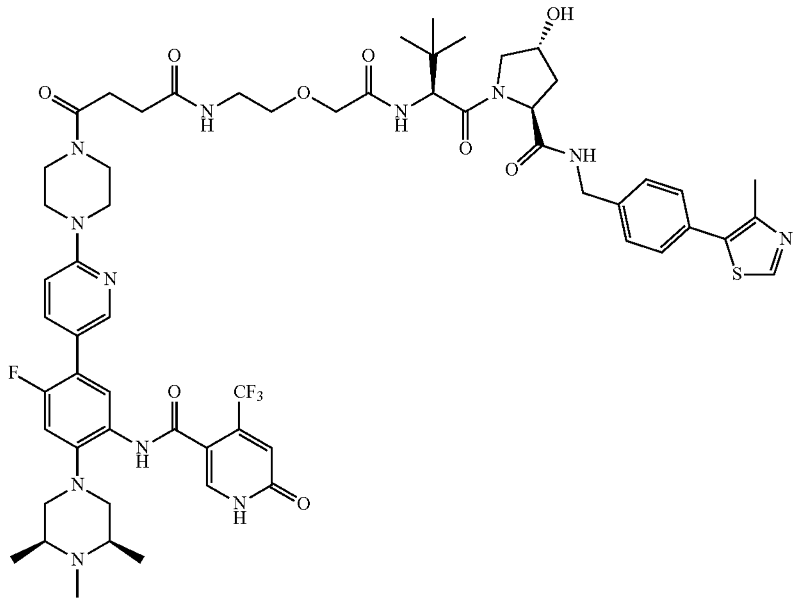 [SMILES: Cc1ncsc1-c1ccc(CNC(=O)[C@@H]2C[C@@H](O)CN2C(=O)[C@@H](NC(=O)COCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 153 | XF067-141 | 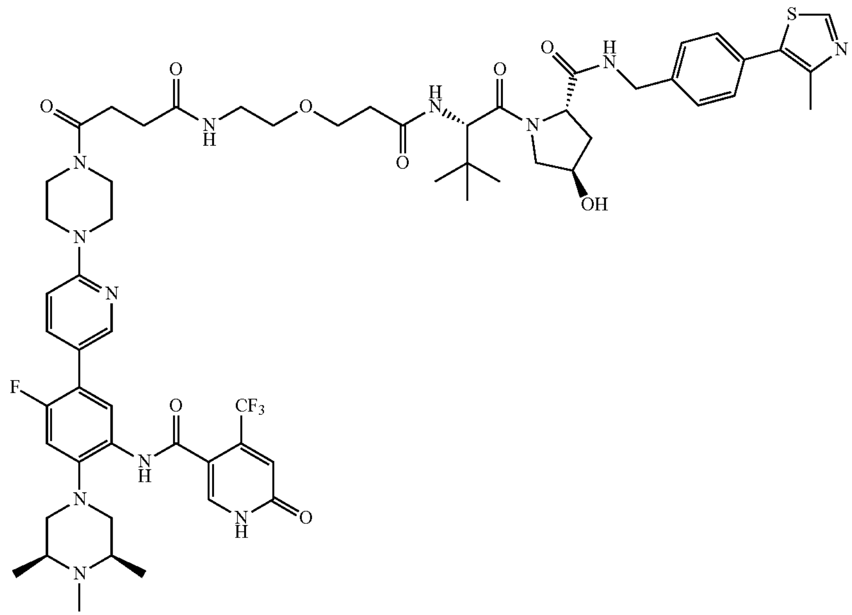 [SMILES: Cc1ncsc1-c1ccc(CNC(=O)[C@@H]2C[C@@H](O)CN2C(=O)[C@@H](NC(=O)CCOCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-((2-(3-((((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| 154 | XF067-142 | 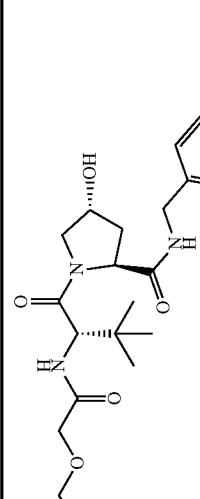 | N-(4-fluoro-5-(6-(4-(4-((S)-3-((2S,4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaheptadecan-17-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 155 | XF067- 143 | 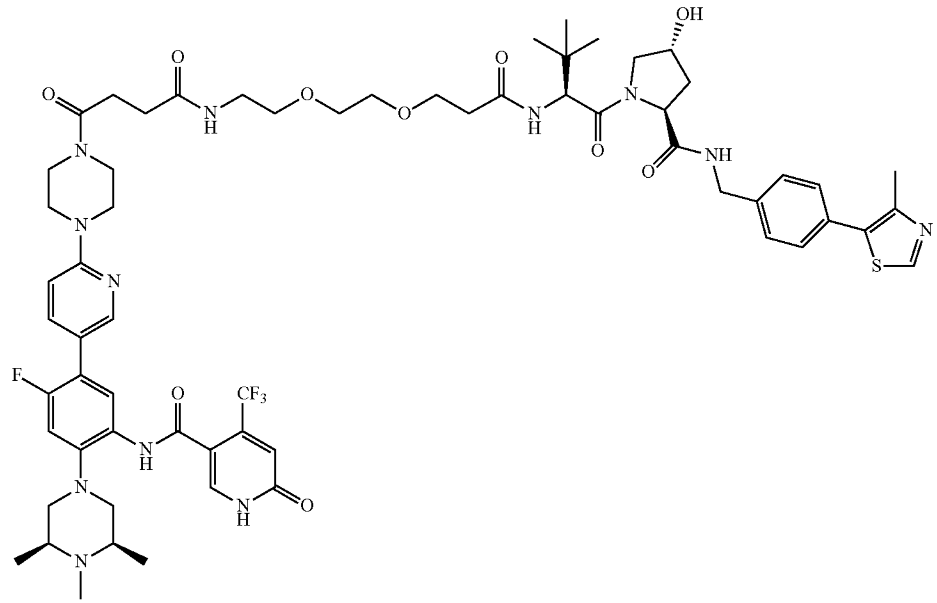 [SMILES: Cc1ncsc1-c1ccc(CNC(=O)[C@@H]2C[C@@H](O)CN2C(=O)[C@@H](NC(=O)CCOCCOCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-((S)-3-((2S,4R)-4-hydroxy-2-((4-(4-methylthiazol-5-yl)benzyl)carbamoyl)pyrrolidine-1-carbonyl)-2,2-dimethyl-5,15-dioxo-8,11-dioxa-4,14-diazaoctadecan-18-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| 156 | XF067-144 | 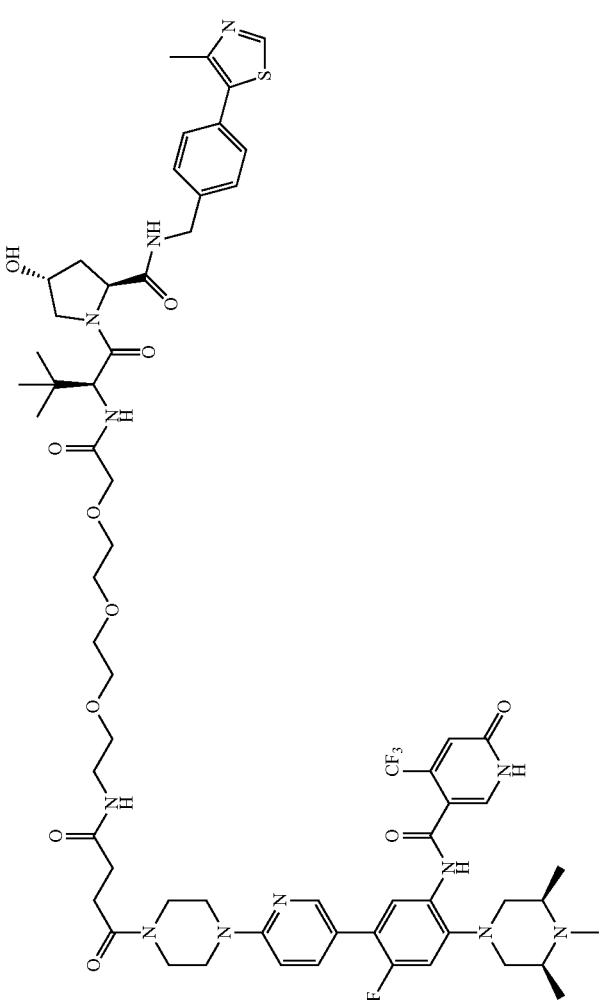 | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,17-dioxo-7,10,13-trioxa-4,16-diazaicosan-20-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 157 | XF067-145 | 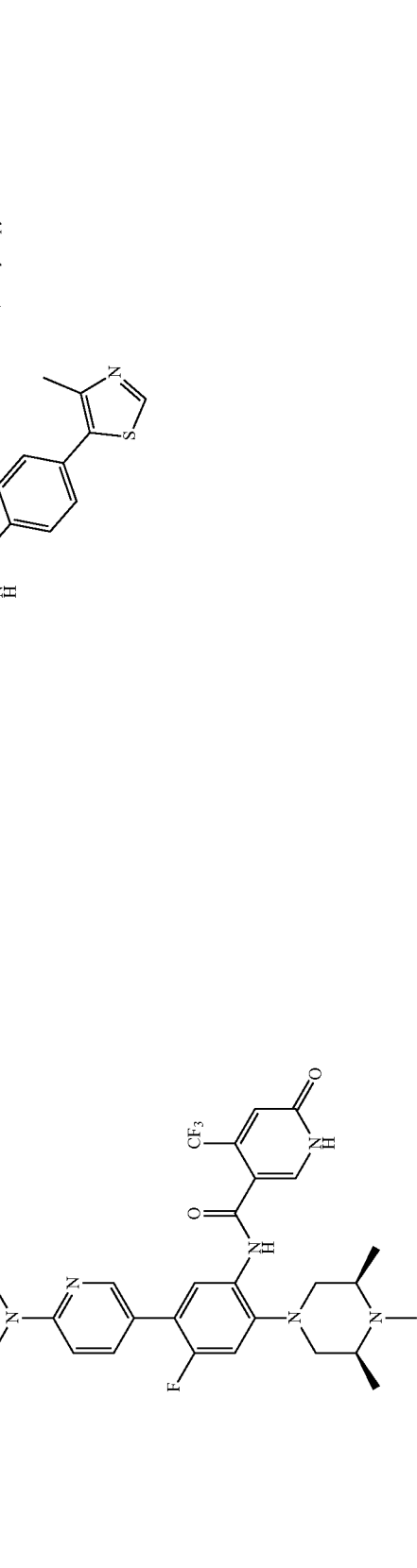 | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,18-dioxo-8,11,14-trioxa-4,17-diazahenicosan-21-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex-am-ples | Compound ID | Structure | Chemical Name |
|---|---|---|---|
| 158 | XF067-146 | 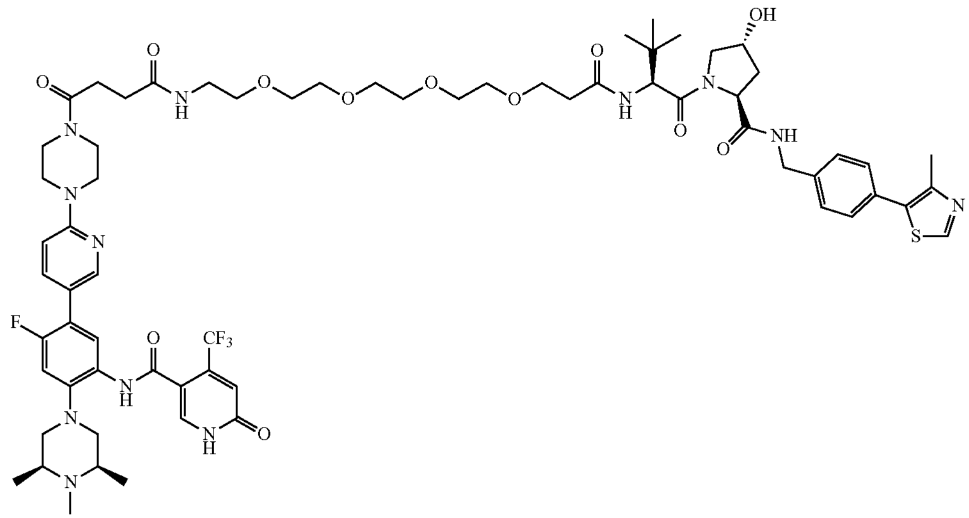 | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,21-dioxo-8,11,14,17-tetraoxa-4,20-diazatetracosan-24-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| 159 | XF067-147 | 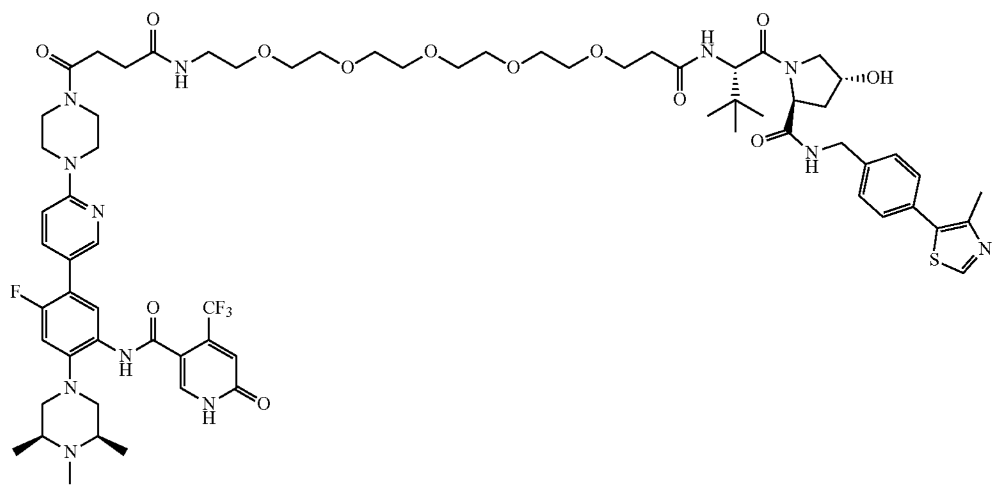 [SMILES: Cc1ncsc1-c1ccc(CNC(=O)[C@@H]2C[C@@H](O)CN2C(=O)[C@@H](NC(=O)CCOCCOCCOCCOCCOCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,24-dioxo-8,11,14,17,20-pentaoxa-4,23-diazaheptacosan-27-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Example | Compound ID | Structure | Chemical Name |
|---|---|---|---|
| 160 | XF067-148 | 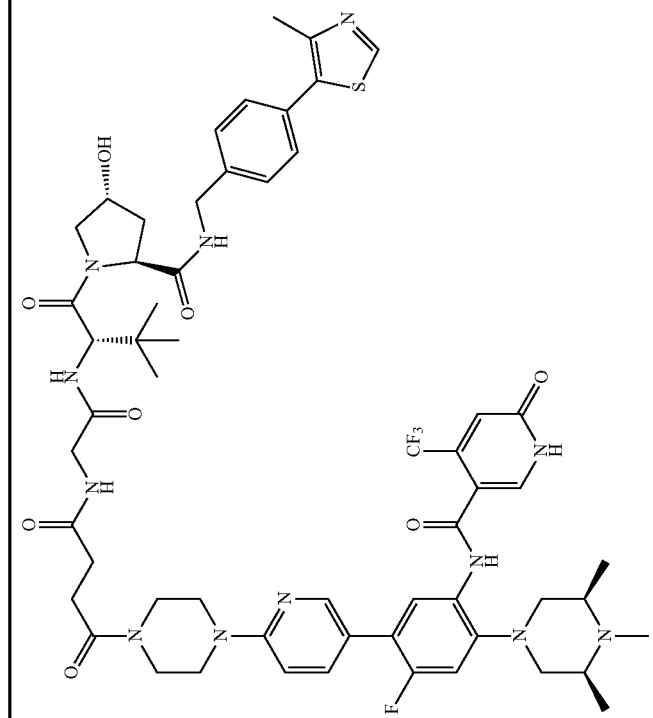 | N-(4-fluoro-5-(6-(4-(4-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 161 | XF067-149 | 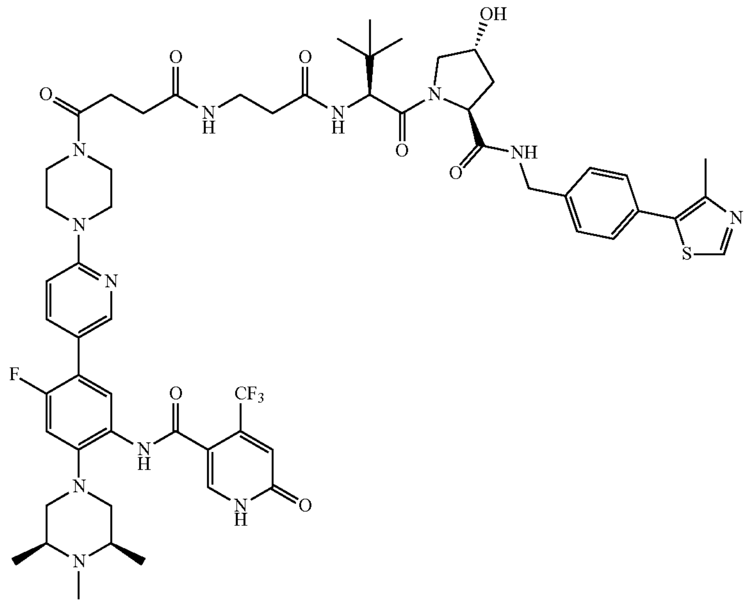 [SMILES: Cc1ncsc1-c1ccc(CNC(=O)[C@@H]2C[C@@H](O)CN2C(=O)[C@@H](NC(=O)CCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Ex-am-ples | Compound ID | Structure | Chemical Name |
|---|---|---|---|
| 162 | XF067-150 | 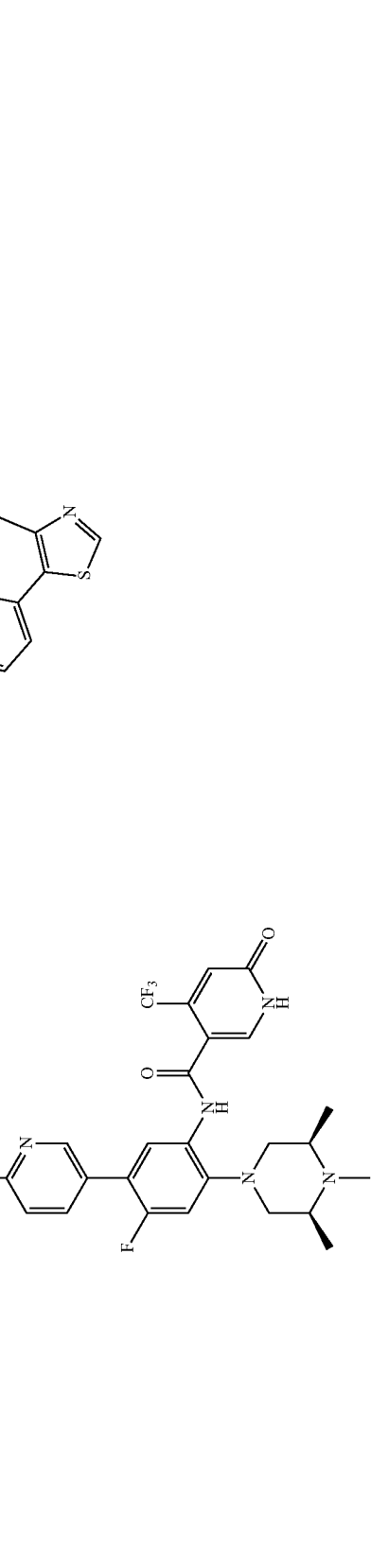 | N-(4-fluoro-5-(6-(4-(4-(4-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 163 | XF067-151 | 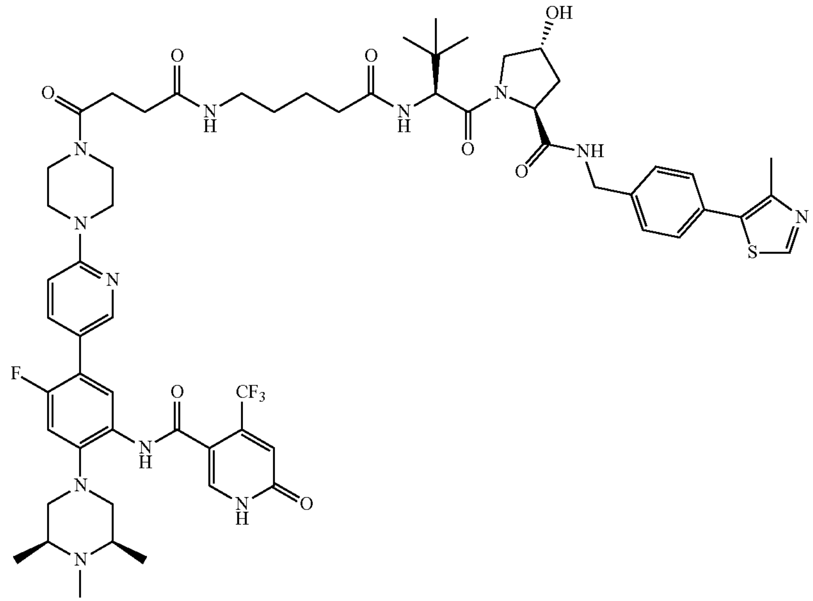 [SMILES: Cc1ncsc1-c1ccc(CNC(=O)[C@@H]2C[C@@H](O)CN2C(=O)[C@@H](NC(=O)CCCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 164 | XF067-152 | 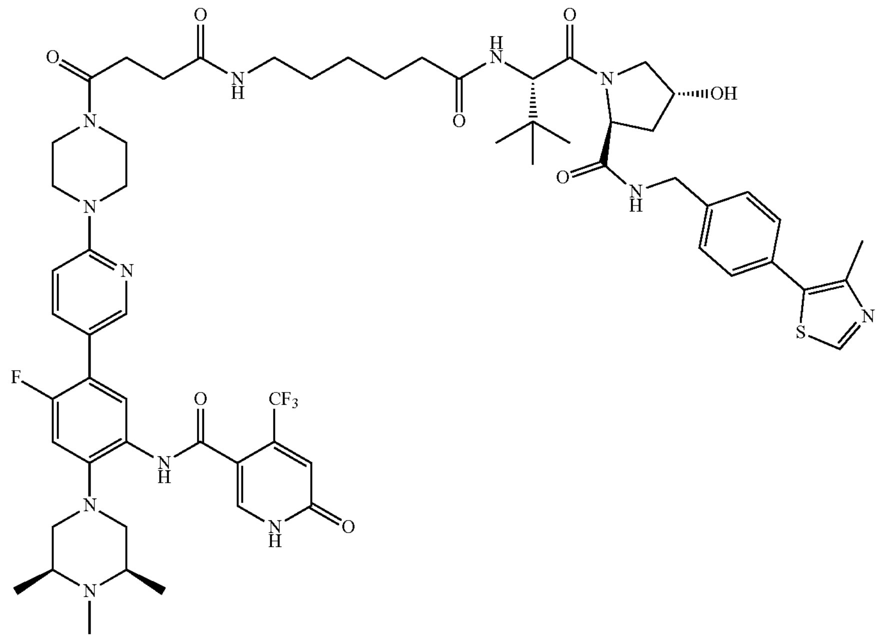 [SMILES: Cc1ncsc1-c1ccc(CNC(=O)[C@@H]2C[C@@H](O)CN2C(=O)[C@@H](NC(=O)CCCCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 165 | XF067-153 | 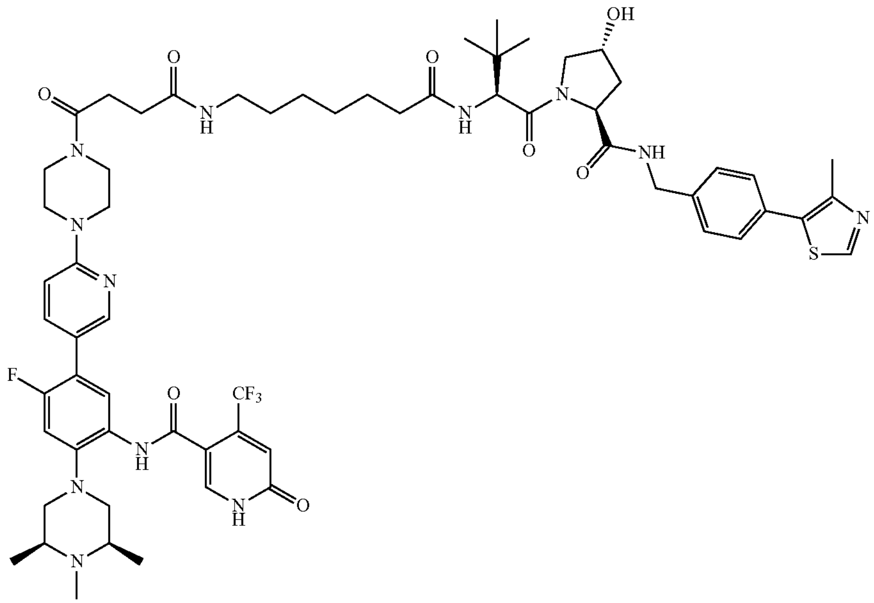 [SMILES: Cc1ncsc1-c1ccc(CNC(=O)[C@@H]2C[C@@H](O)CN2C(=O)[C@@H](NC(=O)CCCCCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| 166 | XF067- 154 | 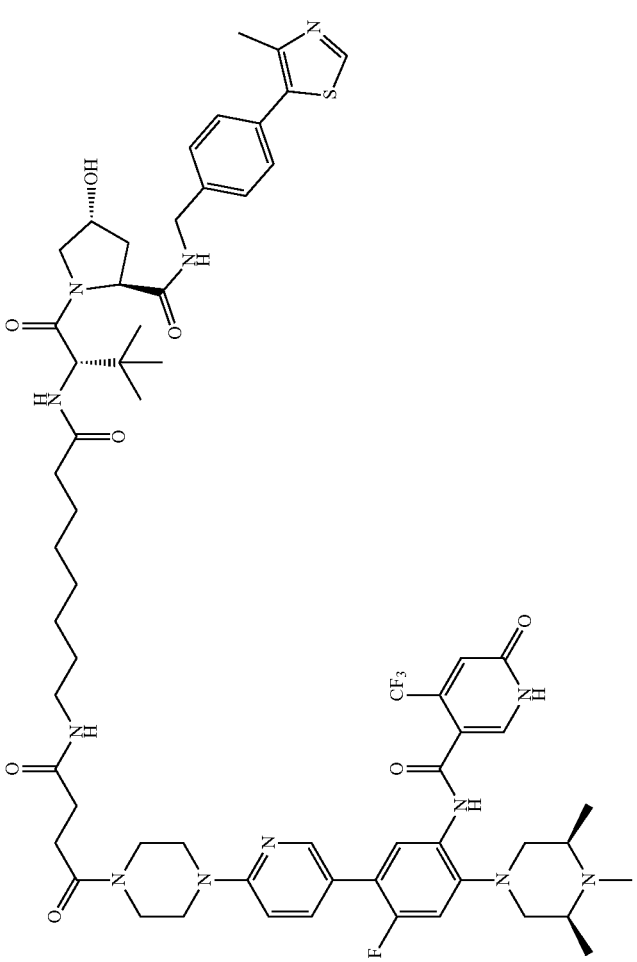 | N-(4-fluoro-5-(6-(4-(4-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 167 | XF067-155 | 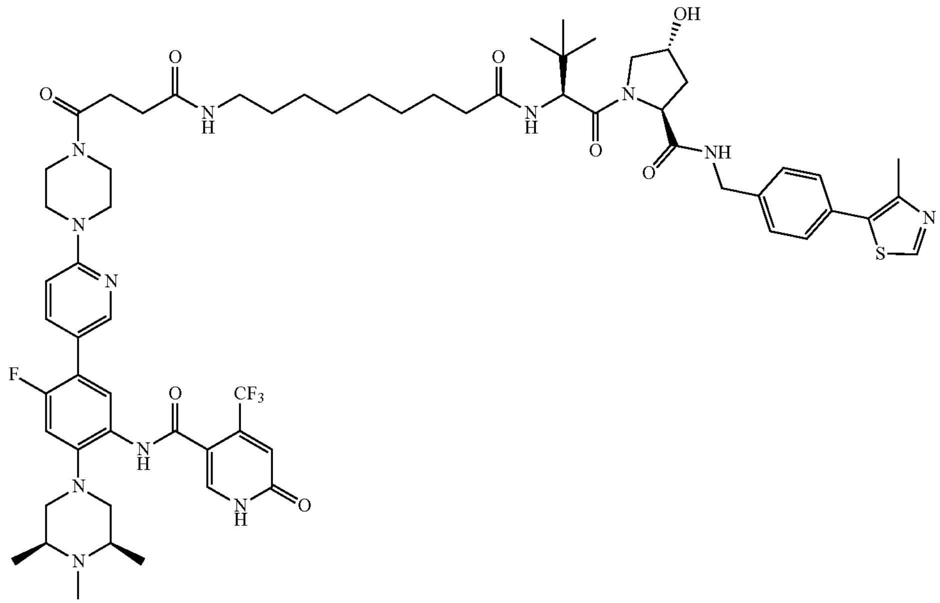 [SMILES: Cc1ncsc1-c1ccc(CNC(=O)[C@@H]2C[C@@H](O)CN2C(=O)[C@@H](NC(=O)CCCCCCCCNC(=O)CCC(=O)N2CCN(c3ccc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(6-(4-(4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 168 | XF067-156 | 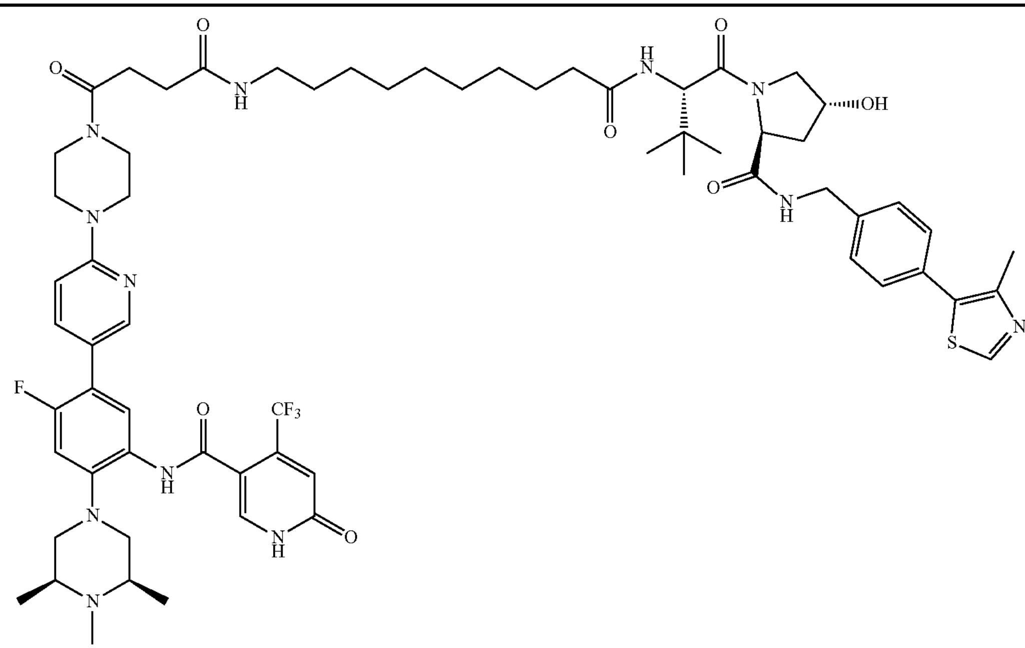 | N-(4-fluoro-5-(6-(4-(4-(4-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 169 | XF067-157 | 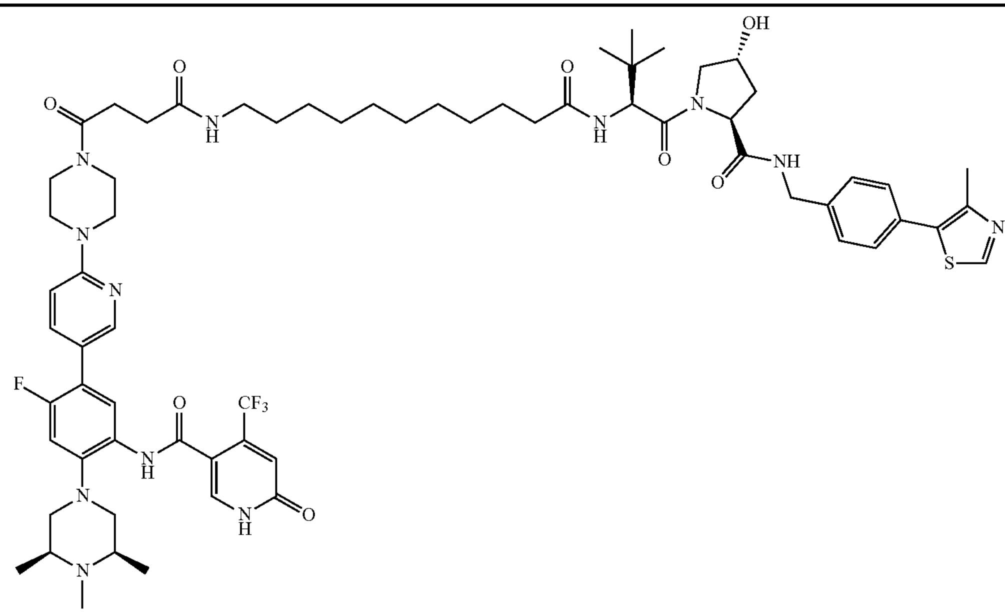 | N-(4-fluoro-5-(6-(4-(4-(4-((11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

| Example | Compound ID | Structure | Chemical Name |
|---|---|---|---|
| 170 | XF067-158 | 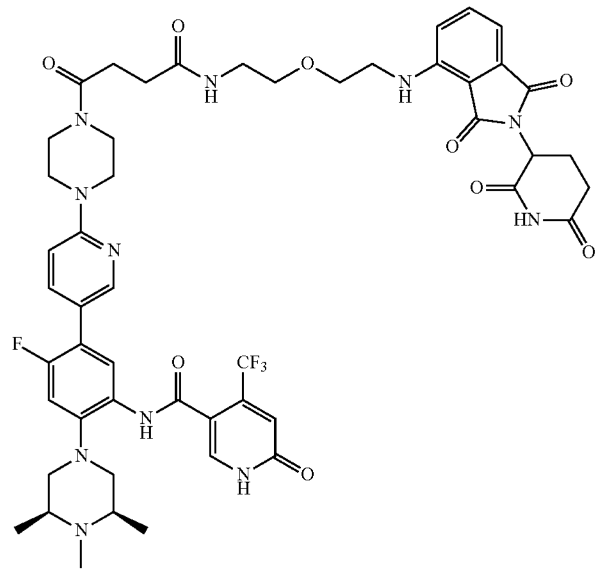 | N-(5-(6-(4-(4-((2-(2-((2-(2,6-dioxopiperidin-3-yl)-1,3-dioxoisoindolin-4-yl)amino)ethoxy)ethyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 171 | XF067-159 | 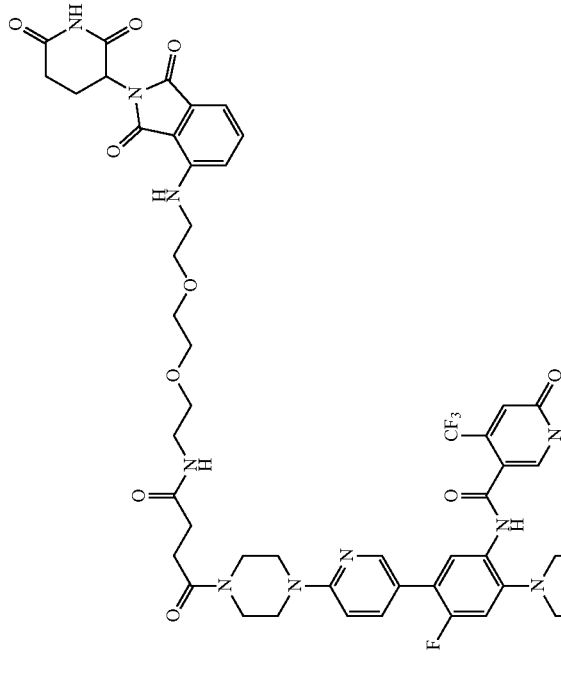 | N-(5-(6-(4-(4-((2-(2-(2-((2-(2,6-dioxopiperidin-3-yl)-1,3-dioxoisoindolin-4-yl)amino)ethoxy)ethoxy)ethyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 172 | XF067-160 | 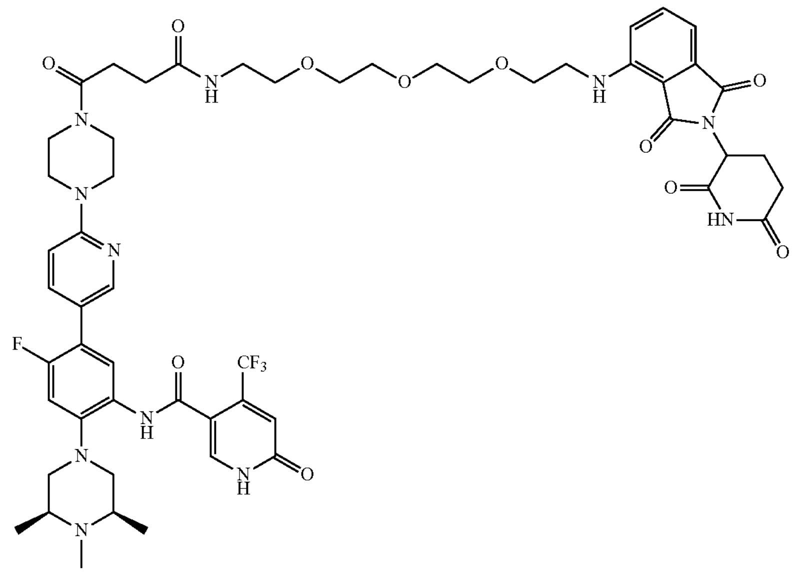 | N-(5-(6-(4-(1-((2-(2,6-dioxopiperidin-3-yl)-1,3-dioxoisoindolin-4-yl)amino)-13-oxo-3,6,9-trioxa-12-azahexadecan-16-oyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 173 | XF067-161 | 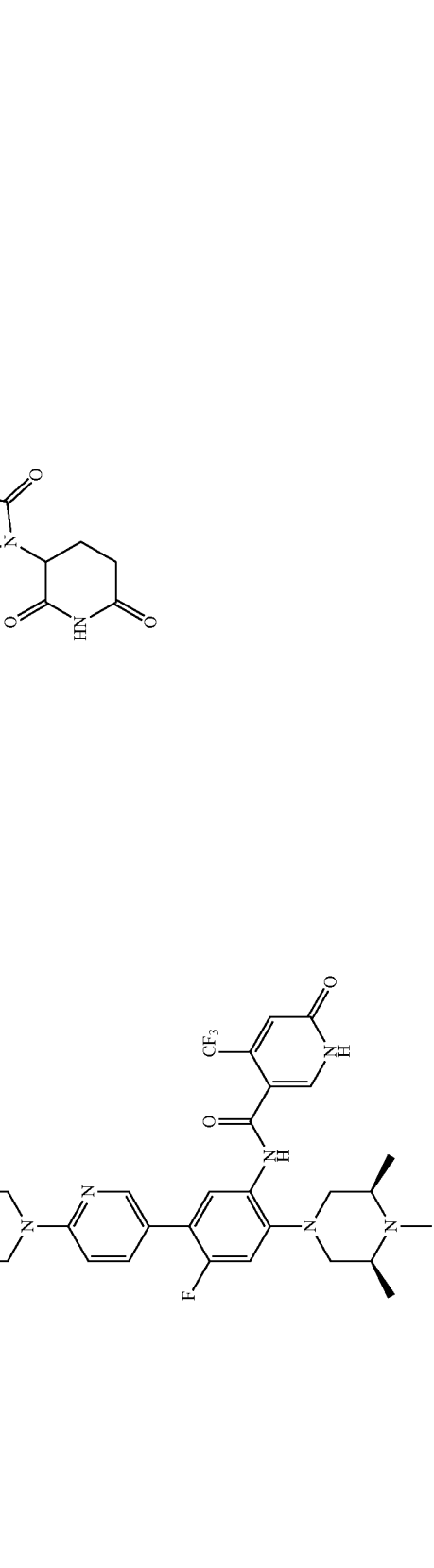 | N-(5-(6-(4-(1-((2-(2,6-dioxopiperidin-3-yl)-1,3-dioxoisoindolin-4-yl)amino)-16-oxo-3,6,9,12-tetraoxa-15-azanonadecan-19-oyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 174 | XF067-162 | 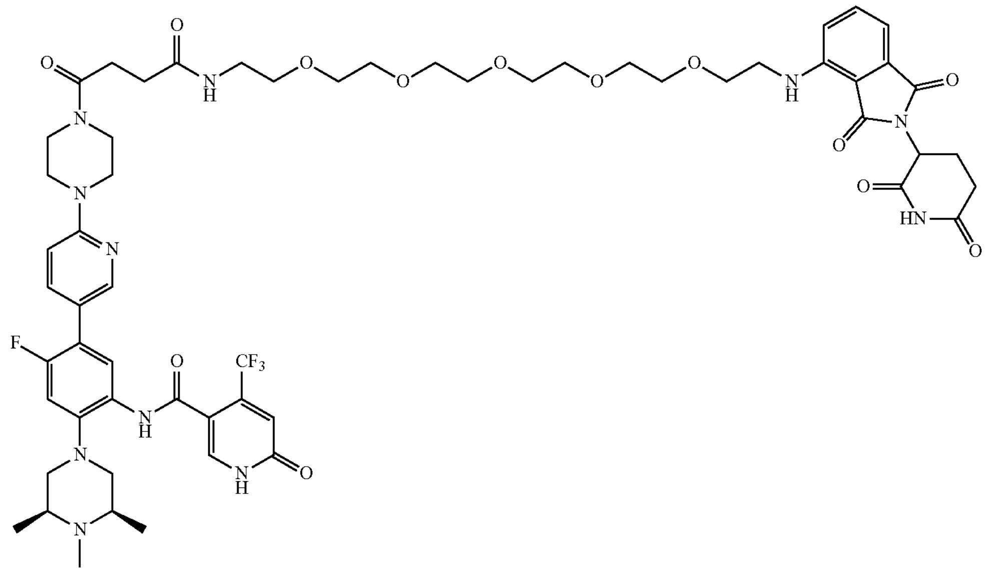 | N-(5-(6-(4-(1-((2-(2,6-dioxopiperidin-3-yl)-1,3-dioxoisoindolin-4-yl)amino)-19-oxo-3,6,9,12,15-pentaoxa-18-azadocosan-22-oyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 175 | XF067-163 | 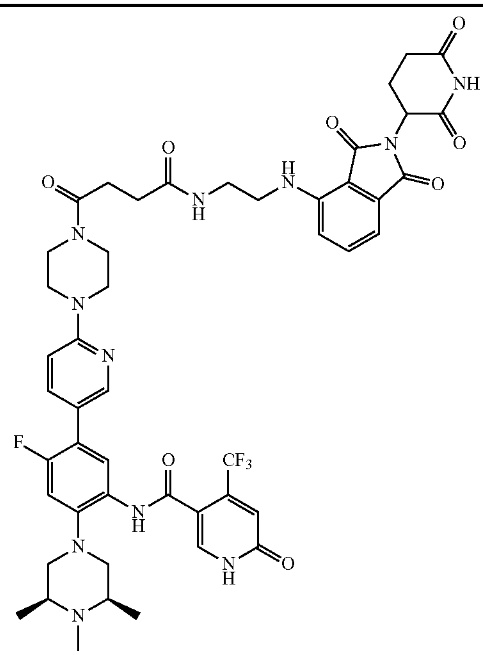 | N-(5-(6-(4-(4-((2-((2-(2,6-dioxopiperidin-3-yl)-1,3-dioxoisoindolin-4-yl)amino)ethyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 176 | XF067-164 | 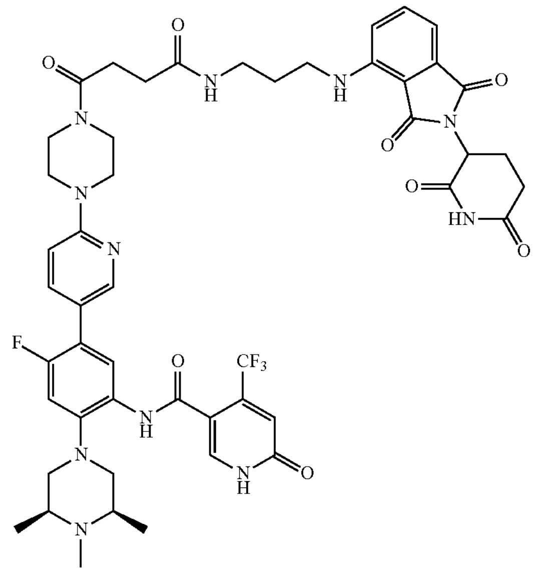 | N-(5-(6-(4-(4-((3-((2-(2,6-dioxopiperidin-3-yl)-1,3-dioxoisoindolin-4-yl)amino)propyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 177 | XF067-165 | 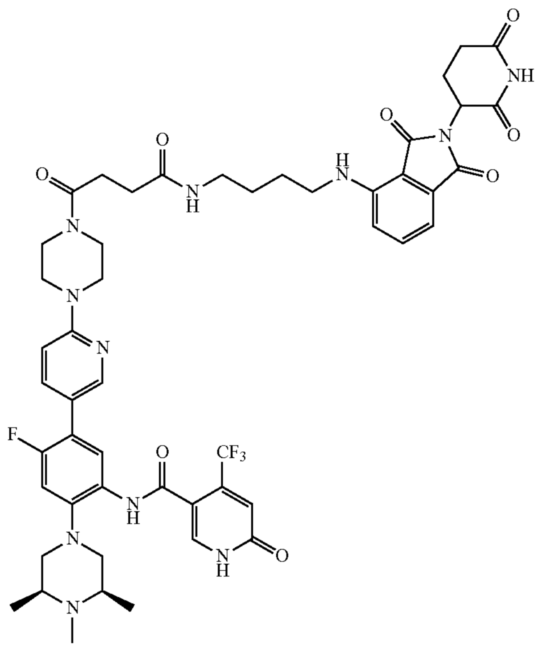 | N-(5-(6-(4-(4-(4-((2-(2,6-dioxopiperidin-3-yl)-1,3-dioxoisoindolin-4-yl)amino)butyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 178 | XF067-166 | 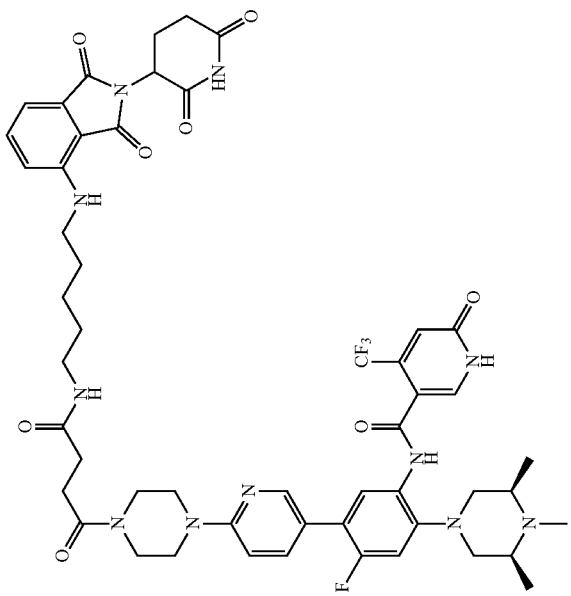 | N-(5-(6-(4-(4-((5-((2-(2,6-dioxopiperidin-3-yl)-1,3-dioxoisoindolin-4-yl)amino)pentyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 179 | XF067-167 | 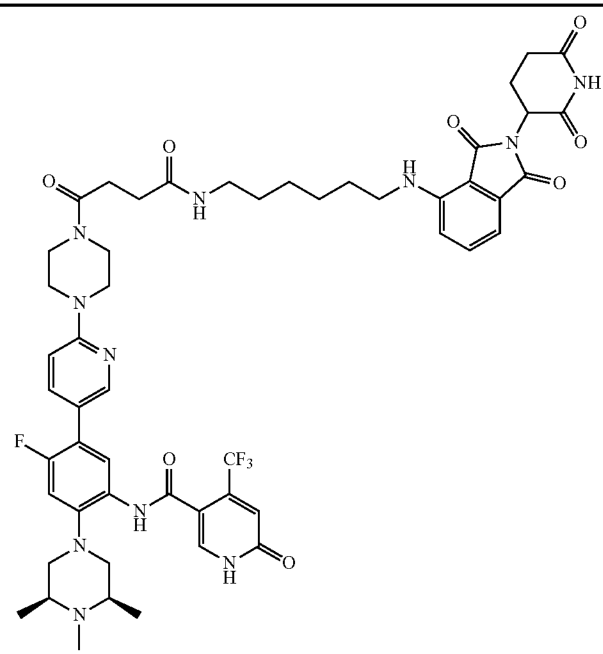 | N-(5-(6-(4-(4-((6-((2-(2,6-dioxopiperidin-3-yl)-1,3-dioxoisoindolin-4-yl)amino)hexyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 180 | XF067-168 | 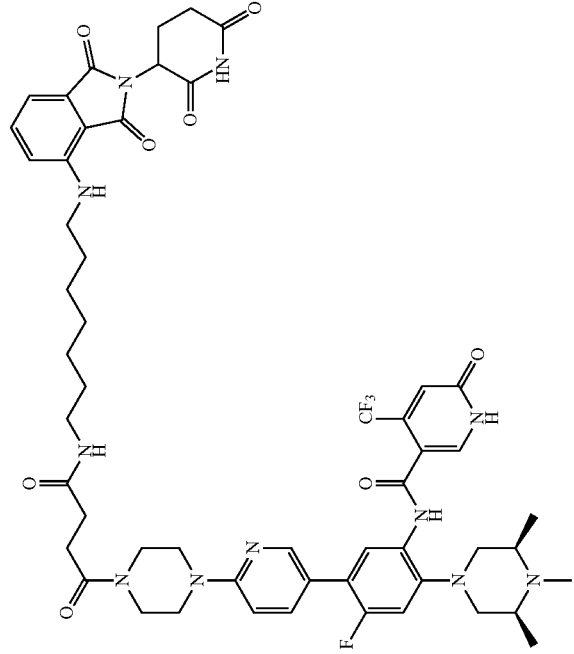 | N-(5-(6-(4-(4-((7-((2-(2,6-dioxopiperidin-3-yl)-1,3-dioxoisoindolin-4-yl)amino)heptyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 181 | XF067-169 | 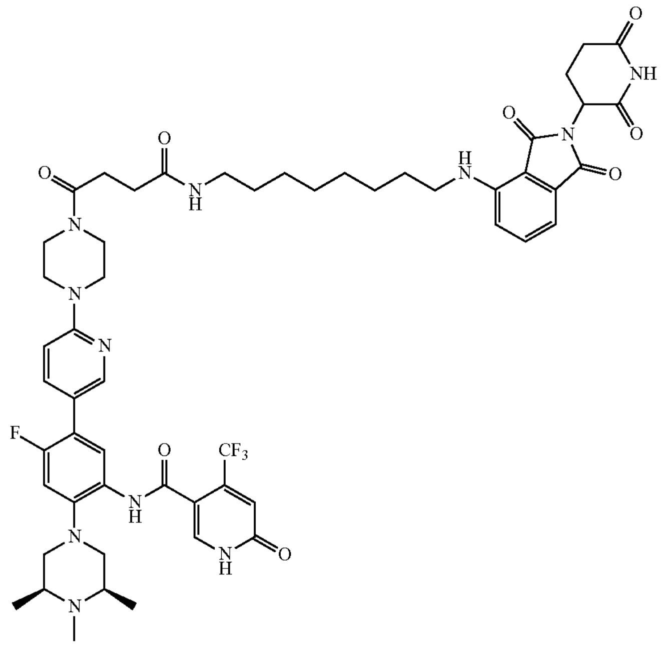 | N-(5-(6-(4-(4-(8-((2-(2,6-dioxopiperidin-3-yl)-1,3-dioxoisoindolin-4-yl)amino)octyl)amino)-4-oxobutanoyl)piperazin-1-yl)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| 183 | XF078-1 | 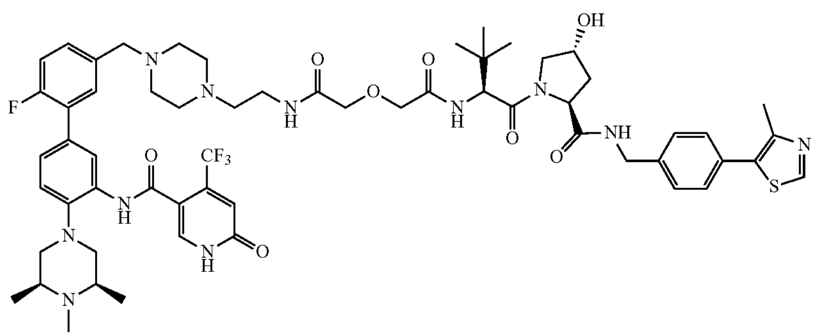 [SMILES: Cc1ncsc1-c1ccc(CNC(=O)[C@@H]2C[C@@H](O)CN2C(=O)[C@@H](NC(=O)COCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N-(2'-fluoro-5'-((4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)ethyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 184 | XF078-2 | 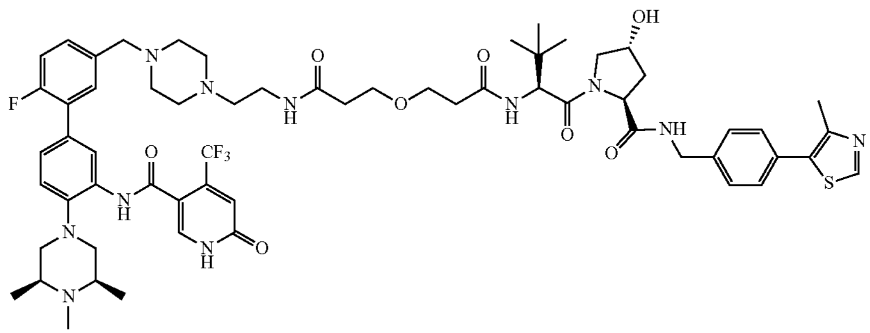 [SMILES: Cc1ncsc1-c1ccc(CNC(=O)[C@@H]2C[C@@H](O)CN2C(=O)[C@@H](NC(=O)CCOCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N-(2'-fluoro-5'-((4-(2-(3-((((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanamido)ethyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 185 | XF078-3 | 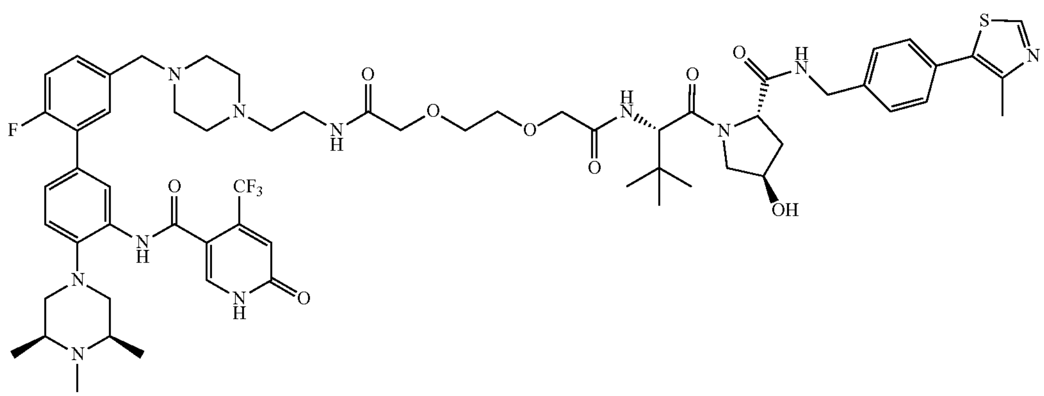 [SMILES: Cc1ncsc1-c1ccc(CNC(=O)[C@@H]2C[C@@H](O)CN2C(=O)[C@@H](NC(=O)COCCOCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N-(2'-fluoro-5'-((4-((S)-13-((2S,4R)-4-hydroxy-2-((4-(4-methylthiazol-5-yl)benzyl)carbamoyl)pyrrolidine-1-carbonyl)-14,14-dimethyl-4,11-dioxo-6,9-dioxa-3,12-diazapentadecyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 186 | XF078-4 | 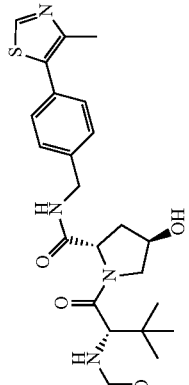 | N-(2'-fluoro-5'-((4-((S)-15-((2S,4R)-4-hydroxy-2-((4-(4-methylthiazol-5-yl)benzyl)carbamoyl)pyrrolidine-1-carbonyl)-16,16-dimethyl-4,13-dioxo-7,10-dioxa-3,14-diazaheptadecyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 187 | XF078-5 | 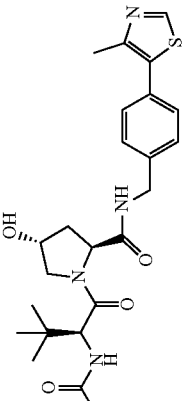 | N-(2'-fluoro-5'-((4-((S)-16-((2S,4R)-4-hydroxy-2-((4-(4-methylthiazol-5-yl)benzyl)carbamoyl)pyrrolidine-1-carbonyl)-17,17-dimethyl-4,14-dioxo-6,9,12-trioxa-3,15-diazaoctadecyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 188 | XF078-6 | 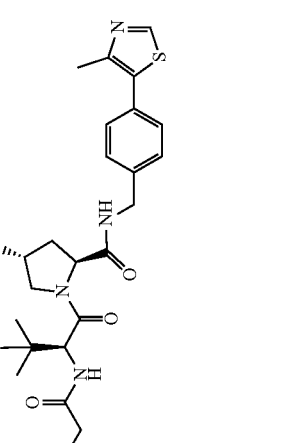 | N-(2'-fluoro-5'-((4-((S)-18-((2S,4R)-4-hydroxy-2-((4-(4-methylthiazol-5-yl)benzyl)carbamoyl)pyrrolidine-1-carbonyl)-19,19-dimethyl-4,16-dioxo-7,10,13-trioxa-3,17-diazaicosyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 189 | XF078-7 | 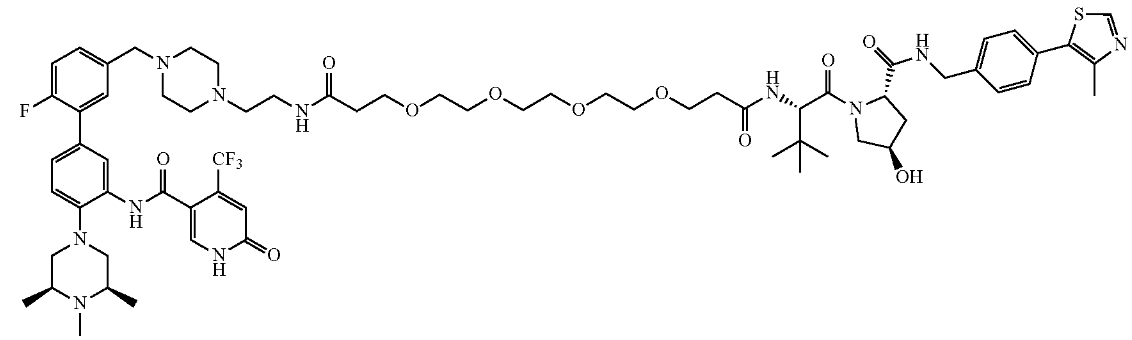 [SMILES: Cc1ncsc1-c1ccc(CNC(=O)[C@@H]2C[C@@H](O)CN2C(=O)[C@@H](NC(=O)CCOCCOCCOCCOCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | $N^1$-(2-(4-((6-fluoro-3'-(6-oxo-4-(trifluoromethyl)-1,6-dihydropyridine-3-carboxamido)-4-((3S,5R)-3,4,5-trimethylpiperazin-1-yl)-[1,1'-biphenyl]-3-yl)methyl)piperazin-1-yl)ethyl)-$N^{16}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |
| 190 | XF078-8 | 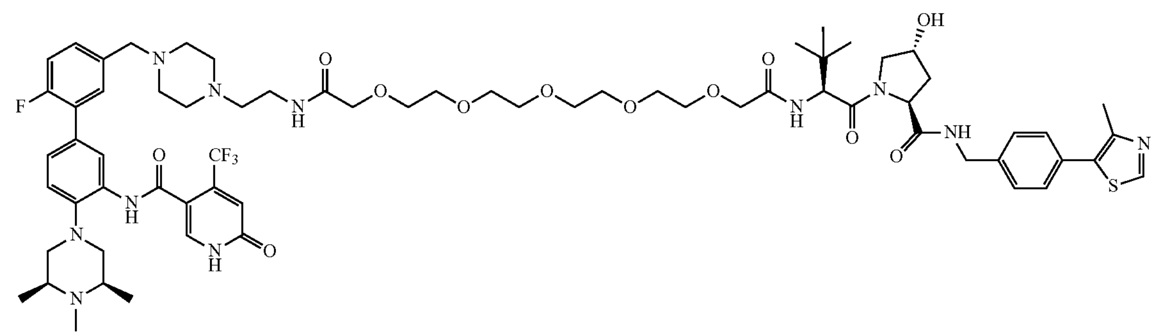 [SMILES: Cc1ncsc1-c1ccc(CNC(=O)[C@@H]2C[C@@H](O)CN2C(=O)[C@@H](NC(=O)COCCOCCOCCOCCOCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | $N^1$-(2-(4-((6-fluoro-3'-(6-oxo-4-(trifluoromethyl)-1,6-dihydropyridine-3-carboxamido)-4-((3S,5R)-3,4,5-trimethylpiperazin-1-yl)-[1,1'-biphenyl]-3-yl)methyl)piperazin-1-yl)ethyl)-$N^{17}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide |
| 191 | XF078-9 | 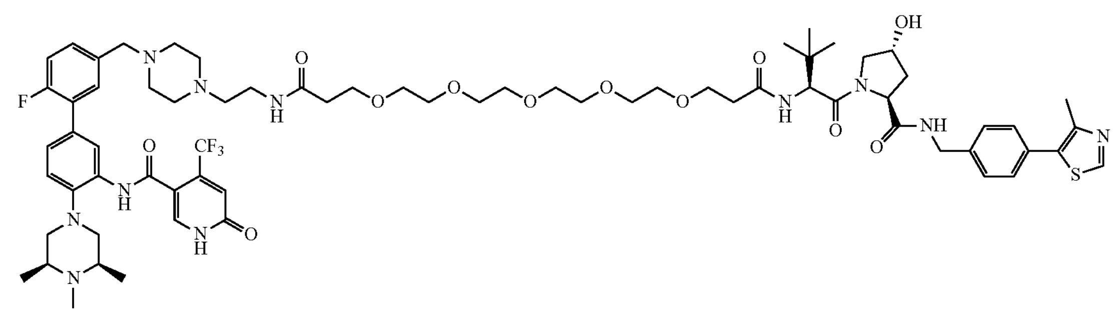 [SMILES: Cc1ncsc1-c1ccc(CNC(=O)[C@@H]2C[C@@H](O)CN2C(=O)[C@@H](NC(=O)CCOCCOCCOCCOCCOCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | $N^1$-(2-(4-((6-fluoro-3'-(6-oxo-4-(trifluoromethyl)-1,6-dihydropyridine-3-carboxamido)-4-((3S,5R)-3,4,5-trimethylpiperazin-1-yl)-[1,1'-biphenyl]-3-yl)methyl)piperazin-1-yl)ethyl)-$N^{19}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |

TABLE 1-continued

| Examples | Compound ID | Structure | Chemical Name |
|---|---|---|---|
| 192 | XF078-10 | 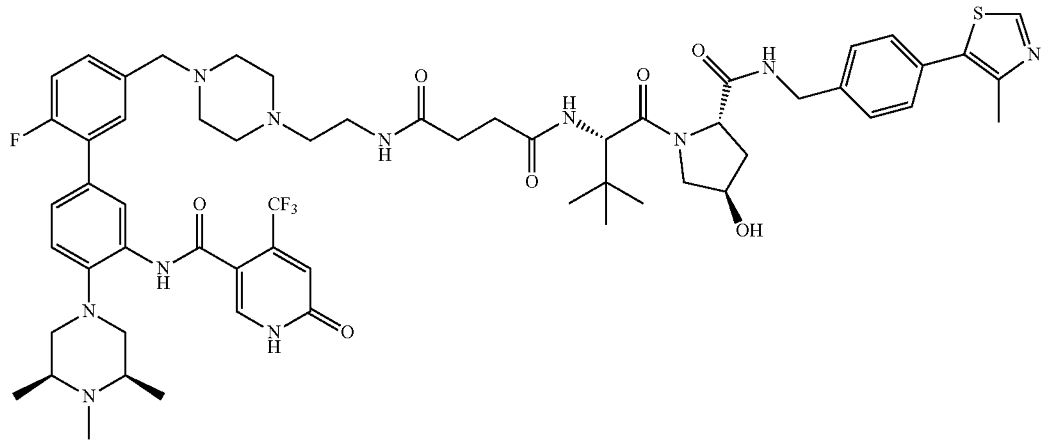 [SMILES: Cc1ncsc1-c1ccc(CNC(=O)[C@@H]2C[C@@H](O)CN2C(=O)[C@@H](NC(=O)CCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N1-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |
| 193 | XF078-11 | 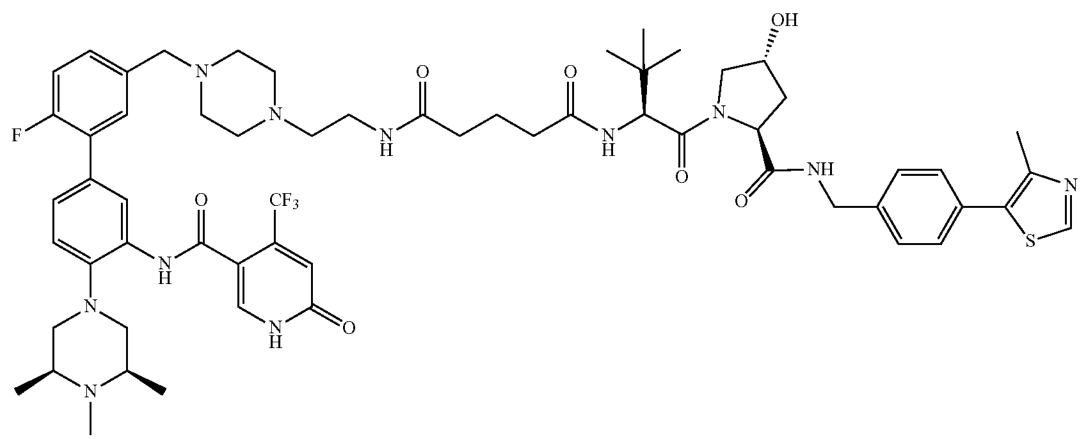 [SMILES: Cc1ncsc1-c1ccc(CNC(=O)[C@@H]2C[C@@H](O)CN2C(=O)[C@@H](NC(=O)CCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N1-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |

TABLE 1-continued

| Examples | Compound ID | Structure | Chemical Name |
|---|---|---|---|
| 194 | XF078-12 | 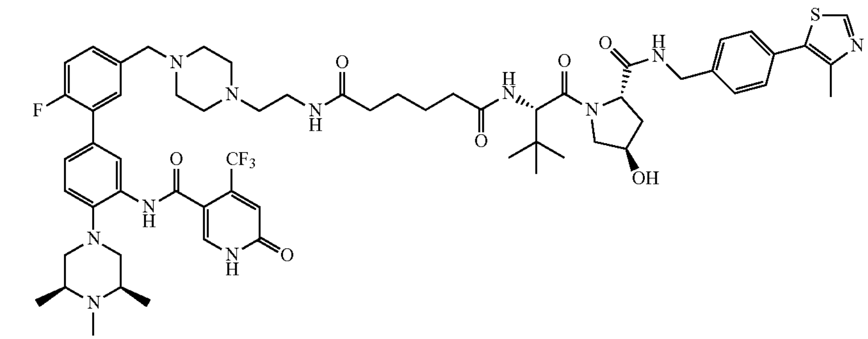 [SMILES: Cc1ncsc1-c1ccc(CNC(=O)[C@@H]2C[C@@H](O)CN2C(=O)[C@@H](NC(=O)CCCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N⁶-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |
| 195 | XF078-13 | 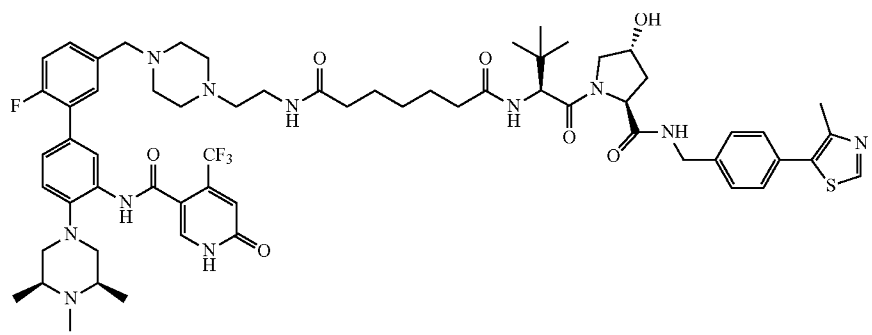 | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N⁷-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
| 196 | XF078-14 | 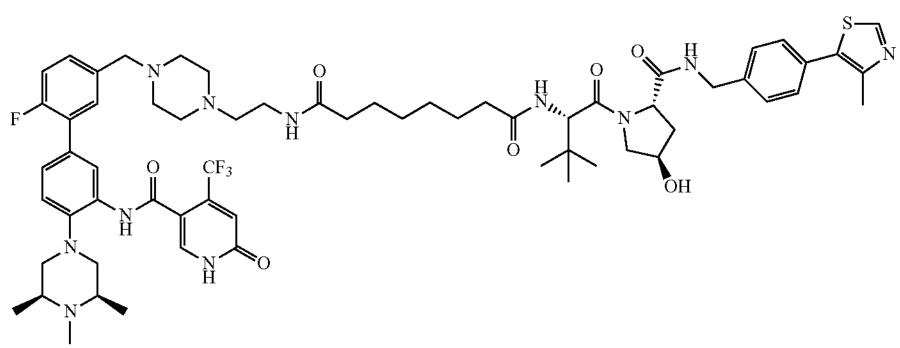 [SMILES: Cc1ncsc1-c1ccc(CNC(=O)[C@@H]2C[C@@H](O)CN2C(=O)[C@@H](NC(=O)CCCCCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N⁸-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |

TABLE 1-continued

| Examples | Compound ID | Structure | Chemical Name |
|---|---|---|---|
| 197 | XF078-15 | 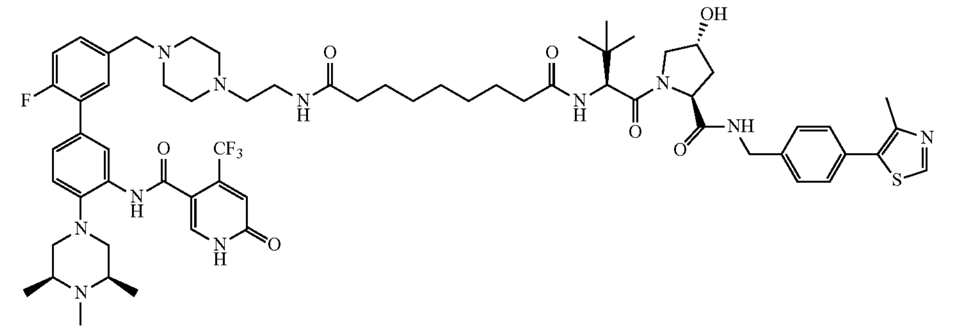 [SMILES: Cc1ncsc1-c1ccc(CNC(=O)[C@@H]2C[C@@H](O)CN2C(=O)[C@@H](NC(=O)CCCCCCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N⁹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |
| 198 | XF078-16 | 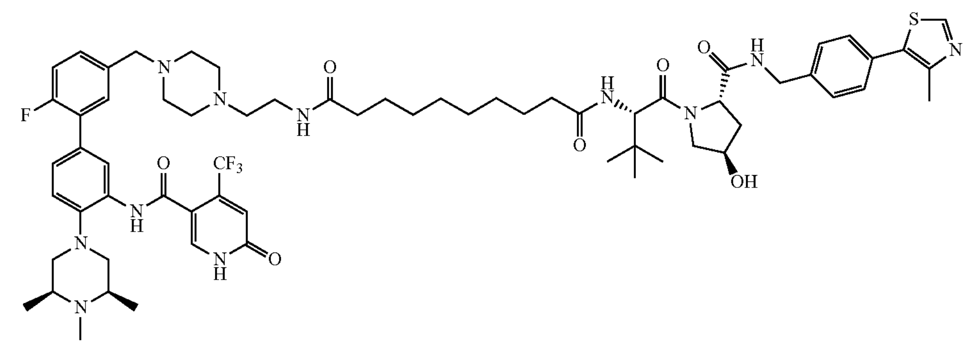 [SMILES: Cc1ncsc1-c1ccc(CNC(=O)[C@@H]2C[C@@H](O)CN2C(=O)[C@@H](NC(=O)CCCCCCCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N¹⁰-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |
| 199 | XF078-17 | 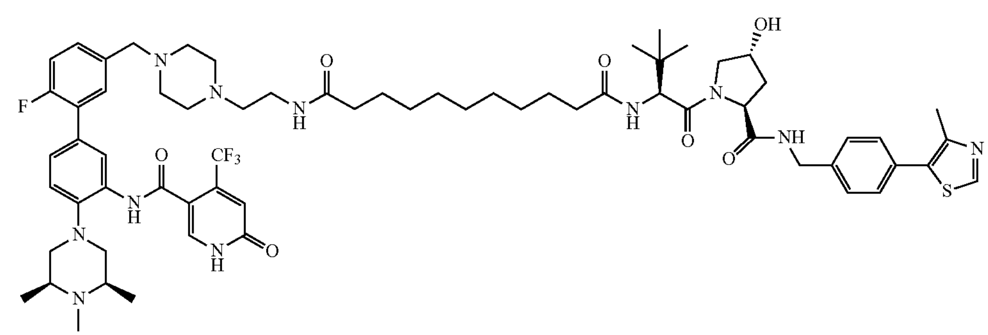 [SMILES: Cc1ncsc1-c1ccc(CNC(=O)[C@@H]2C[C@@H](O)CN2C(=O)[C@@H](NC(=O)CCCCCCCCCC(=O)NCCN2CCN(Cc3ccc(F)c(-c4ccc(N5C[C@@H](C)N(C)[C@@H](C)C5)c(NC(=O)c5c[nH]c(=O)cc5C(F)(F)F)c4)c3)CC2)C(C)(C)C)cc1] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N¹¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |

TABLE 1-continued

| Examples | Compound ID | Structure | Chemical Name |
|---|---|---|---|
| 200 | XF078-18 | 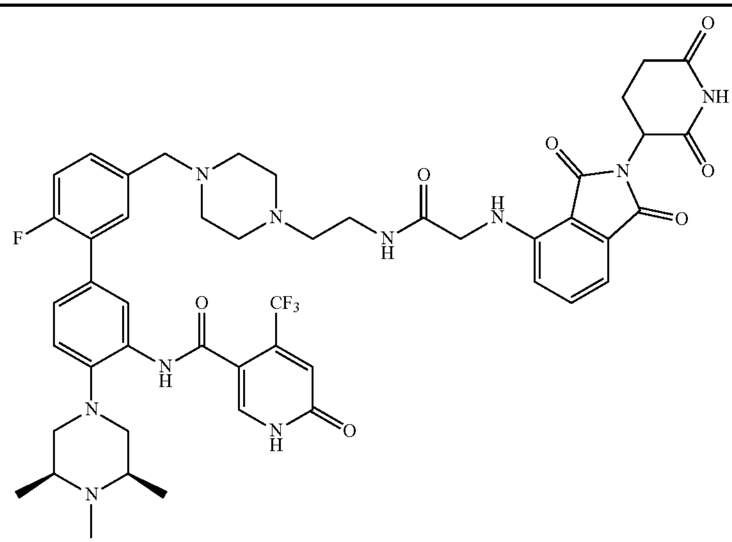 | N-(5'-((4-(2-(2-(2-(2,6-dioxopiperidin-3-yl)-1,3-dioxoisoindolin-4-yl)amino)acetamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 201 | XF078-19 | 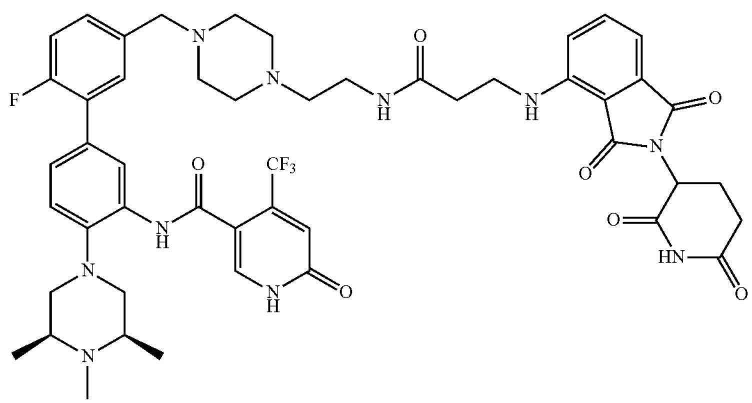 [SMILES: C[C@@H]1CN(c2ccc(-c3cc(CN4CCN(CCNC(=O)CCNc5cccc6c5C(=O)N(C5CCC(=O)NC5=O)C6=O)CC4)ccc3F)cc2NC(=O)c2c[nH]c(=O)cc2C(F)(F)F)C[C@H](C)N1C] | N-(5'-((4-(2-(3-((2-(2,6-dioxopiperidin-3-yl)-1,3-dioxoisoindolin-4-yl)amino)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 202 | XF078-20 | 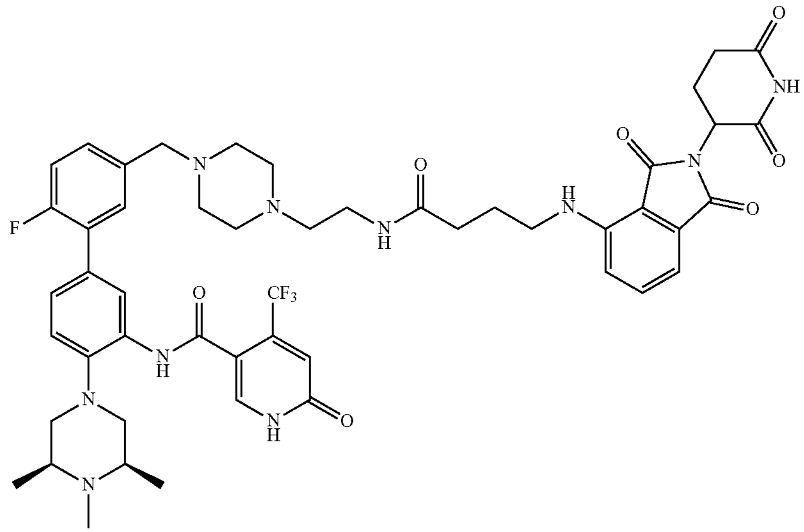 [SMILES: C[C@@H]1CN(c2ccc(-c3cc(CN4CCN(CCNC(=O)CCCNc5cccc6c5C(=O)N(C5CCC(=O)NC5=O)C6=O)CC4)ccc3F)cc2NC(=O)c2c[nH]c(=O)cc2C(F)(F)F)C[C@H](C)N1C] | N-(5'-((4-(2-(4-((2-(2,6-dioxopiperidin-3-yl)-1,3-dioxoisoindolin-4-yl)amino)butanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 203 | XF078-21 | 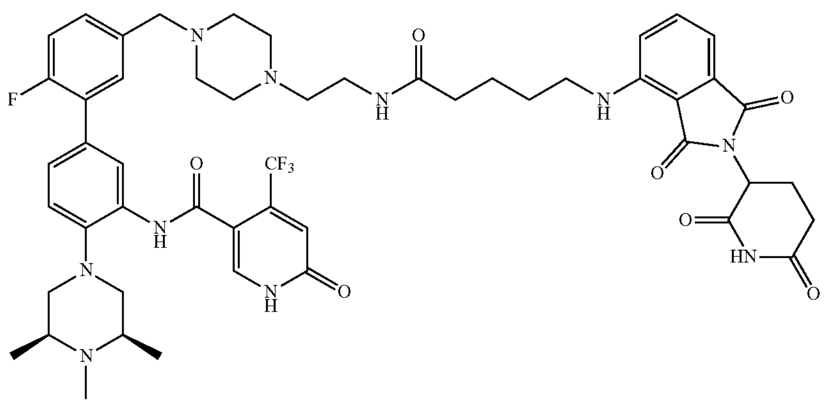 [SMILES: C[C@@H]1CN(c2ccc(-c3cc(CN4CCN(CCNC(=O)CCCCNc5cccc6c5C(=O)N(C5CCC(=O)NC5=O)C6=O)CC4)ccc3F)cc2NC(=O)c2c[nH]c(=O)cc2C(F)(F)F)C[C@H](C)N1C] | N-(5'-((4-(2-(5-((2-(2,6-dioxopiperidin-3-yl)-1,3-dioxoisoindolin-4-yl)amino)pentanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 204 | XF078-22 | 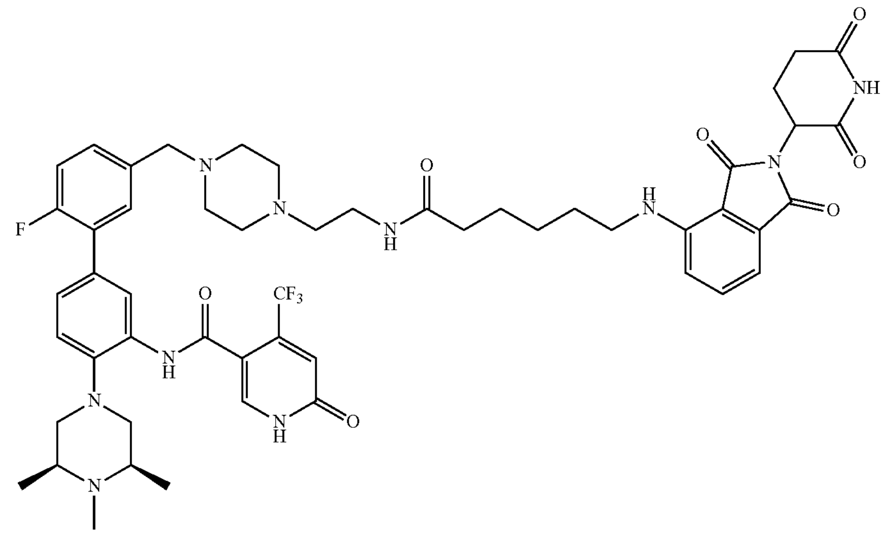 [SMILES: C[C@@H]1CN(c2ccc(-c3cc(CN4CCN(CCNC(=O)CCCCCNc5cccc6c5C(=O)N(C5CCC(=O)NC5=O)C6=O)CC4)ccc3F)cc2NC(=O)c2c[nH]c(=O)cc2C(F)(F)F)C[C@H](C)N1C] | N-(5'-((4-(2-(6-((2-(2,6-dioxopiperidin-3-yl)-1,3-dioxoisoindolin-4-yl)amino)hexanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 205 | XF078-23 | 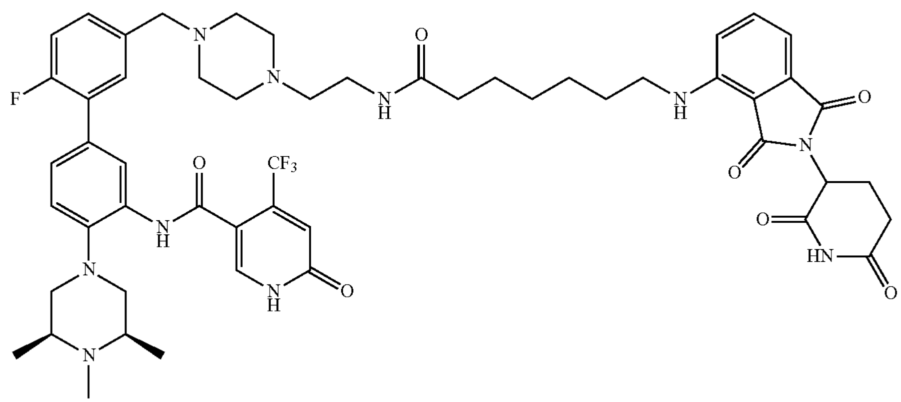 [SMILES: C[C@@H]1CN(c2ccc(-c3cc(CN4CCN(CCNC(=O)CCCCCCNc5cccc6c5C(=O)N(C5CCC(=O)NC5=O)C6=O)CC4)ccc3F)cc2NC(=O)c2c[nH]c(=O)cc2C(F)(F)F)C[C@H](C)N1C] | N-(5'-((4-(2-(7-((2-(2,6-dioxopiperidin-3-yl)-1,3-dioxoisoindolin-4-yl)amino)heptanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 206 | XF078-24 | 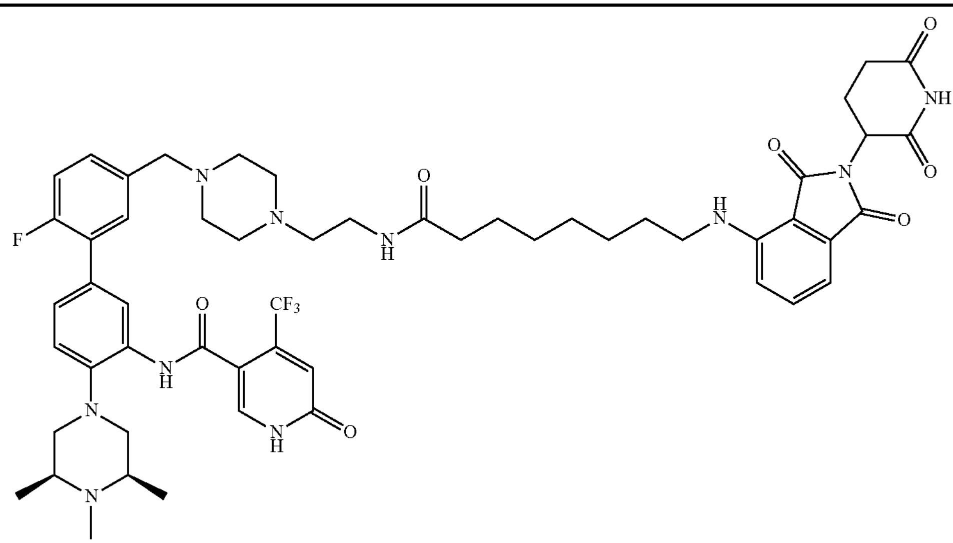 | N-(5'-((4-(2-(8-((2-(2,6-dioxopiperidin-3-yl)-1,3-dioxoisoindolin-4-yl)amino)octanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 207 | XF078-25 | 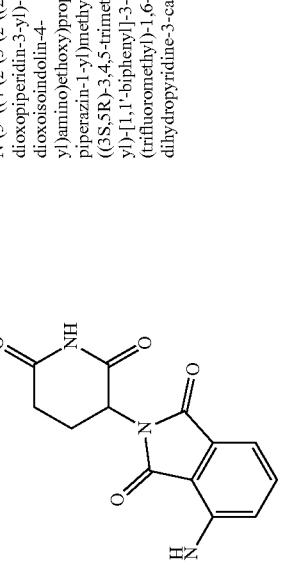 | N-(5'-((4-(2-(3-(2-(2-(2,6-dioxopiperidin-3-yl)-1,3-dioxoisoindolin-4-yl)amino)ethoxy)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 208 | XF078-26 | 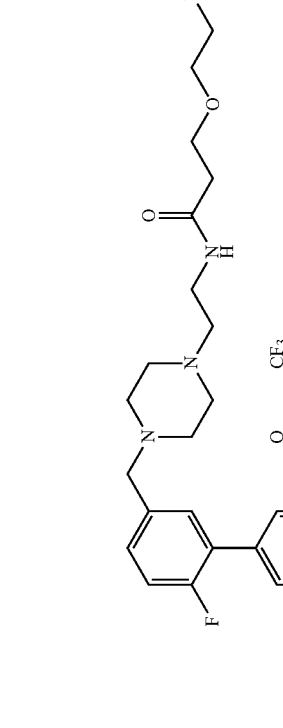 | N-(5'-((4-(2-(3-(2-(2-(2-(2,6-dioxopiperidin-3-yl)-1,3-dioxoisoindolin-4-yl)amino)ethoxy)ethoxy)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 209 | XF078-27 | 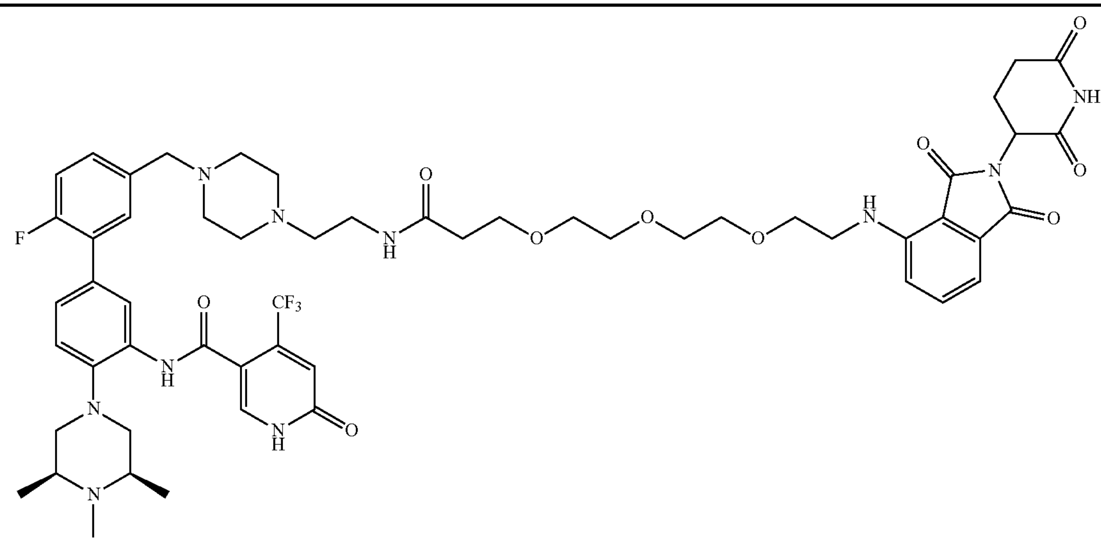 | N-(5'-((4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 210 | XF078-28 | 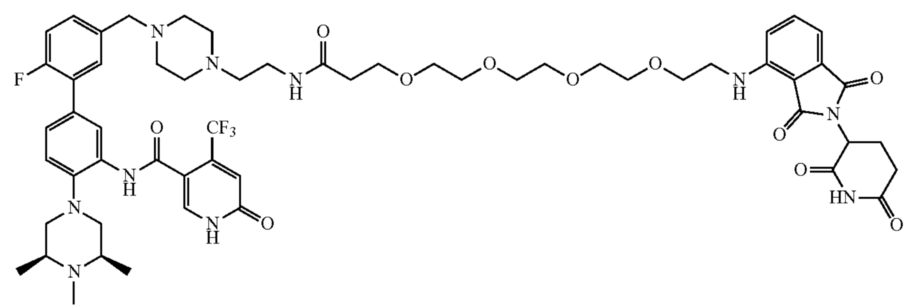 [SMILES: C[C@@H]1CN(c2ccc(-c3cc(CN4CCN(CCNC(=O)CCOCCOCCOCCOCCNc5cccc6c5C(=O)N(C5CCC(=O)NC5=O)C6=O)CC4)ccc3F)cc2NC(=O)c2c[nH]c(=O)cc2C(F)(F)F)C[C@H](C)N1C] | N-(5'-((4-(1-((2-(2,6-dioxopiperidin-3-yl)-1,3-dioxoisoindolin-4-yl)amino)-15-oxo-3,6,9,12-tetraoxa-16-azaoctadecan-18-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 211 | XF078-29 | 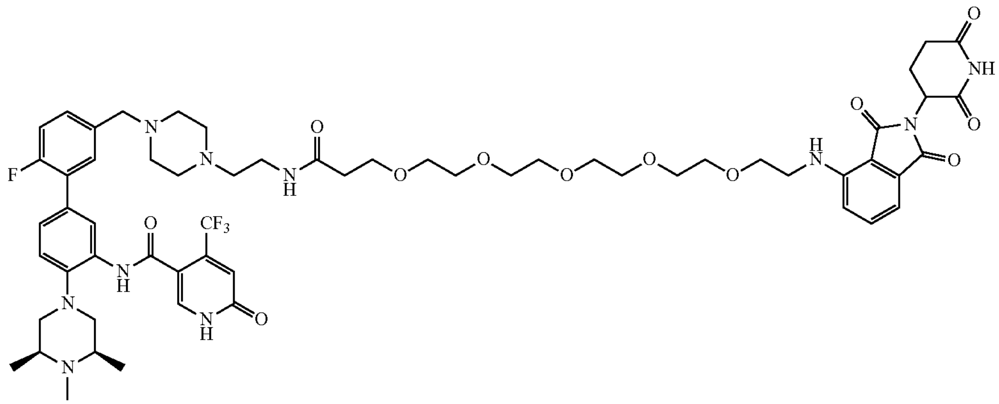 [SMILES: C[C@@H]1CN(c2ccc(-c3cc(CN4CCN(CCNC(=O)CCOCCOCCOCCOCCOCCNc5cccc6c5C(=O)N(C5CCC(=O)NC5=O)C6=O)CC4)ccc3F)cc2NC(=O)c2c[nH]c(=O)cc2C(F)(F)F)C[C@H](C)N1C] | N-(5'-((4-(1-((2-(2-(2,6-dioxopiperidin-3-yl)-1,3-dioxoisoindolin-4-yl)amino)-18-oxo-3,6,9,12,15-pentaoxa-19-azahenicosan-21-yl)methyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 213 | XF078-30 | 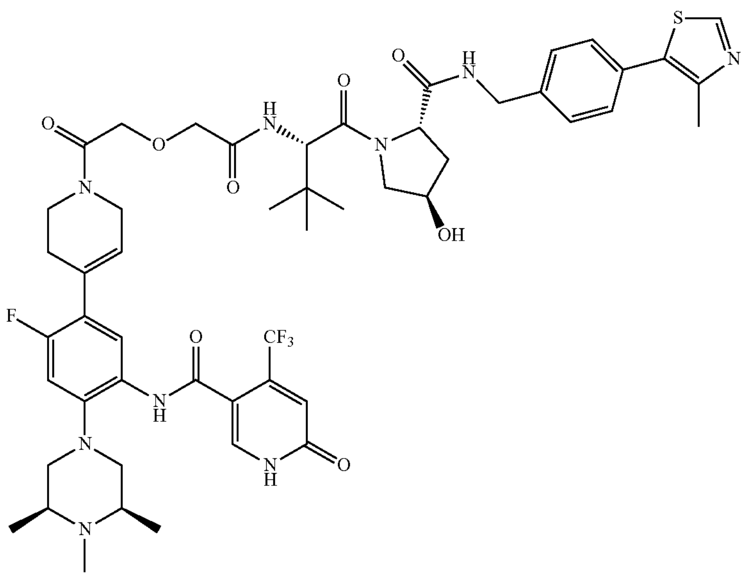 | N-(4-fluoro-5-(1-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 214 | XF078-31 | 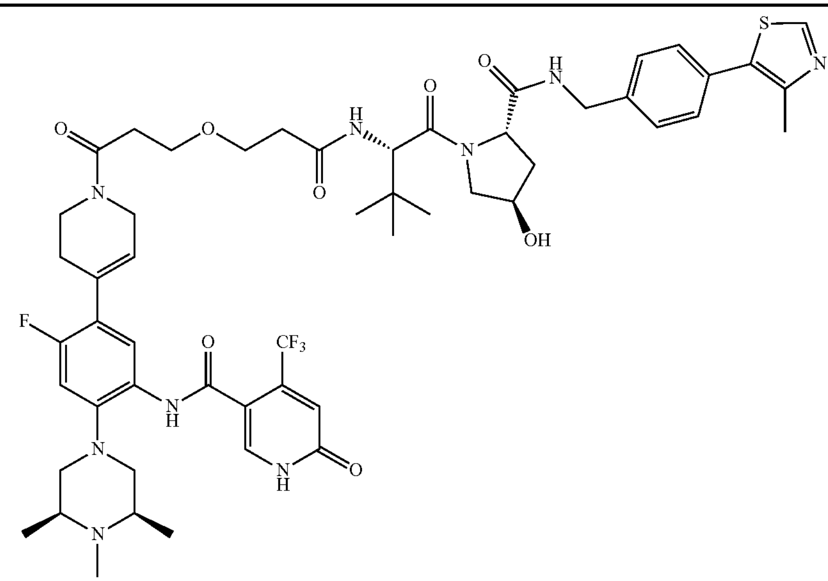 | N-(4-fluoro-5-(1-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 215 | XF078-32 | 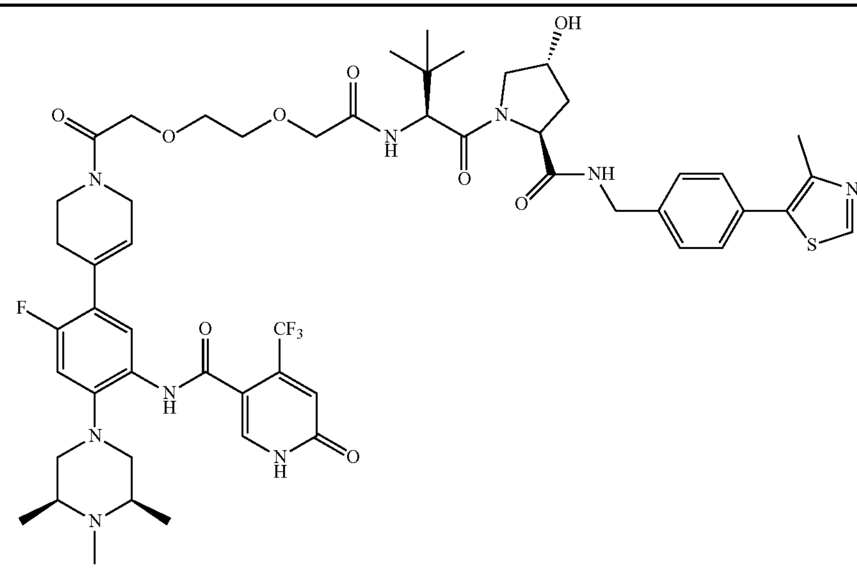 | N-(4-fluoro-5-(1-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 216 | XF078-33 | 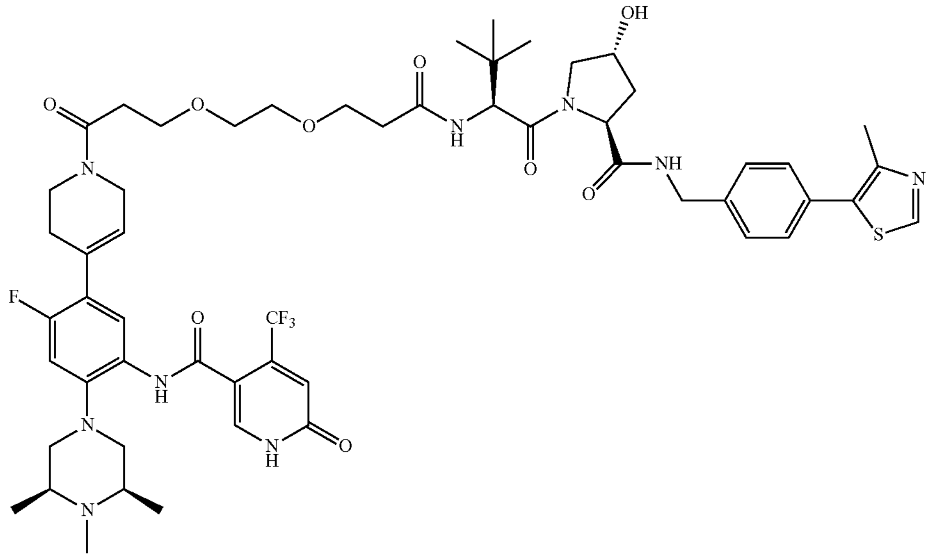 [SMILES: Cc1ncsc1-c1ccc(CNC(=O)[C@@H]2C[C@@H](O)CN2C(=O)[C@@H](NC(=O)CCOCCOCCC(=O)N2CC=C(c3cc(NC(=O)c4c[nH]c(=O)cc4C(F)(F)F)c(N4C[C@@H](C)N(C)[C@@H](C)C4)cc3F)CC2)C(C)(C)C)cc1] | N-(4-fluoro-5-(1-(3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 217 | XF078-34 | 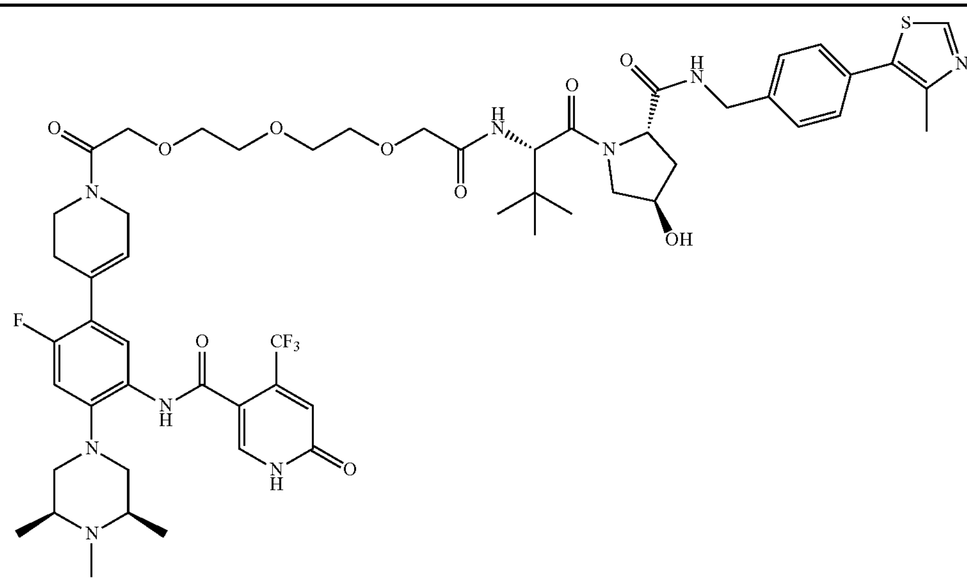 | N-(4-fluoro-5-(1-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 218 | XF078-35 | 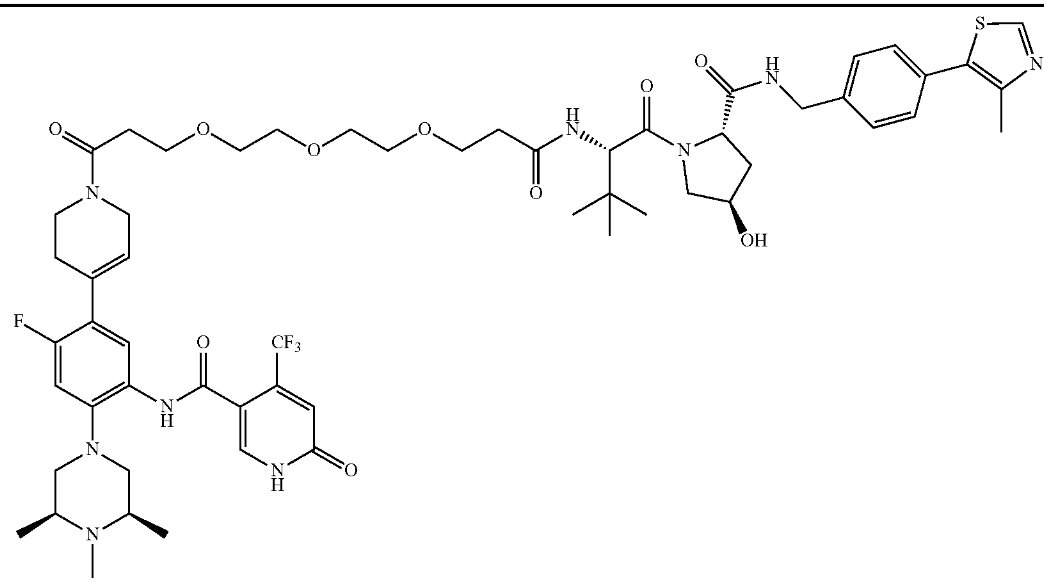 | N-(4-fluoro-5-(1-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| 219 | XF078-36 | 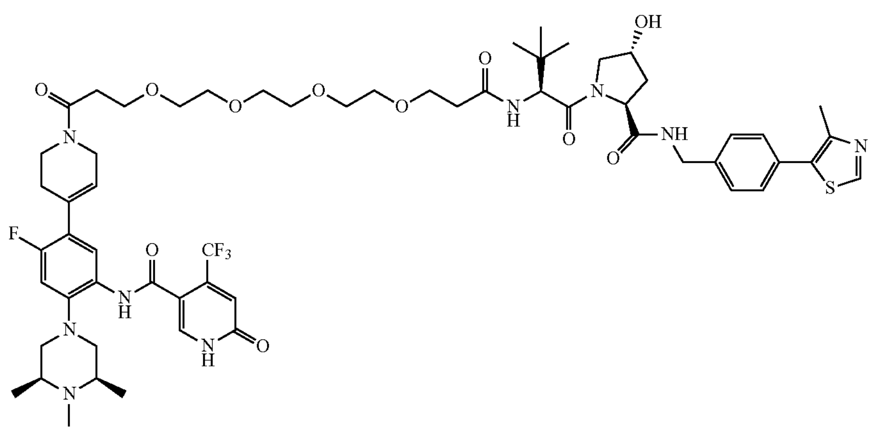 [SMILES: Cc1ncsc1-c1ccc(CNC(=O)[C@@H]2C[C@@H](O)CN2C(=O)[C@@H](NC(=O)CCOCCOCCOCCOCCC(=O)N2CC=C(c3cc(NC(=O)c4c[nH]c(=O)cc4C(F)(F)F)c(N4C[C@@H](C)N(C)[C@@H](C)C4)cc3F)CC2)C(C)(C)C)cc1] | N-(4-fluoro-5-(1-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 220 | XF078-37 | 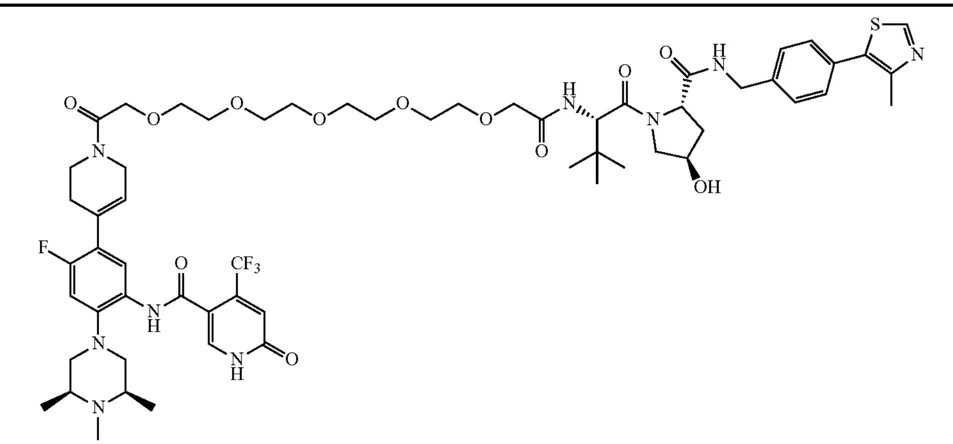 | N-(4-fluoro-5-(1-((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| 221 | XF078-38 | 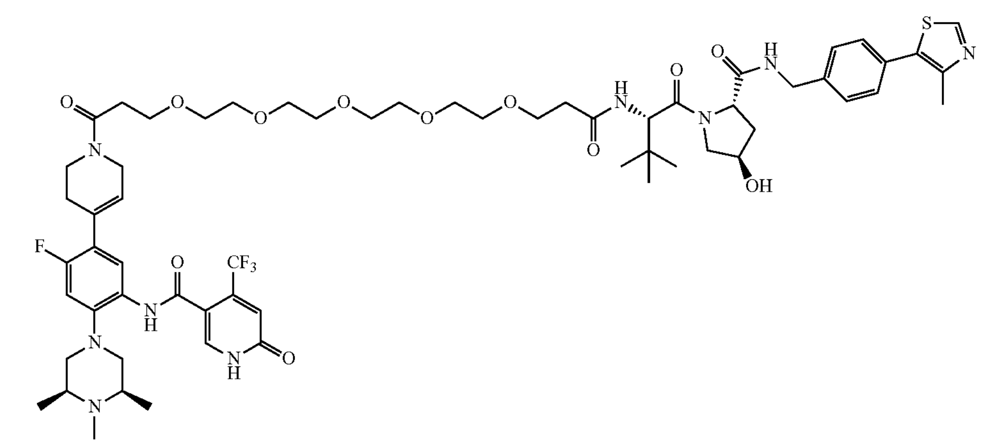 [SMILES: Cc1ncsc1-c1ccc(CNC(=O)[C@@H]2C[C@@H](O)CN2C(=O)[C@@H](NC(=O)CCOCCOCCOCCOCCOCCC(=O)N2CC=C(c3cc(NC(=O)c4c[nH]c(=O)cc4C(F)(F)F)c(N4C[C@@H](C)N(C)[C@@H](C)C4)cc3F)CC2)C(C)(C)C)cc1] | N-(4-fluoro-5-(1-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 222 | XF078-39 | 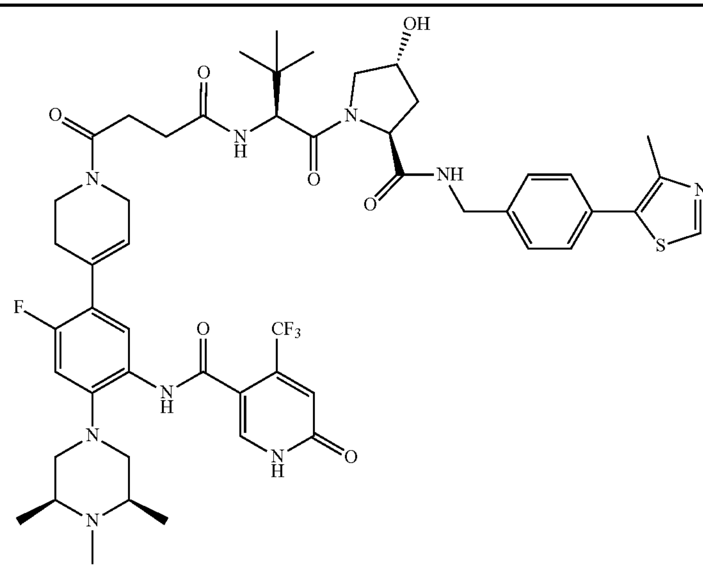 | N-(4-fluoro-5-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 223 | XF078-40 | 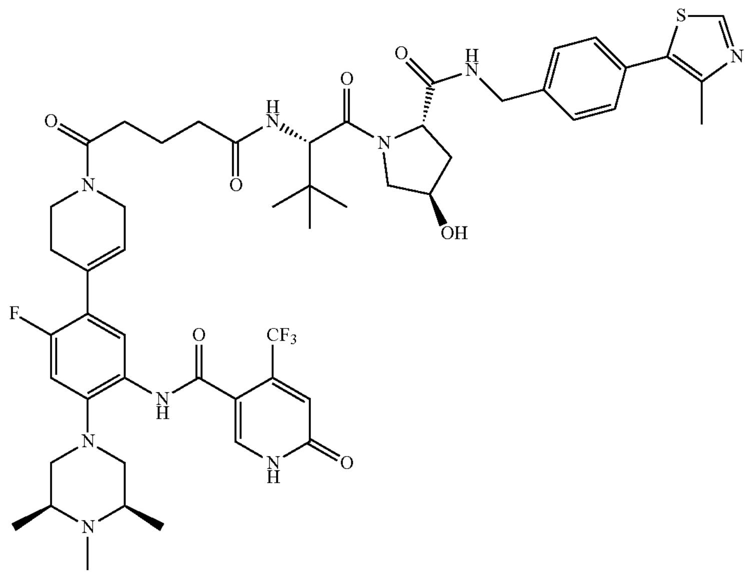 [SMILES: Cc1ncsc1-c1ccc(CNC(=O)[C@@H]2C[C@@H](O)CN2C(=O)[C@@H](NC(=O)CCCC(=O)N2CC=C(c3cc(NC(=O)c4c[nH]c(=O)cc4C(F)(F)F)c(N4C[C@@H](C)N(C)[C@@H](C)C4)cc3F)CC2)C(C)(C)C)cc1] | N-(4-fluoro-5-(1-(5-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 224 | XF078-41 | 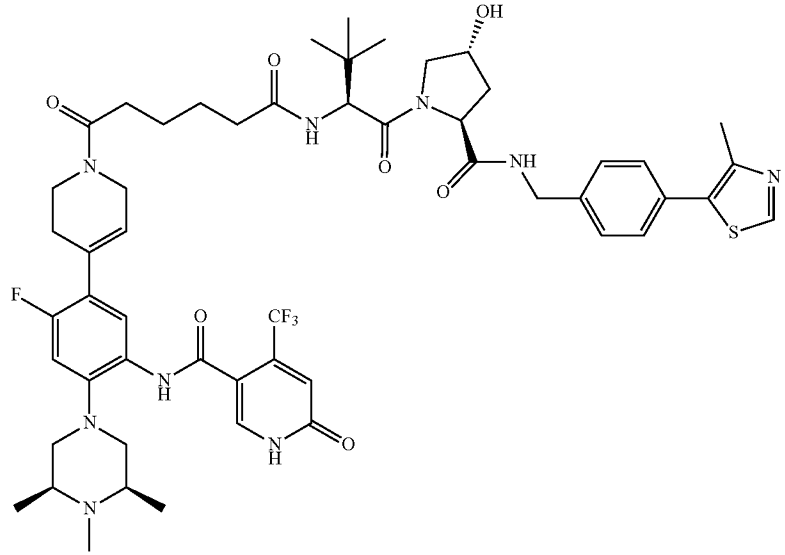 [SMILES: Cc1ncsc1-c1ccc(CNC(=O)[C@@H]2C[C@@H](O)CN2C(=O)[C@@H](NC(=O)CCCCC(=O)N2CC=C(c3cc(NC(=O)c4c[nH]c(=O)cc4C(F)(F)F)c(N4C[C@@H](C)N(C)[C@@H](C)C4)cc3F)CC2)C(C)(C)C)cc1] | N-(4-fluoro-5-(1-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 225 | XF078-42 | 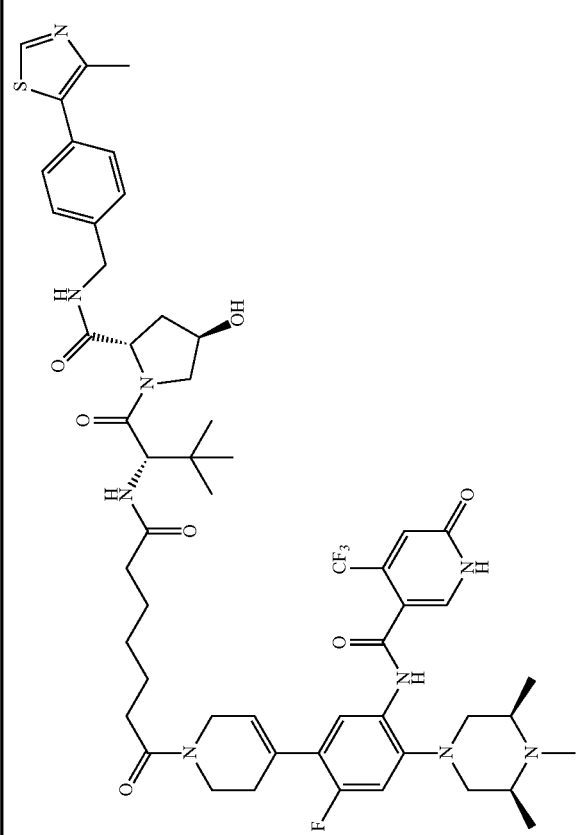 | N-(4-fluoro-5-(1-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 226 | XF078-43 | 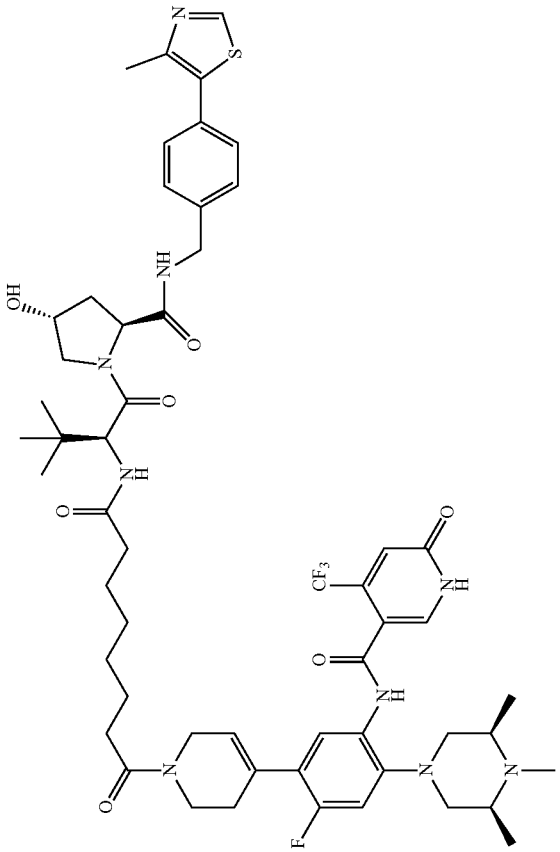 | N-(4-fluoro-5-(1-(8-(((S)-1-(((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 227 | XF078-44 | 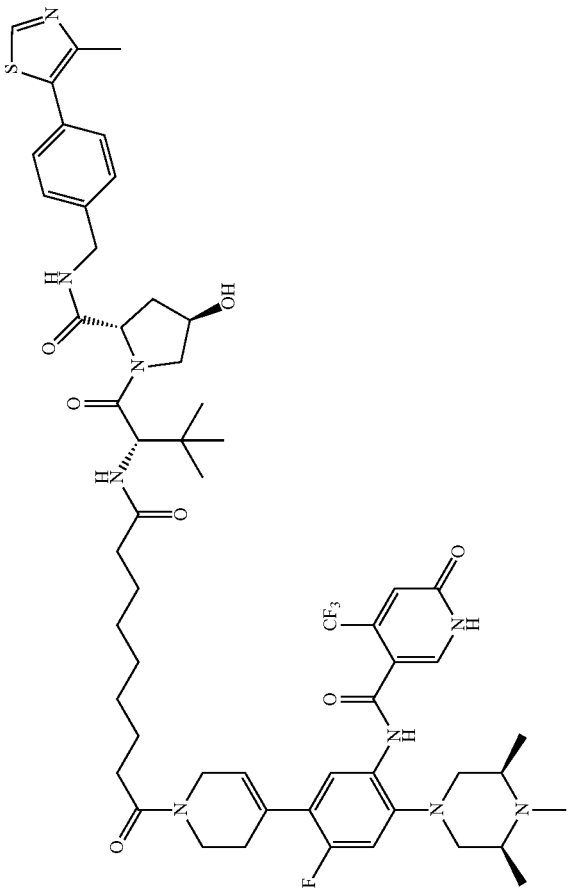 | N-(4-fluoro-5-(1-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 228 | XF078-45 | 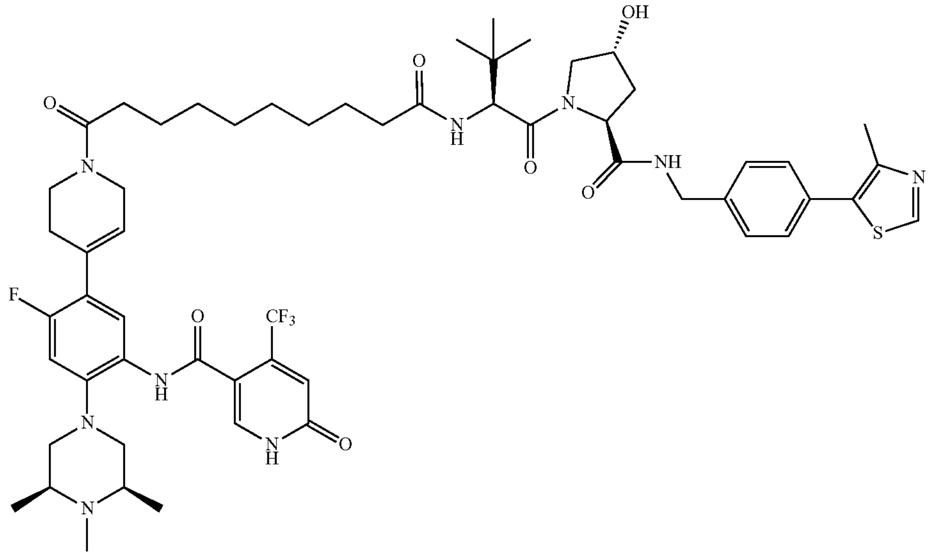 | N-(4-fluoro-5-(1-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 229 | XF078-46 | 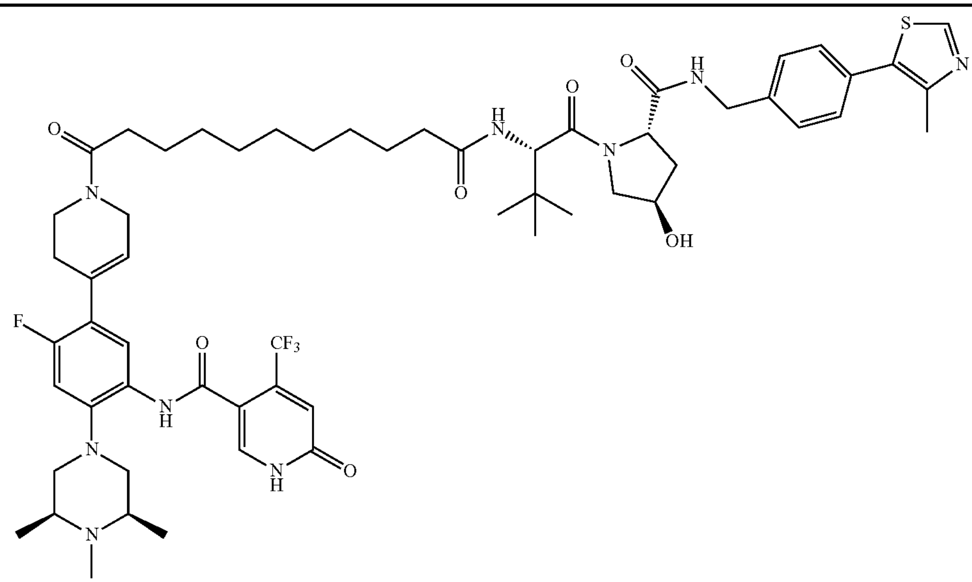 | N-(4-fluoro-5-(1-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 230 | XF078-47 | 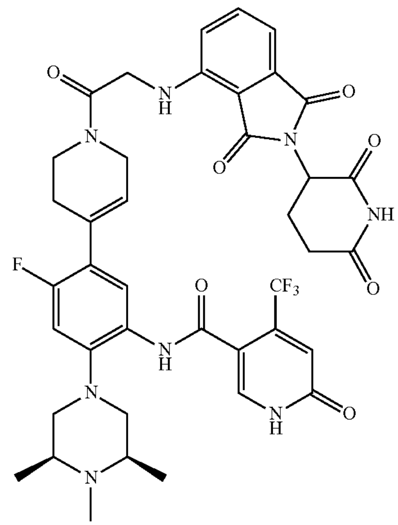 [SMILES: C[C@@H]1CN(c2cc(F)c(C3=CCN(C(=O)CNc4cccc5c4C(=O)N(C4CCC(=O)NC4=O)C5=O)CC3)cc2NC(=O)c2c[nH]c(=O)cc2C(F)(F)F)C[C@H](C)N1C] | N-(5-(1-((2-(2-(2,6-dioxopiperidin-3-yl)-1,3-dioxoisoindolin-4-yl)glycyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 231 | XF078-48 | 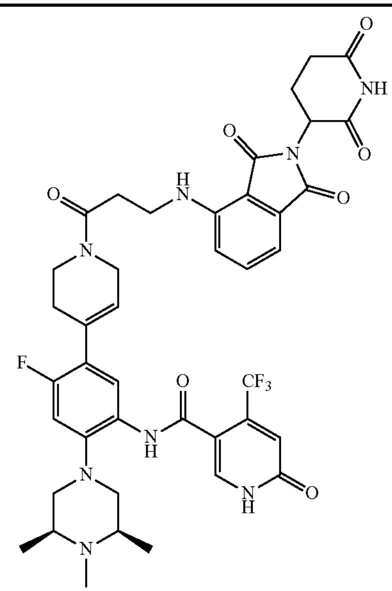 | N-(5-(1-(3-((3-(2-(2,6-dioxopiperidin-3-yl)-1,3-dioxoisoindolin-4-yl)amino)propanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| Examples | Compound ID | Structure | Chemical Name |
|---|---|---|---|
| 232 | XF078-49 | 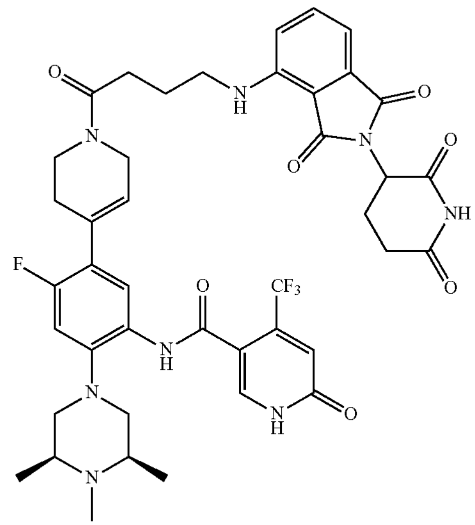 [SMILES: C[C@@H]1CN(c2cc(F)c(C3=CCN(C(=O)CCCNc4cccc5c4C(=O)N(C4CCC(=O)NC4=O)C5=O)CC3)cc2NC(=O)c2c[nH]c(=O)cc2C(F)(F)F)C[C@H](C)N1C] | N-(5-(1-(4-((2-(2,6-dioxopiperidin-3-yl)-1,3-dioxoisoindolin-4-yl)amino)butanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 233 | XF078-50 | 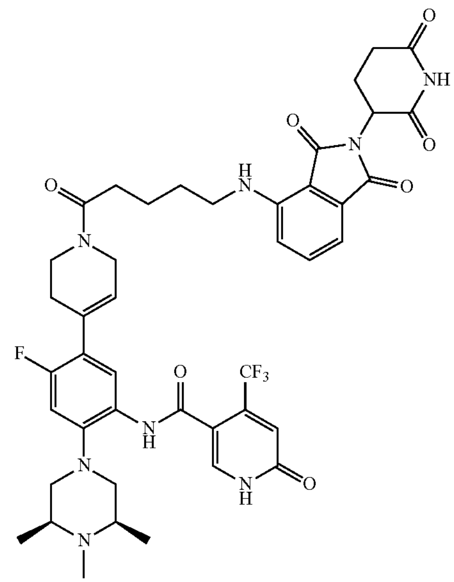 [SMILES: C[C@@H]1CN(c2cc(F)c(C3=CCN(C(=O)CCCCNc4cccc5c4C(=O)N(C4CCC(=O)NC4=O)C5=O)CC3)cc2NC(=O)c2c[nH]c(=O)cc2C(F)(F)F)C[C@H](C)N1C] | N-(5-(1-(5-((2-(2,6-dioxopiperidin-3-yl)-1,3-dioxoisoindolin-4-yl)amino)pentanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 234 | XF078- 51 | 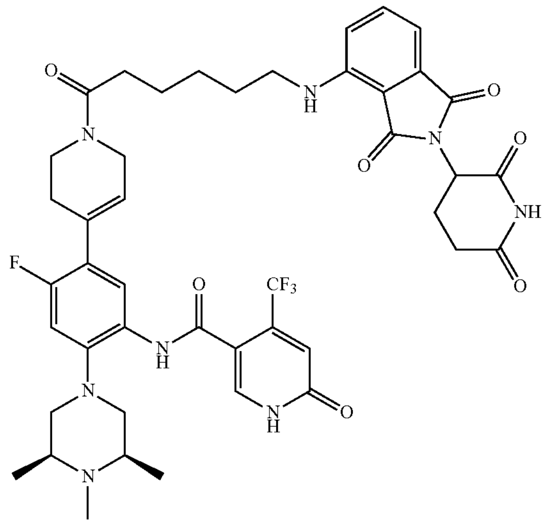 [SMILES: C[C@@H]1CN(c2cc(F)c(C3=CCN(C(=O)CCCCCNc4cccc5c4C(=O)N(C4CCC(=O)NC4=O)C5=O)CC3)cc2NC(=O)c2c[nH]c(=O)cc2C(F)(F)F)C[C@H](C)N1C] | N-(5-(1-(6-((2-(2,6-dioxopiperidin-3-yl)-1,3-dioxoisoindolin-4-yl)amino)hexanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 235 | XF078-52 | 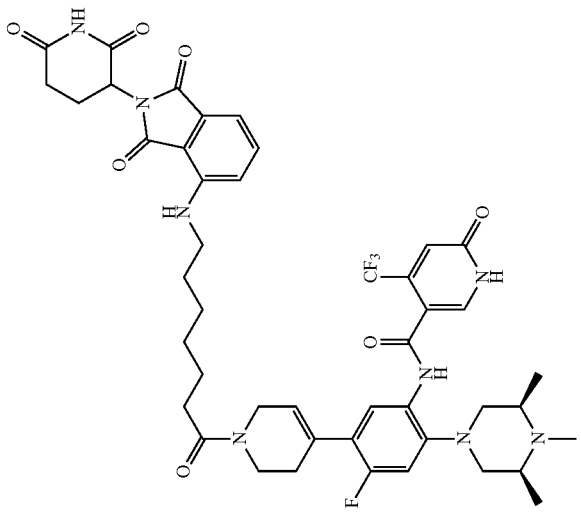 | N-(5-(1-(7-((2-(2,6-dioxopiperidin-3-yl)-1,3-dioxoisoindolin-4-yl)amino)heptanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 236 | XF078-53 | 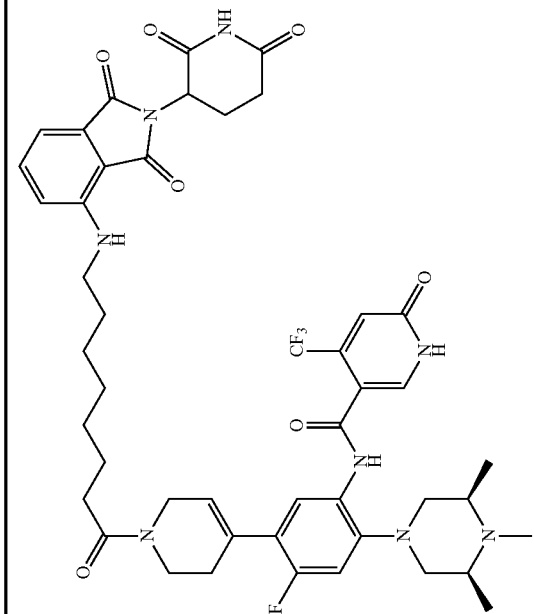 | N-(5-(1-(8-((2-(2,6-dioxopiperidin-3-yl)-1,3-dioxoisoindolin-4-yl)amino)octanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 237 | XF078- 54 | 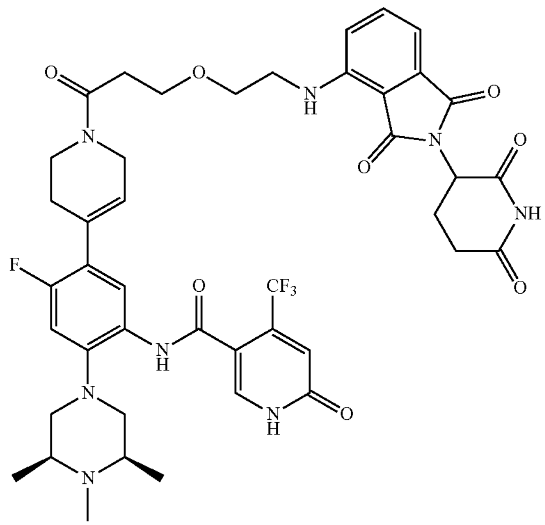 [SMILES: C[C@@H]1CN(c2cc(F)c(C3=CCN(C(=O)CCOCCNc4cccc5c4C(=O)N(C4CCC(=O)NC4=O)C5=O)CC3)cc2NC(=O)c2c[nH]c(=O)cc2C(F)(F)F)C[C@H](C)N1C] | N-(5-(1-(3-(2-(2-((2-(2,6-dioxopiperidin- 3-yl)-1,3-dioxoisoindolin-4- yl)amino)ethoxy)propanoyl)-1,2,3,6- tetrahydropyridin-4-yl)-4-fluoro-2- ((3S,5R)-3,4,5-trimethylpiperazin-1- yl)phenyl)-6-oxo-4-(trifluoromethyl)- 1,6-dihydropyridine-3-carboxamide |

TABLE 1-continued

| Examples | Compound ID | Structure | Chemical Name |
|---|---|---|---|
| 238 | XF078-55 | 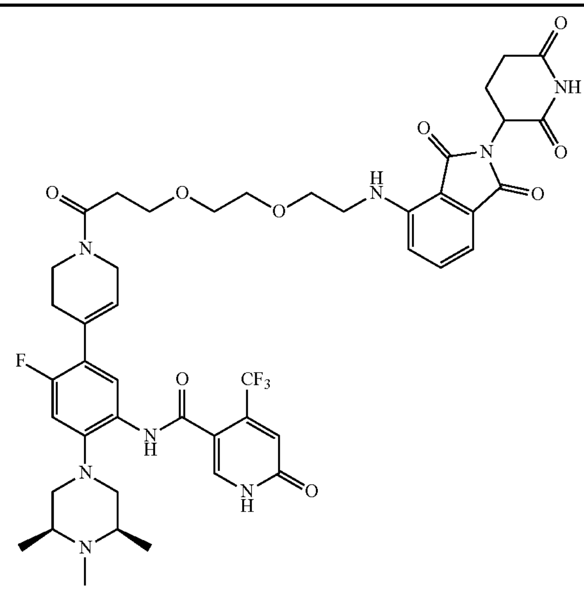 | N-(5-(1-(3-(2-(2-((2-(2,6-dioxopiperidin-3-yl)-1,3-dioxoisoindolin-4-yl)amino)ethoxy)ethoxy)propanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 239 | XF078-56 | 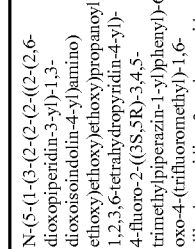 | N-(5-(1-(3-(2-(2-(2-((2-(2,6-dioxopiperidin-3-yl)-1,3-dioxoisoindolin-4-yl)amino)ethoxy)ethoxy)ethoxy)propanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| Ex- am- ples | Com- pound ID | Structure | Chemical Name |
|---|---|---|---|
| 240 | XF078-57 | 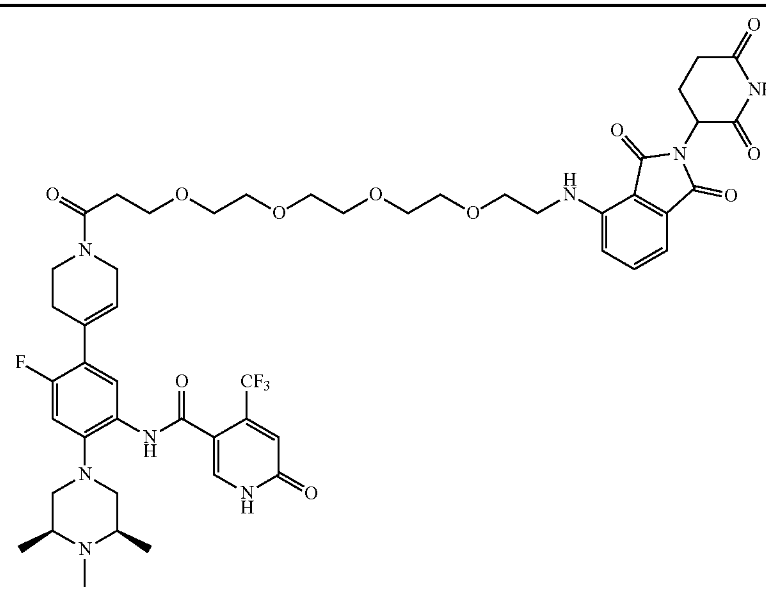 | N-(5-(1-(1-((2-(2,6-dioxopiperidin-3-yl)-1,3-dioxoisoindolin-4-yl)amino)-3,6,9,12-tetraoxapentadecan-15-oyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 241 | XF078-58 | 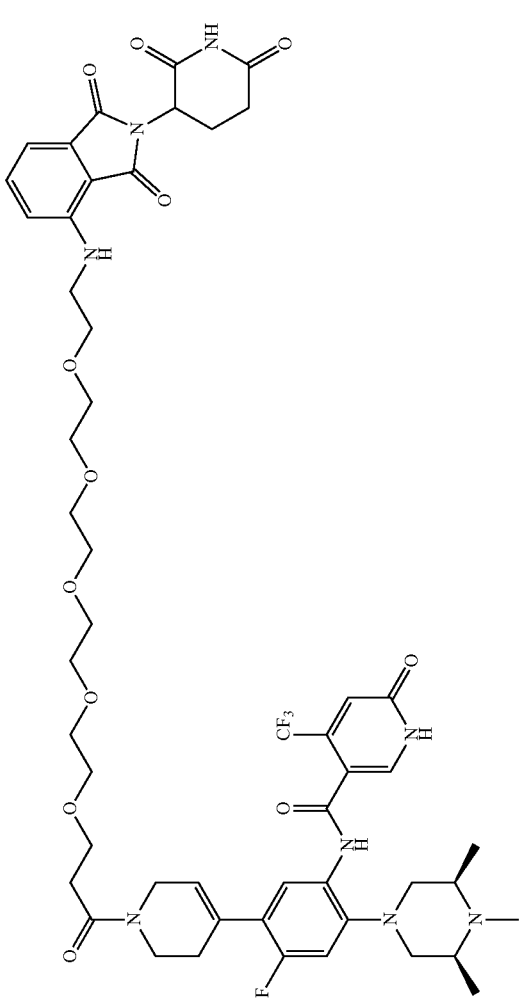 | N-(5-(1-(1-((2-(2,6-dioxopiperidin-3-yl)-1,3-dioxoisoindolin-4-yl)amino)-3,6,9,12,15-pentaoxaoctadecan-18-oyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| Example | Compound ID | Structure | Chemical Name |
|---|---|---|---|
| 243 | XF078-61 | 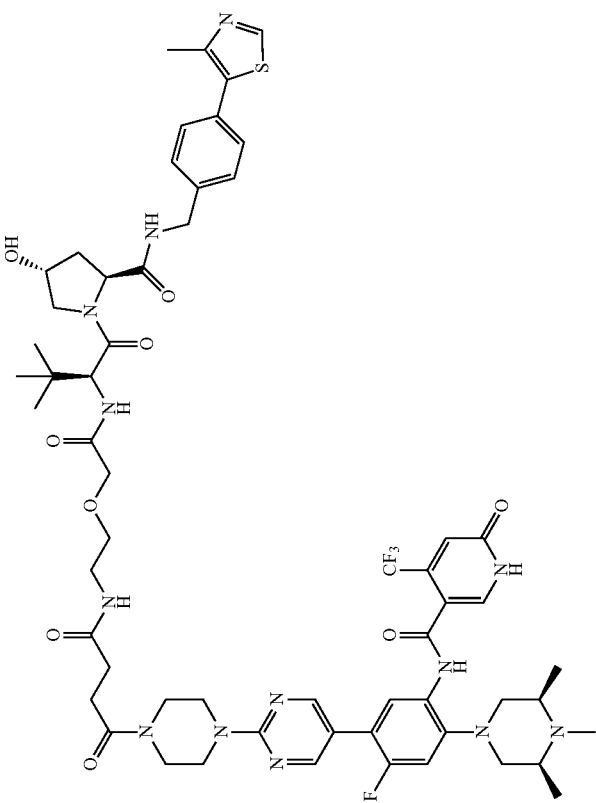 | N-(4-fluoro-5-(2-(4-(4-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 244 | XF078-62 | 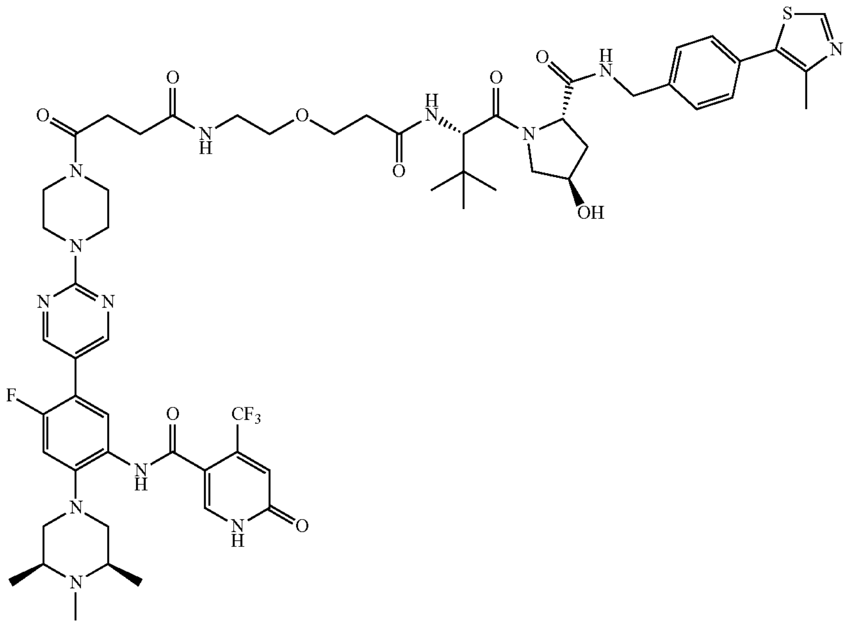 [SMILES: Cc1ncsc1-c1ccc(CNC(=O)[C@@H]2C[C@@H](O)CN2C(=O)[C@@H](NC(=O)CCOCCNC(=O)CCC(=O)N2CCN(c3ncc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(2-(4-(4-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 245 | XF078-63 | 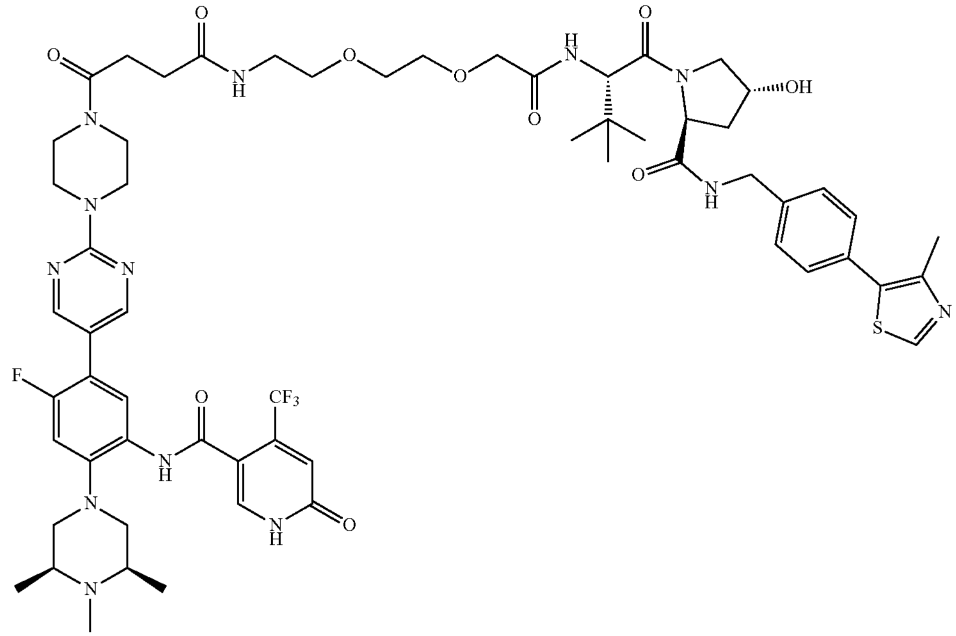 [SMILES: Cc1ncsc1-c1ccc(CNC(=O)[C@@H]2C[C@@H](O)CN2C(=O)[C@@H](NC(=O)COCCOCCNC(=O)CCC(=O)N2CCN(c3ncc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(2-(4-((S)-3-((2S,4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaheptadecan-17-oyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 246 | XF078-64 | 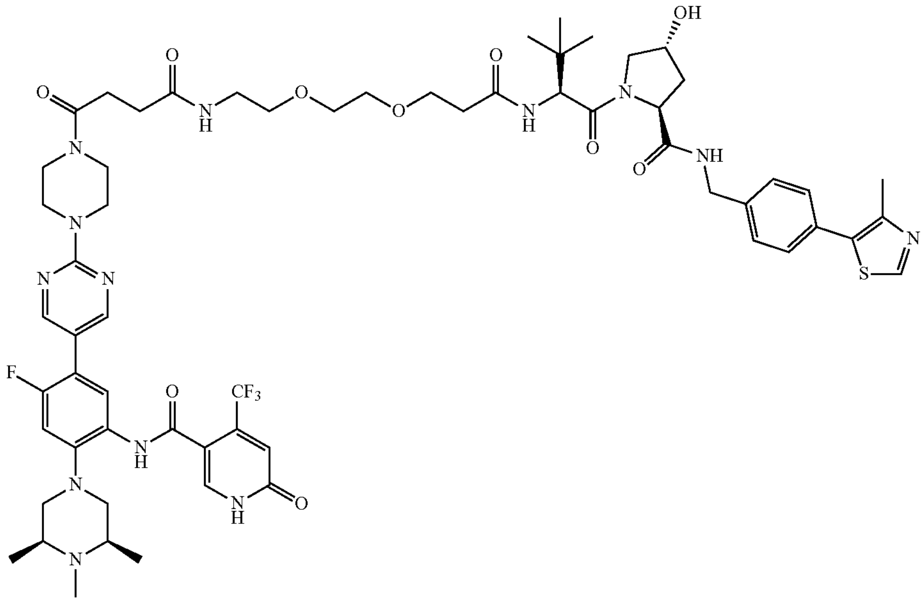 [SMILES: Cc1ncsc1-c1ccc(CNC(=O)[C@@H]2C[C@@H](O)CN2C(=O)[C@@H](NC(=O)CCOCCOCCNC(=O)CCC(=O)N2CCN(c3ncc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(2-(4-((S)-3-((2S,4R)-4-hydroxy-2-((4-(4-methylthiazol-5-yl)benzyl)carbamoyl)pyrrolidine-1-carbonyl)-2,2-dimethyl-5,15-dioxo-8,11-dioxa-4,14-diazaoctadecan-18-oyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 247 | XF078-65 | 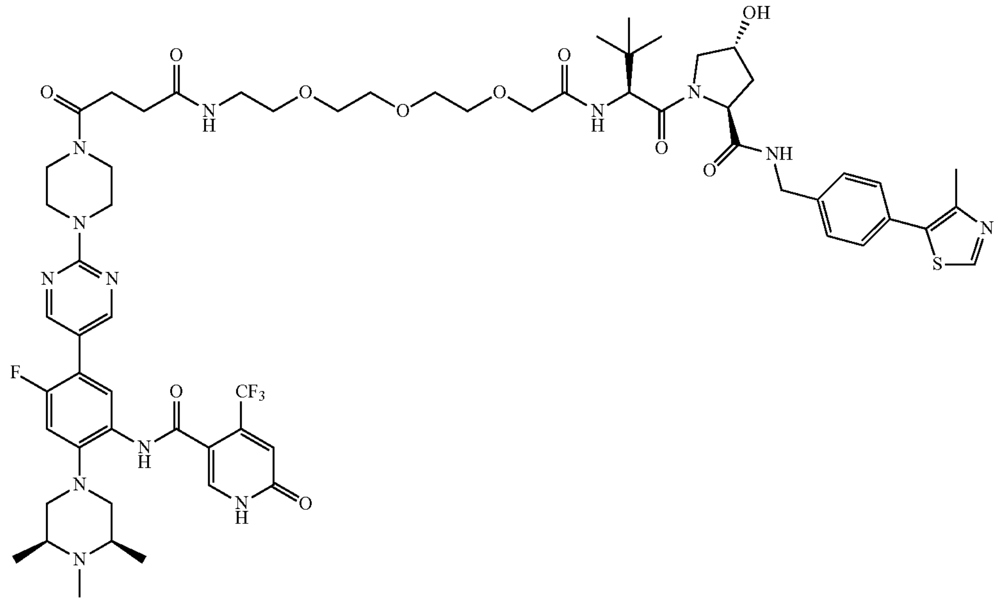 [SMILES: Cc1ncsc1-c1ccc(CNC(=O)[C@@H]2C[C@@H](O)CN2C(=O)[C@@H](NC(=O)COCCOCCOCCNC(=O)CCC(=O)N2CCN(c3ncc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(2-(4-((S)-3-((2S,4R)-4-hydroxy-2-((4-(4-methylthiazol-5-yl)benzyl)carbamoyl)pyrrolidine-1-carbonyl)-2,2-dimethyl-5,17-dioxo-7,10,13-trioxa-4,16-diazaicosan-20-oyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 248 | XF078-66 | 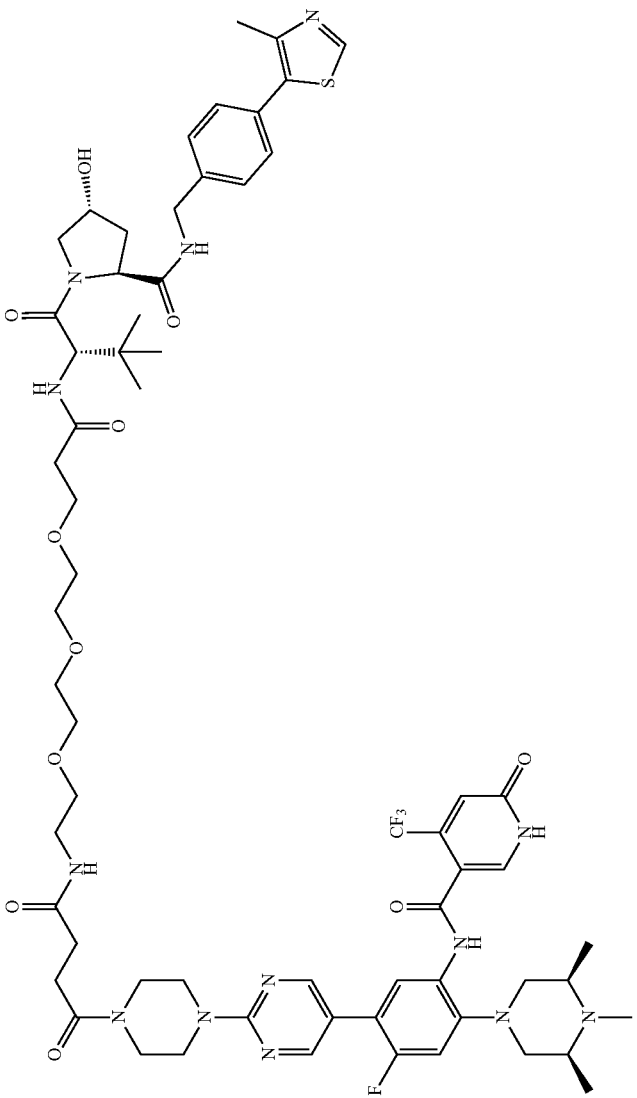 | N-(4-fluoro-5-(2-(4-((S)-3-((2S,4R)-4-hydroxy-2-((4-(4-methylthiazol-5-yl)benzyl)carbamoyl)pyrrolidine-1-carbonyl)-2,2-dimethyl-5,18-dioxo-8,11,14-trioxa-4,17-diazahenicosan-21-oyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 249 | XF078-67 | 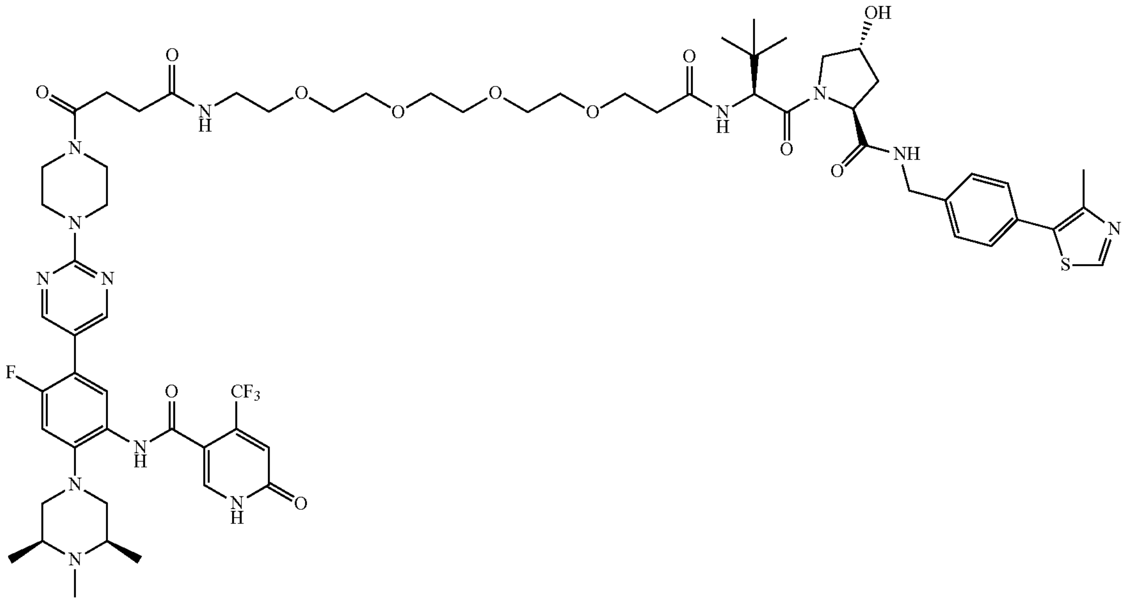 | N-(4-fluoro-5-(2-(4-((S)-3-((2S,4R)-4-hydroxy-2-((4-(4-methylthiazol-5-yl)benzyl)carbamoyl)pyrrolidine-1-carbonyl)-2,2-dimethyl-5,21-dioxo-8,11,14,17-tetraoxa-4,20-diazatetracosan-24-oyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 250 | XF078-68 | 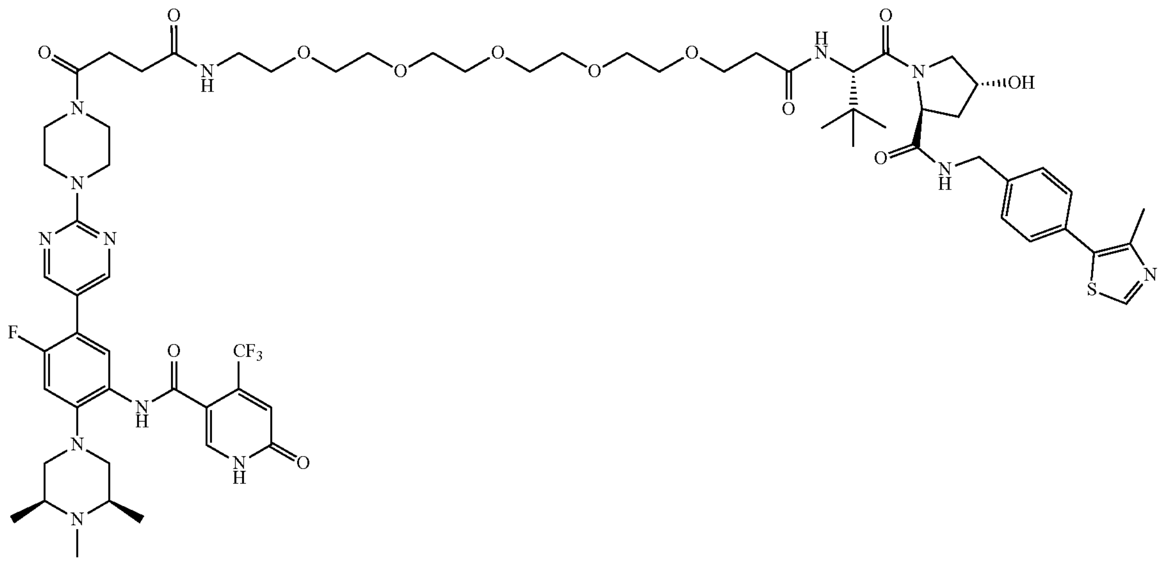 [SMILES: Cc1ncsc1-c1ccc(CNC(=O)[C@@H]2C[C@@H](O)CN2C(=O)[C@@H](NC(=O)CCOCCOCCOCCOCCOCCNC(=O)CCC(=O)N2CCN(c3ncc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(2-(4-((S)-3-((2S,4R)-4-hydroxy-2-((4-(4-methylthiazol-5-yl)benzyl)carbamoyl)pyrrolidine-1-carbonyl)-2,2-dimethyl-5,24-dioxo-8,11,14,17,20-pentaoxa-4,23-diazaheptacosan-27-oyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 251 | XF078-69 | 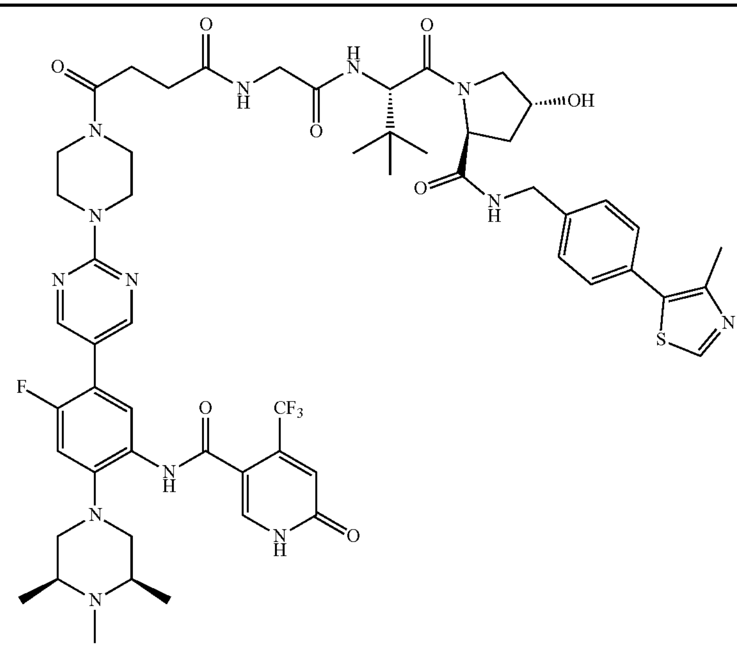 | N-(4-fluoro-5-(2-(4-(4-(2-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 252 | XF078-70 | 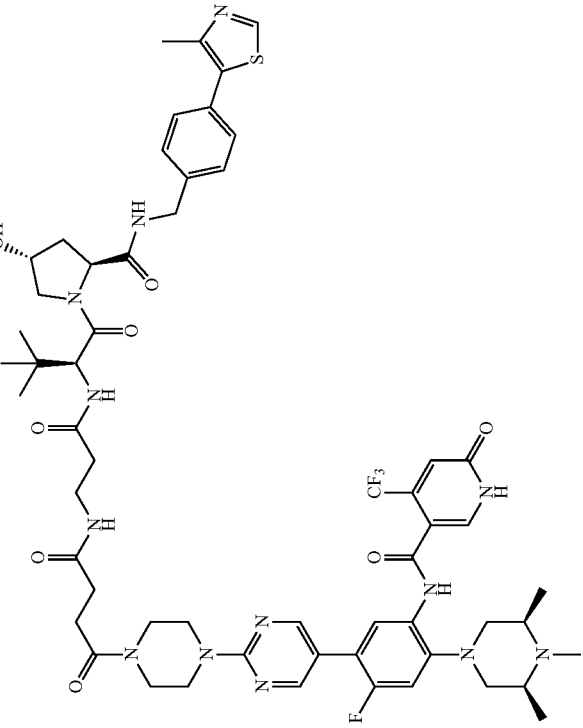 | N-(4-fluoro-5-(2-(4-(4-(3-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Example | Compound ID | Structure | Chemical Name |
|---|---|---|---|
| 253 | XF078-71 | 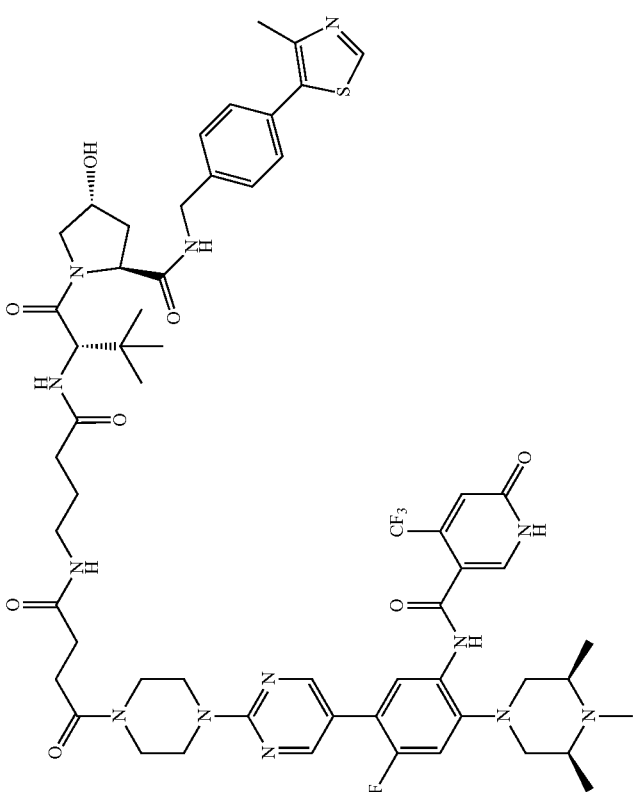 | N-(4-fluoro-5-(2-(4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 254 | XF078-72 | 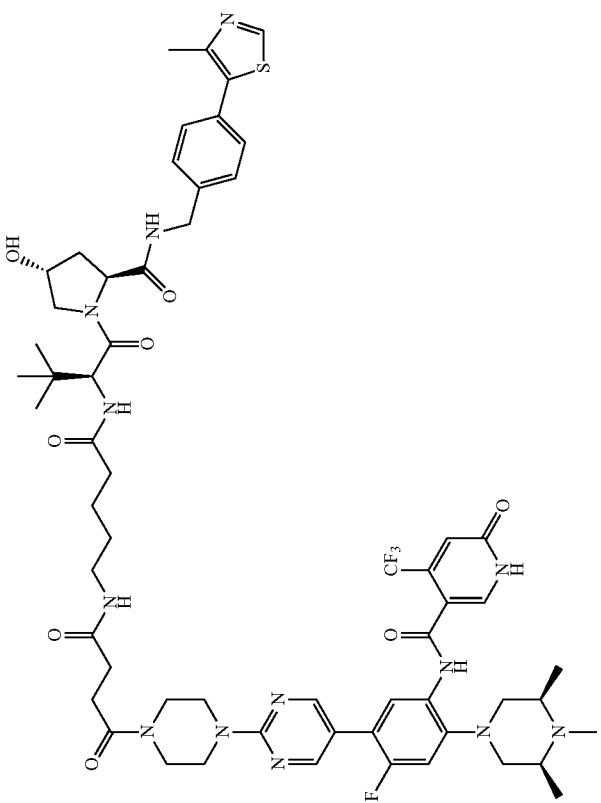 | N-(4-fluoro-5-(2-(4-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 255 | XF078-73 | 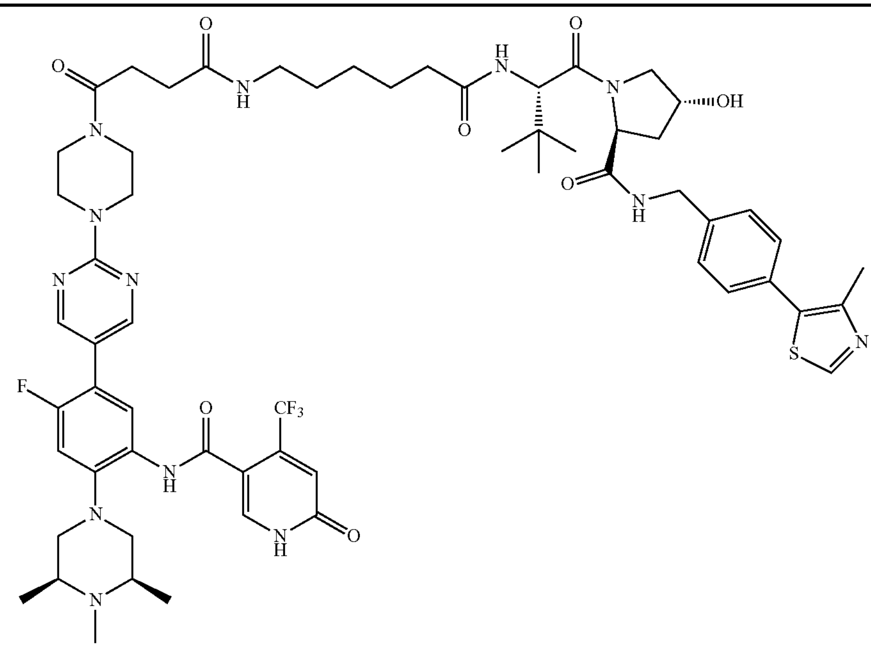 | N-(4-fluoro-5-(2-(4-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

| Ex- am- ples | Com- pound ID | Structure | Chemical Name |
|---|---|---|---|
| 256 | XF078-74 | 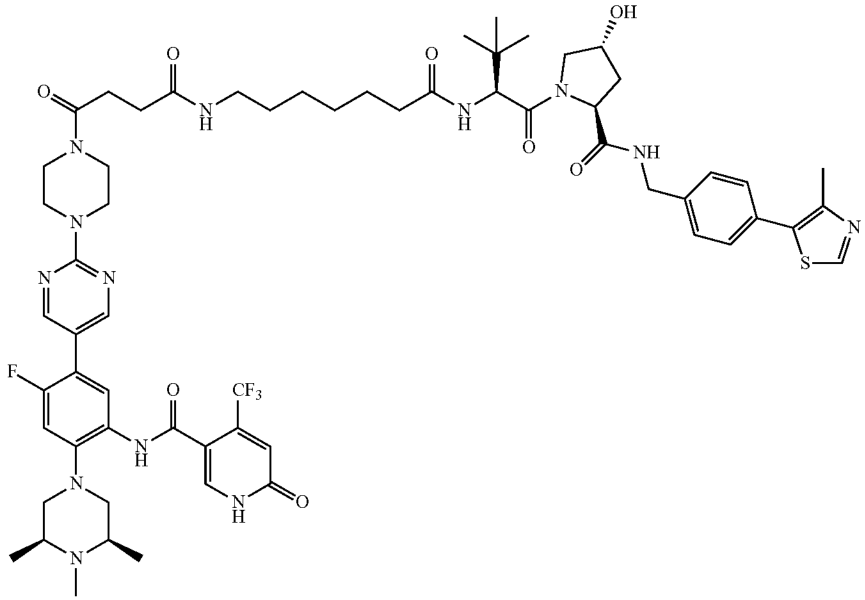 [SMILES: Cc1ncsc1-c1ccc(CNC(=O)[C@@H]2C[C@@H](O)CN2C(=O)[C@@H](NC(=O)CCCCCCNC(=O)CCC(=O)N2CCN(c3ncc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(2-(4-(4-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

| Ex- am- ples | Com- pound ID | Structure | Chemical Name |
|---|---|---|---|
| 257 | XF078-75 | 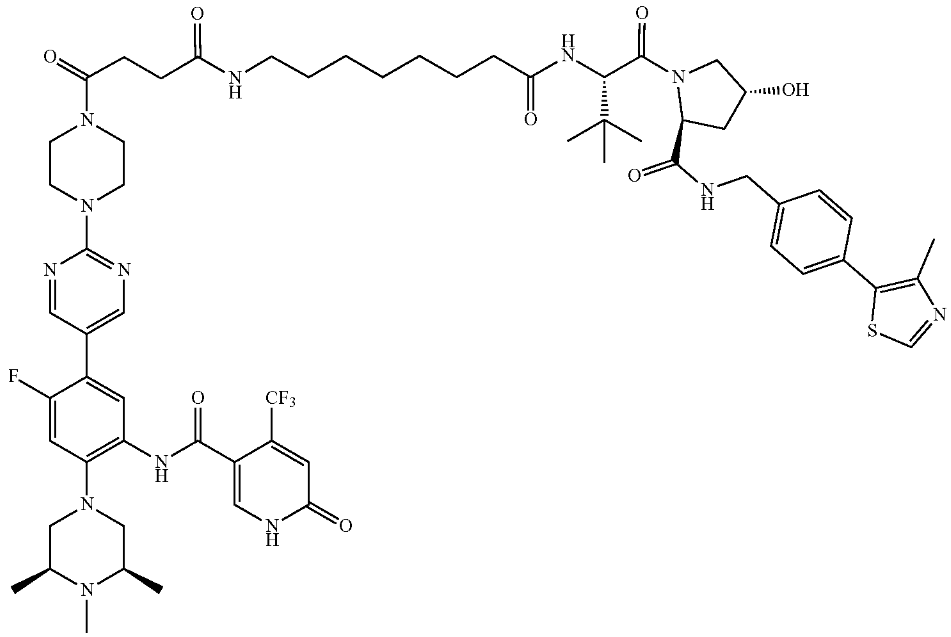 [SMILES: Cc1ncsc1-c1ccc(CNC(=O)[C@@H]2C[C@@H](O)CN2C(=O)[C@@H](NC(=O)CCCCCCCNC(=O)CCC(=O)N2CCN(c3ncc(-c4cc(NC(=O)c5c[nH]c(=O)cc5C(F)(F)F)c(N5C[C@@H](C)N(C)[C@@H](C)C5)cc4F)cn3)CC2)C(C)(C)C)cc1] | N-(4-fluoro-5-(2-(4-(4-(4-((8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 258 | XF078-76 | 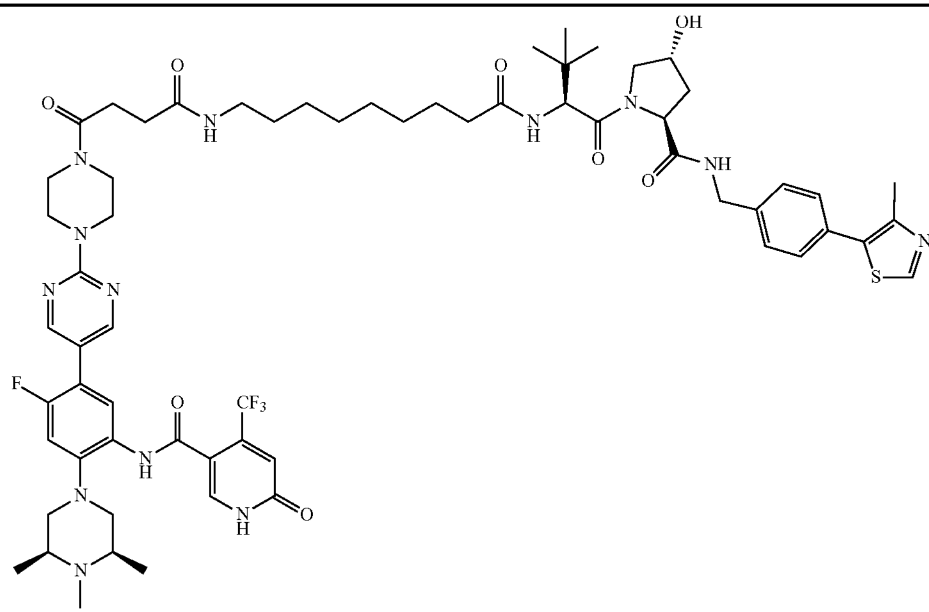 | N-(4-fluoro-5-(2-(4-(4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 259 | XF078-77 | 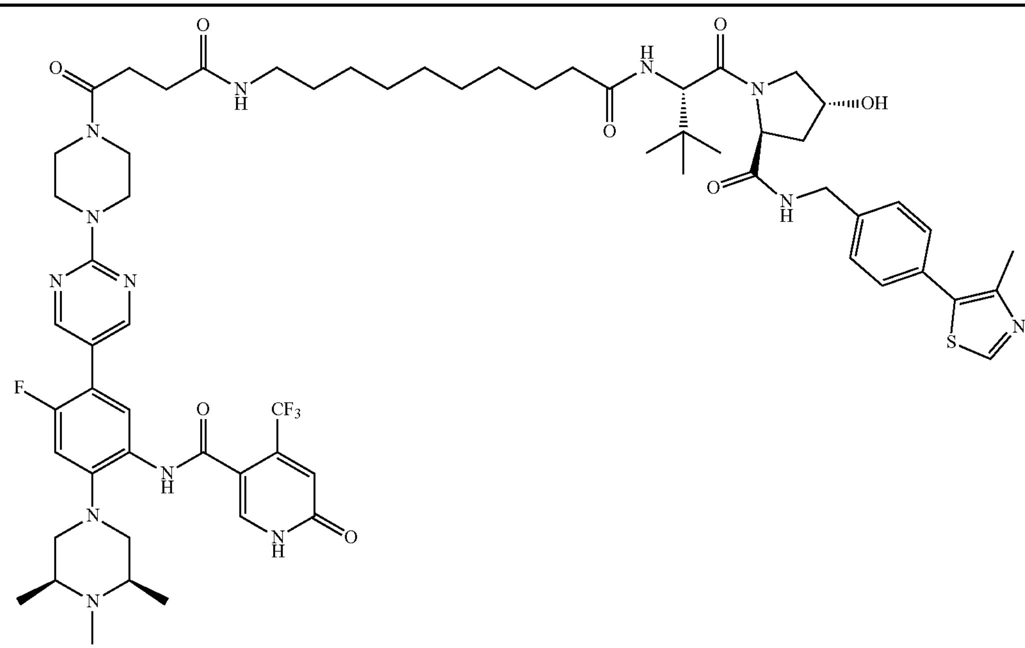 | N-(4-fluoro-5-(2-(4-(4-(4-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| 260 | XF078-78 | 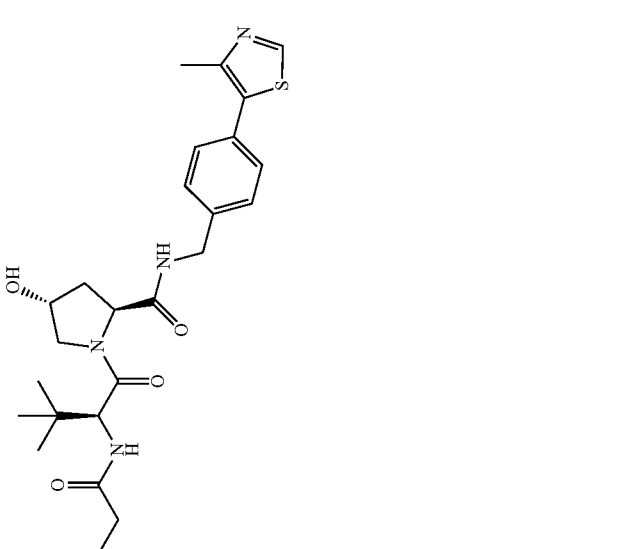 | N-(4-fluoro-5-(2-(4-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 261 | XF078-79 | 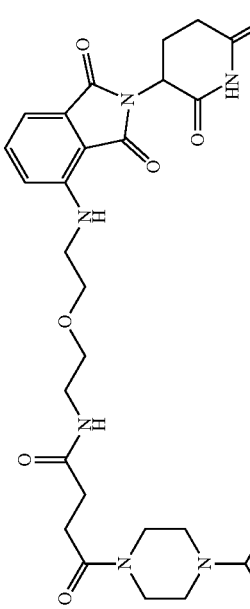 | N-(5-(2-(4-(4-(2-(2-((2-(2,6-dioxopiperidin-3-yl)-1,3-dioxoisoindolin-4-yl)amino)ethoxy)ethyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 262 | XF078-80 | 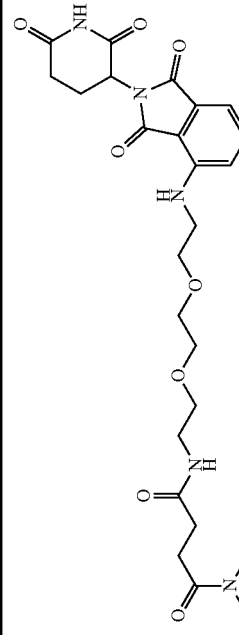 | N-(5-(2-(4-(4-((2-(2-(2-((2-(2,6-dioxopiperidin-3-yl)-1,3-dioxoisoindolin-4-yl)amino)ethoxy)ethoxy)ethyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 263 | XF078-81 | 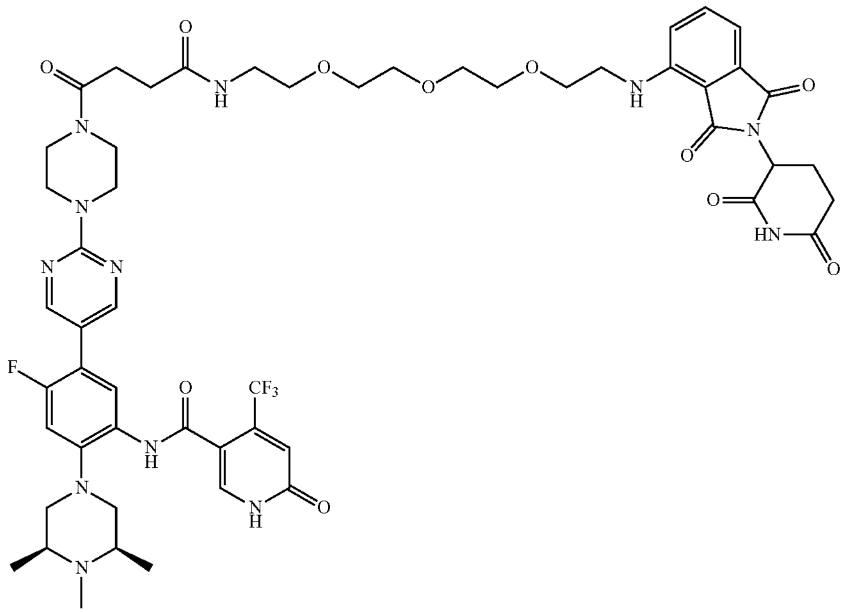 [SMILES: C[C@@H]1CN(c2cc(F)c(-c3cnc(N4CCN(C(=O)CCC(=O)NCCOCCOCCOCCNc5cccc6c5C(=O)N(C5CCC(=O)NC5=O)C6=O)CC4)nc3)cc2NC(=O)c2c[nH]c(=O)cc2C(F)(F)F)C[C@H](C)N1C] | N-(5-(2-(4-(1-((2-(2,6-dioxopiperidin-3-yl)-1,3-dioxoisoindolin-4-yl)amino)-13-oxo-3,6,9-trioxa-12-azahexadecan-16-oyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 264 | XF078-82 | 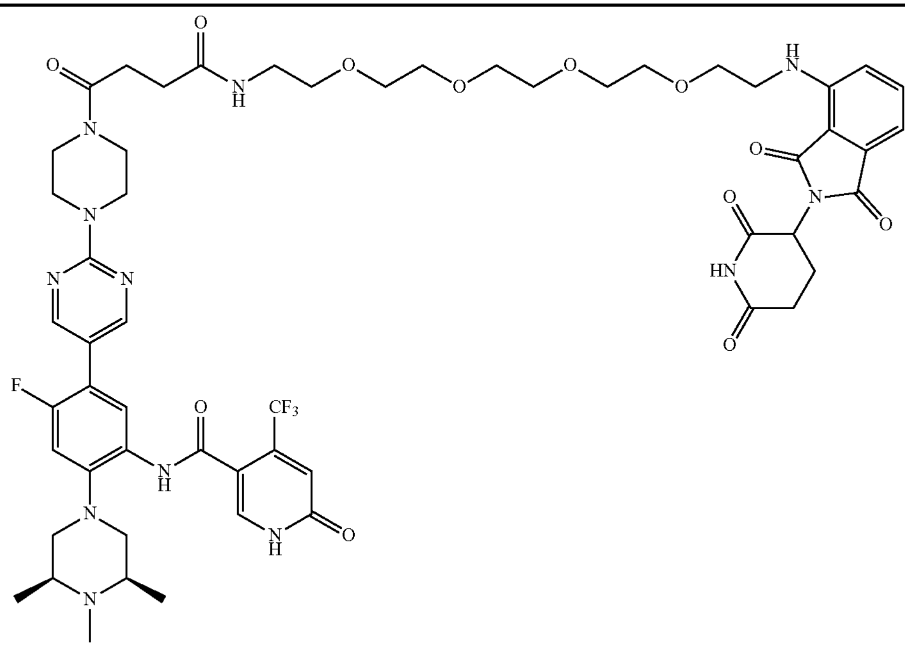 | N-(5-(2-(4-(4-(1-((2-(2,6-dioxopiperidin-3-yl)-1,3-dioxoisoindolin-4-yl)amino)-16-oxo-3,6,9,12-tetraoxa-15-azanonadecan-19-oyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 265 | XF078-83 | 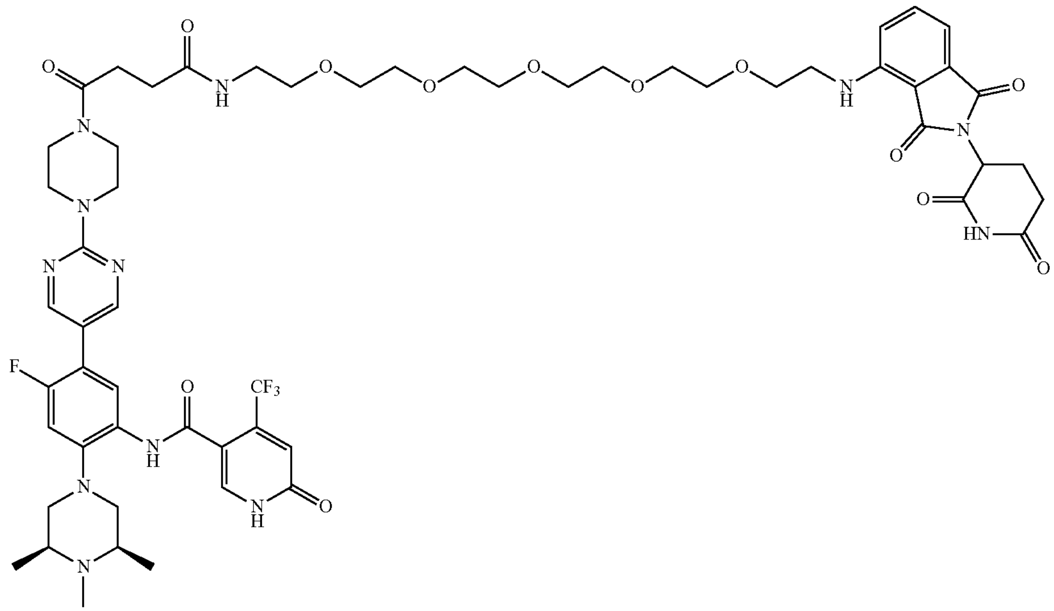 [SMILES: C[C@@H]1CN(c2cc(F)c(-c3cnc(N4CCN(C(=O)CCC(=O)NCCOCCOCCOCCOCCOCCNc5cccc6c5C(=O)N(C5CCC(=O)NC5=O)C6=O)CC4)nc3)cc2NC(=O)c2c[nH]c(=O)cc2C(F)(F)F)C[C@H](C)N1C] | N-(5-(2-(4-(1-((2-(2,6-dioxopiperidin-3-yl)-1,3-dioxoisoindolin-4-yl)amino)-19-oxo-3,6,9,12,15-pentaoxa-18-azadocosan-22-oyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 266 | XF078-84 | 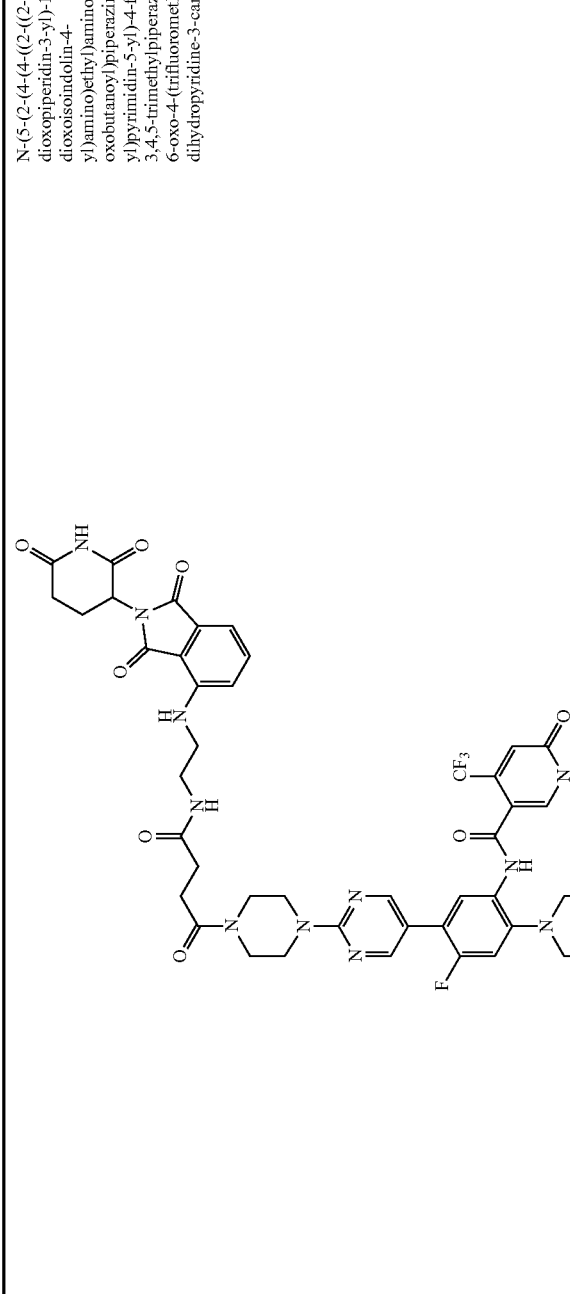 | N-(5-(2-(4-(4-((2-((2-(2,6-dioxopiperidin-3-yl)-1,3-dioxoisoindolin-4-yl)amino)ethyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 267 | XF078-85 | 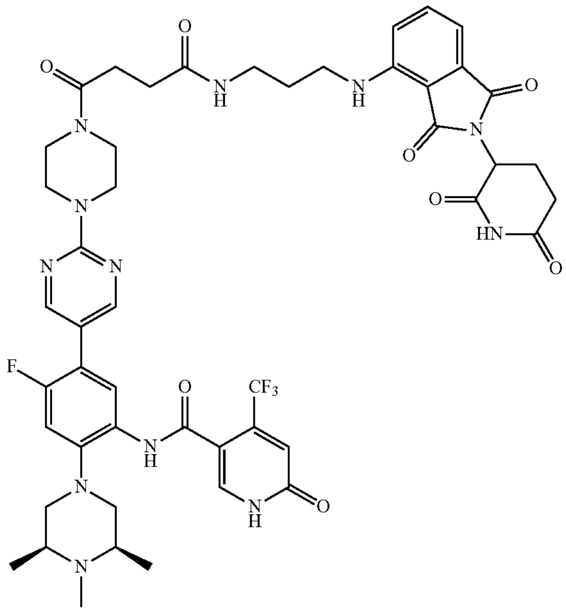 [SMILES: C[C@@H]1CN(c2cc(F)c(-c3cnc(N4CCN(C(=O)CCC(=O)NCCCNc5cccc6c5C(=O)N(C5CCC(=O)NC5=O)C6=O)CC4)nc3)cc2NC(=O)c2c[nH]c(=O)cc2C(F)(F)F)C[C@H](C)N1C] | N-(5-(2-(4-(4-(3-((2-(2,6-dioxopiperidin-3-yl)-1,3-dioxoisoindolin-4-yl)amino)propyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| Example | Compound ID | Structure | Chemical Name |
|---|---|---|---|
| 268 | XF078-86 | 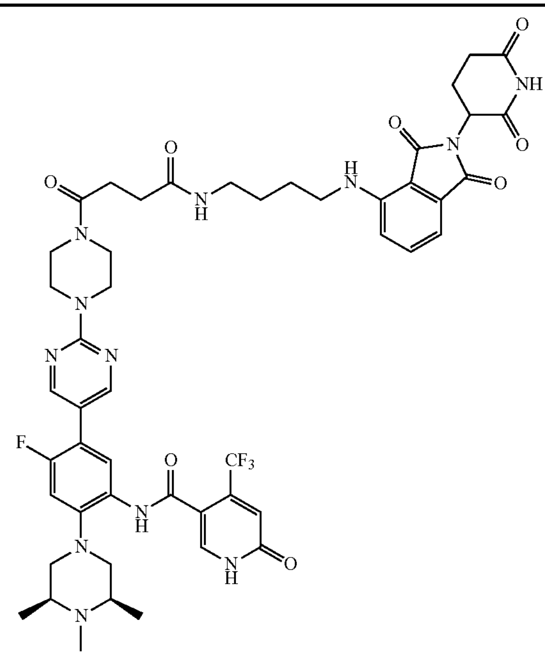 | N-(5-(2-(4-(4-(4-((2-(2,6-dioxopiperidin-3-yl)-1,3-dioxoisoindolin-4-yl)amino)butyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 269 | XF078-87 | 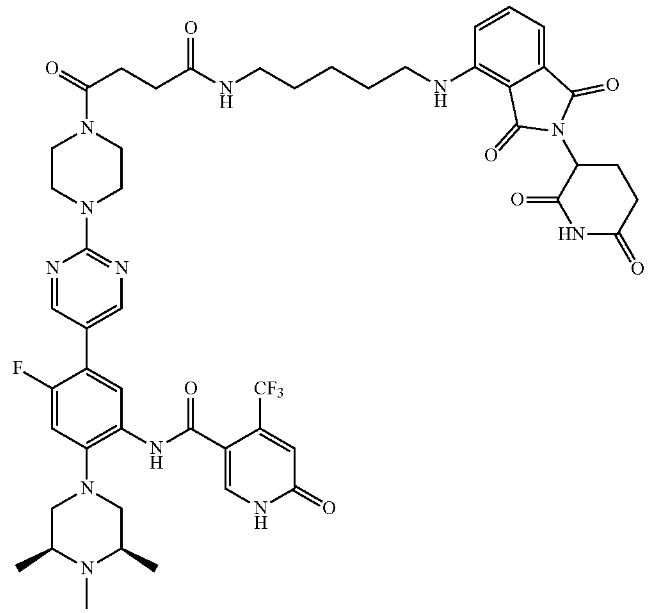 [SMILES: C[C@@H]1CN(c2cc(F)c(-c3cnc(N4CCN(C(=O)CCC(=O)NCCCCCNc5cccc6c5C(=O)N(C5CCC(=O)NC5=O)C6=O)CC4)nc3)cc2NC(=O)c2c[nH]c(=O)cc2C(F)(F)F)C[C@H](C)N1C] | N-(5-(2-(4-(4-((5-((2-(2,6-dioxopiperidin-3-yl)-1,3-dioxoisoindolin-4-yl)amino)pentyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Example | Compound ID | Structure | Chemical Name |
|---|---|---|---|
| 270 | XF078-88 | 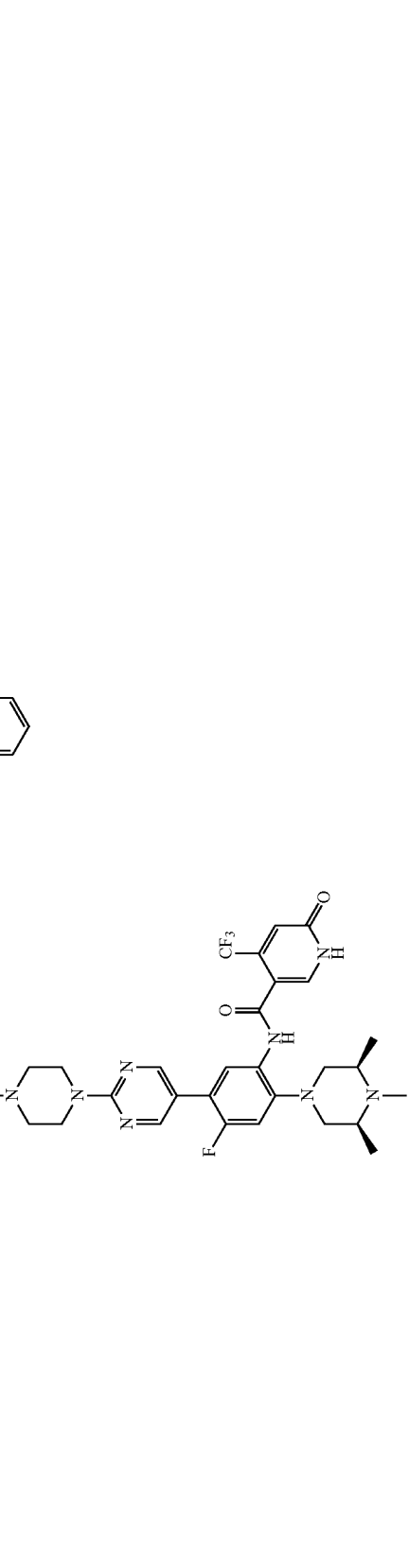 | N-(5-(2-(4-(4-((6-((2-(2,6-dioxopiperidin-3-yl)-1,3-dioxoisoindolin-4-yl)amino)hexyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| Examples | Compound ID | Structure | Chemical Name |
|---|---|---|---|
| 271 | XF078-89 | 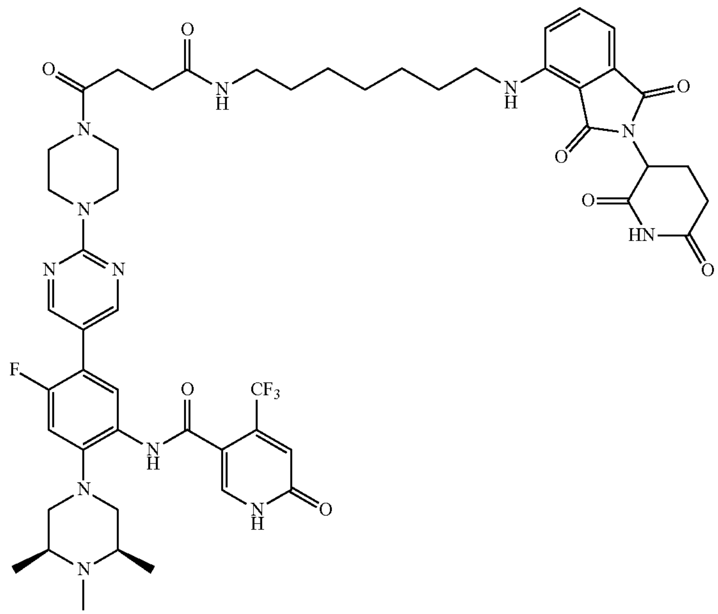 [SMILES: C[C@@H]1CN(c2cc(F)c(-c3cnc(N4CCN(C(=O)CCC(=O)NCCCCCCCNc5cccc6c5C(=O)N(C5CCC(=O)NC5=O)C6=O)CC4)nc3)cc2NC(=O)c2c[nH]c(=O)cc2C(F)(F)F)C[C@H](C)N1C] | N-(5-(2-(4-(4-((7-((2-(2,6-dioxopiperidin-3-yl)-1,3-dioxoisoindolin-4-yl)amino)heptyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 272 | XF078-90 | 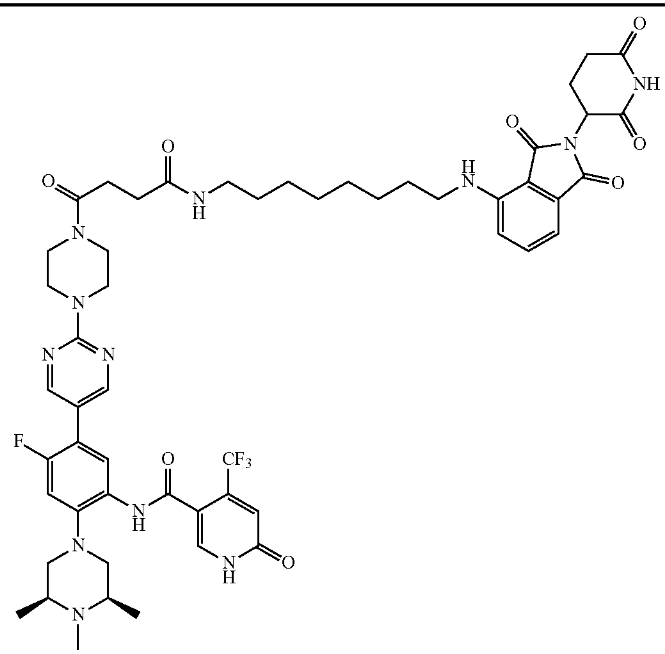 | N-(5-(2-(4-(4-(8-((2-(2,6-dioxopiperidin-3-yl)-1,3-dioxoisoindolin-4-yl)amino)octyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 274 | XF078-99 | 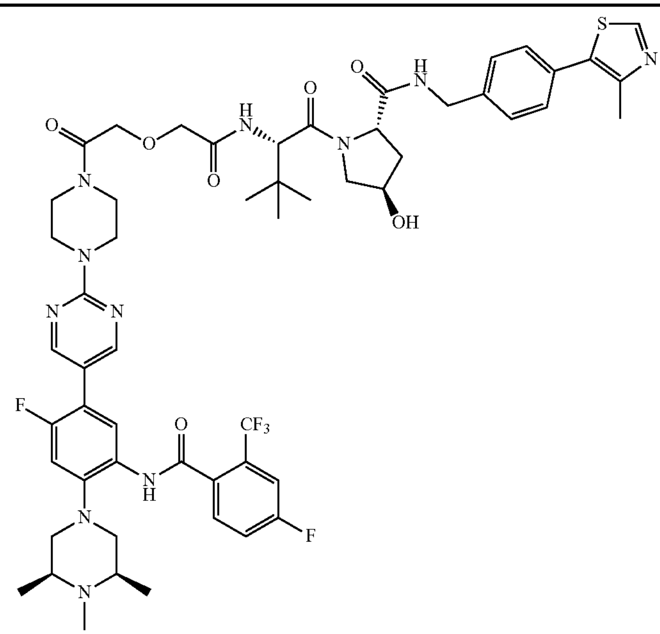 | (2S,4R)-1-((S)-2-(2-(2-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 275 | XF078-100 | 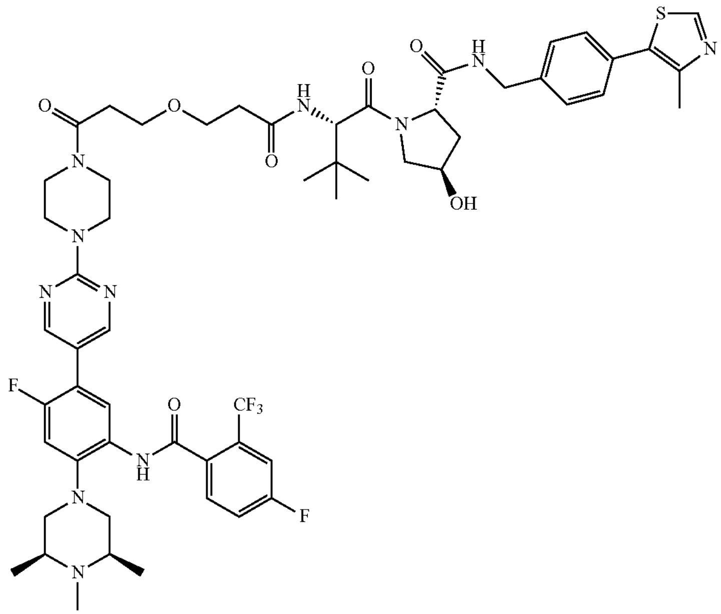 [SMILES: Cc1ncsc1-c1ccc(CNC(=O)[C@@H]2C[C@@H](O)CN2C(=O)[C@@H](NC(=O)CCOCCC(=O)N2CCN(c3ncc(-c4cc(NC(=O)c5ccc(F)cc5C(F)(F)F)c(N5C[C@@H](C)N(C)[C@@H](C)C5)cc4F)cn3)CC2)C(C)(C)C)cc1] | (2S,4R)-1-((S)-2-(3-(3-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide |

TABLE 1-continued
| Ex- am- ples | Com- pound ID | Structure | Chemical Name |
|---|---|---|---|
| 276 | XF078-101 | 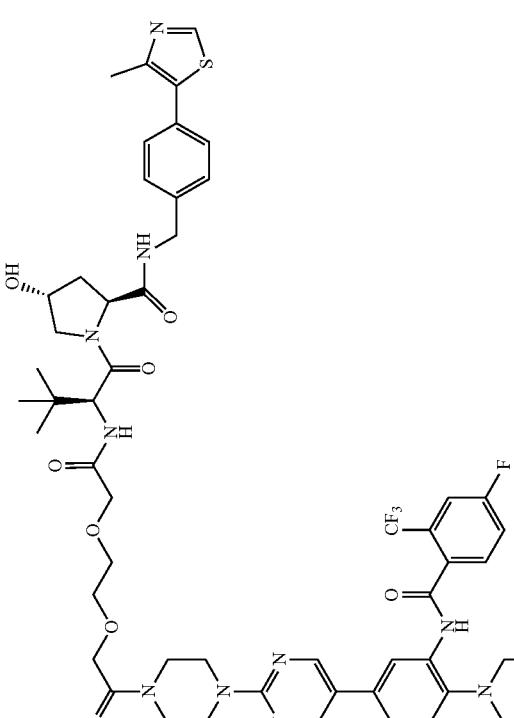 | (2S,4R)-1-((S)-2-(2-(2-(2-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued
| Ex-am-ples | Compound ID | Structure | Chemical Name |
|---|---|---|---|
| 277 | XF078-102 | 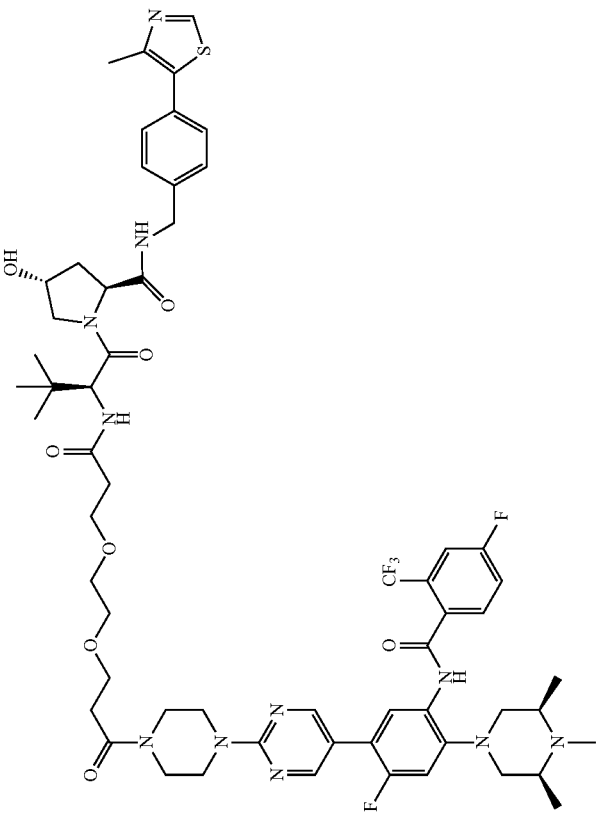 | (2S,4R)-1-((S)-2-(3-(2-(3-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued
| Ex- am- ples | Com- pound ID | Structure | Chemical Name |
|---|---|---|---|
| 278 | XF078-103 | 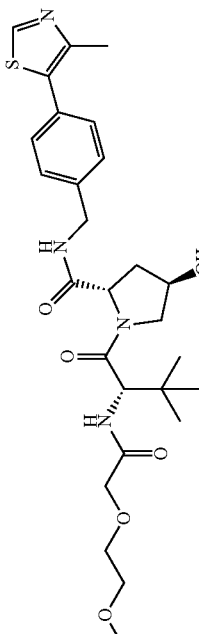 | (2S,4R)-1-((S)-2-(tert-butyl)-14-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide |

| Ex- am- ples | Com- pound ID | Structure | Chemical Name |
|---|---|---|---|
| 279 | XF078-104 | 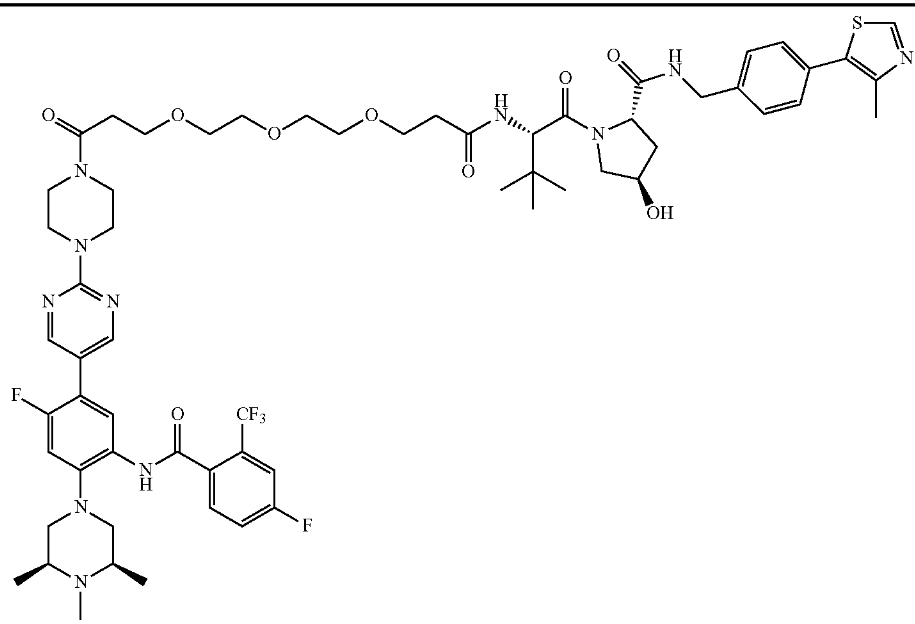 | (2S,4R)-1-((S)-2-(tert-butyl)-16-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |

| Ex-am-ples | Compound ID | Structure | Chemical Name |
|---|---|---|---|
| 280 | XF078-105 | 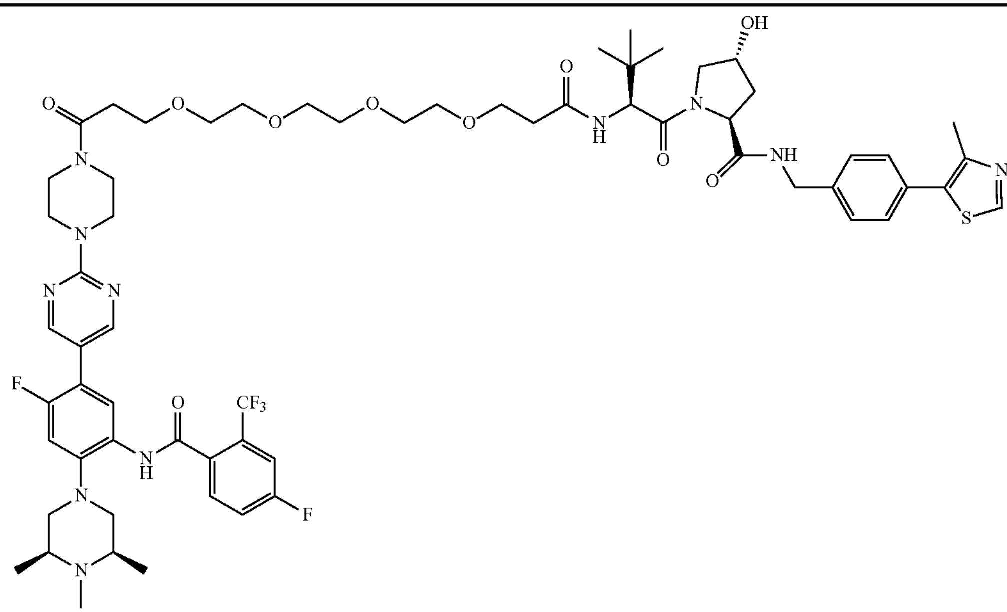 | (2S,4R)-1-((S)-2-(tert-butyl)-19-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 281 | XF078-106 | 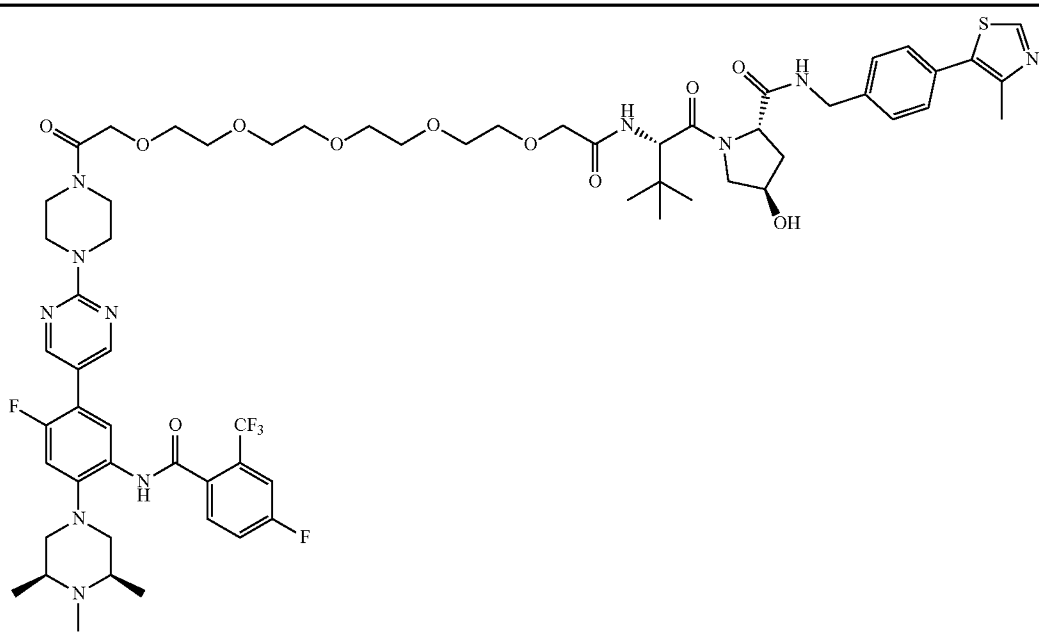 | (2S,4R)-1-((S)-2-(tert-butyl)-20-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 282 | XF078-107 | 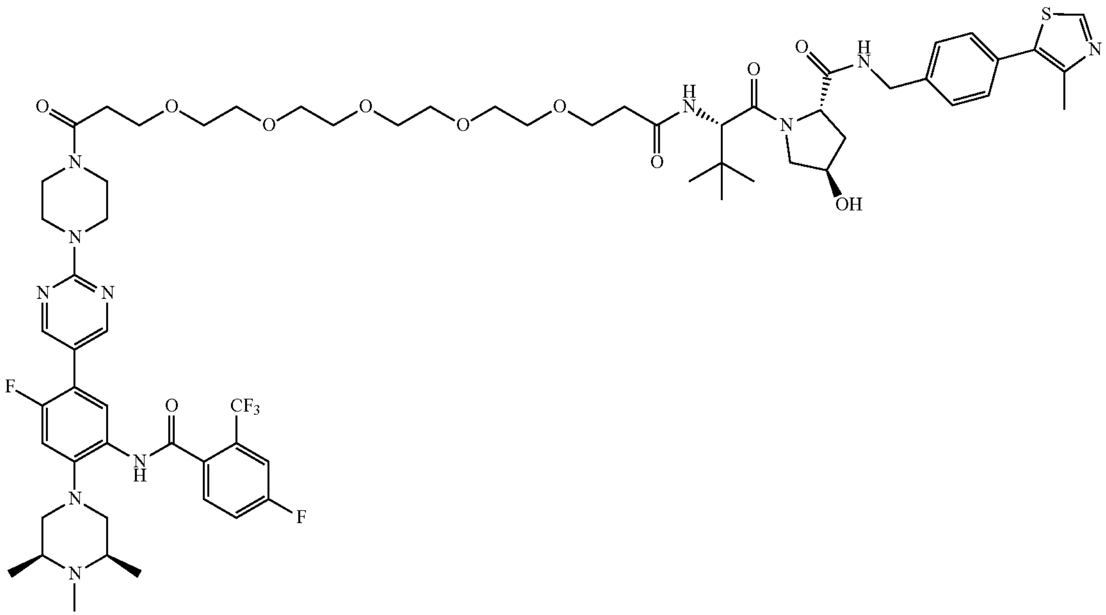 | (2S,4R)-1-((S)-2-(tert-butyl)-22-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 283 | XF078-108 | 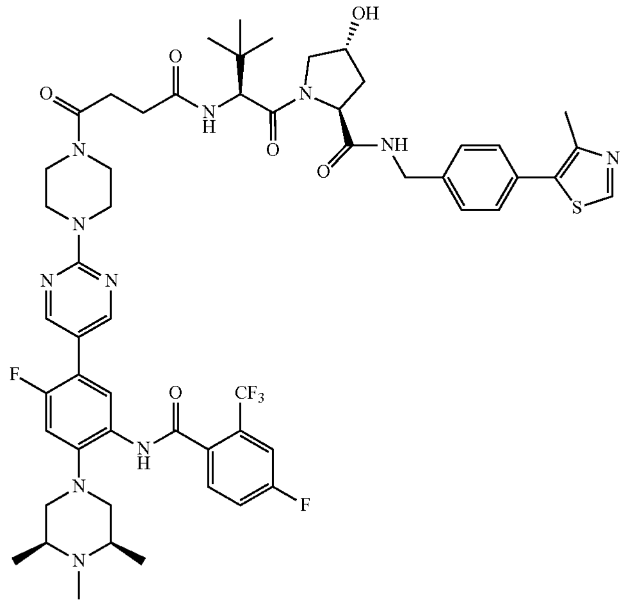 | (2S,4R)-1-((S)-2-(4-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 284 | XF078-109 | 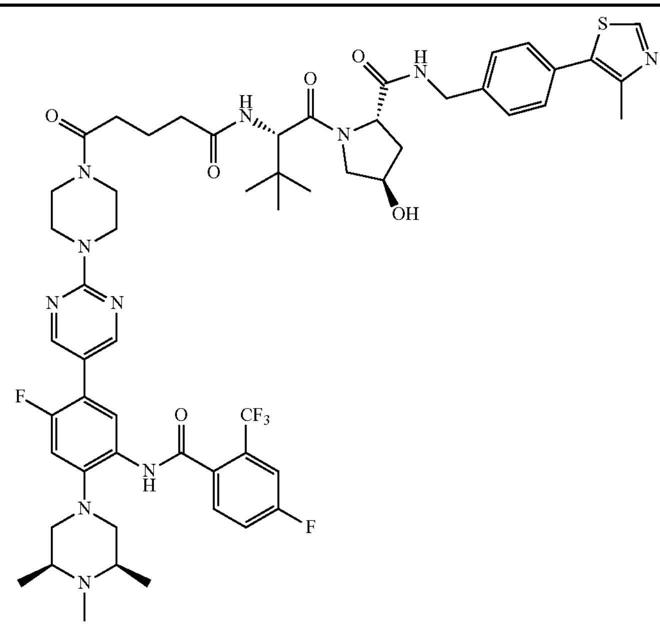 | (2S,4R)-1-((S)-2-(5-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide |

TABLE 1-continued

| Ex- am- ples | Com- pound ID | Structure | Chemical Name |
|---|---|---|---|
| 285 | XF078-110 | 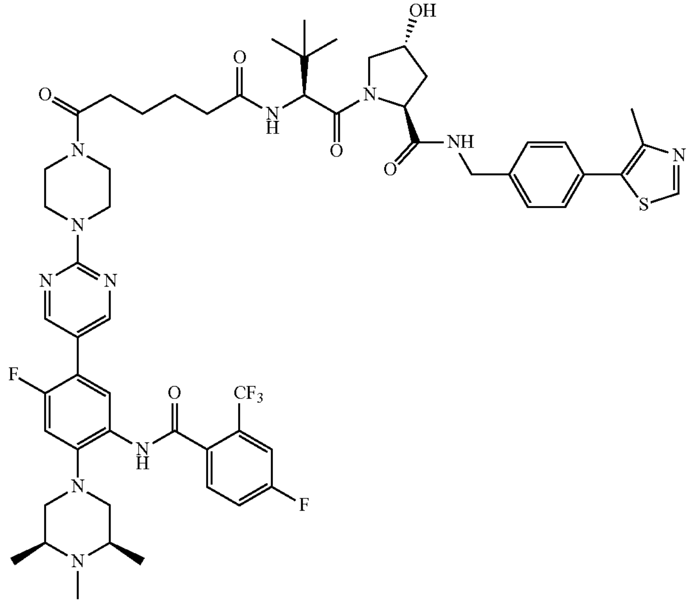 [SMILES: Cc1ncsc1-c1ccc(CNC(=O)[C@@H]2C[C@@H](O)CN2C(=O)[C@@H](NC(=O)CCCCC(=O)N2CCN(c3ncc(-c4cc(NC(=O)c5ccc(F)cc5C(F)(F)F)c(N5C[C@@H](C)N(C)[C@@H](C)C5)cc4F)cn3)CC2)C(C)(C)C)cc1] | (2S,4R)-1-((S)-2-(6-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 286 | XF078-111 | 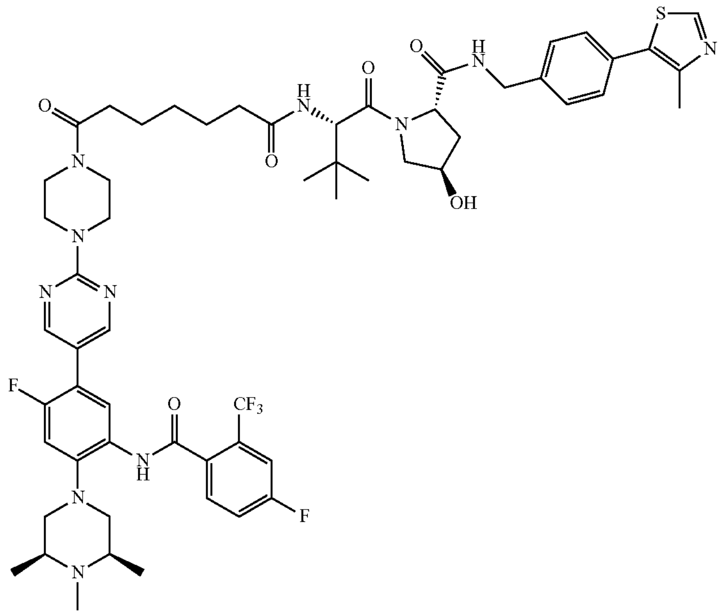 [SMILES: Cc1ncsc1-c1ccc(CNC(=O)[C@@H]2C[C@@H](O)CN2C(=O)[C@@H](NC(=O)CCCCCC(=O)N2CCN(c3ncc(-c4cc(NC(=O)c5ccc(F)cc5C(F)(F)F)c(N5C[C@@H](C)N(C)[C@@H](C)C5)cc4F)cn3)CC2)C(C)(C)C)cc1] | (2S,4R)-1-((S)-2-(7-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |

TABLE 1-continued
| Ex- am- ples | Com- pound ID | Structure | Chemical Name |
|---|---|---|---|
| 287 | XF078- 112 | 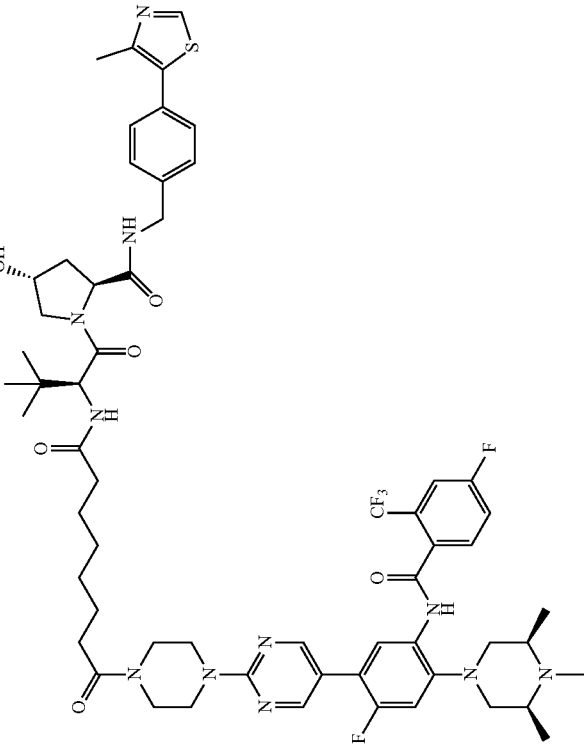 | (2S,4R)-1-((S)-2-(8-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide |

TABLE 1-continued

| Example | Compound ID | Structure | Chemical Name |
|---|---|---|---|
| 288 | XF078-113 | 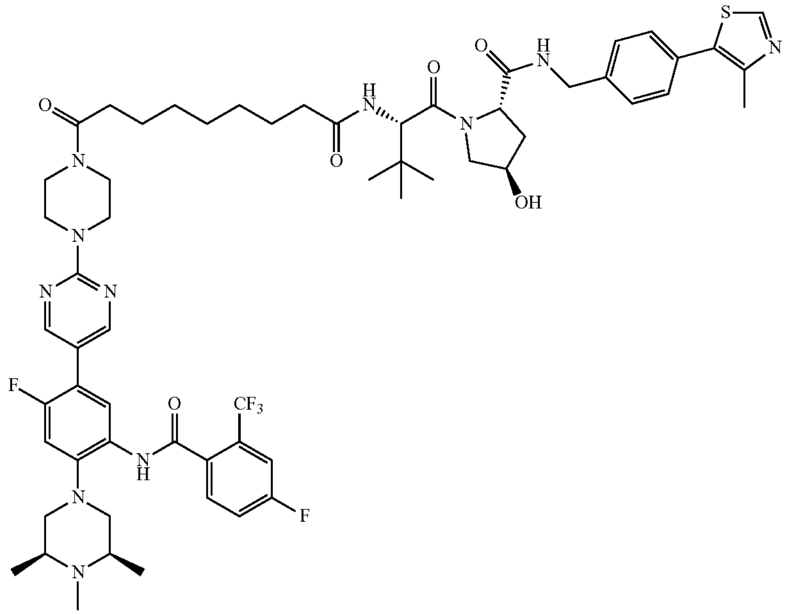 [SMILES: Cc1ncsc1-c1ccc(CNC(=O)[C@@H]2C[C@@H](O)CN2C(=O)[C@@H](NC(=O)CCCCCCCC(=O)N2CCN(c3ncc(-c4cc(NC(=O)c5ccc(F)cc5C(F)(F)F)c(N5C[C@@H](C)N(C)[C@@H](C)C5)cc4F)cn3)CC2)C(C)(C)C)cc1] | (2S,4R)-1-((S)-2-(9-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 289 | XF078-114 | 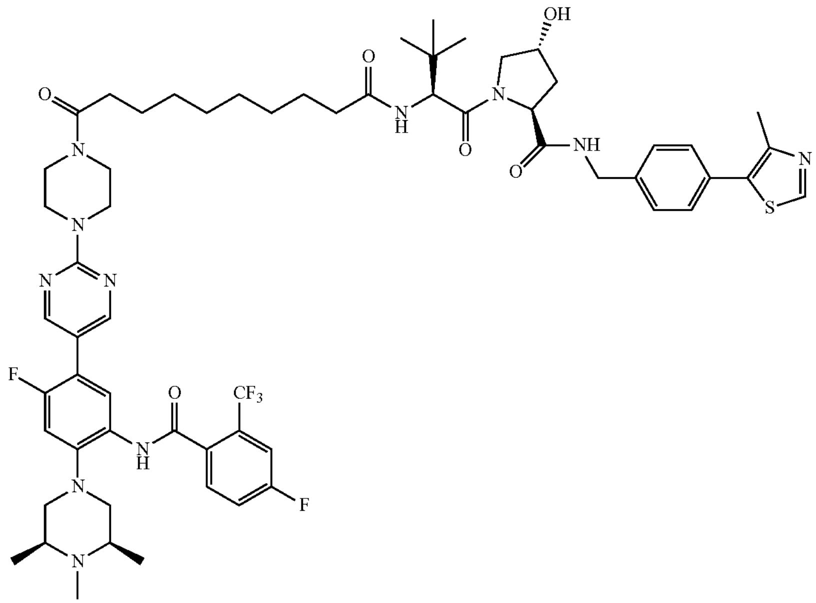 [SMILES: Cc1ncsc1-c1ccc(CNC(=O)[C@@H]2C[C@@H](O)CN2C(=O)[C@@H](NC(=O)CCCCCCCCC(=O)N2CCN(c3ncc(-c4cc(NC(=O)c5ccc(F)cc5C(F)(F)F)c(N5C[C@@H](C)N(C)[C@@H](C)C5)cc4F)cn3)CC2)C(C)(C)C)cc1] | (2S,4R)-1-((S)-2-(10-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |

| Example | Compound ID | Structure | Chemical Name |
|---|---|---|---|
| 290 | XF078-115 | 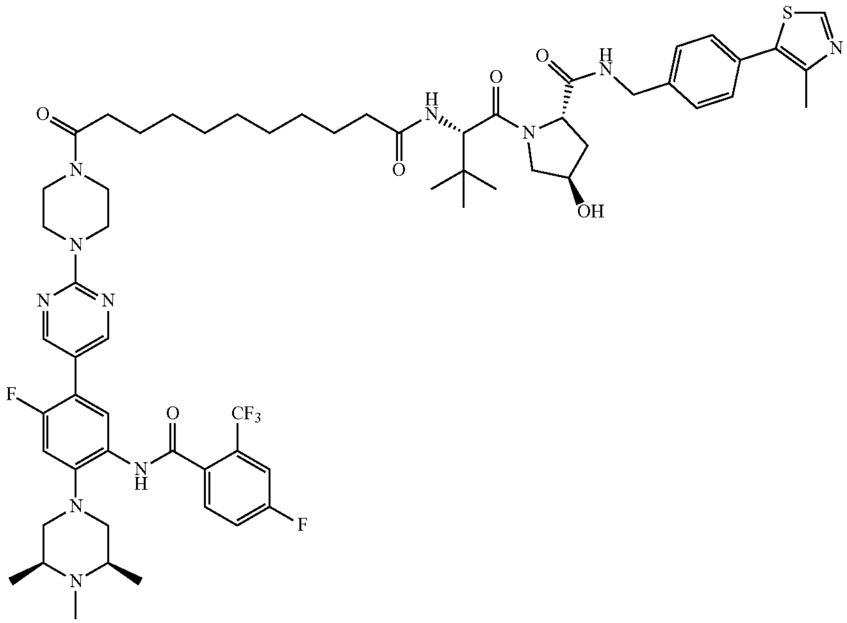 [SMILES: Cc1ncsc1-c1ccc(CNC(=O)[C@@H]2C[C@@H](O)CN2C(=O)[C@@H](NC(=O)CCCCCCCCCC(=O)N2CCN(c3ncc(-c4cc(NC(=O)c5ccc(F)cc5C(F)(F)F)c(N5C[C@@H](C)N(C)[C@@H](C)C5)cc4F)cn3)CC2)C(C)(C)C)cc1] | (2S,4R)-1-((S)-2-(11-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 291 | XF078-116 | 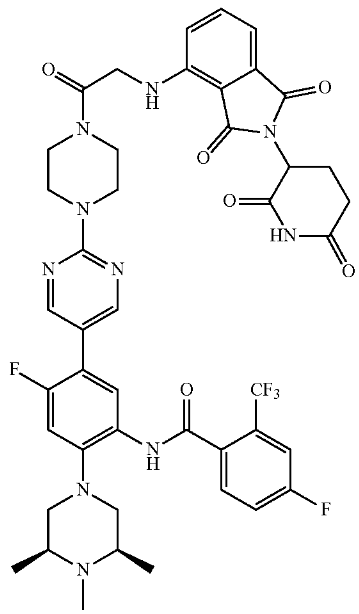 [SMILES: C[C@@H]1CN(c2cc(F)c(-c3cnc(N4CCN(C(=O)CNc5cccc6c5C(=O)N(C5CCC(=O)NC5=O)C6=O)CC4)nc3)cc2NC(=O)c2ccc(F)cc2C(F)(F)F)C[C@H](C)N1C] | N-(5-(2-(4-(4-((2-(2,6-dioxopiperidin-3-yl)-1,3-dioxoisoindolin-4-yl)glycyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued

| Examples | Compound ID | Structure | Chemical Name |
|---|---|---|---|
| 292 | XF078-117 | 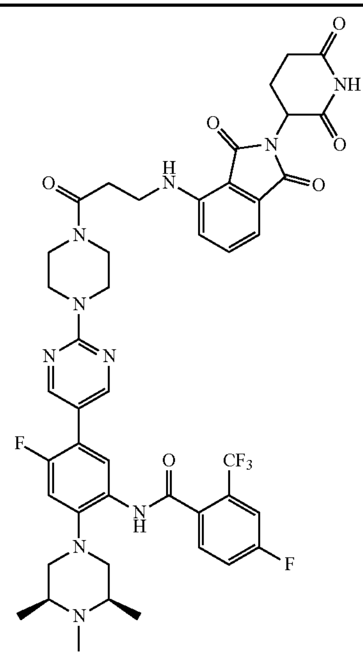 | N-(5-(2-(4-(3-((2-(2,6-dioxopiperidin-3-yl)-1,3-dioxoisoindolin-4-yl)amino)propanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued
| Examples | Compound ID | Structure | Chemical Name |
|---|---|---|---|
| 293 | XF078-118 | 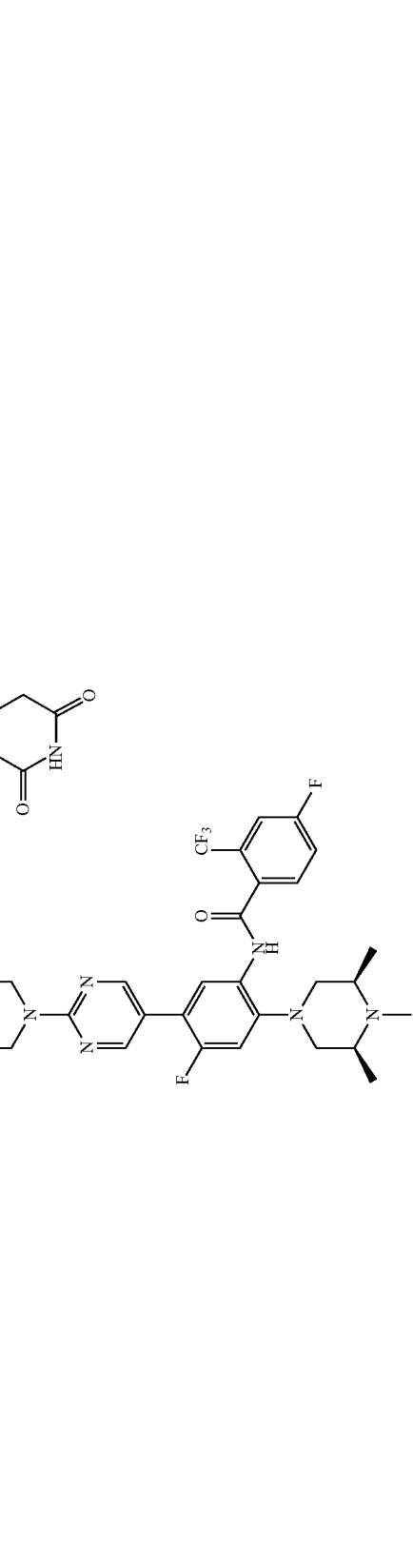 | N-(5-(2-(4-(4-((2-(2,6-dioxopiperidin-3-yl)-1,3-dioxoisoindolin-4-yl)amino)butanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued

| Ex- am- ples | Com- pound ID | Structure | Chemical Name |
|---|---|---|---|
| 294 | XF078-119 | 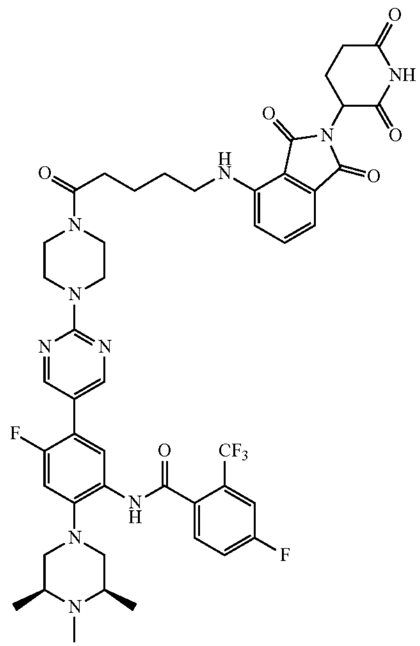 [SMILES: C[C@@H]1CN(c2cc(F)c(-c3cnc(N4CCN(C(=O)CCCCNc5cccc6c5C(=O)N(C5CCC(=O)NC5=O)C6=O)CC4)nc3)cc2NC(=O)c2ccc(F)cc2C(F)(F)F)C[C@H](C)N1C] | N-(5-(2-(4-(5-((2-(2,6-dioxopiperidin-3-yl)-1,3-dioxoisoindolin-4-yl)amino)pentanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued

| Examples | Compound ID | Structure | Chemical Name |
|---|---|---|---|
| 295 | XF078-120 | 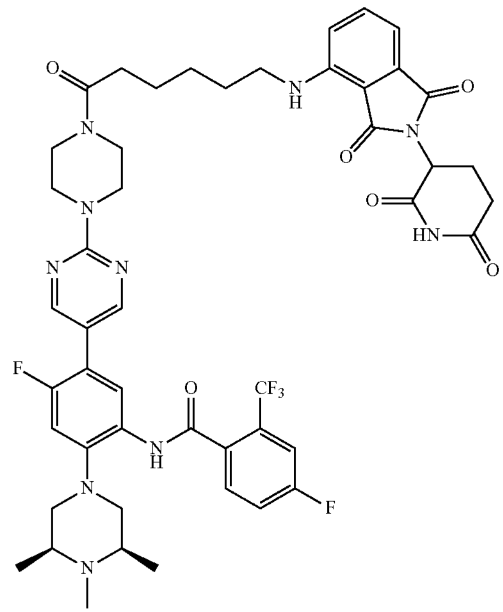 [SMILES: C[C@@H]1CN(c2cc(F)c(-c3cnc(N4CCN(C(=O)CCCCCNc5cccc6c5C(=O)N(C5CCC(=O)NC5=O)C6=O)CC4)nc3)cc2NC(=O)c2ccc(F)cc2C(F)(F)F)C[C@H](C)N1C] | N-(5-(2-(4-(6-((2-(2,6-dioxopiperidin-3-yl)-1,3-dioxoisoindolin-4-yl)amino)hexanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued

| Ex- am- ples | Com- pound ID | Structure | Chemical Name |
|---|---|---|---|
| 296 | XF078-121 | 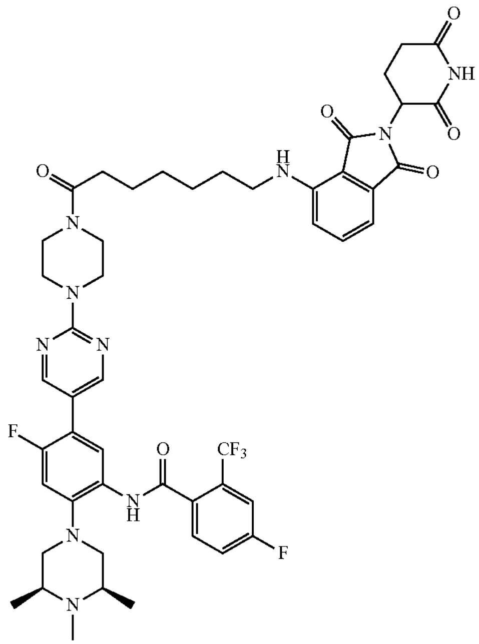 [SMILES: C[C@@H]1CN(c2cc(F)c(-c3cnc(N4CCN(C(=O)CCCCCCNc5cccc6c5C(=O)N(C5CCC(=O)NC5=O)C6=O)CC4)nc3)cc2NC(=O)c2ccc(F)cc2C(F)(F)F)C[C@H](C)N1C] | N-(5-(2-(4-(7-((2-(2,6-dioxopiperidin-3-yl)-1,3-dioxoisoindolin-4-yl)amino)heptanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued

| Example | Compound ID | Structure | Chemical Name |
|---|---|---|---|
| 297 | XF078-122 | 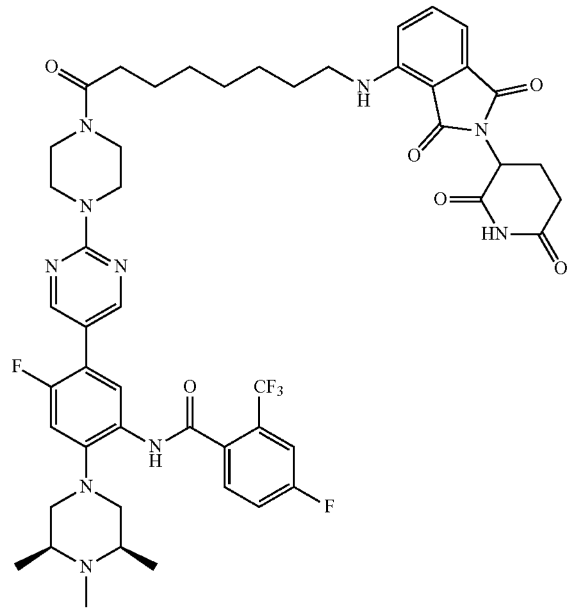 [SMILES: C[C@@H]1CN(c2cc(F)c(-c3cnc(N4CCN(C(=O)CCCCCCCNc5cccc6c5C(=O)N(C5CCC(=O)NC5=O)C6=O)CC4)nc3)cc2NC(=O)c2ccc(F)cc2C(F)(F)F)C[C@H](C)N1C] | N-(5-(2-(4-(8-((2-(2,6-dioxopiperidin-3-yl)-1,3-dioxoisoindolin-4-yl)amino)octanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued
| Example | Compound ID | Structure | Chemical Name |
|---|---|---|---|
| 298 | XF078-123 | 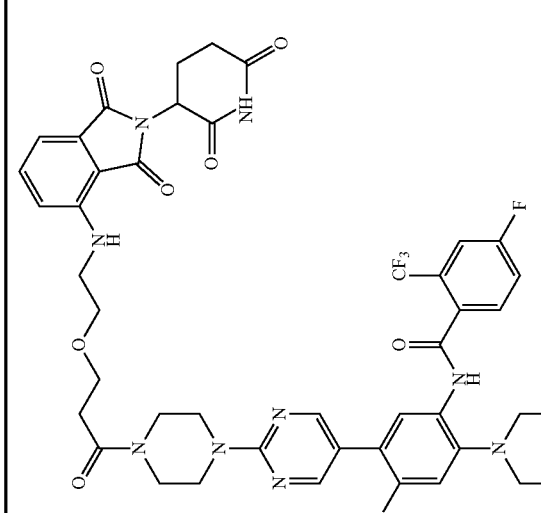 | N-(5-(2-(4-(3-(3-(2-((2-(2,6-dioxopiperidin-3-yl)-1,3-dioxoisoindolin-4-yl)amino)ethoxy)propanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued

| Example | Compound ID | Structure | Chemical Name |
|---|---|---|---|
| 299 | XF078-124 | 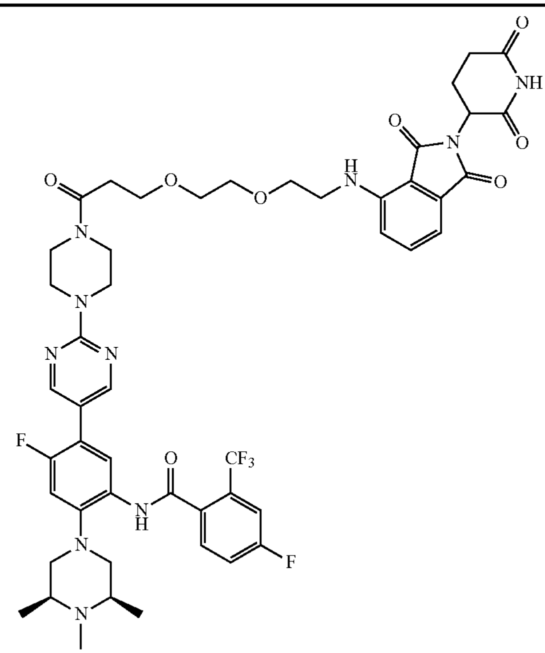 | N-(5-(2-(4-(3-(2-(2-((2-(2,6-dioxopiperidin-3-yl)-1,3-dioxoisoindolin-4-yl)amino)ethoxy)ethoxy)propanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued

| Ex-am-ples | Compound ID | Structure | Chemical Name |
|---|---|---|---|
| 300 | XF078-125 | 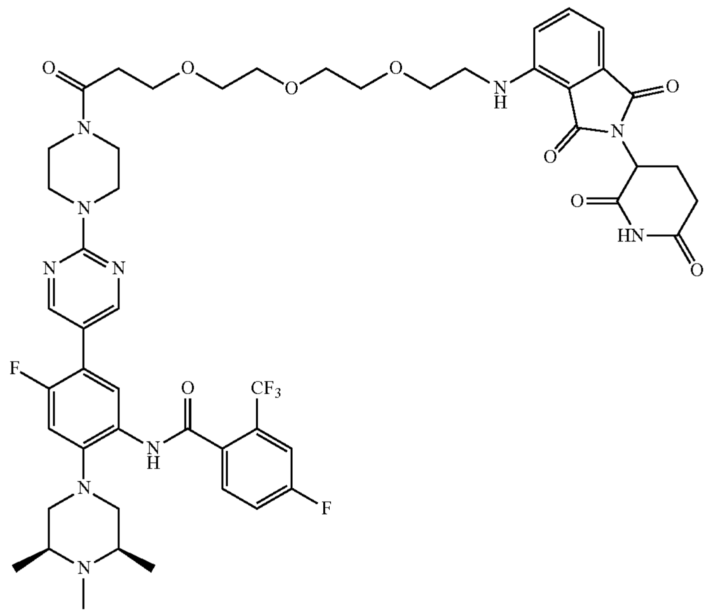 [SMILES: C[C@@H]1CN(c2cc(F)c(-c3cnc(N4CCN(C(=O)CCOCCOCCOCCNc5cccc6c5C(=O)N(C5CCC(=O)NC5=O)C6=O)CC4)nc3)cc2NC(=O)c2ccc(F)cc2C(F)(F)F)C[C@H](C)N1C] | N-(5-(2-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued
| Examples | Compound ID | Structure | Chemical Name |
|---|---|---|---|
| 301 | XF078-126 | 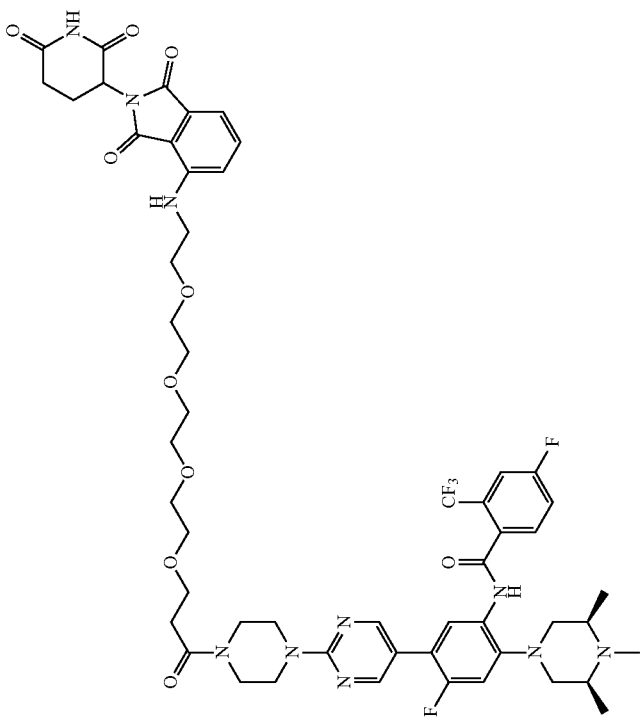 | N-(5-(2-(4-(1-((2-(2,6-dioxopiperidin-3-yl)-1,3-dioxoisoindolin-4-yl)amino)-3,6,9,12-tetraoxapentadecan-15-oyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued
| Examples | Compound ID | Structure | Chemical Name |
|---|---|---|---|
| 302 | XF078-127 | 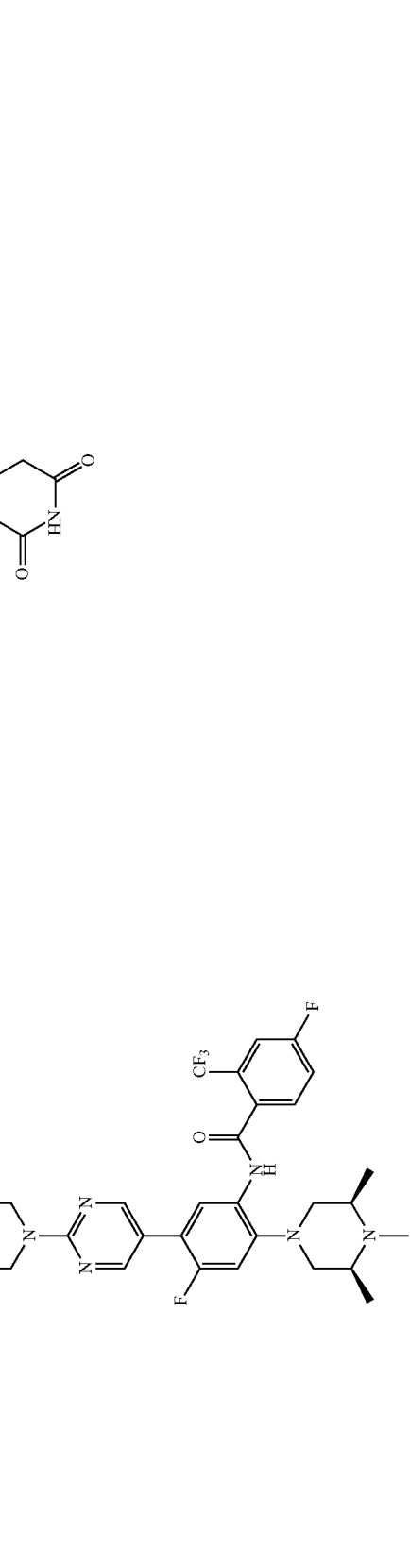 | N-(5-(2-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued
| Example | Compound ID | Structure | Chemical Name |
|---|---|---|---|
| 304 | XF078-132 | 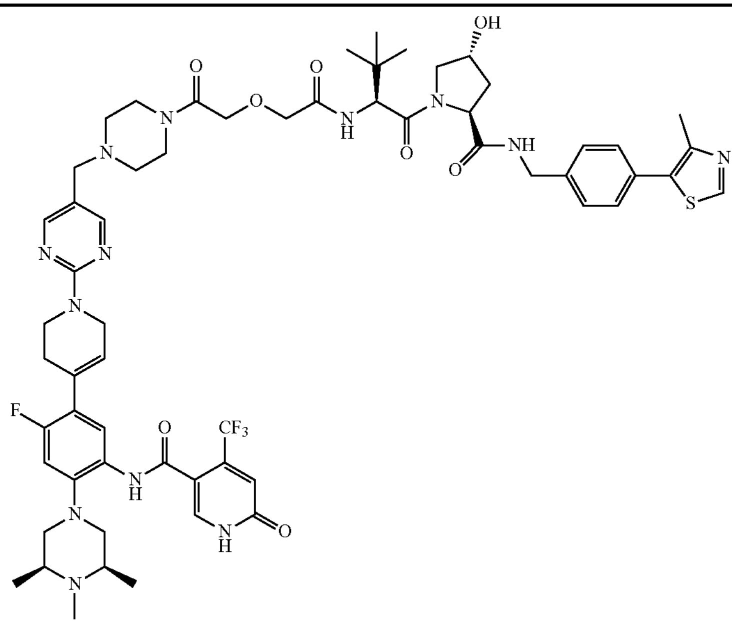 | N-(4-fluoro-5-(1-(5-((4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 305 | XF078-133 | 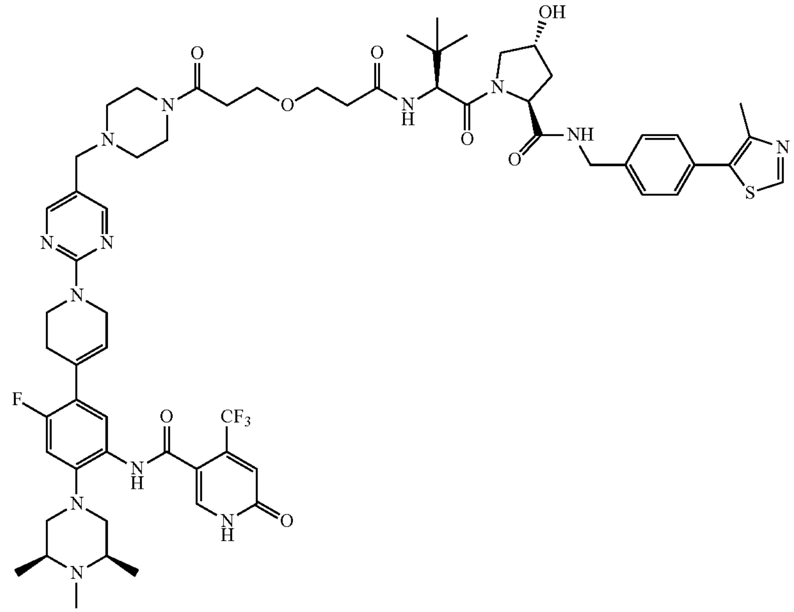 [SMILES: Cc1ncsc1-c1ccc(CNC(=O)[C@@H]2C[C@@H](O)CN2C(=O)[C@@H](NC(=O)CCOCCC(=O)N2CCN(Cc3cnc(N4CC=C(c5cc(NC(=O)c6c[nH]c(=O)cc6C(F)(F)F)c(N6C[C@@H](C)N(C)[C@@H](C)C6)cc5F)CC4)nc3)CC2)C(C)(C)C)cc1] | N-(4-fluoro-5-(1-(5-((4-(3-((4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 306 | XF078-134 | 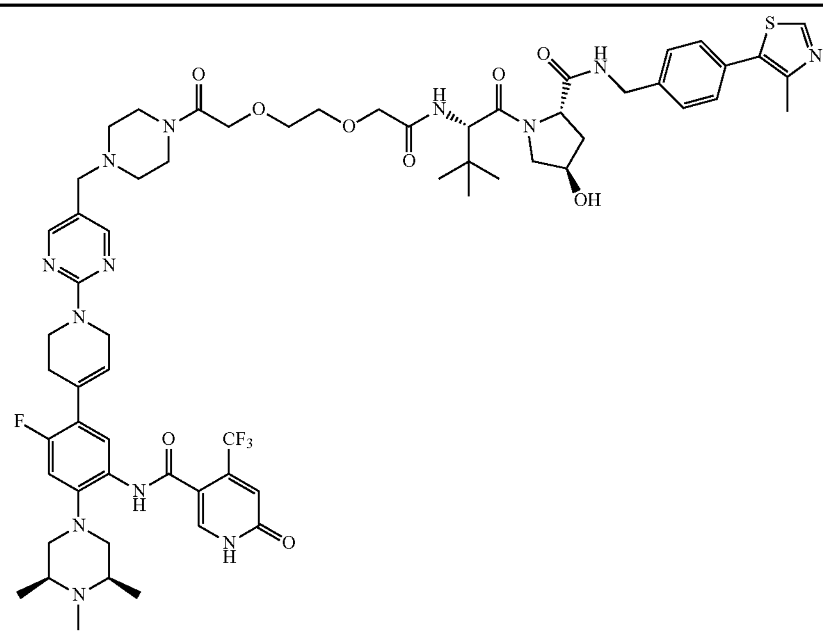 | N-(4-fluoro-5-(1-(5-((4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| 307 | XF078-135 | 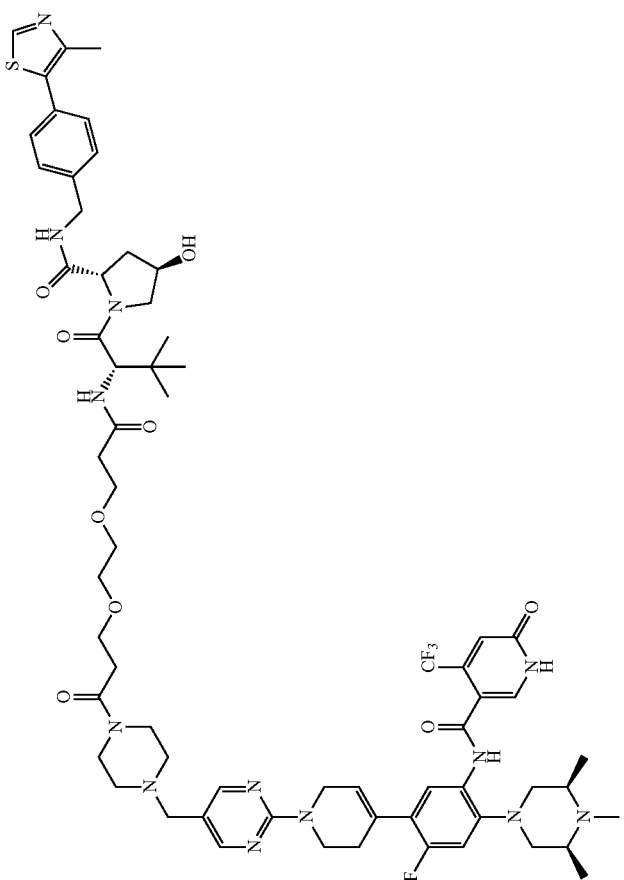 | N-(4-fluoro-5-(1-(5-((4-(3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 308 | XF078-136 | 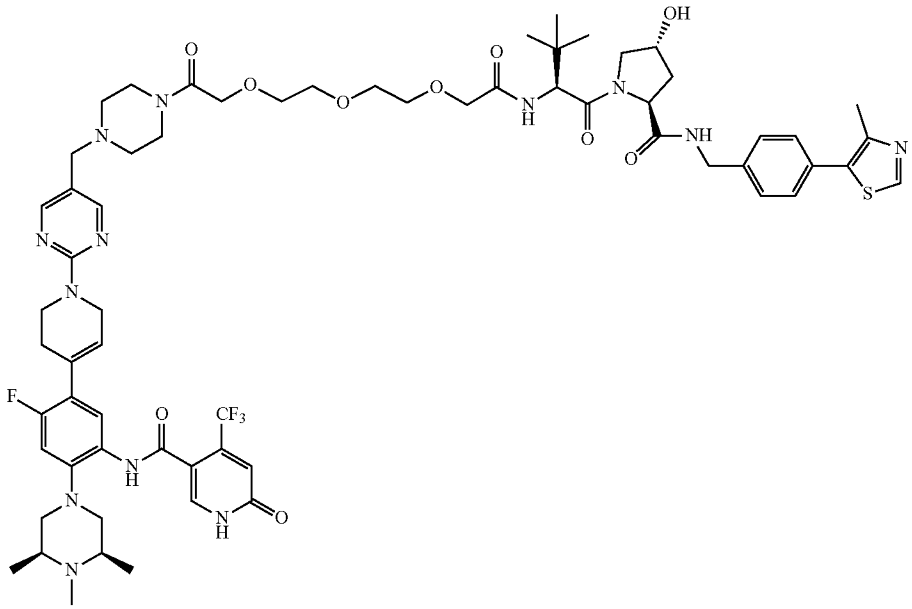 [SMILES: Cc1ncsc1-c1ccc(CNC(=O)[C@@H]2C[C@@H](O)CN2C(=O)[C@@H](NC(=O)COCCOCCOCC(=O)N2CCN(Cc3cnc(N4CC=C(c5cc(NC(=O)c6c[nH]c(=O)cc6C(F)(F)F)c(N6C[C@@H](C)N(C)[C@@H](C)C6)cc5F)CC4)nc3)CC2)C(C)(C)C)cc1] | N-(4-fluoro-5-(1-(5-((4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex-am-ples | Compound ID | Structure | Chemical Name |
|---|---|---|---|
| 309 | XF078-137 | 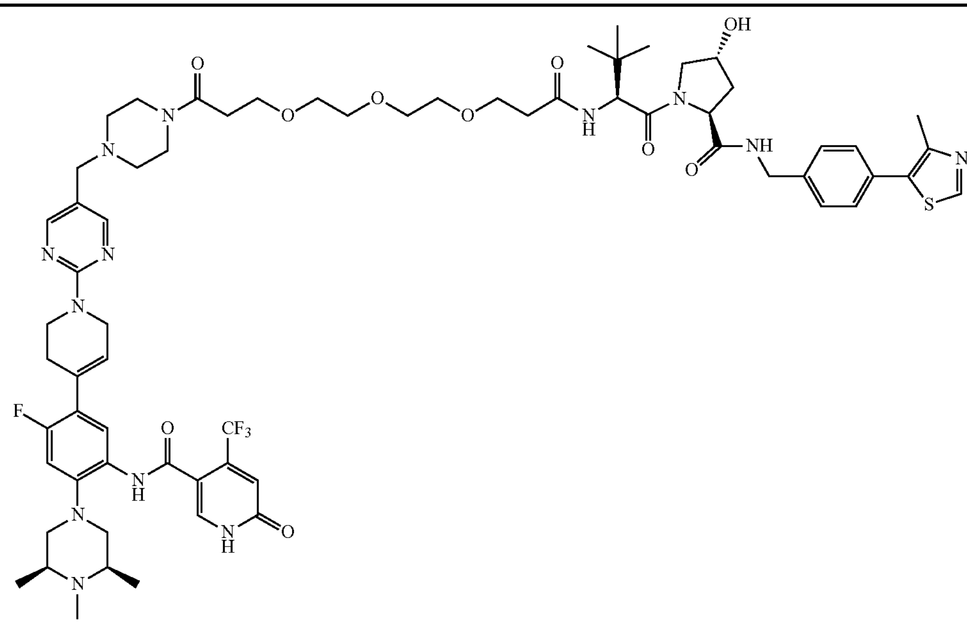 | N-(4-fluoro-5-(1-(5-((4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 310 | XF078-138 | 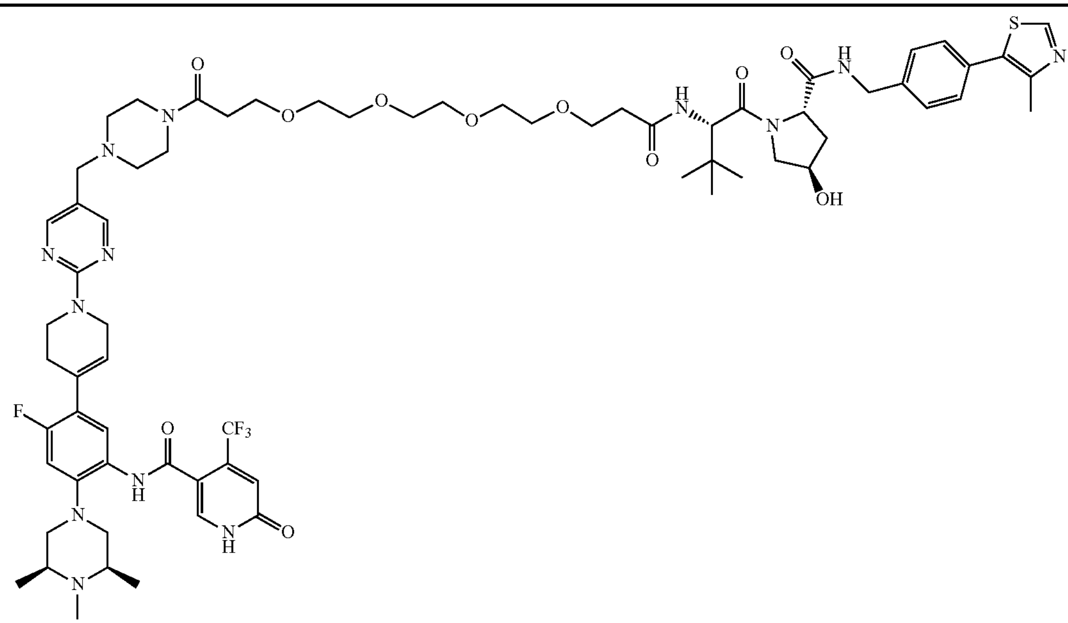 | N-(4-fluoro-5-(1-(5-((4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 311 | XF078- 139 | 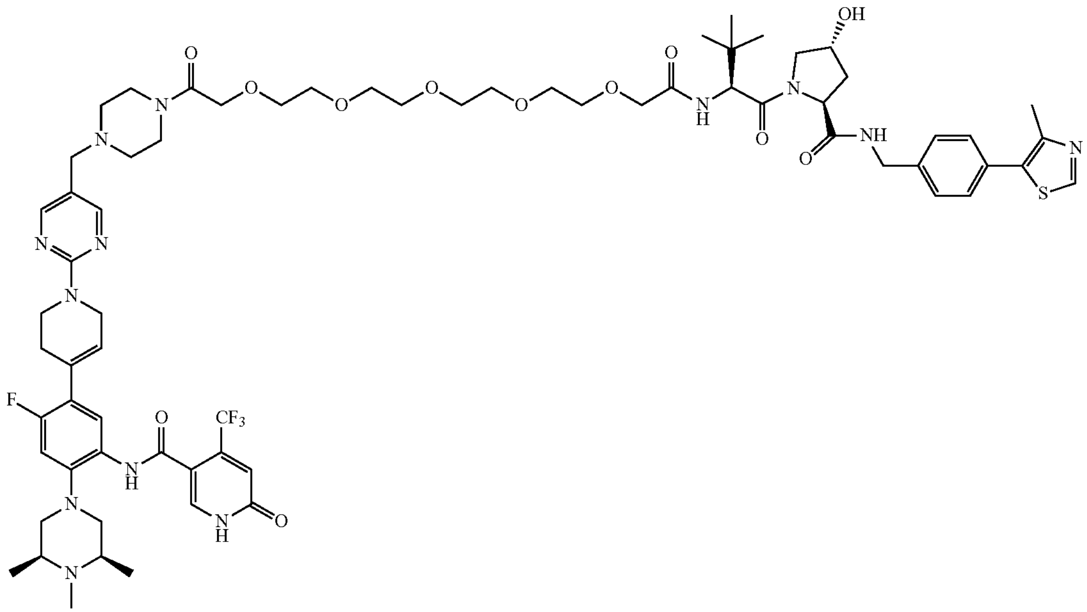 [SMILES: Cc1ncsc1-c1ccc(CNC(=O)[C@@H]2C[C@@H](O)CN2C(=O)[C@@H](NC(=O)COCCOCCOCCOCCOCC(=O)N2CCN(Cc3cnc(N4CC=C(c5cc(NC(=O)c6c[nH]c(=O)cc6C(F)(F)F)c(N6C[C@@H](C)N(C)[C@@H](C)C6)cc5F)CC4)nc3)CC2)C(C)(C)C)cc1] | N-(4-fluoro-5-(1-(5-(((4-((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 312 | XF078-140 | 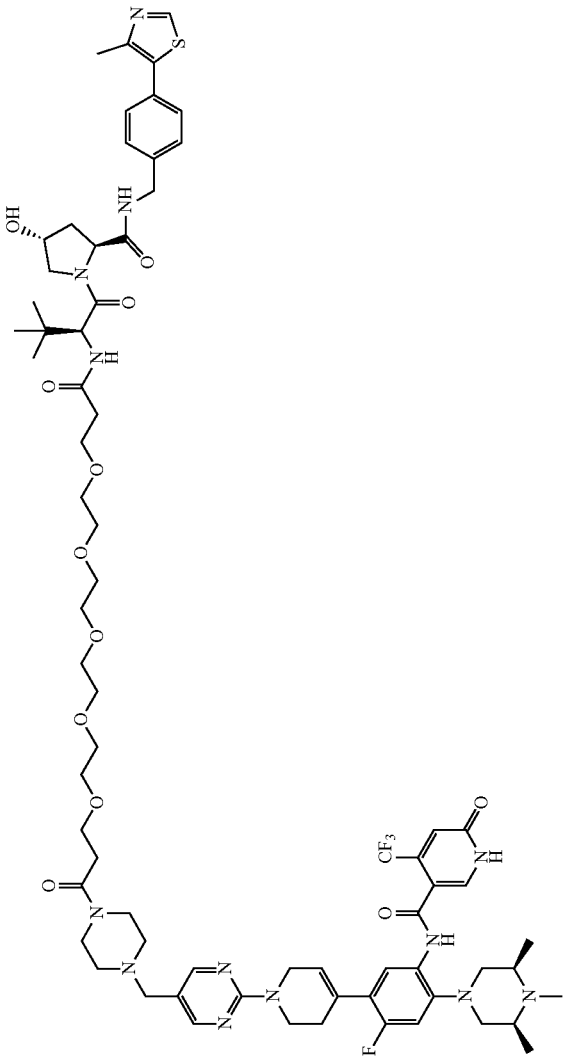 | N-(4-fluoro-5-(1-(5-((4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 313 | XF078-141 | 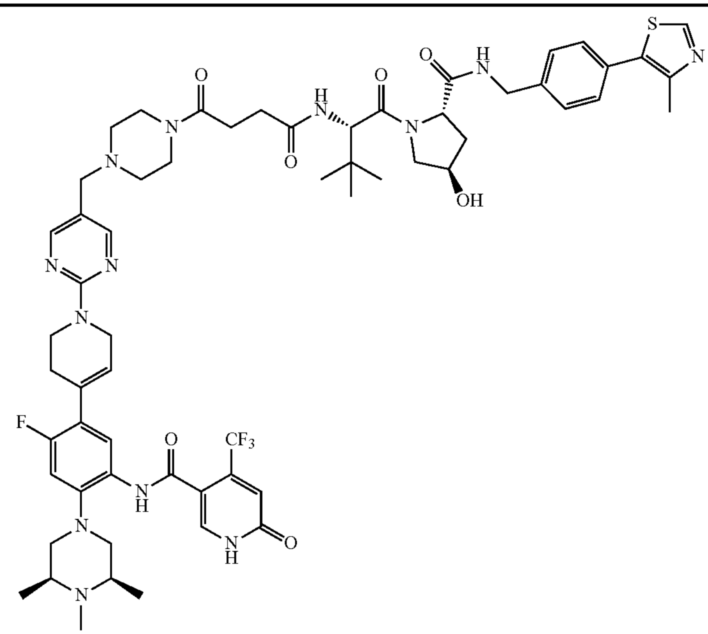 | N-(4-fluoro-5-(1-(5-((4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 314 | XF078-142 | 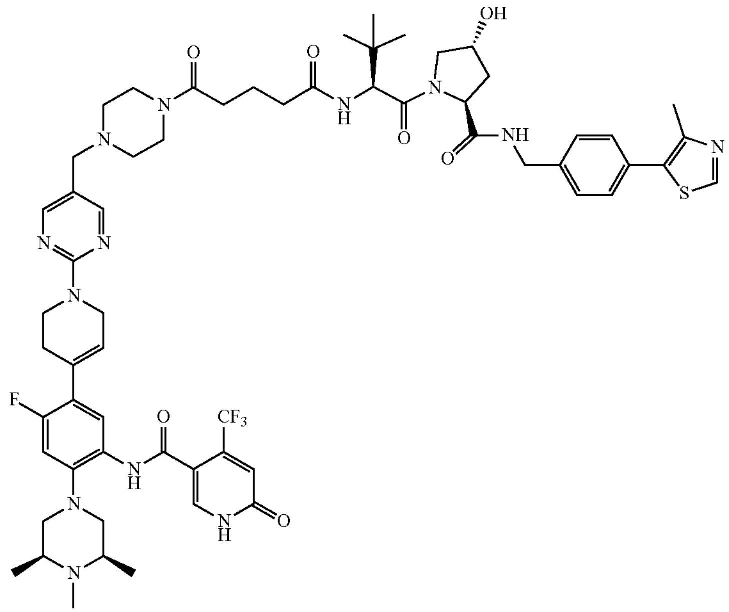 [SMILES: Cc1ncsc1-c1ccc(CNC(=O)[C@@H]2C[C@@H](O)CN2C(=O)[C@@H](NC(=O)CCCC(=O)N2CCN(Cc3cnc(N4CC=C(c5cc(NC(=O)c6c[nH]c(=O)cc6C(F)(F)F)c(N6C[C@@H](C)N(C)[C@@H](C)C6)cc5F)CC4)nc3)CC2)C(C)(C)C)cc1] | N-(4-fluoro-5-(1-(5-((4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 315 | XF078-143 | 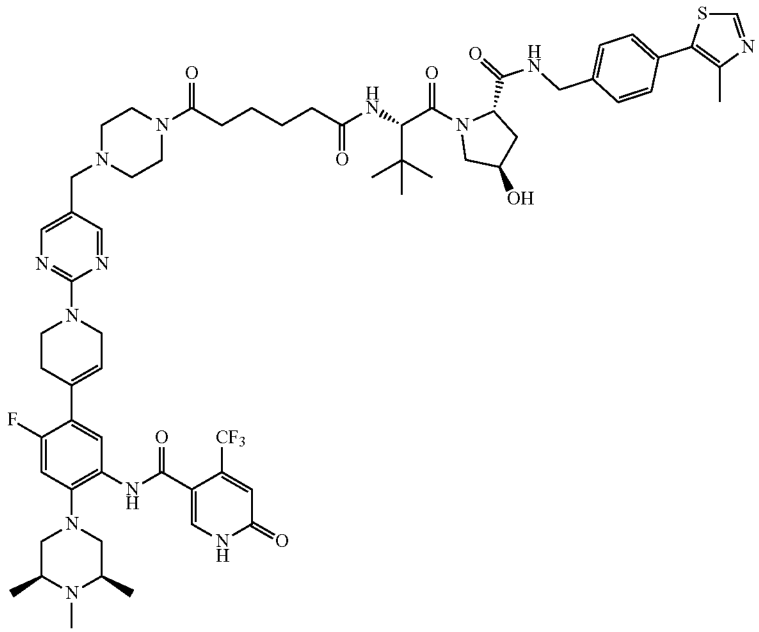 [SMILES: Cc1ncsc1-c1ccc(CNC(=O)[C@@H]2C[C@@H](O)CN2C(=O)[C@@H](NC(=O)CCCCC(=O)N2CCN(Cc3cnc(N4CC=C(c5cc(NC(=O)c6c[nH]c(=O)cc6C(F)(F)F)c(N6C[C@@H](C)N(C)[C@@H](C)C6)cc5F)CC4)nc3)CC2)C(C)(C)C)cc1] | N-(4-fluoro-5-(1-(5-((4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 316 | XF078-144 | 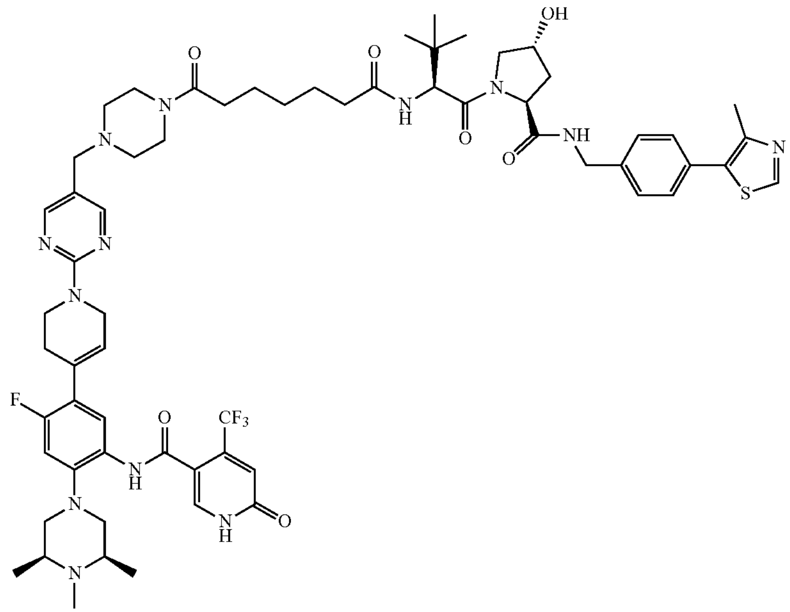 [SMILES: Cc1ncsc1-c1ccc(CNC(=O)[C@@H]2C[C@@H](O)CN2C(=O)[C@@H](NC(=O)CCCCCC(=O)N2CCN(Cc3cnc(N4CC=C(c5cc(NC(=O)c6c[nH]c(=O)cc6C(F)(F)F)c(N6C[C@@H](C)N(C)[C@@H](C)C6)cc5F)CC4)nc3)CC2)C(C)(C)C)cc1] | N-(4-fluoro-5-(1-(5-((4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 317 | XF078-145 | 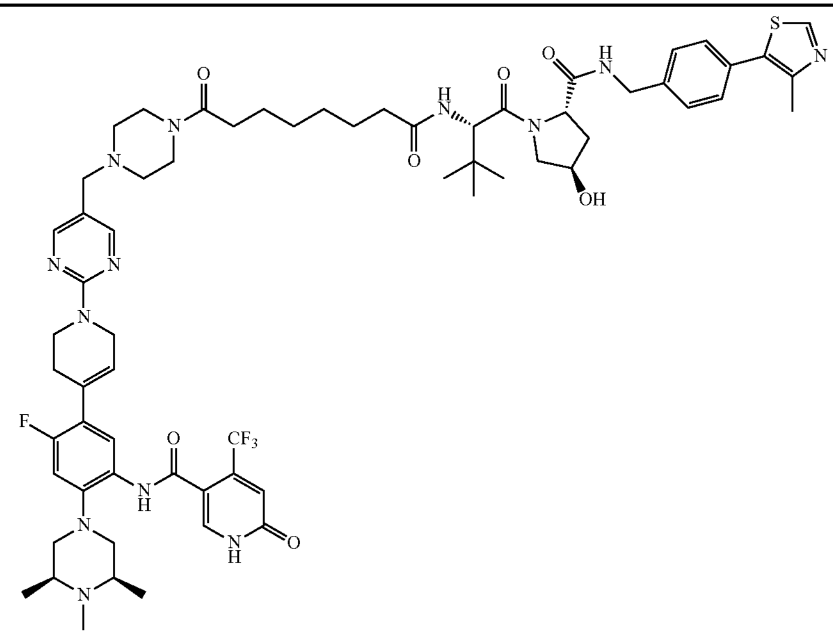 | N-(4-fluoro-5-(1-(5-((4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 318 | XF078-146 | 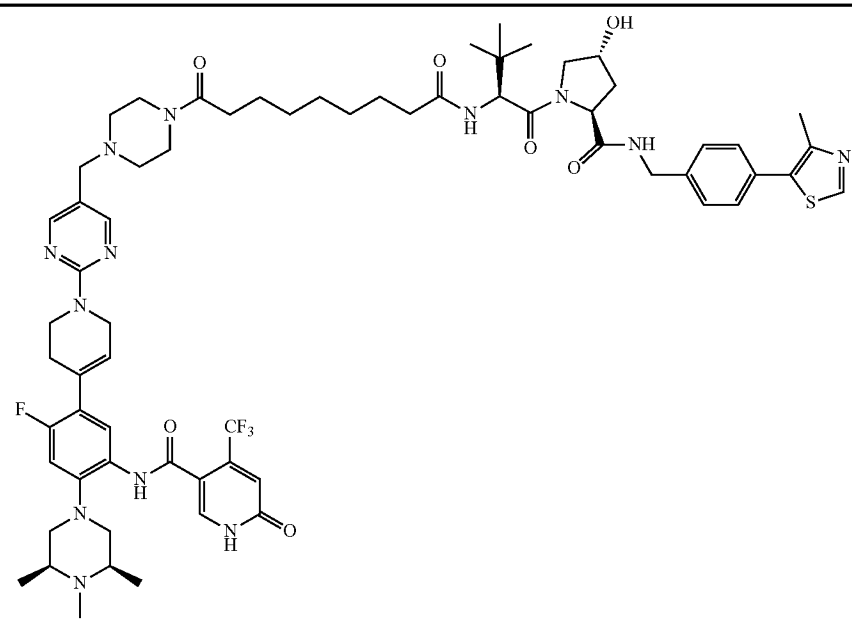 | N-(4-fluoro-5-(1-(5-((4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 319 | XF078-147 | 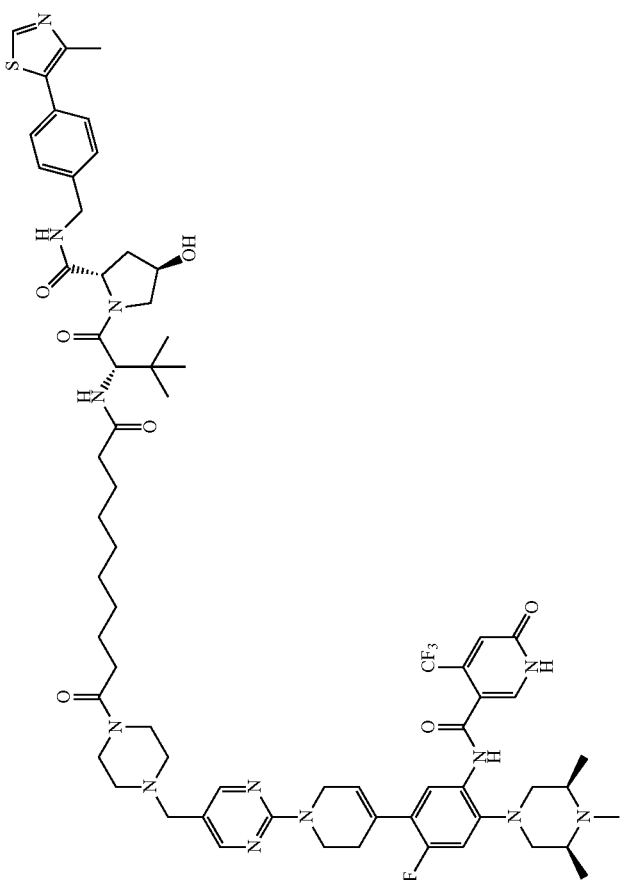 | N-(4-fluoro-5-(1-(5-((4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 320 | XF078-148 | 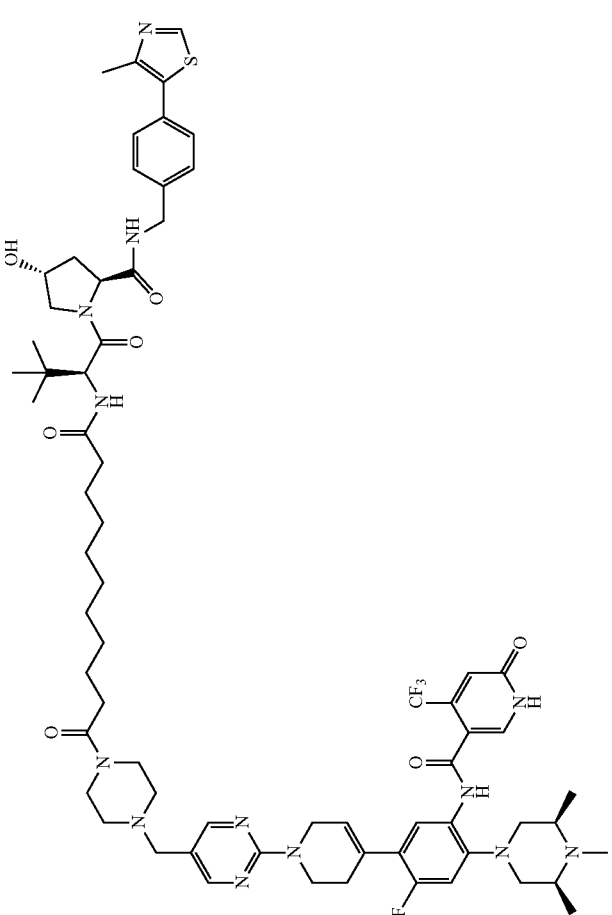 | N-(4-fluoro-5-(1-(5-((4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 321 | XF078-149 | 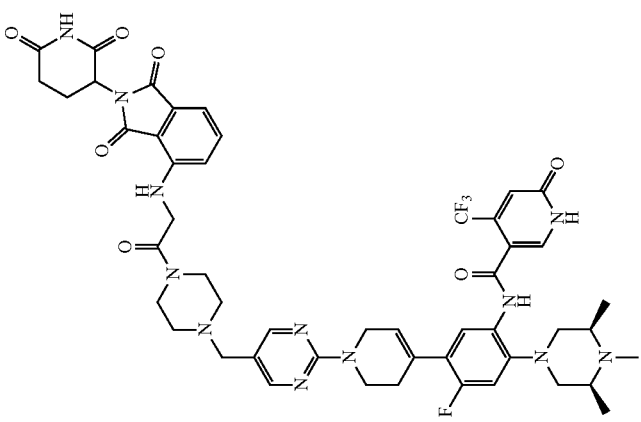 | N-(5-(1-(5-(1-(4-((2-(2,6-dioxopiperidin-3-yl)-1,3-dioxoisoindolin-4-yl)glycyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 322 | XF078-150 | 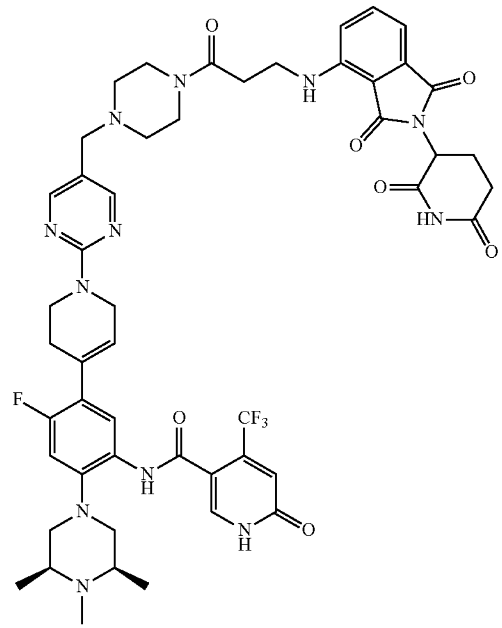 [SMILES: C[C@@H]1CN(c2cc(F)c(C3=CCN(c4ncc(CN5CCN(C(=O)CCNc6cccc7c6C(=O)N(C6CCC(=O)NC6=O)C7=O)CC5)cn4)CC3)cc2NC(=O)c2c[nH]c(=O)cc2C(F)(F)F)C[C@H](C)N1C] | N-(5-(1-(5-((4-(3-((2-(2,6-dioxopiperidin-3-yl)-1,3-dioxoisoindolin-4-yl)amino)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 323 | XF078-151 | 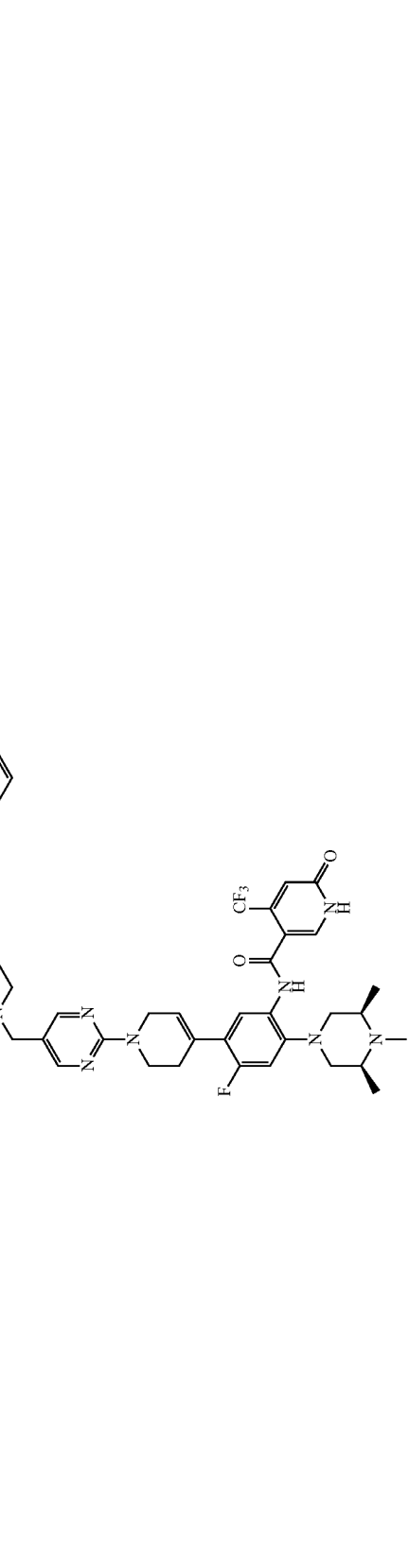 | N-(5-(1-(5-((4-(4-((2-(2,6-dioxopiperidin-3-yl)-1,3-dioxoisoindolin-4-yl)amino)butanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 324 | XF078-152 | 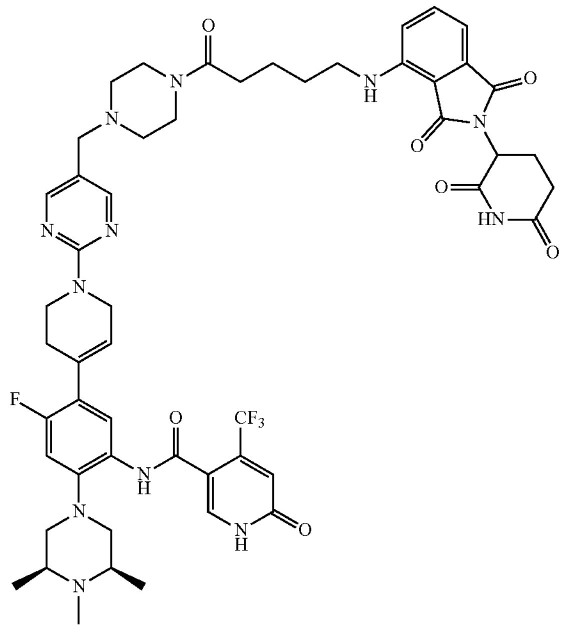 [SMILES: C[C@@H]1CN(c2cc(F)c(C3=CCN(c4ncc(CN5CCN(C(=O)CCCCNc6cccc7c6C(=O)N(C6CCC(=O)NC6=O)C7=O)CC5)cn4)CC3)cc2NC(=O)c2c[nH]c(=O)cc2C(F)(F)F)C[C@H](C)N1C] | N-(5-(1-(5-((4-(5-((2-(2,6-dioxopiperidin-3-yl)-1,3-dioxoisoindolin-4-yl)amino)pentanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 325 | XF078-153 | 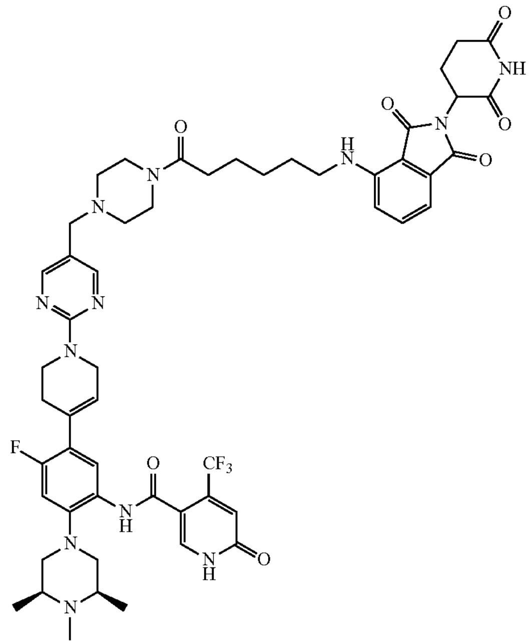 [SMILES: C[C@@H]1CN(c2cc(F)c(C3=CCN(c4ncc(CN5CCN(C(=O)CCCCCNc6cccc7c6C(=O)N(C6CCC(=O)NC6=O)C7=O)CC5)cn4)CC3)cc2NC(=O)c2c[nH]c(=O)cc2C(F)(F)F)C[C@H](C)N1C] | N-(5-(1-(5-((4-(6-((2-(2,6-dioxopiperidin-3-yl)-1,3-dioxoisoindolin-4-yl)amino)hexanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 326 | XF078-154 | 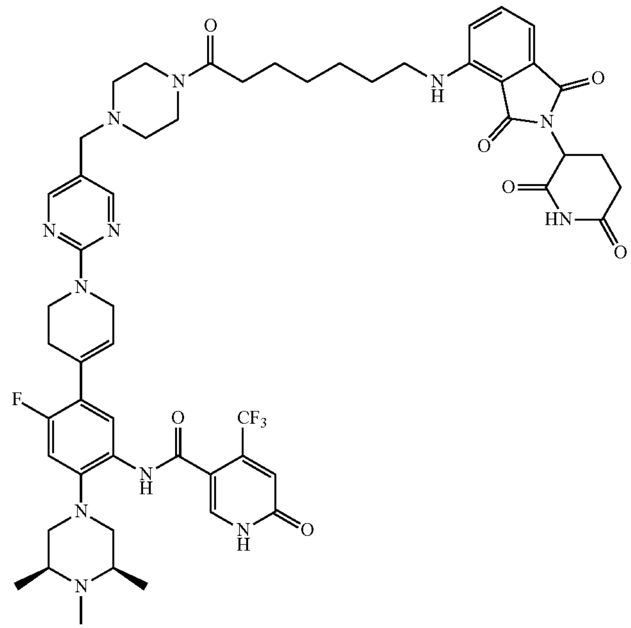 [SMILES: C[C@@H]1CN(c2cc(F)c(C3=CCN(c4ncc(CN5CCN(C(=O)CCCCCCNc6cccc7c6C(=O)N(C6CCC(=O)NC6=O)C7=O)CC5)cn4)CC3)cc2NC(=O)c2c[nH]c(=O)cc2C(F)(F)F)C[C@H](C)N1C] | N-(5-(1-(5-(4-(7-((2-(2,6-dioxopiperidin-3-yl)-1,3-dioxoisoindolin-4-yl)amino)heptanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 327 | XF078-155 | 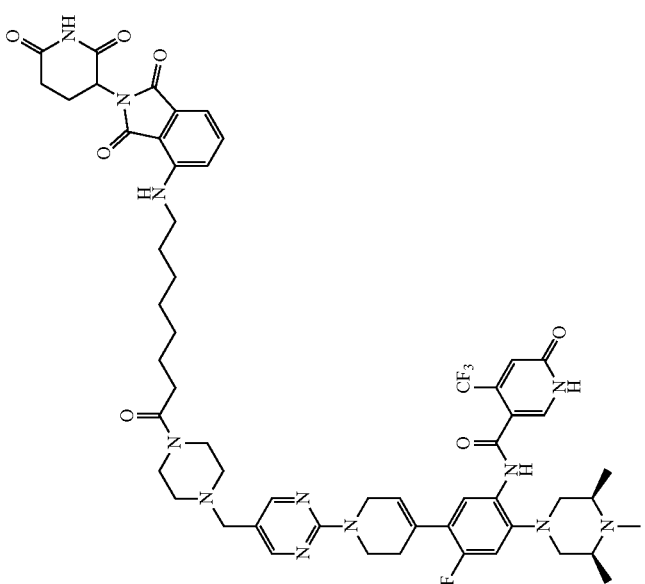 | N-(5-(1-(5-((4-(8-((2-(2,6-dioxopiperidin-3-yl)-1,3-dioxoisoindolin-4-yl)amino)octanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 328 | XF078-156 | 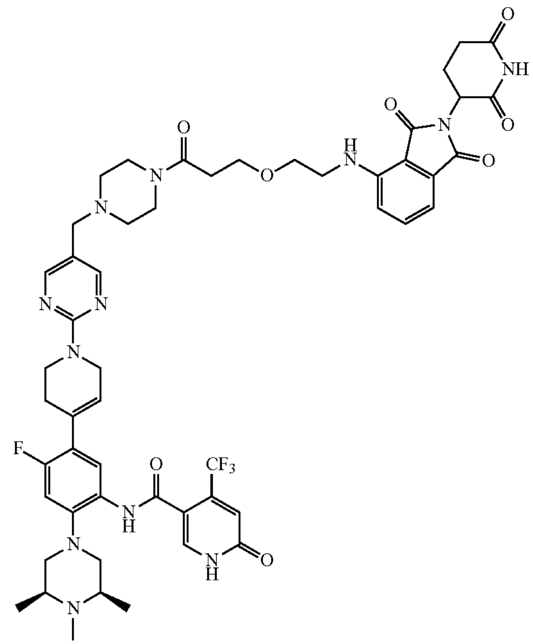 | N-(5-(1-(5-((4-(3-(2-((4-(3-(2-((2,6-dioxopiperidin-3-yl)-1,3-dioxoisoindolin-4-yl)amino)ethoxy)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 329 | XF078-157 | 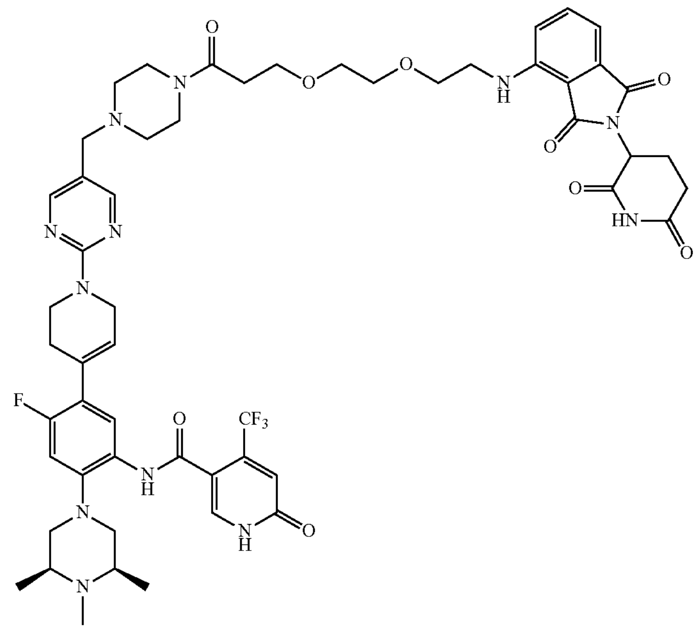 [SMILES: C[C@@H]1CN(c2cc(F)c(C3=CCN(c4ncc(CN5CCN(C(=O)CCOCCOCCNc6cccc7c6C(=O)N(C6CCC(=O)NC6=O)C7=O)CC5)cn4)CC3)cc2NC(=O)c2c[nH]c(=O)cc2C(F)(F)F)C[C@H](C)N1C] | N-(5-(1-(5-((4-(3-(2-(2-(2-((2-(2,6-dioxopiperidin-3-yl)-1,3-dioxoisoindolin-4-yl)amino)ethoxy)ethoxy)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Example | Compound ID | Structure | Chemical Name |
|---|---|---|---|
| 330 | XF078-158 | 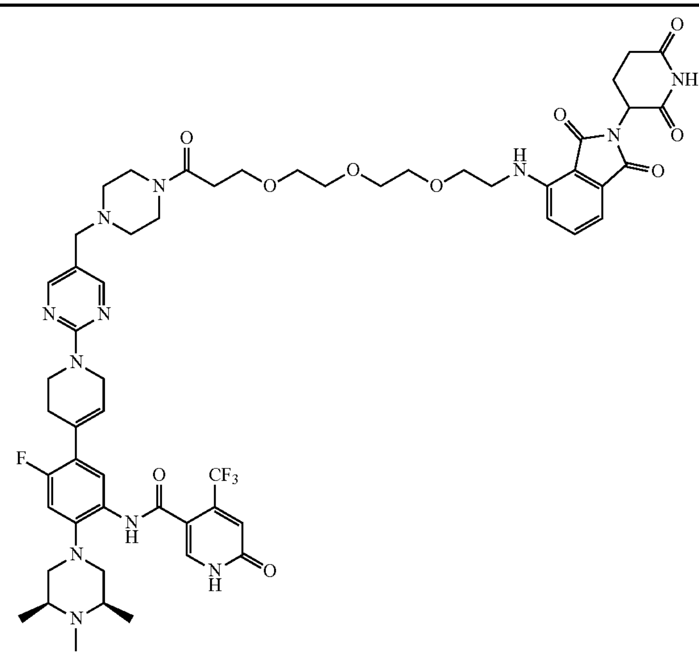 | N-(5-(1-(5-((4-(3-(2-(2-(2-(2-((2-(2,6-dioxopiperidin-3-yl)-1,3-dioxoisoindolin-4-yl)amino)ethoxy)ethoxy)ethoxy)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| Examples | Compound ID | Structure | Chemical Name |
|---|---|---|---|
| 331 | XF078-159 | 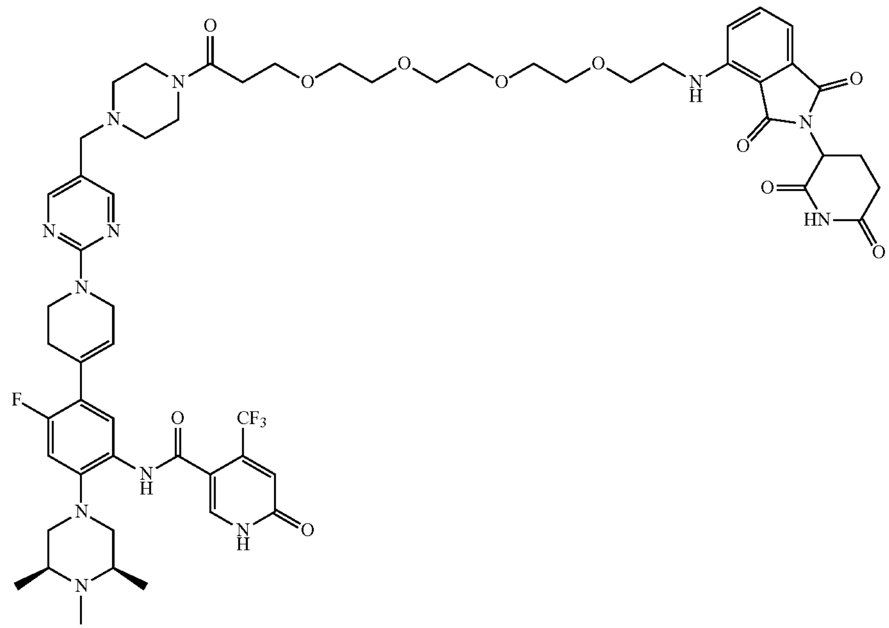 [SMILES: C[C@@H]1CN(c2cc(F)c(C3=CCN(c4ncc(CN5CCN(C(=O)CCOCCOCCOCCOCCNc6cccc7c6C(=O)N(C6CCC(=O)NC6=O)C7=O)CC5)cn4)CC3)cc2NC(=O)c2c[nH]c(=O)cc2C(F)(F)F)C[C@H](C)N1C] | N-(5-(1-(5-((4-(1-((2-(2,6-dioxopiperidin-3-yl)-1,3-dioxoisoindolin-4-yl)amino)-3,6,9,12-tetraoxapentadecan-15-oyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| Examples | Compound ID | Structure | Chemical Name |
|---|---|---|---|
| 332 | XF078-160 | 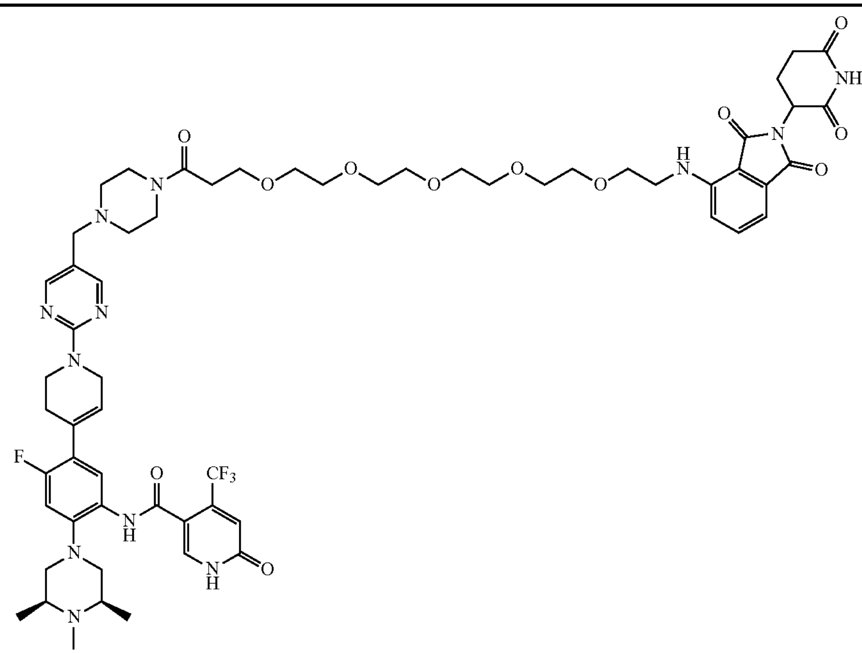 | N-(5-(1-(5-((4-(1-((2-(2,6-dioxopiperidin-3-yl)-1,3-dioxoisoindolin-4-yl)amino)-3,6,9,12,15-pentaoxaoctadecan-18-oyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| 335 | XF061-33 | 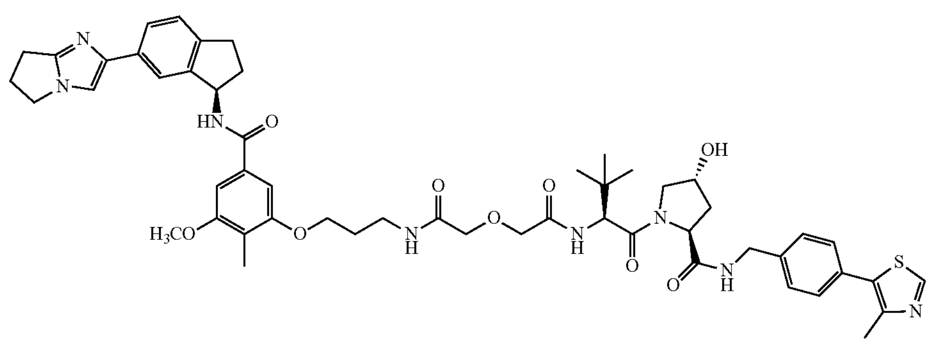 [SMILES: COc1cc(C(=O)N[C@@H]2CCc3ccc(-c4cn5c(n4)CCC5)cc32)cc(OCCCNC(=O)COCC(=O)N[C@H](C(=O)N2C[C@H](O)C[C@H]2C(=O)NCc2ccc(-c3scnc3C)cc2)C(C)(C)C)c1C] | (2S,4R)-1-((S)-2-(2-(2-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)amino)-2-oxoethoxy)acetamido)-3,3-dimethylbutanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 336 | XF061-34 | 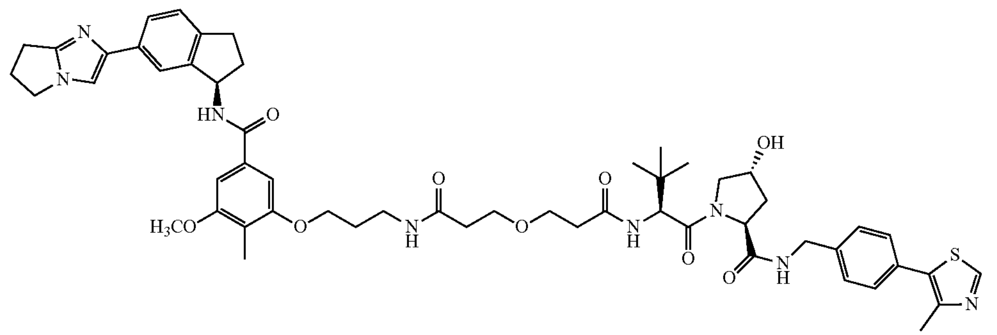 [SMILES: COc1cc(C(=O)N[C@@H]2CCc3ccc(-c4cn5c(n4)CCC5)cc32)cc(OCCCNC(=O)CCOCCC(=O)N[C@H](C(=O)N2C[C@H](O)C[C@H]2C(=O)NCc2ccc(-c3scnc3C)cc2)C(C)(C)C)c1C] | (2S,4R)-1-((S)-2-(3-(3-(3-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)amino)-3-oxopropoxy)propanamido)-3,3-dimethylbutanoyl)-4-hydroxy-N-(4-(4-methylthiazol-5-yl)benzyl)pyrrolidine-2-carboxamide |
| 337 | XF061-35 | 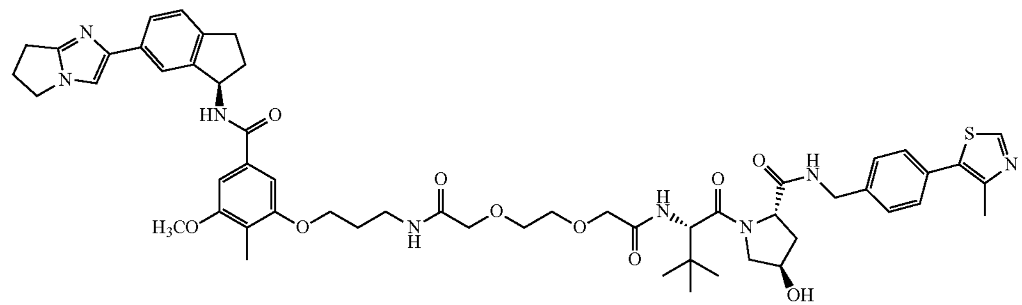 [SMILES: COc1cc(C(=O)N[C@@H]2CCc3ccc(-c4cn5c(n4)CCC5)cc32)cc(OCCCNC(=O)COCCOCC(=O)N[C@H](C(=O)N2C[C@H](O)C[C@H]2C(=O)NCc2ccc(-c3scnc3C)cc2)C(C)(C)C)c1C] | (2S,4R)-1-((S)-2-(tert-butyl)-15-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)-4,11-dioxo-6,9-dioxa-3,12-diazapentadecanoyl)-4-hydroxy-N-(4-(4-methylthiazol-5-yl)benzyl)pyrrolidine-2-carboxamide |
| 338 | XF061-36 | 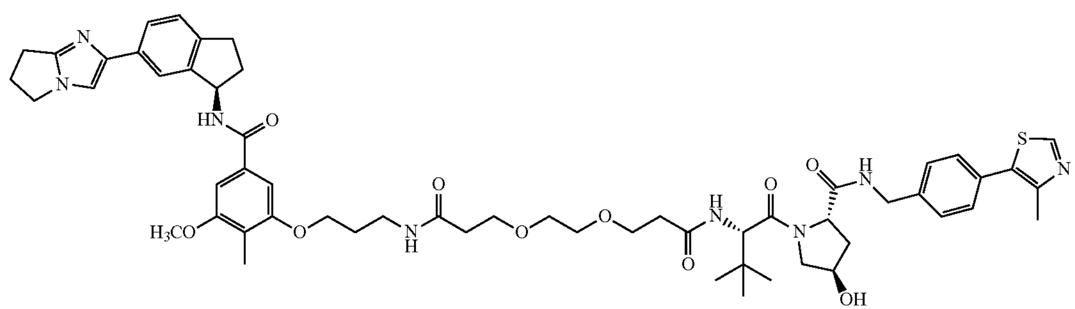 | (2S,4R)-1-((S)-2-(tert-butyl)-17-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)-4,13-dioxo-7,10-dioxa-3,14-diazaheptadecanoyl)-4-hydroxy-N-(4-(4-methylthiazol-5-yl)benzyl)pyrrolidine-2-carboxamide |

TABLE 1-continued

| Examples | Compound ID | Structure | Chemical Name |
|---|---|---|---|
| 339 | XF061-37 | 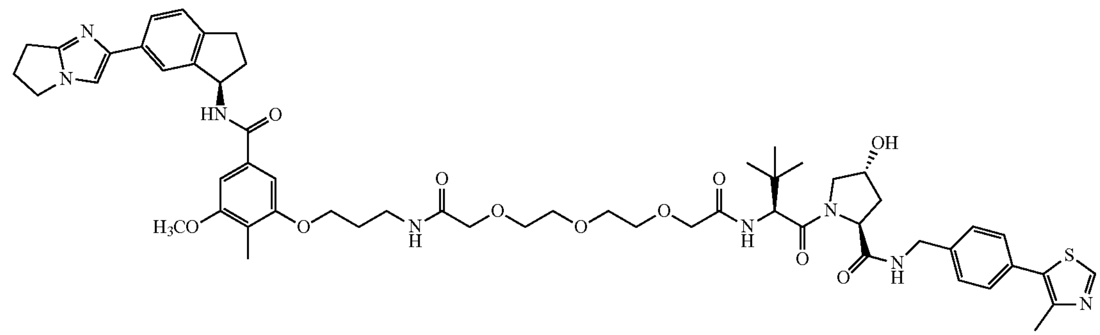 [SMILES: COc1cc(C(=O)N[C@@H]2CCc3ccc(-c4cn5c(n4)CCC5)cc32)cc(OCCCNC(=O)COCCOCCOCC(=O)N[C@H](C(=O)N2C[C@H](O)C[C@H]2C(=O)NCc2ccc(-c3scnc3C)cc2)C(C)(C)C)c1C] | (2S,4R)-1-((S)-2-(tert-butyl)-18-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)-4,14-dioxo-6,9,12-trioxa-3,15-diazaoctadecanoyl)-4-hydroxy-N-(4-(4-methylthiazol-5-yl)benzyl)pyrrolidine-2-carboxamide |
| 340 | XF061-38 | 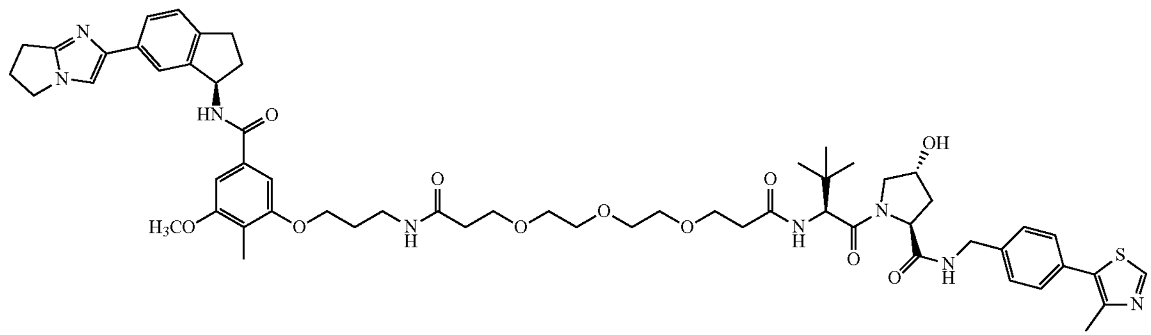 [SMILES: COc1cc(C(=O)N[C@@H]2CCc3ccc(-c4cn5c(n4)CCC5)cc32)cc(OCCCNC(=O)CCOCCOCCOCCC(=O)N[C@H](C(=O)N2C[C@H](O)C[C@H]2C(=O)NCc2ccc(-c3scnc3C)cc2)C(C)(C)C)c1C] | (2S,4R)-1-((S)-2-(tert-butyl)-20-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)-4,16-dioxo-7,10,13-trioxa-3,17-diazaicosanoyl)-4-hydroxy-N-(4-(4-methylthiazol-5-yl)benzyl)pyrrolidine-2-carboxamide |
| 341 | XF061-39 | 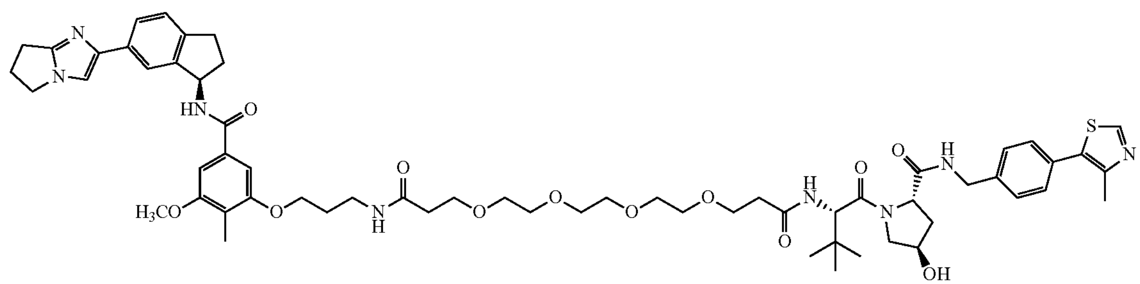 [SMILES: COc1cc(C(=O)N[C@@H]2CCc3ccc(-c4cn5c(n4)CCC5)cc32)cc(OCCCNC(=O)CCOCCOCCOCCOCCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N¹⁶-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |

TABLE 1-continued

| Examples | Compound ID | Structure | Chemical Name |
|---|---|---|---|
| 342 | XF061-40 | 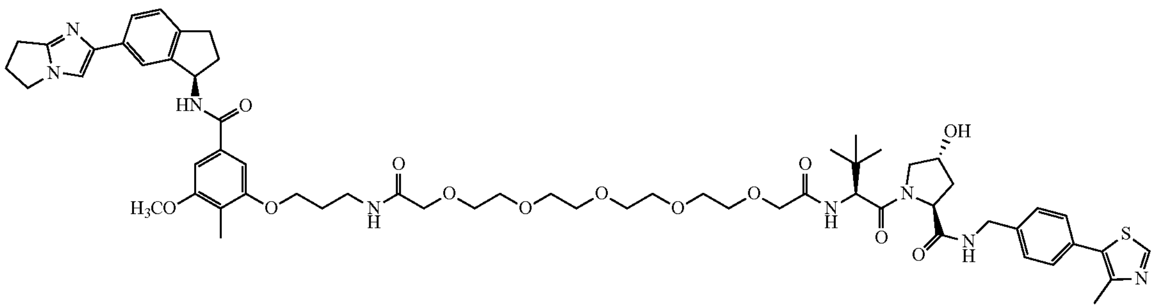 [SMILES: COc1cc(C(=O)N[C@@H]2CCc3ccc(-c4cn5c(n4)CCC5)cc32)cc(OCCCNC(=O)COCCOCCOCCOCCOCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N¹⁷-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide |
| 343 | XF061-41 | 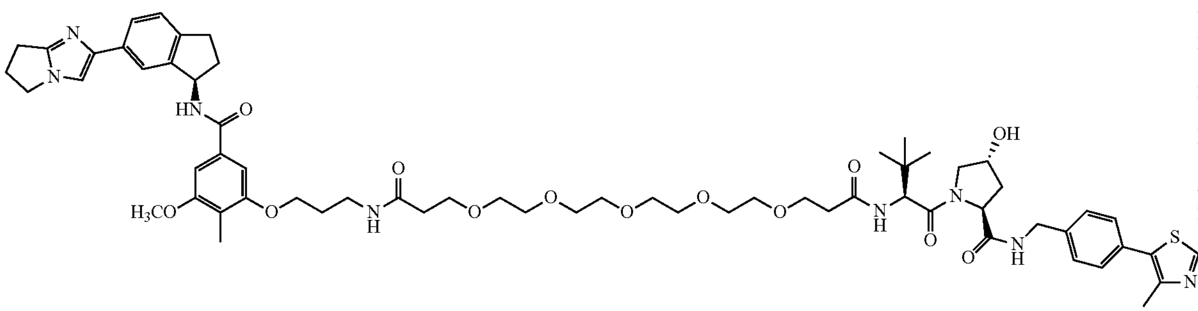 [SMILES: COc1cc(C(=O)N[C@@H]2CCc3ccc(-c4cn5c(n4)CCC5)cc32)cc(OCCCNC(=O)CCOCCOCCOCCOCCOCCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N¹⁹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| 344 | XF061-42 | 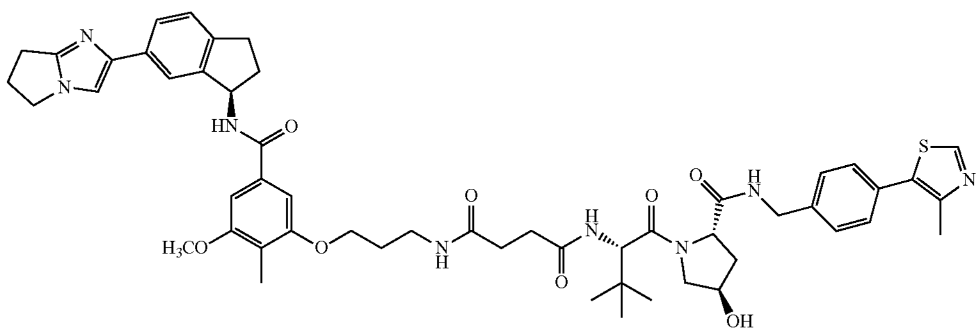 [SMILES: COc1cc(C(=O)N[C@@H]2CCc3ccc(-c4cn5c(n4)CCC5)cc32)cc(OCCCNC(=O)CCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N⁴-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |

TABLE 1-continued

| Examples | Compound ID | Structure | Chemical Name |
|---|---|---|---|
| 345 | XF061-43 | 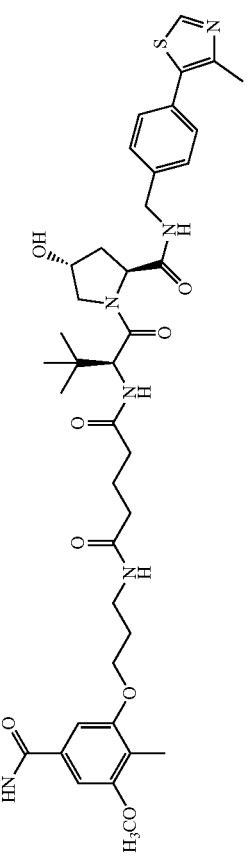 | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N⁵-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |
| 346 | XF061-44 | 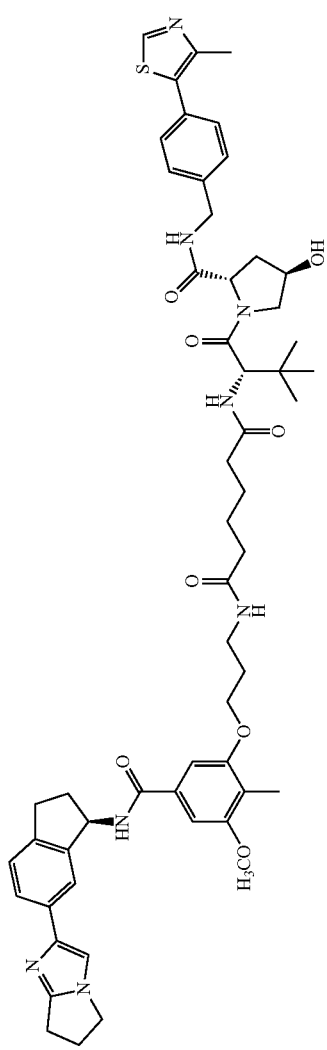 | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N⁶-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |

TABLE 1-continued

| Example | Compound ID | Structure | Chemical Name |
|---|---|---|---|
| 347 | XF061-45 | 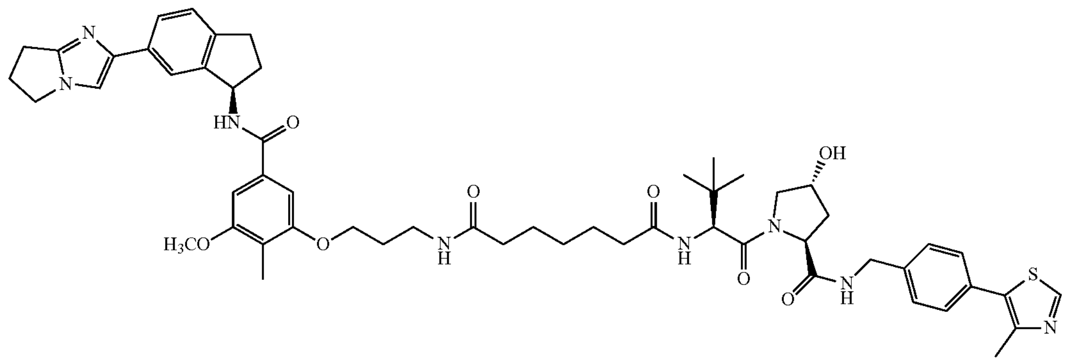 [SMILES: COc1cc(C(=O)N[C@@H]2CCc3ccc(-c4cn5c(n4)CCC5)cc32)cc(OCCCNC(=O)CCCCCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N⁷-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
| 348 | XF061-46 | 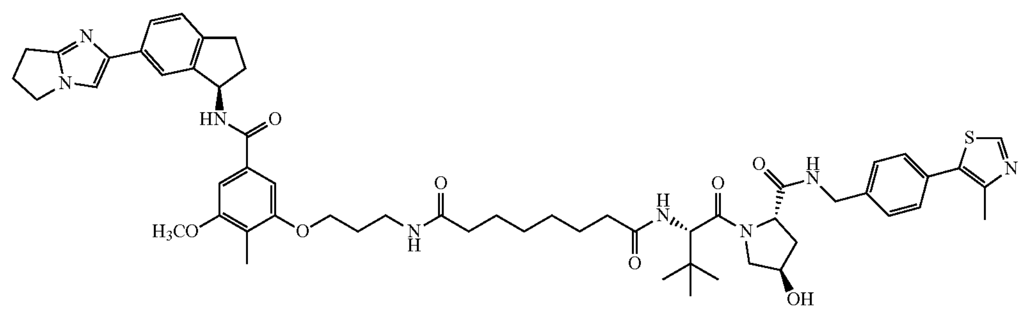 [SMILES: COc1cc(C(=O)N[C@@H]2CCc3ccc(-c4cn5c(n4)CCC5)cc32)cc(OCCCNC(=O)CCCCCCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N⁸-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |
| 349 | XF061-47 | 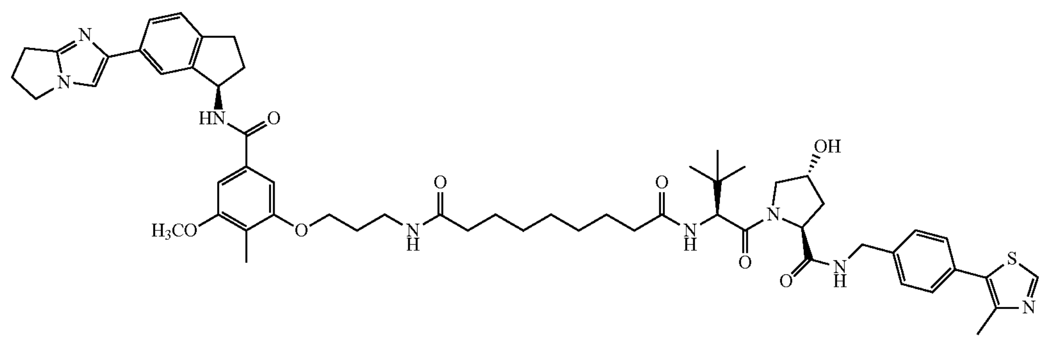 [SMILES: COc1cc(C(=O)N[C@@H]2CCc3ccc(-c4cn5c(n4)CCC5)cc32)cc(OCCCNC(=O)CCCCCCCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N⁹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |

TABLE 1-continued

| Examples | Compound ID | Structure | Chemical Name |
|---|---|---|---|
| 350 | XF061-48 | 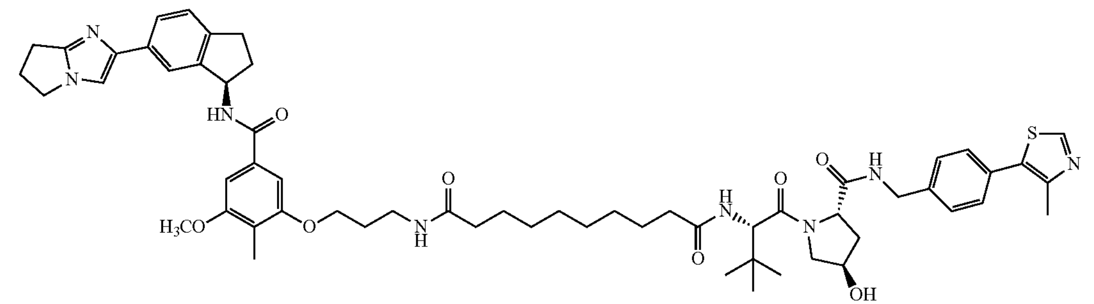 [SMILES: COc1cc(C(=O)N[C@@H]2CCc3ccc(-c4cn5c(n4)CCC5)cc32)cc(OCCCNC(=O)CCCCCCCCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N¹⁰-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |
| 351 | XF061-49 | 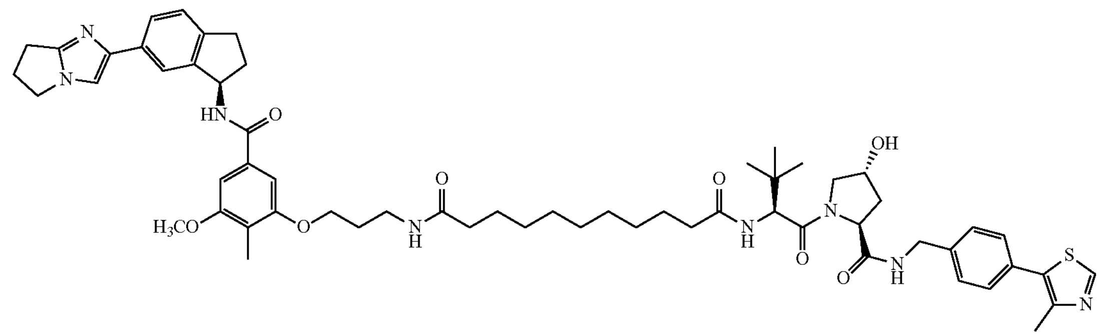 [SMILES: COc1cc(C(=O)N[C@@H]2CCc3ccc(-c4cn5c(n4)CCC5)cc32)cc(OCCCNC(=O)CCCCCCCCCC(=O)N[C@H](C(=O)N2C[C@H](O)C[C@H]2C(=O)NCc2ccc(-c3scnc3C)cc2)C(C)(C)C)c1C] | N¹-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-N¹¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| 352 | XF061-50 | 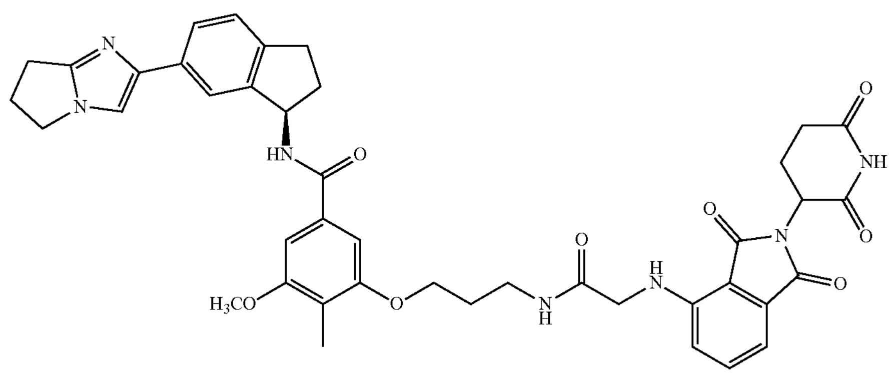 [SMILES: COc1cc(C(=O)N[C@@H]2CCc3ccc(-c4cn5c(n4)CCC5)cc32)cc(OCCCNC(=O)CNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(3-(2-((2-(2,6-dioxopiperidin-3-yl)-1,3-dioxoisoindolin-4-yl)amino)acetamido)propoxy)-5-methoxy-4-methylbenzamide |

TABLE 1-continued

| Examples | Compound ID | Structure | Chemical Name |
|---|---|---|---|
| 353 | XF061-51 | 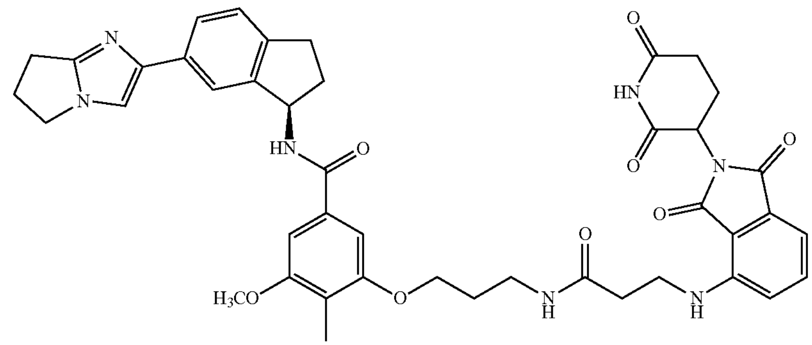 [SMILES: COc1cc(C(=O)N[C@@H]2CCc3ccc(-c4cn5c(n4)CCC5)cc32)cc(OCCCNC(=O)CCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(3-((2-(2,6-dioxopiperidin-3-yl)-1,3-dioxoisoindolin-4-yl)amino)propanamido)propoxy)-5-methoxy-4-methylbenzamide |
| 354 | XF061-52 | 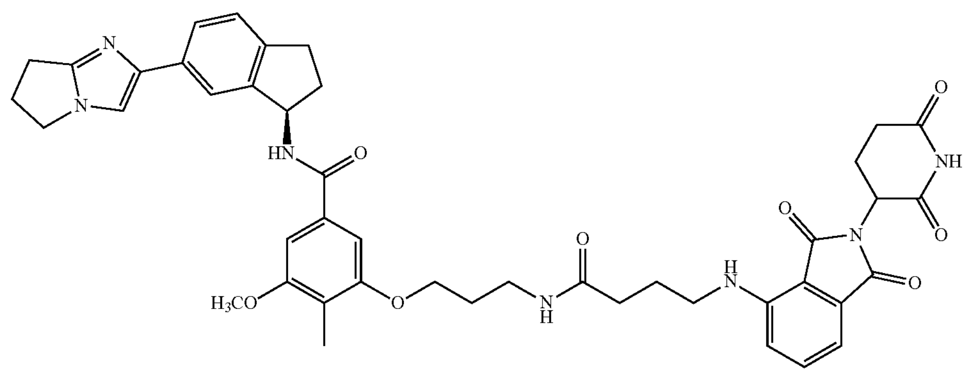 [SMILES: COc1cc(C(=O)N[C@@H]2CCc3ccc(-c4cn5c(n4)CCC5)cc32)cc(OCCCNC(=O)CCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(4-((2-(2,6-dioxopiperidin-3-yl)-1,3-dioxoisoindolin-4-yl)amino)butanamido)propoxy)-5-methoxy-4-methylbenzamide |

TABLE 1-continued

| Examples | Compound ID | Structure | Chemical Name |
|---|---|---|---|
| 355 | XF061-53 | 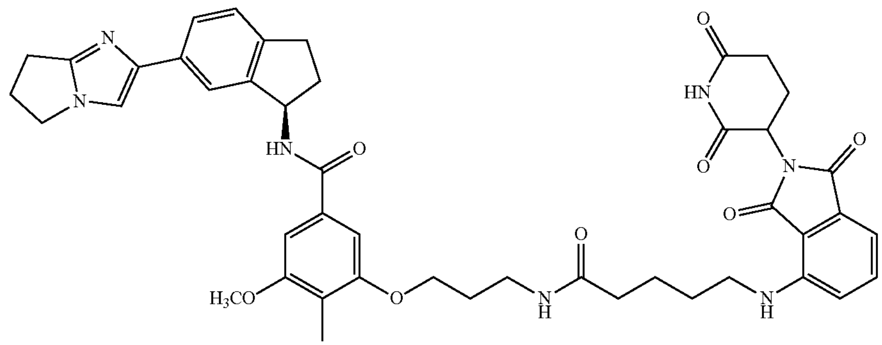 [SMILES: COc1cc(C(=O)N[C@@H]2CCc3ccc(-c4cn5c(n4)CCC5)cc32)cc(OCCCNC(=O)CCCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(5-((2-(2,6-dioxopiperidin-3-yl)-1,3-dioxoisoindolin-4-yl)amino)pentanamido)propoxy)-5-methoxy-4-methylbenzamide |
| 356 | XF061-54 | 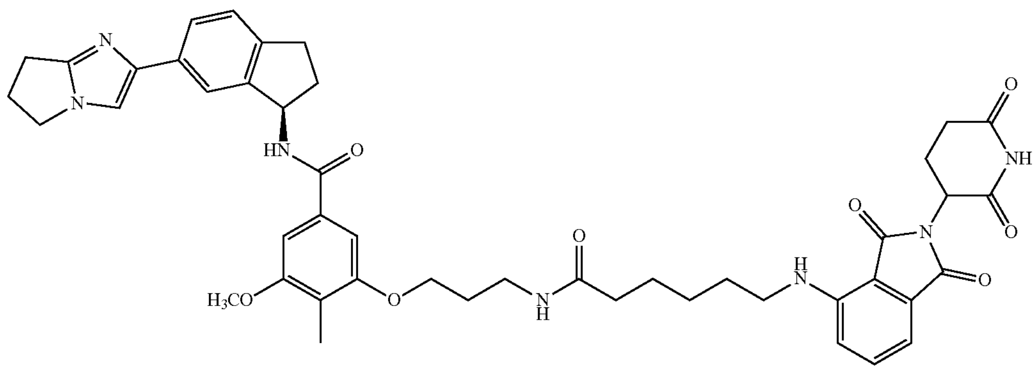 [SMILES: COc1cc(C(=O)N[C@@H]2CCc3ccc(-c4cn5c(n4)CCC5)cc32)cc(OCCCNC(=O)CCCCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(6-((2-(2,6-dioxopiperidin-3-yl)-1,3-dioxoisoindolin-4-yl)amino)hexanamido)propoxy)-5-methoxy-4-methylbenzamide |

TABLE 1-continued

| Examples | Compound ID | Structure | Chemical Name |
|---|---|---|---|
| 357 | XF061-55 | 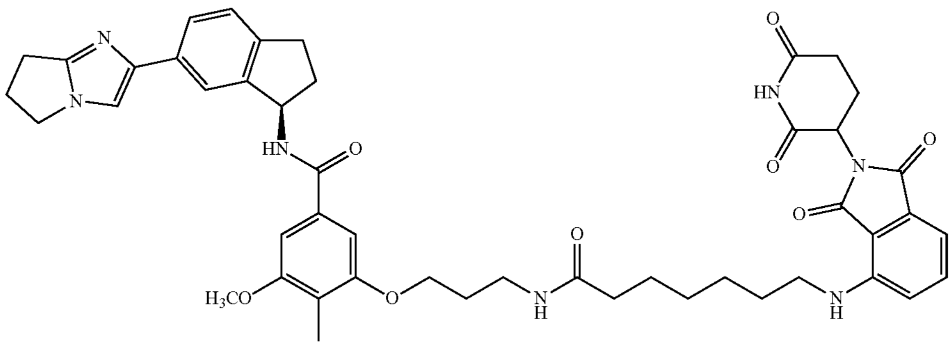 [SMILES: COc1cc(C(=O)N[C@@H]2CCc3ccc(-c4cn5c(n4)CCC5)cc32)cc(OCCCNC(=O)CCCCCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(7-((2-(2,6-dioxopiperidin-3-yl)-1,3-dioxoisoindolin-4-yl)amino)heptanamido)propoxy)-5-methoxy-4-methylbenzamide |
| 358 | XF061-56 | 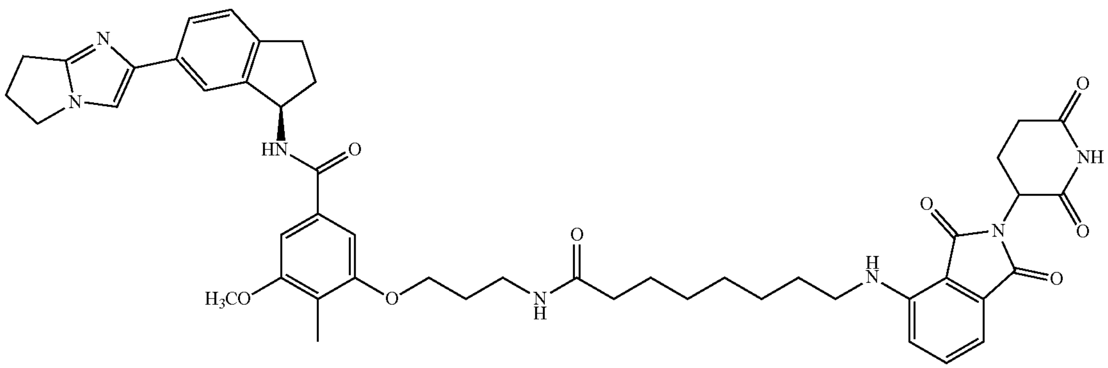 [SMILES: COc1cc(C(=O)N[C@@H]2CCc3ccc(-c4cn5c(n4)CCC5)cc32)cc(OCCCNC(=O)CCCCCCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(8-((2-(2,6-dioxopiperidin-3-yl)-1,3-dioxoisoindolin-4-yl)amino)octanamido)propoxy)-5-methoxy-4-methylbenzamide |

TABLE 1-continued

| Examples | Compound ID | Structure | Chemical Name |
|---|---|---|---|
| 359 | XF061-57 | 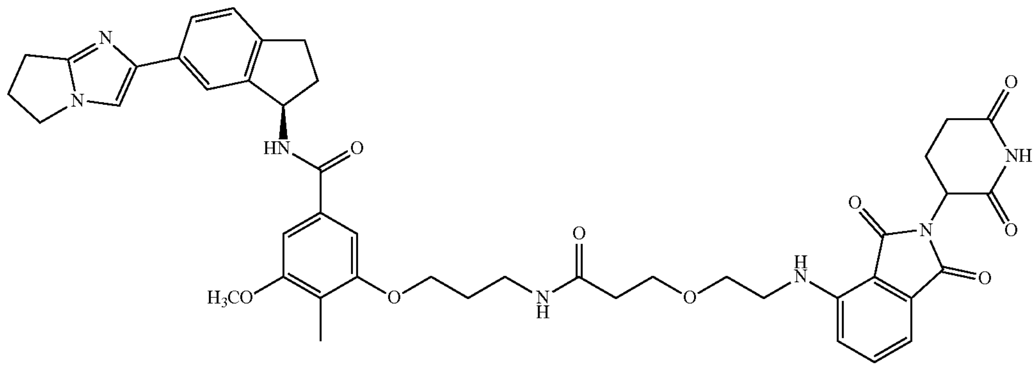 [SMILES: COc1cc(C(=O)N[C@@H]2CCc3ccc(-c4cn5c(n4)CCC5)cc32)cc(OCCCNC(=O)CCOCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(3-(2-((2-(2,6-dioxopiperidin-3-yl)-1,3-dioxoisoindolin-4-yl)amino)ethoxy)propanamido)propoxy)-5-methoxy-4-methylbenzamide |
| 360 | XF061-58 | 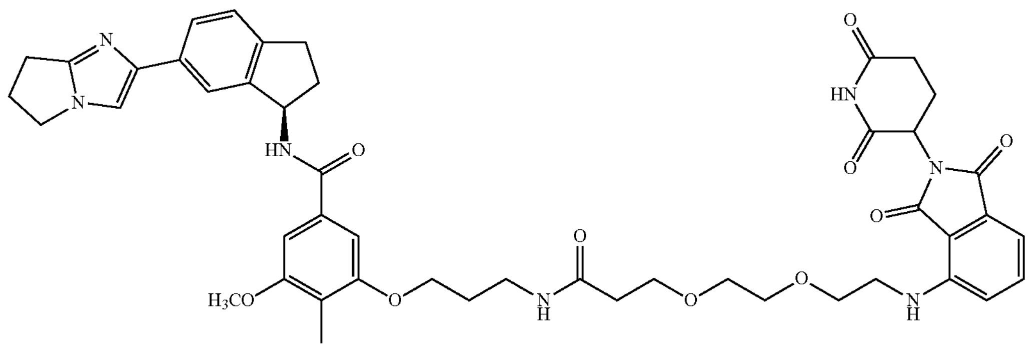 [SMILES: COc1cc(C(=O)N[C@@H]2CCc3ccc(-c4cn5c(n4)CCC5)cc32)cc(OCCCNC(=O)CCOCCOCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-(3-(2-(2-((2-(2,6-dioxopiperidin-3-yl)-1,3-dioxoisoindolin-4-yl)amino)ethoxy)ethoxy)propanamido)propoxy)-5-methoxy-4-methylbenzamide |
| 361 | XF061-59 | 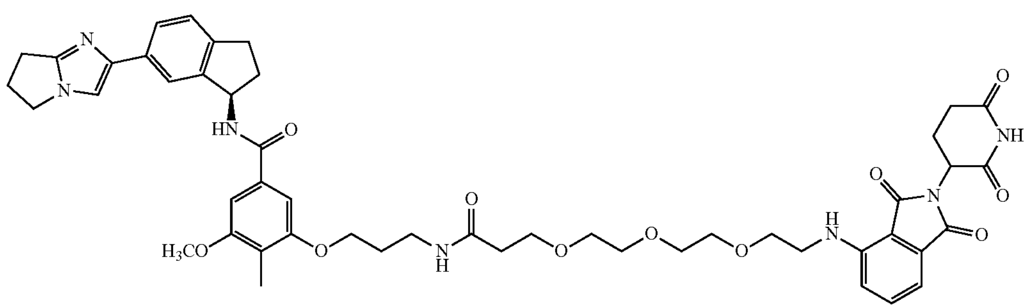 [SMILES: COc1cc(C(=O)N[C@@H]2CCc3ccc(-c4cn5c(n4)CCC5)cc32)cc(OCCCNC(=O)CCOCCOCCOCCNc2cccc3c2C(=O)N(C2CCC(=O)NC2=O)C3=O)c1C] | N-((R)-6-(6,7-dihydro-5H-pyrrolo[1,2-a]imidazol-2-yl)-2,3-dihydro-1H-inden-1-yl)-3-((1-((2-(2,6-dioxopiperidin-3-yl)-1,3-dioxoisoindolin-4-yl)amino)-12-oxo-3,6,9-trioxa-13-azahexadecan-16-yl)oxy)-5-methoxy-4-methylbenzamide |

TABLE 1-continued

| Examples | Compound ID | Structure | Chemical Name |
|---|---|---|---|
| 362 | XF061-60 | 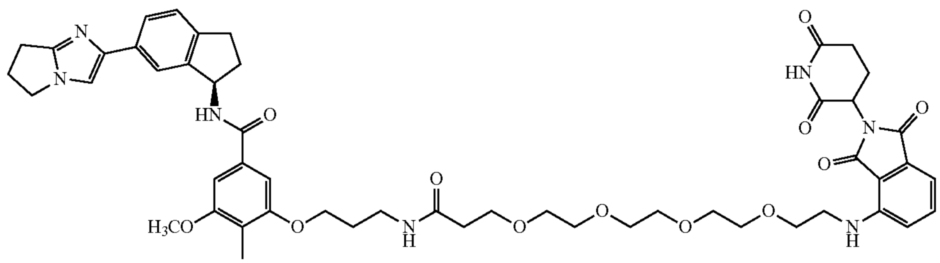 [SMILES: COc1cc(C(=O)N[C@@H]2CCc3ccc(-c4cn5c(n4)CCC5)cc32)cc(OCCCNC(=O)CCOCCOCCOCCOCCNc2cccc3c2C(=O)N(C2CCC(=O)NC2=O)C3=O)c1C] | N-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-1-((2-(2,6-dioxopiperidin-3-yl)-1,3-dioxoisoindolin-4-yl)amino)-3,6,9,12-tetraoxapentadecan-15-amide |
| 363 | XF061-61 | 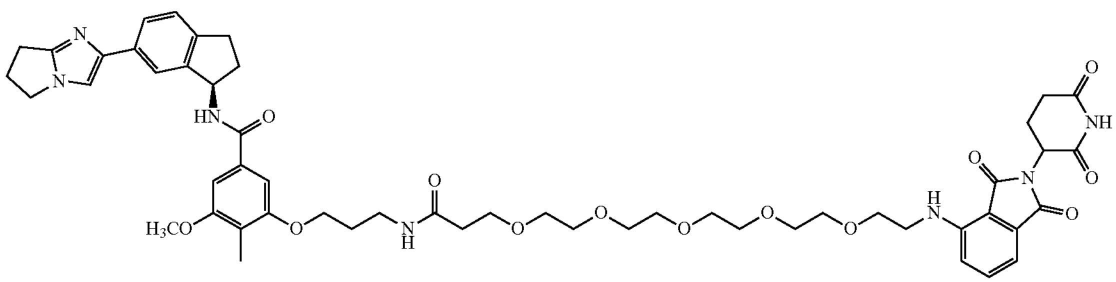 [SMILES: COc1cc(C(=O)N[C@@H]2CCc3ccc(-c4cn5c(n4)CCC5)cc32)cc(OCCCNC(=O)CCOCCOCCOCCOCCOCCNc2cccc3c2C(=O)N(C2CCC(=O)NC2=O)C3=O)c1C] | N-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)-1-((2-(2,6-dioxopiperidin-3-yl)-1,3-dioxoisoindolin-4-yl)amino)-3,6,9,12,15-pentaoxaoctadecan-18-amide |
| 365 | XF082-33 | 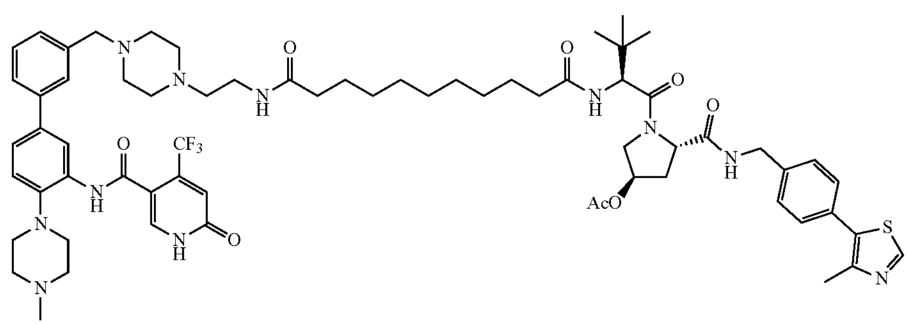 | (3R,5S)-1-((S)-3,3-dimethyl-2-(11-((2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)amino)-11-oxoundecanamido)butanoyl)-5-((4-(4-methylthiazol-5-yl)benzyl)carbamoyl)pyrrolidin-3-yl acetate |

TABLE 1-continued

| Examples | Compound ID | Structure | Chemical Name |
|---|---|---|---|
| 366 | XF082-34 | 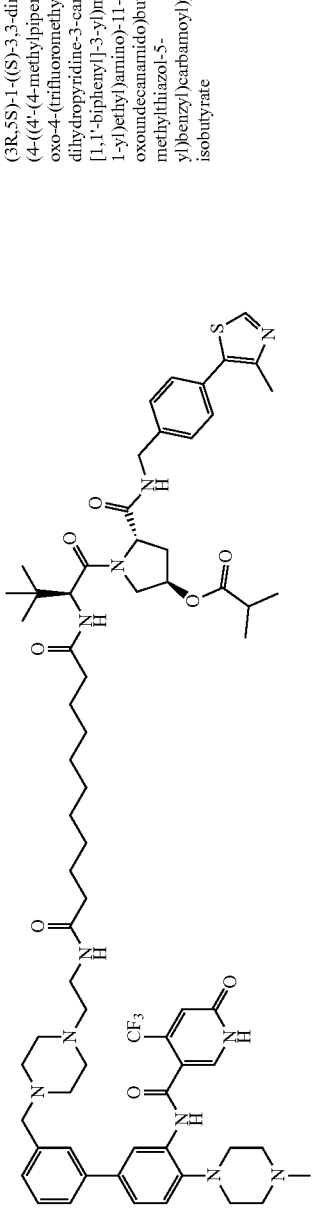 | (3R,5S)-1-((S)-3,3-dimethyl-2-(11-((2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)amino)-11-oxoundecanamido)butanoyl)-5-((4-(4-methylthiazol-5-yl)benzyl)carbamoyl)pyrrolidin-3-yl isobutyrate |
| 369 | | 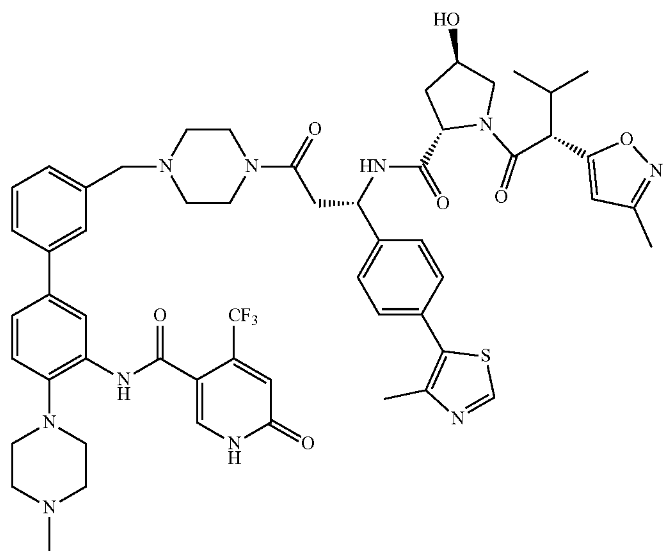 [SMILES: Cc1cc([C@H](C(=O)N2C[C@H](O)C[C@H]2C(=O)N[C@@H](CC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Example Compound ID | Structure | Chemical Name |
|---|---|---|
| 370 | 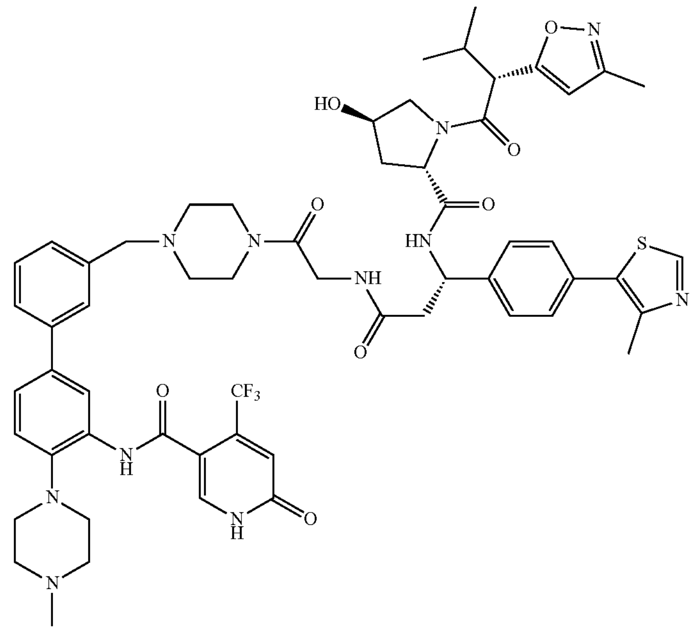 [SMILES: Cc1cc([C@H](C(=O)N2C[C@H](O)C[C@H]2C(=O)N[C@@H](CC(=O)NCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)glycyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Example | Compound ID | Structure | Chemical Name |
|---|---|---|---|
| | 371 | | N-(3'-((4-(3-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 372 | | 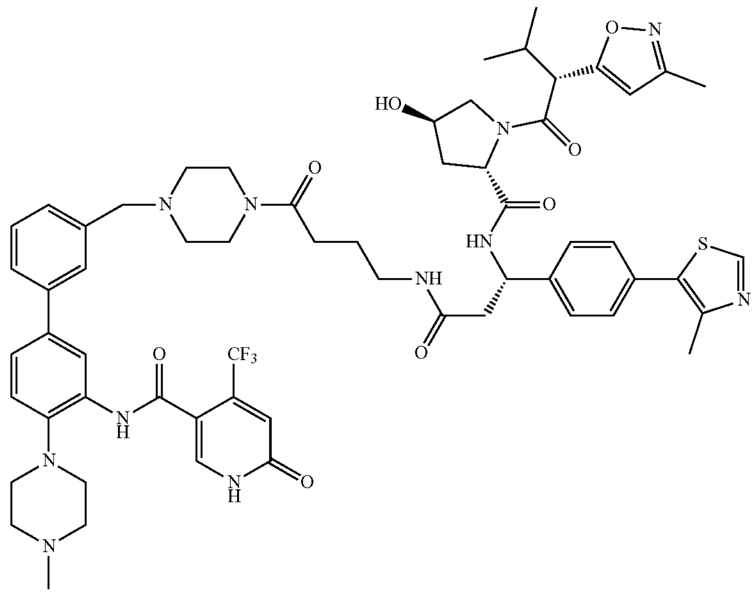 [SMILES: Cc1cc([C@H](C(=O)N2C[C@H](O)C[C@H]2C(=O)N[C@@H](CC(=O)NCCCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)butanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 373 | | 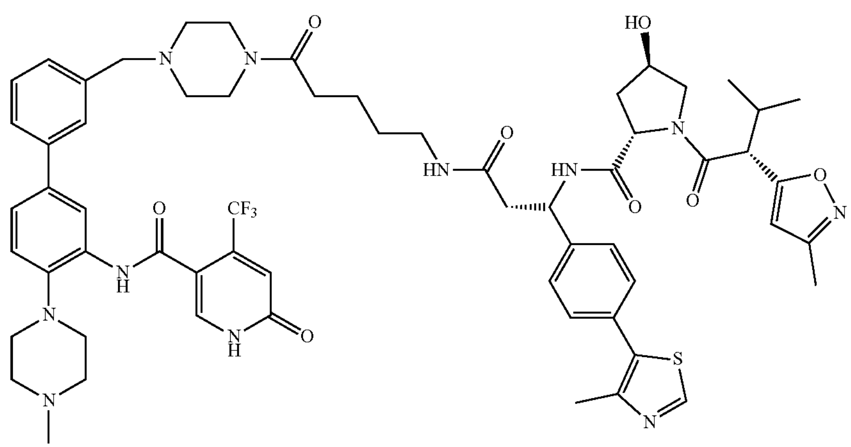 | N-(3'-((4-(5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples Compound ID | Structure | Chemical Name |
|---|---|---|
| 374 | 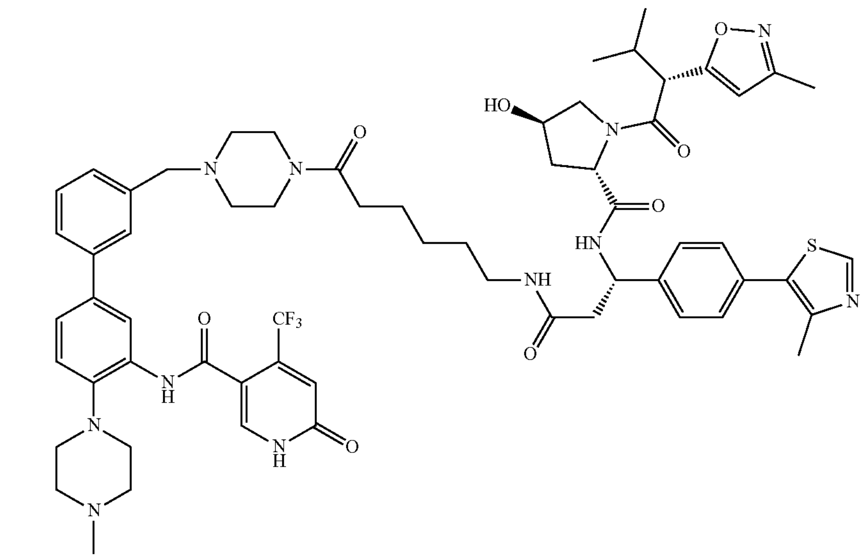 [SMILES: Cc1cc([C@H](C(=O)N2C[C@H](O)C[C@H]2C(=O)N[C@@H](CC(=O)NCCCCCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 375 | 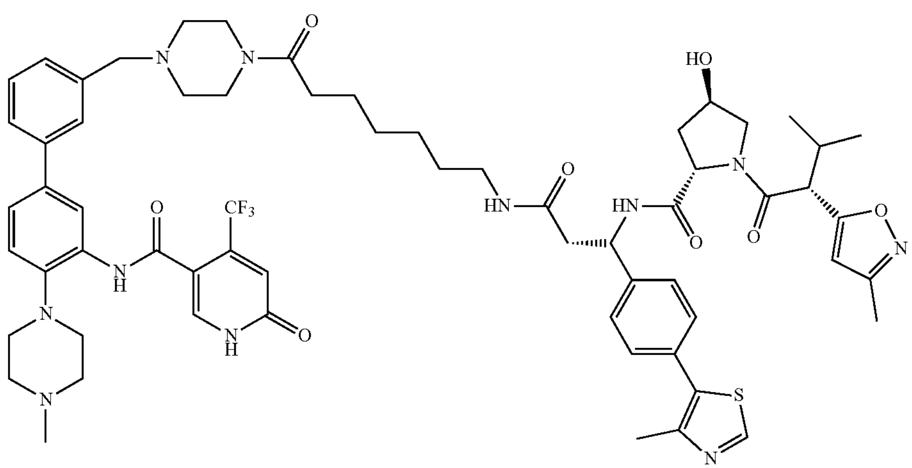 | N-(3'-((4-(7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Ex-am-ples | Com-pound ID | Structure | Chemical Name |
|---|---|---|---|
| | 376 | 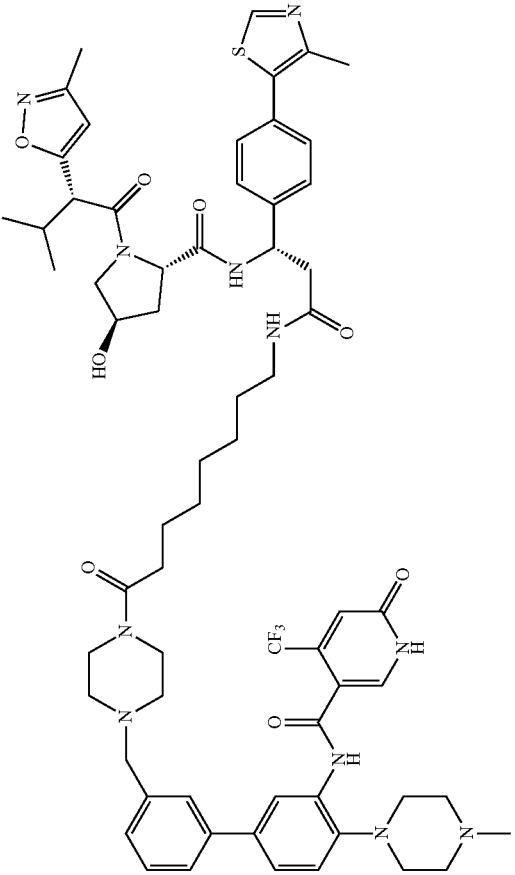 | N-(3'-((4-(8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| | 377 | 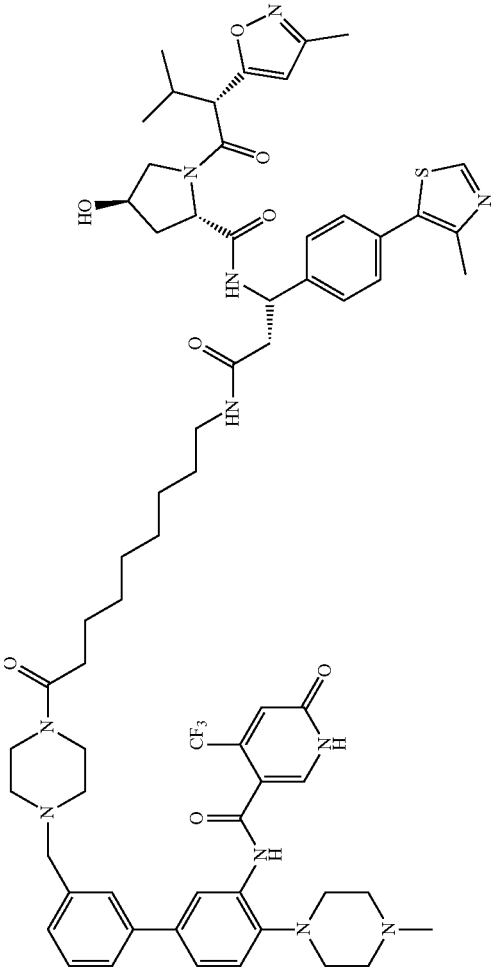 | N-(3'-((4-(9-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)nonanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| | 378 | 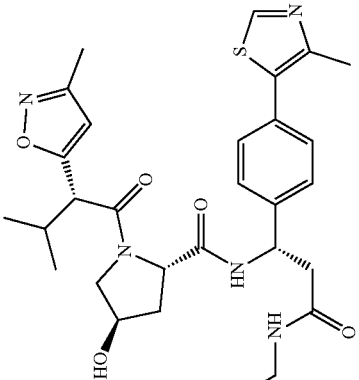 | N-(3'-((4-(10-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)decanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| | 379 | 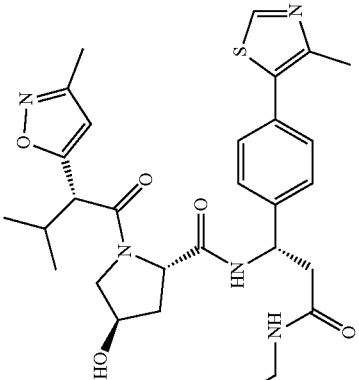 | N-(3'-((4-(11-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)undecanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 380 | | N-(3'-((4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| | 381 | 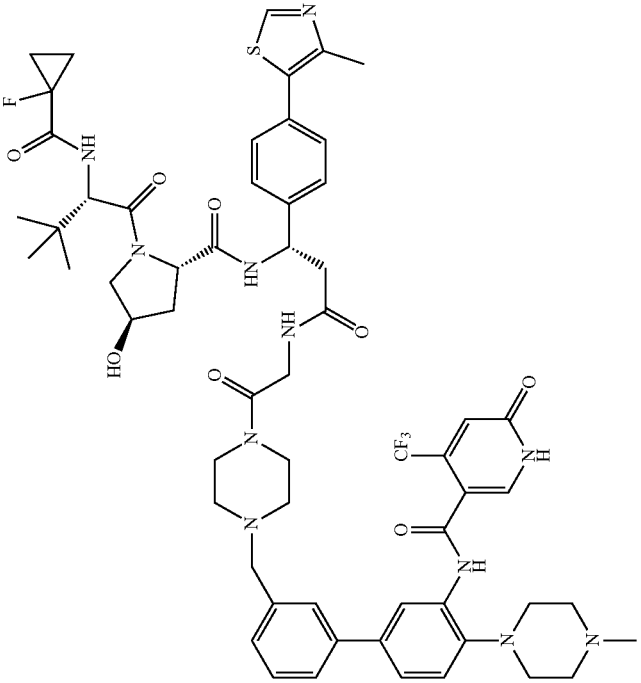 | N-(3'-((4-(((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanoyl)glycyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| | 382 | 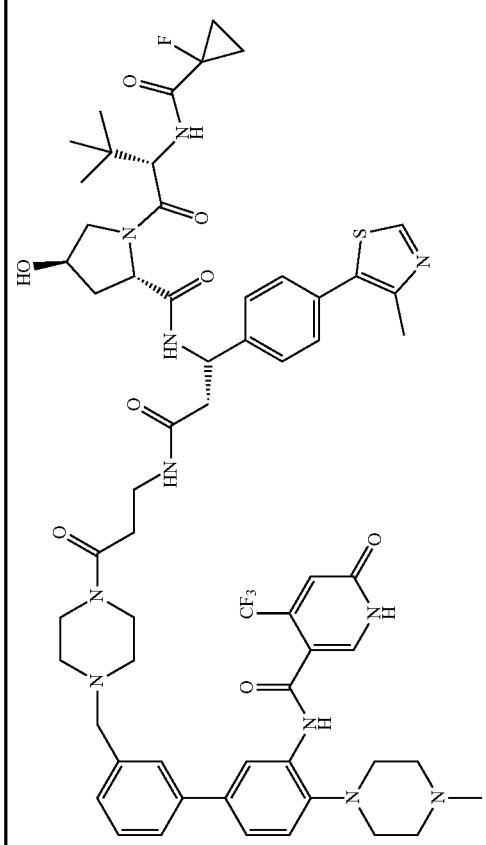 | N-(3'-((4-(3-((S)-3-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 383 | | N-(3'-((4-(4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)butanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 384 | | N-(3'-((4-(5-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)pentanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| | 385 | | N-(3'-((4-(6-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)hexanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 386 | | N-(3'-((4-(7-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)heptanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| | 387 | | N-(3'-((4-(8-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)octanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 388 | 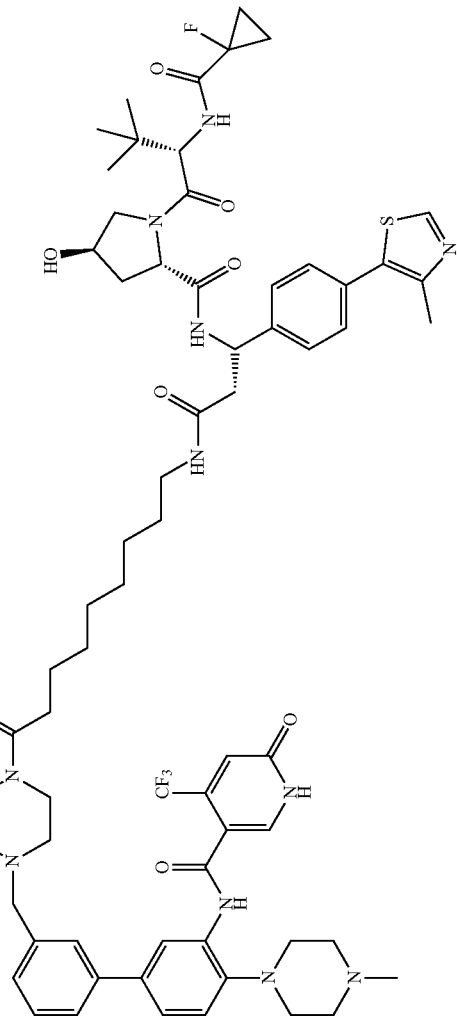 | N-(3'-((4-(9-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)nonanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| | 389 | 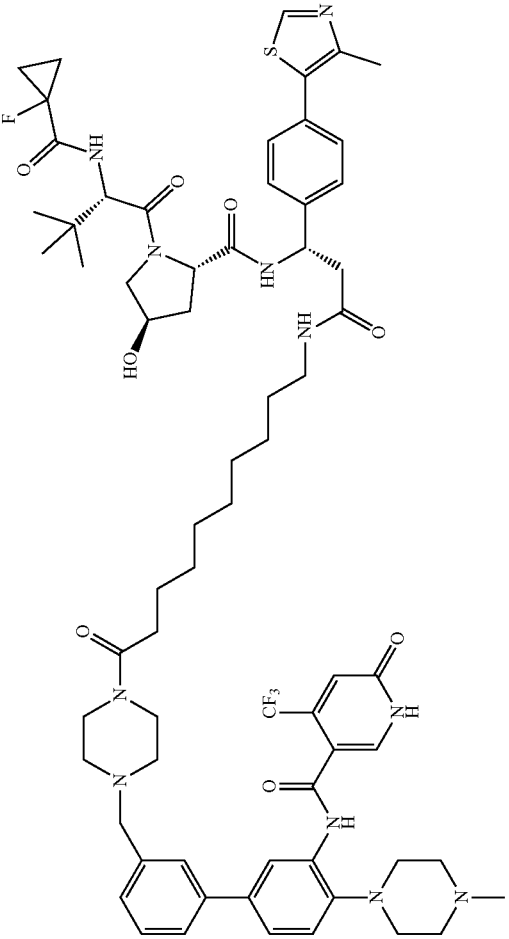 | N-(3'-((4-(10-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)decanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Example | Compound ID | Structure | Chemical Name |
|---|---|---|---|
| | 390 | | N-(3'-((4-(11-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)undecanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| 391 | | 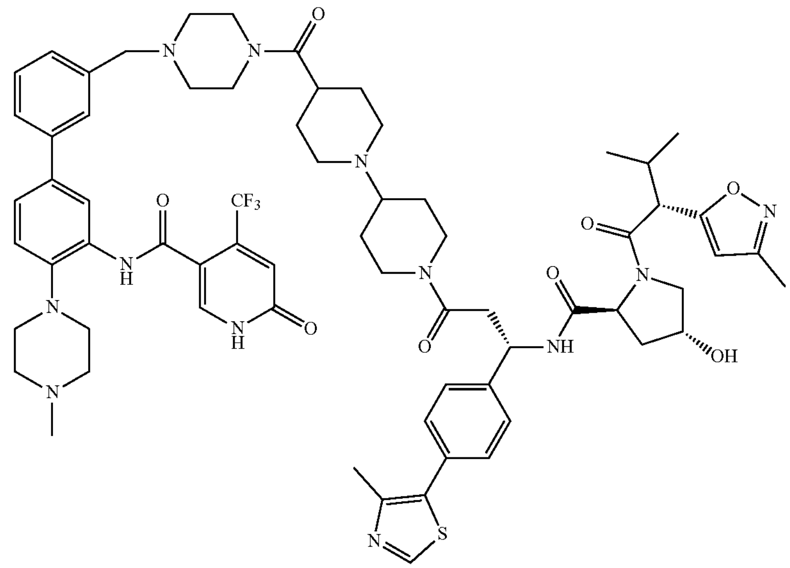 [SMILES: Cc1cc([C@H](C(=O)N2C[C@H](O)C[C@H]2C(=O)N[C@@H](CC(=O)N2CCC(N3CCC(C(=O)N4CCN(Cc5cccc(-c6ccc(N7CCN(C)CC7)c(NC(=O)c7c[nH]c(=O)cc7C(F)(F)F)c6)c5)CC4)CC3)CC2)c2ccc(-c3scnc3C)cc2)C(C)C)on1] | N-(3'-((4-(1'-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)-[1,4'-bipiperidine]-4-carbonyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 392 | | 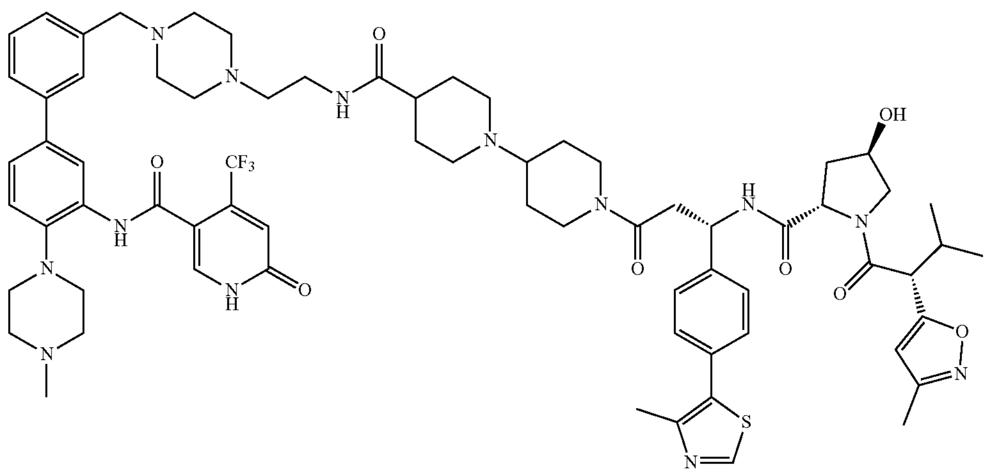 [SMILES: Cc1cc([C@H](C(=O)N2C[C@H](O)C[C@H]2C(=O)N[C@@H](CC(=O)N2CCC(N3CCC(C(=O)NCCN4CCN(Cc5cccc(-c6ccc(N7CCN(C)CC7)c(NC(=O)c7c[nH]c(=O)cc7C(F)(F)F)c6)c5)CC4)CC3)CC2)c2ccc(-c3scnc3C)cc2)C(C)C)on1] | 1'-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)-N-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)-[1,4'-bipiperidine]-4-carboxamide |

TABLE 1-continued

| Examples | Compound ID | Structure | Chemical Name |
|---|---|---|---|
| | 393 | | N-(3'-((4-(1'-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanoyl)-[1,4'-bipiperidine]-4-carbonyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| Ex-am-ples | Com-pound ID | Structure | Chemical Name |
|---|---|---|---|
| | 394 | | 1'-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanoyl)-N-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)-[1,4'-bipiperidine]-4-carboxamide |
| | 395 | | N-(2'-fluoro-5'-((2-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| | 396 | | N-(2'-fluoro-5'-((3-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 397 | | N-(2'-fluoro-5'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| | 398 | | N-(2'-fluoro-5'-((5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| | 399 | 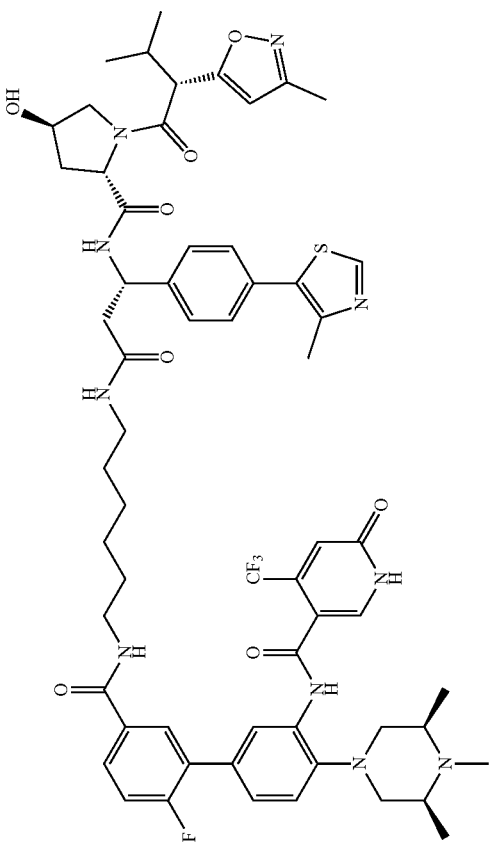 | N-(2'-fluoro-5'-((6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Example | Compound ID | Structure | Chemical Name |
|---|---|---|---|
| | 400 | 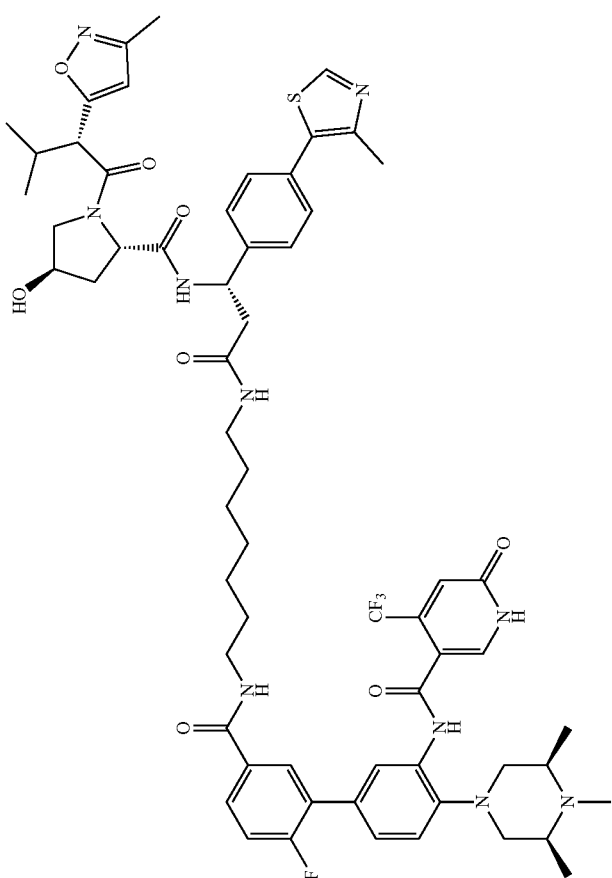 | N-(2'-fluoro-5'-((7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| | 401 | | N-(2'-fluoro-5'-((8-((S)-3-((2S,4R)-4-hydroxy-1-((R)-3-methyl-2-(3-methylisoxazol-5-yl)butanoyl)pyrrolidine-2-carboxamido)-2-(4-(4-methylthiazol-5-yl)phenyl)propanamido)octyl) carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Ex- amples | Compound ID | Structure | Chemical Name |
|---|---|---|---|
| | 402 | 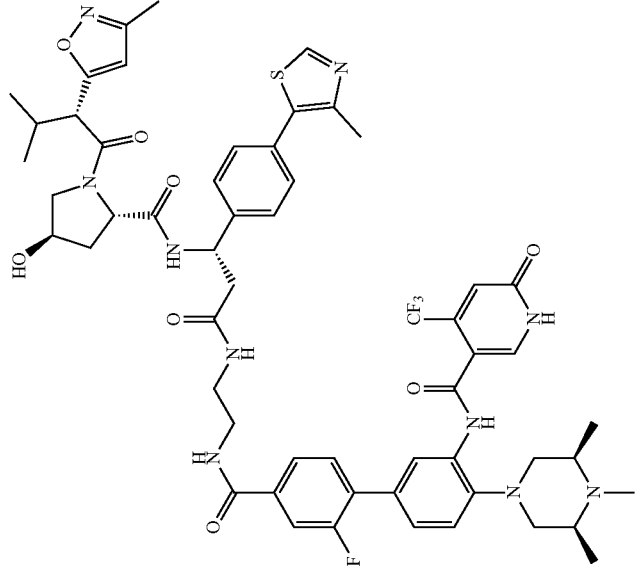 | N-(2'-fluoro-4'-((2-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| | 403 | 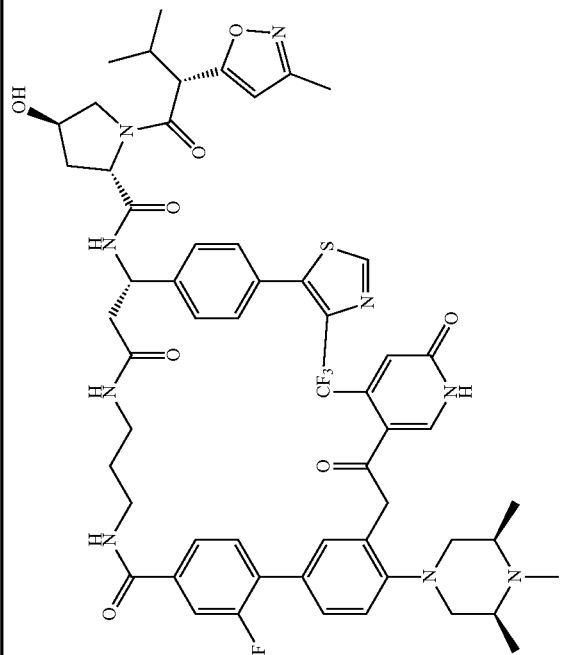 | N-(2'-fluoro-4'-((3-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 404 | | N-(2'-fluoro-4'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 405 | | N-(2'-fluoro-4'-((5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| | 406 | 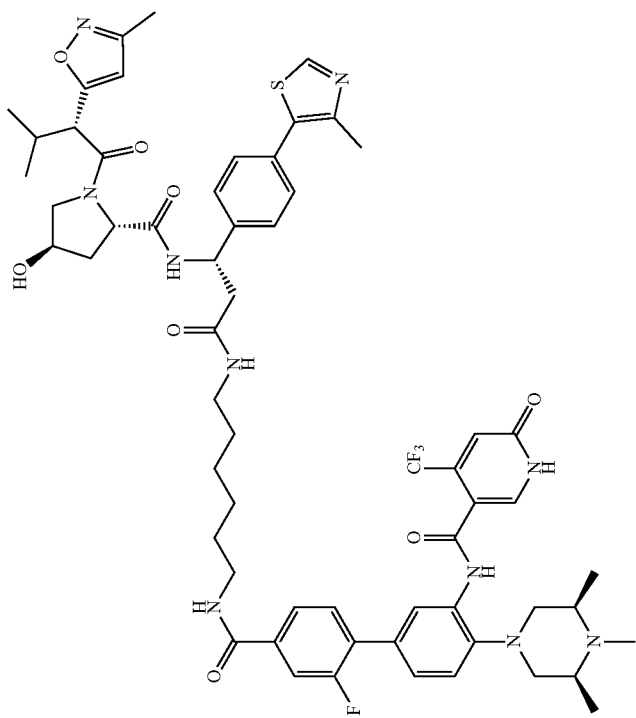 | N-(2'-fluoro-4'-((6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| | 407 | 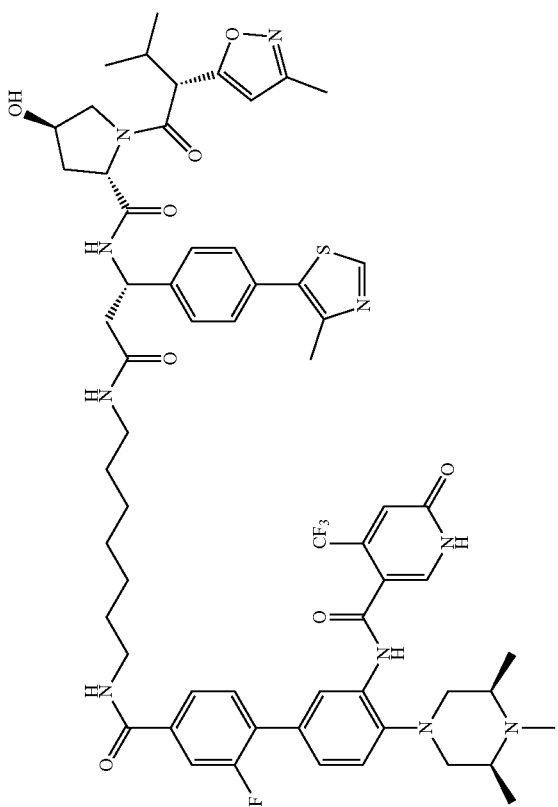 | N-(2'-fluoro-4'-((7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 408 | | N-(2'-fluoro-4'-((8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 409 | | N-(2'-fluoro-5'-((2-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Ex- am- ples | Com- pound ID | Structure | Chemical Name |
|---|---|---|---|
| | 410 | 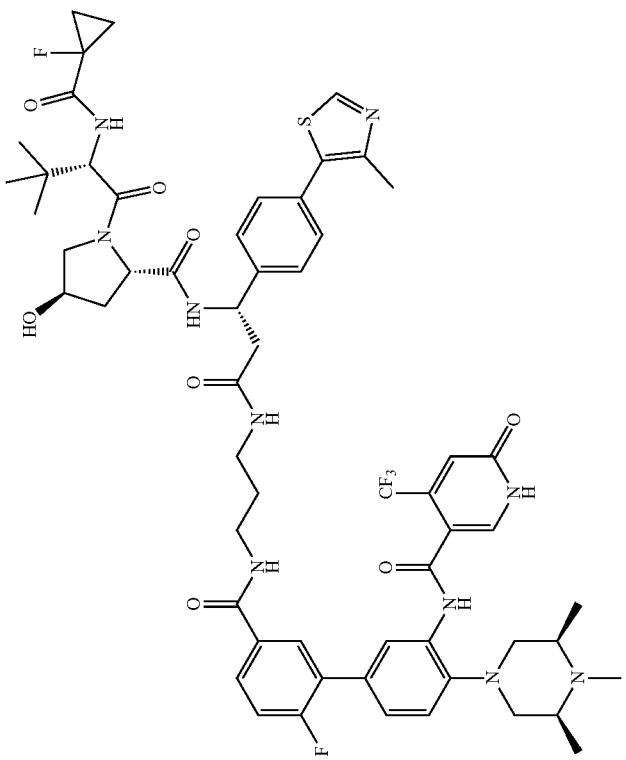 | N-(2'-fluoro-5'-((3-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Example Compound ID | Structure | Chemical Name |
|---|---|---|
| 411 | 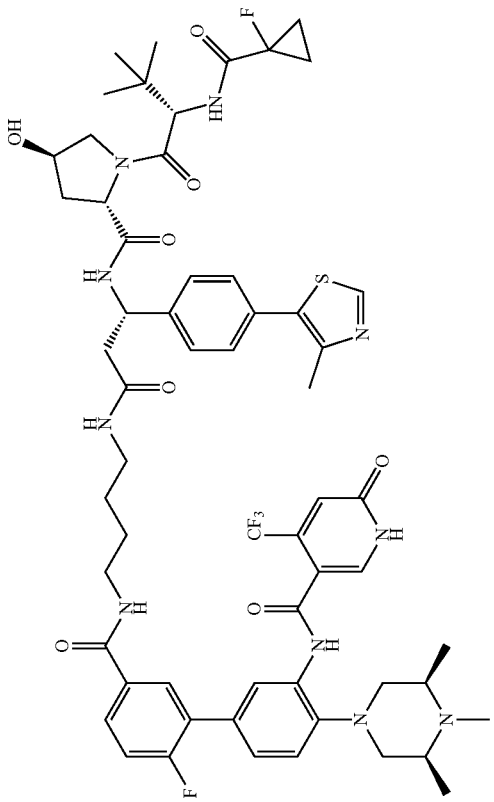 | N-(2'-fluoro-5'-((4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Example Compound ID | Structure | Chemical Name |
|---|---|---|
| 412 | 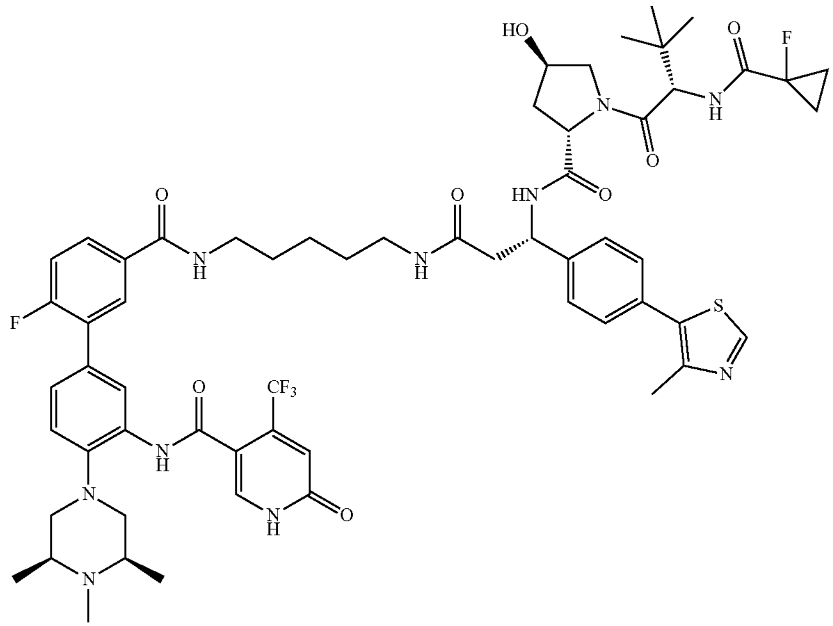 [SMILES: Cc1ncsc1-c1ccc([C@H](CC(=O)NCCCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)NC(=O)[C@@H]2C[C@@H](O)CN2C(=O)[C@@H](NC(=O)C2(F)CC2)C(C)(C)C)cc1] | N-(2'-fluoro-5'-((5-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| 413 | | 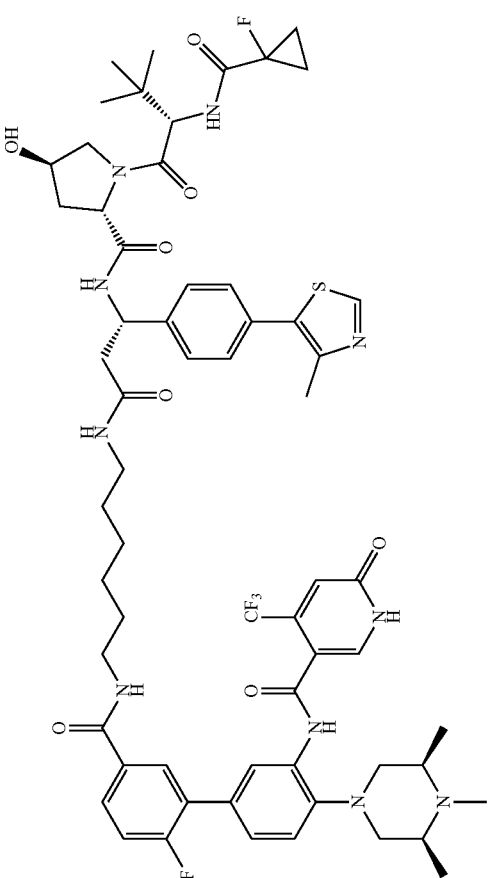 | N-(2'-fluoro-5'-((6-(((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Example | Compound ID | Structure | Chemical Name |
|---|---|---|---|
| | 414 | 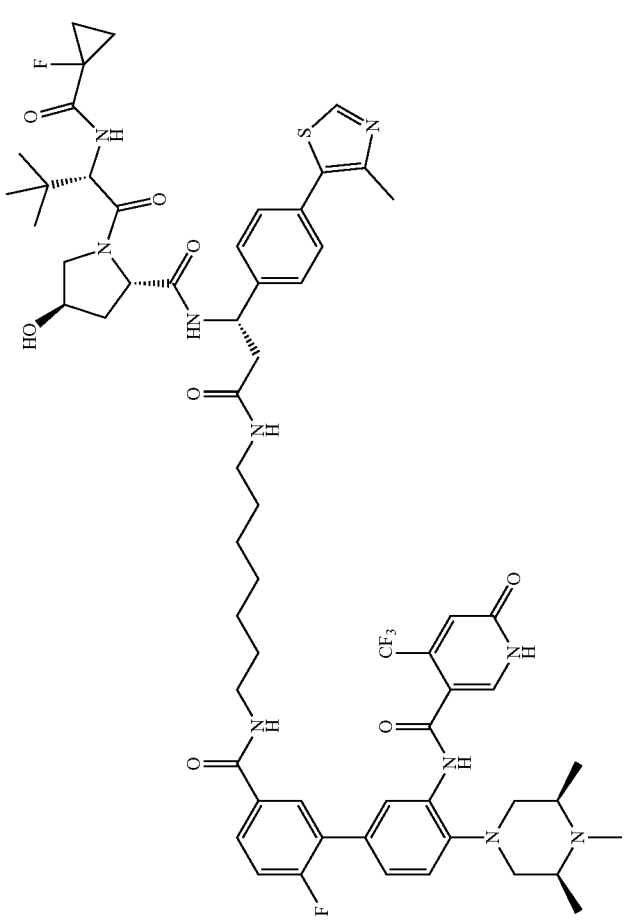 | N-(2'-fluoro-5'-((7-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex- am- ples | Com- pound ID | Structure | Chemical Name |
|---|---|---|---|
| 415 | | 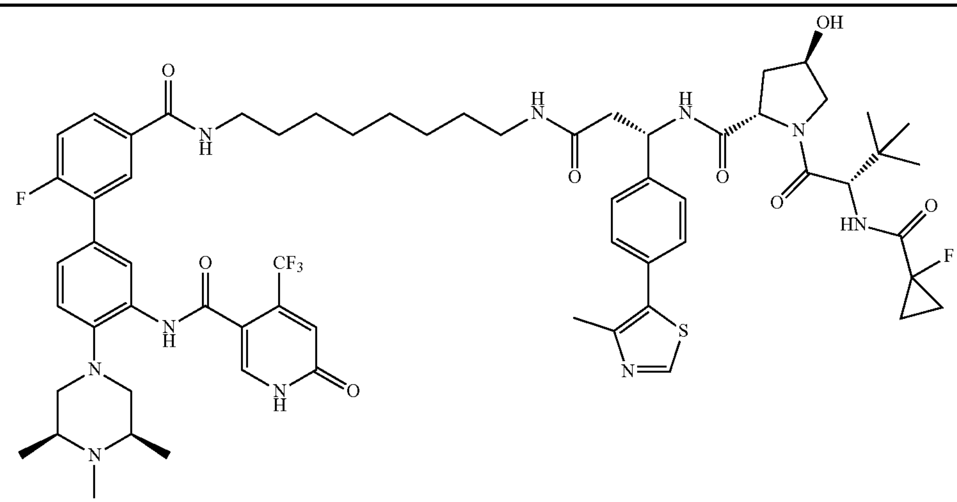 | N-(2'-fluoro-5'-((8-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| | 416 | 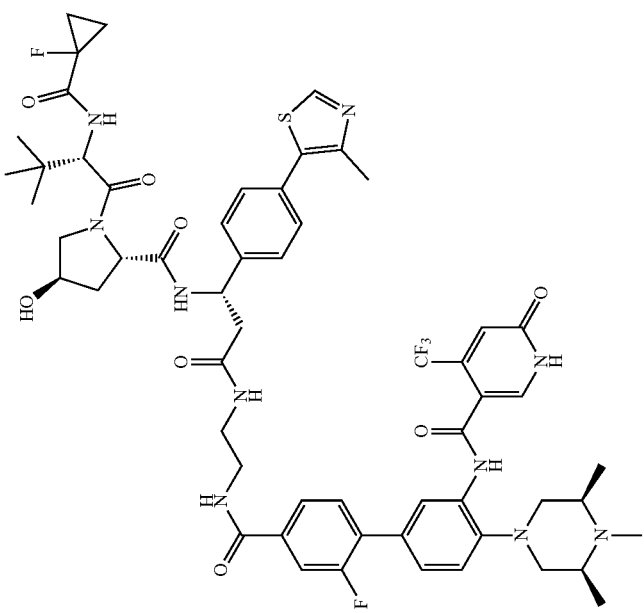 | N-(2'-fluoro-4'-((2-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Example Compound ID | Structure | Chemical Name |
|---|---|---|
| 417 | 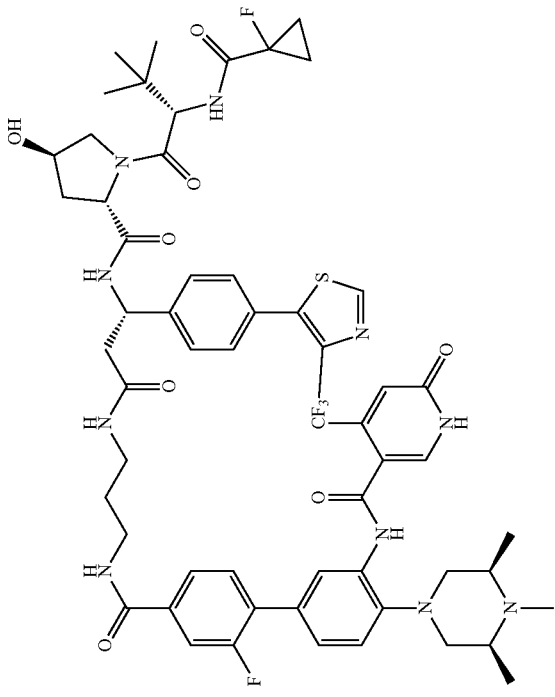 | N-(2'-fluoro-4'-((3-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| | 418 | 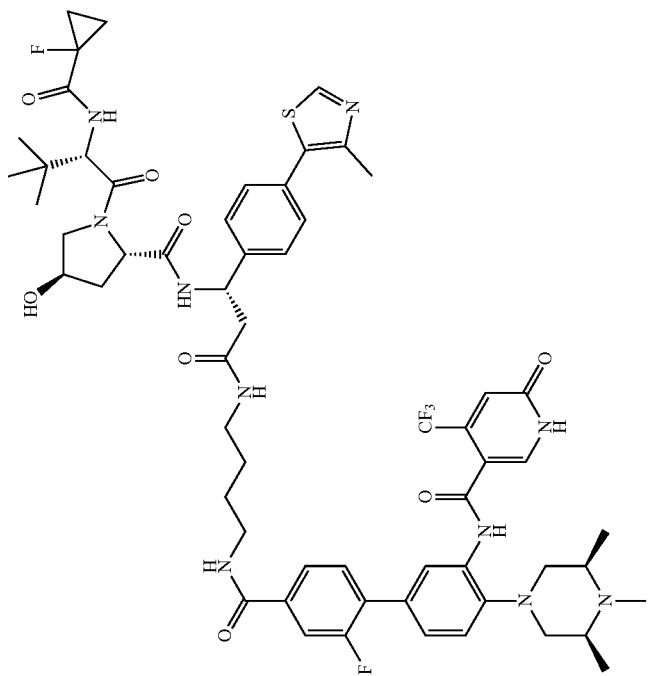 | N-(2'-fluoro-4'-((4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| Examples | Compound ID | Structure | Chemical Name |
|---|---|---|---|
| | 419 | 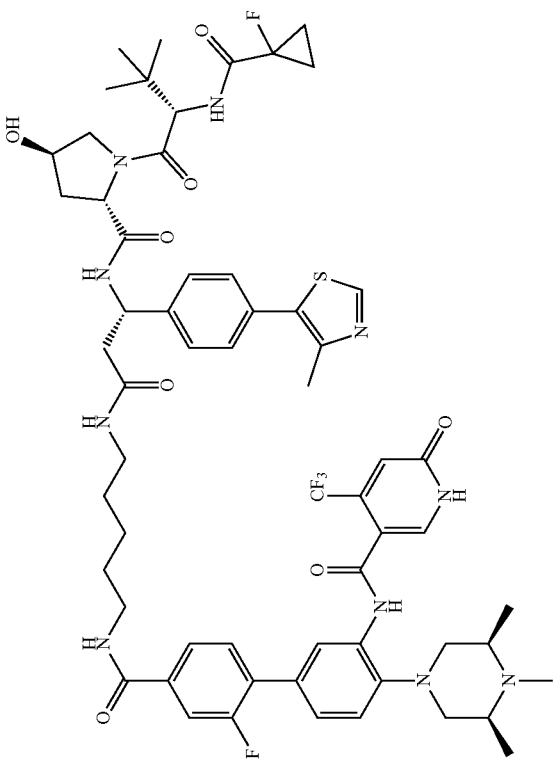 | N-(2'-fluoro-4'-((5-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Ex-am-ples | Compound ID | Structure | Chemical Name |
|---|---|---|---|
| | 420 | | N-(2'-fluoro-4'-((6-(((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued
| Examples | Compound ID | Structure | Chemical Name |
|---|---|---|---|
| | 421 | 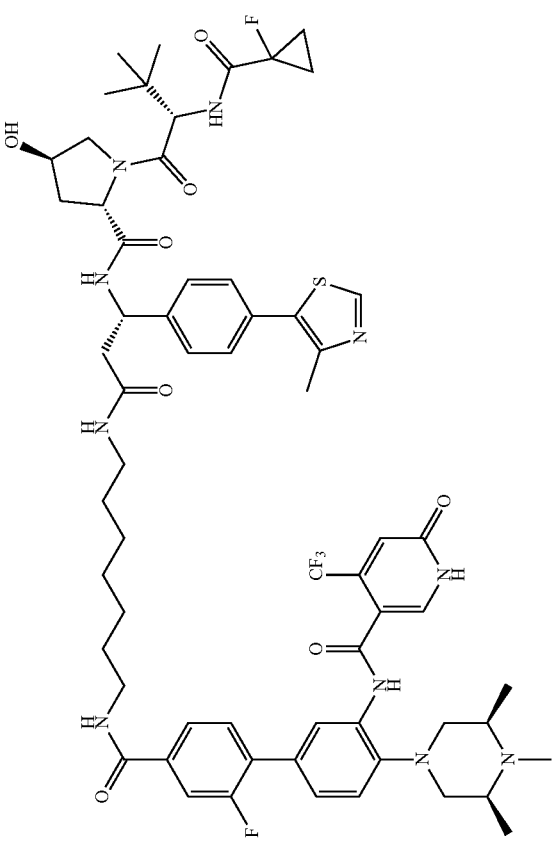 | N-(2'-fluoro-4'-((7-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 422 | | N-(2'-fluoro-4'-((8-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| Examples | Compound ID | Structure | Chemical Name |
|---|---|---|---|
| | 423 | 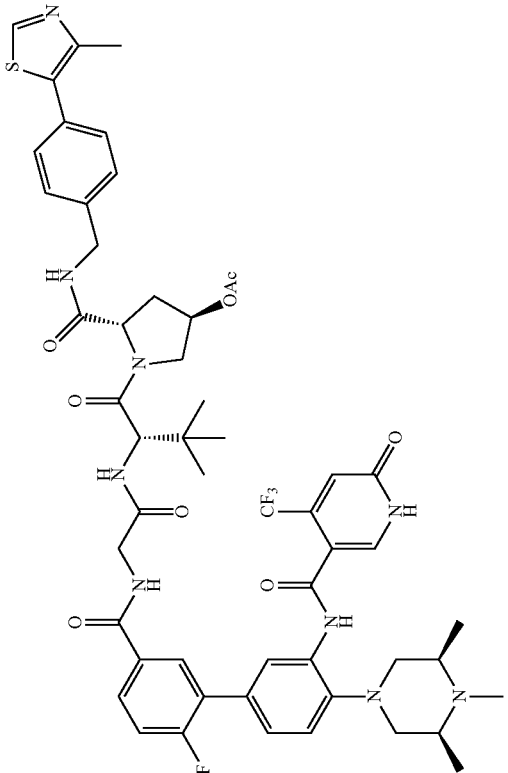 | (3R,5S)-1-((S)-2-(2-(6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-carboxamido)acetamido)-3,3-dimethylbutanoyl)-5-((4-(4-methylthiazol-5-yl)benzyl)carbamoyl)pyrrolidin-3-yl acetate |
| | 424 | 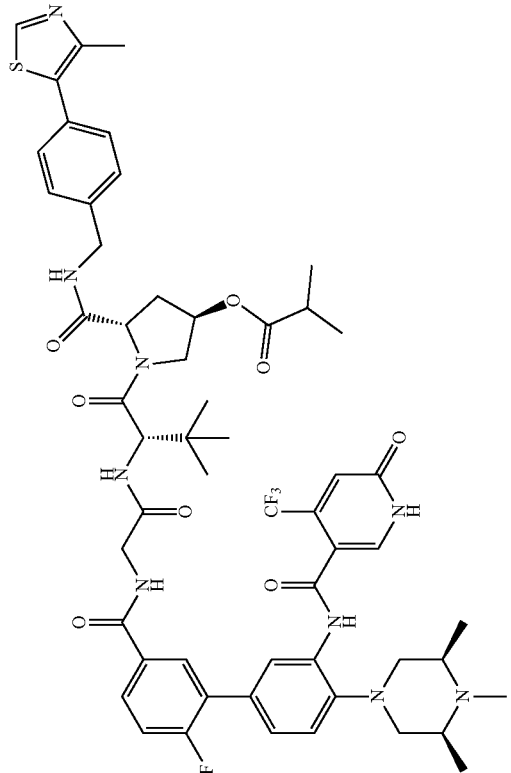 | (3R,5S)-1-((S)-2-(2-(6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-carboxamido)acetamido)-3,3-dimethylbutanoyl)-5-((4-(4-methylthiazol-5-yl)benzyl)carbamoyl)pyrrolidin-3-yl isobutyrate |

TABLE 1-continued

| Examples | Compound ID | Structure | Chemical Name |
|---|---|---|---|
| | 425 | | (3R,5S)-1-((S)-2-(2-(6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-carboxamido)acetamido)-3,3-dimethylbutanoyl)-5-((4-(4-methylthiazol-5-yl)benzyl)carbamoyl)pyrrolidin-3-yl D-prolinate |
| | 426 | | (3R,5S)-1-((S)-3,3-dimethyl-2-(11-((2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)amino)-11-oxoundecanamido)butanoyl)-5-((((S)-1-(4-(4-methylthiazol-5-yl)phenyl)ethyl)carbamoyl)pyrrolidin-3-yl acetate |

| Examples | Compound ID | Structure | Chemical Name |
|---|---|---|---|
| | 427 | 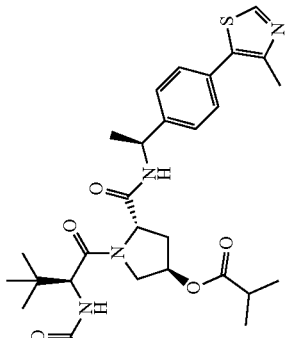 | (3R,5S)-1-((S)-3,3-dimethyl-2-(11-((2-(4-((4'-(4-methylpiperazin-1-yl)-3'-(6-oxo-4-(trifluoromethyl)-1,6-dihydropyridine-3-carboxamido)[1,1'-biphenyl]-3-yl)methyl)piperazin-1-yl)ethyl)amino)-11-oxoundecanamido)butanoyl)-5-(((S)-1-(4-(4-methylthiazol-5-yl)phenyl)ethyl)carbamoyl)pyrrolidin-3-yl isobutyrate |
| | 428 | 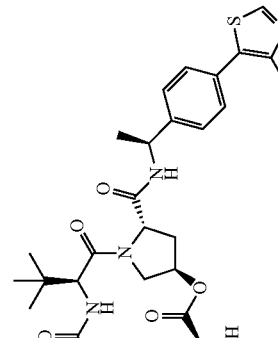 | (3R,5S)-1-((S)-3,3-dimethyl-2-(11-((2-(4-((4'-(4-methylpiperazin-1-yl)-3'-(6-oxo-4-(trifluoromethyl)-1,6-dihydropyridine-3-carboxamido)[1,1'-biphenyl]-3-yl)methyl)piperazin-1-yl)ethyl)amino)-11-oxoundecanamido)butanoyl)-5-(((S)-1-(4-(4-methylthiazol-5-yl)phenyl)ethyl)carbamoyl)pyrrolidin-3-yl L-prolinate |
| | 429 | 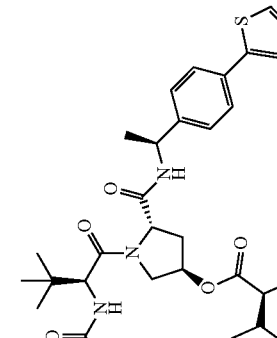 | (3R,5S)-1-((S)-3,3-dimethyl-2-(11-((2-(4-((4'-(4-methylpiperazin-1-yl)-3'-(6-oxo-4-(trifluoromethyl)-1,6-dihydropyridine-3-carboxamido)[1,1'-biphenyl]-3-yl)methyl)piperazin-1-yl)ethyl)amino)-11-oxoundecanamido)butanoyl)-5-(((S)-1-(4-(4-methylthiazol-5-yl)phenyl)ethyl)carbamoyl)pyrrolidin-3-yl L-valinate |

| Examples Compound ID | Structure | Chemical Name |
|---|---|---|
| 430 | 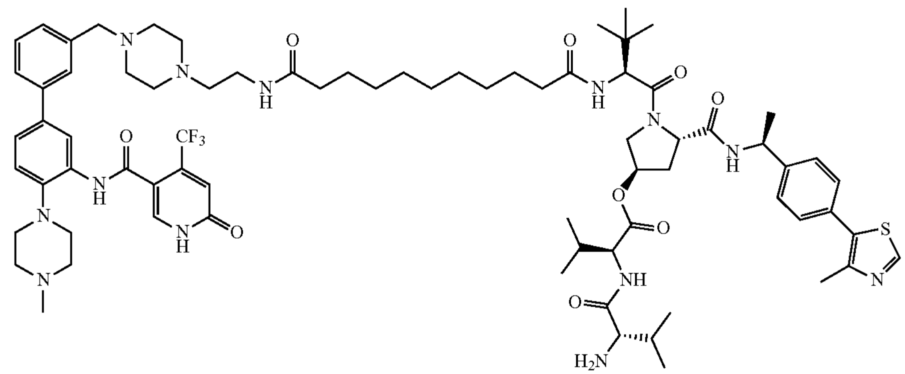 [SMILES: Cc1ncsc1-c1ccc([C@H](C)NC(=O)[C@@H]2C[C@@H](OC(=O)[C@@H](NC(=O)[C@@H](N)C(C)C)C(C)C)CN2C(=O)[C@@H](NC(=O)CCCCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | (3R,5S)-1-((S)-3,3-dimethyl-2-(11-((2-(4'-((4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)amino)-11-oxoundecanamido)butanoyl)-5-(((S)-1-(4-(4-methylthiazol-5-yl)phenyl)ethyl)carbamoyl)pyrrolidin-3-yl L-valyl-L-valinate |
| 431 | 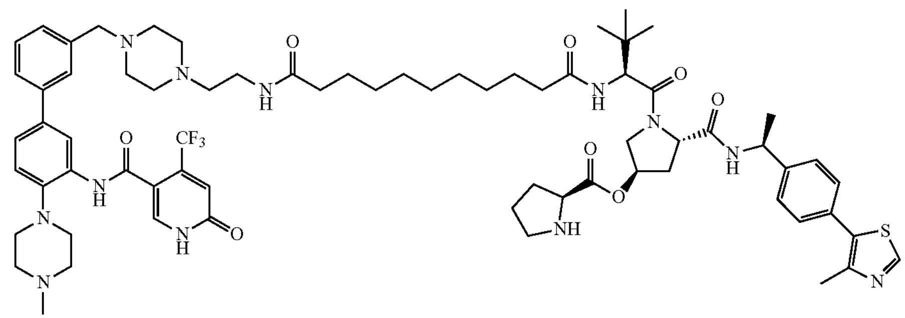 [SMILES: Cc1ncsc1-c1ccc([C@H](C)NC(=O)[C@@H]2C[C@@H](OC(=O)[C@@H]3CCCN3)CN2C(=O)[C@@H](NC(=O)CCCCCCCCCC(=O)NCCN2CCN(Cc3cccc(-c4ccc(N5CCN(C)CC5)c(NC(=O)c5c[nH]c(=O)cc5C(F)(F)F)c4)c3)CC2)C(C)(C)C)cc1] | (3R,5S)-1-((S)-3,3-dimethyl-2-(11-((2-(4'-((4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)amino)-11-oxoundecanamido)butanoyl)-5-(((S)-1-(4-(4-methylthiazol-5-yl)phenyl)ethyl)carbamoyl)pyrrolidin-3-yl L-prolinate |

TABLE 1-continued
| Example | Compound ID | Structure | Chemical Name |
|---|---|---|---|
| | 432 | 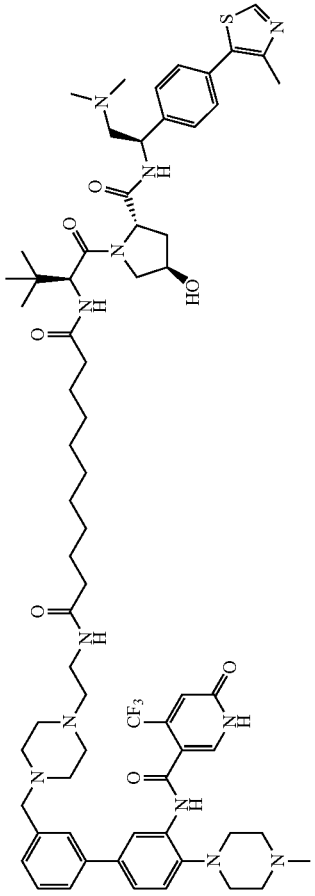 | N[1]-((S)-1-((2S,4R)-2-(((R)-2-(dimethylamino)-1-(4-(4-methylthiazol-5-yl)phenyl)ethyl)carbamoyl)-4-hydroxypyrrolidin-1-yl)-3,3-dimethyl-1-oxobutan-2-yl)-N[11]-(2-(4-(4'-((4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |

As used herein, in case of discrepancy between the structure and chemical name provided for a particular compound, the structure shall control.

Example 433. Assessing the Effect of Selected Compounds on Reducing WDR5 Protein Levels in MV4;11 Cells (FIG. 1)

MV4;11 cells were treated with DMSO or indicated compounds at 1 µM and 10 µM for 18 hours. The Western blot results showed that multiple compounds significantly reduced WDR5 protein levels at 1 µM, while the WDR5 protein-protein inhibitor OICR-9429 had no effect on WDR5 protein levels. And 1 µM treatment of Hela cells with these compounds showed similar results.

Example 434. WDR5 Degraders Concentration-Dependently Reduced WDR5 Protein Levels in MV4;11 Cells (FIG. 2)

MV4;11 cells were treated with DMSO or indicated compounds at 0.1 µM, 0.5 µM, 1 µM, 5 µM, and 10 µM for 18 hours. The Western blot results showed that XF048-133 and XF048-145 significantly reduced WDR5 protein levels at concentrations as low as 0.5 µM, while the WDR5 protein-protein inhibitor OICR-9429 had no effect on WDR5 protein levels.

Example 435. WDR5 Degraders Time-Dependently Reduced WDR5 Protein Levels in MV4;11 Cells (FIGS. 3A and 3B)

MV4;11 cells were treated with DMSO or indicated compounds at a fixed concentration of 0.5 µM for 1, 2, 4, 8, 16, or 24 hours. The results showed that WDR5 degraders time-dependently reduced WDR5 protein levels in MV4;11 cells while the WDR5 inhibitor OICR-9429 had no effect on reducing WDR5 protein levels.

Example 436. XF048-133 Significantly Reduced the Viability of MV4;11 Cells (FIG. 4)

MV4;11 cells were treated with DMSO or the indicated compounds at indicated concentration of 0.1 µM, 0.5 µM, 1 µM, 5 µM, and 10 µM for 72 hours. The WDR5 degrader XF048-133 reduced the viability of MV4;11 cells much more significantly than the WDR5 inhibitor OICR-9429.

Example 437. WDR5 Degraders Concentration-Dependently Reduced WDR5 Protein Levels in MIAPACA2 Cells (FIG. 5)

MIAPACA2 cells were treated with DMSO or indicated compounds at 0.1 µM, 0.5 µM, 1 µM, 5 µM, and 10 µM for 18 hours. The Western blot results showed that XF048-133 and XF048-140 reduced WDR5 protein levels, while the WDR5 inhibitor OICR-9429 had no effect on WDR5 protein levels.

Figure 6:
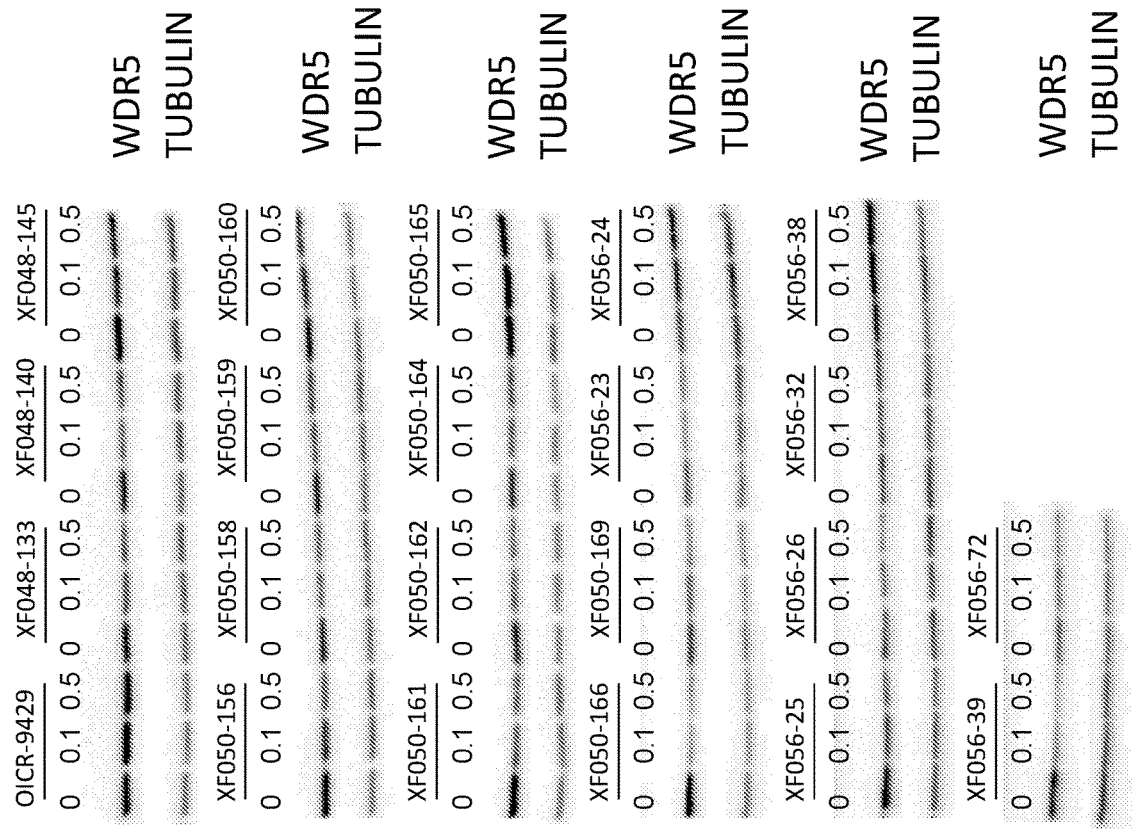
FIG. 6 is a series of Western blots showing the effect of selected WDR5 degraders in reducing WDR5 protein levels at 0, 0.1 µM, and 0.5 µM in MV4;11 cells after 18 h treatment.

Example 438. Assessing the Effect of Selected Compounds on Reducing WDR5 Protein Levels in MV4;11 Cells (FIG. 6)

MV4;11 cells were treated with DMSO or indicated compounds at 0.1 µM and 0.5 µM for 18 hours. The Western blot results showed that multiple compounds significantly reduced WDR5 protein levels at 0.1 µM, while the WDR5 protein-protein inhibitor OICR-9429 had no effect on WDR5 protein levels. And some of the compounds exhibited better degradation effects than XF048-133 and XF048-140.

Figure 7:
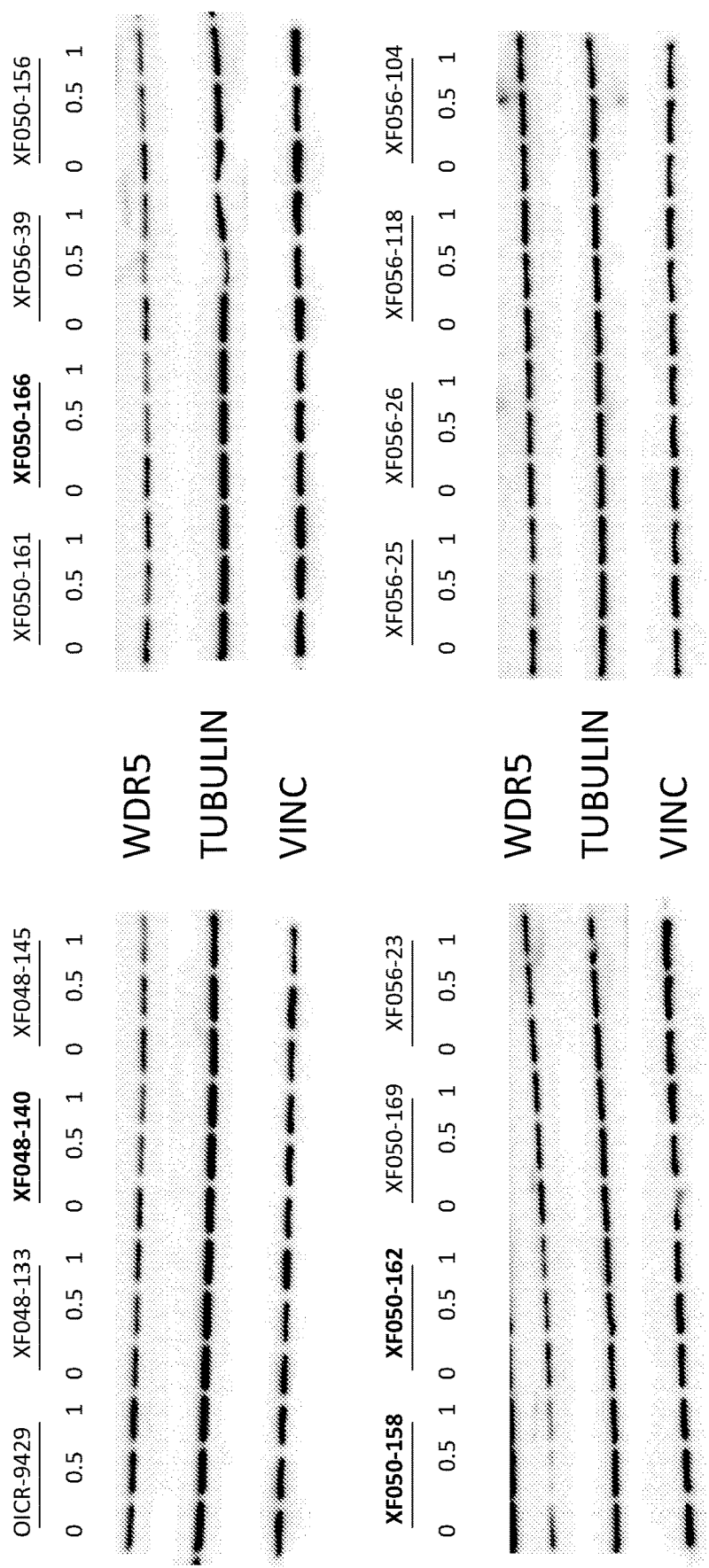
FIG. 7 is a series of Western blots showing the effect of selected degraders from FIG. 6 in reducing WDR5 protein levels at 0, 0.5 µM, and 1.0 µM in MIAPACA2 cells after 18 h treatment.

Example 439. Assessing the Effect of 10 Selected Compounds on Reducing WDR5 Protein Levels in MIAPACA2 Cells (FIG. 7)

MIAPACA2 cells were treated with DMSO or indicated compounds at 0.5 µM and 1.0 µM for 18 hours. The Western blot results showed that XF050-166 exhibited better WDR5 degradation effects than XF048-132 and XF048-140.

Figure 8A:
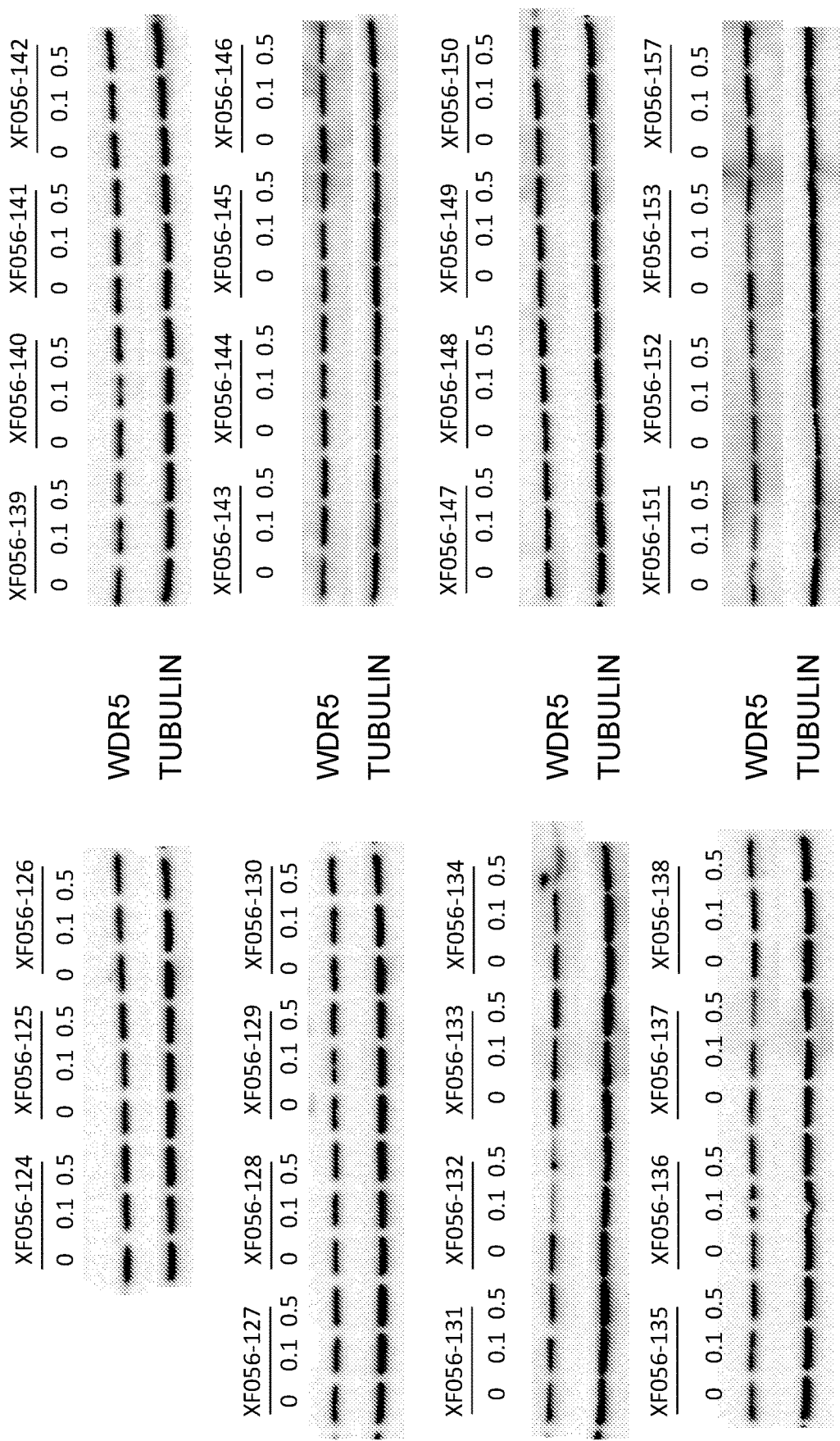
FIGS. 8A-C are a series of Western blots showing the effect of selected degraders in reducing WDR5 protein levels at 0, 0.1 µM, and 0.5 µM in MIAPACA2 cells after 18 h treatment.
Figure 8B:
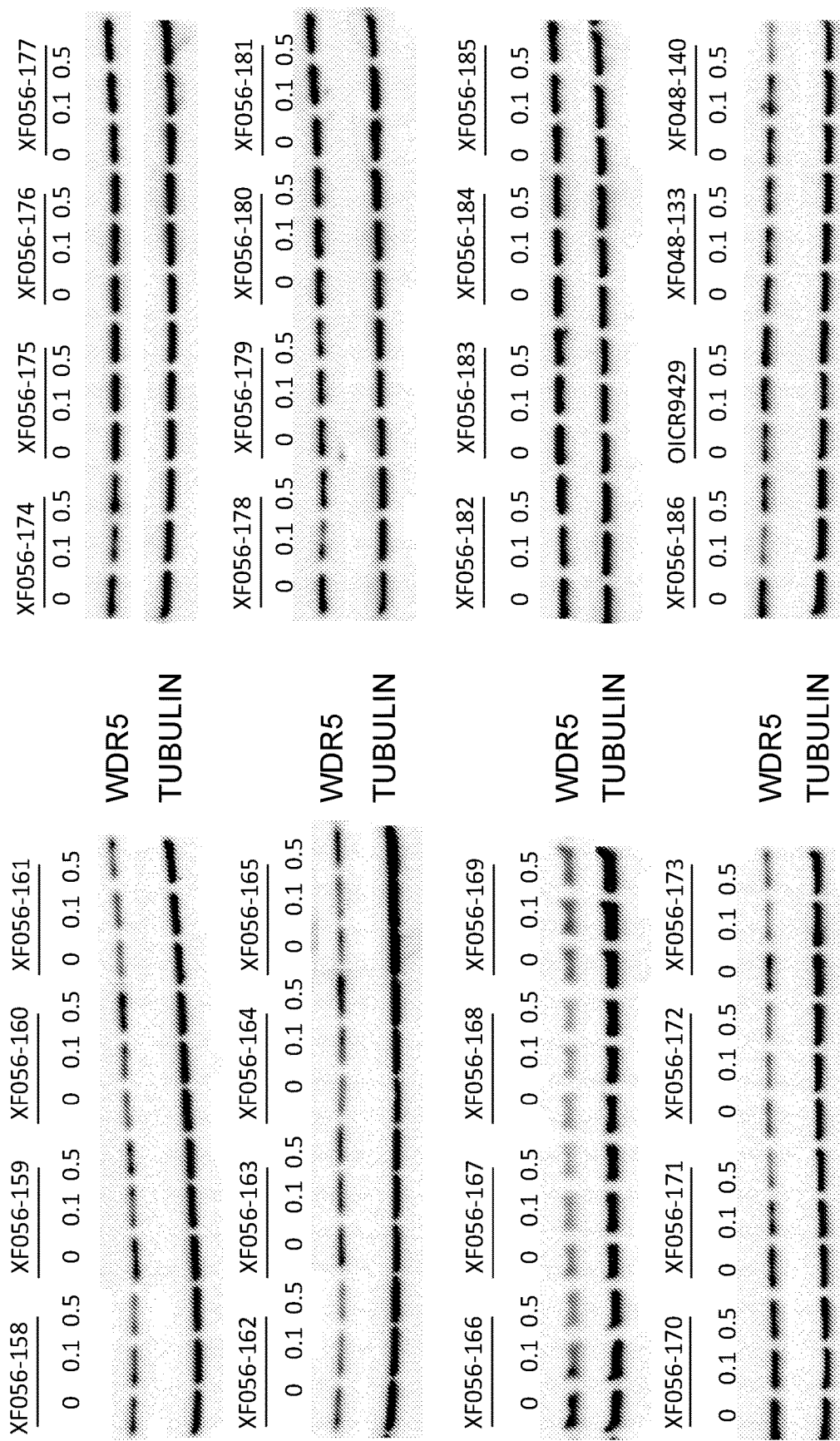
Figure 8C:
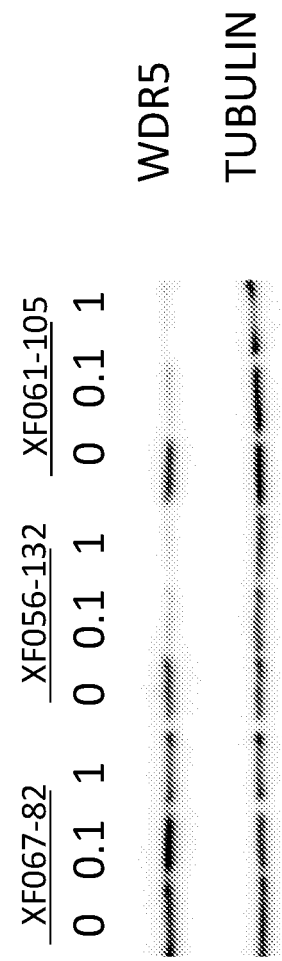

Example 440. Assessing the Effect of Selected Compounds on Reducing WDR5 Protein Levels in MIAPACA2 Cells (FIG. 8A-8C)

MIAPACA2 cells were treated with DMSO or indicated compounds at 0.1 µM and 0.5 µM for 18 hours. The Western blot results showed both XF056-132 and XF061-105, can effectively degrade WDR5 at 0.1 µM and 0.5 µM, while the WDR5 inhibitor, XF067-82, showed no effects on the degradation of WDR5.

Figure 9A:
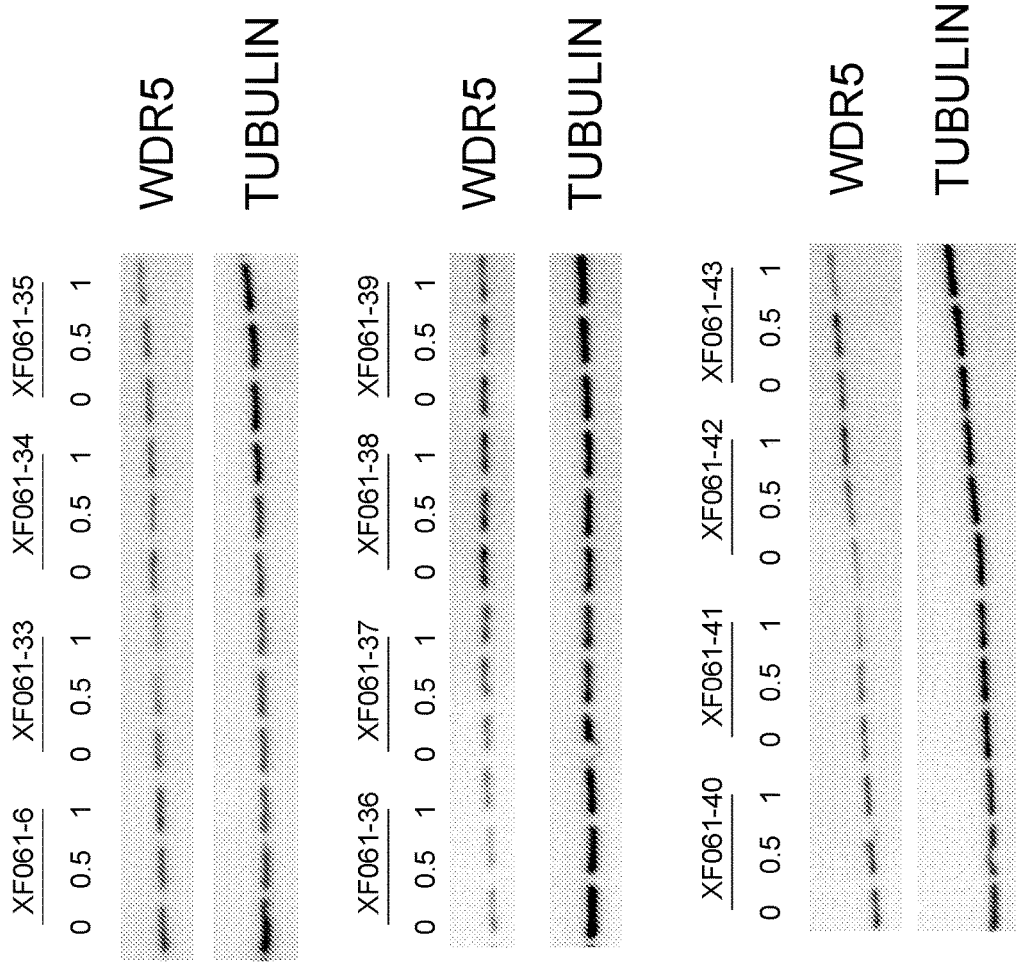
FIGS. 9A-C are is a series of Western blots showing the effect of selected degraders in reducing WDR5 protein levels at 0, 0.5 µM, and 1.0 µM or at 0, 1.0 µM, and 10 µM in MIAPACA2 cells after 18 h treatment.
Figure 9B:
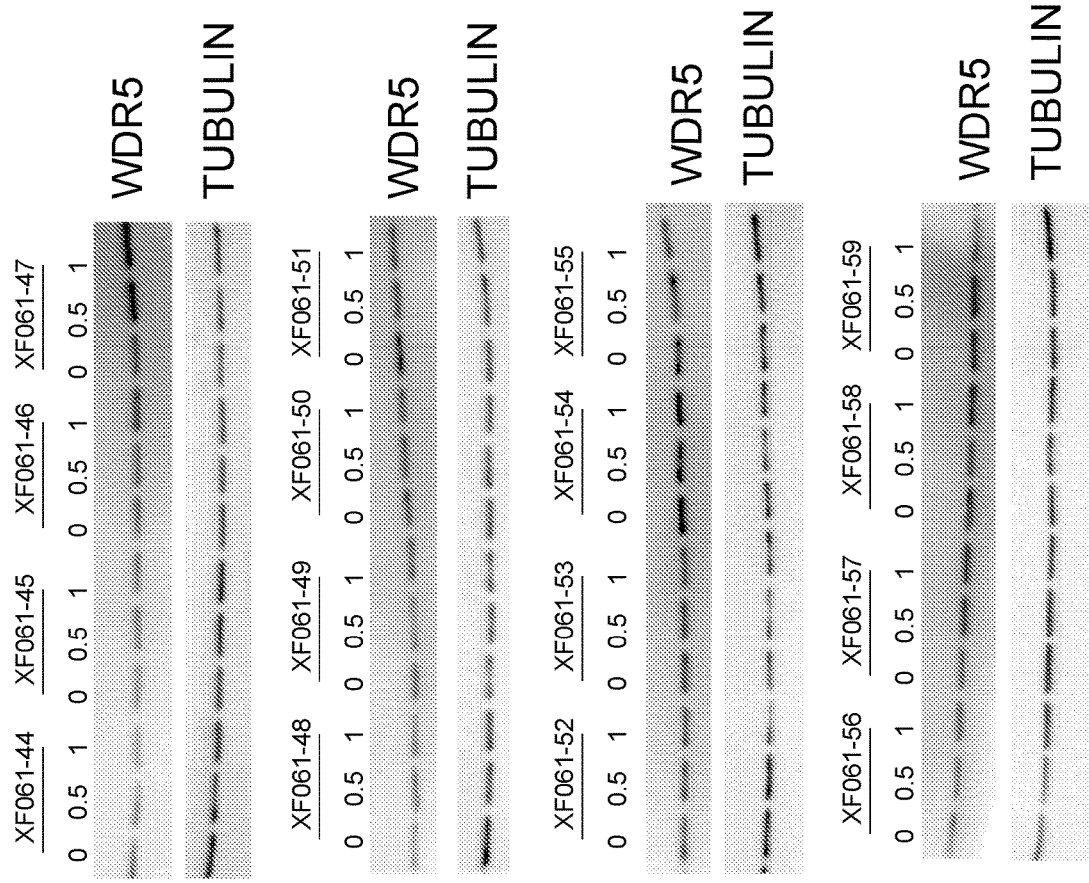
Figure 9C:
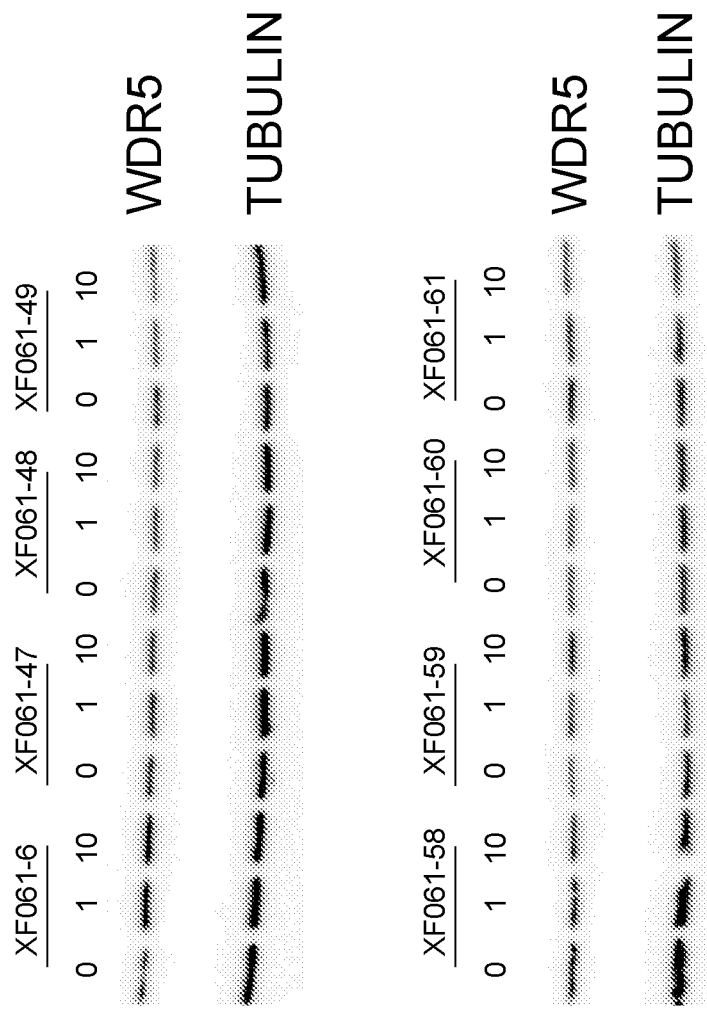
Figure 10A:
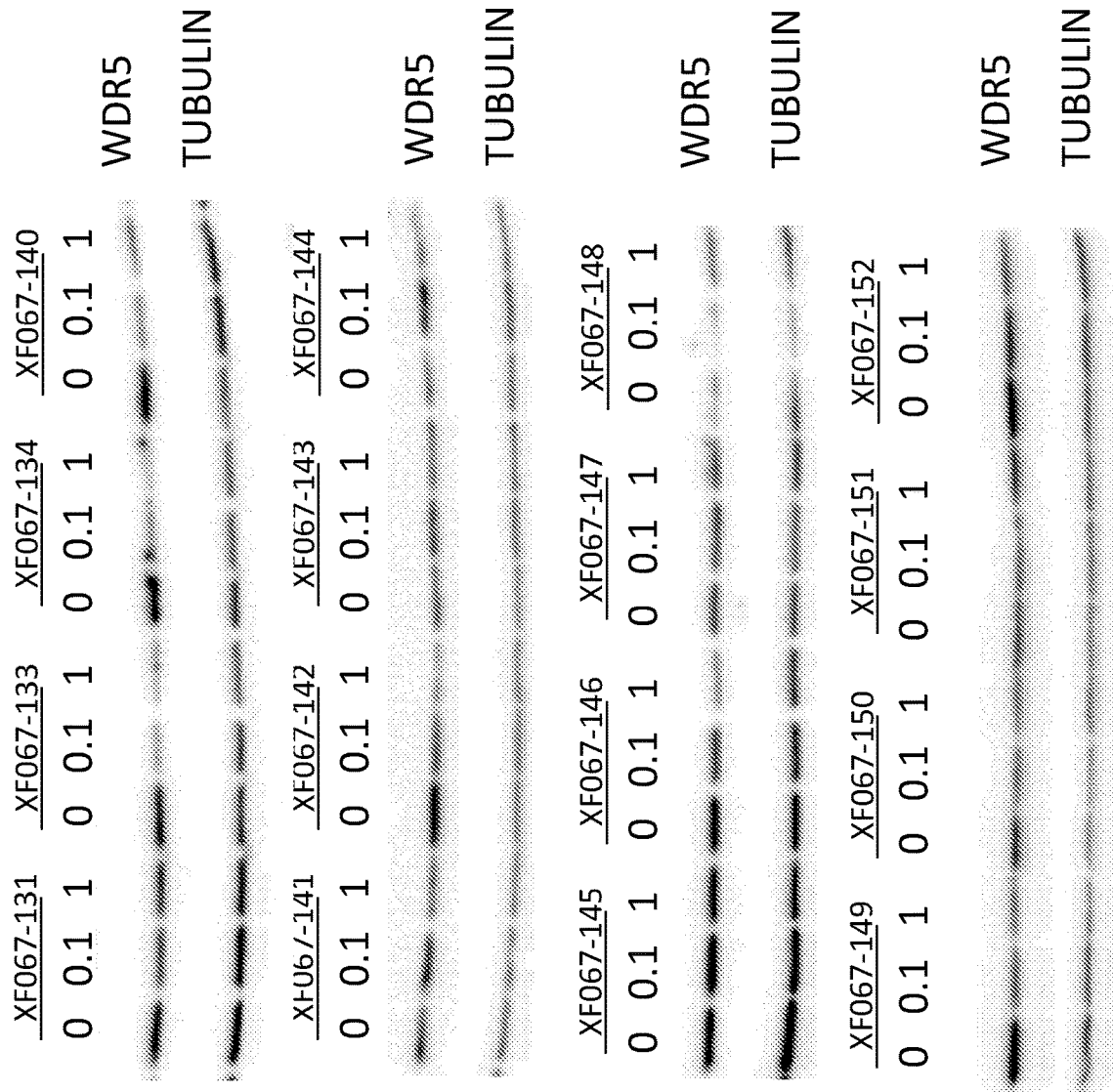
FIGS. 10A-L are a series of Western blots showing the effect of selected degraders in reducing WDR5 protein levels at 0, 0.1 µM, and 1.0 µM in MV4;11 cells after 18 h treatment.
Figure 10B:
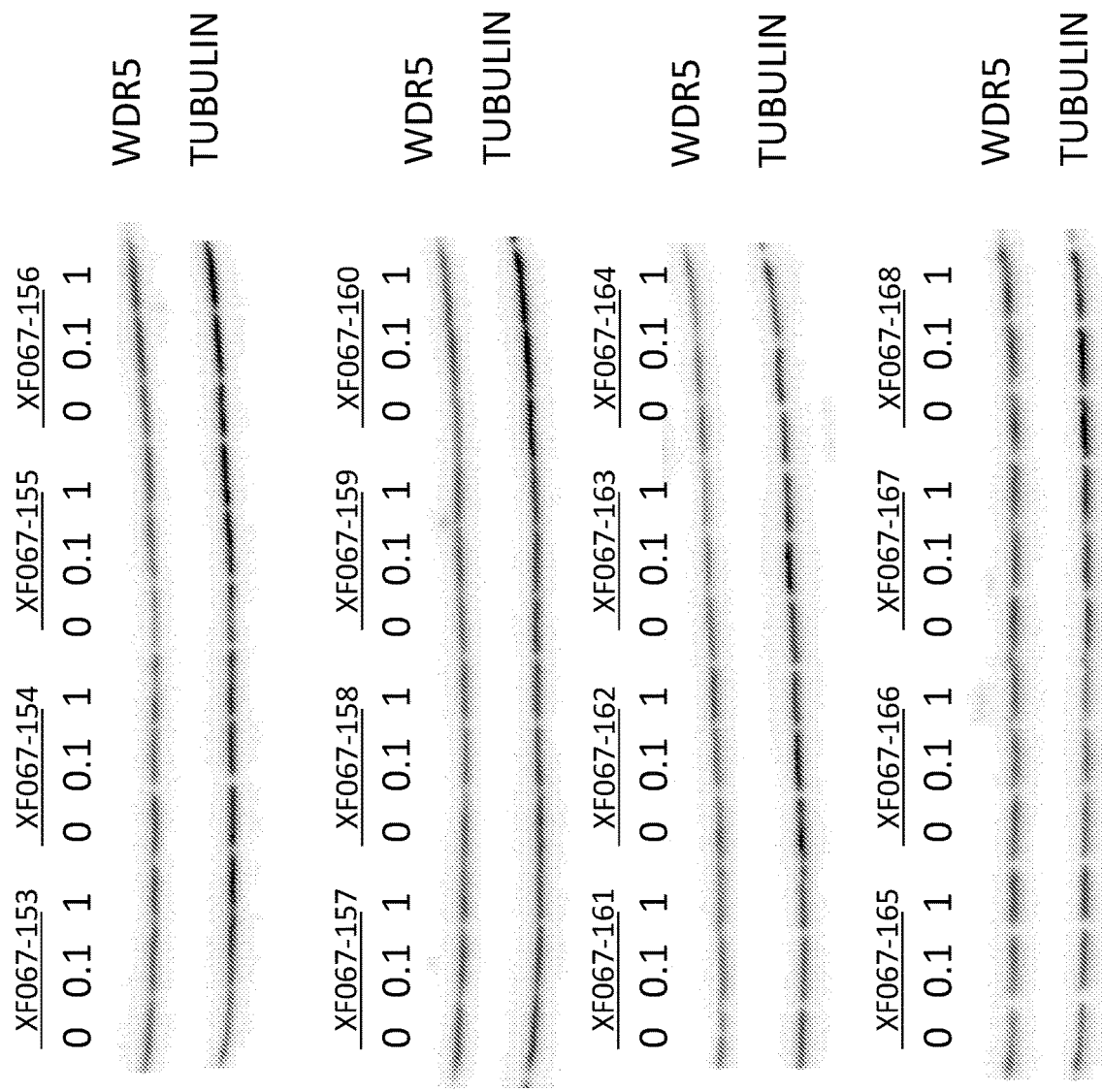
Figure 10C:
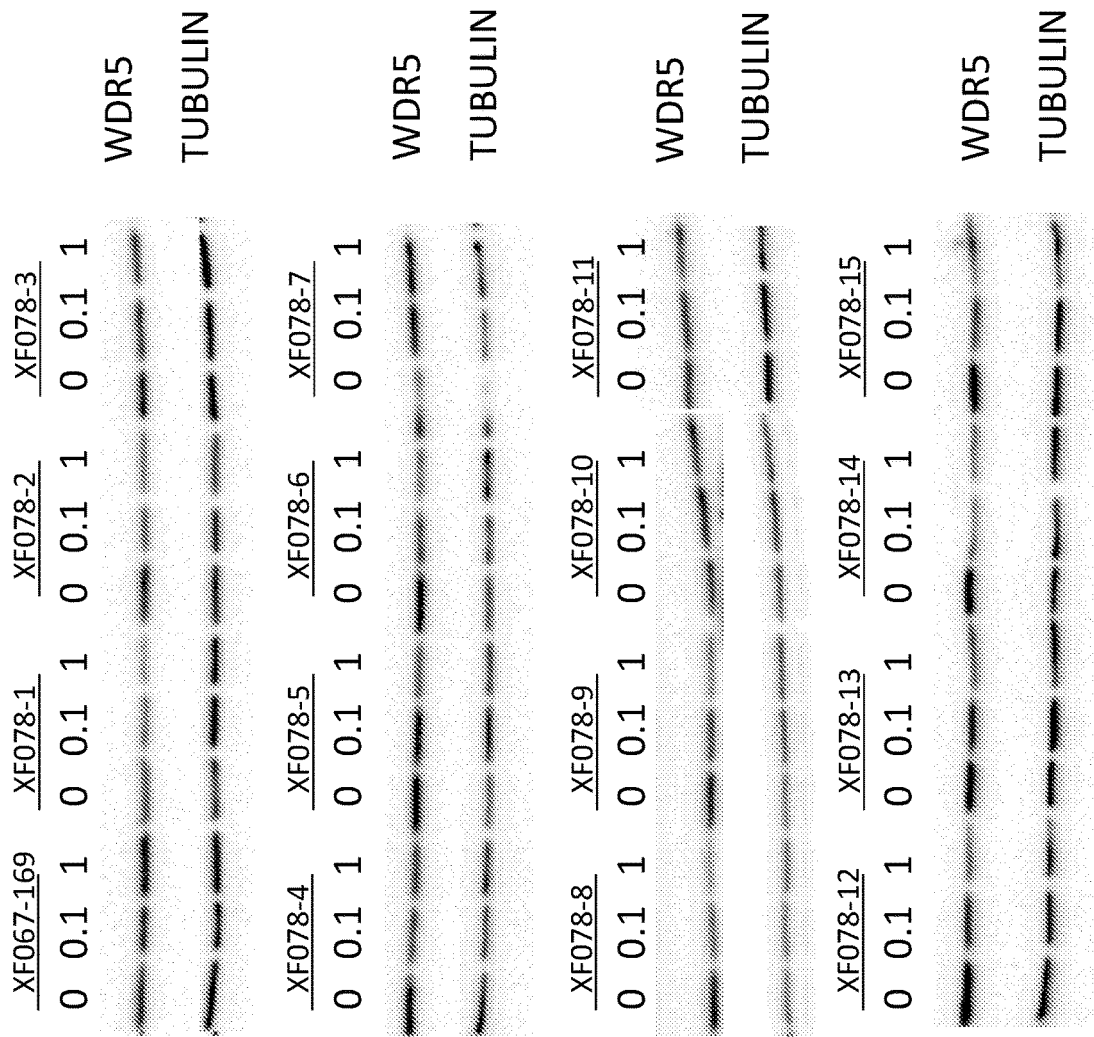
Figure 10D:
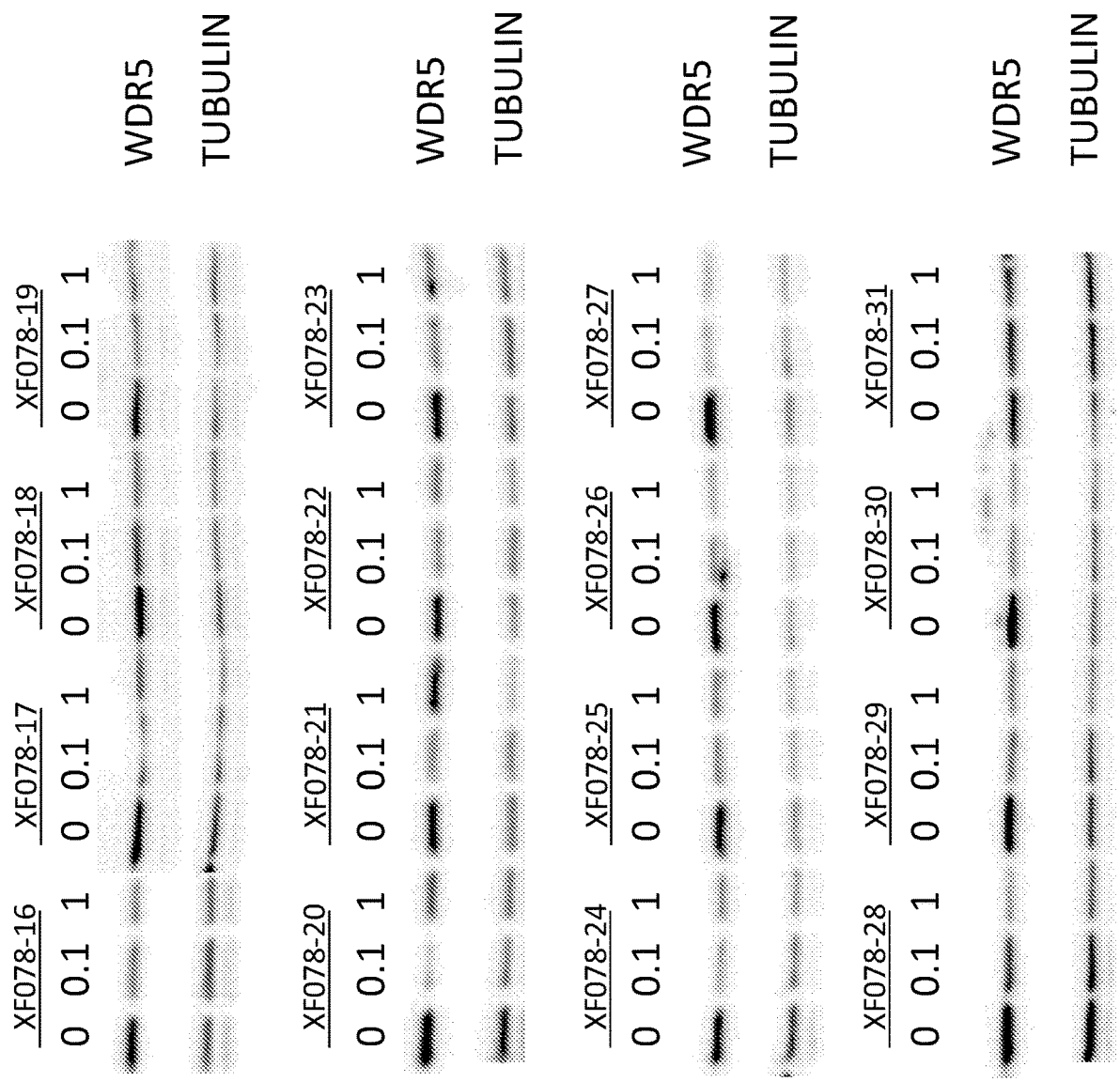
Figure 10E:
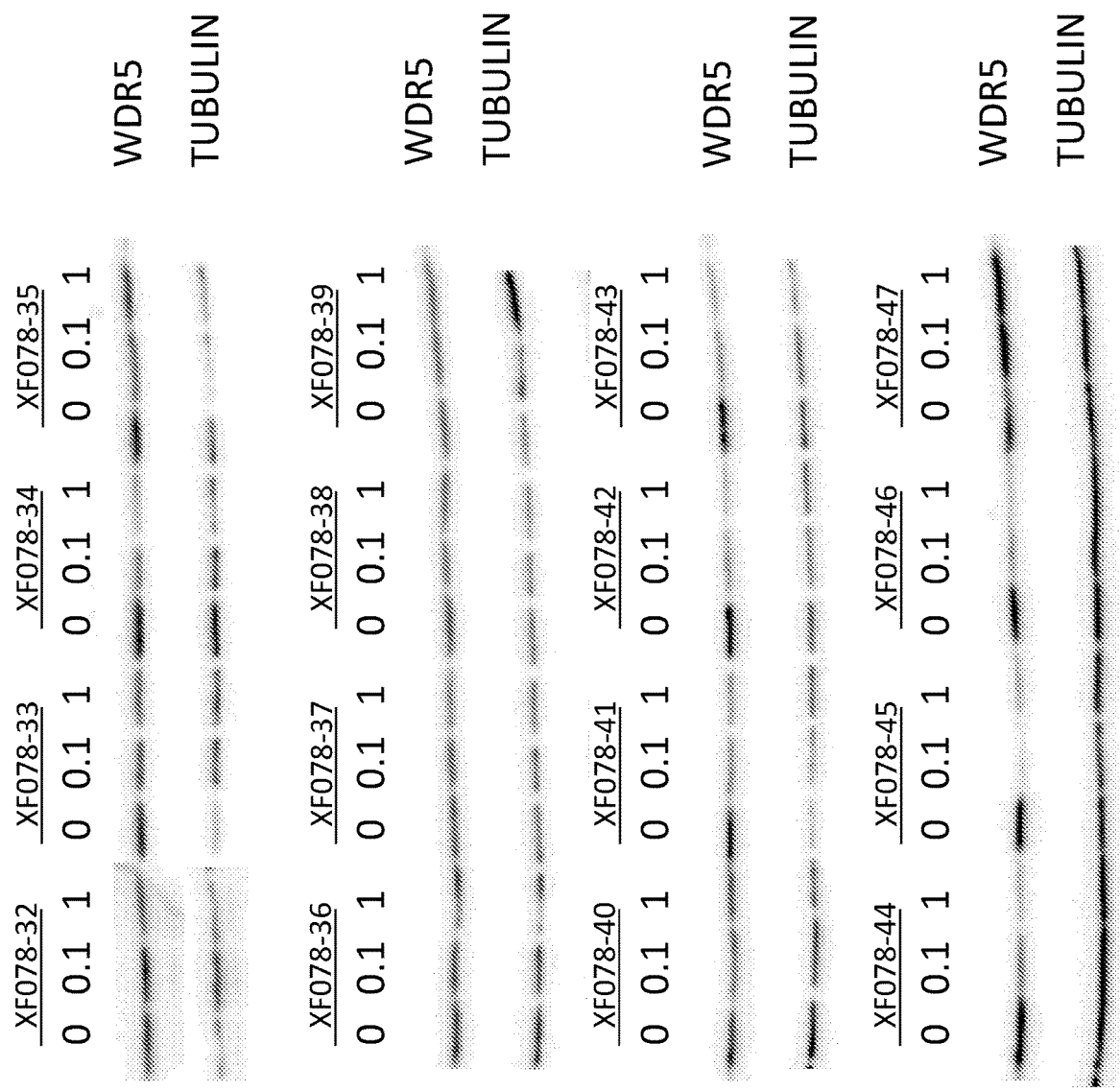
Figure 10F:
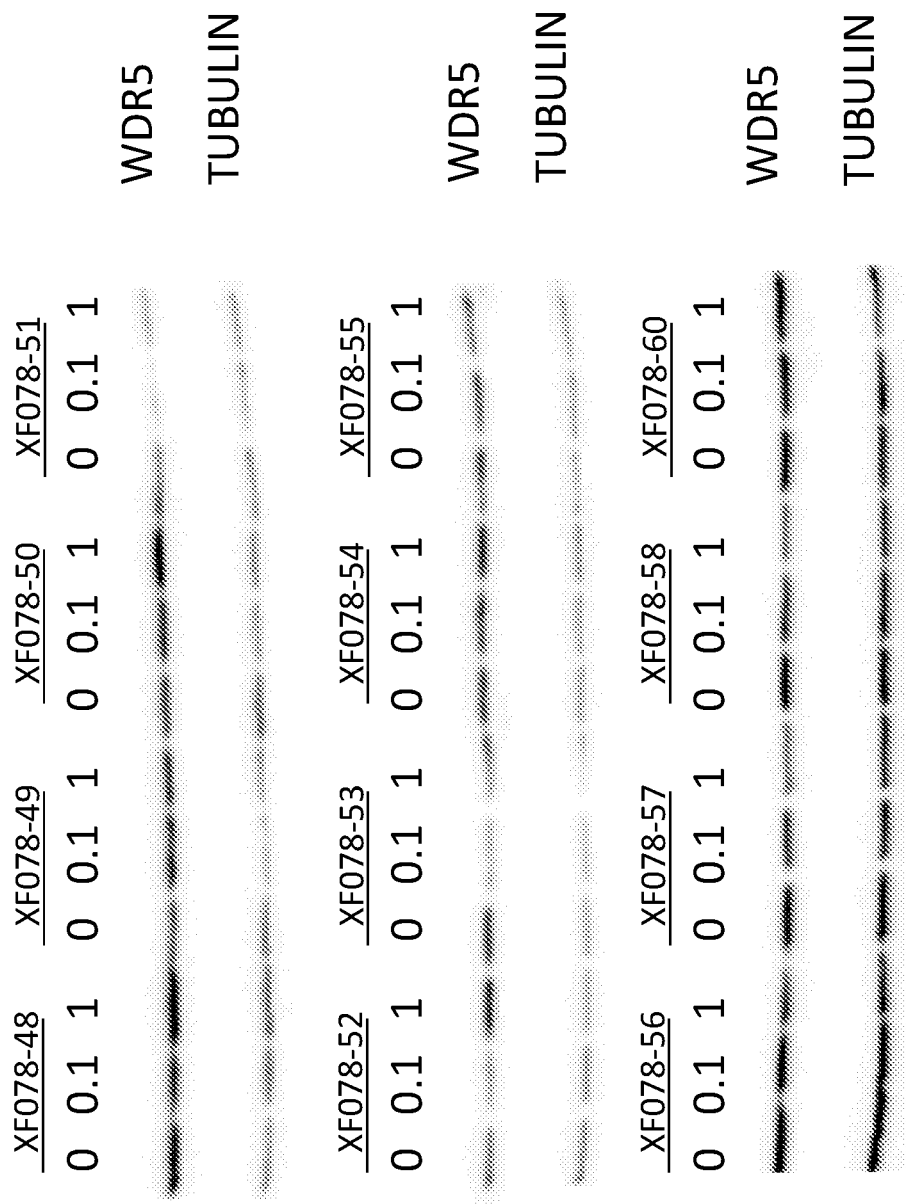
Figure 10G:
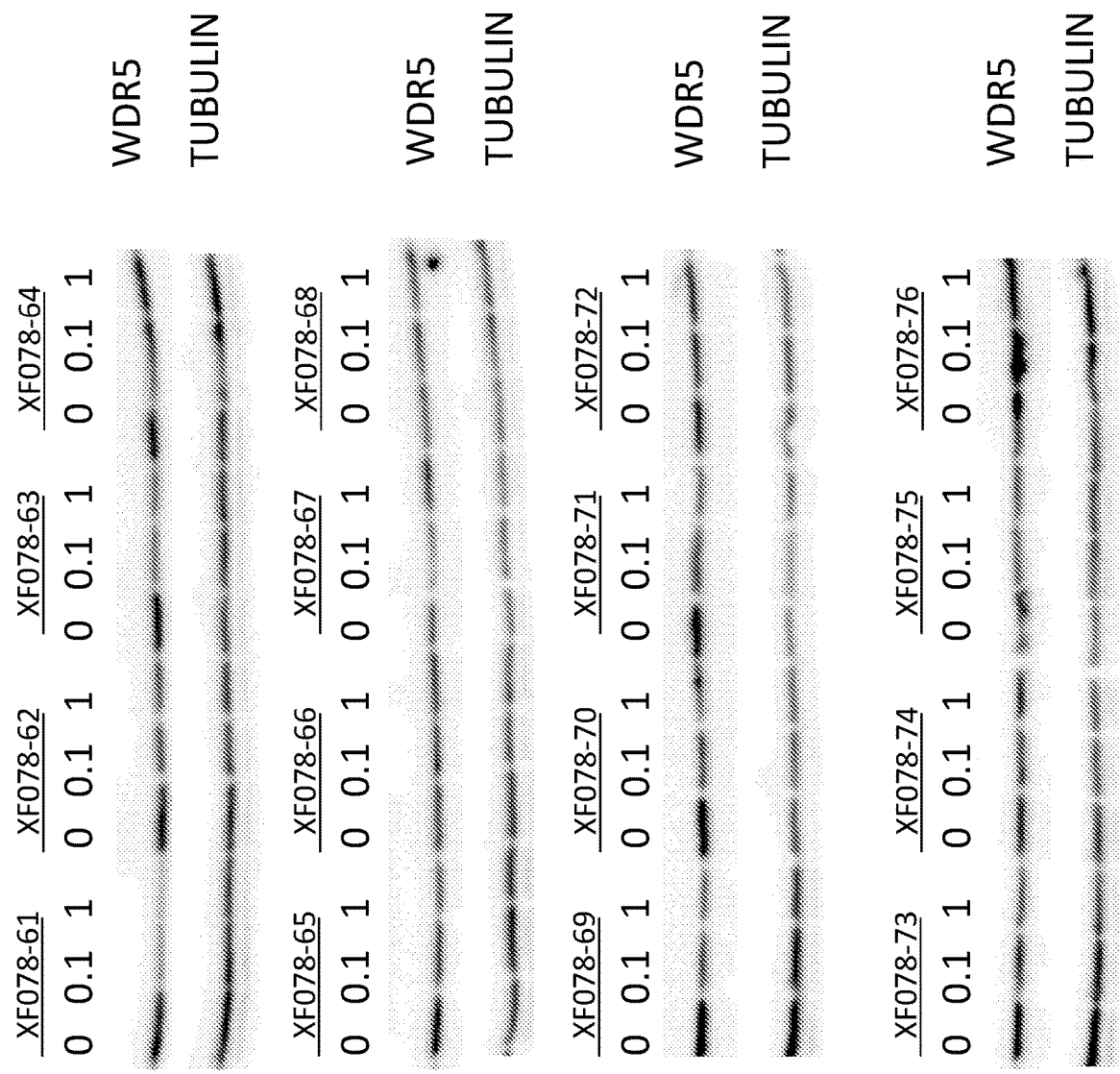
Figure 10H:
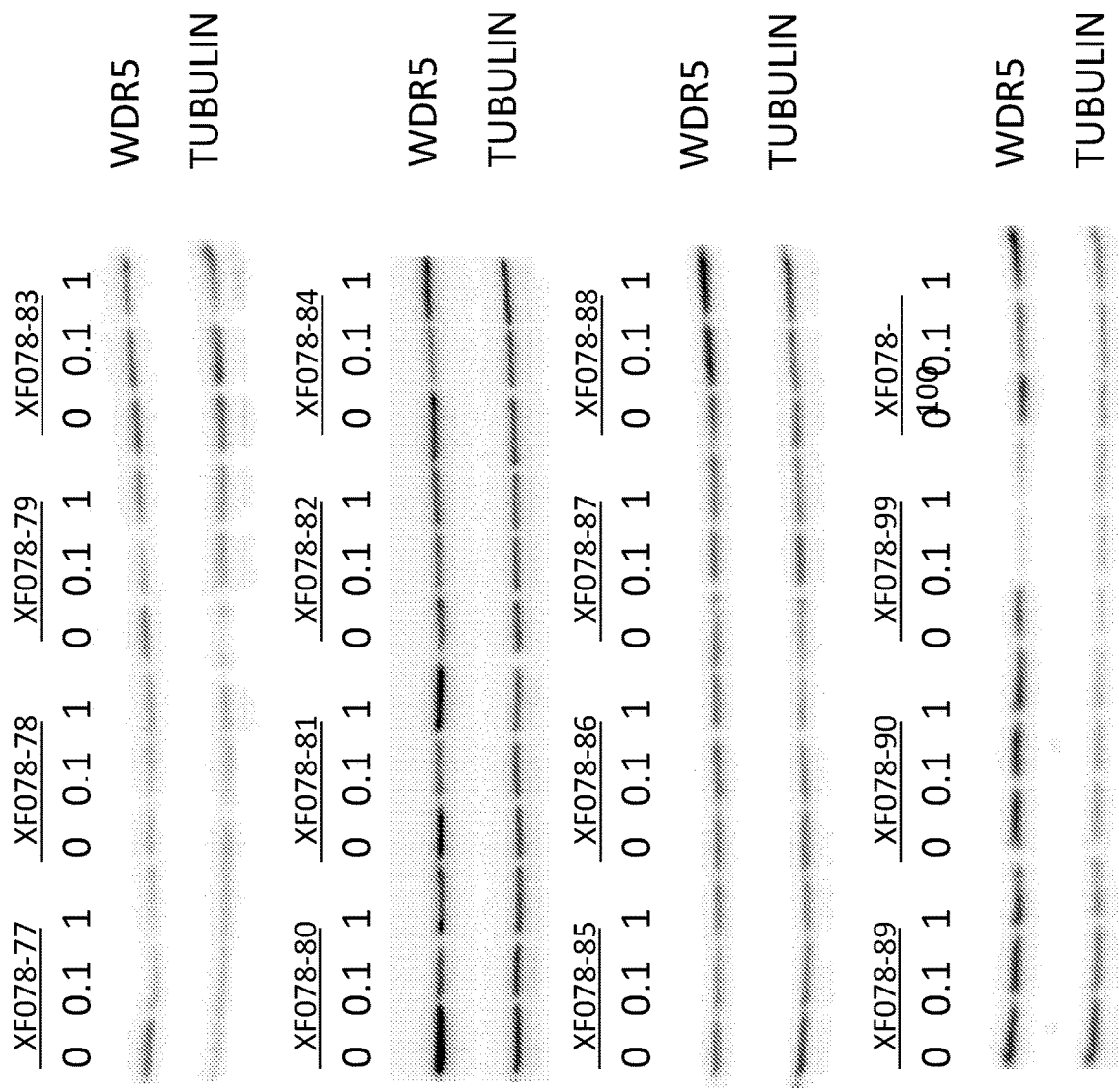
Figure 10I:
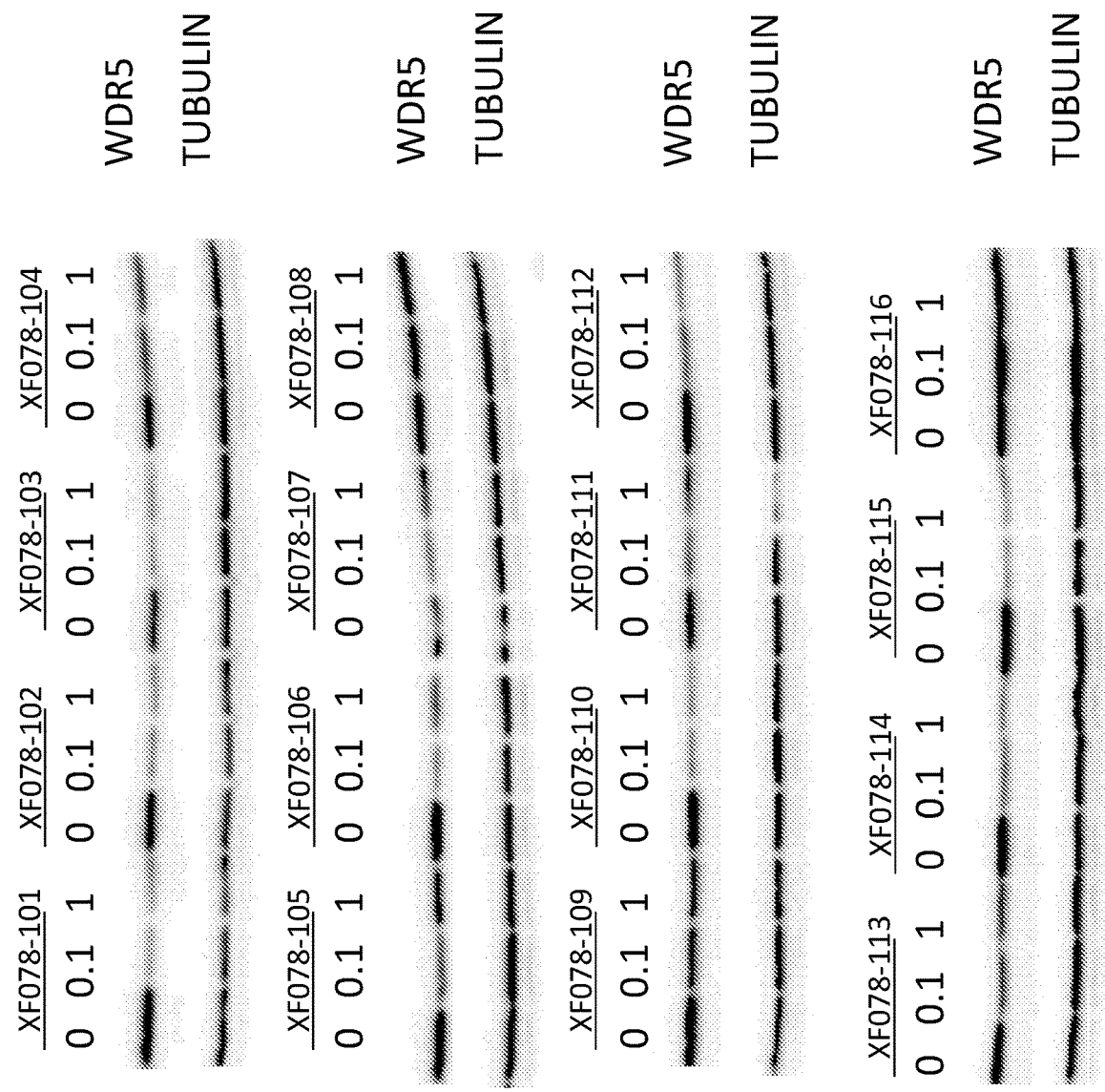
Figure 10J:
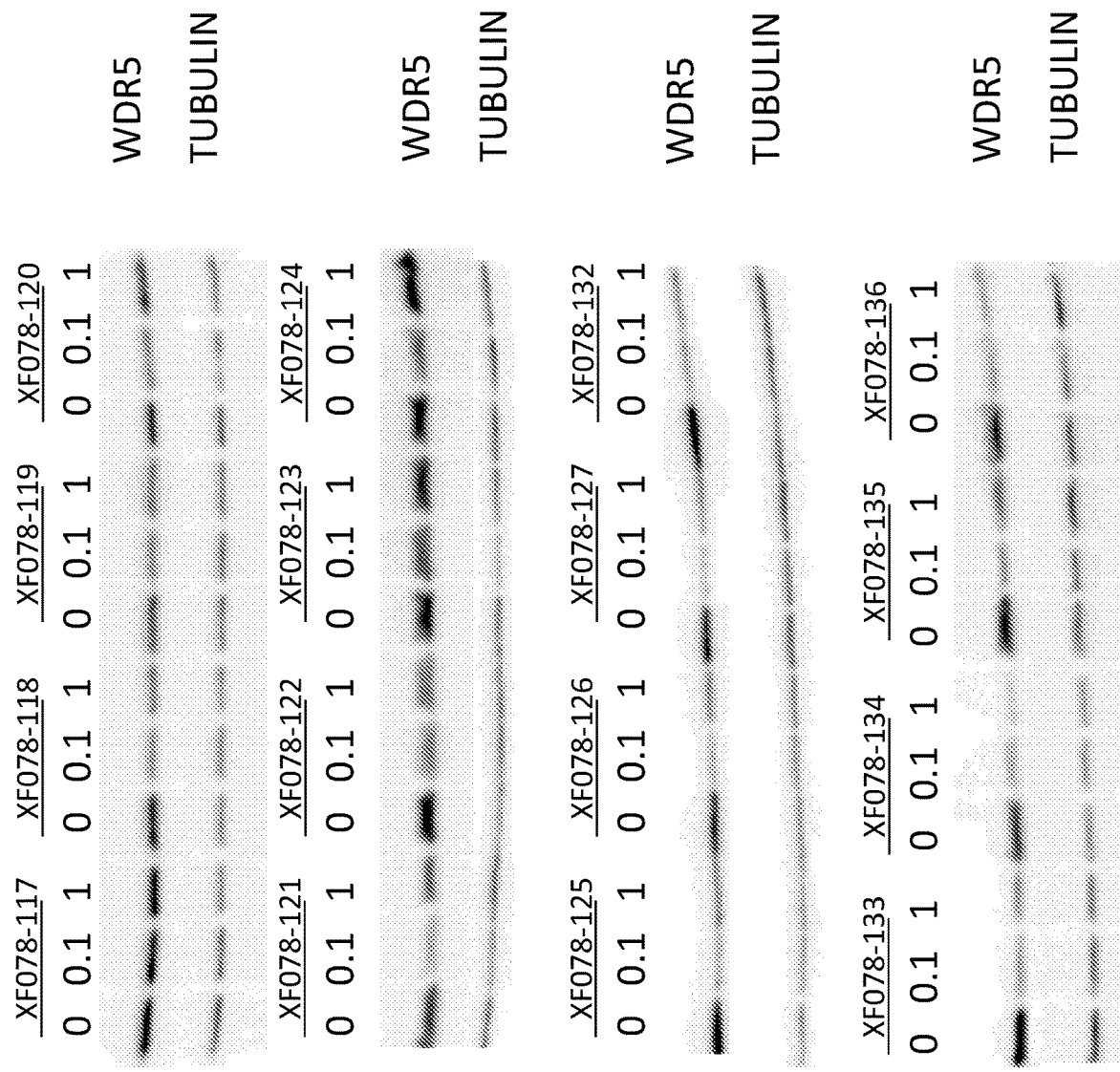
Figure 10K:
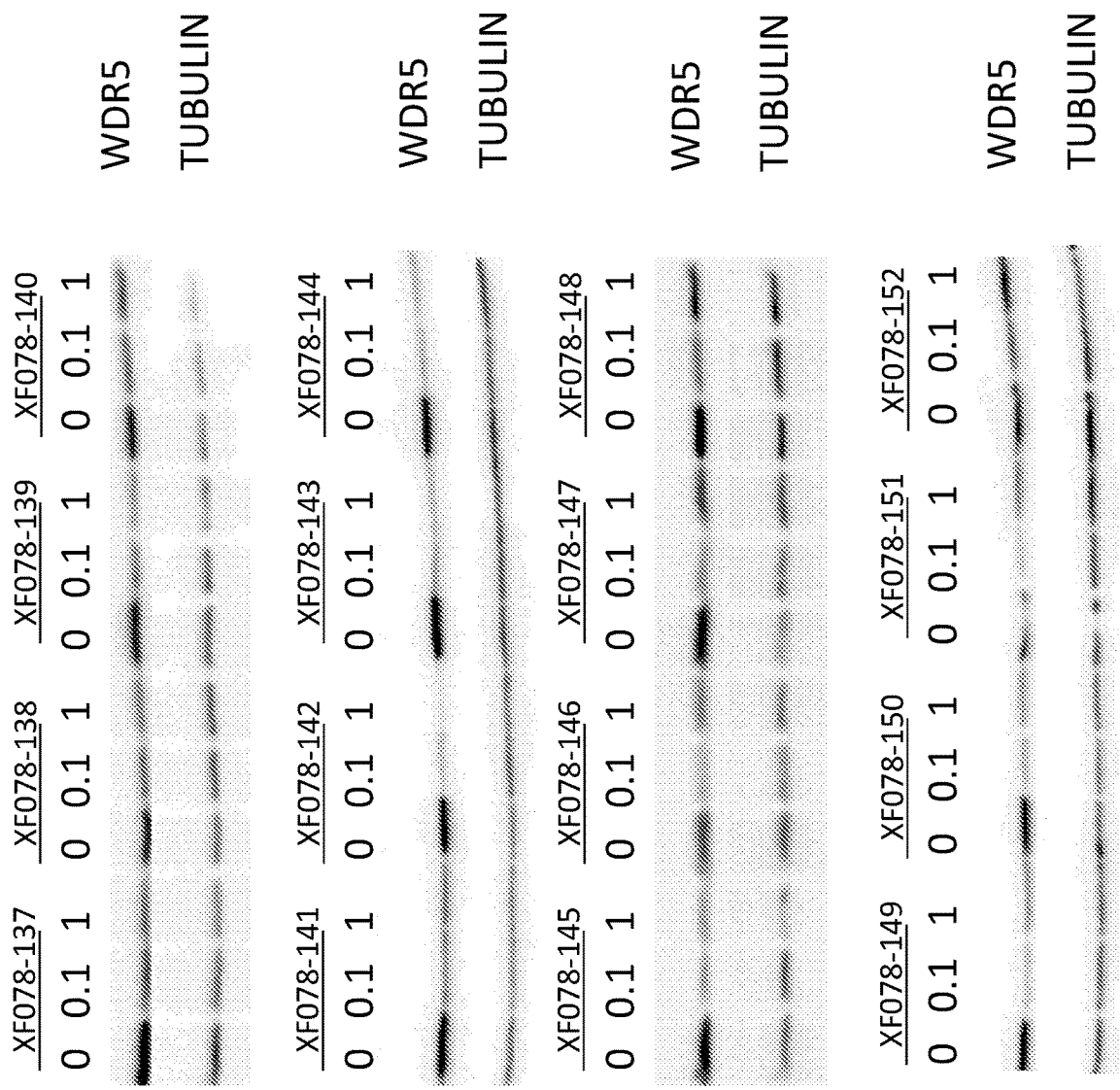
Figure 10L:
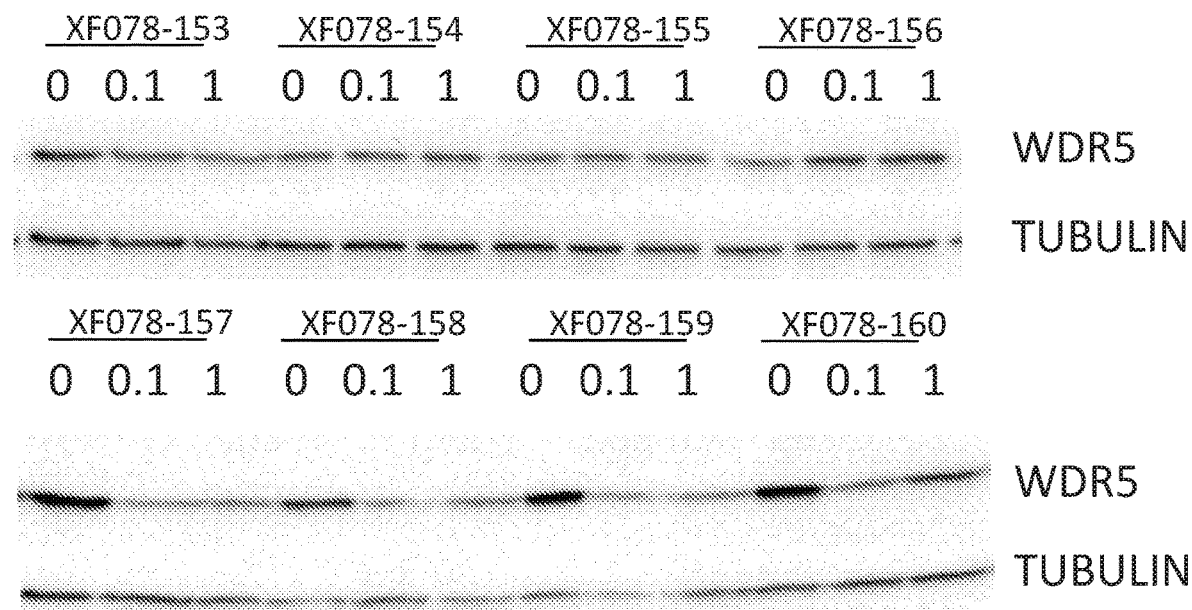

Example 441. Assessing the Effect of Selected Compounds on Reducing WDR5 Protein Levels in MIAPACA2 Cells (FIG. 9A-9C)

MIAPACA2 cells were treated with DMSO or indicated compounds at 0.5 µM and 1.0 µM or at 1.0 µM and 10 µM for 18 hours. The Western blot results showed that these selected compounds did not effectively degrade WDR5.

Example 442. Assessing the Effect of Selected Compounds on Reducing WDR5 Protein Levels in MV4;11 Cells (FIG. 10A-10L)

MV4;11 cells were treated with DMSO or indicated compounds at 0.1 µM and 1.0 µM for 18 hours. The Western blot results showed that multiple compounds were excellent WDR5 degraders.

Example 443

Figure 11:
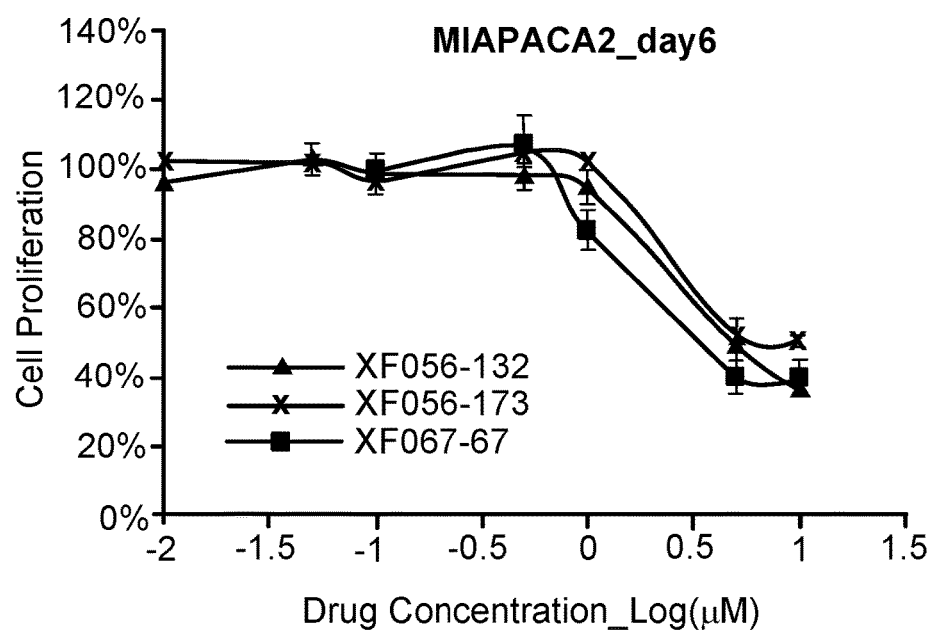
FIG. 11 Shows that WDR5 degraders XF056-132, XF056-173 and XF067-67 significantly decreased the cell proliferation in a pancreatic cancer cell line, MIAPACA2.

Assessment of the cell proliferation effects of WDR5 degraders XF056-132, XF056-173 and XF067-67 in MIAPACA2 cells (FIG. 11). MIAPACA2 cells were treated with DMSO or indicated compounds at 0.01 µM, 0.03 µM, 0.1 µM, 0.5 µM, 1 µM, 5 µM, and 10 µM for 6 days. MTT assay was used for detecting cell proliferation effects. The results showed that XF056-132, XF056-173 and XF067-67 significantly reduced the proliferation of MIAPACA2 cells. XF067-67 exhibited the best cell killing effect among the 3 compounds.

Materials and Methods:
General Chemistry Methods:
All chemicals and reagents were purchased from commercial suppliers and used without further purification. HPLC spectra for all compounds were acquired using an Agilent 1200 Series system with DAD detector. Chromatography was performed on a 2.1×150 mm Zorbax 300SB-C18 5 µm column with water containing 0.1% formic acid as solvent A and acetonitrile containing 0.1% formic acid as solvent B at a flow rate of 0.4 ml/min. The linear gradient was as follows: 1% B (0-1 min), 1-99% B (1-4 min), and 99% B (4-8 min). High-resolution mass spectra (HRMS)

data were acquired in positive ion mode using an Agilent G1969A API-TOF with an electrospray ionization (ESI) source. Proton Nuclear Magnetic Resonance ($^1$H-NMR) spectra were recorded on a Bruker DRX-500, Bruker DRX-600 and Bruker DRX-800 spectrometer. Chemical shifts are expressed in parts per million (ppm) and reported as δ value (chemical shift 6). Coupling constants are reported in units of hertz (Jvalue, Hz; Integration and splitting patterns: where s=singlet, d=double, t=triplet, q=quartet, brs=broad singlet, m=multiple). Preparative HPLC was performed on Agilent Prep 1200 series with UV detector set to 254 nm. Samples were injected onto a Phenomenex Luna 75×30 mm, 5 µm, C18 column at room temperature. The flow rate was 40 ml/min. A linear gradient was used with 10% (or 50%) of MeOH (A) in $H_2O$ (with 0.1% TFA) (B) to 100% of MeOH (A). HPLC was used to establish the purity of target compounds. All compounds showed >95% purity using the HPLC methods described above.

Cell Lines

MV4;11 cells were purchased from ATCC and cultured in RPMI 1640 supplemented with 10% FBS and 1% Penicillin/Streptomycin.

MIAPACA2 and Hela cells were cultured in DMEM supplemented with 10% FBS and 1% Penicillin/Streptomycin.

Compound Treatment

WDR5 degraders were dissolved in DMSO and DMSO with no degraders was used as the control. $1×10^6$ MV4;11 cells or $1×10^5$ MIAPACA2 or $2×10^5$ Hela cells were seeded in 2 mL medium for each well in 24-well plates.

For prescreening of all the compounds, each test compound was added to the medium at indicated concentrations. After 18 h treatment, cells were collected.

For the concentration-dependent treatment (FIG. 2), candidate compounds were added to the medium at a series of concentration: 0.1 µM, 0.5 µM, 1 µM, 5 µM, and 10 µM. After 18 h treatment, cells were collected.

For the time-course treatment (FIG. 3), candidate compounds were added to the medium at a final concentration of 0.5 µM. And cells were collected at indicated timepoints: 1 h, 2 h, 4 h, 8 h, 16 h, and 24 h.

Immunoblotting

After WDR5 degrader treatment, cells were collected and lysed. Total cell lysates were used for western blot. The following primary antibodies were used: WDR5 (Santa Cruz), vinculin (Cell Signaling Technology), tubulin (Cell Signaling Technology), GAPDH (Santa Cruz). Blots were imaged using fluorescence-labeled secondary antibodies on ChemiDoc™ Imaging Systems.

Cell Viability Assay $0.5×10^6$ MV4;11 cells were seeded in 2 mL medium for each well in 12-well plates. WDR5 degraders in DMSO were added to the medium at indicated concentrations. DMSO was used as the control. Each treatment was done in duplicate wells. After 72 h treatment, 1 part cell suspension from each treatment was mixed with 1 part 0.4% trypan blue respectively. The mixture was allowed to incubate for ~3 min at room temperature and live cells were counted by automated cell counter.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Aguilar, A., Lu, J., Liu, L., Du, D., Bernard, D., McEachern, D., Przybranowski, S., Li, X., Luo, R., Wen, B., et al. (2017). Discovery of 4-((3'R,4'S,5'R)-6''-Chloro-4'-(3-chloro-2-fluorophenyl)-1'-ethyl-2''-oxodispiro[cyclohexane-1,2'-pyrrolidine-3',3''-indoline]-5'-carboxamido) bicyclo[2.2.2]octane-1-carboxylic Acid (AA-115/APG-115): A Potent and Orally Active Murine Double Minute 2 (MDM2) Inhibitor in Clinical Development. J Med Chem 60, 2819-2839.

Bolshan, Y., Getlik, M., Kuznetsova, E., Wasney, G. A., Hajian, T., Poda, G., Nguyen, K. T., Wu, H., Dombrovski, L., Dong, A., et al. (2013). Synthesis, Optimization, and Evaluation of Novel Small Molecules as Antagonists of WDR5-MLL Interaction. ACS medicinal chemistry letters 4, 353-357.

Bondeson, D. P., Mares, A., Smith, I. E., Ko, E., Campos, S., Miah, A. H., Mulholland, K. E., Routly, N., Buckley, D. L., Gustafson, J. L., et al. (2015). Catalytic in vivo protein knockdown by small-molecule PROTACs. Nat Chem Biol 11, 611-617.

Buckley, D. L., and Crews, C. M. (2014). Small-molecule control of intracellular protein levels through modulation of the ubiquitin proteasome system. Angew Chem Int Ed Engl 53, 2312-2330.

Buckley, D. L., Gustafson, J. L., Van Molle, I., Roth, A. G., Tae, H. S., Gareiss, P. C., Jorgensen, W. L., Ciulli, A., and Crews, C. M. (2012a). Small-molecule inhibitors of the interaction between the E3 ligase VHL and HIFlalpha. Angew Chem Int Ed Engl 51, 11463-11467.

Buckley, D. L., Raina, K., Darricarrere, N., Hines, J., Gustafson, J. L., Smith, I. E., Miah, A. H., Harling, J. D., and Crews, C. M. (2015). HaloPROTACS: Use of Small Molecule PROTACs to Induce Degradation of HaloTag Fusion Proteins. ACS Chem Biol 10, 1831-1837.

Buckley, D. L., Van Molle, I., Gareiss, P. C., Tae, H. S., Michel, J., Noblin, D. J., Jorgensen, W. L., Ciulli, A., and Crews, C. M. (2012b). Targeting the von Hippel-Lindau E3 ubiquitin ligase using small molecules to disrupt the VHL/HIF-1alpha interaction. J Am Chem Soc 134, 4465-4468.

Cai, Y., Jin, J., Swanson, S. K., Cole, M. D., Choi, S. H., Florens, L., Washburn, M. P., Conaway, J. W., and Conaway, R. C. (2010). Subunit composition and substrate specificity of a MOF-containing histone acetyltransferase distinct from the male-specific lethal (MSL) complex. J Biol Chem 285, 4268-4272.

Cao, F., Townsend, E. C., Karatas, H., Xu, J., Li, L., Lee, S., Liu, L., Chen, Y., Ouillette, P., Zhu, J., et al. (2014). Targeting MLL1 H3K4 Methyltransferase Activity in Mixed-Lineage Leukemia. Molecular cell 53, 247-261.

Carugo, A., Genovese, G., Seth, S., Nezi, L., Rose, J. L., Bossi, D., Cicalese, A., Shah, P. K., Viale, A., Pettazzoni, P. F., et al. (2016). In Vivo Functional Platform Targeting Patient-Derived Xenografts Identifies WDR5-Myc Association as a Critical Determinant of Pancreatic Cancer. Cell Rep 16, 133-147.

Chamberlain, P. P., Lopez-Girona, A., Miller, K., Carmel, G., Pagarigan, B., Chie-Leon, B., Rychak, E., Corral, L. G., Ren, Y. J., Wang, M., et al. (2014). Structure of the human Cereblon-DDB1-lenalidomide complex reveals basis for responsiveness to thalidomide analogs. Nat Struct Mol Biol 21, 803-809.

Chen, W. L., Li, D. D., Wang, Z. H., Xu, X. L., Zhang, X. J., Jiang, Z. Y., Guo, X. K., and You, Q. D. (2018). Design, synthesis, and initial evaluation of affinity-based small molecular probe for detection of WDR5. Bioorganic chemistry 76, 380-385.

Chen, X., Gu, P., Li, K., Xie, W., Chen, C., Lin, T., and Huang, J. (2015a). Gene expression profiling of WDR5 regulated genes in bladder cancer. Genom Data 5, 27-29.

Chen, X., Xie, W., Gu, P., Cai, Q., Wang, B., Xie, Y., Dong, W., He, W., Zhong, G., Lin, T., et al. (2015b). Upregulated WDR5 promotes proliferation, self-renewal and chemoresistance in bladder cancer via mediating H3K4 trimethylation. Sci Rep 5, 8293.

Chung, C. Y., Sun, Z., Mullokandov, G., Bosch, A., Qadeer, Z. A., Cihan, E., Rapp, Z., Parsons, R., Aguirre-Ghiso, J. A., Farias, E. F., et al. (2016). Cbx8 Acts Non-canonically with Wdr5 to Promote Mammary Tumorigenesis. Cell reports 16, 472-486.

Dai, X., Guo, W., Zhan, C., Liu, X., Bai, Z., and Yang, Y. (2015). WDR5 Expression Is Prognostic of Breast Cancer Outcome. PLoS One 10, e0124964.

Davies, T. G., Wixted, W. E., Coyle, J. E., Griffiths-Jones, C., Hearn, K., McMenamin, R., Norton, D., Rich, S. J., Richardson, C., Saxty, G., et al. (2016). Monoacidic Inhibitors of the Kelch-like ECH-Associated Protein 1: Nuclear Factor Erythroid 2-Related Factor 2 (KEAP1: NRF2) Protein-Protein Interaction with High Cell Potency Identified by Fragment-Based Discovery. J Med Chem 59, 3991-4006.

Dias, J., Van Nguyen, N., Georgiev, P., Gaub, A., Brettschneider, J., Cusack, S., Kadlec, J., and Akhtar, A. (2014). Structural analysis of the KANSL1/WDR5/KANSL2 complex reveals that WDR5 is required for efficient assembly and chromatin targeting of the NSL complex. Genes & development 28, 929-942.

E. Wakeling, A. (1995). Use of pure antioestrogens to elucidate the mode of action of oestrogens. Biochem Pharmacol 49, 1545-1549.

Ee, L. S., McCannell, K. N., Tang, Y., Fernandes, N., Hardy, W. R., Green, M. R., Chu, F., and Fazzio, T. G. (2017). An Embryonic Stem Cell-Specific NuRD Complex Functions through Interaction with WDR5. Stem Cell Reports 8, 1488-1496.

Fan, Q., Aksoy, O., Wong, R. A., Ilkhanizadeh, S., Novotny, C. J., Gustafson, W. C., Truong, A. Y., Cayanan, G., Simonds, E. F., Haas-Kogan, D., et al. (2017). A Kinase Inhibitor Targeted to mTORC1 Drives Regression in Glioblastoma. Cancer Cell 31, 424-435.

Fischer, E. S., Bohm, K., Lydeard, J. R., Yang, H., Stadler, M. B., Cavadini, S., Nagel, J., Serluca, F., Acker, V., Lingaraju, G. M., et al. (2014). Structure of the DDB1-CRBN E3 ubiquitin ligase in complex with thalidomide. Nature 512, 49-53.

Galdeano, C., Gadd, M. S., Soares, P., Scaffidi, S., Van Molle, I., Birced, I., Hewitt, S., Dias, D. M., and Ciulli, A. (2014). Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem 57, 8657-8663.

Ge, Z., Song, E. J., Kawasawa, Y. I., Li, J., Dovat, S., and Song, C. (2016). WDR5 high expression and its effect on tumorigenesis in leukemia. Oncotarget 7, 37740-37754.

Getlik, M., Smil, D., Zepeda-Velazquez, C., Bolshan, Y., Poda, G., Wu, H., Dong, A., Kuznetsova, E., Marcellus, R., Senisterra, G., et al. (2016). Structure-Based Optimization of a Small Molecule Antagonist of the Interaction Between WD Repeat-Containing Protein 5 (WDR5) and Mixed-Lineage Leukemia 1 (MLL1). J Med Chem 59, 2478-2496.

Grebien, F., Vedadi, M., Getlik, M., Giambruno, R., Grover, A., Avellino, R., Skucha, A., Vittori, S., Kuznetsova, E., Smil, D., et al. (2015). Pharmacological targeting of the Wdr5-MLL interaction in C/EBPalpha N-terminal leukemia. Nat Chem Biol 11, 571-578.

Guarnaccia, A. D., and Tansey, W. P. (2018). Moonlighting with WDR5: A Cellular Multitasker. Journal of clinical medicine 7.

Higa, L. A., Wu, M., Ye, T., Kobayashi, R., Sun, H., and Zhang, H. (2006). CUL4-DDB1 ubiquitin ligase interacts with multiple WD40-repeat proteins and regulates histone methylation. Nature cell biology 8, 1277-1283.

Hiroyuki Suda, Tomohisa Takita, Takaaki Aoyagi, and Umezawa, H. (1976). The structure of bestatin. The Journal of Antibiotic 20, 100-101.

Ito, T., Ando, H., Suzuki, T., Ogura, T., Hotta, K., Imamura, Y., Yamaguchi, Y., and Handa, H. (2010). Identification of a primary target of thalidomide teratogenicity. Science 327, 1345-1350.

Karatas, H., Li, Y., Liu, L., Ji, J., Lee, S., Chen, Y., Yang, J., Huang, L., Bernard, D., Xu, J., et al. (2017). Discovery of a Highly Potent, Cell-Permeable Macrocyclic Peptidomimetic (MM-589) Targeting the WD Repeat Domain 5 Protein (WDR5)-Mixed Lineage Leukemia (MLL) Protein-Protein Interaction. J Med Chem 60, 4818-4839.

Lai, A. C., Toure, M., Hellerschmied, D., Salami, J., Jaime-Figueroa, S., Ko, E., Hines, J., and Crews, C. M. (2016). Modular PROTAC Design for the Degradation of Oncogenic BCR-ABL. Angew Chem Int Ed Engl 55, 807-810.

Li, D. D., Chen, W. L., Wang, Z. H., Xie, Y. Y., Xu, X. L., Jiang, Z. Y., Zhang, X. J., You, Q. D., and Guo, X. K. (2016a). High-affinity small molecular blockers of mixed lineage leukemia 1 (MLL1)-WDR5 interaction inhibit MLL1 complex H3K4 methyltransferase activity. European journal of medicinal chemistry 124, 480-489.

Li, D. D., Chen, W. L., Xu, X. L., Jiang, F., Wang, L., Xie, Y. Y., Zhang, X. J., Guo, X. K., You, Q. D., and Sun, H. P. (2016b). Structure-based design and synthesis of small molecular inhibitors disturbing the interaction of MLL1-WDR5. European journal of medicinal chemistry 118, 1-8.

Liu, J., Farmer, J. D., Jr., Lane, W. S., Friedman, J., Weissman, I., and Schreiber, S. L. (1991). Calcineurin is a common target of cyclophilin-cyclosporin A and FKBP-FK506 complexes. Cell 66, 807-815.

Lu, J., Qian, Y., Altieri, M., Dong, H., Wang, J., Raina, K., Hines, J., Winkler, J. D., Crew, A. P., Coleman, K., et al. (2015). Hijacking the E3 Ubiquitin Ligase Cereblon to Efficiently Target BRD4. Chemistry & biology 22, 755-763.

Maniaci, C., Hughes, S. J., Testa, A., Chen, W., Lamont, D. J., Rocha, S., Alessi, D. R., Romeo, R., and Ciulli, A. (2017). Homo-PROTACs: bivalent small-molecule dimerizers of the VHL E3 ubiquitin ligase to induce self-degradation. Nat Commun 8, 830.

Migliori, V., Muller, J., Phalke, S., Low, D., Bezzi, M., Mok, W. C., Sahu, S. K., Gunaratne, J., Capasso, P., Bassi, C., et al. (2012). Symmetric dimethylation of H3R2 is a newly identified histone mark that supports euchromatin maintenance. Nat Struct Mol Biol 19, 136-144.

Miller, T., Krogan, N. J., Dover, J., Erdjument-Bromage, H., Tempst, P., Johnston, M., Greenblatt, J. F., and Shilatifard, A. (2001). COMPASS: a complex of proteins associated with a trithorax-related SET domain protein. Proc Natl Acad Sci USA 98, 12902-12907.

Odho, Z., Southall, S. M., and Wilson, J. R. (2010). Characterization of a novel WDR5-binding site that recruits RbBP5 through a conserved motif to enhance methylation of histone H3 lysine 4 by mixed lineage leukemia protein-1. The Journal of biological chemistry 285, 32967-32976.

Ohoka, N., Okuhira, K., Ito, M., Nagai, K., Shibata, N., Hattori, T., Ujikawa, O., Shimokawa, K., Sano, O., Koyama, R., et al. (2017). In Vivo Knockdown of Pathogenic Proteins via Specific and Nongenetic Inhibitor of Apoptosis Protein (IAP)-dependent Protein Erasers (SNIPERs). J Biol Chem 292, 4556-4570.

Okuhira, K., Ohoka, N., Sai, K., Nishimaki-Mogami, T., Itoh, Y., Ishikawa, M., Hashimoto, Y., and Naito, M. (2011). Specific degradation of CRABP-II via cIAP1-mediated ubiquitylation induced by hybrid molecules that crosslink cIAP1 and the target protein. FEBS Lett 585, 1147-1152.

Patel, A., Dharmarajan, V., and Cosgrove, M. S. (2008a). Structure of WDR5 bound to mixed lineage leukemia protein-1 peptide. The Journal of biological chemistry 283, 32158-32161.

Patel, A., Vought, V. E., Dharmarajan, V., and Cosgrove, M. S. (2008b). A conserved arginine-containing motif crucial for the assembly and enzymatic activity of the mixed lineage leukemia protein-1 core complex. The Journal of biological chemistry 283, 32162-32175.

Rodrik-Outmezguine, V. S., Okaniwa, M., Yao, Z., Novotny, C. J., McWhirter, C., Banaji, A., Won, H., Wong, W., Berger, M., de Stanchina, E., et al. (2016). Overcoming mTOR resistance mutations with a new-generation mTOR inhibitor. Nature 534, 272-276.

Roguev, A., Schaft, D., Shevchenko, A., Pijnappel, W. W., Wilm, M., Aasland, R., and Stewart, A. F. (2001). The *Saccharomyces cerevisiae* Set1 complex includes an Ash2 homologue and methylates histone 3 lysine 4. The EMBO journal 20, 7137-7148.

Senisterra, G., Wu, H., Allali-Hassani, A., Wasney, G. A., Barsyte-Lovejoy, D., Dombrovski, L., Dong, A., Nguyen, K. T., Smil, D., Bolshan, Y., et al. (2013). Small-molecule inhibition of MLL activity by disruption of its interaction with WDR5. Biochem J 449, 151-159.

Shibata, N., Miyamoto, N., Nagai, K., Shimokawa, K., Sameshima, T., Ohoka, N., Hattori, T., Imaeda, Y., Nara, H., Cho, N., et al. (2017). Development of protein degradation inducers of oncogenic BCR-ABL protein by conjugation of ABL kinase inhibitors and IAP ligands. Cancer Sci 108, 1657-1666.

Song, J. J., and Kingston, R. E. (2008). WDR5 interacts with mixed lineage leukemia (MLL) protein via the histone H3-binding pocket. The Journal of biological chemistry 283, 35258-35264.

Sun, D., Li, Z., Rew, Y., Gribble, M., Bartberger, M. D., Beck, H. P., Canon, J., Chen, A., Chen, X., Chow, D., et al. (2014). Discovery of AMG 232, a potent, selective, and orally bioavailable MDM2-p53 inhibitor in clinical development. J Med Chem 57, 1454-1472.

Sun, W., Guo, F., and Liu, M. (2018). Up-regulated WDR5 promotes gastric cancer formation by induced cyclin D1 expression. J Cell Biochem 119, 3304-3316.

Sun, Y., Bell, J. L., Carter, D., Gherardi, S., Poulos, R. C., Milazzo, G., Wong, J. W., Al-Awar, R., Tee, A. E., Liu, P. Y., et al. (2015). WDR5 Supports anN-Myc Transcriptional Complex That Drives a Protumorigenic Gene Expression Signature in Neuroblastoma. Cancer Res 75, 5143-5154.

Tan, X., Chen, S., Wu, J., Lin, J., Pan, C., Ying, X., Pan, Z., Qiu, L., Liu, R., Geng, R., et al. (2017). PI3K/AKT-mediated upregulation of WDR5 promotes colorectal cancer metastasis by directly targeting ZNF407. Cell Death Dis 8, e2686.

Thomas, L. R., Foshage, A. M., Weissmiller, A. M., and Tansey, W. P. (2015a). The MYC-WDR5 Nexus and Cancer. Cancer Res 75, 4012-4015.

Thomas, L. R., Wang, Q., Grieb, B. C., Phan, J., Foshage, A. M., Sun, Q., Olejniczak, E. T., Clark, T., Dey, S., Lorey, S., et al. (2015b). Interaction with WDR5 promotes target gene recognition and tumorigenesis by MYC. Molecular cell 58, 440-452.

Trievel, R. C., and Shilatifard, A. (2009). WDR5, a complexed protein. Nature structural & molecular biology 16, 678-680.

Varfolomeev, E., Blankenship, J. W., Wayson, S. M., Fedorova, A. V., Kayagaki, N., Garg, P., Zobel, K., Dynek, J. N., Elliott, L. O., Wallweber, H. J., et al. (2007). IAP antagonists induce autoubiquitination of c-IAPs, NF-kappaB activation, and TNFalpha-dependent apoptosis. Cell 131, 669-681.

Vassilev, L. T., Vu, B. T., Graves, B., Carvajal, D., Podlaski, F., Filipovic, Z., Kong, N., Kammlott, U., Lukacs, C., Klein, C., et al. (2004). In vivo activation of the p53 pathway by small-molecule antagonists of MDM2. Science 303, 844-848.

Vu, B., Wovkulich, P., Pizzolato, G., Lovey, A., Ding, Q., Jiang, N., Liu, J. J., Zhao, C., Glenn, K., Wen, Y., et al. (2013). Discovery of RG7112: A Small-Molecule MDM2 Inhibitor in Clinical Development. ACS Med Chem Lett 4, 466-469.

Weisberg, E., Ray, A., Barrett, R., Nelson, E., Christie, A. L., Porter, D., Straub, C., Zawel, L., Daley, J. F., Lazo-Kallanian, S., et al. (2010). Smac mimetics: implications for enhancement of targeted therapies in leukemia. Leukemia 24, 2100-2109.

Winter, G. E., Buckley, D. L., Paulk, J., Roberts, J. M., Souza, A., Dhe-Paganon, S., and Bradner, J. E. (2015). Phthalimide conjugation as a strategy for in vivo target protein degradation. Science 348, 1376-1381.

Wu, Y., Diao, P., Li, Z., Zhang, W., Wang, D., Wang, Y., and Cheng, J. (2018). Overexpression of WD repeat domain 5 associates with aggressive clinicopathological features and unfavorable prognosis in head neck squamous cell carcinoma. J Oral Pathol Med.

Xie, Q., Li, Z., and Chen, J. (2017). WDR5 positively regulates p53 stability by inhibiting p53 ubiquitination. Biochem Biophys Res Commun 487, 333-338.

Xie, T., Lim, S. M., Westover, K. D., Dodge, M. E., Ercan, D., Ficarro, S. B., Udayakumar, D., Gurbani, D., Tae, H. S., Riddle, S. M., et al. (2014). Pharmacological targeting of the pseudokinase Her3. Nat Chem Biol 10, 1006-1012.

Zengerle, M., Chan, K. H., and Ciulli, A. (2015). Selective Small Molecule Induced Degradation of the BET Bromodomain Protein BRD4. ACS Chem Biol 10, 1770-1777.

What is claimed is:

1. A bivalent compound comprising a WD40 repeat domain protein 5 (WDR5) ligand conjugated to a degradation/disruption tag through a linker, said linker selected from the group consisting of:

FORMULA 8

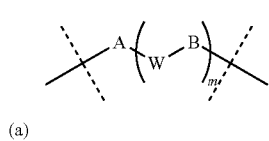

(a)

FORMULA 8A

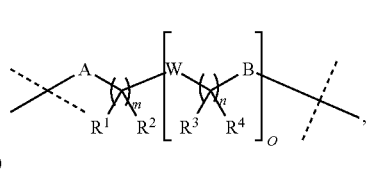

(b)

wherein

A, W and B, at each occurrence, are independently selected from null, or bivalent moiety selected from R'-R", R'COR", R'CO$_2$R", R'C(O)N(R$^1$)R", R'C(S)N(R$^1$)R", R'OR", R'OC(O)R", R'OC(O)OR", R'OCON(R$^1$)R", R'SR", R'SOR", R'SO$_2$R", R'SO$_2$N(R$^1$)R", R'N(R$^1$)R", R'NR"COR", R'NR$^1$C(O)OR", R'NR"CON(R$^2$)R", R'NR"C(S)R", R'NR$^1$S(O)R", R'NR$^1$S(O)$_2$R", and R'NR$^1$S(O)$_2$N(R$^2$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_5$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_5$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^1$ and R$^2$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^1$ and R$^2$, R' and R$^1$, R$^1$ and R$^2$, R" and R$^1$, R" and R$^2$ together with the atom to which they are connected form a 3-20 membered cycloalkyl or 4-20 membered heterocyclyl ring; and m is 0 to 15;

wherein

R$^1$, R$^2$, R$^3$ and R$^4$, at each occurrence, are independently selected from hydrogen, halogen, hydroxyl, amino, cyano, nitro, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$ alkylamino, and optionally substituted C$_1$-C$_8$ alkylaminoC$_1$-C$_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl, or R$^1$ and R$^2$, R$^3$ and R$^4$ together with the atom to which they are connected form a 3-20 membered cycloalkyl or 4-20 membered heterocyclyl ring;

A, W and B, at each occurrence, are independently selected from null, or bivalent moiety selected from R'-R", R'COR", R'CO$_2$R", R'C(O)N(R$^5$)R", R'C(S)N(R$^5$)R", R'OR", R'OC(O)R", R'OC(O)OR", R'OCONR$^5$R", R'SR", R'SOR", R'SO$_2$R", R'SO$_2$N(R$^5$)R", R'N(R$^5$)R", R'NR$^5$COR", R'NR$^5$C(O)OR", R'NR$^5$CON(R$^6$)R", R'NR$^5$C(S)R", R'NR$^5$S(O)R", R'NR$^5$S(O)$_2$R", and R'NR$^5$S(O)$_2$N(R$^6$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted $C_3$-$C_{13}$ spiro heterocyclyl, optionally substituted aryl, and optionally substituted heteroaryl;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;
n, at each occurrence, is 0 to 15; and
o is 0 to 15;

FORMULA 8B

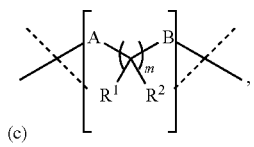

(c)

wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'-R", R'COR", R'CO$_2$R", R'C(O)NR$^3$R", R'C(S)NR$^3$R", R'OR", R'OC(O)R", R'OC(O)OR", R'OCON(R$^3$)R", R'SR", R'SOR", R'SO$_2$R", R'SO$_2$N(R$^3$)R", R'N(R$^3$)R", R'NR$^3$COR", R'NR$^3$C(O)OR", R'NR$^3$CON(R$^4$)R', R'NR$^3$C(S)R", R'NR$^3$S(O)R", R'NR$^3$S(O)$_2$R", and R'NR$^3$S(O)$_2$N(R$^4$)R", wherein R' and R" are independently selected from null, optionally substituted R$^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^3$ and $R^4$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

m, at each occurrence, is 0 to 15; and
n is 0 to 15;

FORMULA 8C

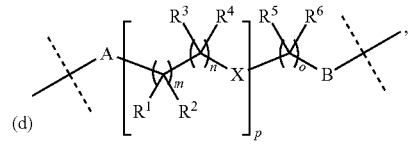

(d)

wherein

X is selected from O, NH, and NR$^7$;

$R^1$, $R^2$, $R^3$, $R^4$, $R^5$, and $R^6$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'-R", R'COR", R'CO$_2$R", R'C(O)N(R$^8$)R", R'C(S)N(R$^8$)R", R'OR", R'OC(O)R", R'OC(O)OR", R'OCON(R$^8$)R", R'SR", R'SOR", R'SO$_2$R", R'SO$_2$N(R$^8$)R", R'N(R$^8$)R", R'NR$^B$COR", R'NR$^B$C(O)OR", R'NR$^B$CON(R$^9$)R", R'NR$^B$C(S)R", R'NR$^B$S(O)R", R'NR$^B$S(O)$_2$R", and R'NR$^B$S(O)$_2$N(R$^9$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^7$, R$^8$ and R$^9$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^8$ and R$^9$, R' and R$^8$, R' and R$^9$, R" and R$^8$, R" and R$^9$ together with the atom to which they are connected form a 3-20 membered cycloalkyl or 4-20 membered heterocyclyl ring;

m, at each occurrence, is 0 to 15;
n, at each occurrence, is 0 to 15;
o is 0 to 15; and
p is 0 to 15;

(e) the linker comprises a ring selected from the group consisting of a 3 to 13 membered ring, a 3 to 13 membered fused ring, a 3 to 13 membered bridged ring, and a 3 to 13 membered spiro ring;

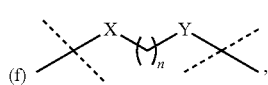

FORMULA A wherein X is C═O or CH$_2$,

Y is C═O or CH$_2$, and n is 0-15;

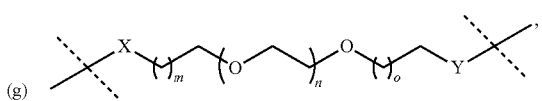

Formula B wherein X is C═O or CH$_2$,

Y is C═O or CH$_2$, m is 0-15, n is 0-6, and o is 0-15; or

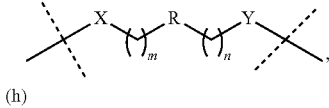

Formula C wherein

X is C═O or CH$_2$,

Y is C═O or CH$_2$,

R is —CH$_2$—, —CF$_2$—, —CH(C$_{1-3}$ alkyl)-, —C(C$_{1-3}$ alkyl)(C$_{1-3}$ alkyl)-, —CH═CH—, —C(C$_{1-3}$ alkyl)═C(C$_{1-3}$ alkyl)-, —C═C—, —O—, —NH—, —N(C$_{1-3}$ alkyl)-, —C(O)NH—, —C(O)N(C$_{1-3}$ alkyl)-, a 3-13 membered ring, a 3-13 membered fused ring, a 3-13 membered bridged ring, and/or a 3-13 membered spiro ring, m is 0-15, and n is 0-15; and wherein the WDR5 ligand is selected from

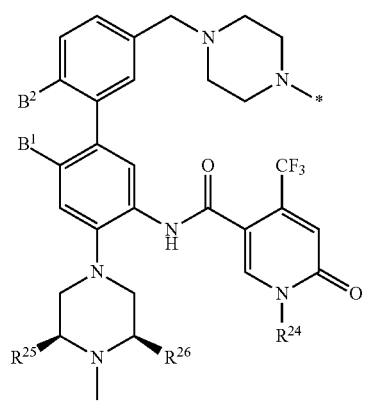

FORMULA 1A

FORMULA 1B
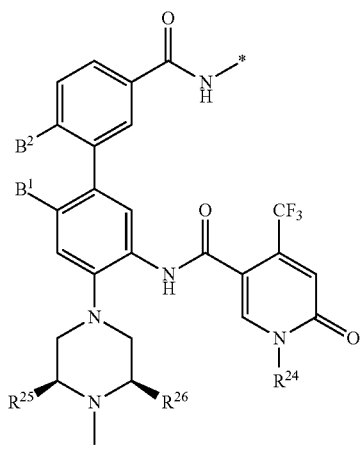
FORMULA 1E
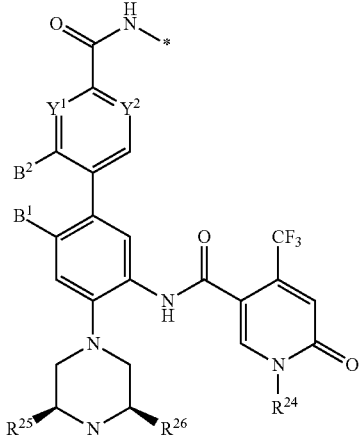
FORMULA 1C
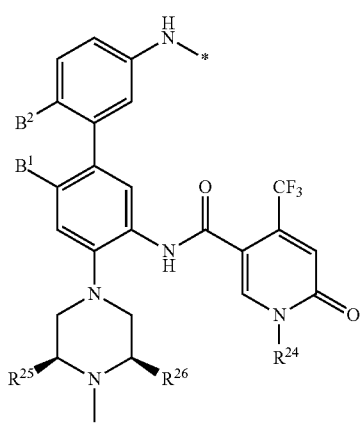
FORMULA 1F
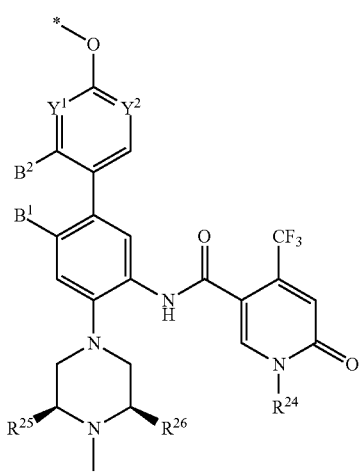
FORMULA 1D
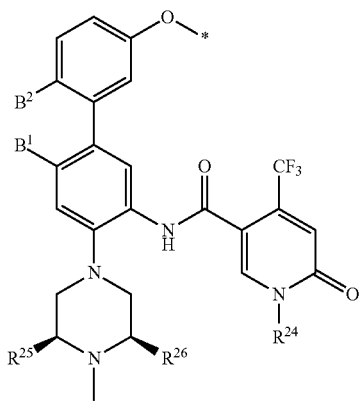
FORMULA 1G
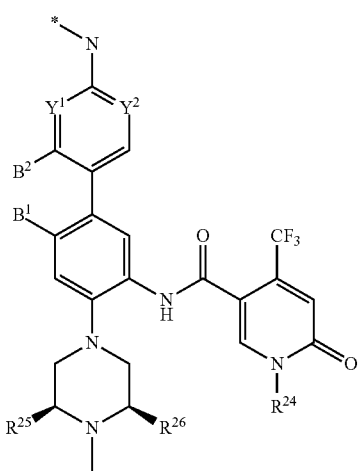

FORMULA 1H
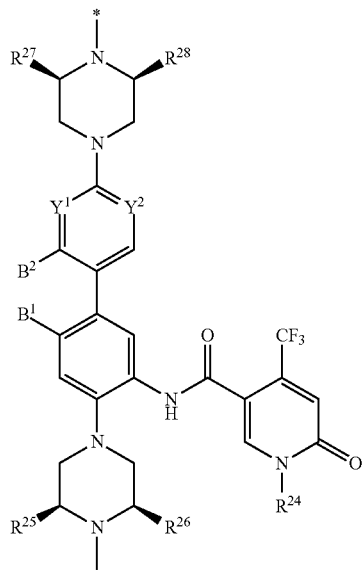
FORMULA 1J
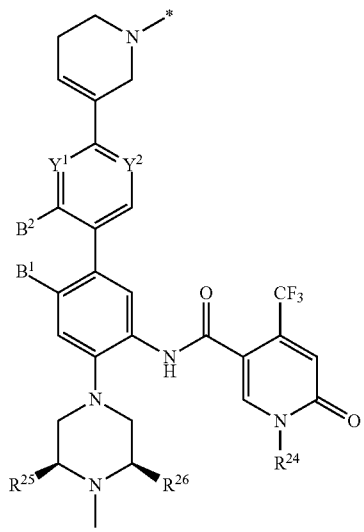
FORMULA 1K
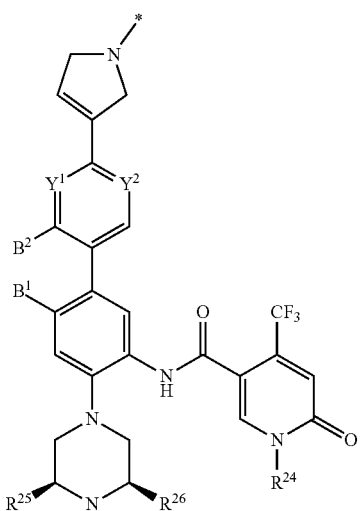
FORMULA 1I
FORMULA 1L
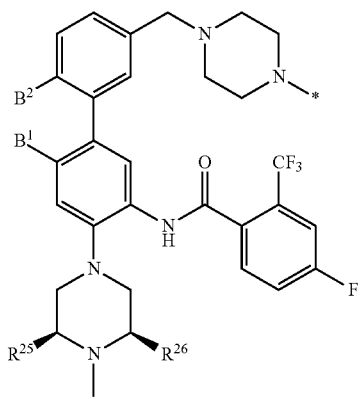

FORMULA 1M
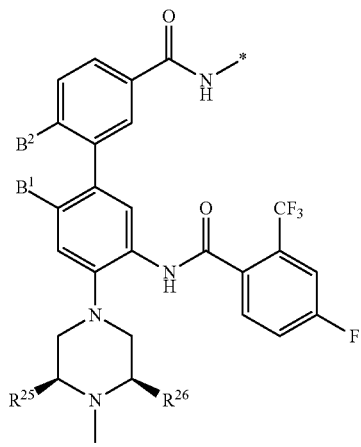
FORMULA 1P
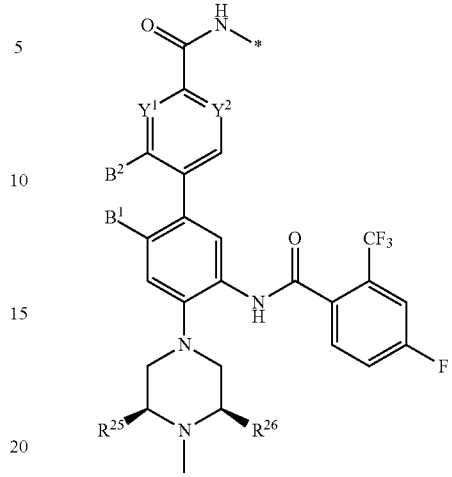
FORMULA 1N
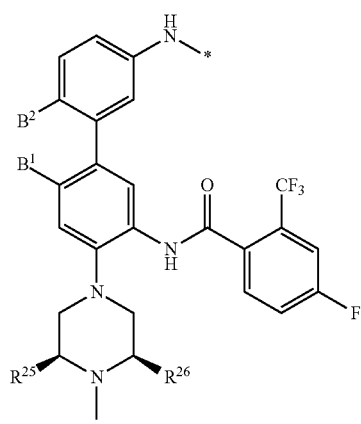
FORMULA 1Q
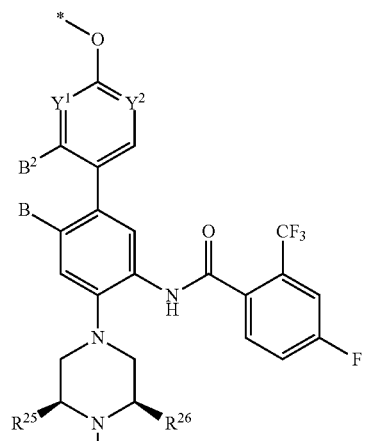
FORMULA 1O
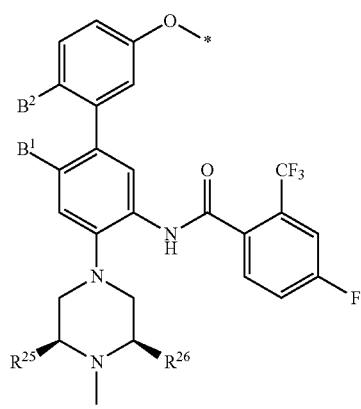
FORMULA 1R
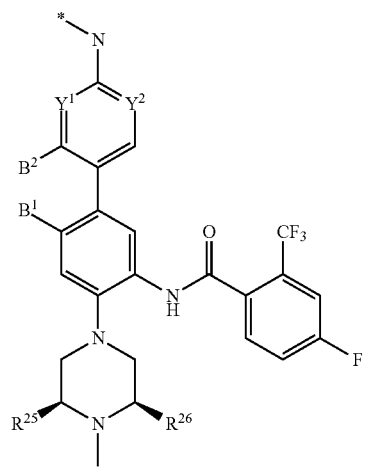

FORMULA 1S
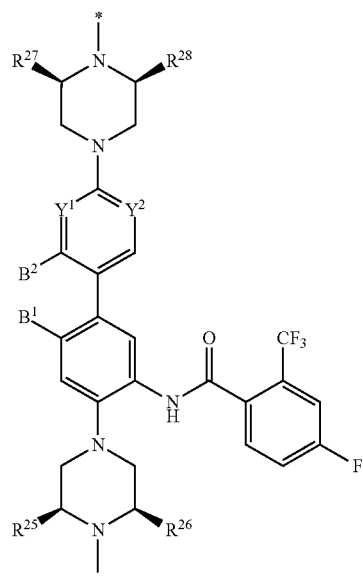
FORMULA 1T
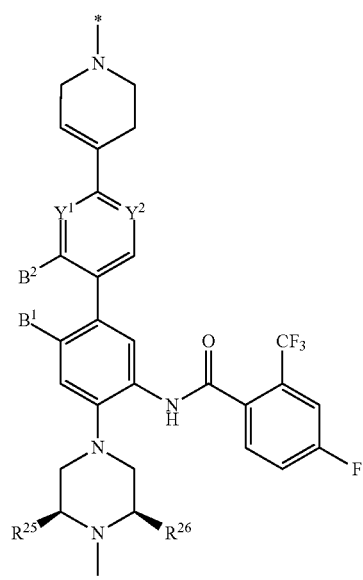
FORMULA 1U
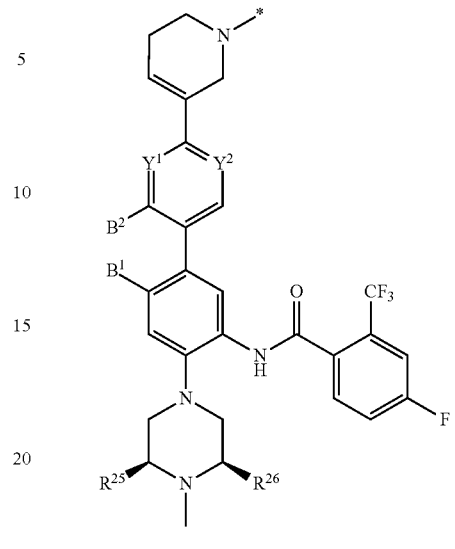
FORMULA 1V
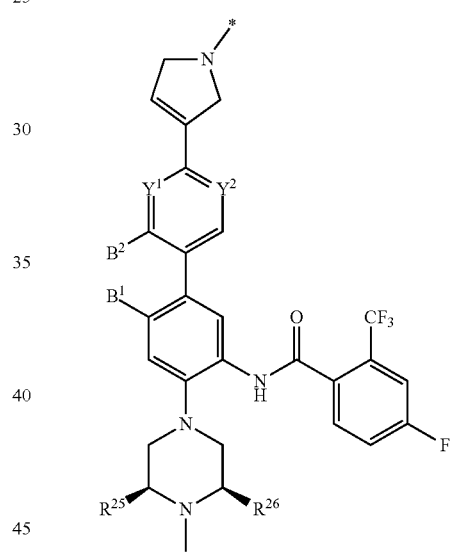
FORMULA 1W
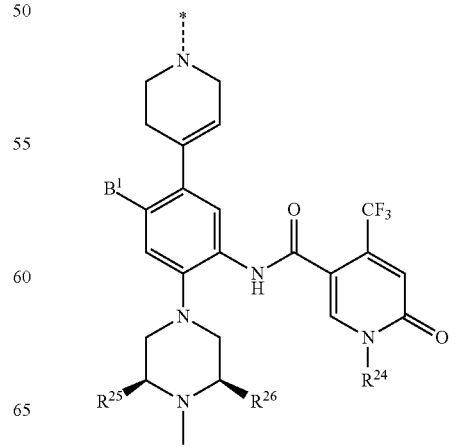

1461 -continued
FORMULA 1X
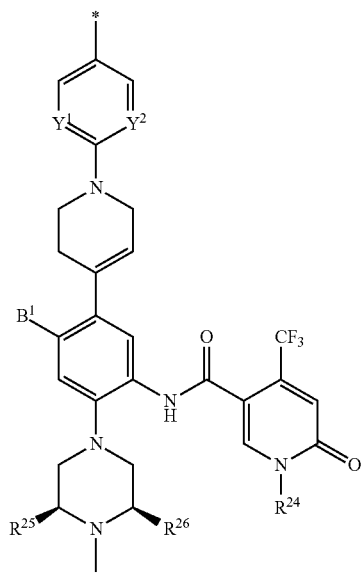
1462 -continued
FORMULA 1Z
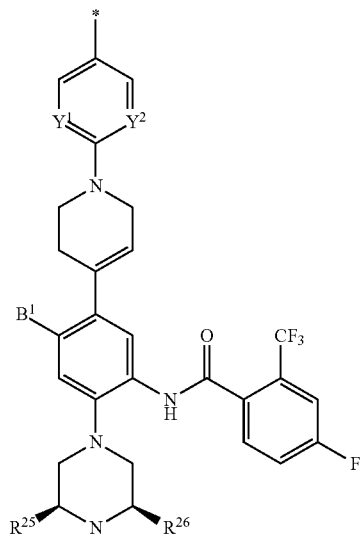
FORMULA 1Y
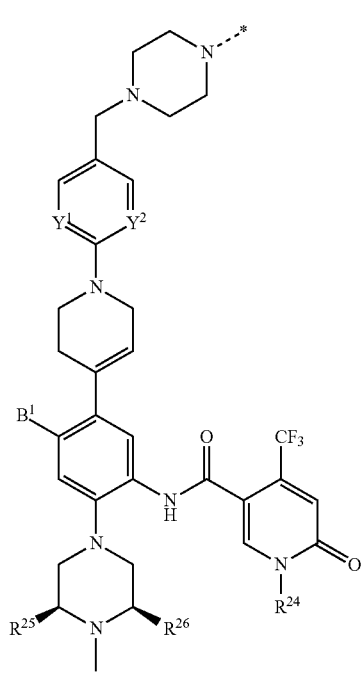
FORMULA 1AA
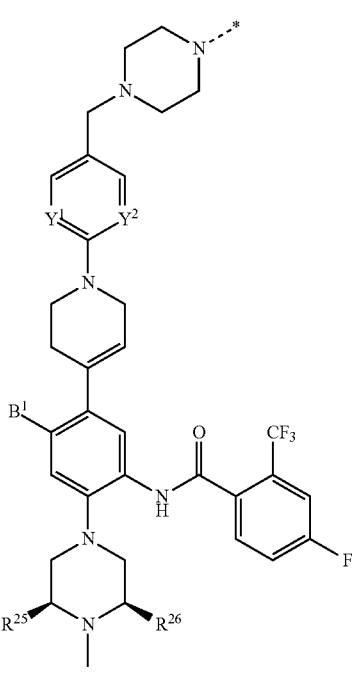

1463
-continued
FORMULA 1AB
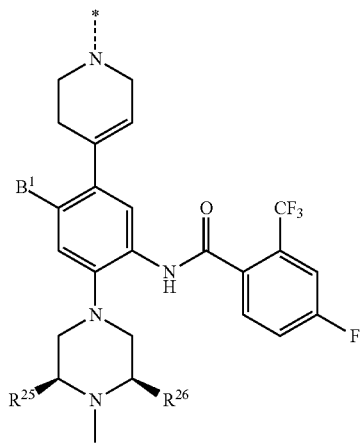
FORMULA 1AC
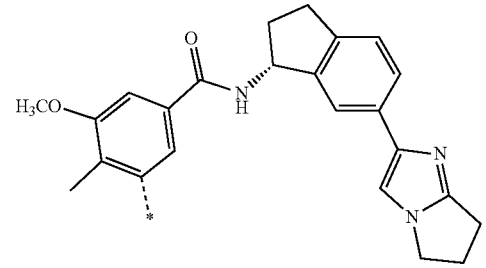
FORMULA 1AD
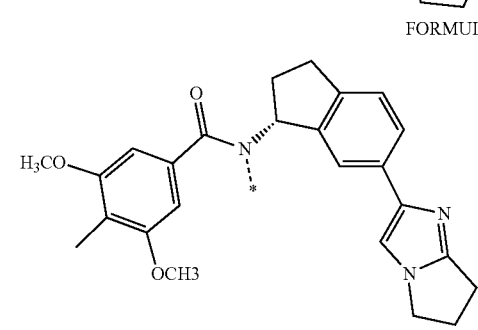
FORMULA 1AE
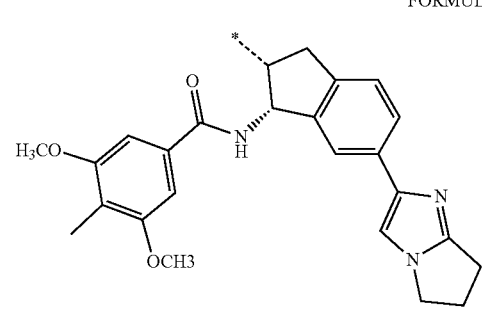
FORMULA 1AF
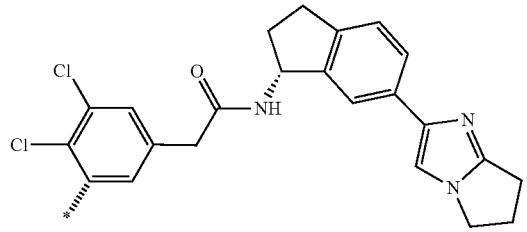
1464
-continued
FORMULA 1AG
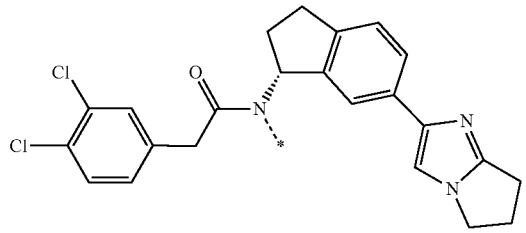
FORMULA 1AH
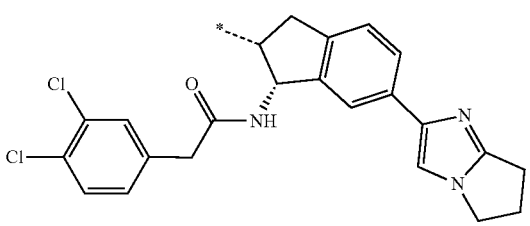
FORMULA 1AI
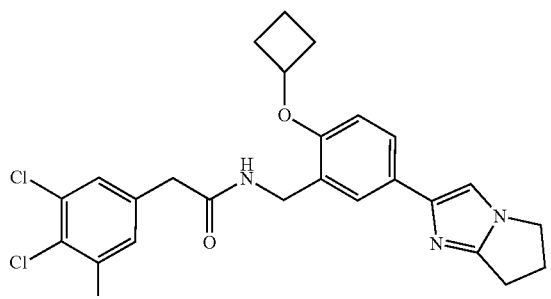
FORMULA 1AJ
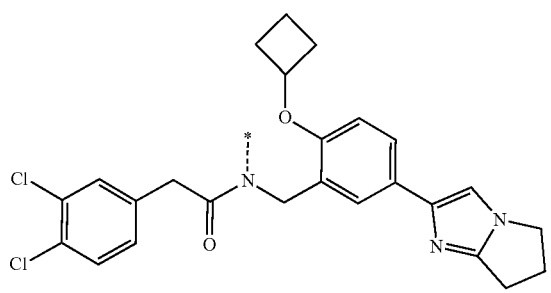
FORMULA 1AK
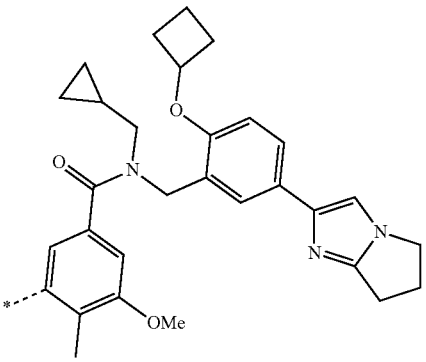

-continued

FORMULA 1AL

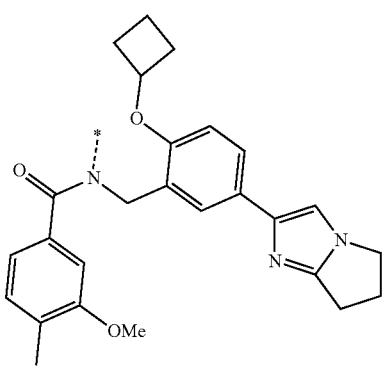

FORMULA 1AM

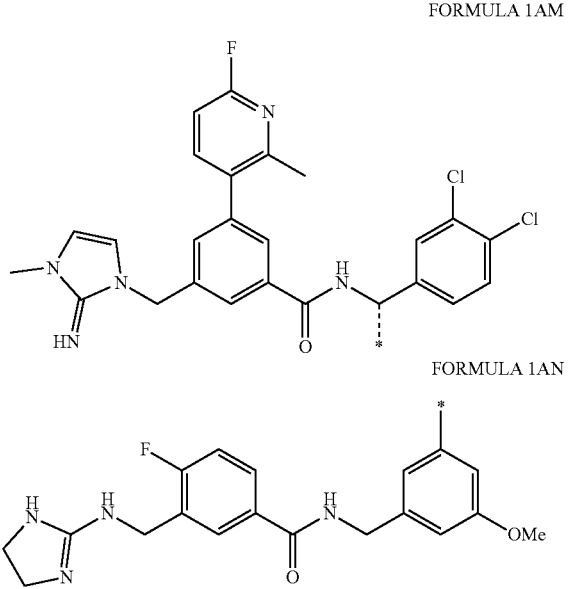

FORMULA 1AN

wherein $R^{24}$, $R^{25}$, $R^{26}$, $R^{27}$, and $R^{28}$ are independently selected from H and $CH_3$;

$B^1$ and $B^2$ are independently selected from H and F; and $Y^1$ and $Y^2$ are independently selected from CH and N;

and wherein the degradation/disruption tag is selected from

FORMULA 5A

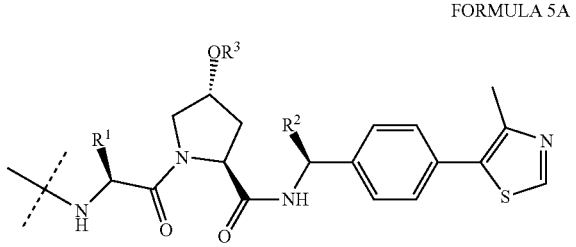

wherein $R^1$ and $R^2$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_1$-$C_8$ aminoalkyl, $C_1$-$C_8$ alkylaminoalkyl, $C_3$-$C_7$ cycloalkyl, $C_3$-$C_7$ heterocyclyl, $C_2$-$C_8$ alkenyl, or $C_2$-$C_8$ alkynyl;

$R^3$ is H, $C(O)C_1$-$C_8$ alkyl, $C(O)C_1$-$C_8$ alkoxyalkyl, $C(O)C_1$-$C_8$ haloalkyl, $C(O)C_1$-$C_8$ hydroxyalkyl, $C(O)C_1$-$C_8$ aminoalkyl, $C(O)C_1$-$C_8$ alkylaminoalkyl, $C(O)C_3$-$C_7$ cycloalkyl, $C(O)C_3$-$C_7$ heterocyclyl, $C(O)C_2$-$C_5$ alkenyl, $C(O)C_2$-$C_5$ alkynyl, $C(O)OC_1$-$C_8$ alkoxyalkyl, $C(O)OC_1$-$C_8$ haloalkyl, $C(O)OC_1$-$C_8$ hydroxyalkyl, $C(O)OC_1$-$C_8$ aminoalkyl, $C(O)OC_1$-$C_8$ alkylaminoalkyl, $C(O)OC_3$-$C_7$ cycloalkyl, $C(O)OC_3$-$C_7$ heterocyclyl, $C(O)OC_2$-$C_8$ alkenyl, $C(O)OC_2$-$C_8$ alkynyl, $C(O)NC_1$-$C_8$ alkoxyalkyl, $C(O)NC_1$-$C_8$ haloalkyl, $C(O)NC_1$-$C_8$ hydroxyalkyl, $C(O)NC_1$-$C_8$ aminoalkyl, $C(O)NC_1$-$C_8$ alkylaminoalkyl, $C(O)NC_3$-$C_7$ cycloalkyl, $C(O)NC_3$-$C_7$ heterocyclyl, $C(O)NC_2$-$C_8$ alkenyl, $C(O)NC_2$-$C_8$ alkynyl, $P(O)(OH)_2$, $P(O)(OC_1$-$C_8$ alkyl$)_2$, or $P(O)(OC_1$-$C_8$ aryl$)_2$.

2. The bivalent compound of claim 1, wherein the linker comprises:

FORMULA 8

wherein

A, W and B, at each occurrence, are independently selected from null, or bivalent moiety selected from R'-R", R'COR", R'CO$_2$R", R'C(O)N(R$^1$)R", R'C(S)N(R$^1$)R", R'OR", R'OC(O)R", R'OC(O)OR", R'OCON(R$^1$)R", R'SR", R'SOR", R'SO$_2$R", R'SO$_2$N(R$^1$)R", R'N(R$^1$)R", R'NR"COR", R'NR$^1$C(O)OR", R'NR"CON(R$^2$)R", R'NR"C(S)R", R'NR$^1$S(O)R", R'NR$^1$S(O)$_2$R", and R'NR$^1$S(O)$_2$N(R$^2$)R", wherein R' and R" are independently selected from null, optionally substituted R$^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^1$ and $R^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^1$ and $R^2$, R' and $R^1$, R' and $R^2$, R" and $R^1$, R" and $R^2$ together with the atom to which they are connected form a 3-20 membered cycloalkyl or 4-20 membered heterocyclyl ring; and m is 0 to 15.

3. The bivalent compound of claim 1, wherein the linker comprises:

FORMULA 8A

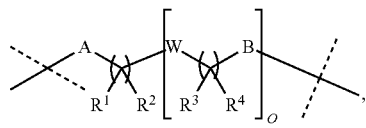

wherein $R^1$, $R^2$, $R^3$ and $R^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl, or $R^1$ and $R^2$, $R^3$ and $R^4$ together with the atom to which they are connected form a 3-20 membered cycloalkyl or 4-20 membered heterocyclyl ring;

A, W and B, at each occurrence, are independently selected from null, or bivalent moiety selected from R'-R", R'COR", R'CO$_2$R", R'C(O)N($R^5$)R", R'C(S)N($R^5$)R", R'OR", R'OC(O)R", R'OC(O)OR", R'OCONR$^5$R", R'SR", R'SOR", R'SO$_2$R', R'SO$_2$N($R^5$)R", R'N($R^5$)R", R'NR$^5$COR", R'NR$^5$C(O)OR", R'NR$^5$CON($R^6$)R", R'NR$^5$C(S)R", R'NR$^5$S(O)R", R'NR$^5$S(O)$_2$R", and R'NR$^5$S(O)$_2$N($R^6$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;

n, at each occurrence, is 0 to 15; and o is 0 to 15.

4. The bivalent compound of claim 1, wherein the linker comprises:

FORMULA 8B

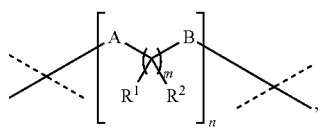

wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'-R", R'COR", R'CO$_2$R", R'C(O)NR$^3$R", R'C(S)NR$^3$R", R'OR", R'OC(O)R", R'OC(O)OR", R'OCON($R^3$)R", R'SR", R'SOR", R'SO$_2$R", R'SO$_2$N($R^3$)R", R'N($R^3$)R", R'NR$^3$COR", R'NR$^3$C(O)OR", R'NR$^3$CON($R^4$)R', R'NR³C(S)R", R'NR³S(O)R", R'NR³S(O)₂R", and R'NR³S(O)₂N(R⁴)R", wherein R' and R" are independently selected from null, optionally substituted R$^r$—(C₁-C₈ alkyl), or a moiety comprising of optionally substituted C₁-C₈ alkyl, optionally substituted C₂-C₈ alkenyl, optionally substituted C₂-C₈ alkynyl, optionally substituted C₁-C₈ hydroxyalkyl, optionally substituted C₁-C₈alkoxyC₁-C₈alkyl, optionally substituted C₁-C₈alkylaminoC₁-C₈alkyl, optionally substituted C₁-C₈ haloalkyl, optionally substituted C₁-C₈ alkylene, optionally substituted C₂-C₈ alkenylene, optionally substituted C₂-C₈ alkynylene, optionally substituted C₁-C₈ hydroxyalkylene, optionally substituted C₁-C₈alkoxyC₁-C₈alkylene, optionally substituted C₁-C₈alkylaminoC₁-C₈alkylene, optionally substituted C₁-C₈ haloalkylene, optionally substituted 3-10 membered carbocyclyl, optionally substituted 4-10 membered heterocyclyl, optionally substituted C₃-C₁₃ fused cycloalkyl, optionally substituted C₃-C₁₃ fused heterocyclyl, optionally substituted C₃-C₁₃ bridged cycloalkyl, optionally substituted C₃-C₁₃ bridged heterocyclyl, optionally substituted C₃-C₁₃ spiro cycloalkyl, optionally substituted C₃-C₁₃ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C₃-C₁₃ fused cycloalkyl, optionally substituted C₃-C₁₃ fused heterocyclyl, optionally substituted C₃-C₁₃ bridged cycloalkyl, optionally substituted C₃-C₁₃ bridged heterocyclyl, optionally substituted C₃-C₁₃ spiro cycloalkyl, optionally substituted C₃-C₁₃ spiro heterocyclyl, optionally substituted aryl, and optionally substituted heteroaryl;

R³ and R⁴ are independently selected from hydrogen, optionally substituted C₁-C₈ alkyl, optionally substituted C₂-C₈ alkenyl, optionally substituted C₂-C₈ alkynyl, optionally substituted C₁-C₈ alkoxyalkyl, optionally substituted C₁-C₈ haloalkyl, optionally substituted C₁-C₈ hydroxyalkyl, optionally substituted C₁-C₈alkylaminoC₁-C₈alkyl, optionally substituted 3-10 membered carbocyclyl, optionally substituted 4-10 membered heterocyclyl, optionally substituted aryl, and optionally substituted heteroaryl;

R' and R", R³ and R⁴, R' and R³, R' and R⁴, R" and R³, R" and R⁴ together with the atom to which they are connected form a 3-20 membered cycloalkyl or 4-20 membered heterocyclyl ring;

m, at each occurrence, is 0 to 15; and n is 0 to 15.

5. The bivalent compound of claim 1, wherein the linker comprises:

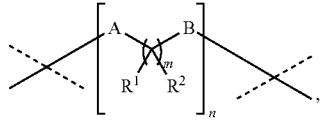

FORMULA 8B wherein

R¹ and R², at each occurrence, are independently selected from hydrogen, halogen, hydroxyl, amino, cyano, nitro, and optionally substituted C₁-C₈ alkyl, optionally substituted C₁-C₈ alkoxy, optionally substituted C₁-C₈ alkoxy C₁-C₈ alkyl, optionally substituted C₁-C₈ haloalkyl, optionally substituted C₁-C₈ hydroxyalkyl, optionally substituted C₁-C₈ alkylamino, C₁-C₈alkylaminoC₁-C₈alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or R¹ and R² together with the atom to which they are connected form a 3-20 membered cycloalkyl or 4-20 membered heterocyclyl ring;

A and B, at each occurrence, are independently selected from null, or bivalent moiety selected from R'-R", R'COR", R'CO₂R", R'C(O)NR³R", R'C(S)NR³R", R'OR", R'OC(O)R", R'OC(O)OR", R'OCON(R³)R", R'SR", R'SOR", R'SO₂R", R'SO₂N(R³)R", R'N(R³)R", R'NR³COR", R'NR³C(O)OR", R'NR³CON(R⁴)R', R'NR³C(S)R", R'NR³S(O)R", R'NR³S(O)₂R", and R'NR³S(O)₂N(R⁴)R", wherein R' and R" are independently selected from null, optionally substituted R$^r$—(C₁-C₈ alkyl), or a moiety comprising of optionally substituted C₁-C₈ alkyl, optionally substituted C₂-C₈ alkenyl, optionally substituted C₂-C₈ alkynyl, optionally substituted C₁-C₈ hydroxyalkyl, optionally substituted C₁-C₈alkoxyC₁-C₈alkyl, optionally substituted C₁-C₈alkylaminoC₁-C₈alkyl, optionally substituted C₁-C₈ haloalkyl, optionally substituted C₁-C₈ alkylene, optionally substituted C₂-C₈ alkenylene, optionally substituted C₂-C₈ alkynylene, optionally substituted C₁-C₈ hydroxyalkylene, optionally substituted C₁-C₈alkoxyC₁-C₈alkylene, optionally substituted C₁-C₈alkylaminoC₁-C₈alkylene, optionally substituted C₁-C₈ haloalkylene, optionally substituted 3-10 membered carbocyclyl, optionally substituted 4-10 membered heterocyclyl, optionally substituted C₃-C₁₃ fused cycloalkyl, optionally substituted C₃-C₁₃ fused heterocyclyl, optionally substituted C₃-C₁₃ bridged cycloalkyl, optionally substituted C₃-C₁₃ bridged heterocyclyl, optionally substituted C₃-C₁₃ spiro cycloalkyl, optionally substituted C₃-C₁₃ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C₃-C₁₃ fused cycloalkyl, optionally substituted C₃-C₁₃ fused heterocyclyl, optionally substituted C₃-C₁₃ bridged cycloalkyl, optionally substituted C₃-C₁₃ bridged heterocyclyl, optionally substituted C₃-C₁₃ spiro cycloalkyl, optionally substituted C₃-C₁₃ spiro heterocyclyl, optionally substituted aryl, and optionally substituted heteroaryl;

R³ and R⁴ are independently selected from hydrogen, optionally substituted C₁-C₈ alkyl, optionally substituted C₂-C₈ alkenyl, optionally substituted C₂-C₈ alkynyl, optionally substituted C₁-C₈ alkoxyalkyl, optionally substituted C₁-C₈ haloalkyl, optionally substituted C₁-C₈ hydroxyalkyl, optionally substituted C₁-C₈alkylaminoC₁-C₈alkyl, optionally substituted 3-10 membered carbocyclyl, optionally substituted 4-10 membered heterocyclyl, optionally substituted aryl, and optionally substituted heteroaryl;

R' and R", R³ and R⁴, R' and R³, R' and R⁴, R" and R³, R" and R⁴ together with the atom to which they are connected form a 3-20 membered cycloalkyl or 4-20 membered heterocyclyl ring;

m, at each occurrence, is 0 to 15; and n is 0 to 15.

6. The bivalent compound of claim 1, wherein the linker comprises:

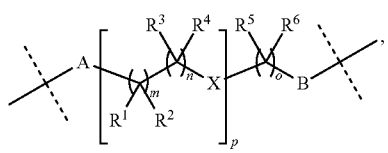

FORMULA 8C wherein
R⁵ and R⁶ are at each occurrence, hydrogen;
A is R'C(O)NR"R¹ or R'NR¹C(O)R", wherein R' is optionally substituted C₁-C₈ alkylene and R" is null;
B is R'C(O)R", wherein both R' and R" are null, or B is null;
R¹ is hydrogen; and
o is 6 to 10; and
p is 0.

7. The bivalent compound of claim 1, wherein the linker comprises:

FORMULA 8C

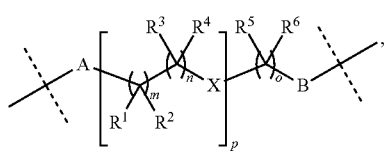

wherein
R⁵ and R⁶ are at each occurrence, hydrogen;
A is R'C(O)R", wherein R' is optionally substituted 4-10 membered heterocyclyl and R" is optionally substituted C₁-C₈ alkylene;
B is R'C(O)R", wherein R' and R" are each null;
o is 4 to 12; and
p is 0.

8. A method of treating a WD40 repeat domain protein 5 (WDR5)-mediated disease, comprising administering to a subject with a WDR5-mediated disease, a bivalent compound comprising a WDR5 ligand conjugated to a degradation/disruption tag through a linker, wherein said disease is selected from the group consisting of leukemia, lymphoma, ovarian cancer, stomach cancer, cervical cancer, uterine cancer, gastric cancer, head neck squamous cell carcinoma (HNSCC), colorectal cancer (CRC), lung cancer, pancreatic cancer, bladder cancer, breast cancer, and neuroblastoma.

9. A method for identifying a bivalent compound which mediates degradation/disruption of WDR5, the method comprising:
providing a heterobifunctional test compound comprising a WDR5 ligand conjugated to a degradation/disruption tag through a linker;
contacting the heterobifunctional test compound with a cell comprising a ubiquitin ligase and WDR5;
determining whether WDR5 levels decrease in the cell; and
identifying the heterobifunctional test compound as a bivalent compound which mediates degradation/reduction of WDR5 levels decrease in the cell.

10. A bivalent compound selected from the group consisting of:

| 369 | 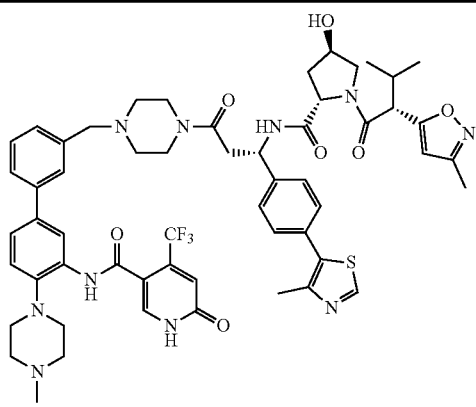 | N-(3'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
|---|---|---|
| 373 | 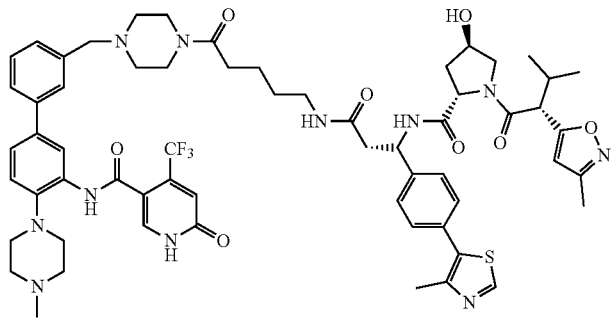 | N-(3'-((4-(5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| # | | |
|---|---|---|
| 374 | 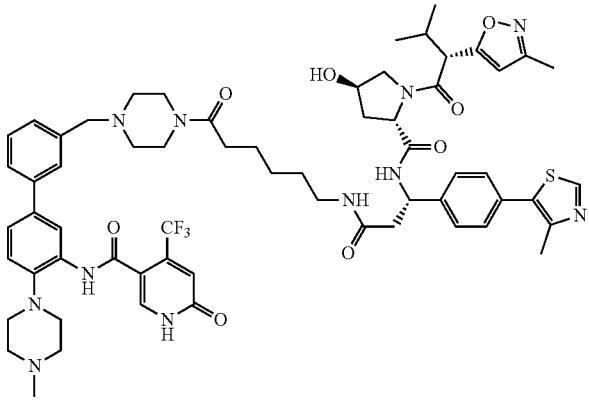 [SMILES: Cc1cc([C@H](C(=O)N2C[C@H](O)C[C@H]2C(=O)N[C@@H](CC(=O)NCCCCCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 375 | 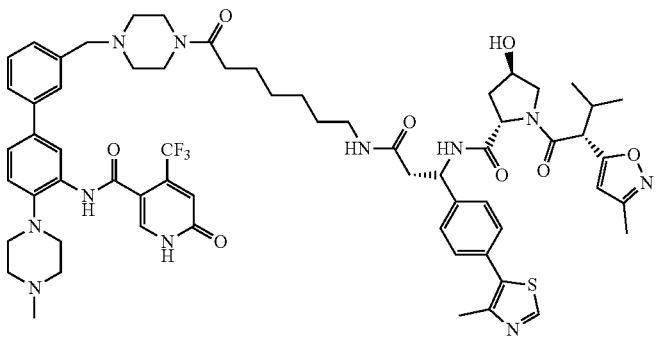 | N-(3'-((4-(7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 376 | 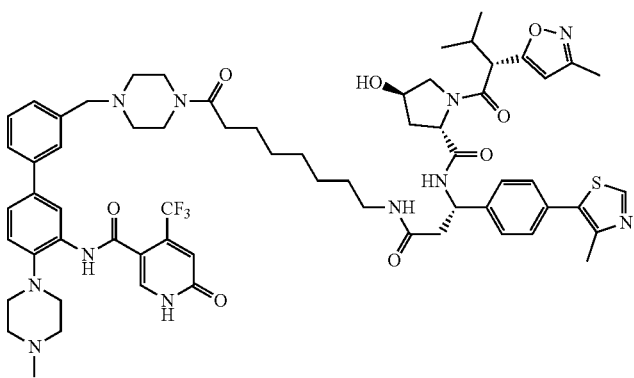 [SMILES: Cc1cc([C@H](C(=O)N2C[C@H](O)C[C@H]2C(=O)N[C@@H](CC(=O)NCCCCCCCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 377 | 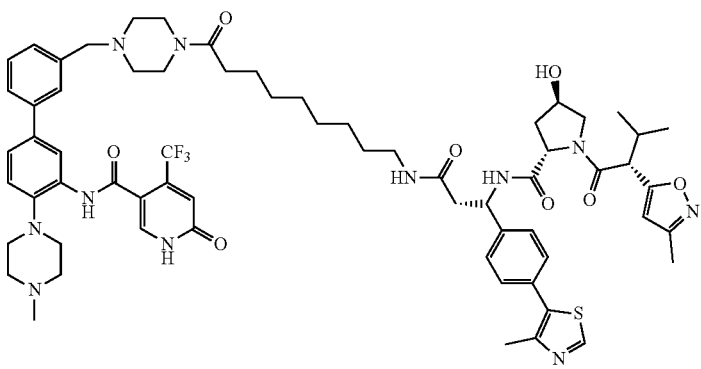 | N-(3'-((4-(9-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)nonanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| 378 | 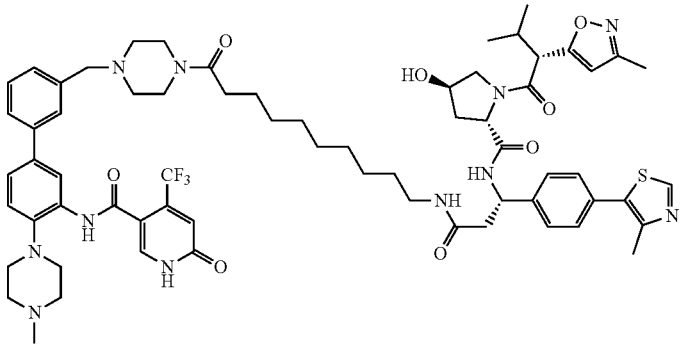 [SMILES: Cc1cc([C@H](C(=O)N2C[C@H](O)C[C@H]2C(=O)N[C@@H](CC(=O)NCCCCCCCCCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(10-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)decanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 379 | 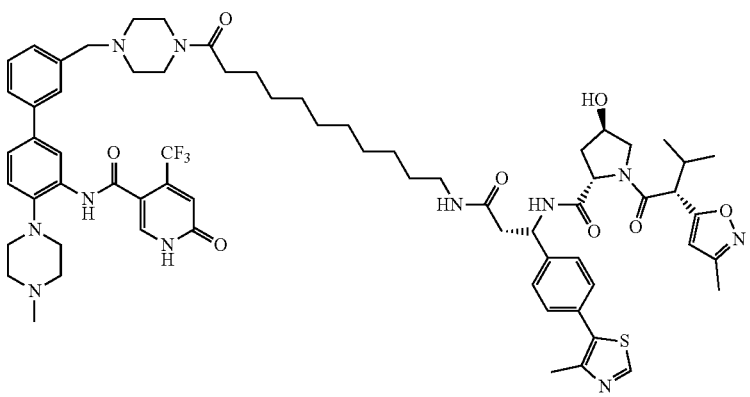 | N-(3'-((4-(11-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)undecanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 380 | 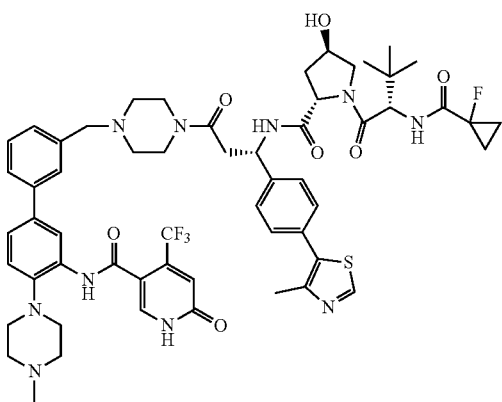 [SMILES: Cc1ncsc1-c1ccc([C@H](CC(=O)N2CCN(Cc3cccc(-c4ccc(N5CCN(C)CC5)c(NC(=O)c5c[nH]c(=O)cc5C(F)(F)F)c4)c3)CC2)NC(=O)[C@@H]2C[C@@H](O)CN2C(=O)[C@@H](NC(=O)C2(F)CC2)C(C)(C)C)cc1] | N-(3'-((4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 387 | 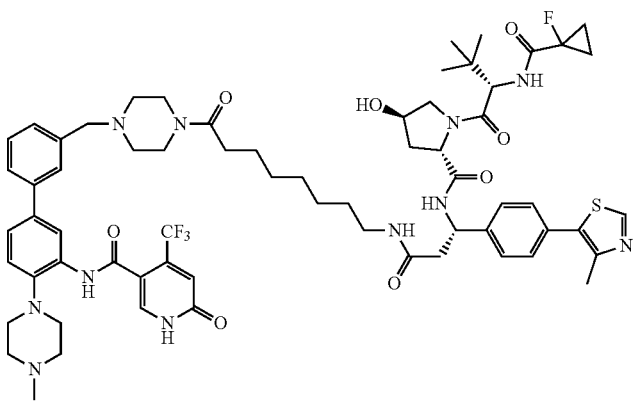 [SMILES: Cc1ncsc1-c1ccc([C@H](CC(=O)NCCCCCCCC(=O)N2CCN(Cc3cccc(-c4ccc(N5CCN(C)CC5)c(NC(=O)c5c[nH]c(=O)cc5C(F)(F)F)c4)c3)CC2)NC(=O)[C@@H]2C[C@@H](O)CN2C(=O)[C@@H](NC(=O)C2(F)CC2)C(C)(C)C)cc1] | N-(3'-((4-(8-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)octanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| 388 | 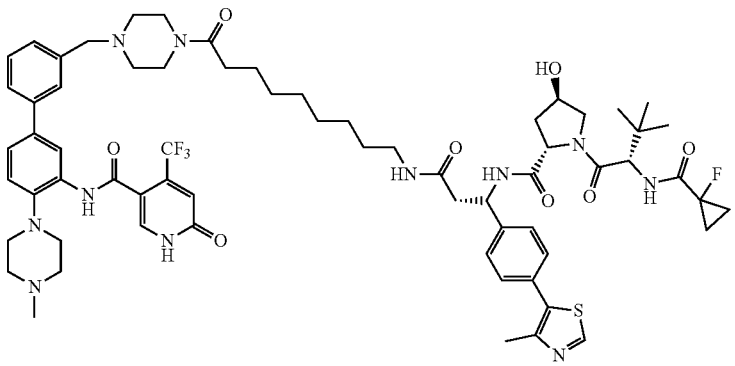 | N-(3'-((4-(9-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)nonanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 389 | 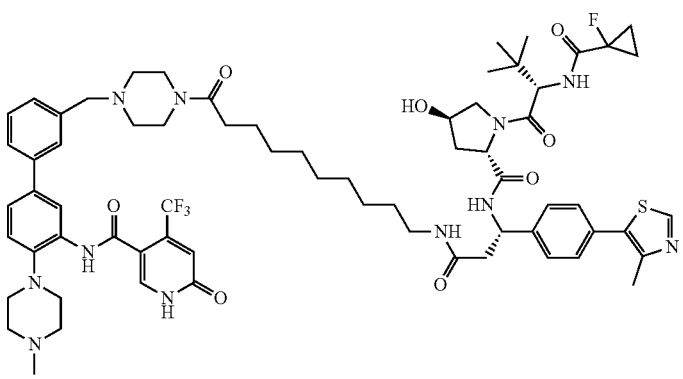 [SMILES: Cc1ncsc1-c1ccc([C@H](CC(=O)NCCCCCCCCCC(=O)N2CCN(Cc3cccc(-c4ccc(N5CCN(C)CC5)c(NC(=O)c5c[nH]c(=O)cc5C(F)(F)F)c4)c3)CC2)NC(=O)[C@@H]2C[C@@H](O)CN2C(=O)[C@@H](NC(=O)C2(F)CC2)C(C)(C)C)cc1] | N-(3'-((4-(10-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)decanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 391 | 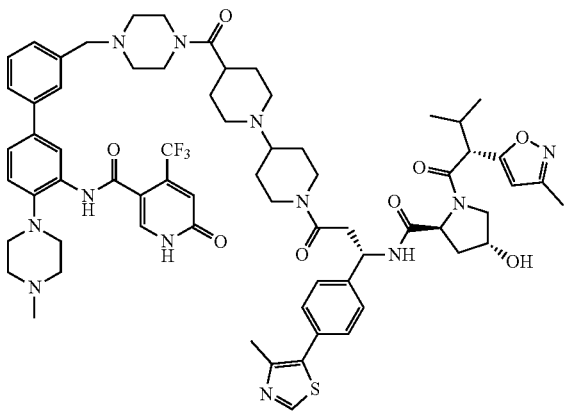 [SMILES: Cc1cc([C@H](C(=O)N2C[C@H](O)C[C@H]2C(=O)N[C@@H](CC(=O)N2CCC(N3CCC(C(=O)N4CCN(Cc5cccc(-c6ccc(N7CCN(C)CC7)c(NC(=O)c7c[nH]c(=O)cc7C(F)(F)F)c6)c5)CC4)CC3)CC2)c2ccc(-c3scnc3C)cc2)C(C)C)on1] | N-(3'-((4-(1'-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)-[1,4'-bipiperidine]-4-carbonyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 392 | 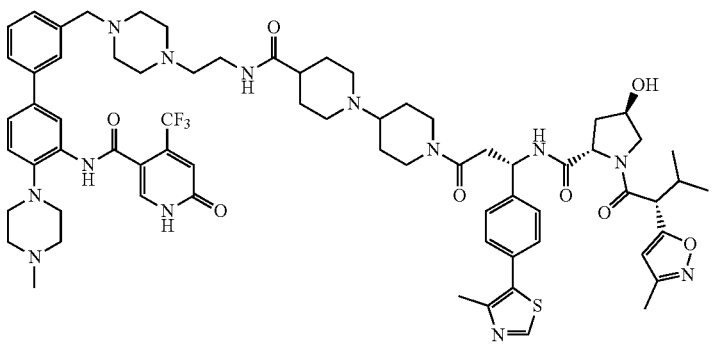 [SMILES: Cc1cc([C@H](C(=O)N2C[C@H](O)C[C@H]2C(=O)N[C@@H](CC(=O)N2CCC(N3CCC(C(=O)NCCN4CCN(Cc5cccc(-c6ccc(N7CCN(C)CC7)c(NC(=O)c7c[nH]c(=O)cc7C(F)(F)F)c6)c5)CC4)CC3)CC2)c2ccc(-c3scnc3C)cc2)C(C)C)on1] | 1'-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)-N-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)-[1,4'-bipiperidine]-4-carboxamide |

| | | |
|---|---|---|
| 396 | 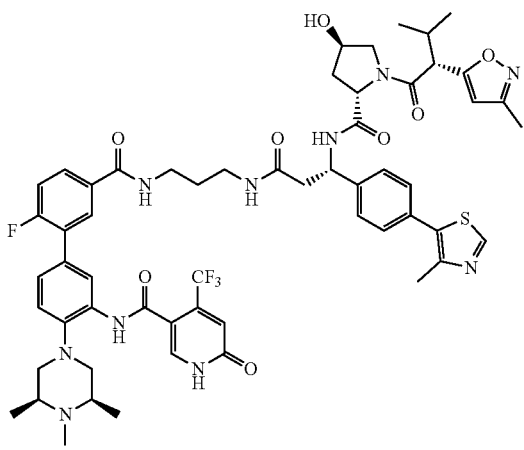 [SMILES: Cc1cc([C@H](C(=O)N2C[C@H](O)C[C@H]2C(=O)N[C@@H](CC(=O)NCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)c2ccc(-c3scnc3C)cc2)C(C)C)on1] | N-(2'-fluoro-5'-((3-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 397 | 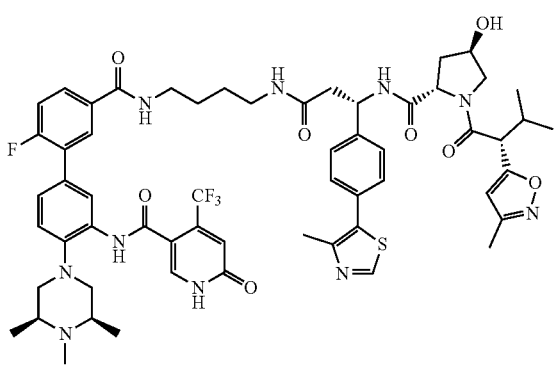 [SMILES: Cc1cc([C@H](C(=O)N2C[C@H](O)C[C@H]2C(=O)N[C@@H](CC(=O)NCCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)c2ccc(-c3scnc3C)cc2)C(C)C)on1] | N-(2'-fluoro-5'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 398 | 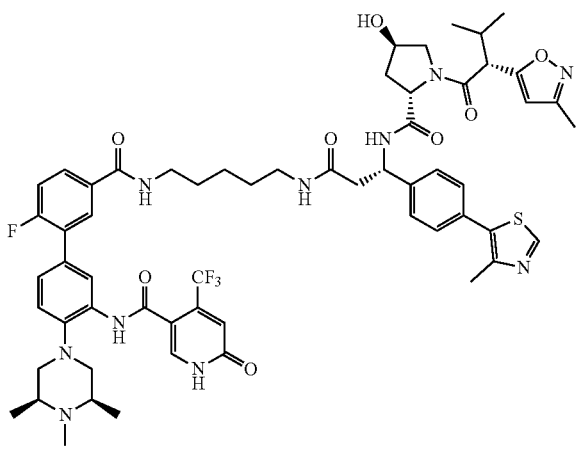 | N-(2'-fluoro-5'-((5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 399 | 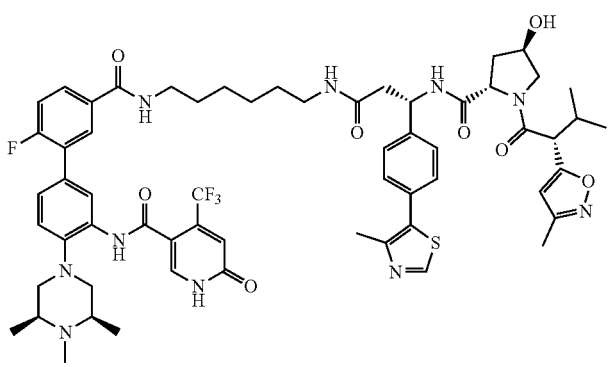 [SMILES: Cc1cc([C@H](C(=O)N2C[C@H](O)C[C@H]2C(=O)N[C@@H](CC(=O)NCCCCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)c2ccc(-c3scnc3C)cc2)C(C)C)on1] | N-(2'-fluoro-5'-((6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 400 | 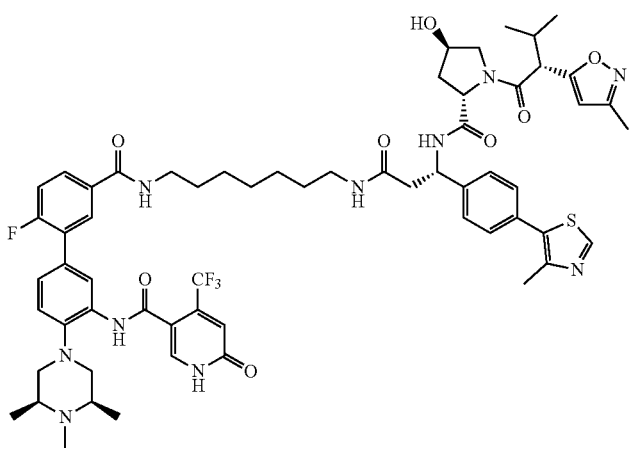 | N-(2'-fluoro-5'-((7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 401 | 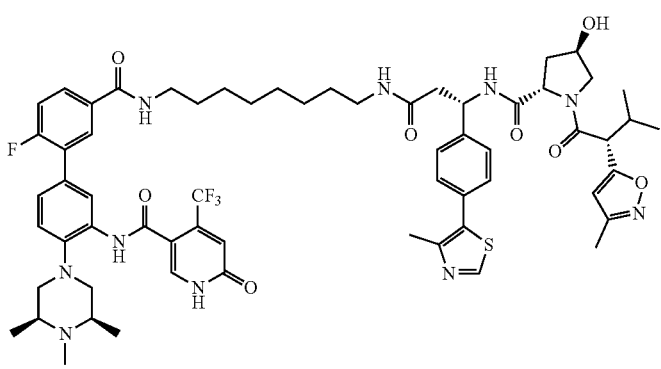 [SMILES: Cc1cc([C@H](C(=O)N2C[C@H](O)C[C@H]2C(=O)N[C@@H](CC(=O)NCCCCCCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)c2ccc(-c3scnc3C)cc2)C(C)C)on1] | N-(2'-fluoro-5'-((8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 402 | 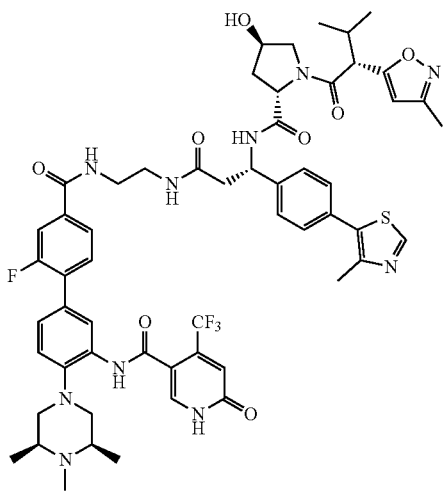 | N-(2'-fluoro-4'-((2-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 403 | 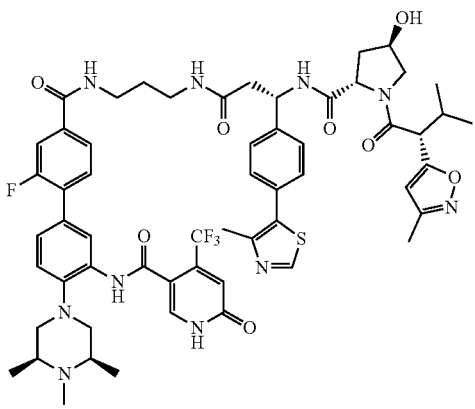 [SMILES: Cc1cc([C@H](C(=O)N2C[C@H](O)C[C@H]2C(=O)N[C@@H](CC(=O)NCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)c2ccc(-c3scnc3C)cc2)C(C)C)on1] | N-(2'-fluoro-4'-((3-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 404 | 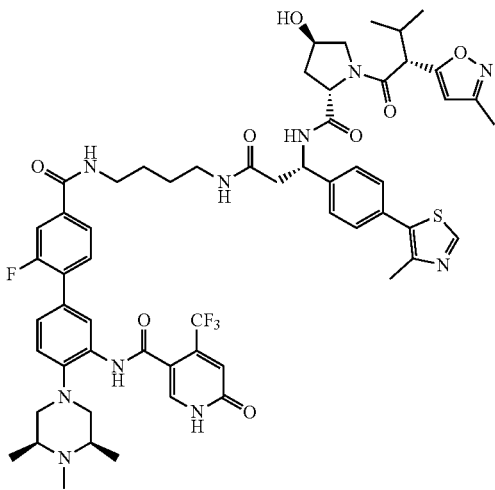 [SMILES: Cc1cc([C@H](C(=O)N2C[C@H](O)C[C@H]2C(=O)N[C@@H](CC(=O)NCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)c2ccc(-c3scnc3C)cc2)C(C)C)on1] | N-(2'-fluoro-4'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 405 | 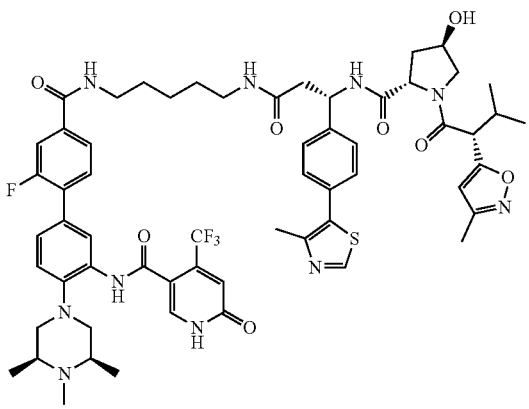 [SMILES: Cc1cc([C@H](C(=O)N2C[C@H](O)C[C@H]2C(=O)N[C@@H](CC(=O)NCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)c2ccc(-c3scnc3C)cc2)C(C)C)on1] | N-(2'-fluoro-4'-((5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 406 | 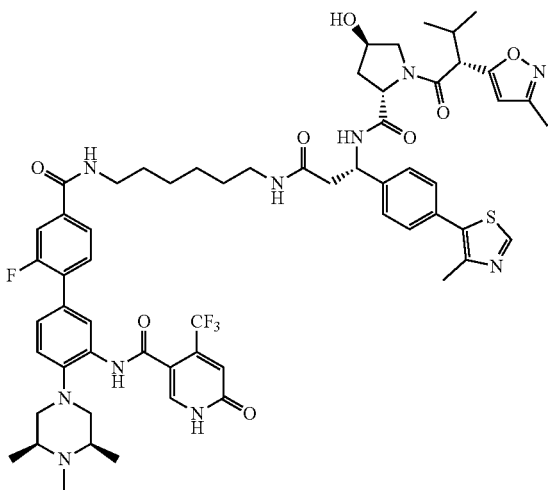 | N-(2'-fluoro-4'-((6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 407 | 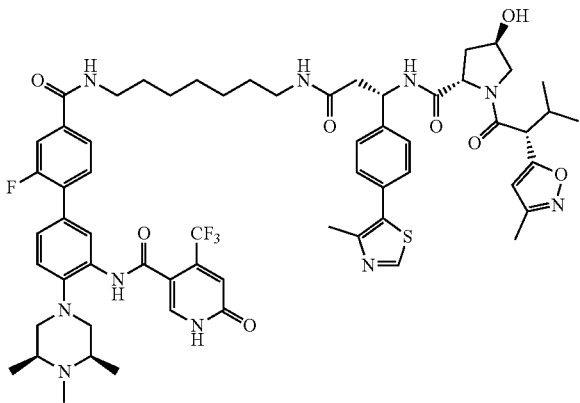 [SMILES: Cc1cc([C@H](C(=O)N2C[C@H](O)C[C@H]2C(=O)N[C@@H](CC(=O)NCCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)c2ccc(-c3scnc3C)cc2)C(C)C)on1] | N-(2'-fluoro-4'-((7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 408 | 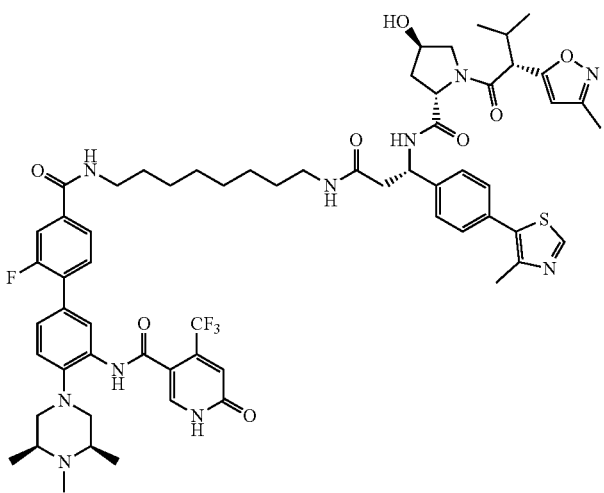 | N-(2'-fluoro-4'-((8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | |
|---|---|
| 409 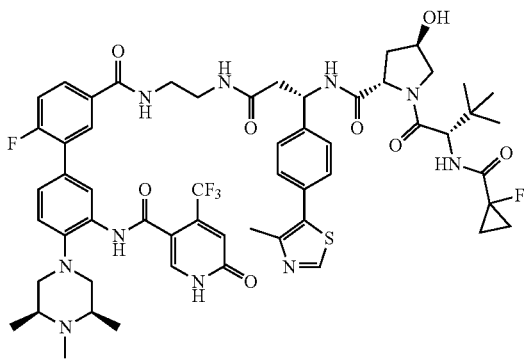 [SMILES: Cc1ncsc1-c1ccc([C@H](CC(=O)NCCNC(=O)c2ccc(F)c(-c3ccc(N4C[C@@H](C)N(C)[C@@H](C)C4)c(NC(=O)c4c[nH]c(=O)cc4C(F)(F)F)c3)c2)NC(=O)[C@@H]2C[C@@H](O)CN2C(=O)[C@@H](NC(=O)C2(F)CC2)C(C)(C)C)cc1] | N-(2'-fluoro-5'-((2-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 416 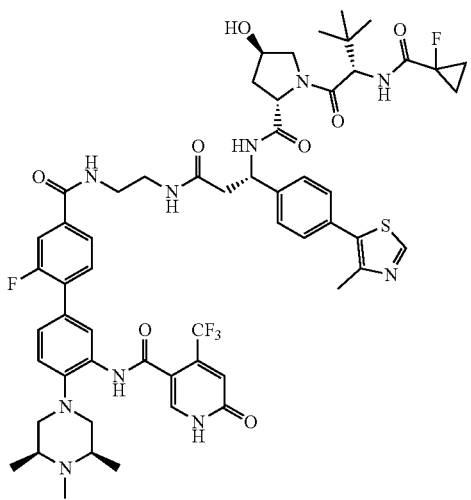 [SMILES: Cc1ncsc1-c1ccc([C@H](CC(=O)NCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((2-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 417 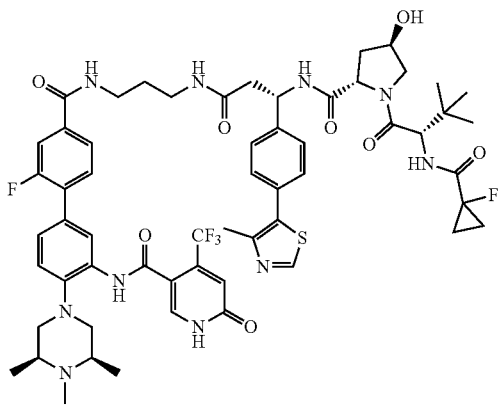 [SMILES: Cc1ncsc1-c1ccc([C@H](CC(=O)NCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((3-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 418 | 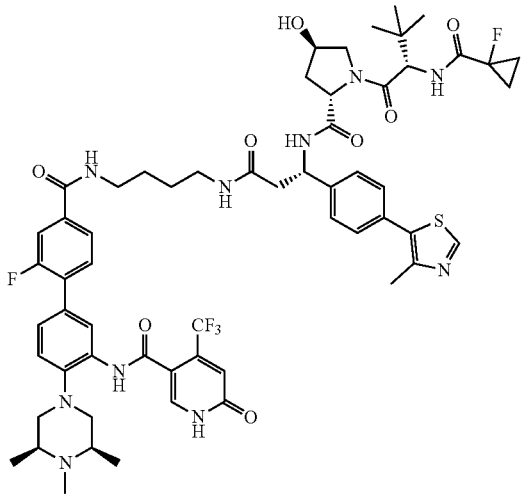 [SMILES: Cc1ncsc1-c1ccc([C@H](CC(=O)NCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 419 | 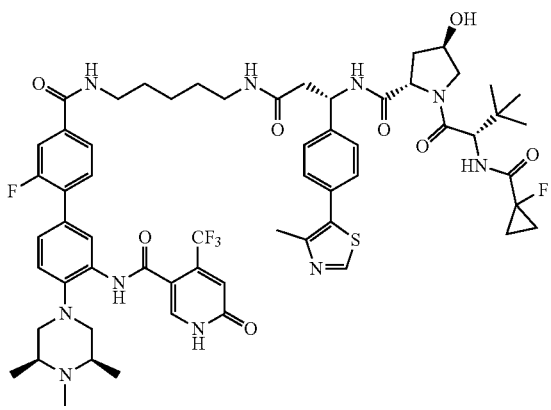 [SMILES: Cc1ncsc1-c1ccc([C@H](CC(=O)NCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((5-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 420 | 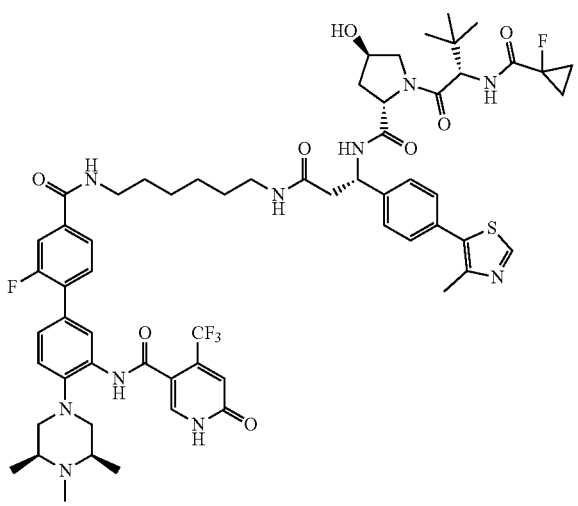 [SMILES: Cc1ncsc1-c1ccc([C@H](CC(=O)NCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((6-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 421 | 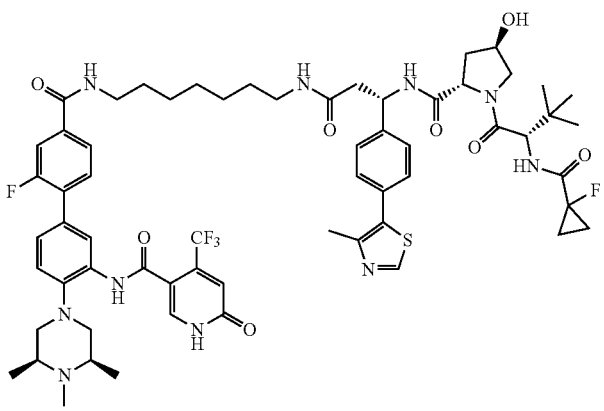 [SMILES: Cc1ncsc1-c1ccc([C@H](CC(=O)NCCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((7-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 422 | 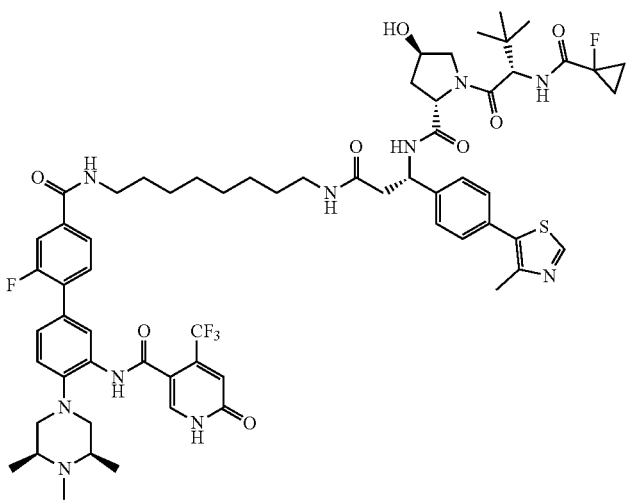 [SMILES: Cc1ncsc1-c1ccc([C@H](CC(=O)NCCCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((8-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 423 | 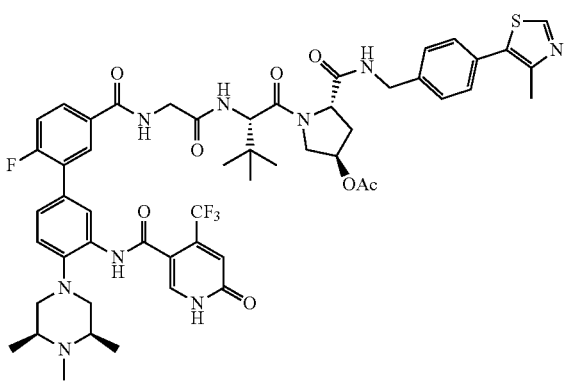 [SMILES: CC(=O)O[C@@H]1C[C@@H](C(=O)NCc2ccc(-c3scnc3C)cc2)N(C(=O)[C@@H](NC(=O)CNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)C1] | (3R,5S)-1-((S)-2-(2-(6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-carboxamido)acetamido)-3,3-dimethylbutanoyl)-5-((4-(4-methylthiazol-5-yl)benzyl)carbamoyl)pyrrolidin-3-yl acetate |

| | | |
|---|---|---|
| 424 | 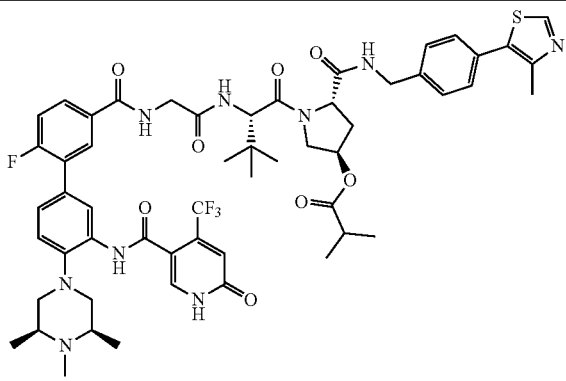 | (3R,5S)-1-((S)-2-(2-(6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-carboxamido)acetamido)-3,3-dimethylbutanoyl)-5-((4-(4-methylthiazol-5-yl)benzyl)carbamoyl)pyrrolidin-3-yl isobutyrate. |

11. A bivalent compound selected from the group consisting of:

| | | |
|---|---|---|
| 369 | 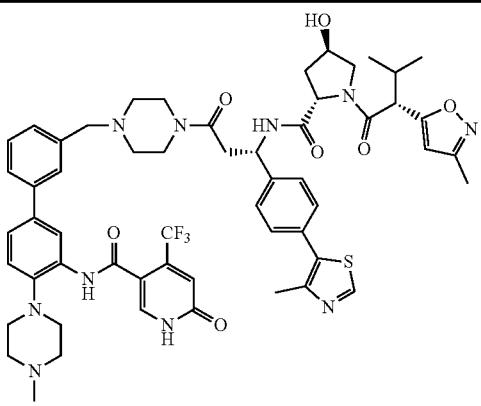 | N-(3'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 374 | 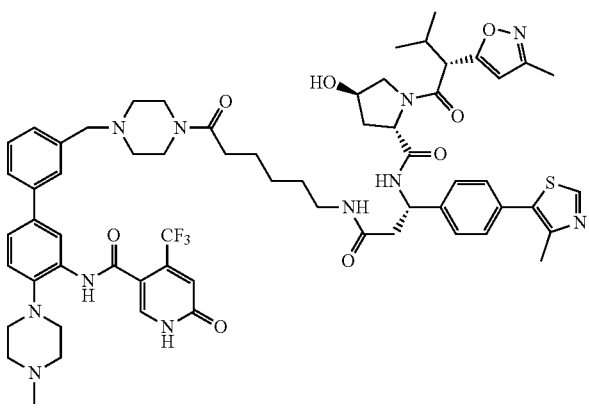 [SMILES: Cc1cc([C@H](C(=O)N2C[C@H](O)C[C@H]2C(=O)N[C@@H](CC(=O)NCCCCCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 375 | 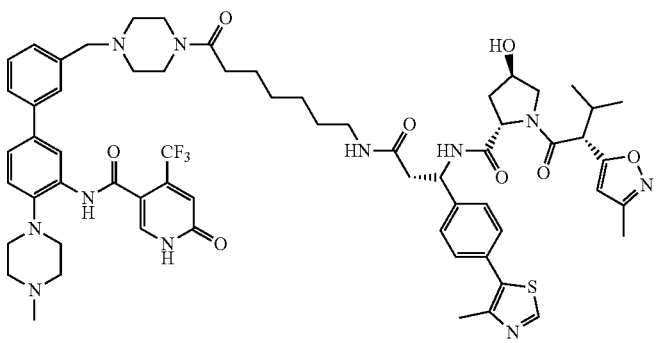 | N-(3'-((4-(7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| 376 | 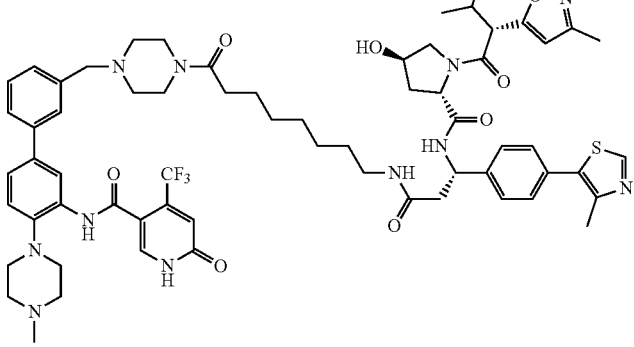 | N-(3'-((4-(8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 377 | 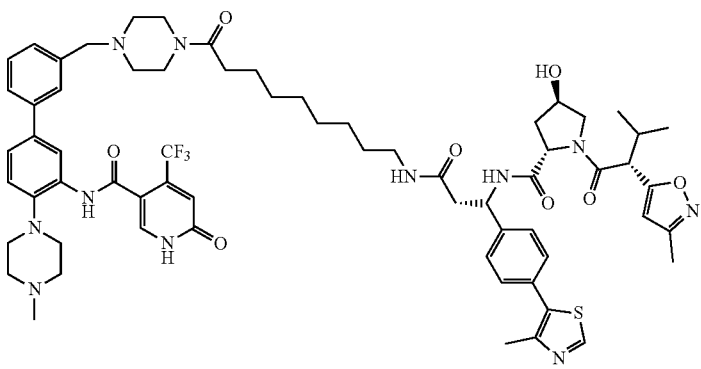 | N-(3'-((4-(9-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)nonanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 378 | 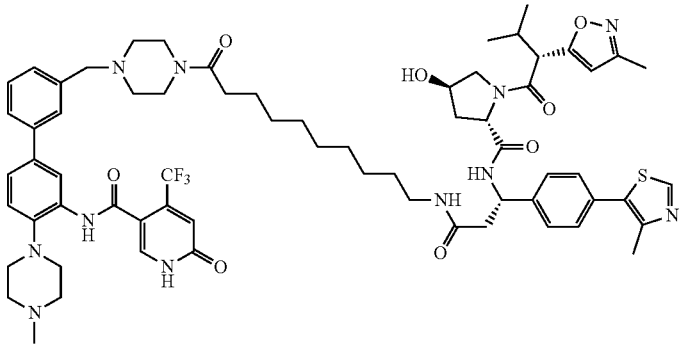 [SMILES: Cc1cc([C@H](C(=O)N2C[C@H](O)C[C@H]2C(=O)N[C@@H](CC(=O)NCCCCCCCCCC(=O)N2CCN(Cc3cccc(-c4ccc(N5CCN(C)CC5)c(NC(=O)c5c[nH]c(=O)cc5C(F)(F)F)c4)c3)CC2)c2ccc(-c3scnc3C)cc2)C(C)C)on1] | N-(3'-((4-(10-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)decanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 379 | 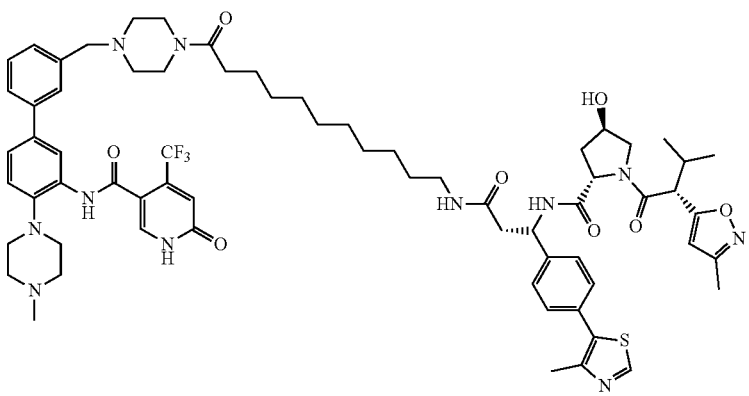 | N-(3'-((4-(11-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)undecanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| 380 | 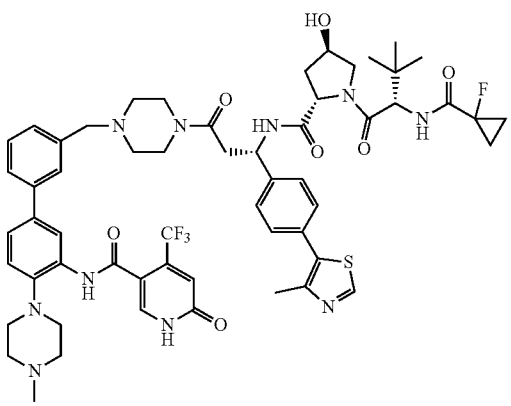 [SMILES: Cc1ncsc1-c1ccc([C@H](CC(=O)N2CCN(Cc3cccc(-c4ccc(N5CCN(C)CC5)c(NC(=O)c5c[nH]c(=O)cc5C(F)(F)F)c4)c3)CC2)NC(=O)[C@@H]2C[C@@H](O)CN2C(=O)[C@@H](NC(=O)C2(F)CC2)C(C)(C)C)cc1] | N-(3'-((4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 388 | 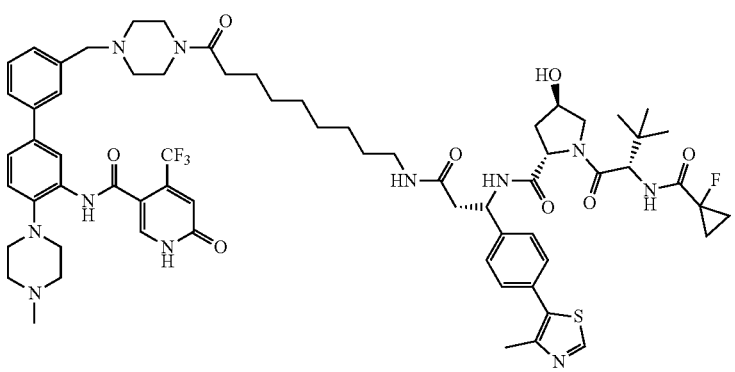 | N-(3'-((4-(9-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)nonanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 389 | 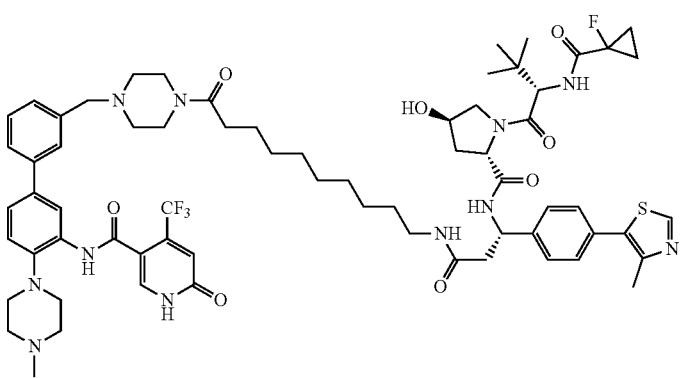 [SMILES: Cc1ncsc1-c1ccc([C@H](CC(=O)NCCCCCCCCCC(=O)N2CCN(Cc3cccc(-c4ccc(N5CCN(C)CC5)c(NC(=O)c5c[nH]c(=O)cc5C(F)(F)F)c4)c3)CC2)NC(=O)[C@@H]2C[C@@H](O)CN2C(=O)[C@@H](NC(=O)C2(F)CC2)C(C)(C)C)cc1] | N-(3'-((4-(10-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)decanoyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| 392 | 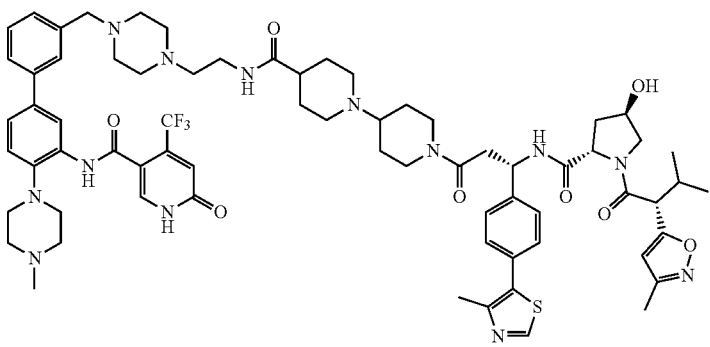 [SMILES: Cc1cc([C@H](C(=O)N2C[C@H](O)C[C@H]2C(=O)N[C@@H](CC(=O)N2CCC(N3CCC(C(=O)NCCN4CCN(Cc5cccc(-c6ccc(N7CCN(C)CC7)c(NC(=O)c7c[nH]c(=O)cc7C(F)(F)F)c6)c5)CC4)CC3)CC2)c2ccc(-c3scnc3C)cc2)C(C)C)on1] | 1'-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanoyl)-N-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)-[1,4'-bipiperidine]-4-carboxamide |

| | | |
|---|---|---|
| 397 | 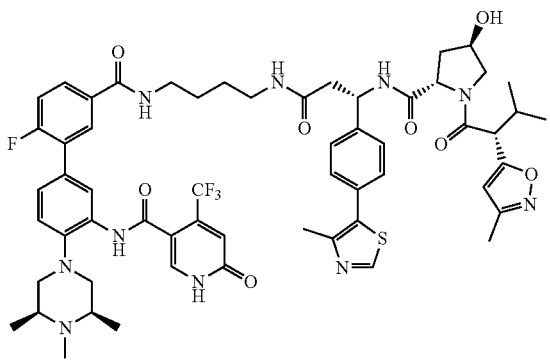 [SMILES: Cc1cc([C@H](C(=O)N2C[C@H](O)C[C@H]2C(=O)N[C@@H](CC(=O)NCCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)c2ccc(-c3scnc3C)cc2)C(C)C)on1] | N-(2'-fluoro-5'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 398 | 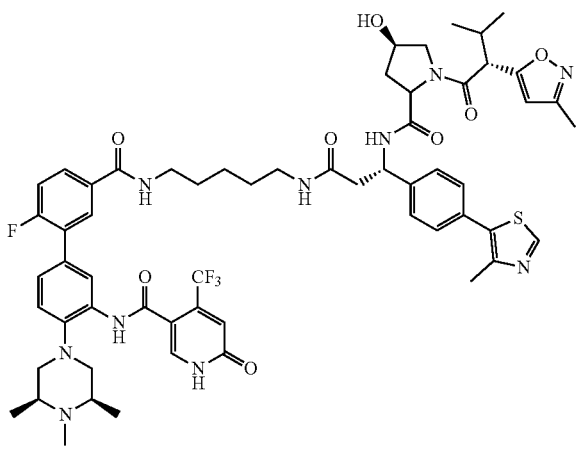 | N-(2'-fluoro-5'-((5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 399 | 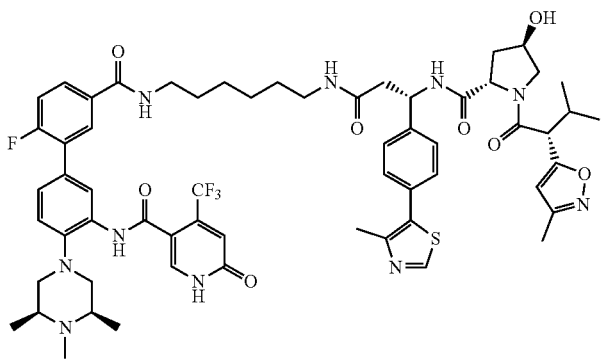 [SMILES: Cc1cc([C@H](C(=O)N2C[C@H](O)C[C@H]2C(=O)N[C@@H](CC(=O)NCCCCCCNC(=O)c2ccc(F)c(-c3ccc(N4C[C@@H](C)N(C)[C@@H](C)C4)c(NC(=O)c4c[nH]c(=O)cc4C(F)(F)F)c3)c2)c2ccc(-c3scnc3C)cc2)C(C)C)on1] | N-(2'-fluoro-5'-((6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 400 | 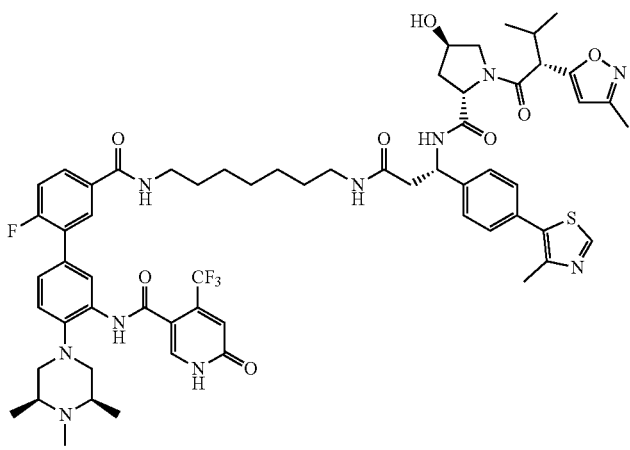 | N-(2'-fluoro-5'-((7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 401 | 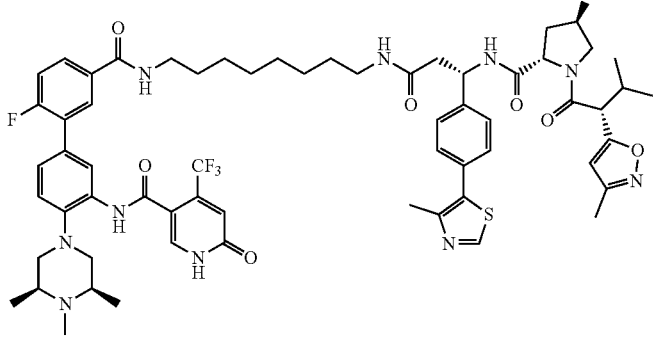 | N-(2'-fluoro-5'-((8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 402 | 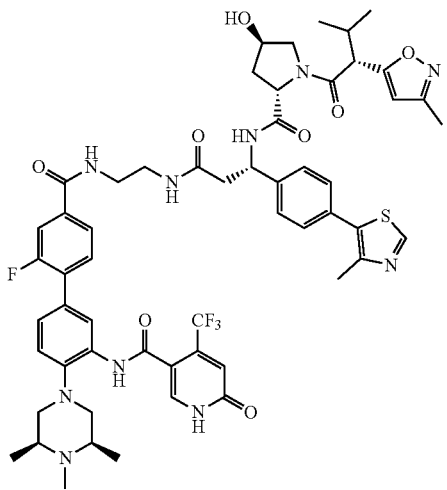 | N-(2'-fluoro-4'-((2-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)ethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 403 | 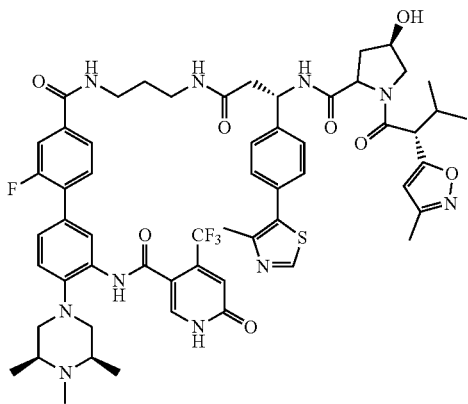 [SMILES: Cc1cc([C@H](C(=O)N2C[C@H](O)CC2C(=O)N[C@@H](CC(=O)NCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)c2ccc(-c3scnc3C)cc2)C(C)C)on1] | N-(2'-fluoro-4'-((3-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

-continued

| | | |
|---|---|---|
| 404 | 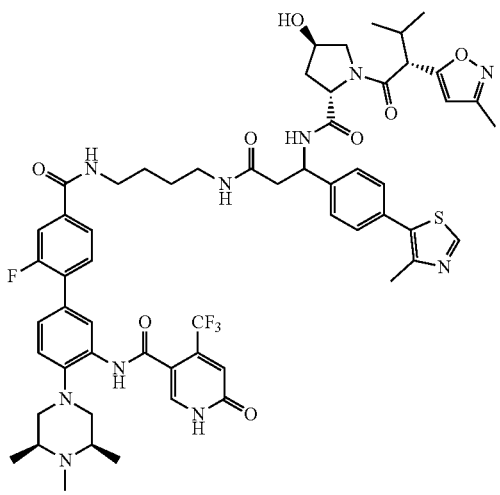 | N-(2'-fluoro-4'-((4-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)butyl) carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 405 | 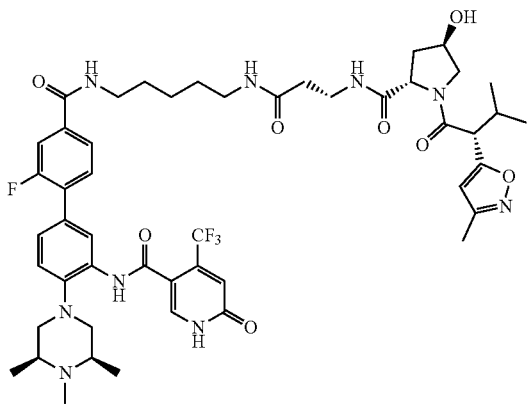 | N-(2'-fluoro-4'-((5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentyl) carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 406 | 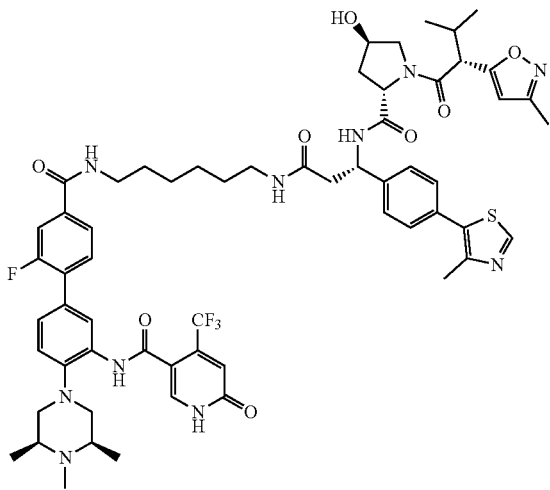 | N-(2'-fluoro-4'-((6-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)hexyl) carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 407 | 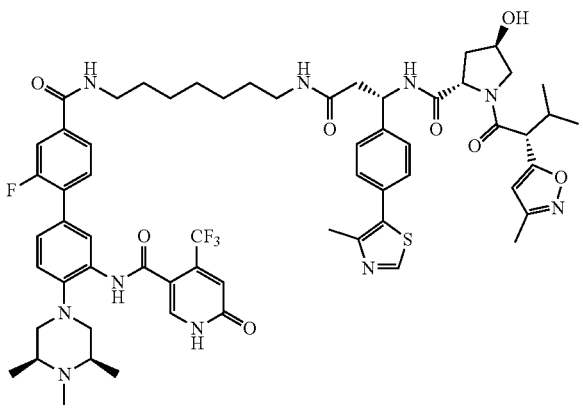 | N-(2'-fluoro-4'-((7-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)heptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 408 | 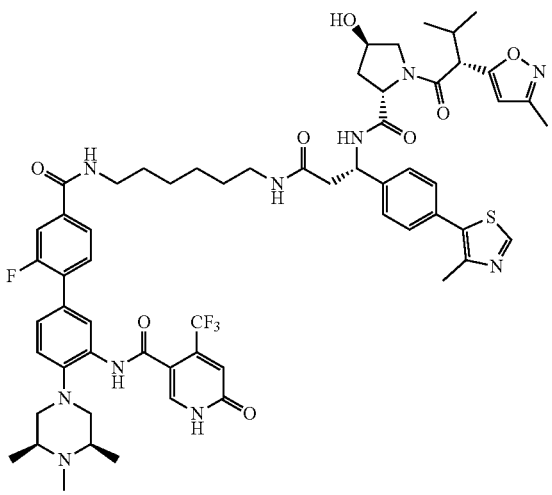 | N-(2'-fluoro-4'-((8-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)octyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 417 | 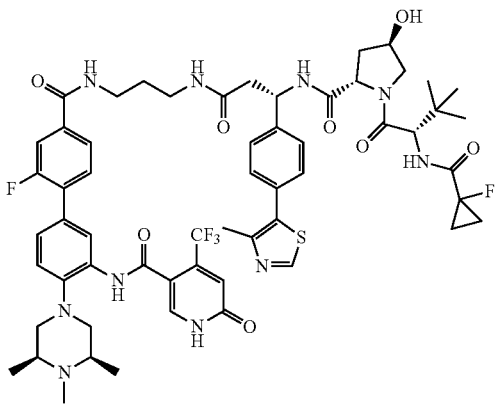 [SMILES: Cc1ncsc1-c1ccc([C@H](CC(=O)NCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((3-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)propyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 418 | 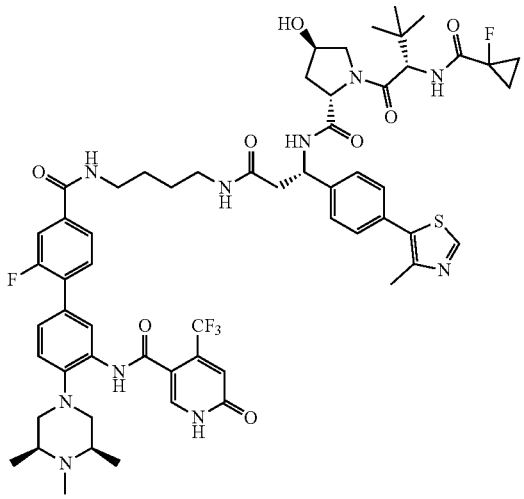 [SMILES: Cc1ncsc1-c1ccc([C@H](CC(=O)NCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((4-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)butyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 419 | 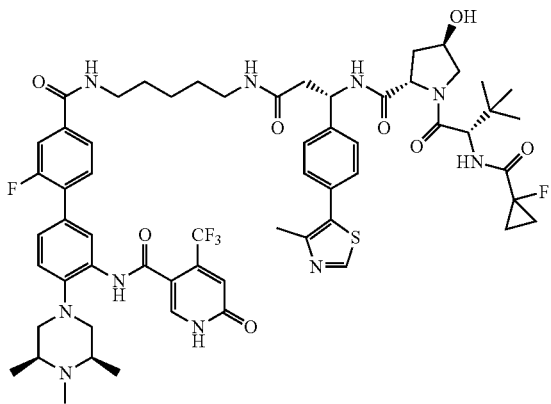 [SMILES: Cc1ncsc1-c1ccc([C@H](CC(=O)NCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((5-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)pentyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| 420 | 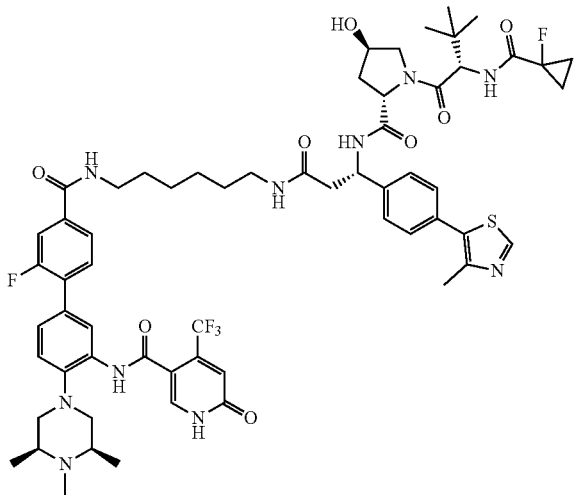 [SMILES: Cc1ncsc1-c1ccc([C@H](CC(=O)NCCCCCCNC(=O)c2ccc(-c3ccc(N4C[C@@H](C)N(C)[C@@H](C)C4)c(NC(=O)c4c[nH]c(=O)cc4C(F)(F)F)c3)c(F)c2)NC(=O)[C@@H]2C[C@@H](O)CN2C(=O)[C@@H](NC(=O)C2(F)CC2)C(C)(C)C)cc1] | N-(2'-fluoro-4'-((6-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanamido)hexyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| 423 | 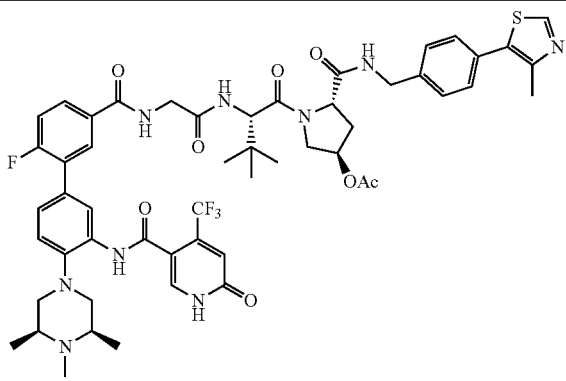 | (3R,5S)-1-((S)-2-(2-(6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-carboxamido)acetamido)-3,3-dimethylbutanoyl)-5-((4-(4-methylthiazol-5-yl)benzyl)carbamoyl)pyrrolidin-3-yl acetate |
| 424 | 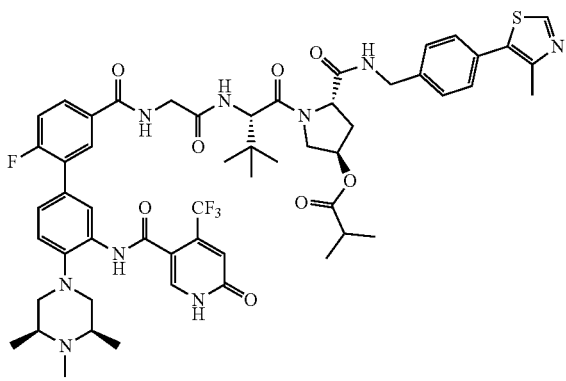 [SMILES: Cc1ncsc1-c1ccc(CNC(=O)[C@@H]2C[C@@H](OC(=O)C(C)C)CN2C(=O)[C@@H](NC(=O)CNC(=O)c2ccc(F)c(-c3ccc(N4C[C@@H](C)N(C)[C@@H](C)C4)c(NC(=O)c4c[nH]c(=O)cc4C(F)(F)F)c3)c2)C(C)(C)C)cc1] | (3R,5S)-1-((S)-2-(2-(6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-carboxamido)acetamido)-3,3-dimethylbutanoyl)-5-((4-(4-methylthiazol-5-yl)benzyl)carbamoyl)pyrrolidin-3-yl isobutyrate. |

12. A bivalent compound selected from the group consisting of:

| ID | Structure | Name |
|---|---|---|
| XF048-133 | 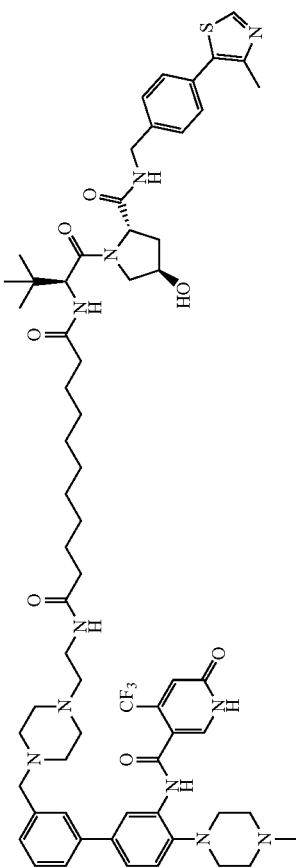 | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{11}$-(2-(4-((4-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |
| XF048-140 | 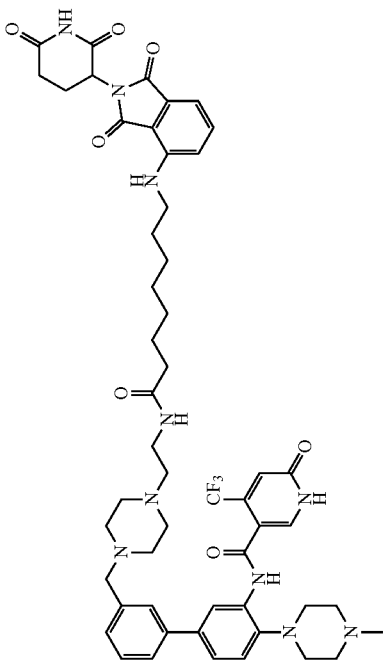 | N-(3'-((4-(2-(8-((2-(2,6-dioxopiperidin-3-yl)-1,3-dioxoisoindolin-4-yl)amino)octanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-145 | 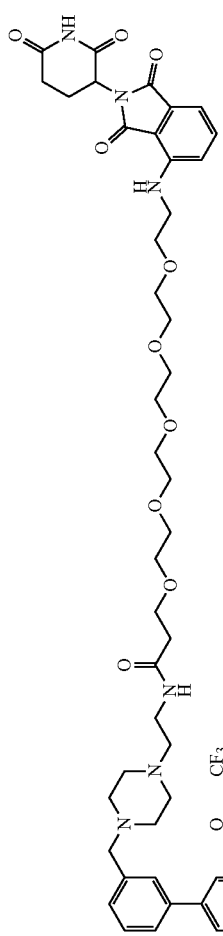 | N-(3'-((4-(1-((2-(2,6-dioxopiperidin-3-yl)-1,3-dioxoisoindolin-4-yl)amino)-18-oxo-3,6,9,12,15-pentaoxa-19-azahenicosan-21-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| XF050-169 | 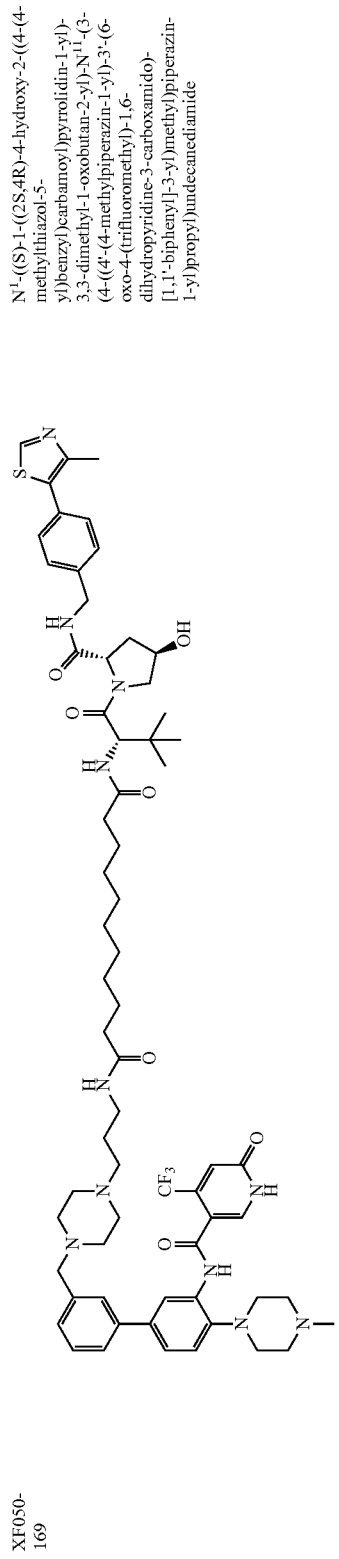 | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N¹¹-(3-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)propyl)undecanediamide |
| XF056-132 | 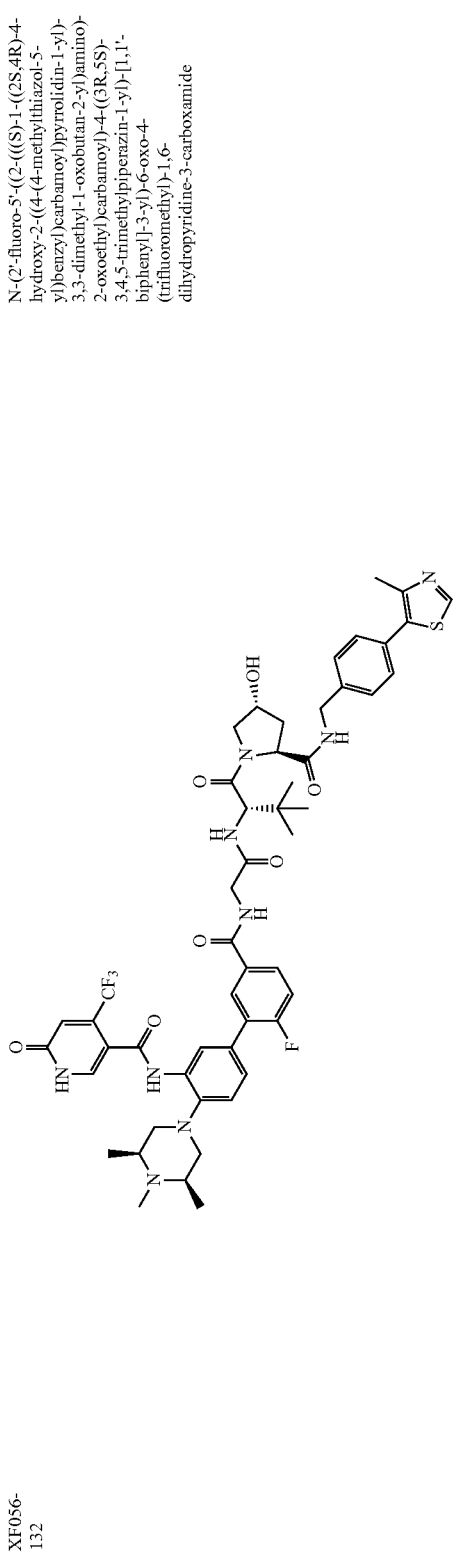 | N-(2'-fluoro-5'-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF067-67 | 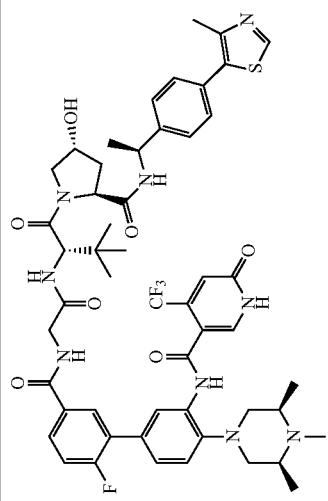 | N-(2'-fluoro-5'-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

13. Bivalent compound:
| | | |
|---|---|---|
| XF067-67 | 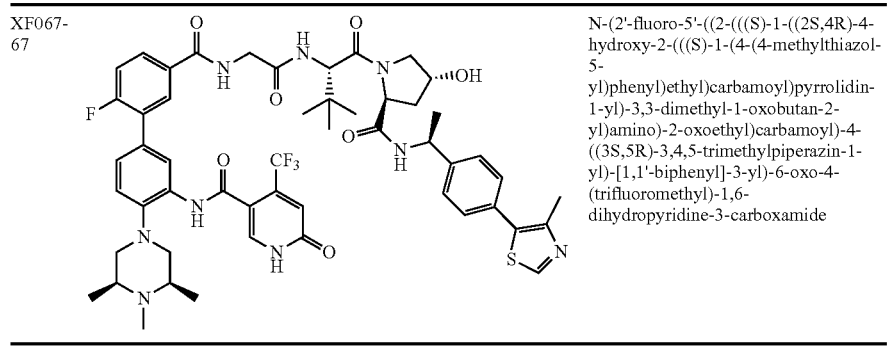 | N-(2'-fluoro-5'-((2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
14. A bivalent compound selected from the group consisting of

| | | |
|---|---|---|
| XF048-117 | 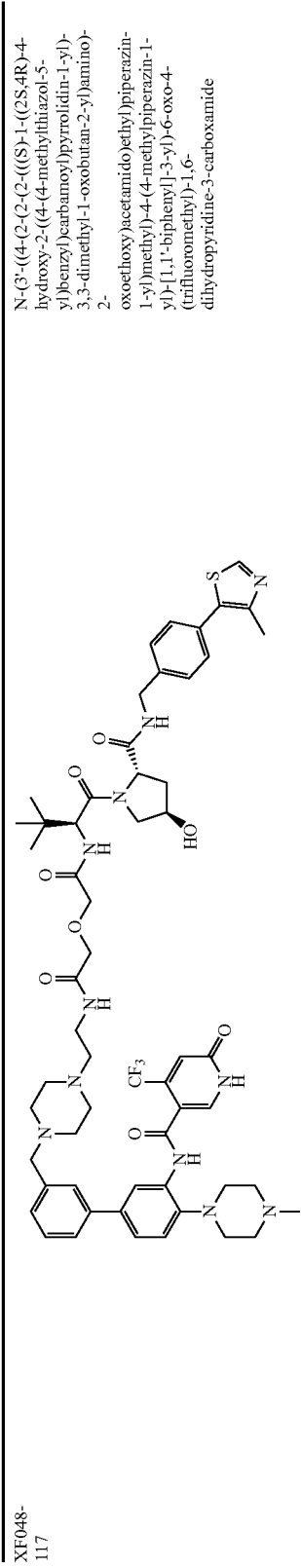 | N-(3'-((4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-118 | 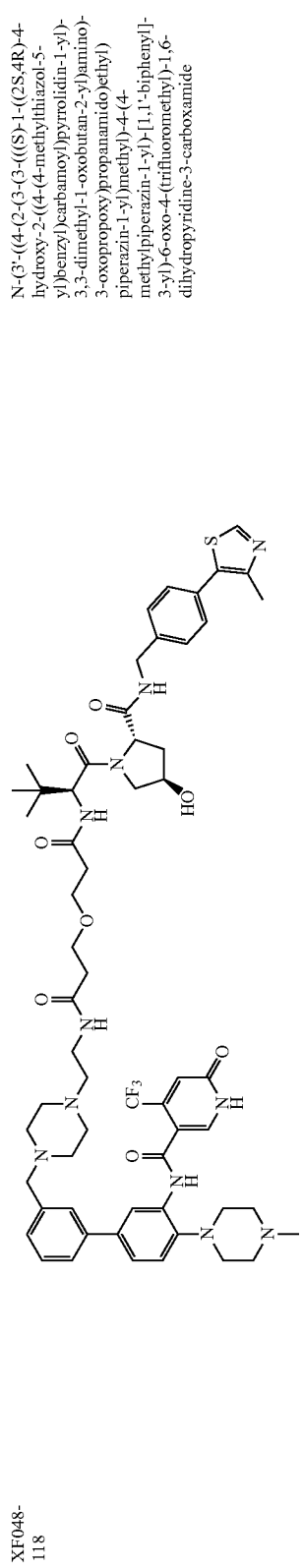 | N-(3'-((4-(2-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-130 | 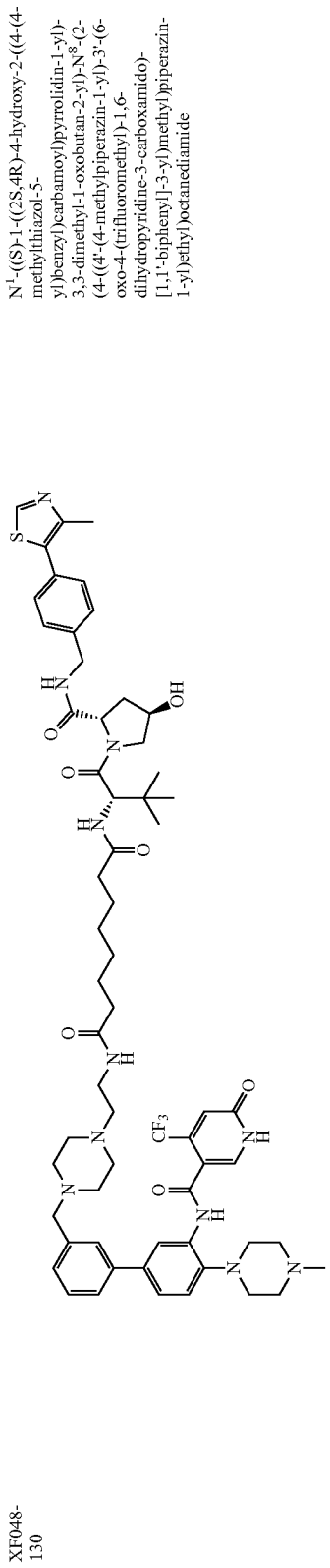 | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^8$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)octanediamide |

-continued

| | | |
|---|---|---|
| XF048-131 | 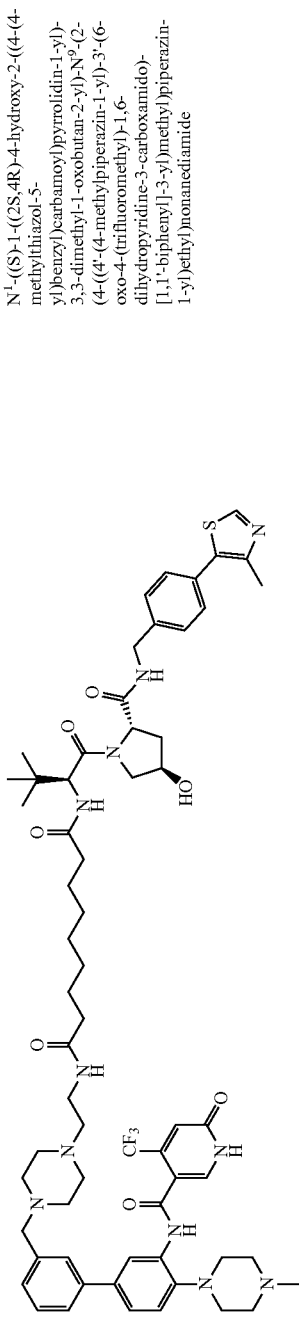 | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁹-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)nonanediamide |
| XF048-132 | 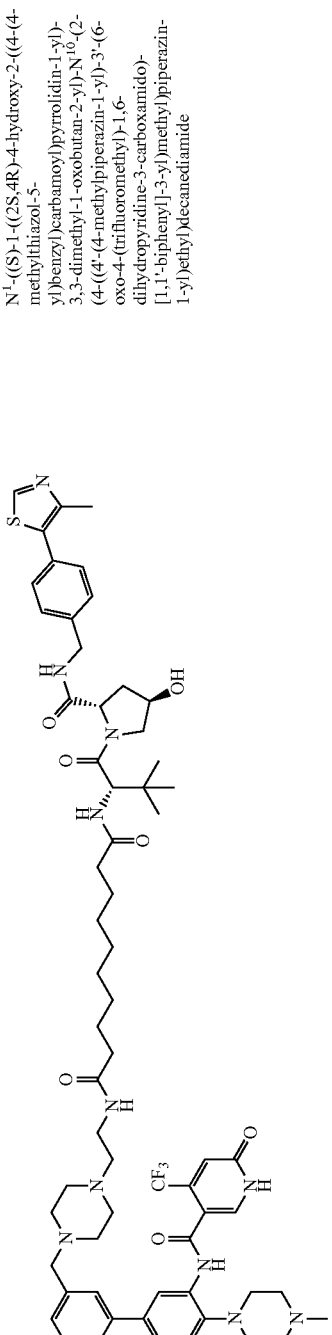 | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N¹⁰-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)decanediamide |
| XF048-133 | 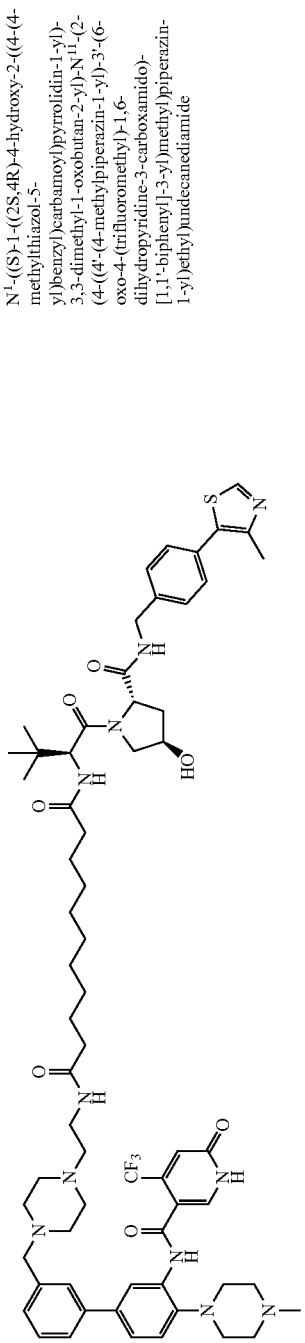 | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N¹¹-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |

-continued

| | | |
|---|---|---|
| XF048-136 | 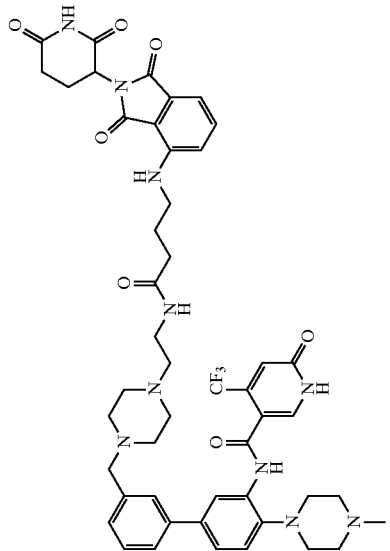 | N-(3'-((4-(2-(4-((2-(2,6-dioxopiperidin-3-yl)-1,3-dioxoisoindolin-4-yl)amino)butanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-139 | 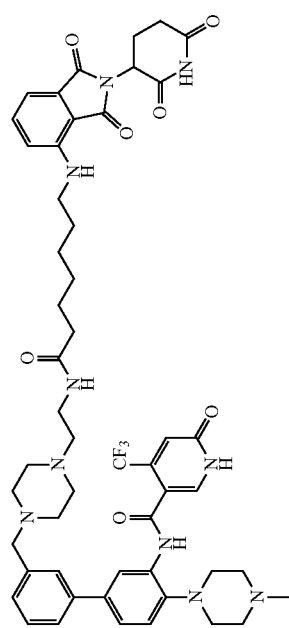 | N-(3'-((4-(2-(7-((2-(2,6-dioxopiperidin-3-yl)-1,3-dioxoisoindolin-4-yl)amino)heptanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-140 | 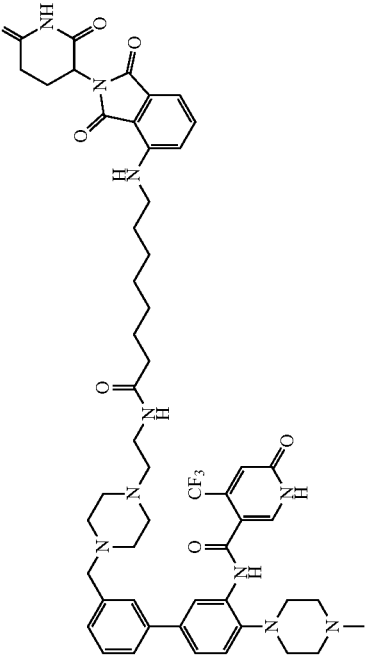 | N-(3'-((4-(2-(8-((2-(2,6-dioxopiperidin-3-yl)-1,3-dioxoisoindolin-4-yl)amino)octanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| XF048-141 | 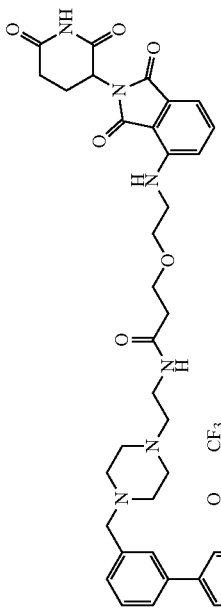 | N-(3'-((4-(2-(3-(2-((2-(2,6-dioxopiperidin-3-yl)-1,3-dioxoisoindolin-4-yl)amino)ethoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-142 | 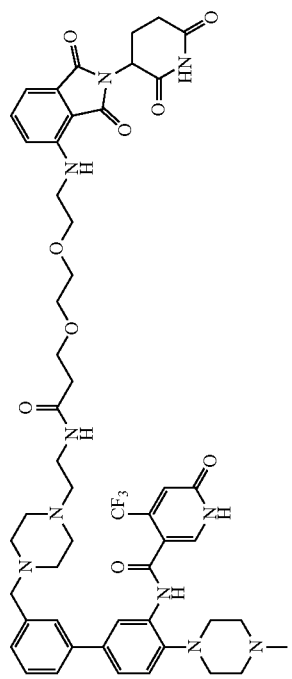 | N-(3'-((4-(2-(3-(2-(2-((2-(2,6-dioxopiperidin-3-yl)-1,3-dioxoisoindolin-4-yl)amino)ethoxy)ethoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-143 | 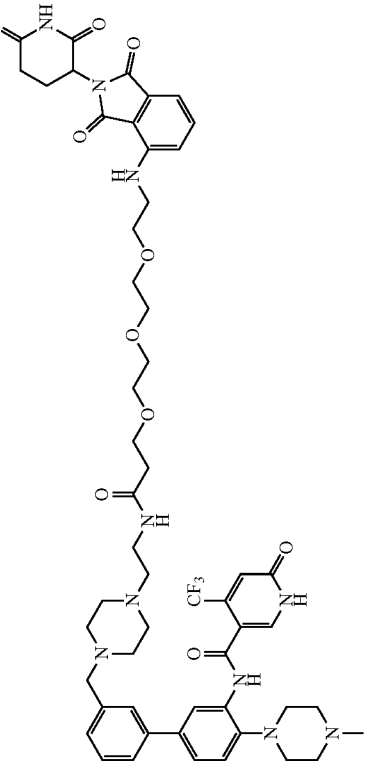 | N-(3'-((4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| XF048-144 | 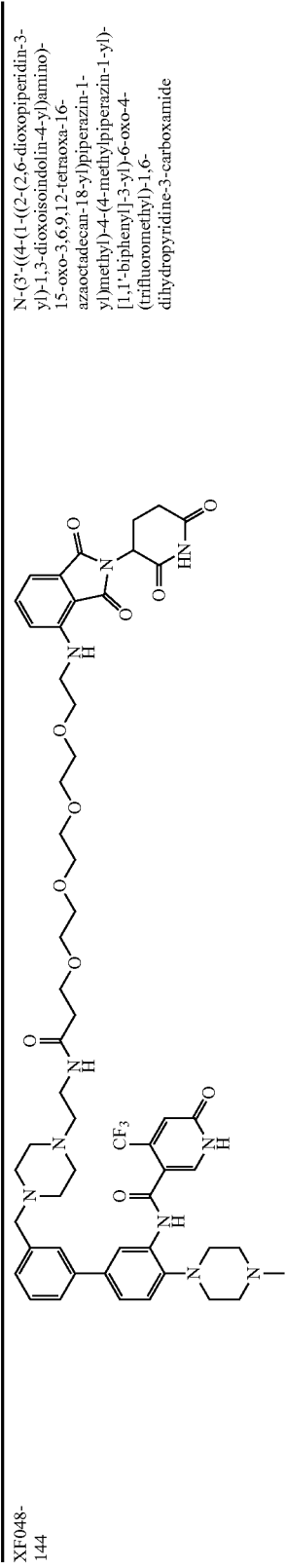 | N-(3'-((4-(1-((2-(2,6-dioxopiperidin-3-yl)-1,3-dioxoisoindolin-4-yl)amino)-15-oxo-3,6,9,12-tetraoxa-16-azaoctadecan-18-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-145 | 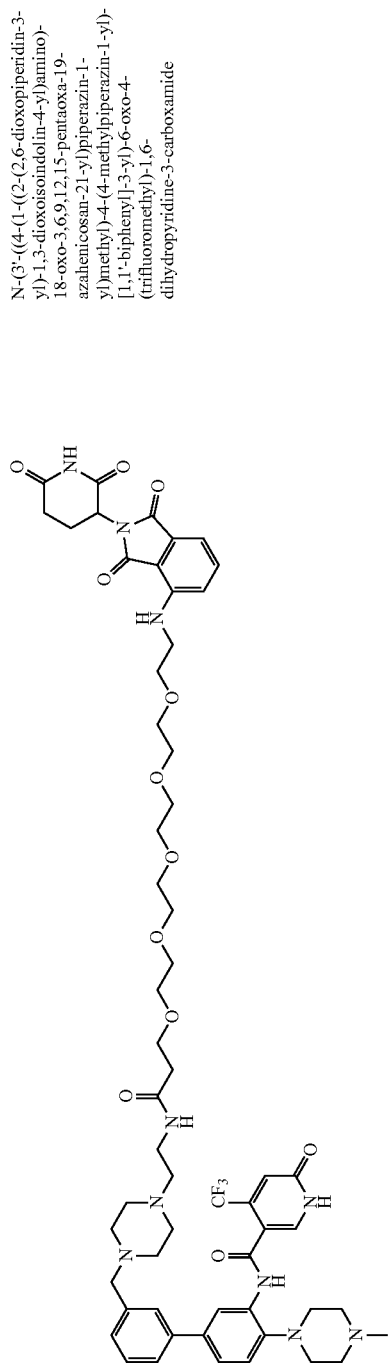 | N-(3'-((4-(1-((2-(2,6-dioxopiperidin-3-yl)-1,3-dioxoisoindolin-4-yl)amino)-18-oxo-3,6,9,12,15-pentaoxa-19-azahenicosan-21-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF050-166 | 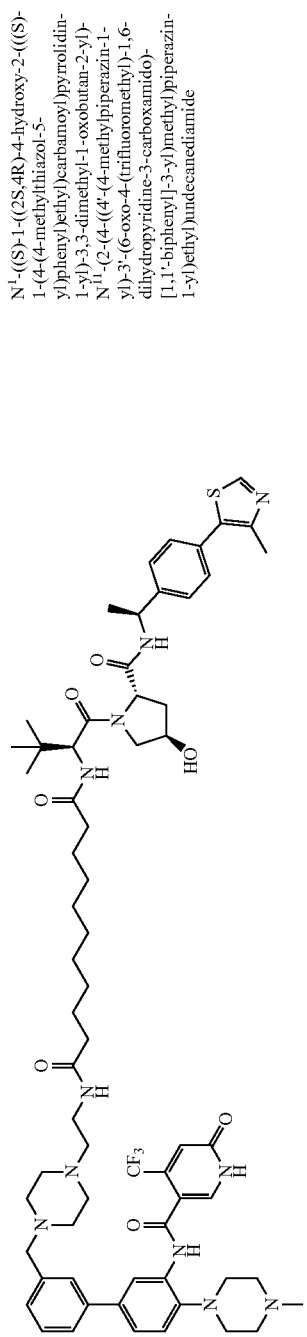 | N¹-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-N¹¹-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |

| | | |
|---|---|---|
| XF050-169 | 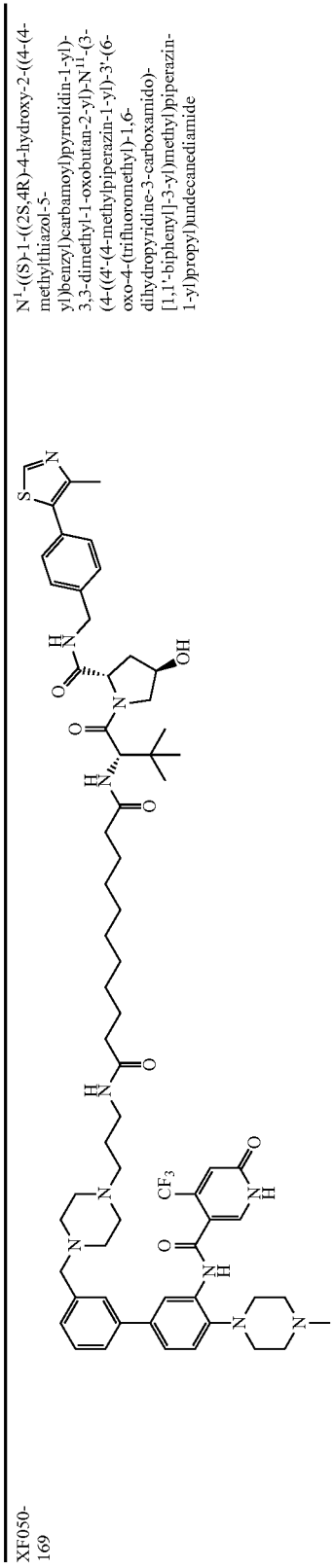 | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{11}$-(3-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)propyl)undecanediamide |
| XF050-161 | 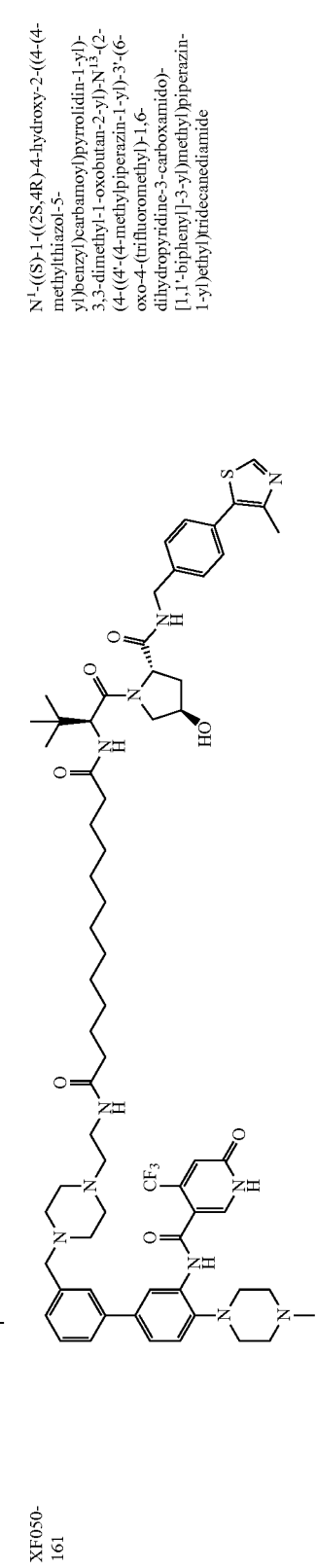 | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{13}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)tridecanediamide |
| XF050-162 | 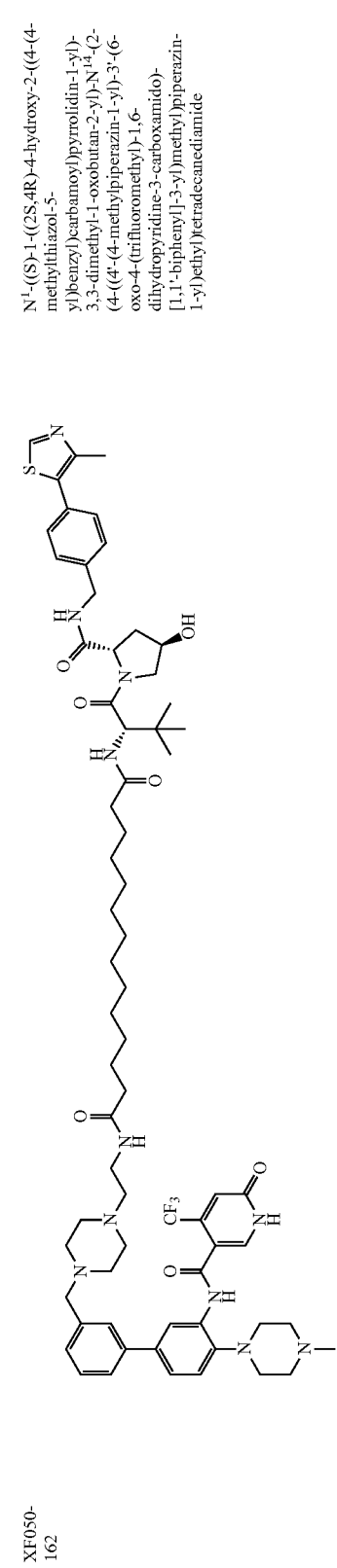 | $N^1$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^{14}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)tetradecanediamide |

| | | |
|---|---|---|
| XF050-156 | 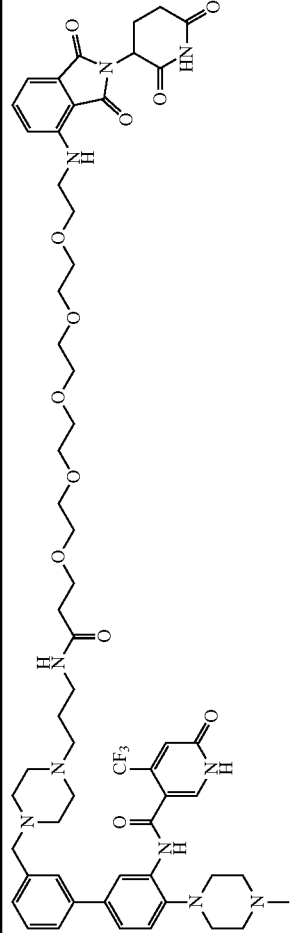 | N-(3'-((4-(1-(2-(2,6-dioxopiperidin-3-yl)-1,3-dioxoisoindolin-4-yl)amino)-18-oxo-3,6,9,12,15-pentaoxa-19-azadocosan-22-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF050-158 | 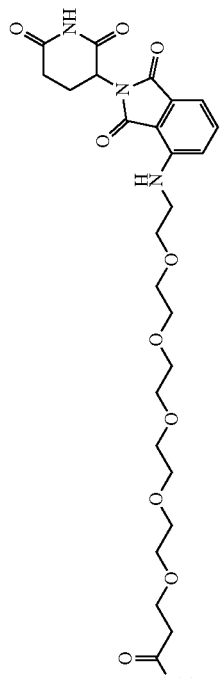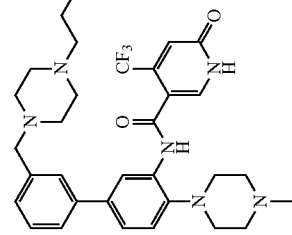 | N-(3'-((4-(1-((2-(2,6-dioxopiperidin-3-yl)-1,3-dioxoisoindolin-4-yl)amino)-18-oxo-3,6,9,12,15-pentaoxa-19-azapentacosan-25-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF056-23 | 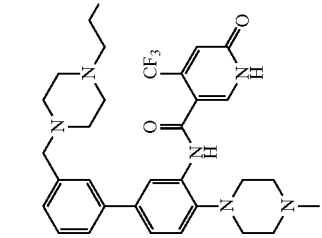 | N-(3'-((4-(1-((2-(2,6-dioxopiperidin-3-yl)-1,3-dioxoisoindolin-4-yl)oxy)-18-oxo-3,6,9,12,15-pentaoxa-19-azahenicosan-21-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| XF056-25 | 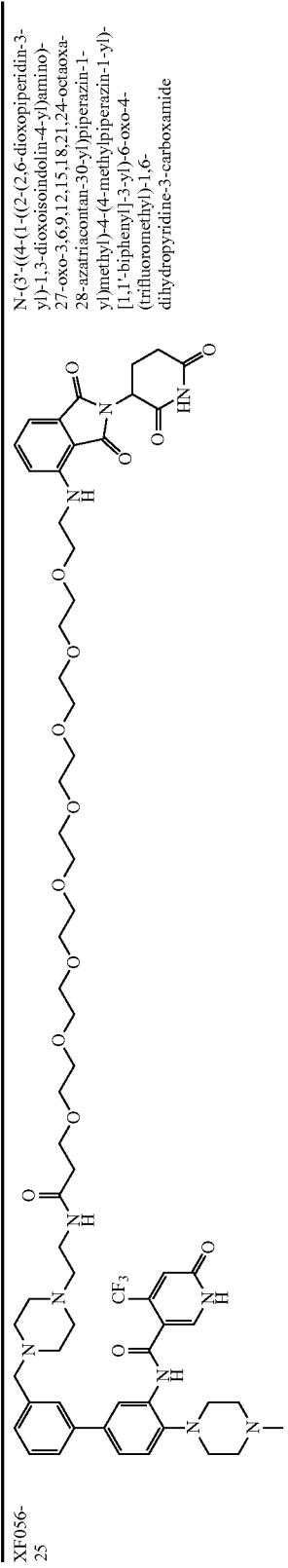 N-(3'-((4-(1-(2-(2,6-dioxopiperidin-3-yl)-1,3-dioxoisoindolin-4-yl)amino)-27-oxo-3,6,9,12,15,18,21,24-octaoxa-28-azatriacontan-30-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide | |
| XF056-26 | 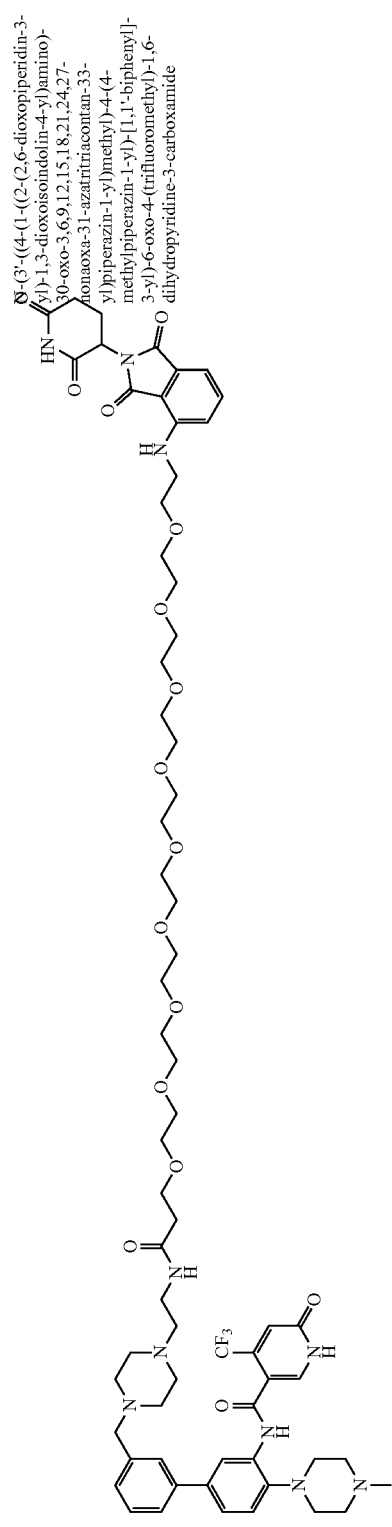 N-(3'-((4-(1-((2-(2,6-dioxopiperidin-3-yl)-1,3-dioxoisoindolin-4-yl)amino)-30-oxo-3,6,9,12,15,18,21,24,27-nonaoxa-31-azatritriacontan-33-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide | |
| XF056-39 | | 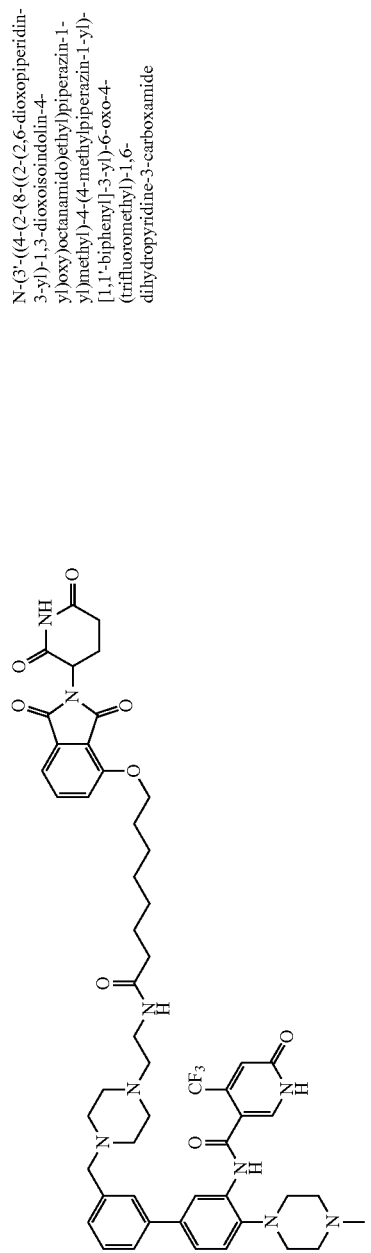 N-(3'-((4-(2-(8-((2-(2,6-dioxopiperidin-3-yl)-1,3-dioxoisoindolin-4-yl)oxy)octanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

| | | |
|---|---|---|
| XF056-132 | 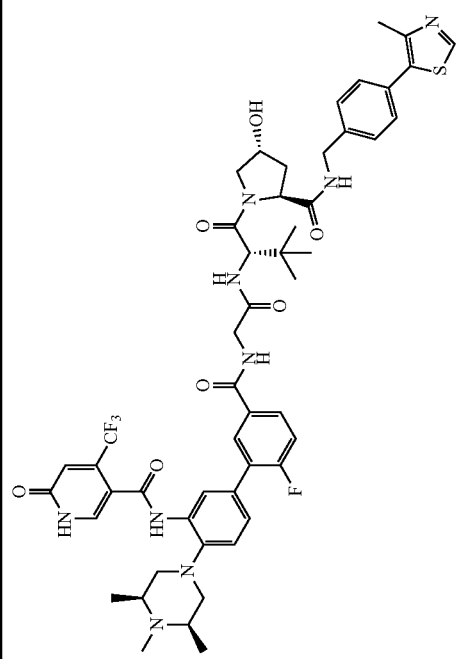 | N-(2'-fluoro-5'-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-134 | 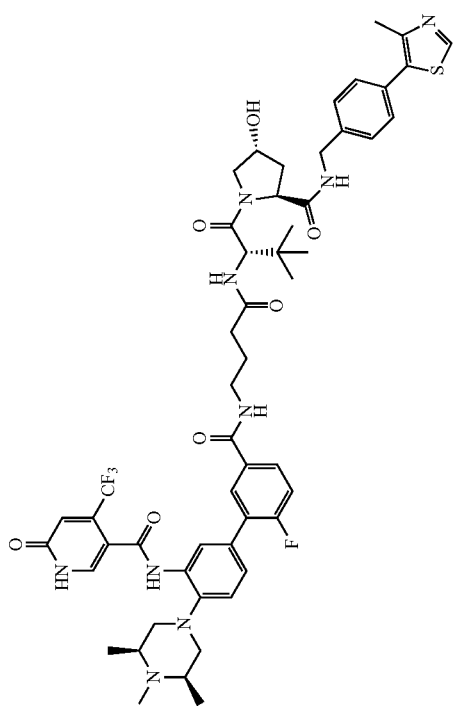 | N-(2'-fluoro-5'-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF056-137 | 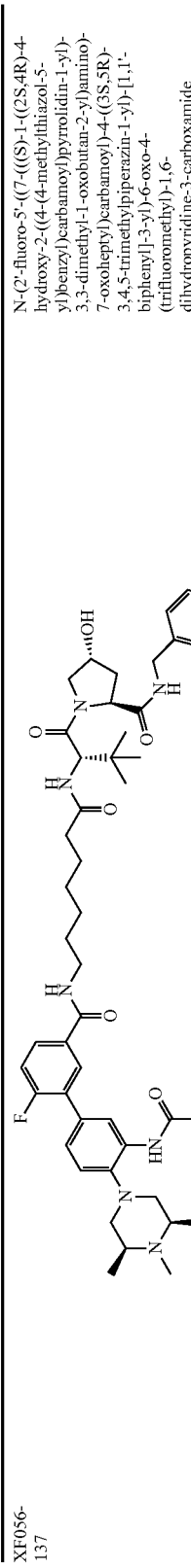 | N-(2'-fluoro-5'-((7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF056-140 |  | N-(2'-fluoro-5'-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-151 | 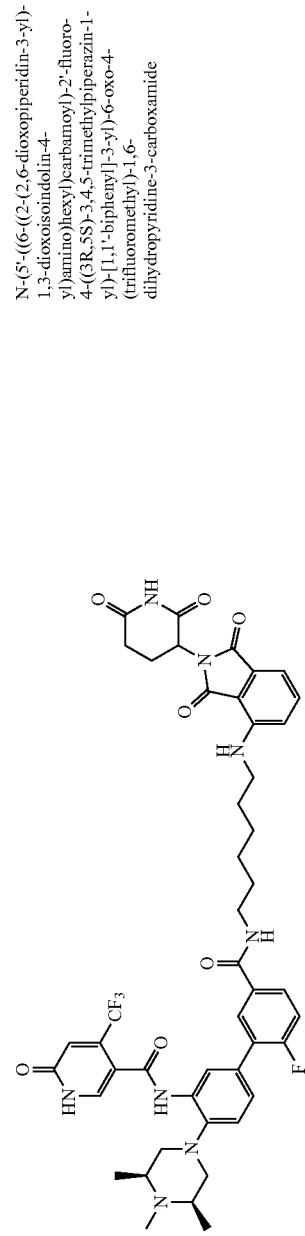 | N-(5'-((6-((2-(2,6-dioxopiperidin-3-yl)-1,3-dioxoisoindolin-4-yl)amino)hexyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF056-152 | 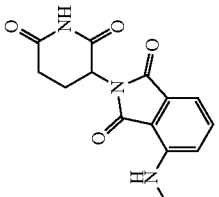 | N-(5'-((7-(2-(2,6-dioxopiperidin-3-yl)-1,3-dioxoisoindolin-4-yl)amino)heptyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF056-153 | | N-(5'-((8-(2-(2,6-dioxopiperidin-3-yl)-1,3-dioxoisoindolin-4-yl)amino)octyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-158 | | N-(2'-fluoro-4'-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF056-159 | 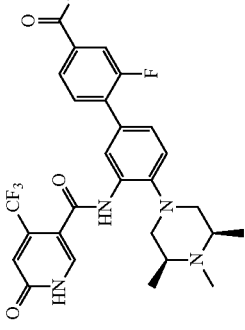 | N-(2'-fluoro-4'-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethylcarbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-162 | 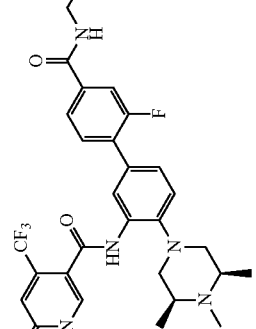 | N-(2'-fluoro-4'-((S)-14-((2S,4R)-4-hydroxy-2-((4-(4-methylthiazol-5-yl)benzyl)carbamoyl)pyrrolidine-1-carbonyl)-15,15-dimethyl-12-oxo-3,6,9-trioxa-13-azahexadecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-166 | 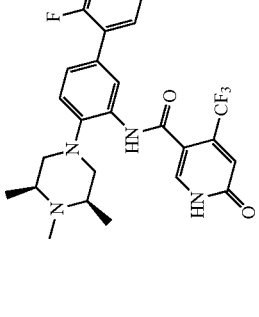 | N-(2'-fluoro-4'-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF056-171 | | N-(2'-fluoro-4'-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-173 | | N-(2'-fluoro-4'-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-178 | | N-(4'-(14-((2-(2,6-dioxopiperidin-3-yl)-1,3-dioxoisoindolin-4-yl)amino)-3,6,9,12-tetraoxatetradecyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF056-186 | 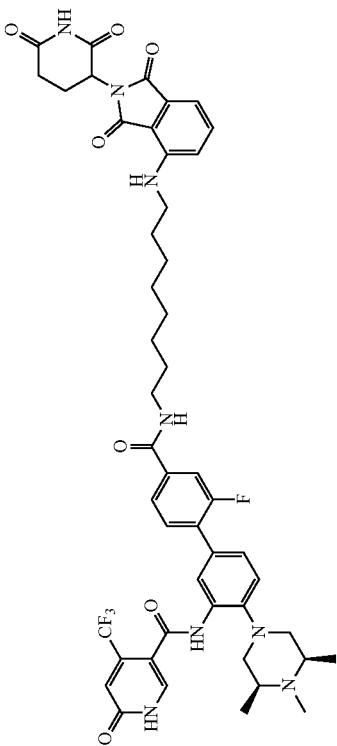 | N-(4'-((8-((2-(2,6-dioxopiperidin-3-yl)-1,3-dioxoisoindolin-4-yl)amino)octyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF067-67 | 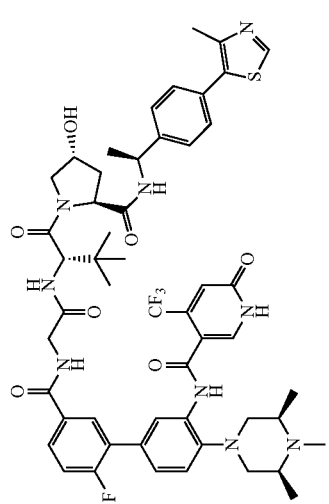 | N-(2'-fluoro-5'-((2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF067-131 | 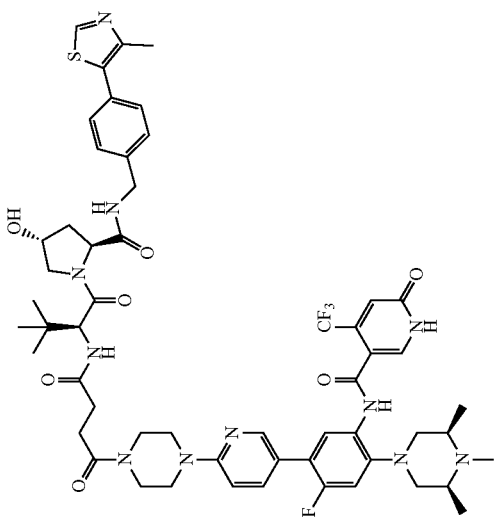 | N-(4-fluoro-5-(6-(4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| XF067-133 | 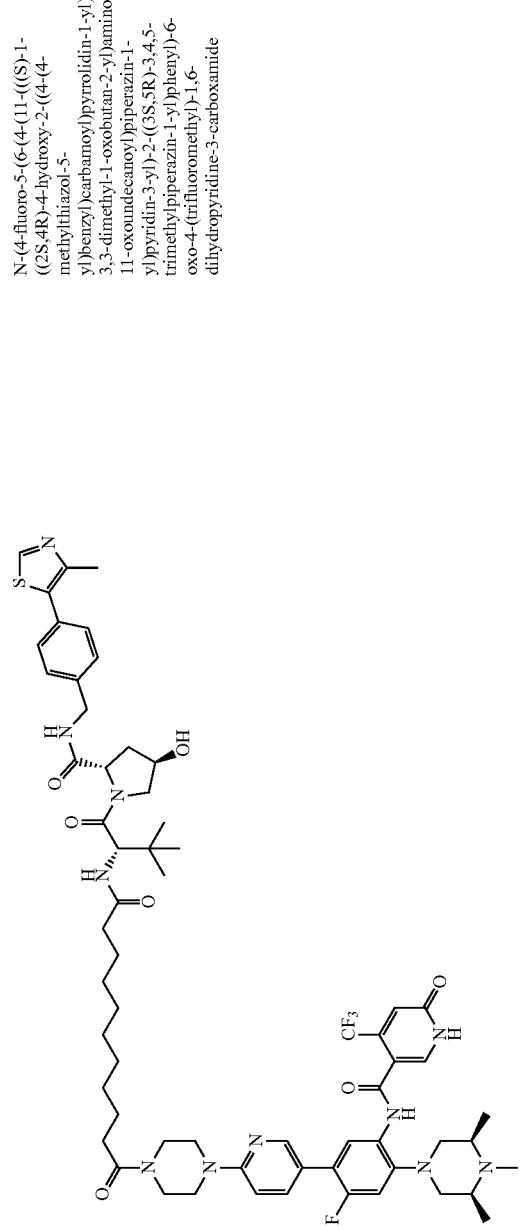 | N-(4-fluoro-5-(6-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF067-134 | 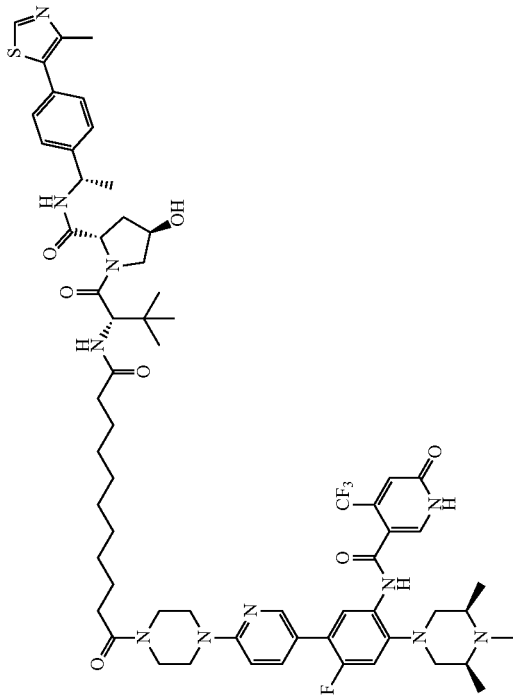 | N-(4-fluoro-5-(6-(4-(11-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-11-oxoundecanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| XF067-140 | 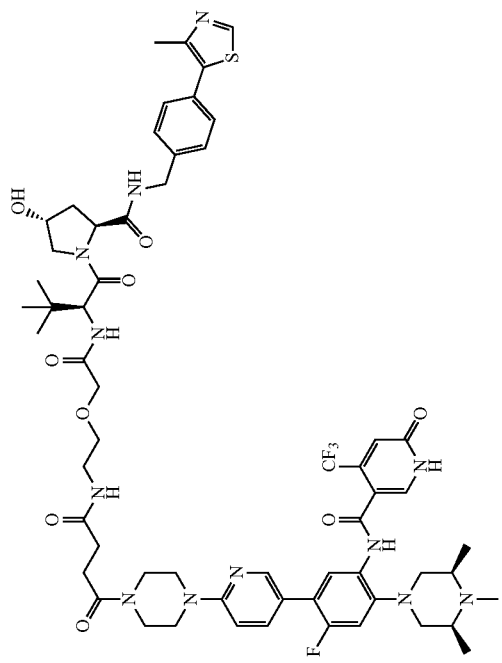 | N-(4-fluoro-5-(6-(4-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF067-142 | 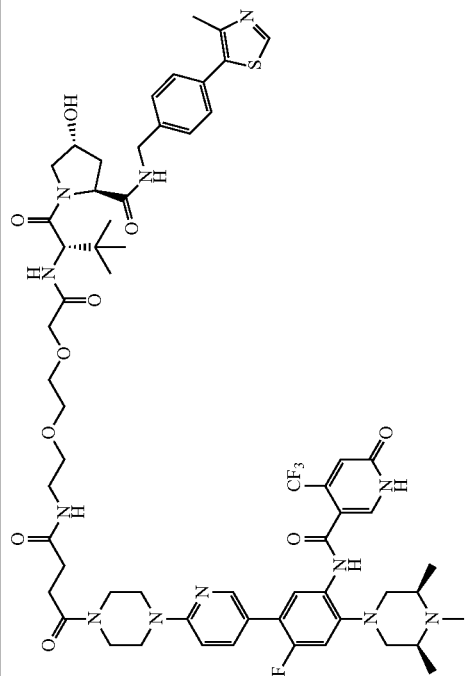 | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaheptadecan-17-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| XF067-146 | 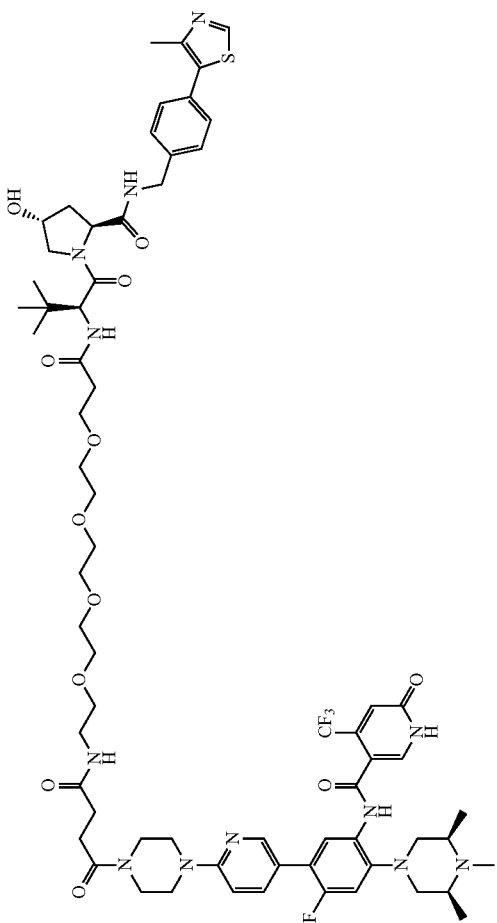 | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,21-dioxo-8,11,14,17-tetraoxa-4,20-diazatetracosan-24-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF067-149 | 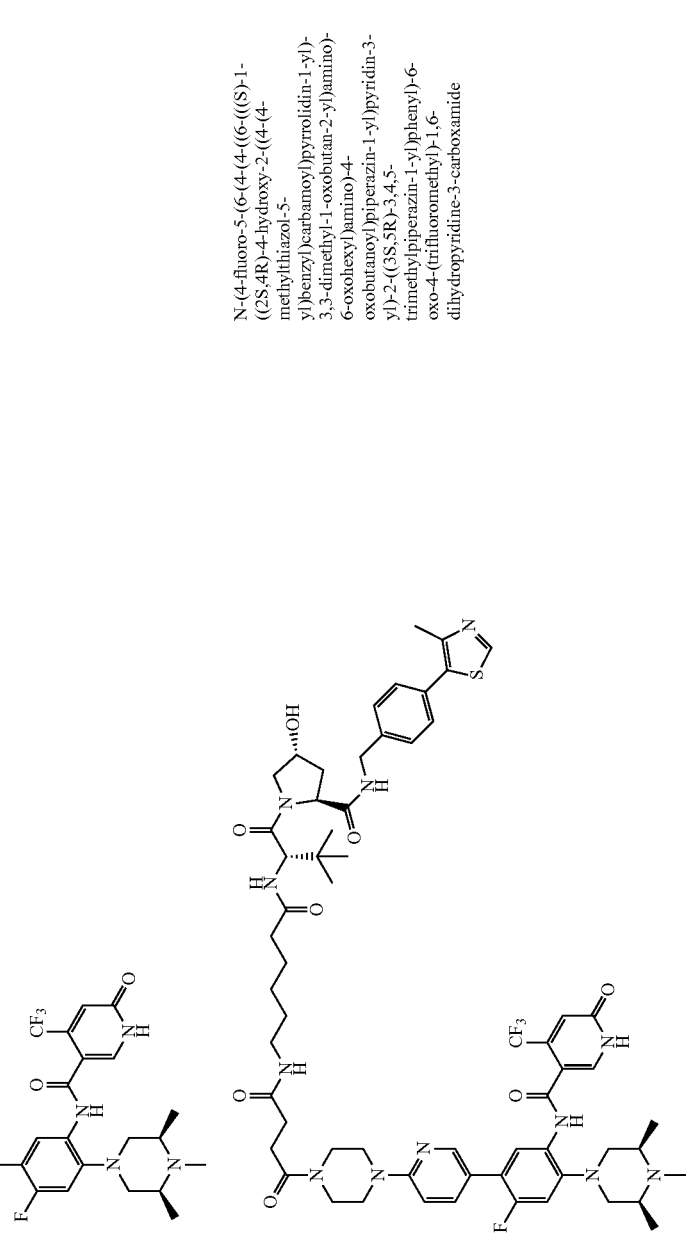 | N-(4-fluoro-5-(6-(4-(4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| XF067-152 | | N-(4-fluoro-5-(6-(4-(4-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-1 | 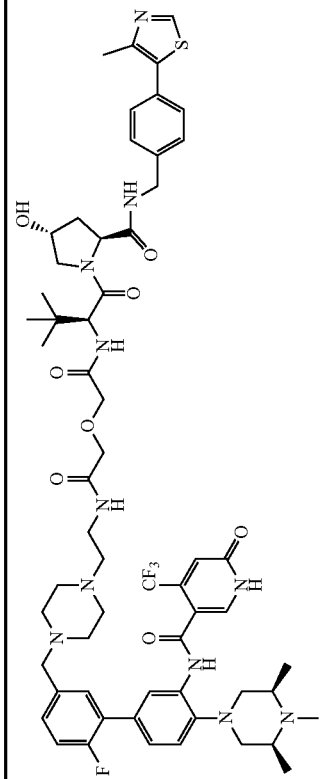 | N-(2'-fluoro-5'-((4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)ethyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-2 | 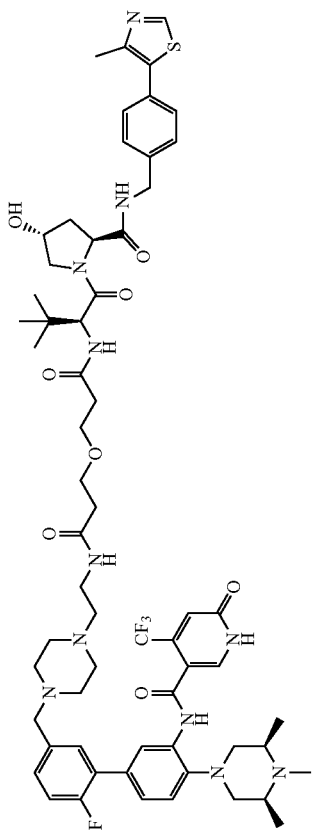 | N-(2'-fluoro-5'-((4-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanamido)ethyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-3 | 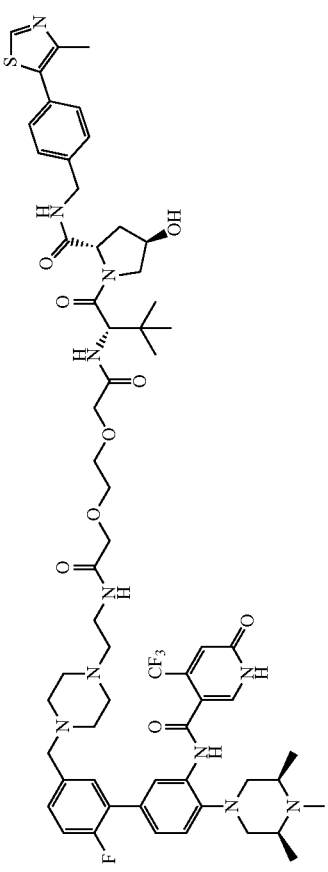 | N-(2'-fluoro-5'-((4-((S)-13-((2S,4R)-4-hydroxy-2-((4-(4-methylthiazol-5-yl)benzyl)carbamoyl)pyrrolidine-1-carbonyl)-14,14-dimethyl-4,11-dioxo-6,9-dioxa-3,12-diazapentadecyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

-continued

| | | |
|---|---|---|
| XF078-4 | 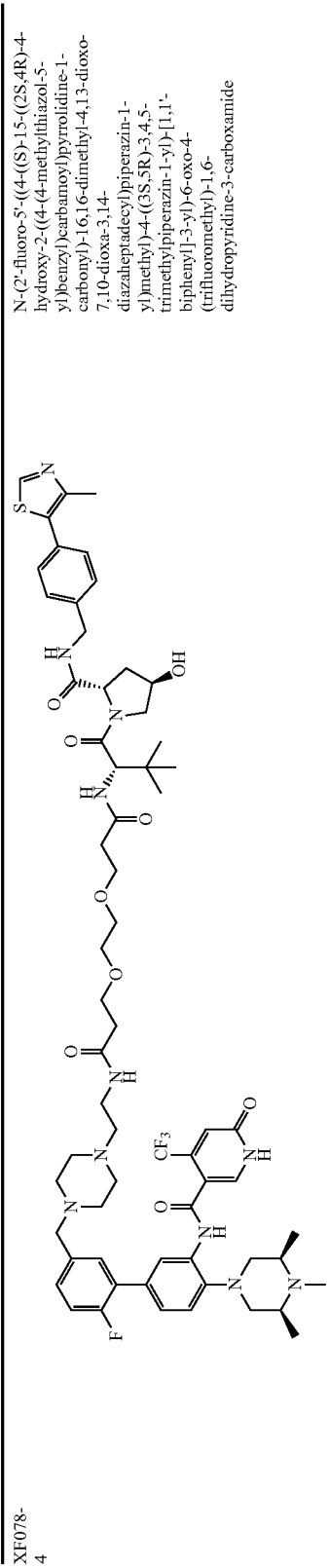 | N-(2'-fluoro-5'-((4-((S)-15-((2S,4R)-4-hydroxy-2-((4-(4-methylthiazol-5-yl)benzyl)carbamoyl)pyrrolidine-1-carbonyl)-16,16-dimethyl-4,13-dioxo-7,10-dioxa-3,14-diazaheptadecyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-5 | 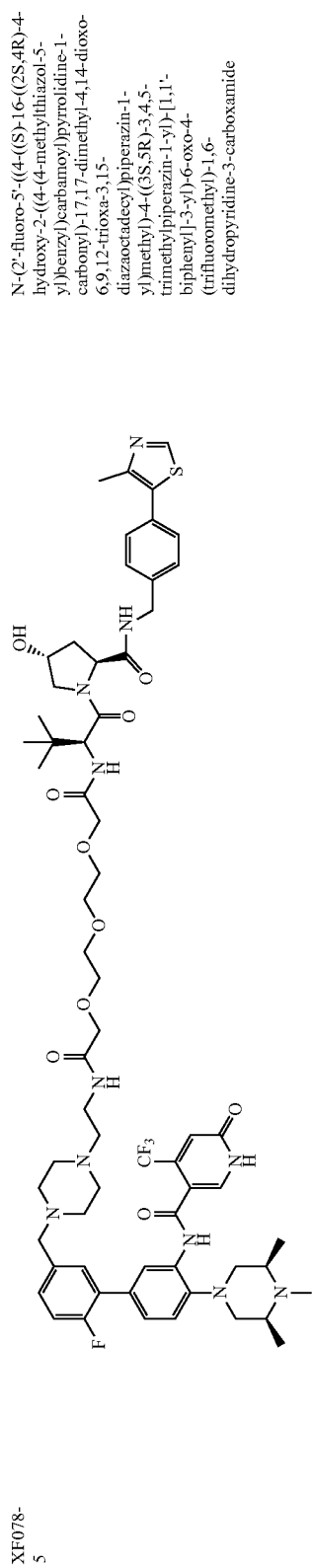 | N-(2'-fluoro-5'-((4-((S)-16-((2S,4R)-4-hydroxy-2-((4-(4-methylthiazol-5-yl)benzyl)carbamoyl)pyrrolidine-1-carbonyl)17,17-dimethyl-4,14-dioxo-6,9,12-trioxa-3,15-diazaoctadecyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-6 | 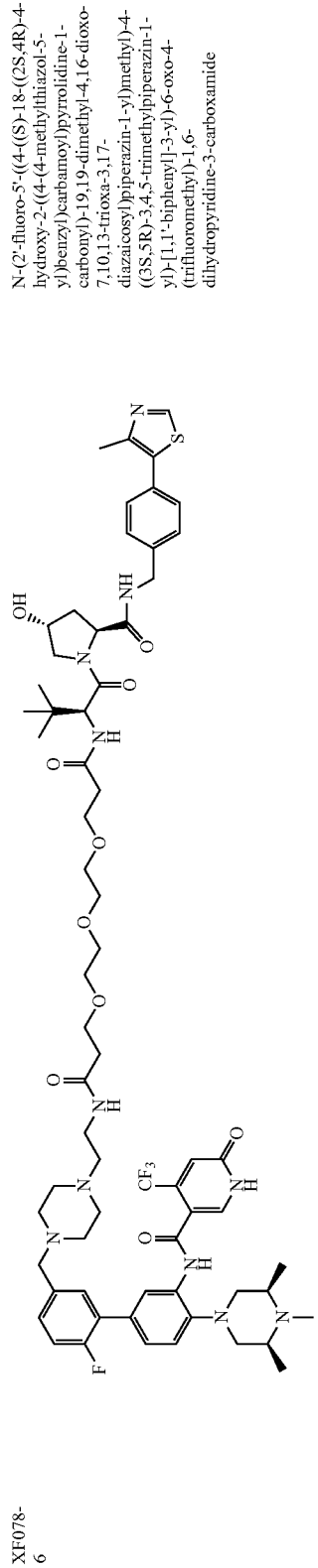 | N-(2'-fluoro-5'-((4-((S)-18-((2S,4R)-4-hydroxy-2-((4-(4-methylthiazol-5-yl)benzyl)carbamoyl)pyrrolidine-1-carbonyl)-19,19-dimethyl-4,16-dioxo-7,10,13-trioxa-3,17-diazaicosyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF078-8 | 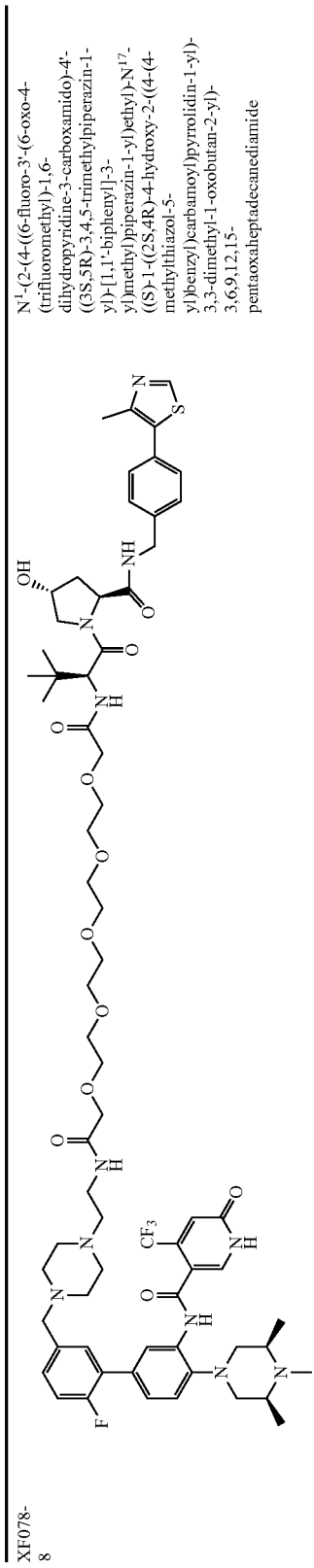 | N$^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N$^{17}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide |
| XF078-9 | 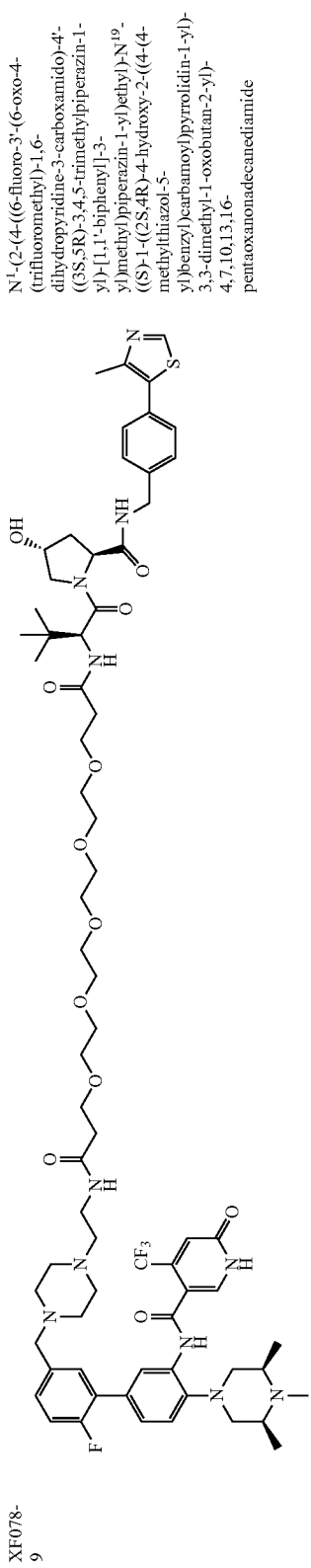 | N$^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N$^{19}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| XF078-12 | 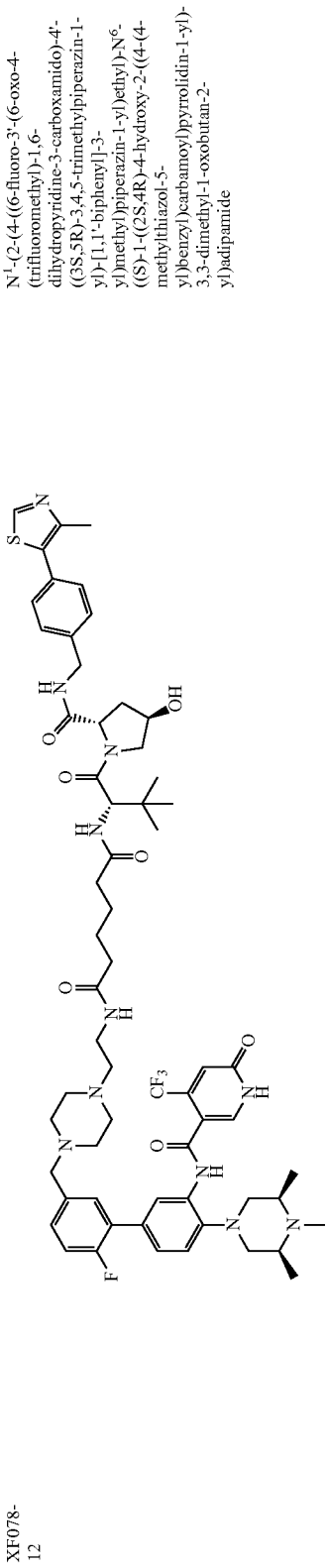 | N$^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N$^6$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |

| | | |
|---|---|---|
| XF078-13 | 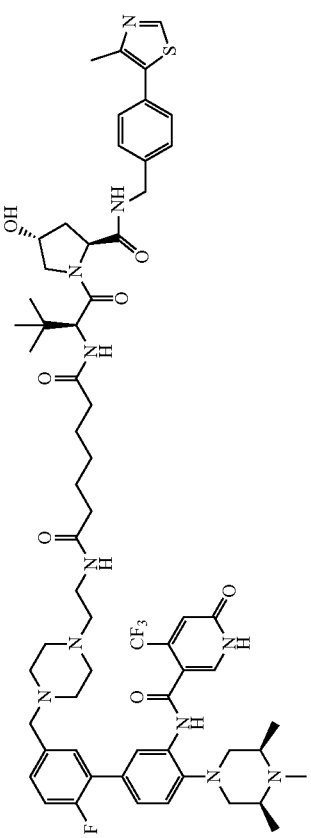 | $N^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-$N^7$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
| XF078-14 | 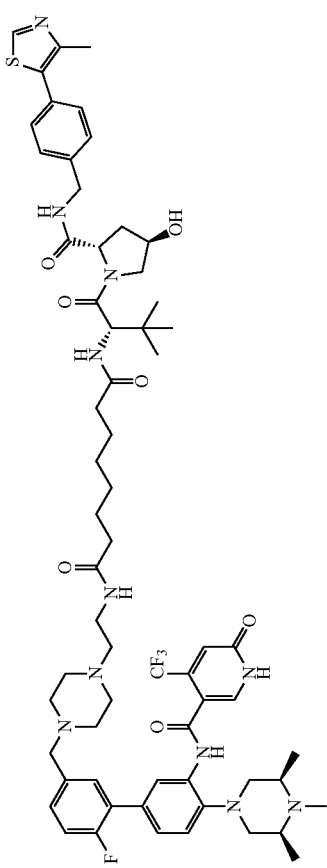 | $N^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-$N^8$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |
| XF078-15 | 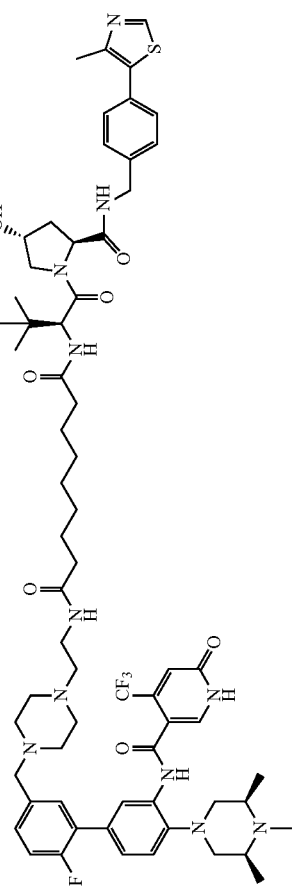 | $N^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-$N^9$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |

| | |
|---|---|
| XF078-16 | N¹-(2-(4-((6-fluoro-3'-(6-oxo-4-(trifluoromethyl)-1,6-dihydropyridine-3-carboxamido)-4-((3S,5R)-3,4,5-trimethylpiperazin-1-yl)-[1,1'-biphenyl]-3-yl)methyl)piperazin-1-yl)ethyl)-N¹⁰-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |
| XF078-17 | N¹-(2-(4-((6-fluoro-3'-(6-oxo-4-(trifluoromethyl)-1,6-dihydropyridine-3-carboxamido)-4-((3S,5R)-3,4,5-trimethylpiperazin-1-yl)-[1,1'-biphenyl]-3-yl)methyl)piperazin-1-yl)ethyl)-N¹¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| XF078-18 | N-(5'-((4-(2-(2-(2-(2,6-dioxopiperidin-3-yl)-1,3-dioxoisoindolin-4-yl)amino)acetamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF078-19 | | N-(5'-((4-(2-(3-((2-(2,6-dioxopiperidin-3-yl)-1,3-dioxoisoindolin-4-yl)amino)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-20 | | N-(5'-((4-(2-(4-((2-(2,6-dioxopiperidin-3-yl)-1,3-dioxoisoindolin-4-yl)amino)butanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-21 | | N-(5'-((4-(2-(5-((2-(2,6-dioxopiperidin-3-yl)-1,3-dioxoisoindolin-4-yl)amino)pentanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF078-22 | 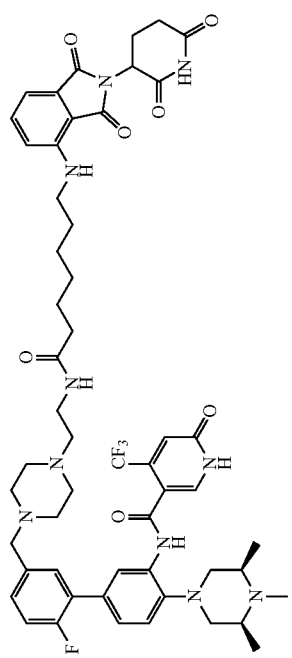 | N-(5'-((4-(2-(6-((2-(2,6-dioxopiperidin-3-yl)-1,3-dioxoisoindolin-4-yl)amino)hexanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-23 | 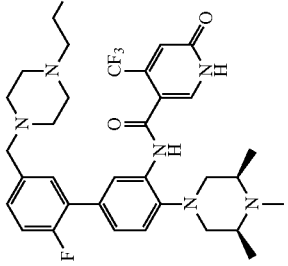 | N-(5'-((4-(2-(7-((2-(2,6-dioxoisoindolin-3-yl)-1,3-dioxoisoindolin-4-yl)amino)heptanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-24 | 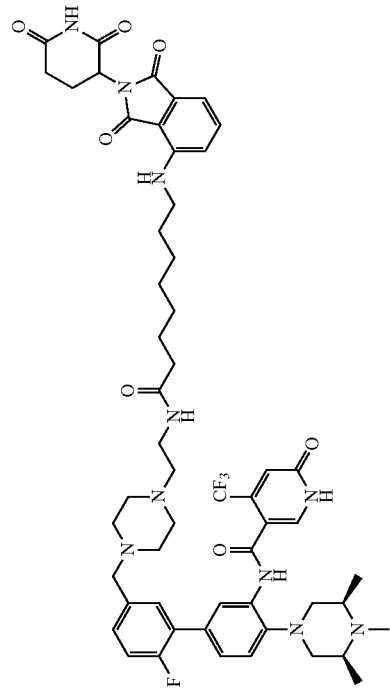 | N-(5'-((4-(2-(8-((2-(2,6-dioxopiperidin-3-yl)-1,3-dioxoisoindolin-4-yl)amino)octanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF078-25 | 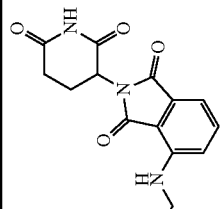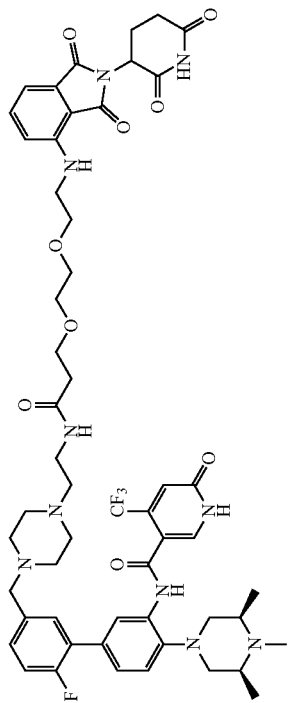 | N-(5'-((4-(2-(3-(2-((2-(2,6-dioxopiperidin-3-yl)-1,3-dioxoisoindolin-4-yl)amino)ethoxy)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-26 | 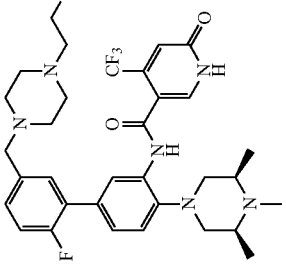 | N-(5'-((4-(2-(3-(2-((2-(2,6-dioxopiperidin-3-yl)-1,3-dioxoisoindolin-4-yl)amino)ethoxy)ethoxy)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-27 | 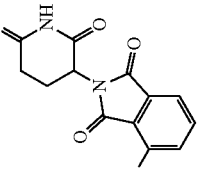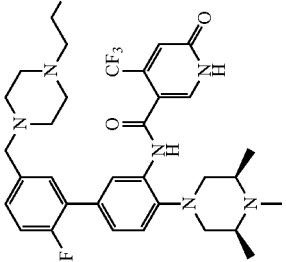 | N-(5'-((4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF078-28 | 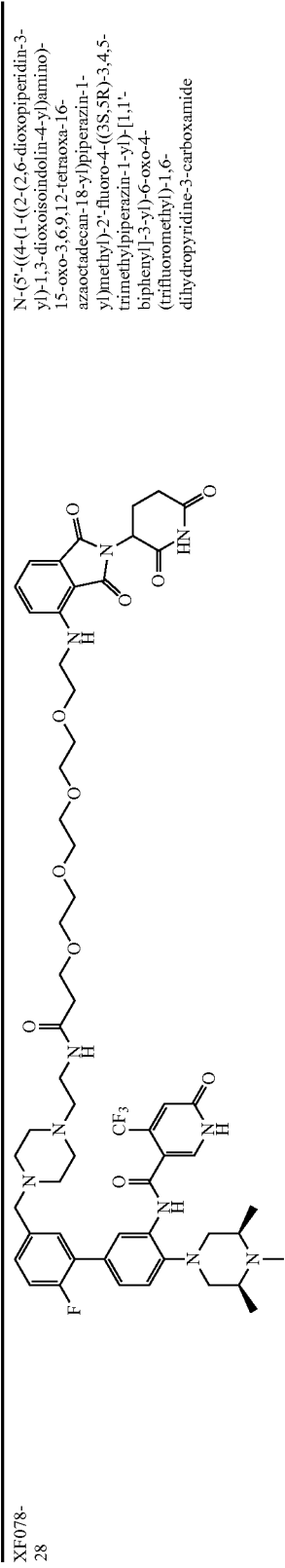 | N-(5'-((4-(1-((2-(2,6-dioxopiperidin-3-yl)-1,3-dioxoisoindolin-4-yl)amino)-15-oxo-3,6,9,12-tetraoxa-16-azaoctadecan-18-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-29 | 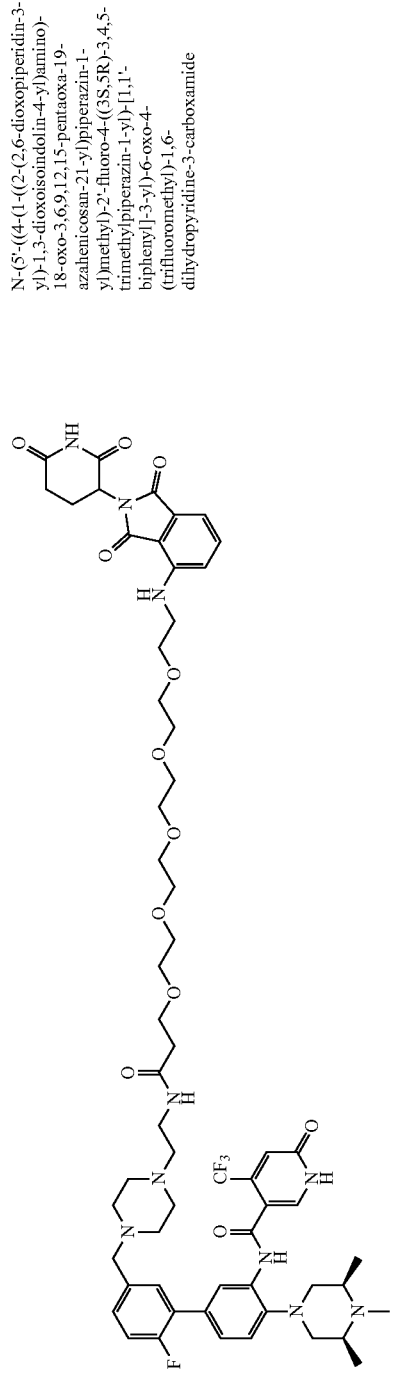 | N-(5'-((4-(1-((2-(2,6-dioxopiperidin-3-yl)-1,3-dioxoisoindolin-4-yl)amino)-18-oxo-3,6,9,12,15-pentaoxa-19-azahenicosan-21-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-30 | 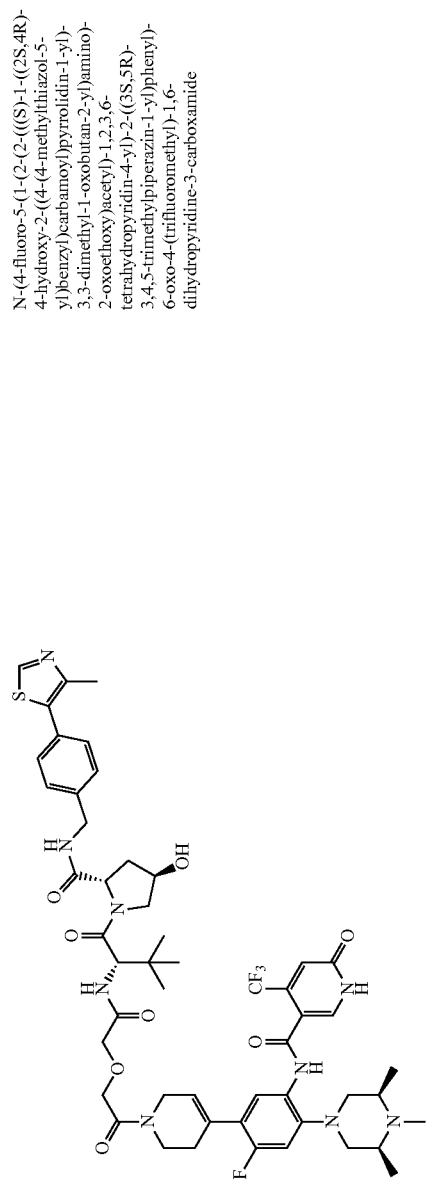 | N-(4-fluoro-5-(1-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-34 | 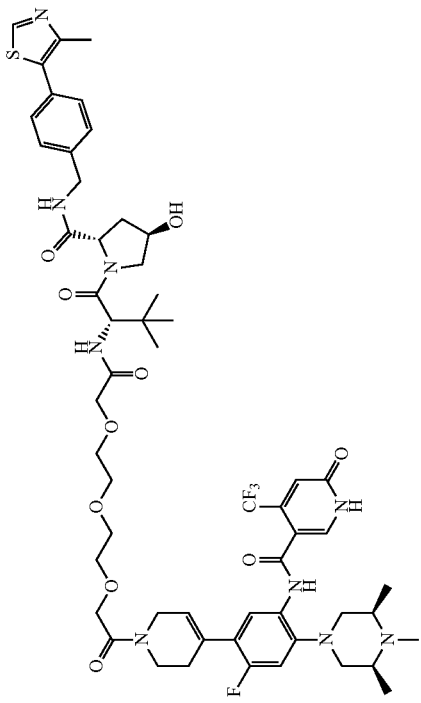 | N-(4-fluoro-5-(1-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-35 | 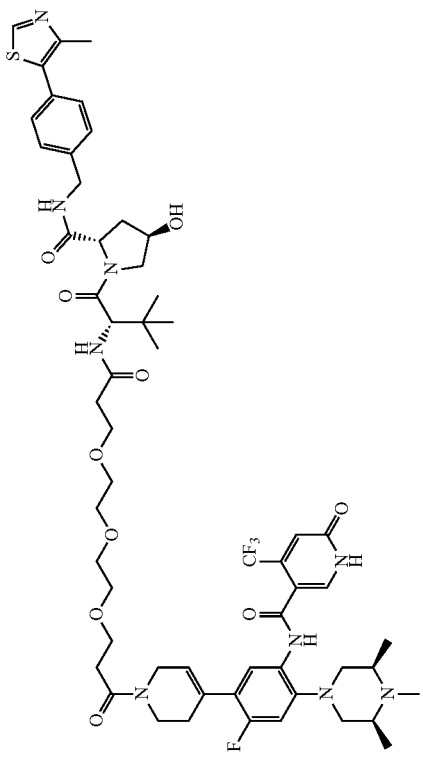 | N-(4-fluoro-5-(1-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-41 | 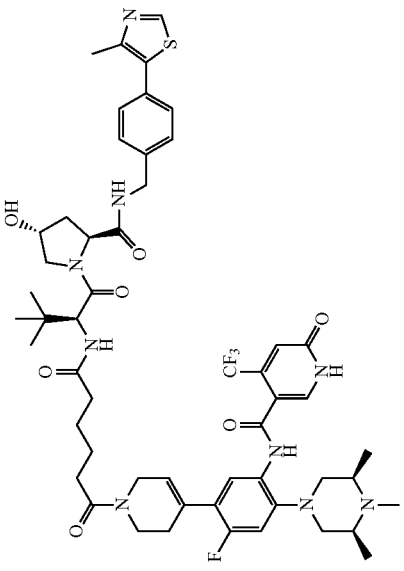 | N-(4-fluoro-5-(1-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-42 | 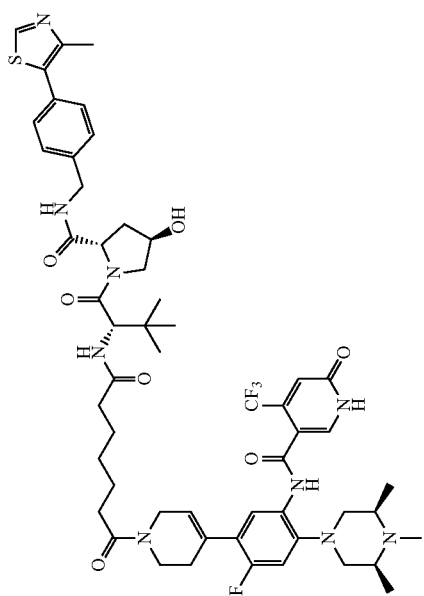 | N-(4-fluoro-5-(1-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-43 | 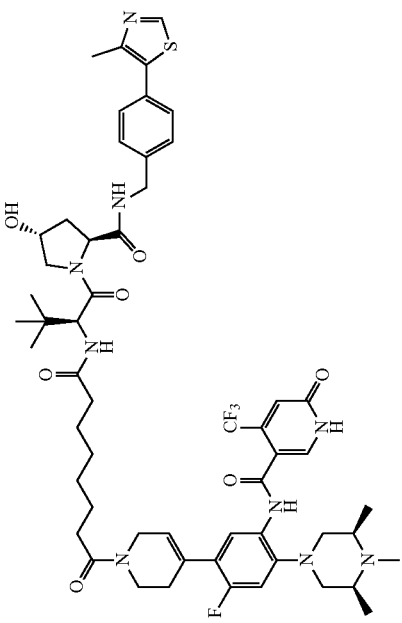 | N-(4-fluoro-5-(1-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-44 | 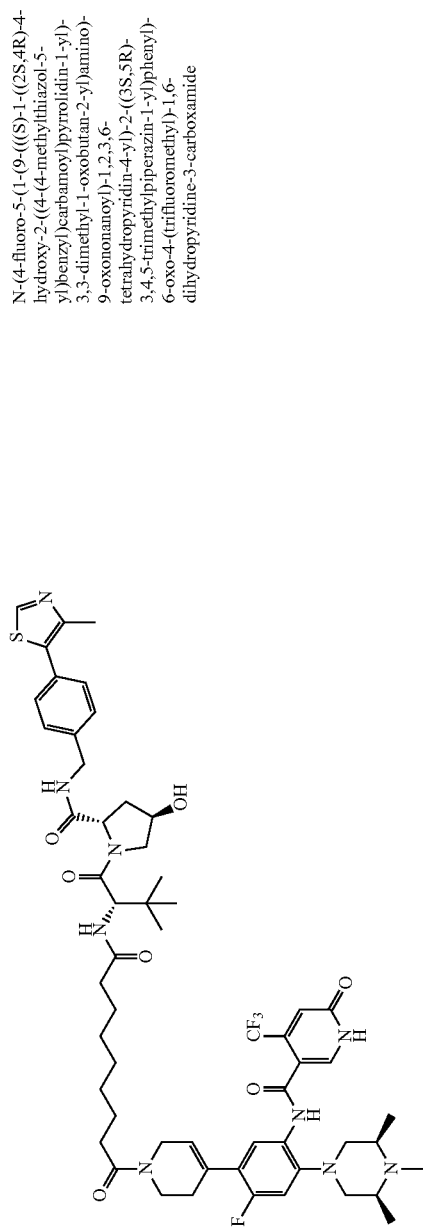 | N-(4-fluoro-5-(1-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-45 | 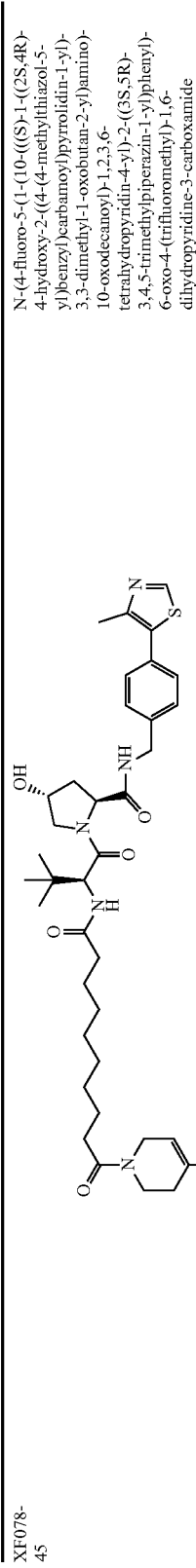 | N-(4-fluoro-5-(1-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-46 | 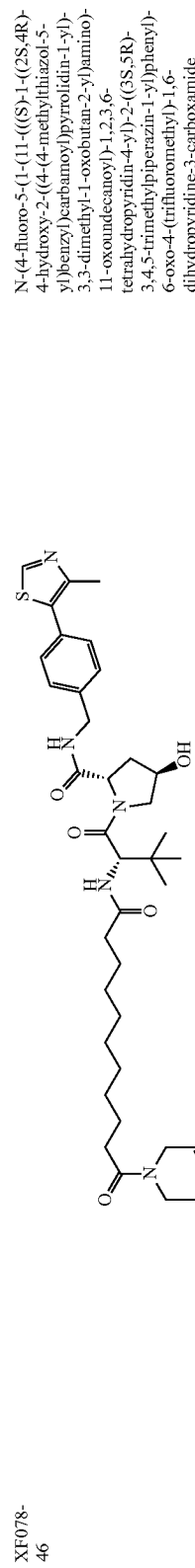 | N-(4-fluoro-5-(1-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-51 | 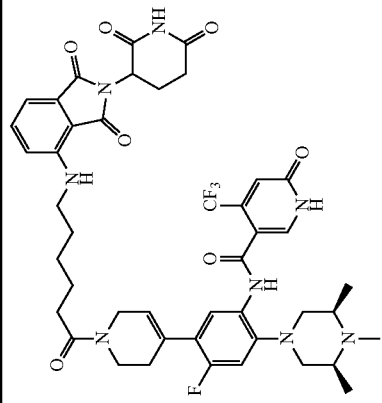 | N-(5-(1-(6-((2-(2,6-dioxopiperidin-3-yl)-1,3-dioxoisoindolin-4-yl)amino)hexanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF078-52 | 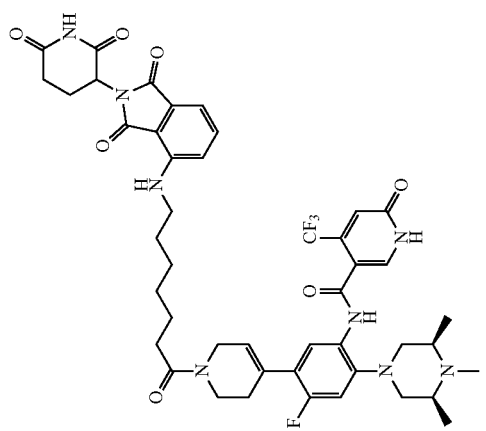 | N-(5-(1-(7-((2-(2,6-dioxopiperidin-3-yl)-1,3-dioxoisoindolin-4-yl)amino)heptanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| XF078-53 | 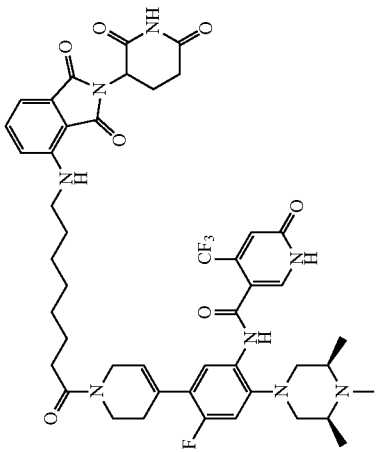 | N-(5-(1-(8-((2-(2,6-dioxopiperidin-3-yl)-1,3-dioxoisoindolin-4-yl)amino)octanoyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF078-57 | 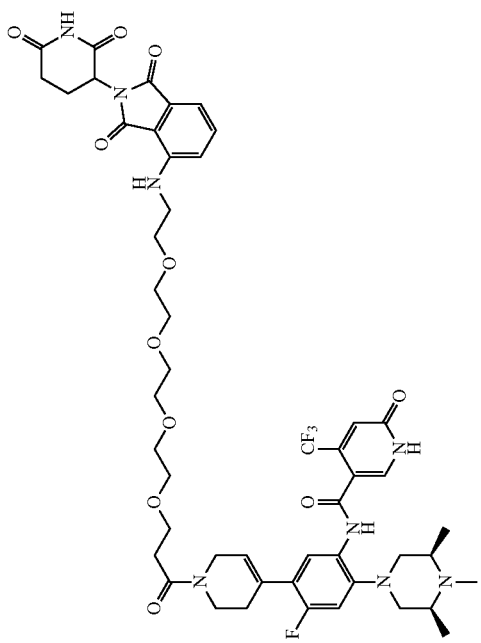 | N-(5-(1-(1-((2-(2,6-dioxopiperidin-3-yl)-1,3-dioxoisoindolin-4-yl)amino)-3,6,9,12-tetraoxapentadecan-15-oyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-58 | 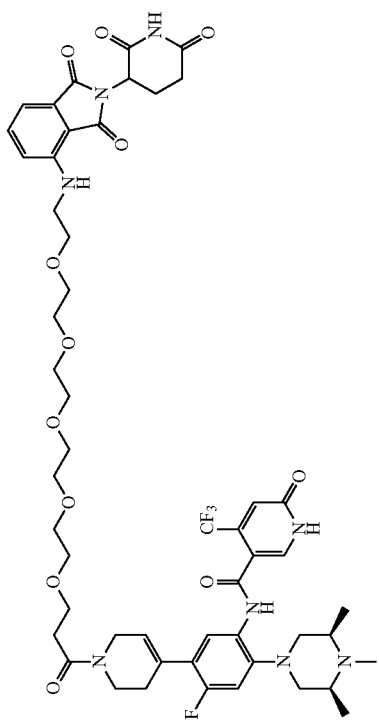 | N-(5-(1-(1-((2-(2,6-dioxopiperidin-3-yl)-1,3-dioxoisoindolin-4-yl)amino)-3,6,9,12,15-pentaoxaoctadecan-18-oyl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF078-61 | 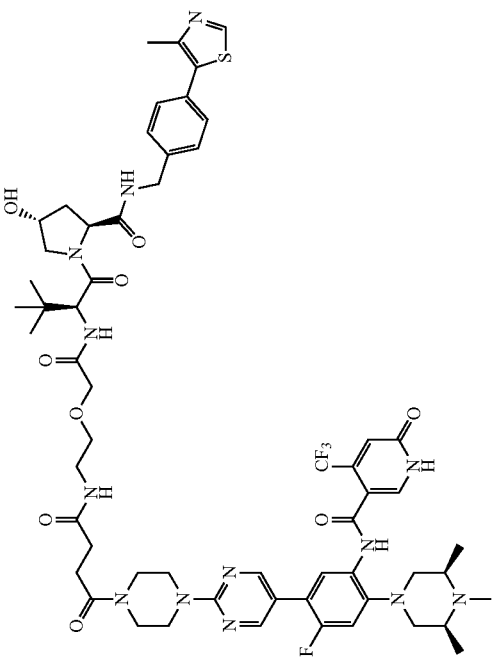 | N-(4-fluoro-5-(2-(4-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

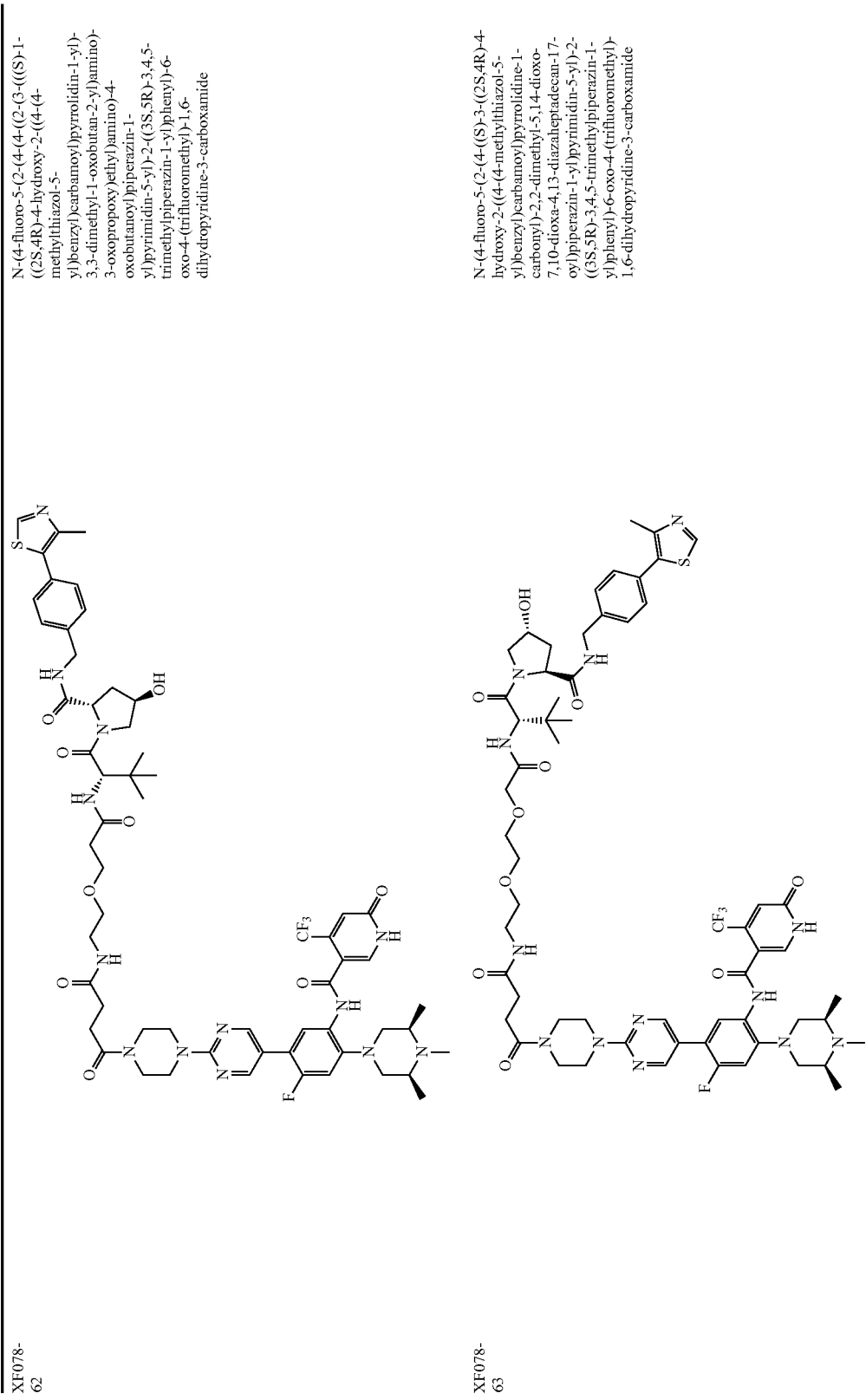

| | | |
|---|---|---|
| XF078-69 | 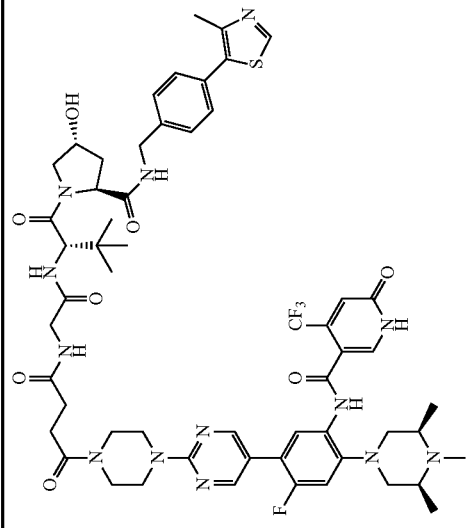 | N-(4-fluoro-5-(2-(4-(4-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |
| XF078-70 | 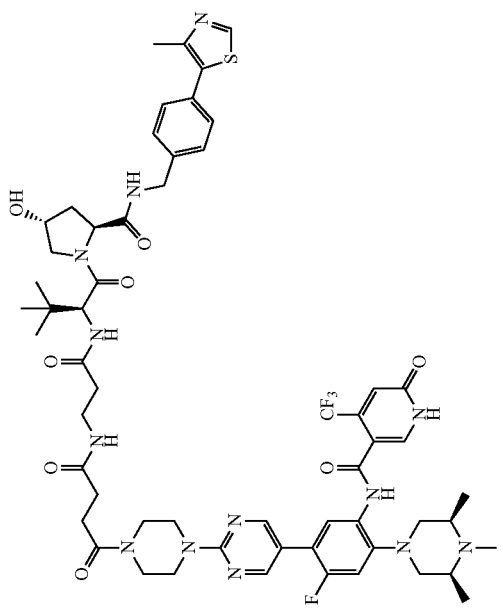 | N-(4-fluoro-5-(2-(4-(4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

| | |
|---|---|
| XF078-71 | N-(4-fluoro-5-(2-(4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide 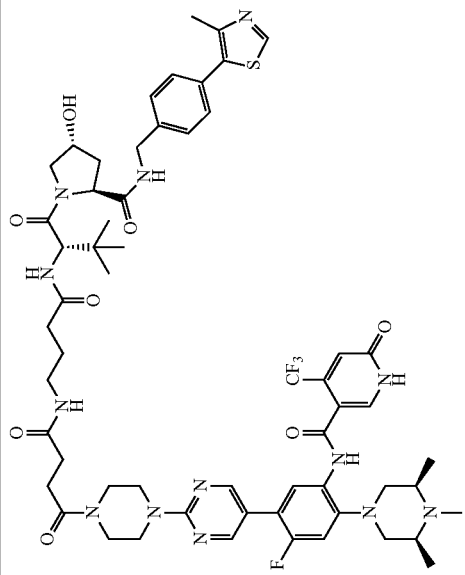 |
| XF078-79 | N-(5-(2-(4-(4-(2-(2-(2,6-dioxopiperidin-3-yl)-1,3-dioxoisoindolin-4-yl)amino)ethoxy)ethyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide 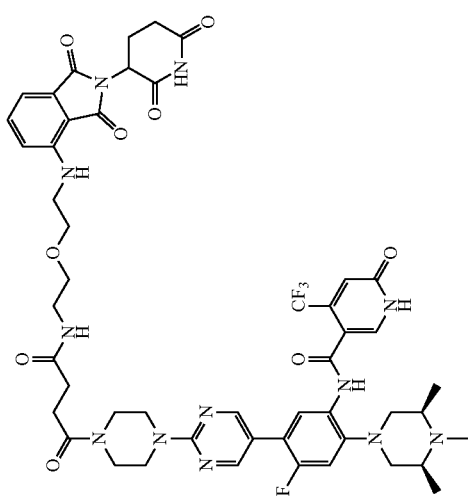 |

| | | |
|---|---|---|
| XF078-80 | 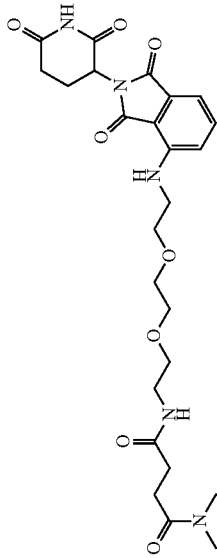 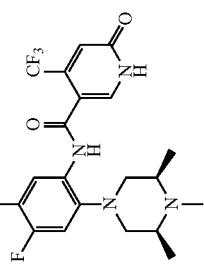 | N-(5-(2-(4-(4-((2-(2-(2-(2-(2,6-dioxopiperidin-3-yl)-1,3-dioxoisoindolin-4-yl)amino)ethoxy)ethyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF078-81 | 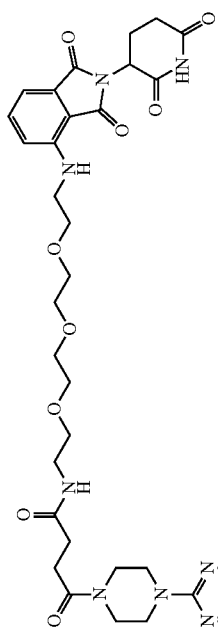 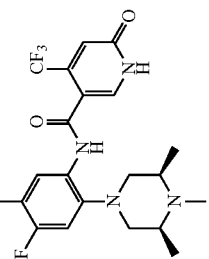 | N-(5-(2-(4-(1-((2-(2,6-dioxopiperidin-3-yl)-1,3-dioxoisoindolin-4-yl)amino)-13-oxo-3,6,9-trioxa-12-azahexadecan-16-oyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| | -continued | |
|---|---|---|
| XF078-84 | 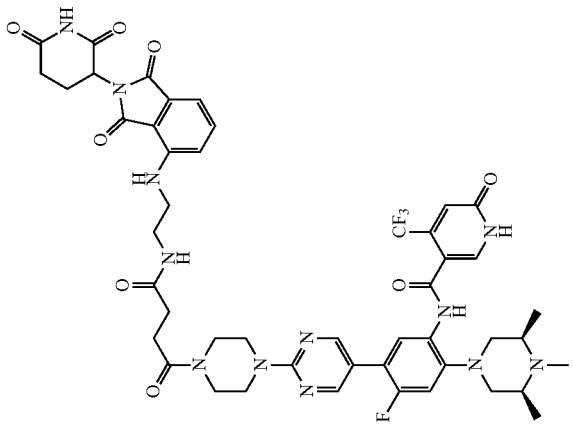 | N-(5-(2-(4-(4-((2-(2,6-dioxopiperidin-3-yl)-1,3-dioxoisoindolin-4-yl)amino)ethyl)amino)-4-oxobutanoyl)piperazin-1-yl)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF078-99 | 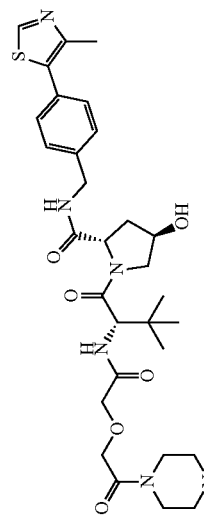 | (2S,4R)-1-((S)-2-(2-(2-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |

| | | |
|---|---|---|
| XF078-101 | [structure] | (2S,4R)-1-((S)-2-(2-(2-(2-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| XF078-102 | [structure] | (2S,4R)-1-((S)-2-(3-(2-(3-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

| XF078-103 | 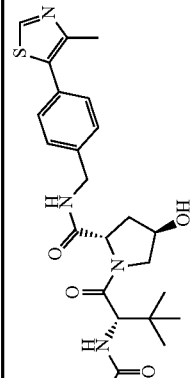 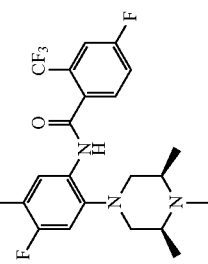 | (2S,4R)-1-((S)-2-(tert-butyl)-14-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide |
|---|---|---|
| XF078-104 | 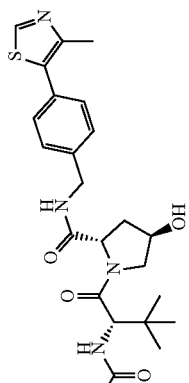 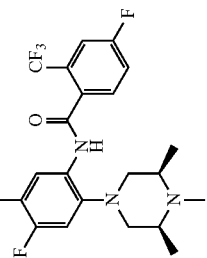 | (2S,4R)-1-((S)-2-(tert-butyl)-16-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |

| | | |
|---|---|---|
| XF078-105 | 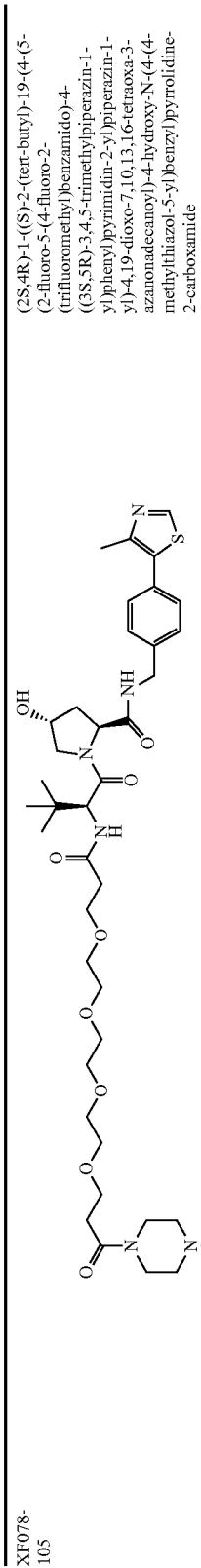 | (2S,4R)-1-((S)-2-(tert-butyl)-19-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| XF078-106 | 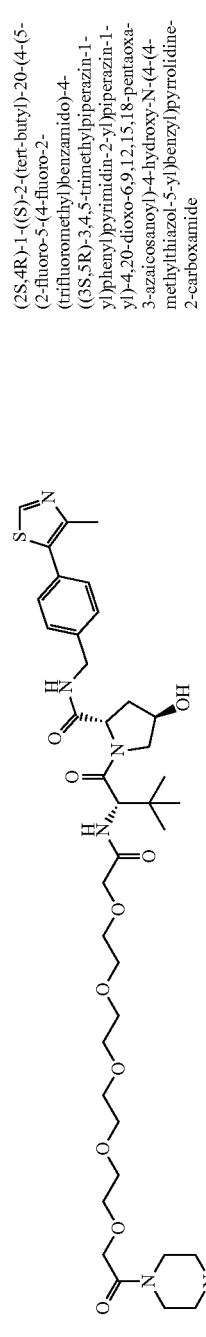 | (2S,4R)-1-((S)-2-(tert-butyl)-20-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |

| | | |
|---|---|---|
| XF078-110 | [structure] | (2S,4R)-1-((S)-2-(6-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |
| XF078-111 | [structure] | (2S,4R)-1-((S)-2-(7-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |

| | | |
|---|---|---|
| XF078-112 | 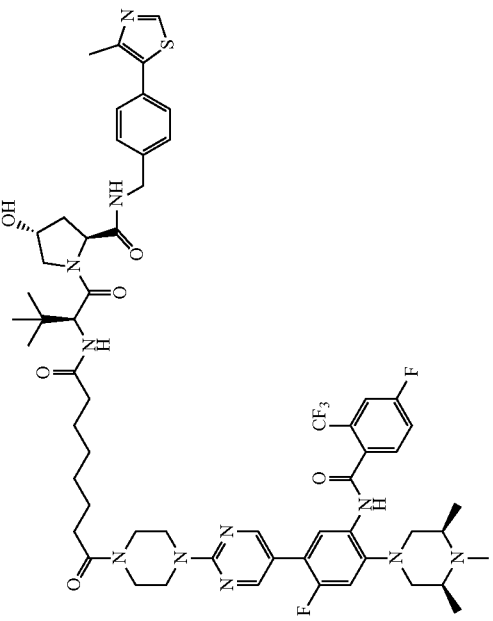 | (2S,4R)-1-((S)-2-(8-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| XF078-113 | 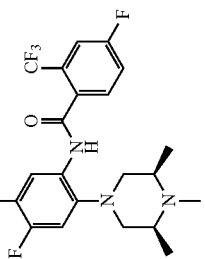 | (2S,4R)-1-((S)-2-(9-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |

| | | |
|---|---|---|
| XF078-114 | 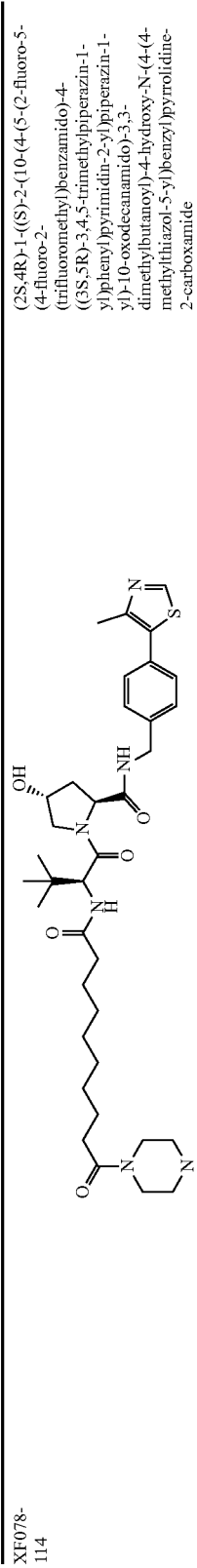 | (2S,4R)-1-((S)-2-(10-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |
| XF078-115 | | (2S,4R)-1-((S)-2-(11-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |

| | | -continued | |
|---|---|---|---|
| XF078-118 | 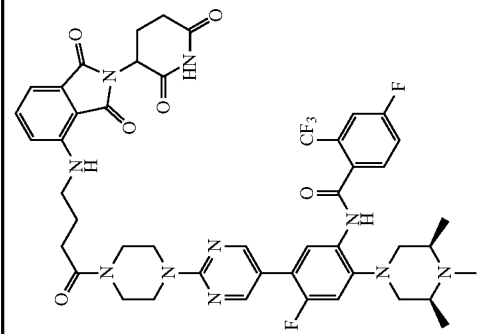 | | N-(5-(2-(4-(4-((2-(2,6-dioxopiperidin-3-yl)-1,3-dioxoisoindolin-4-yl)amino)butanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |
| XF078-119 | 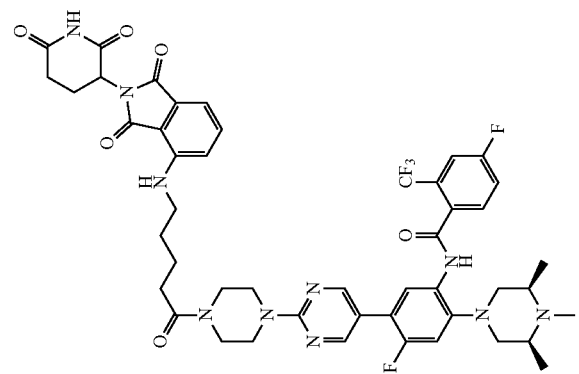 | | N-(5-(2-(4-(5-((2-(2,6-dioxopiperidin-3-yl)-1,3-dioxoisoindolin-4-yl)amino)pentanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

-continued
| | | |
|---|---|---|
| XF078-120 | 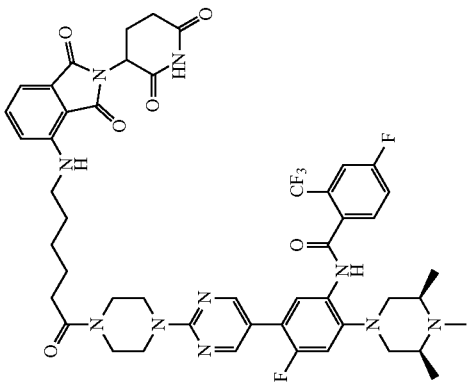 | N-(5-(2-(4-(6-((2-(2,6-dioxopiperidin-3-yl)-1,3-dioxoisoindolin-4-yl)amino)hexanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |
| XF078-121 | 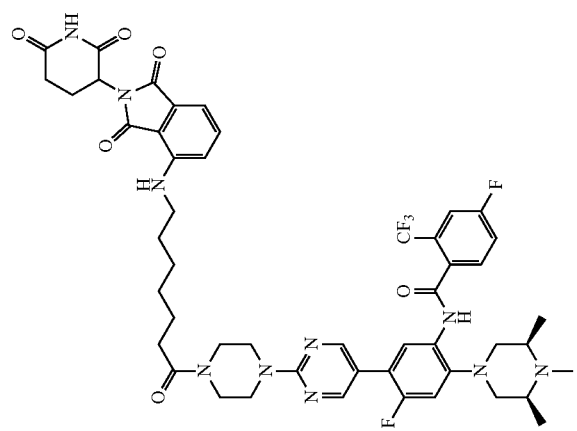 | N-(5-(2-(4-(7-((2-(2,6-dioxopiperidin-3-yl)-1,3-dioxoisoindolin-4-yl)amino)heptanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

| | | |
|---|---|---|
| XF078-122 | 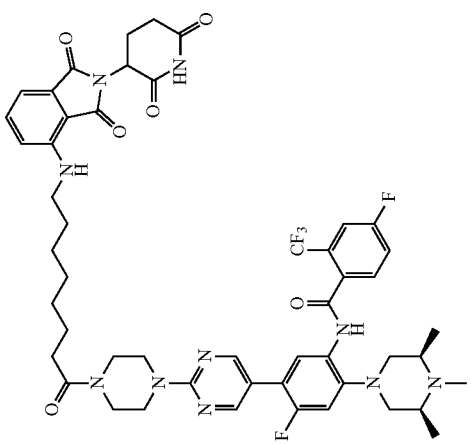 | N-(5-(2-(4-(8-((2-(2,6-dioxopiperidin-3-yl)-1,3-dioxoisoindolin-4-yl)amino)octanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |
| XF078-123 | 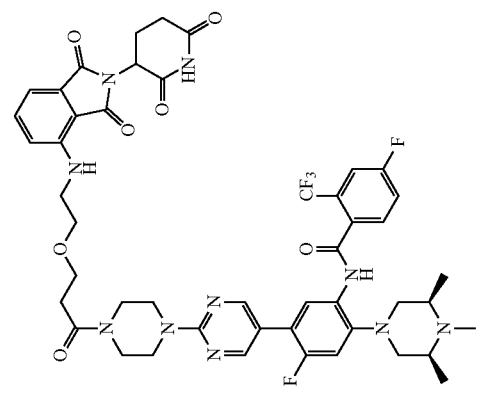 | N-(5-(2-(4-(3-(2-(2-(2,6-dioxopiperidin-3-yl)-1,3-dioxoisoindolin-4-yl)amino)ethoxy)propanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

| | | |
|---|---|---|
| XF078-124 | 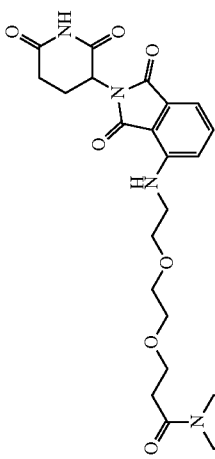 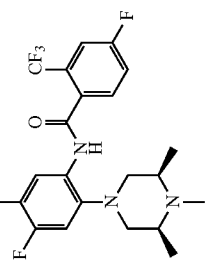 | N-(5-(2-(4-(3-(2-(2-(2-(2,6-dioxopiperidin-3-yl)-1,3-dioxoisoindolin-4-yl)amino)ethoxy)ethoxy)propanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |
| XF078-125 | 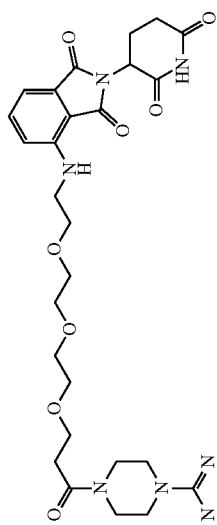 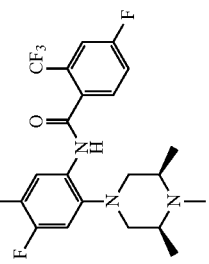 | N-(5-(2-(4-(3-(2-(2-(2-(2,6-dioxopiperidin-3-yl)-1,3-dioxoisoindolin-4-yl)amino)ethoxy)ethoxy)propanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

| | | |
|---|---|---|
| XF078-126 | 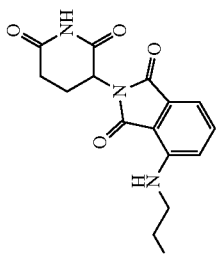 | N-(5-(2-(4-(1-(2-(2,6-dioxopiperidin-3-yl)-1,3-dioxoisoindolin-4-yl)amino)-3,6,9,12-tetraoxapentadecan-15-oyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |
| XF078-127 | 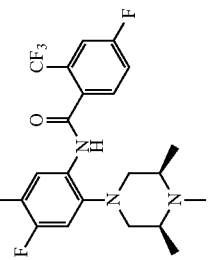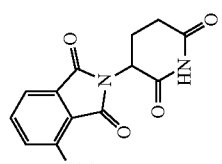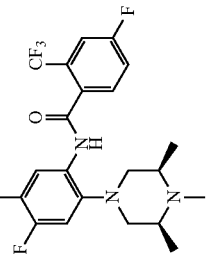 | N-(5-(2-(4-(1-(2-(2,6-dioxopiperidin-3-yl)-1,3-dioxoisoindolin-4-yl)amino)-3,6,9,12,15-pentaoxaoctadecan-18-oyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

-continued

| | | |
|---|---|---|
| XF078-132 | 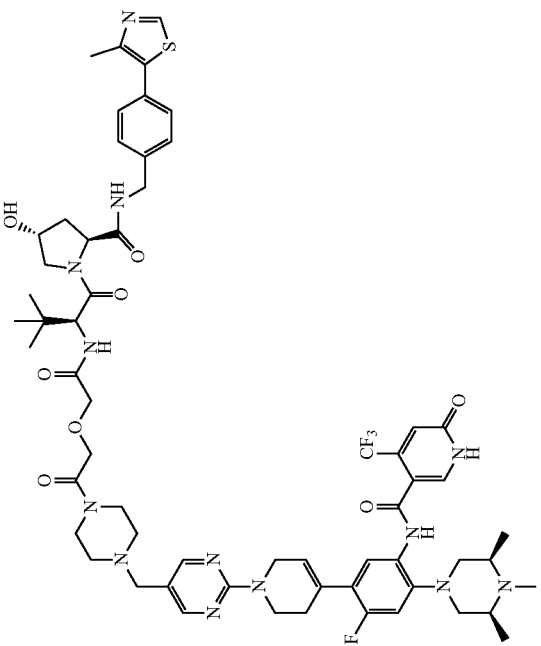 | N-(4-fluoro-5-(1-(5-((4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-133 | 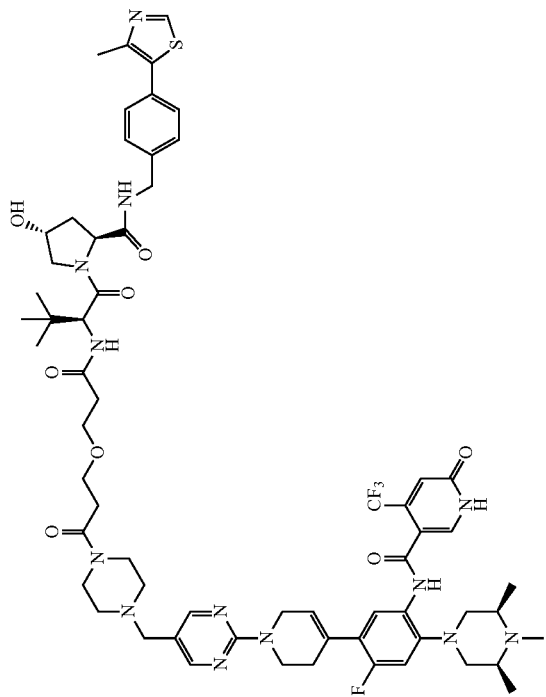 | N-(4-fluoro-5-(1-(5-((4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

-continued

| | | |
|---|---|---|
| XF078-134 | 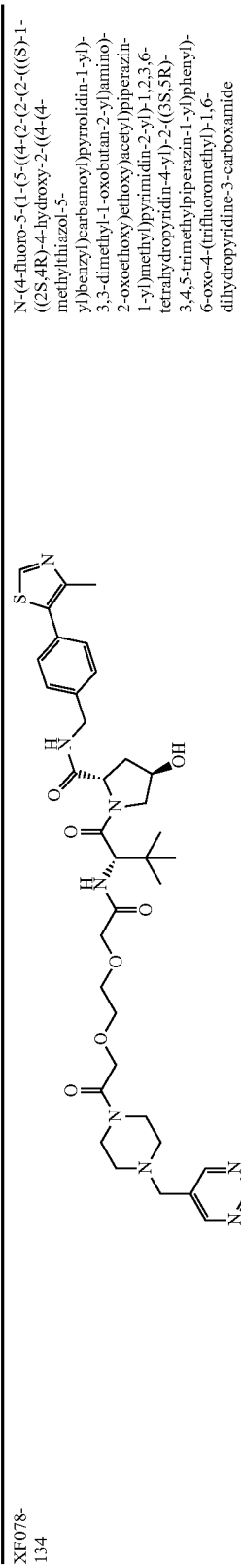 | N-(4-fluoro-5-(1-(5-((4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-135 | 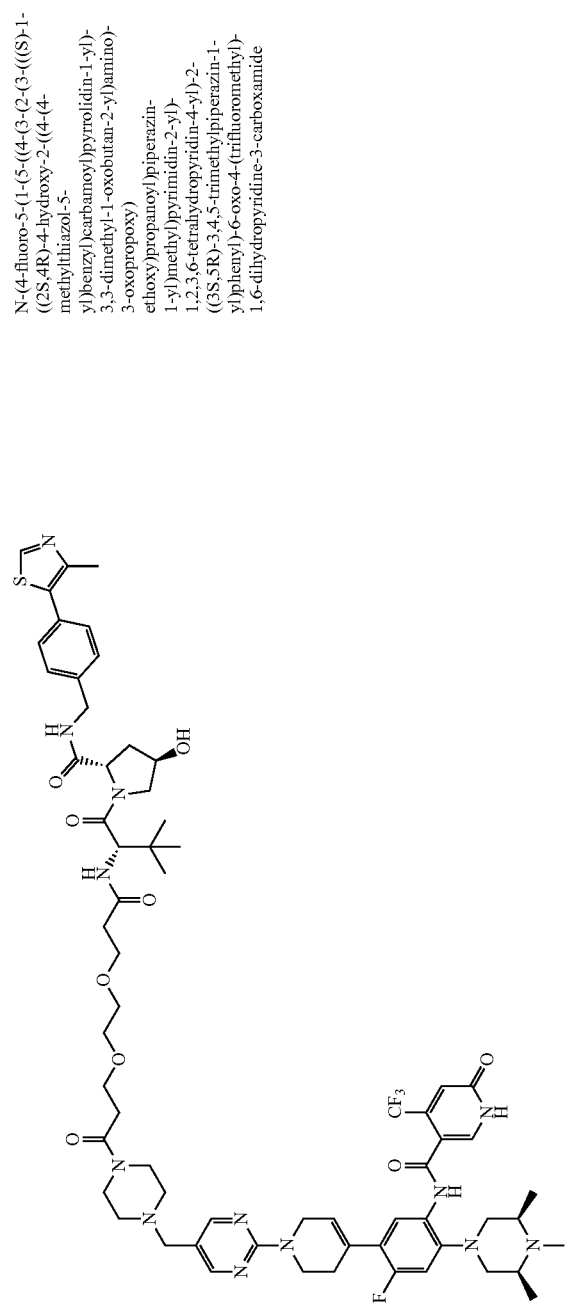 | N-(4-fluoro-5-(1-(5-((4-(3-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoyl)piperazin-1-yl)methyl)pyrimidin-4-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-136 | 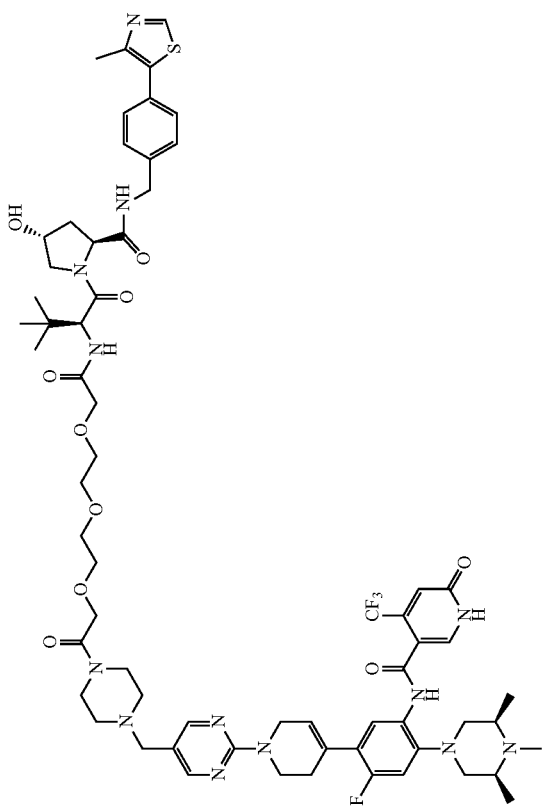 | N-(4-fluoro-5-(1-(5-((4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-137 | 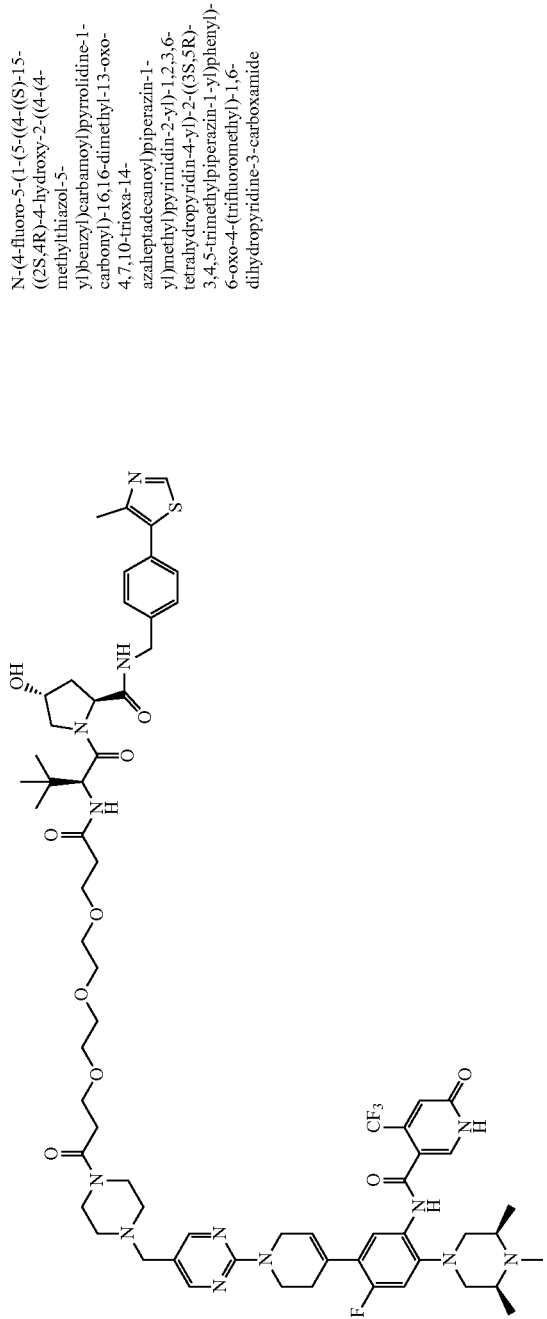 | N-(4-fluoro-5-(1-(5-((4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-138 | 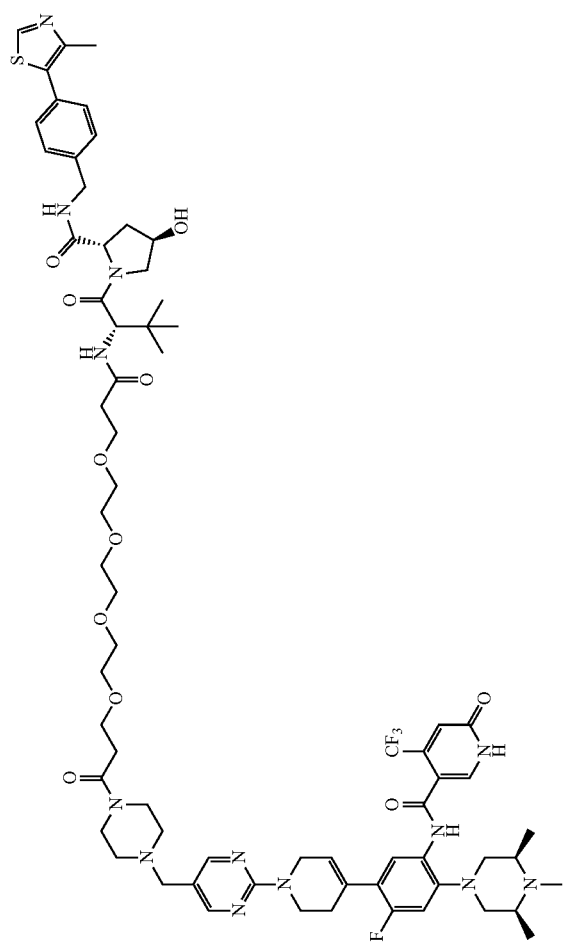 | N-(4-fluoro-5-(1-(5-((4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-139 | 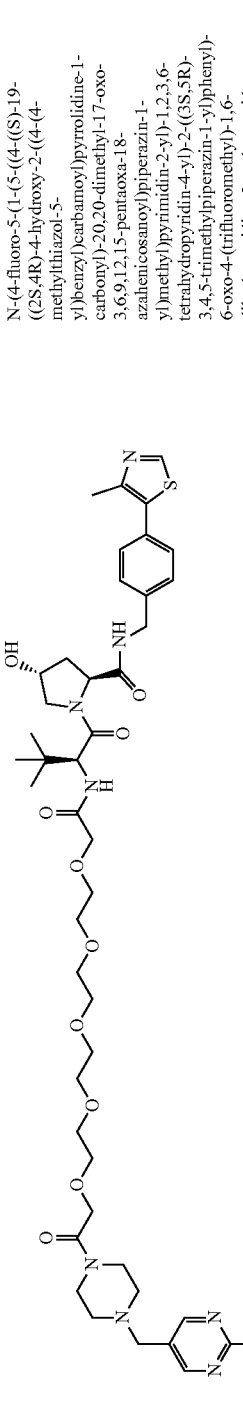 | N-(4-fluoro-5-(1-(5-((4-((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-140 | 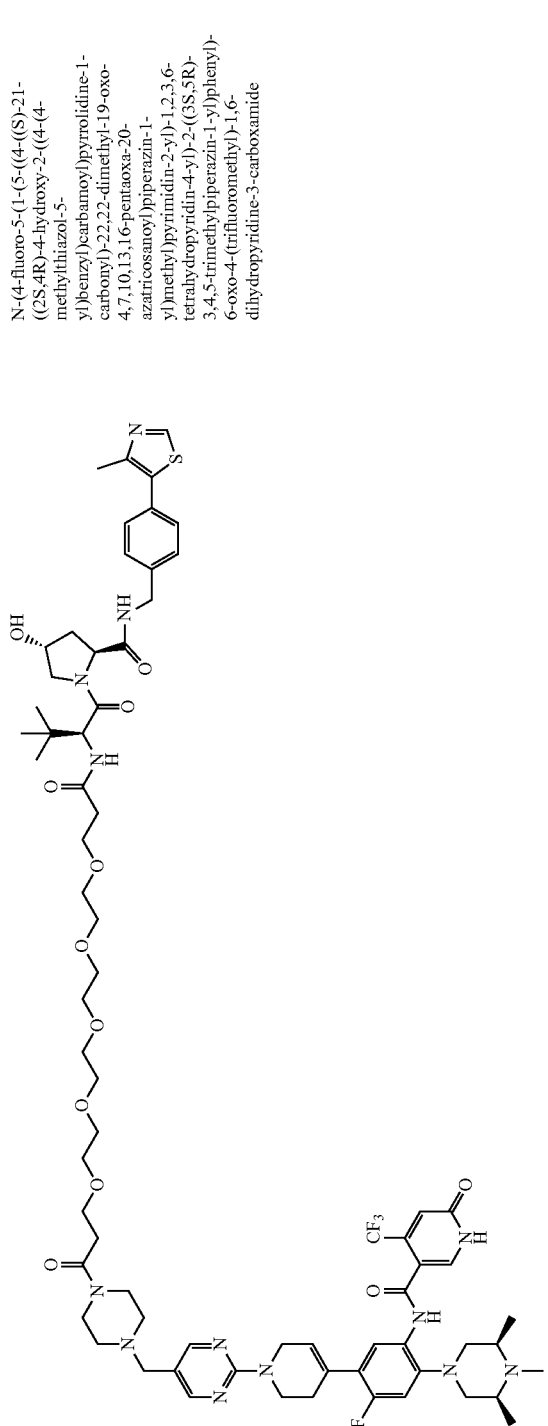 | N-(4-fluoro-5-(1-(5-((4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-141 | 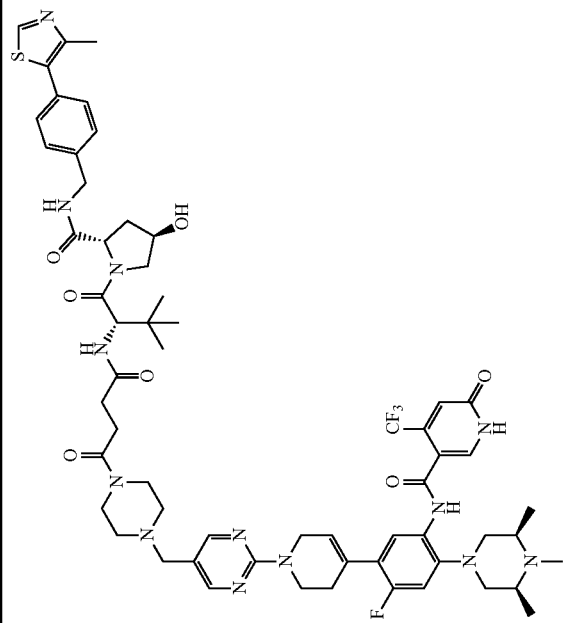 | N-(4-fluoro-5-(1-(5-((4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-142 | 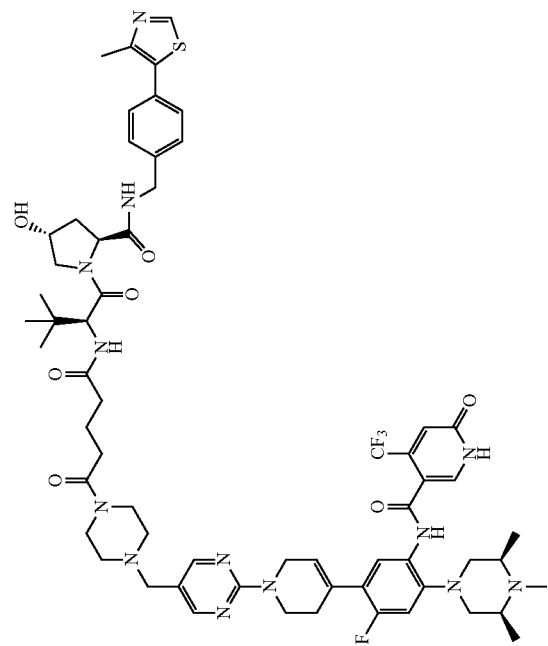 | N-(4-fluoro-5-(1-(5-((4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| XF078-143 | 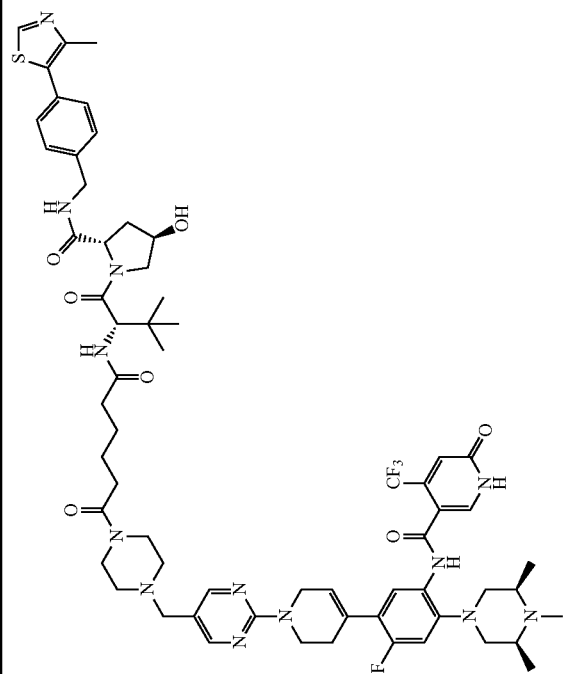 | N-(4-fluoro-5-(1-(5-((4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
|---|---|---|
| XF078-144 | 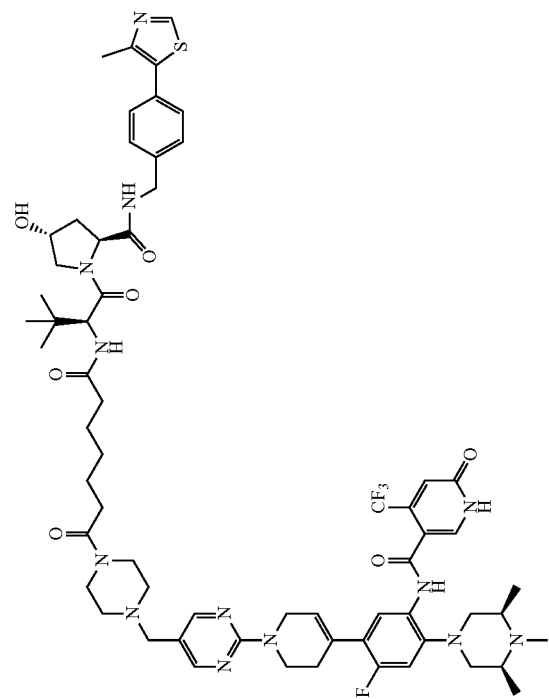 | N-(4-fluoro-5-(1-(5-((4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

XF078-145
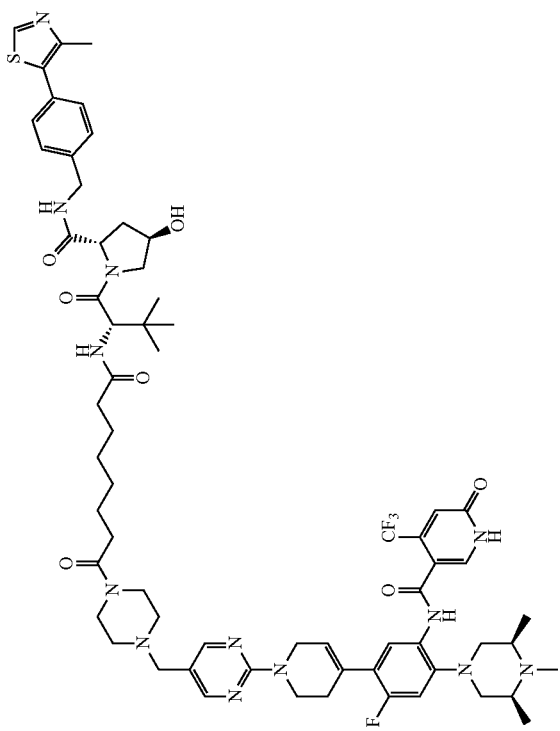
N-(4-fluoro-5-(1-(5-((4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide

| | | |
|---|---|---|
| XF078-146 | 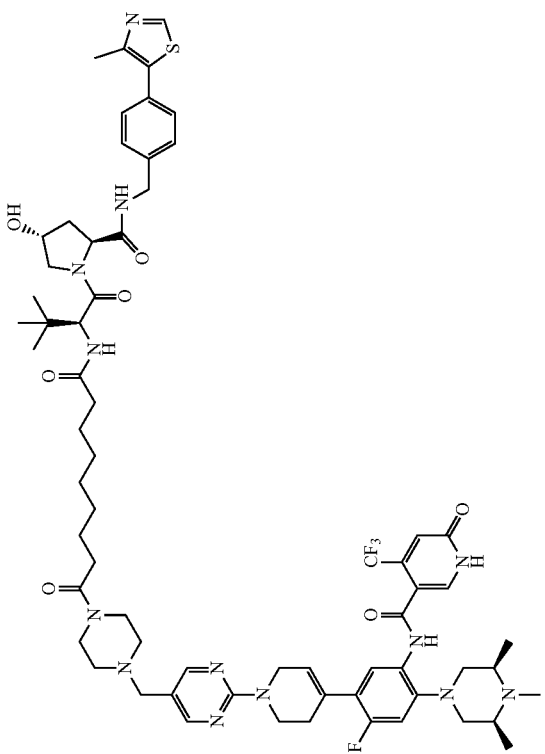 | N-(4-fluoro-5-(1-(5-((4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-147 | 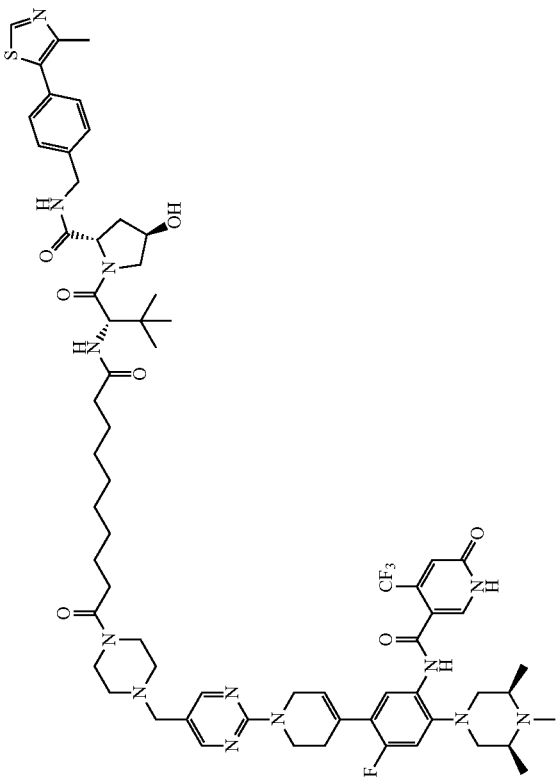 | N-(4-fluoro-5-(1-(5-((4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| XF078-148 | 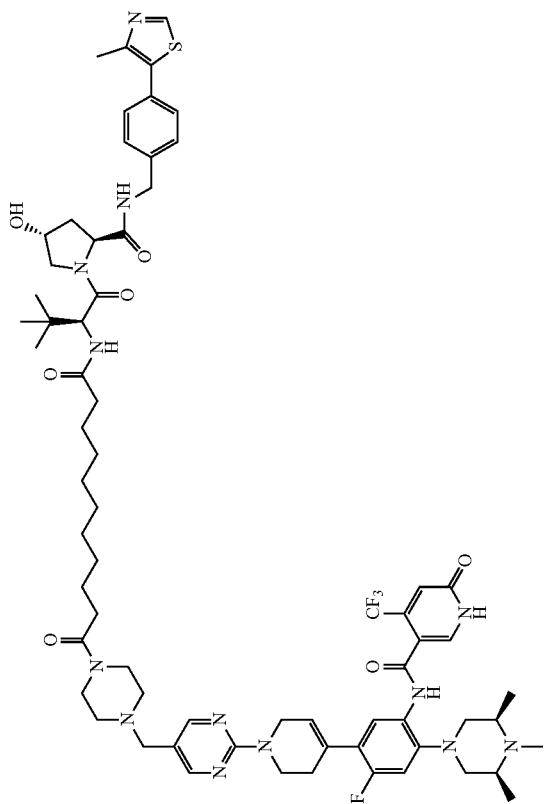 | N-(4-fluoro-5-(1-(5-((4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | -continued | |
|---|---|---|
| XF078-149 | 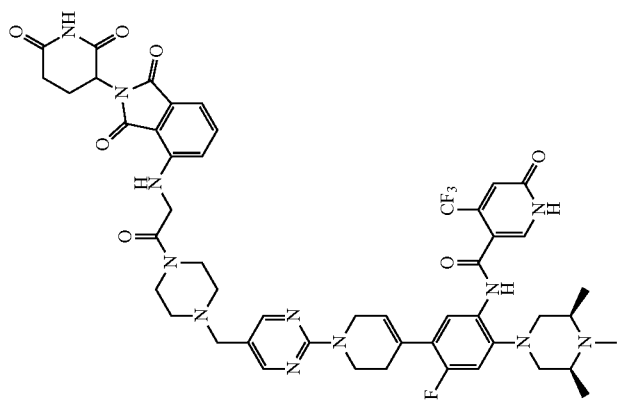 | N-(5-(1-(5-((4-((2-(2,6-dioxopiperidin-3-yl)-1,3-dioxoisoindolin-4-yl)glycyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-150 | 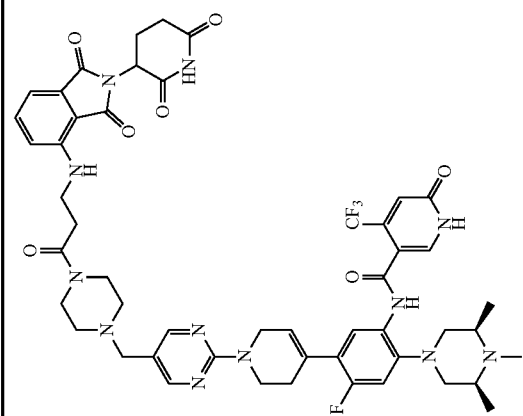 | N-(5-(1-(5-((4-(3-(2-(2,6-dioxopiperidin-3-yl)-1,3-dioxoisoindolin-4-yl)amino)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| XF078-151 | 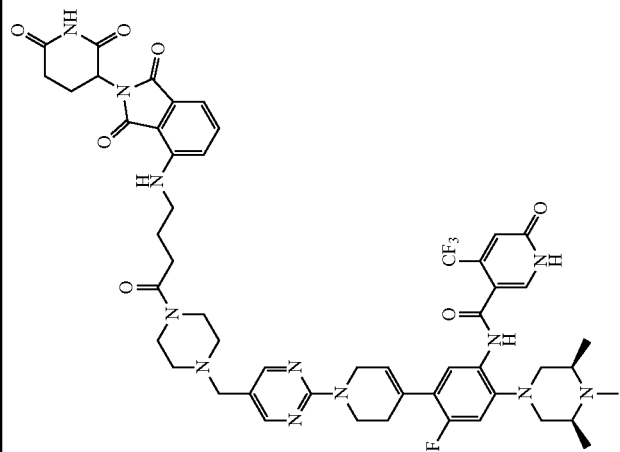 | N-(5-(1-(5-((4-(4-((2-(2,6-dioxopiperidin-3-yl)-1,3-dioxoisoindolin-4-yl)amino)butanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-152 | 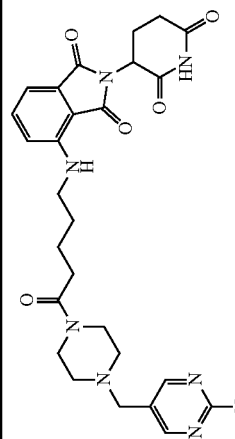 | N-(5-(1-(5-((4-(5-(2-(2,6-dioxopiperidin-3-yl)-1,3-dioxoisoindolin-4-yl)amino)pentanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF078-157 | 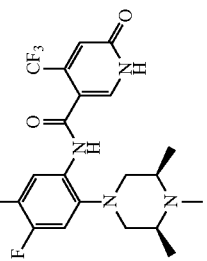 | N-(5-(1-(5-((4-(3-(2-(2-(2-(2,6-dioxopiperidin-3-yl)-1,3-dioxoisoindolin-4-yl)amino)ethoxy)ethoxy)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-158 | 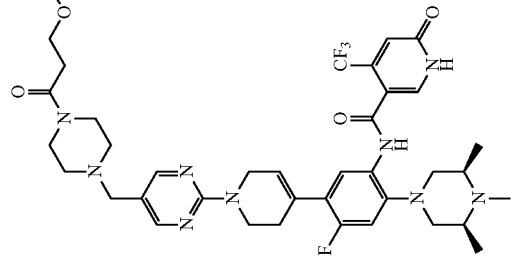 | N-(5-(1-(5-((4-(3-(2-(2-(2-(2-(2,6-dioxopiperidin-3-yl)-1,3-dioxoisoindolin-4-yl)amino)ethoxy)ethoxy)ethoxy)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-159 | 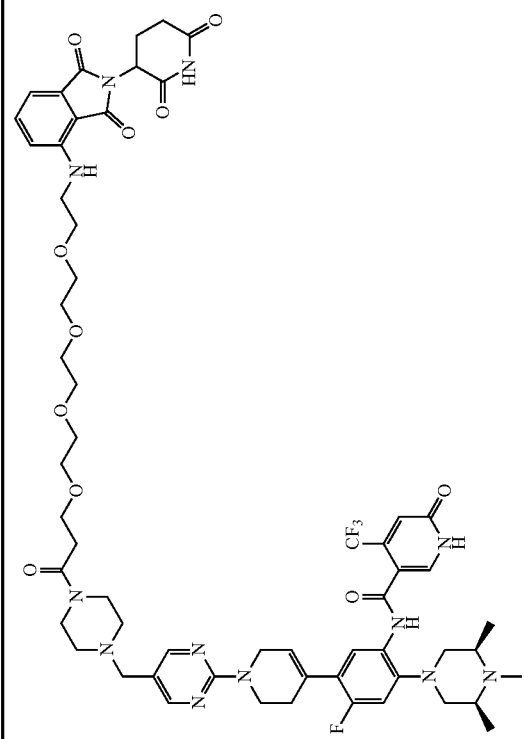 | N-(5-(1-(5-((4-(1-(2-(2,6-dioxopiperidin-3-yl)-1,3-dioxoisoindolin-4-yl)amino)-3,6,9,12-tetraoxapentadecan-15-oyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-160 | 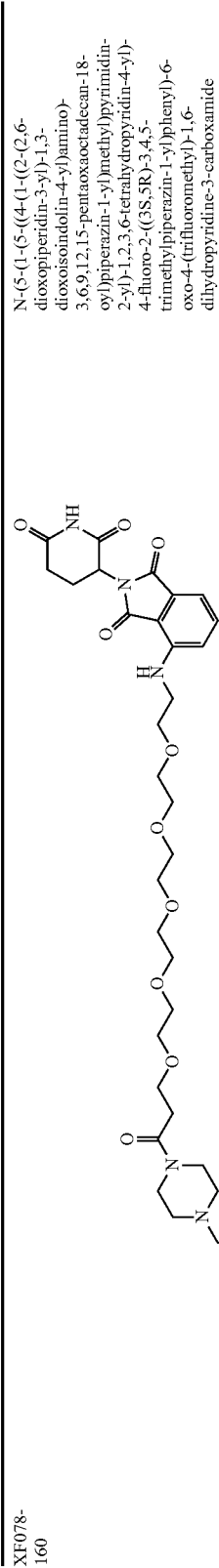 | N-(5-(1-(5-((4-(1-((2-(2,6-dioxopiperidin-3-yl)-1,3-dioxoisoindolin-4-yl)amino)-3,6,9,12,15-pentaoxaoctadecan-18-oyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF061-33 | 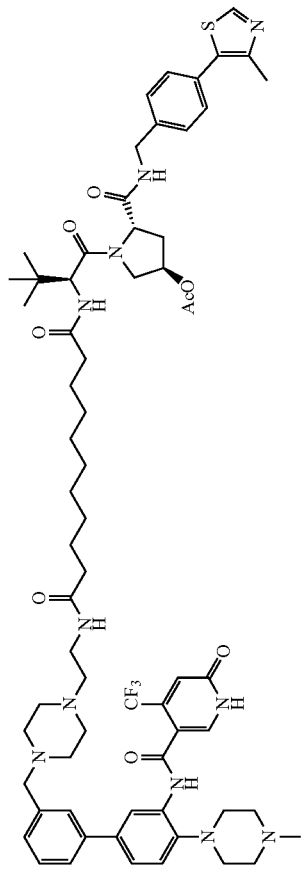 | (2S,4R)-1-((S)-2-(2-(2-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)amino)-2-oxoethoxy)acetamido)-3,3-dimethylbutanoyl)-4-hydroxy-N-(4-(4-methylthiazol-5-yl)benzyl)pyrrolidine-2-carboxamide |

| | | |
|---|---|---|
| XF061-34 | 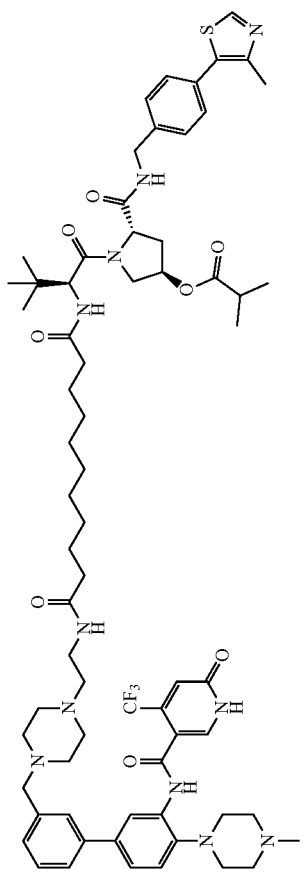 | (2S,4R)-1-((S)-2-(3-(3-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)amino)-3-oxopropoxy)propanamido)-3,3-dimethylbutanoyl)-4-hydroxy-N-(4-(4-methylthiazol-5-yl)benzyl)pyrrolidine-2-carboxamide |

15. A bivalent compound selected from the group consisting of:

TABLE 1

| | | |
|---|---|---|
| XF048-130 | [structure] | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁸-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)octanediamide |
| XF048-131 | [structure] | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁹-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)nonanediamide |
| XF048-132 | [structure] | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N¹⁰-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)decanediamide |

TABLE 1-continued

| | | |
|---|---|---|
| XF048-133 | 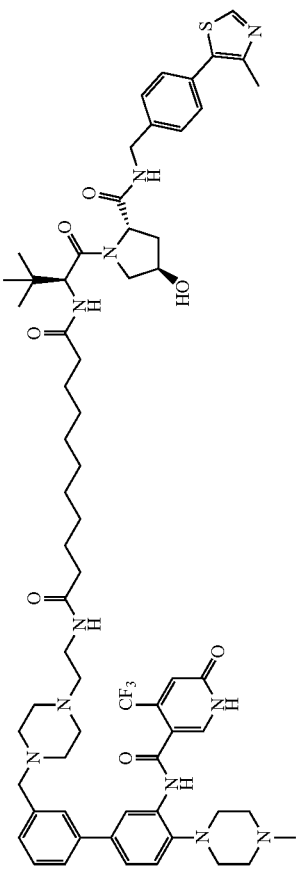 | N¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N¹¹-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |
| XF048-139 | 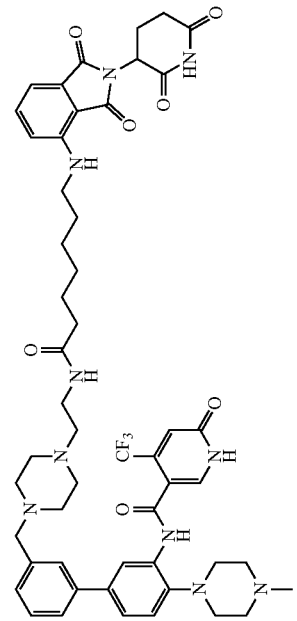 | N-(3'-((4-(2-(7-((2-(2,6-dioxopiperidin-3-yl)-1,3-dioxoisoindolin-4-yl)amino)heptanamido)ethyl)piperazin-1-yl)methyl)-4-(4-methylpiperazin-1-yl)[1,1'-biphenyl]-3-yl)-6-oxo-4-(trifluoromethyl)-1,6-dihydropyridine-3-carboxamide |
| XF048-140 | 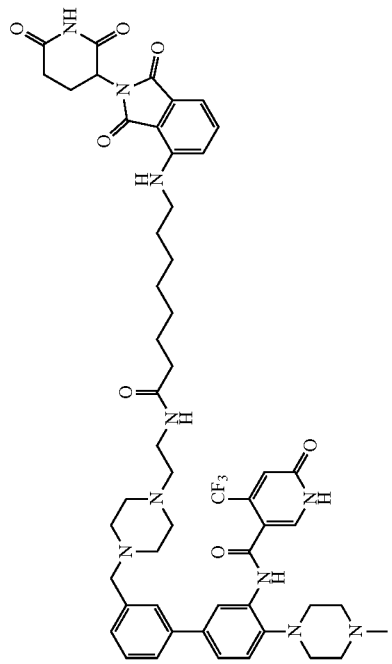 | N-(3'-((4-(2-(8-((2-(2,6-dioxopiperidin-3-yl)-1,3-dioxoisoindolin-4-yl)amino)octanamido)ethyl)piperazin-1-yl)methyl)-4-(4-methylpiperazin-1-yl)[1,1'-biphenyl]-3-yl)-6-oxo-4-(trifluoromethyl)-1,6-dihydropyridine-3-carboxamide |

TABLE 1-continued

| | | |
|---|---|---|
| XF048-141 | 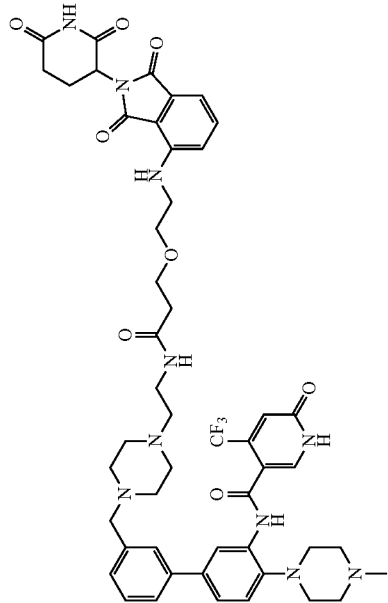 | N-(3'-((4-(2-(3-(2-((2-(2,6-dioxopiperidin-3-yl)-1,3-dioxoisoindolin-4-yl)amino)ethoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-142 | 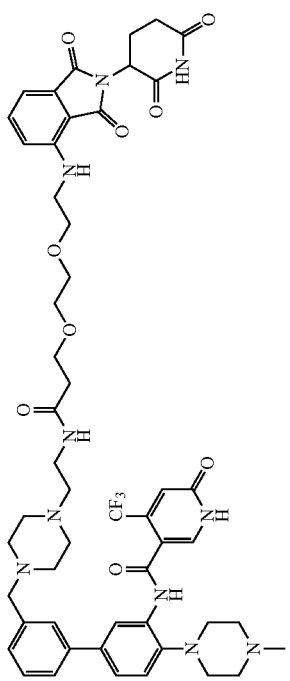 | N-(3'-((4-(2-(3-(2-(2-((2-(2,6-dioxopiperidin-3-yl)-1,3-dioxoisoindolin-4-yl)amino)ethoxy)ethoxy)propanamido)ethyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-143 | 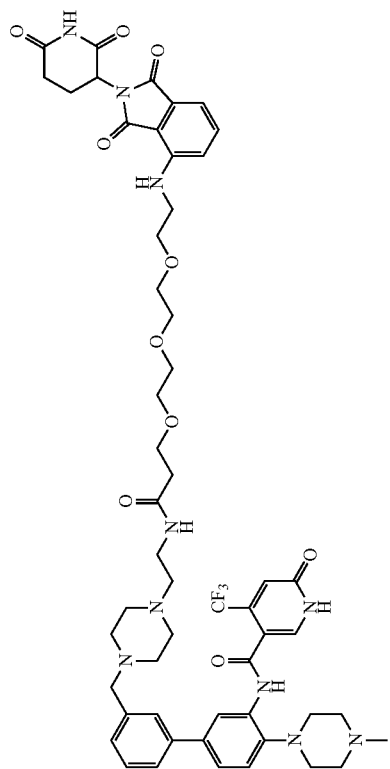 | N-(3'-((4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |

TABLE 1-continued

| | | |
|---|---|---|
| XF048-144 | 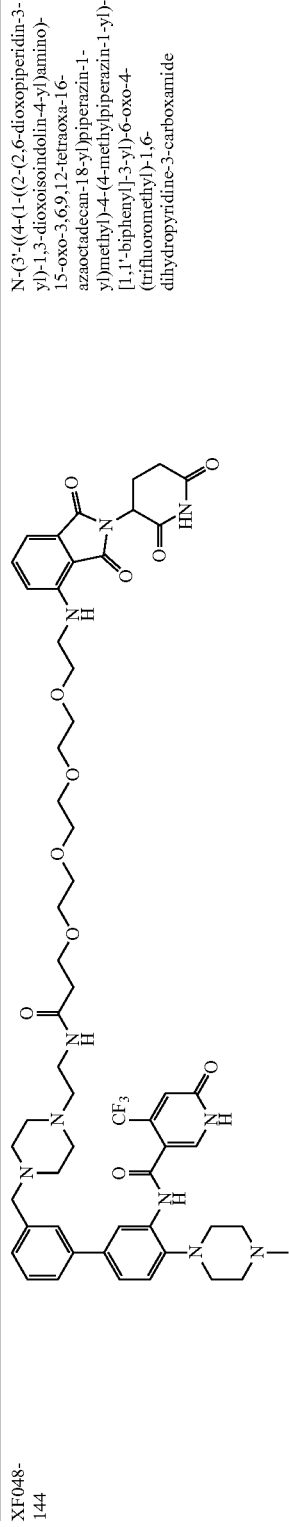 | N-(3'-((4-(1-((2-(2,6-dioxopiperidin-3-yl)-1,3-dioxoisoindolin-4-yl)amino)-15-oxo-3,6,9,12-tetraoxa-16-azaoctadecan-18-yl)methyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF048-145 | 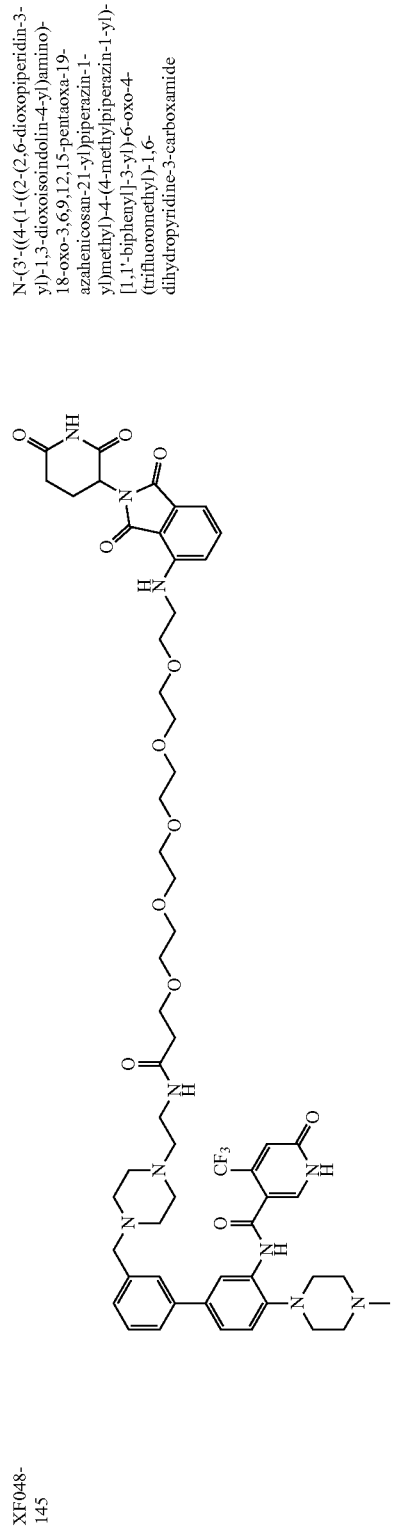 | N-(3'-((4-(1-((2-(2,6-dioxopiperidin-3-yl)-1,3-dioxoisoindolin-4-yl)amino)-18-oxo-3,6,9,12,15-pentaoxa-19-azahenicosan-21-yl)methyl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF050-166 | 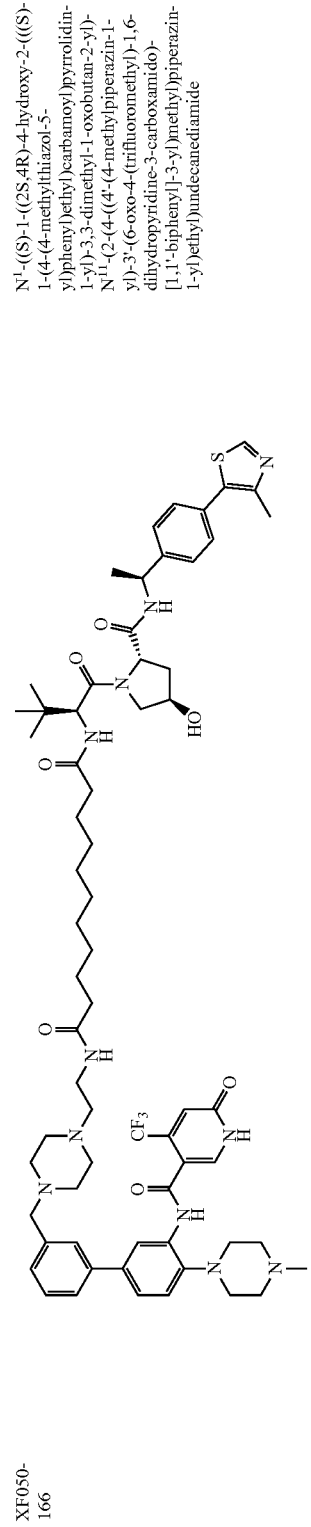 | $N^1$-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-$N^{11}$-(2-(4-((4'-(4-methylpiperazin-1-yl)-3'-(6-oxo-4-(trifluoromethyl)-1,6-dihydropyridine-3-carboxamido)-[1,1'-biphenyl]-3-yl)methyl)piperazin-1-yl)ethyl)undecanediamide |

TABLE 1-continued

| | | |
|---|---|---|
| XF050-158 | 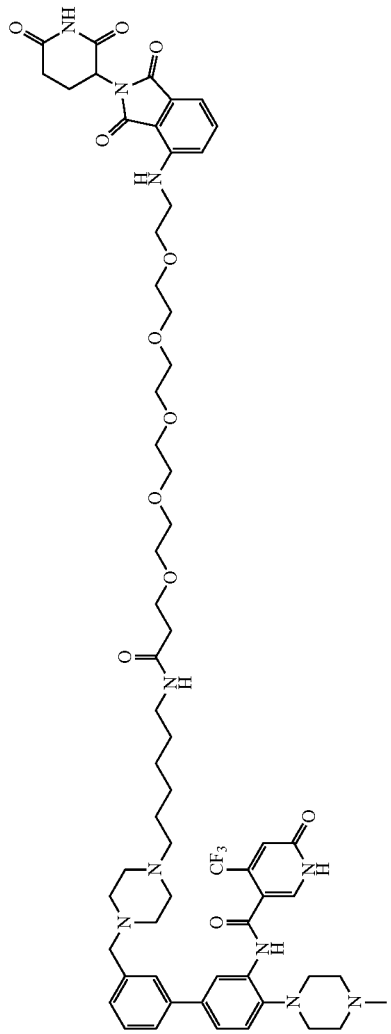 | N-(3'-((4-(1-((2-(2,6-dioxopiperidin-3-yl)-1,3-dioxoisoindolin-4-yl)amino)-18-oxo-3,6,9,12,15-pentaoxa-19-azapentacosan-25-yl)piperazin-1-yl)methyl)-4-(4-methylpiperazin-1-yl)-[1,1'-biphenyl]-3-yl)-6-oxo-4-(trifluoromethyl)-1,6-dihydropyridine-3-carboxamide |
| XF056-132 | 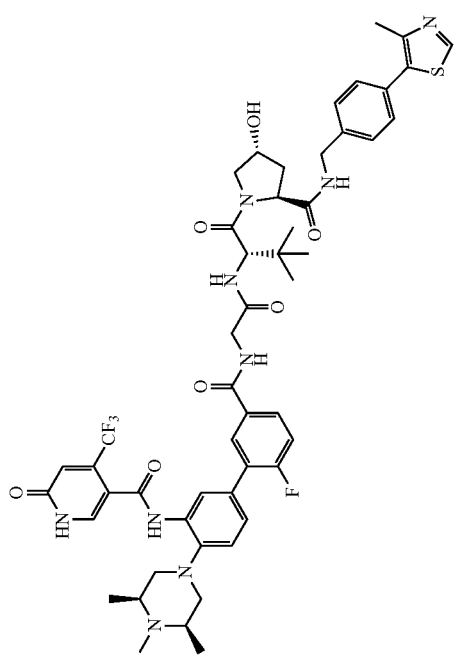 | N-(2'-fluoro-5'-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| | | |
|---|---|---|
| XF056-162 | | N-(2'-fluoro-4'-(((S)-14-((2S,4R)-4-hydroxy-2-((4-(4-methylthiazol-5-yl)benzyl)carbamoyl)pyrrolidine-1-carbonyl)-15,15-dimethyl-12-oxo-3,6,9-trioxa-13-azahexadecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-171 | | N-(2'-fluoro-4'-((8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-173 | | N-(2'-fluoro-4'-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)carbamoyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| XF056-178 | 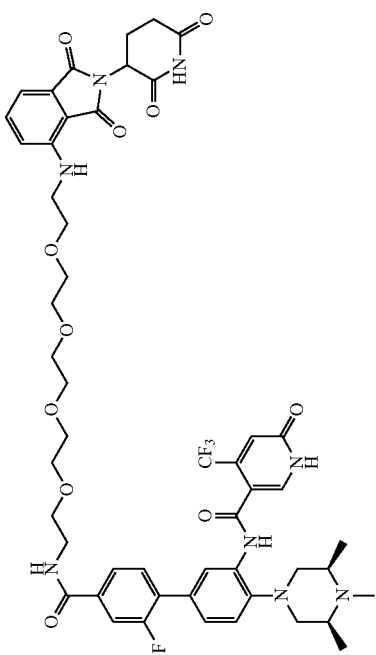 | N-(4'-((14-((2-(2,6-dioxopiperidin-3-yl)-1,3-dioxoisoindolin-4-yl)amino)-3,6,9,12-tetraoxatetradecyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF056-186 | 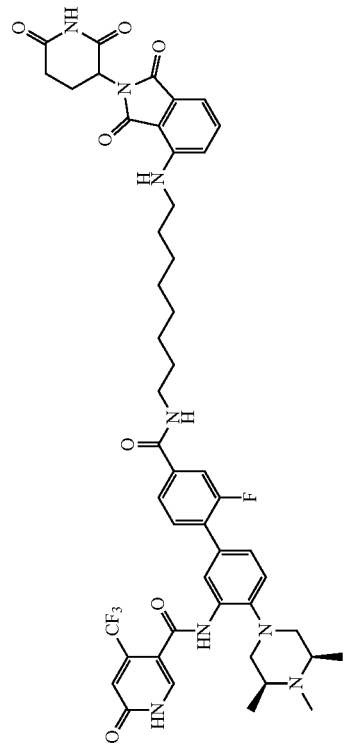 | N-(4'-((8-((2-(2,6-dioxopiperidin-3-yl)-1,3-dioxoisoindolin-4-yl)amino)octyl)carbamoyl)-2'-fluoro-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide |
| XF067-67 | 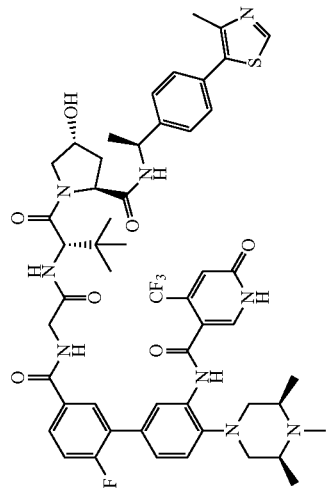 | N-(2'-fluoro-5'-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| XF067-131 | 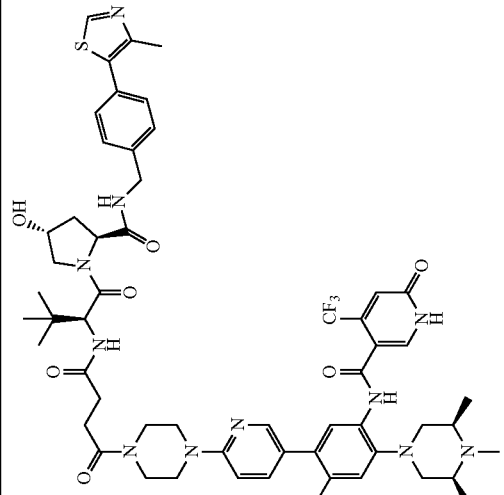 | N-(4-fluoro-5-(6-(4-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| XF067-133 | 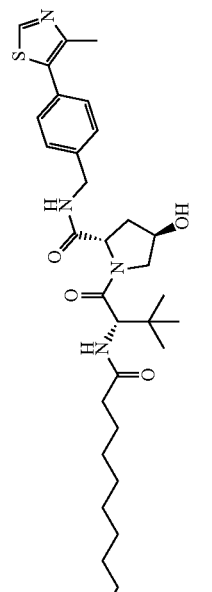 | N-(4-fluoro-5-(6-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF067-134 | 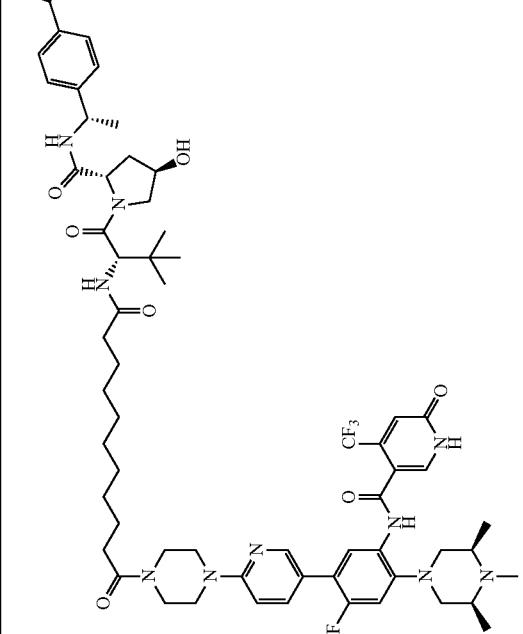 | N-(4-fluoro-5-(6-(4-(11-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-11-oxoundecanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| XF067-140 | 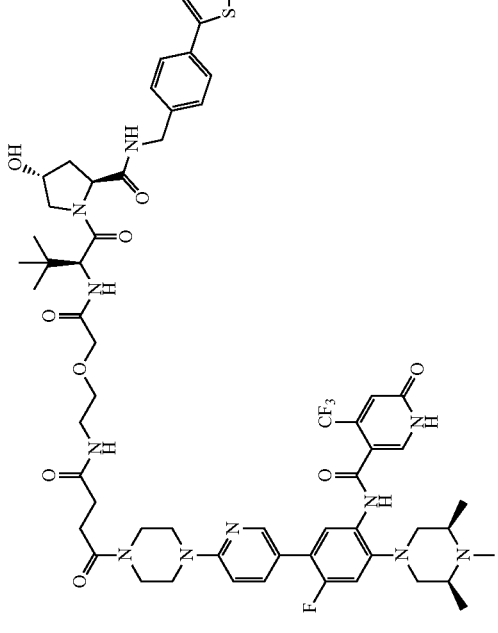 | N-(4-fluoro-5-(6-(4-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutanoyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF067-142 | 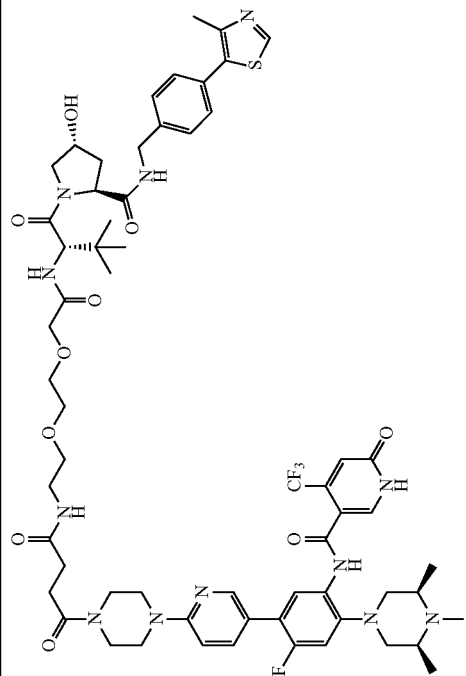 | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaheptadecan-17-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |
| XF067-146 | 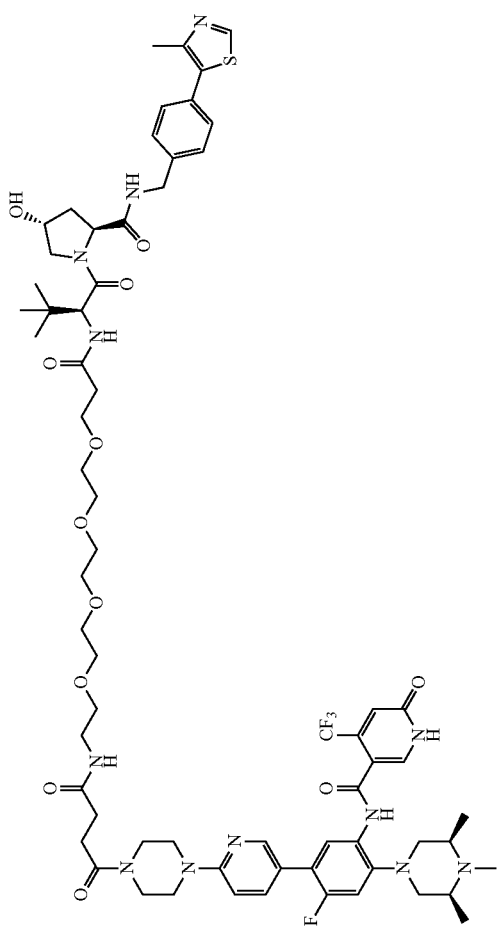 | N-(4-fluoro-5-(6-(4-((S)-3-((2S,4R)-4-hydroxy-2-((4-(4-methylthiazol-5-yl)benzyl)carbamoyl)pyrrolidine-1-carbonyl)-2,2-dimethyl-5,21-dioxo-8,11,14,17-tetraoxa-4,20-diazatetracosan-24-oyl)piperazin-1-yl)pyridin-3-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF067-149 | 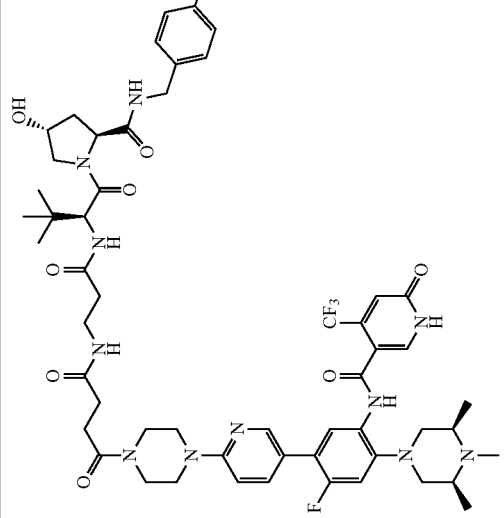 | N-(4-fluoro-5-(6-(4-(4-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-4-oxobutanoyl)piperazin-1-yl)pyridin-3-yl)-2-((3S,5R)-3,4,5-trimethylpiperazin-1-yl)phenyl)-1,6-oxo-4-(trifluoromethyl)-dihydropyridine-3-carboxamide |
| XF078-1 | 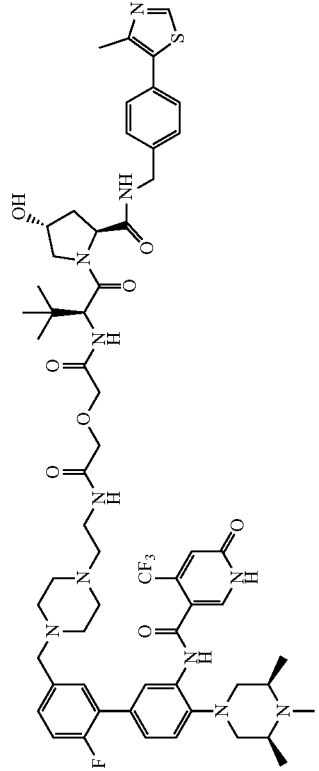 | N-(2'-fluoro-5'-((4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)ethyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

| | | |
|---|---|---|
| XF078-2 | 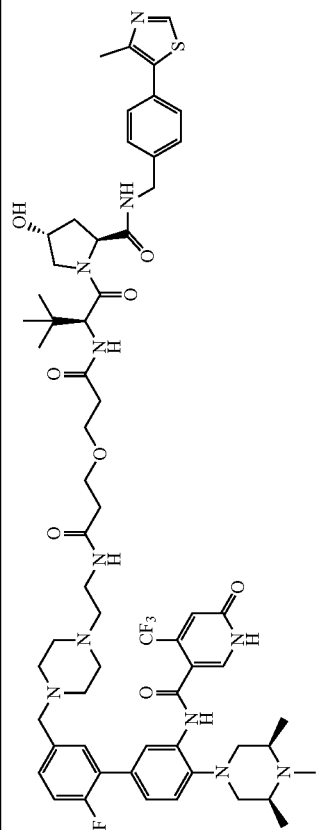 | N-(2'-fluoro-5'-((4-(2-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanamido)ethyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-6 | 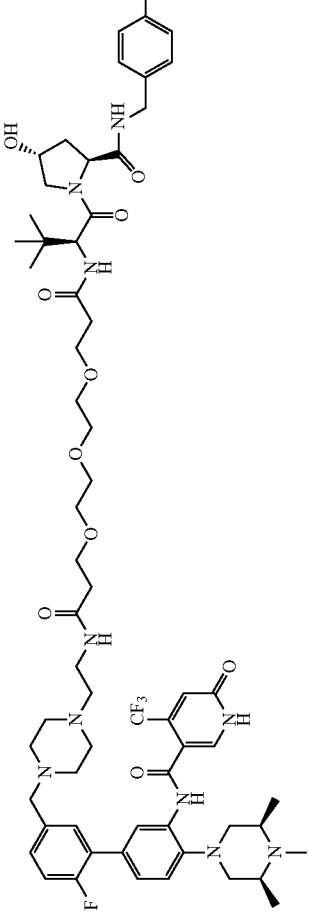 | N-(2'-fluoro-5'-((4-((S)-18-((2S,4R)-4-hydroxy-2-((4-(4-methylthiazol-5-yl)benzyl)carbamoyl)pyrrolidine-1-carbonyl)-19,19-dimethyl-4,16-dioxo-7,10,13-trioxa-3,17-diazaicosyl)piperazin-1-yl)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-8 | 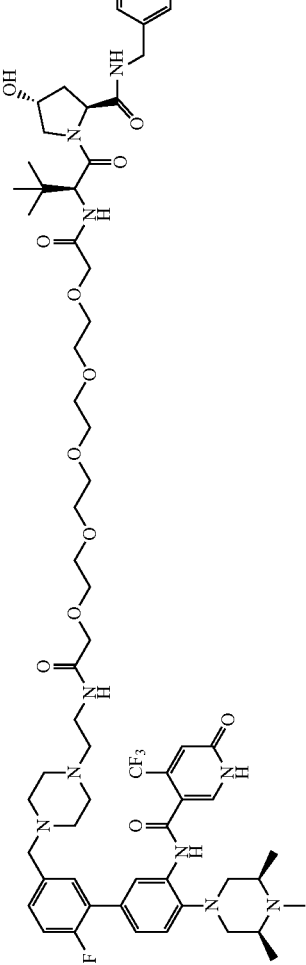 | $N^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-$N^{17}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide |

| | | |
|---|---|---|
| XF078-14 | [structure] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N⁸-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |
| XF078-15 | [structure] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N⁹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |
| XF078-16 | [structure] | N¹-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N¹⁰-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |

| | | |
|---|---|---|
| XF078-17 | 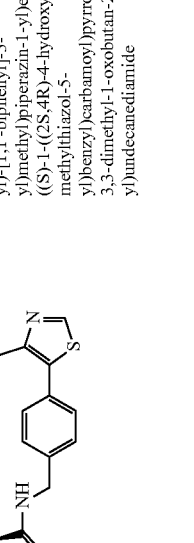 | N$^1$-(2-(4-((6-fluoro-3'-(6-oxo-4-(trifluoromethyl)-1,6-dihydropyridine-3-carboxamido)-4'-((3S,5R)-3,4,5-trimethylpiperazin-1-yl)-[1,1'-biphenyl]-3-yl)methyl)piperazin-1-yl)ethyl)-N$^{11}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| XF078-18 | 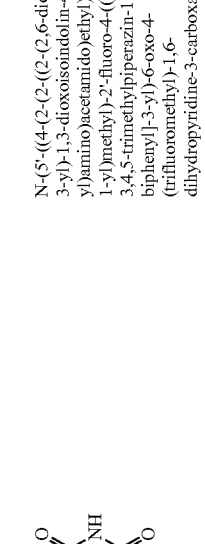 | N-(5'-((4-(2-(2-(2-(2,6-dioxopiperidin-3-yl)-1,3-dioxoisoindolin-4-yl)amino)acetamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-19 |  | N-(5'-((4-(2-(3-((2-(2,6-dioxopiperidin-3-yl)-1,3-dioxoisoindolin-4-yl)amino)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| XF078-20 | 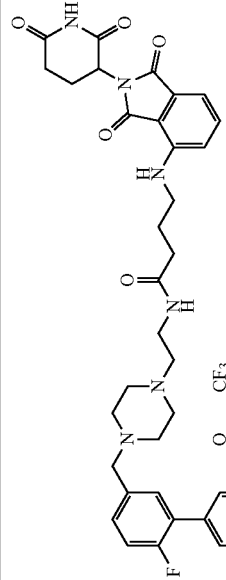 | N-(5'-((4-(2-(4-((2-(2,6-dioxopiperidin-3-yl)-1,3-dioxoisoindolin-4-yl)amino)butanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| --- | --- | --- |
| XF078-21 | 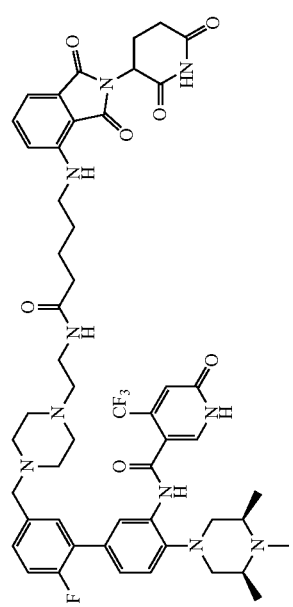 | N-(5'-((4-(2-(5-((2-(2,6-dioxopiperidin-3-yl)-1,3-dioxoisoindolin-4-yl)aminopentanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-22 | 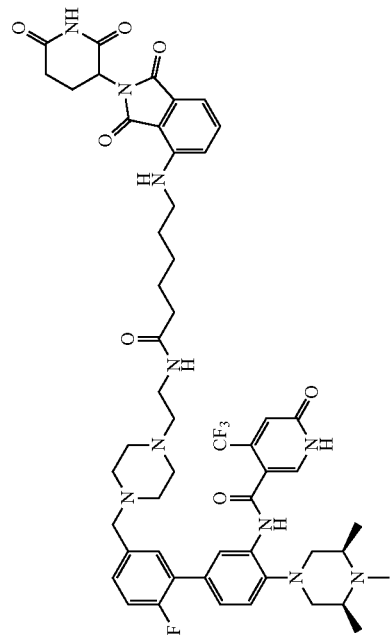 | N-(5'-((4-(2-(6-((2-(2,6-dioxopiperidin-3-yl)-1,3-dioxoisoindolin-4-yl)amino)hexanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| | | |
|---|---|---|
| XF078-23 | [structure] | N-(5'-((4-(2-(7-((2-(2,6-dioxopiperidin-3-yl)-1,3-dioxoisoindolin-4-yl)aminoheptanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-24 | [structure] | N-(5'-((4-(2-(8-((2-(2,6-dioxopiperidin-3-yl)-1,3-dioxoisoindolin-4-yl)amino)octanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-25 | [structure] | N-(5'-((4-(2-(3-(2-((2-(2,6-dioxopiperidin-3-yl)-1,3-dioxoisoindolin-4-yl)amino)ethoxy)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| | | |
|---|---|---|
| XF078-26 | 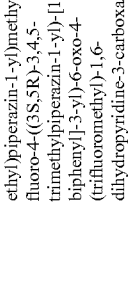 | N-(5'-((4-(2-(3-(2-(2-((2-(2,6-dioxopiperidin-3-yl)-1,3-dioxoisoindolin-4-yl)amino)ethoxy)ethoxy)propanamido)ethyl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-27 | 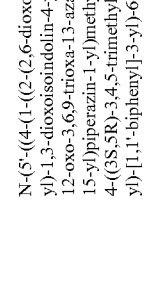 | N-(5'-((4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-28 |  | N-(5'-((4-(1-((2-(2,6-dioxopiperidin-3-yl)-1,3-dioxoisoindolin-4-yl)amino)-15-oxo-3,6,9,12-tetraoxa-16-azaoctadecan-18-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |

TABLE 1-continued

| | | |
|---|---|---|
| XF078-29 | 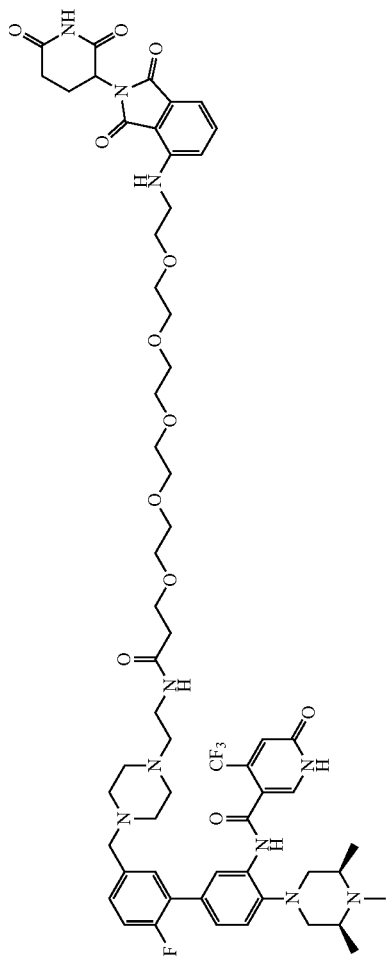 | N-(5'-((4-(1-((2-(2,6-dioxopiperidin-3-yl)-1,3-dioxoisoindolin-4-yl)amino)-18-oxo-3,6,9,12,15-pentaoxa-19-azahenicosan-21-yl)piperazin-1-yl)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide |
| XF078-30 | 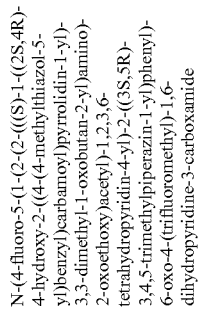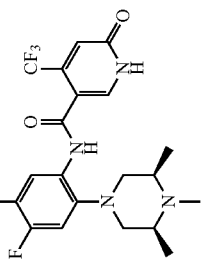 | N-(4-fluoro-5-(1-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF078-34 | 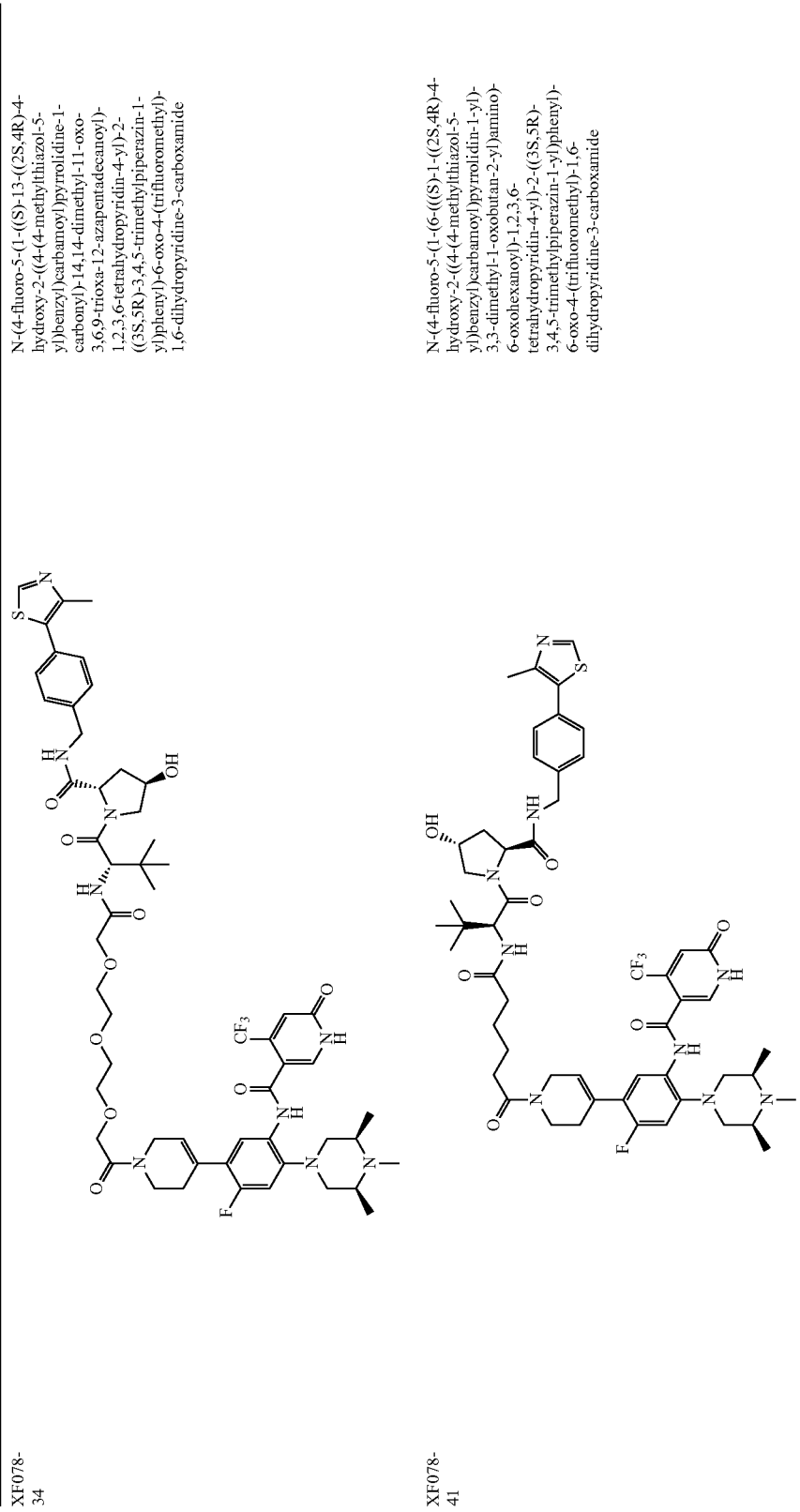 | N-(4-fluoro-5-(1-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-41 | | N-(4-fluoro-5-(1-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)-1,2,3,6-tetrahydropyridin-4-yl)-2-((3S,5R)-3,4,5-trimethylpiperazin-1-yl)phenyl)-1,6-dihydropyridine-3-carboxamide |

TABLE 1-continued

| | | |
|---|---|---|
| XF078-42 | 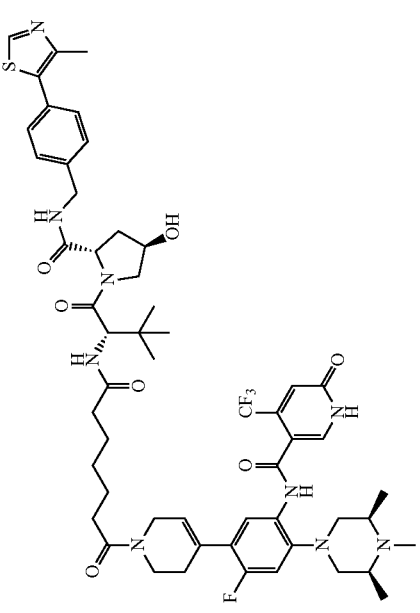 | N-(4-fluoro-5-(1-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-43 | 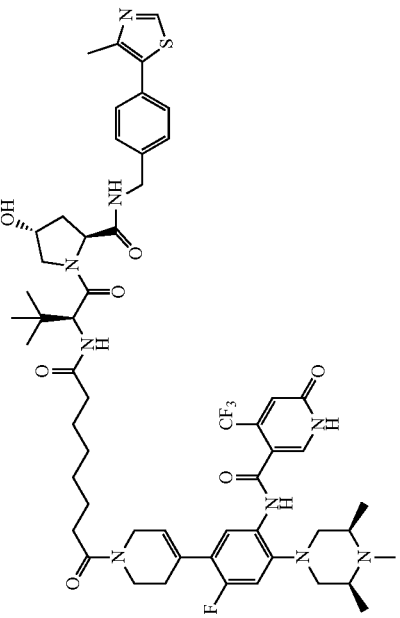 | N-(4-fluoro-5-(1-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | | |
|---|---|---|
| XF078-44 | | N-(4-fluoro-5-(1-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-45 | | N-(4-fluoro-5-(1-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF078-46 | | N-(4-fluoro-5-(1-(11-((((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-61 | | N-(4-fluoro-5-(2-(4-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-4-oxobutanoyl)piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| XF078-99 | [structure] | (2S,4R)-1-((S)-2-(2-(2-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |
| XF078-101 | [structure] | (2S,4R)-1-((S)-2-(2-(2-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

| | | |
|---|---|---|
| XF078-102 | 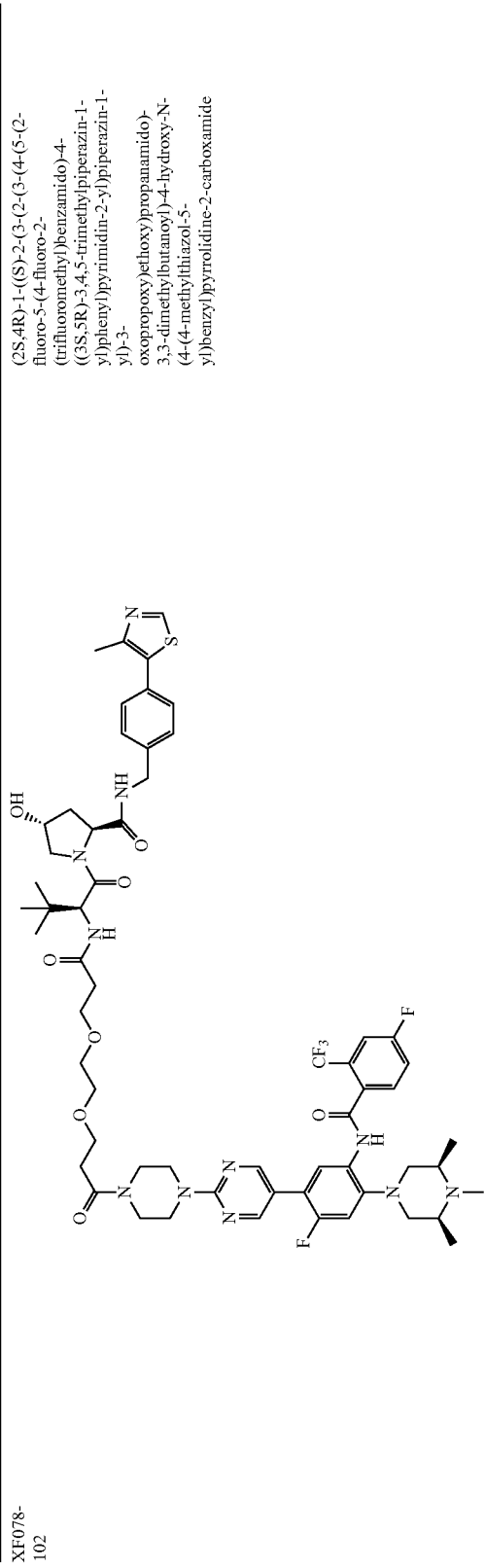 | (2S,4R)-1-((S)-2-(3-(2-(3-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |
| XF078-103 | 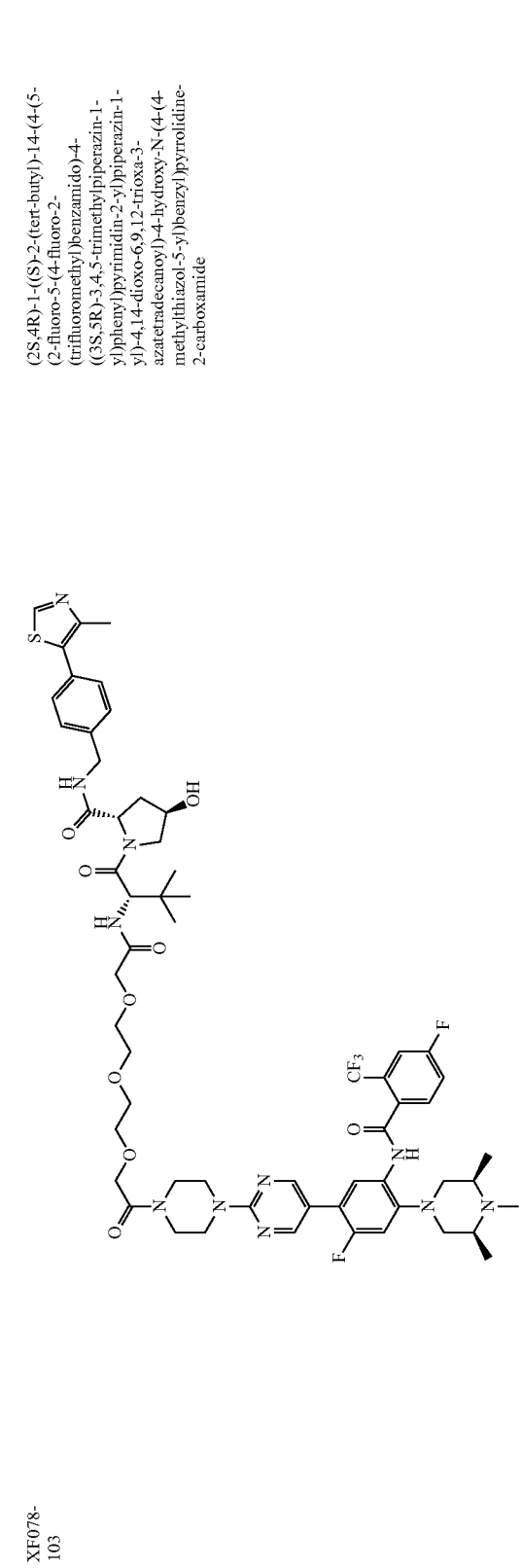 | (2S,4R)-1-((S)-2-(tert-butyl)-14-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide |

TABLE 1-continued

| | | |
|---|---|---|
| XF078-105 | 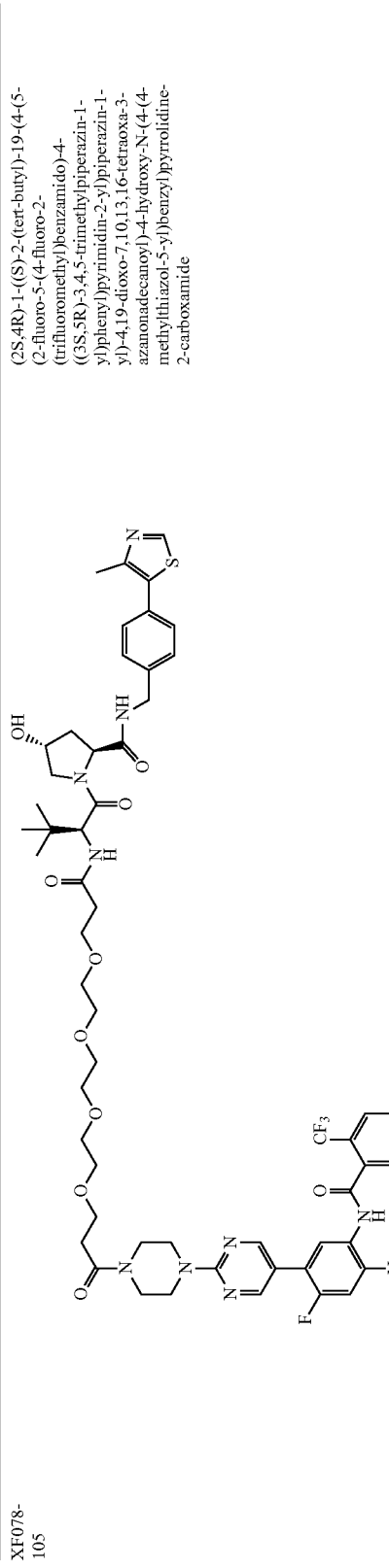 | (2S,4R)-1-((S)-2-(tert-butyl)-19-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| XF078-106 | 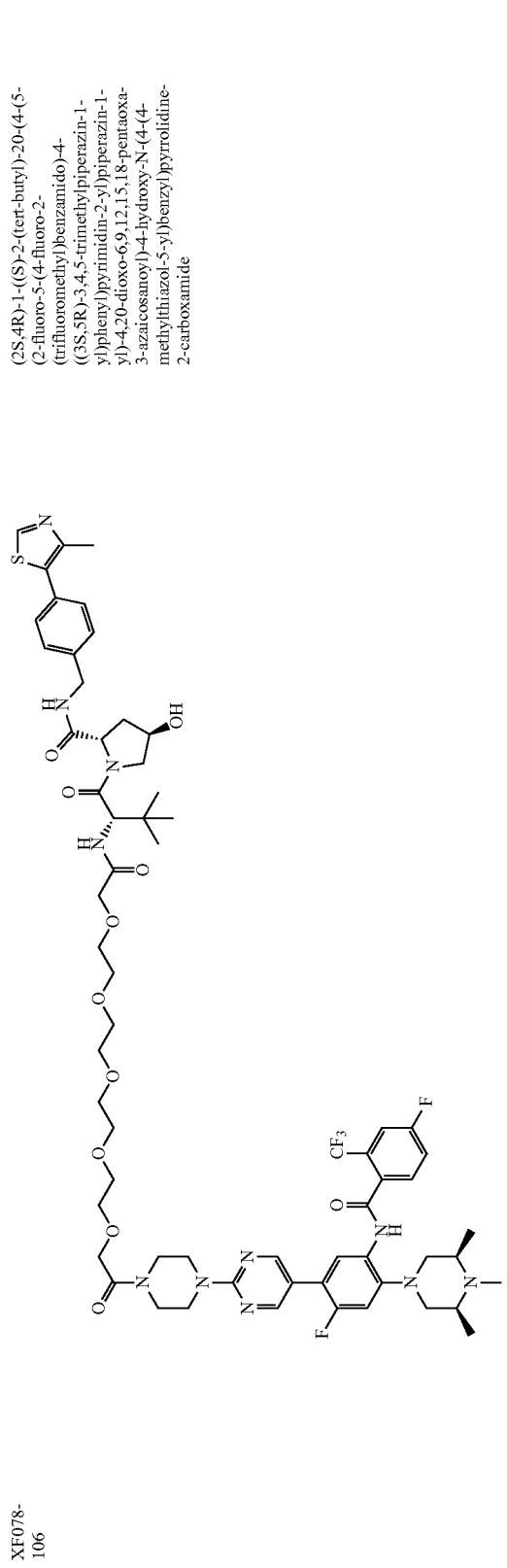 | (2S,4R)-1-((S)-2-(tert-butyl)-20-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |

| | | |
|---|---|---|
| XF078-110 | 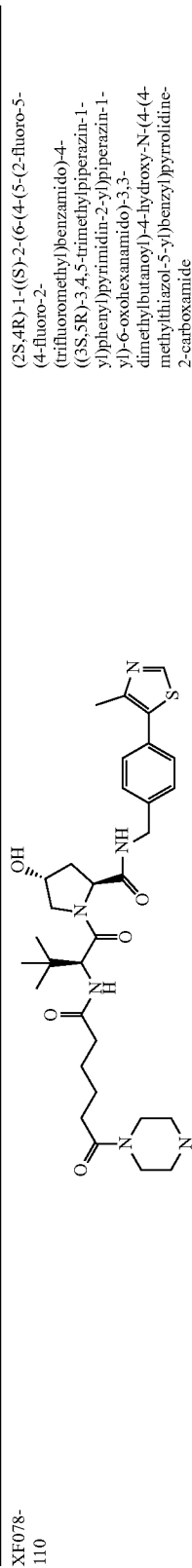 | (2S,4R)-1-((S)-2-(6-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |
| XF078-111 | 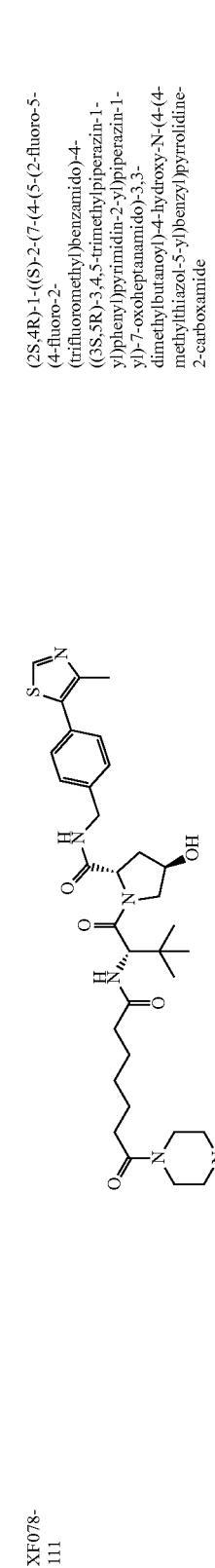 | (2S,4R)-1-((S)-2-(7-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |

TABLE 1-continued

| XF078-112 | 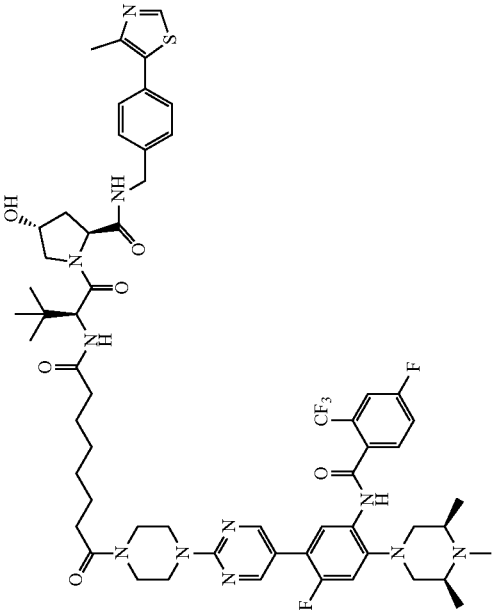 | (2S,4R)-1-((S)-2-(8-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| --- | --- | --- |
| XF078-113 | 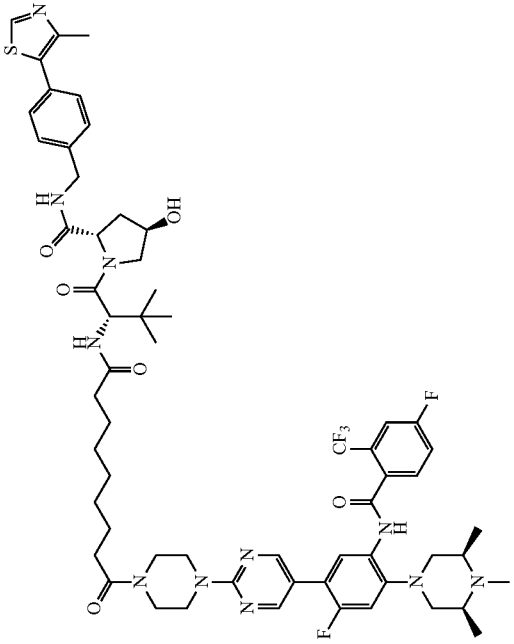 | (2S,4R)-1-((S)-2-(9-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |

TABLE 1-continued

| | | |
|---|---|---|
| XF078-114 | 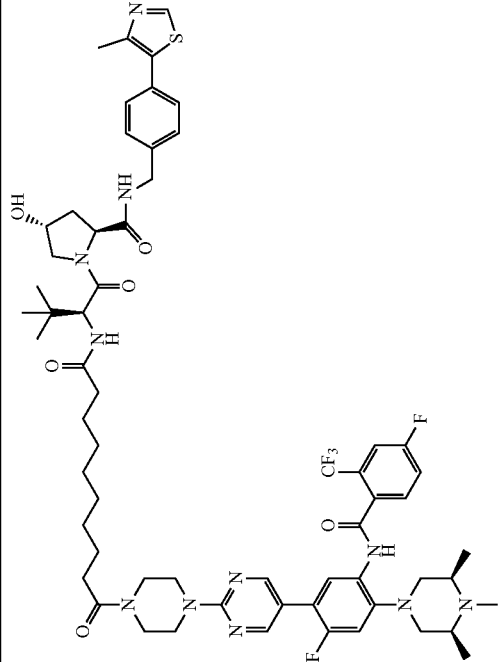 | (2S,4R)-1-((S)-2-(10-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |
| XF078-115 | 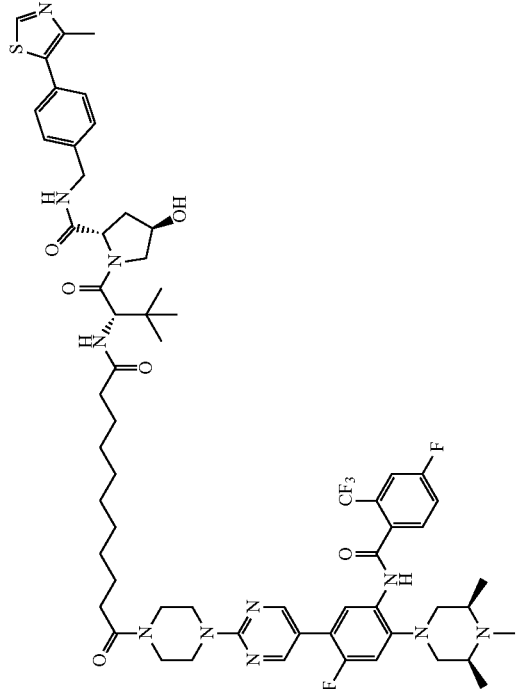 | (2S,4R)-1-((S)-2-(11-(4-(5-(2-fluoro-5-(4-fluoro-2-(trifluoromethyl)benzamido)-4-((3S,5R)-3,4,5-trimethylpiperazin-1-yl)phenyl)pyrimidin-2-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |

TABLE 1-continued

| | | |
|---|---|---|
| XF078-121 | 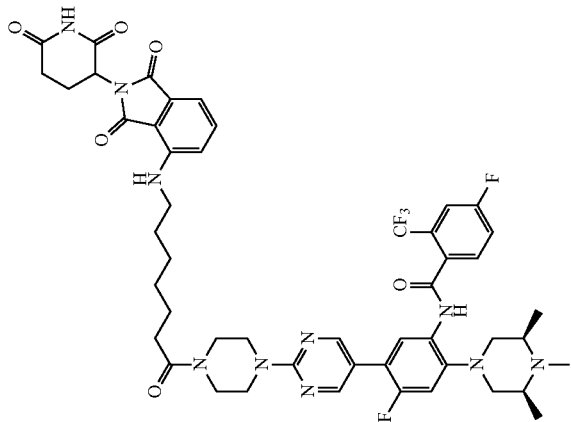 | N-(5-(2-(4-(7-((2-(2,6-dioxopiperidin-3-yl)-1,3-dioxoisoindolin-4-yl)amino)heptanoyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |
| XF078-125 | 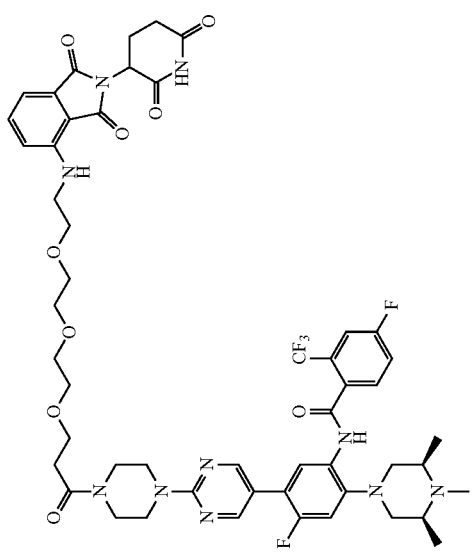 | N-(5-(2-(4-(3-(2-(2-(2-(2-(2,6-dioxopiperidin-3-yl)-1,3-dioxoisoindolin-4-yl)amino)ethoxy)ethoxy)ethoxy)propanoyl)piperazin-1-yl)pyrimidin-5-yl)-3,4,5-trimethylpiperazin-1-yl)phenyl)-4-fluoro-2-((3S,5R)-3,4,5-trimethylpiperazin-1-yl)phenyl)-4-fluoro-2-(trifluoromethyl)benzamide |

TABLE 1-continued

| XF078-126 | [structure] | N-(5-(2-(4-(1-((2-(2,6-dioxopiperidin-3-yl)-1,3-dioxoisoindolin-4-yl)amino)-3,6,9,12-tetraoxapentadecan-15-oyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |
| --- | --- | --- |
| XF078-127 | [structure] | N-(5-(2-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)pyrimidin-5-yl)-4-fluoro-2-((3S,5R)-3,4,5-trimethylpiperazin-1-yl)phenyl)-4-fluoro-2-(trifluoromethyl)benzamide |

TABLE 1-continued
| | | |
|---|---|---|
| XF078-132 | 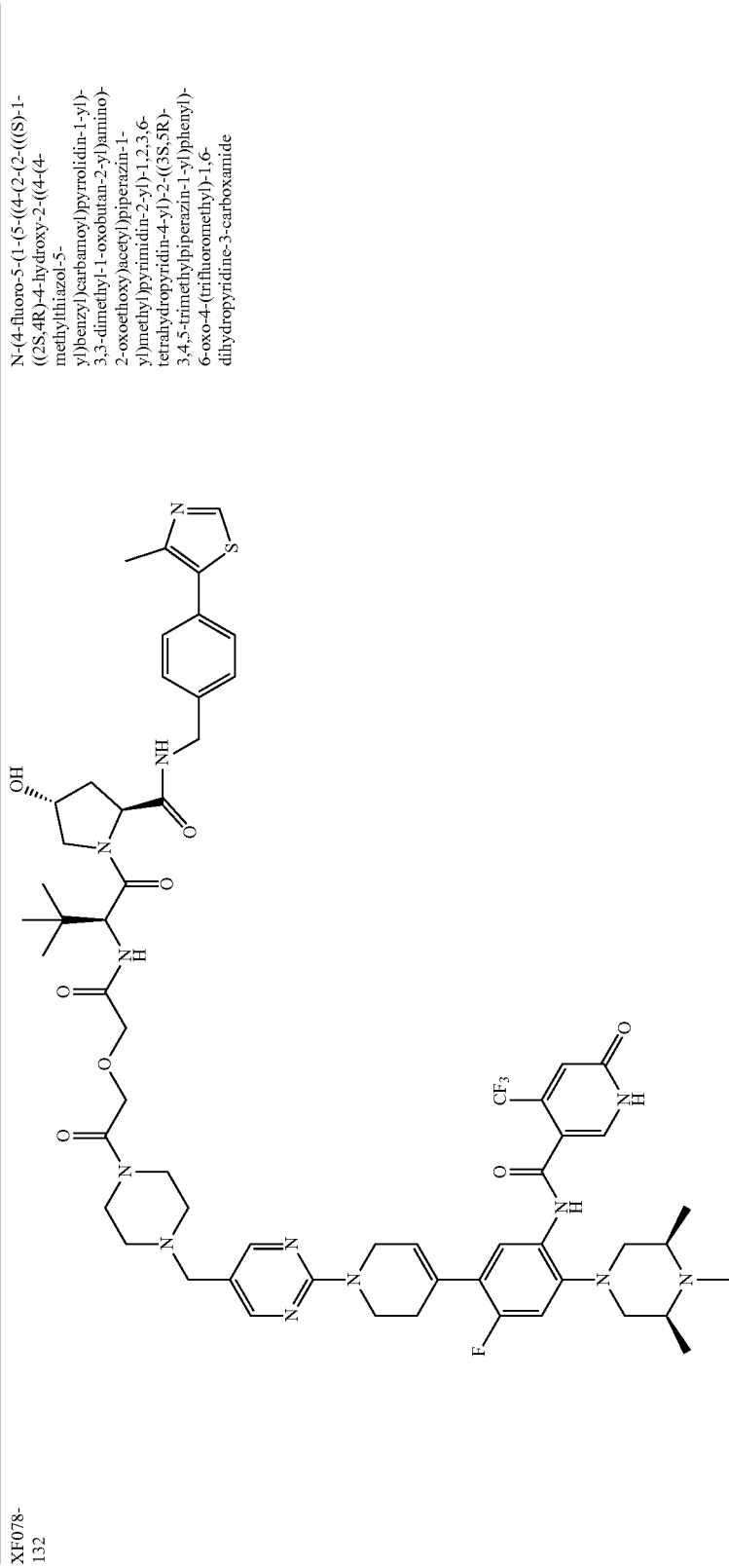 | N-(4-fluoro-5-(1-(5-((4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF078-133 | 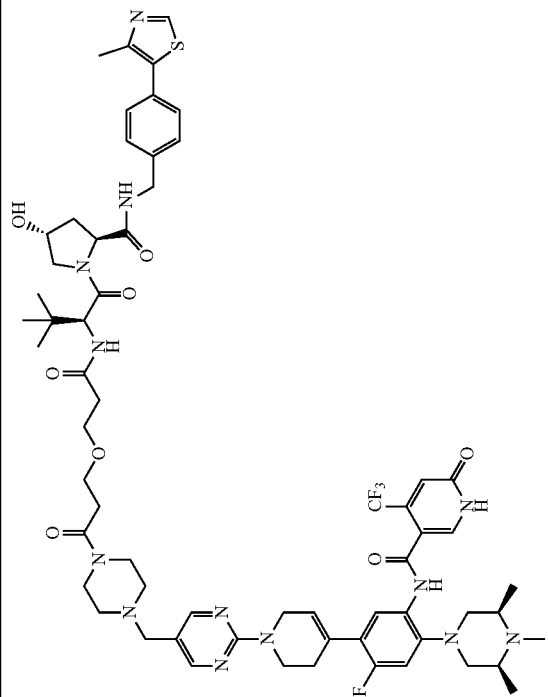 | N-(4-fluoro-5-(1-(5-((4-(3-(((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-134 | 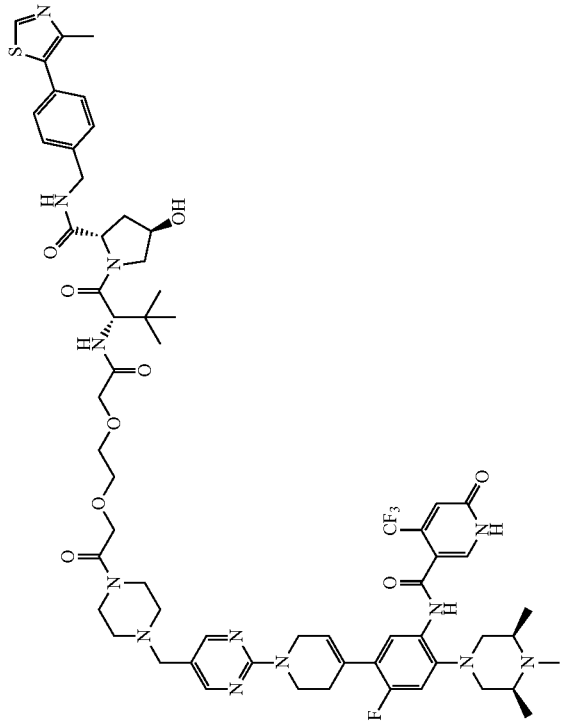 | N-(4-fluoro-5-(1-(5-((4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | |
|---|---|
| XF078-135 | 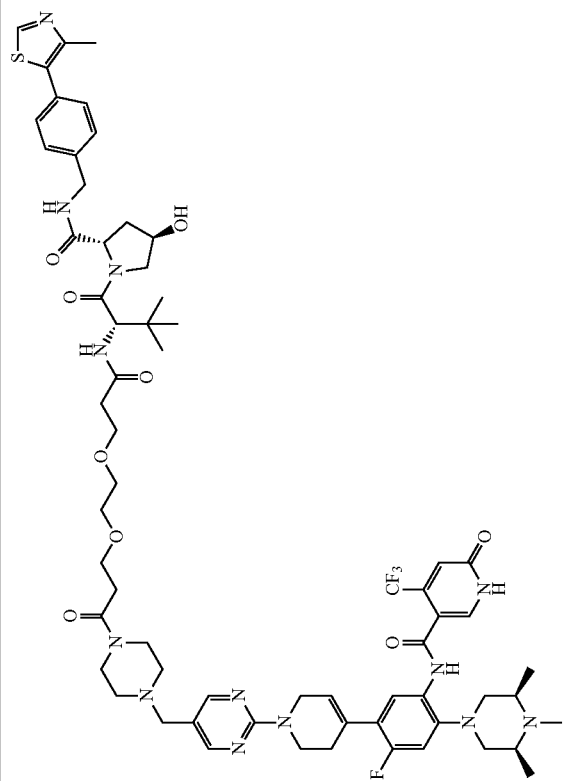 N-(4-fluoro-5-(1-(5-((4-(3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-136 | 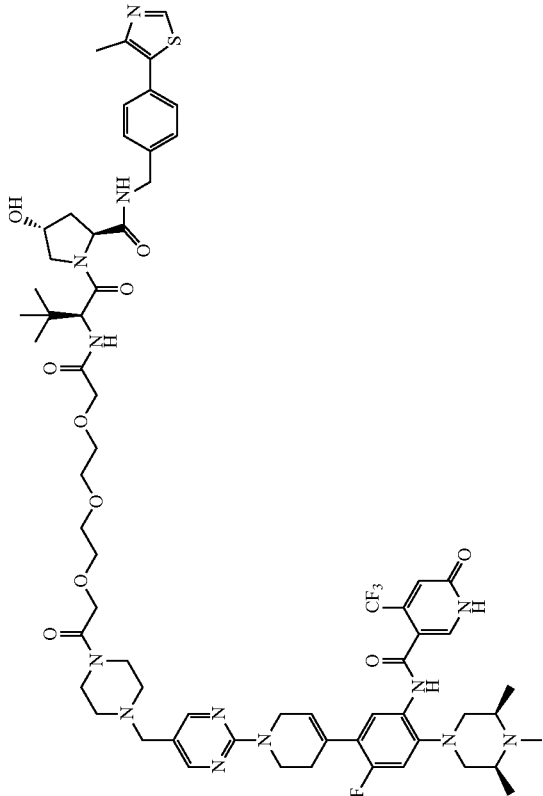 N-(4-fluoro-5-(1-(5-((4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF078-137 | 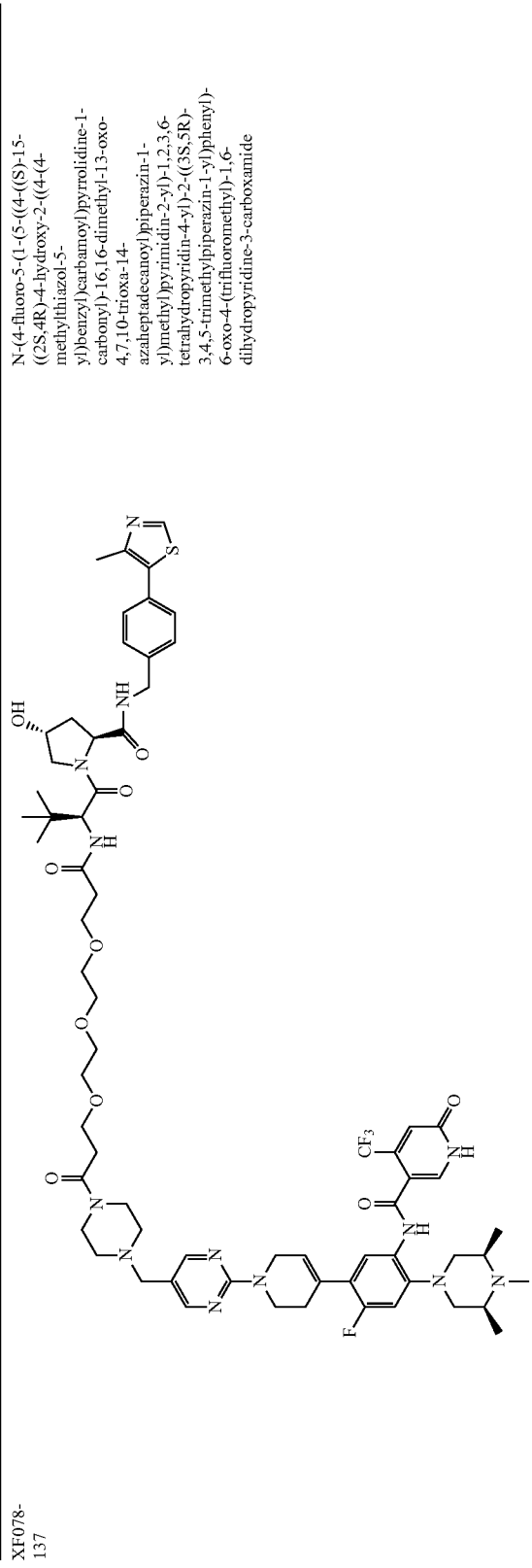 | N-(4-fluoro-5-(1-(5-((4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-138 | 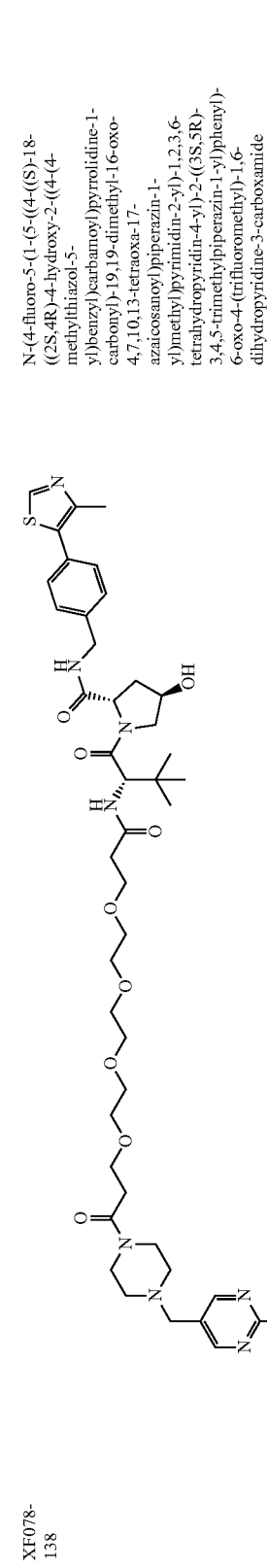 | N-(4-fluoro-5-(1-(5-((4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF078-139 | 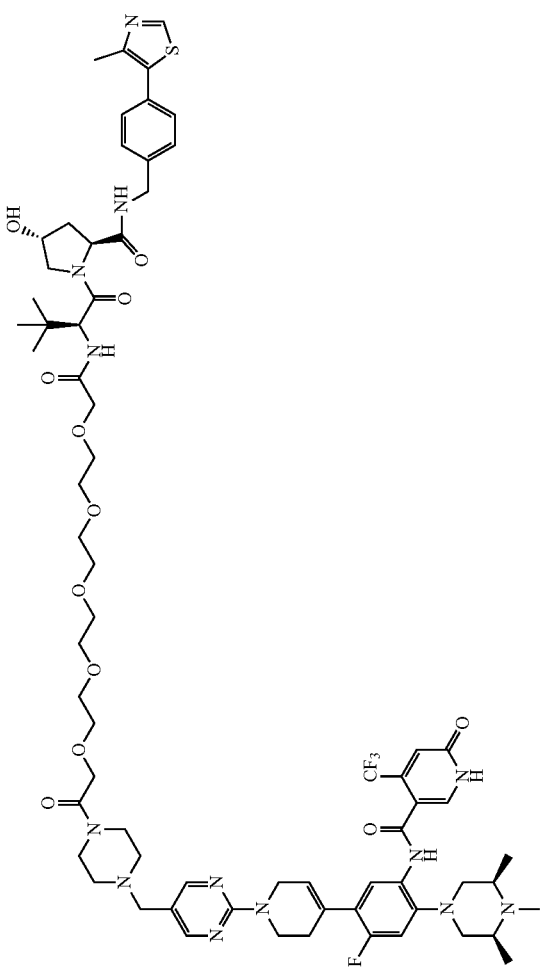 | N-(4-fluoro-5-(1-(5-(((4-((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-141 | 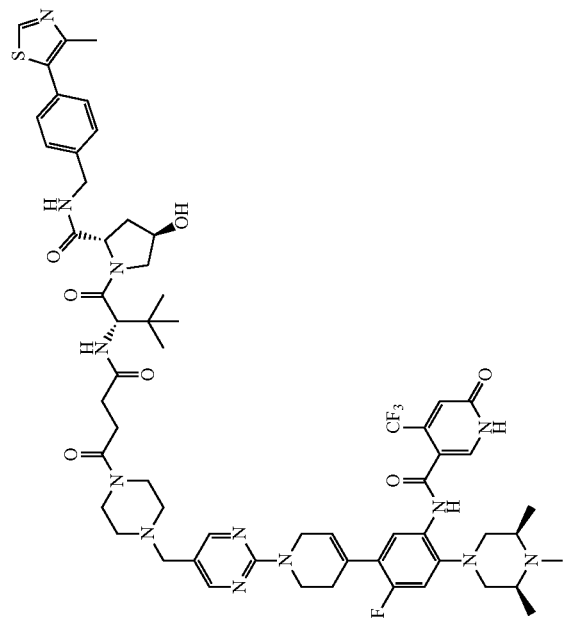 | N-(4-fluoro-5-(1-(5-((4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| XF078-142 | 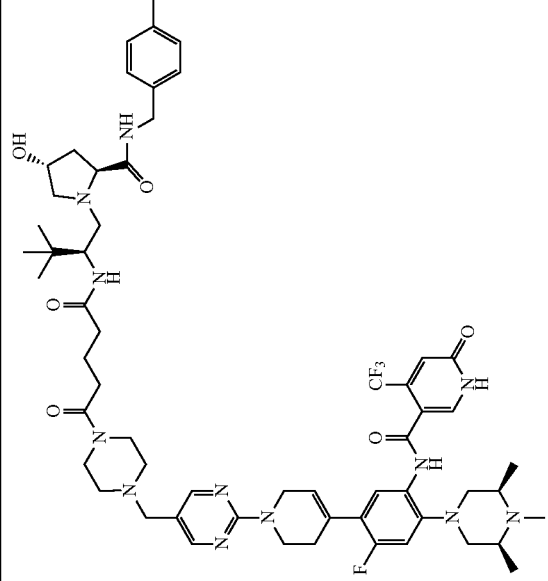 | N-(4-fluoro-5-(1-(5-((4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-143 | 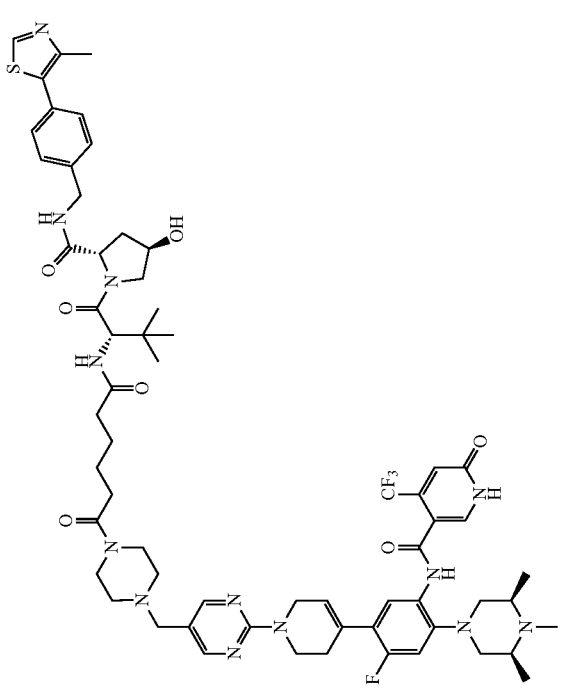 | N-(4-fluoro-5-(1-(5-((4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

| | |
|---|---|
| XF078-144 | 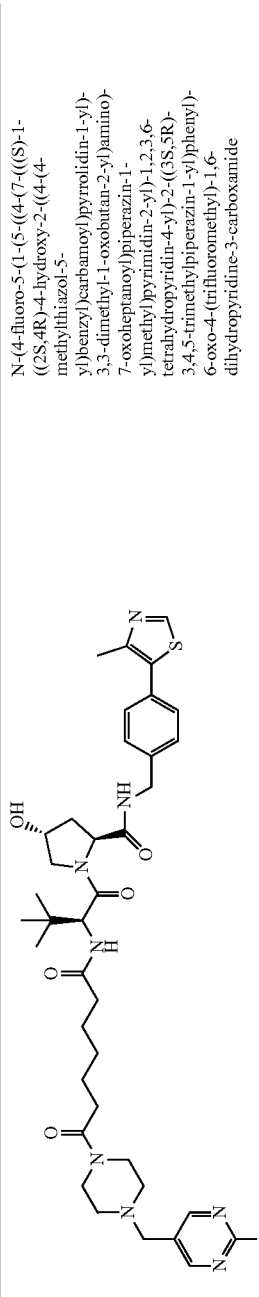 N-(4-fluoro-5-(1-(5-((4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-145 | 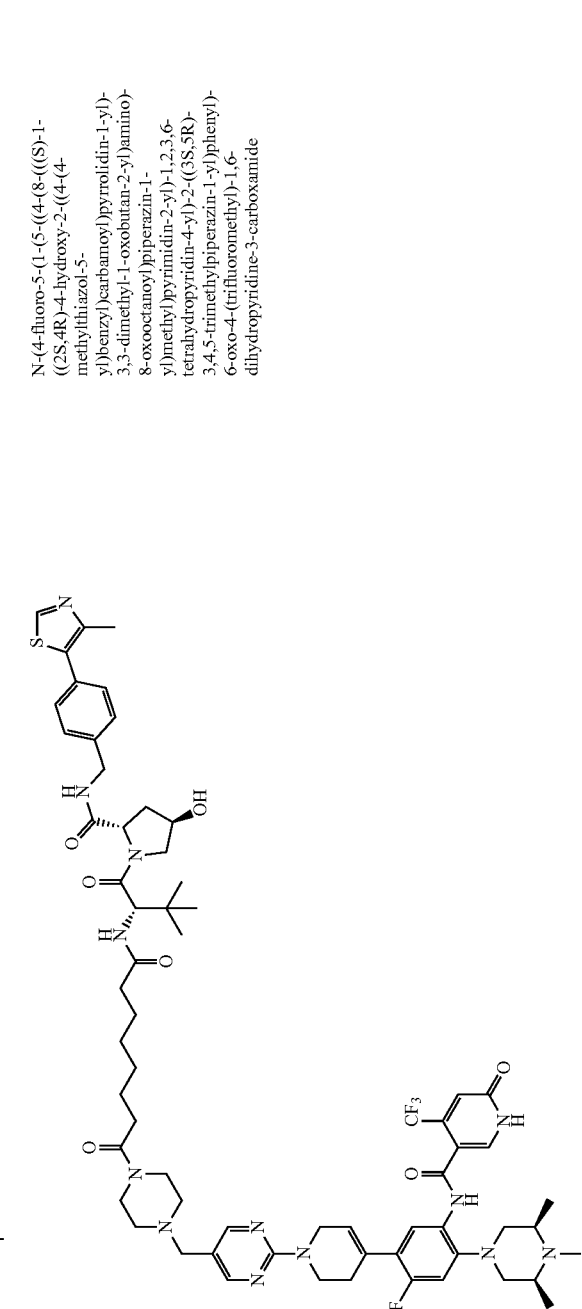 N-(4-fluoro-5-(1-(5-((4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF078-146 | 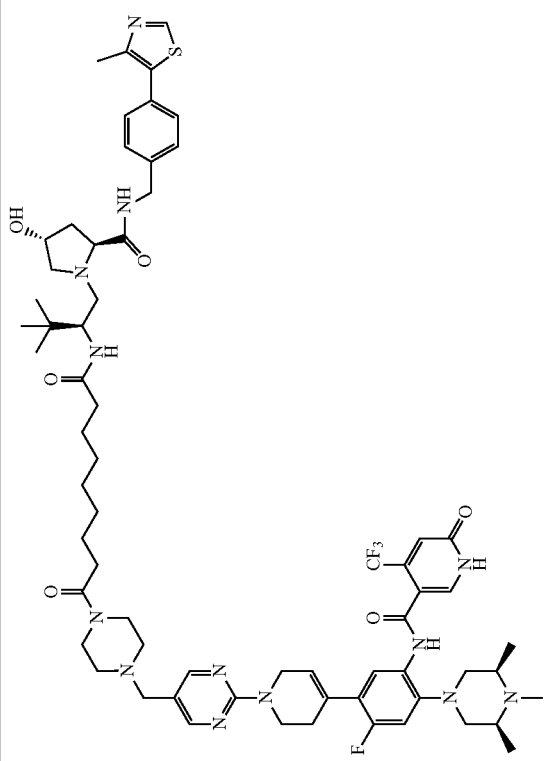 | N-(4-fluoro-5-(1-(5-((4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |
| XF078-147 | 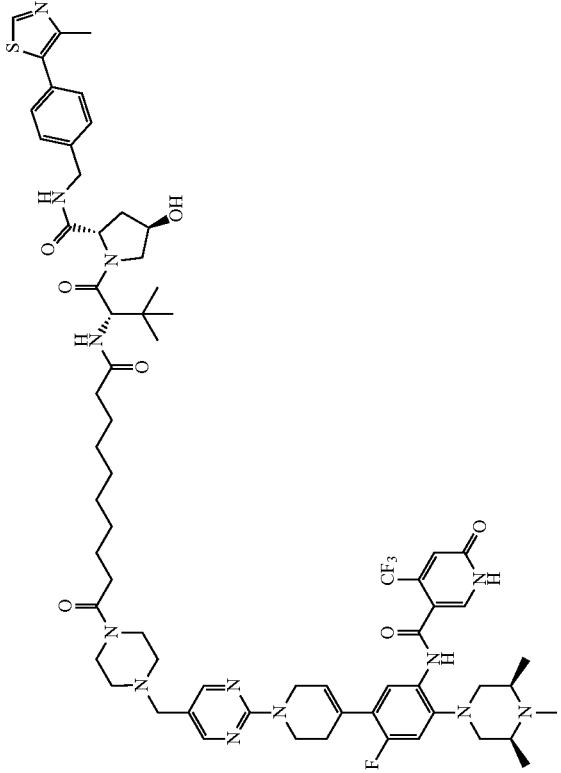 | N-(4-fluoro-5-(1-(5-((4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| | |
|---|---|
| XF078-148 | 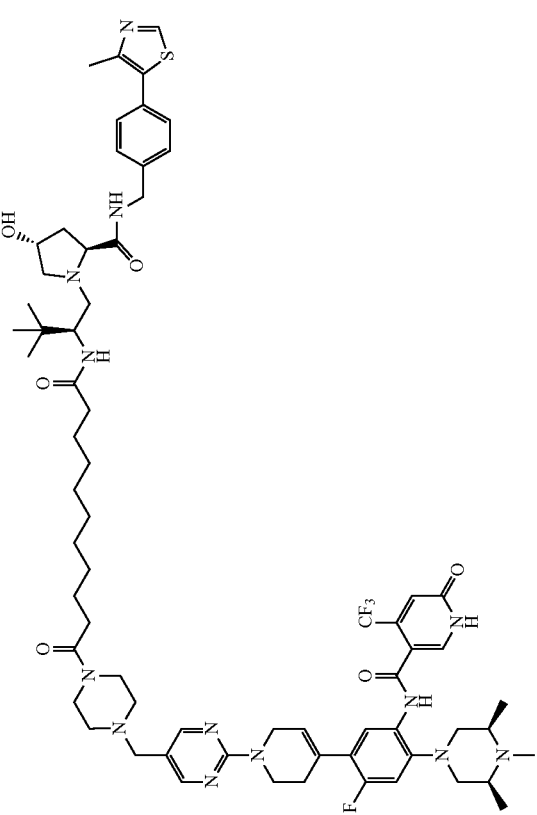 N-(4-fluoro-5-(1-(5-((4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)methyl)pyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide |

TABLE 1-continued
| | | |
|---|---|---|
| XF078-149 | 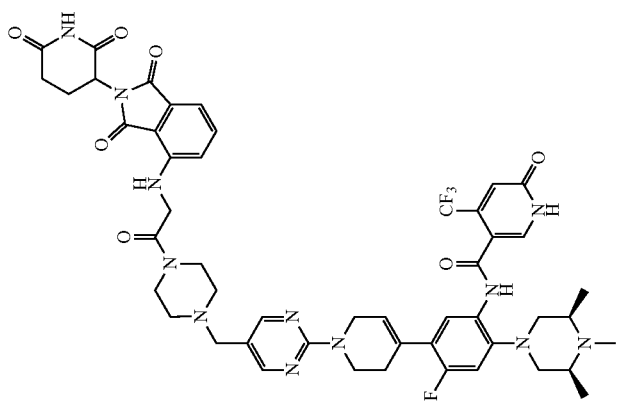 | N-(5-(1-(5-((4-((2-(2,6-dioxopiperidin-3-yl)-1,3-dioxoisoindolin-4-yl)glycyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| | |
|---|---|
| XF078-150 | 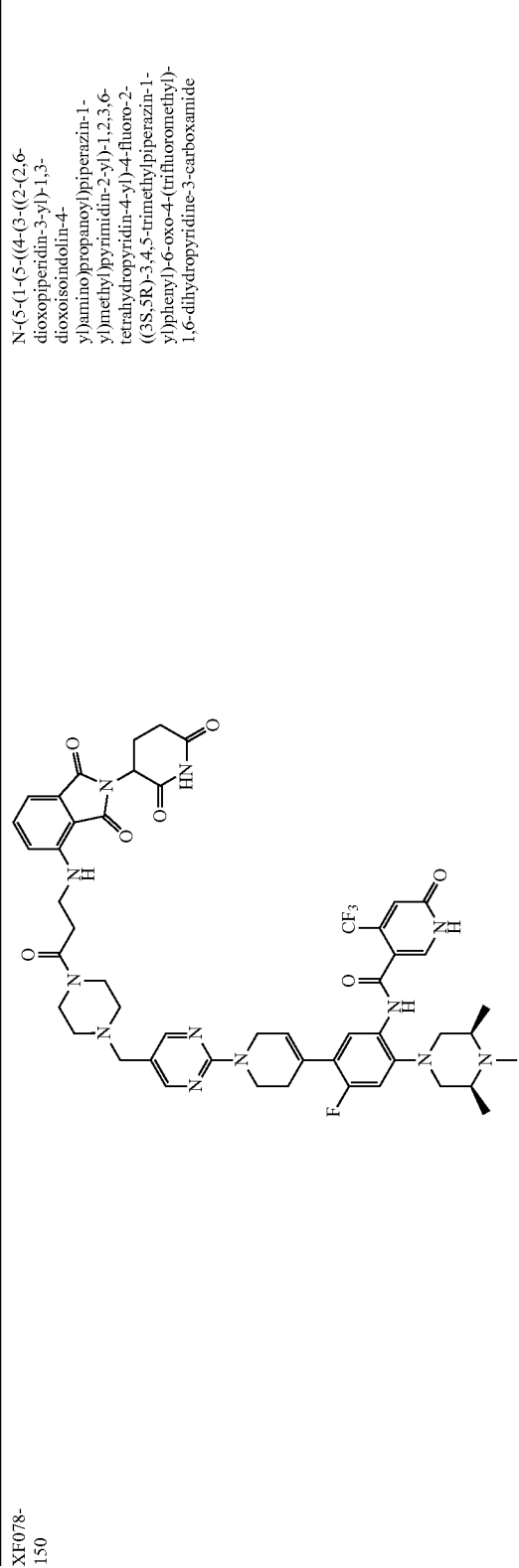 N-(5-(1-(5-((4-(3-((2-(2,6-dioxopiperidin-3-yl)-1,3-dioxoisoindolin-4-yl)amino)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| | | |
|---|---|---|
| XF078-151 | 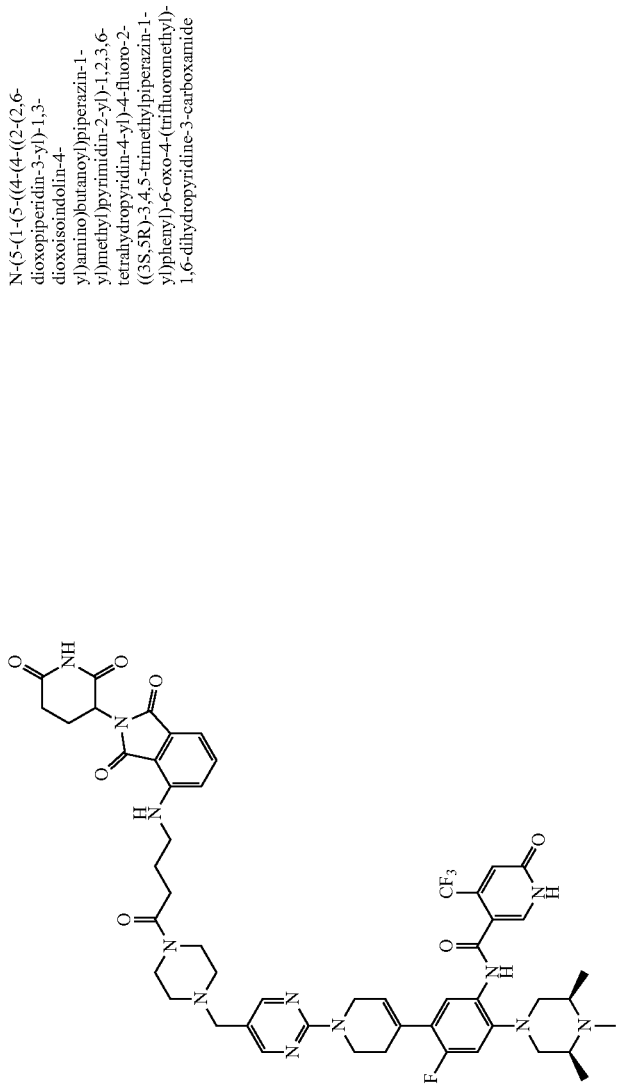 | N-(5-(1-(5-(4-(4-((2-(2-(2,6-dioxopiperidin-3-yl)-1,3-dioxoisoindolin-4-yl)amino)butanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| | | |
|---|---|---|
| XF078-157 | 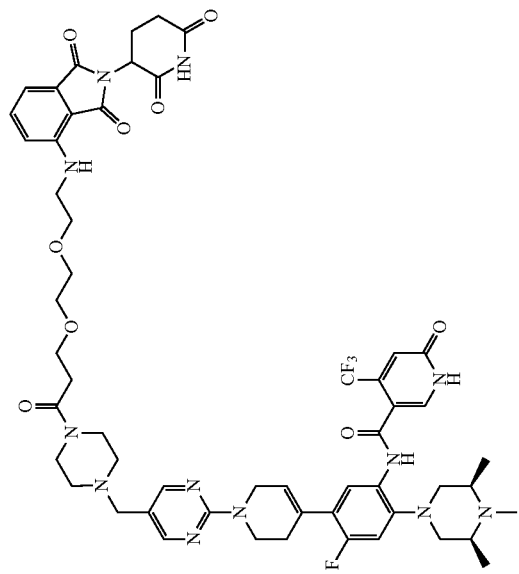 | N-(5-(1-(5-(4-(3-(2-(2-((2-(2,6-dioxopiperidin-3-yl)-1,3-dioxoisoindolin-4-yl)amino)ethoxy)ethoxy)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| | | |
|---|---|---|
| XF078-158 | 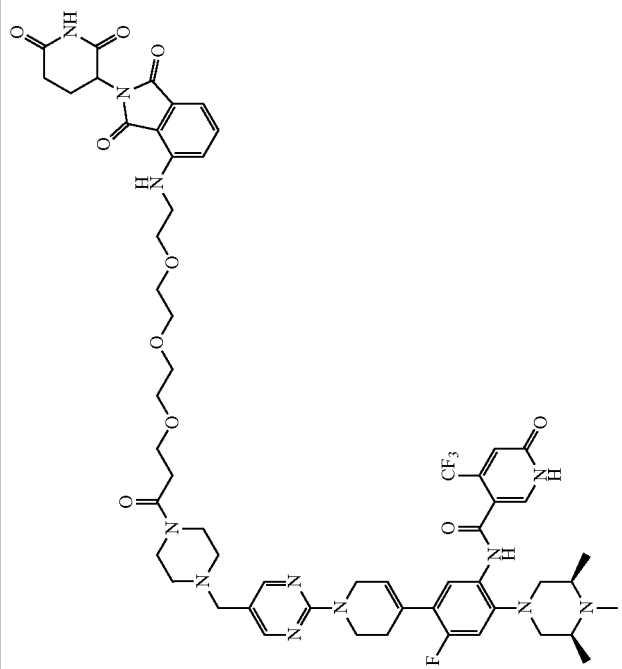 | N-(5-(1-(5-(4-(3-(2-(2-(2-(2-(2,6-dioxopiperidin-3-yl)-1,3-dioxoisoindolin-4-yl)amino)ethoxy)ethoxy)ethoxy)propanoyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued
| | | |
|---|---|---|
| XF078-159 | 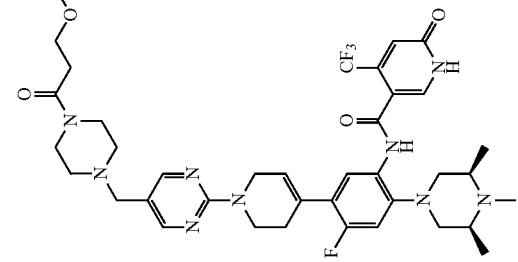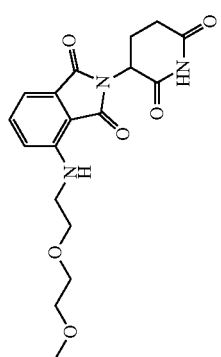 | N-(5-(1-(5-((4-(1-((2-(2,6-dioxopiperidin-3-yl)-1,3-dioxoisoindolin-4-yl)amino)-3,6,9,12-tetraoxapentadecan-15-oyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |

TABLE 1-continued

| | | |
|---|---|---|
| XF078-160 | 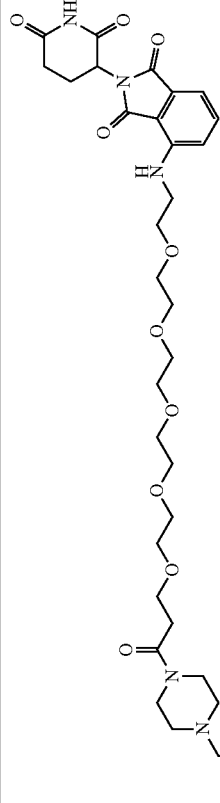 | N-(5-(1-(5-((4-(1-((2-(2,6-dioxopiperidin-3-yl)-1,3-dioxoisoindolin-4-yl)amino)-3,6,9,12,15-pentaoxaoctadecan-18-oyl)piperazin-1-yl)methyl)pyrimidin-2-yl)-1,2,3,6-tetrahydropyridin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide |
| XF061-33 | 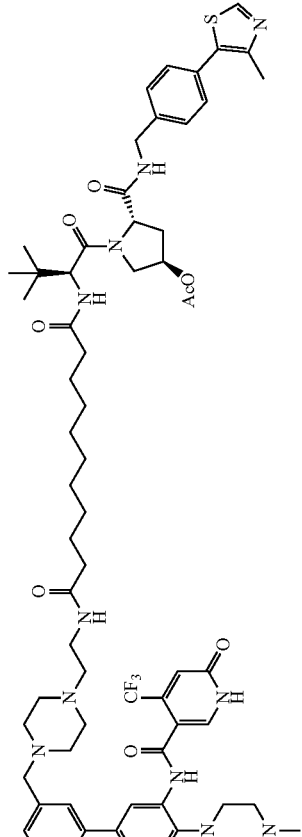 | (2S,4R)-1-((S)-2-(2-(2-(3-(5-(((R)-6-(6,7-dihydro-5H-pyrrolo[1,2-a]imidazol-2-yl)-2,3-dihydro-1H-inden-1-yl)carbamoyl)-3-methoxy-2-methylphenoxy)propyl)amino)-2-oxoethoxy)acetamido)-3,3-dimethylbutanoyl)-4-hydroxy-N-(4-(4-methylthiazol-5-yl)benzyl)pyrrolidine-2-carboxamide |

* * * * *